US012364466B2

(12) United States Patent
Schmid et al.

(10) Patent No.: US 12,364,466 B2
(45) Date of Patent: Jul. 22, 2025

(54) IMPLANTABLE LAYER COMPRISING A PLURALITY OF LAYERS

(71) Applicant: Cilag GmbH International, Zug (CH)

(72) Inventors: Katherine J. Schmid, Loveland, OH (US); Jerome R. Morgan, Cincinnati, OH (US); Donna L. Korvick, San Antonio, TX (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/586,148

(22) Filed: Feb. 23, 2024

(65) Prior Publication Data
US 2024/0252159 A1 Aug. 1, 2024

Related U.S. Application Data

(63) Continuation of application No. 17/396,911, filed on Aug. 9, 2021, now abandoned, which is a
(Continued)

(51) Int. Cl.
A61B 17/072 (2006.01)
A61B 17/00 (2006.01)
(Continued)

(52) U.S. Cl.
CPC ...... *A61B 17/00491* (2013.01); *A61B 17/064* (2013.01); *A61B 17/0643* (2013.01); *A61B 17/0644* (2013.01); *A61B 17/068* (2013.01); *A61B 17/072* (2013.01); *A61B 17/07207* (2013.01); *A61B 17/07292* (2013.01); *A61B 17/105* (2013.01); *A61B 17/1155* (2013.01);

*A61B 17/30* (2013.01); *A61B 2017/00004* (2013.01); *A61B 2017/00495* (2013.01); *A61B 2017/00526* (2013.01);
(Continued)

(58) Field of Classification Search
CPC . A61B 17/064; A61B 17/0643; A61B 17/068; A61B 17/072; A61B 17/07207
USPC .................................................. 227/175.1
See application file for complete search history.

(56) References Cited

U.S. PATENT DOCUMENTS 3,643,851 A 2/1972 Green et al.
4,964,863 A 10/1990 Kanshin et al.
(Continued)

FOREIGN PATENT DOCUMENTS

AU 2012200178 B2 7/2013
BR 112013027777 A2 1/2017
(Continued)

OTHER PUBLICATIONS

ASTM procedure D2240-00, "Standard Test Method for Rubber Property-Durometer Hardness," (Published Aug. 2000).
(Continued)

*Primary Examiner* — Michelle Lopez

(57) ABSTRACT

An implantable layer for use with a surgical stapler is disclosed. The implantable layer includes a first layer including a first side, wherein the first side includes an opening. The implantable layer further includes a second layer including a second side, wherein the second side extends at least partially through the opening to hold the second layer relative to the first layer, and wherein a pocket is defined between the first layer and the second layer. The implantable layer further includes a bioabsorbable material in the pocket.

20 Claims, 331 Drawing Sheets

Related U.S. Application Data continuation of application No. 16/158,501, filed on Oct. 12, 2018, now Pat. No. 11,083,452, which is a continuation of application No. 15/789,615, filed on Oct. 20, 2017, now Pat. No. 10,258,332, which is a continuation of application No. 14/746,360, filed on Jun. 22, 2015, now Pat. No. 9,883,861, which is a continuation of application No. 13/433,114, filed on Mar. 28, 2012, now Pat. No. 9,386,988, which is a continuation-in-part of application No. 13/097,891, filed on Apr. 29, 2011, now Pat. No. 8,864,009, which is a continuation-in-part of application No. 12/894,377, filed on Sep. 30, 2010, now Pat. No. 8,393,514.

(51) Int. Cl.
| | |
|---|---|
| *A61B 17/064* | (2006.01) |
| *A61B 17/068* | (2006.01) |
| *A61B 17/10* | (2006.01) |
| *A61B 17/115* | (2006.01) |
| *A61B 17/30* | (2006.01) |
| *A61B 17/29* | (2006.01) |
| *A61B 17/32* | (2006.01) |

(52) U.S. Cl.
CPC ............... *A61B 2017/0053* (2013.01); *A61B 2017/00818* (2013.01); *A61B 2017/00884* (2013.01); *A61B 2017/00893* (2013.01); *A61B 2017/00991* (2013.01); *A61B 2017/07228* (2013.01); *A61B 2017/07235* (2013.01); *A61B 2017/07242* (2013.01); *A61B 2017/0725* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2017/2908* (2013.01); *A61B 17/2909* (2013.01); *A61B 2017/2916* (2013.01); *A61B 2017/2919* (2013.01); *A61B 2017/2923* (2013.01); *A61B 2017/2927* (2013.01); *A61B 2017/2933* (2013.01); *A61B 2017/2936* (2013.01); *A61B 2017/2937* (2013.01); *A61B 2017/320052* (2013.01)

(56) References Cited

U.S. PATENT DOCUMENTS

| | | |
|---|---|---|
| 5,024,671 A | 6/1991 | Tu et al. |
| 5,158,222 A | 10/1992 | Green et al. |
| 5,263,629 A | 11/1993 | Trumbull et al. |
| 5,285,945 A | 2/1994 | Brinkerhoff et al. |
| 5,397,324 A | 3/1995 | Carroll et al. |
| 5,468,253 A | 11/1995 | Bezwada et al. |
| 5,542,594 A | 8/1996 | McKean et al. |
| 5,549,621 A | 8/1996 | Bessler et al. |
| 5,662,260 A | 9/1997 | Yoon |
| 5,702,409 A | 12/1997 | Rayburn et al. |
| 5,713,920 A | 2/1998 | Bezwada et al. |
| 5,769,892 A | 6/1998 | Kingwell |
| 5,810,855 A | 9/1998 | Rayburn et al. |
| 5,814,057 A | 9/1998 | Oi et al. |
| 5,833,695 A | 11/1998 | Yoon |
| 5,865,361 A | 2/1999 | Milliman et al. |
| 6,099,551 A | 8/2000 | Gabbay |
| 6,273,897 B1 | 8/2001 | Dalessandro et al. |
| 6,319,510 B1 | 11/2001 | Yates |
| 6,325,810 B1 | 12/2001 | Hamilton et al. |
| 6,330,965 B1 | 12/2001 | Milliman et al. |
| 6,450,989 B2 | 9/2002 | Dubrul et al. |
| 6,503,257 B2 | 1/2003 | Grant et al. |
| 6,517,566 B1 | 2/2003 | Hovland et al. |
| 6,592,597 B2 | 7/2003 | Grant et al. |
| 6,596,304 B1 | 7/2003 | Bayon et al. |
| 6,656,193 B2 | 12/2003 | Grant et al. |
| 6,736,854 B2 | 5/2004 | Vadurro et al. |
| 6,818,018 B1 | 11/2004 | Sawhney |
| 6,835,336 B2 | 12/2004 | Watt |
| 6,866,668 B2 | 3/2005 | Giannetti et al. |
| 7,000,818 B2 | 2/2006 | Shelton, IV et al. |
| 7,067,038 B2 | 6/2006 | Trokhan et al. |
| 7,070,083 B2 | 7/2006 | Jankowski |
| 7,083,075 B2 | 8/2006 | Swayze et al. |
| 7,128,748 B2 | 10/2006 | Mooradian et al. |
| 7,143,925 B2 | 12/2006 | Shelton, IV et al. |
| 7,147,138 B2 | 12/2006 | Shelton, IV |
| 7,364,061 B2 | 4/2008 | Swayze et al. |
| 7,371,403 B2 | 5/2008 | McCarthy et al. |
| 7,380,696 B2 | 6/2008 | Shelton, IV et al. |
| 7,398,908 B2 | 7/2008 | Holsten et al. |
| 7,401,721 B2 | 7/2008 | Holsten et al. |
| 7,419,321 B2 | 9/2008 | Tereschouk |
| 7,431,730 B2 | 10/2008 | Viola |
| 7,500,979 B2 | 3/2009 | Hueil et al. |
| 7,506,791 B2 | 3/2009 | Omaits et al. |
| 7,517,356 B2 | 4/2009 | Heinrich |
| 7,547,312 B2 | 6/2009 | Bauman et al. |
| 7,635,074 B2 | 12/2009 | Olson et al. |
| 7,665,646 B2 | 2/2010 | Prommersberger |
| 7,708,180 B2 | 5/2010 | Murray et al. |
| 7,718,180 B2 | 5/2010 | Karp |
| 7,722,527 B2 | 5/2010 | Bouchier et al. |
| 7,744,627 B2 | 6/2010 | Orban, III et al. |
| 7,780,685 B2 | 8/2010 | Hunt et al. |
| 7,794,475 B2 | 9/2010 | Hess et al. |
| 7,823,592 B2 | 11/2010 | Bettuchi et al. |
| 7,832,612 B2 | 11/2010 | Baxter, III et al. |
| 7,845,533 B2 | 12/2010 | Marczyk et al. |
| 7,845,536 B2 | 12/2010 | Viola et al. |
| 7,886,951 B2 | 2/2011 | Hessler |
| 7,905,381 B2 | 3/2011 | Baxter et al. |
| 7,922,743 B2 | 4/2011 | Heinrich et al. |
| 7,926,691 B2 | 4/2011 | Viola et al. |
| 7,934,630 B2 | 5/2011 | Shelton, IV et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,988,779 B2 | 8/2011 | Disalvo et al. |
| 7,992,757 B2 | 8/2011 | Wheeler et al. |
| 7,997,469 B2 | 8/2011 | Olson et al. |
| 8,016,178 B2 | 9/2011 | Olson et al. |
| 8,028,883 B2 | 10/2011 | Stopek |
| 8,028,884 B2 | 10/2011 | Sniffin et al. |
| 8,034,363 B2 | 10/2011 | Li et al. |
| 8,038,045 B2 | 10/2011 | Bettuchi et al. |
| 8,062,330 B2 | 11/2011 | Prommersberger et al. |
| 8,091,756 B2 | 1/2012 | Viola |
| 8,114,100 B2 | 2/2012 | Smith et al. |
| 8,123,103 B2 | 2/2012 | Milliman |
| 8,157,151 B2 | 4/2012 | Ingmanson et al. |
| 8,167,895 B2 | 5/2012 | D'Agostino et al. |
| 8,231,040 B2 | 7/2012 | Zemlok et al. |
| 8,245,901 B2 | 8/2012 | Stopek |
| 8,256,654 B2 | 9/2012 | Bettuchi et al. |
| 8,302,323 B2 | 11/2012 | Fortier et al. |
| 8,319,002 B2 | 11/2012 | Daniels et al. |
| 8,348,131 B2 | 1/2013 | Omaits et al. |
| 8,365,976 B2 | 2/2013 | Hess et al. |
| 8,371,491 B2 | 2/2013 | Huitema et al. |
| 8,372,094 B2 | 2/2013 | Bettuchi et al. |
| 8,377,029 B2 | 2/2013 | Nagao et al. |
| 8,388,633 B2 | 3/2013 | Rousseau et al. |
| 8,393,514 B2 | 3/2013 | Shelton, IV et al. |
| 8,413,870 B2 | 4/2013 | Pastorelli et al. |
| 8,464,925 B2 | 6/2013 | Hull et al. |
| 8,470,355 B2 | 6/2013 | Skalla et al. |
| 8,474,677 B2 | 7/2013 | Woodard, Jr. et al. |
| 8,479,968 B2 | 7/2013 | Hodgkinson et al. |
| 8,496,153 B2 | 7/2013 | Demmy et al. |
| 8,521,273 B2 | 8/2013 | Kliman |
| 8,529,600 B2 | 9/2013 | Woodard, Jr. et al. |
| 8,529,819 B2 | 9/2013 | Ostapoff et al. |

(56) References Cited

U.S. PATENT DOCUMENTS

| | | | |
|---|---|---|---|
| 8,561,870 B2 | 10/2013 | Baxter, III et al. |
| 8,657,176 B2 | 2/2014 | Shelton, IV et al. |
| 8,668,129 B2 | 3/2014 | Olson |
| 8,678,263 B2 | 3/2014 | Viola |
| 8,701,958 B2 | 4/2014 | Shelton, IV et al. |
| 8,727,199 B2 | 5/2014 | Wenchell |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,535 B2 | 6/2014 | Shelton, IV et al. |
| 8,752,699 B2 | 6/2014 | Morgan et al. |
| 8,757,465 B2 | 6/2014 | Woodard, Jr. et al. |
| 8,763,877 B2 | 7/2014 | Schall et al. |
| 8,777,004 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,741 B2 | 7/2014 | Baxter, III et al. |
| 8,808,274 B2 | 8/2014 | Hartwell |
| 8,814,024 B2 | 8/2014 | Woodard, Jr. et al. |
| 8,840,003 B2 | 9/2014 | Morgan et al. |
| 8,857,694 B2 | 10/2014 | Shelton, IV et al. |
| 8,864,007 B2 | 10/2014 | Widenhouse et al. |
| 8,864,009 B2 | 10/2014 | Shelton, IV et al. |
| 8,893,949 B2 | 11/2014 | Shelton, IV et al. |
| 8,899,463 B2 | 12/2014 | Schall et al. |
| 8,920,443 B2 | 12/2014 | Hiles et al. |
| 8,925,782 B2 | 1/2015 | Shelton, IV |
| 8,967,448 B2 | 3/2015 | Carter et al. |
| 8,978,954 B2 | 3/2015 | Shelton, IV et al. |
| 8,978,956 B2 | 3/2015 | Schall et al. |
| 8,991,676 B2 | 3/2015 | Hess et al. |
| 9,016,542 B2 | 4/2015 | Shelton, IV et al. |
| 9,033,203 B2 | 5/2015 | Woodard, Jr. et al. |
| 9,044,227 B2 | 6/2015 | Shelton, IV et al. |
| 9,044,228 B2 | 6/2015 | Woodard, Jr. et al. |
| 9,050,084 B2 | 6/2015 | Schmid et al. |
| 9,055,941 B2 | 6/2015 | Schmid et al. |
| 9,055,942 B2 | 6/2015 | Balbierz et al. |
| 9,084,602 B2 | 7/2015 | Gleiman |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,168,038 B2 | 10/2015 | Shelton, IV et al. |
| 9,204,880 B2 | 12/2015 | Baxter, III et al. |
| 9,204,881 B2 | 12/2015 | Penna |
| 9,211,120 B2 | 12/2015 | Scheib et al. |
| 9,216,019 B2 | 12/2015 | Schmid et al. |
| 9,220,500 B2 | 12/2015 | Swayze et al. |
| 9,220,501 B2 | 12/2015 | Baxter et al. |
| 9,226,754 B2 | 1/2016 | D'Agostino et al. |
| 9,232,941 B2 | 1/2016 | Mandakolathur Vasudevan et al. |
| 9,241,714 B2 | 1/2016 | Timm et al. |
| 9,277,919 B2 | 3/2016 | Timmer et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,320,523 B2 | 4/2016 | Shelton, IV et al. |
| 9,332,974 B2 | 5/2016 | Henderson et al. |
| 9,351,730 B2 | 5/2016 | Schmid et al. |
| 9,351,731 B2 | 5/2016 | Carter et al. |
| 9,364,229 B2 | 6/2016 | D'Agostino et al. |
| 9,364,233 B2 | 6/2016 | Alexander et al. |
| 9,386,988 B2 | 7/2016 | Baxter et al. |
| 9,414,838 B2 | 8/2016 | Shelton, IV et al. |
| 9,433,419 B2 | 9/2016 | Gonzalez et al. |
| 9,463,260 B2 | 10/2016 | Stopek |
| 9,480,476 B2 | 11/2016 | Aldridge et al. |
| 9,517,063 B2 | 12/2016 | Swayze et al. |
| 9,629,626 B2 | 4/2017 | Soltz et al. |
| 9,839,420 B2 | 12/2017 | Shelton, IV et al. |
| 9,883,861 B2 | 2/2018 | Shelton, IV et al. |
| 9,888,924 B2 | 2/2018 | Ebersole et al. |
| 9,889,230 B2 | 2/2018 | Bennett et al. |
| 10,022,125 B2 | 7/2018 | (Prommersberger) Stopek et al. |
| 10,085,754 B2 | 10/2018 | Sniffin et al. |
| 10,117,652 B2 | 11/2018 | Schmid et al. |
| 10,123,798 B2 | 11/2018 | Baxter et al. |
| 10,136,890 B2 | 11/2018 | Shelton, IV et al. |
| 10,172,616 B2 | 1/2019 | Murray et al. |
| 10,258,332 B2 | 4/2019 | Schmid et al. |
| 10,258,336 B2 | 4/2019 | Baxter, III et al. |
| 10,271,846 B2 | 4/2019 | Shelton, IV et al. |
| 10,307,161 B2 | 6/2019 | Jankowski |
| 10,912,575 B2 | 2/2021 | Shelton, IV et al. |
| 11,083,452 B2 | 8/2021 | Schmid et al. |
| 2002/0116063 A1 | 8/2002 | Giannetti et al. |
| 2002/0165562 A1 | 11/2002 | Grant et al. |
| 2004/0254590 A1 | 12/2004 | Hoffman et al. |
| 2005/0059997 A1 | 3/2005 | Bauman et al. |
| 2005/0070929 A1 | 3/2005 | Dalessandro et al. |
| 2005/0129668 A1 | 6/2005 | Giannetti et al. |
| 2005/0145671 A1 | 7/2005 | Viola |
| 2005/0245965 A1 | 11/2005 | Orban, III et al. |
| 2006/0085034 A1 | 4/2006 | Bettuchi |
| 2006/0173470 A1 | 8/2006 | Oray et al. |
| 2007/0243227 A1 | 10/2007 | Gertner |
| 2007/0246505 A1 | 10/2007 | Pace-Floridia et al. |
| 2008/0086078 A1 | 4/2008 | Powell et al. |
| 2008/0128469 A1 | 6/2008 | Dalessandro et al. |
| 2008/0140115 A1 | 6/2008 | Stopek |
| 2008/0190989 A1 | 8/2008 | Crews et al. |
| 2008/0308608 A1 | 12/2008 | Prommersberger |
| 2009/0078739 A1 | 3/2009 | Viola |
| 2009/0120994 A1 | 5/2009 | Murray et al. |
| 2009/0143855 A1 | 6/2009 | Weber et al. |
| 2009/0196903 A1 | 8/2009 | Kliman |
| 2009/0206125 A1 | 8/2009 | Huitema et al. |
| 2009/0206126 A1 | 8/2009 | Huitema et al. |
| 2009/0206131 A1 | 8/2009 | Weisenburgh et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0308907 A1 | 12/2009 | Nalagatla et al. |
| 2010/0016888 A1 | 1/2010 | Calabrese et al. |
| 2010/0076489 A1 | 3/2010 | Stopek et al. |
| 2010/0100123 A1 | 4/2010 | Bennett |
| 2010/0147921 A1 | 6/2010 | Olson |
| 2010/0331880 A1 | 12/2010 | Stopek |
| 2011/0114697 A1 | 5/2011 | Baxter, III et al. |
| 2011/0293690 A1 | 12/2011 | Griffin et al. |
| 2012/0004636 A1 | 1/2012 | Lo |
| 2012/0016467 A1 | 1/2012 | Chen et al. |
| 2012/0074200 A1 | 3/2012 | Schmid et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0125792 A1 | 5/2012 | Cassivi |
| 2012/0187179 A1 | 7/2012 | Gleiman |
| 2012/0248169 A1 | 10/2012 | Widenhouse et al. |
| 2012/0273547 A1 | 11/2012 | Hodgkinson et al. |
| 2013/0153639 A1 | 6/2013 | Hodgkinson et al. |
| 2013/0256373 A1 | 10/2013 | Schmid et al. |
| 2014/0048580 A1 | 2/2014 | Merchant et al. |
| 2022/0211367 A1 | 7/2022 | Schmid et al. |

FOREIGN PATENT DOCUMENTS

| | | |
|---|---|---|
| CN | 1777406 A | 5/2006 |
| CN | 2796654 Y | 7/2006 |
| CN | 101273908 A | 10/2008 |
| CN | 101378791 A | 3/2009 |
| CN | 101721236 A | 6/2010 |
| CN | 102217963 A | 10/2011 |
| EP | 0669104 A1 | 8/1995 |
| EP | 1064882 A1 | 1/2001 |
| EP | 1837041 A1 | 9/2007 |
| EP | 0922435 B1 | 10/2007 |
| EP | 2039302 A2 | 3/2009 |
| EP | 1719461 B1 | 6/2009 |
| FR | 2598905 A1 | 11/1987 |
| GB | 2024012 A | 1/1980 |

(56) References Cited

FOREIGN PATENT DOCUMENTS

| JP | 2005187954 A | 7/2005 |
|---|---|---|
| JP | 2009189846 A | 8/2009 |
| JP | 2010069307 A | 4/2010 |
| RU | 2161450 C1 | 1/2001 |
| RU | 2186714 C2 | 8/2002 |
| SU | 1377052 A1 | 2/1988 |
| SU | 1503766 A1 | 8/1989 |
| WO | WO-9827870 A1 | 7/1998 |

OTHER PUBLICATIONS

ASTM procedure D2240-05, "Standard Test Method for Rubber Property-Durometer Hardness," (Published Apr. 2010).

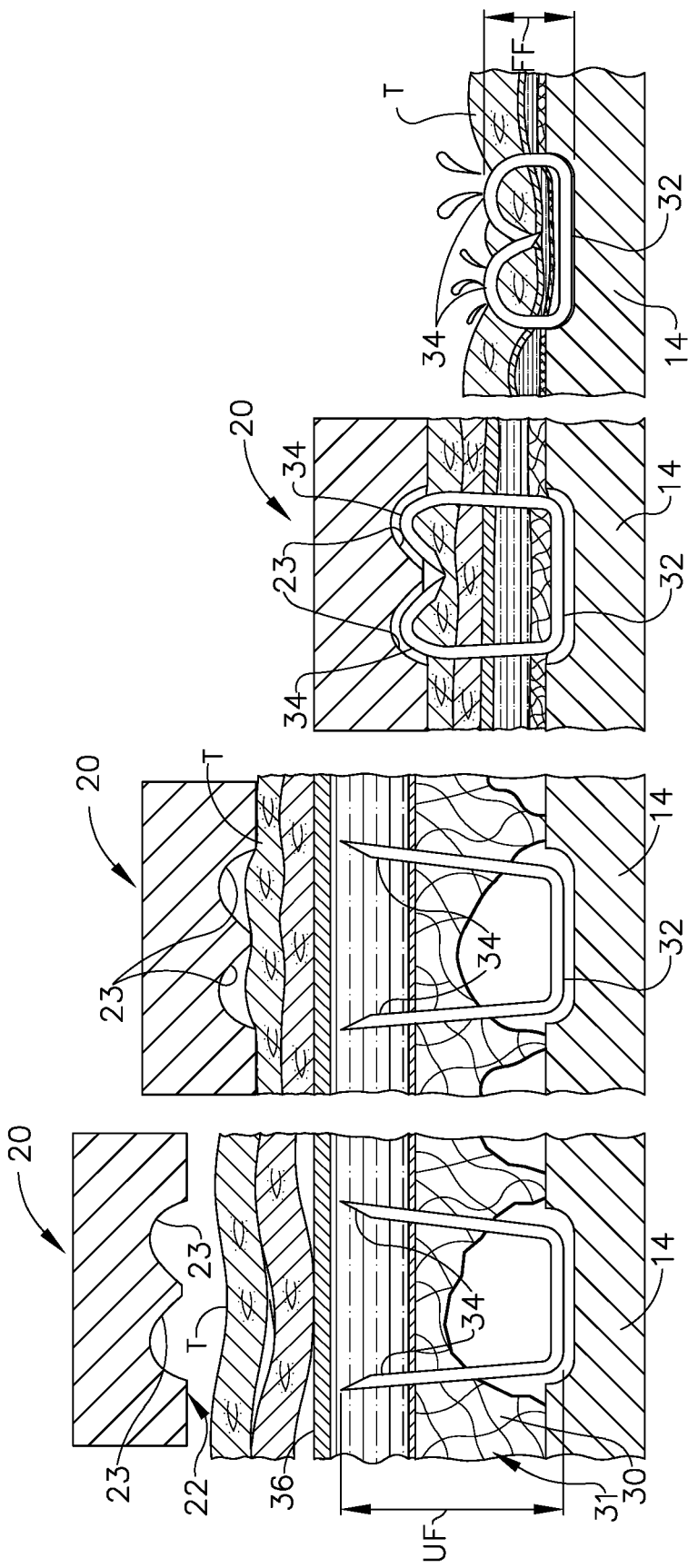

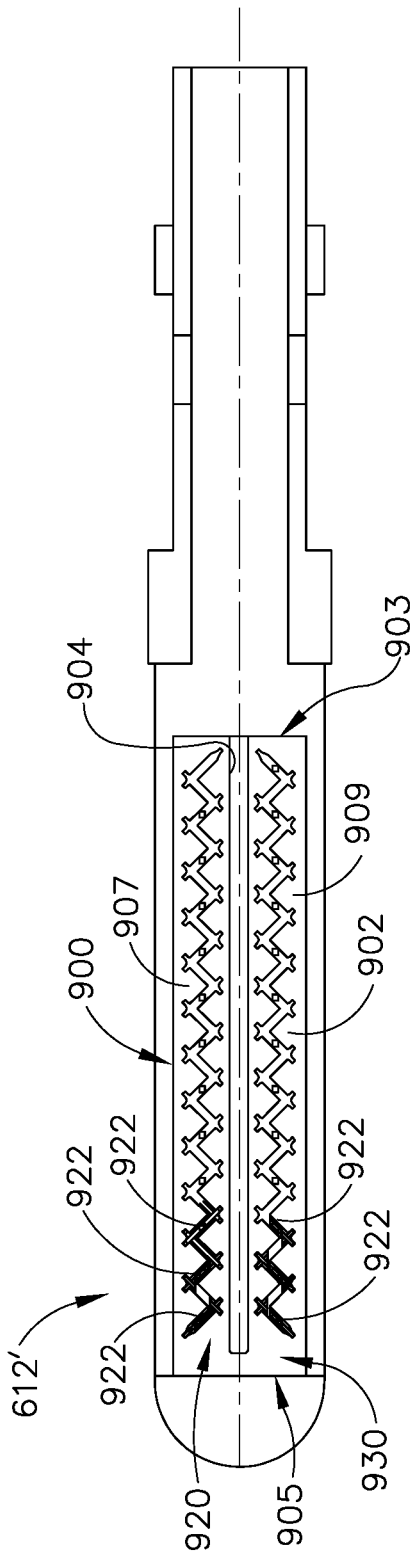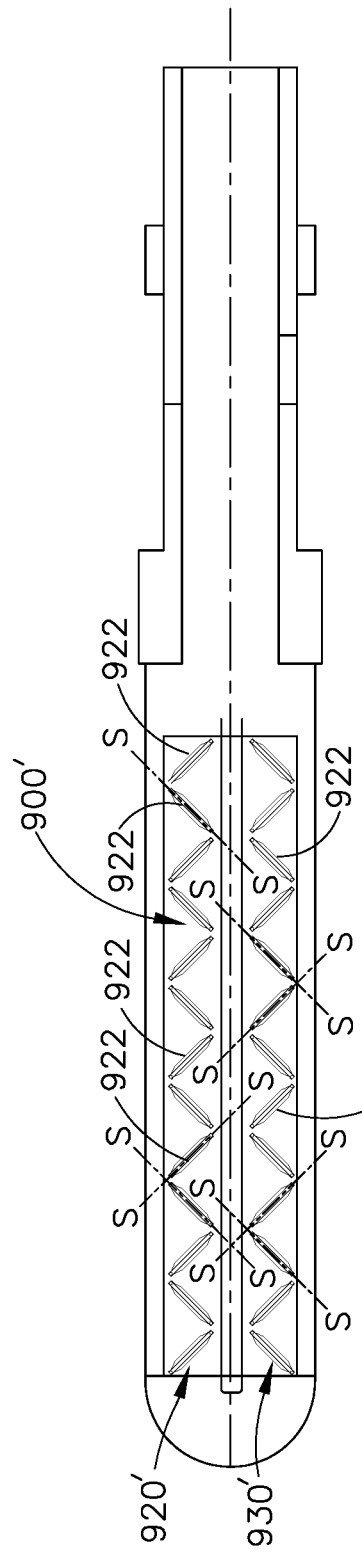

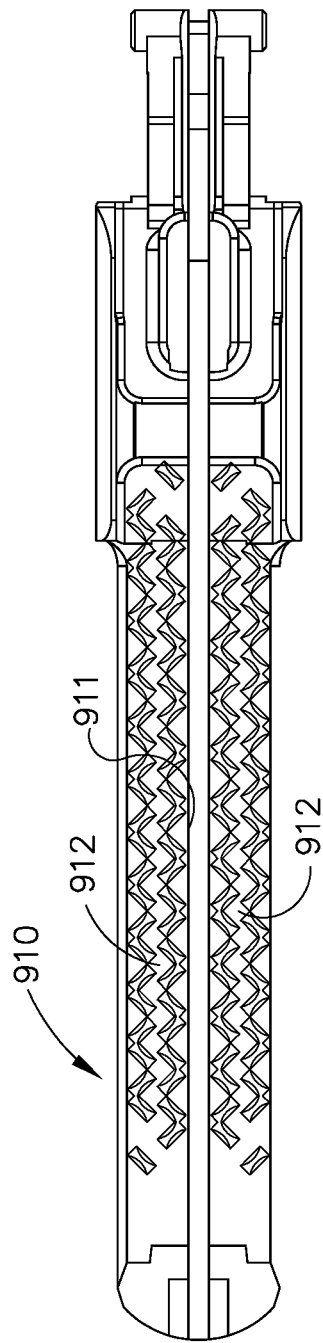
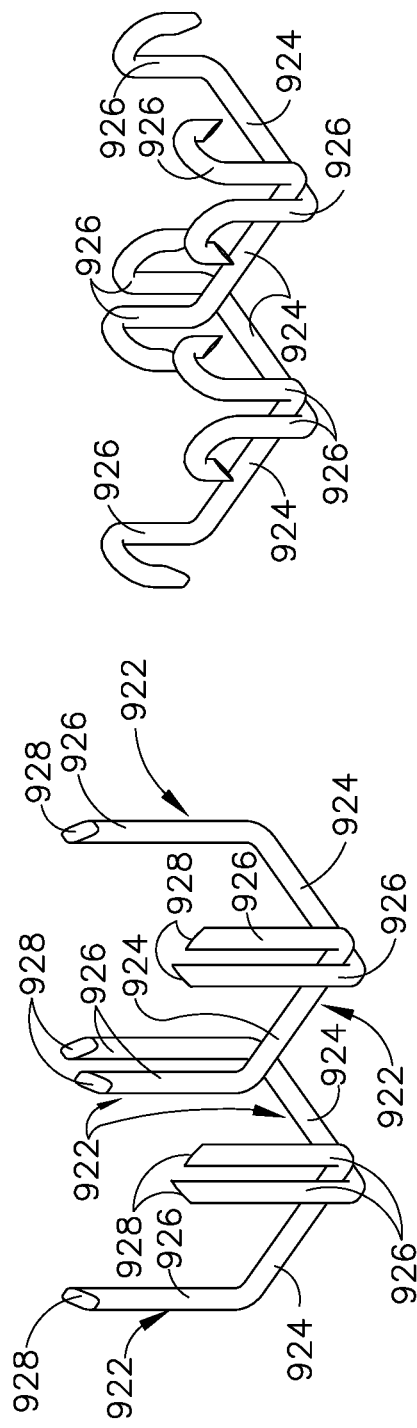
FIG. 9
FIG. 10
FIG. 11

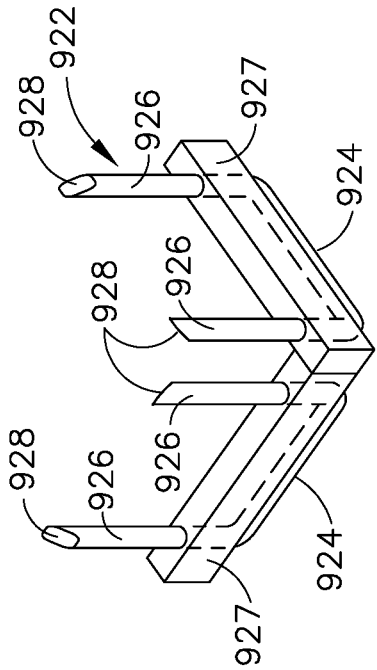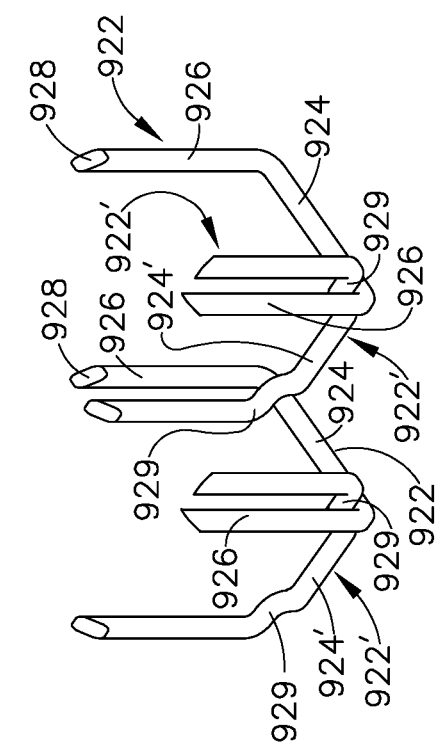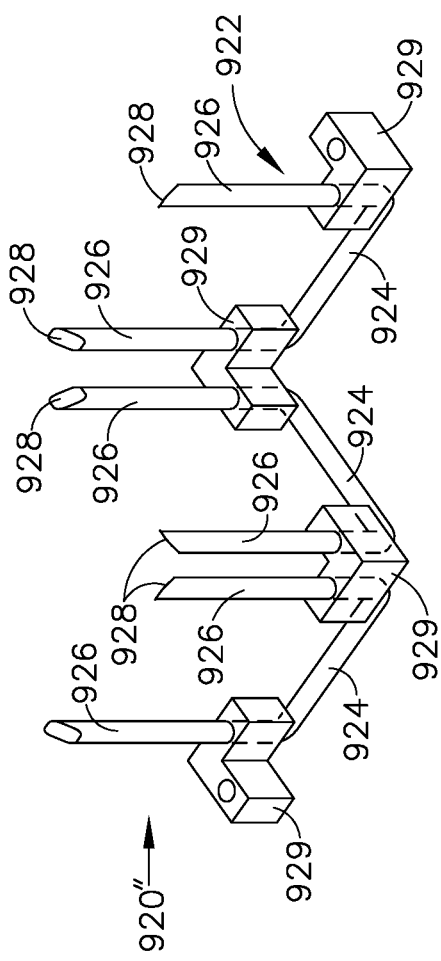

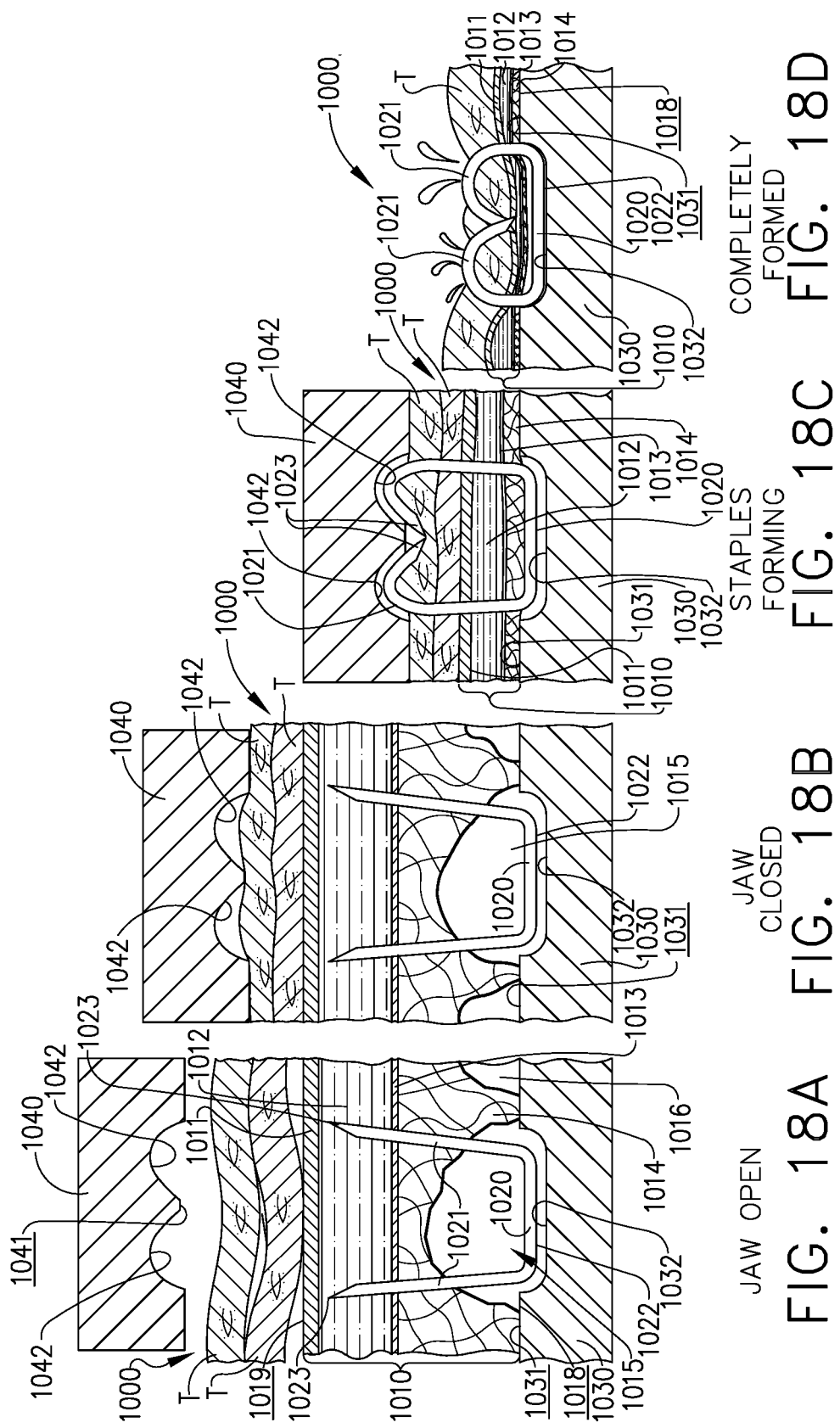

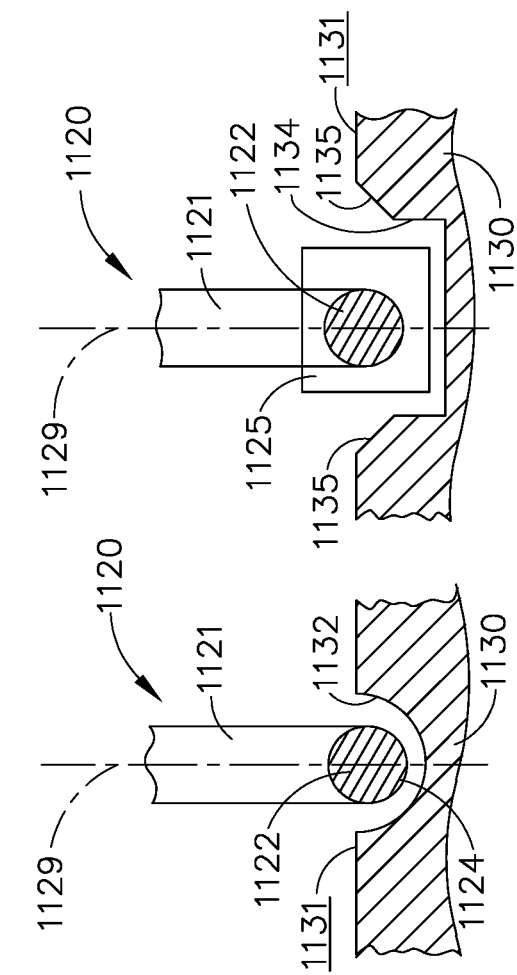
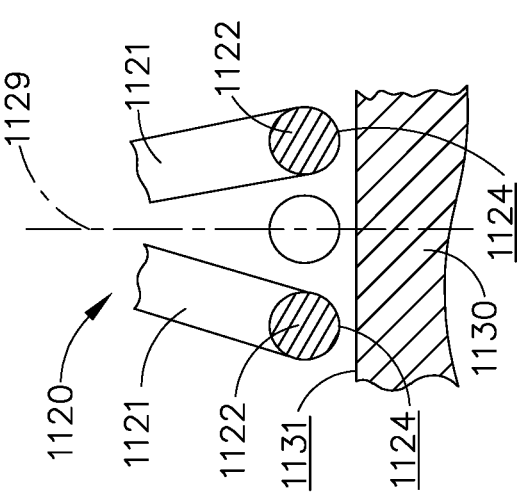

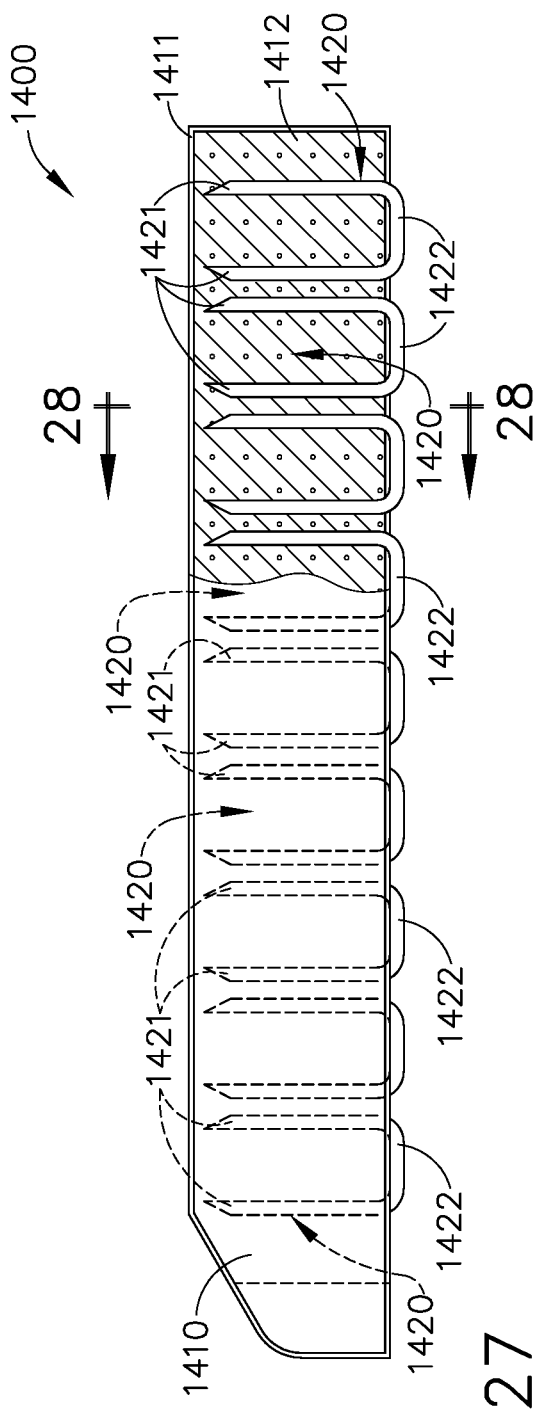
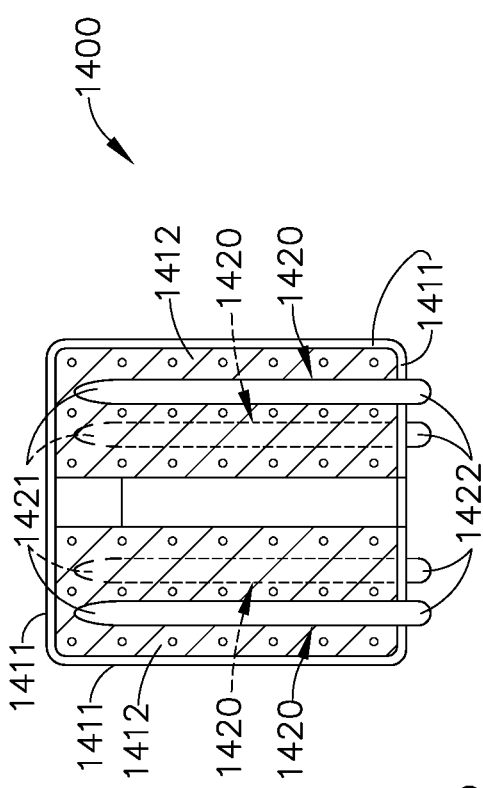
FIG. 27
FIG. 28

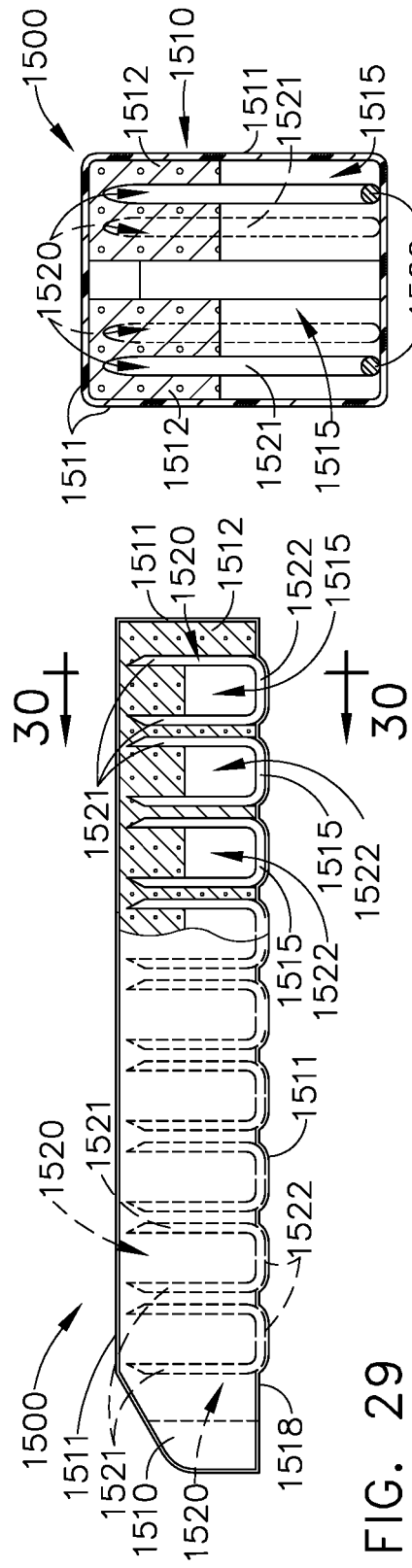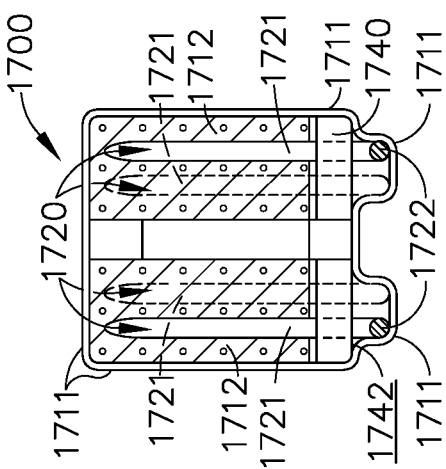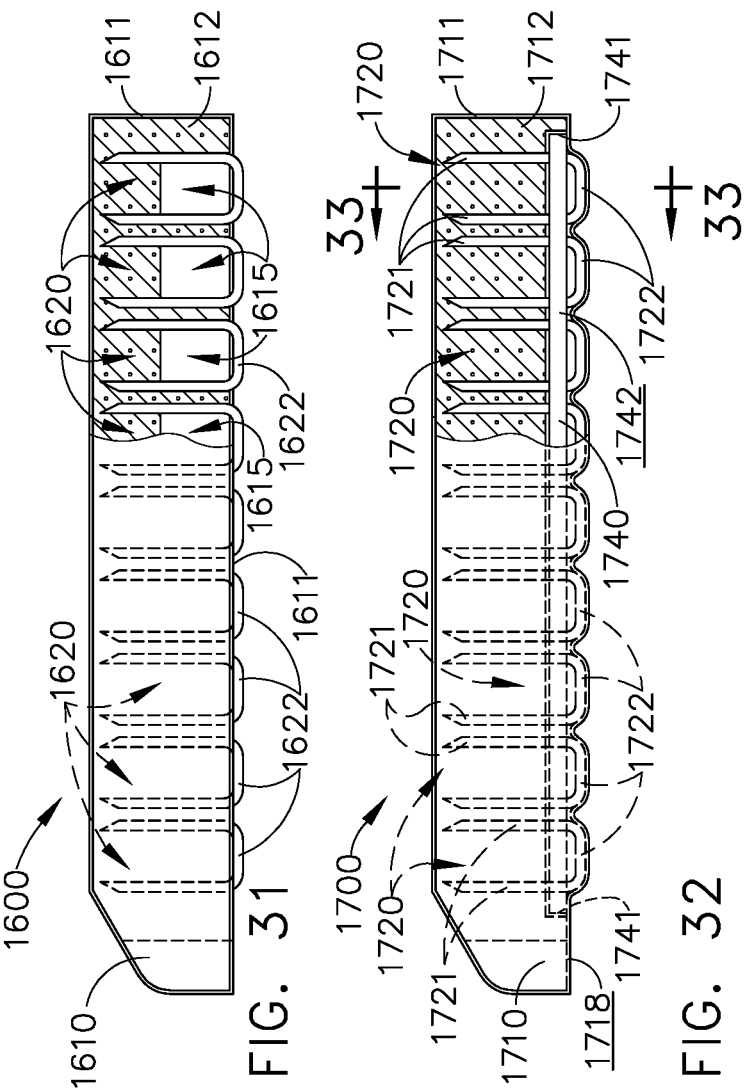

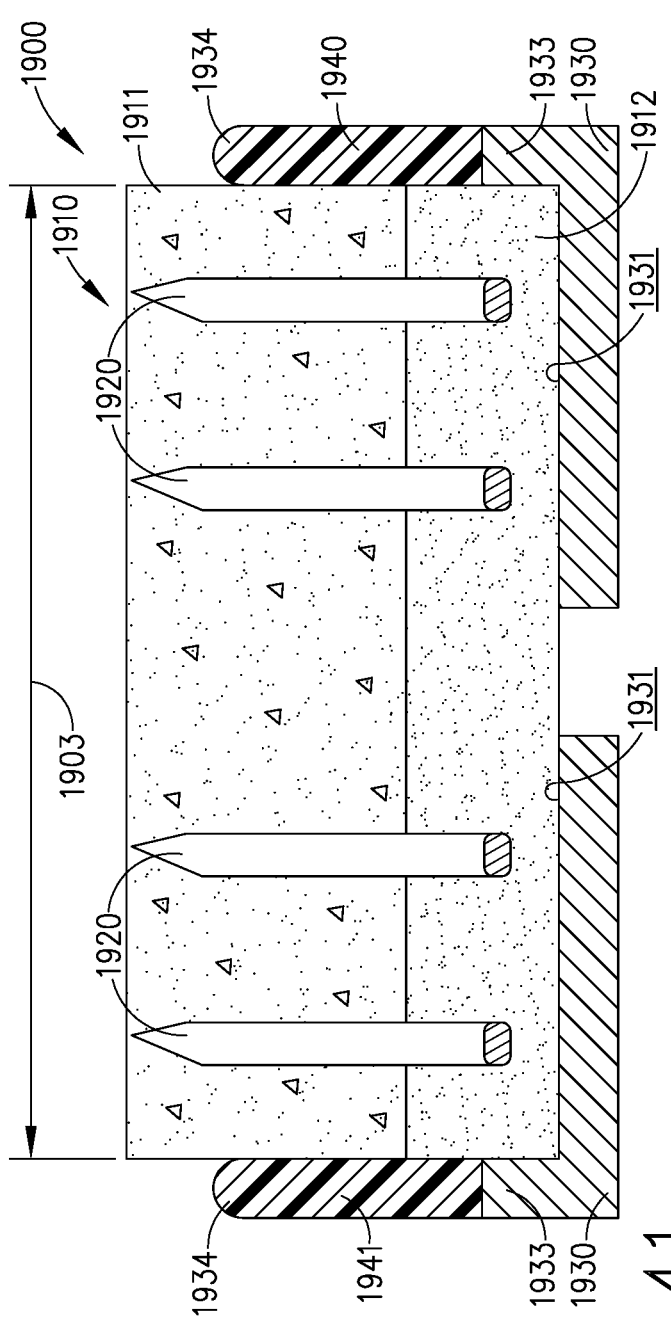
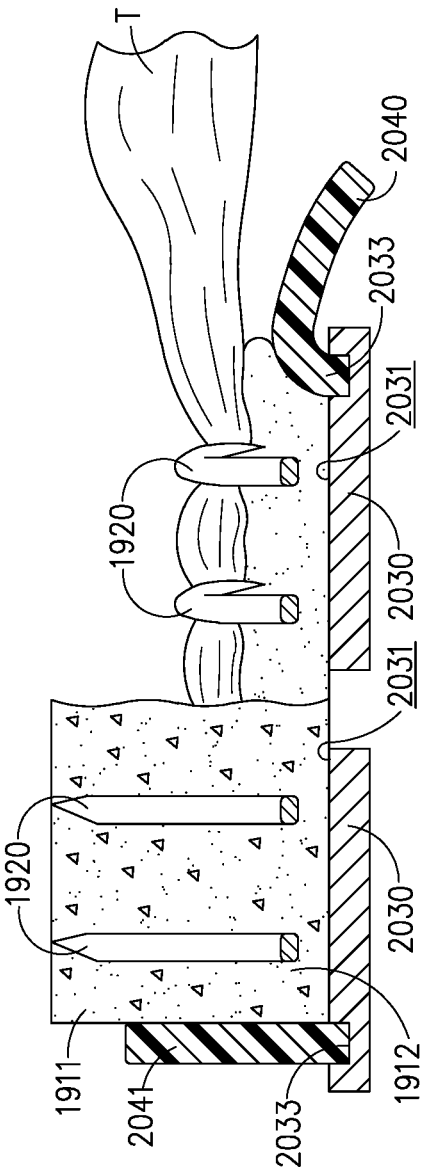
FIG. 41
FIG. 42

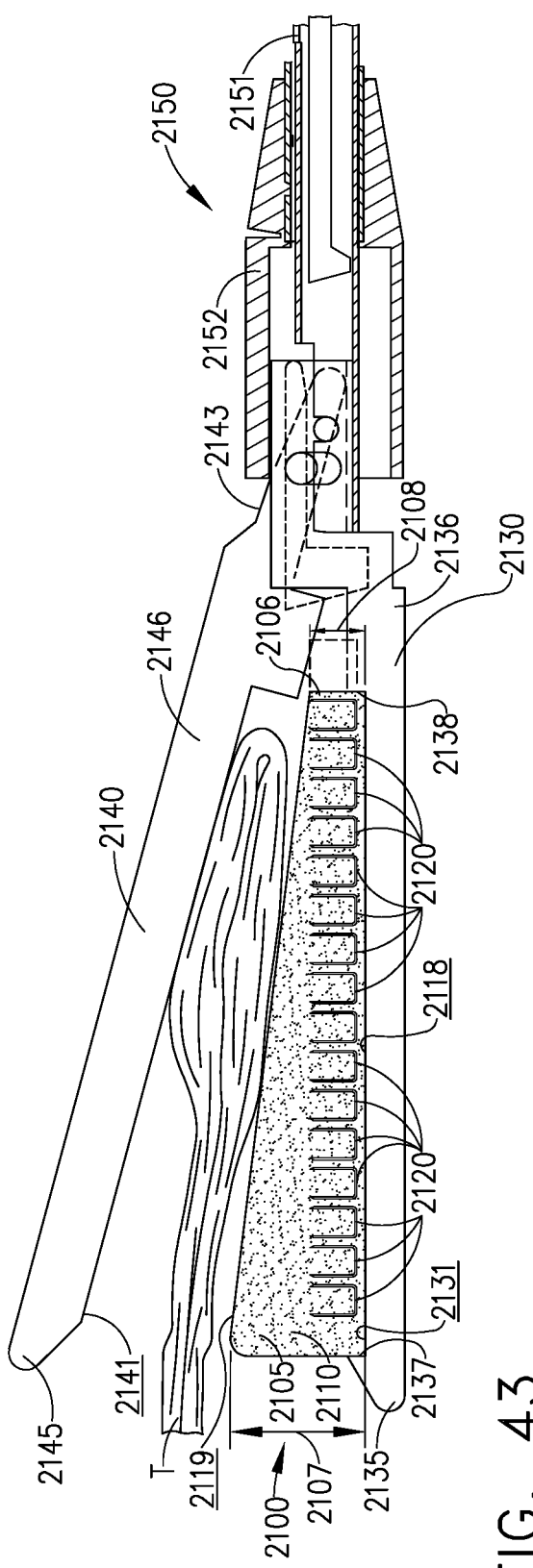
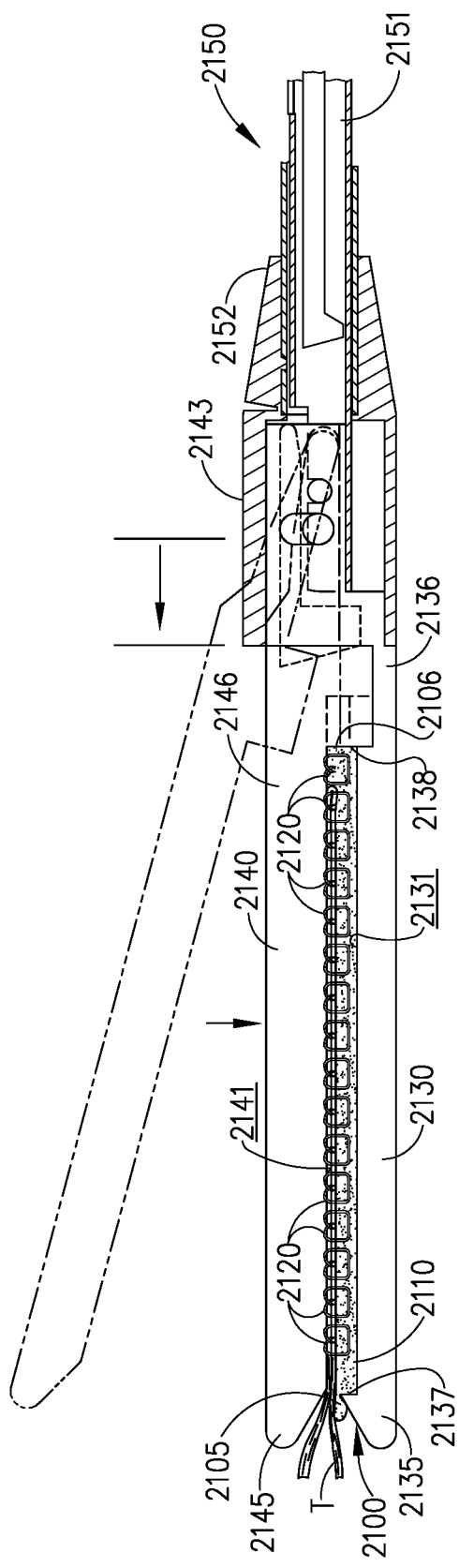
FIG. 43
FIG. 44

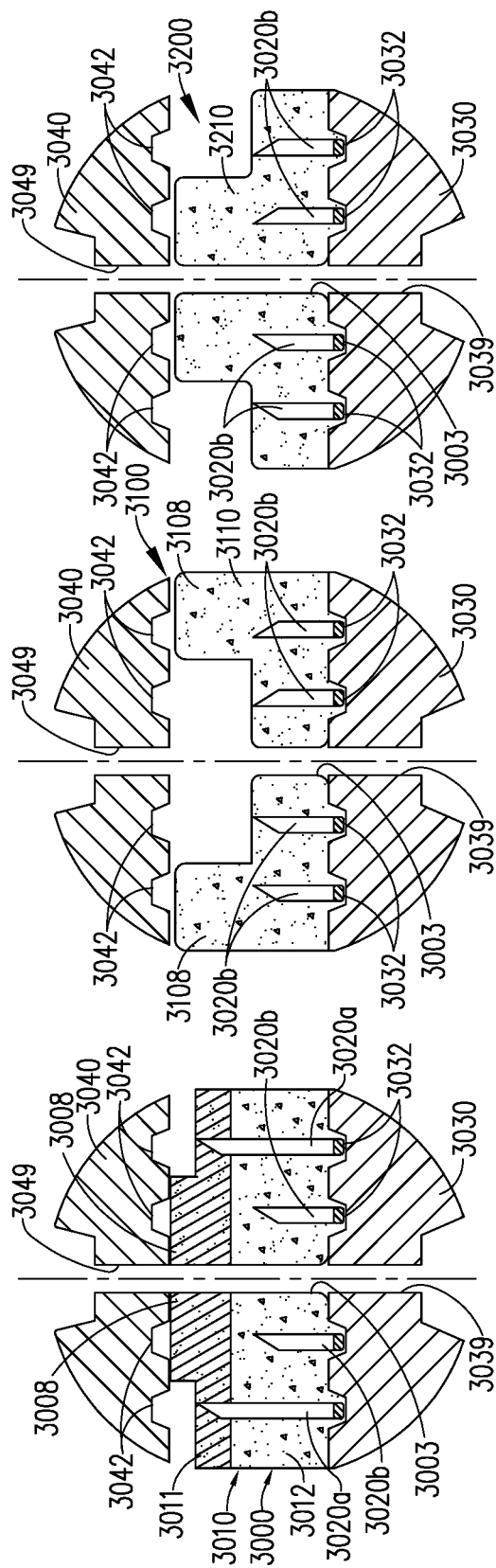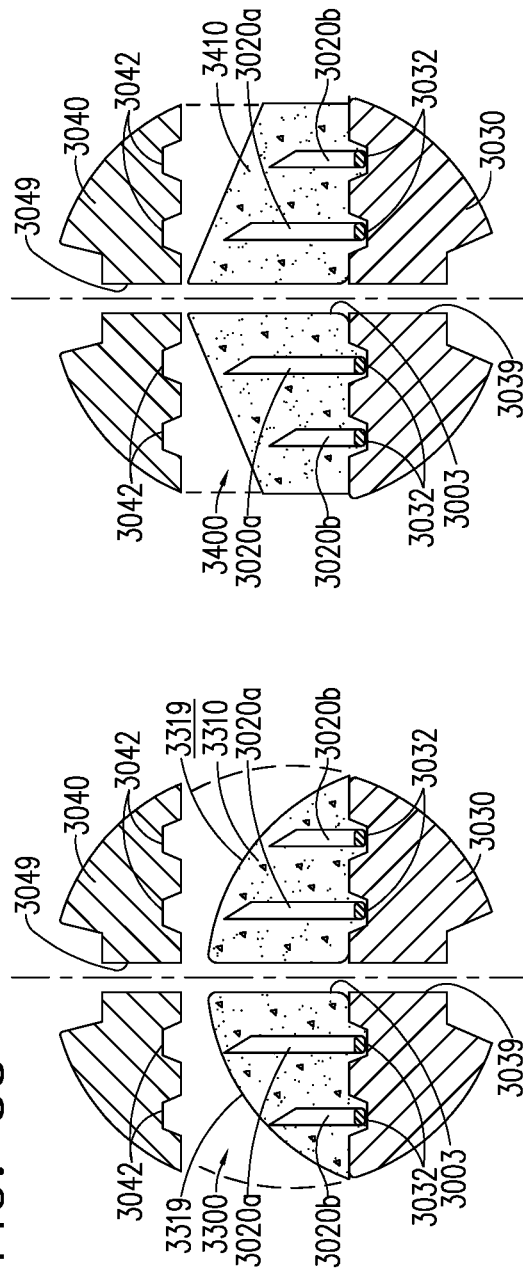

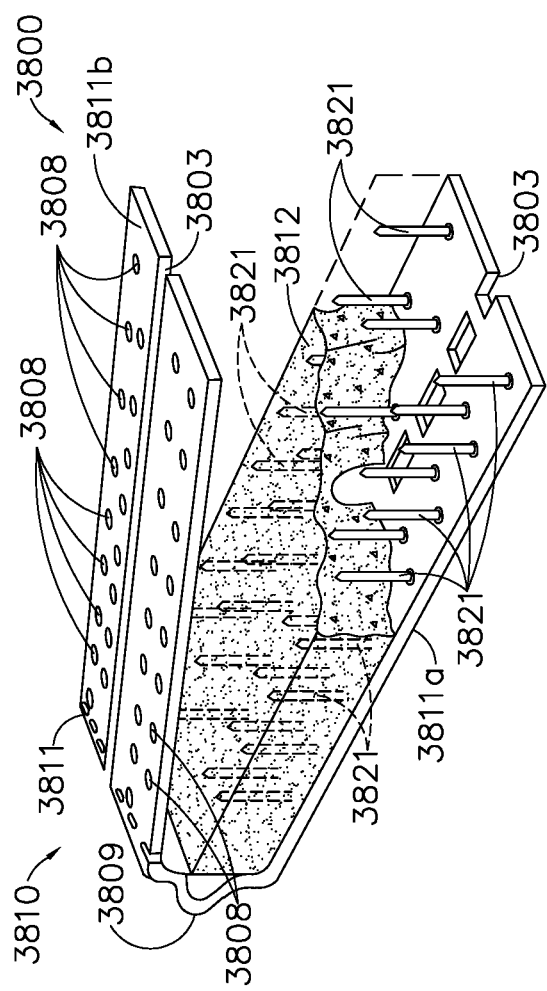
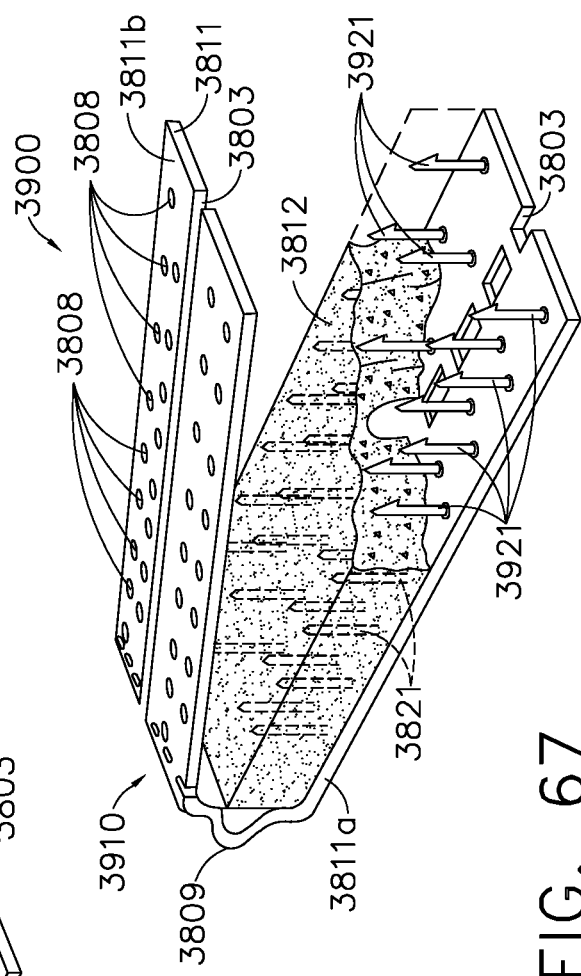
FIG. 66
FIG. 67

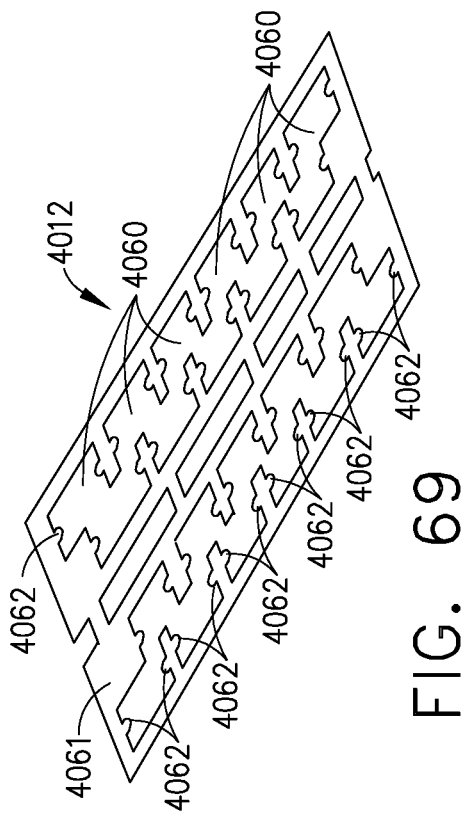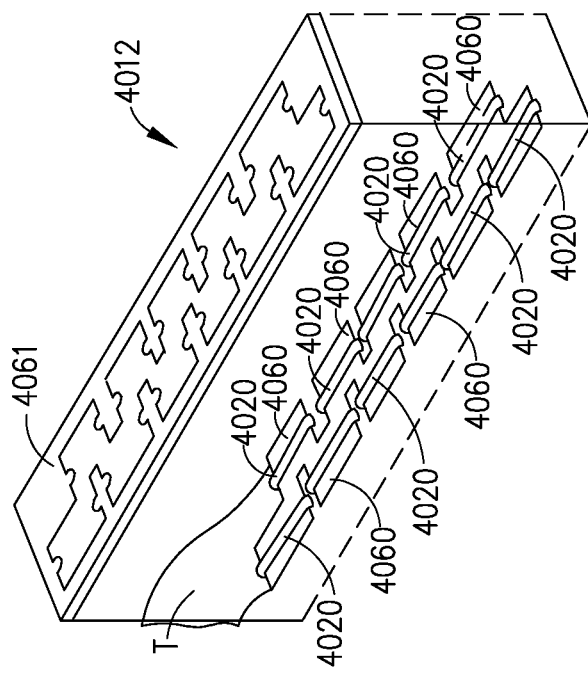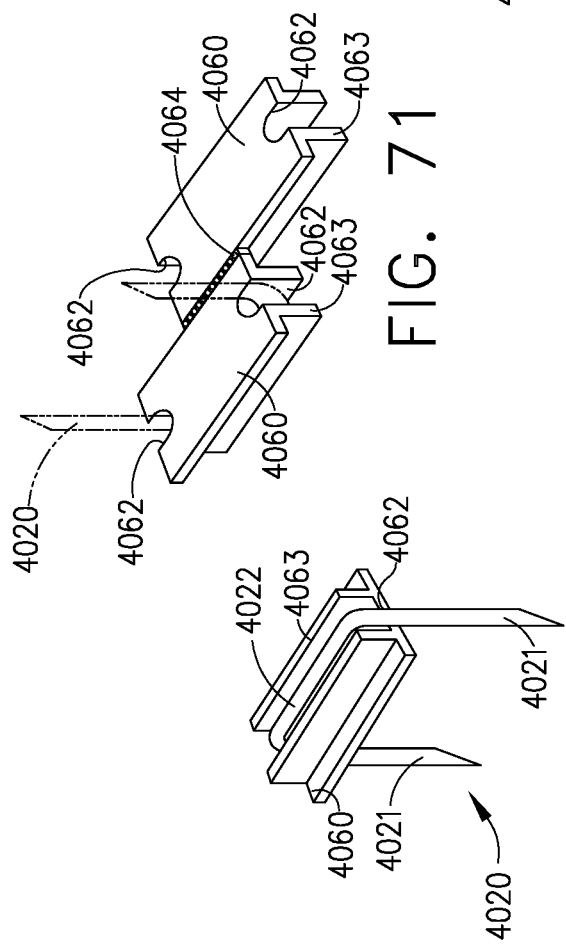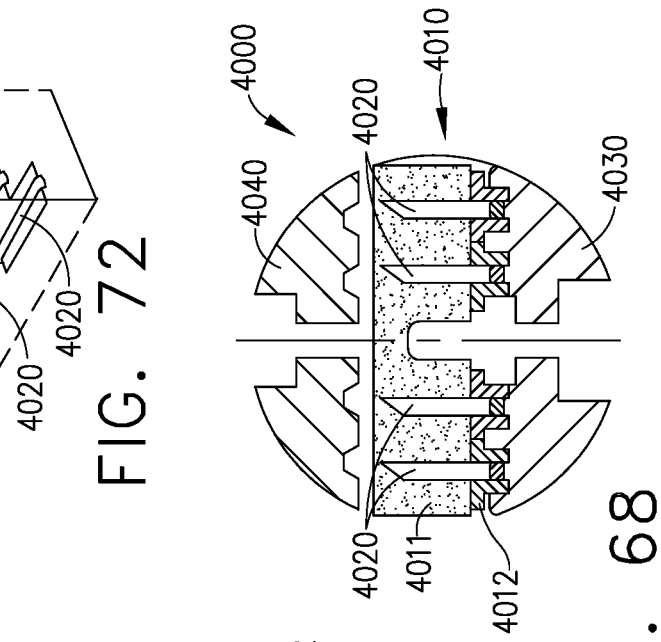

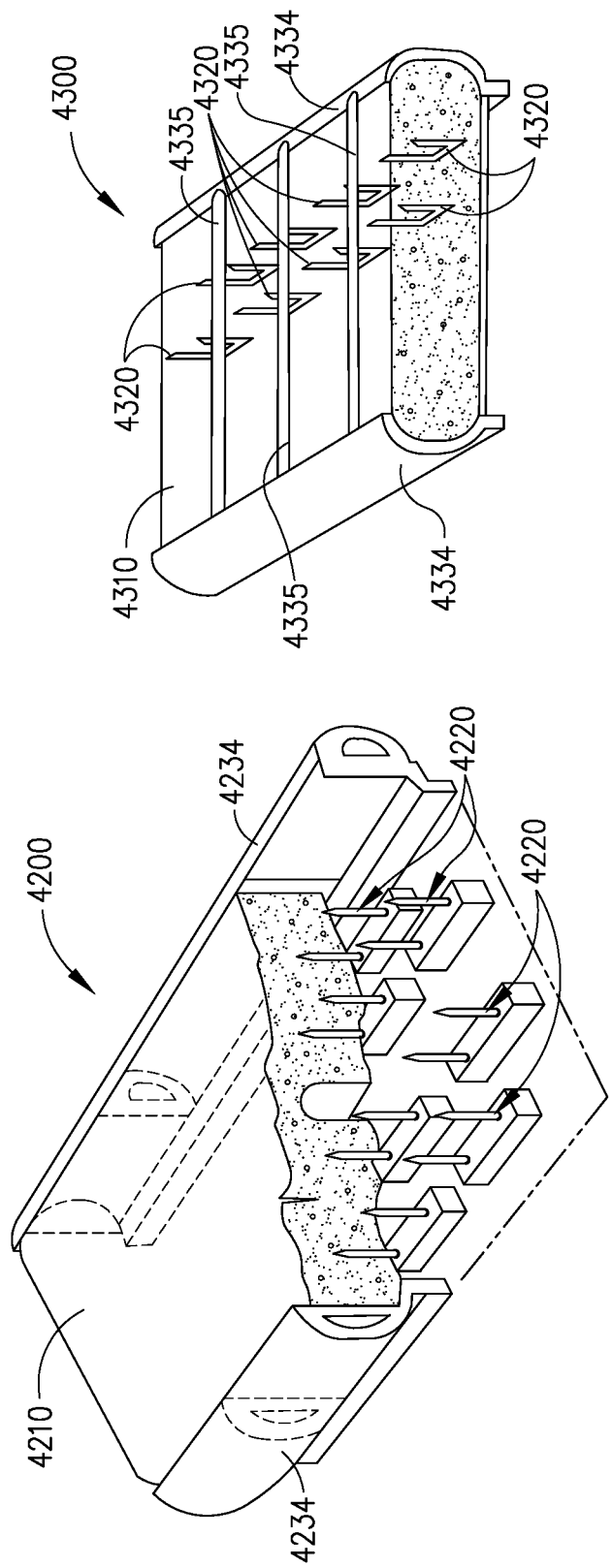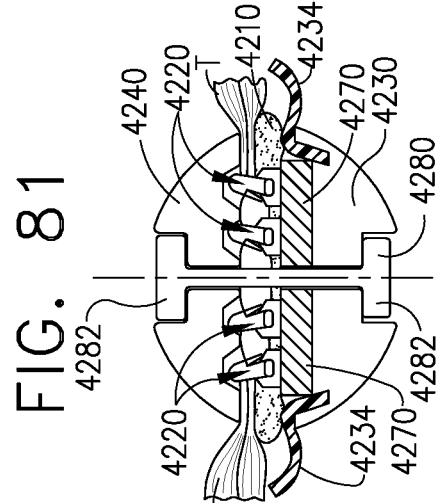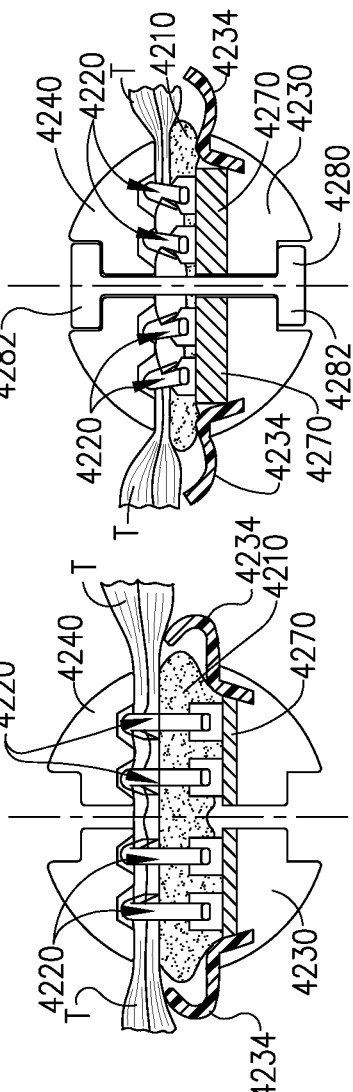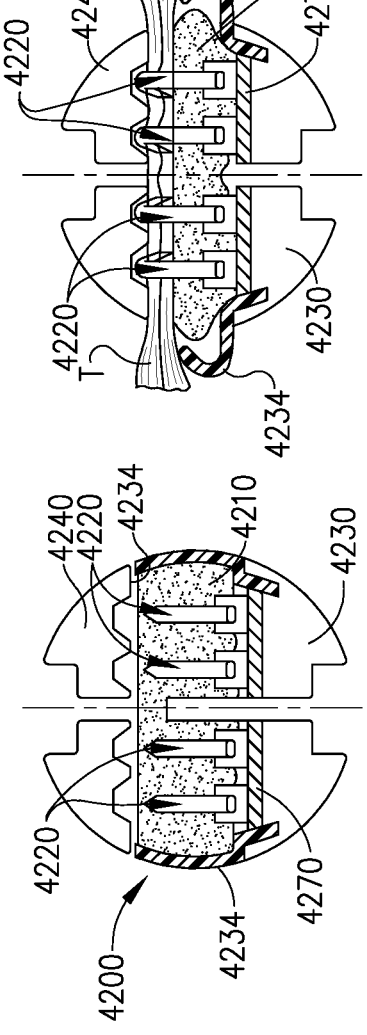

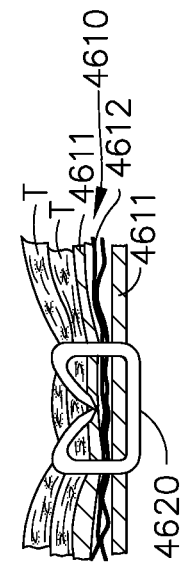
FIG. 88
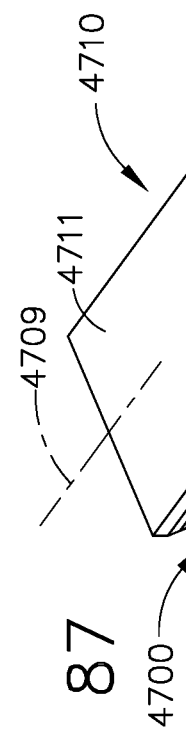
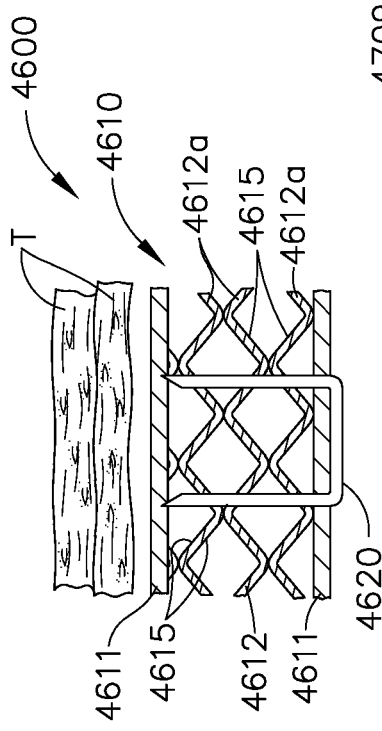
FIG. 87
FIG. 89

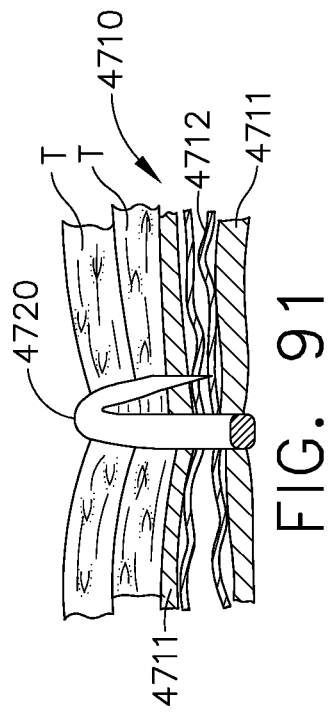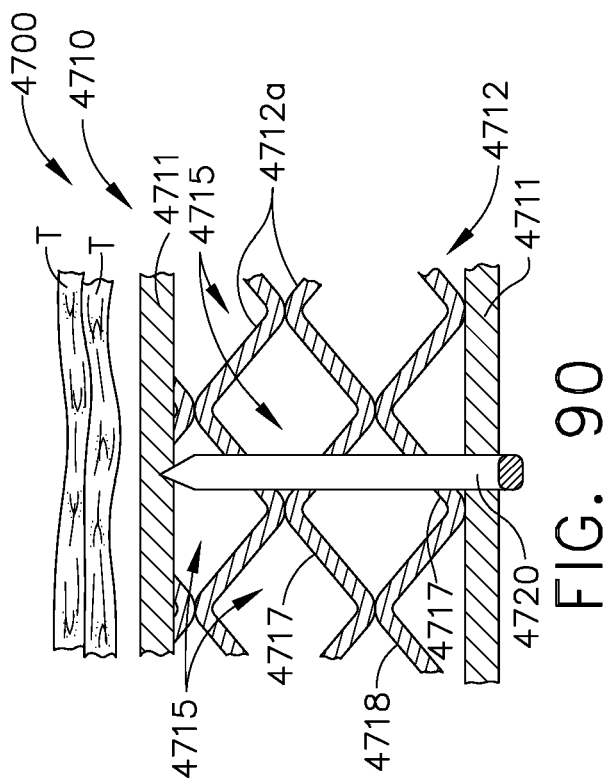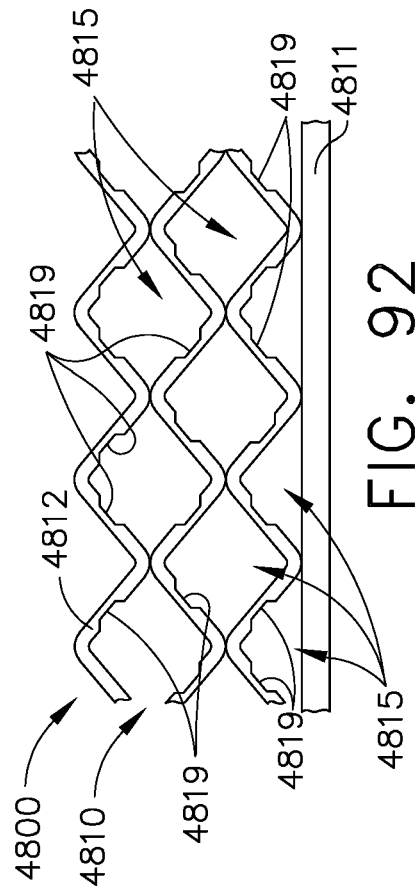

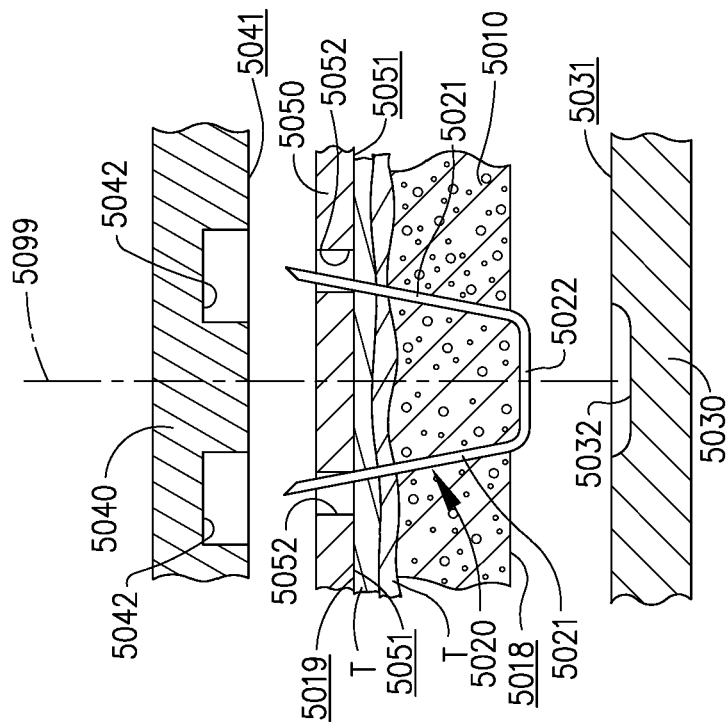
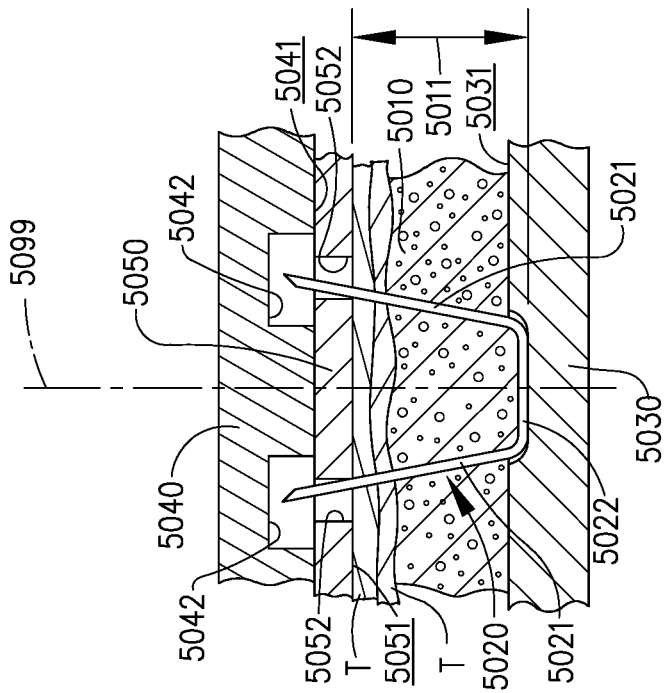

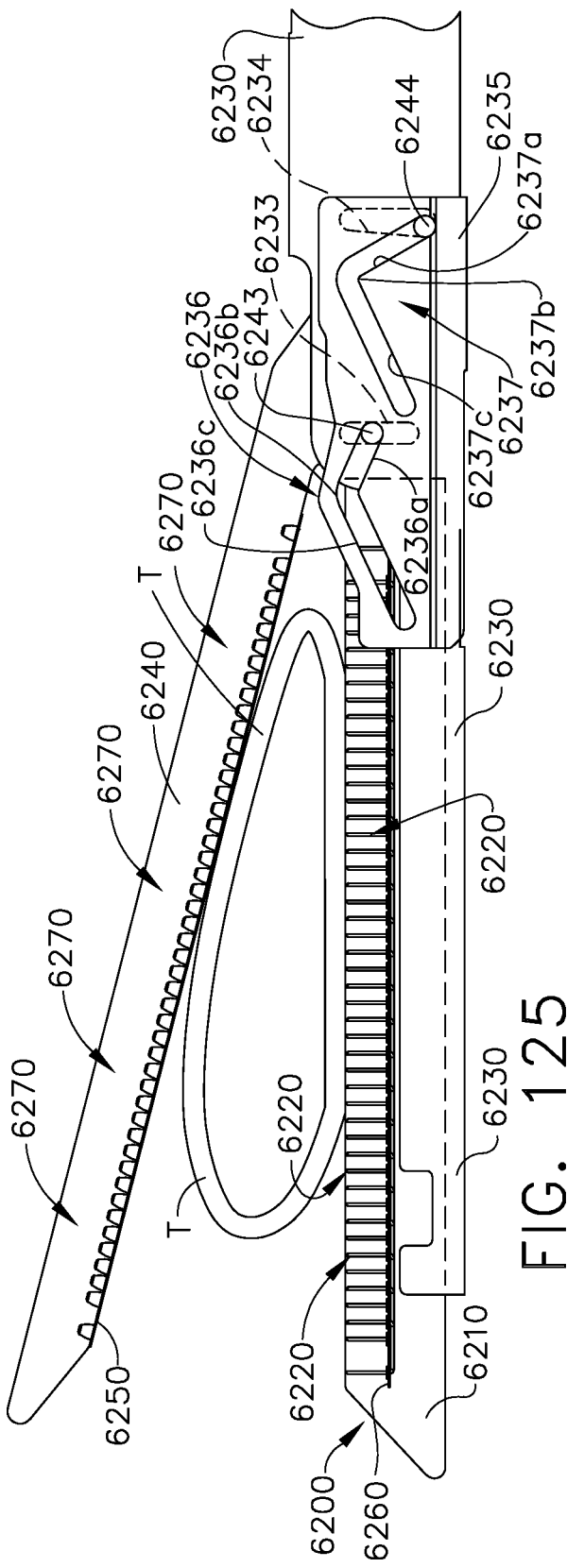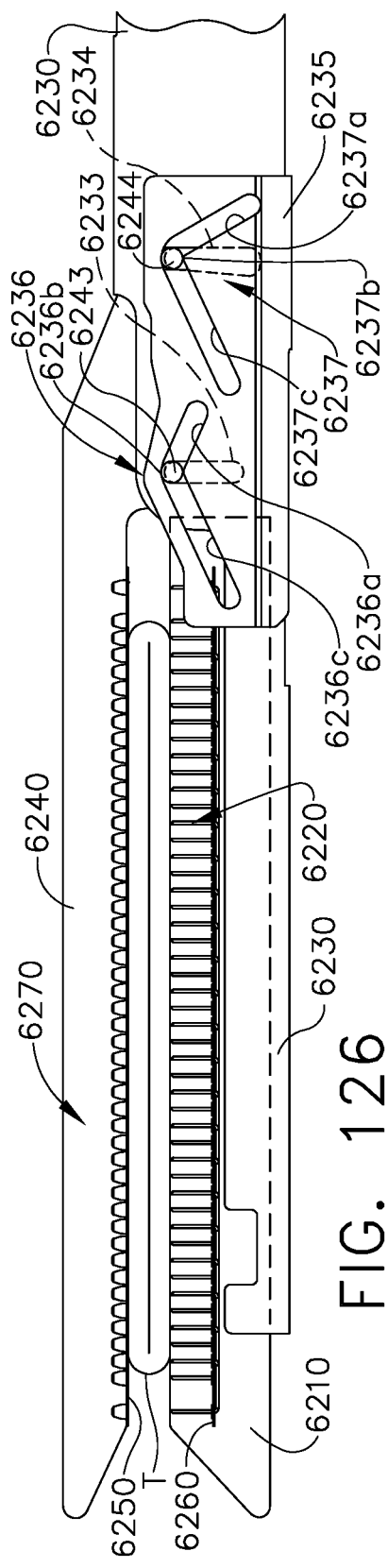

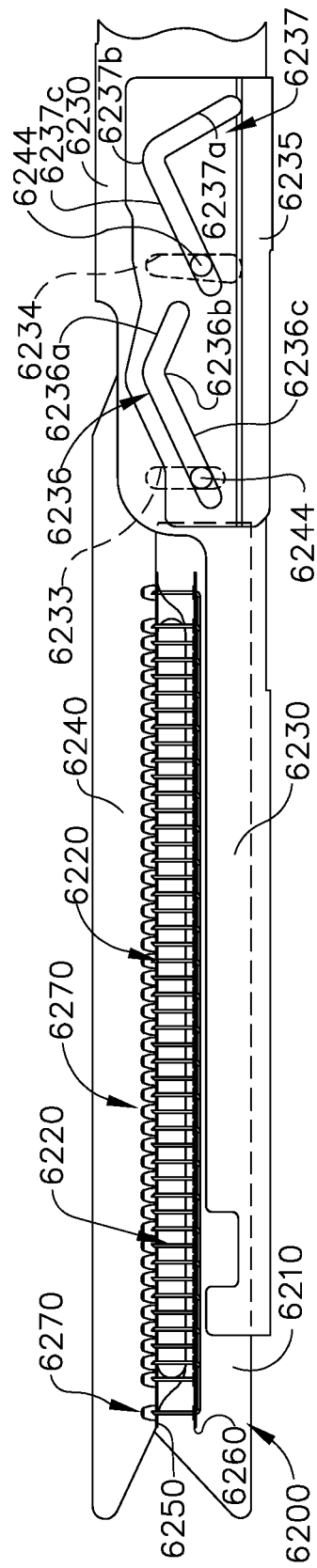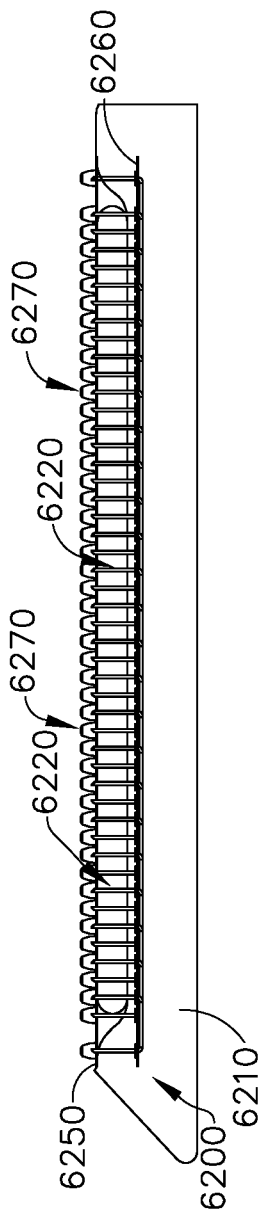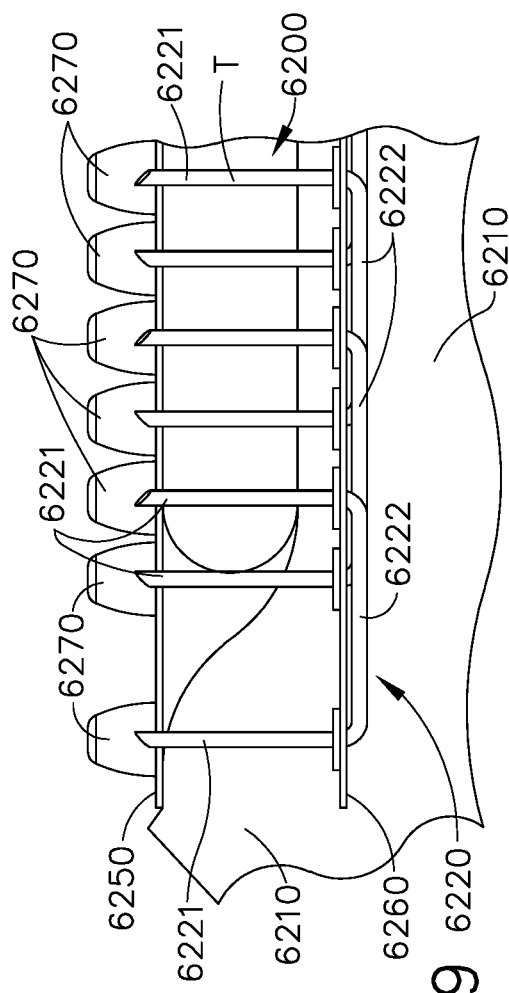
FIG. 127
FIG. 128
FIG. 129

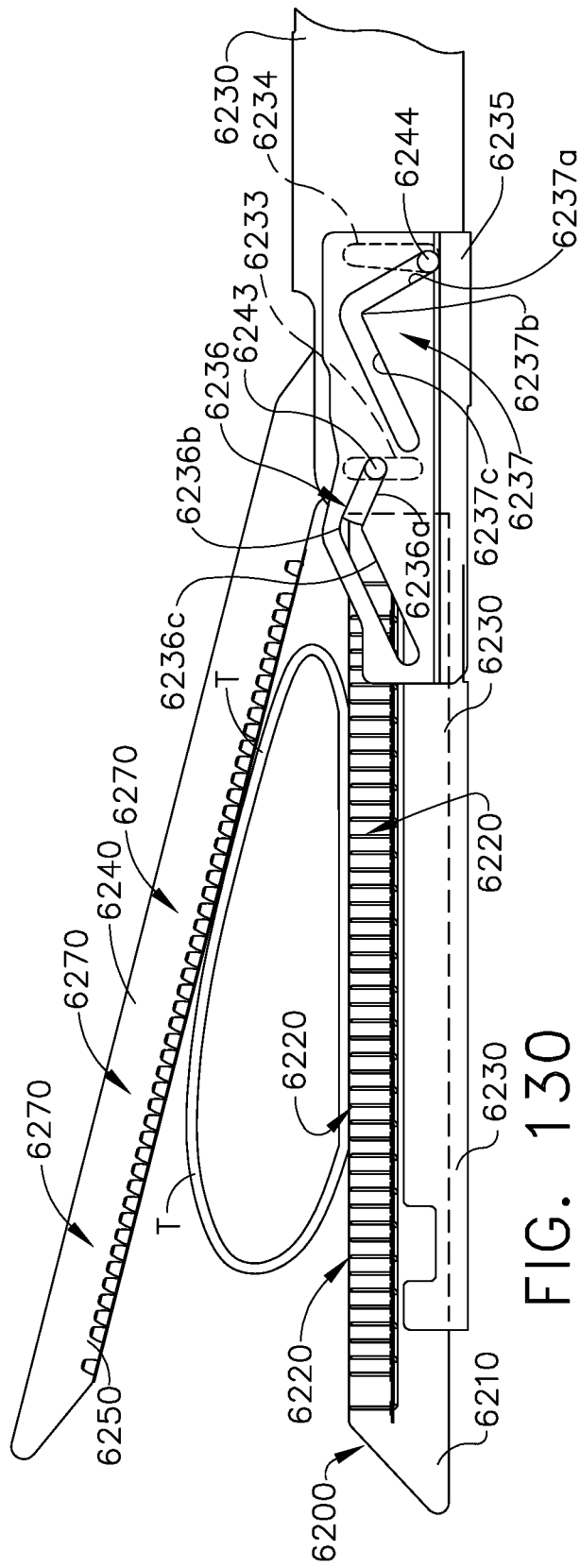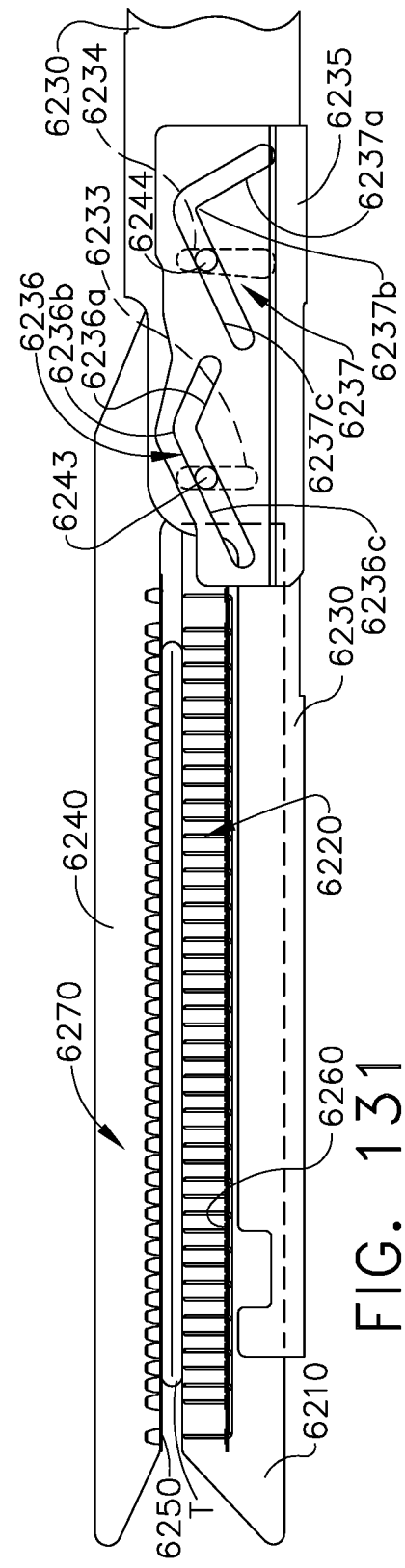

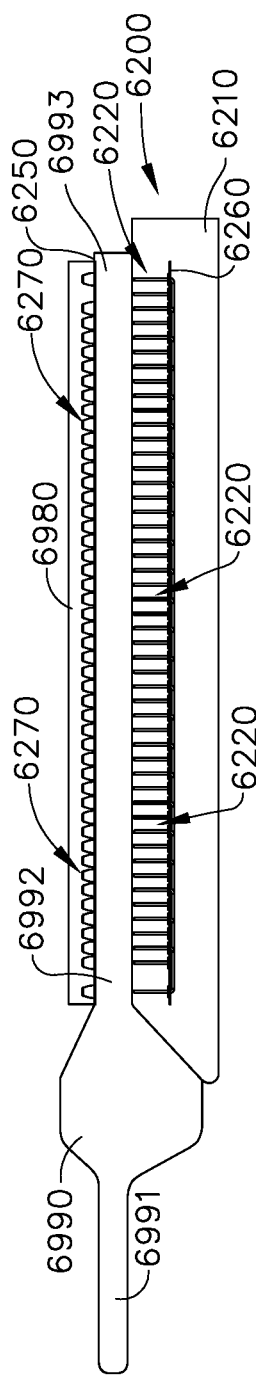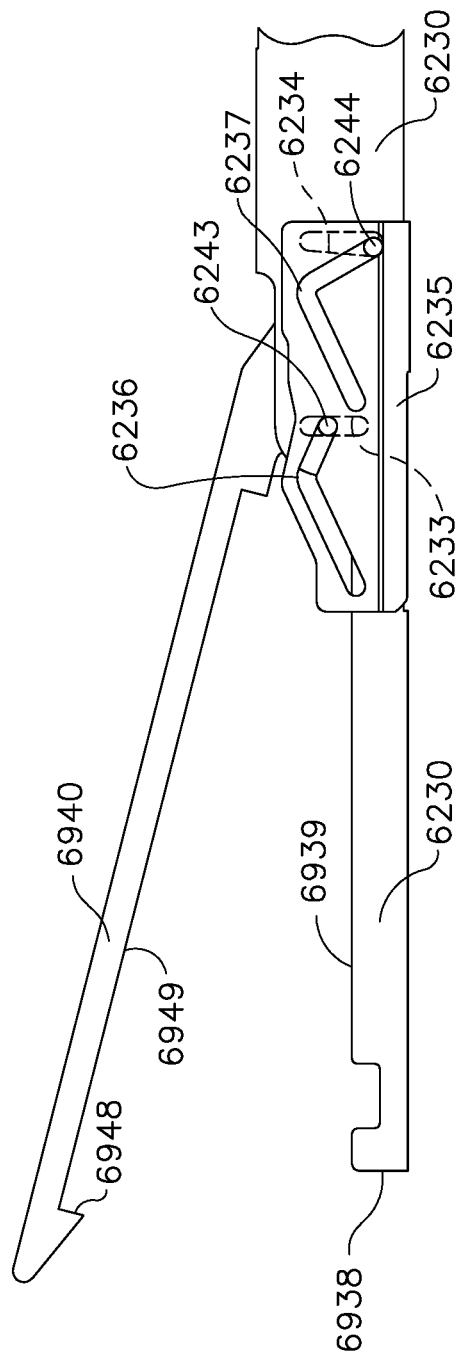
FIG. 151
FIG. 152

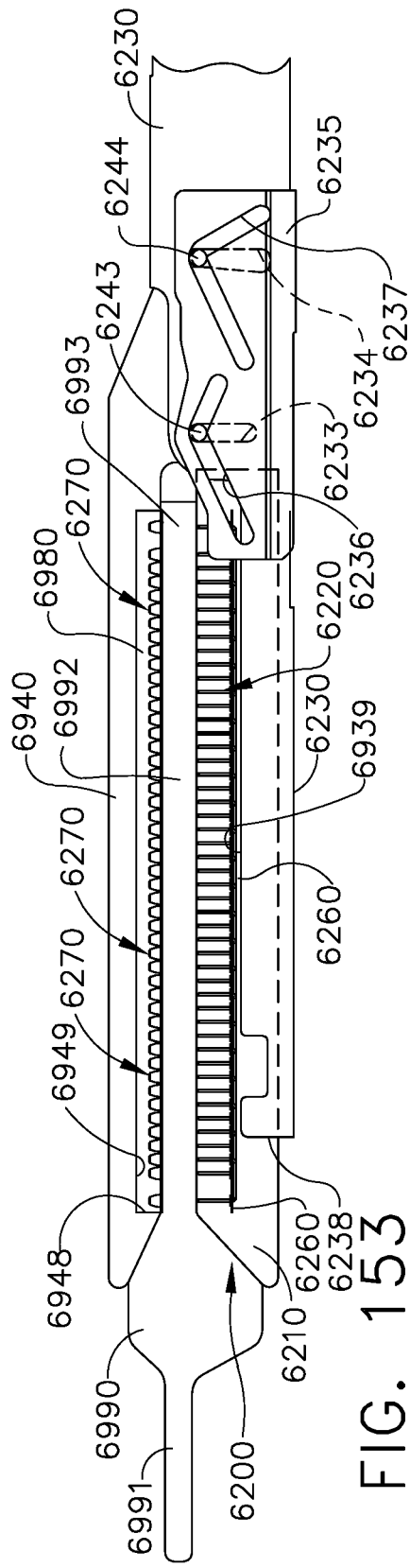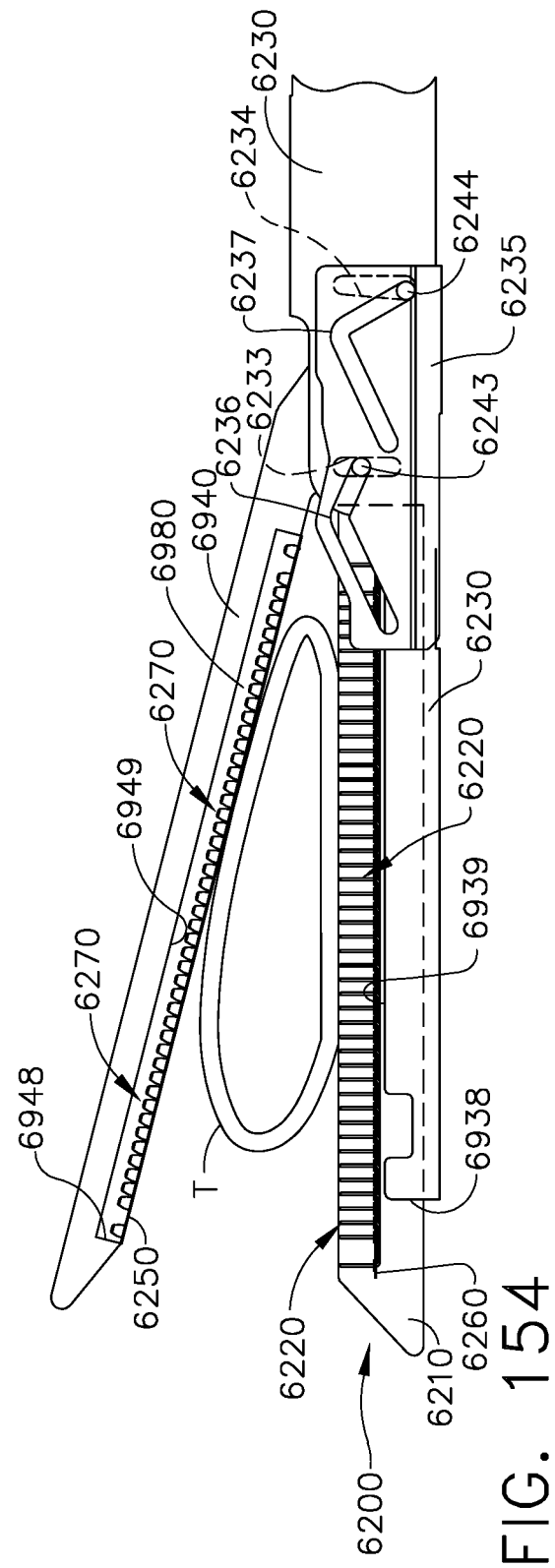

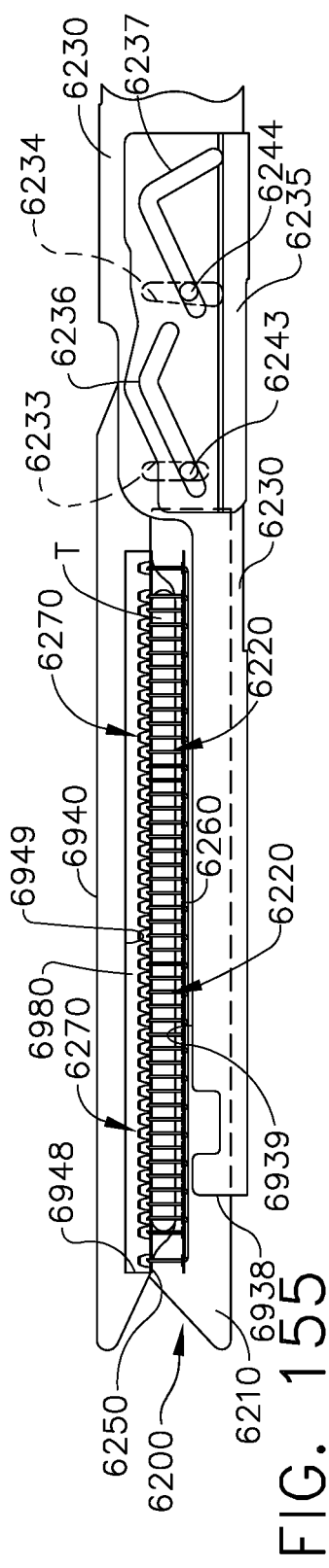
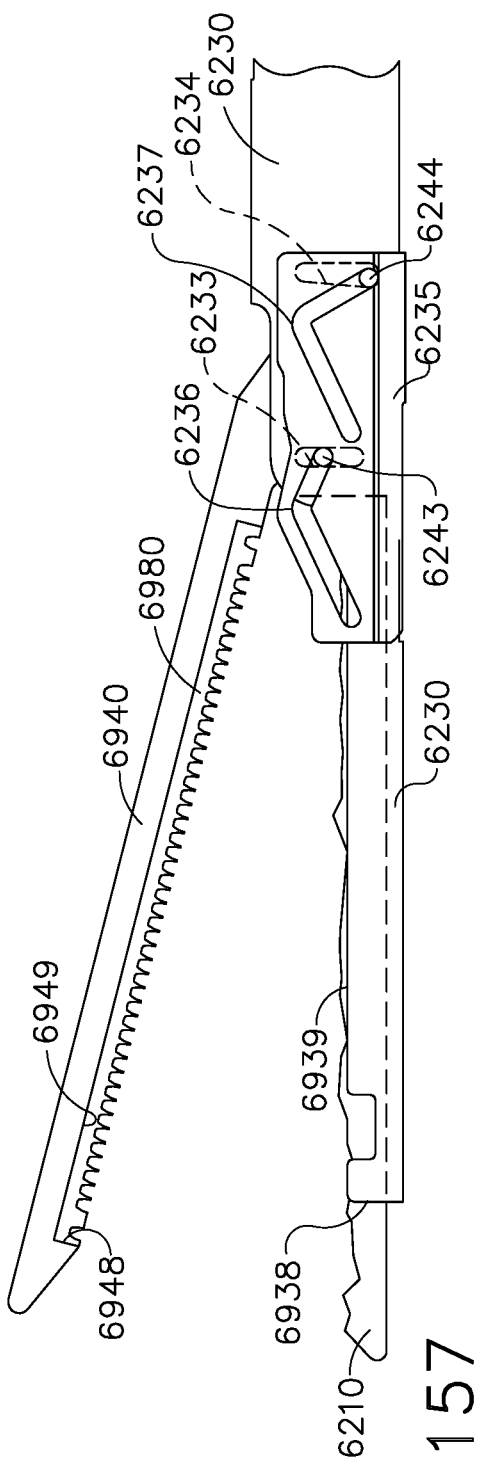
FIG. 155
FIG. 156
FIG. 157

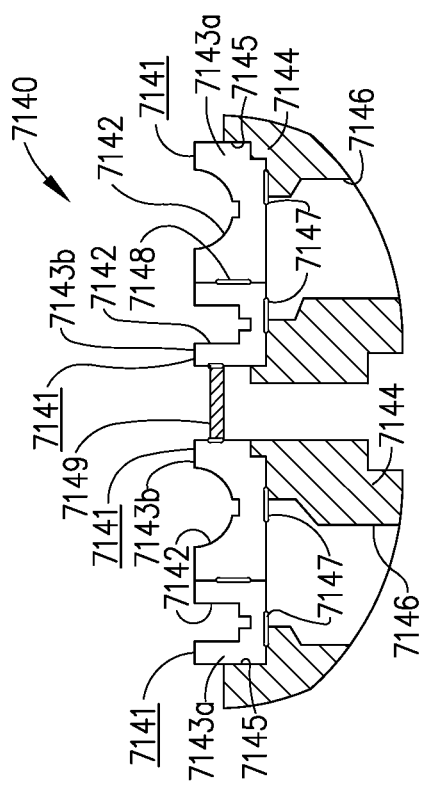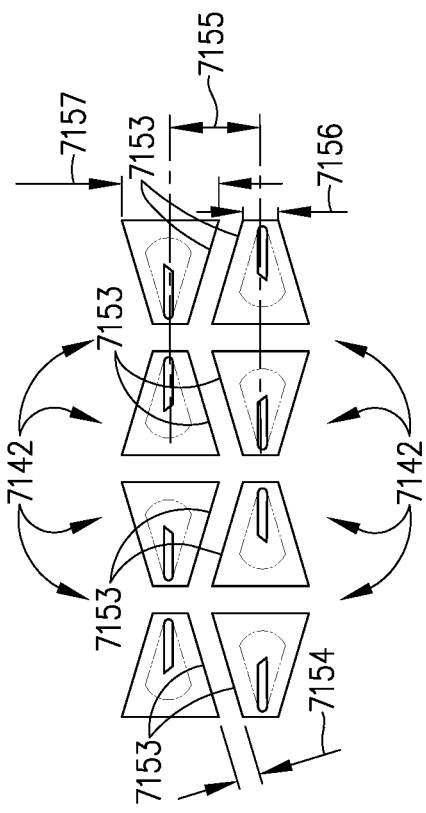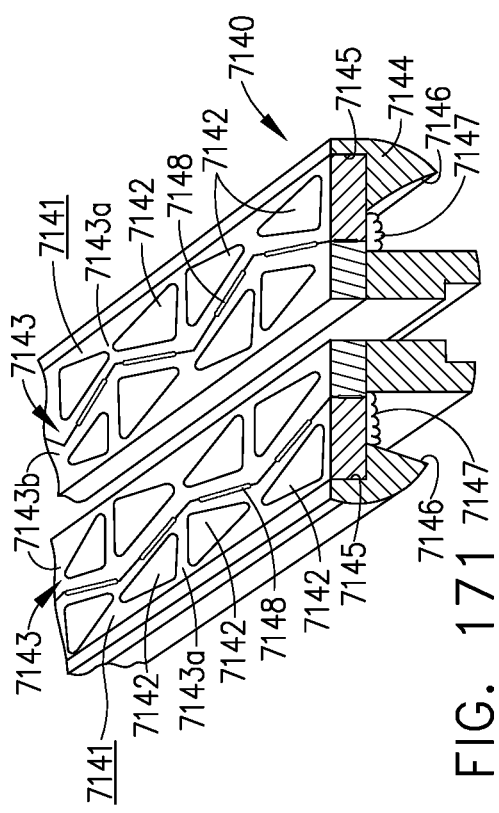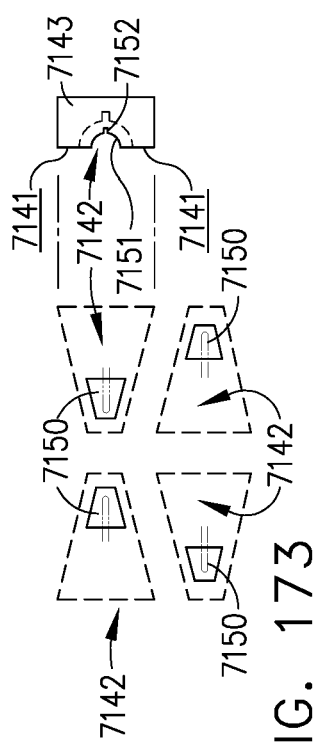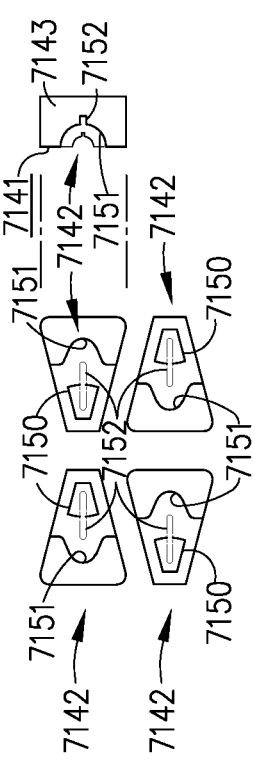

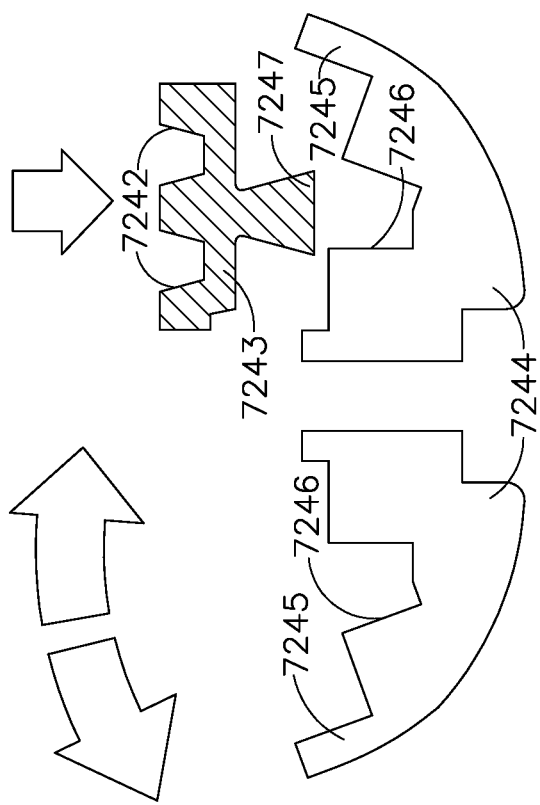
FIG. 176
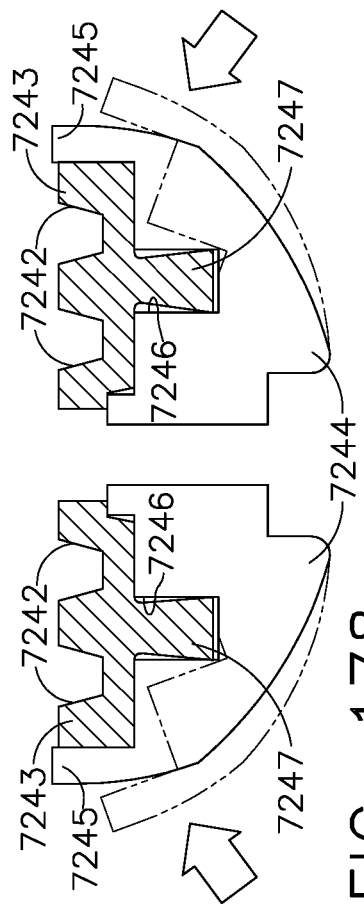
FIG. 177
FIG. 178
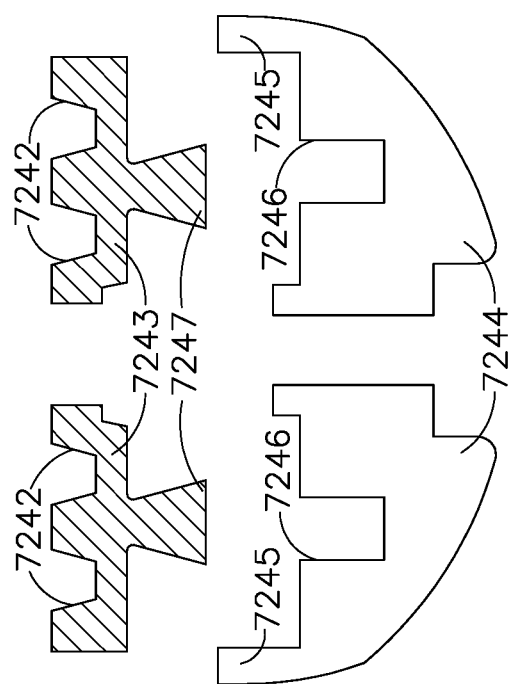

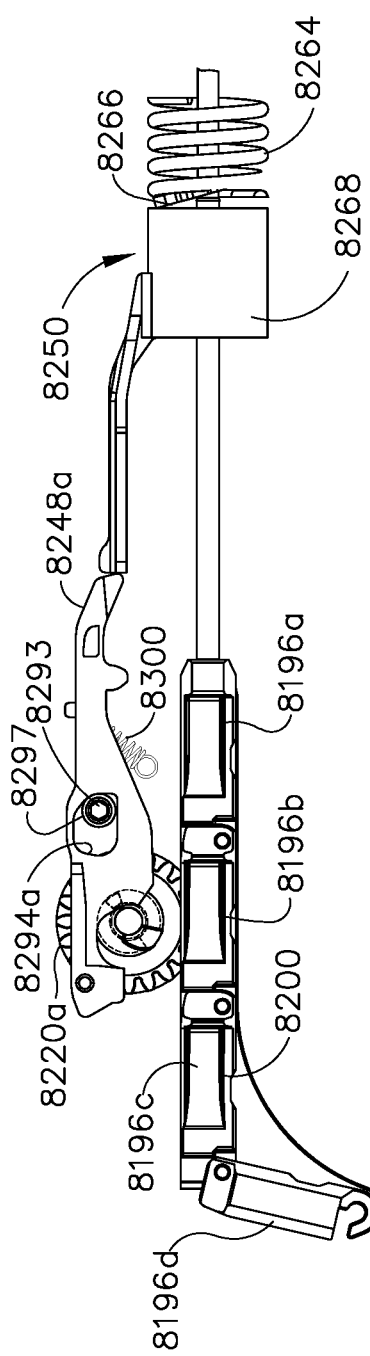
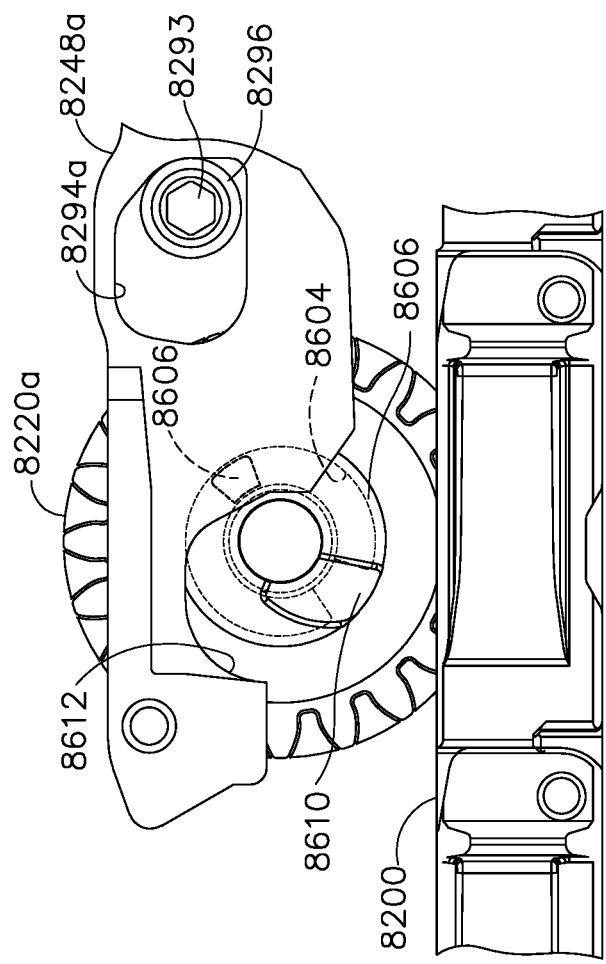
FIG. 199
FIG. 199A

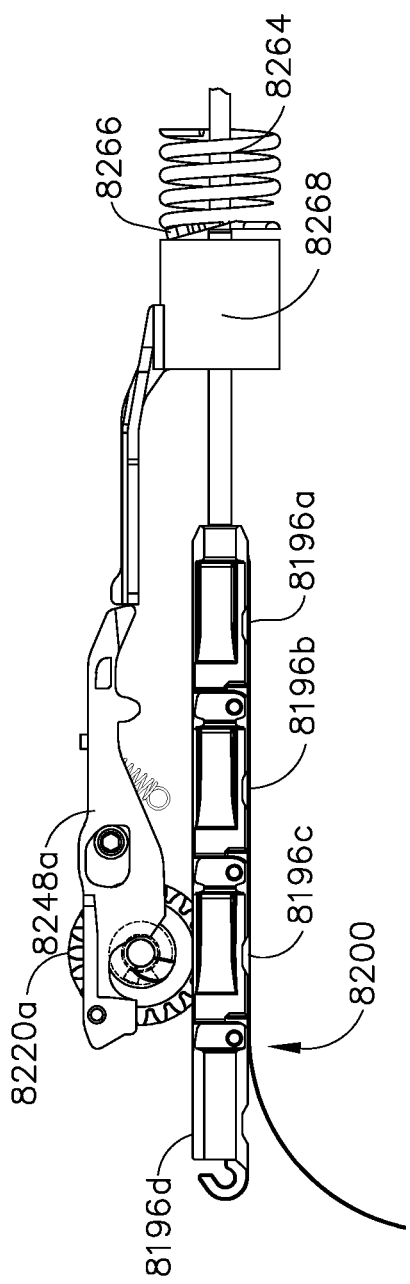
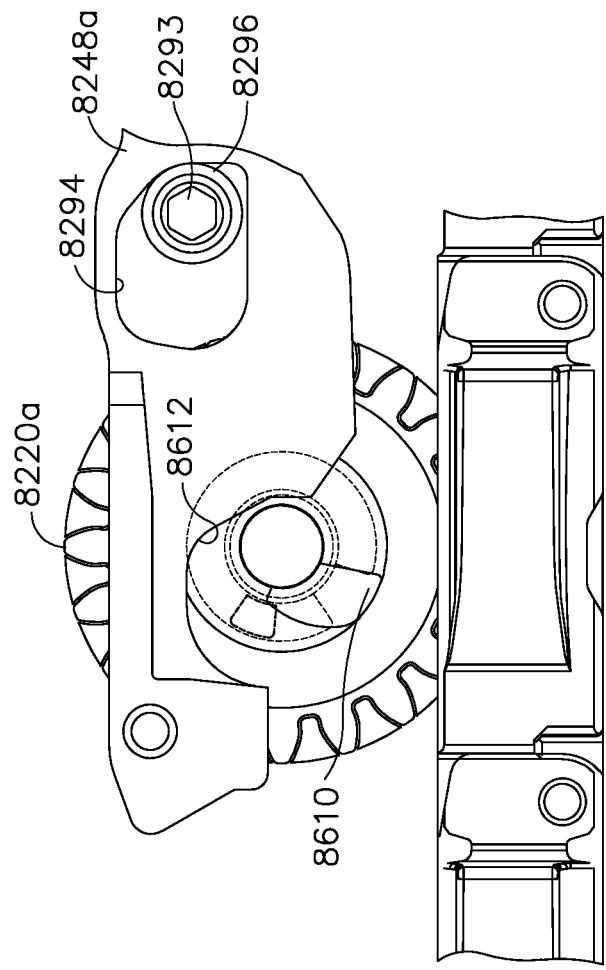
FIG. 200
FIG. 200A

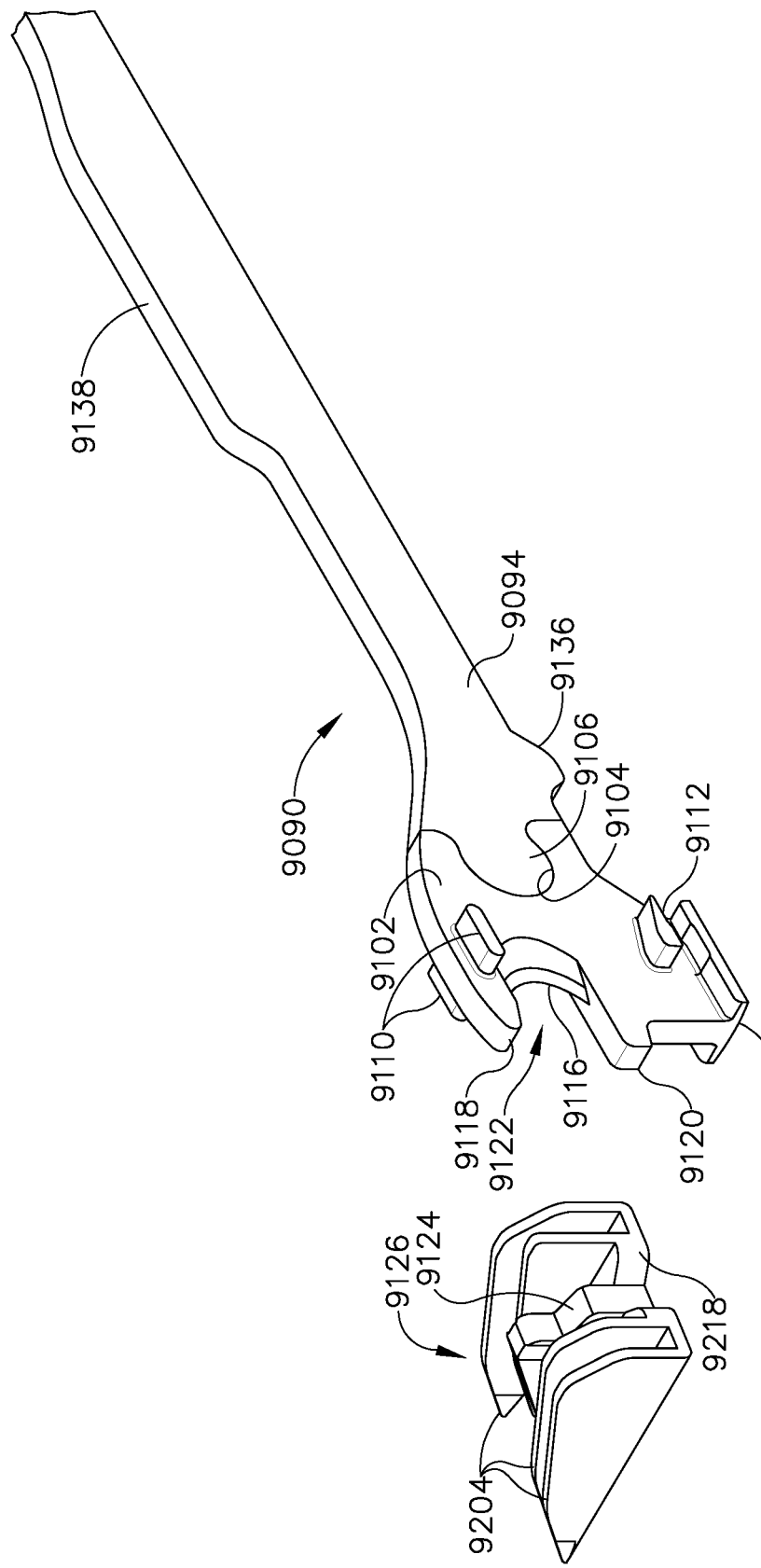

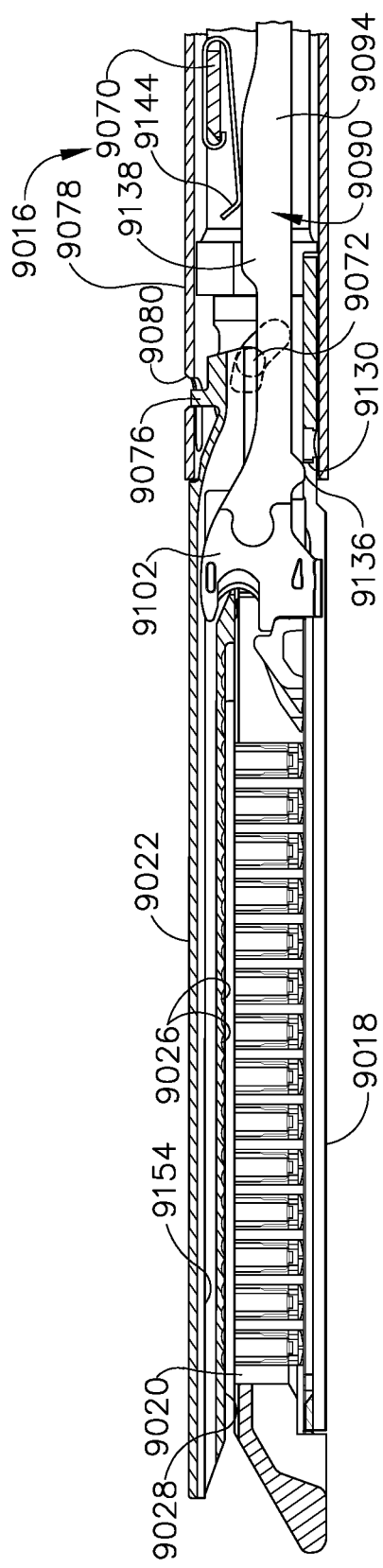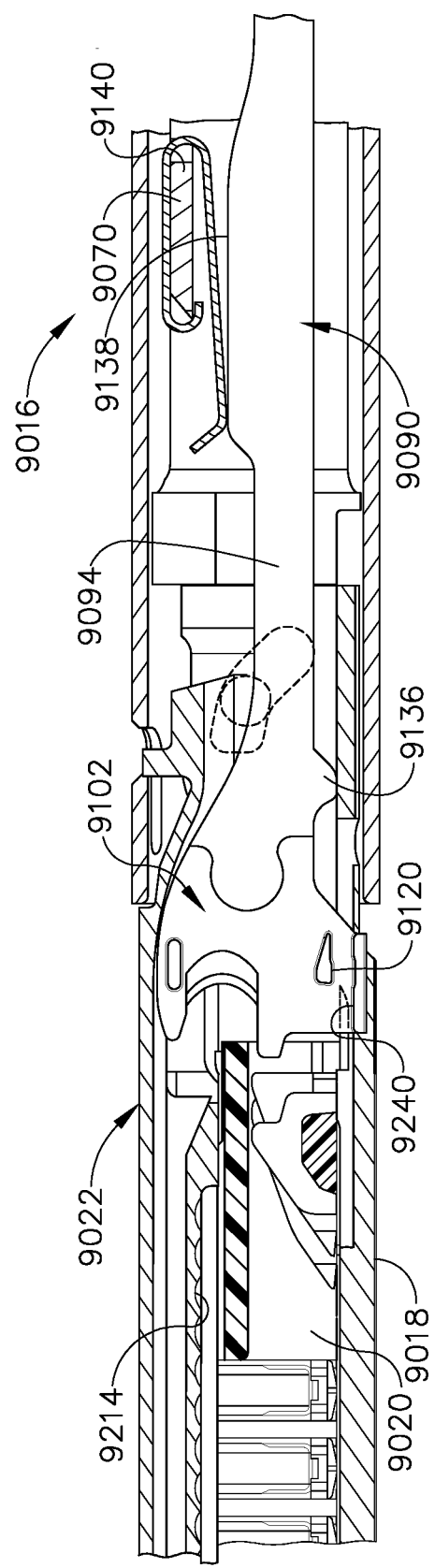

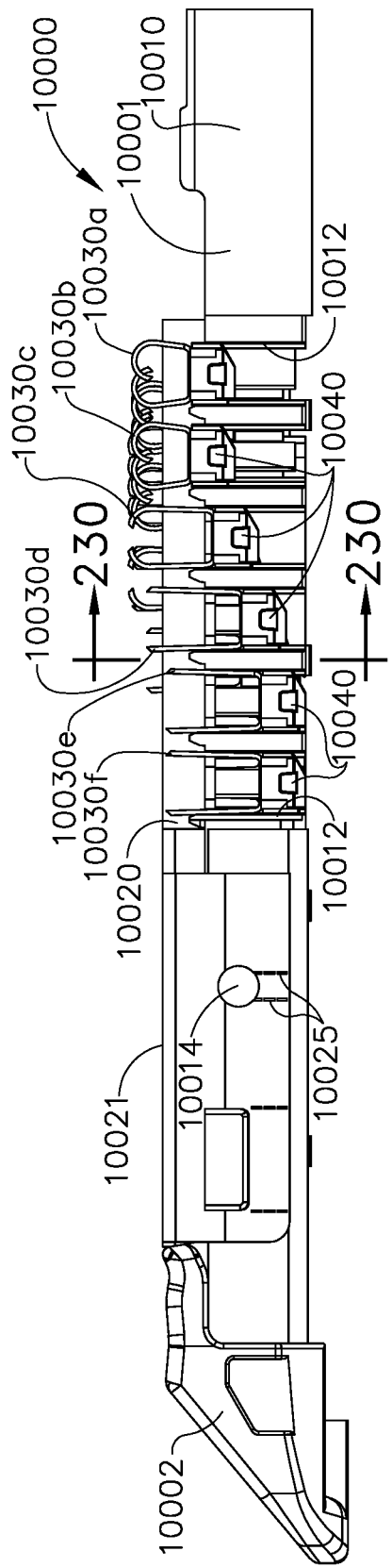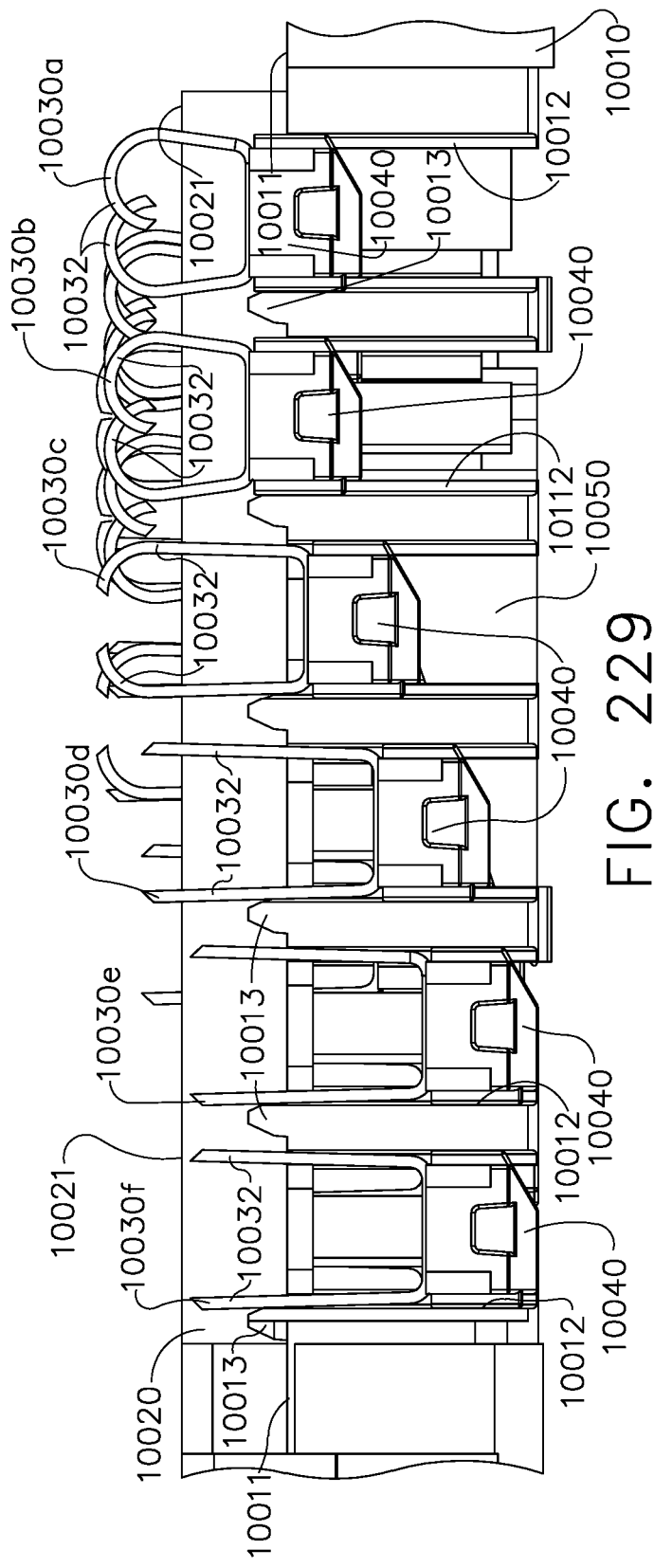

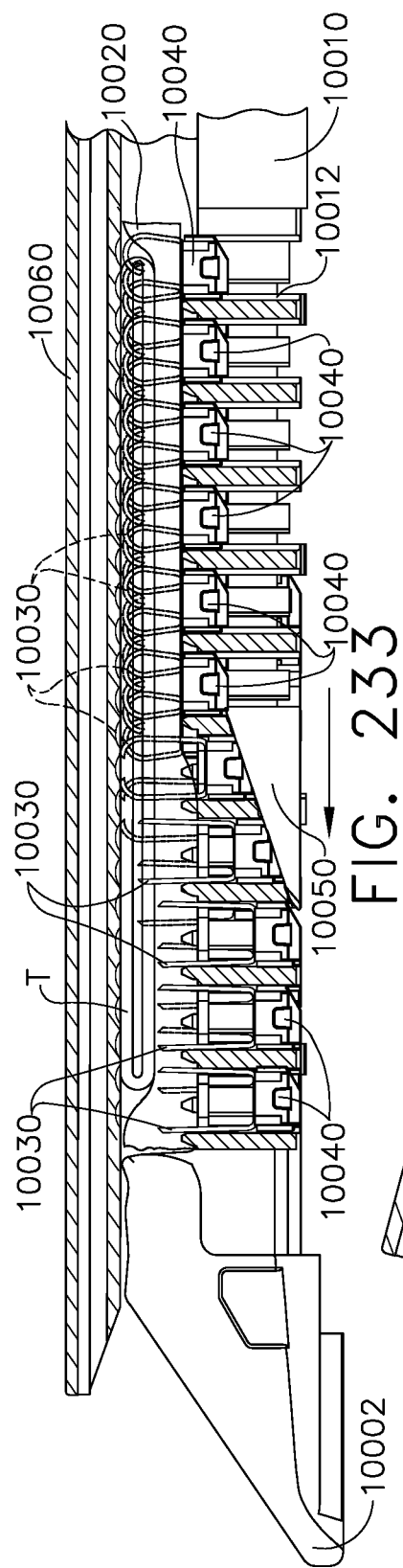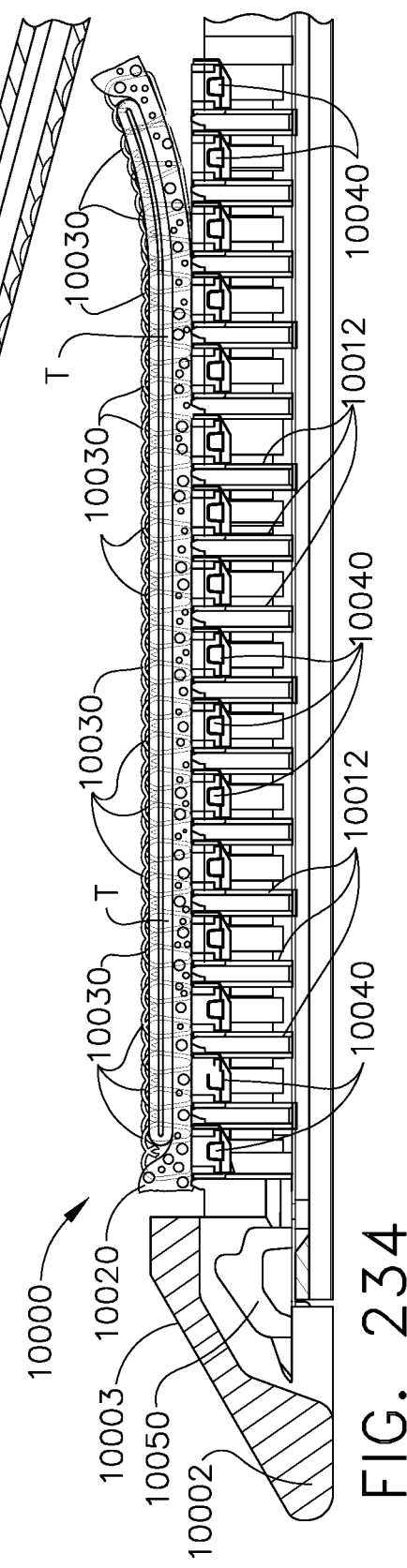

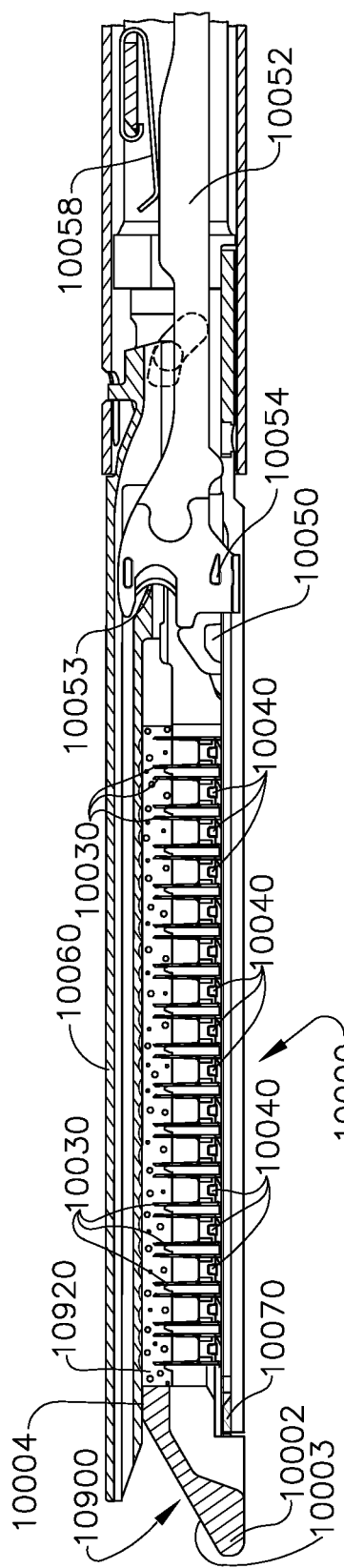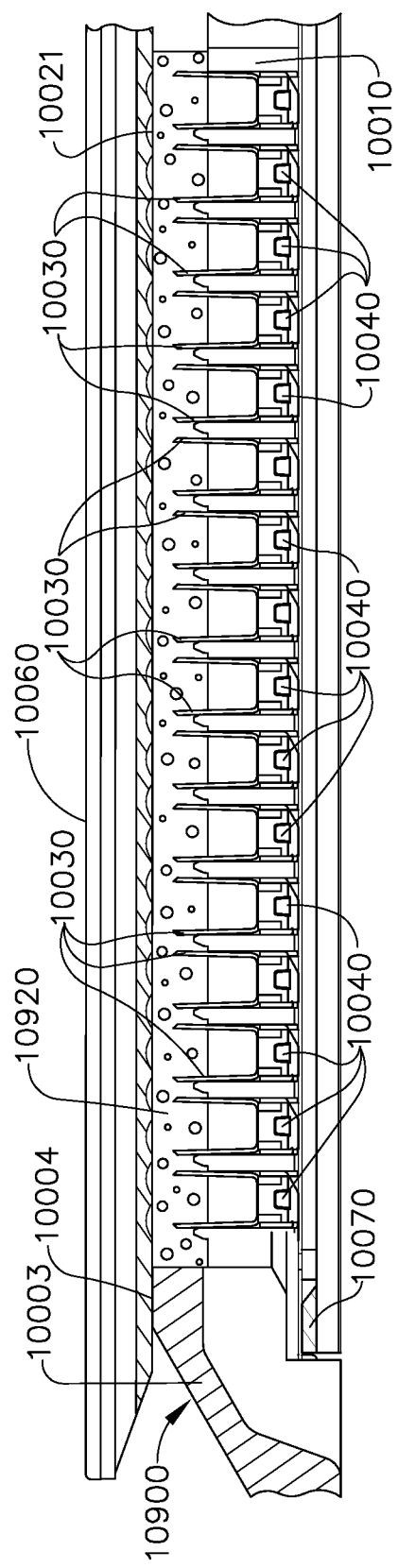

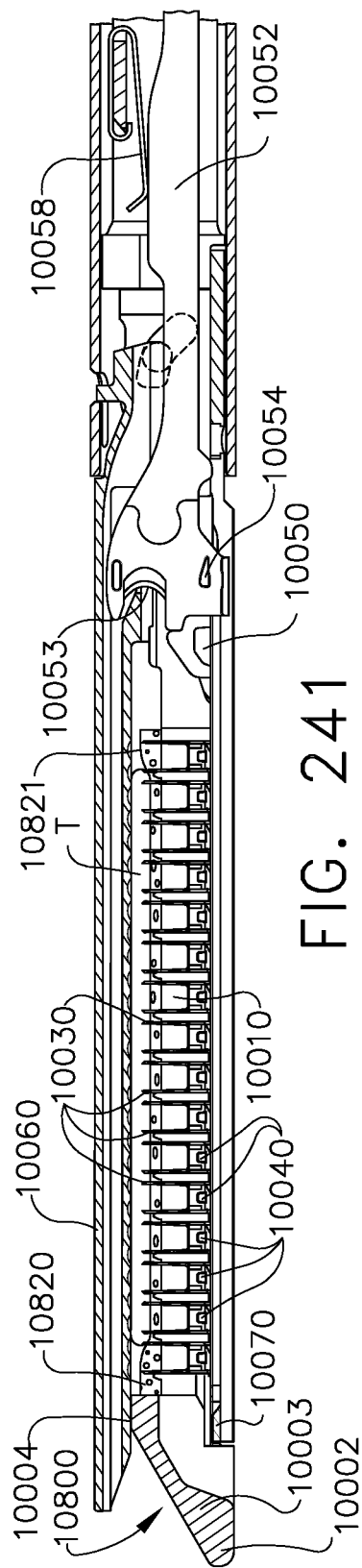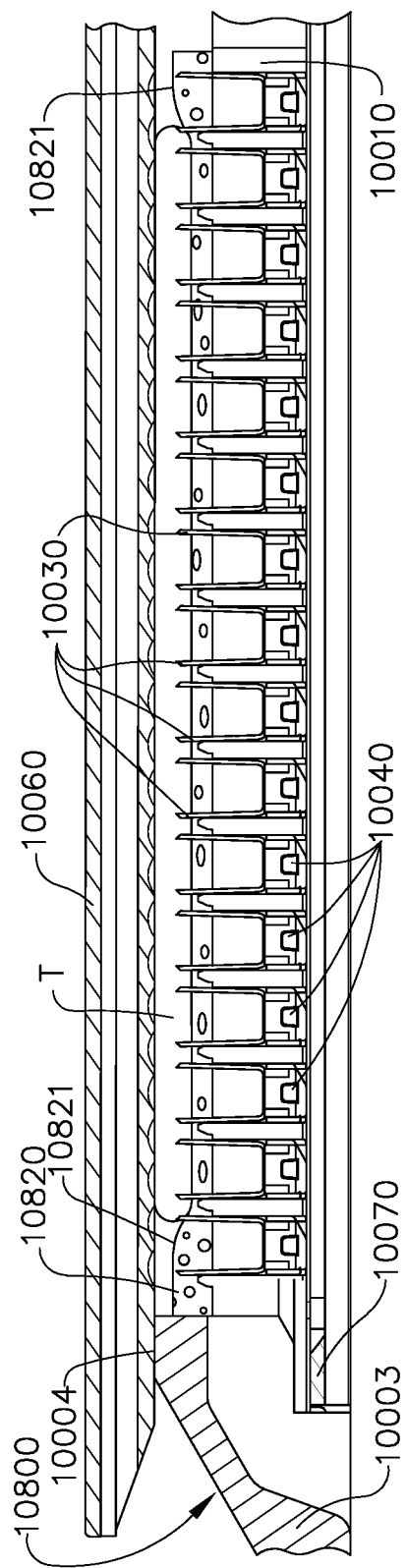

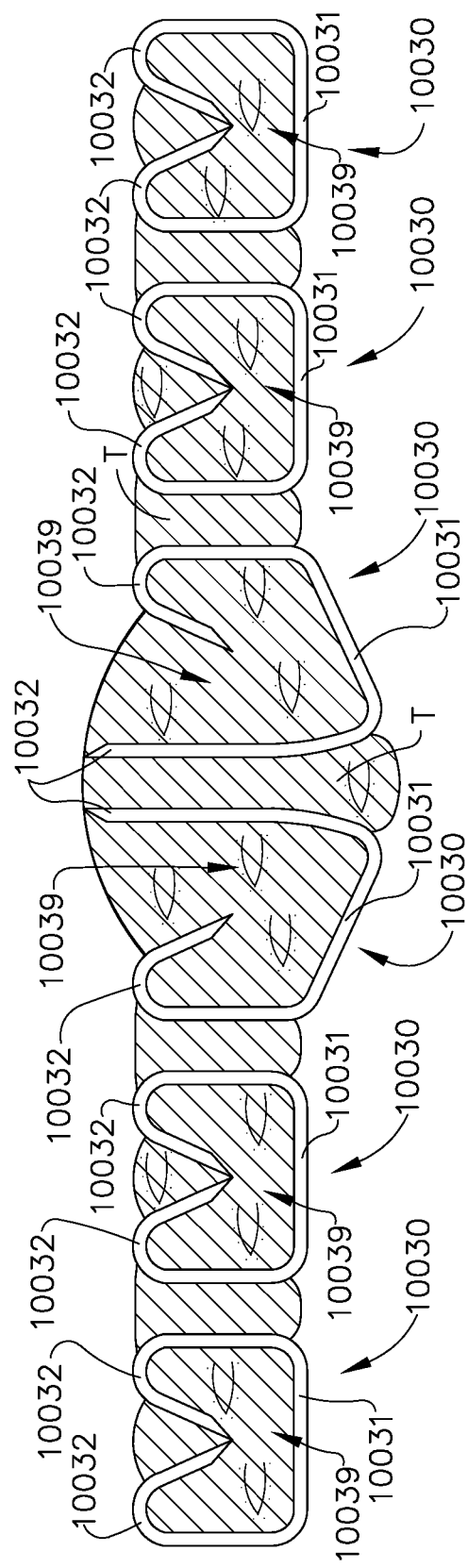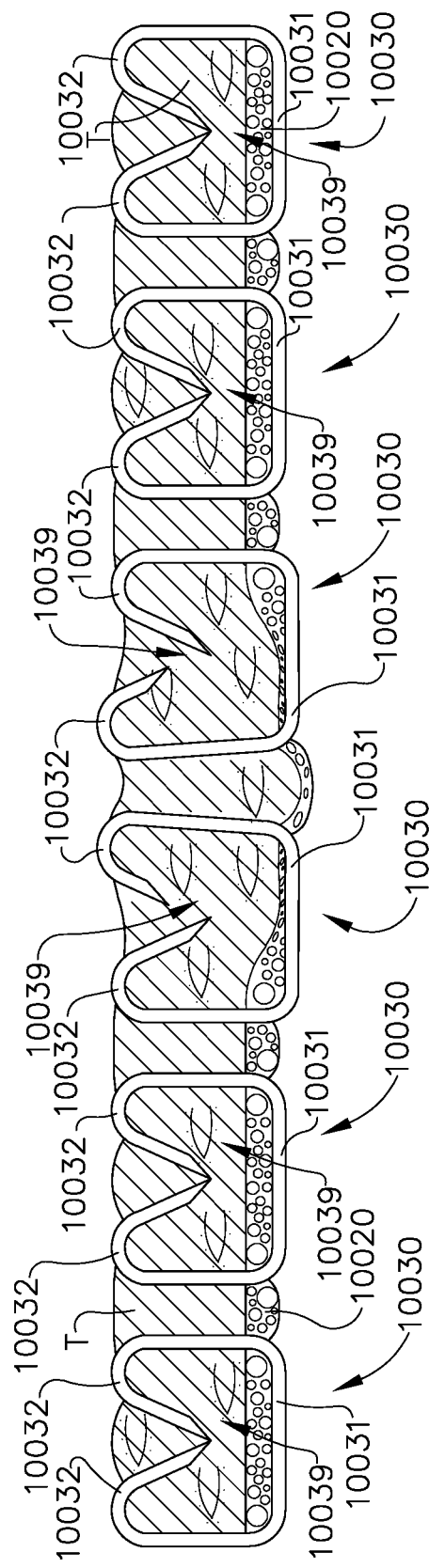

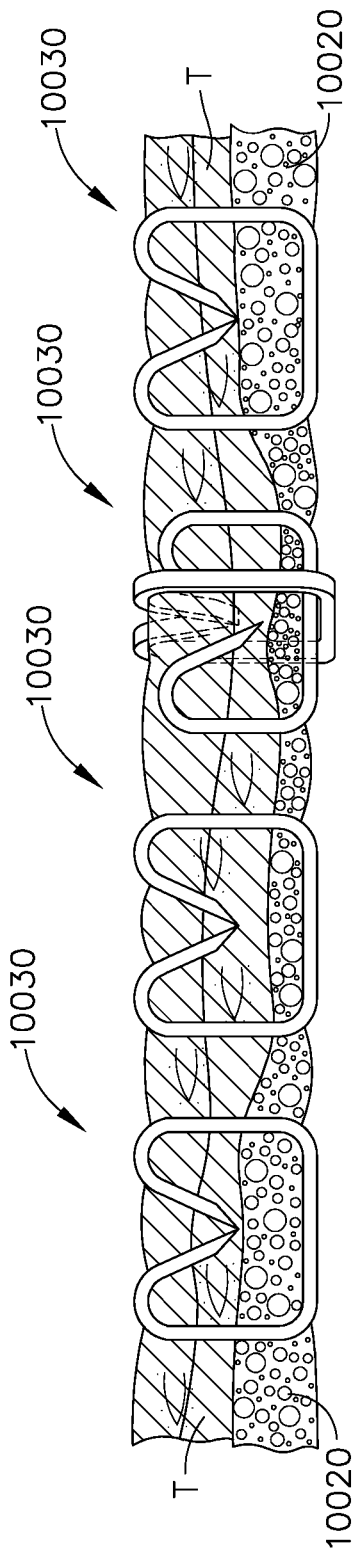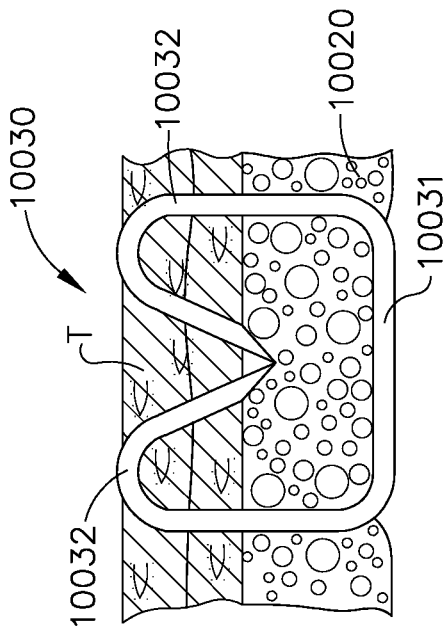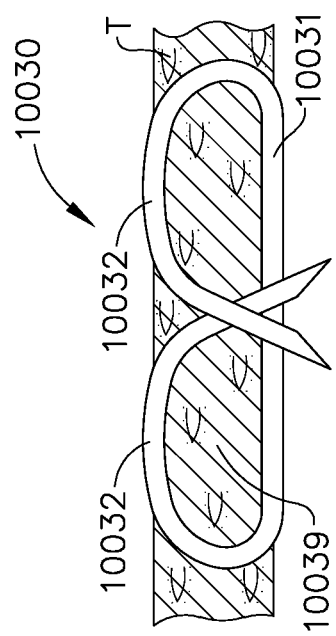
FIG. 249
FIG. 251
FIG. 250

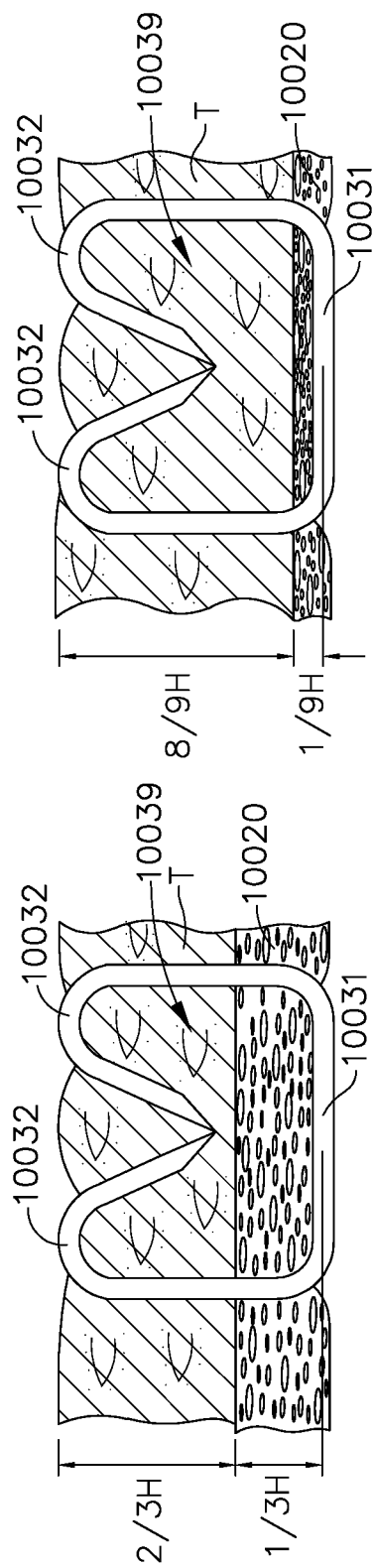
FIG. 256
FIG. 257
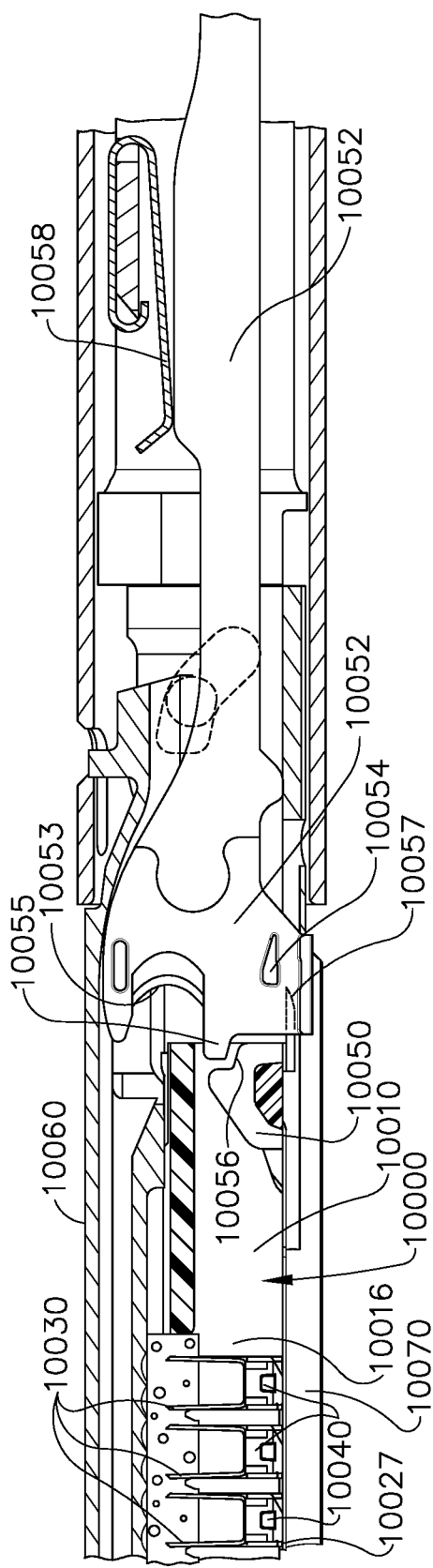
FIG. 258

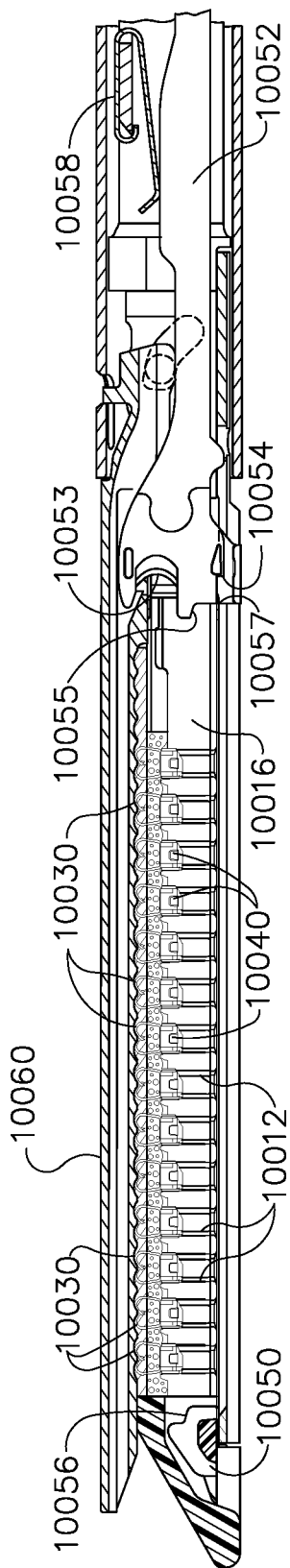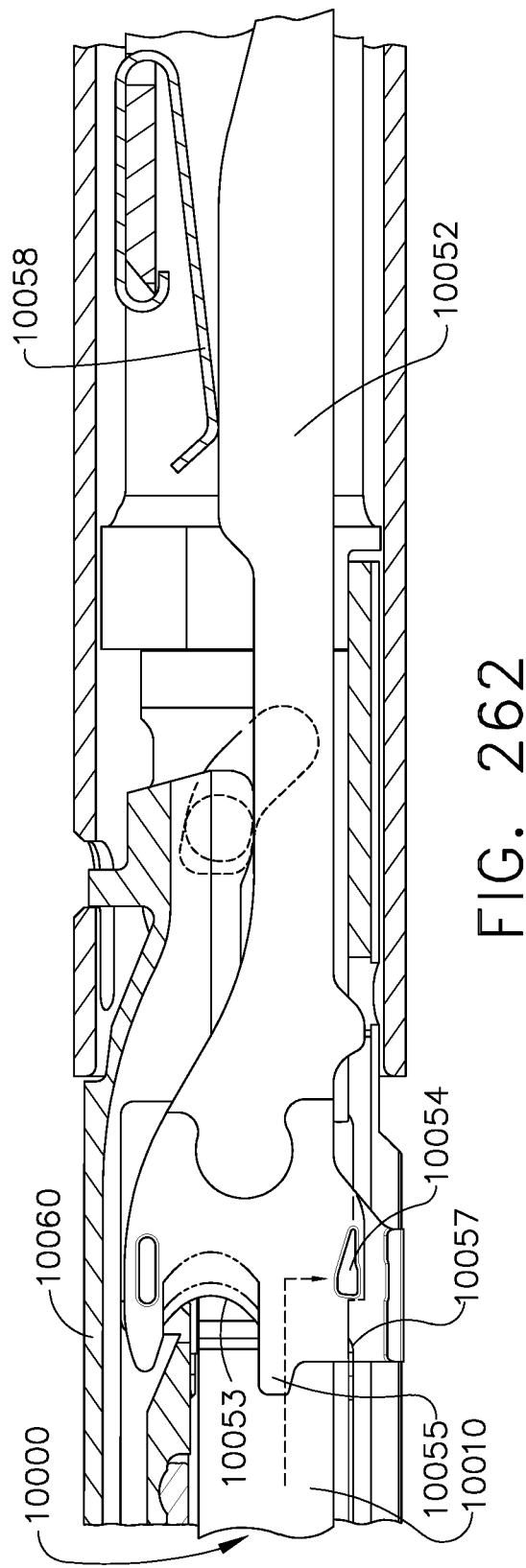
FIG. 261
FIG. 262

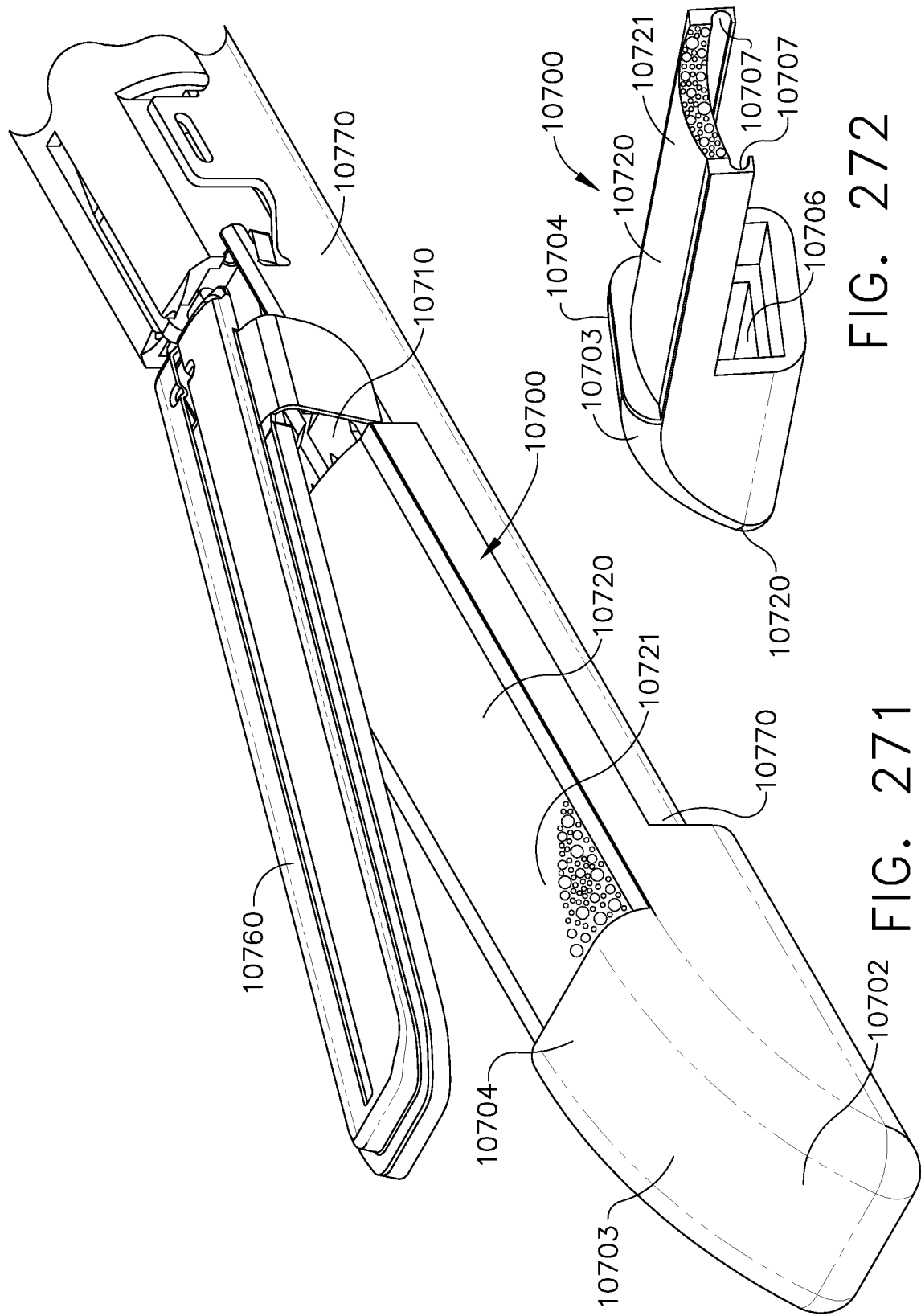

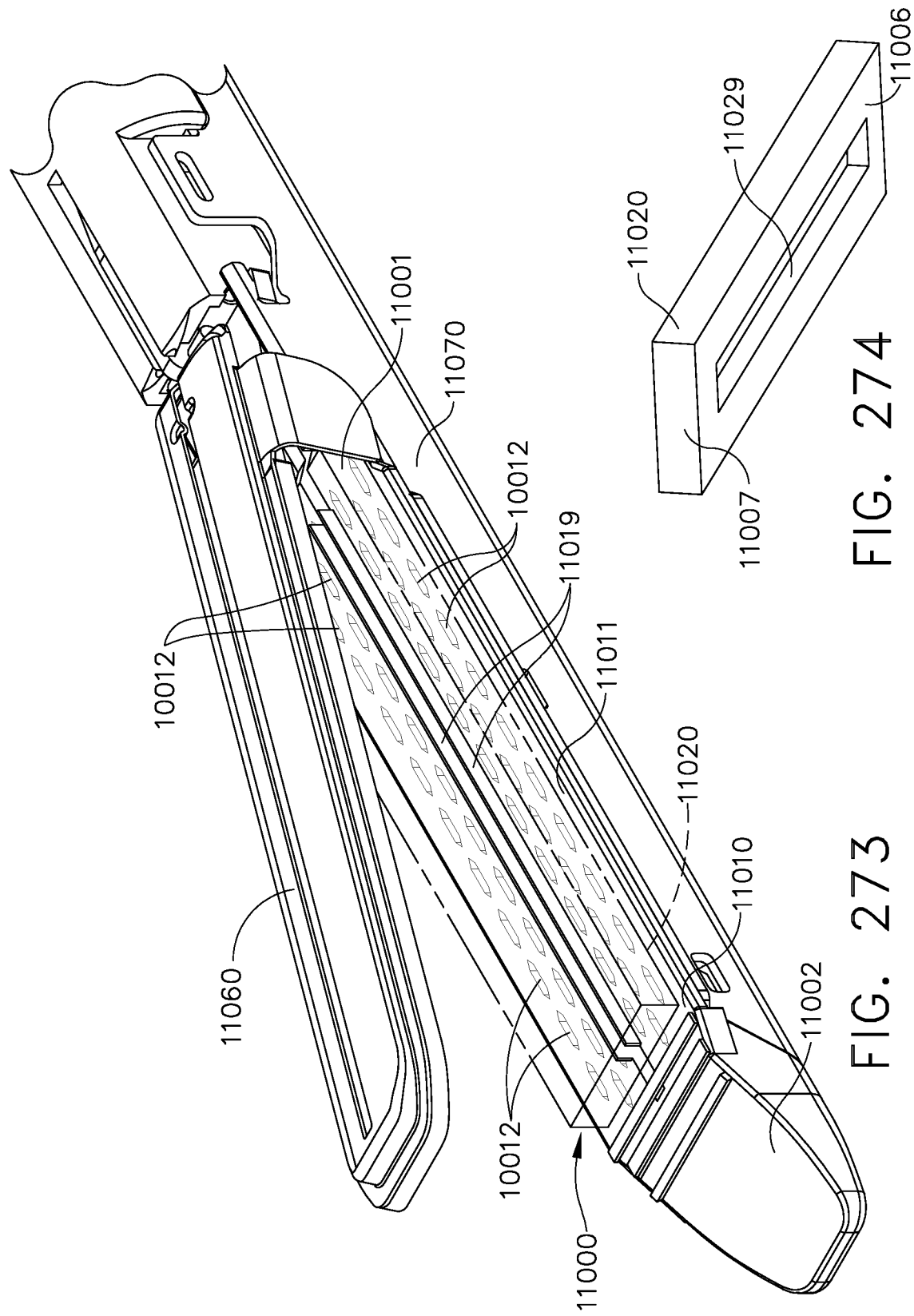

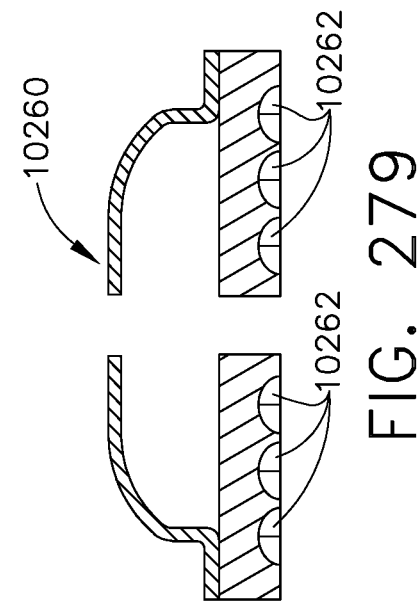
FIG. 279
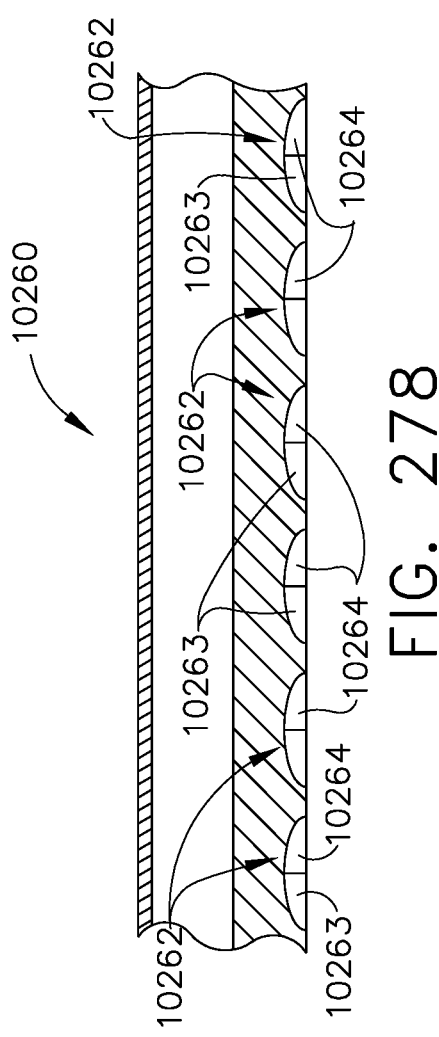
FIG. 278
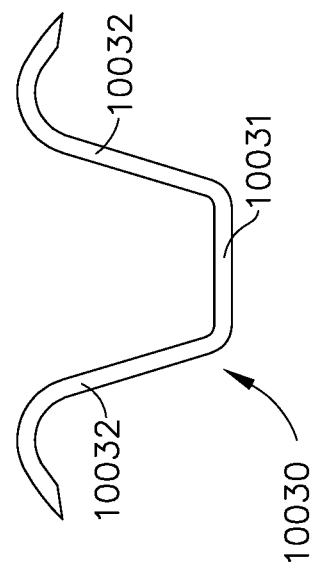
FIG. 282
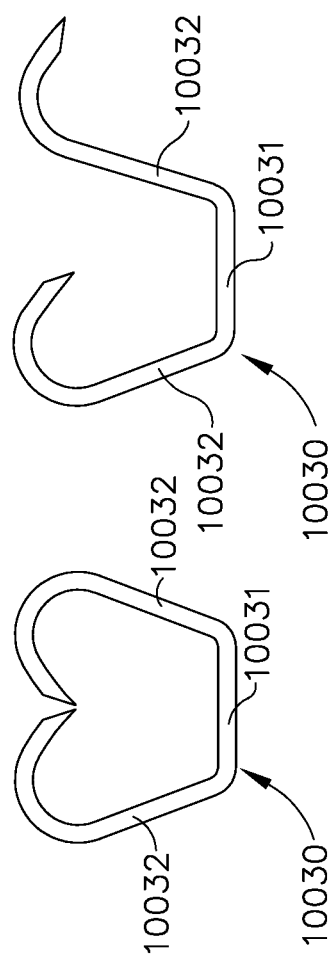
FIG. 281
FIG. 280

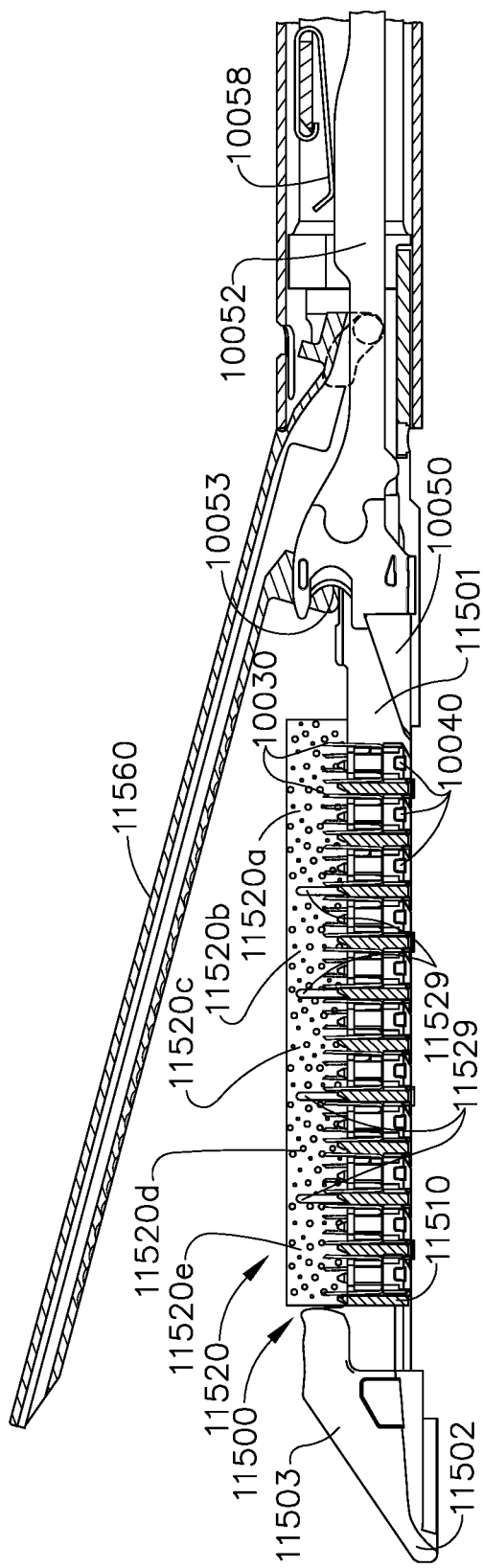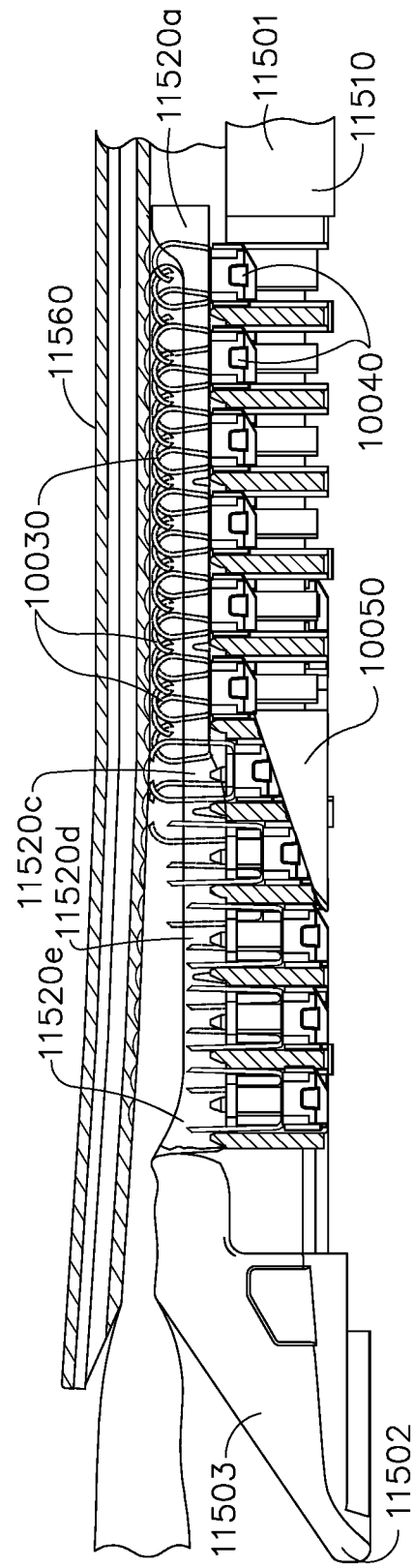

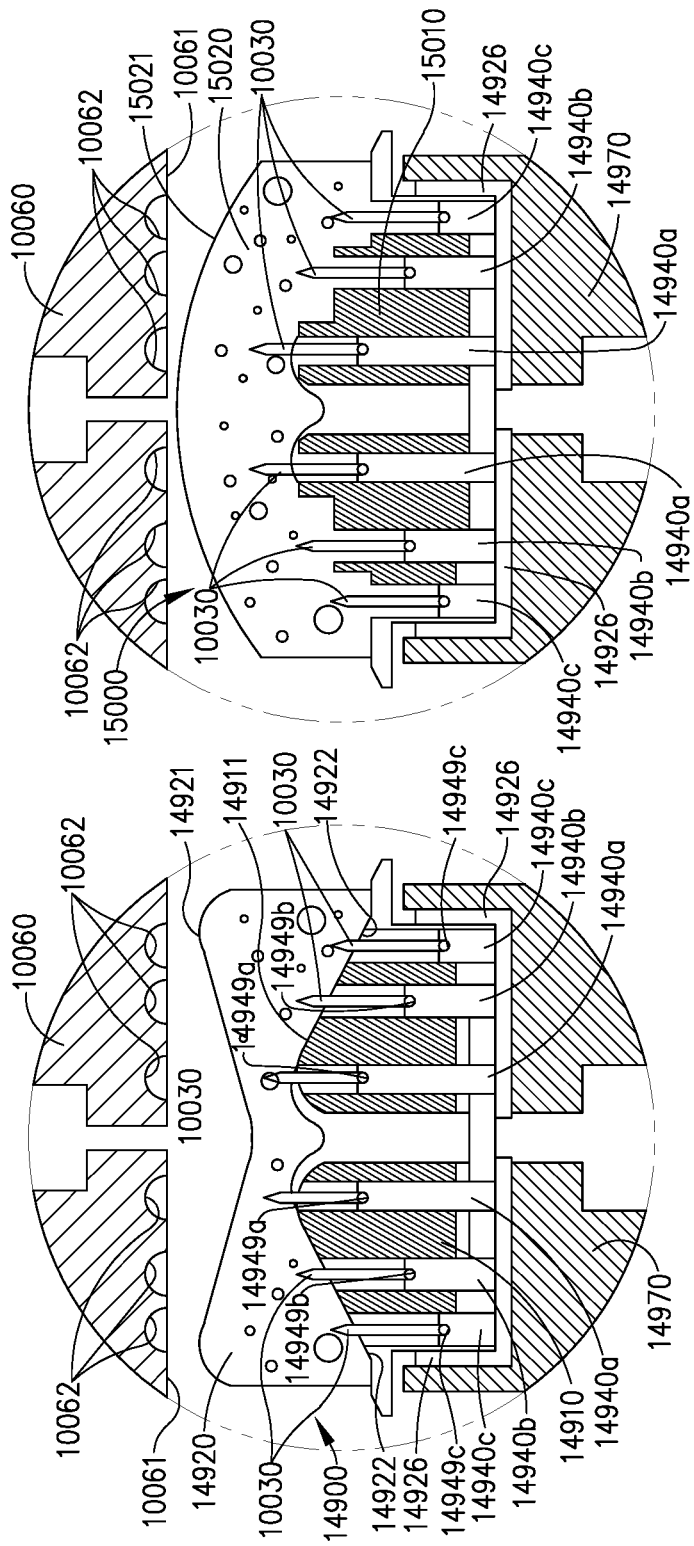

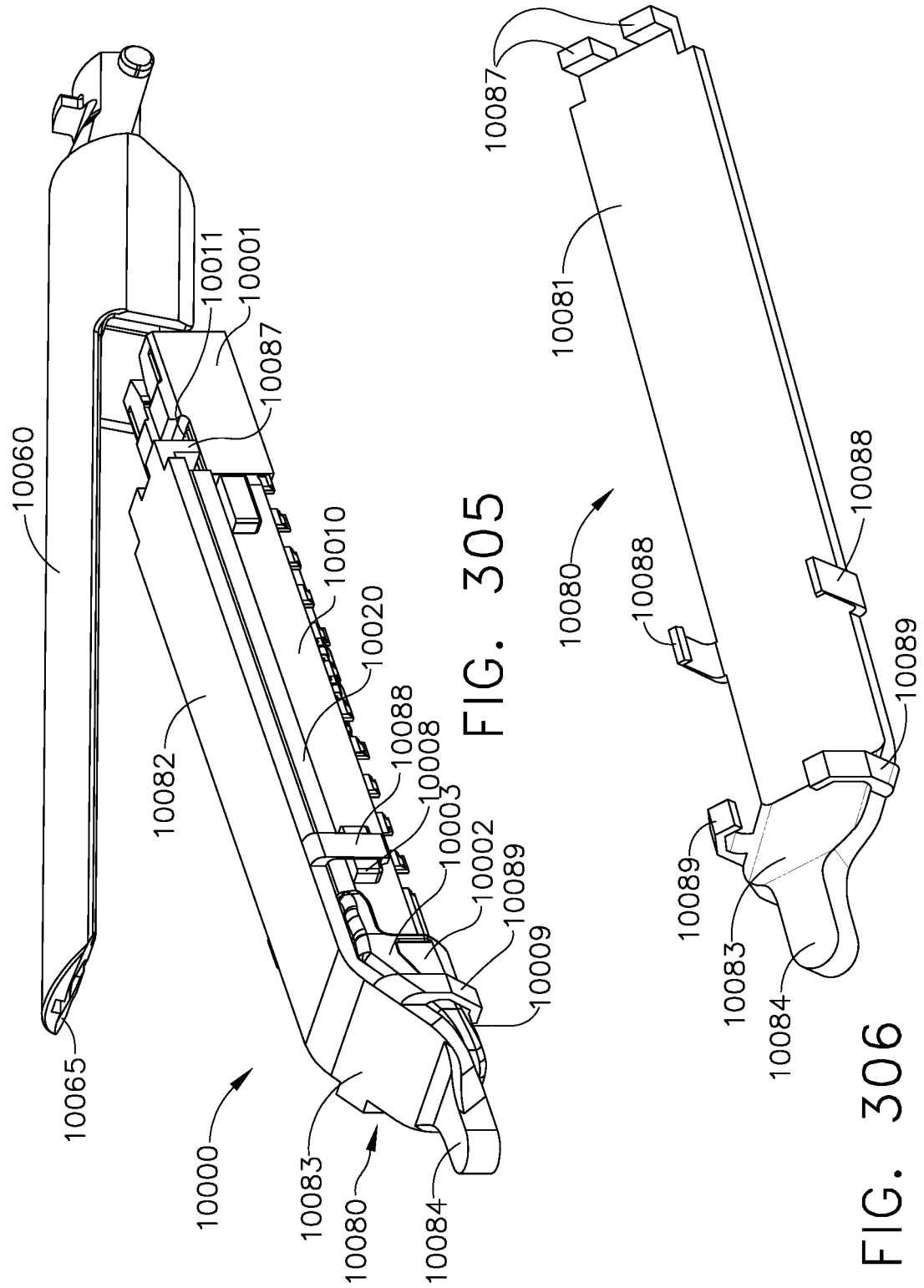

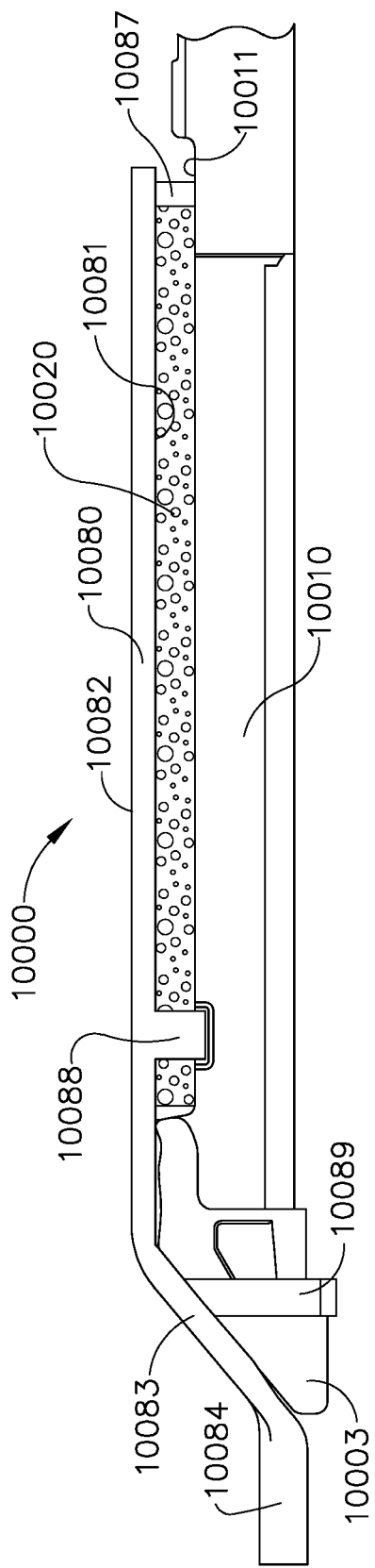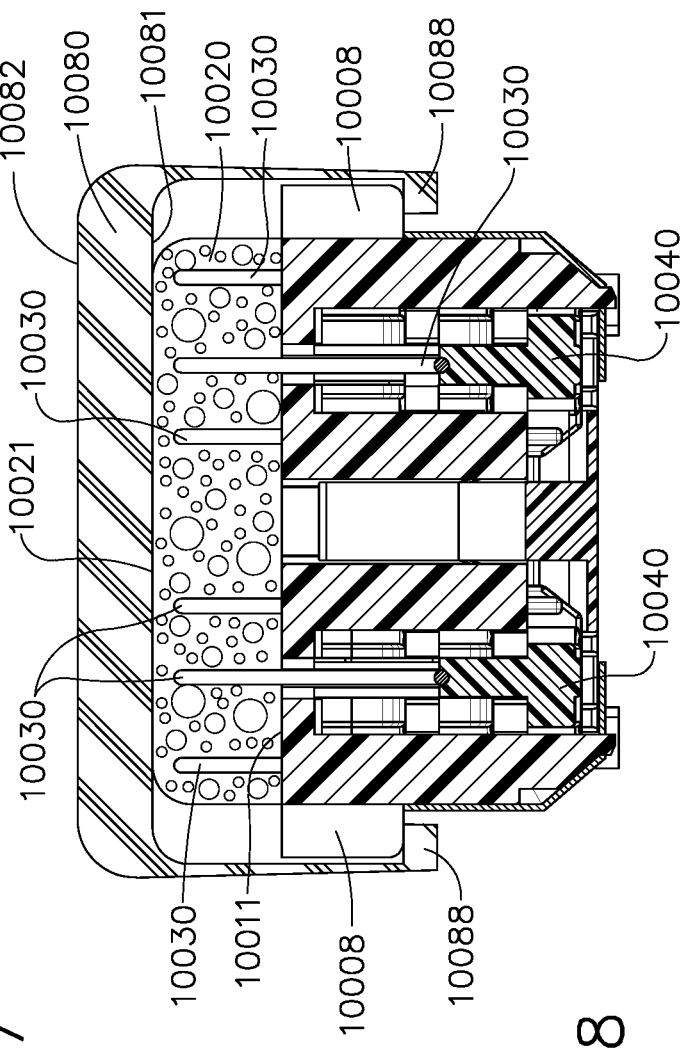
FIG. 307
FIG. 308

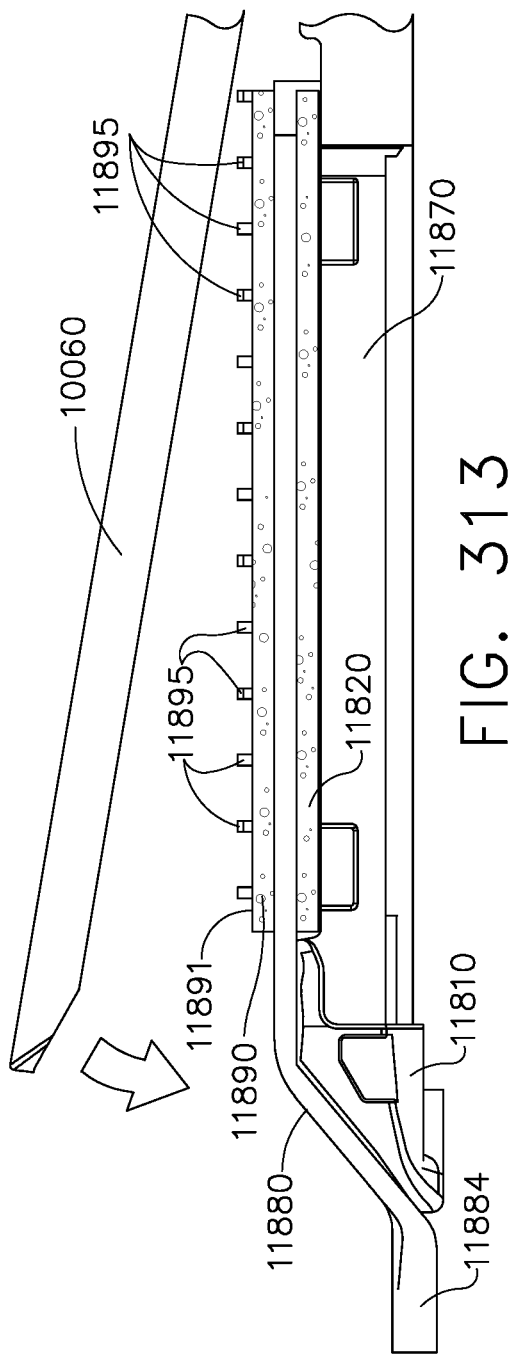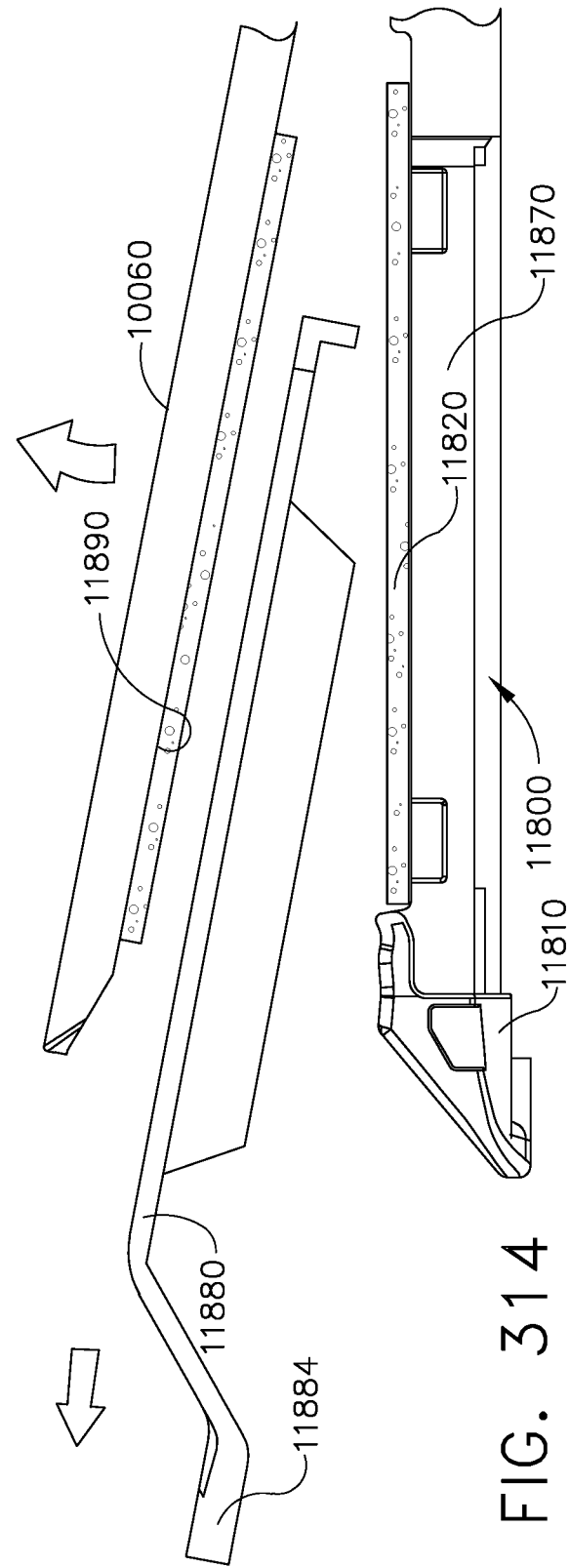

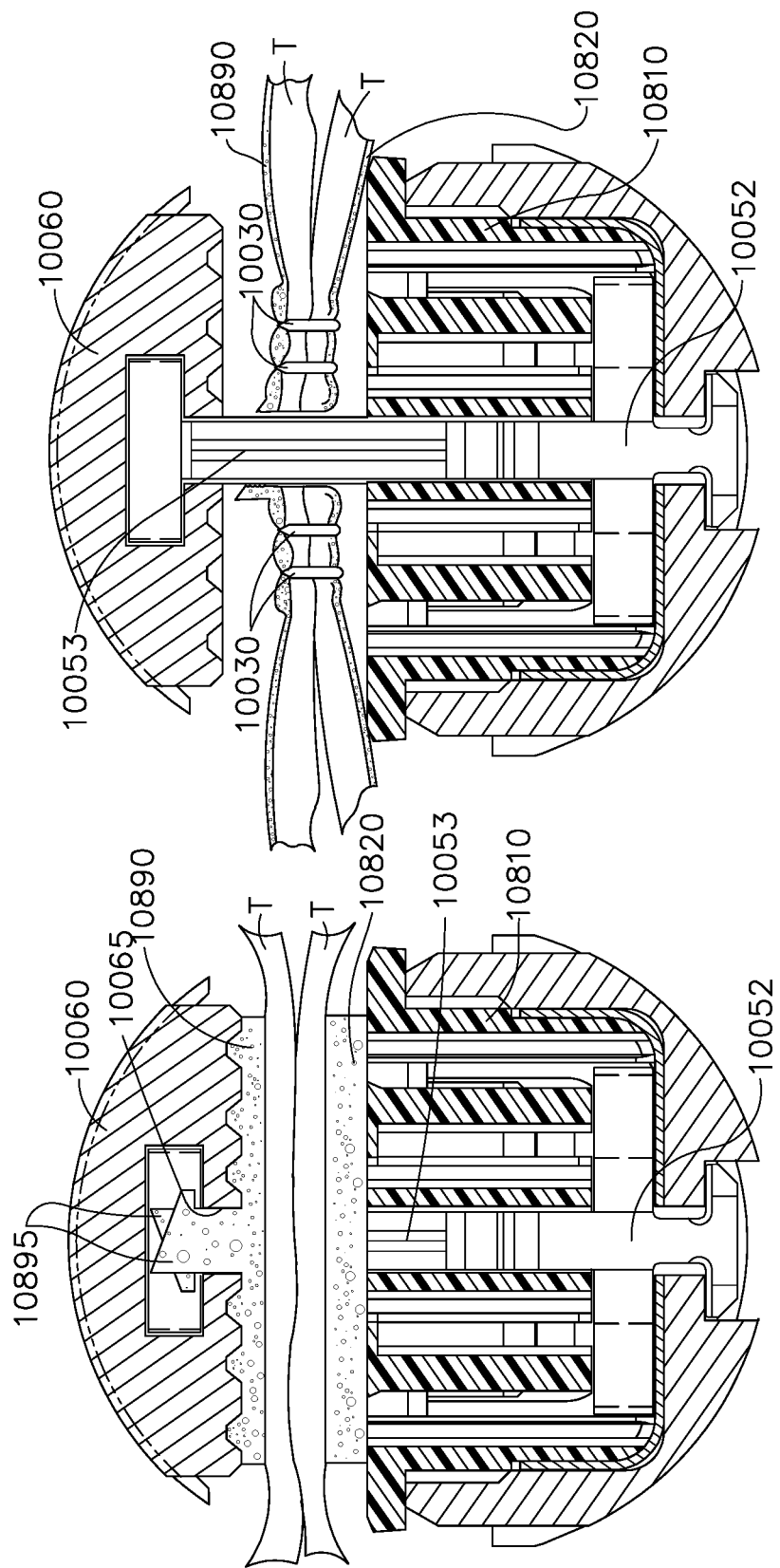

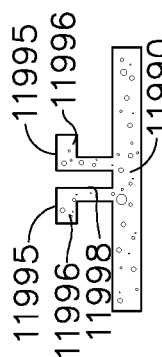
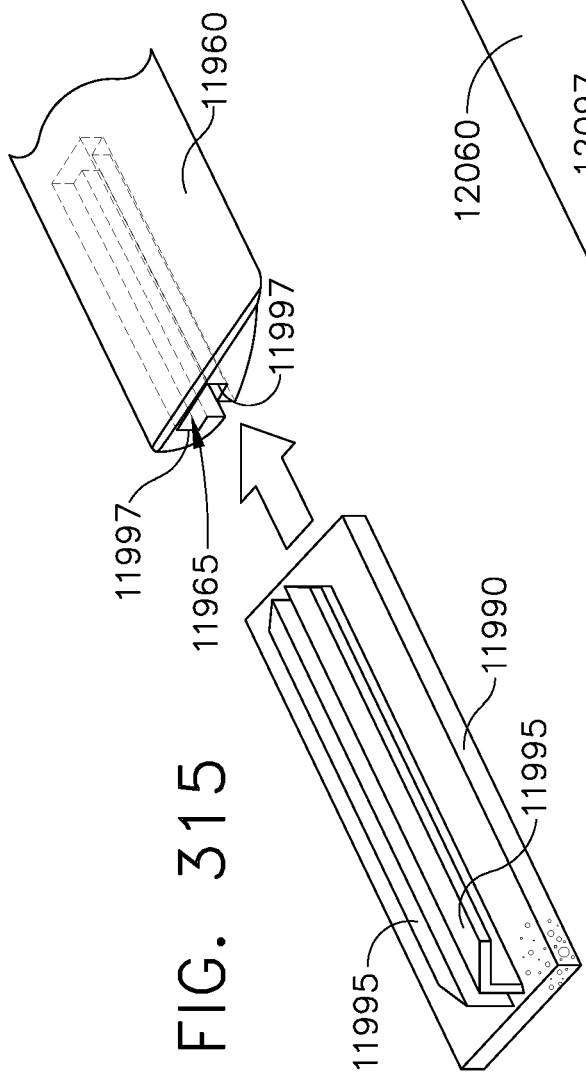
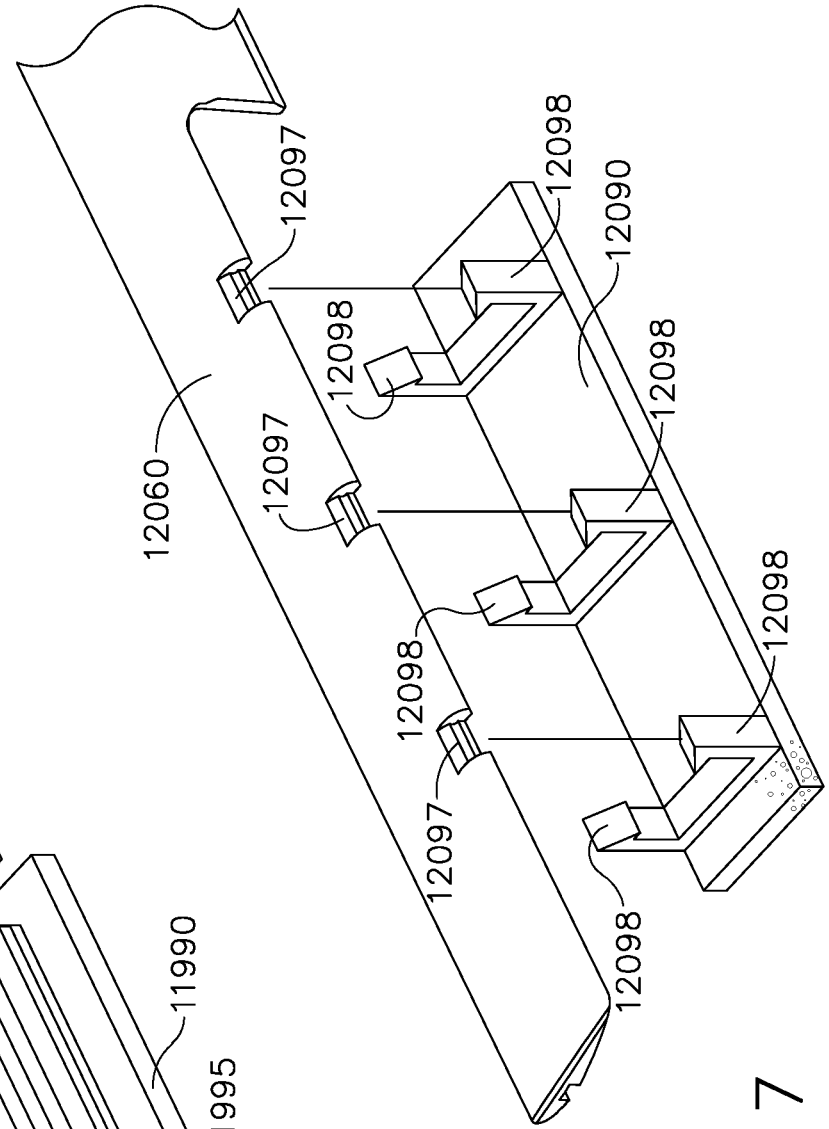
FIG. 316
FIG. 315
FIG. 317

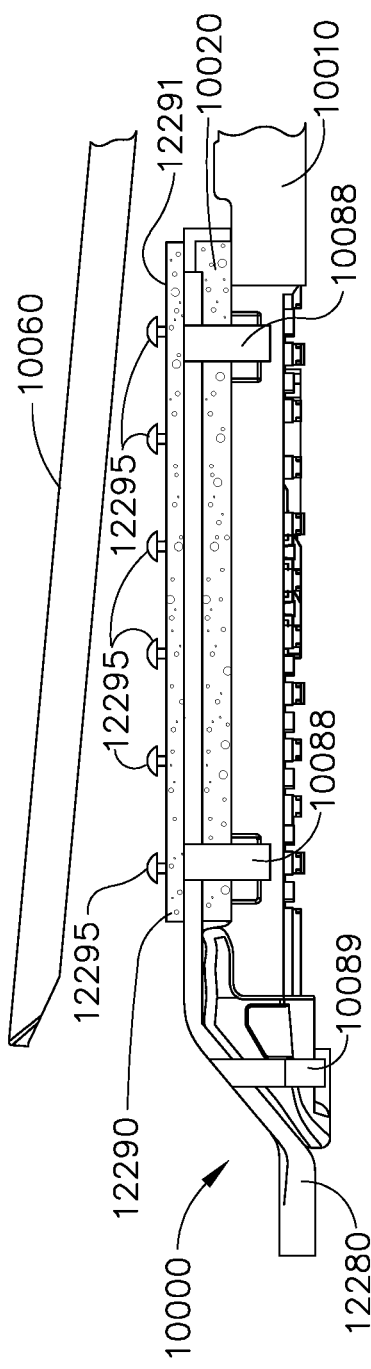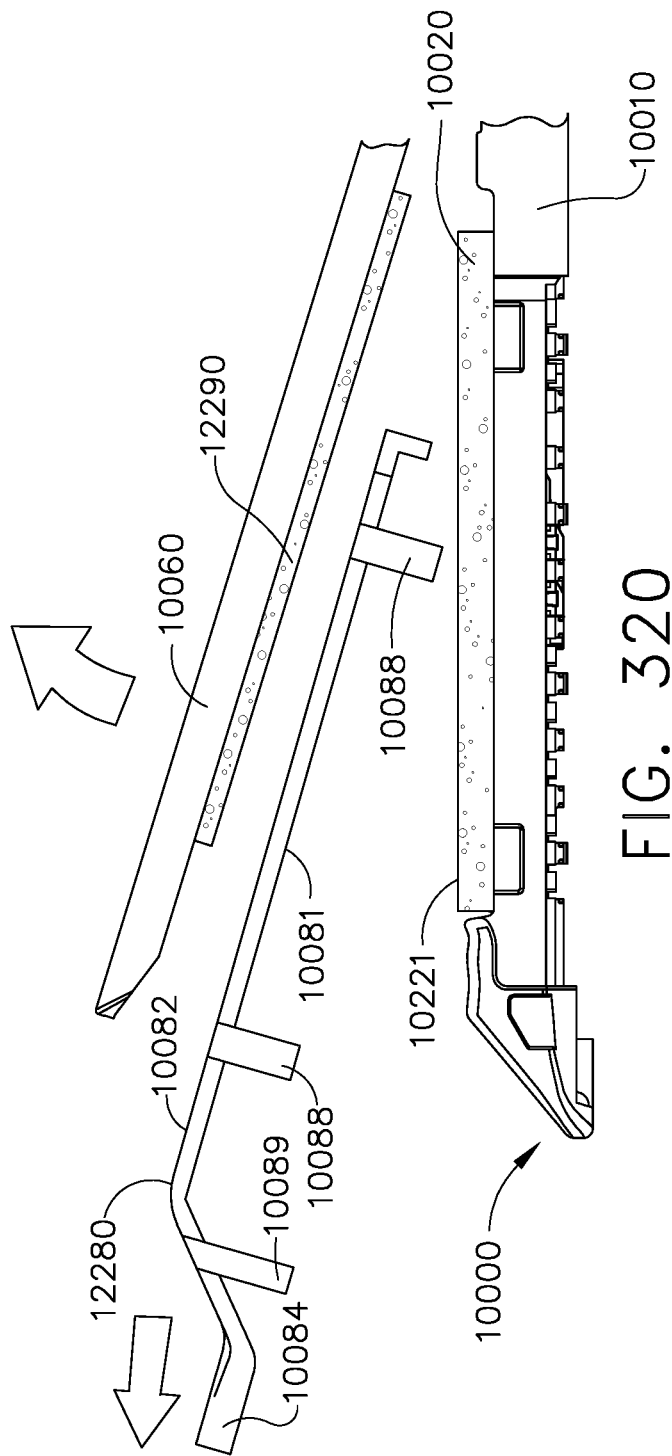

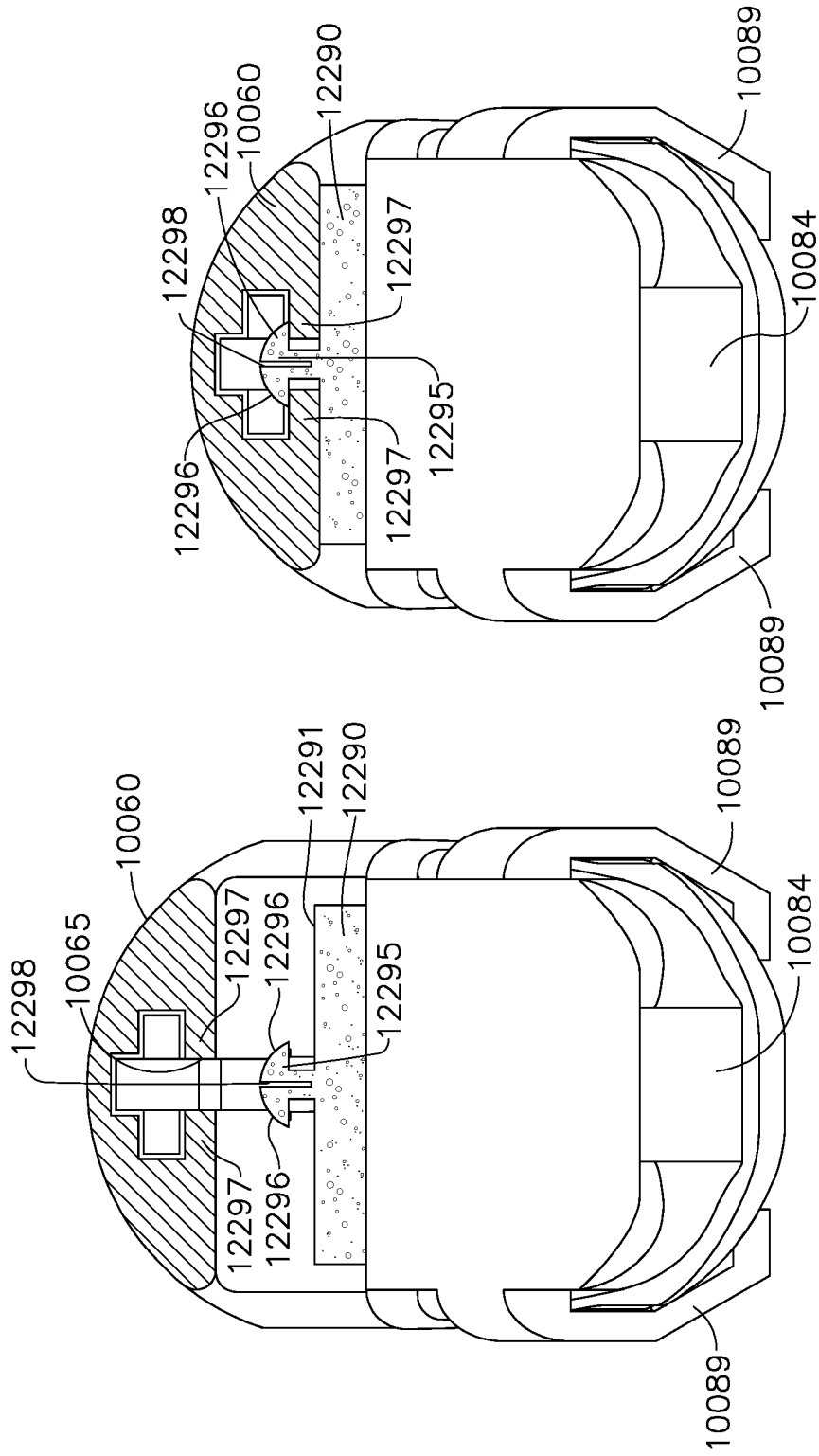

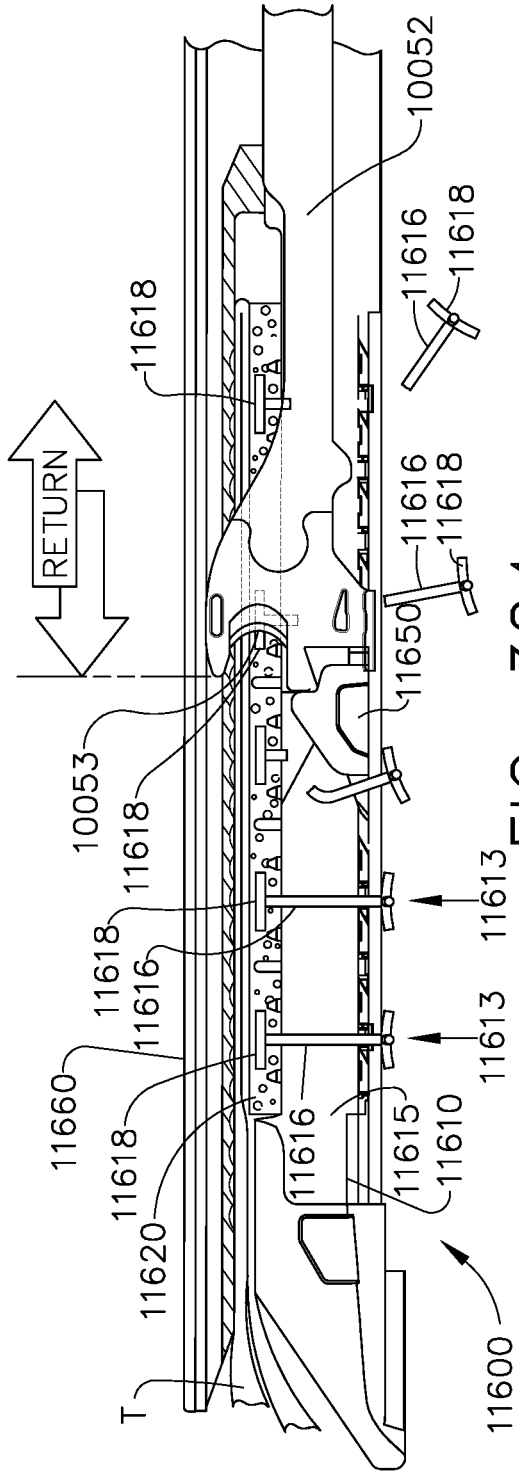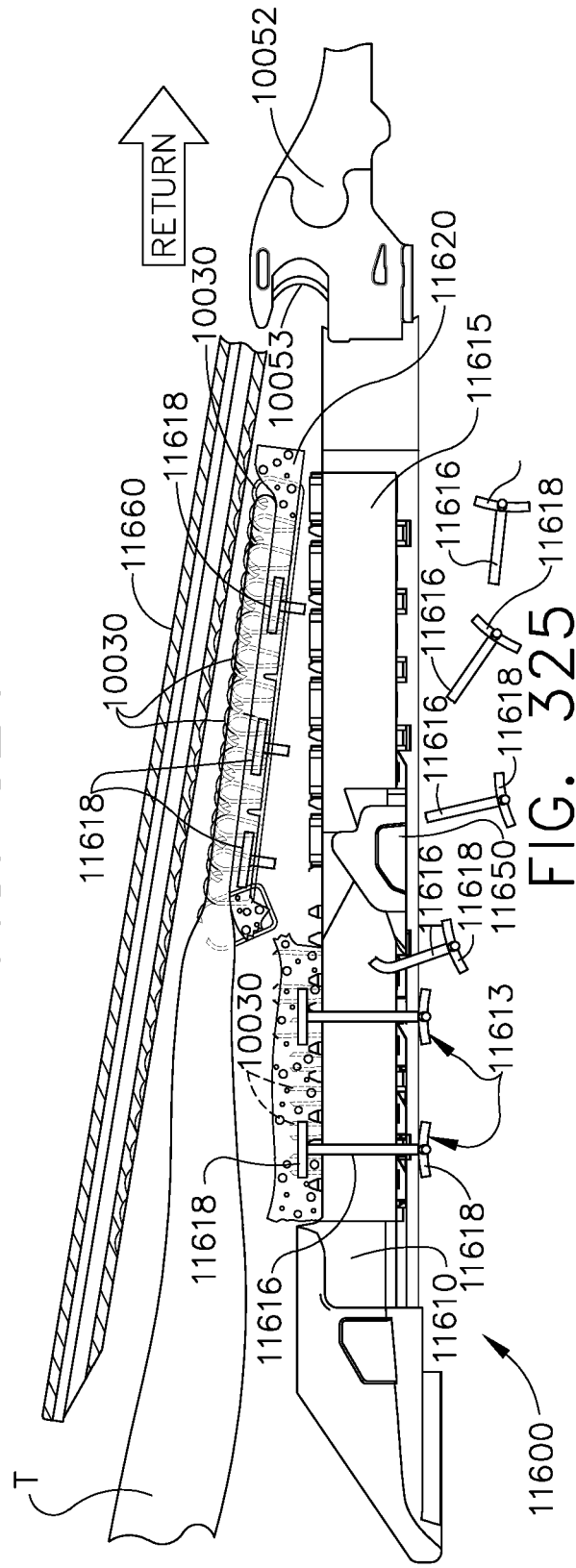

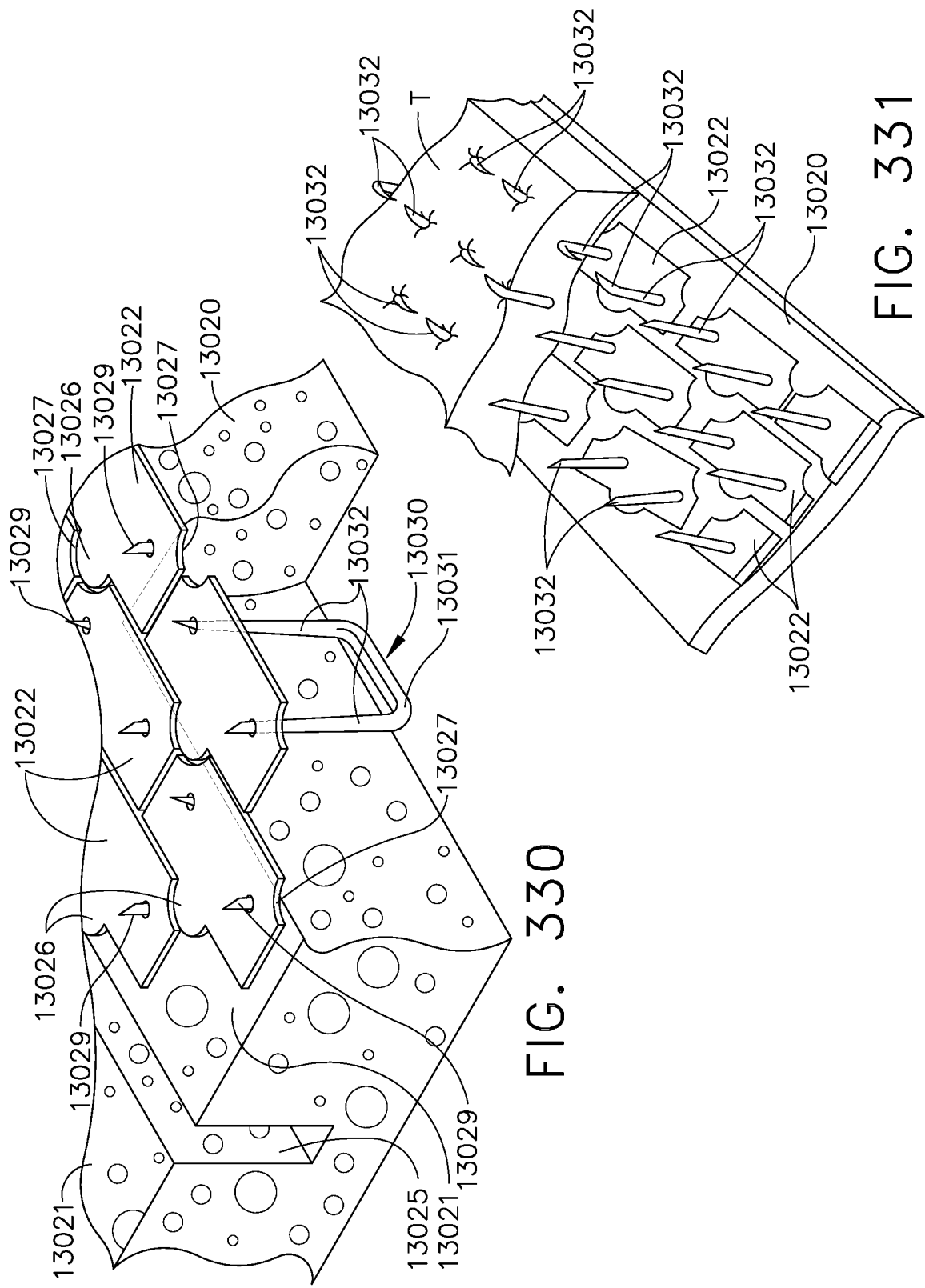

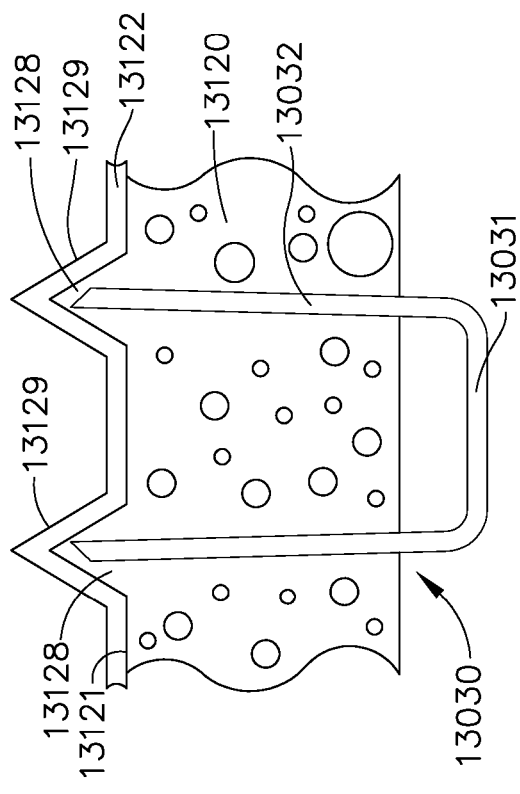
FIG. 332
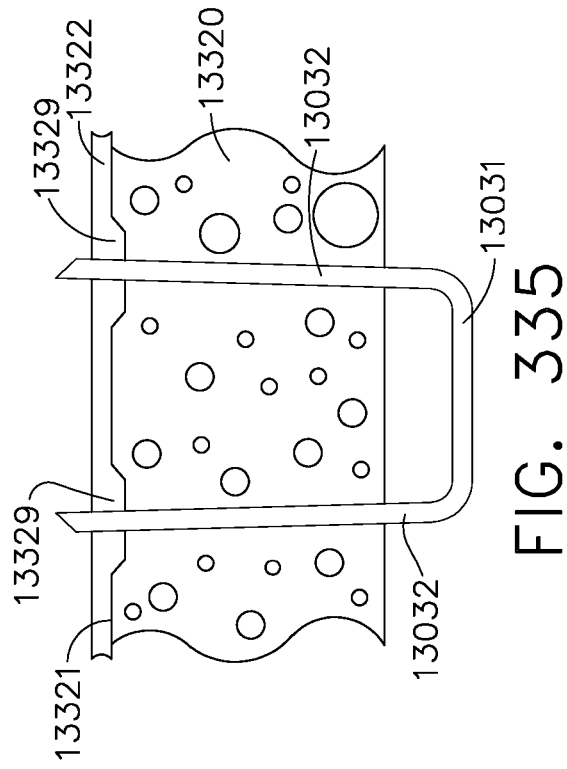
FIG. 333
FIG. 334
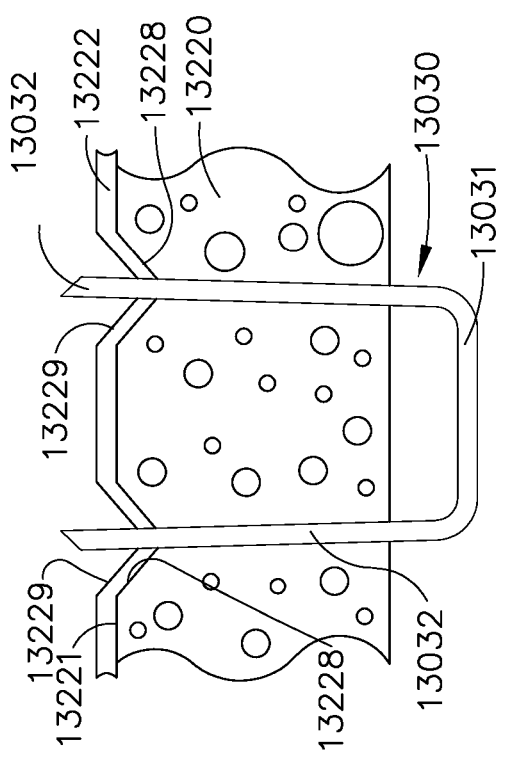
FIG. 335

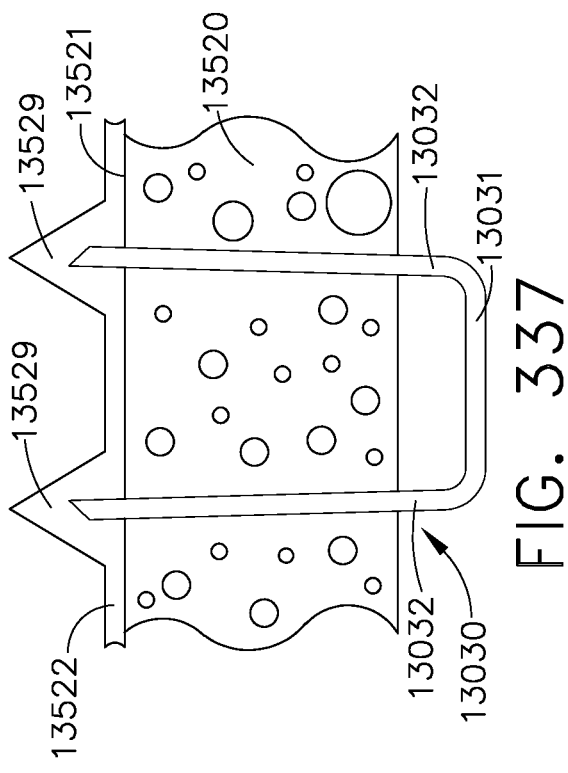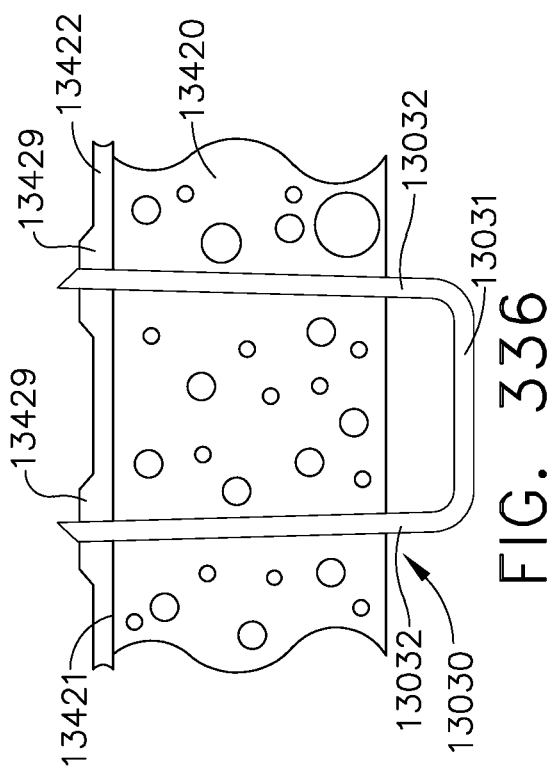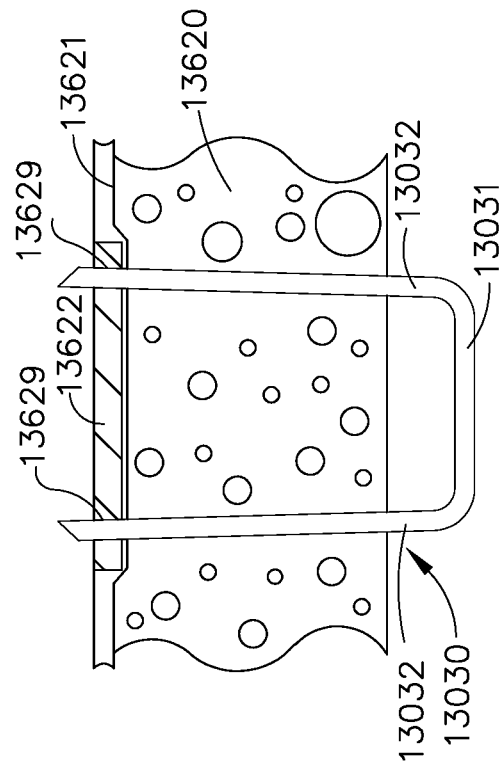
FIG. 337
FIG. 336
FIG. 338

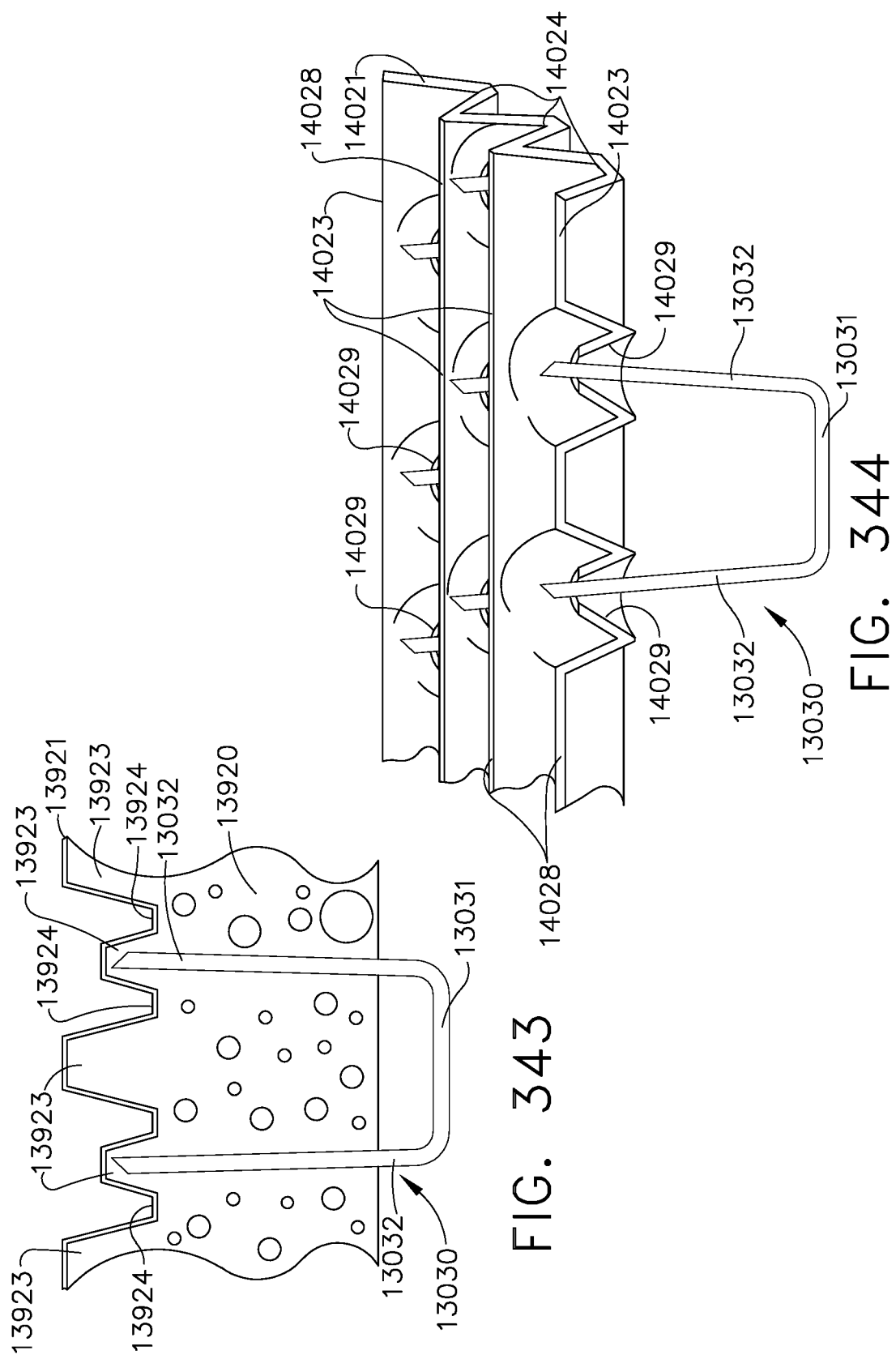

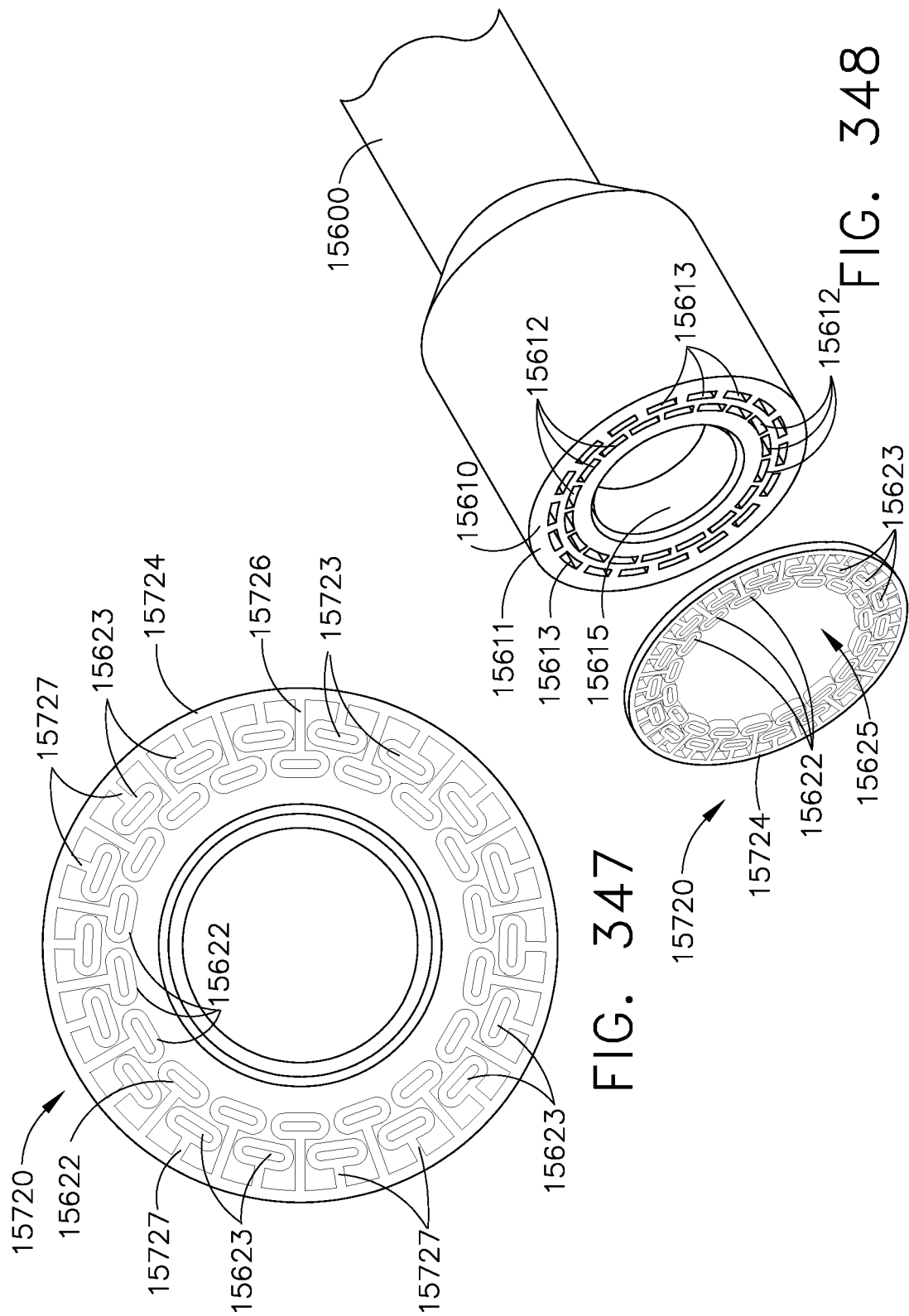

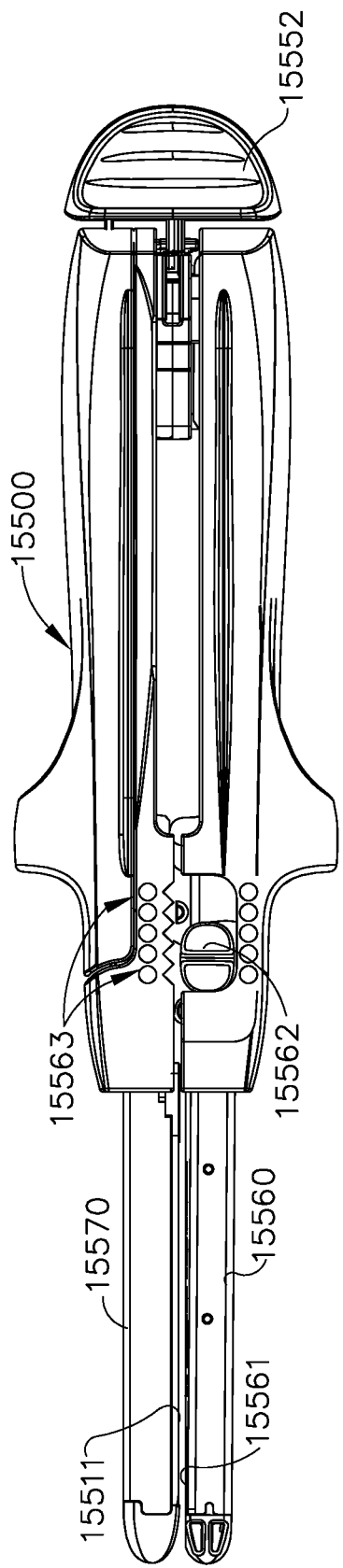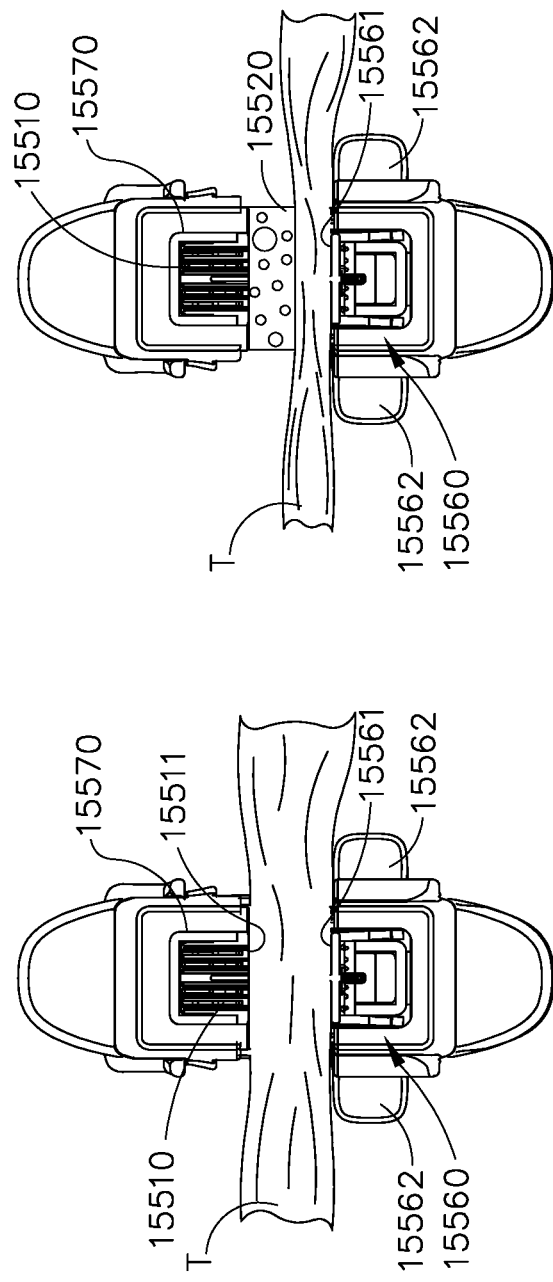
FIG. 351
FIG. 352
FIG. 353

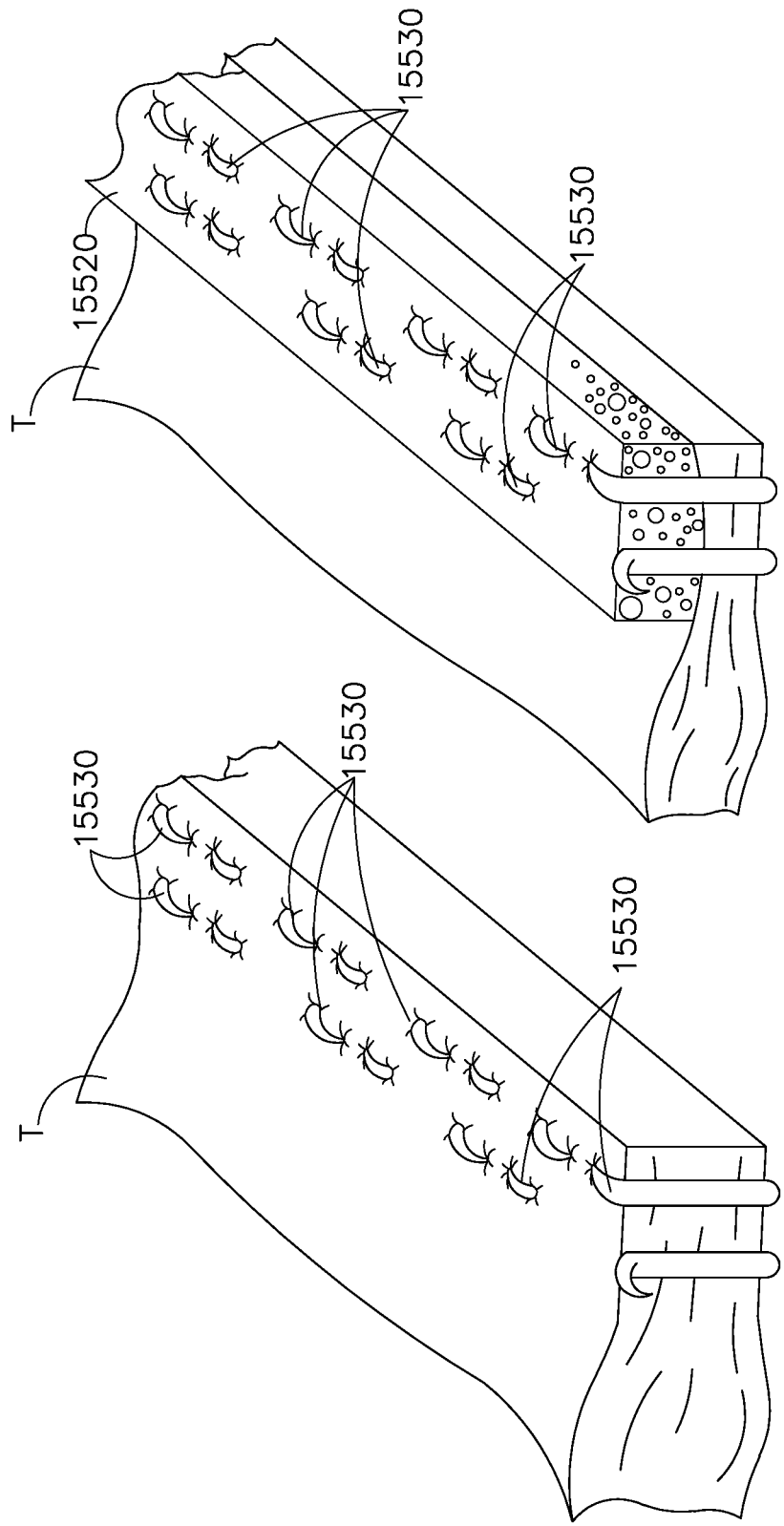

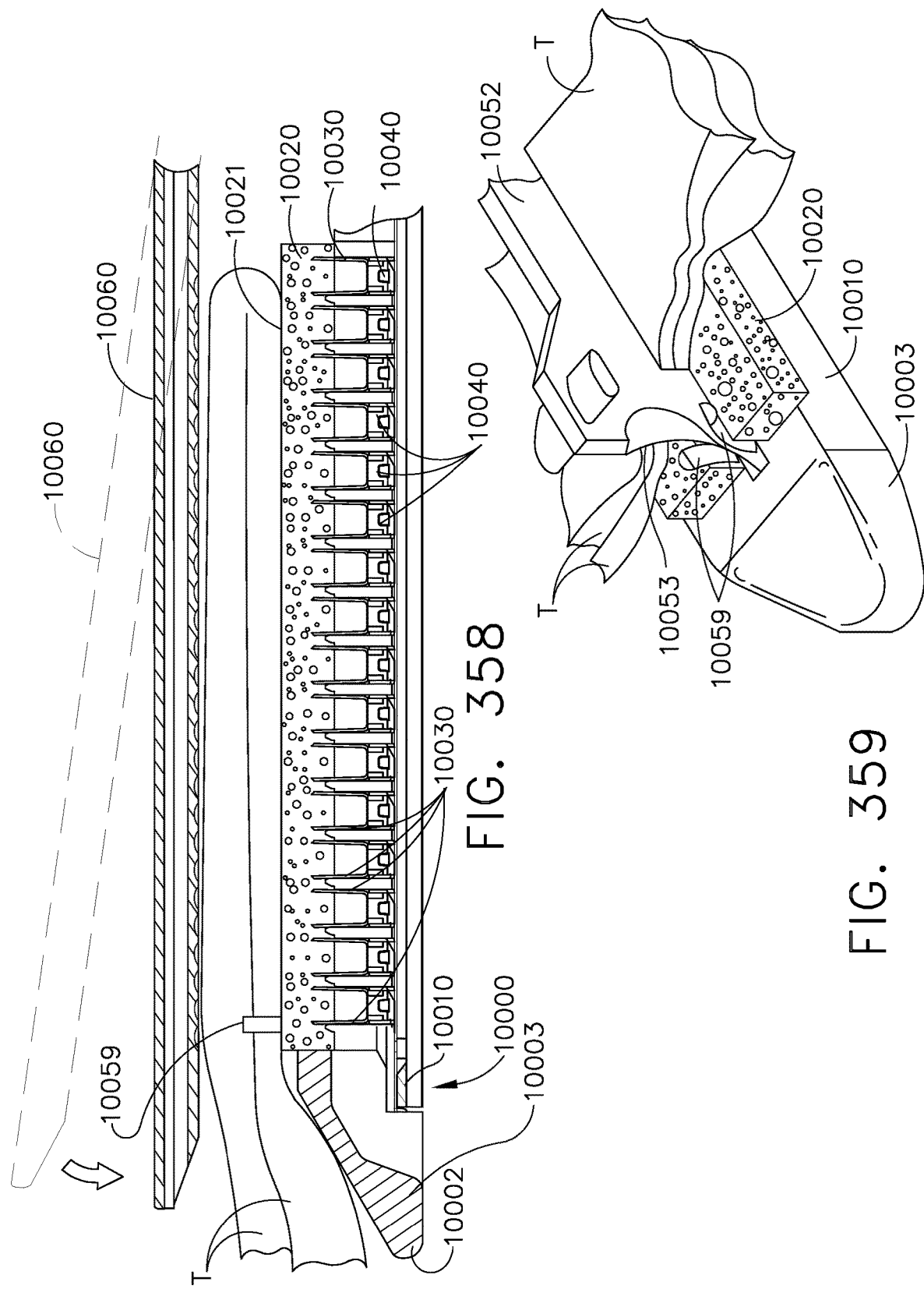

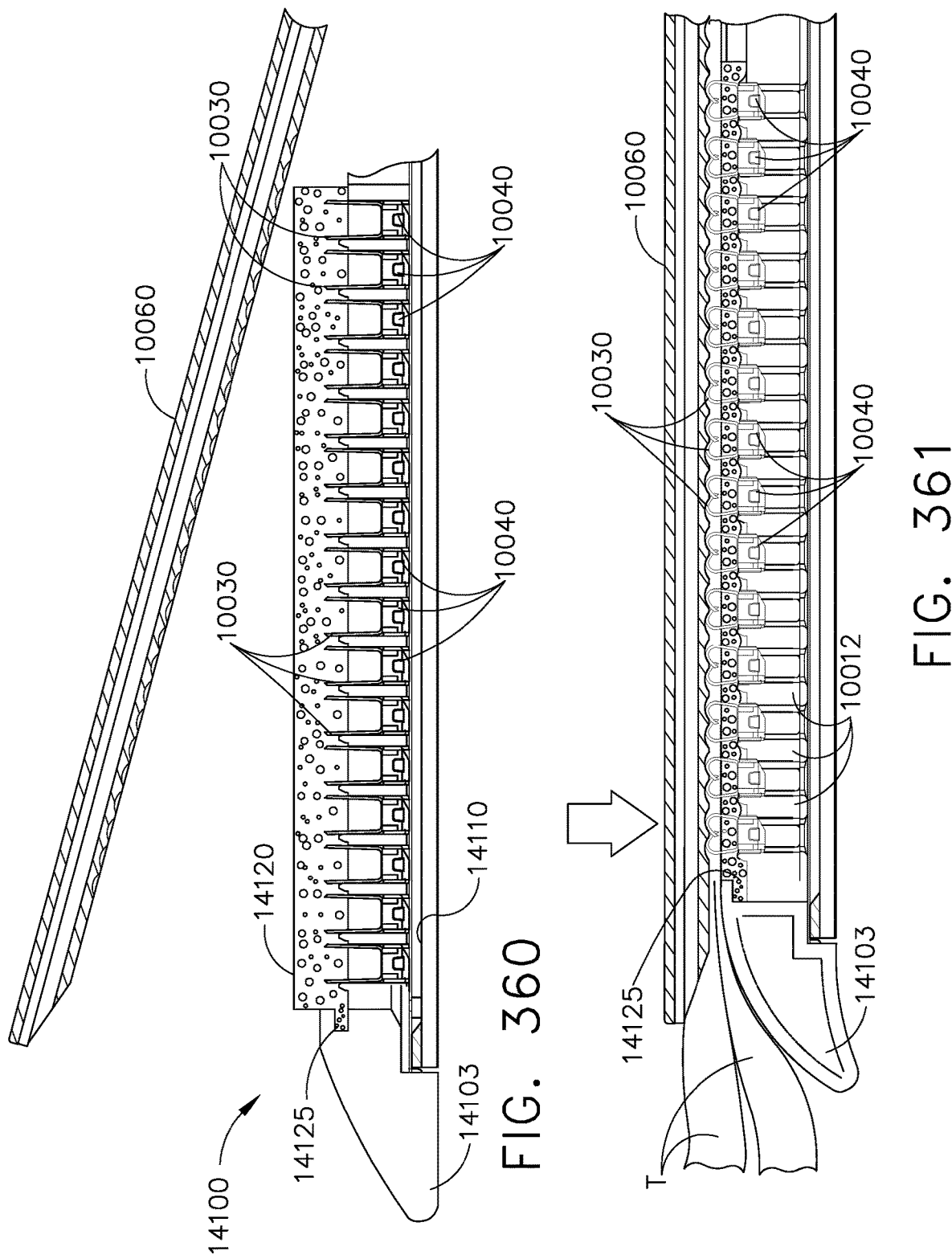

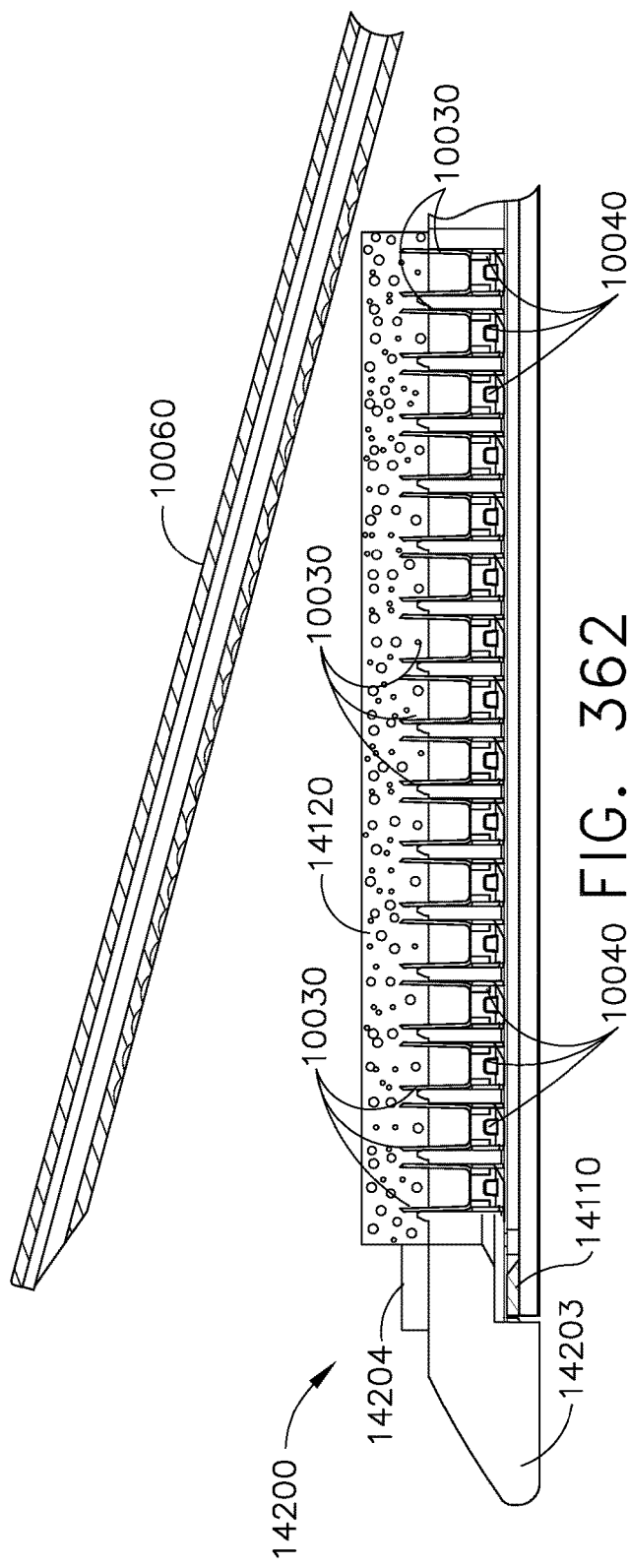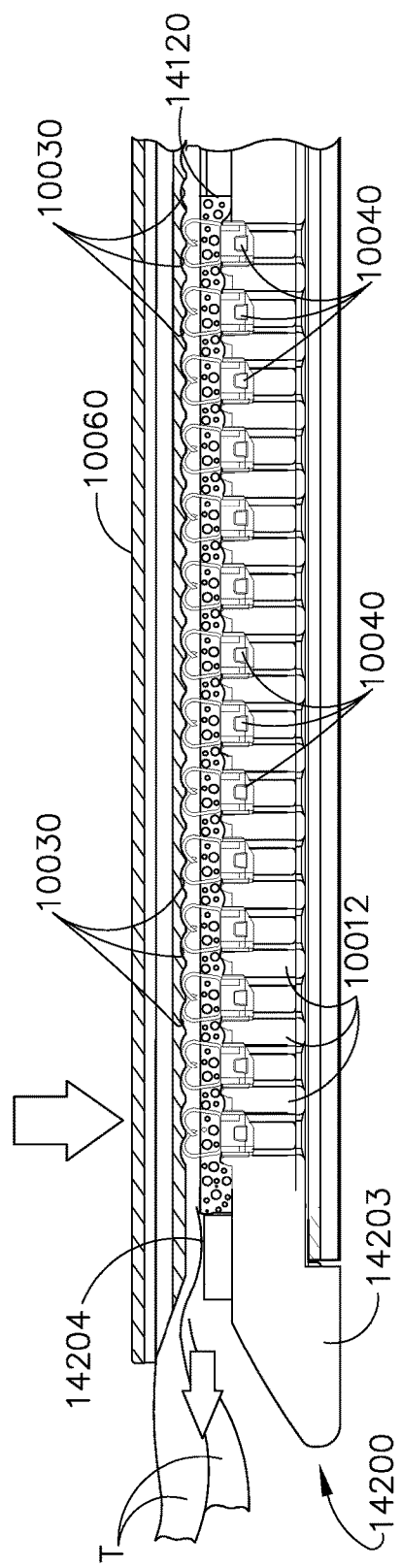

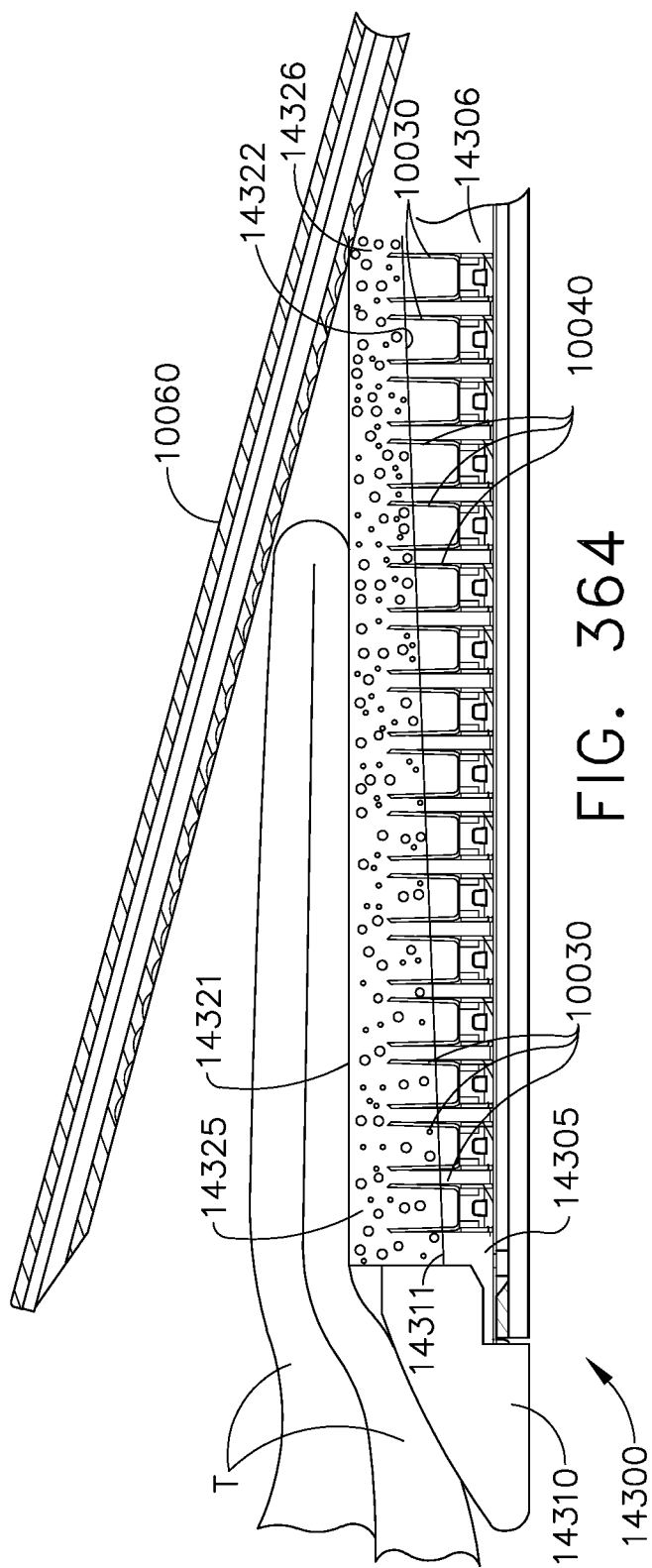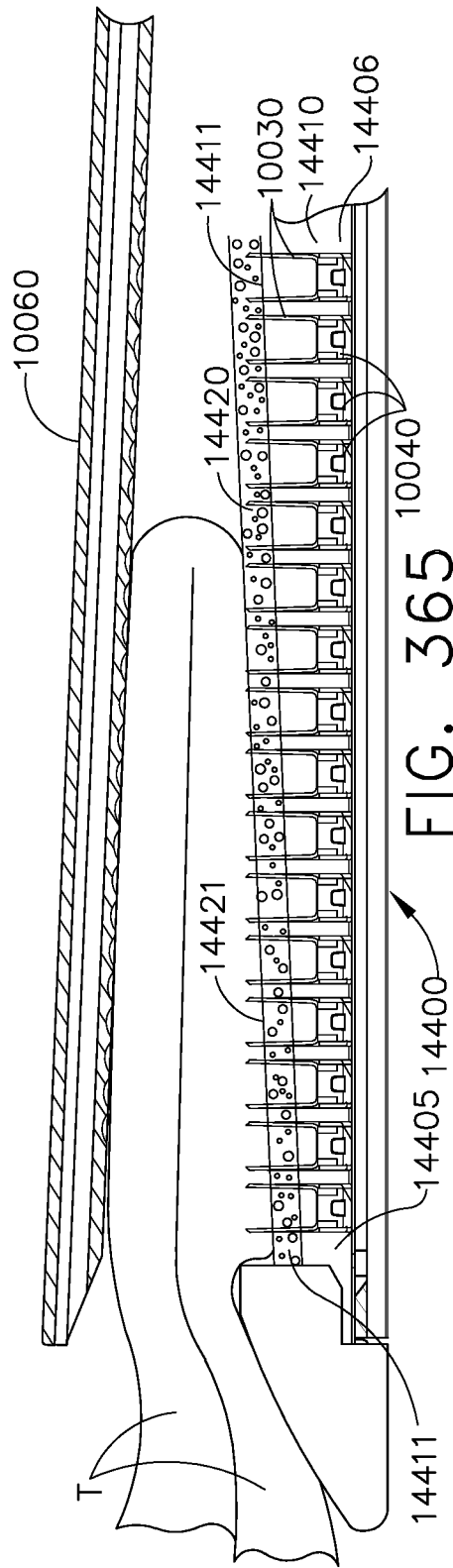

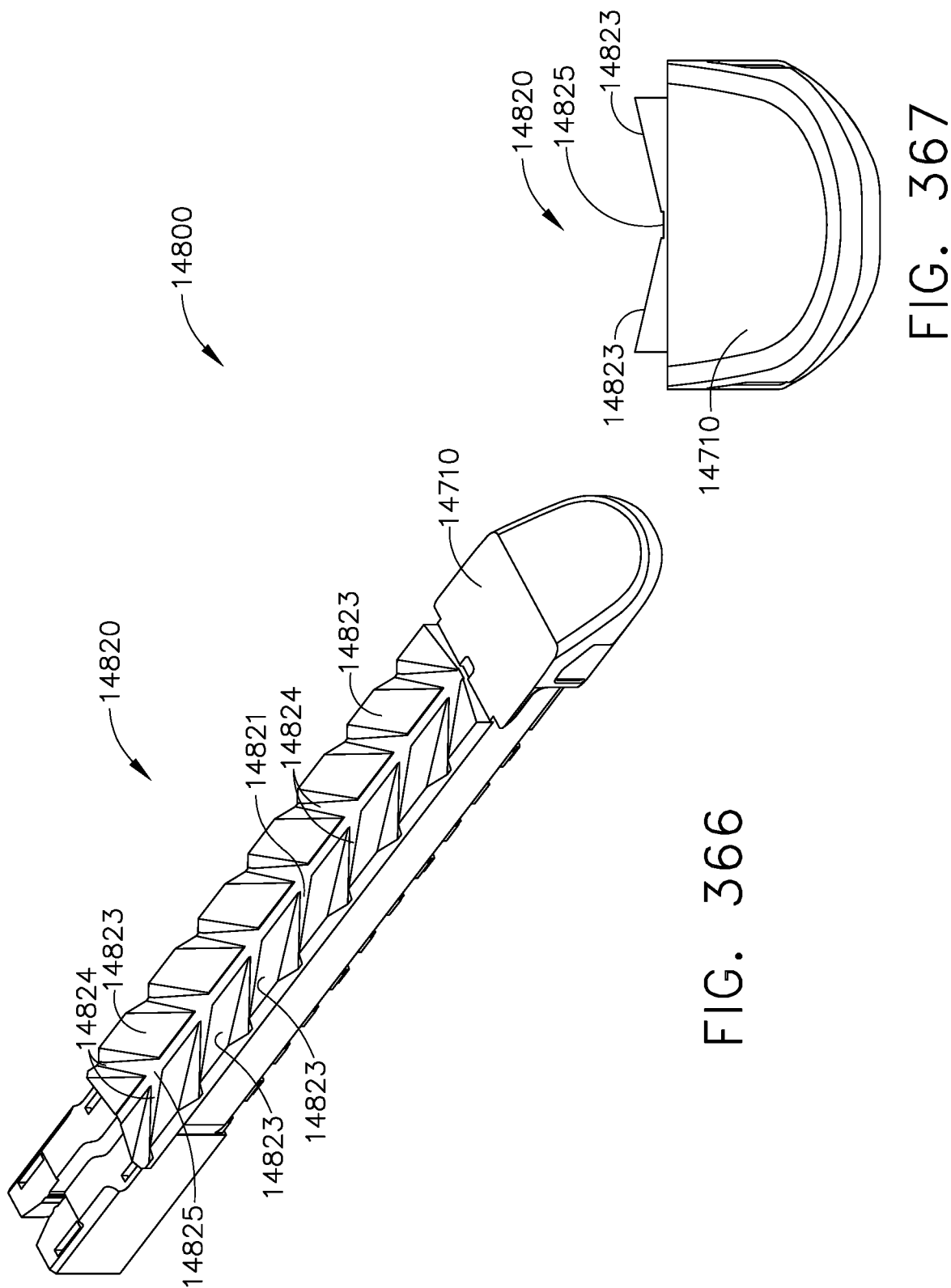

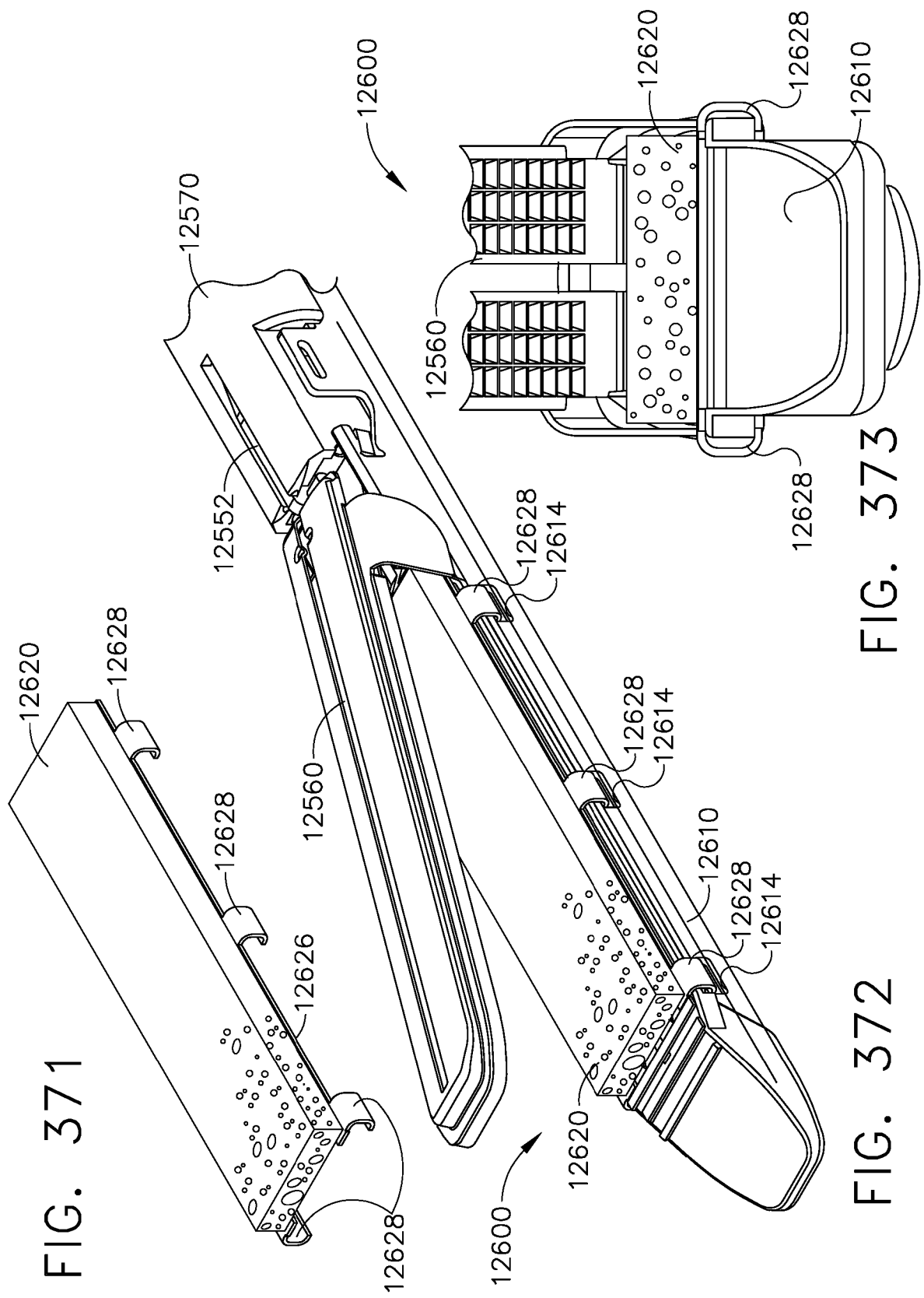

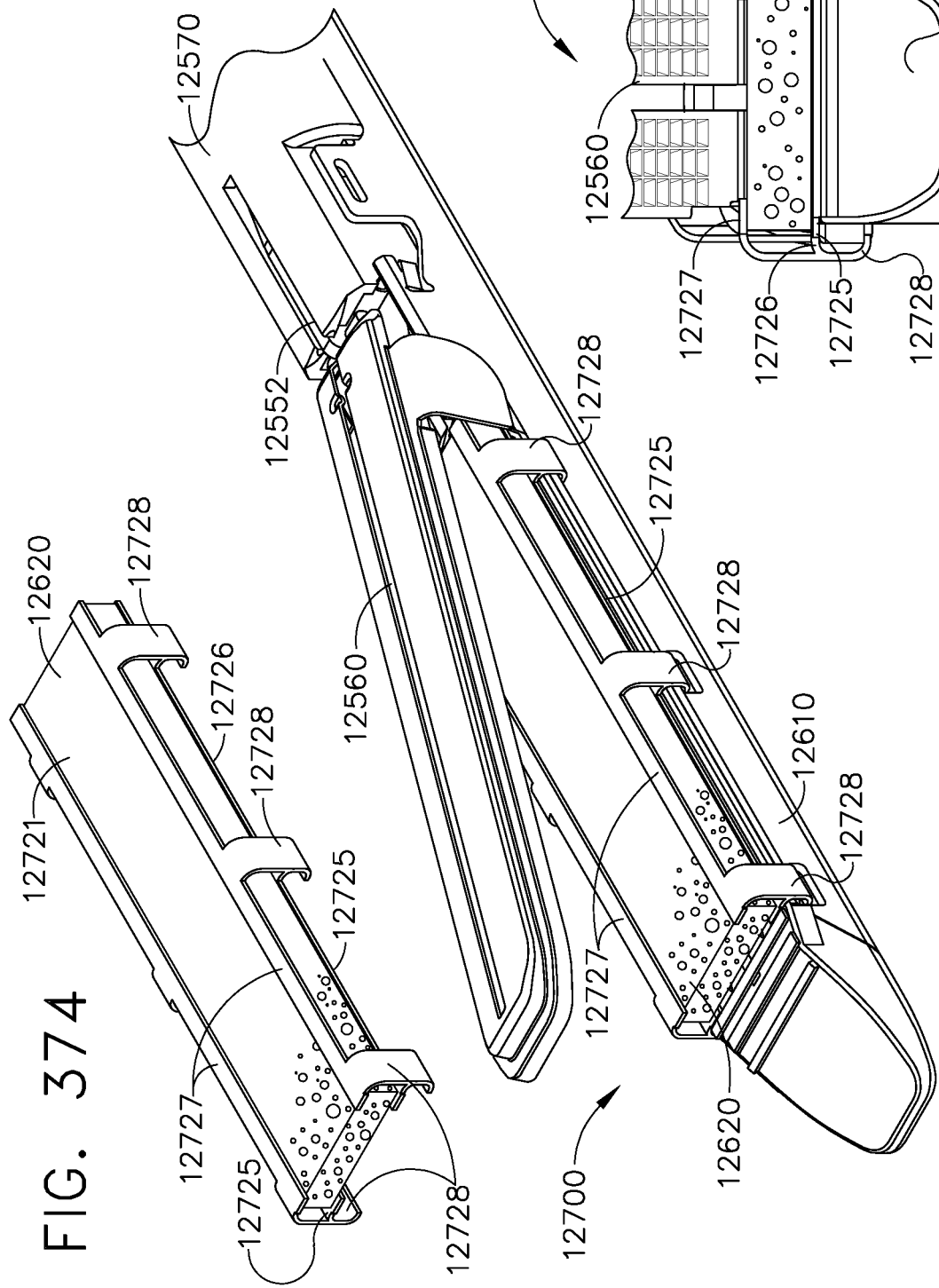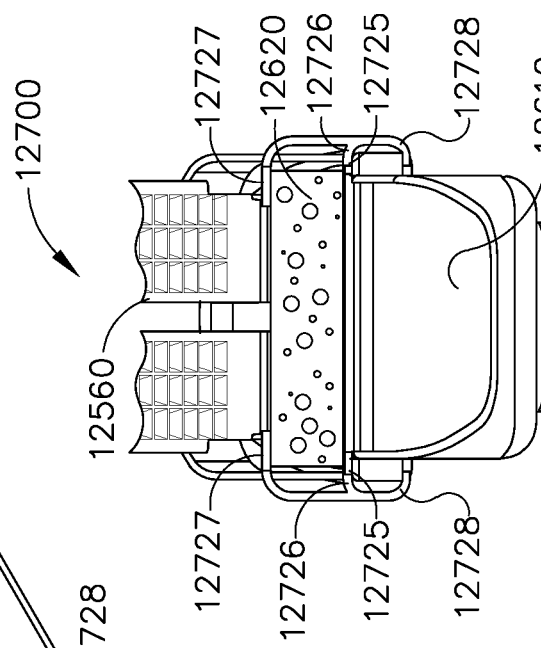

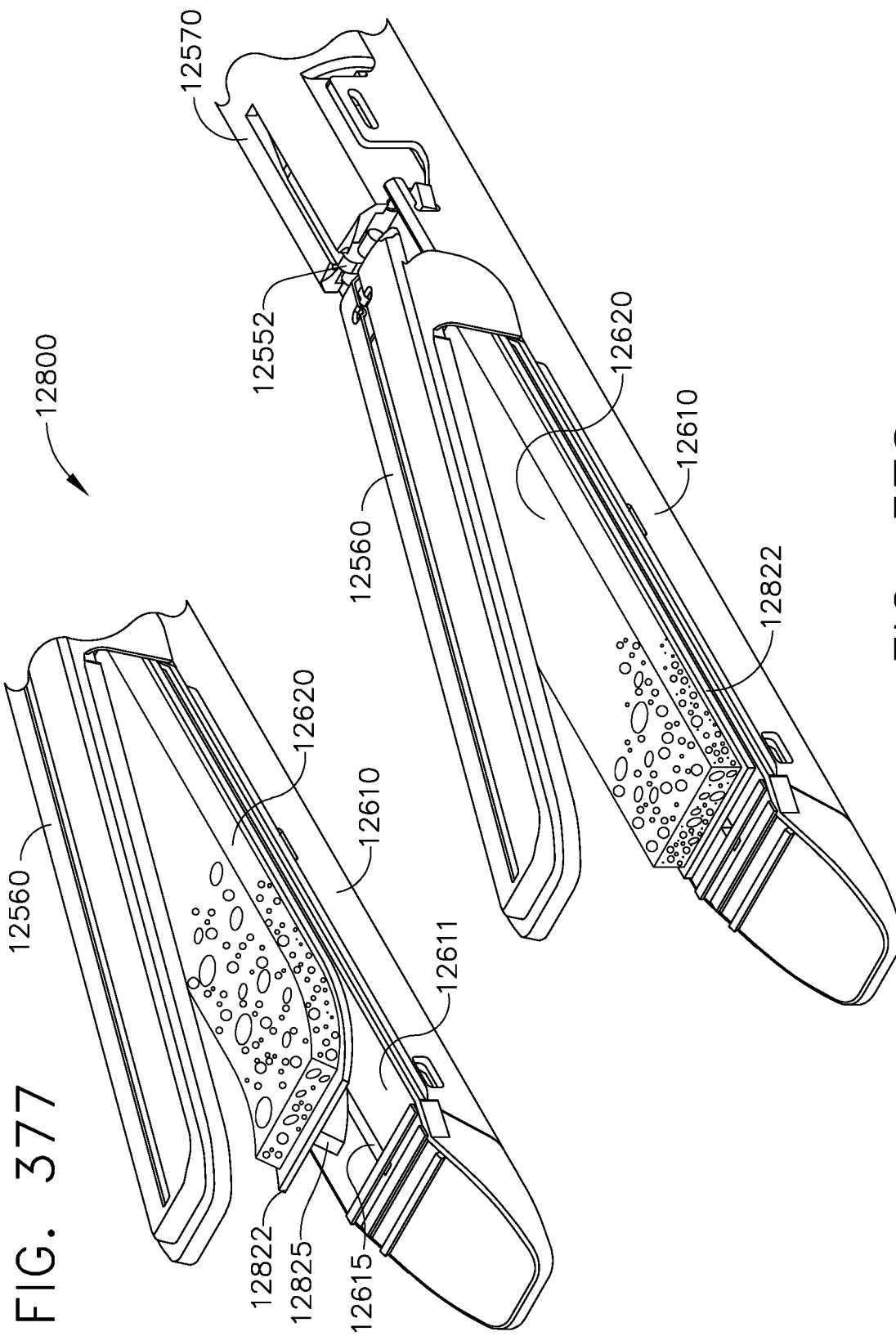

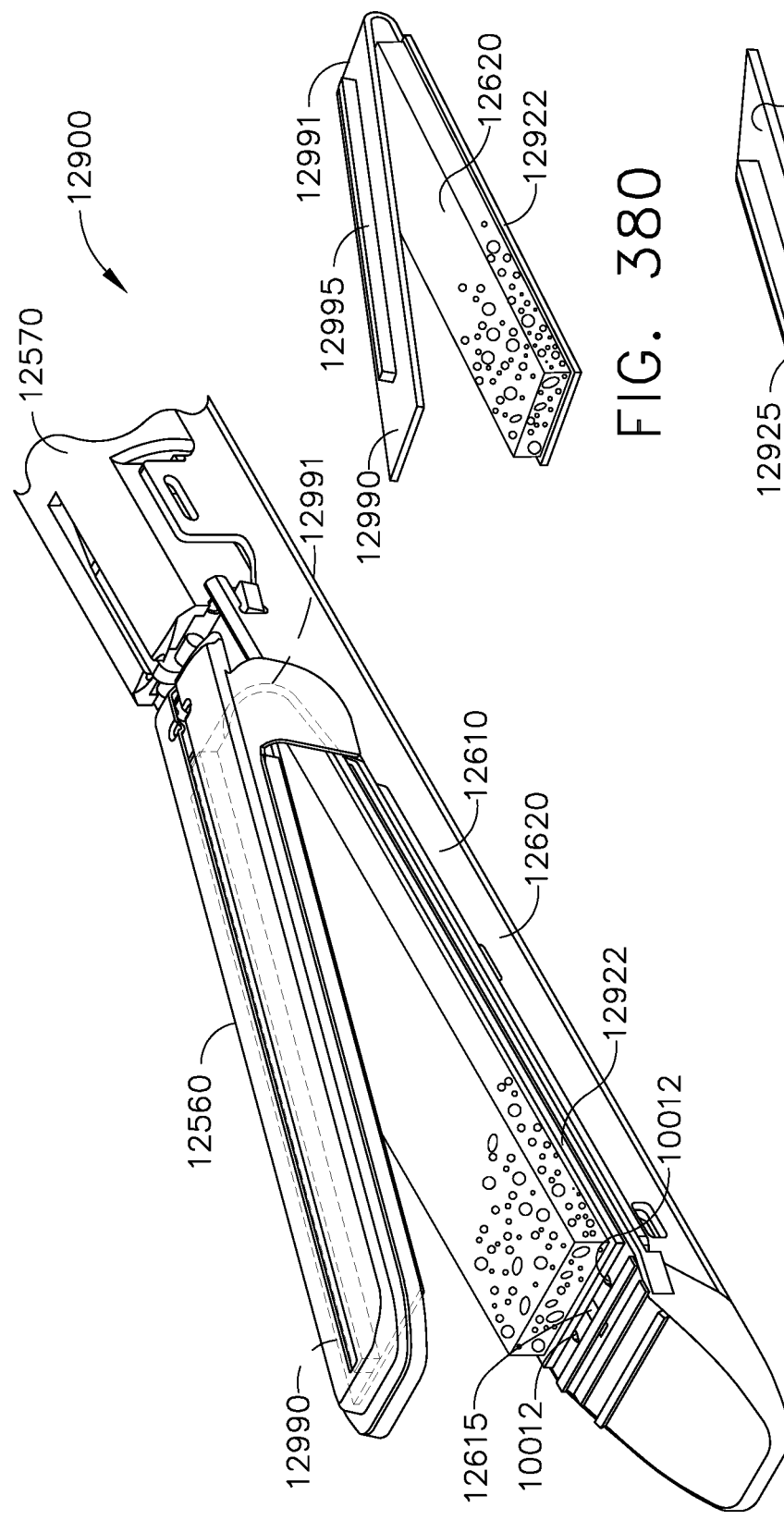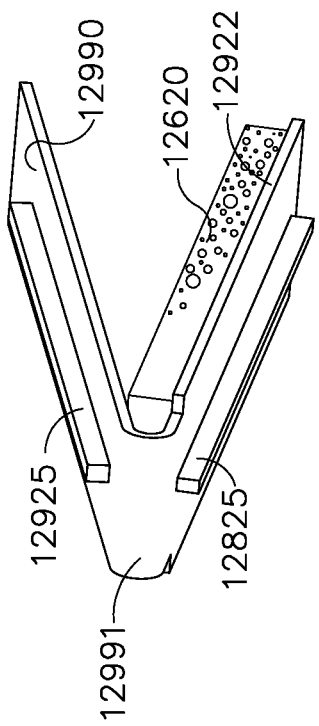

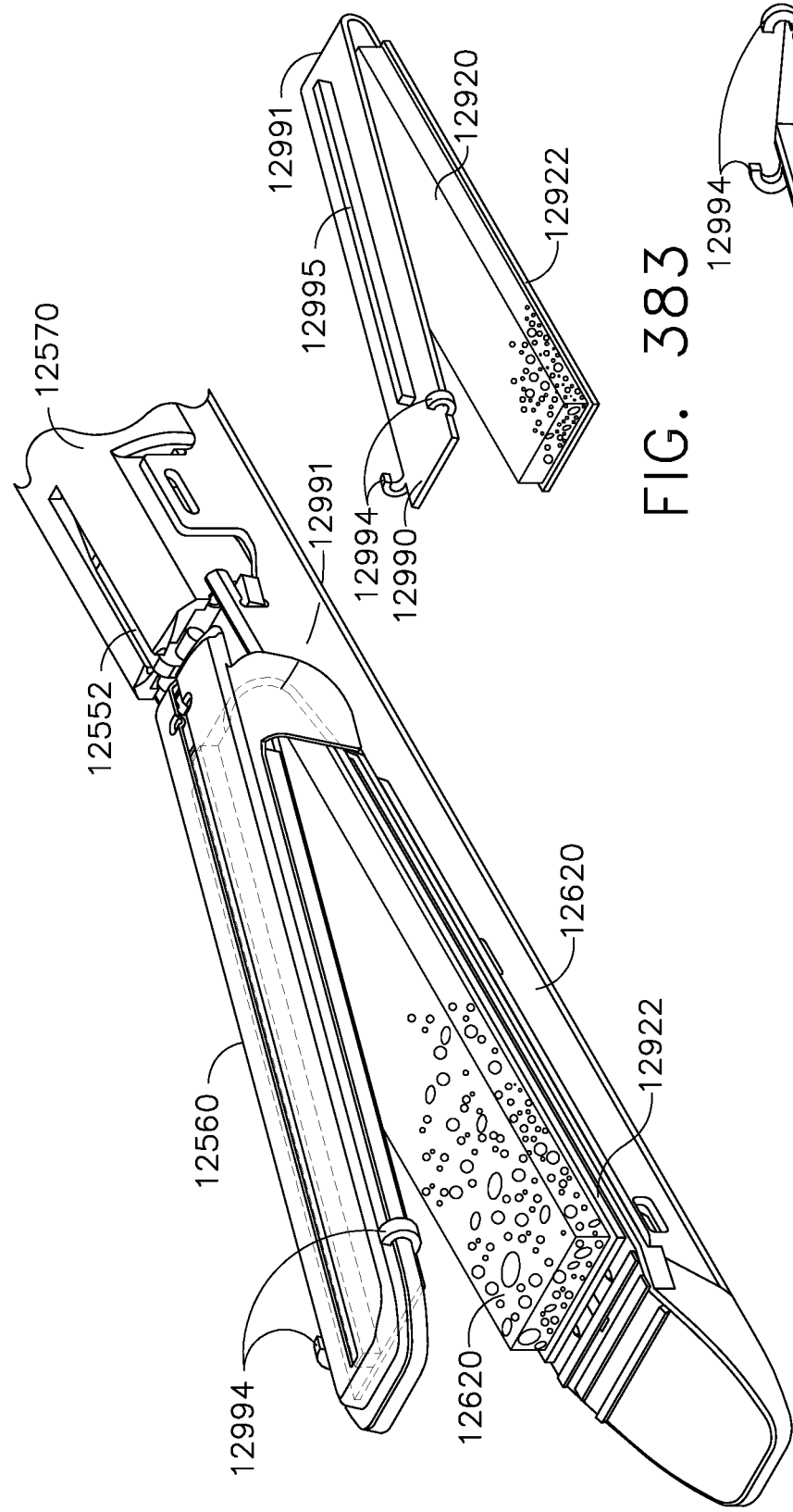
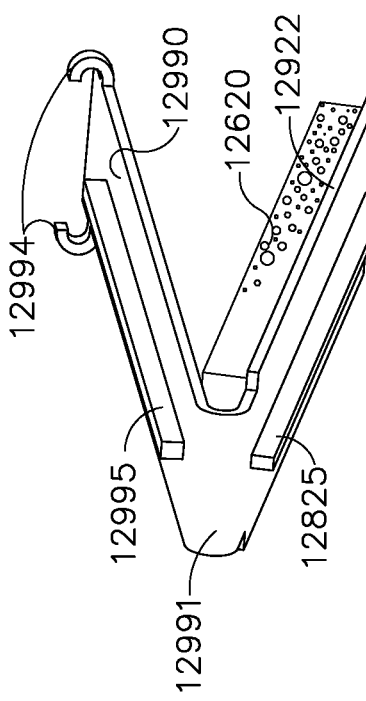
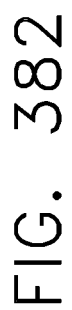
FIG. 382
FIG. 383
FIG. 384

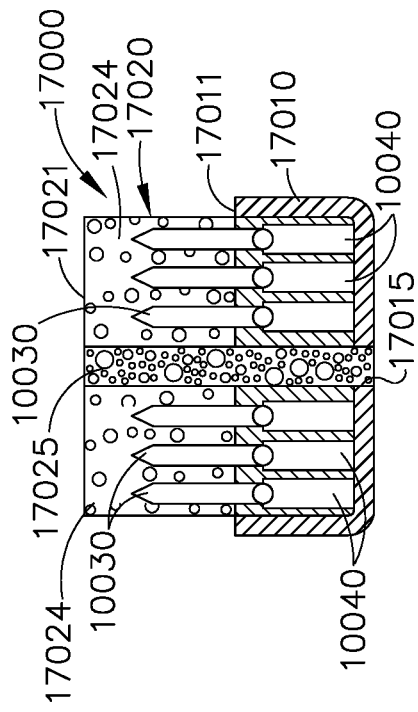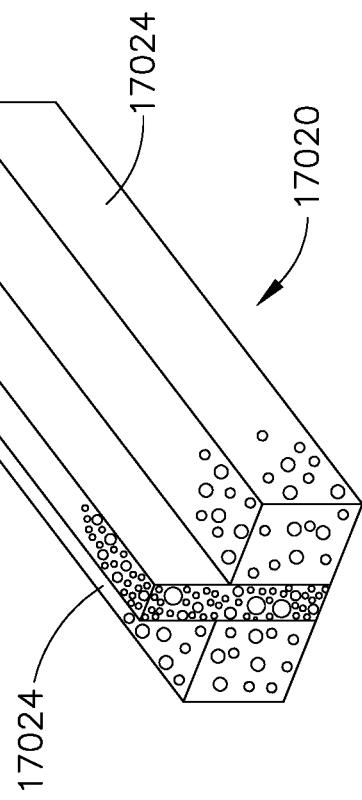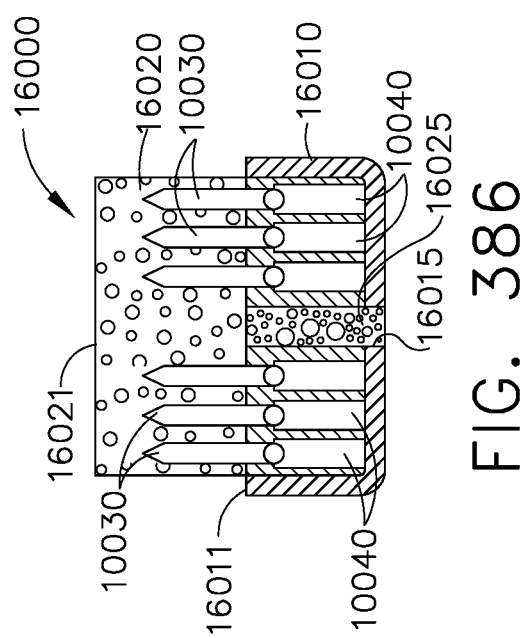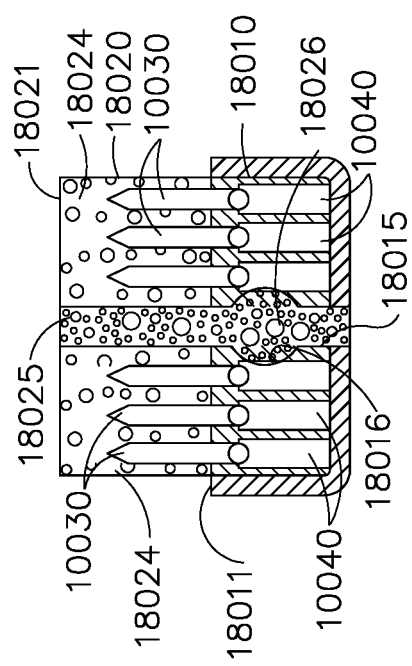

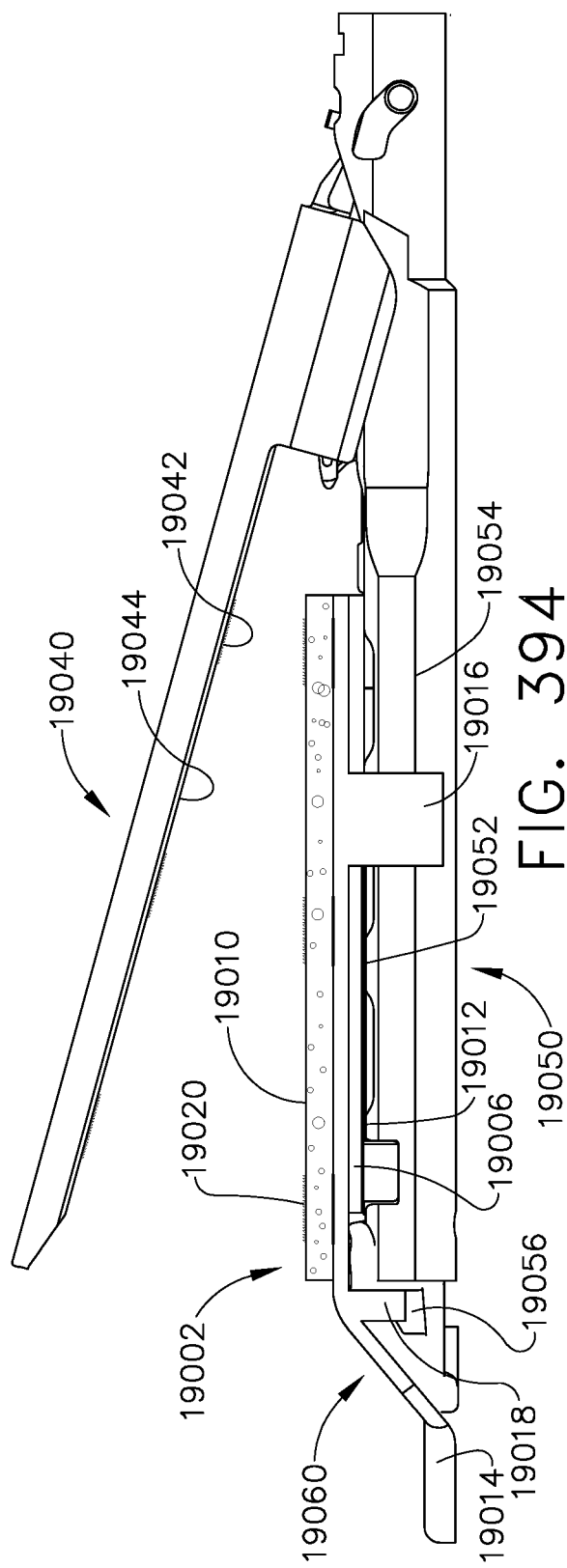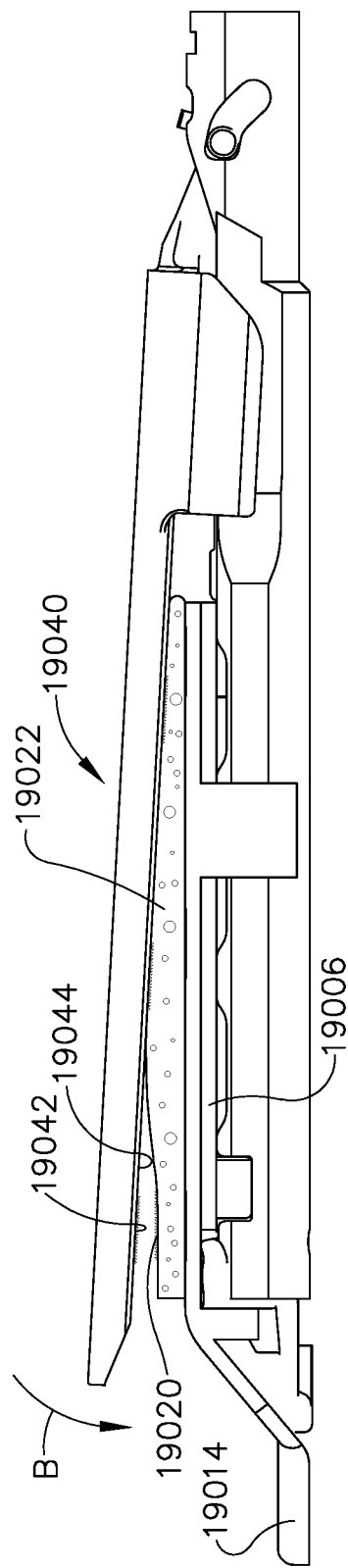

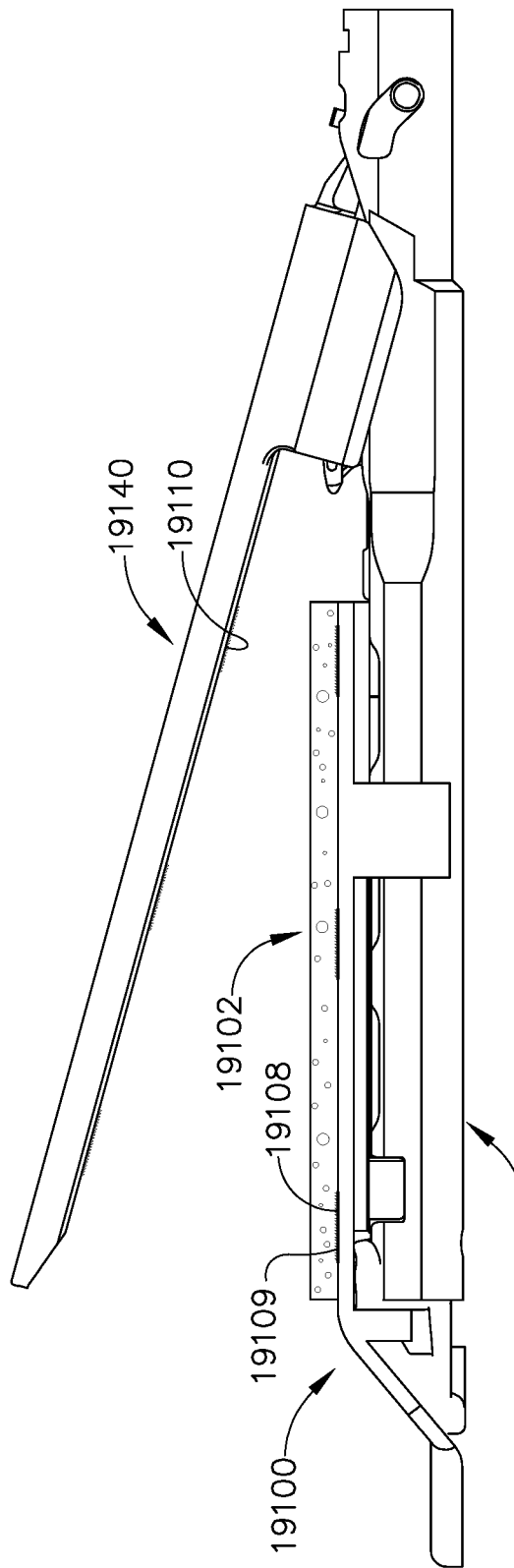
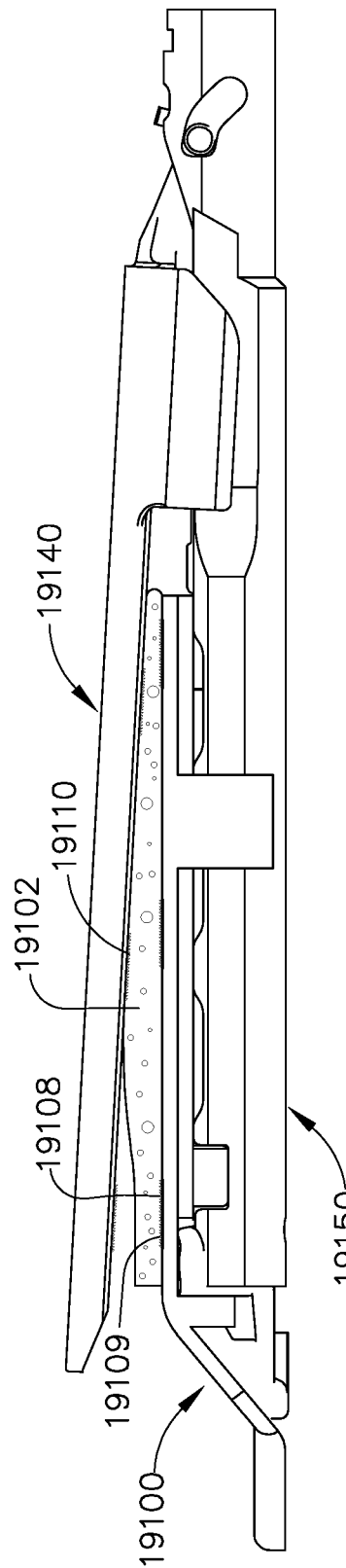
FIG. 398
FIG. 399

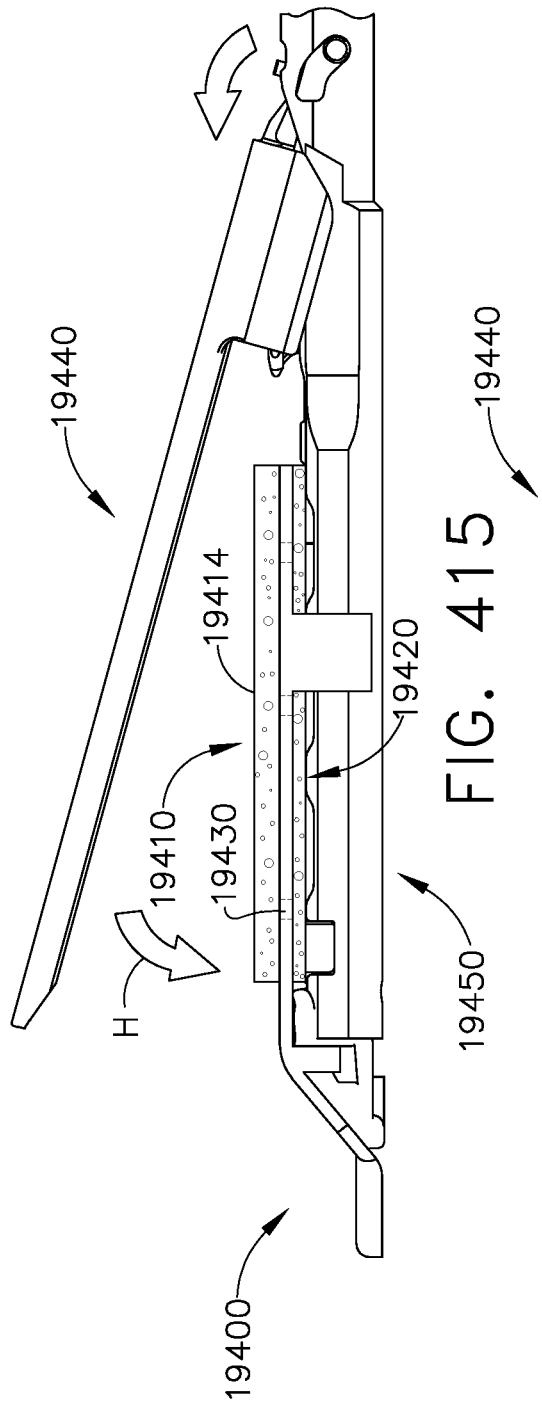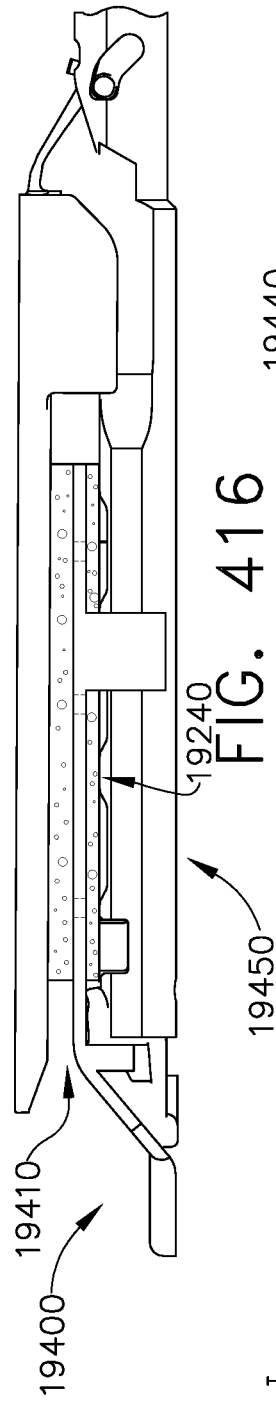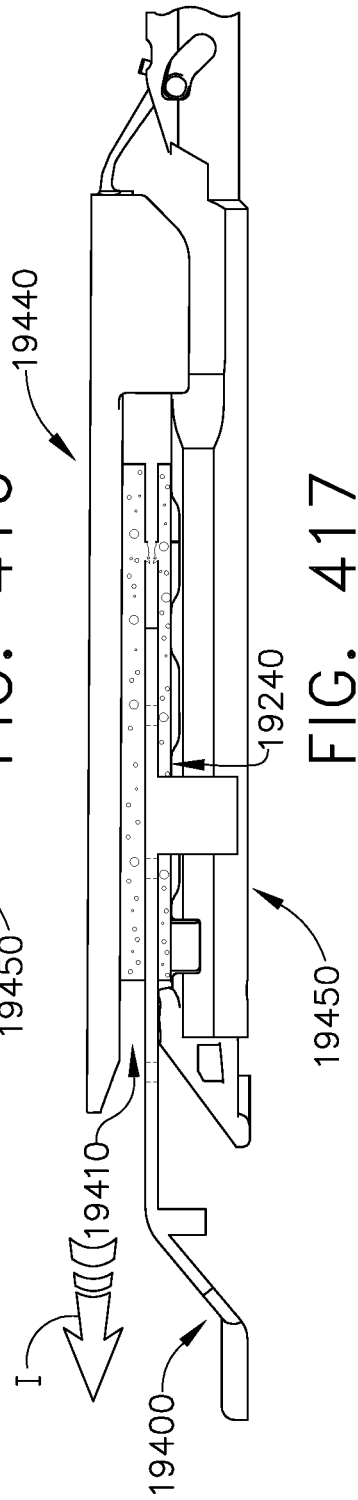

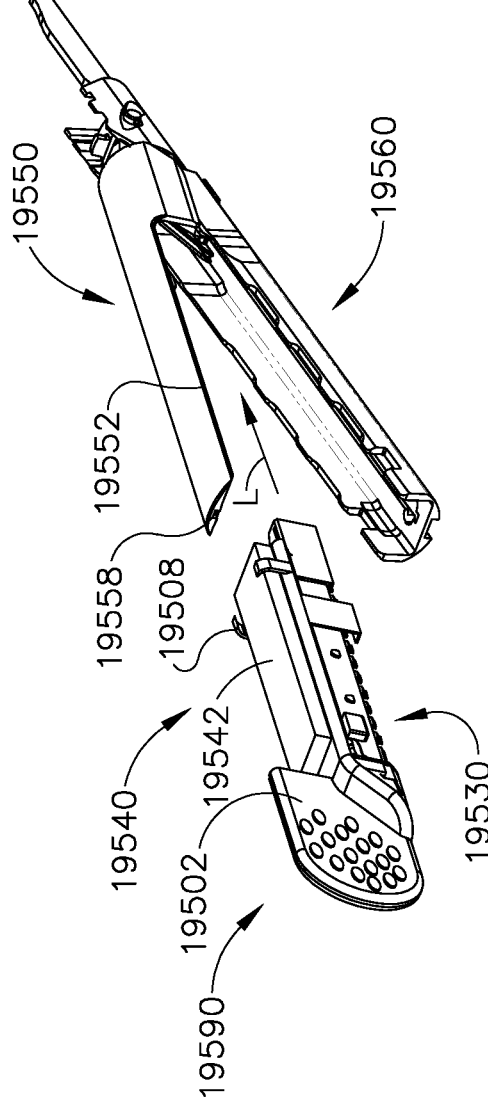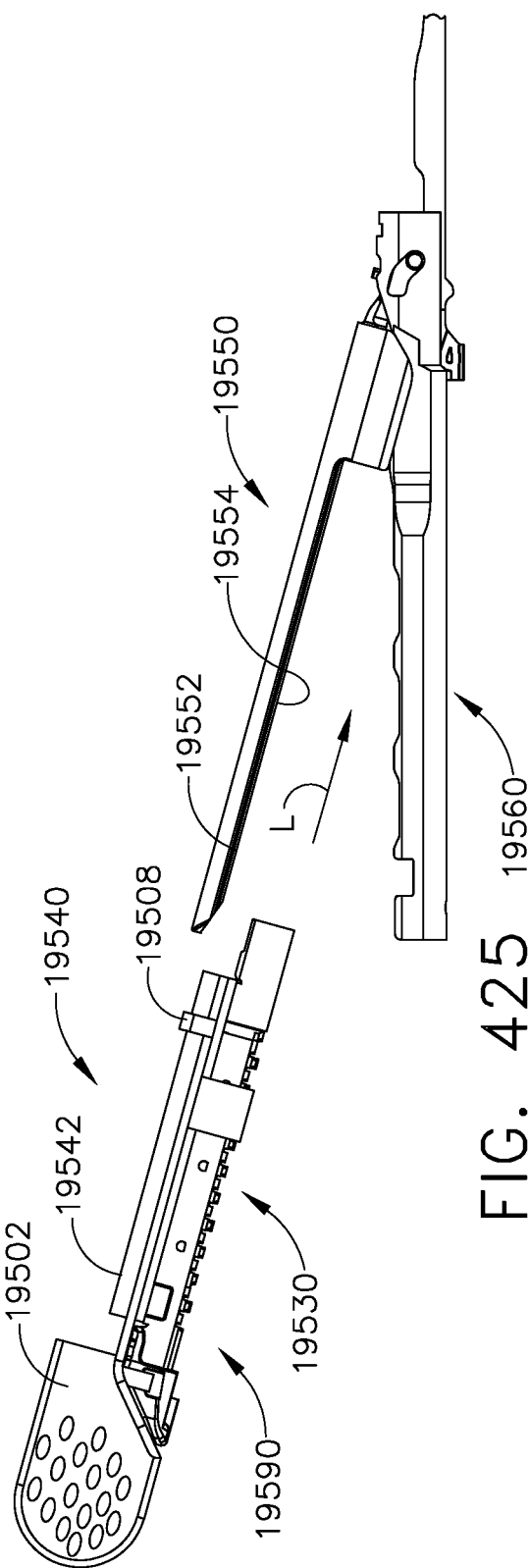
FIG. 424
FIG. 425

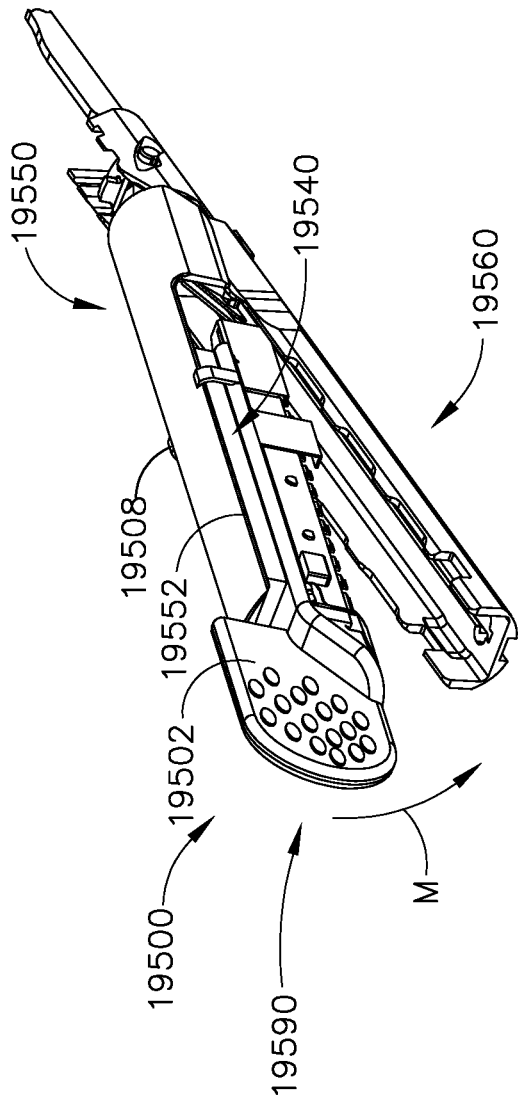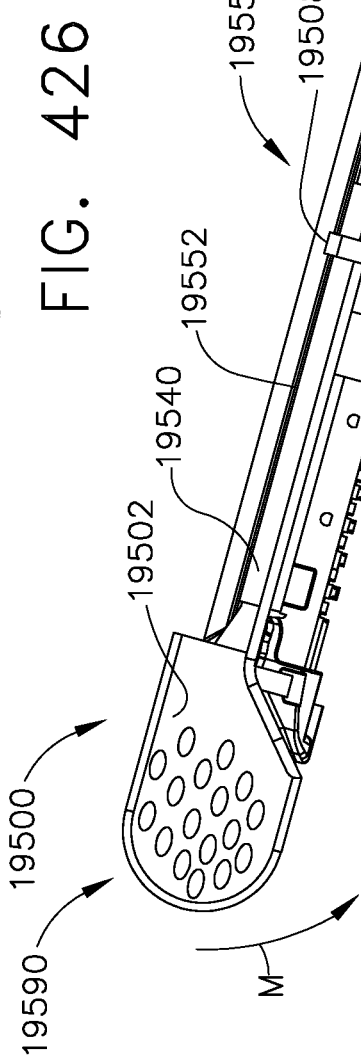

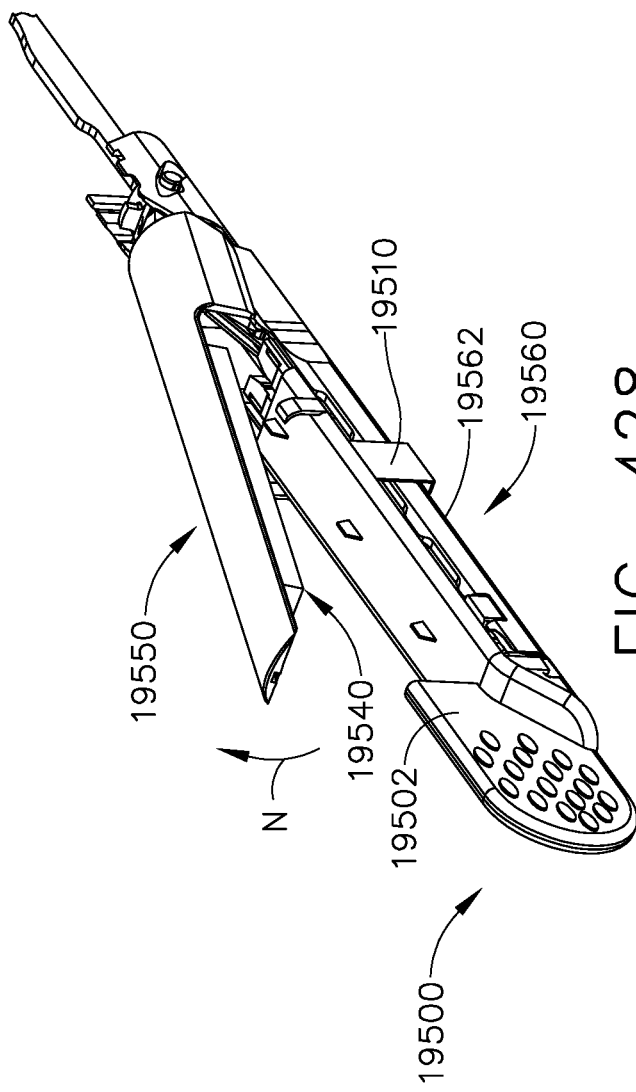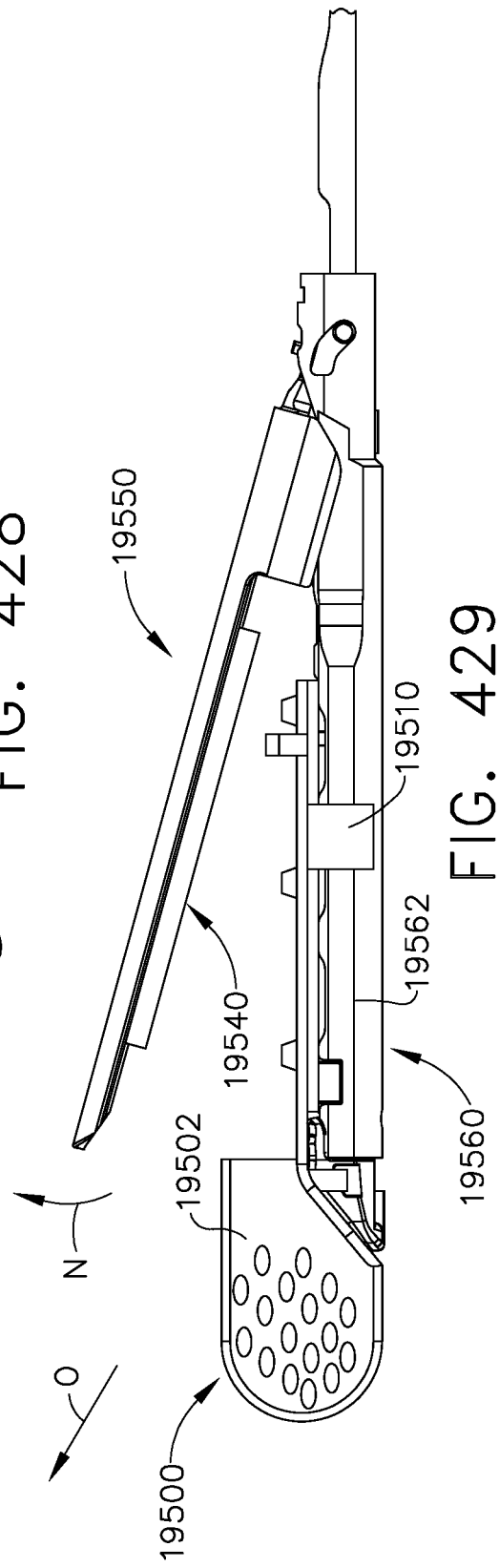

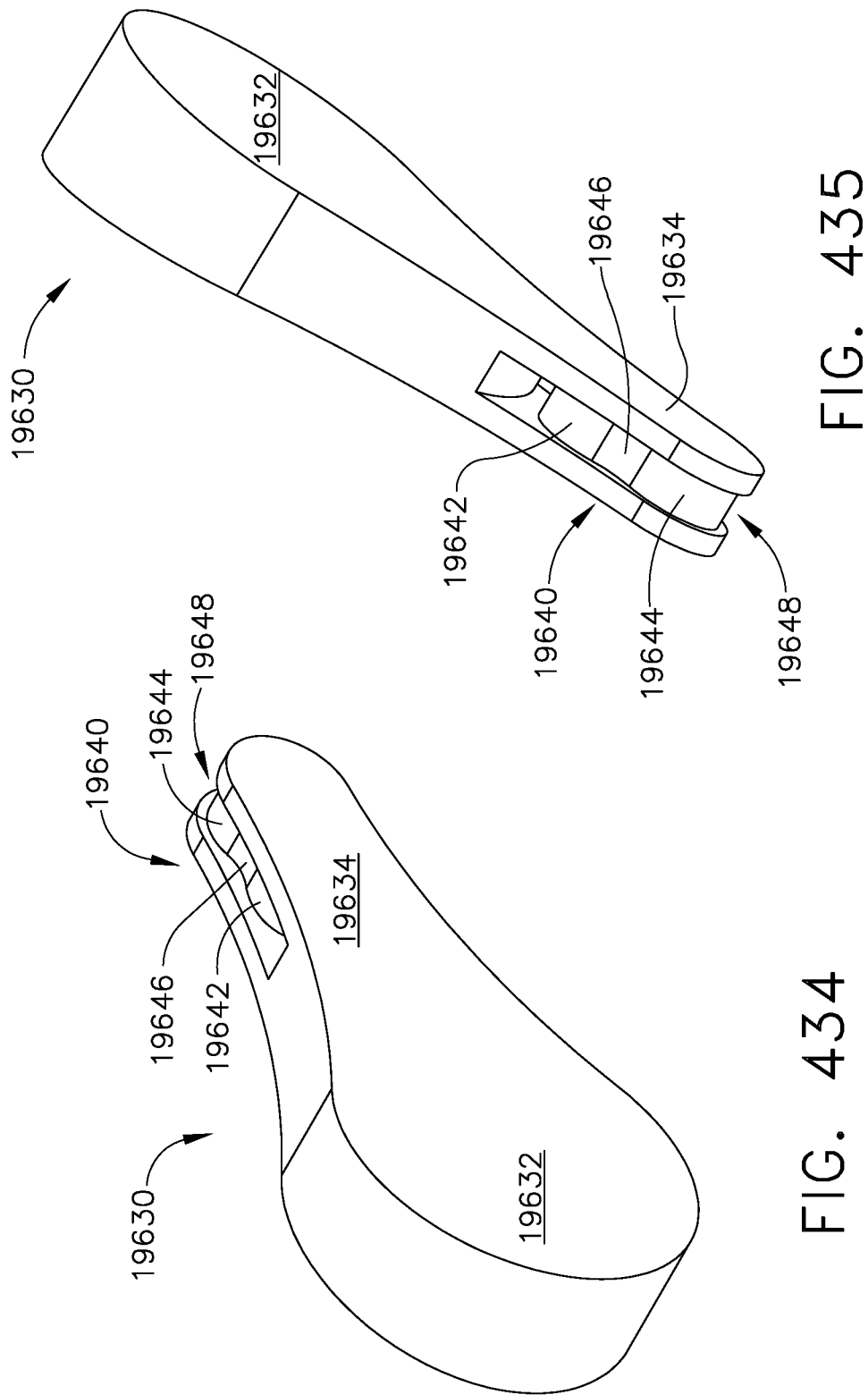

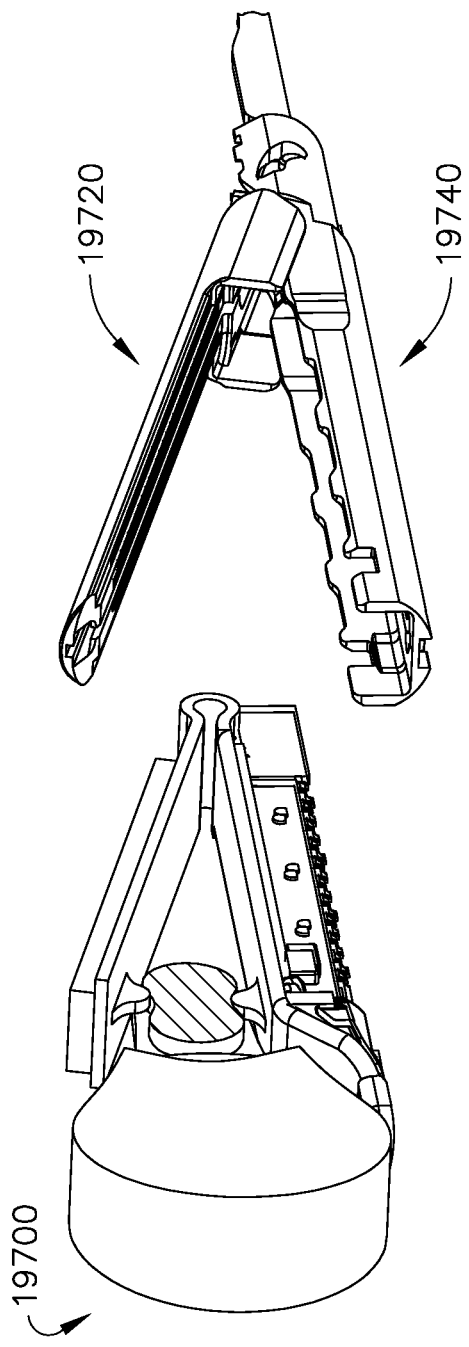
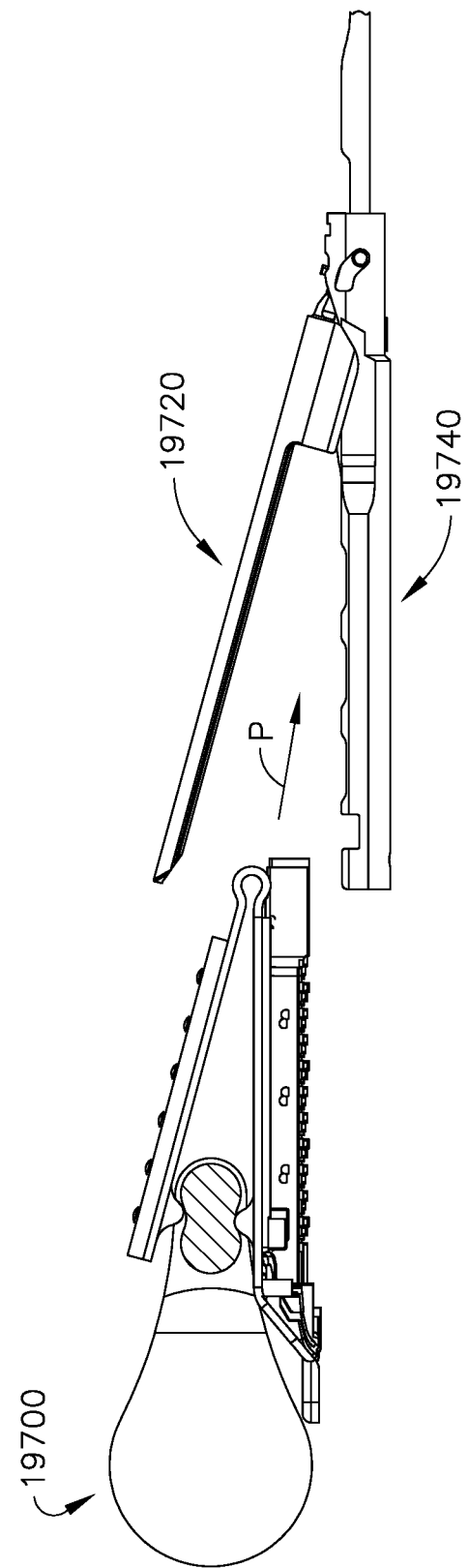

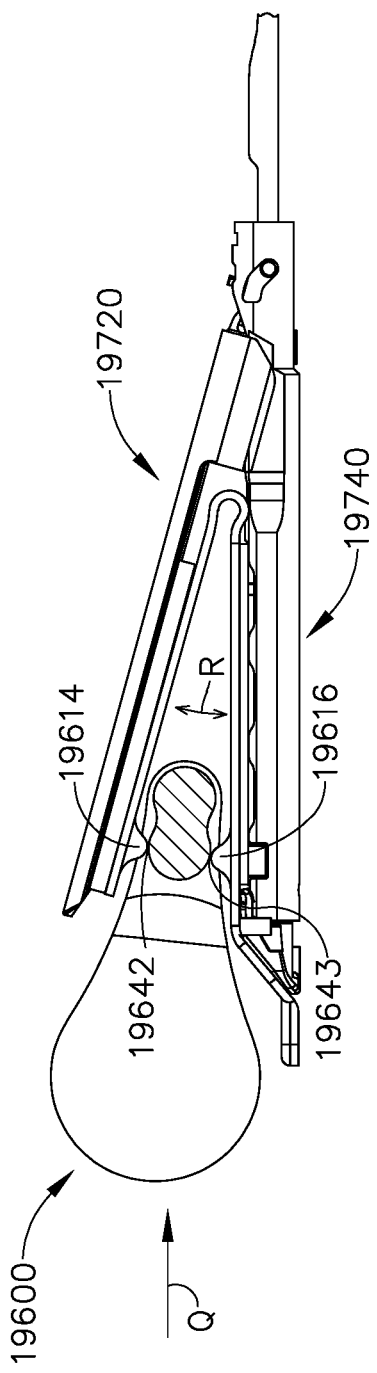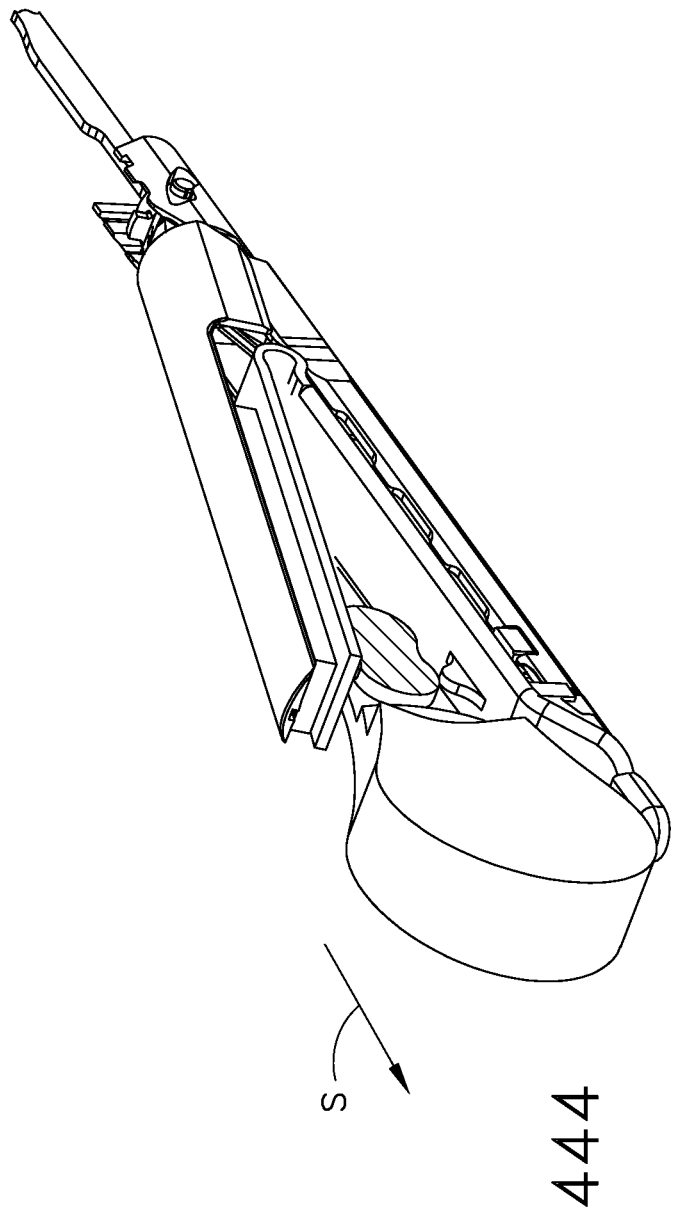
FIG. 443
FIG. 444

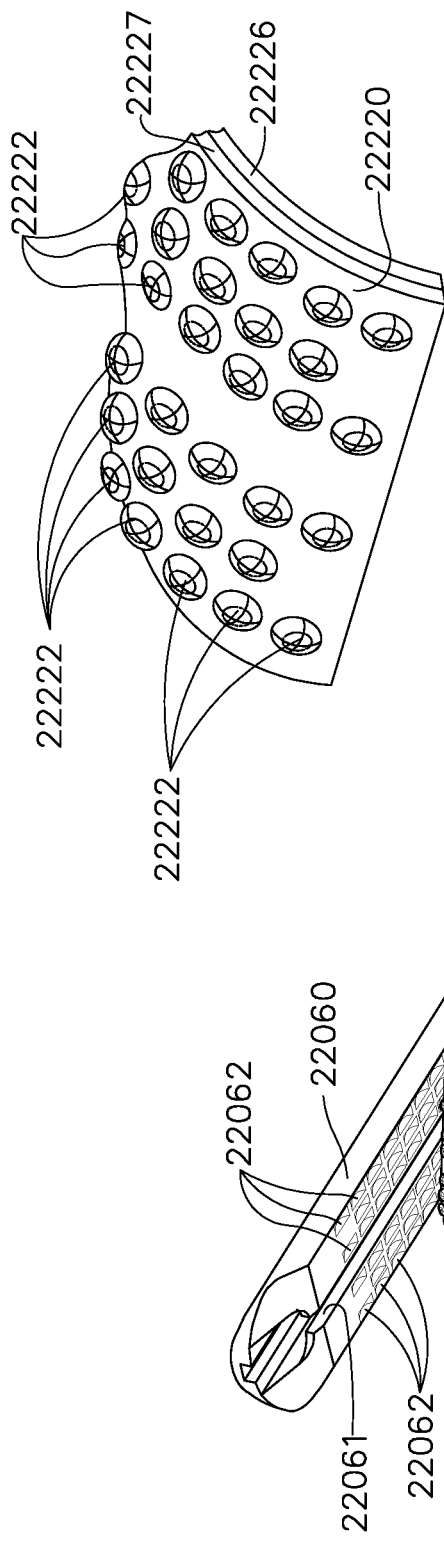
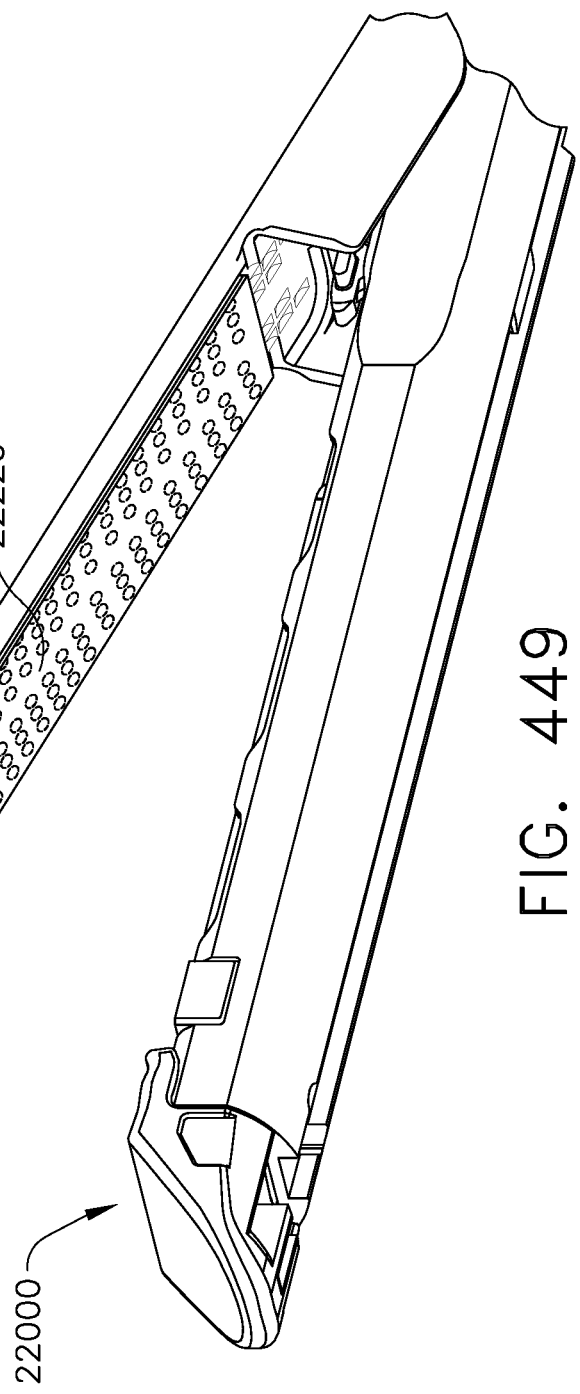
FIG. 449a
FIG. 449

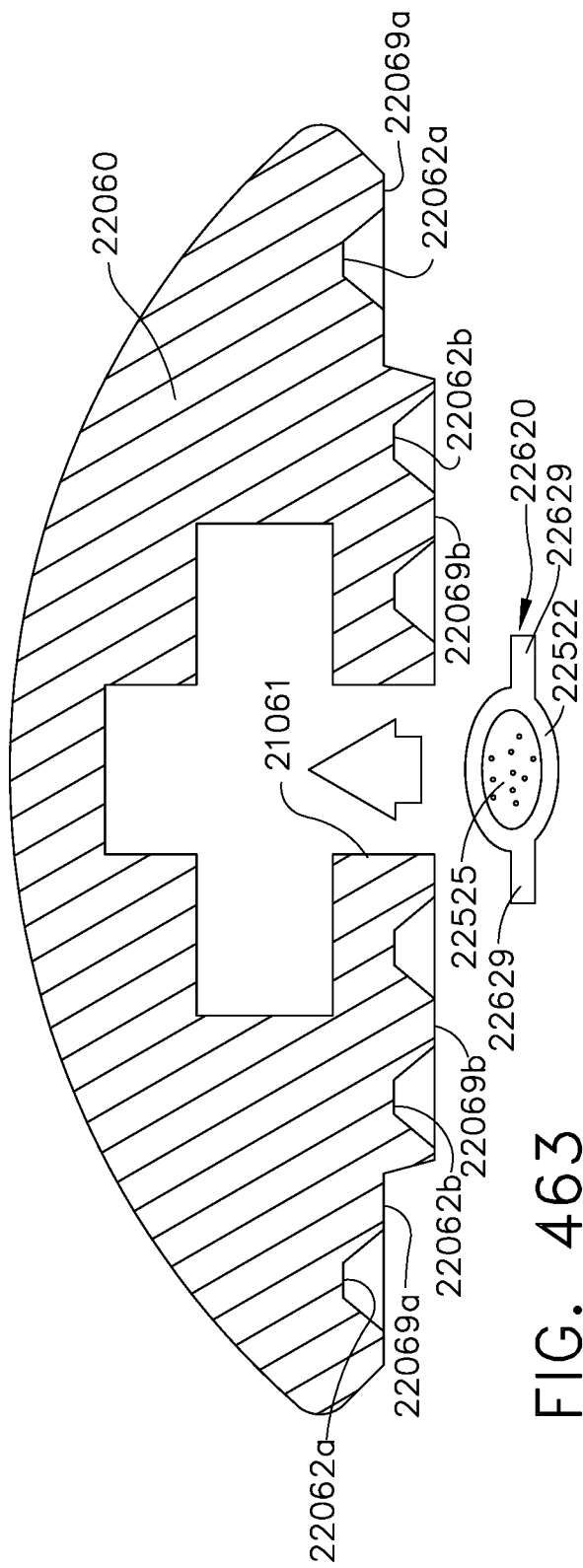
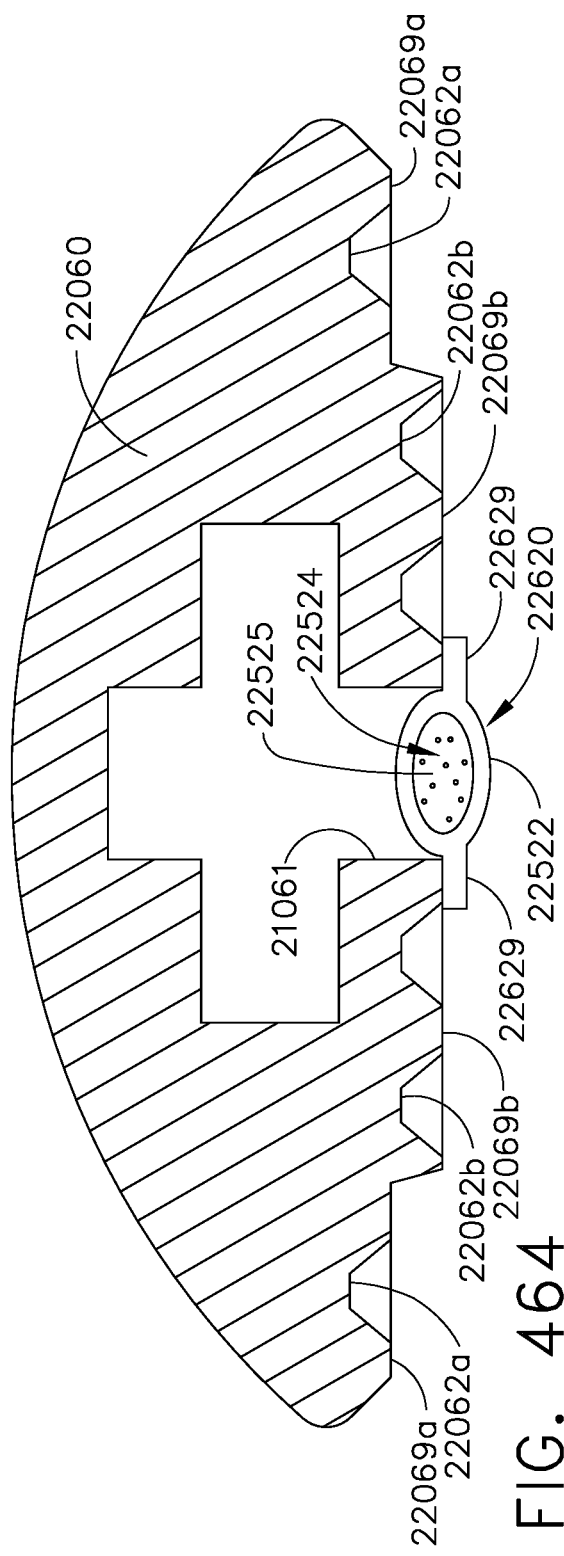
FIG. 463
FIG. 464

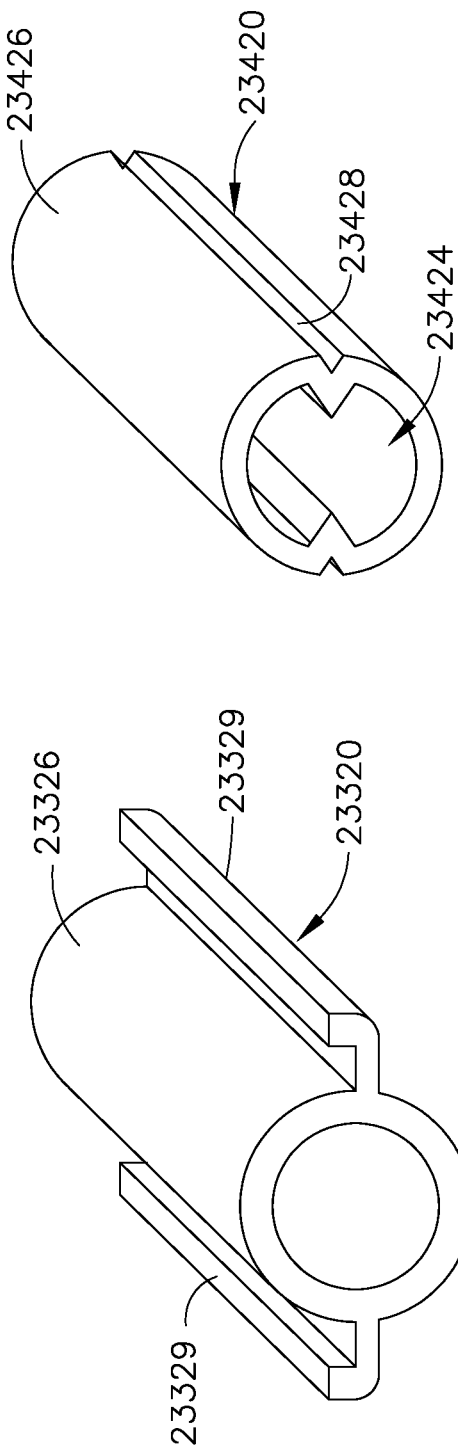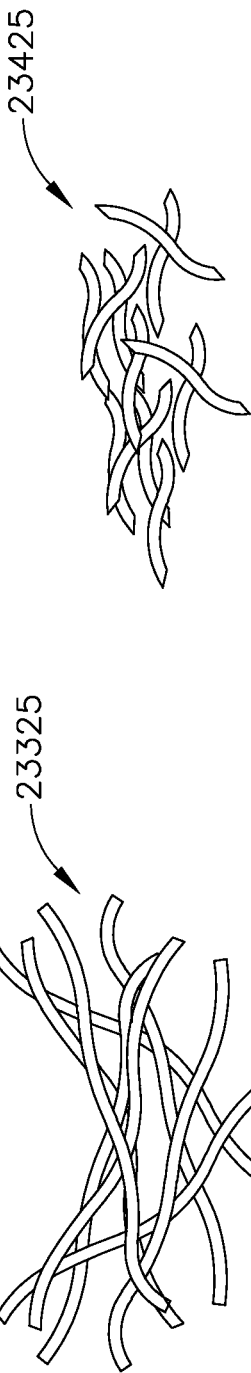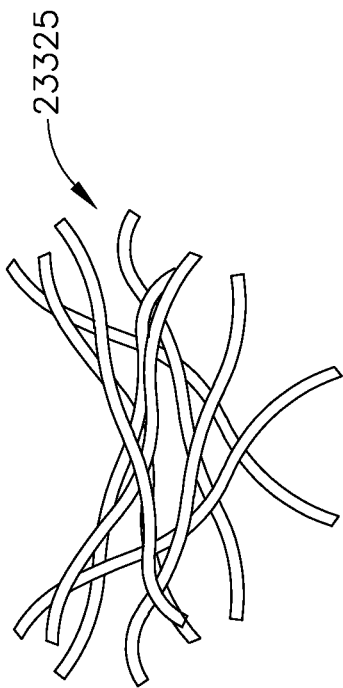
FIG. 473
FIG. 475
FIG. 472
FIG. 474

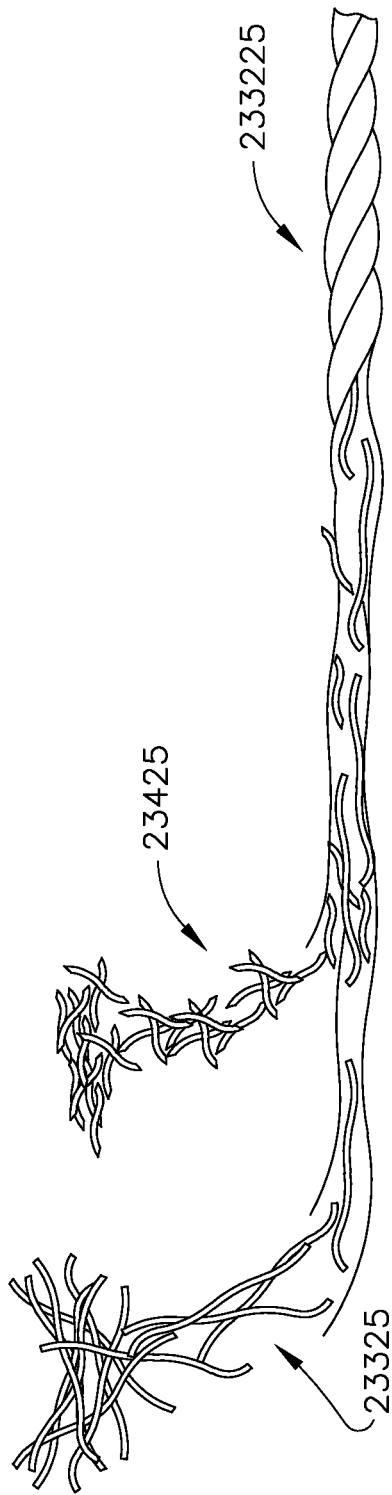
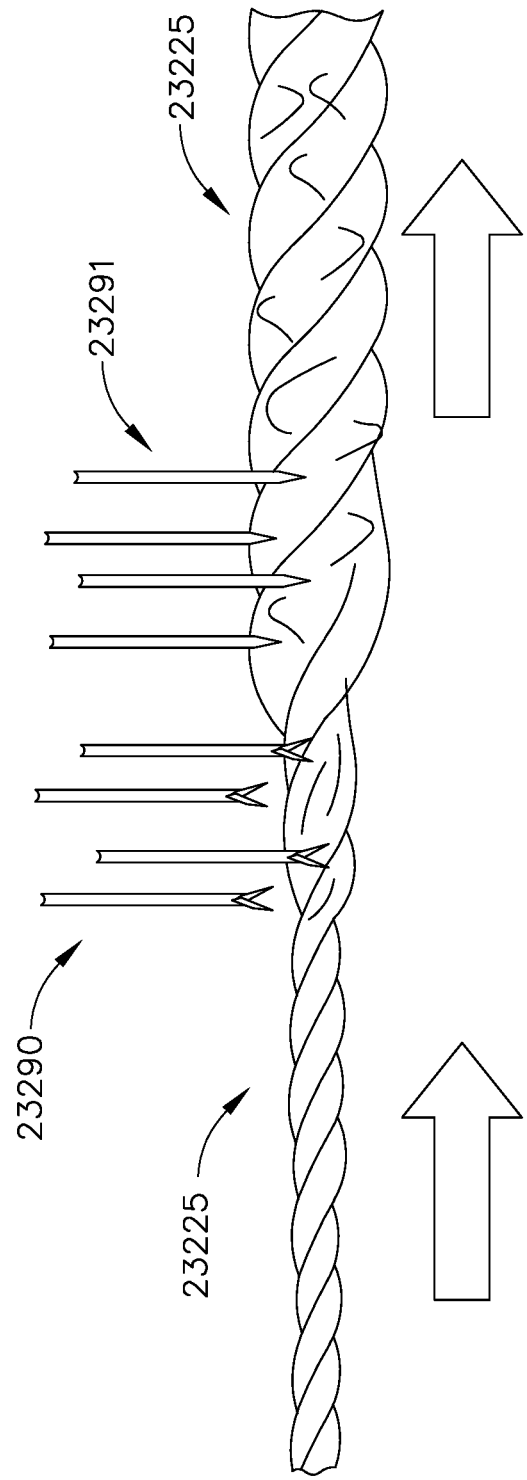

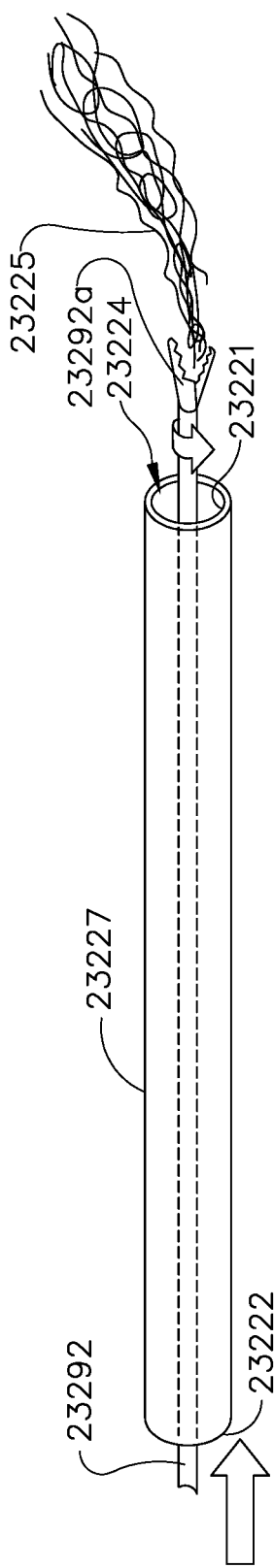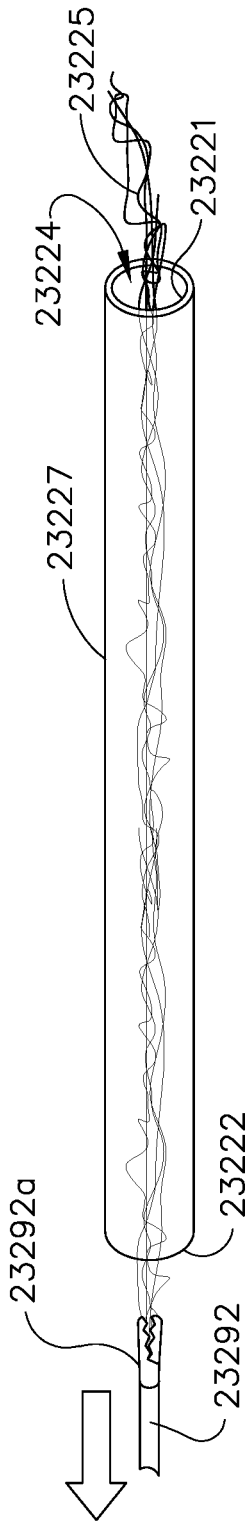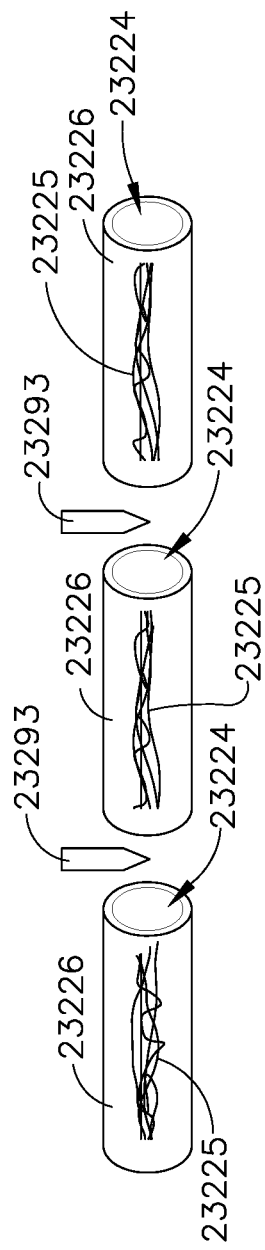
FIG. 478
FIG. 479
FIG. 480

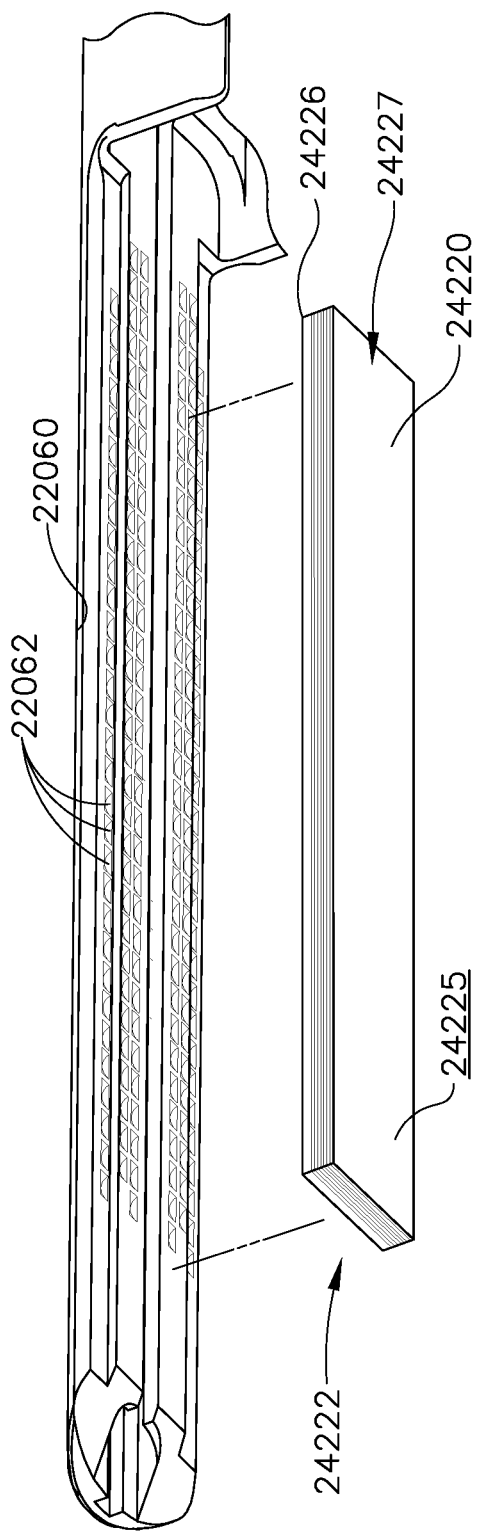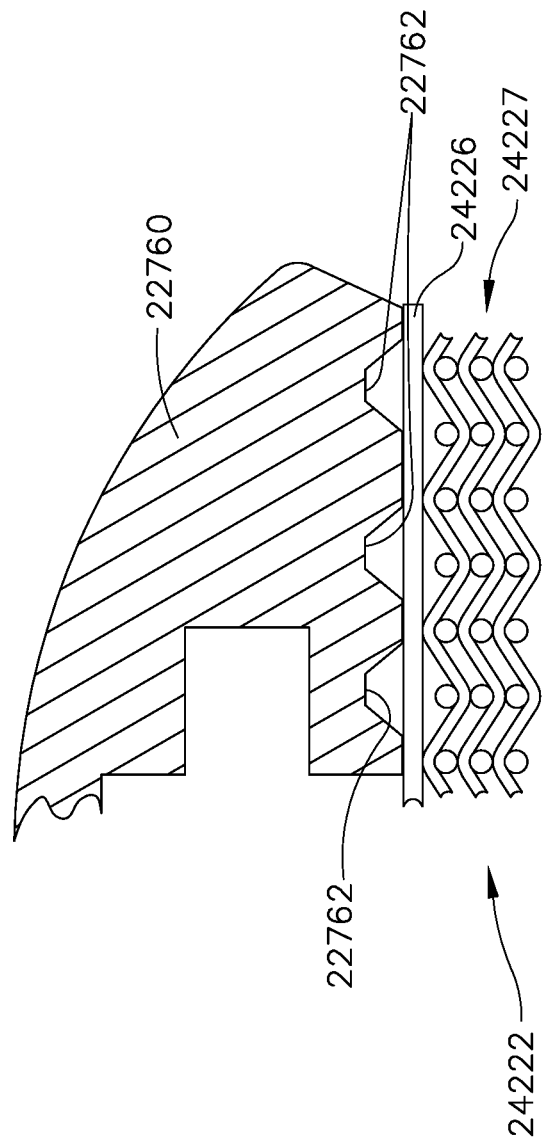

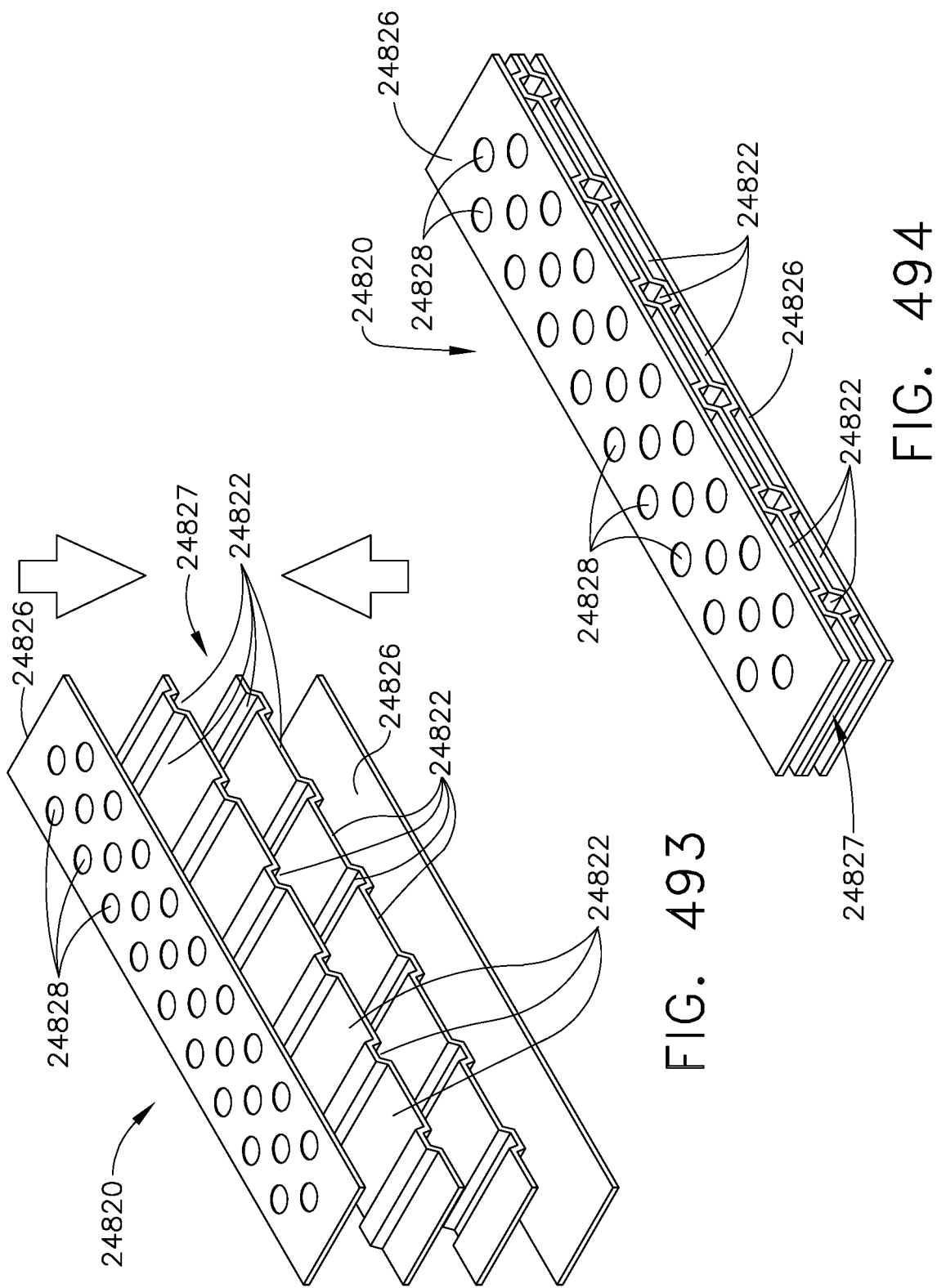

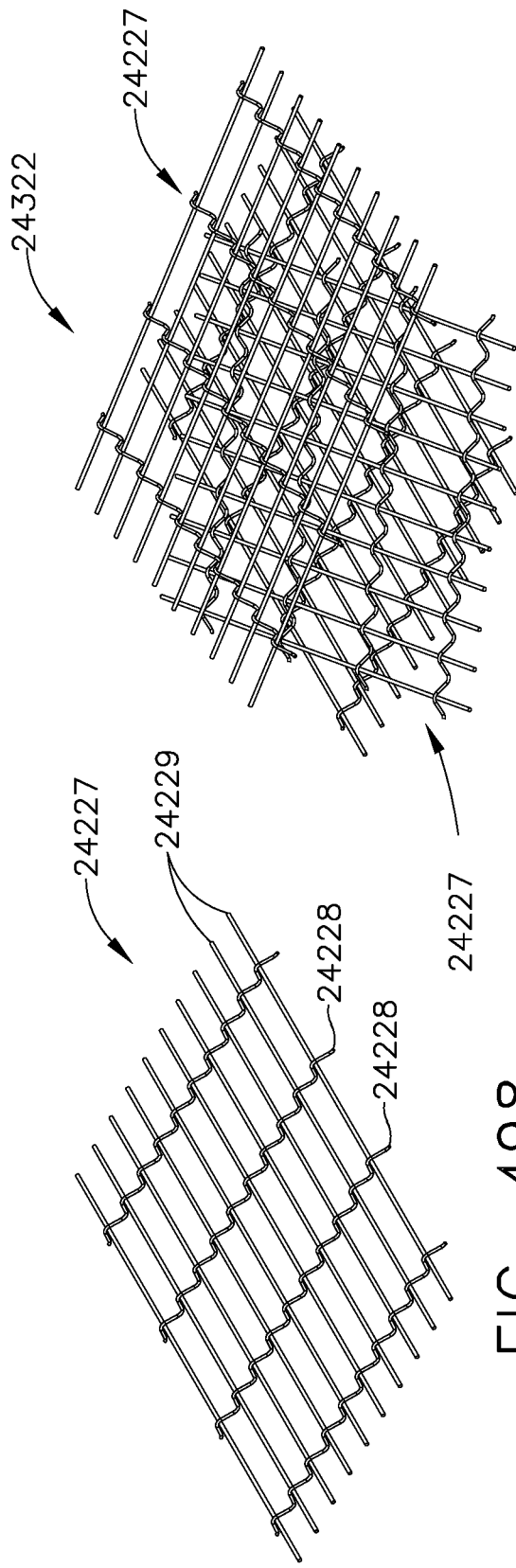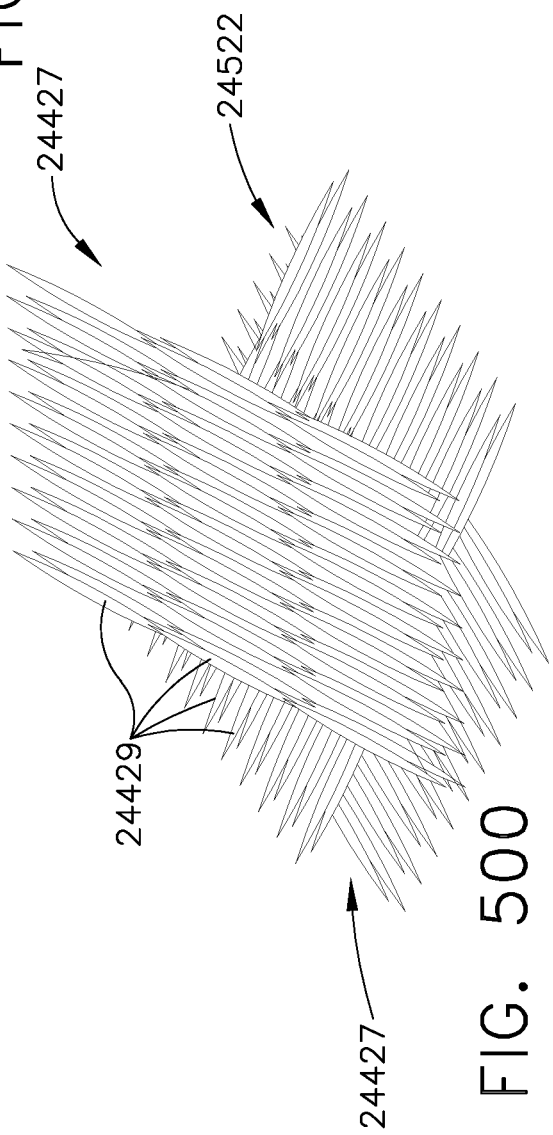

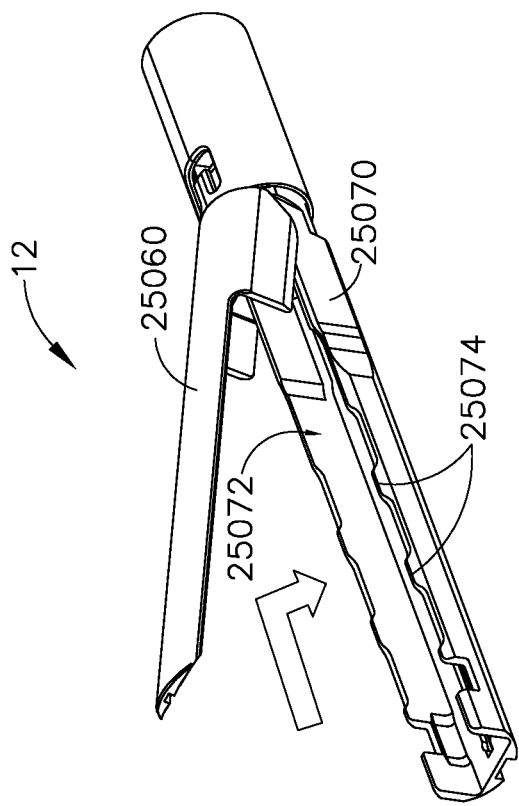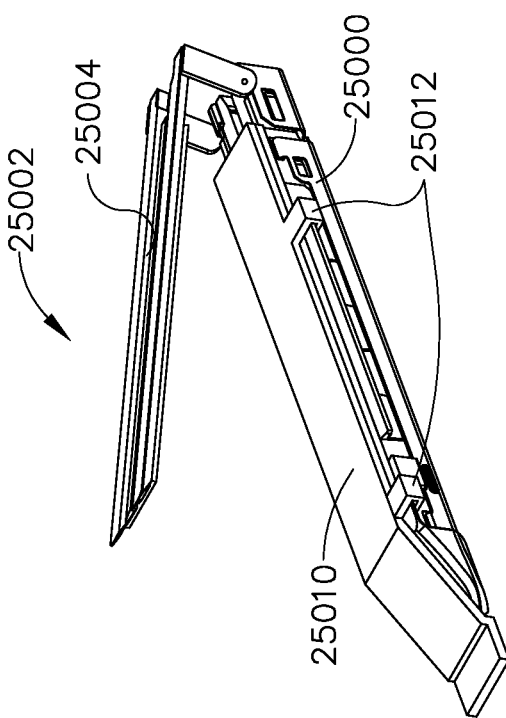
FIG. 501

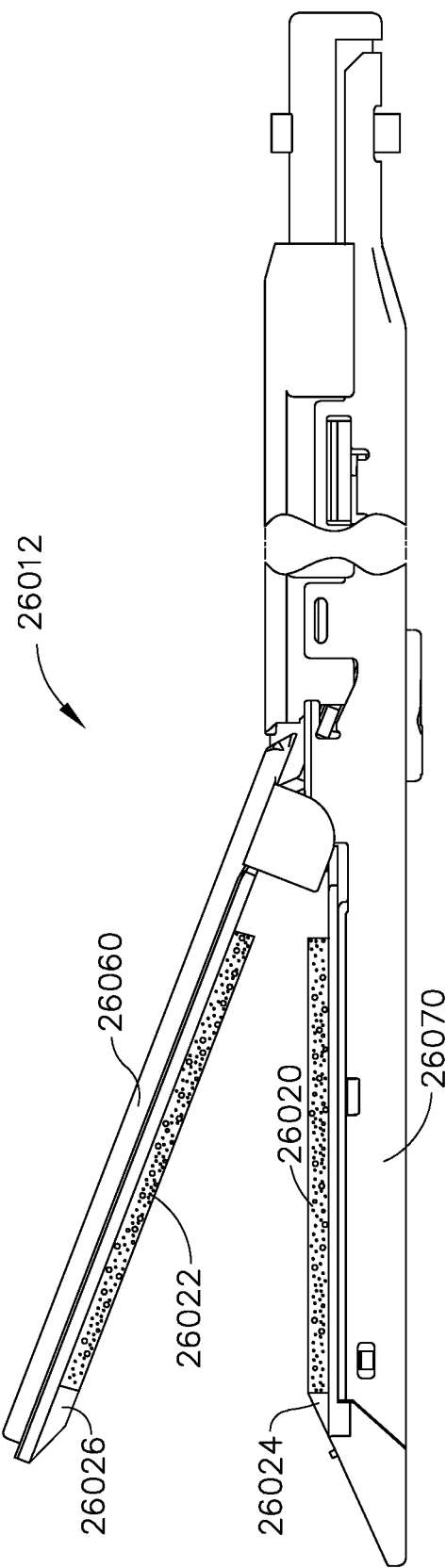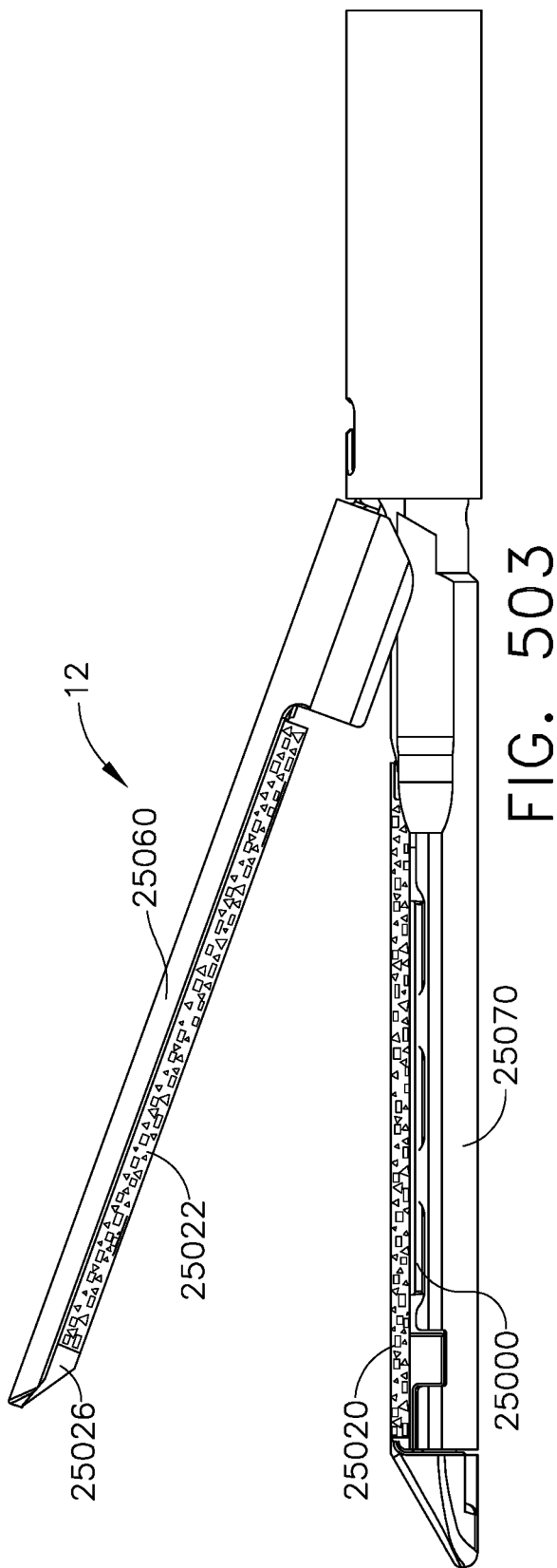

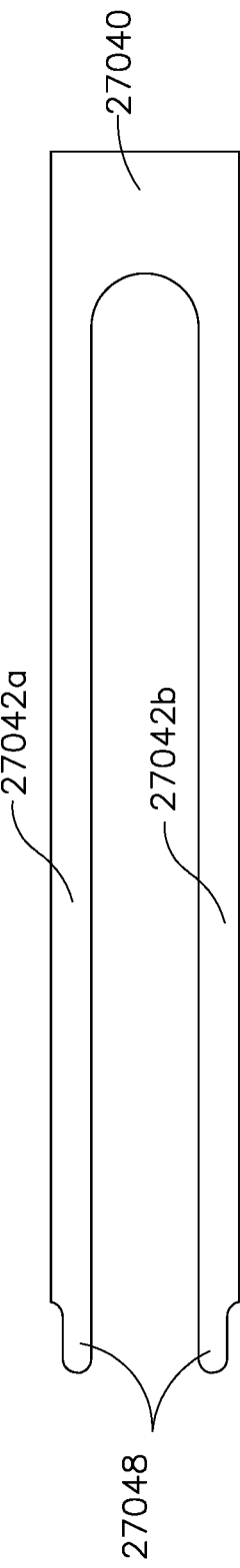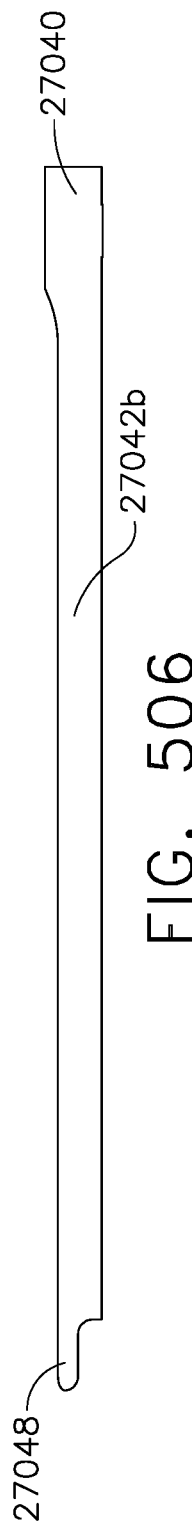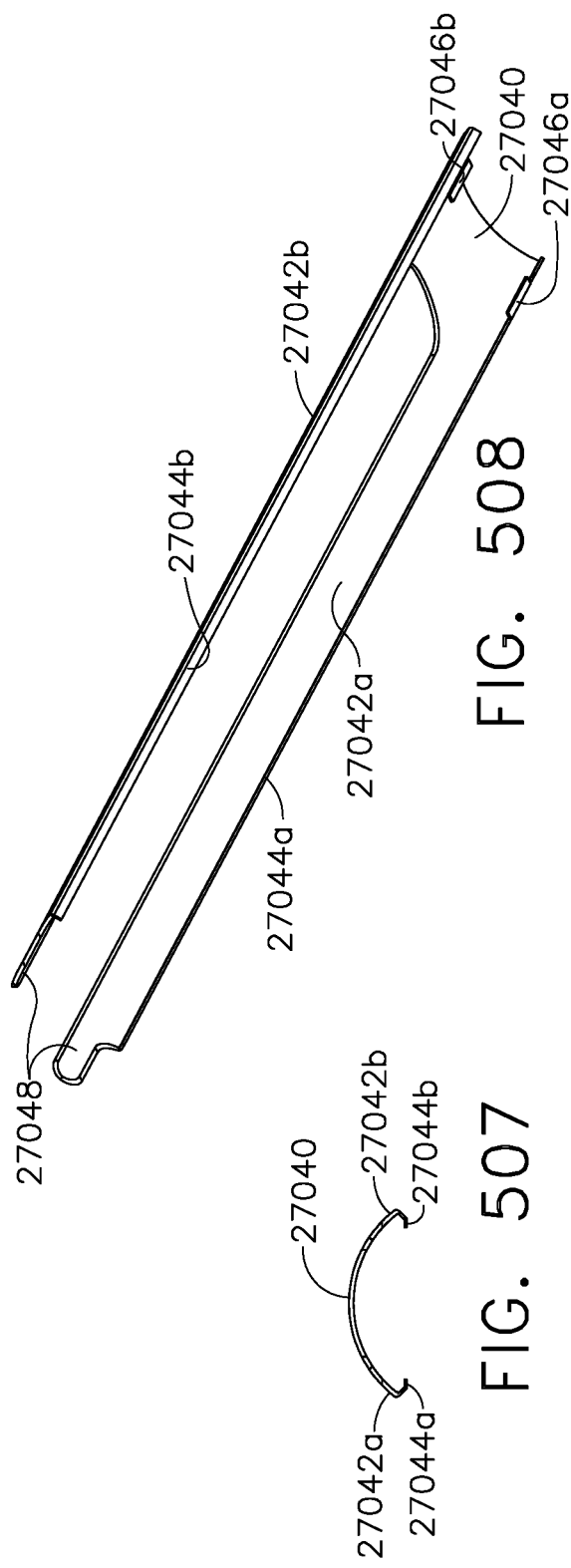

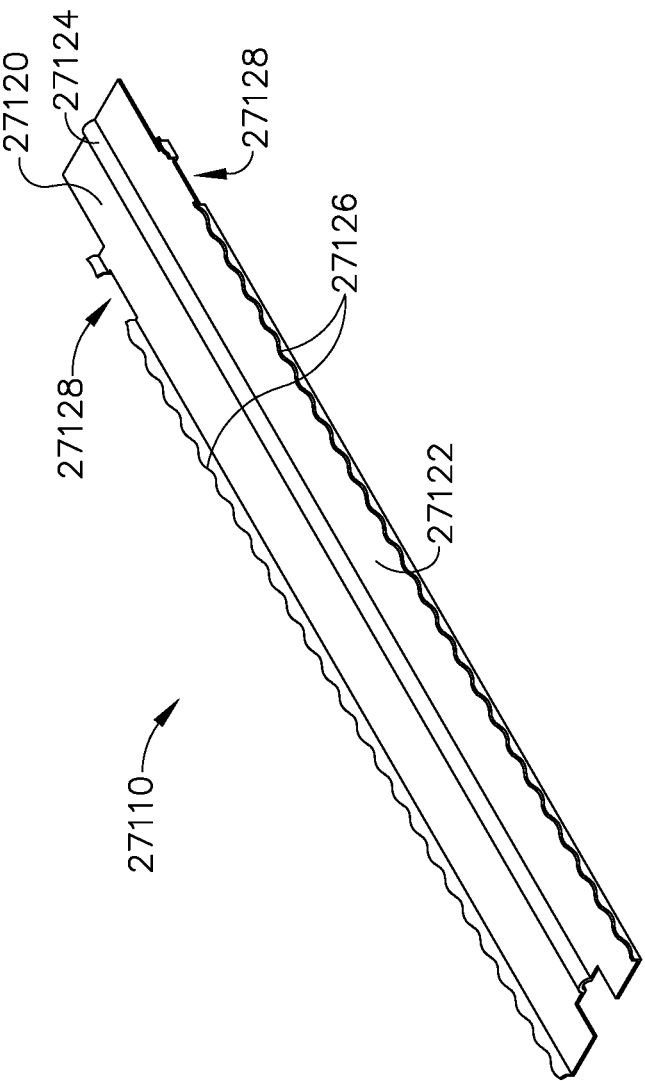
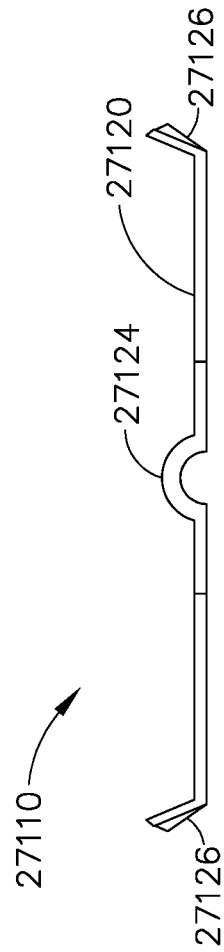
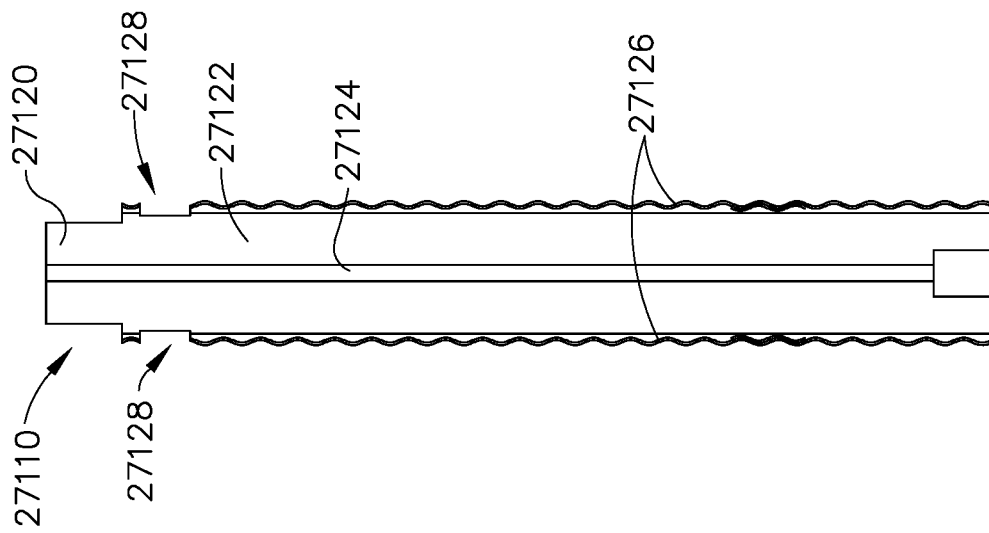

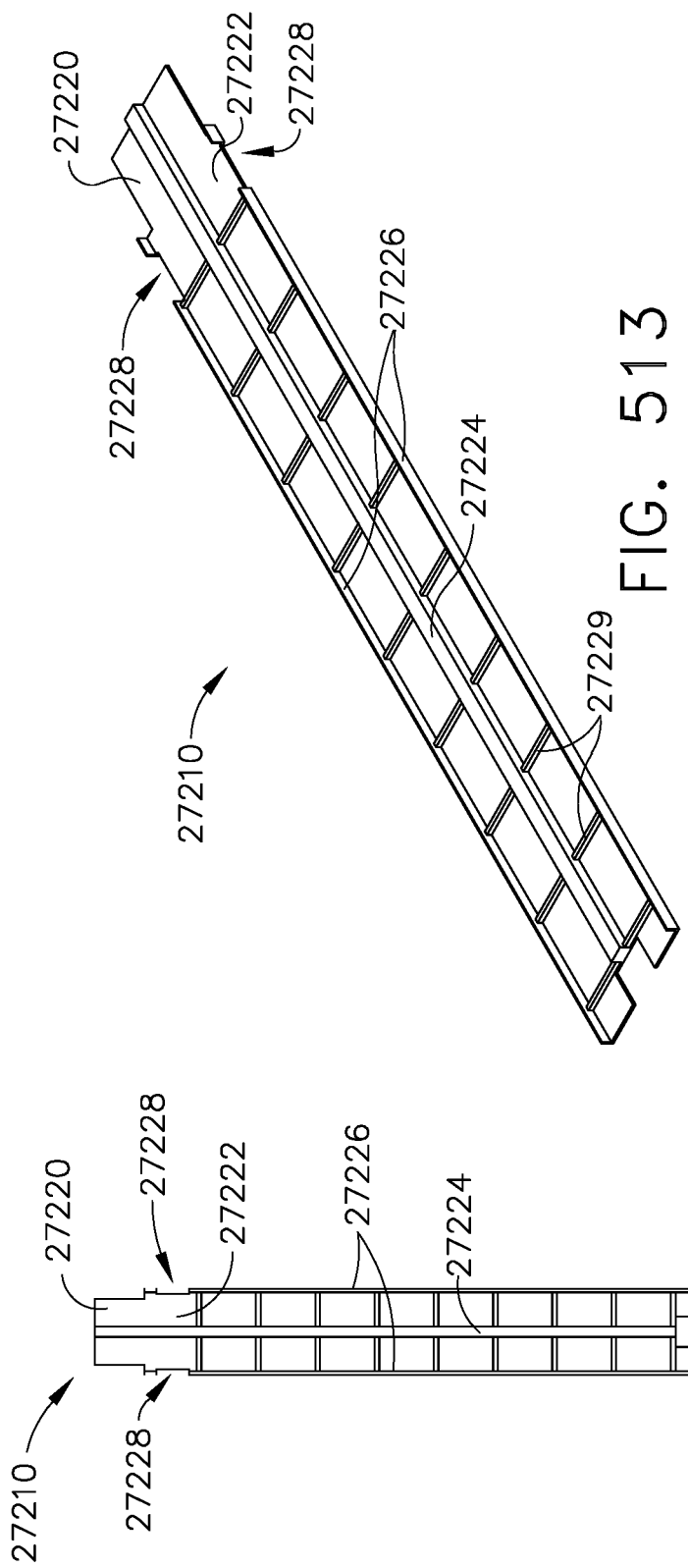
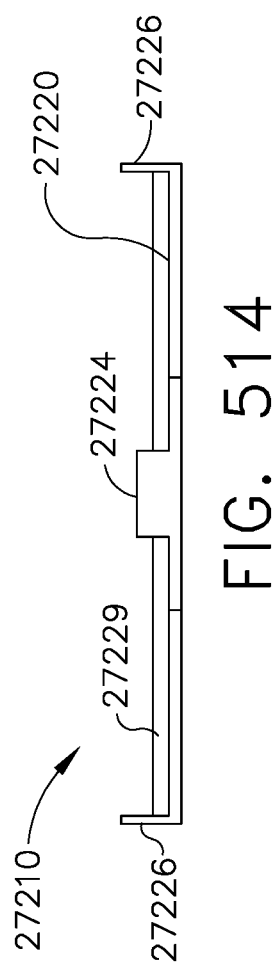

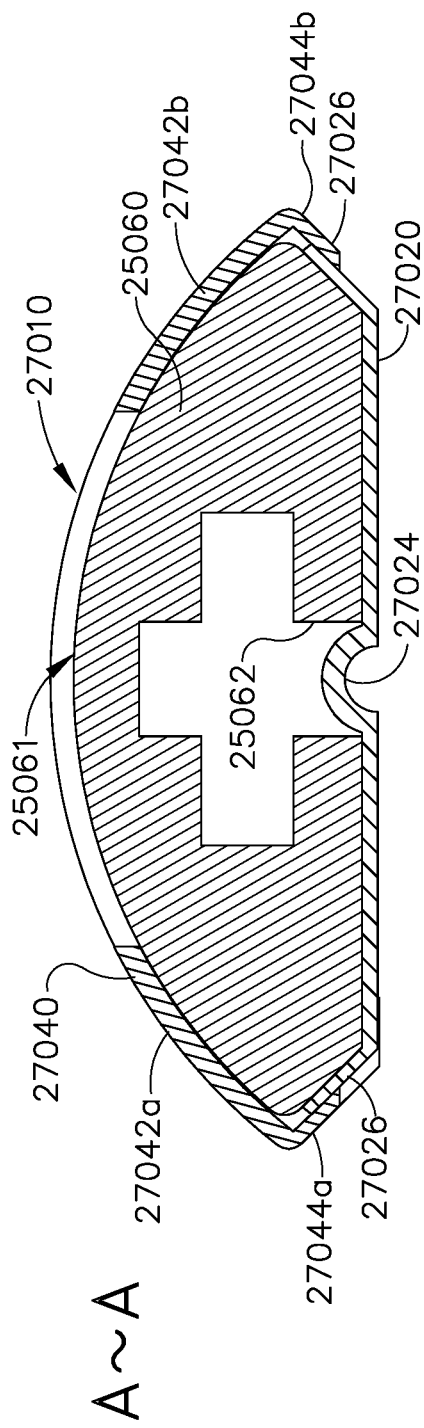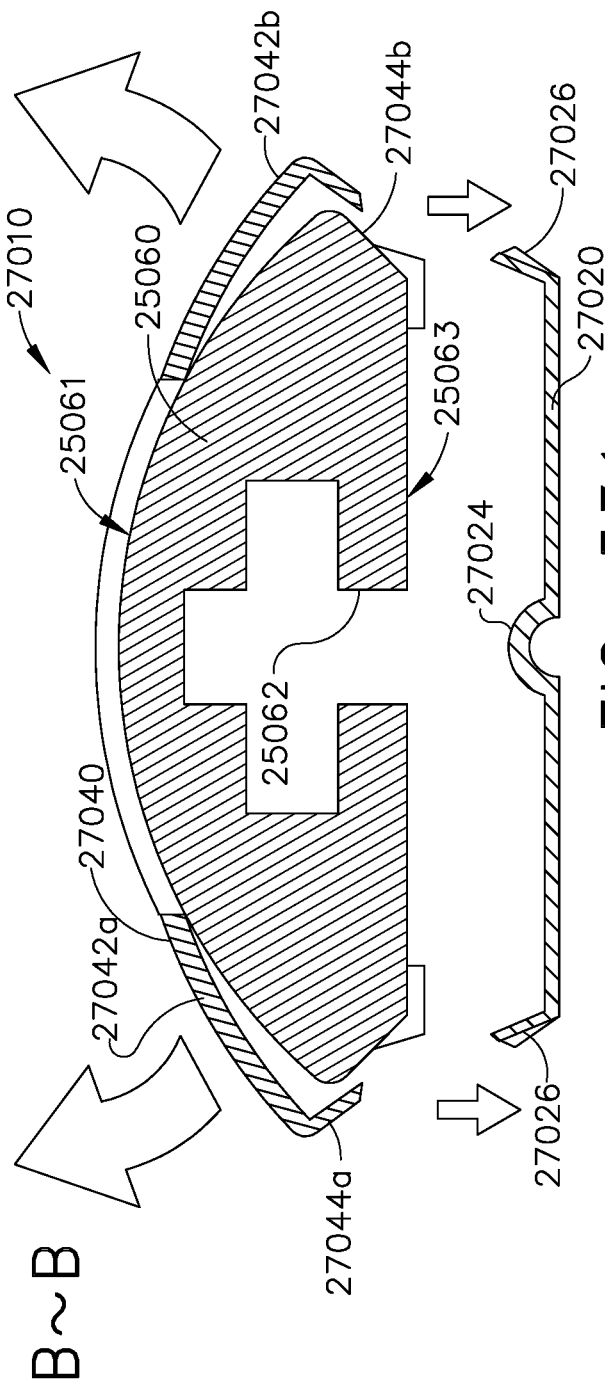

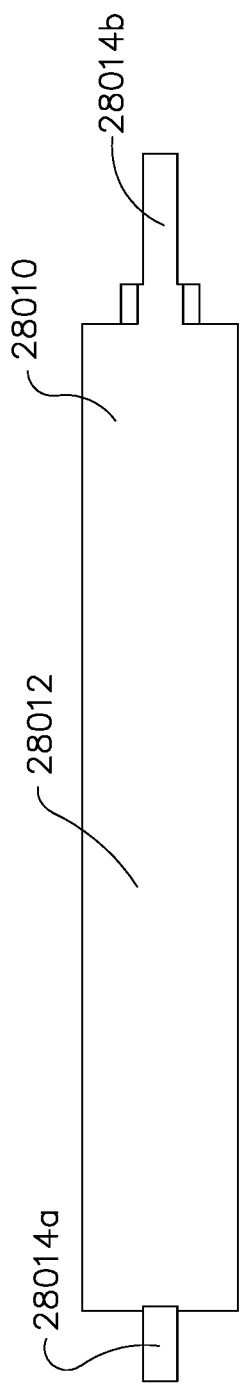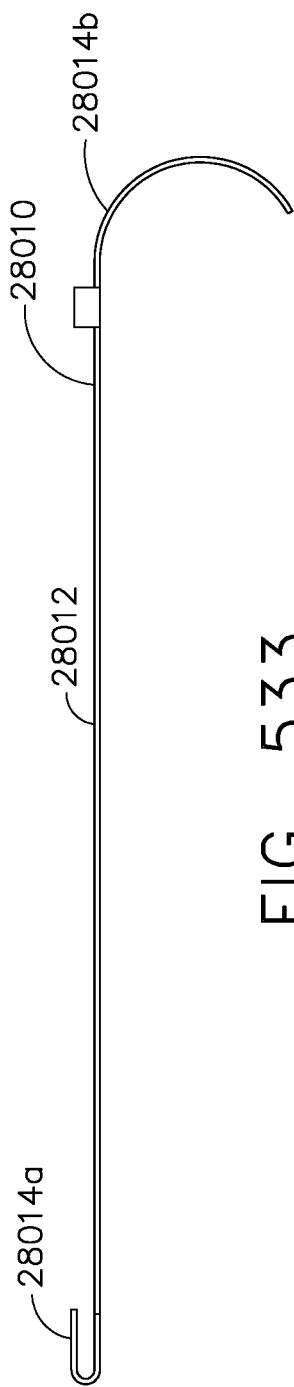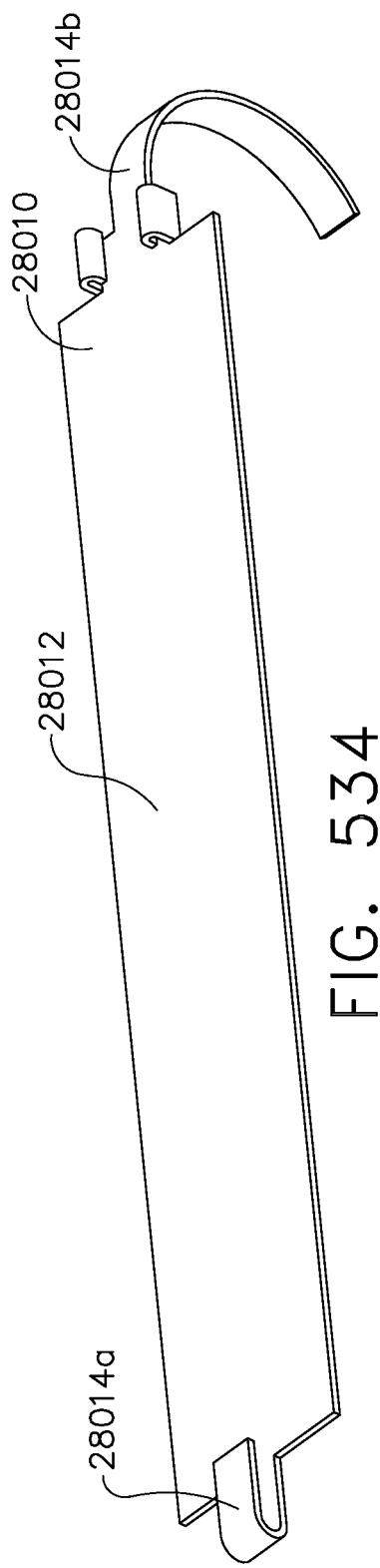

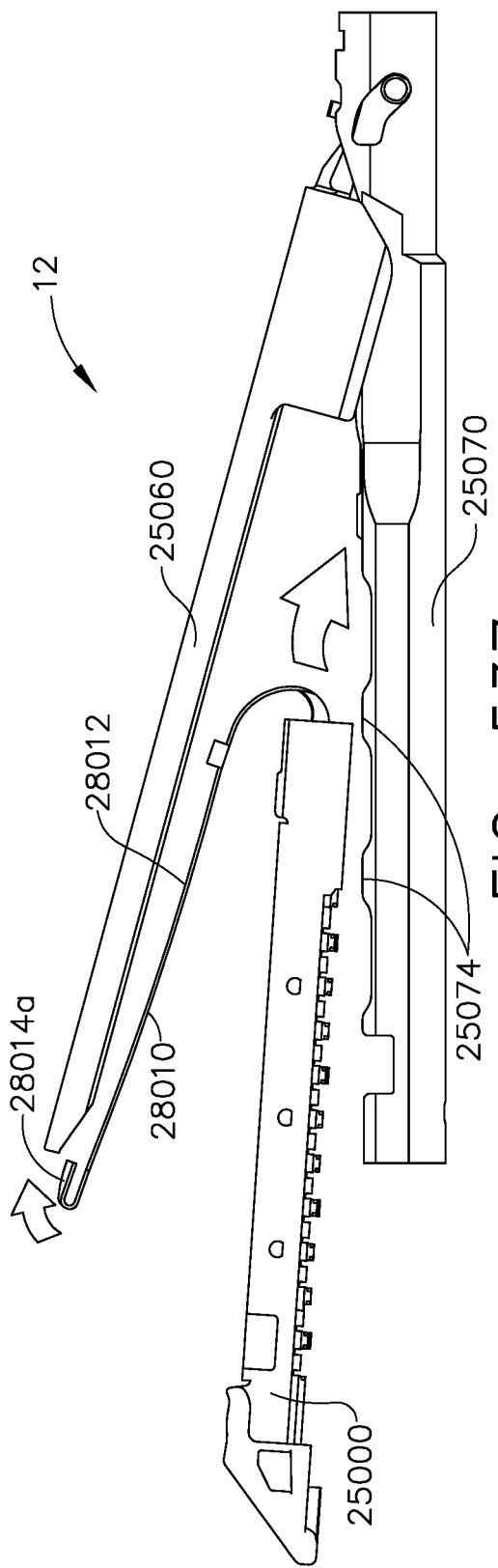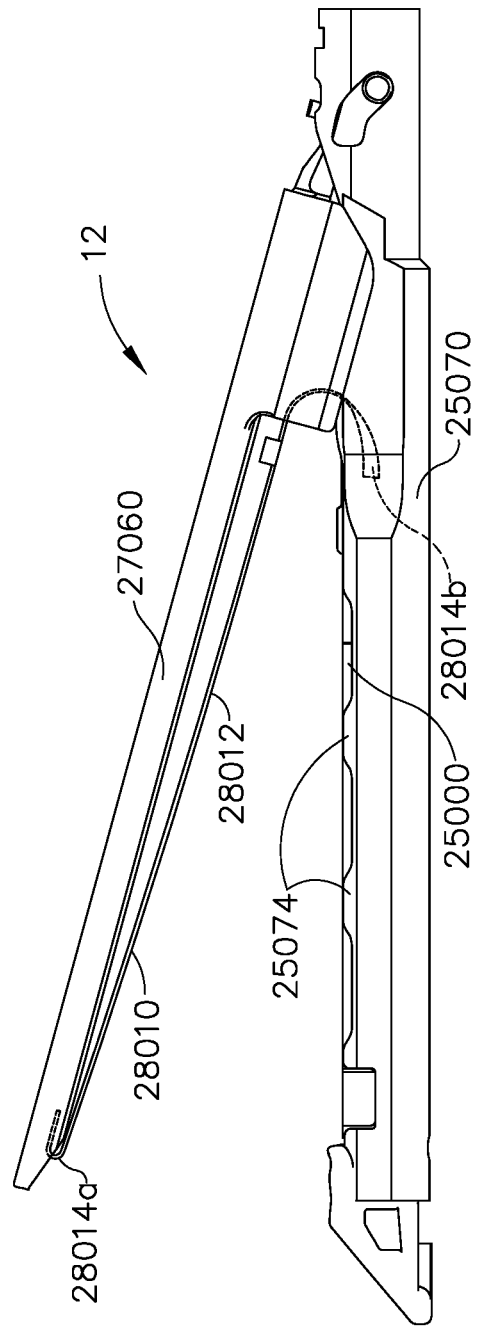
FIG. 537
FIG. 538

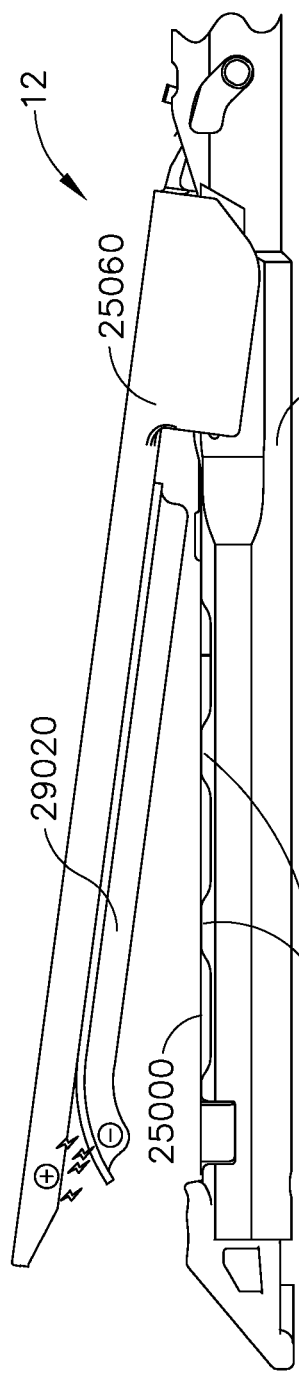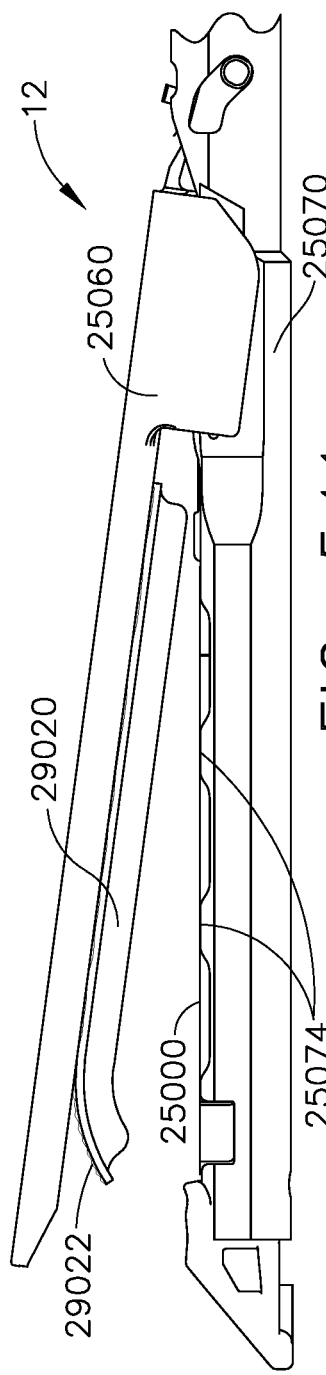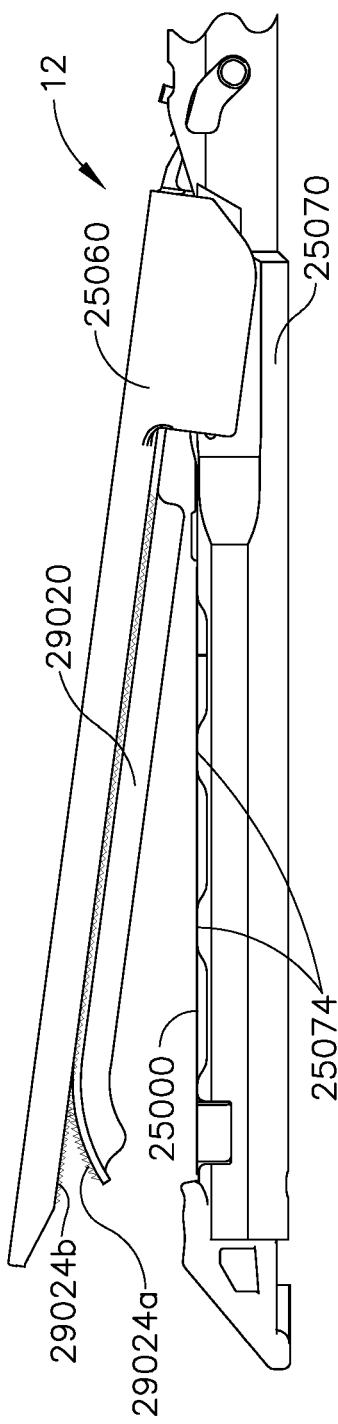

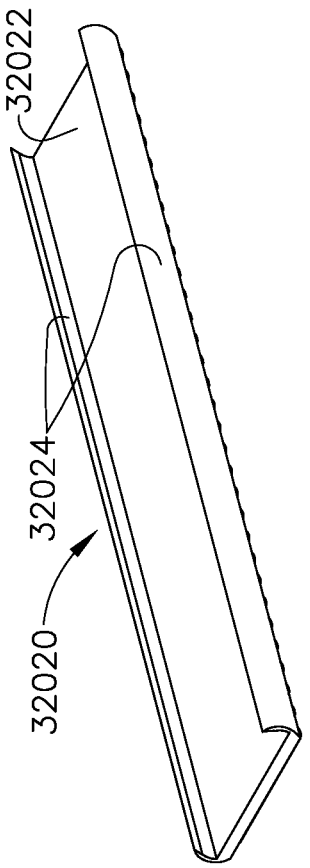
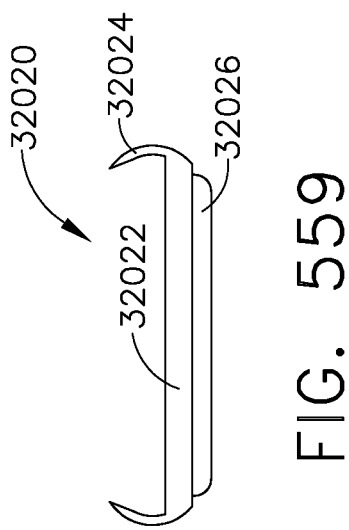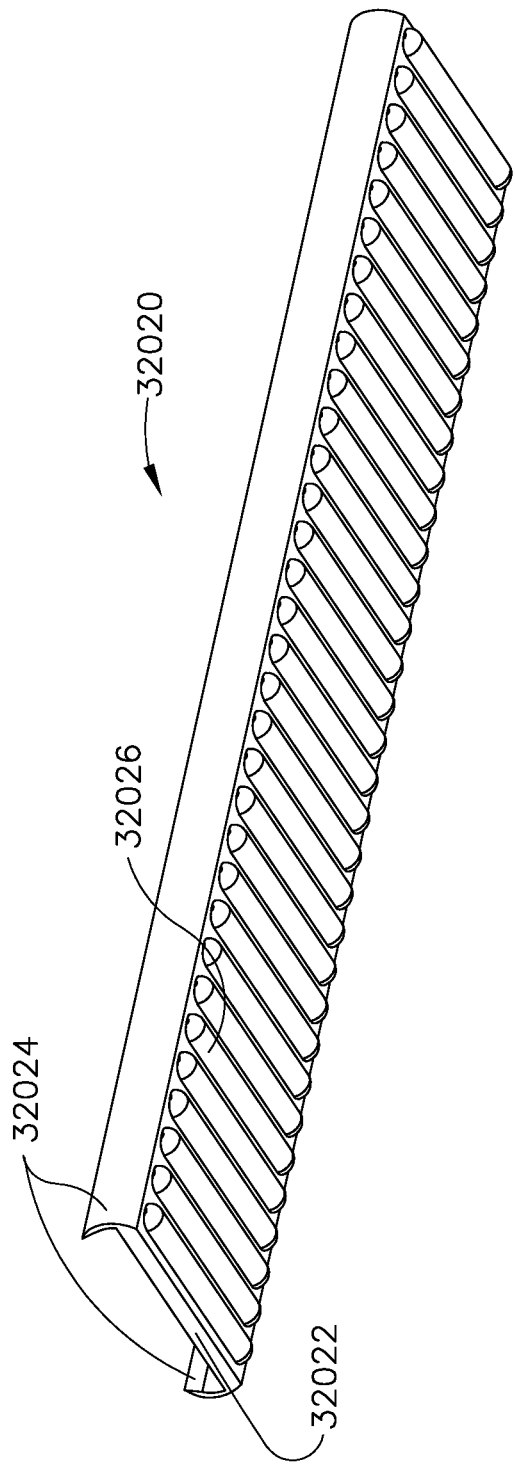
FIG. 560
FIG. 561
FIG. 559

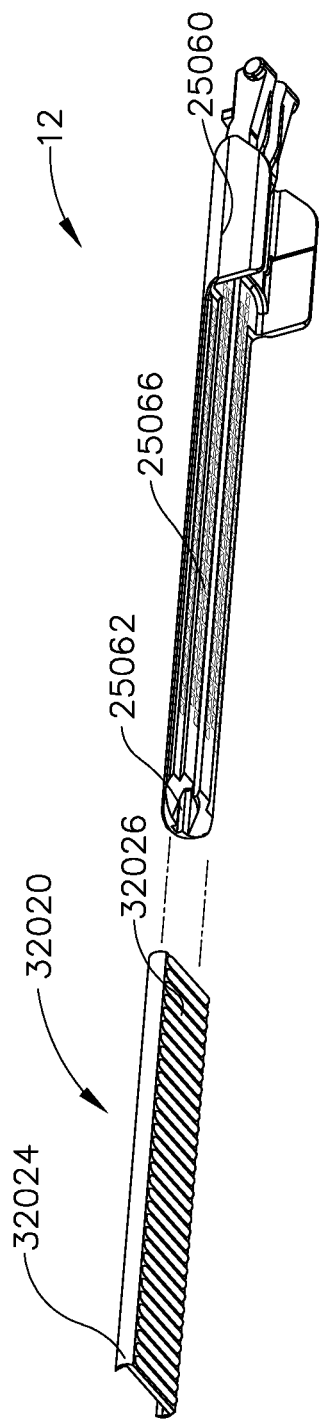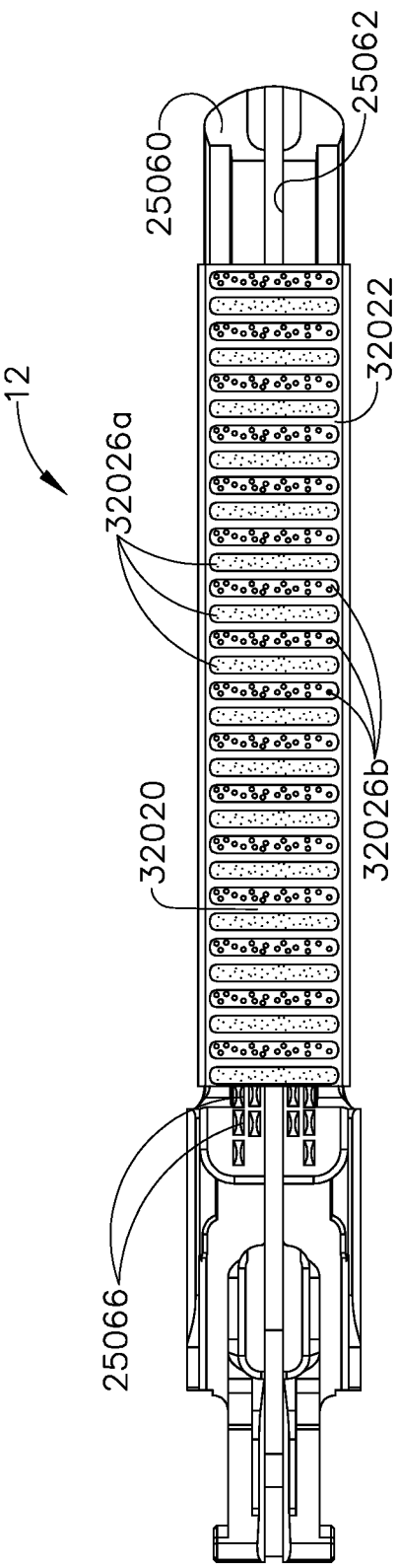
FIG. 562
FIG. 563

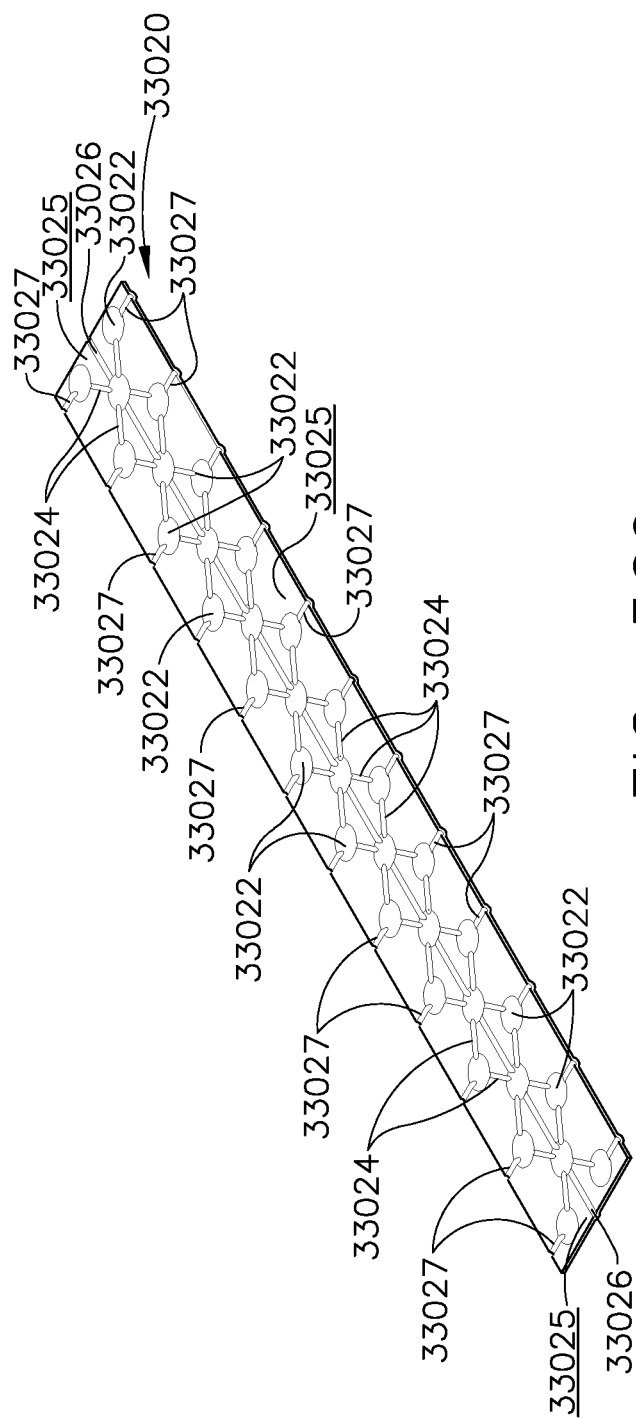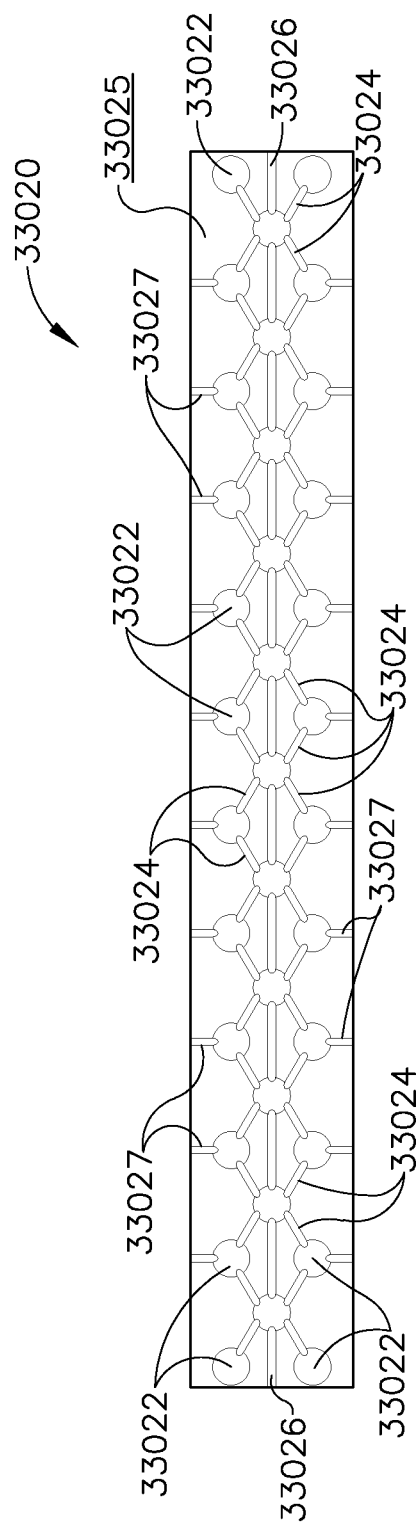

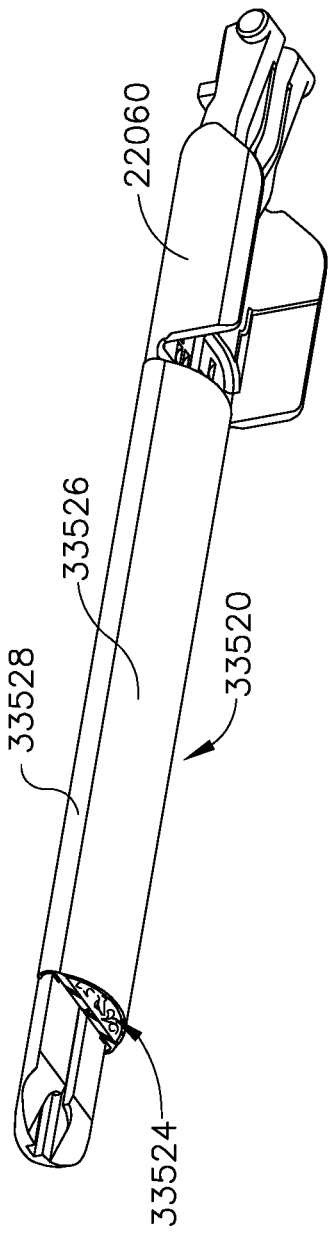
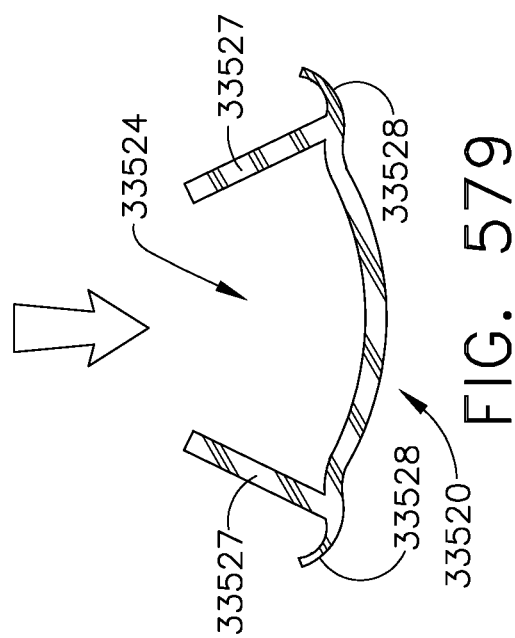
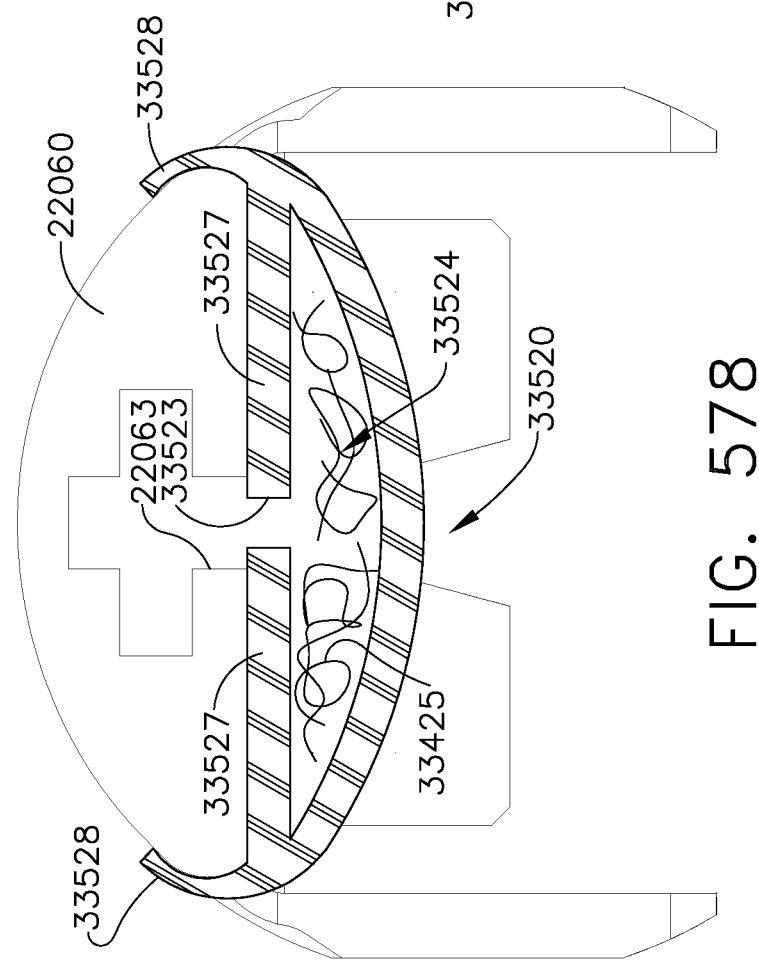
FIG. 577
FIG. 579
FIG. 578

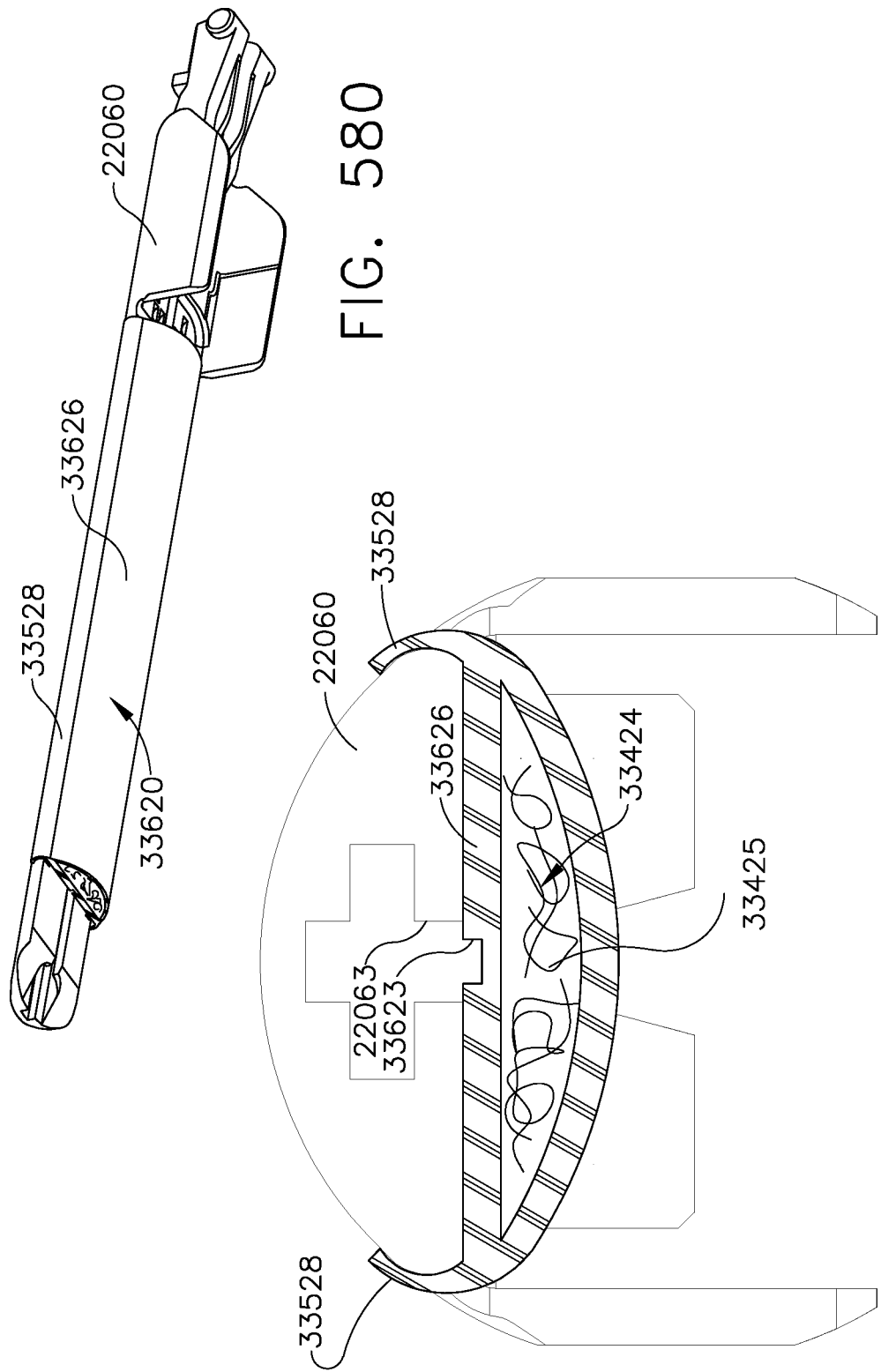

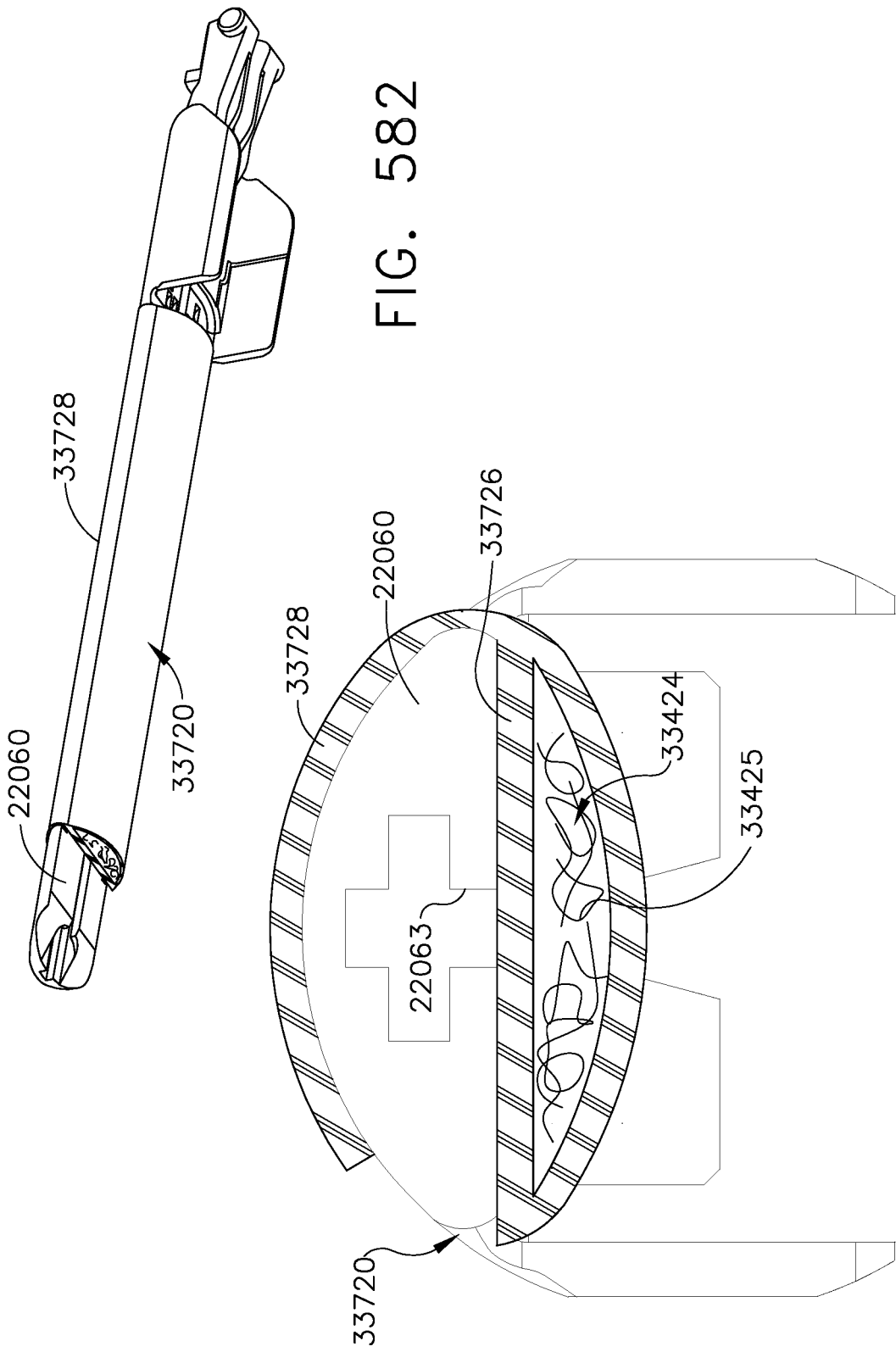

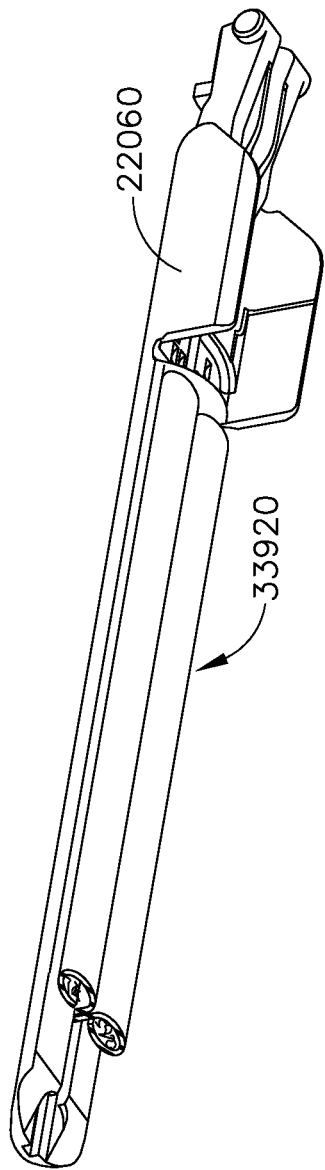
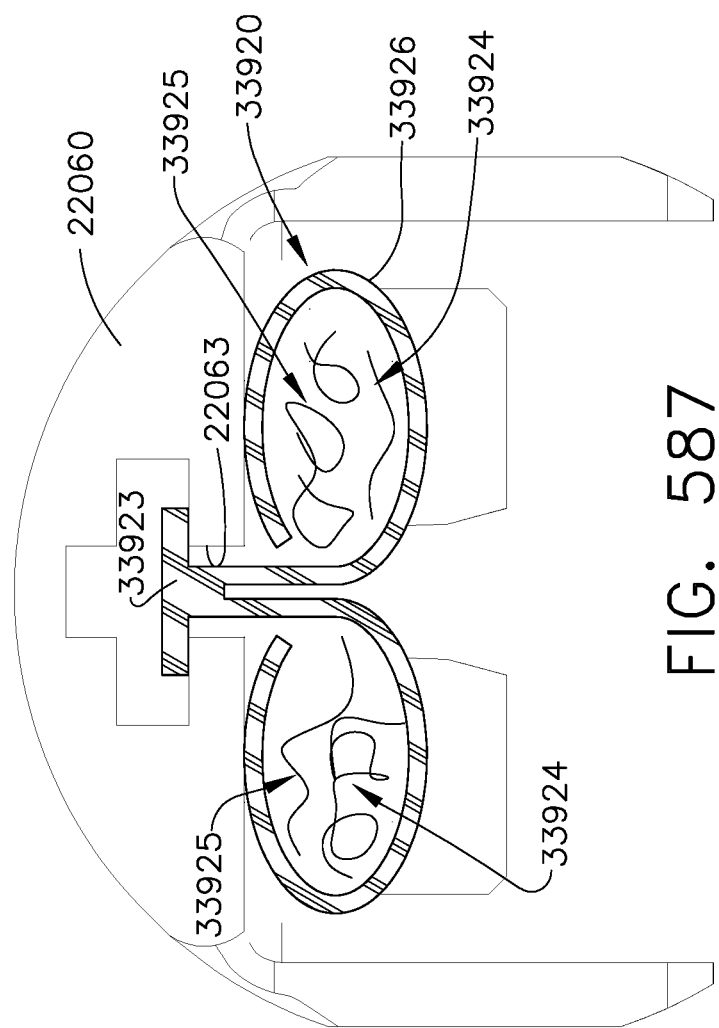
FIG. 586
FIG. 587

IMPLANTABLE LAYER COMPRISING A PLURALITY OF LAYERS

CROSS-REFERENCE TO RELATED APPLICATIONS

This application is a continuation application claiming priority under 35 U.S.C. § 120 to U.S. patent application Ser. No. 17/396,911, entitled RETAINER ASSEMBLY INCLUDING A TISSUE THICKNESS COMPENSATOR, filed on Aug. 9, 2021, now U.S. Patent Application Publication No. 2022/0211367, which is a continuation application claiming priority under 35 U.S.C. § 120 to U.S. patent application Ser. No. 16/158,501, entitled STAPLE CARTRIDGE INCLUDING A TISSUE THICKNESS COMPENSATOR, filed on Oct. 12, 2018, which issued on Aug. 10, 2021 as U.S. Pat. No. 11,083,452, which is a continuation application claiming priority under 35 U.S.C. § 120 to U.S. patent application Ser. No. 15/789,615, entitled RETAINER ASSEMBLY INCLUDING A TISSUE THICKNESS COMPENSATOR, filed on Oct. 20, 2017, which issued on Apr. 16, 2019 as U.S. Pat. No. 10,258,332, which is a continuation application under 35 U.S.C. § 120 to U.S. patent application Ser. No. 14/746,360, entitled RETAINER ASSEMBLY INCLUDING A TISSUE THICKNESS COMPENSATOR, filed on Jun. 22, 2015, which issued on Feb. 6, 2018 as U.S. Pat. No. 9,883,861, which is a continuation application under 35 U.S.C. § 120 to U.S. patent application Ser. No. 13/433,114, entitled RETAINER ASSEMBLY INCLUDING A TISSUE THICKNESS COMPENSATOR, filed on Mar. 28, 2012, which issued on Jul. 12, 2016 as U.S. Pat. No. 9,386,988, which is a continuation-in-part application under 35 U.S.C. § 120 to U.S. patent application Ser. No. 13/097,891, entitled TISSUE THICKNESS COMPENSATOR FOR A SURGICAL STAPLER COMPRISING AN ADJUSTABLE ANVIL, filed on Apr. 29, 2011, which issued on Oct. 21, 2014 as U.S. Pat. No. 8,864,009, which is a continuation-in-part application under 35 U.S.C. § 120 to U.S. patent application Ser. No. 12/894,377, entitled SELECTIVELY ORIENTABLE IMPLANTABLE FASTENER CARTRIDGE, filed on Sep. 30, 2010, which issued on Mar. 12, 2013 as U.S. Pat. No. 8,393,514, the entire disclosures of which are hereby incorporated by reference herein.

BACKGROUND

The present invention relates to surgical instruments and, in various embodiments, to surgical cutting and stapling instruments and staple cartridges therefor that are designed to cut and staple tissue.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIGS. 1B-1E illustrate portions of an end effector clamping and stapling tissue with an implantable staple cartridge;

FIG. 7 is a top view of the surgical staple cartridge and elongated channel of the device depicted in FIG. 6;

FIG. 8 is a top view of another surgical staple cartridge embodiment installed in an elongated channel of an end effector;

FIG. 9 is a bottom view of an anvil;

FIG. 10 is a partial perspective view of a plurality of staples forming a portion of a staple line;

FIG. 11 is another partial perspective view of the staple line of FIG. 10 with the staples thereof after being formed by being contacted by the anvil of the surgical cutting and stapling device;

FIG. 12 is a partial perspective view of alternative staples forming a portion of another staple line;

FIG. 13 is a partial perspective view of alternative staples forming a portion of another staple line;

FIG. 14 is a partial perspective view of alternative staples forming a portion of another staple line embodiment;

FIGS. 18A-18D diagram the deformation of a surgical staple positioned within a collapsible staple cartridge body in accordance with at least one embodiment;

FIG. 20 is a diagram depicting a staple positioned against a staple cartridge support surface and illustrating potential relative movement therebetween;

FIG. 21 is a cross-sectional view of a staple cartridge support surface comprising a slot, or trough, configured to stabilize the base of the staple of FIG. 20;

FIG. 22 is a cross-sectional view of a staple comprising an overmolded crown and a slot, or trough, configured to receive a portion of the crown in accordance with at least one alternative embodiment;

FIG. 27 is an elevational view of a staple cartridge in accordance with at least one embodiment comprising staples at least partially extending outside of a collapsible staple cartridge body and a protective layer surrounding the staple cartridge body;

FIG. 28 is a cross-sectional view of the staple cartridge of FIG. 27 taken along line 28-28 in FIG. 27;

FIG. 29 is a partial break-away view of a staple cartridge in accordance with at least one embodiment comprising staples at least partially embedded in a collapsible staple cartridge body, the staples being at least partially positioned in a staple cavity void in the staple cartridge body;

FIG. 30 is a cross-sectional view of the staple cartridge of FIG. 29 taken along line 30-30 in FIG. 29;

FIG. 31 is a partial break-away view of a staple cartridge in accordance with at least one embodiment;

FIG. 32 is a partial break-away view of a staple cartridge in accordance with at least one embodiment comprising staples at least partially embedded within a collapsible staple cartridge body and an alignment matrix connecting the staples and aligning the staples with respect to each other;

FIG. 33 is a cross-sectional view of the staple cartridge of FIG. 32 taken along line 33-33 in FIG. 32;

FIG. 41 is a cross-sectional view of a staple cartridge and staple cartridge channel in accordance with at least one embodiment;

FIG. 42 is a diagram illustrating a portion of the staple cartridge of FIG. 41 in a deformed state;

FIG. 43 is an elevational view of an end effector of a surgical stapler comprising an anvil in an open position and a staple cartridge positioned within a staple cartridge channel;

FIG. 44 is an elevational view of the end effector of FIG. 43 illustrating the anvil in a closed position and the staple cartridge compressed between the anvil and the staple cartridge channel;

FIG. 55 is a cross-sectional view of an alternative embodiment of an end effector of a surgical stapler comprising a staple cartridge comprising a plurality of compressible layers;

FIG. 56 is a cross-sectional view of an alternative embodiment of an end effector of a surgical stapler comprising a staple cartridge comprising a stepped compressible cartridge body;

FIG. 57 is a cross-sectional view of another alternative embodiment of an end effector of a surgical stapler comprising a staple cartridge comprising a stepped compressible cartridge body;

FIG. 58 is a cross-sectional view of an alternative embodiment of an end effector of a surgical stapler comprising a staple cartridge comprising a curved tissue-contacting surface;

FIG. 59 is a cross-sectional view of an alternative embodiment of an end effector of a surgical stapler comprising a staple cartridge having an inclined tissue-contacting surface;

FIG. 66 is a perspective view of an alternative embodiment of a staple cartridge comprising deformable members extending from an outer layer of the staple cartridge;

FIG. 67 is a perspective view of an alternative embodiment of a staple cartridge comprising an outer layer of the staple cartridge being assembled to an inner layer;

FIG. 68 is a cross-sectional view of an alternative embodiment of a staple cartridge comprising a plurality of staples, a compressible layer, and a pledget layer;

FIG. 69 is a perspective view of the pledget layer of FIG. 68;

FIG. 70 is a perspective view of a pledget singulated from the pledget layer of FIG. 68 and a staple aligned with a groove in the pledget;

FIG. 71 is a perspective view of two connected pledgets from the pledget layer of FIG. 68;

FIG. 72 is a perspective view of a pledget support frame of the pledget layer of FIG. 68 being removed from the singulated pledgets;

FIG. 77 is a break-away view of a staple cartridge in accordance with at least one alternative embodiment comprising staples positioned within staple drivers;

FIG. 78 is a cross-sectional view of the staple cartridge of FIG. 77 positioned within a staple cartridge channel;

FIG. 79 is a cross-sectional view of the staple cartridge of FIG. 77 illustrating an anvil moved into a closed position and staples contained within the staple cartridge deformed by the anvil;

FIG. 80 is a cross-sectional view of the staple cartridge of FIG. 77 illustrating the staples moved upwardly toward the anvil;

FIG. 81 is a perspective view of an alternative embodiment of a staple cartridge comprising straps connecting the flexible sides of the staple cartridge;

FIG. 87 is a partial cross-sectional view of a compressible staple cartridge in accordance with at least one alternative embodiment;

FIG. 88 is a diagram illustrating the staple cartridge of FIG. 87 in an implanted condition;

FIG. 89 is a partial cut-away view of a compressible staple cartridge in accordance with at least one alternative embodiment;

FIG. 90 is a partial cross-sectional view of the staple cartridge of FIG. 89;

FIG. 91 is a diagram illustrating the staple cartridge of FIG. 89 in an implanted condition;

FIG. 92 is a partial cross-sectional view of a crushable staple cartridge in accordance with at least one alternative embodiment;

FIG. 96C is a partial cross-sectional view of the end effector of FIG. 96A illustrating the jaw in a final position and the retention matrix engaged with the staple of FIG. 96B;

FIG. 96D is a partial cross-sectional view of the end effector of FIG. 96A illustrating the jaw and the staple cartridge channel being moved away from the implanted staple cartridge and retention matrix;

FIG. 110 is a top view of a retention aperture of a retention matrix comprising a retention tab extending into the retention aperture in accordance with at least one embodiment;

FIG. 111 is a top view of a retention aperture of a retention matrix comprising a retention tab extending into the retention aperture in accordance with at least one alternative embodiment;

FIG. 112 is a perspective view of a fastening system comprising a plurality of staples, a retention matrix engaged with the staples, and an alignment matrix configured to align the staples;

FIG. 113 is a perspective view of the retention matrix of FIG. 112;

FIG. 114 is a perspective view of the alignment matrix of FIG. 112;

FIG. 115 is a partial top view of the retention matrix of FIG. 112 engaged with the staples of FIG. 112;

FIG. 116 is a partial bottom view of the retention matrix of FIG. 112 engaged with the staples of FIG. 112;

FIG. 117 is a partial elevational view of the fastening system of FIG. 112;

FIG. 118 is a partial perspective view of the fastening system of FIG. 112;

FIG. 119 is a partial cross-sectional view of the retention matrix of FIG. 112 engaged with the staples of FIG. 112;

FIG. 120 is a partial cross-sectional view of the fastening system of FIG. 112;

FIG. 121 is a perspective view of the fastening system of FIG. 112 further comprising protective caps assembled to the legs of the staples;

Figure 121:
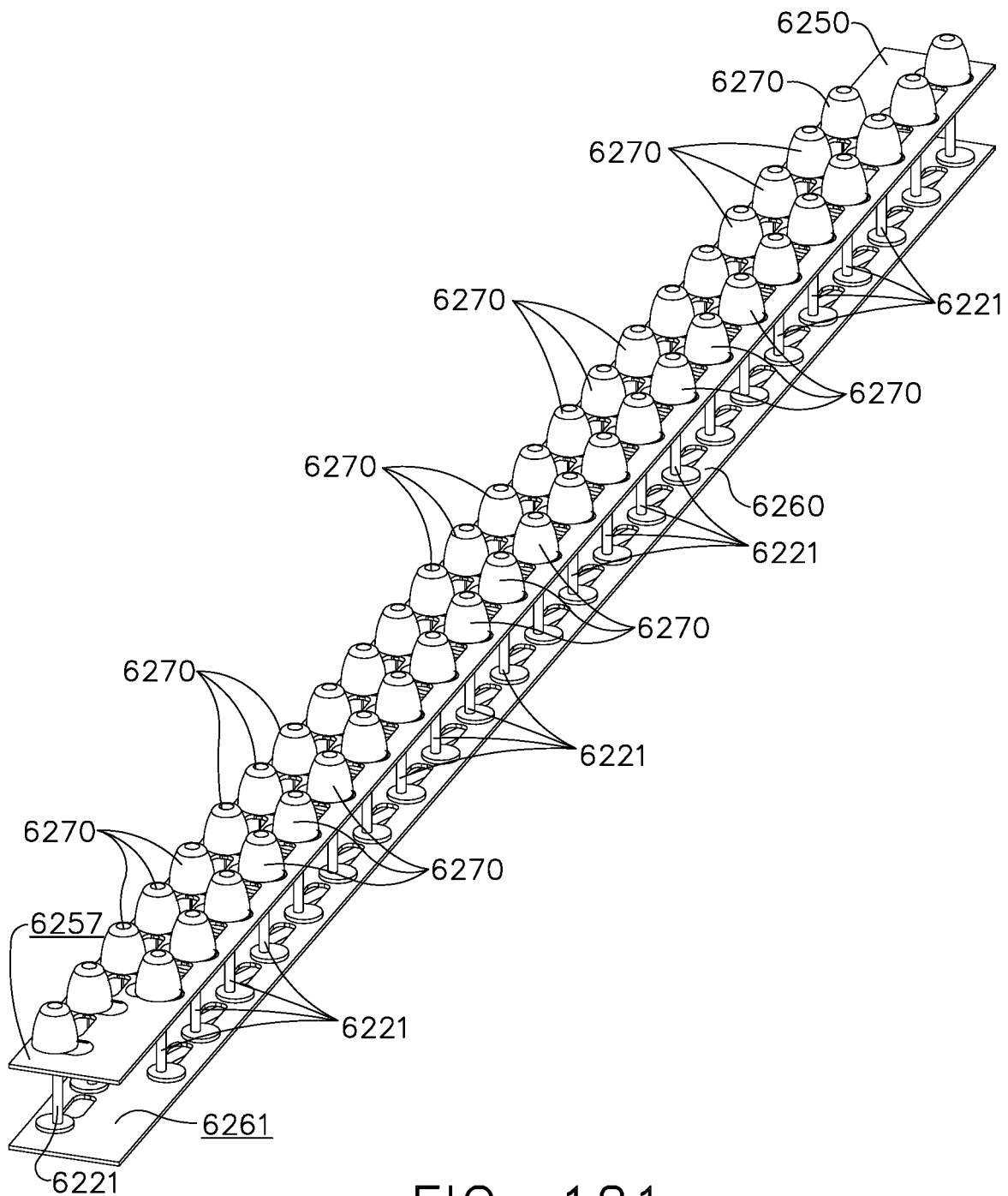
Figure 122:
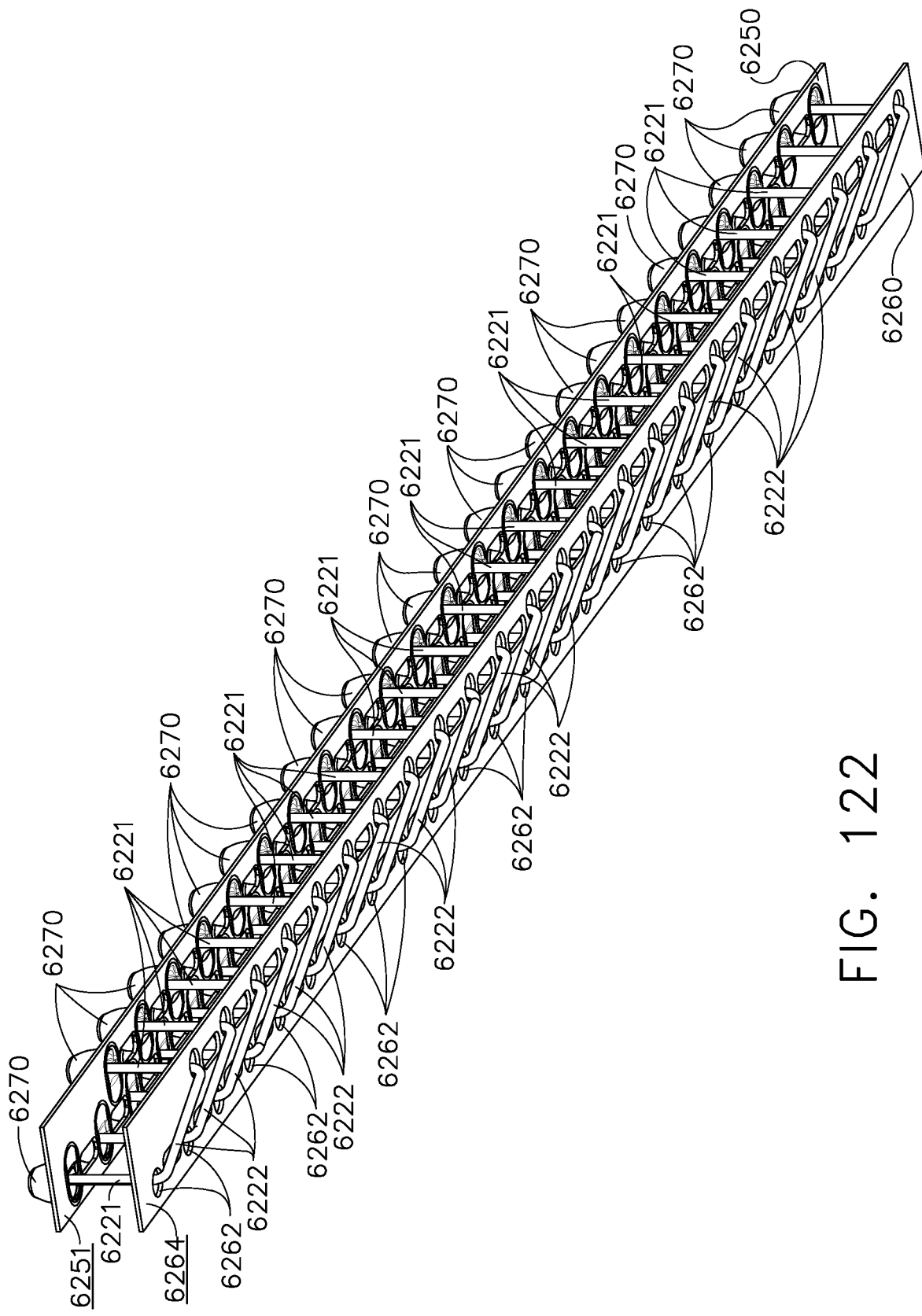
Figure 123:
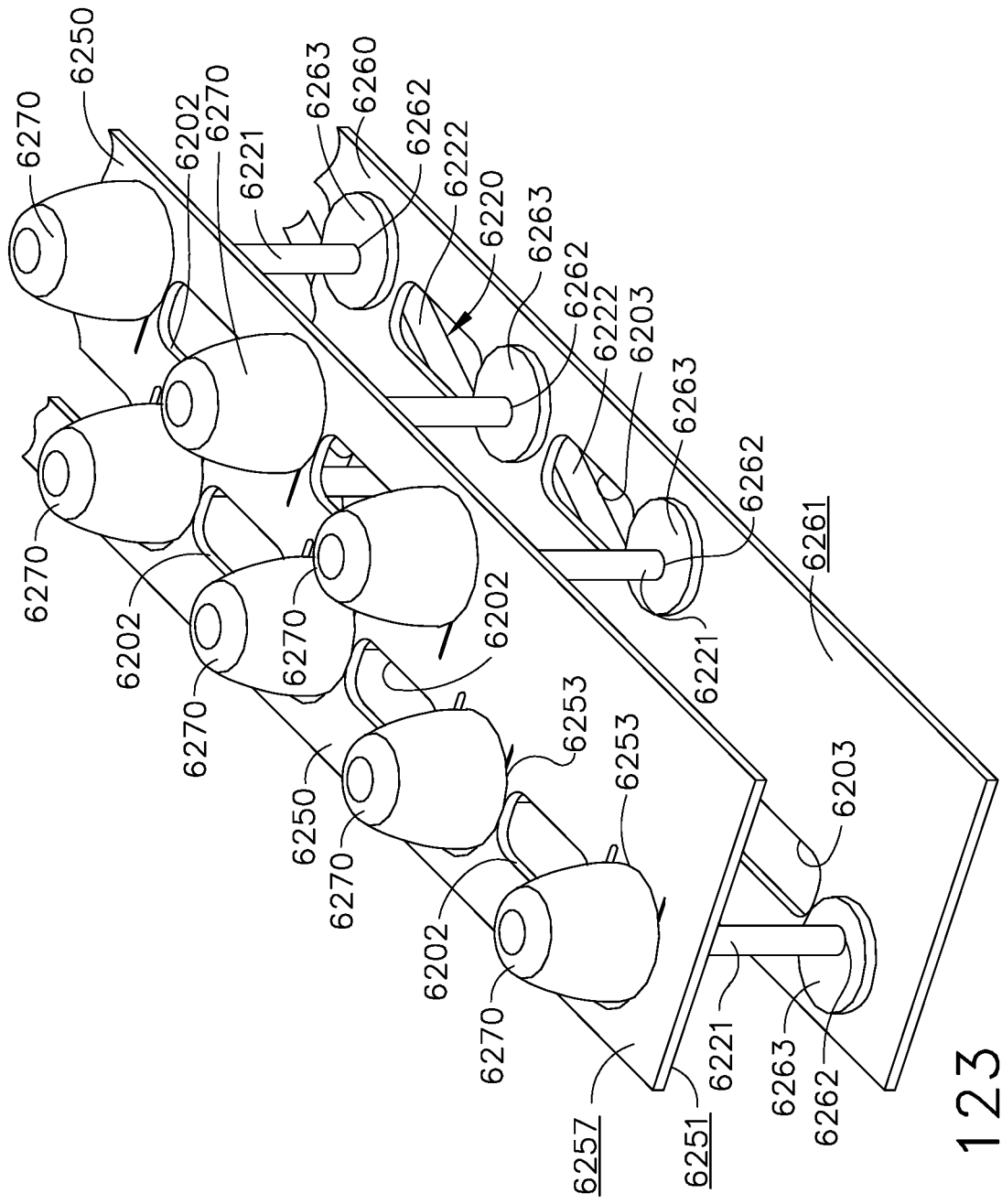
Figure 124:
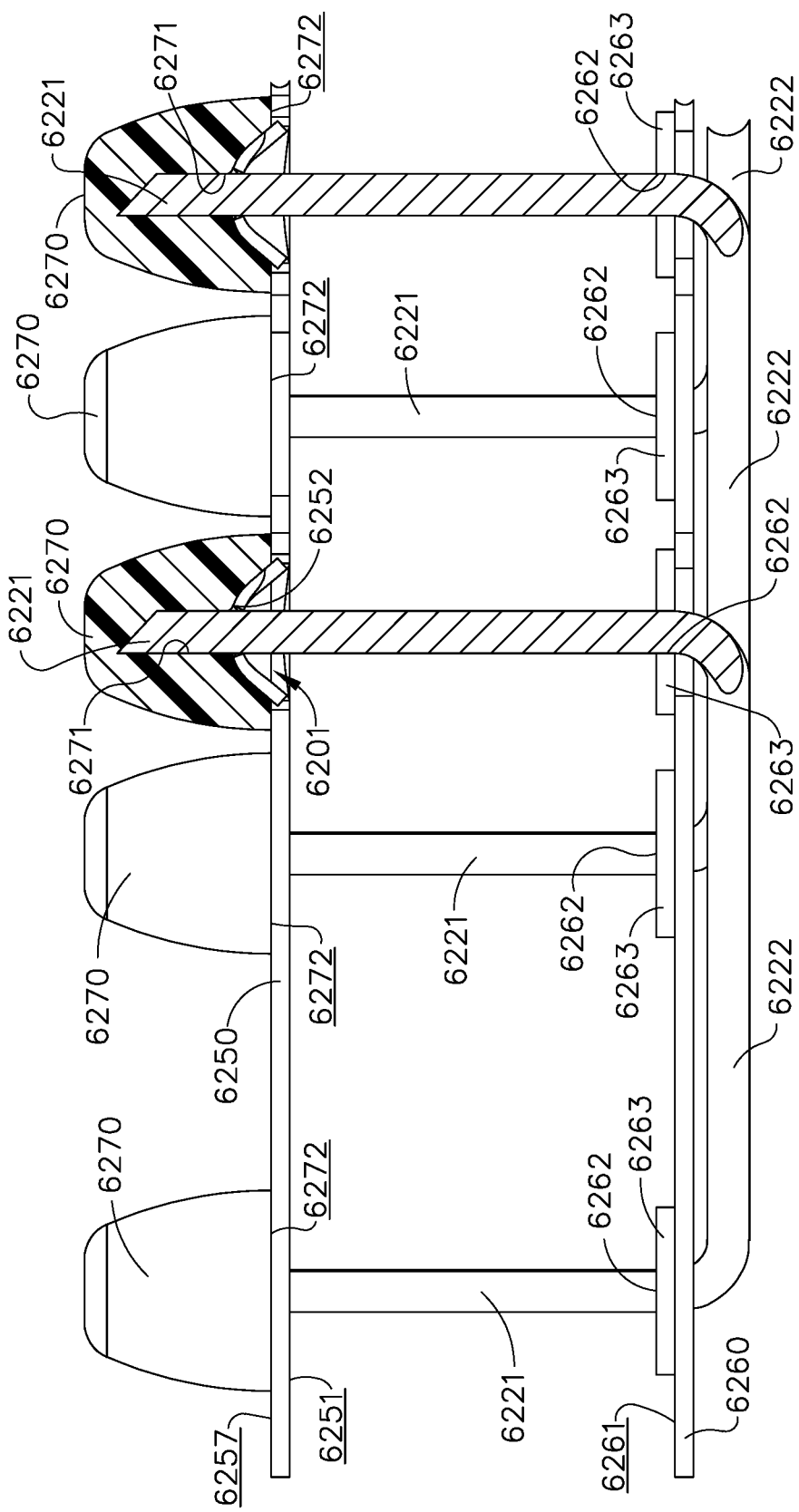
Figure 132:
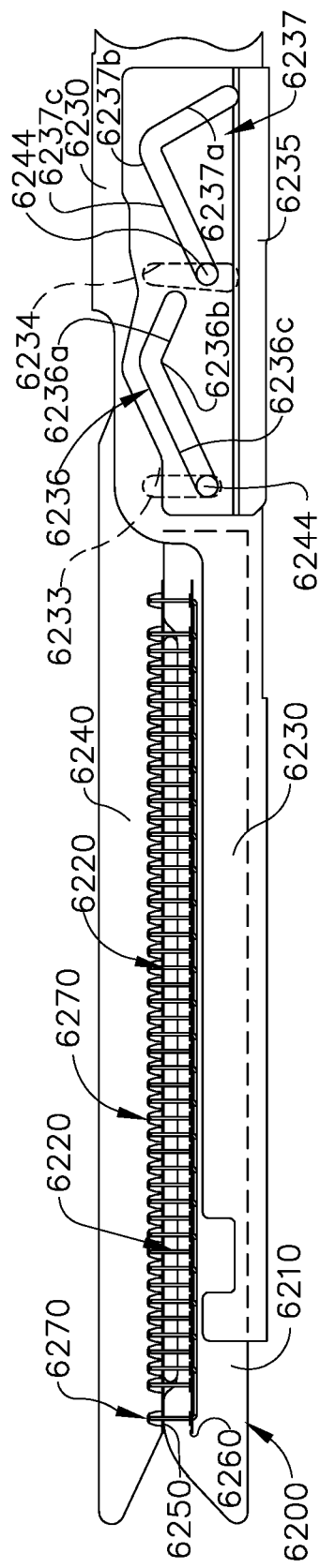
Figure 133:
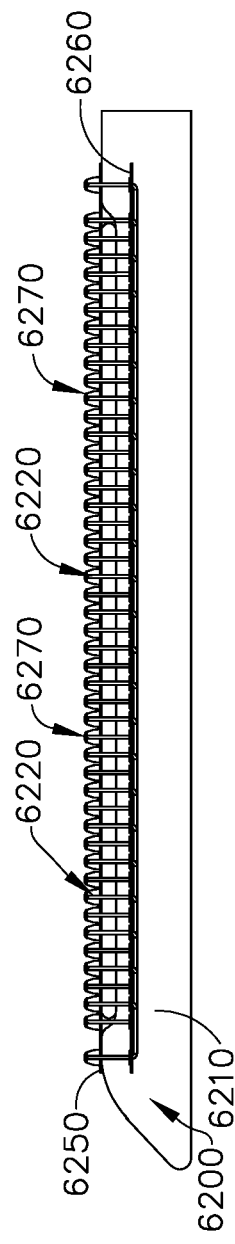
Figure 134:
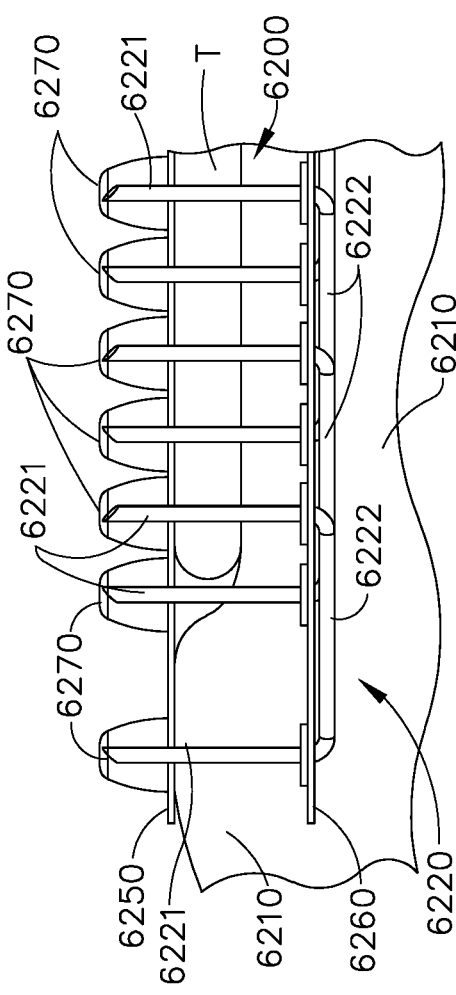
Figure 135:
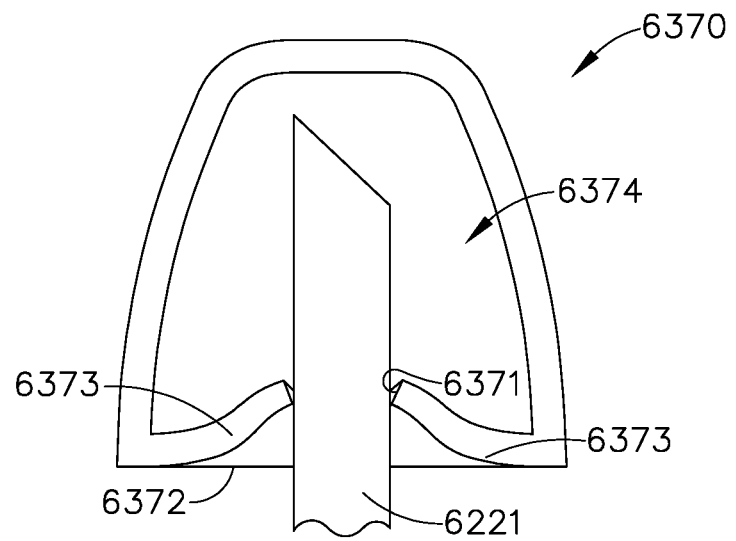
Figure 136:
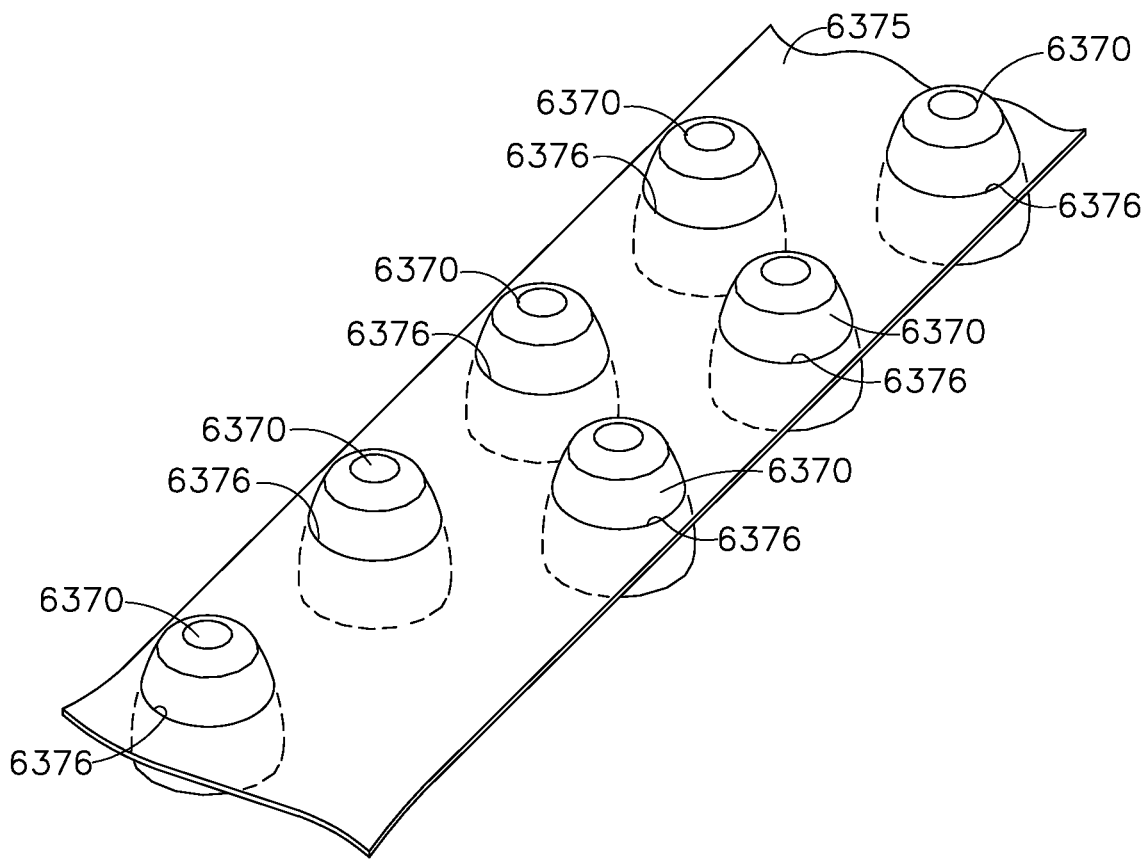
Figure 137:
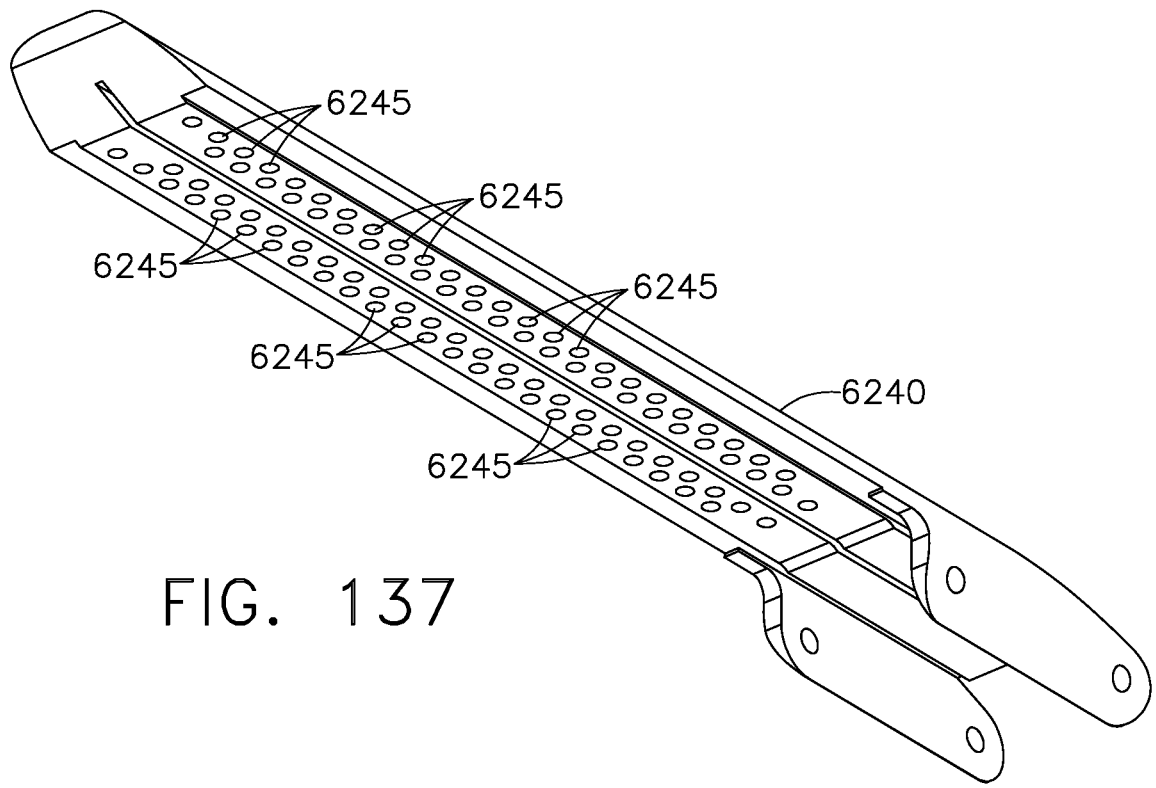
Figure 138:
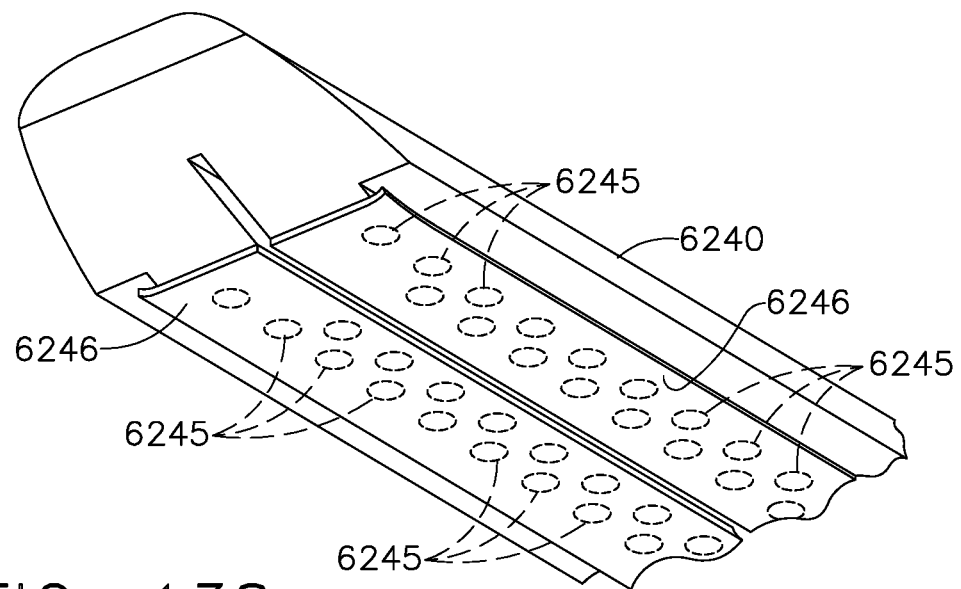
Figure 139:
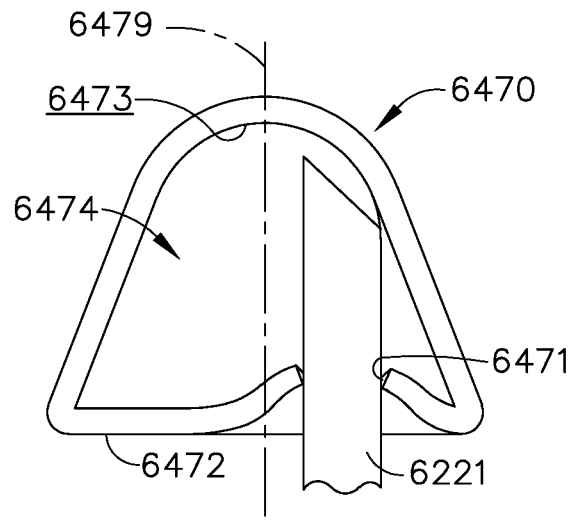
Figure 140:
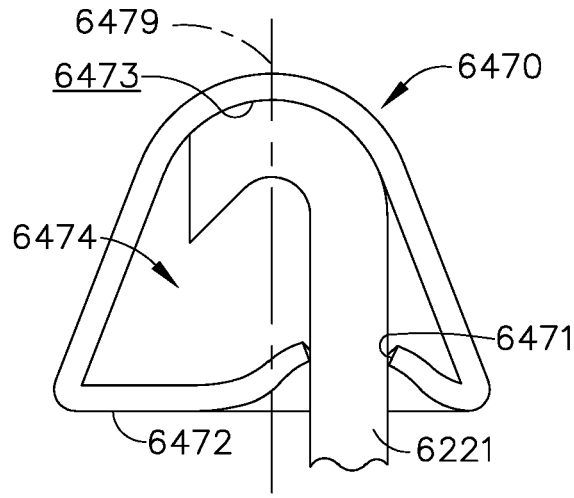
Figure 141:
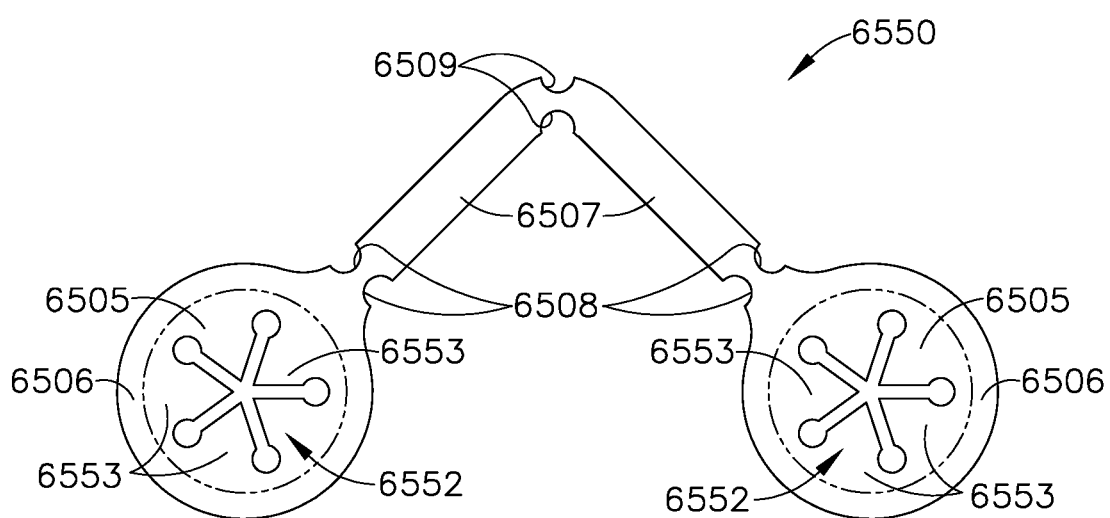
Figure 142:
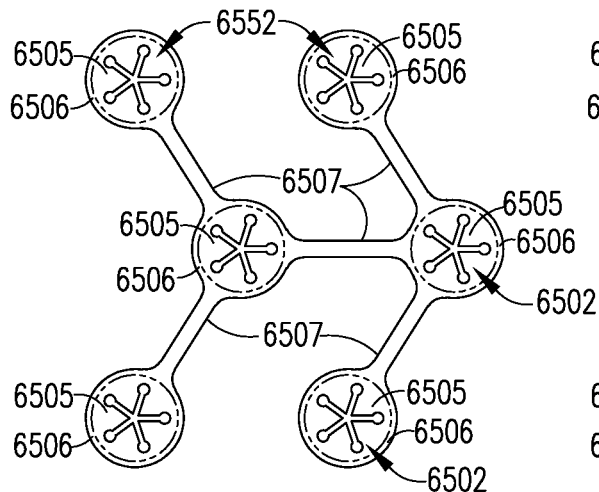
Figure 143:
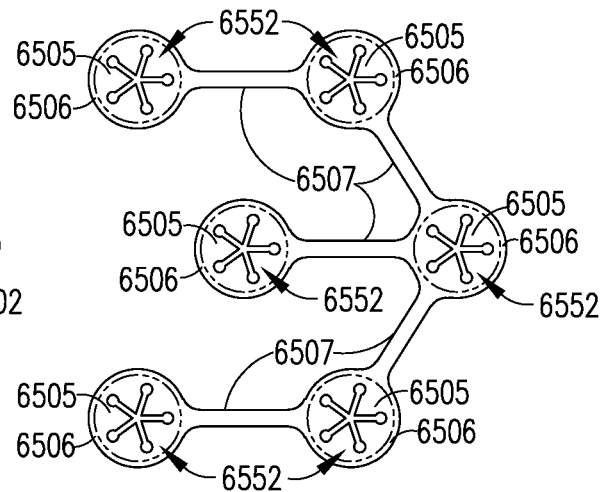
Figure 144:
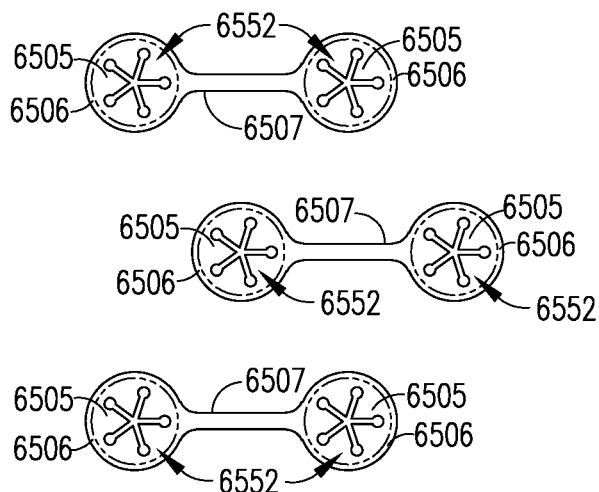
Figure 145:
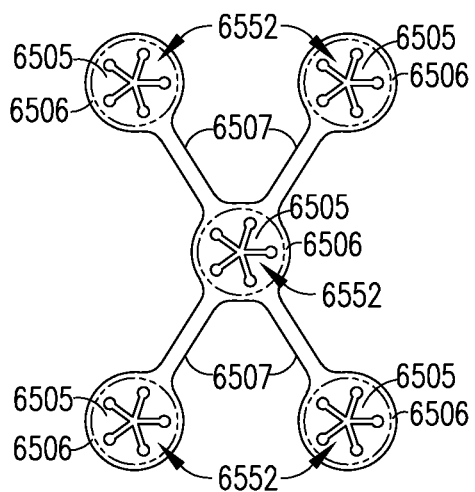
Figure 146:
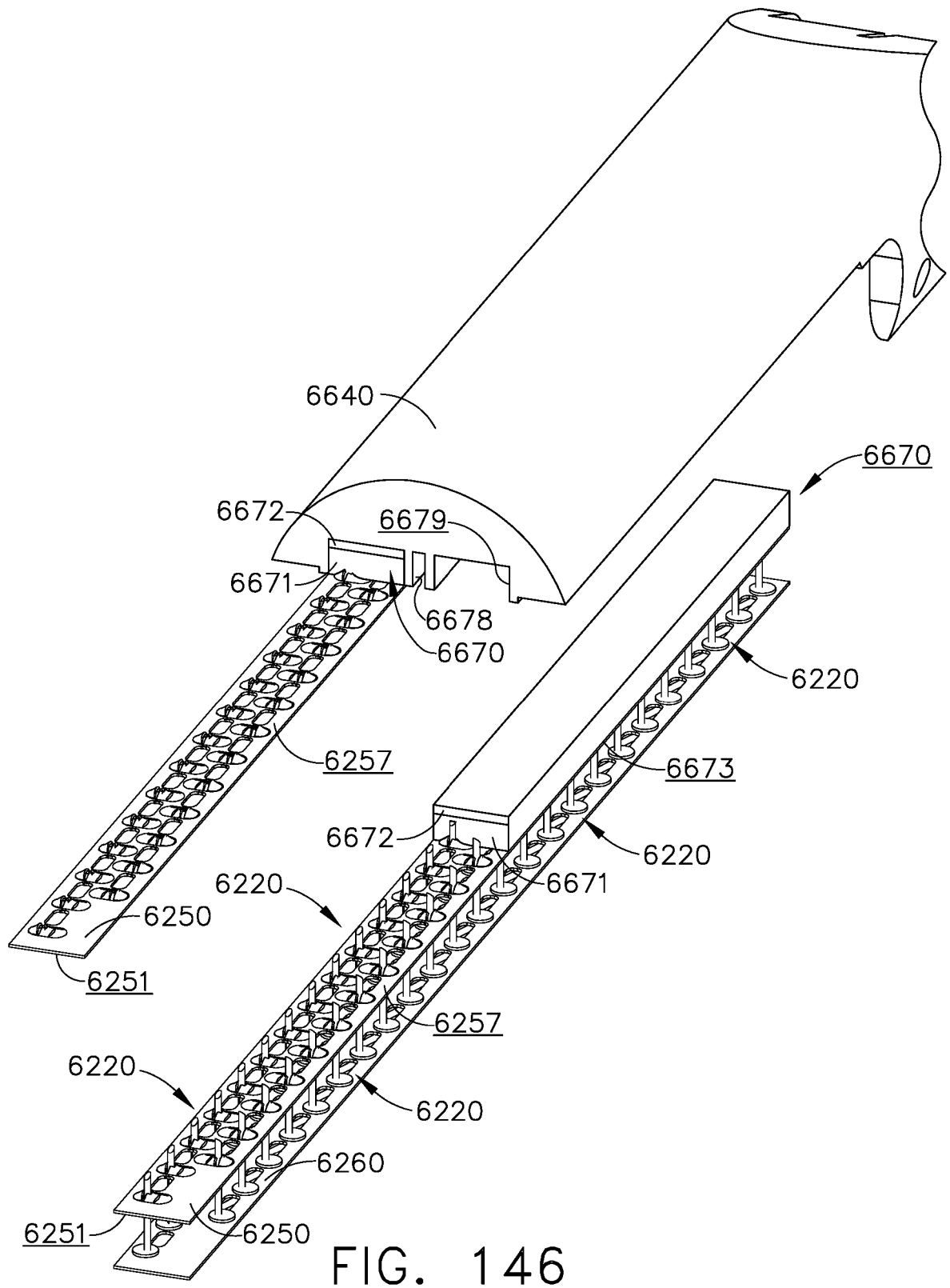
Figure 147:
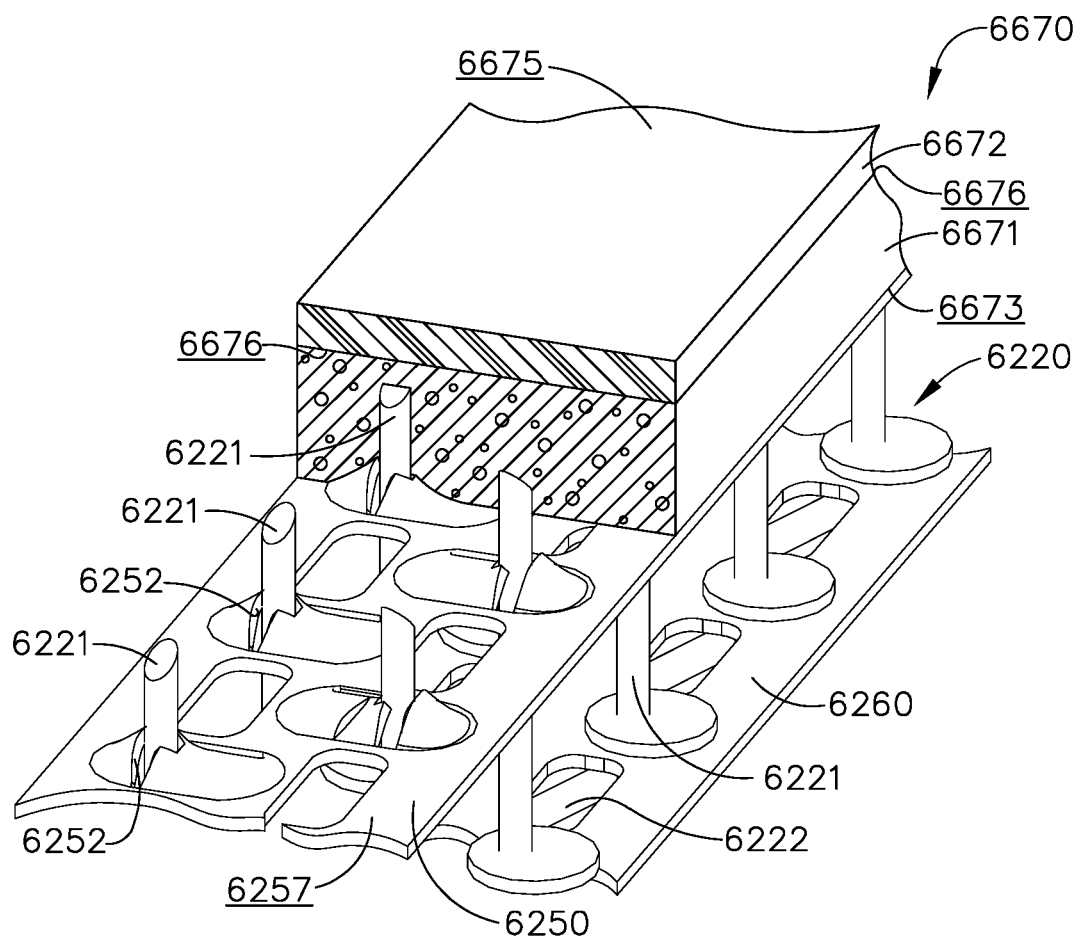
Figure 148:
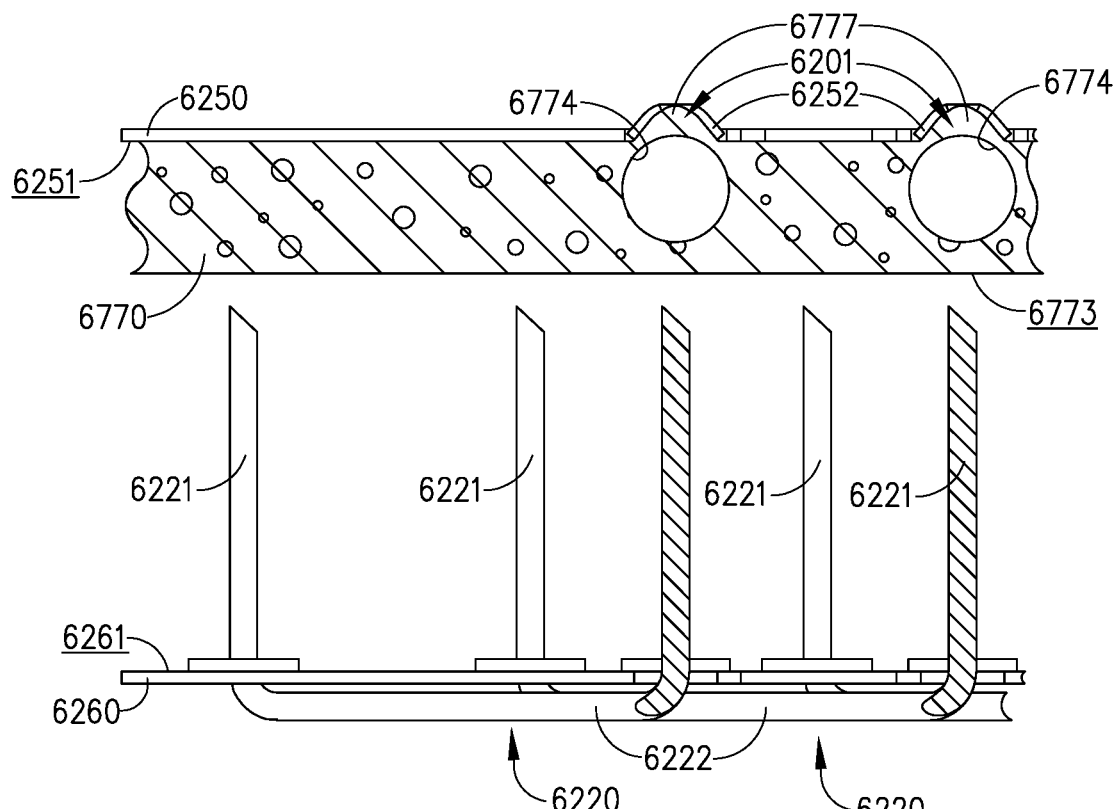
Figure 149:
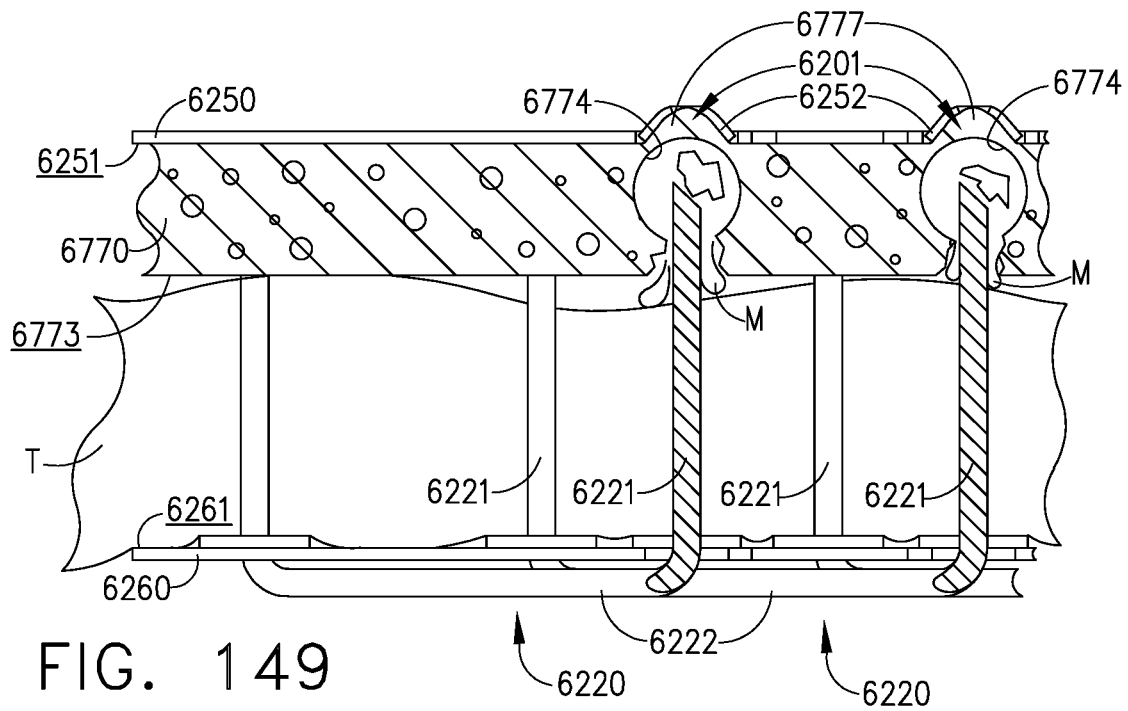
Figure 150:
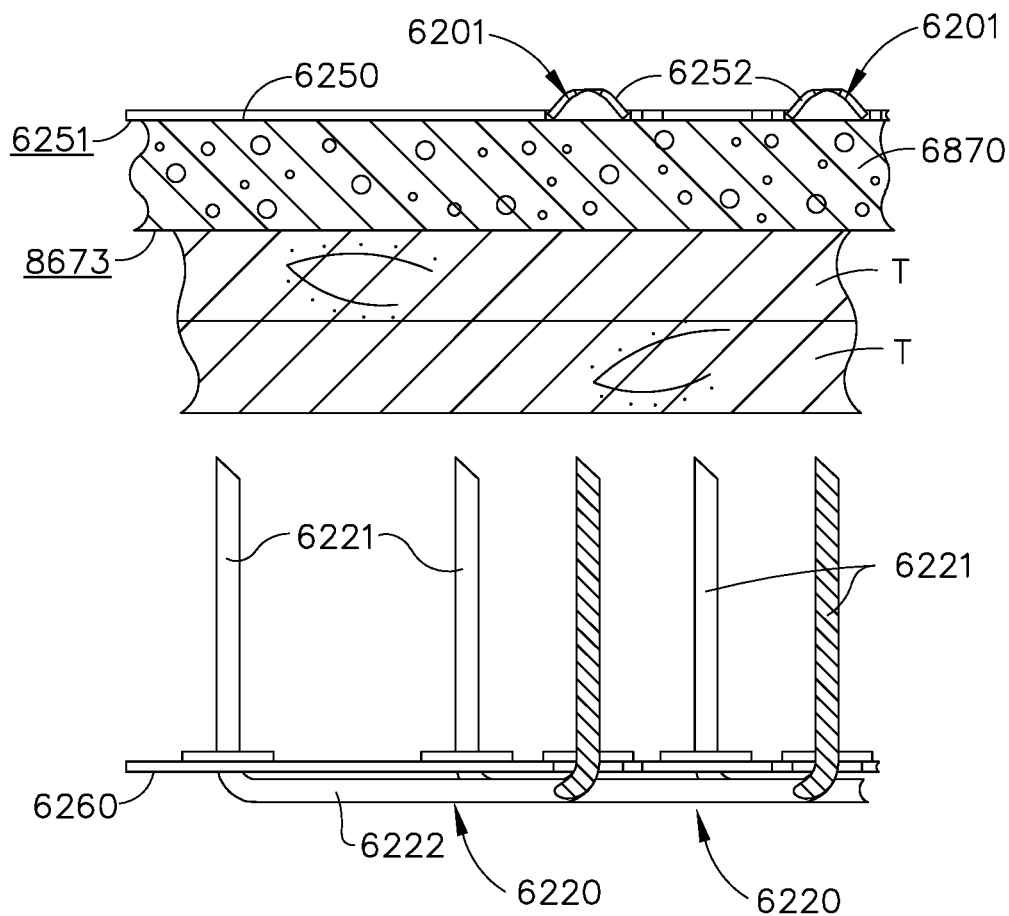
Figure 158:
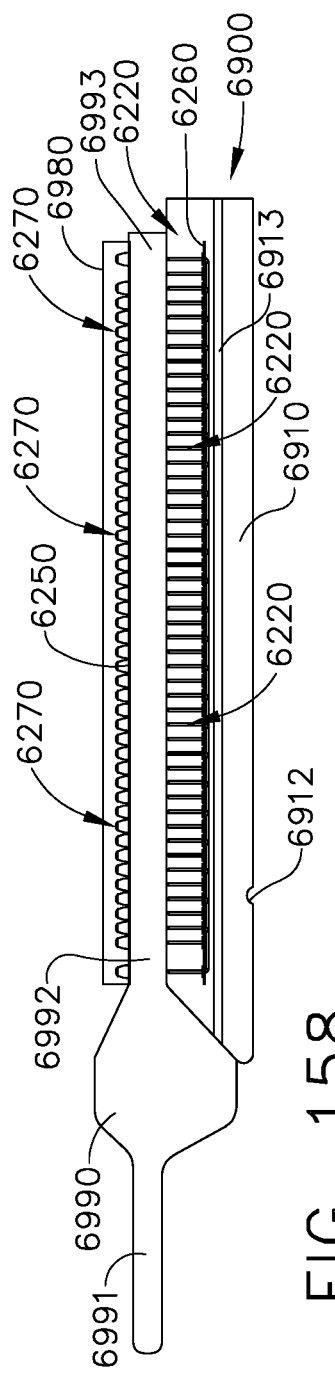
Figure 159:
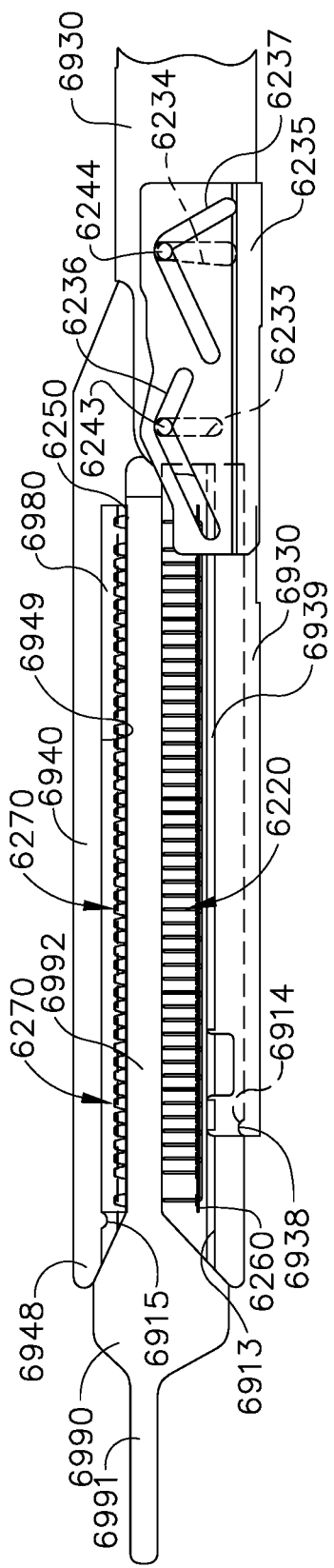
Figure 160:
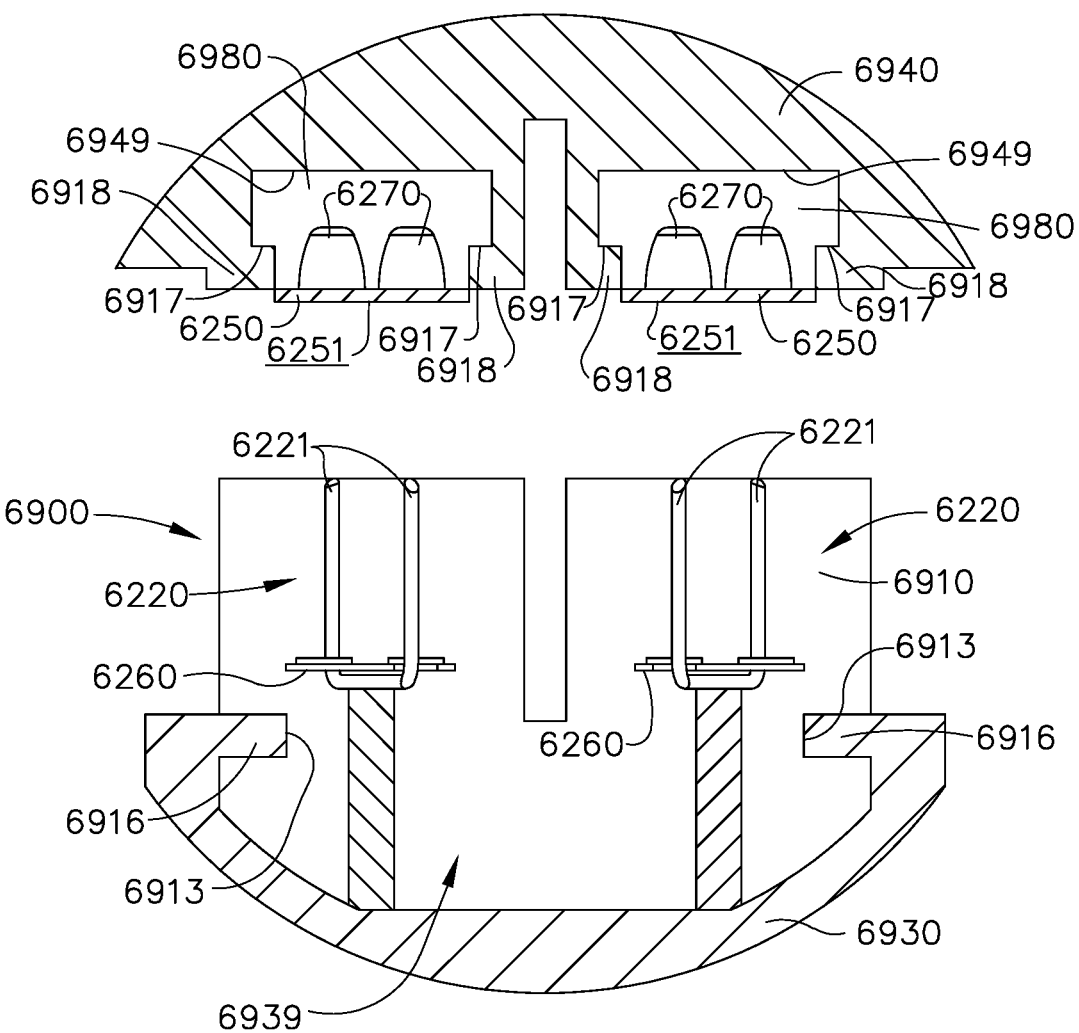
Figure 161:
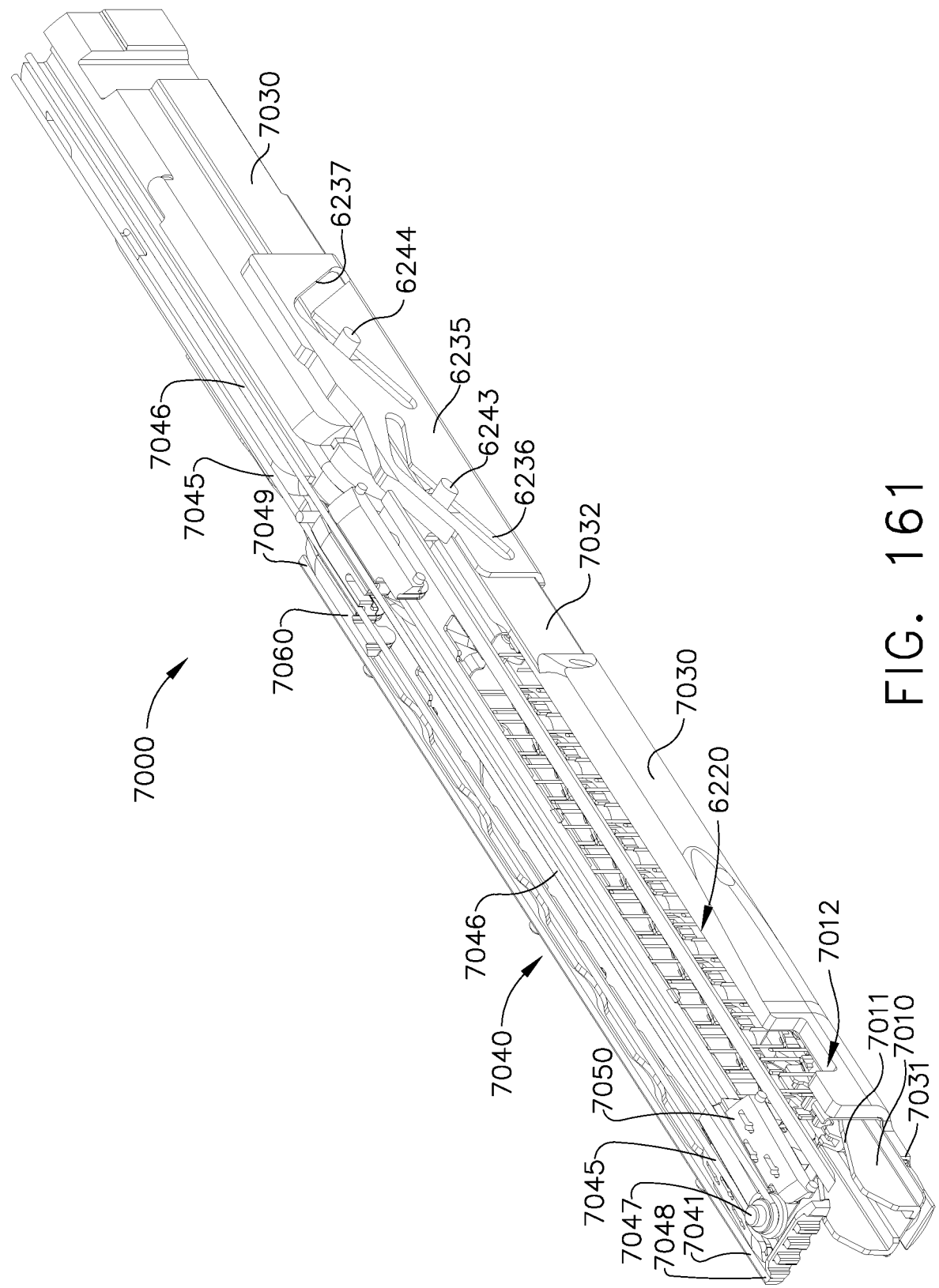
Figure 162:
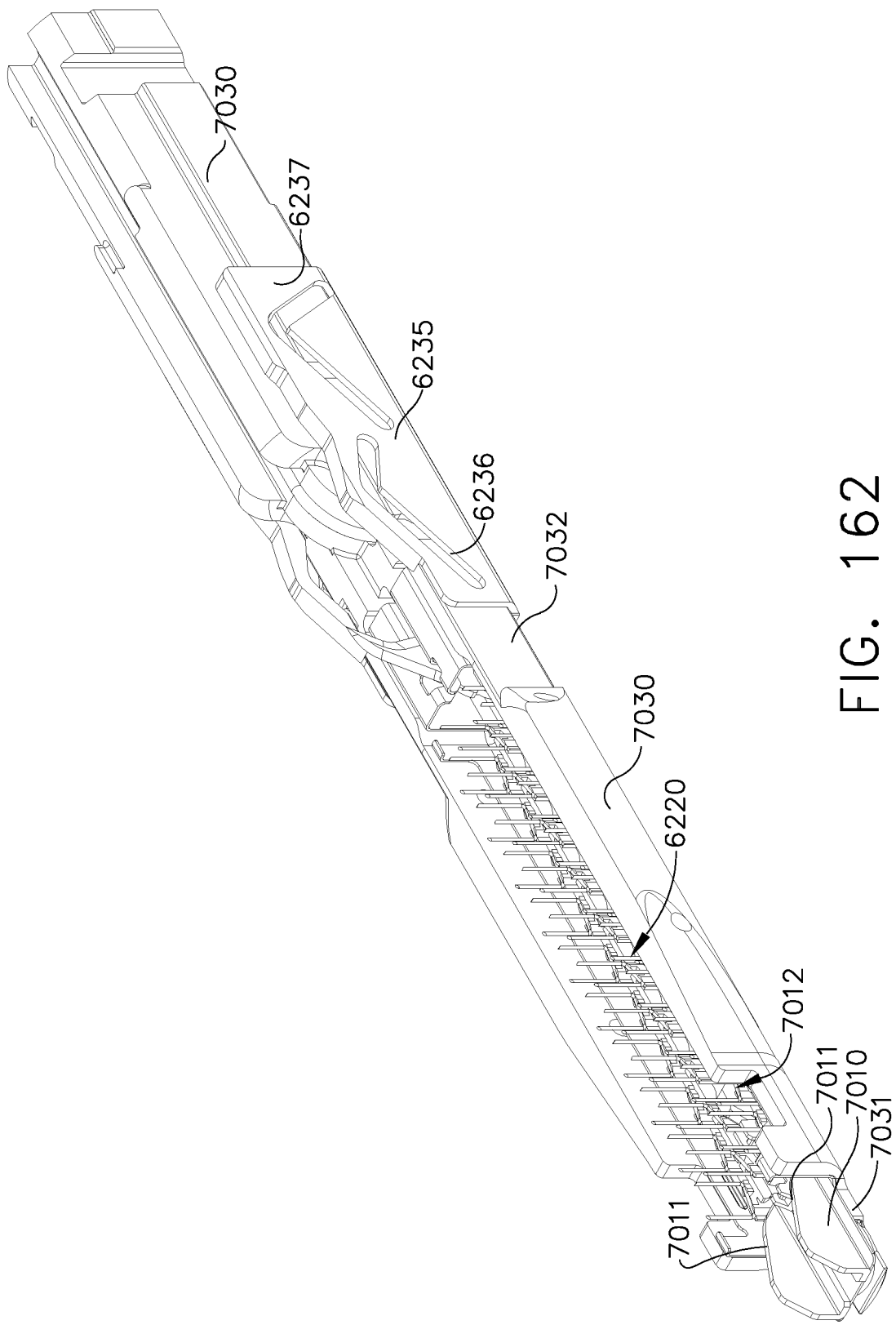
Figure 163:
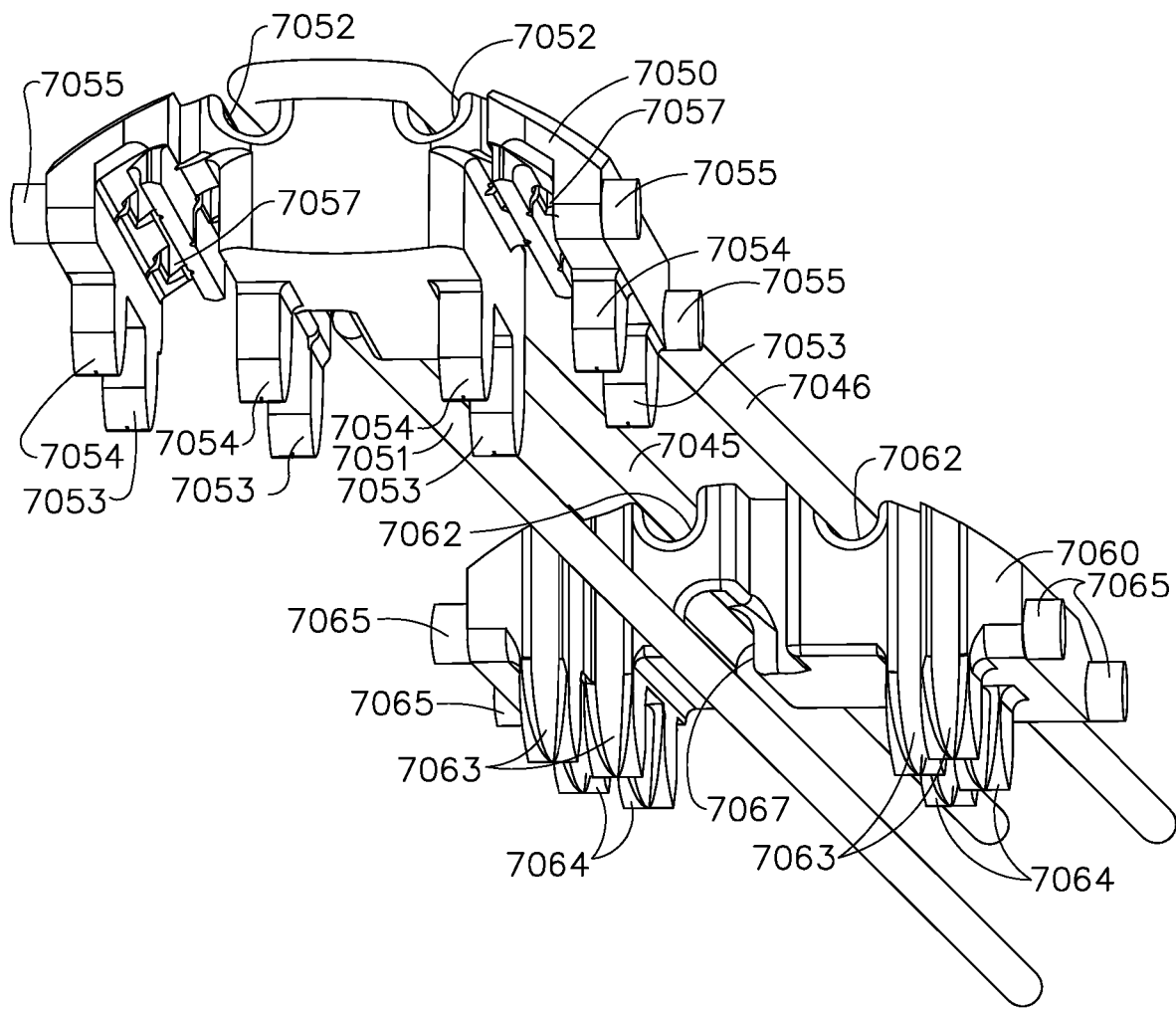
Figure 164:
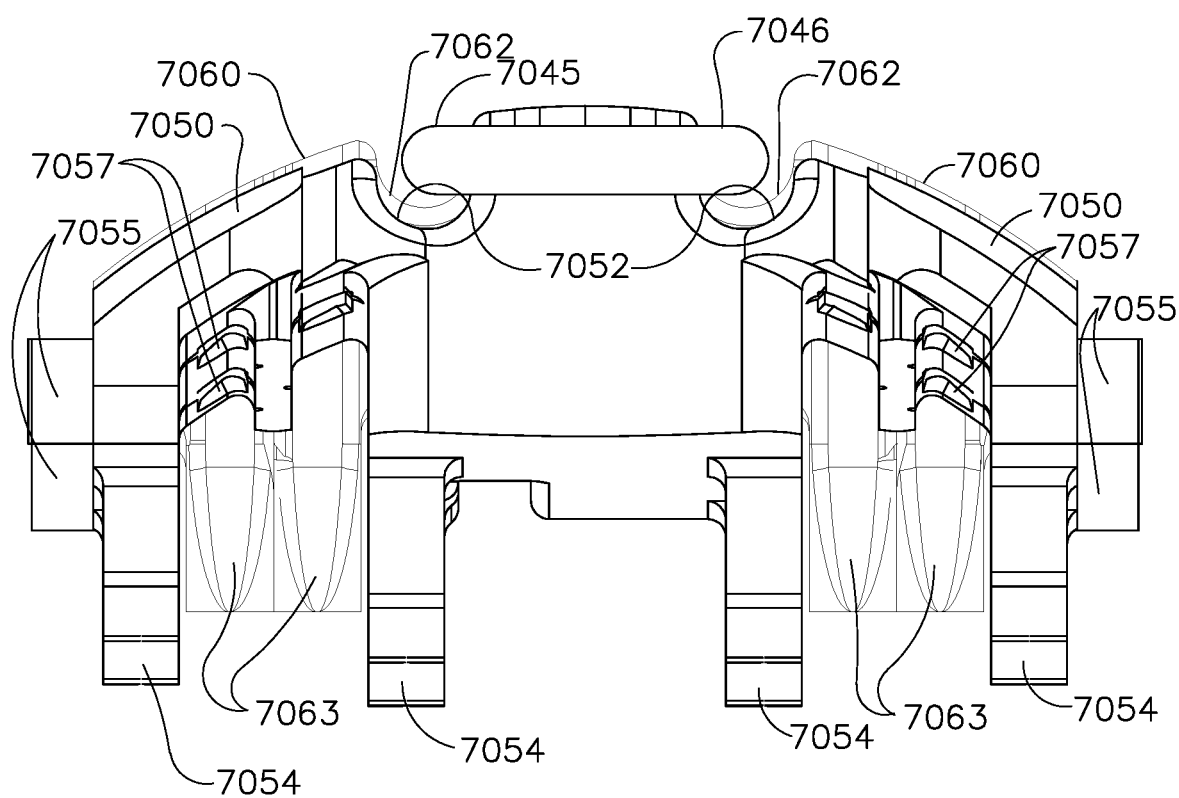
Figure 165:
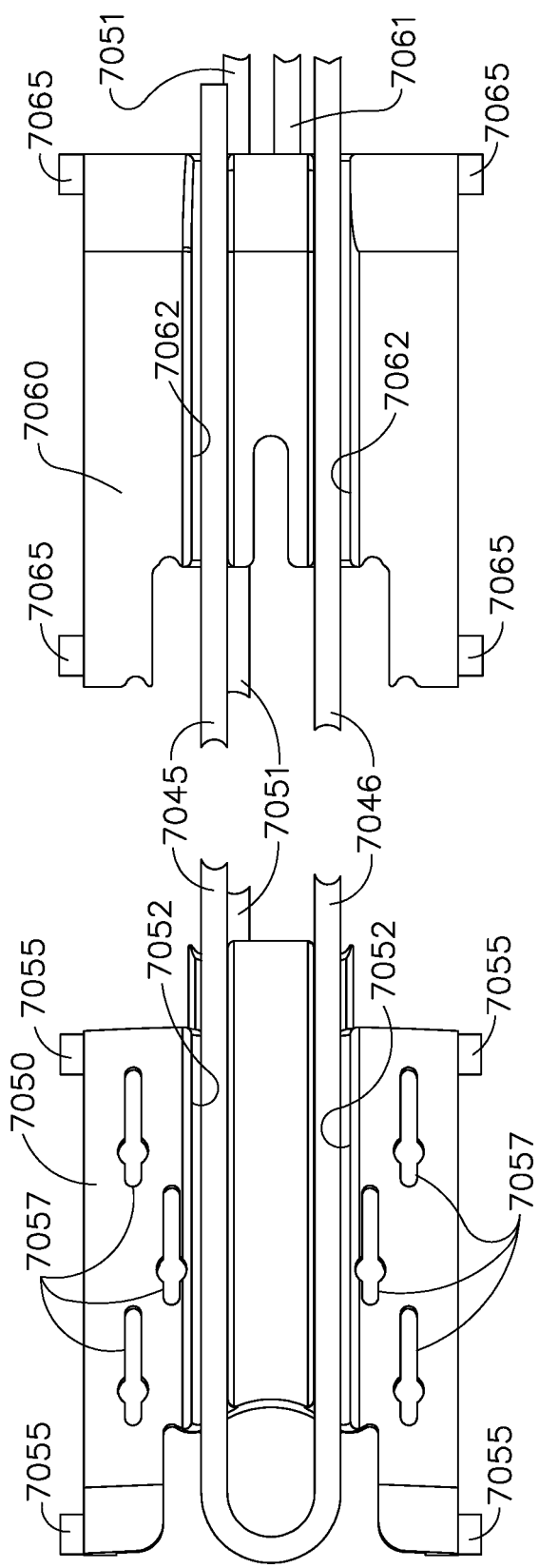
Figure 166:
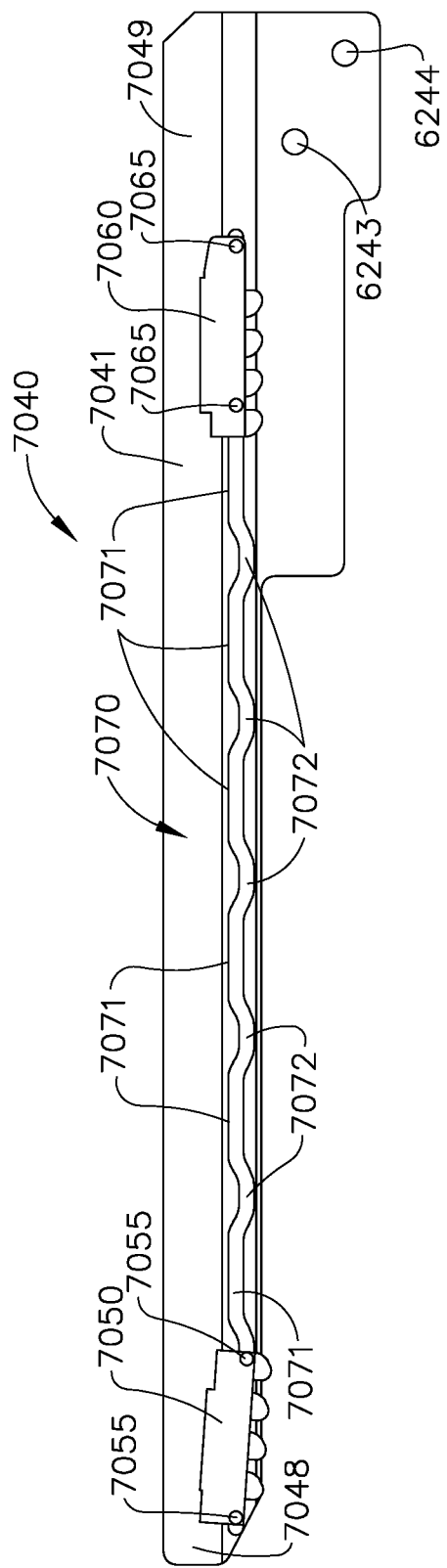
Figure 167:
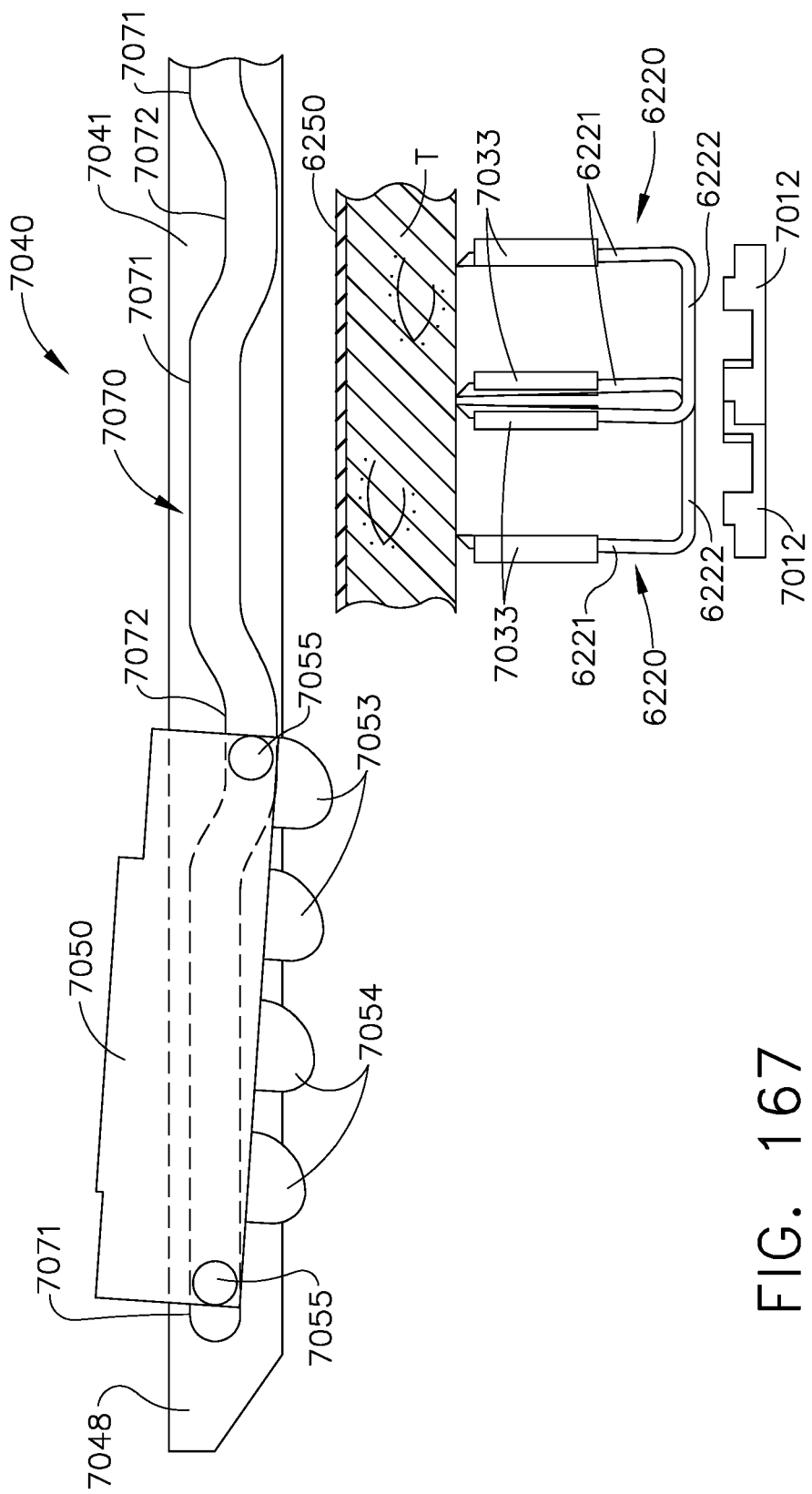
Figure 168:
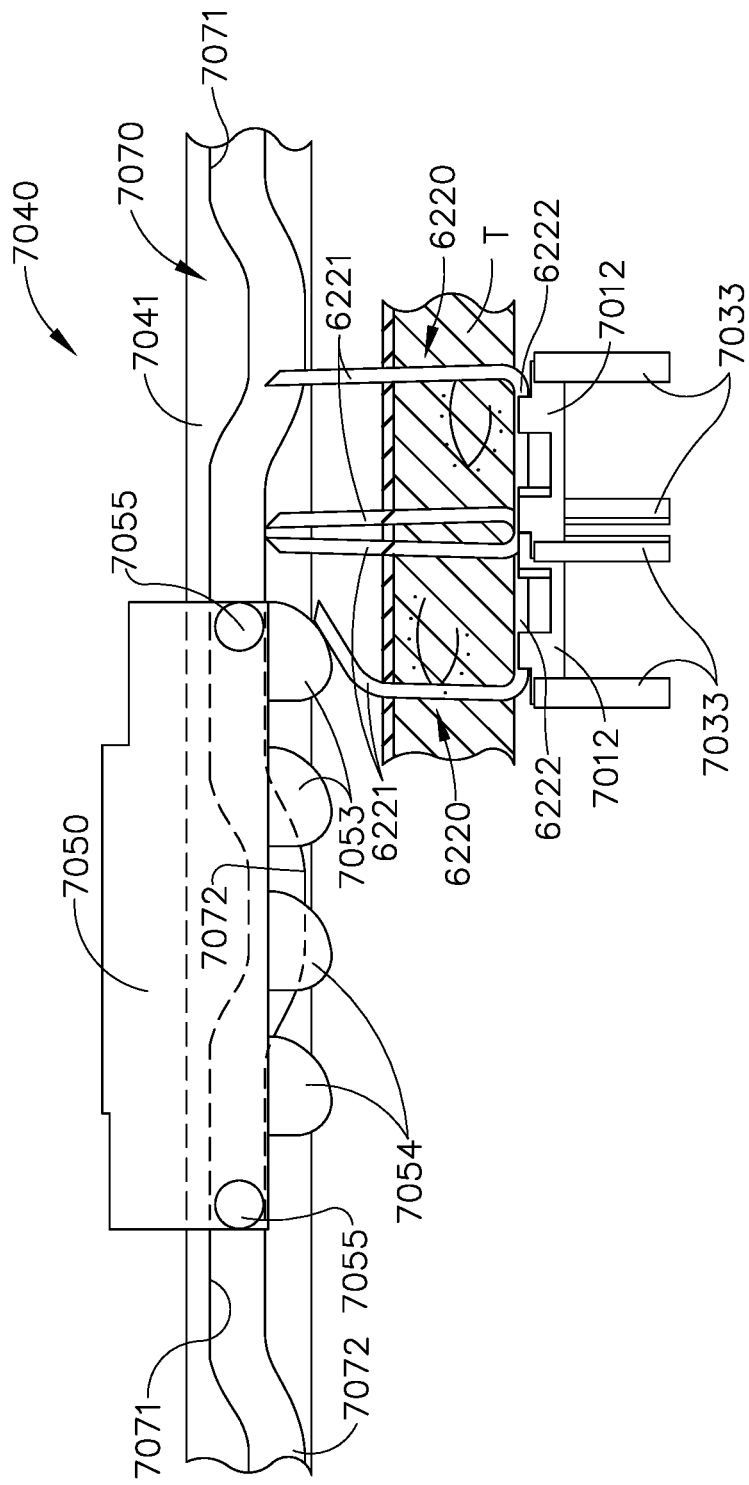
Figure 169:
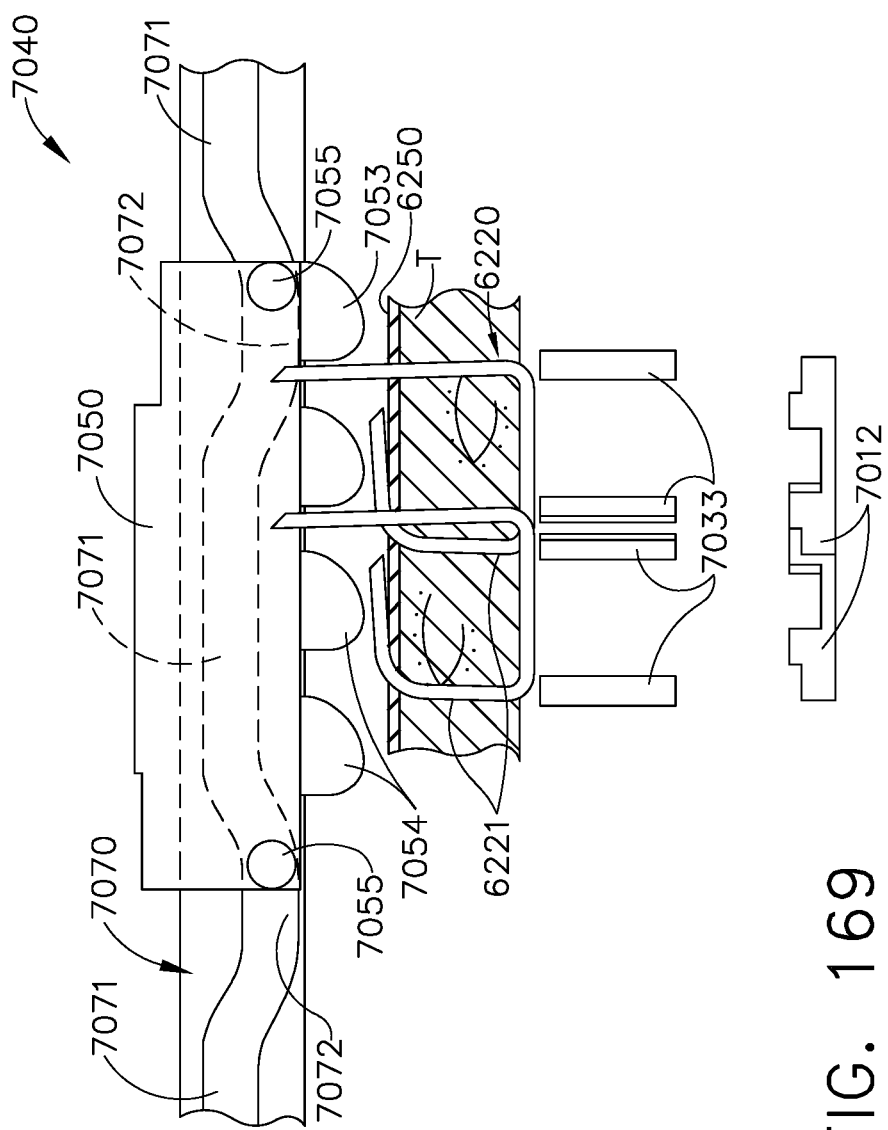
Figure 170:
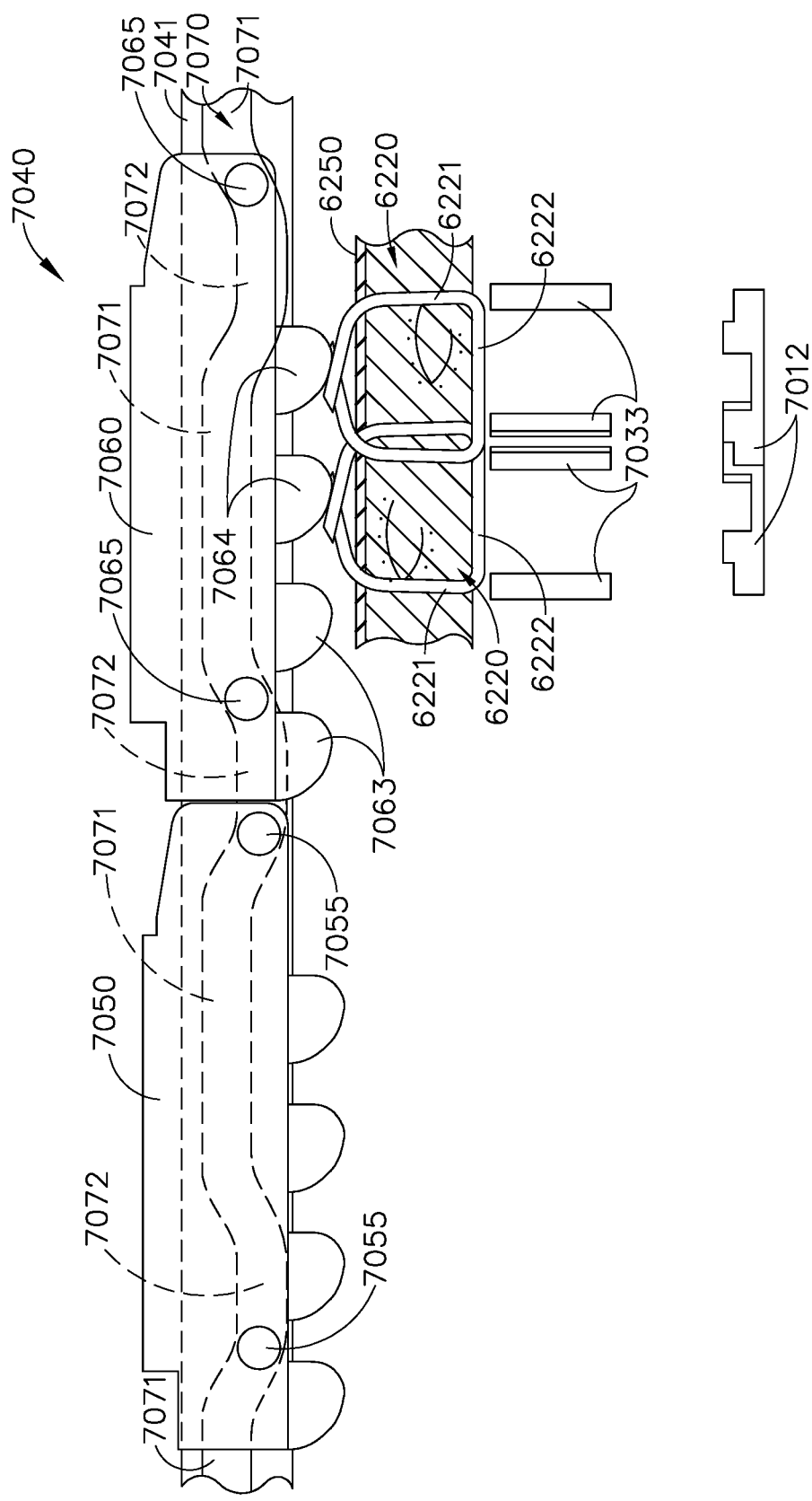
Figure 179:
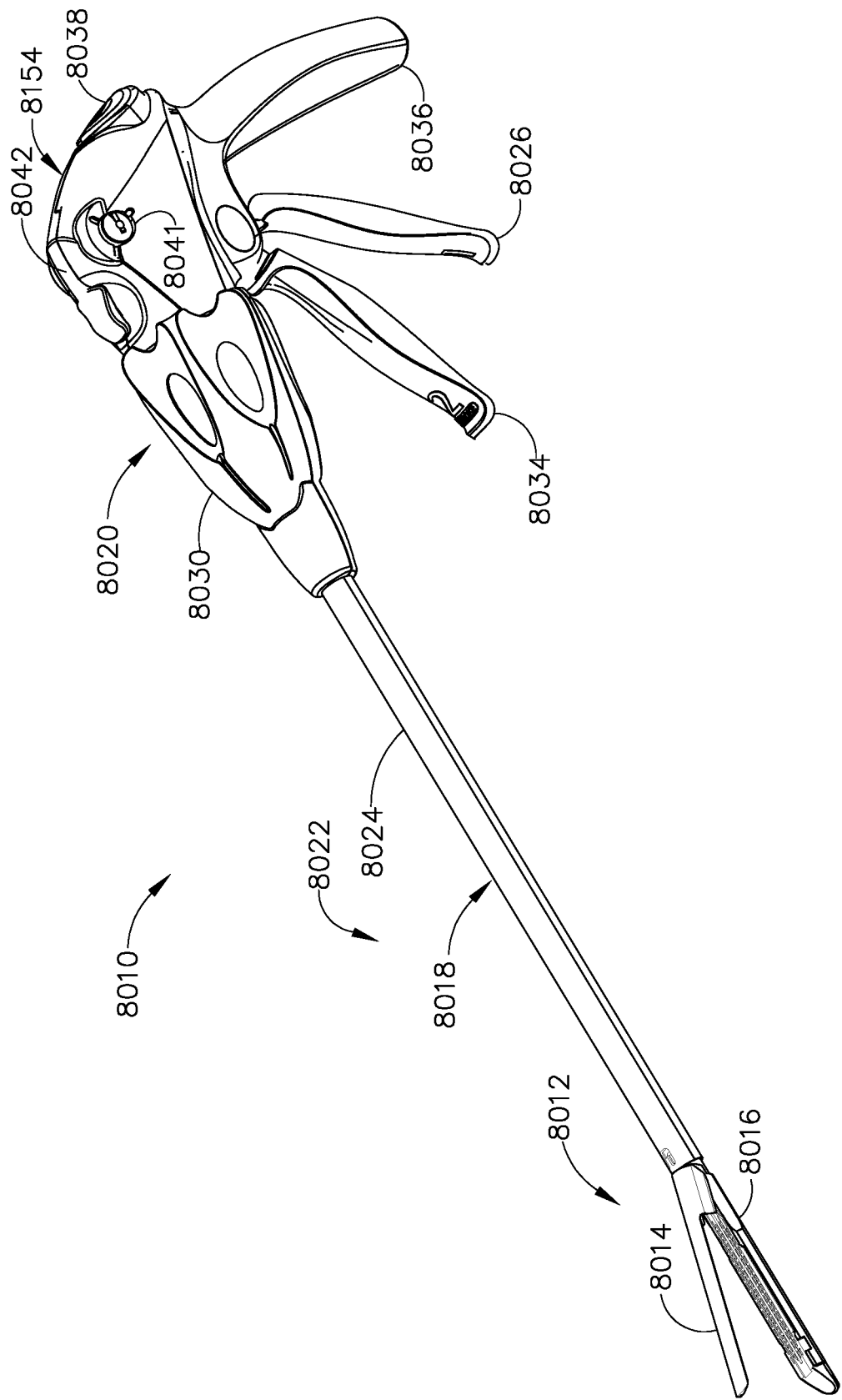
Figure 180:
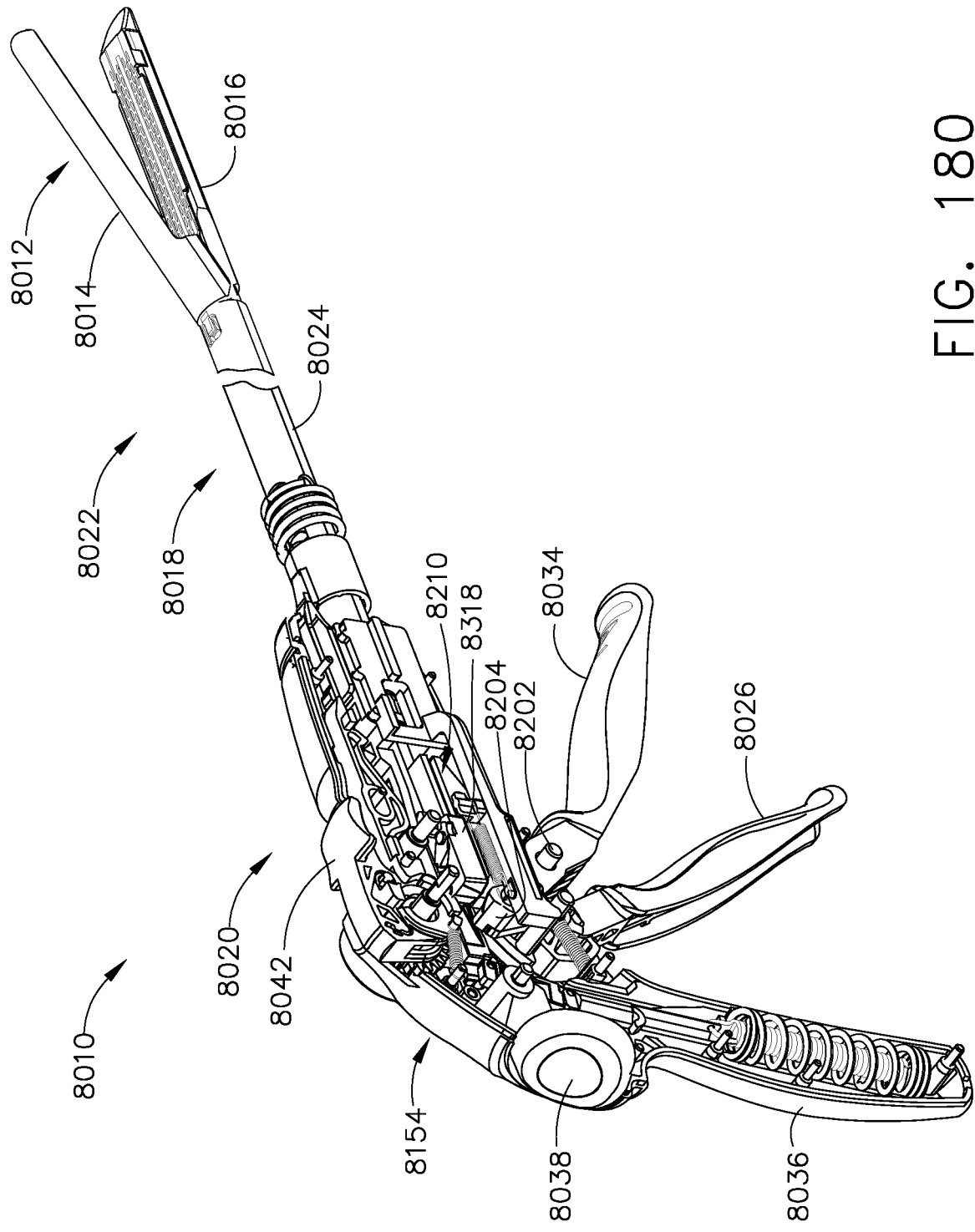
Figure 181:
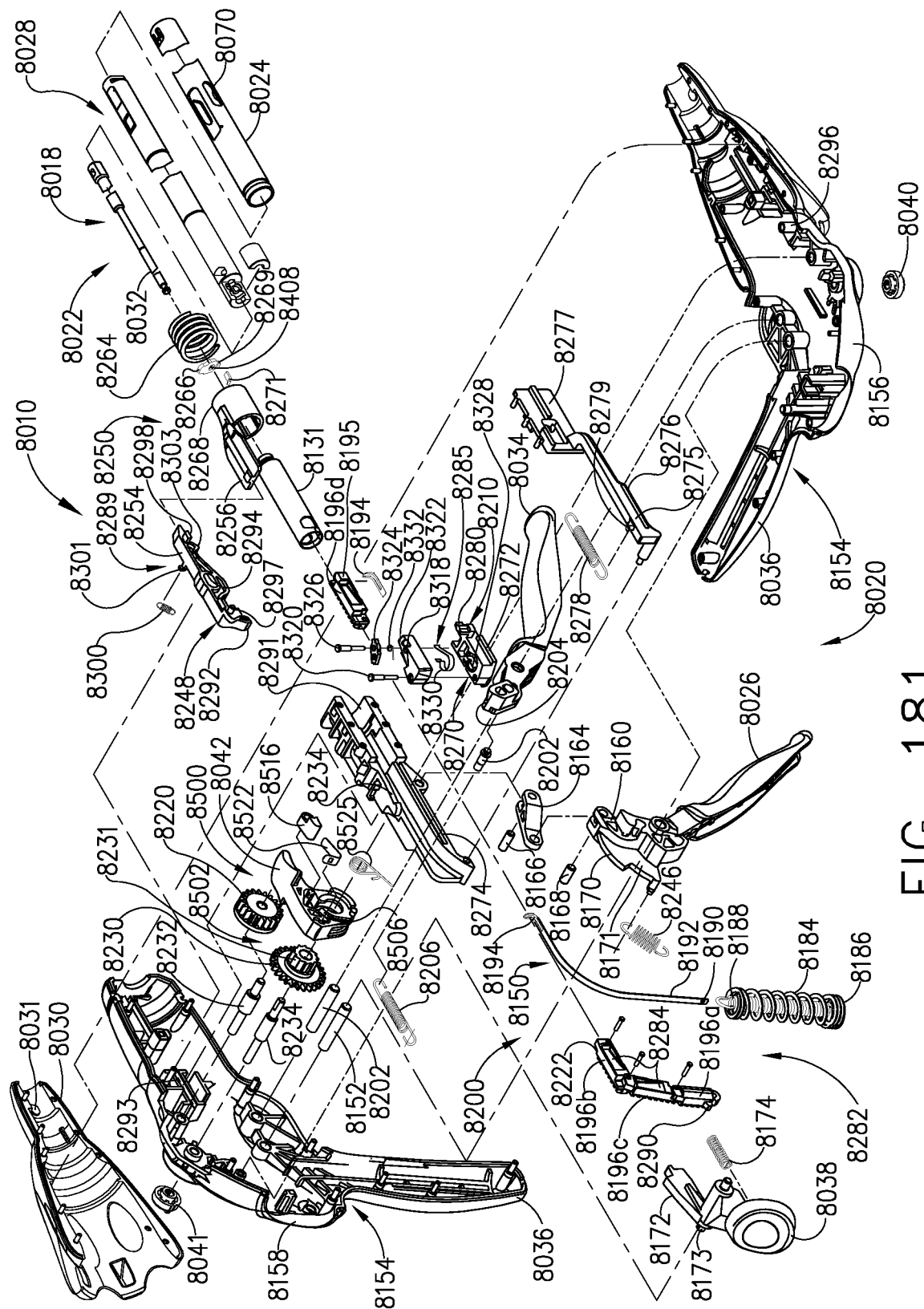
Figure 182:
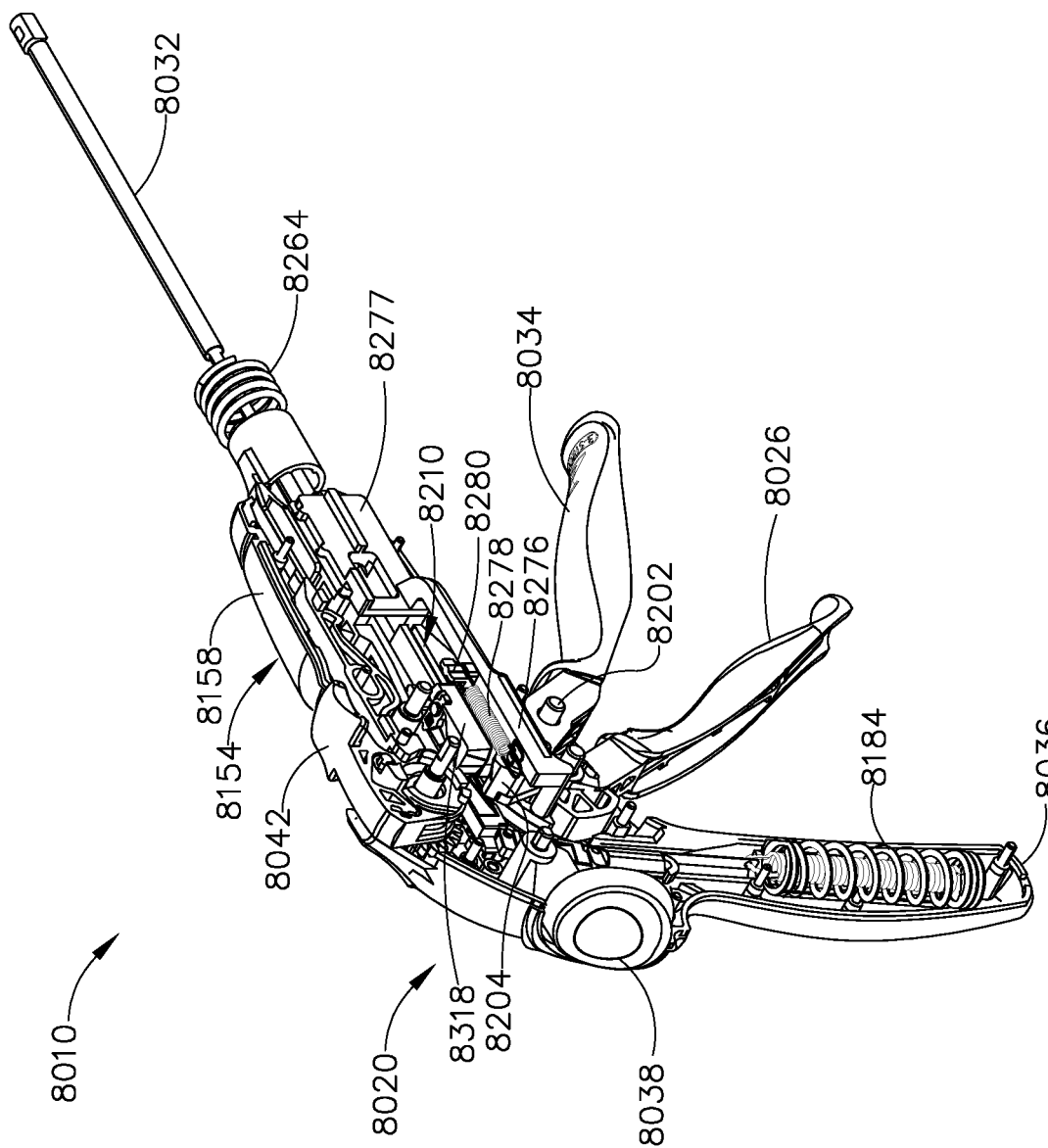
Figure 183:
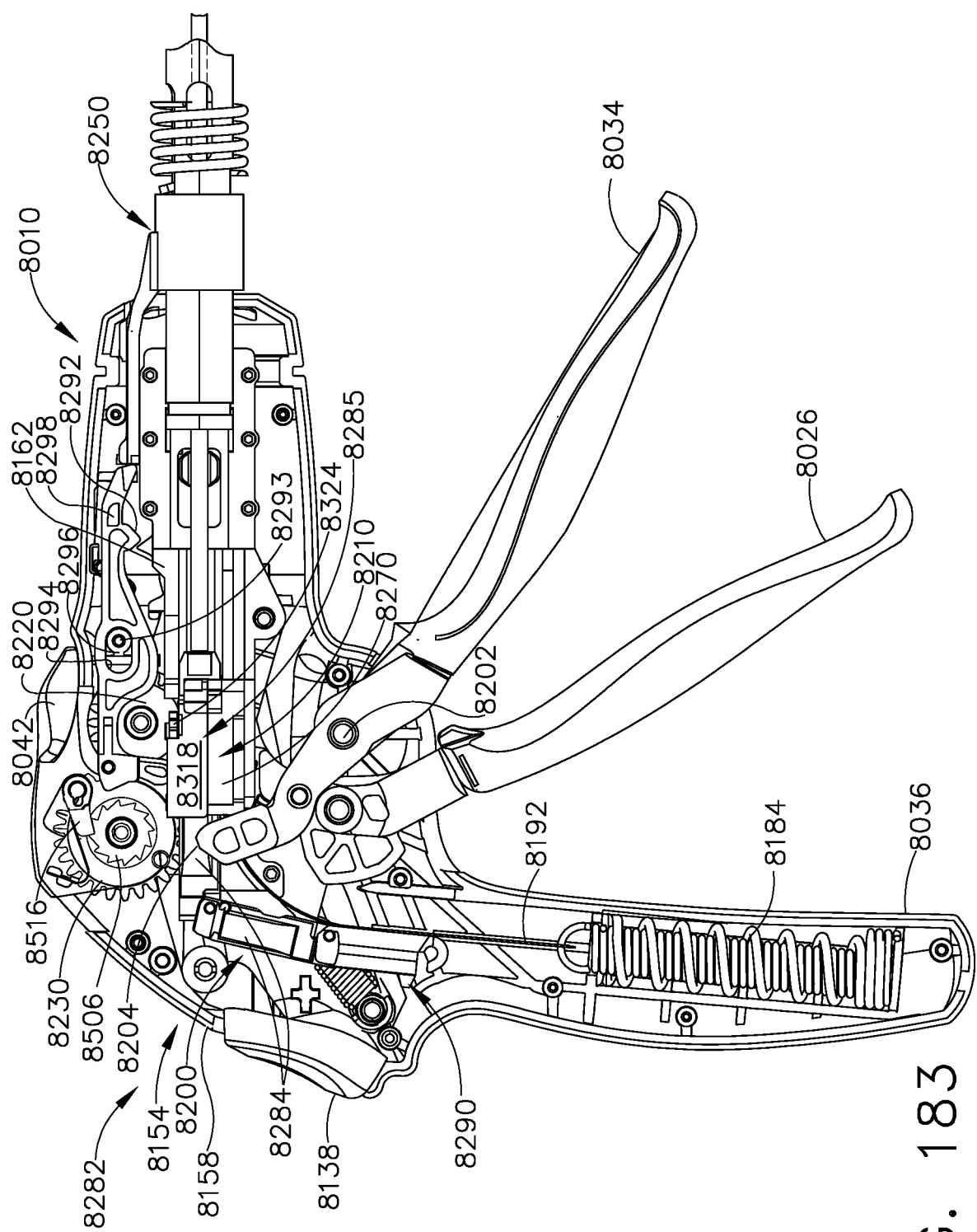
Figure 184:
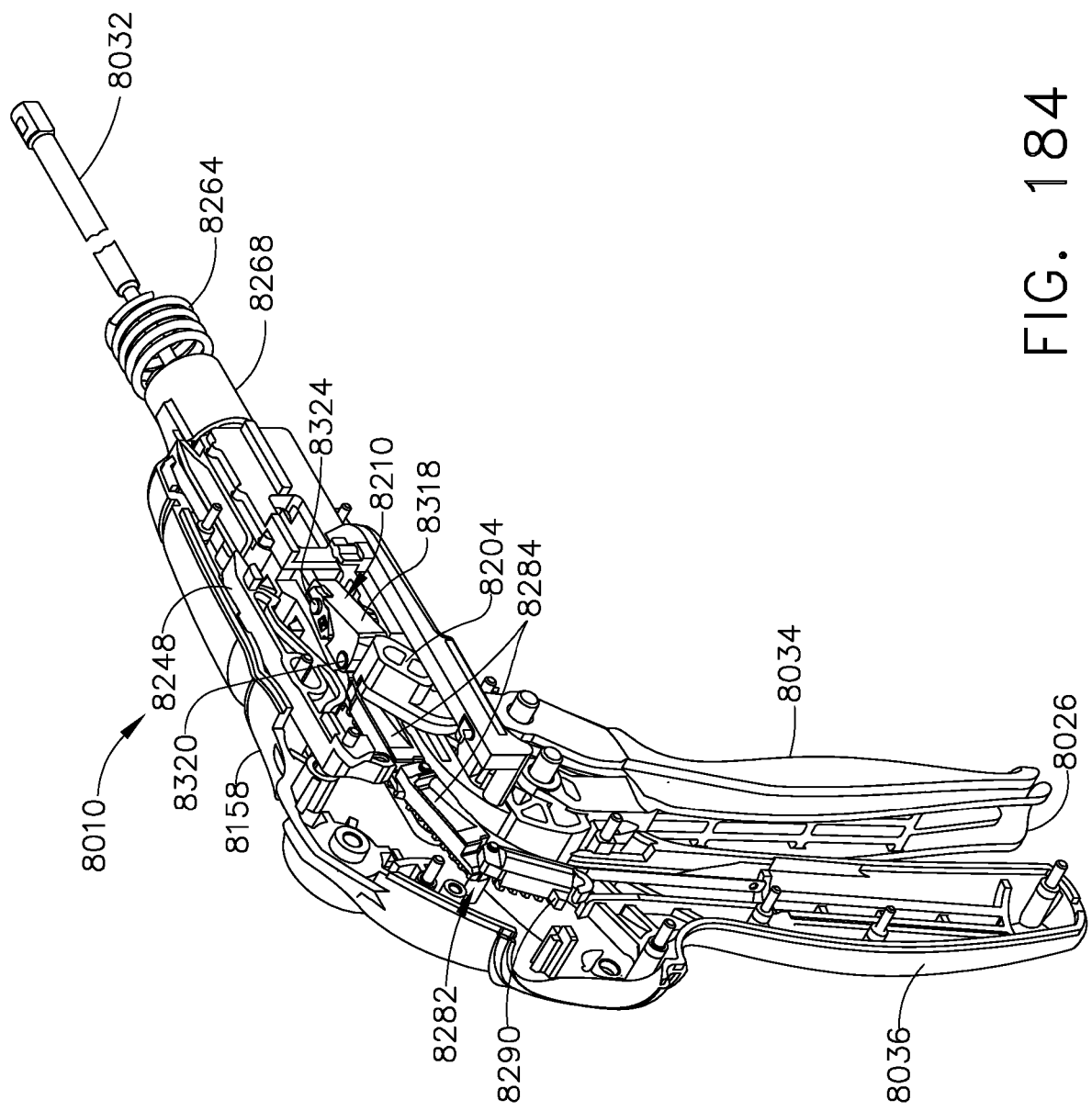
Figure 185:
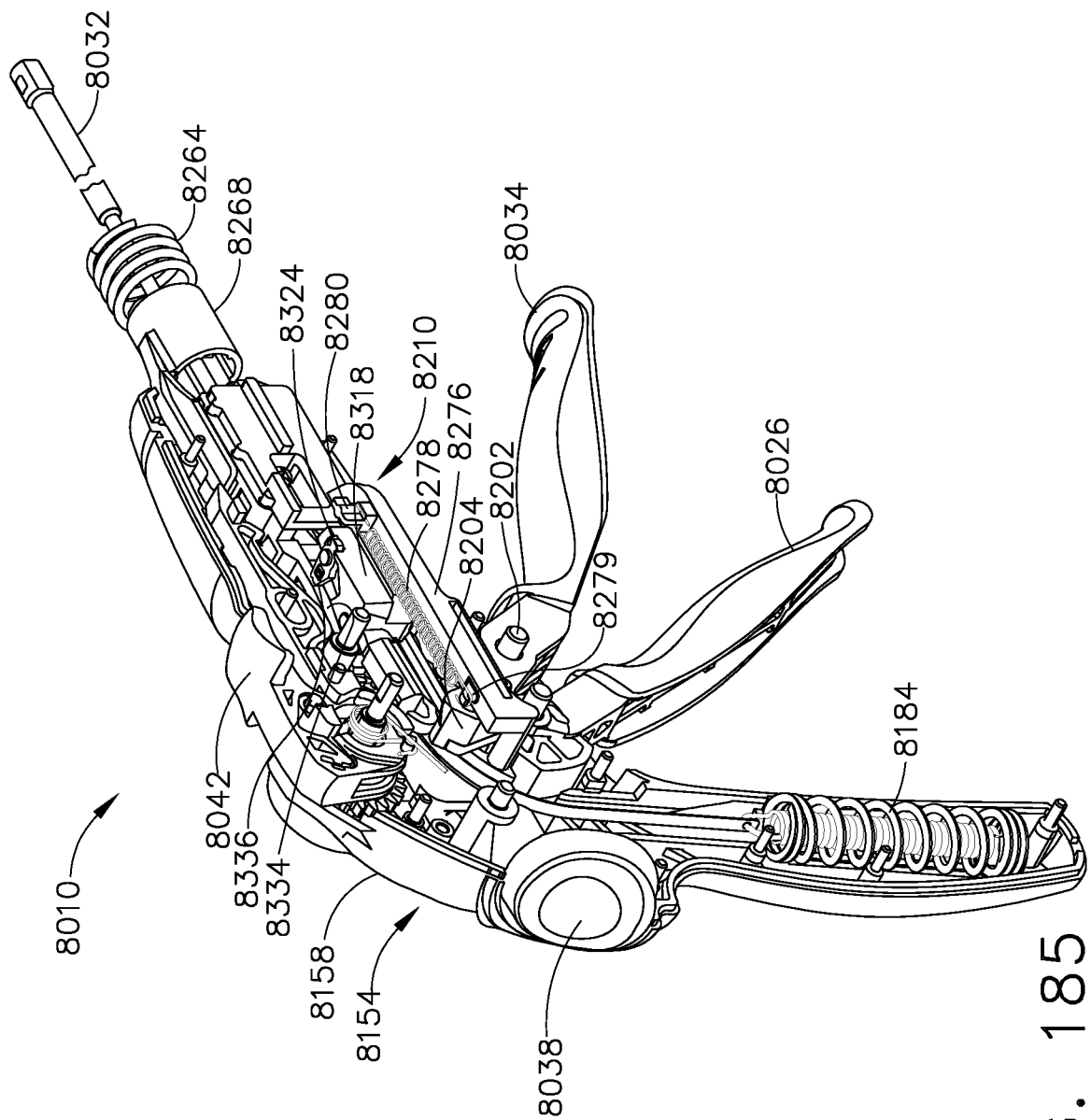
Figure 186:
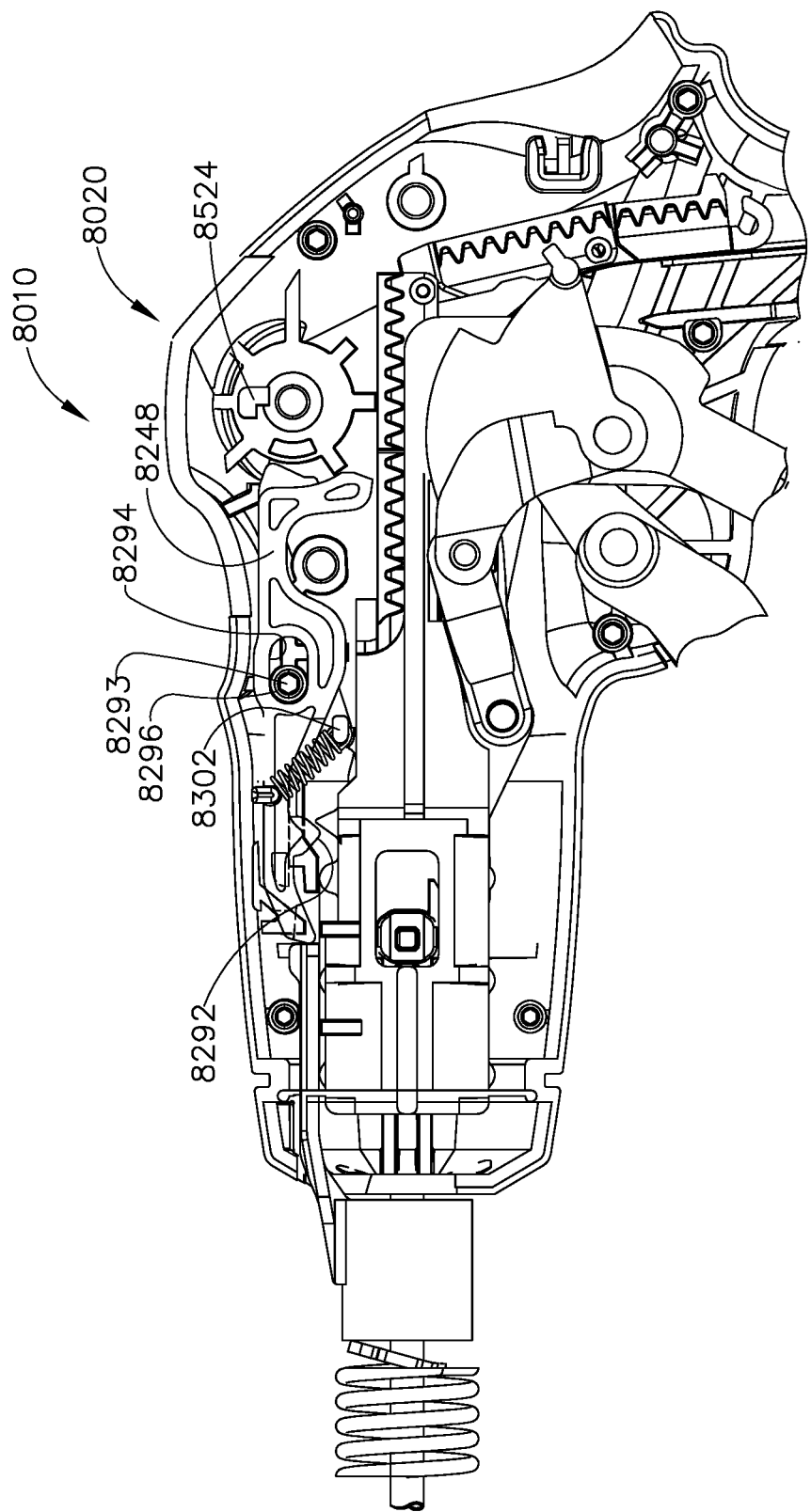
Figure 187:
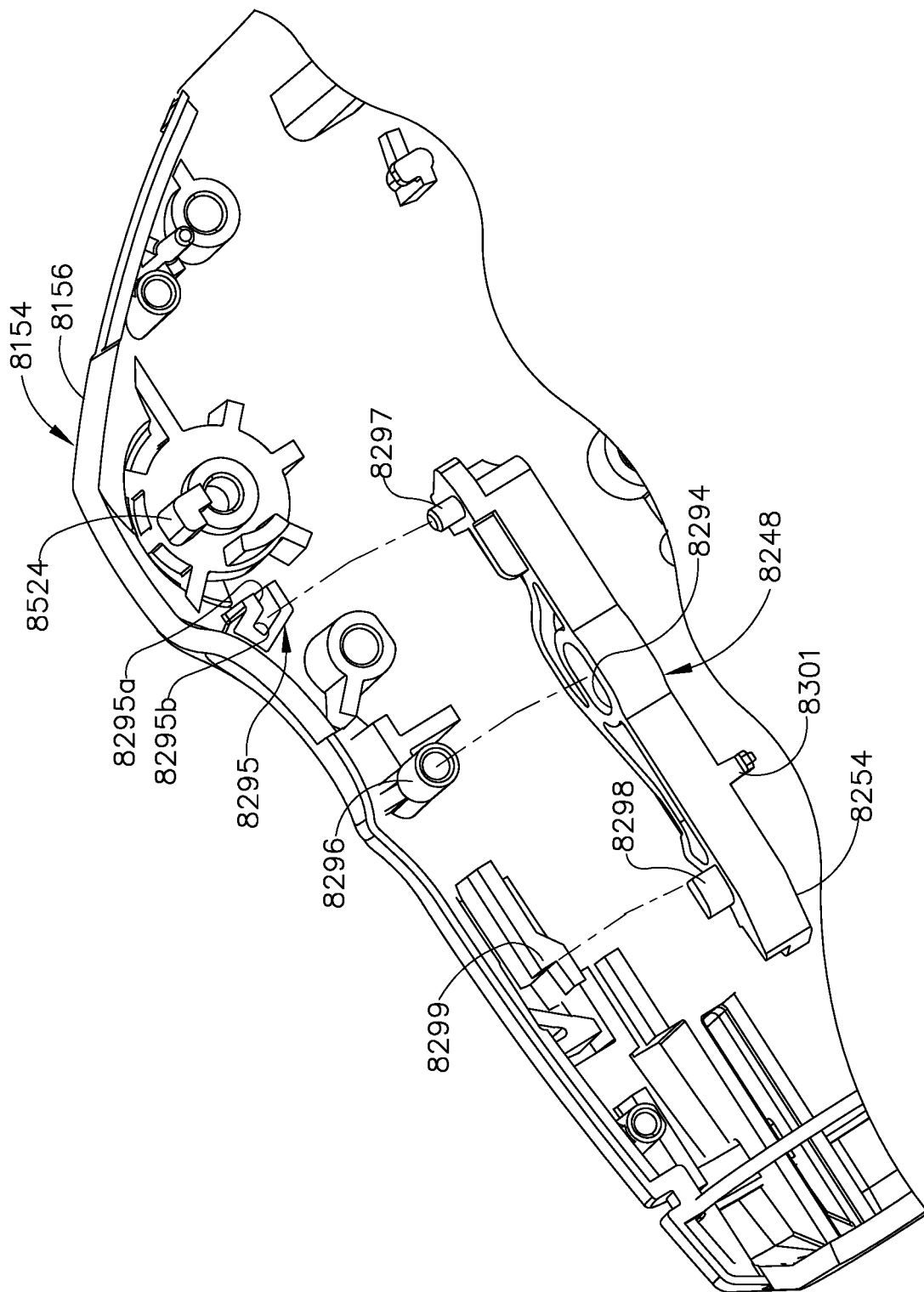
Figure 188:
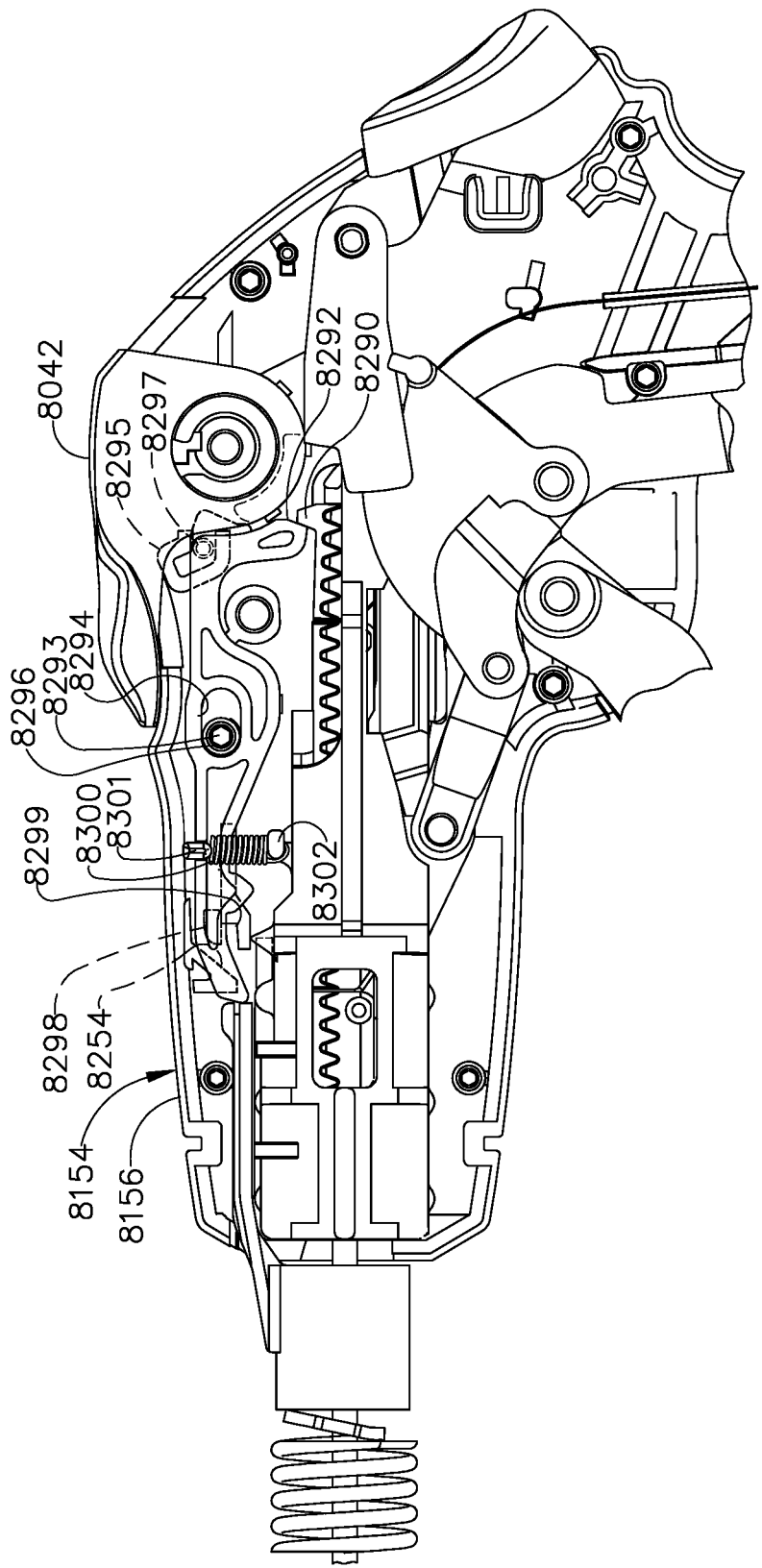
Figure 189:
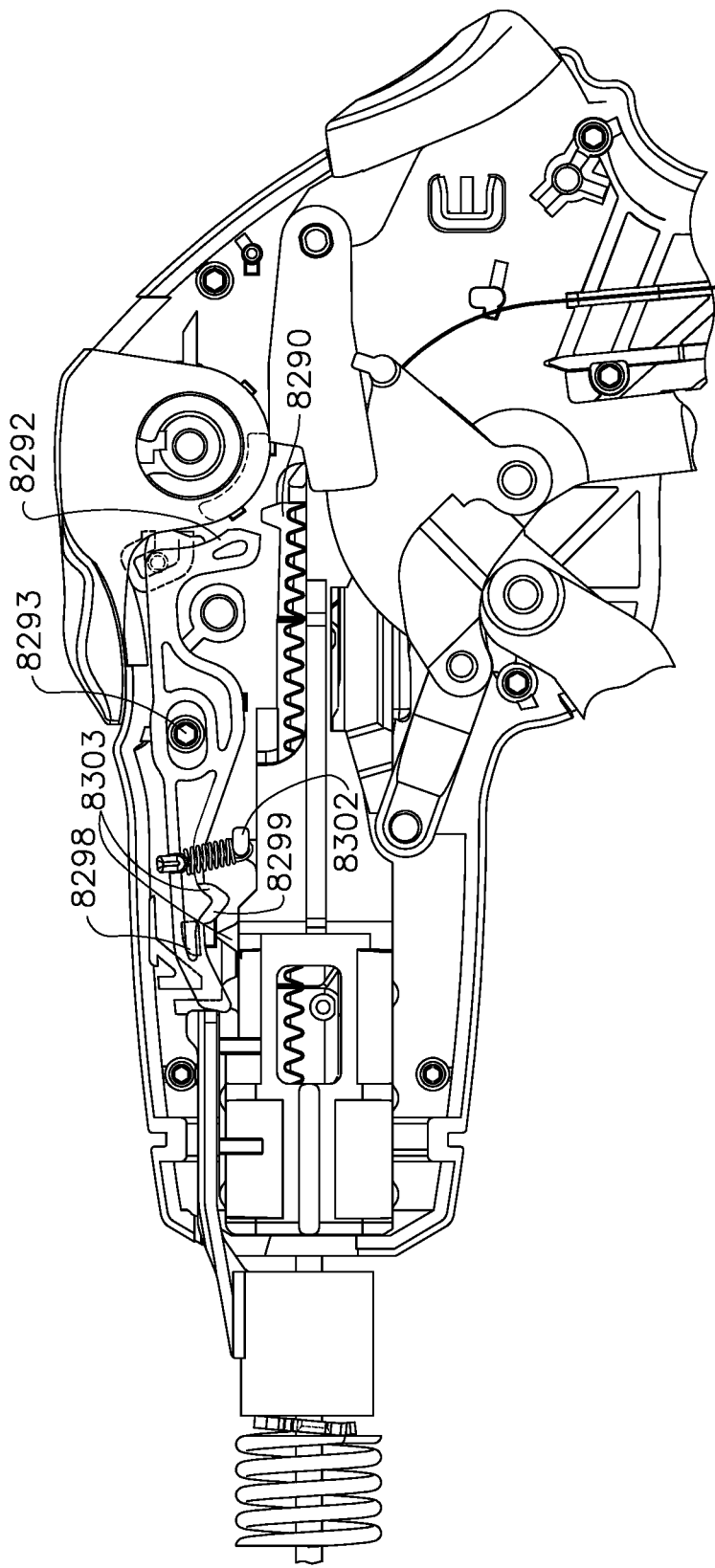
Figure 190:
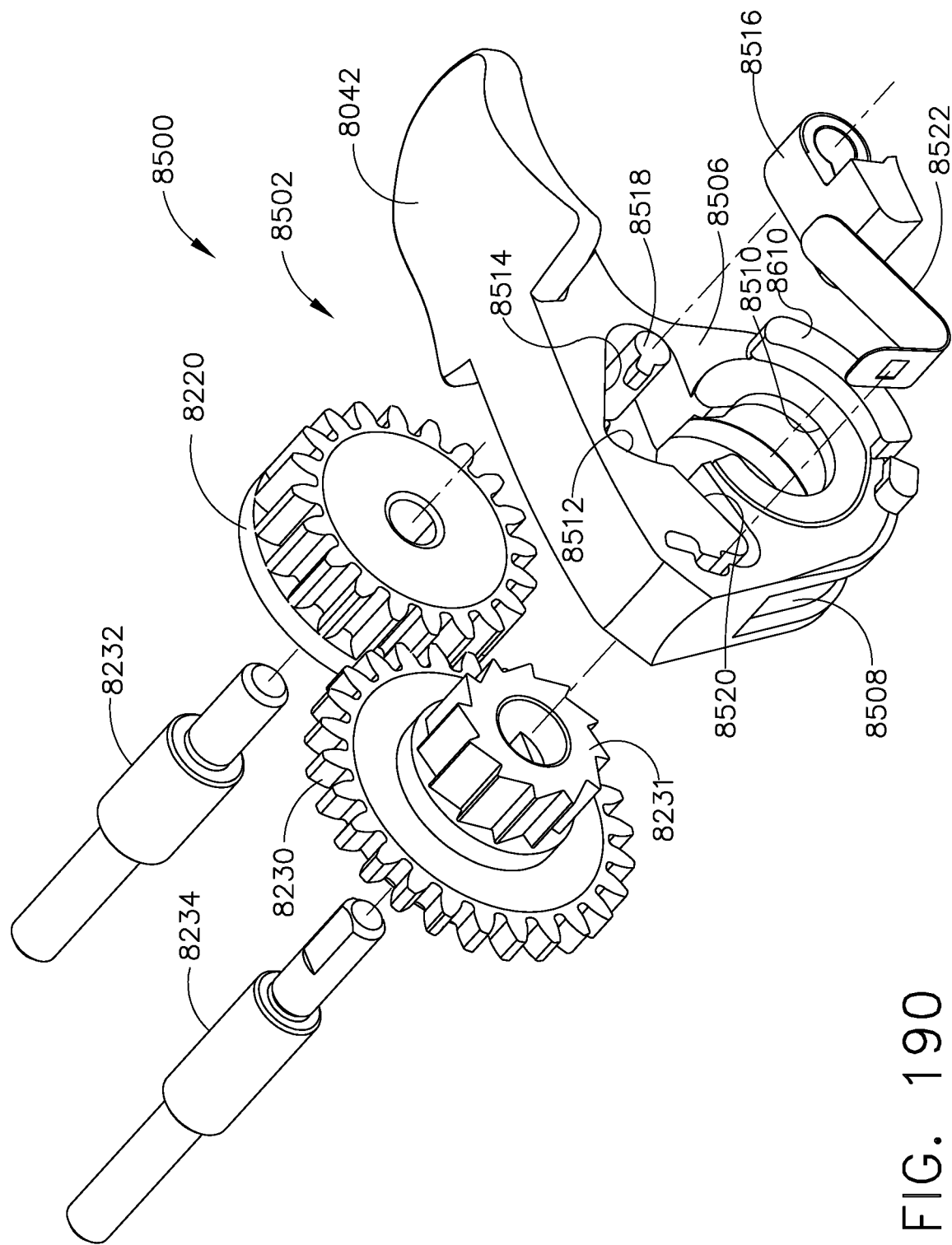
Figure 191:
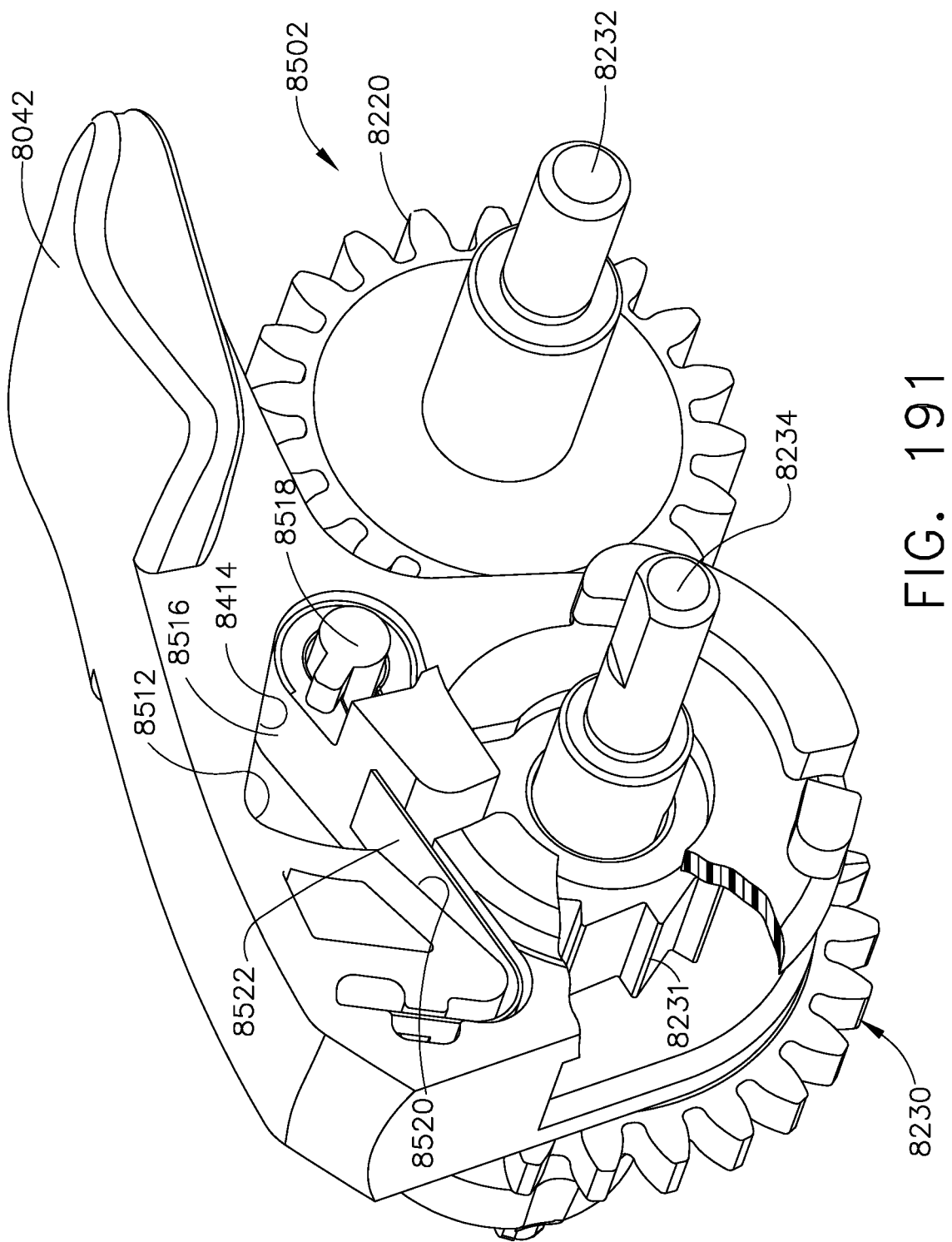
Figure 192:
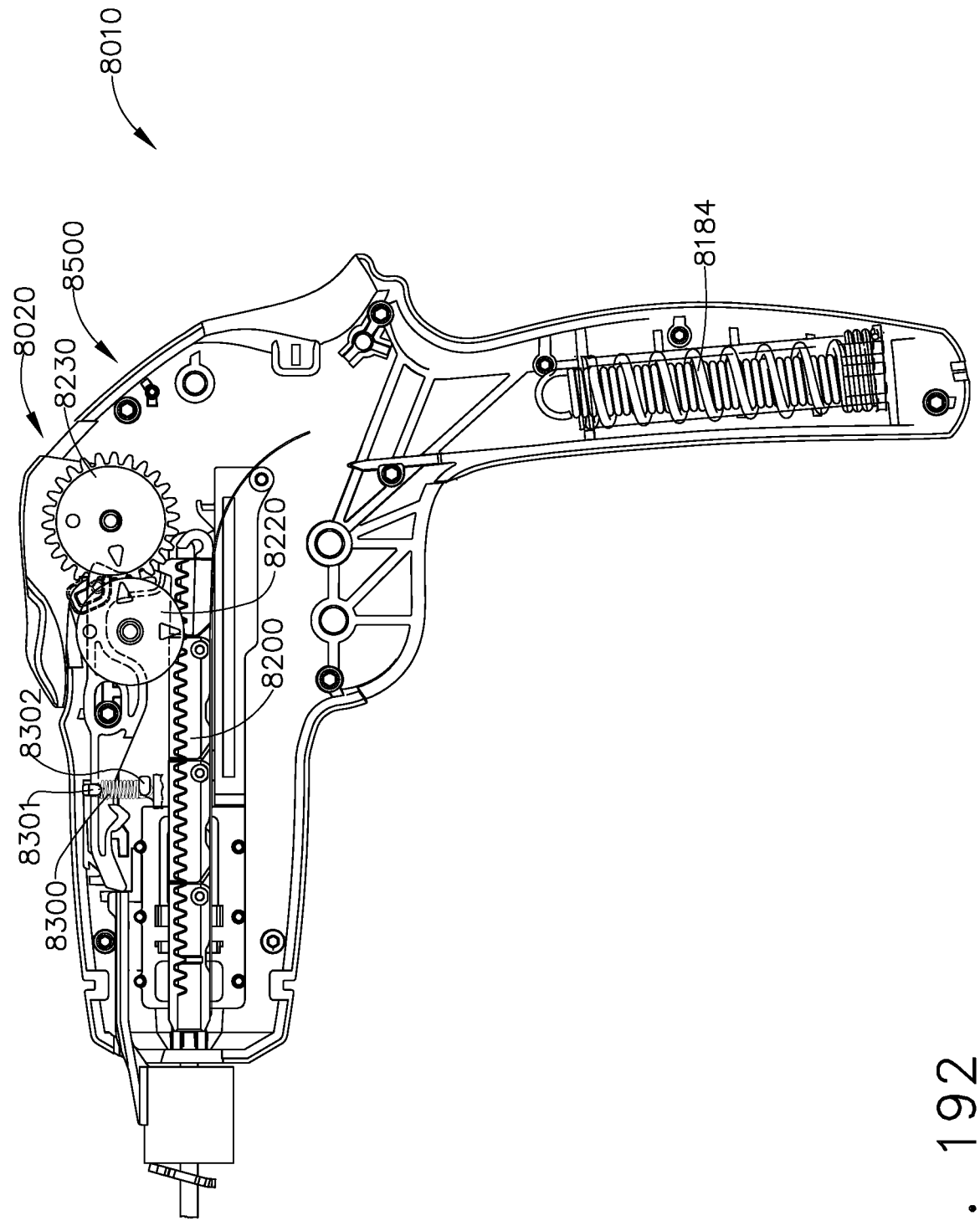
Figure 193:
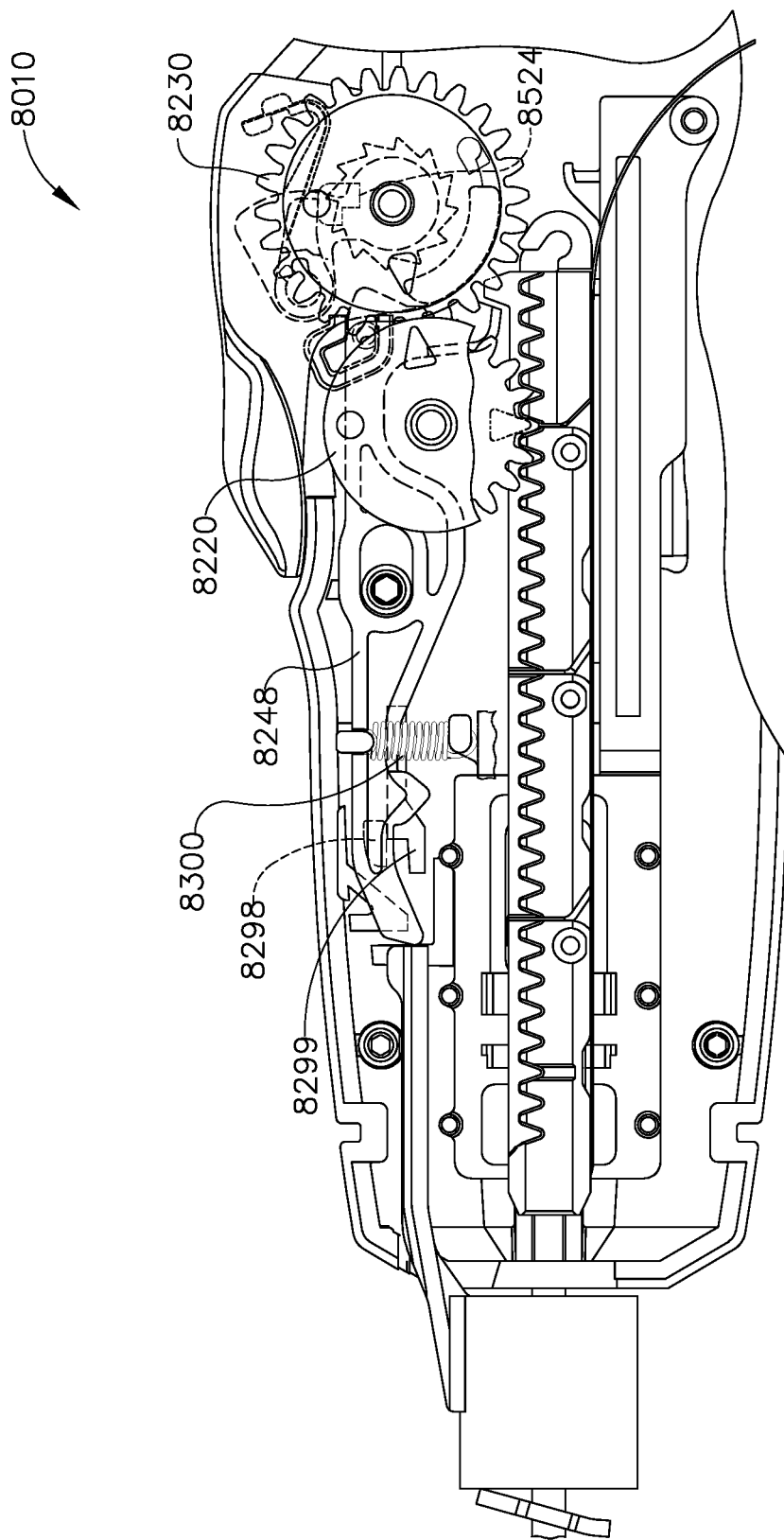
Figure 194:
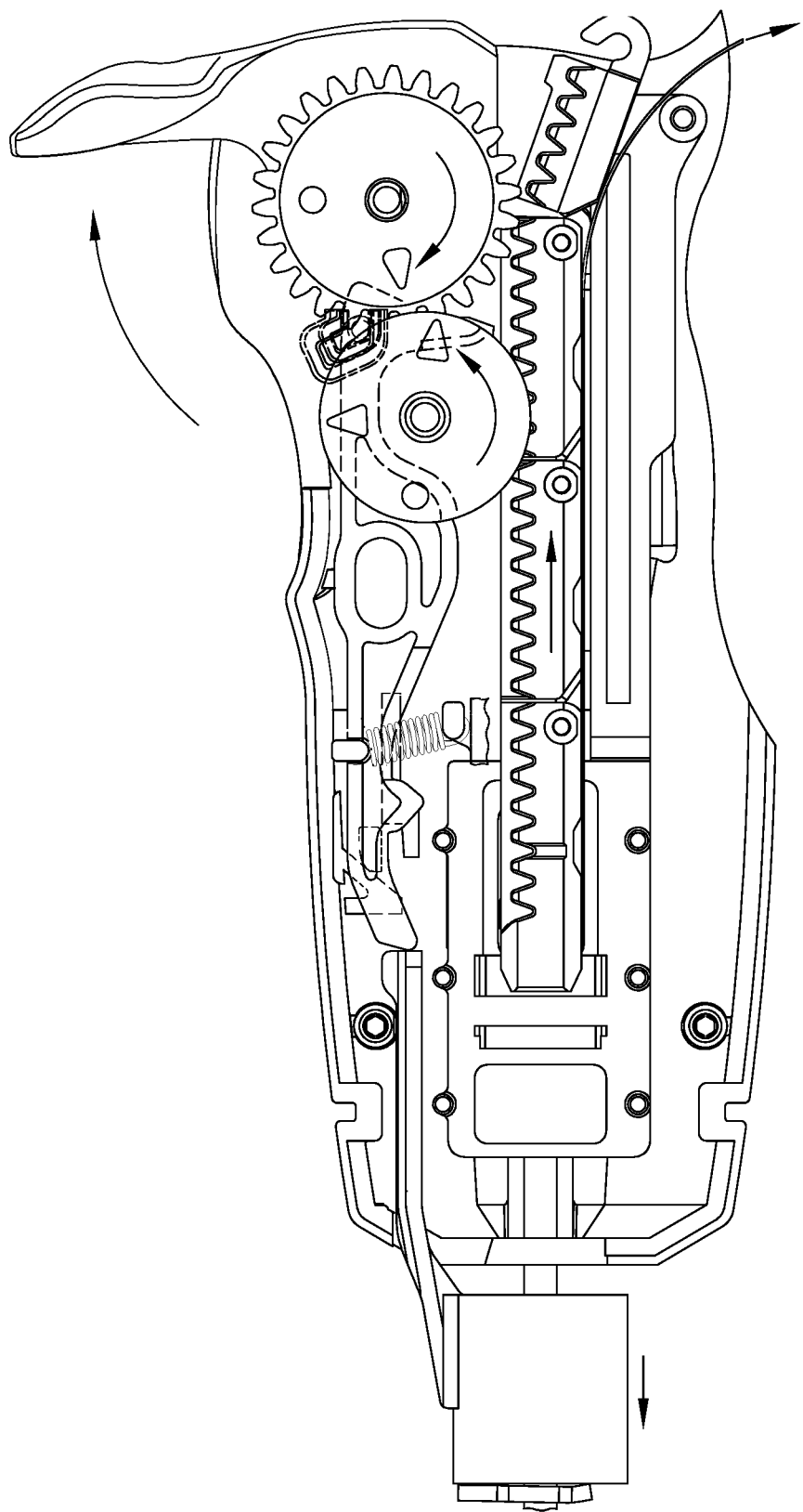
Figure 195:
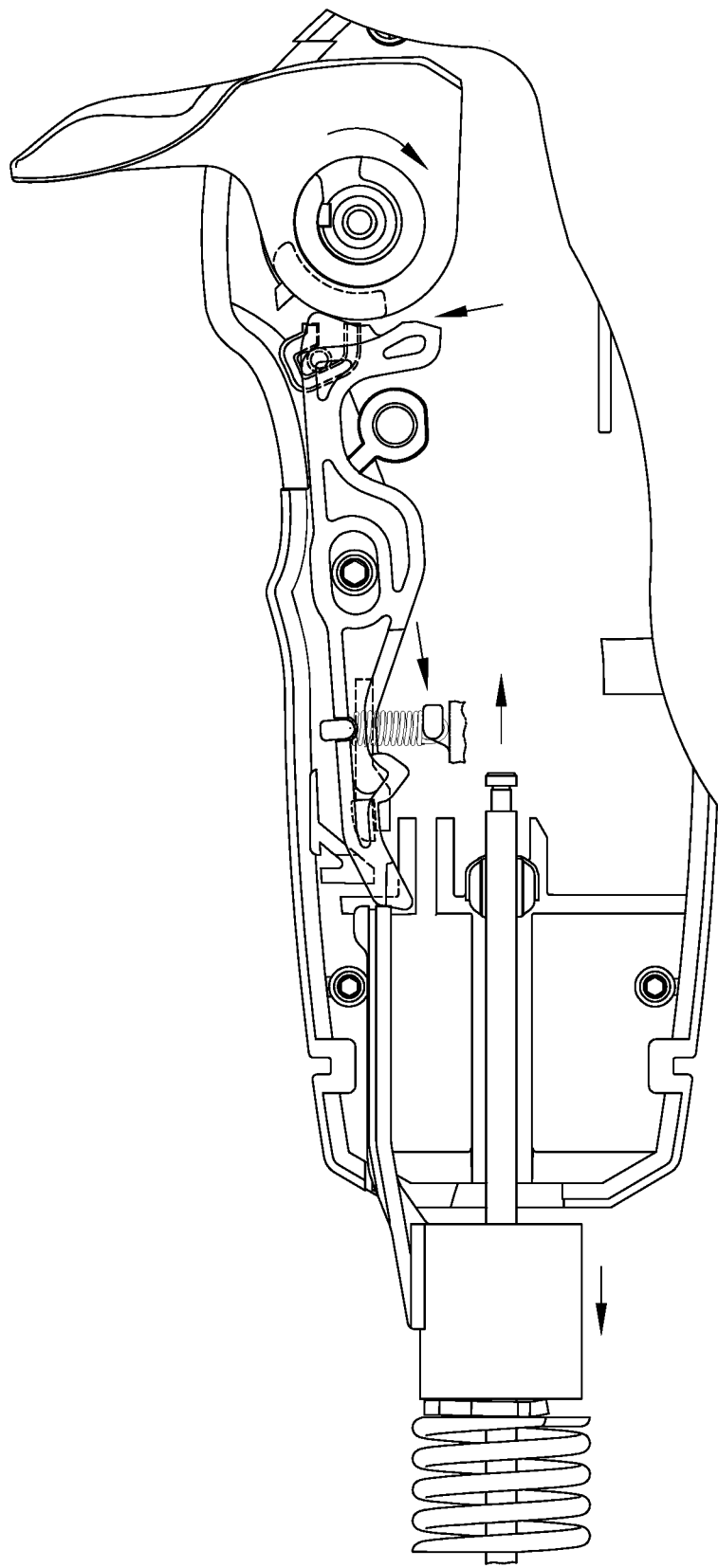
Figure 196:
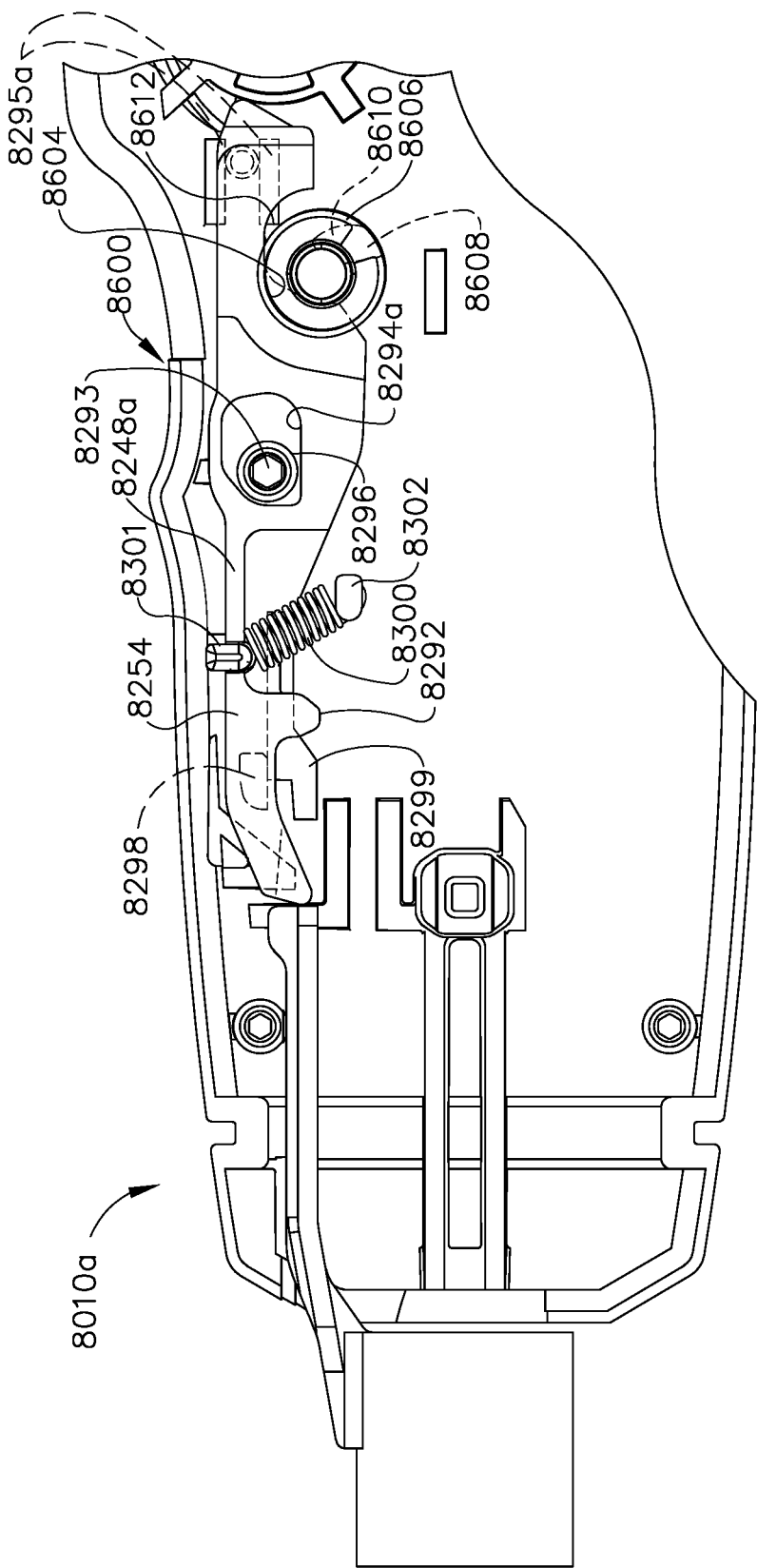
Figure 197:
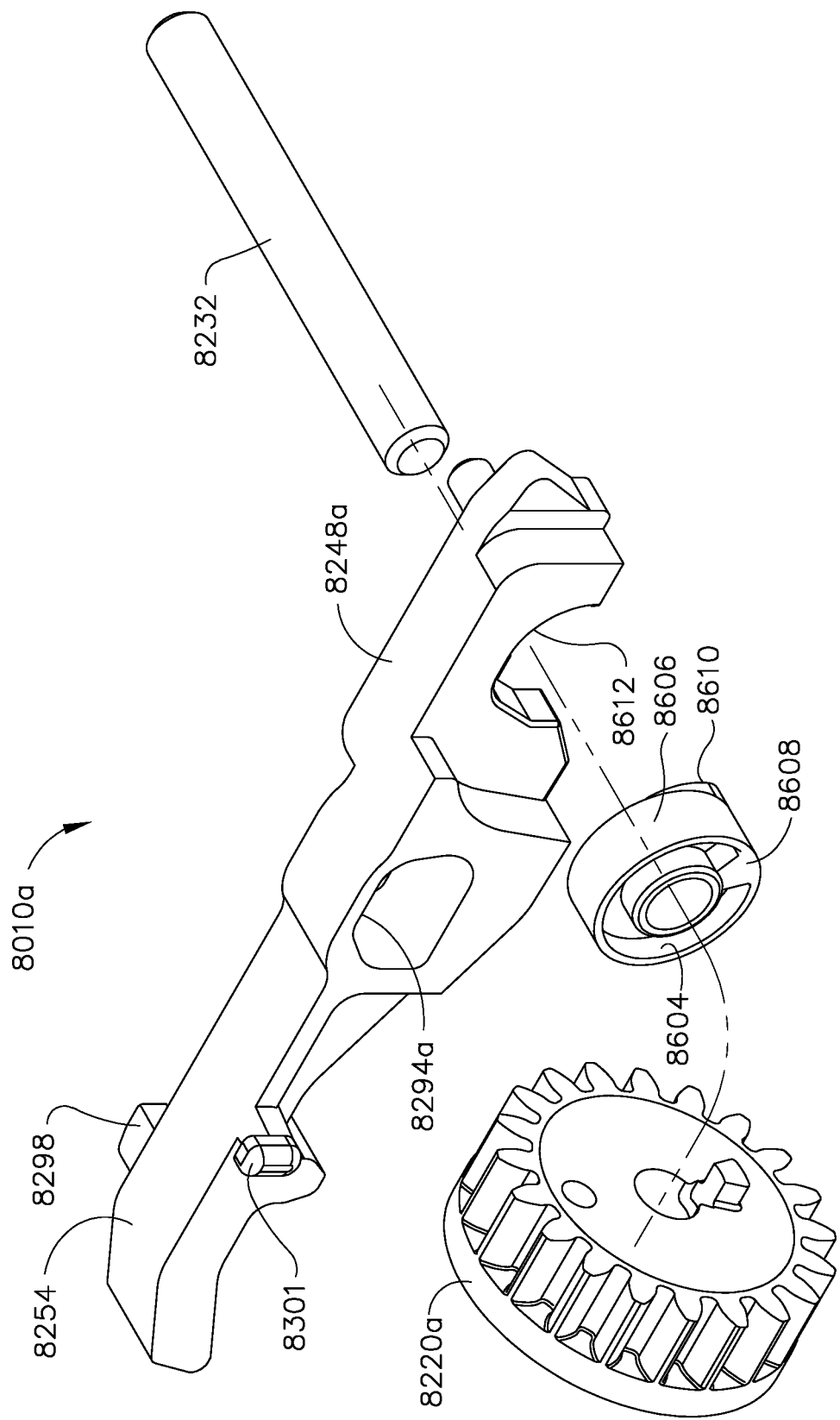
Figure 198:
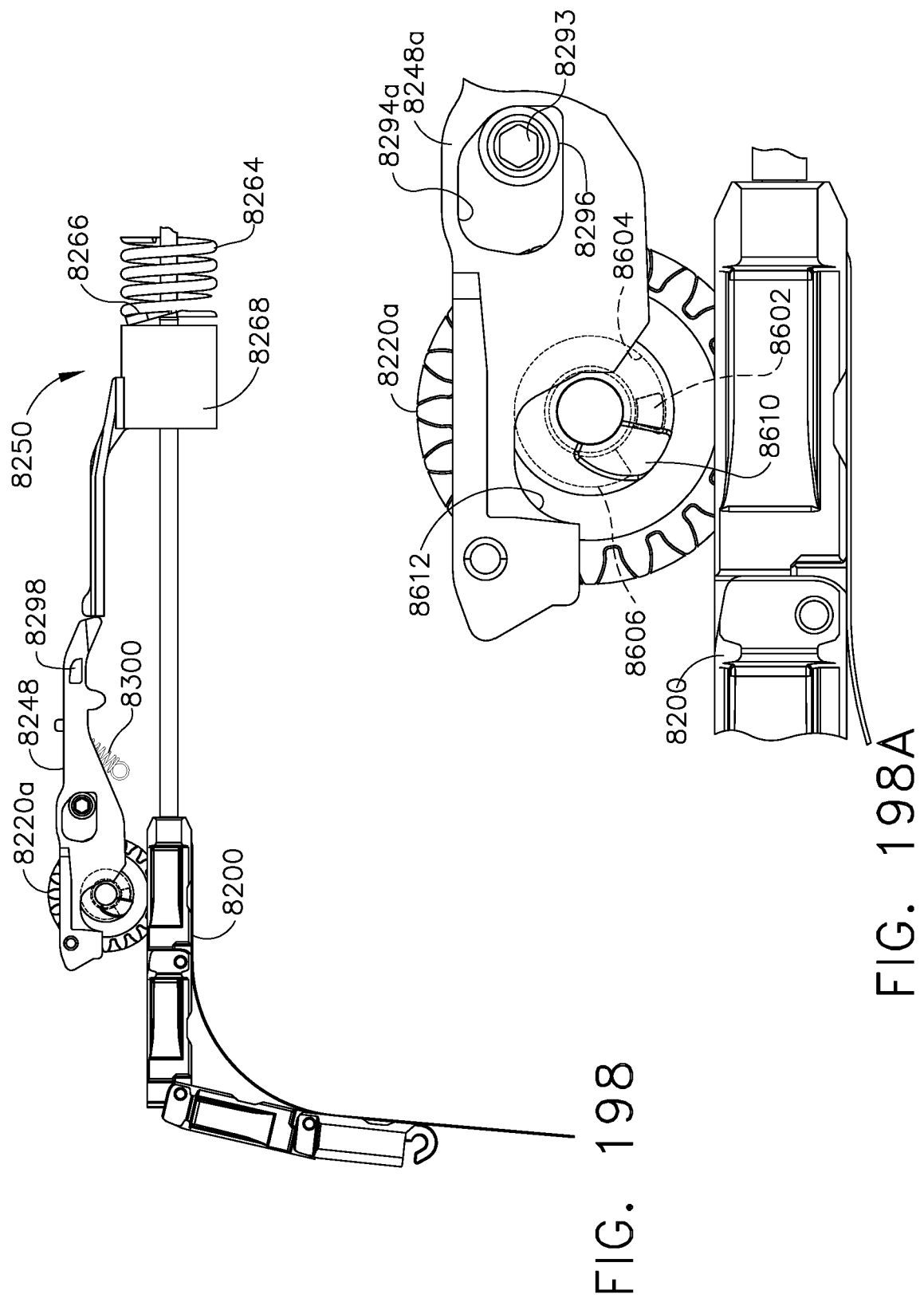
Figure 201:
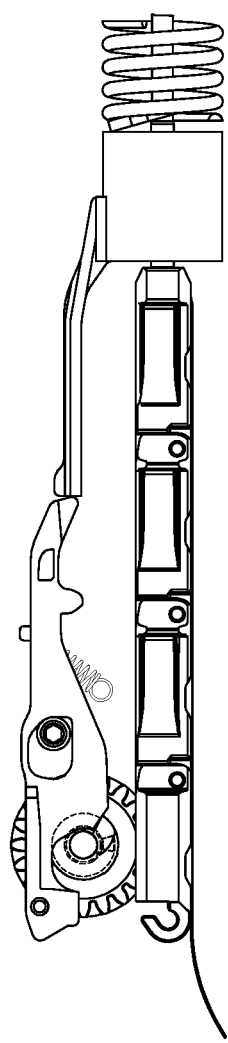
Figure 201A:
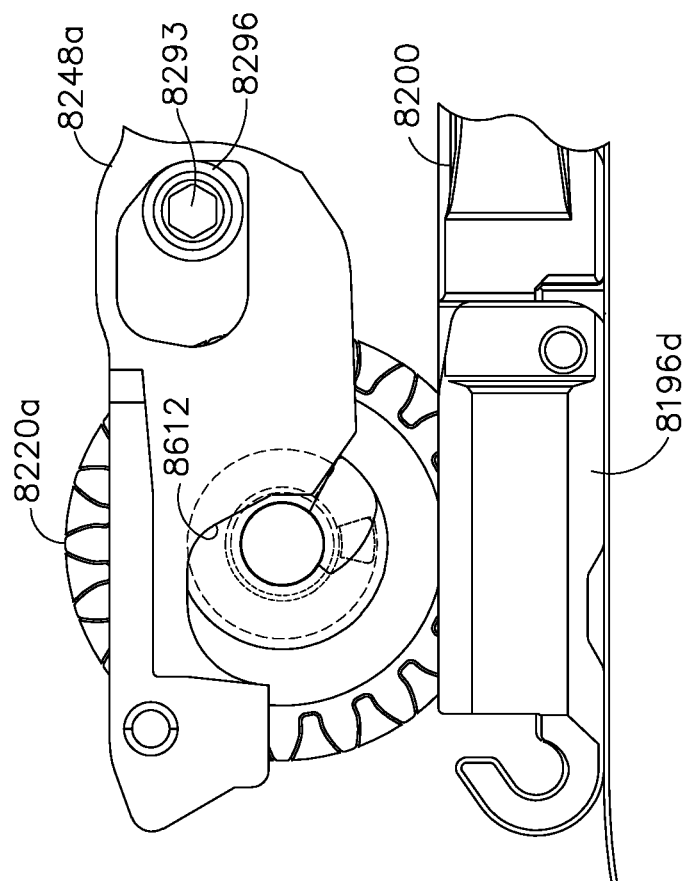
Figure 202:
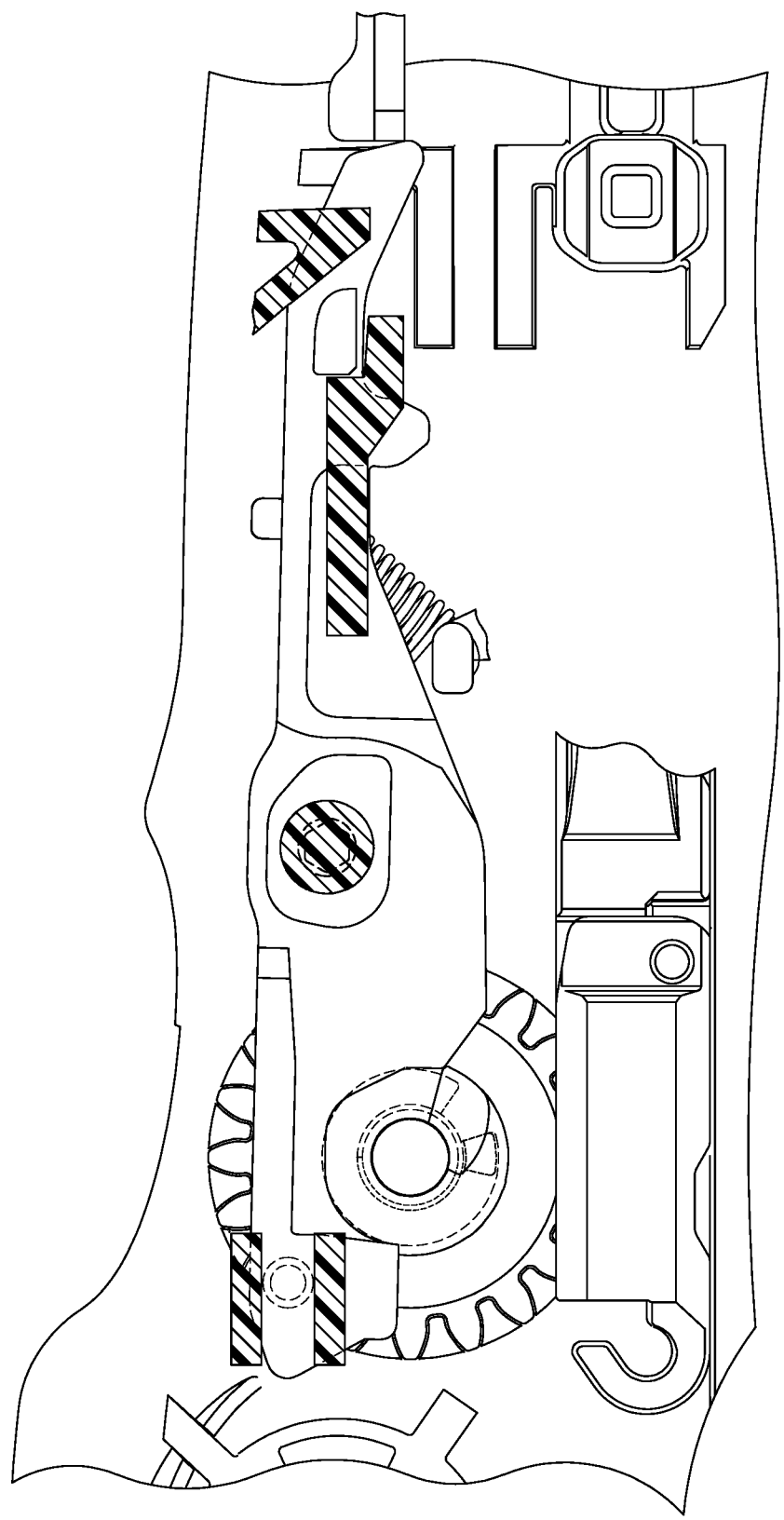
Figure 203:
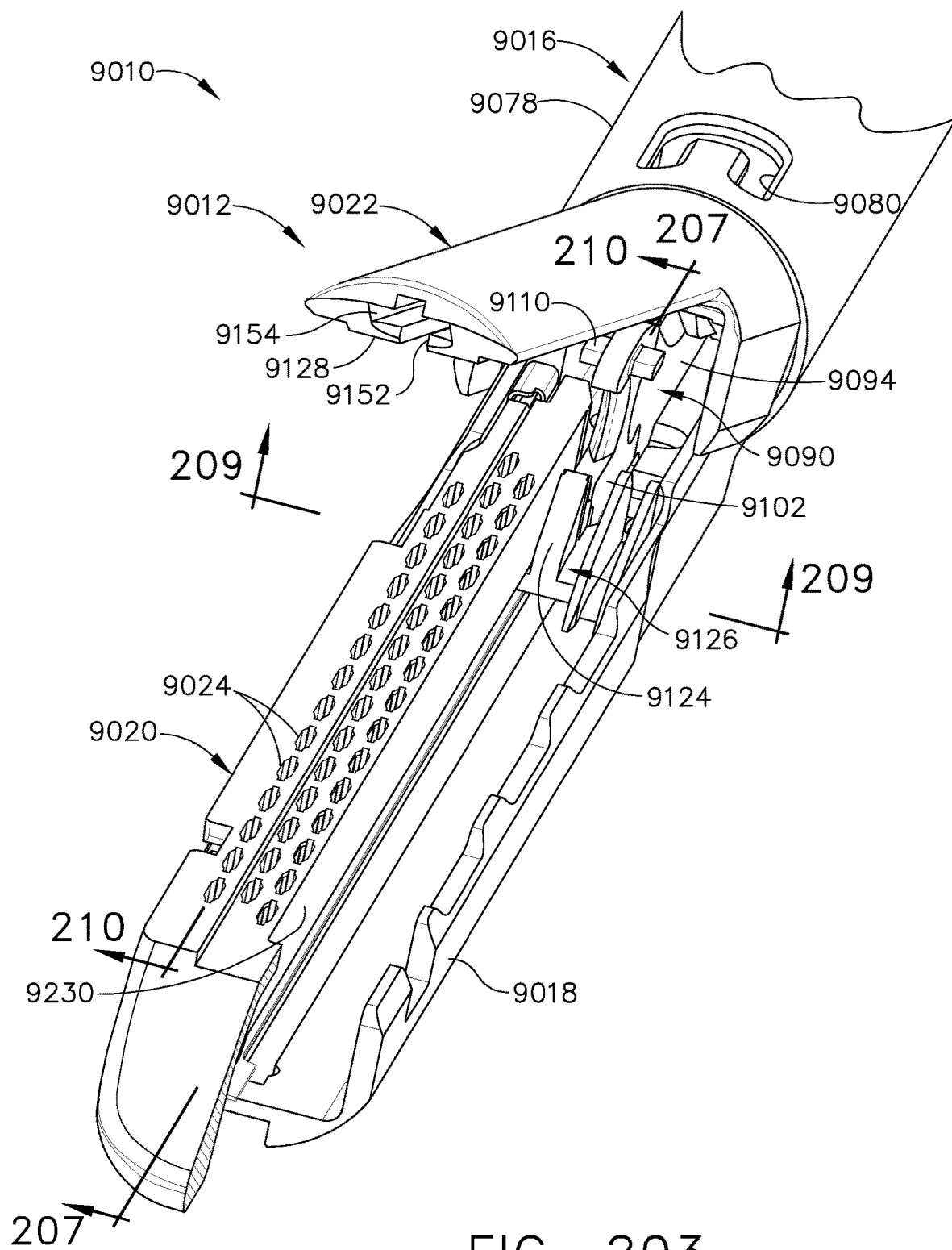
Figure 204:
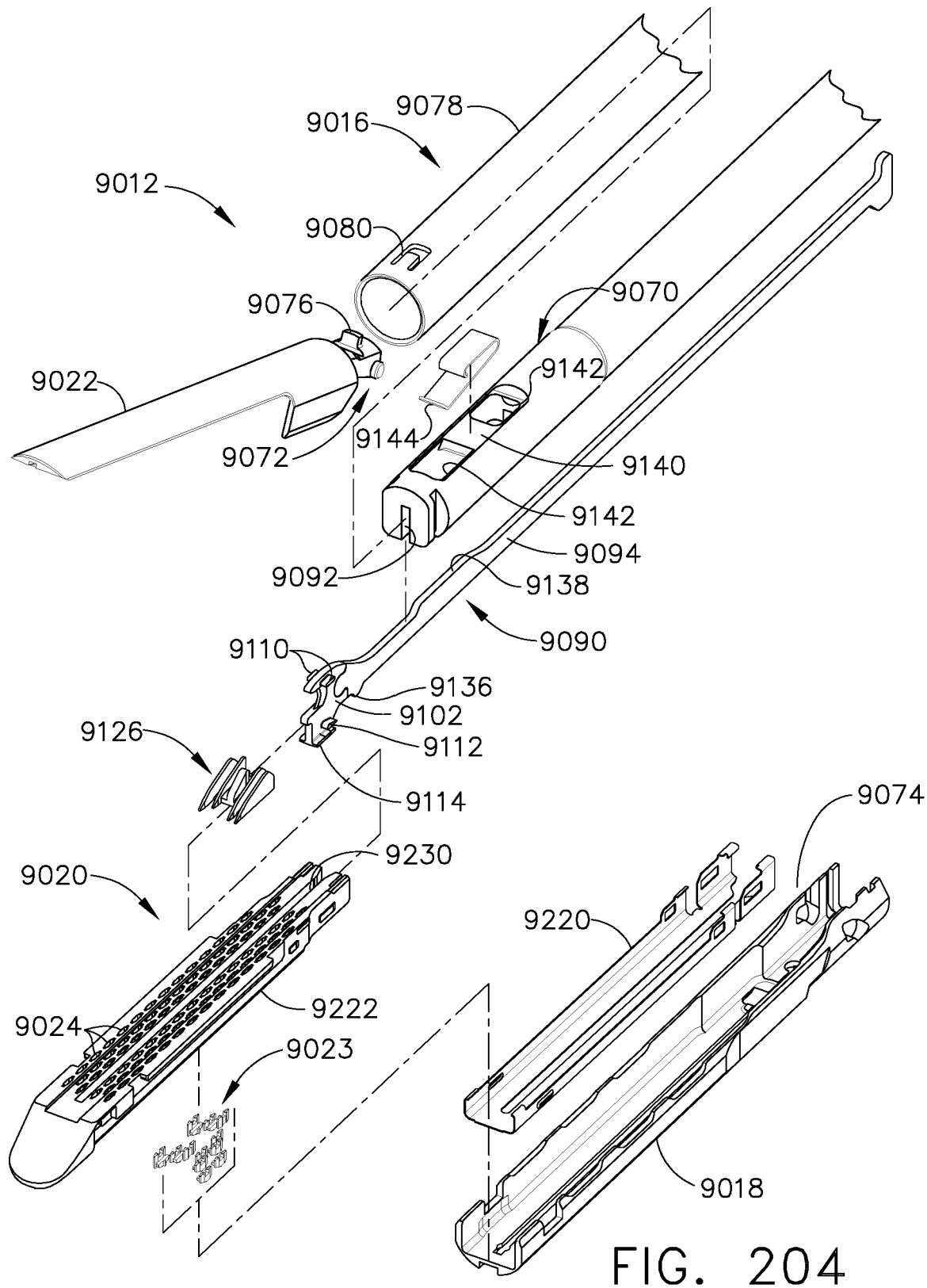
Figure 207:
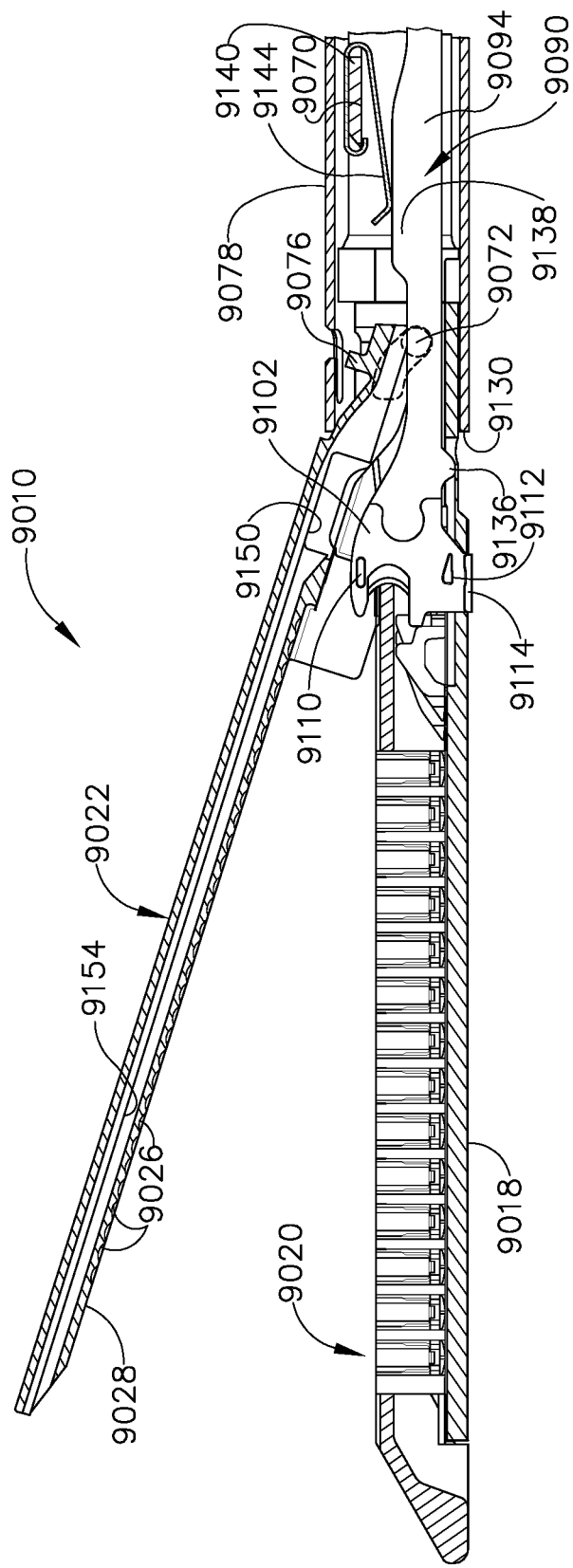
Figure 208:
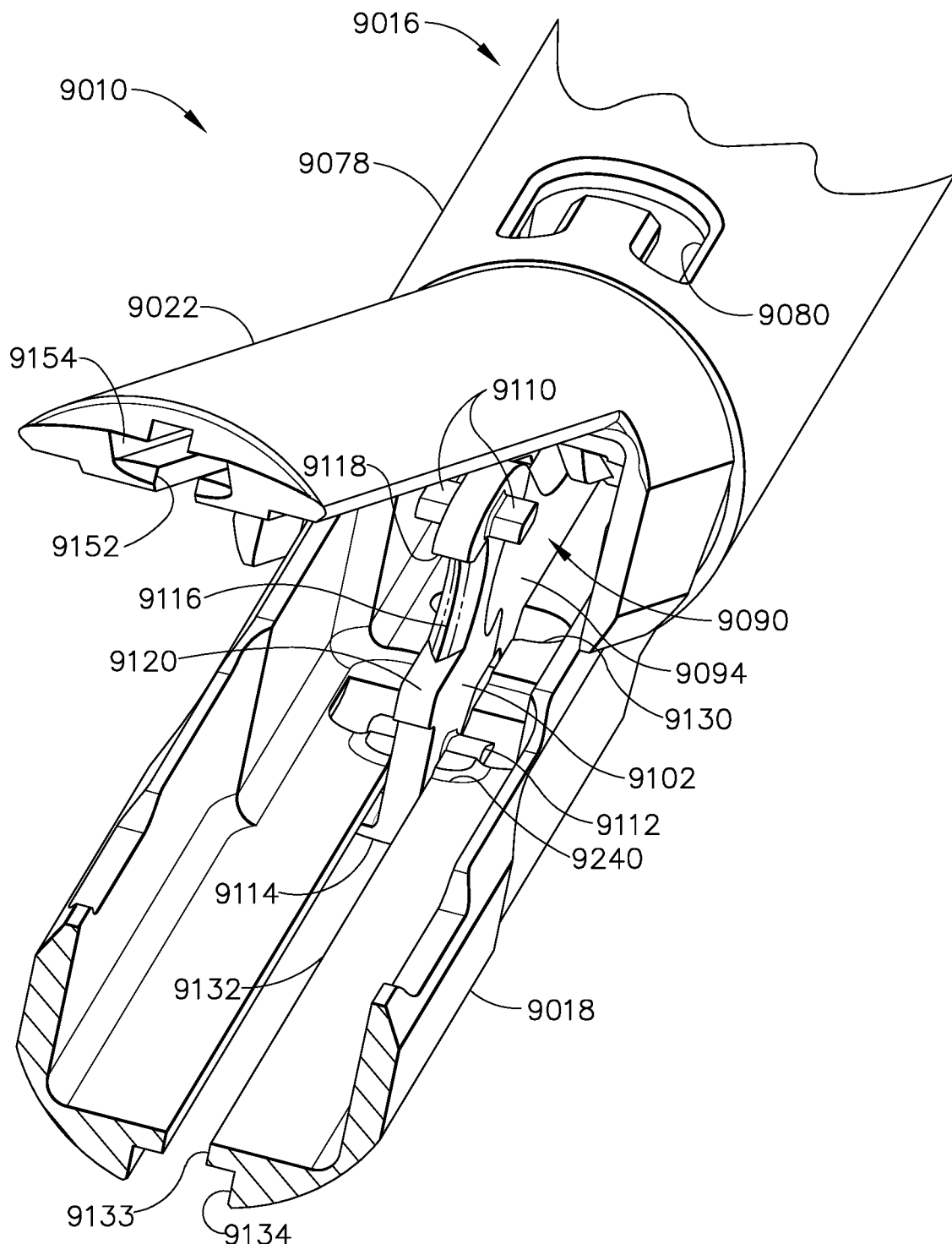
Figure 209:
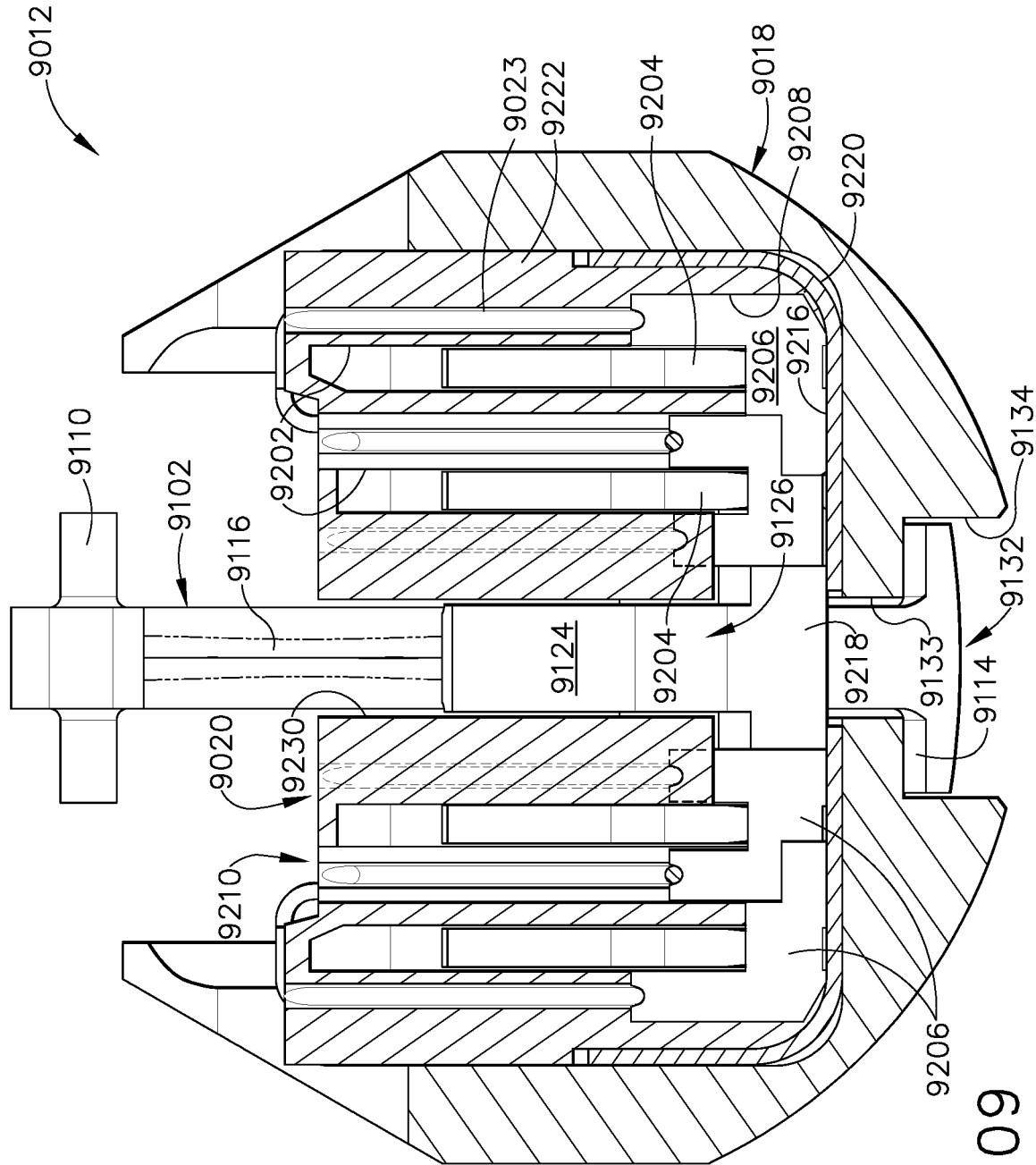
Figure 212:
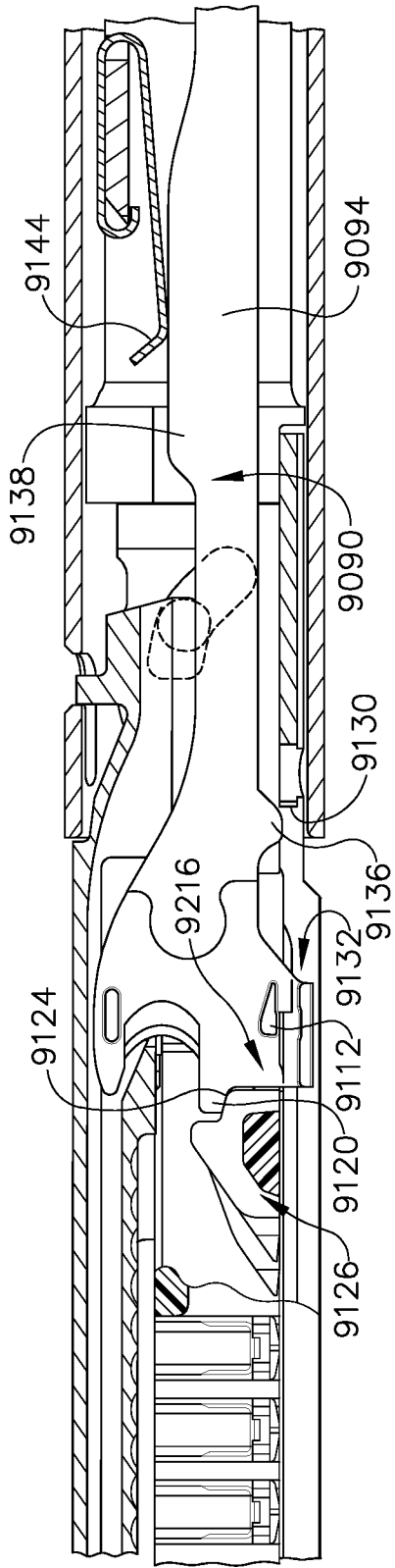
Figure 213:
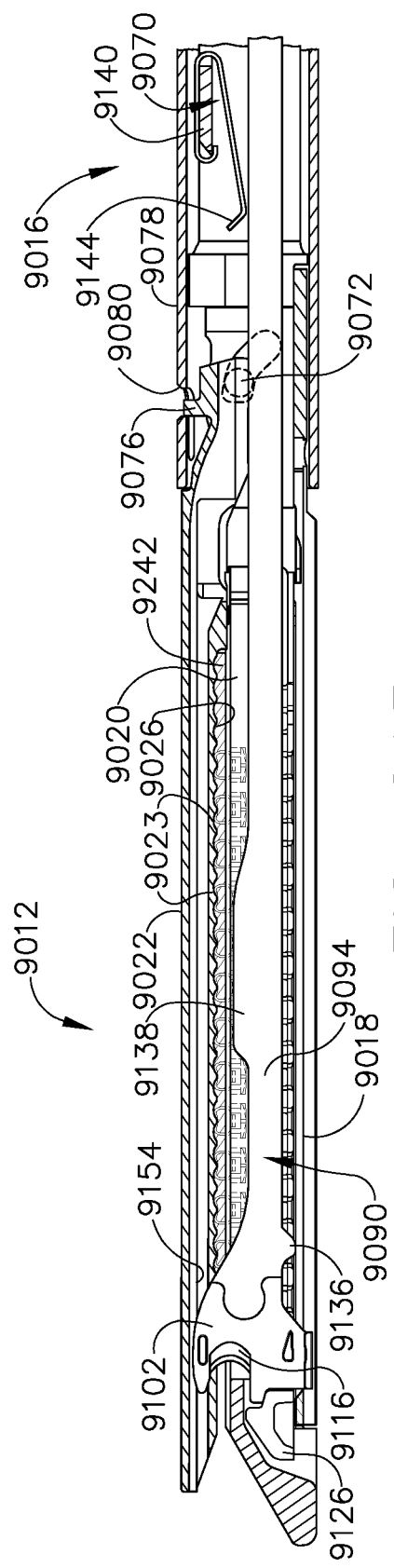
Figure 214:
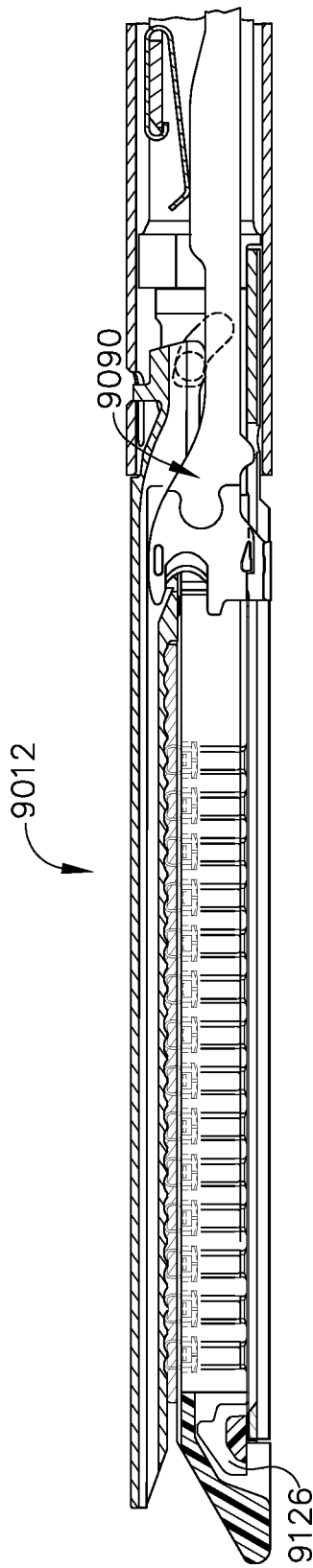
Figure 215:
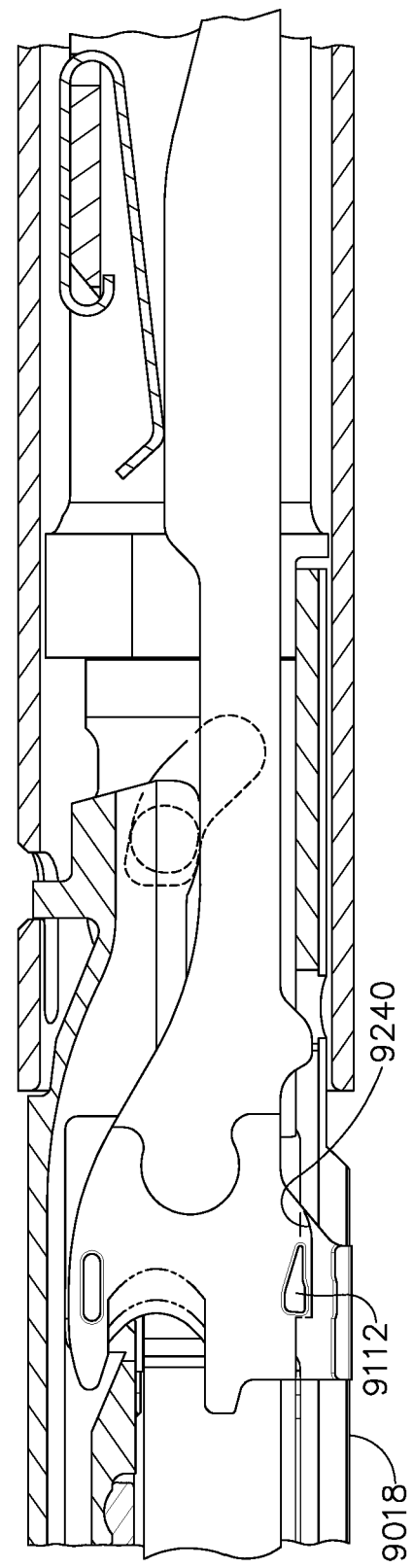
Figure 216:
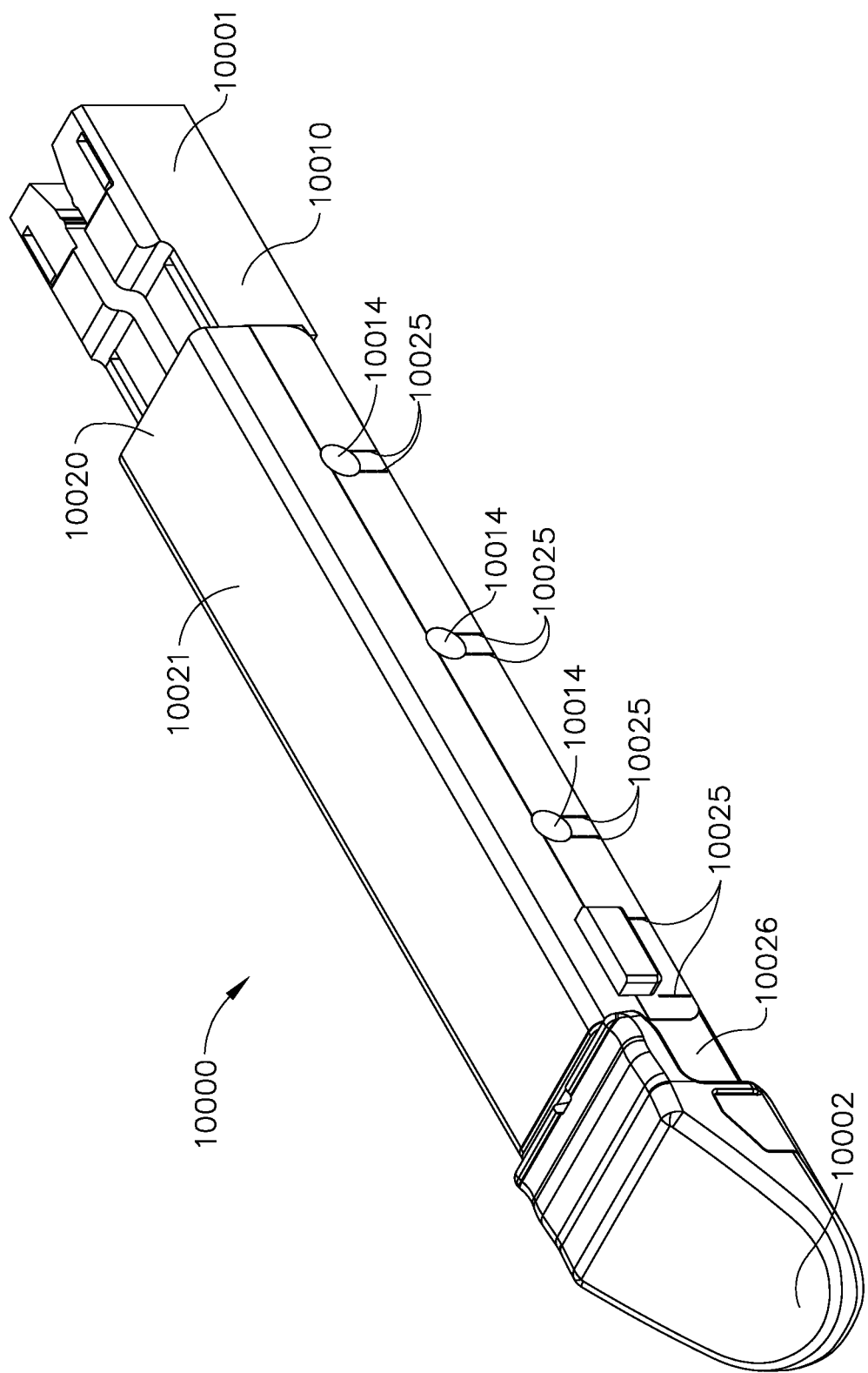
Figure 217:
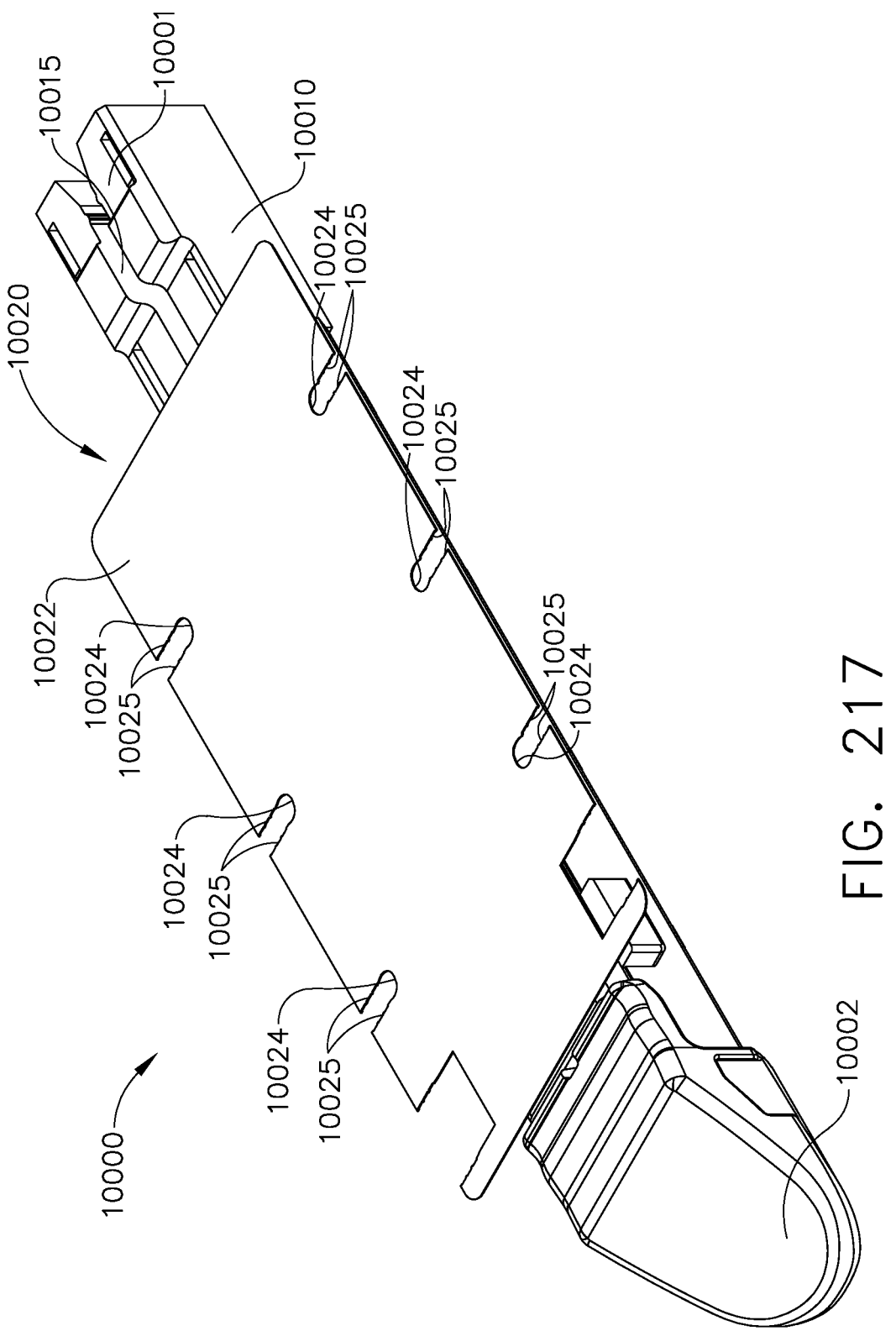
Figure 218:
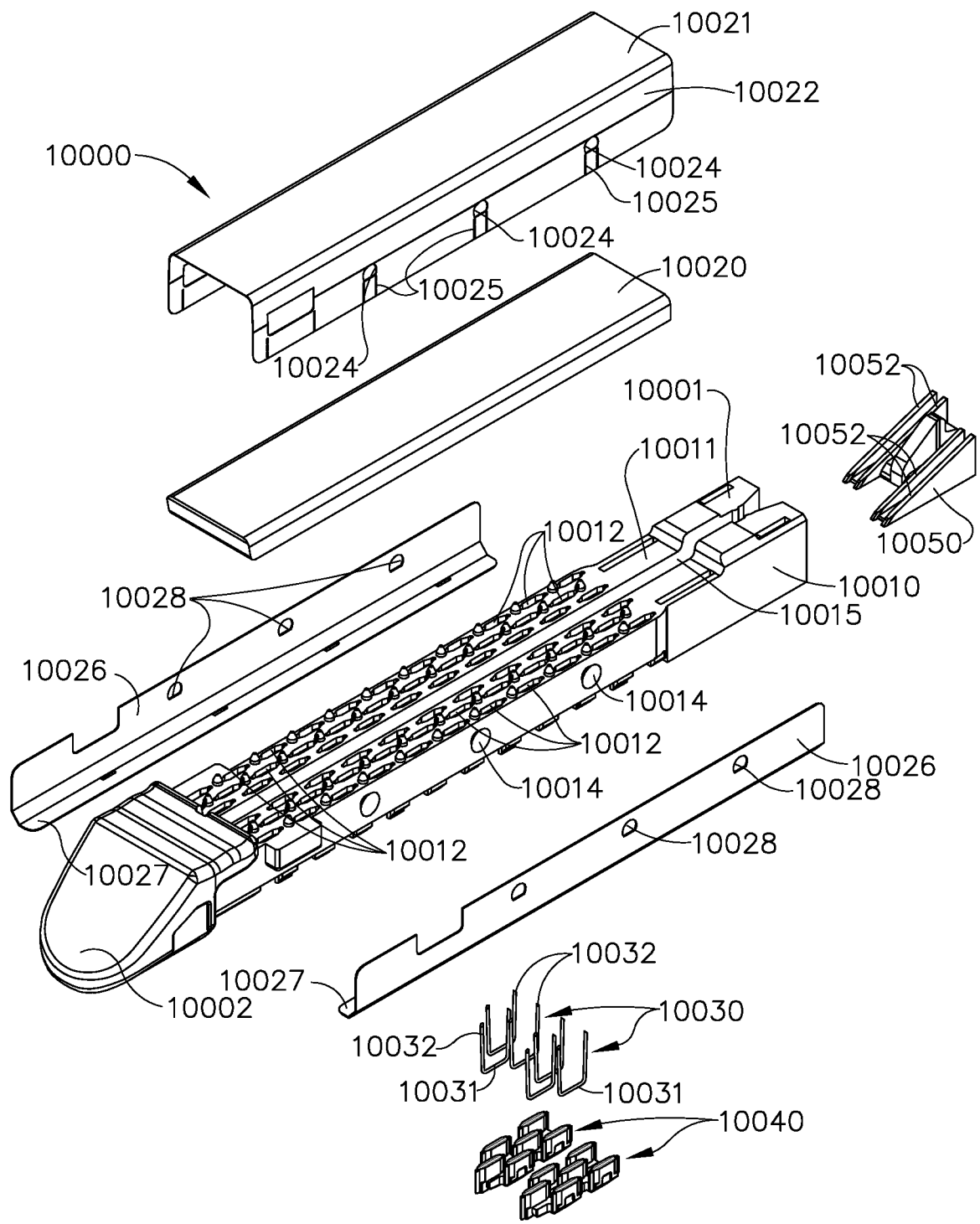
Figure 219:
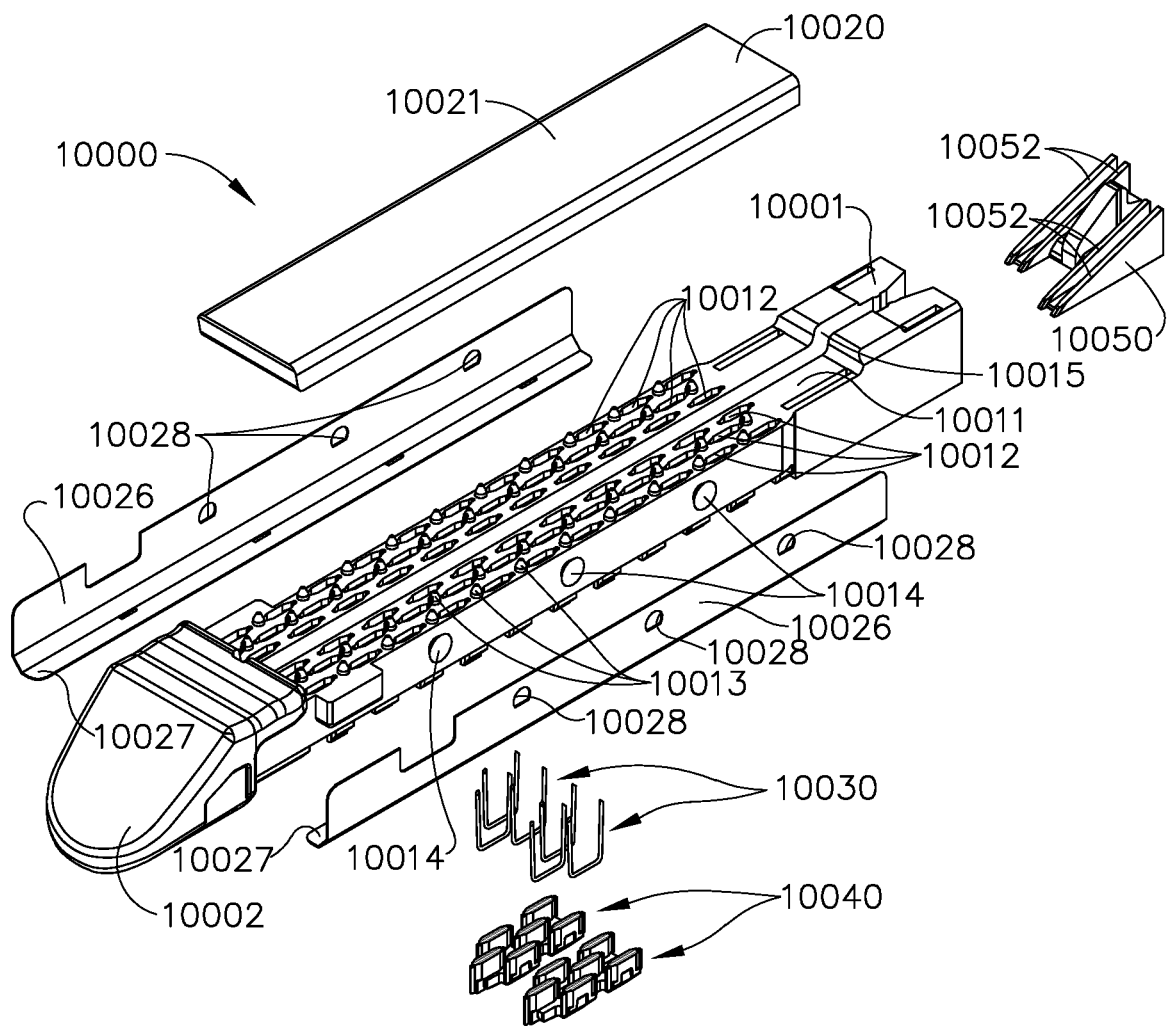
Figure 220:
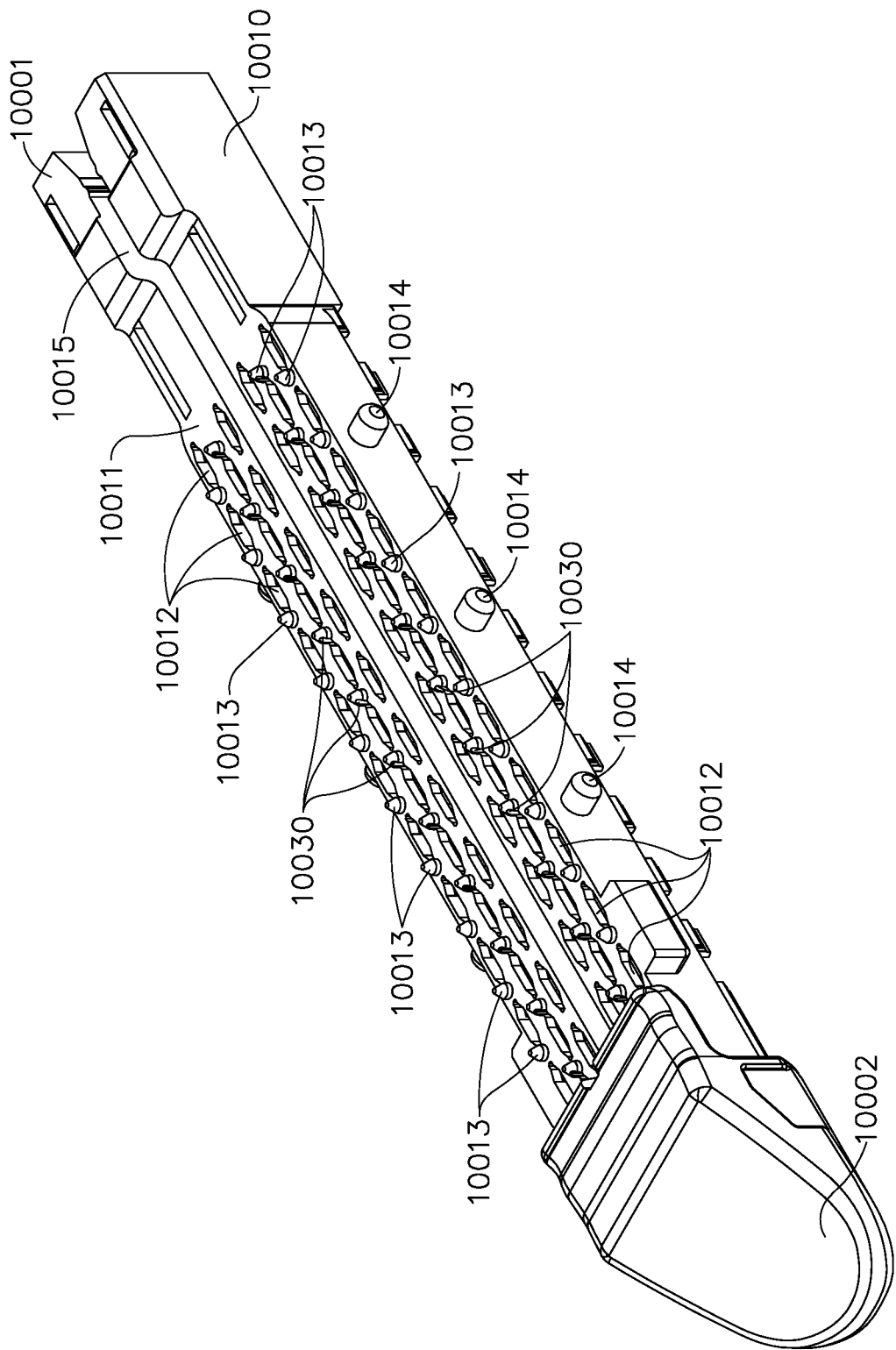
Figure 221:
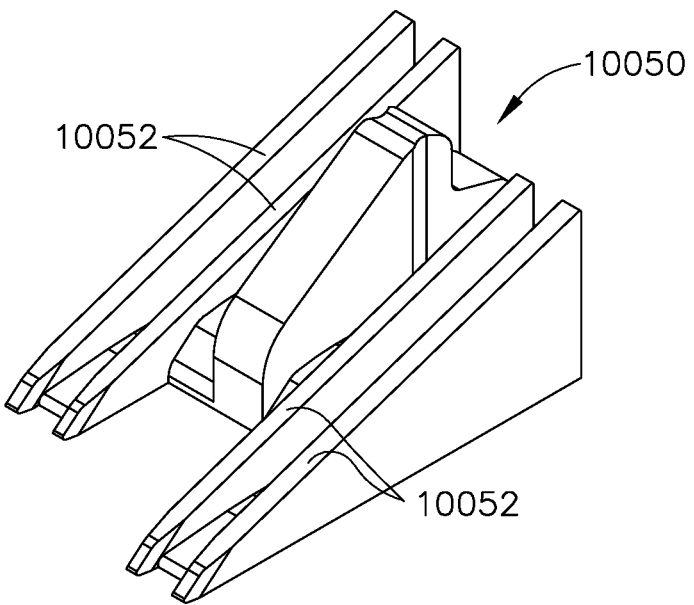
Figure 222:
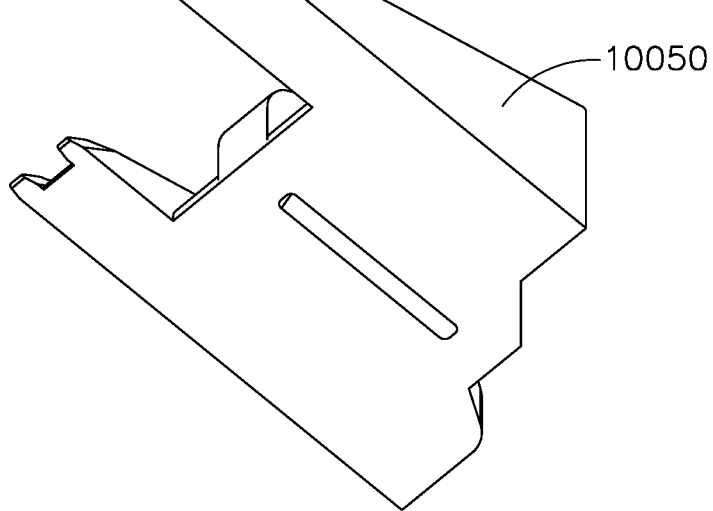
Figure 223:
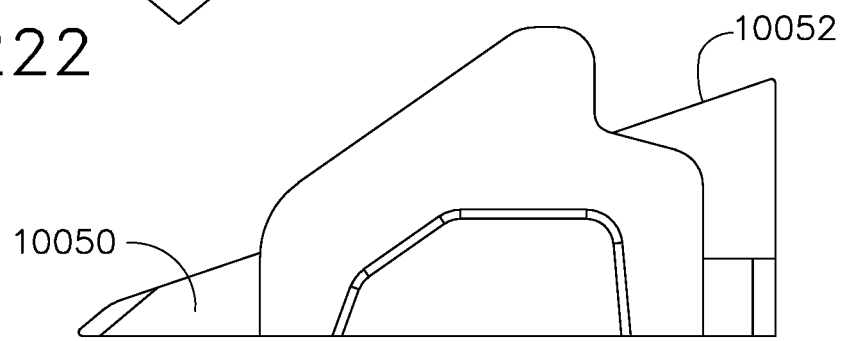
Figure 224:
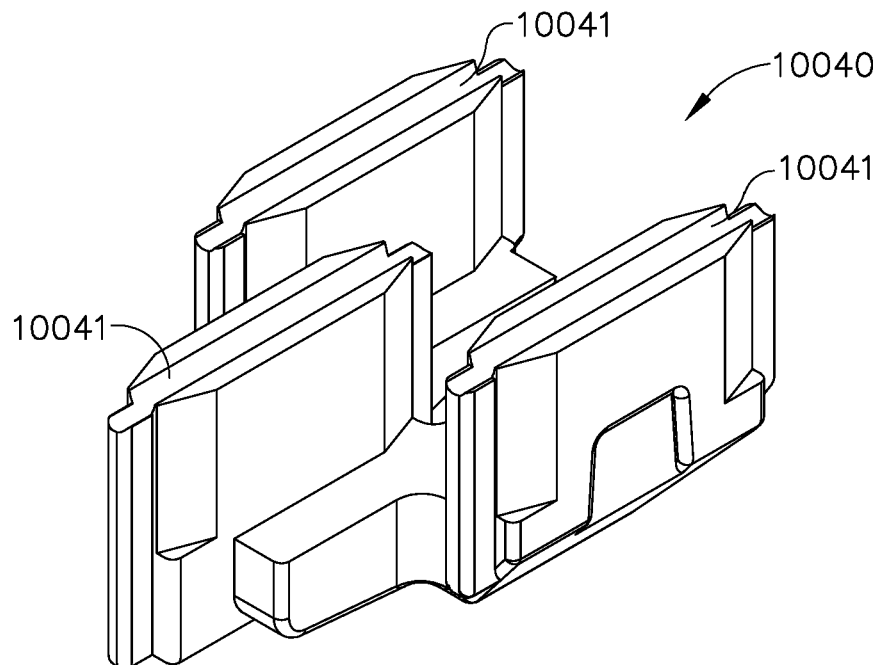
Figure 225:
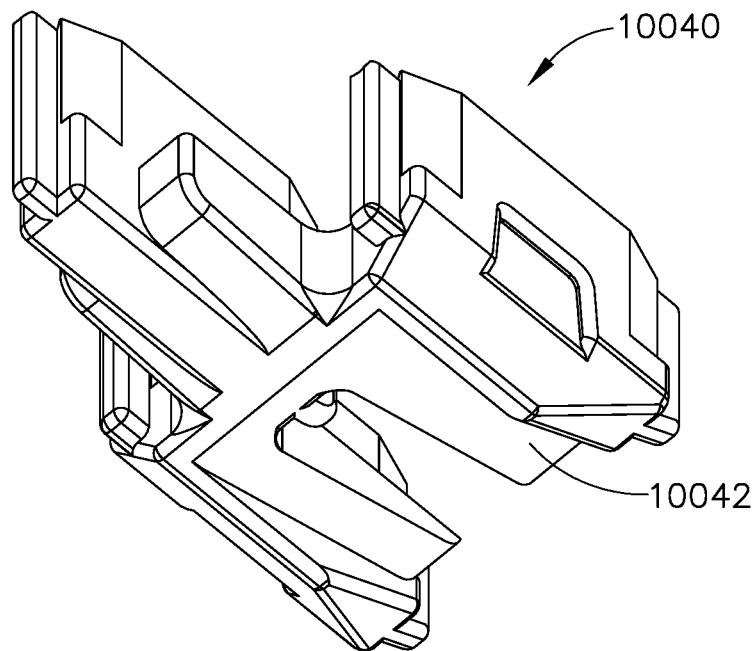
Figure 226:
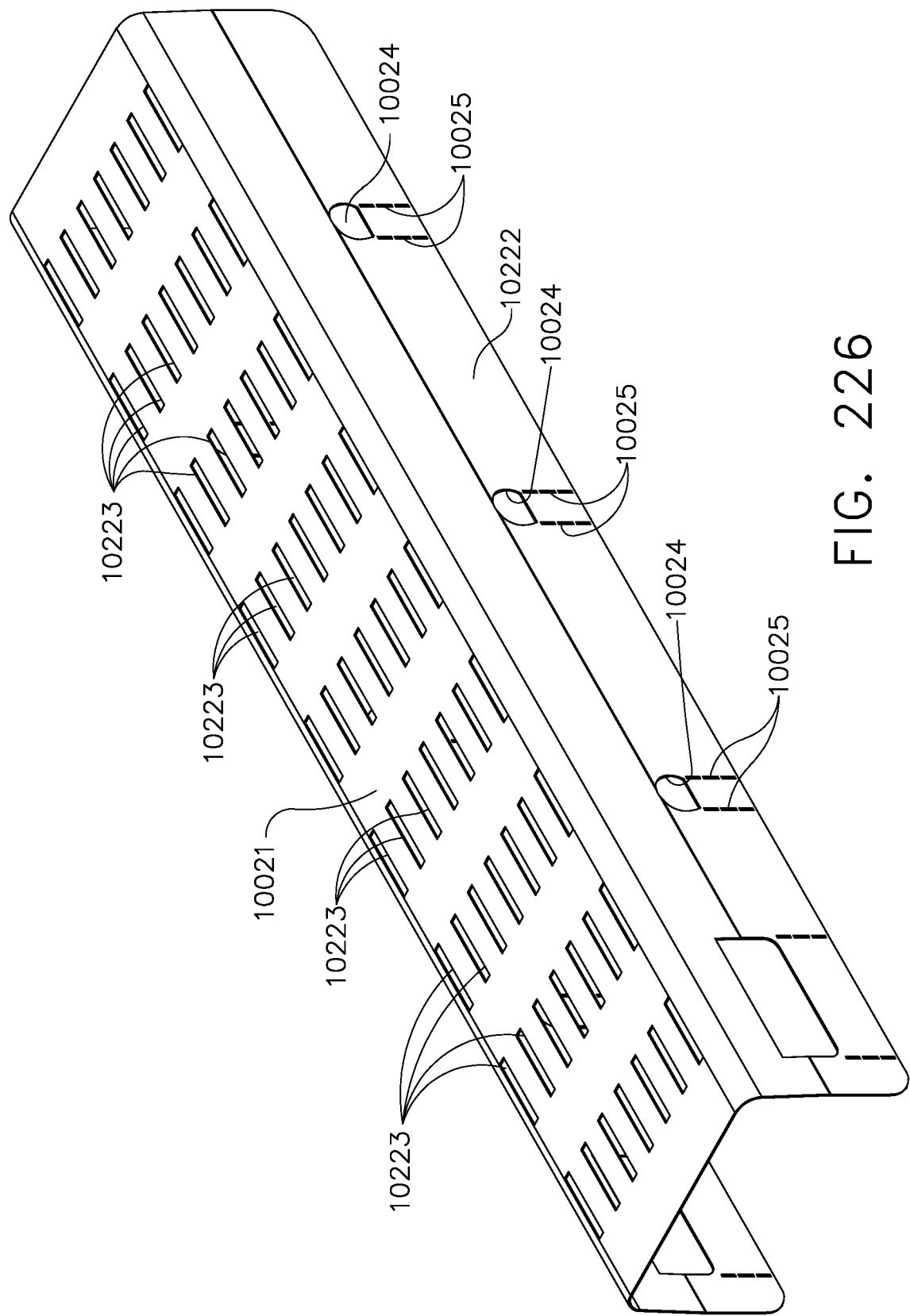
Figure 227:
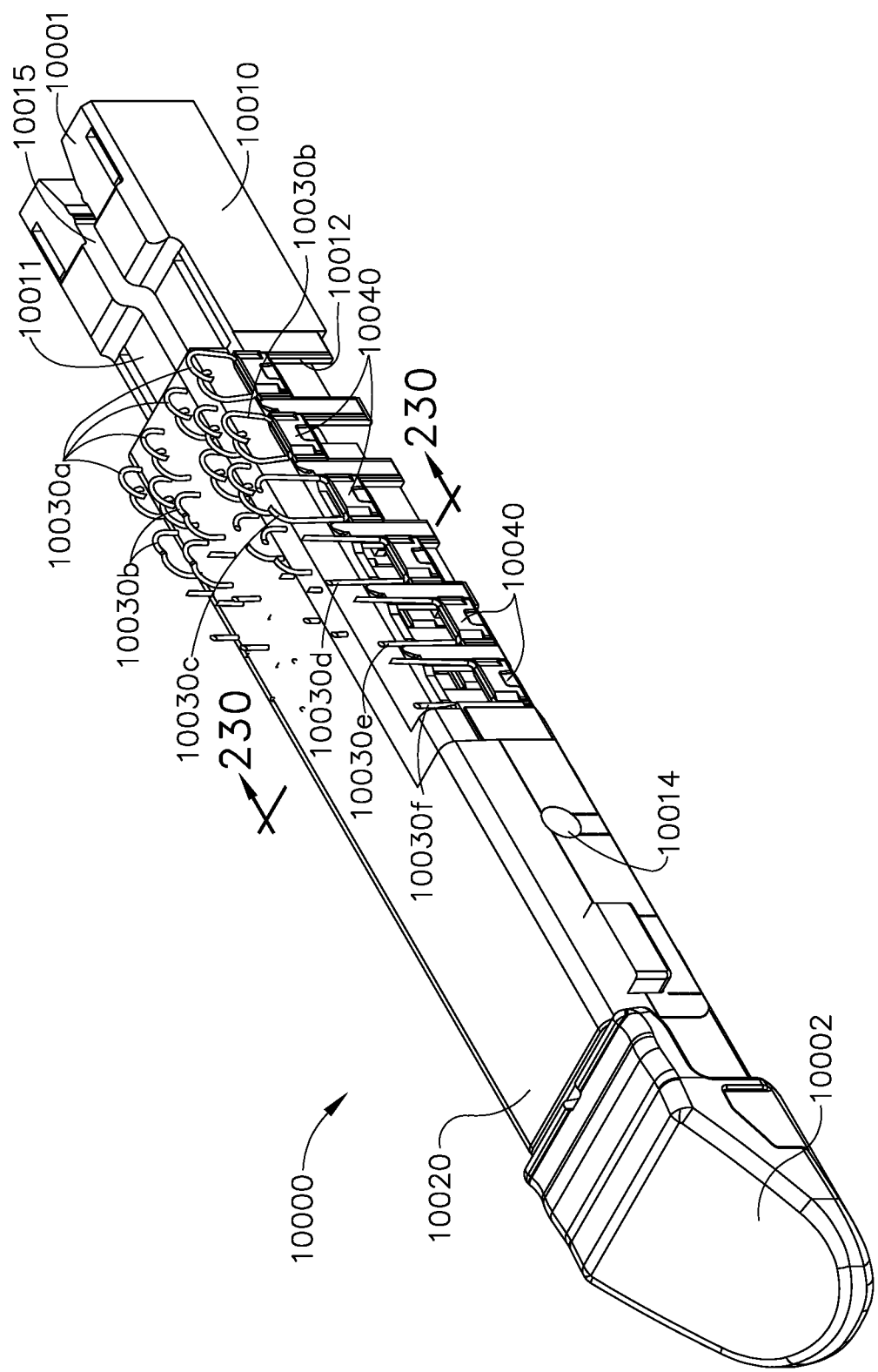
Figure 230:
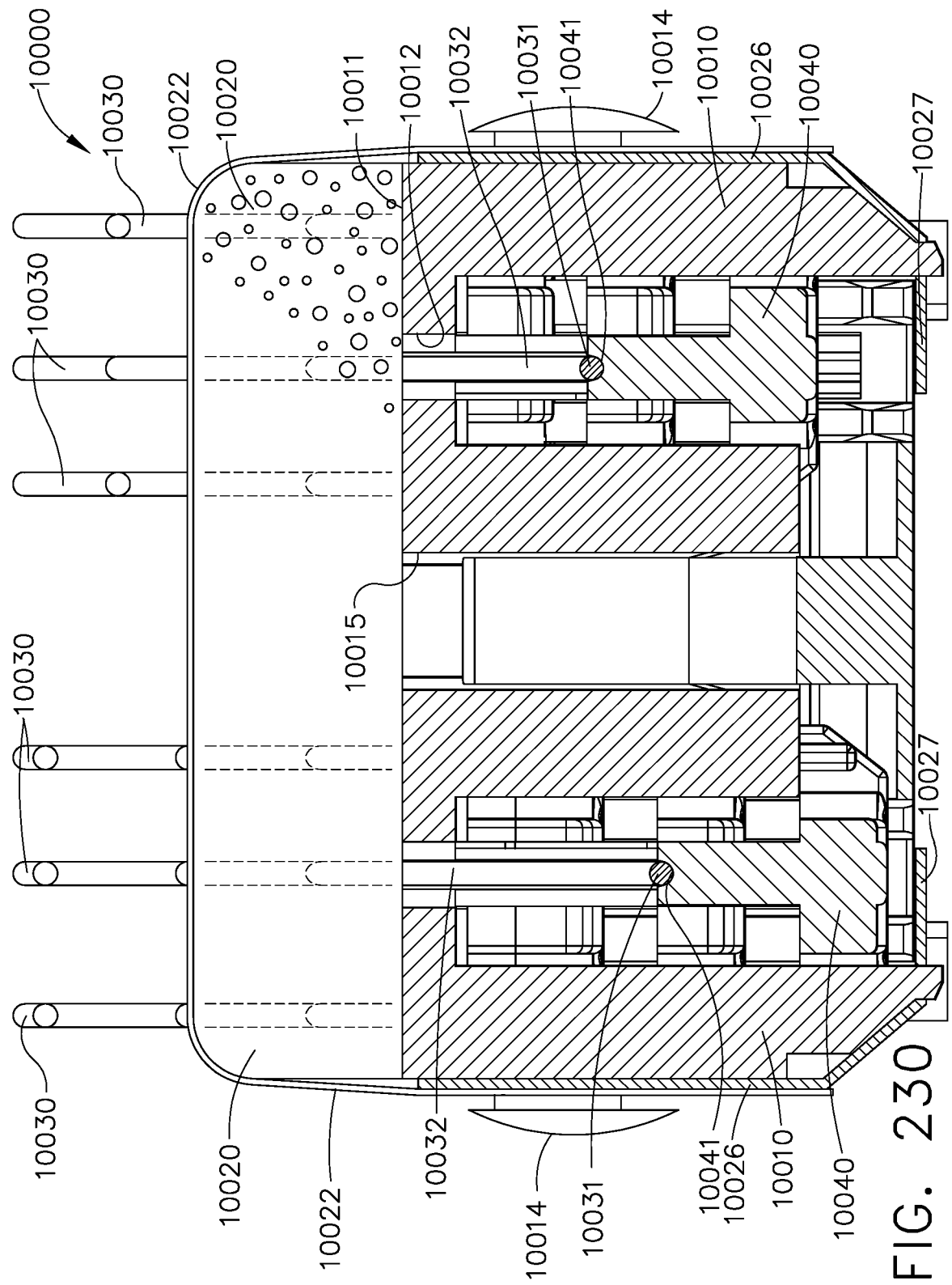
Figure 231:
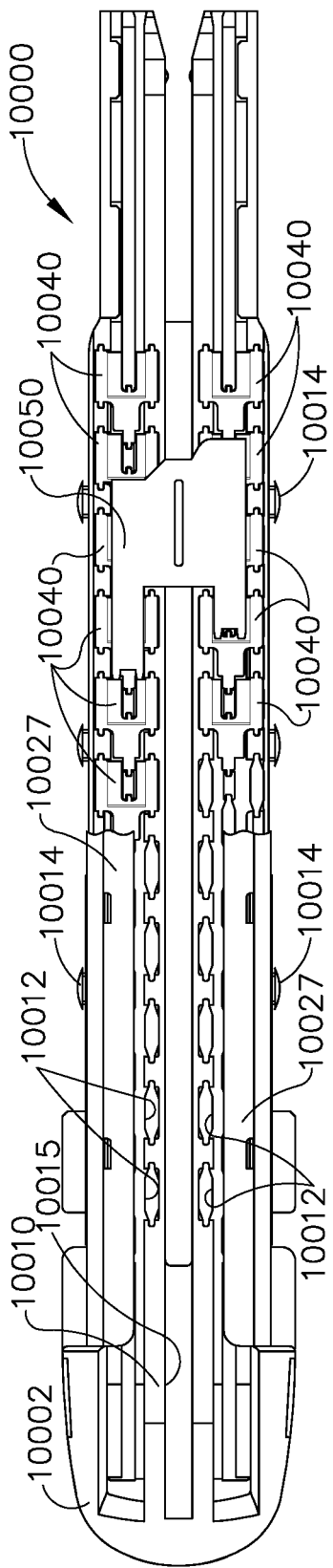
Figure 232:
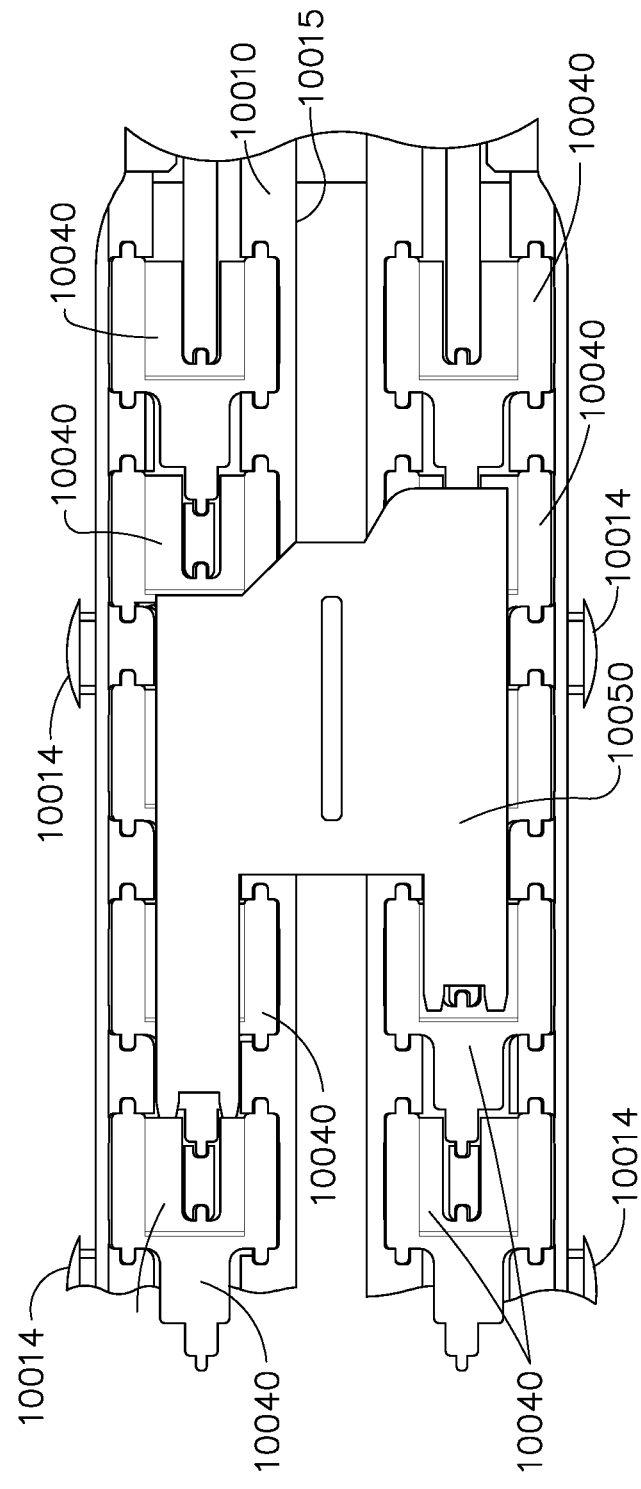
Figure 235:
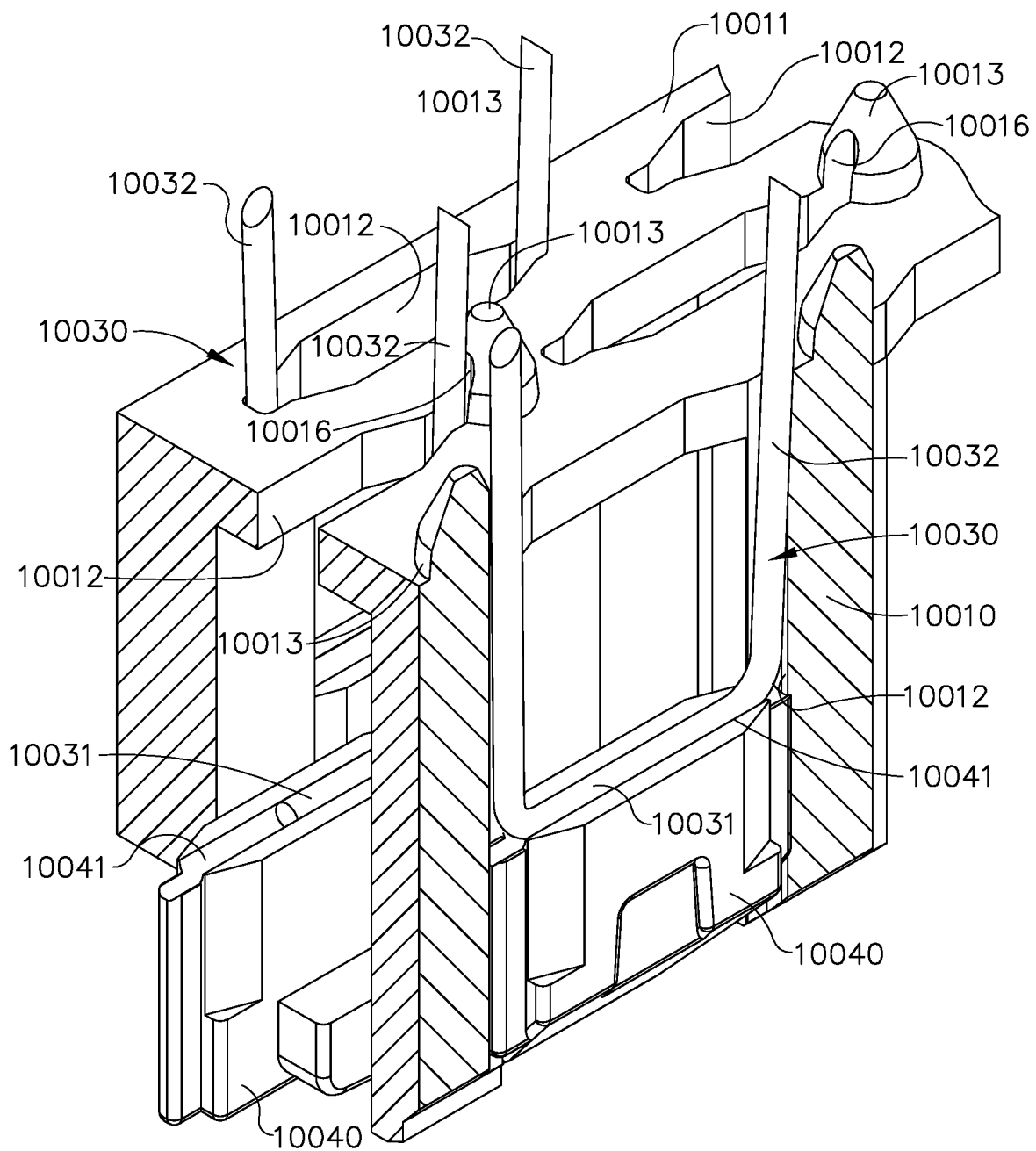
Figure 238:
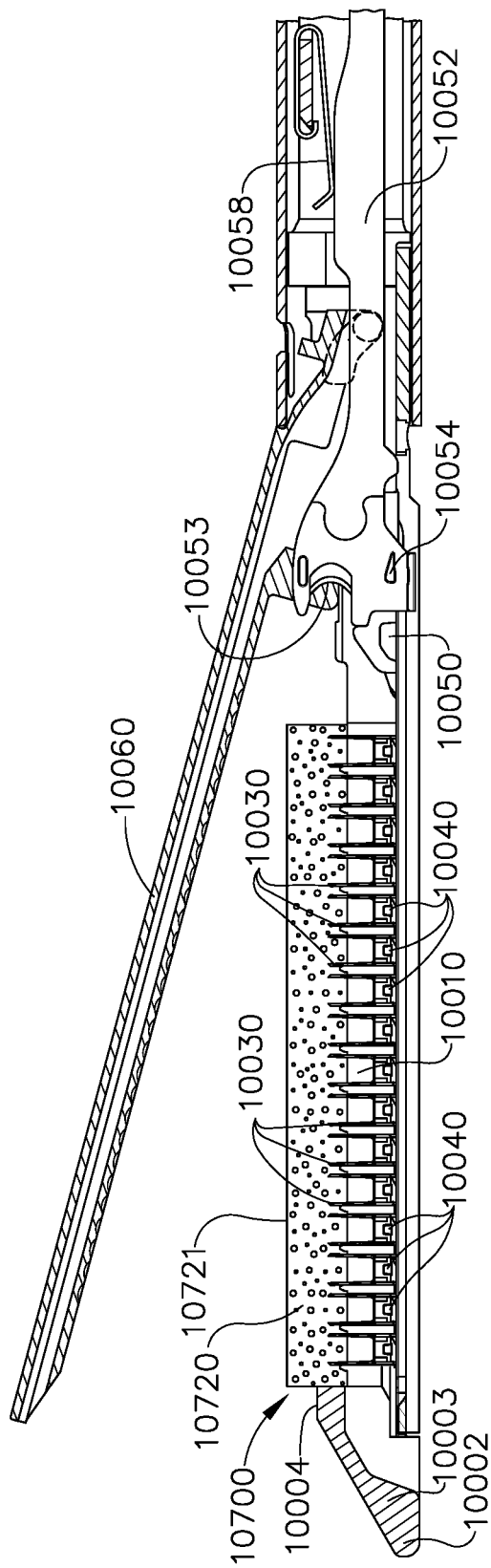
Figure 239:
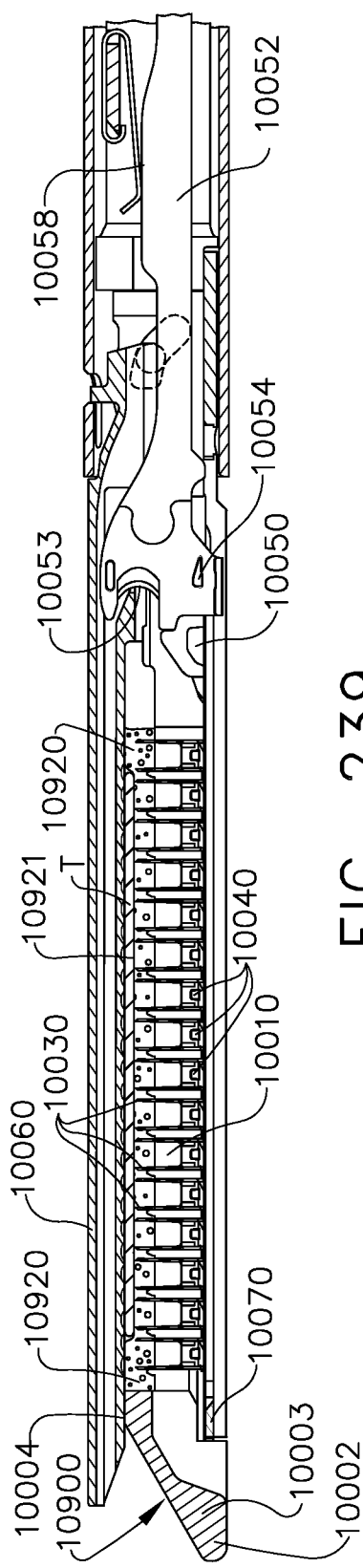
Figure 240:
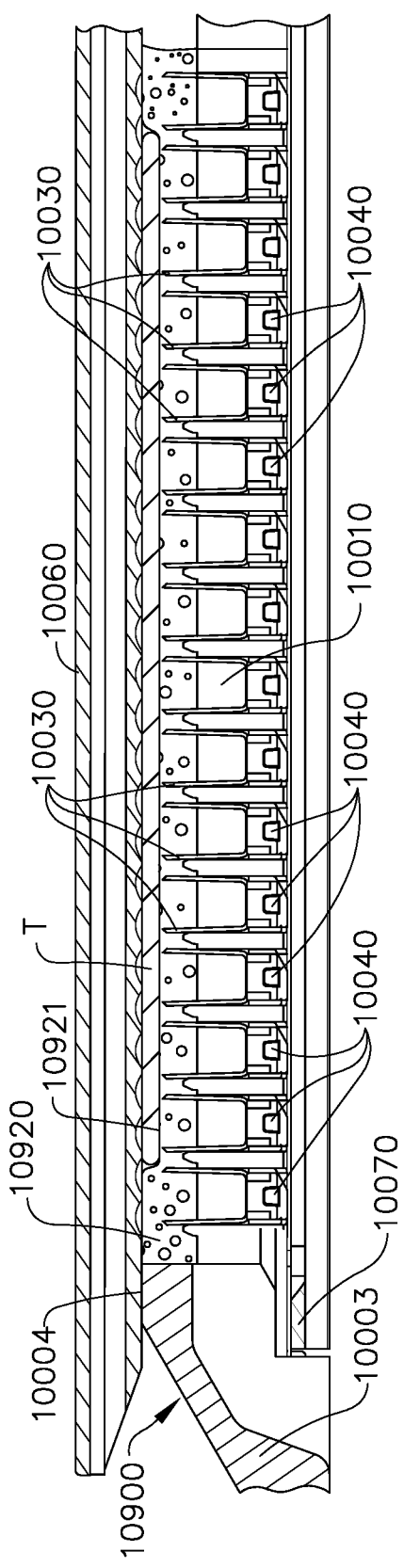
Figure 243:
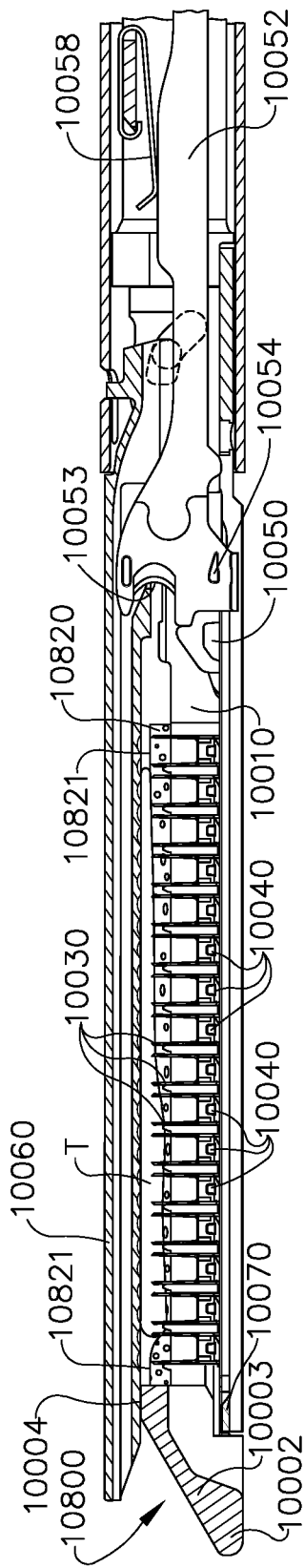
Figure 244:
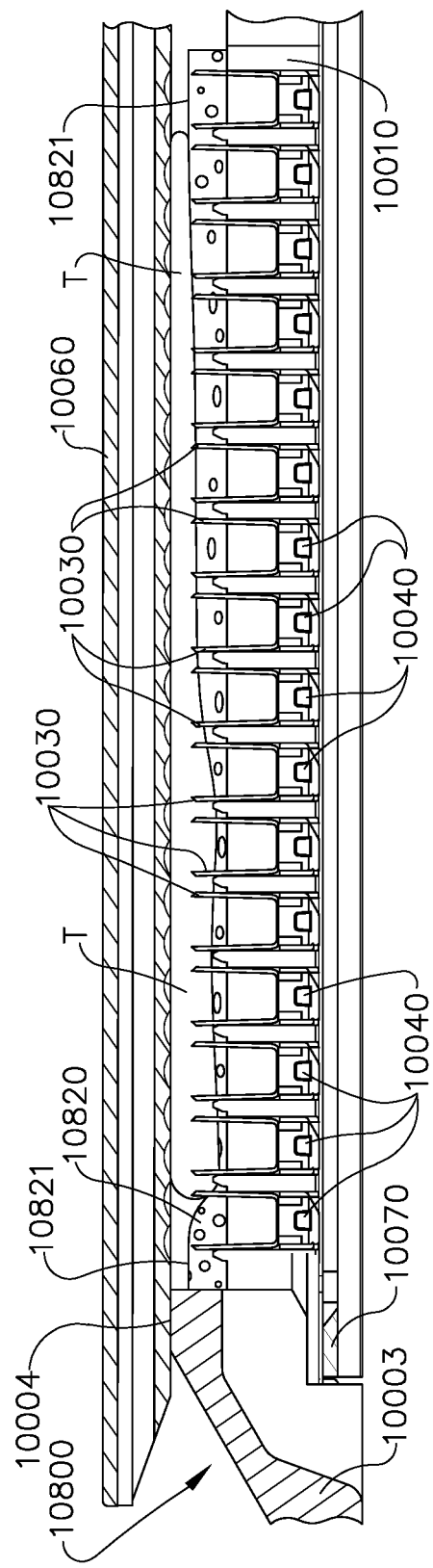
Figure 245:
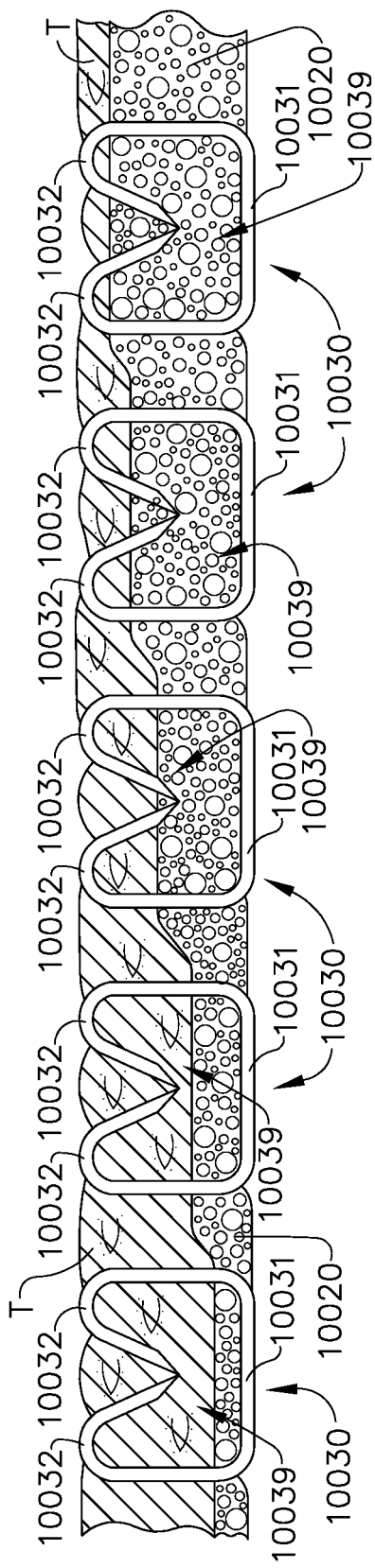
Figure 246:
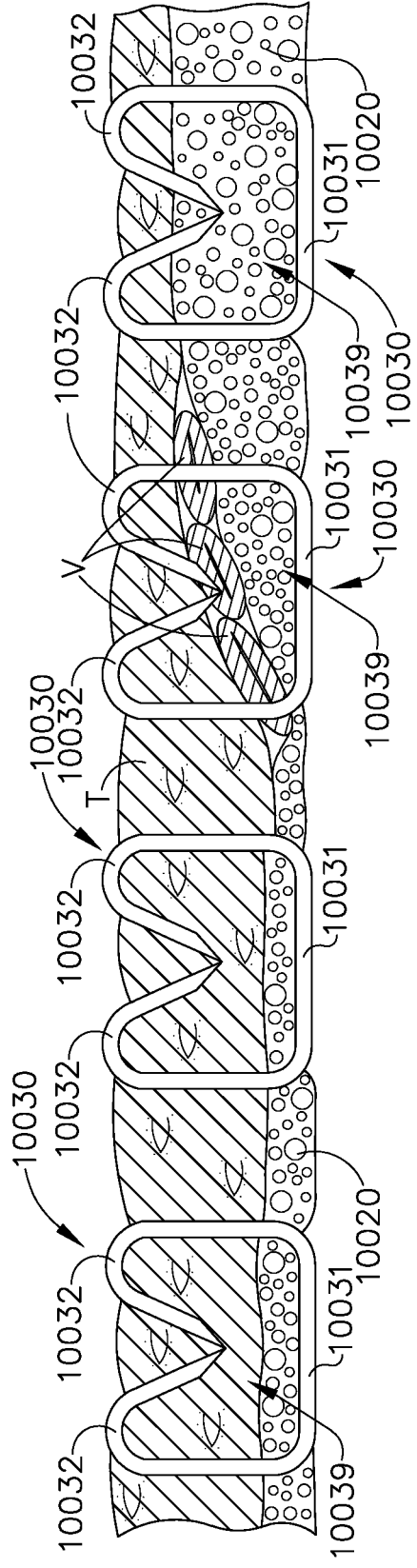
Figure 252:
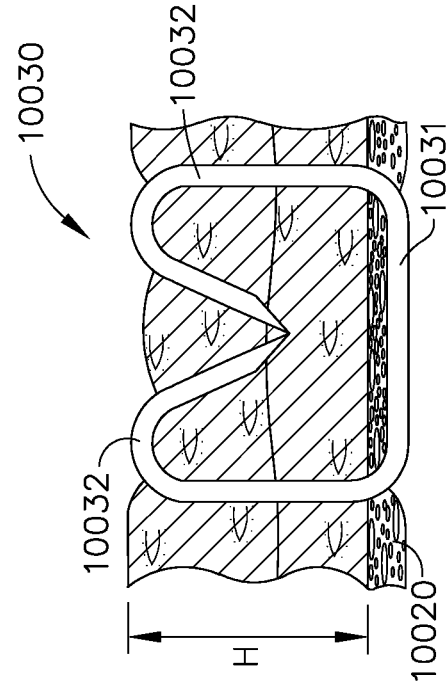
Figure 253:
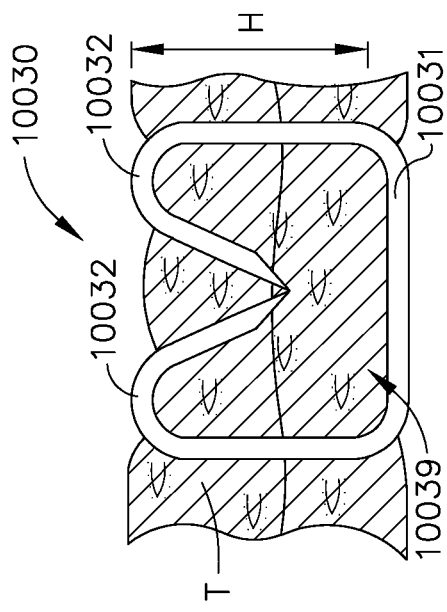
Figure 254:
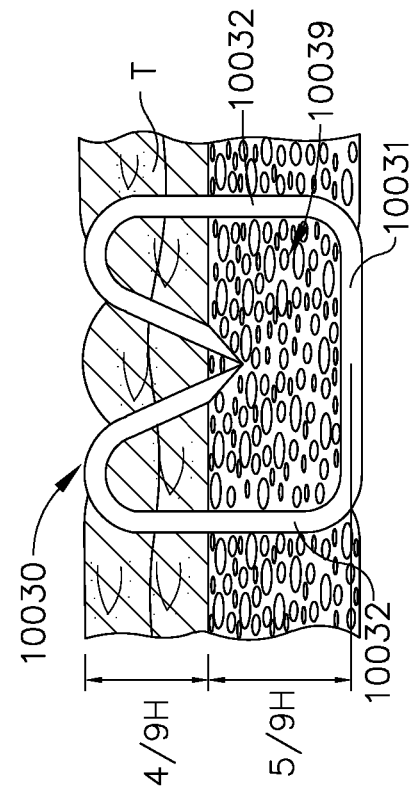
Figure 255:
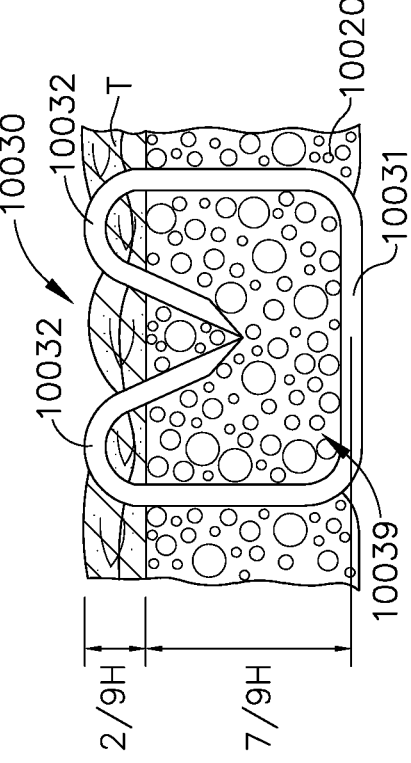
Figure 259:
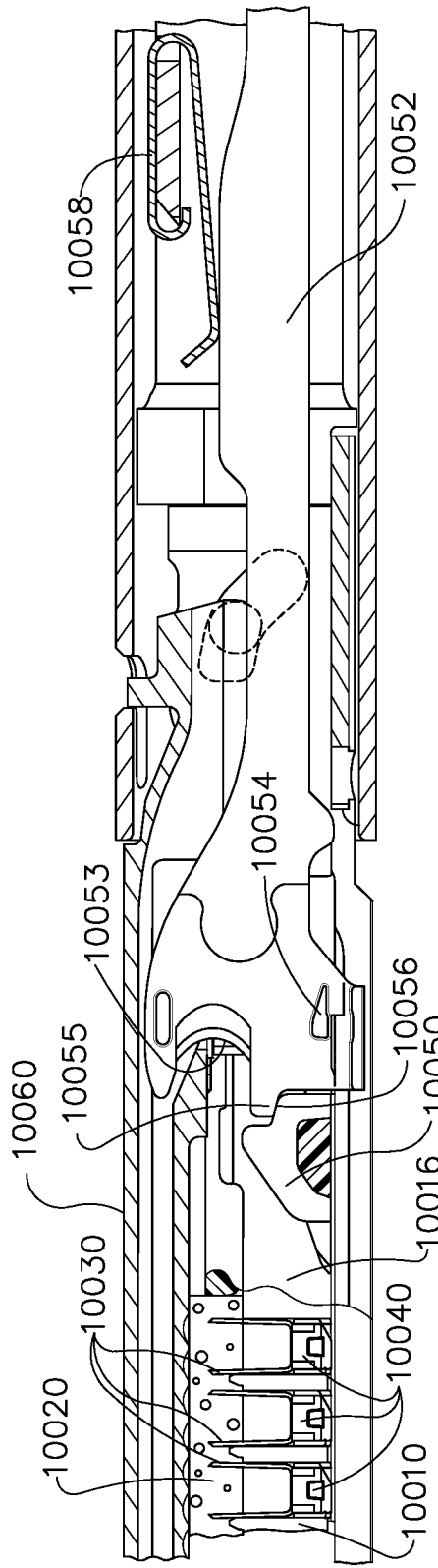
Figure 260:
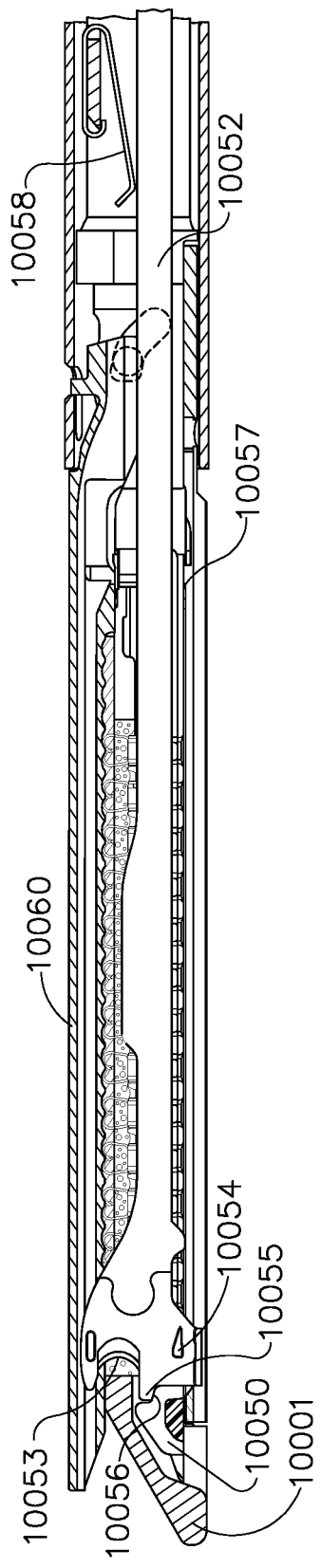
Figure 263:
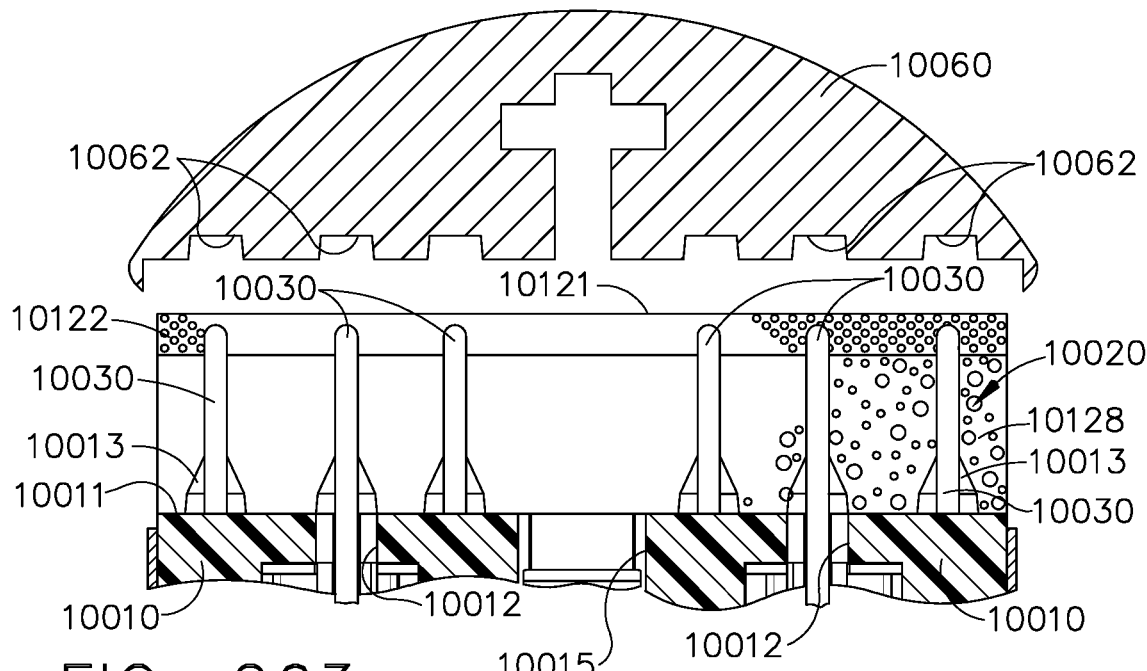
Figure 264:
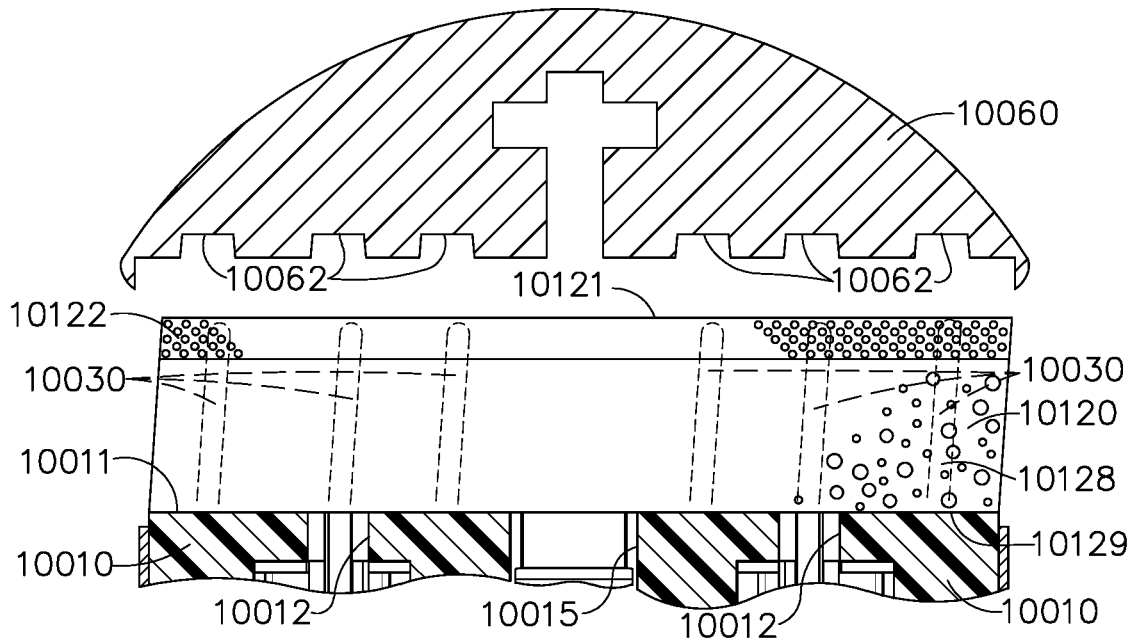
Figure 265:
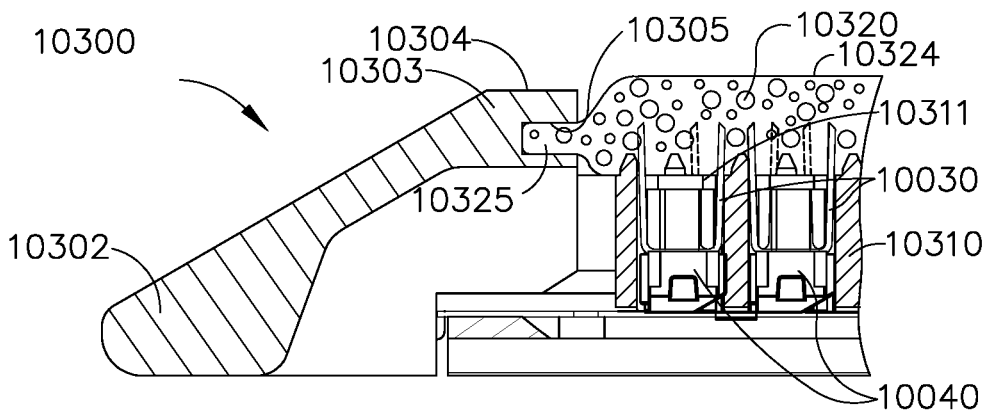
Figure 266:
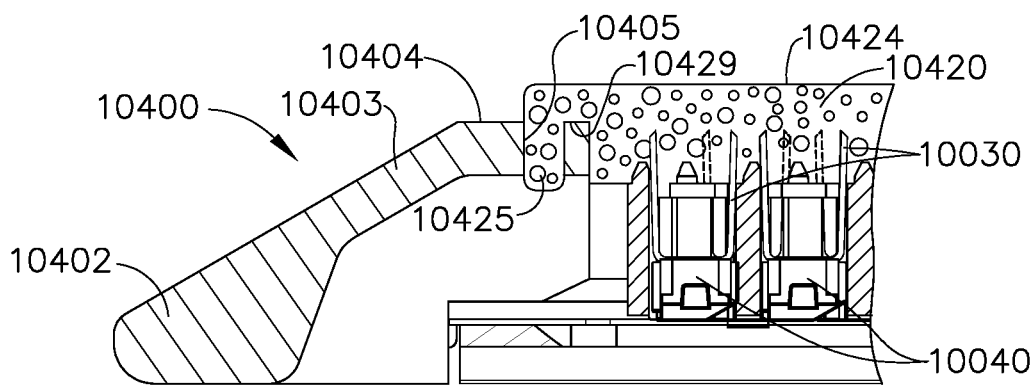
Figure 267:
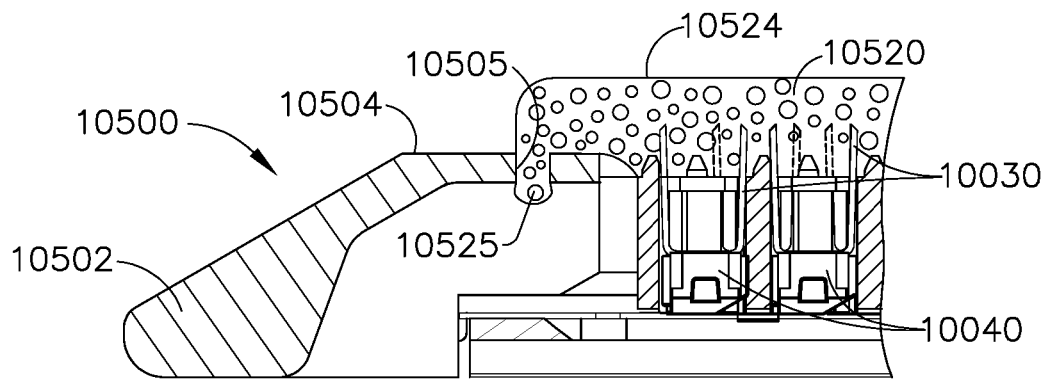
Figure 268:
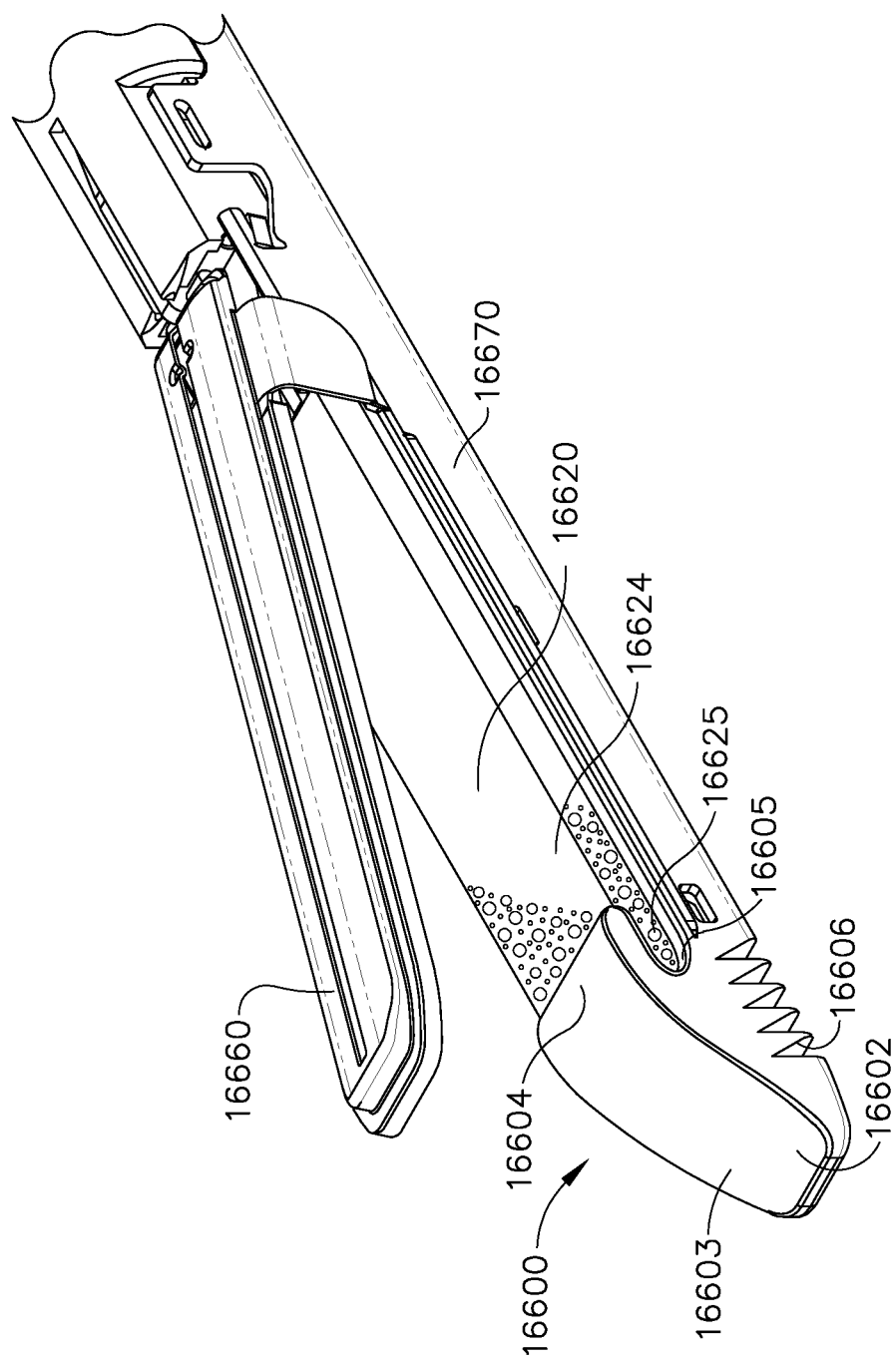
Figure 269:
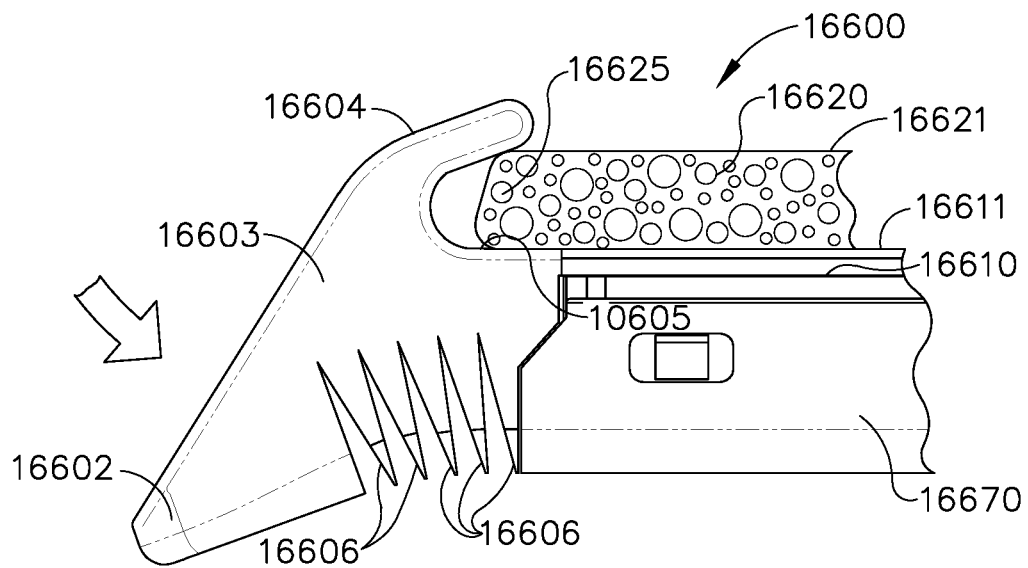
Figure 270:
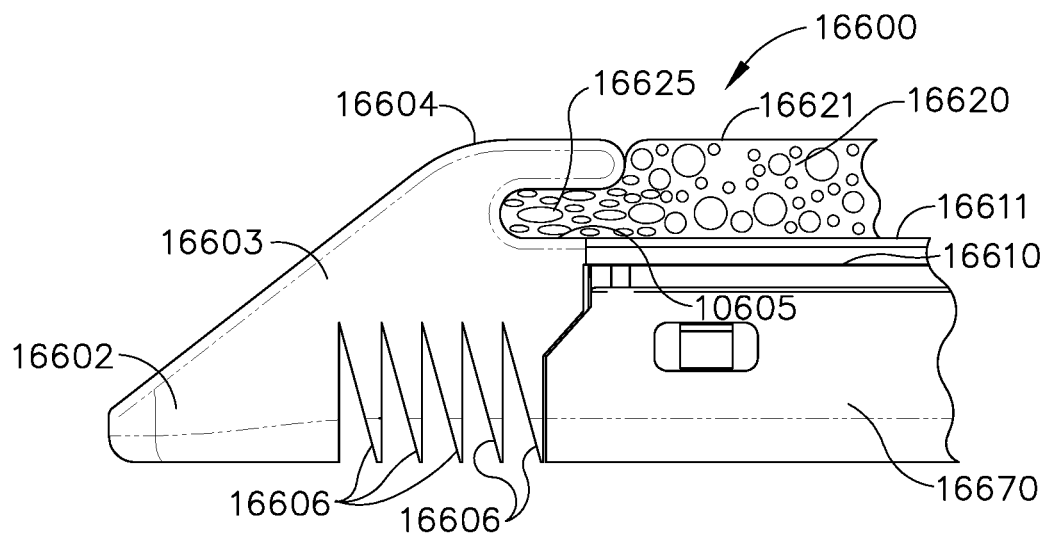
Figure 275:
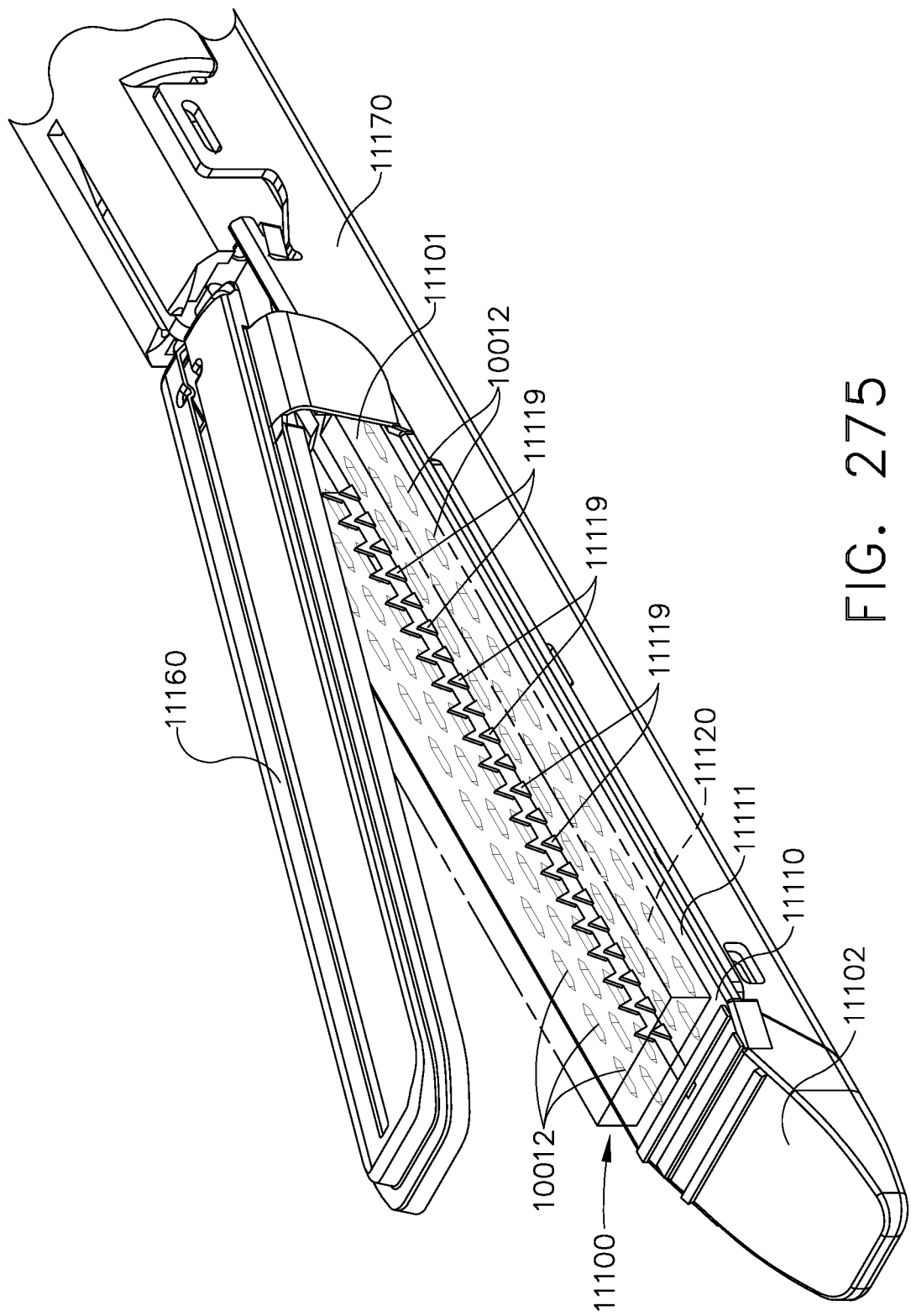
Figure 276:
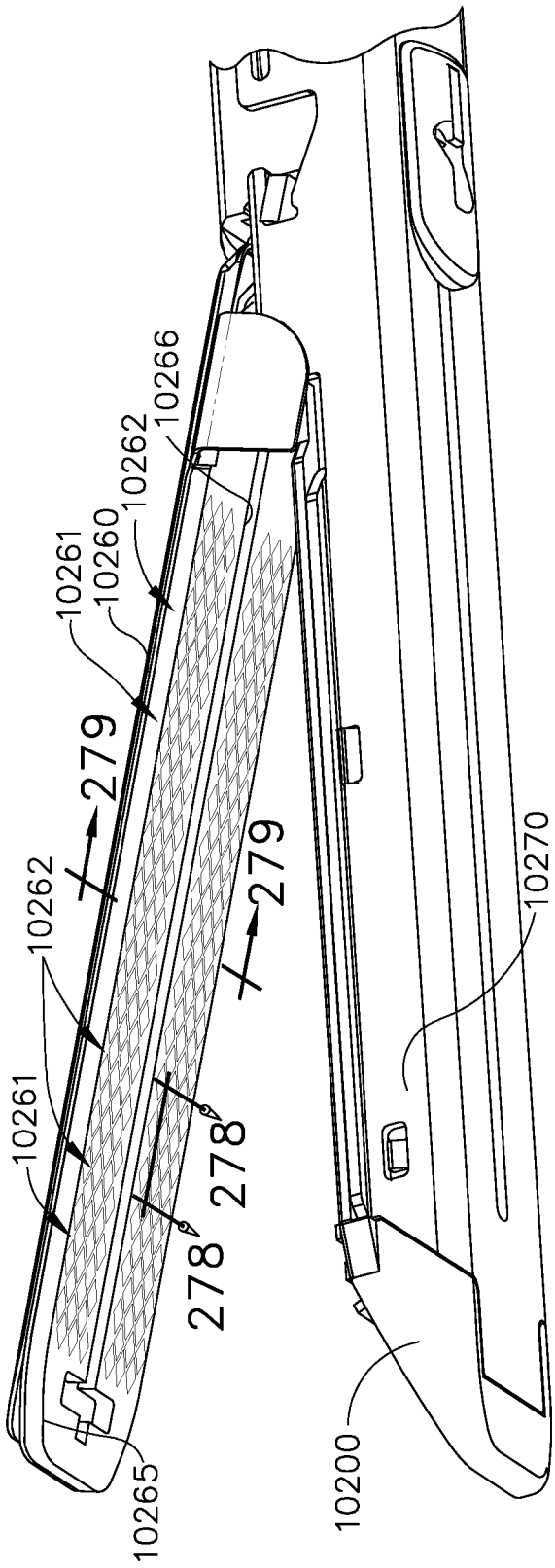
Figure 277:
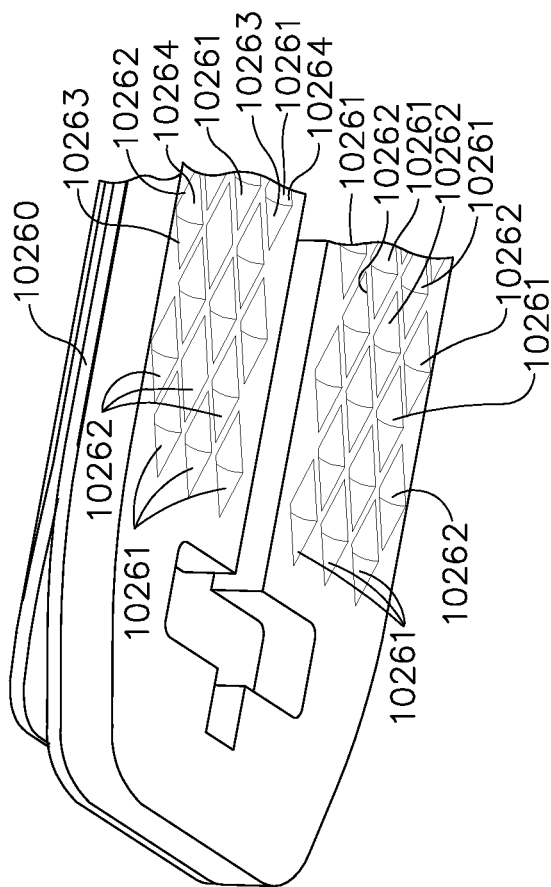
Figure 283:
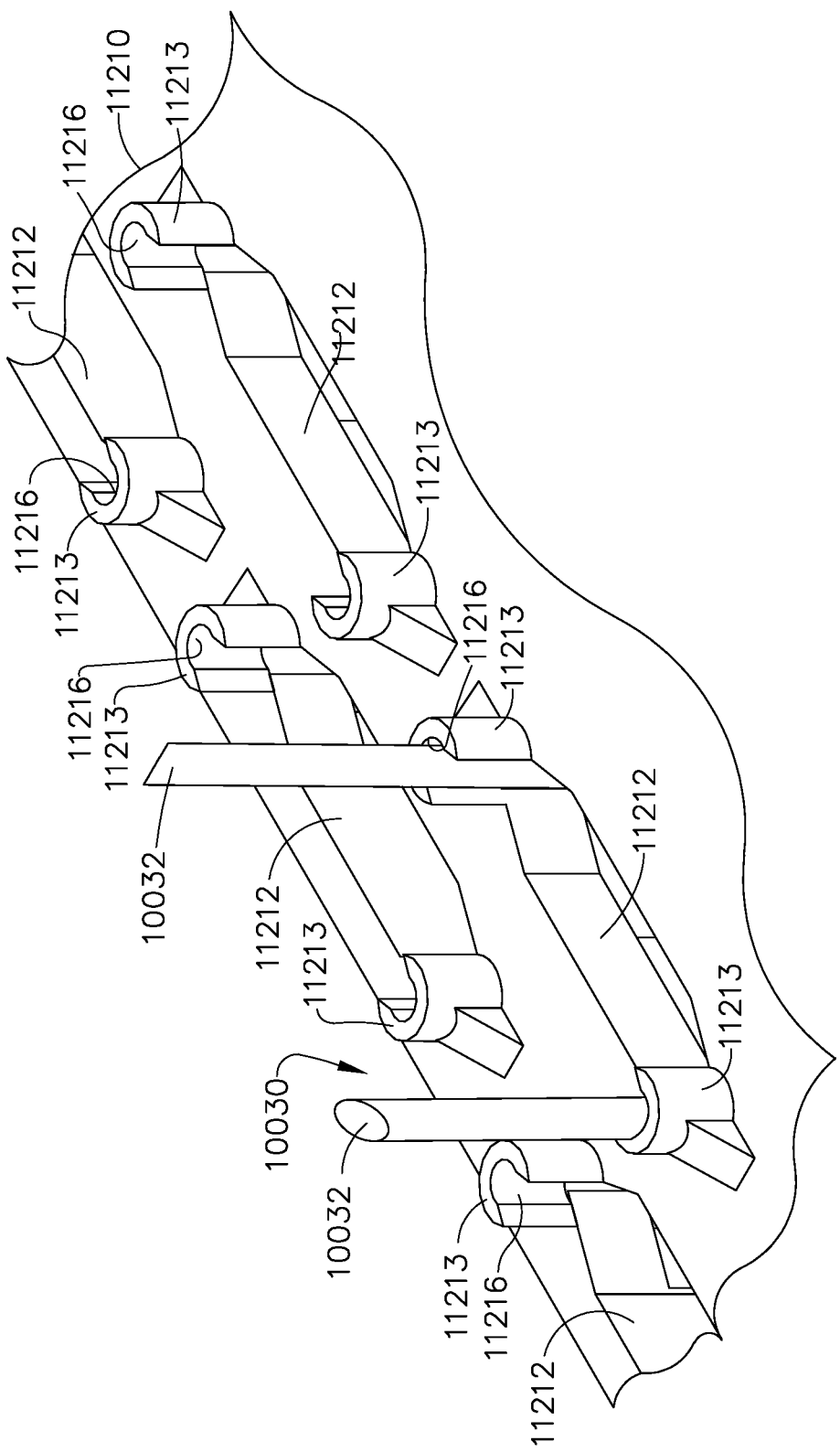
Figure 284:
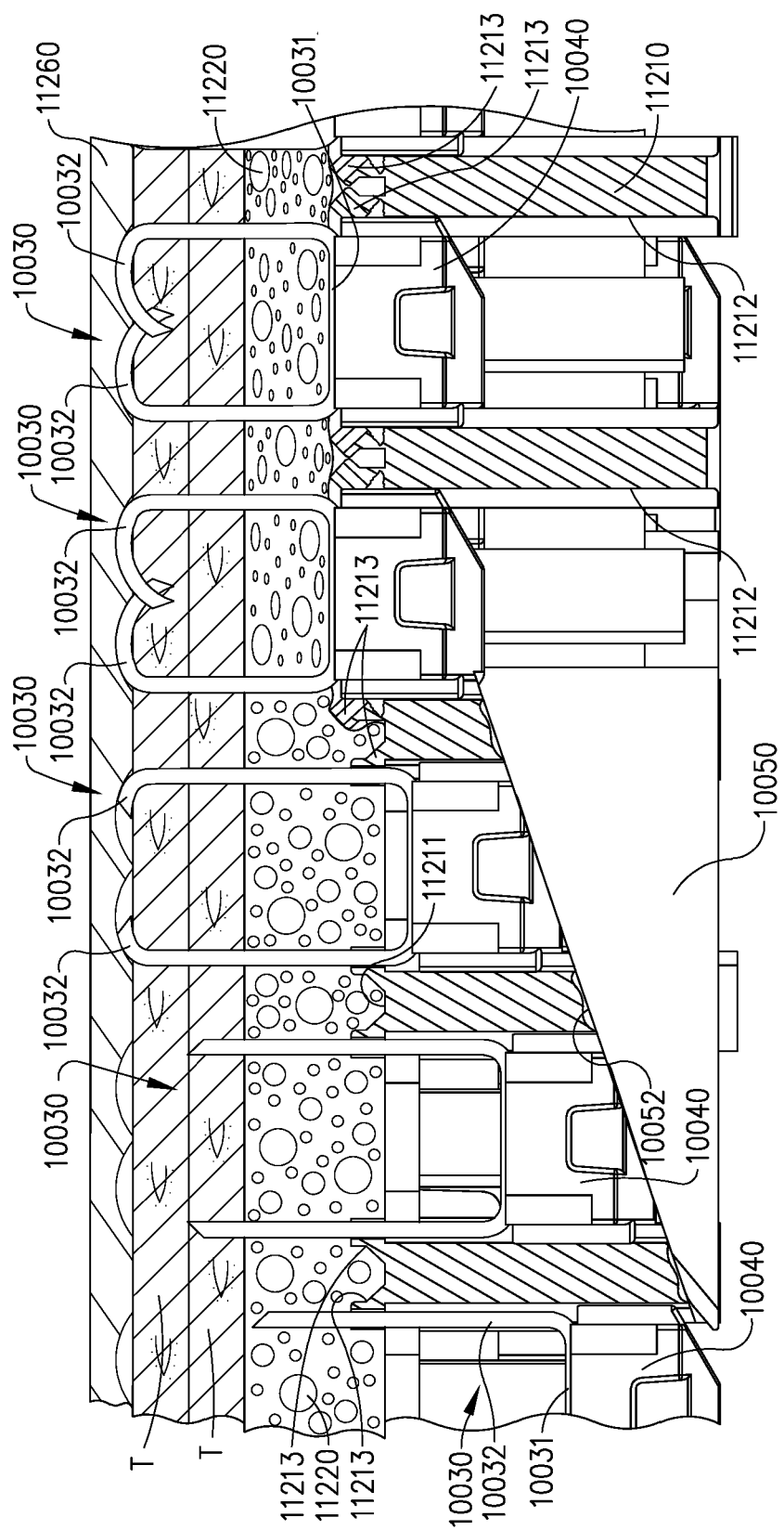
Figure 285:
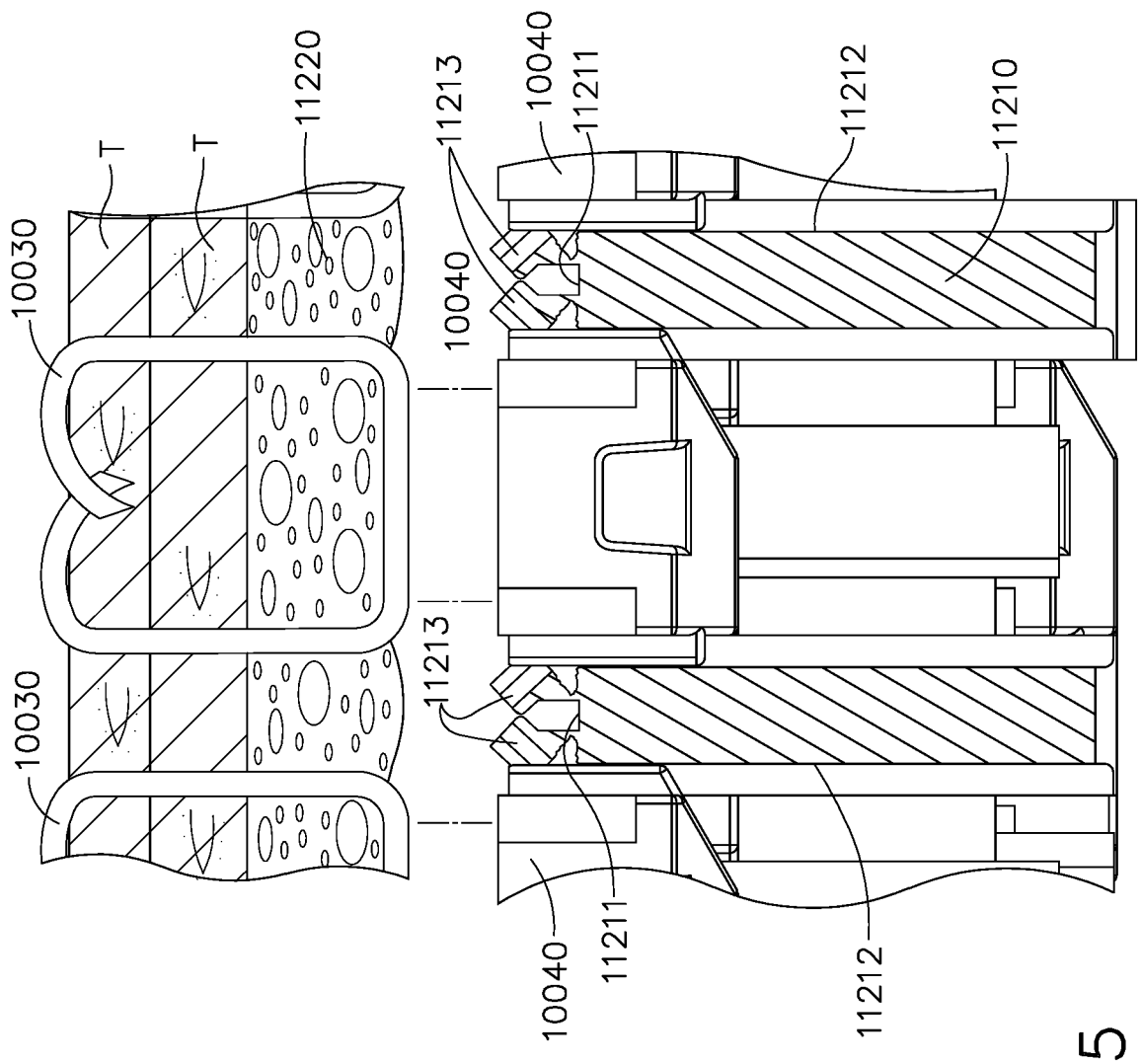
Figure 286:
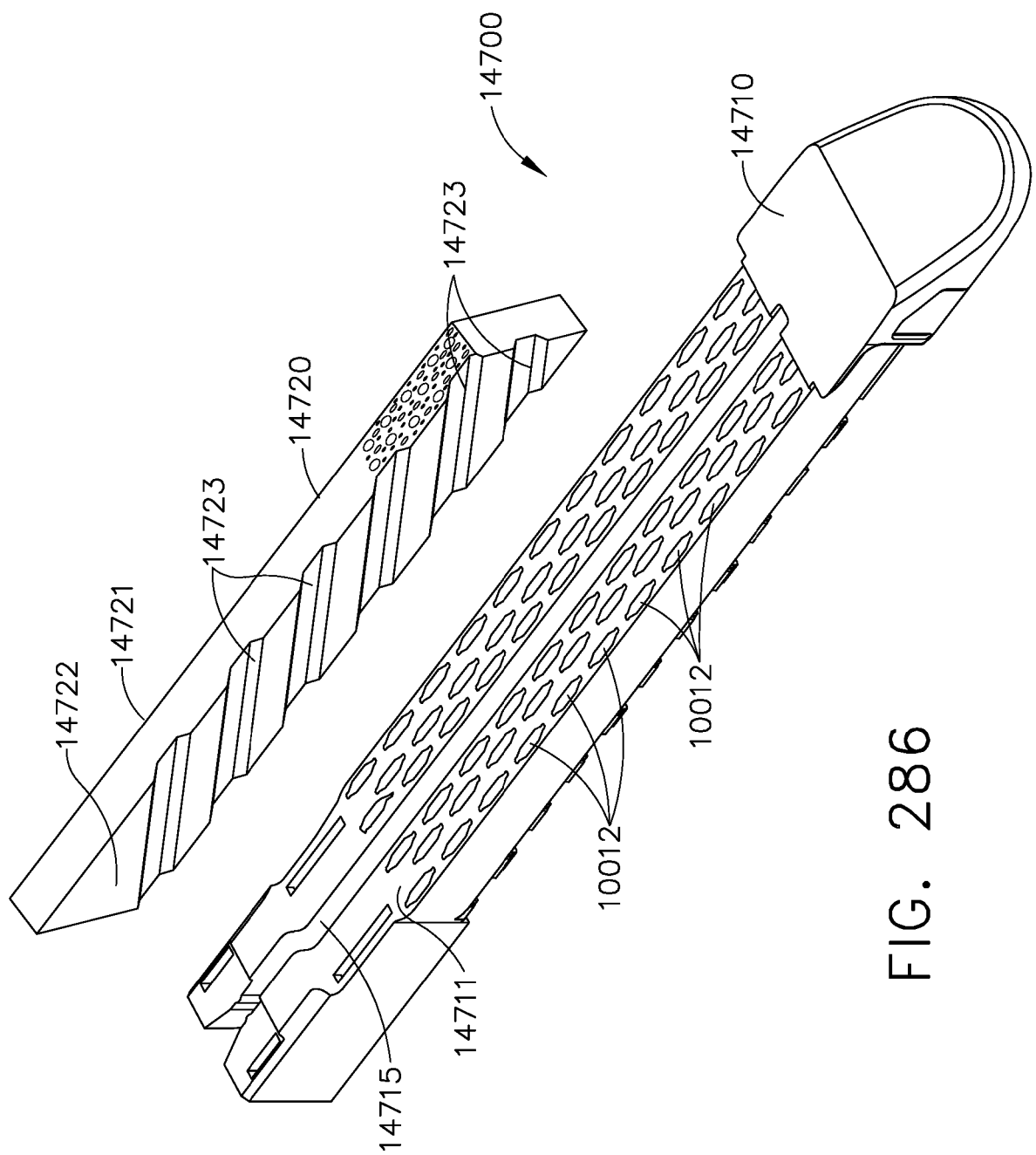
Figure 287:
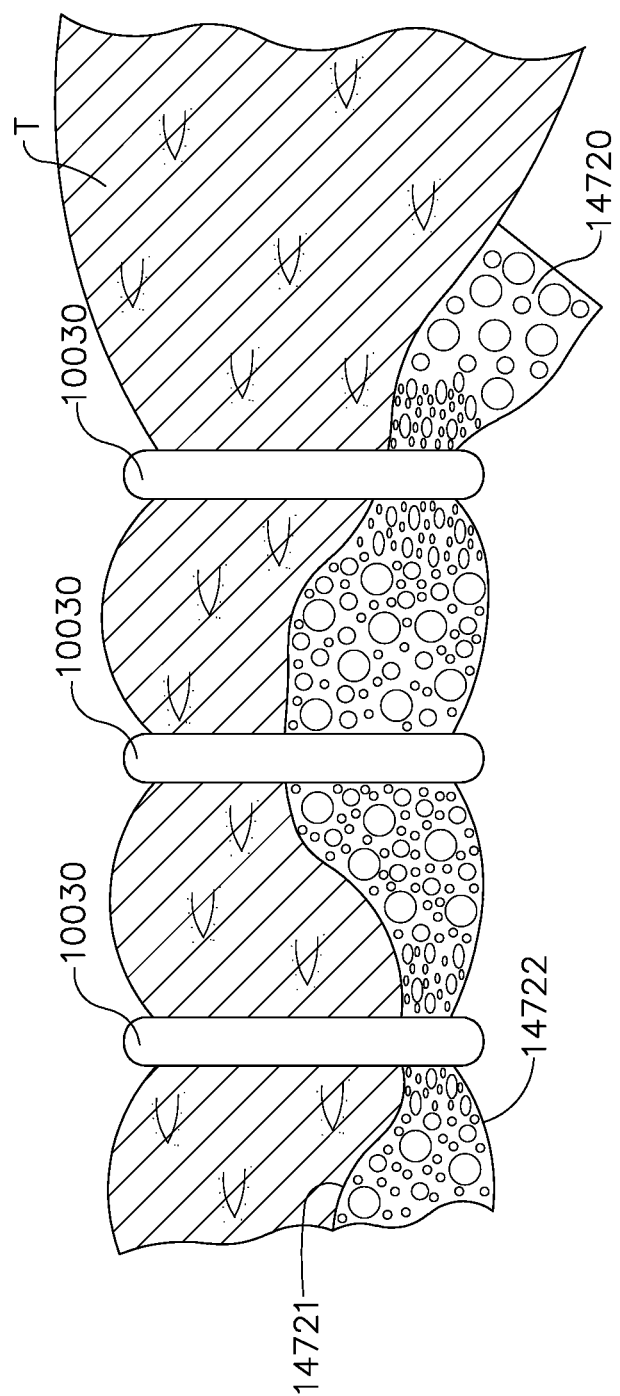
Figure 288:
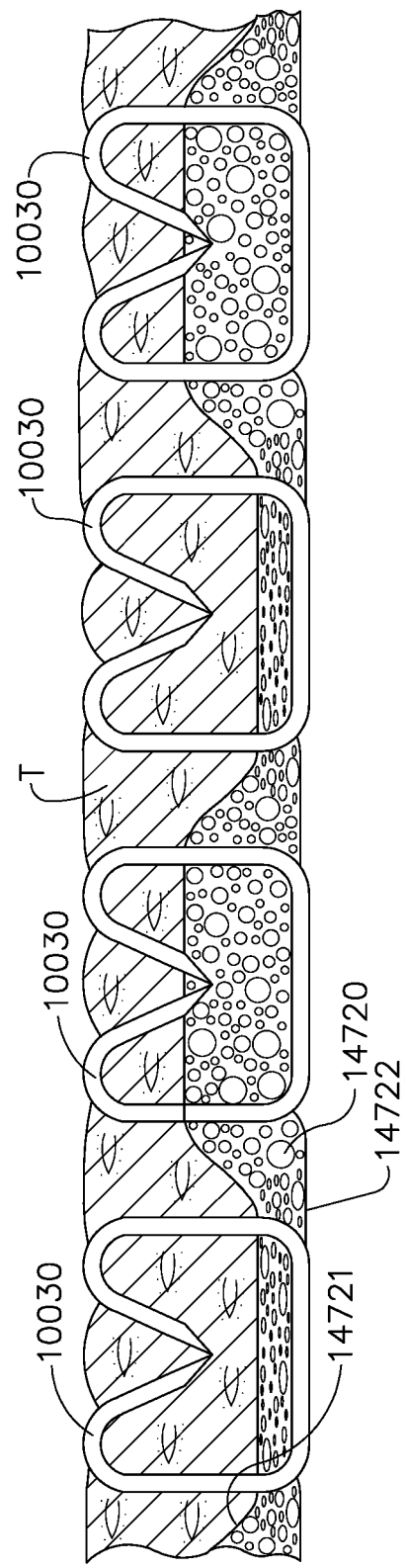
Figure 289:
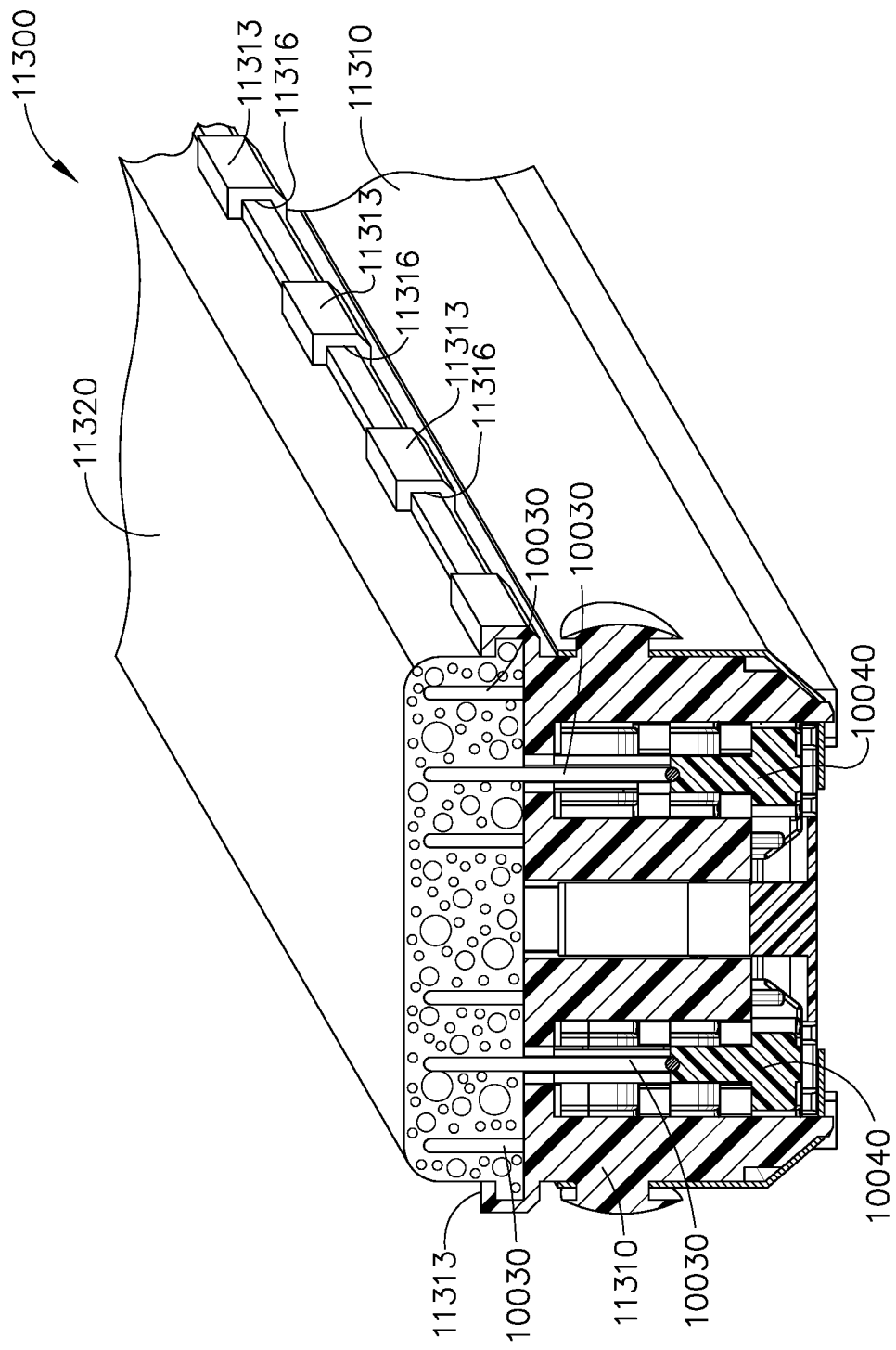
Figure 290:
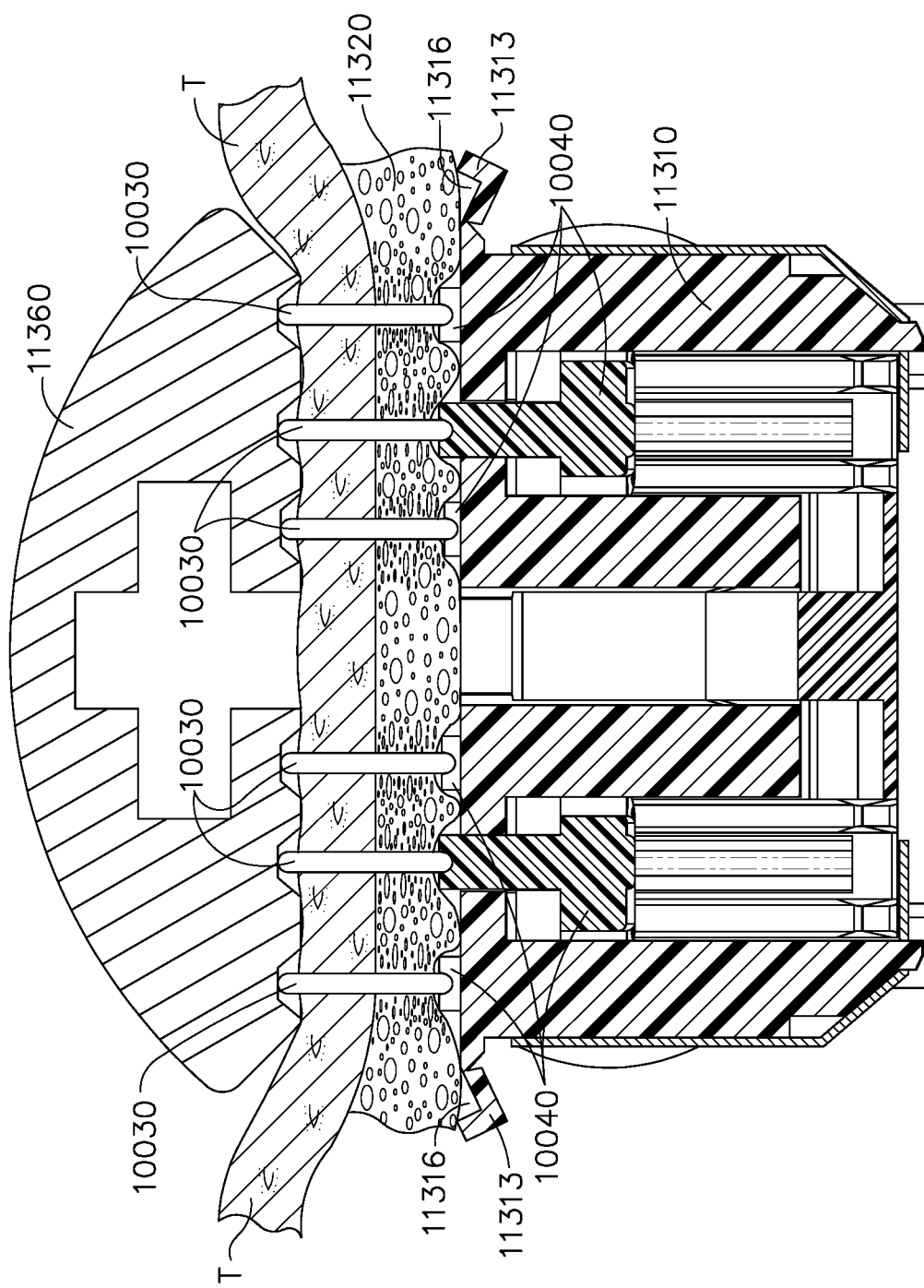
Figure 291:
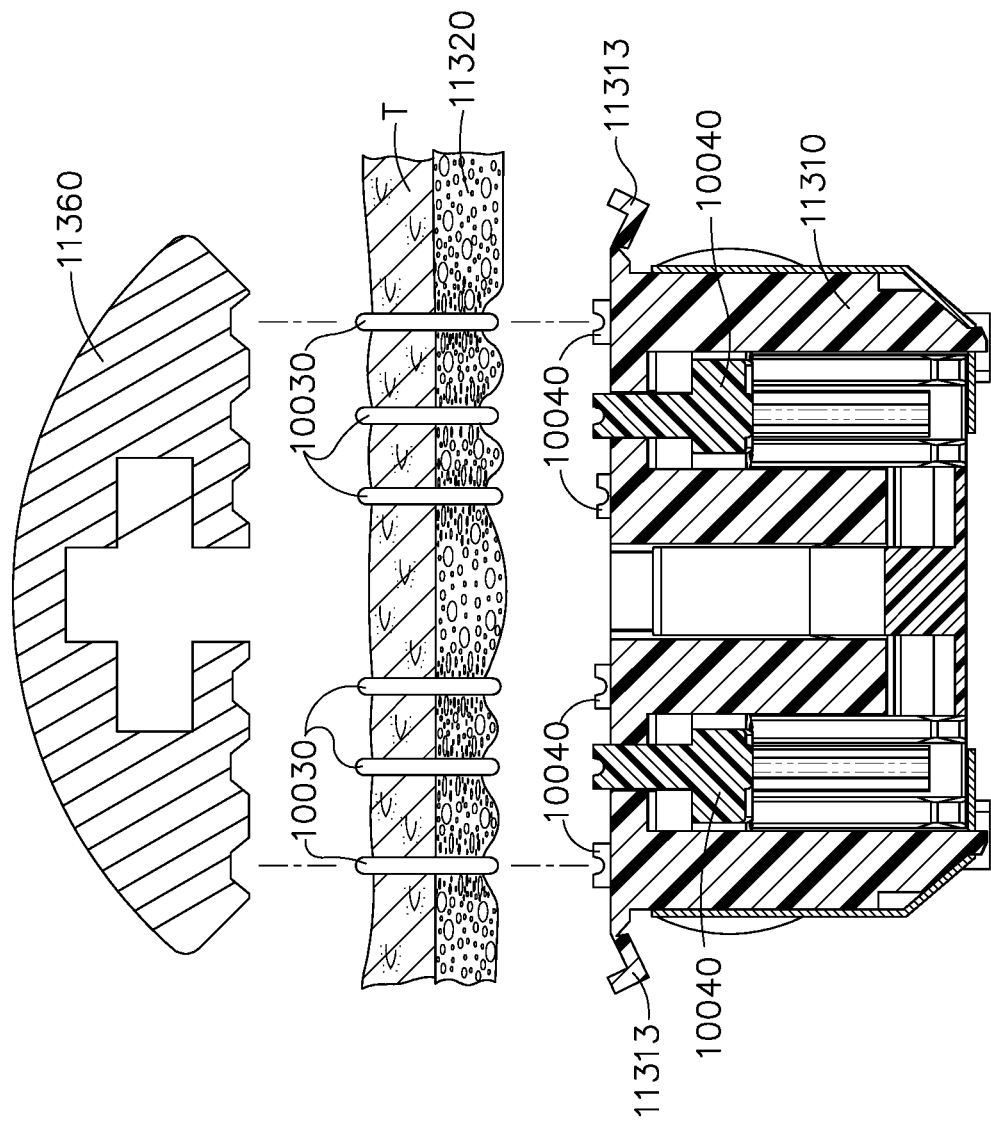
Figure 292:
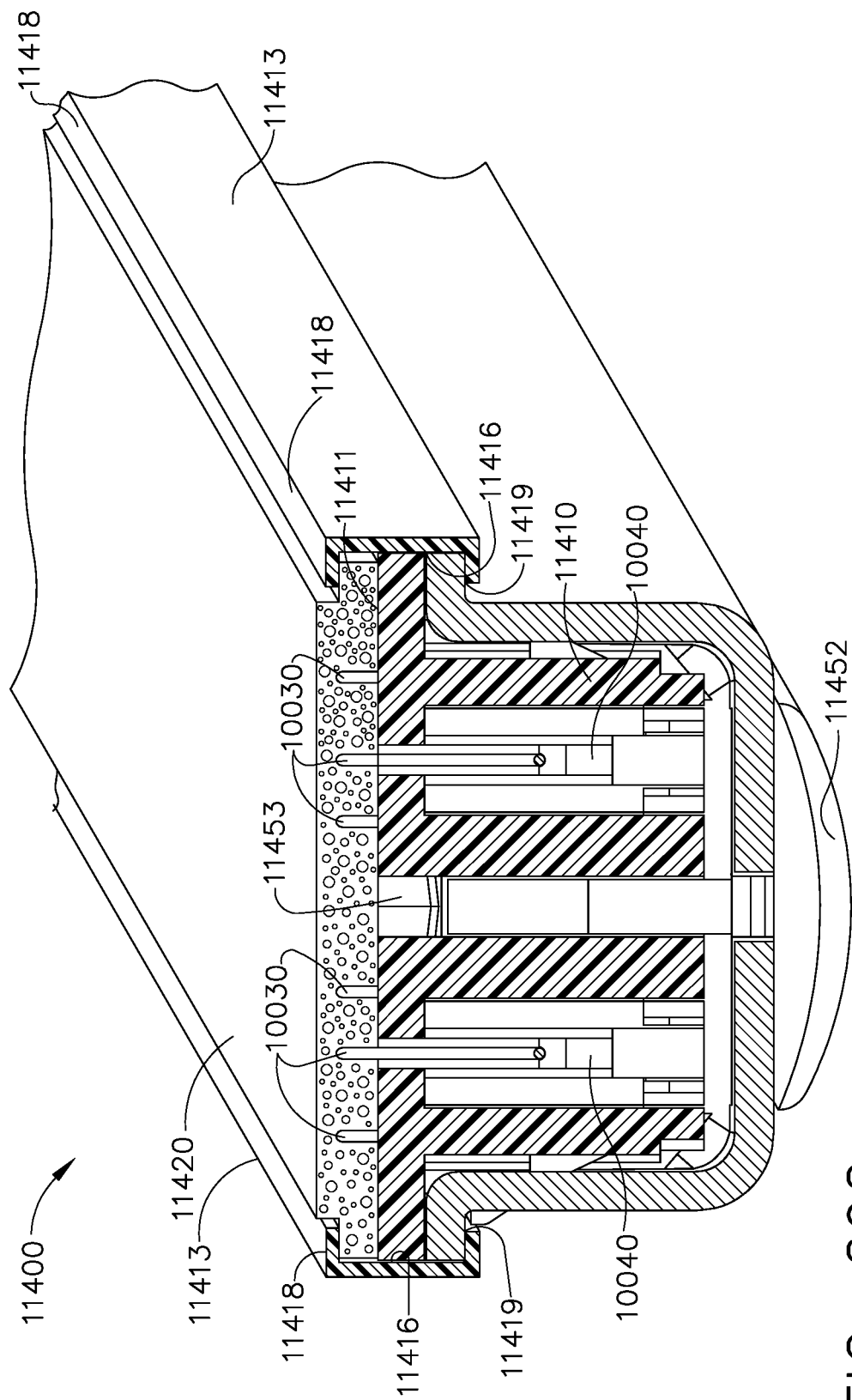
Figure 293:
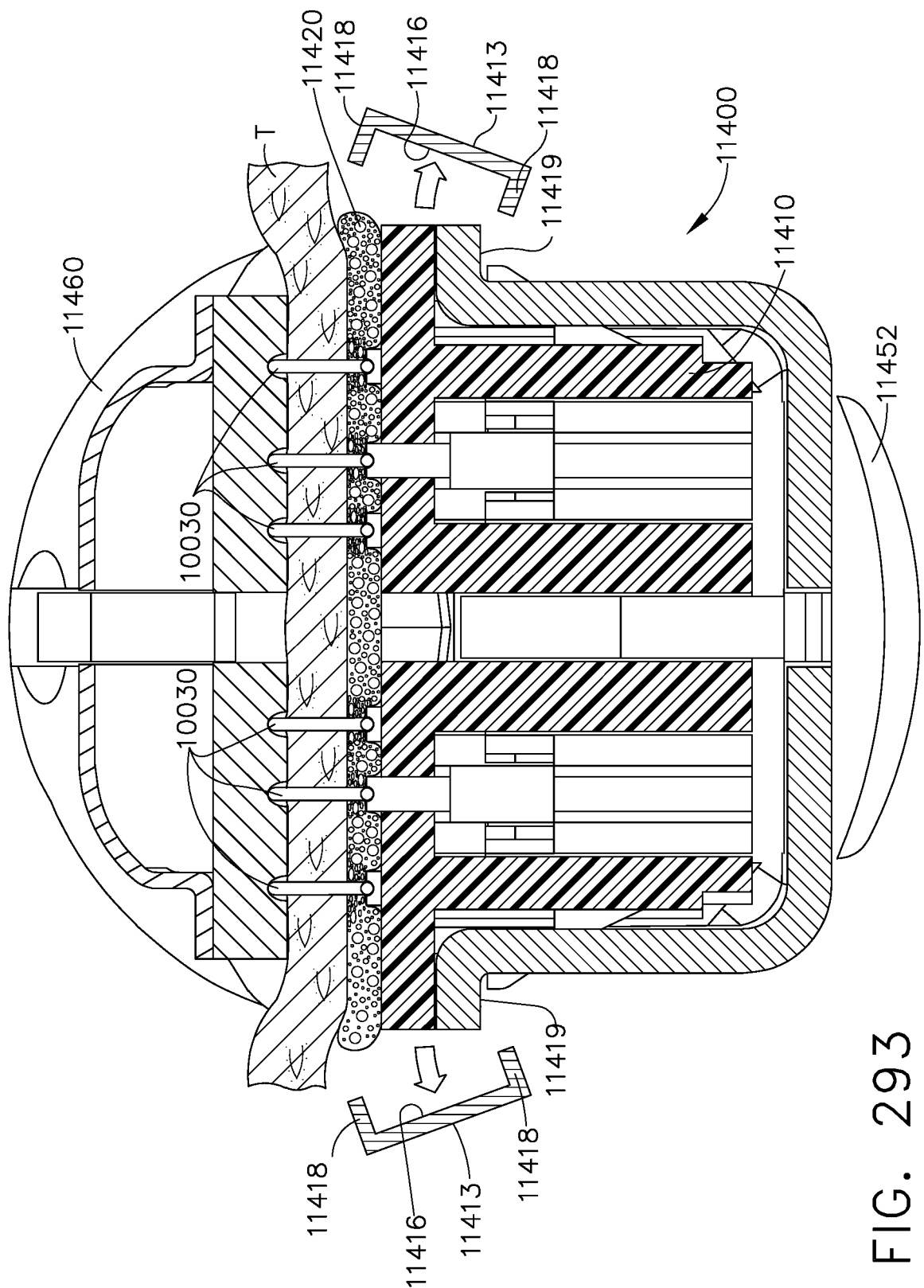
Figure 294:
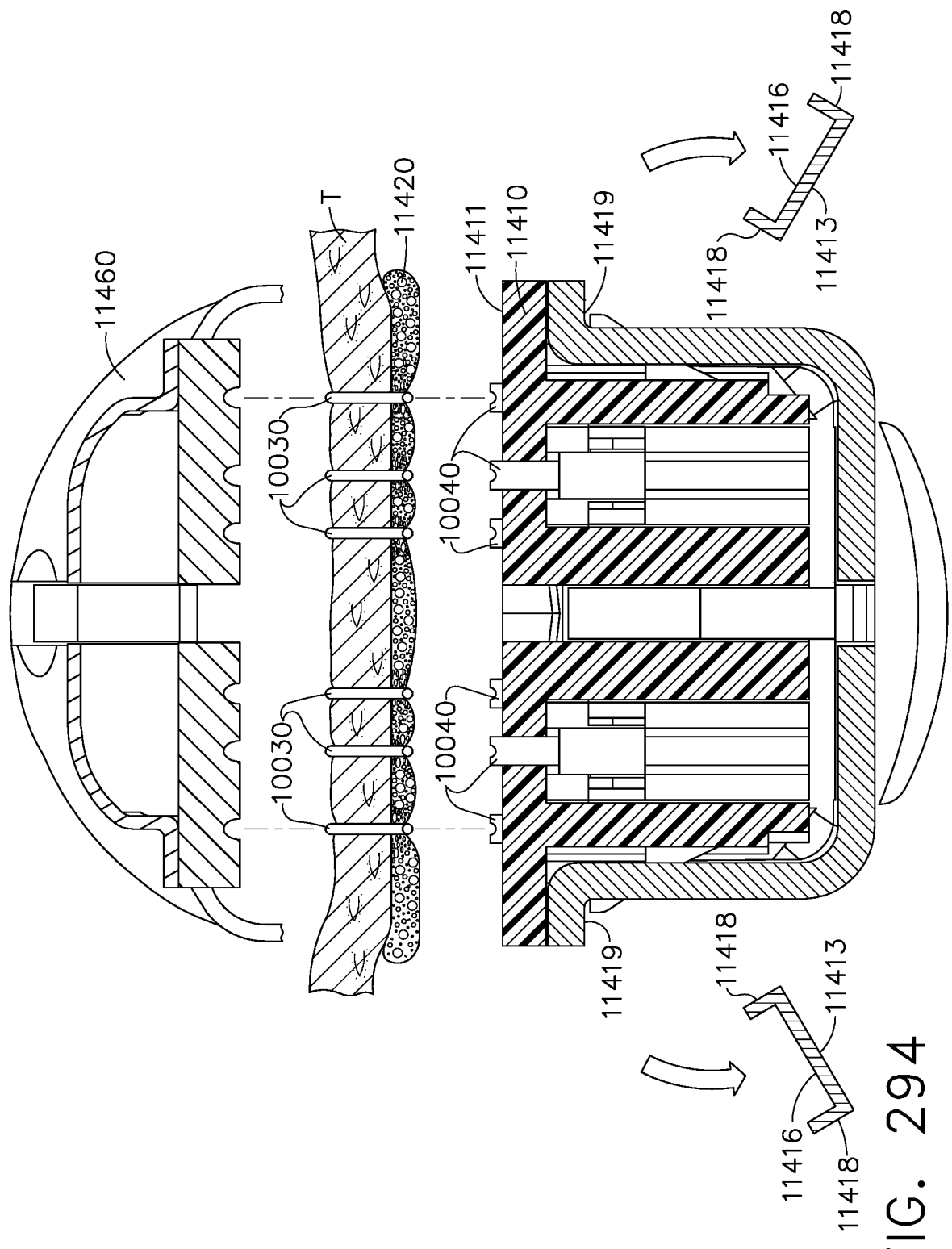
Figure 295:
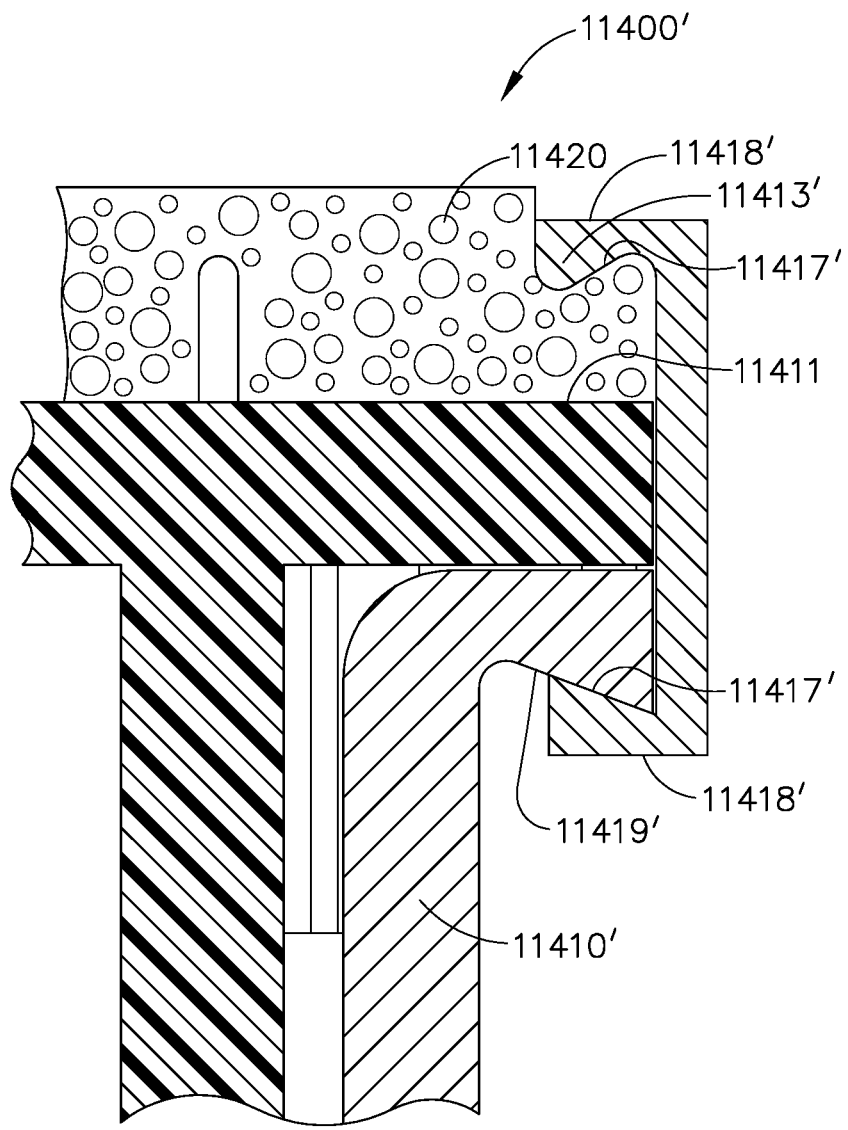
Figure 296:
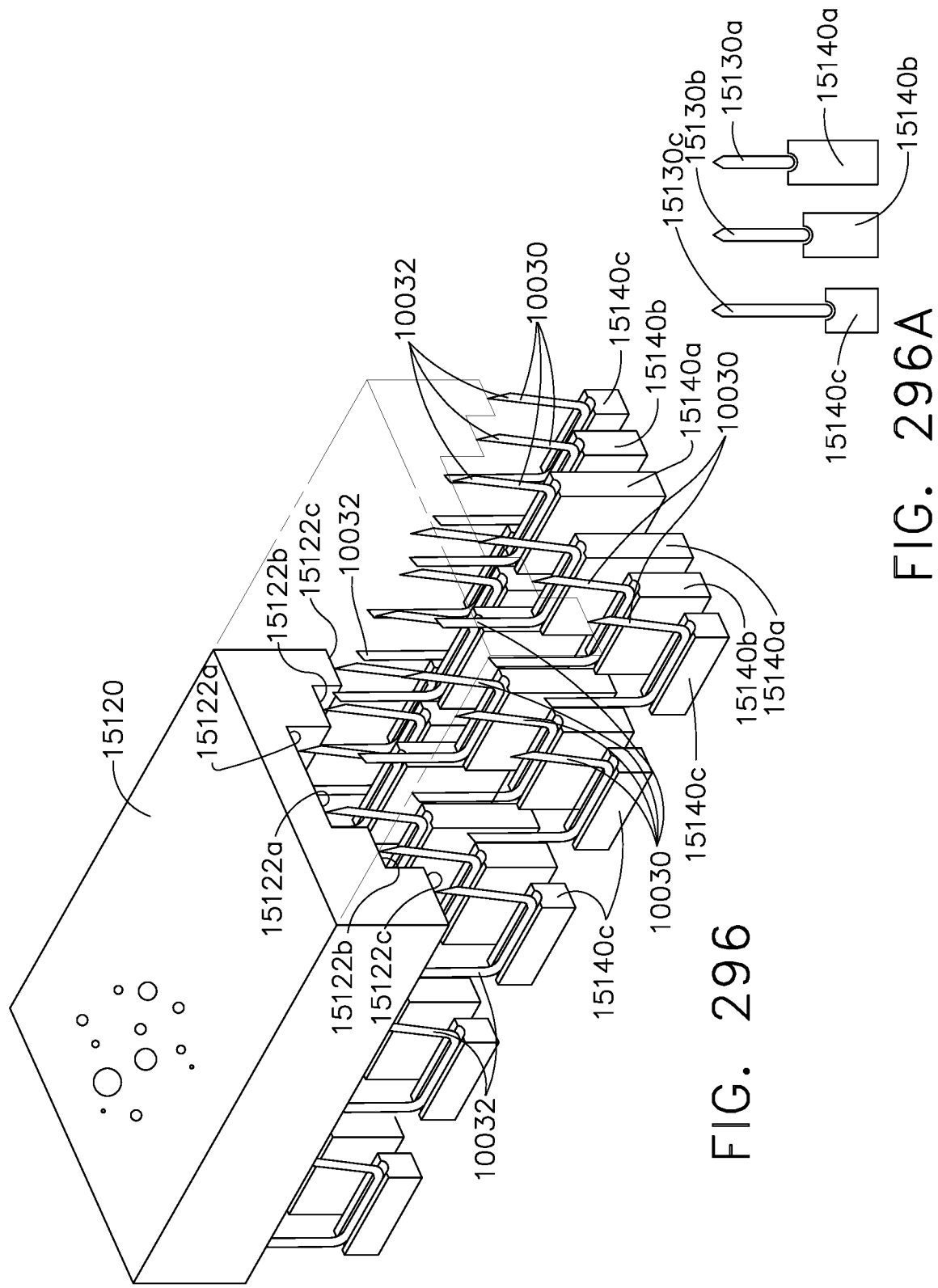
Figure 297:
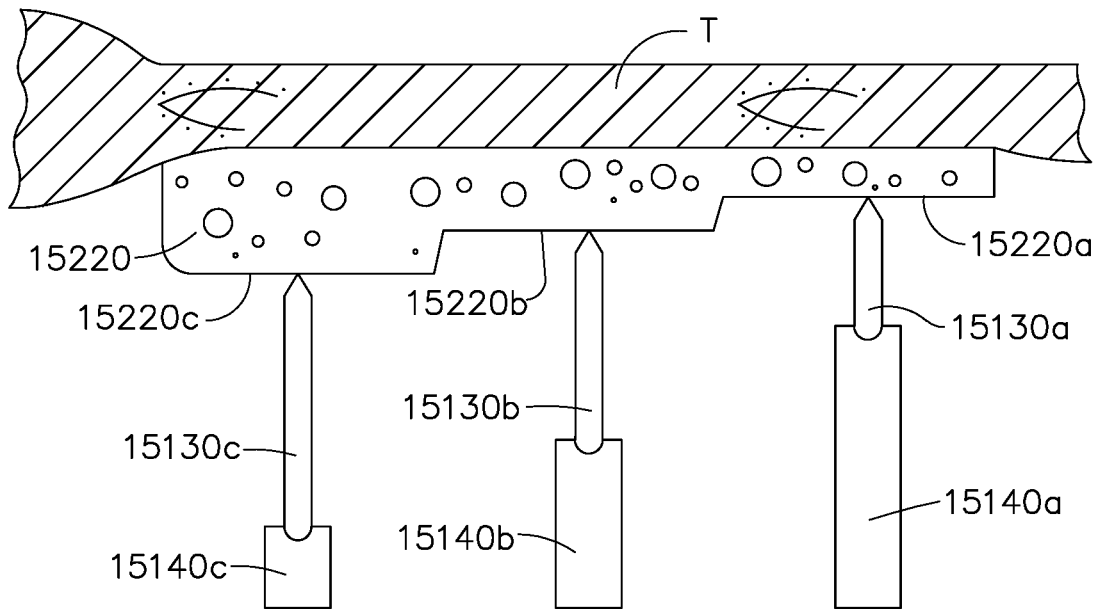
Figure 298:
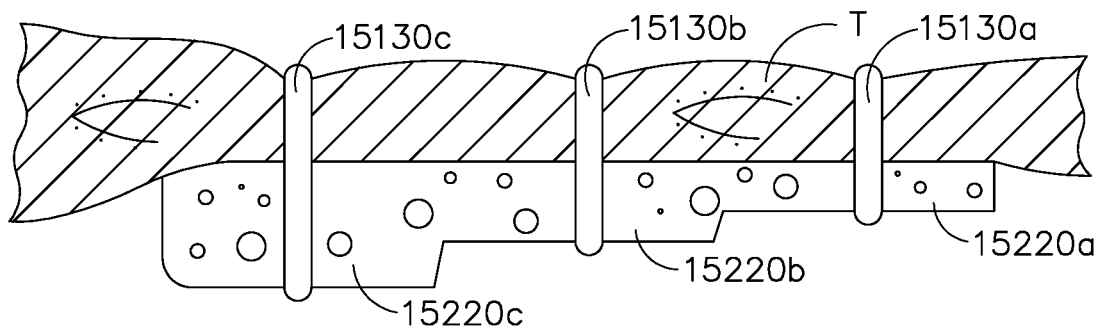
Figure 299:
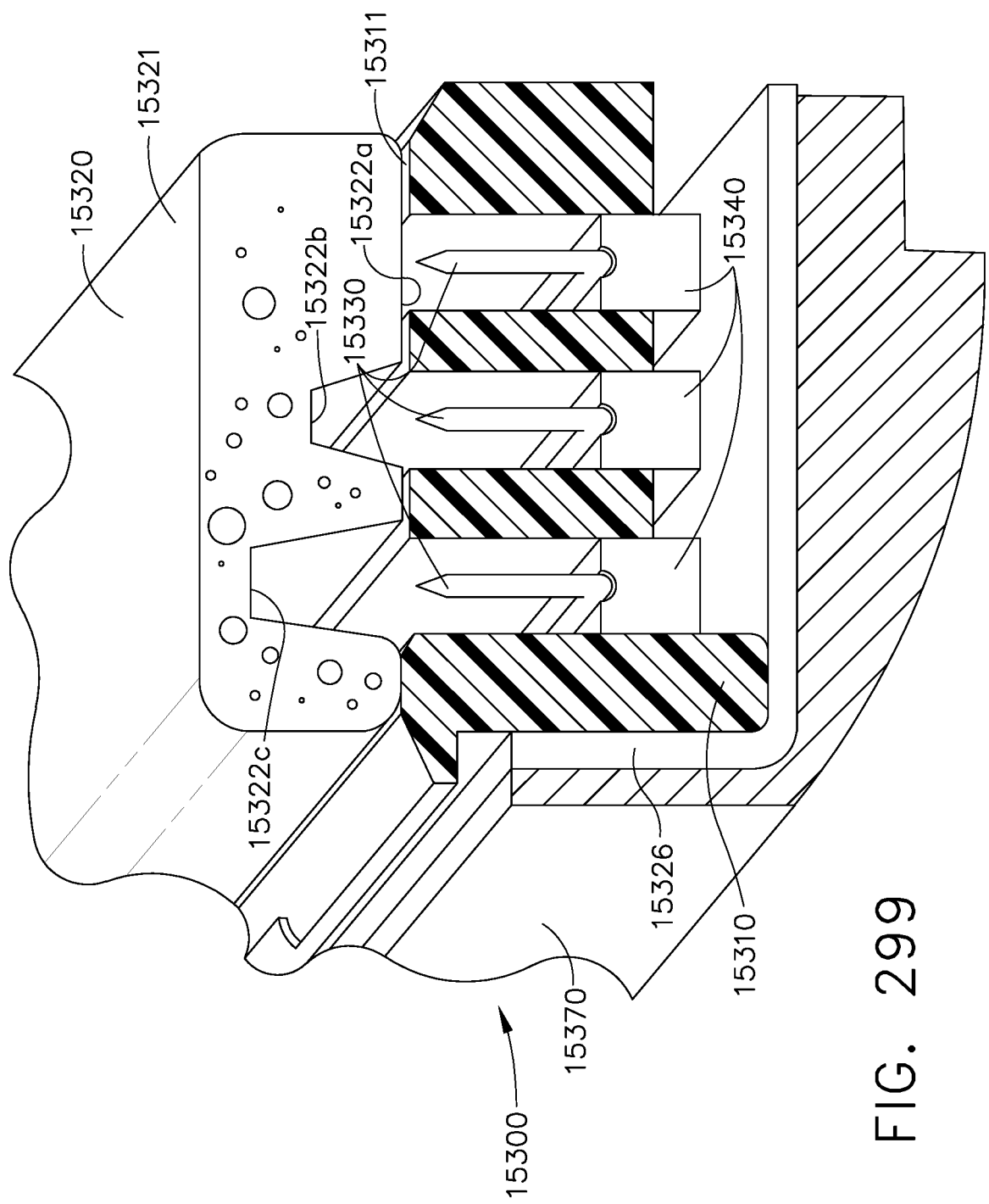
Figure 302:
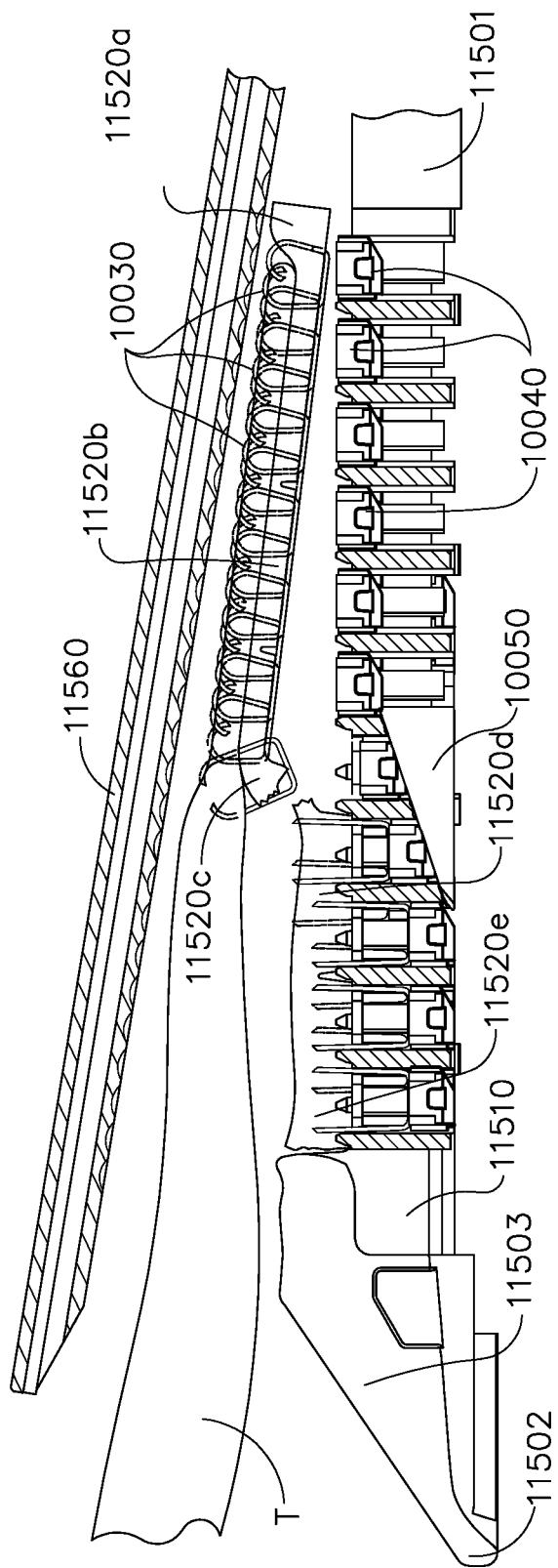
Figure 309:
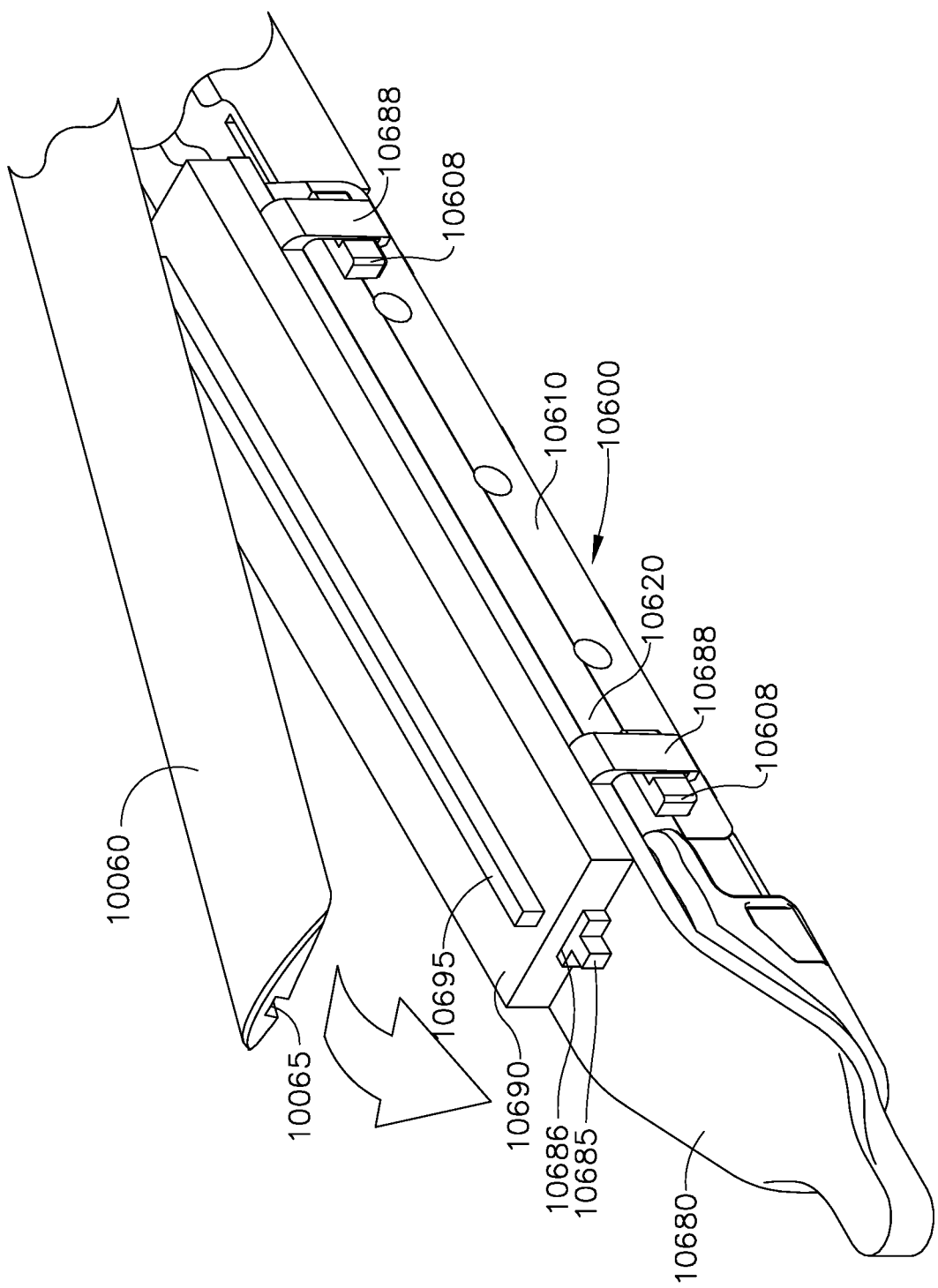
Figure 310:
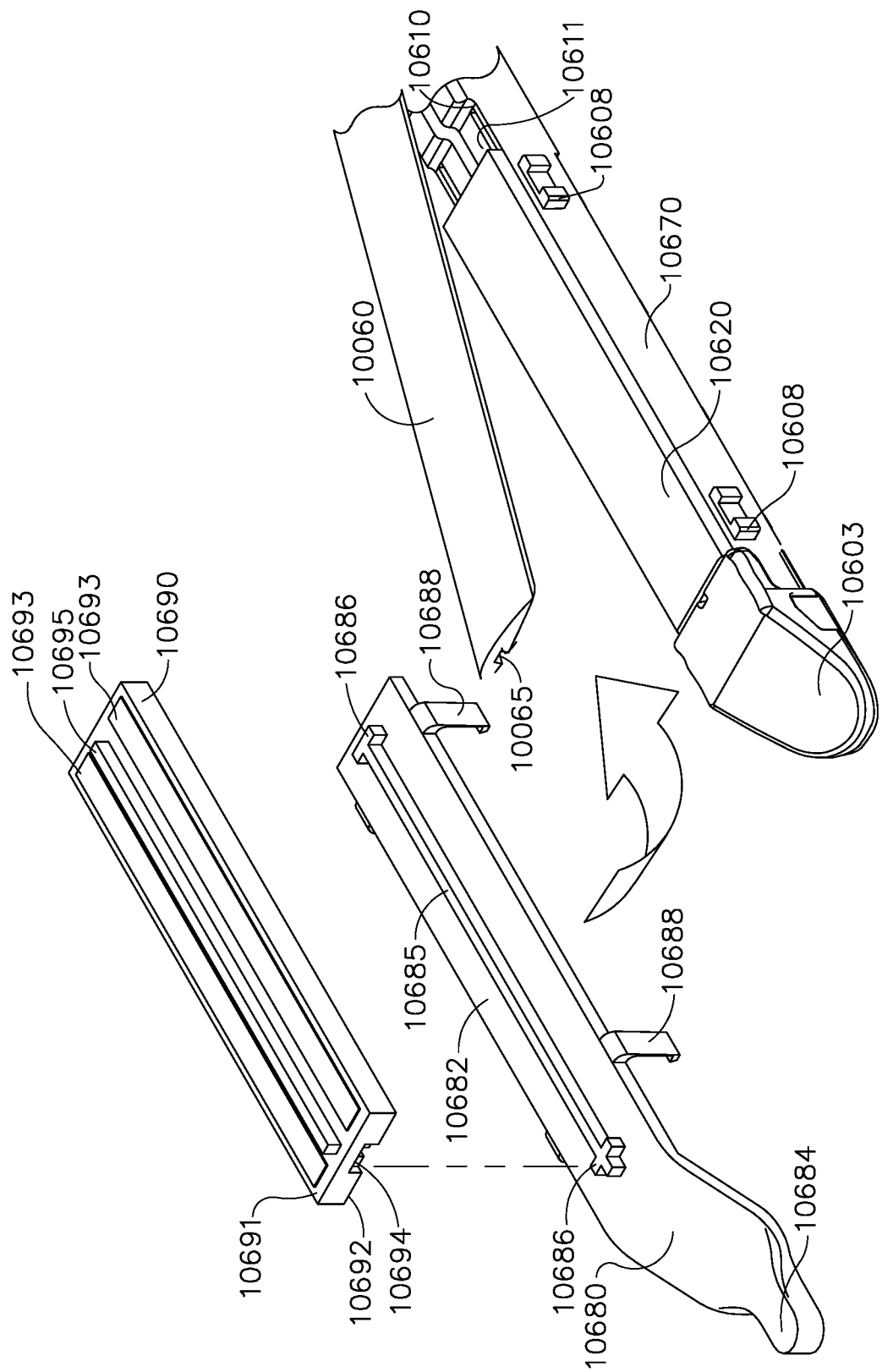
Figure 310A:
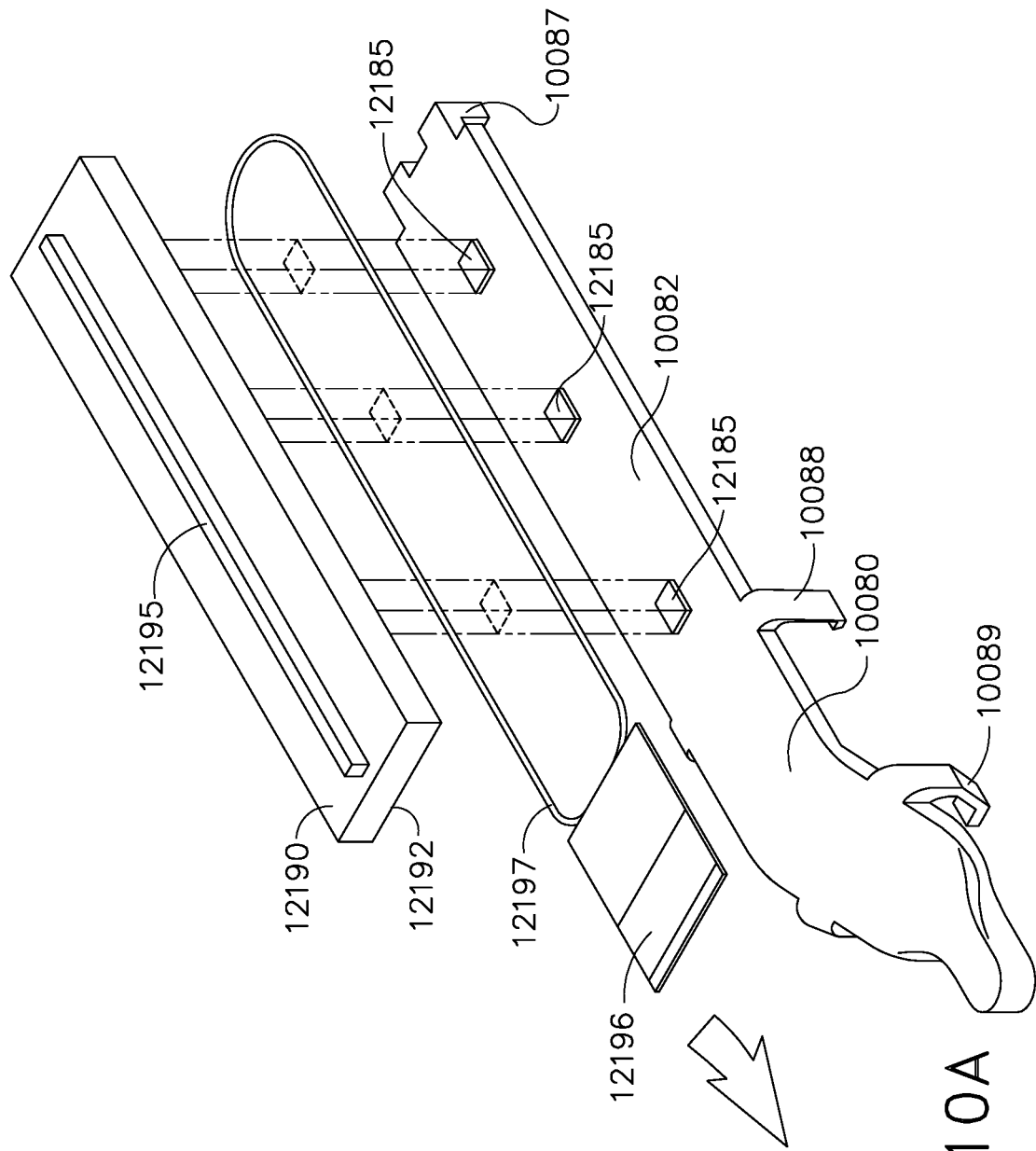
Figure 311:
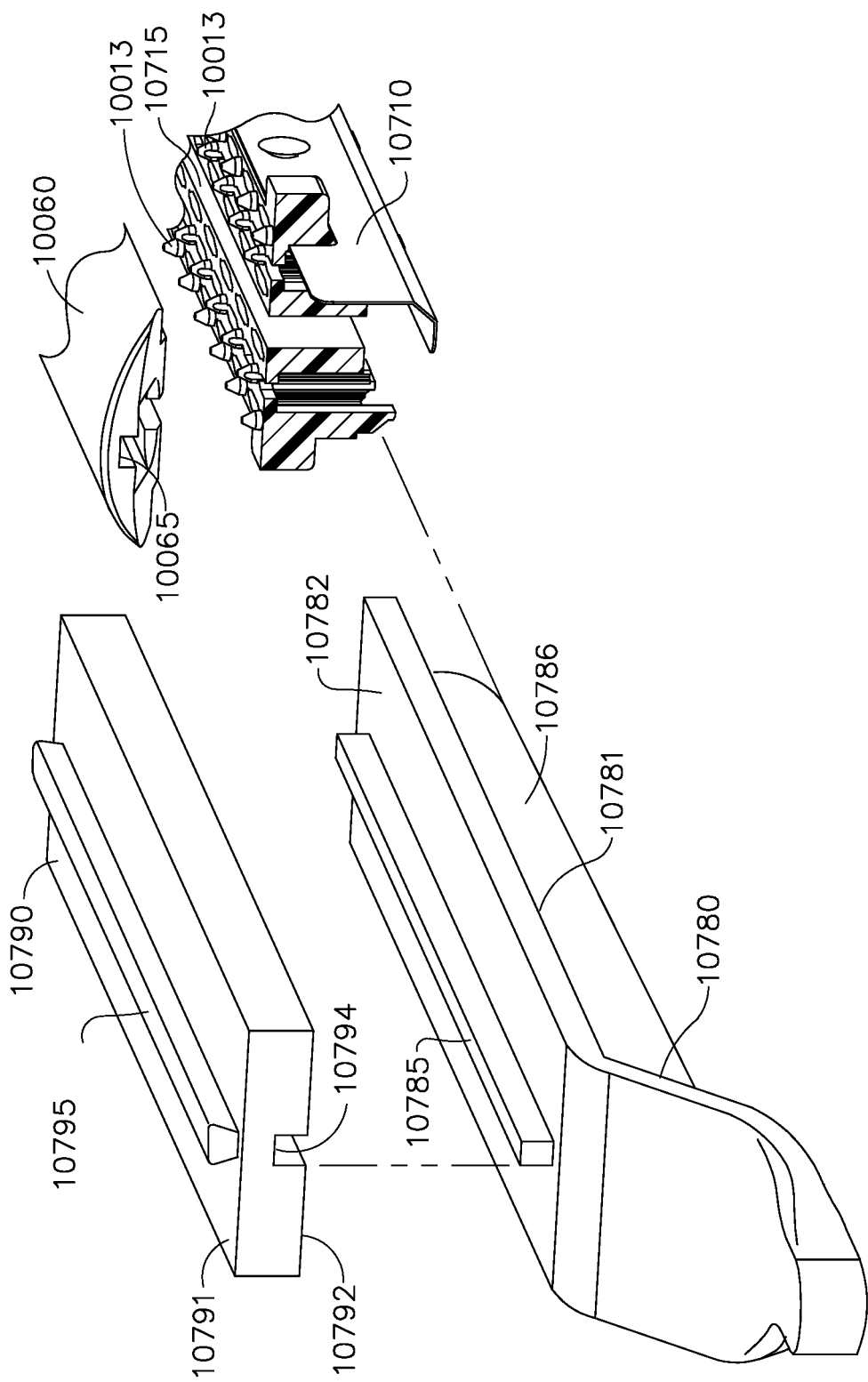
Figure 312:
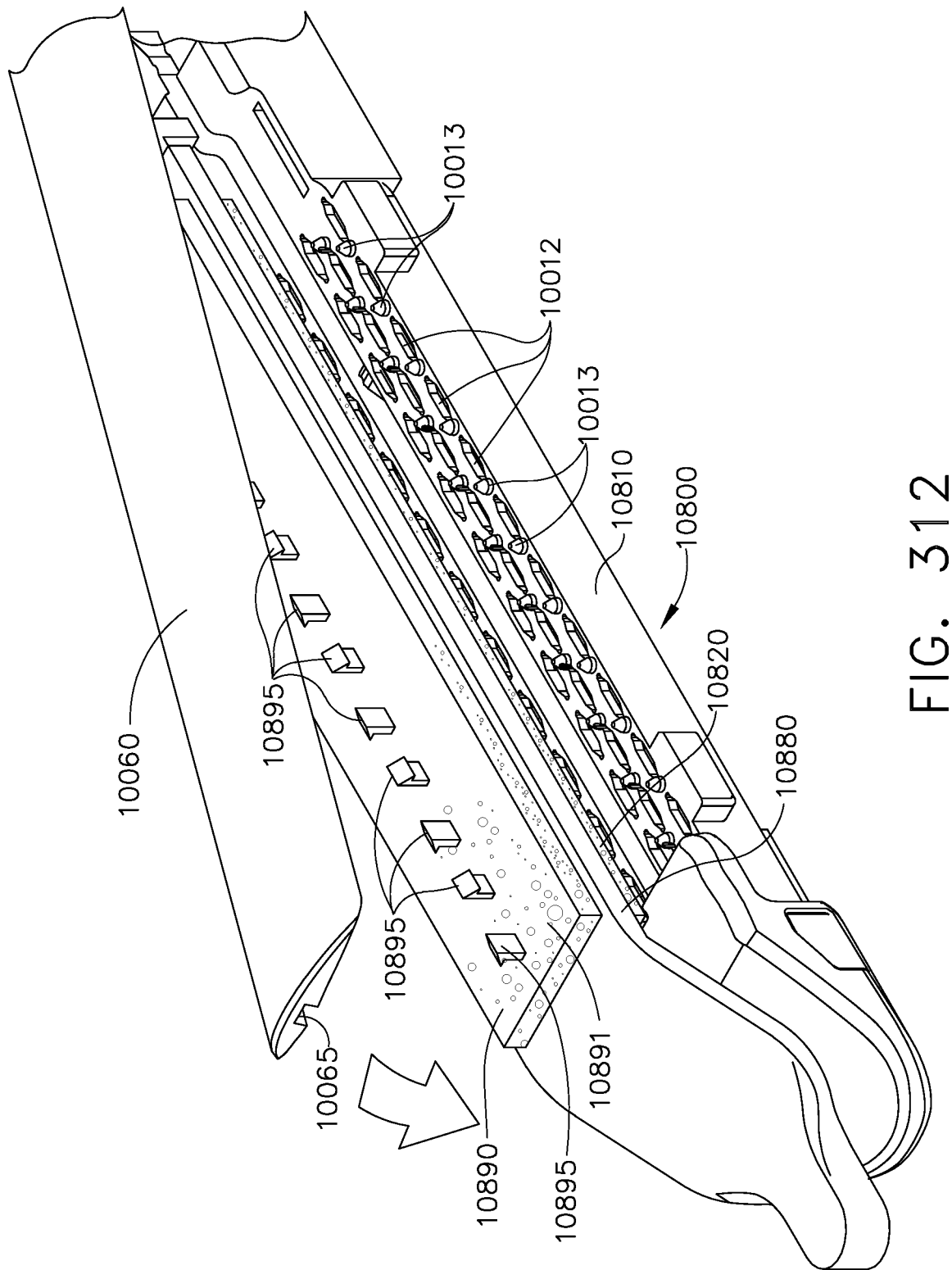
Figure 318:
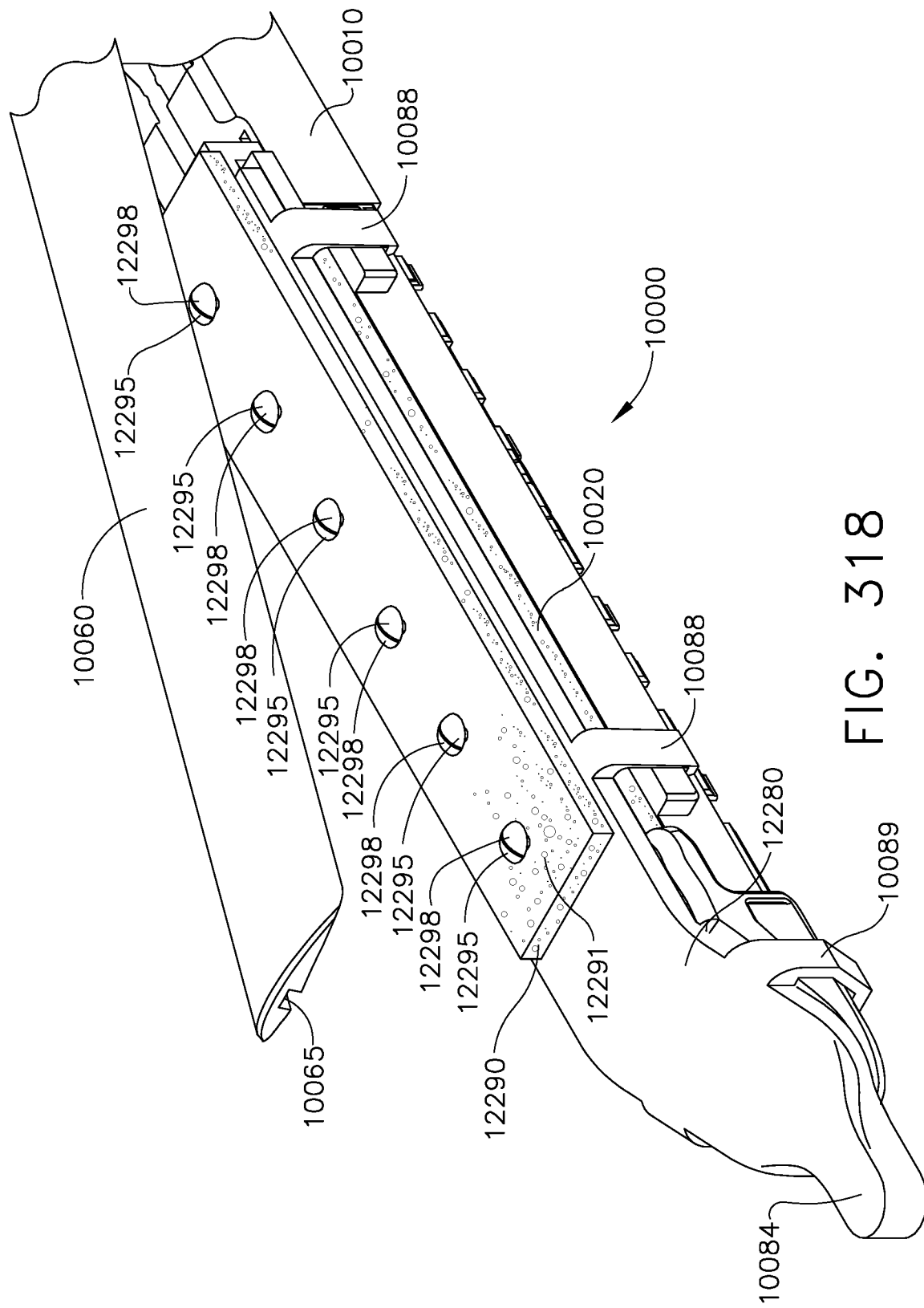
Figure 323:
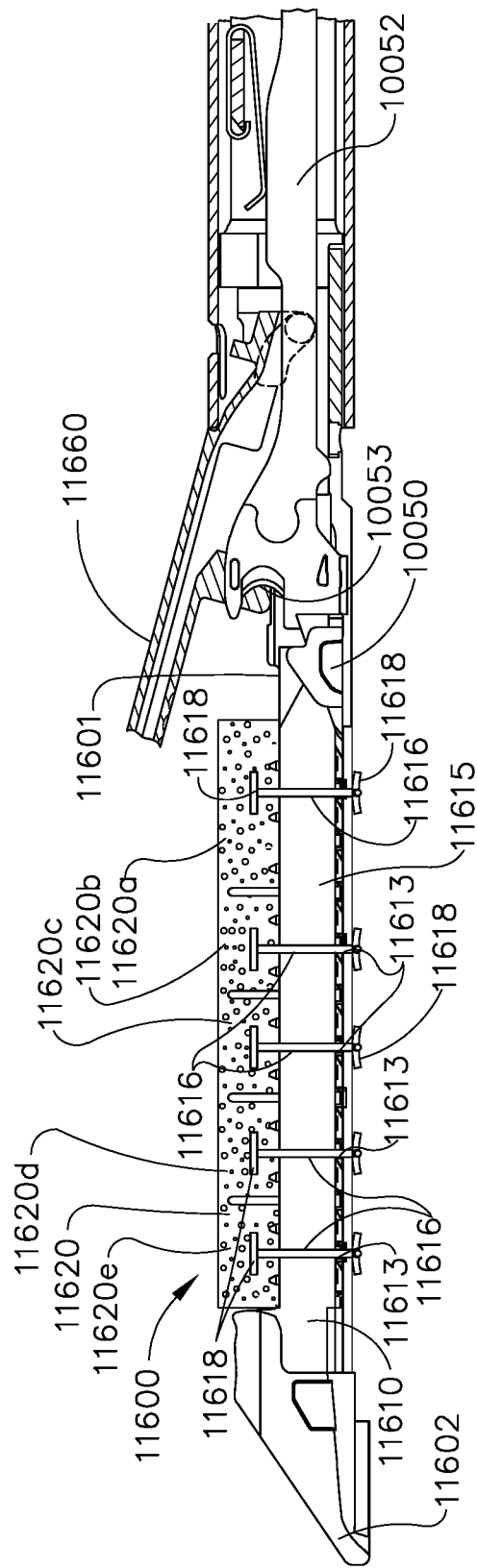
Figure 326:
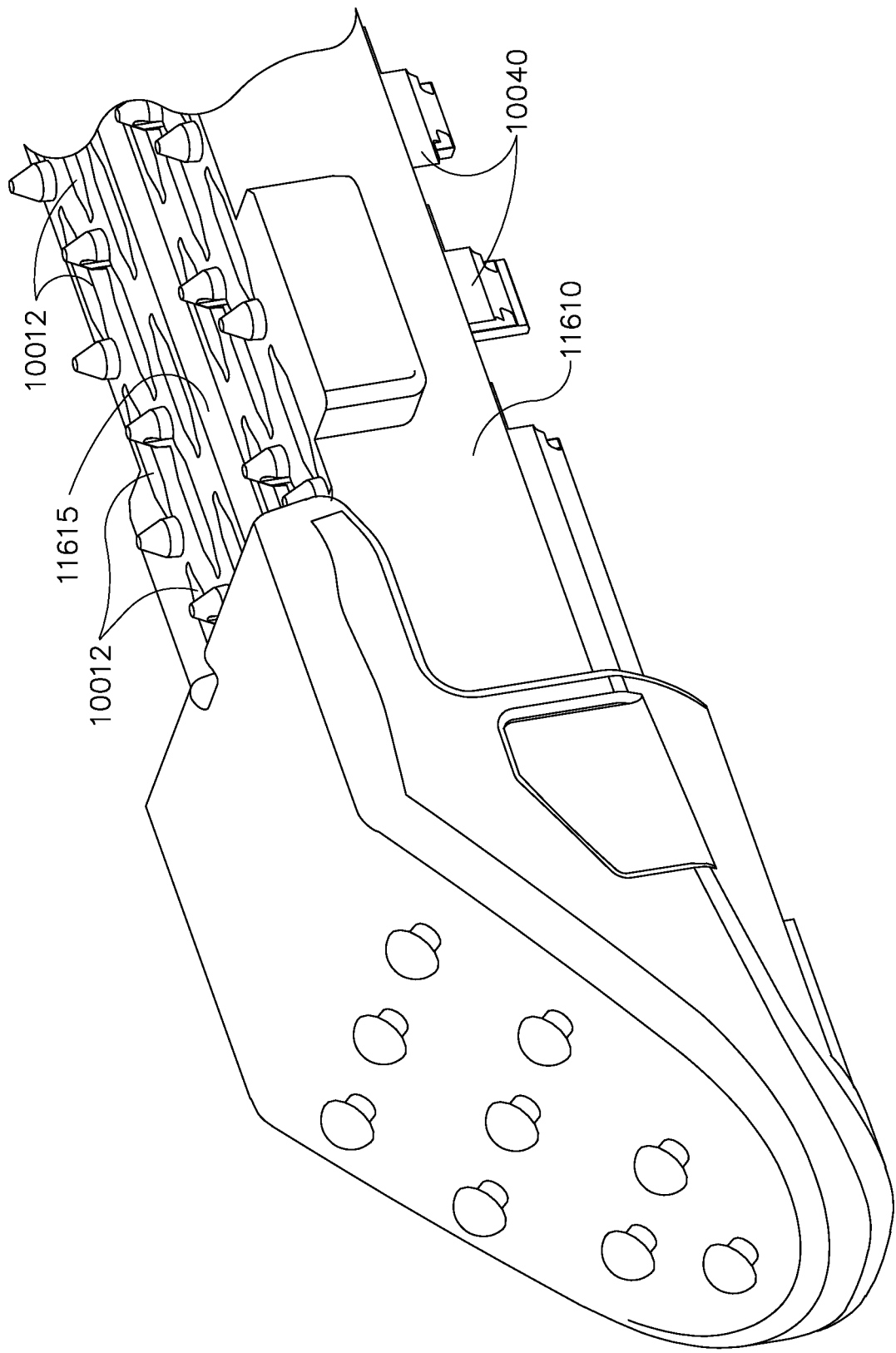
Figure 327:
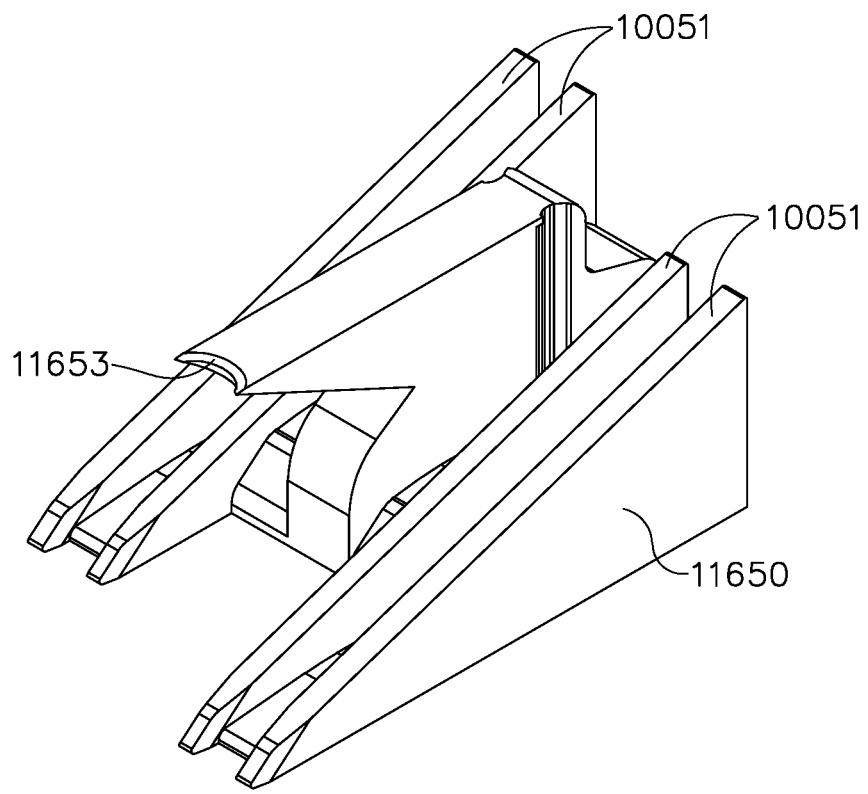
Figure 328:
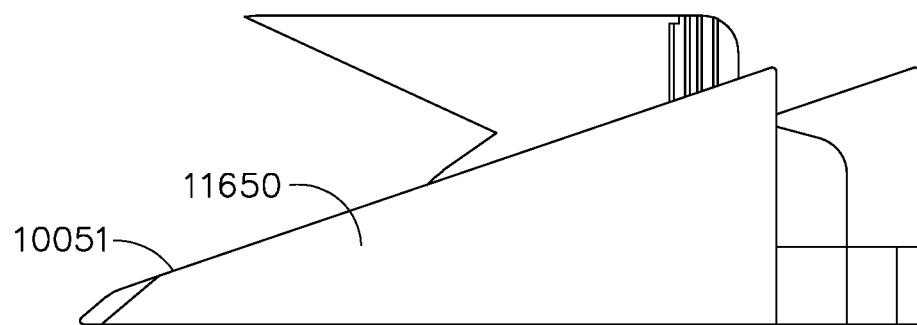
Figure 329:
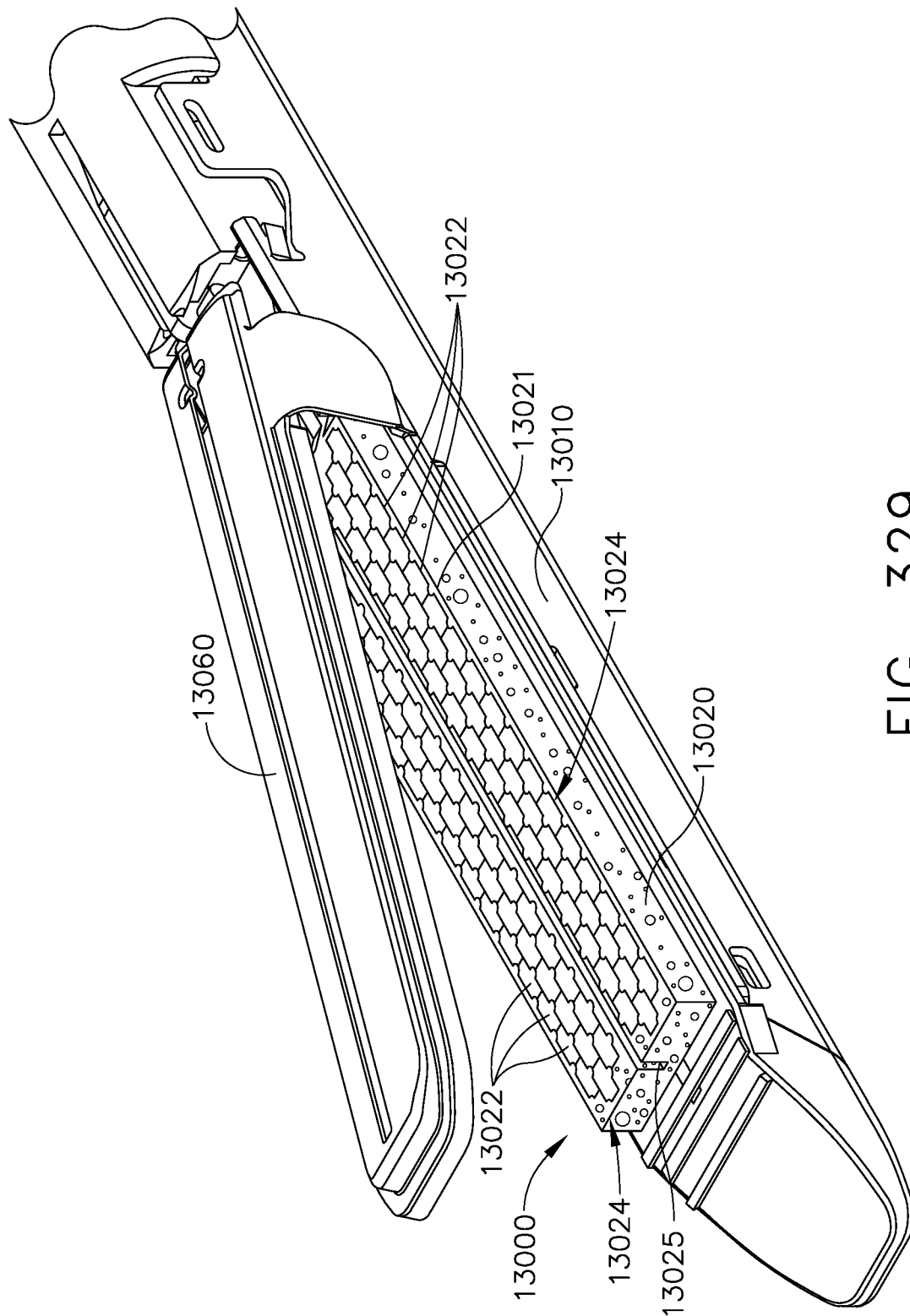
Figure 340:
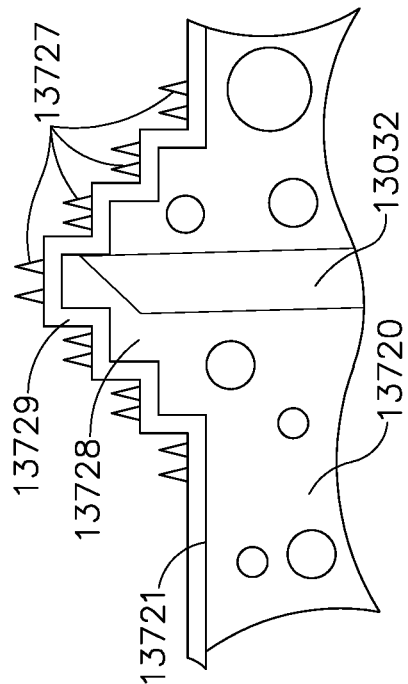
Figure 342:
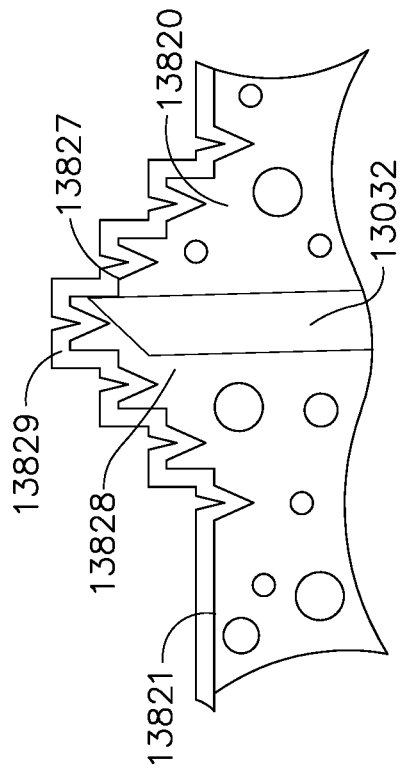
Figure 339:
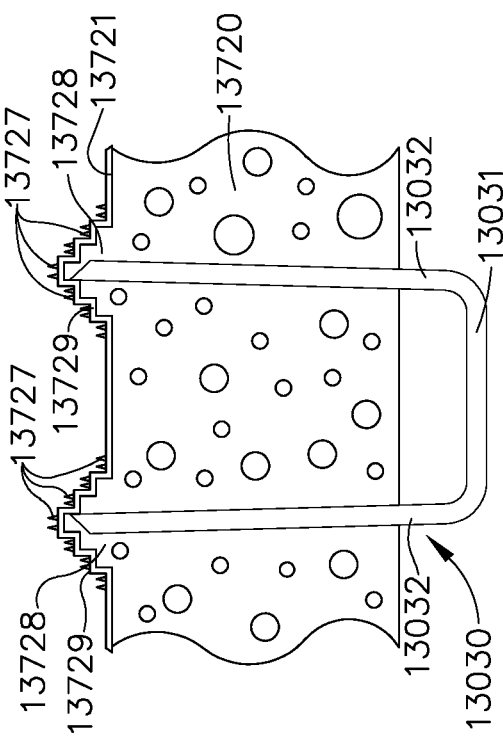
Figure 341:
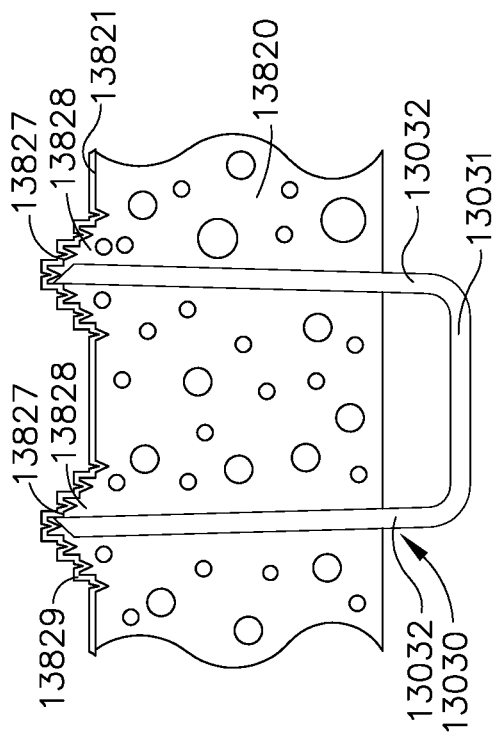
Figures 345, 346:
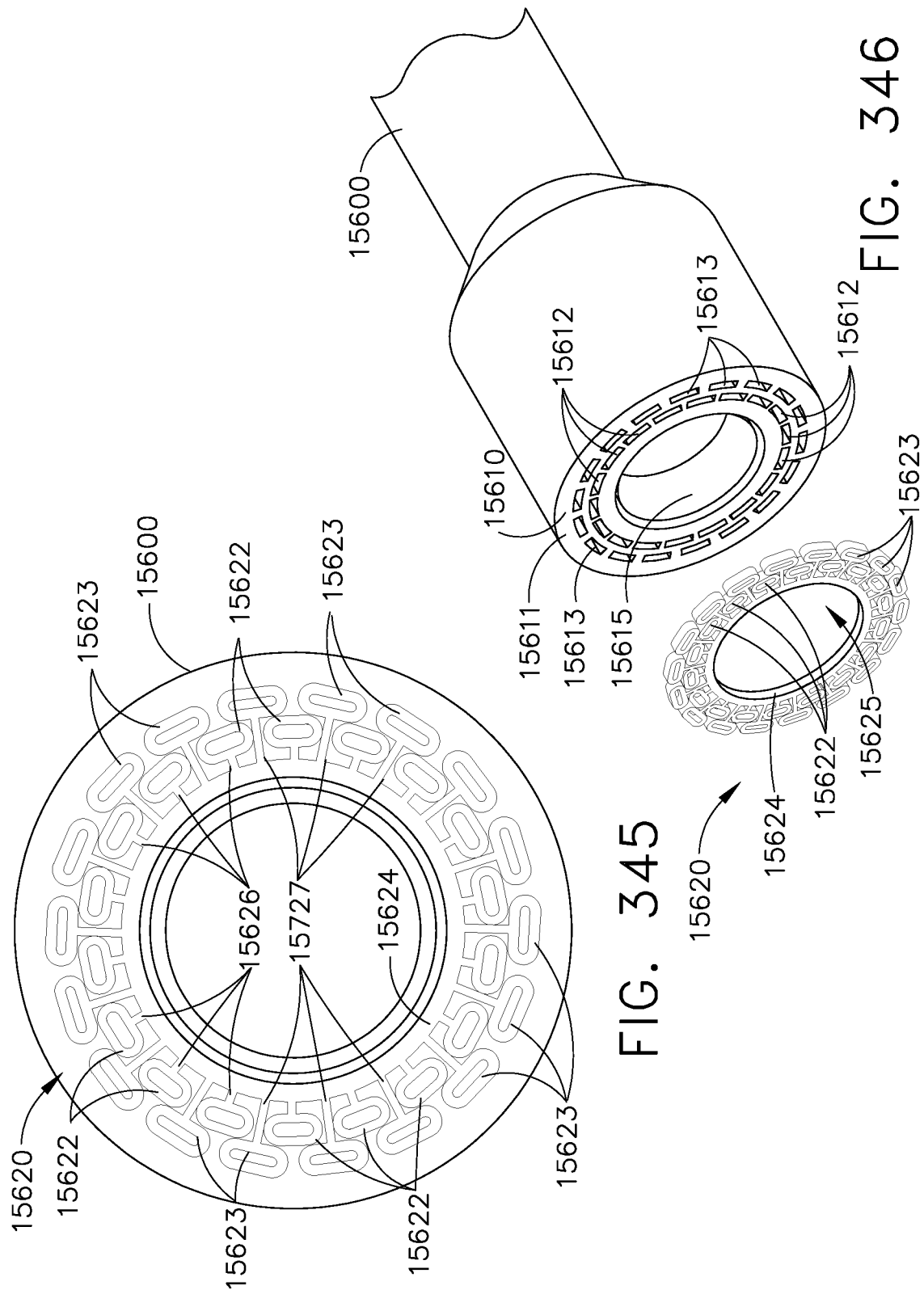
Figures 349, 350:
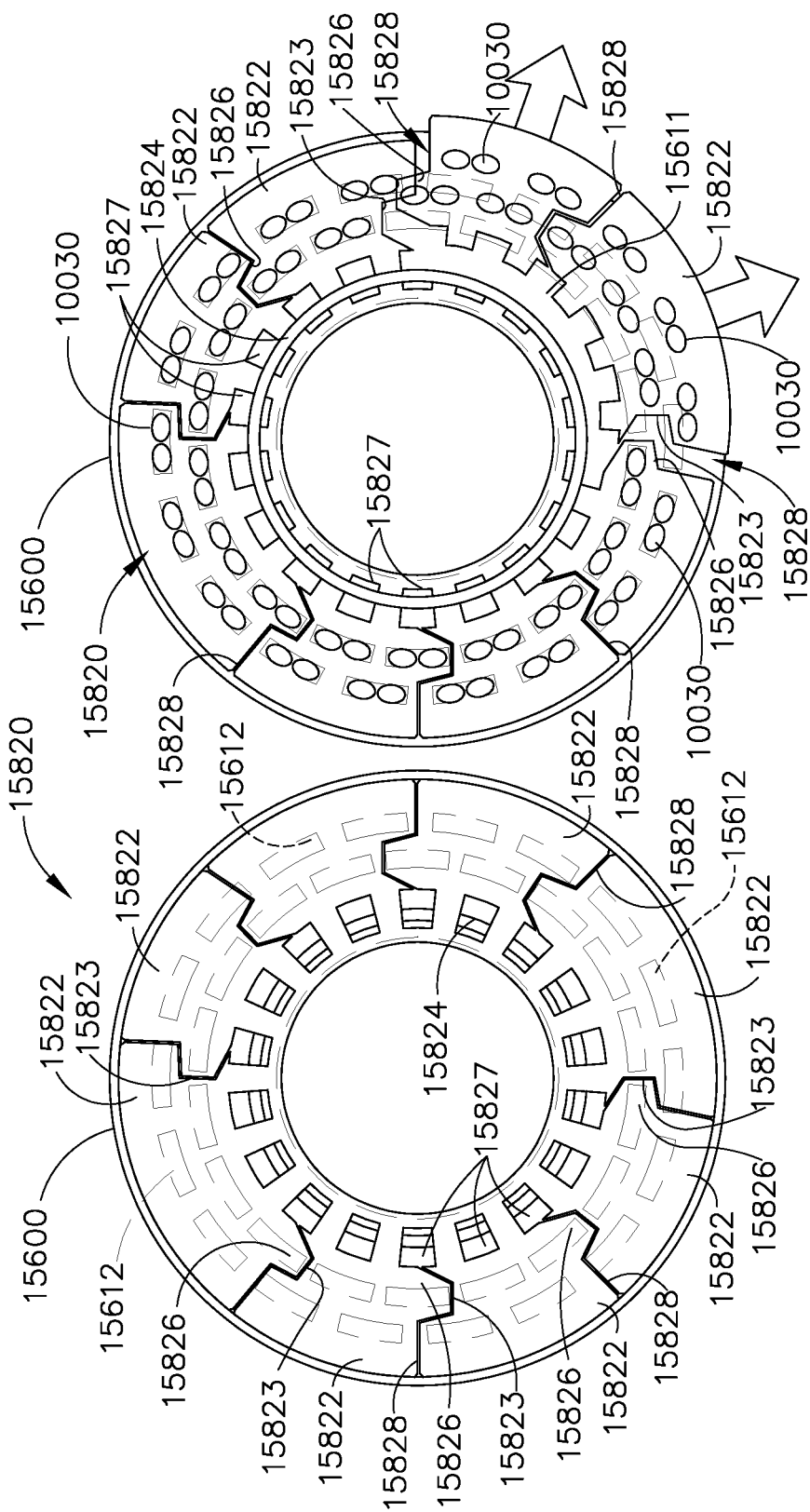
Figure 356:
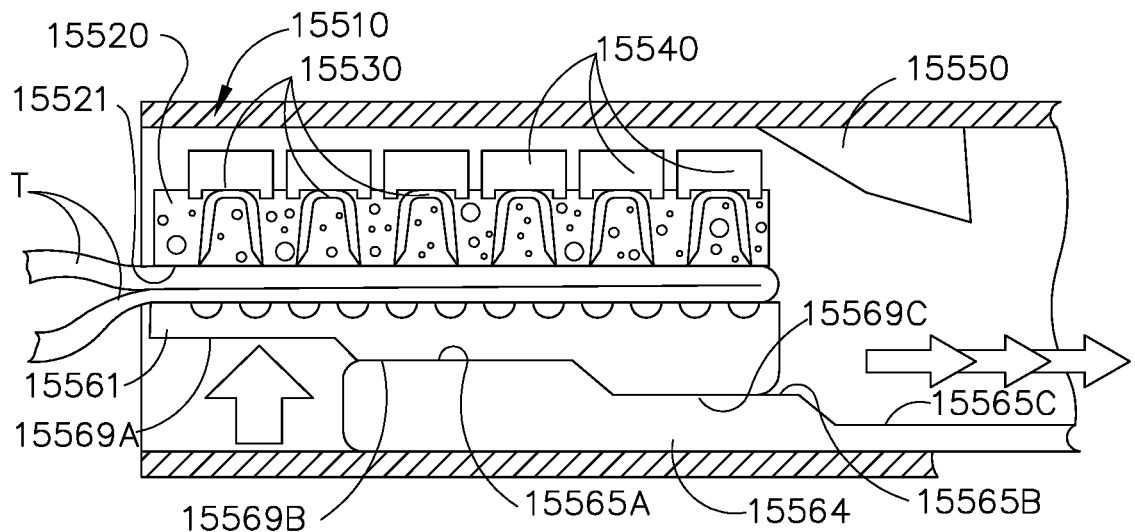
Figure 357:
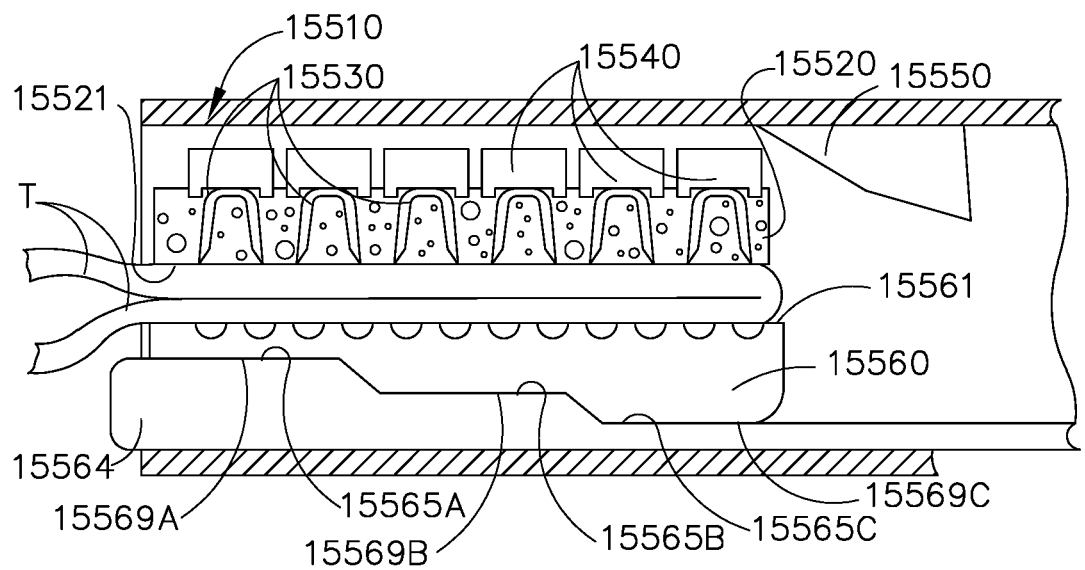
Figure 368:
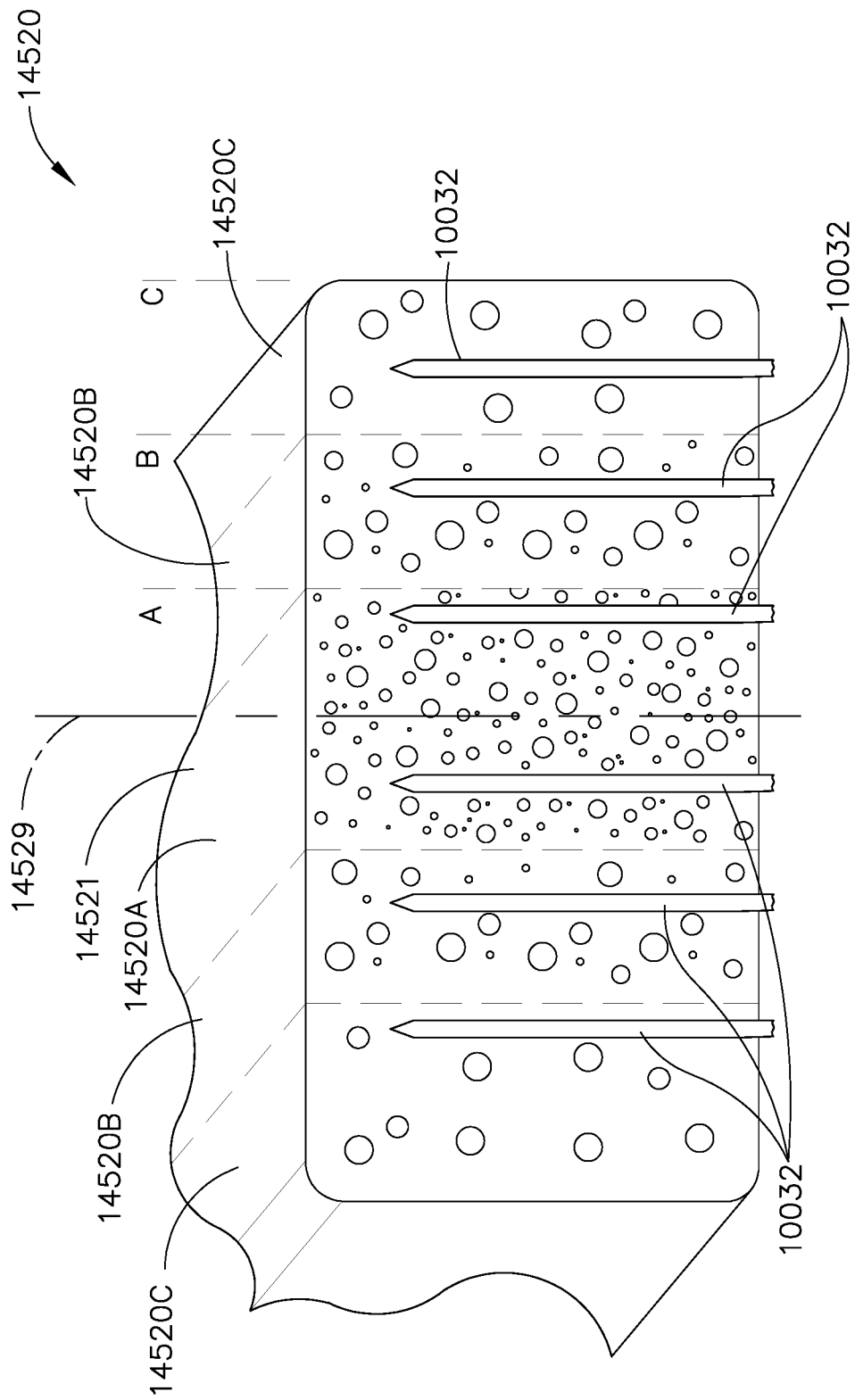
Figure 369:
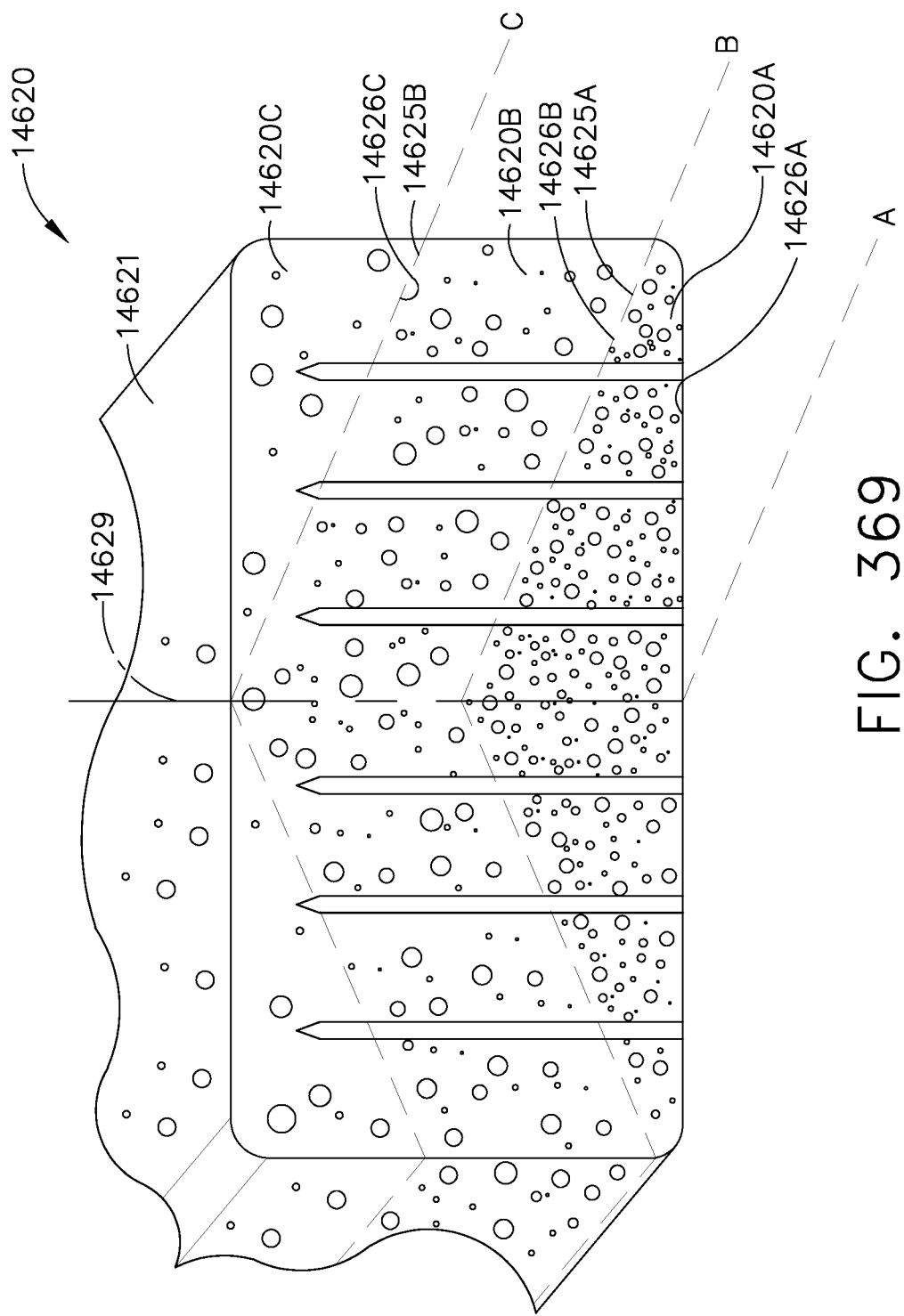
Figure 370:
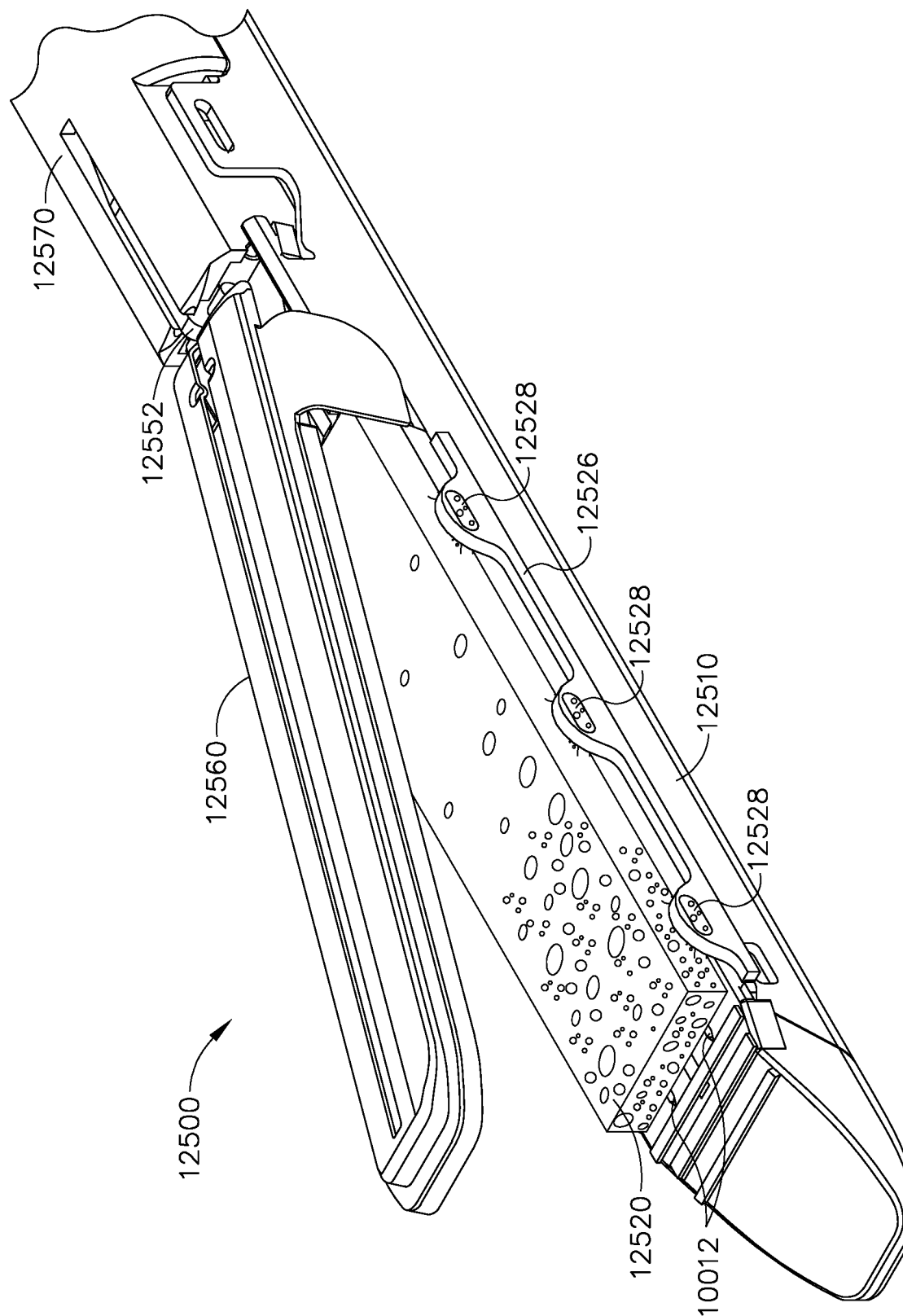
Figure 385:
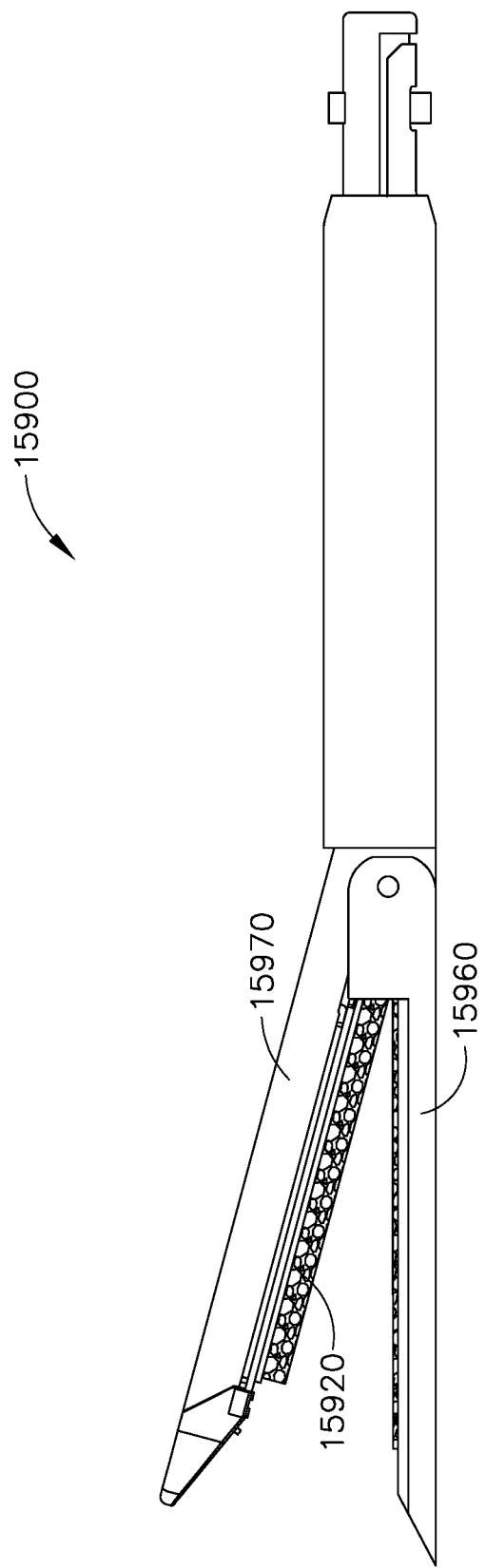
Figure 390:
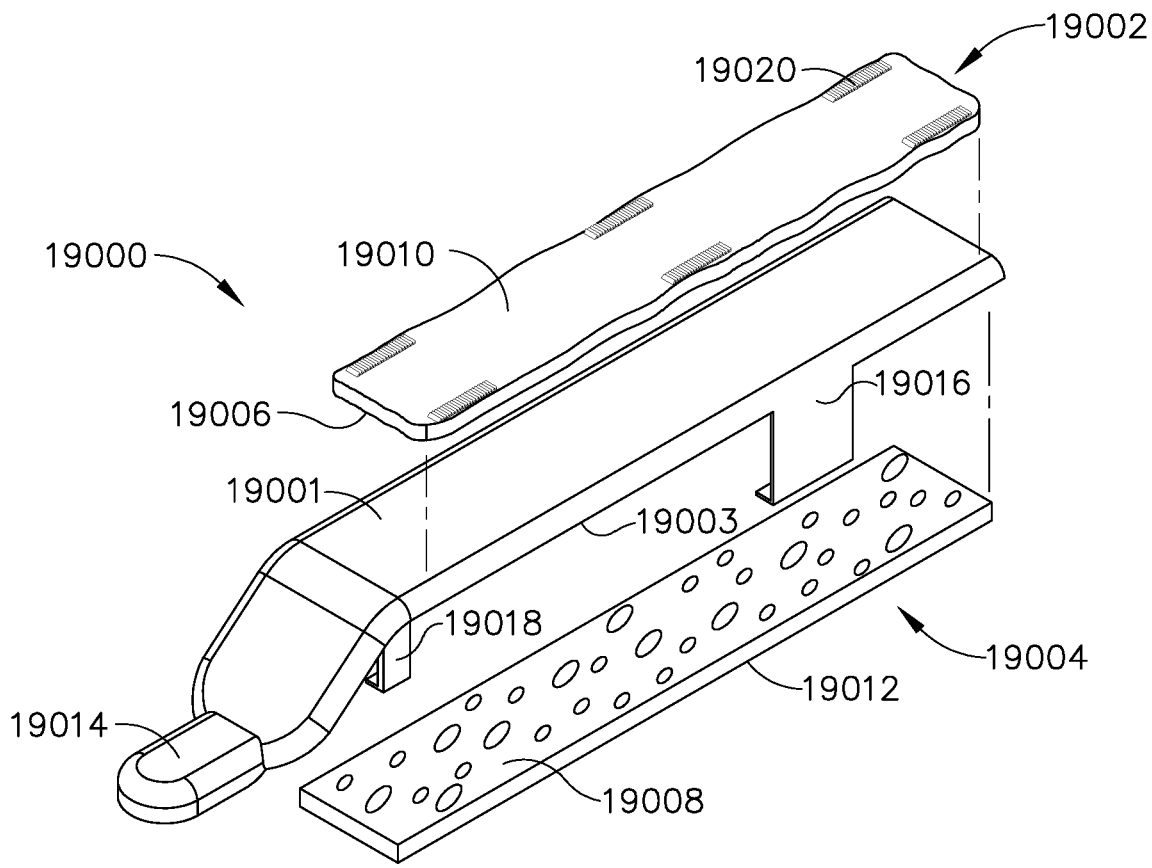
Figure 391:
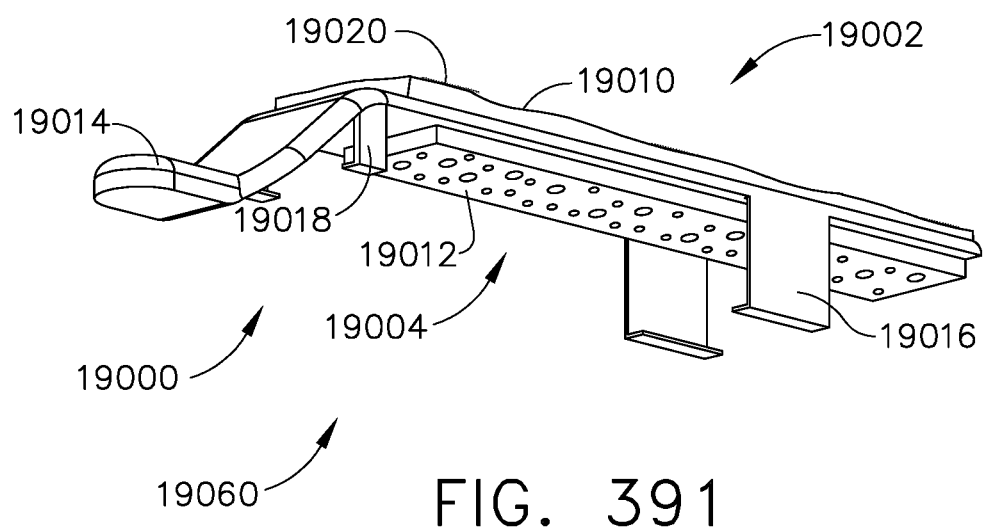
Figure 392:
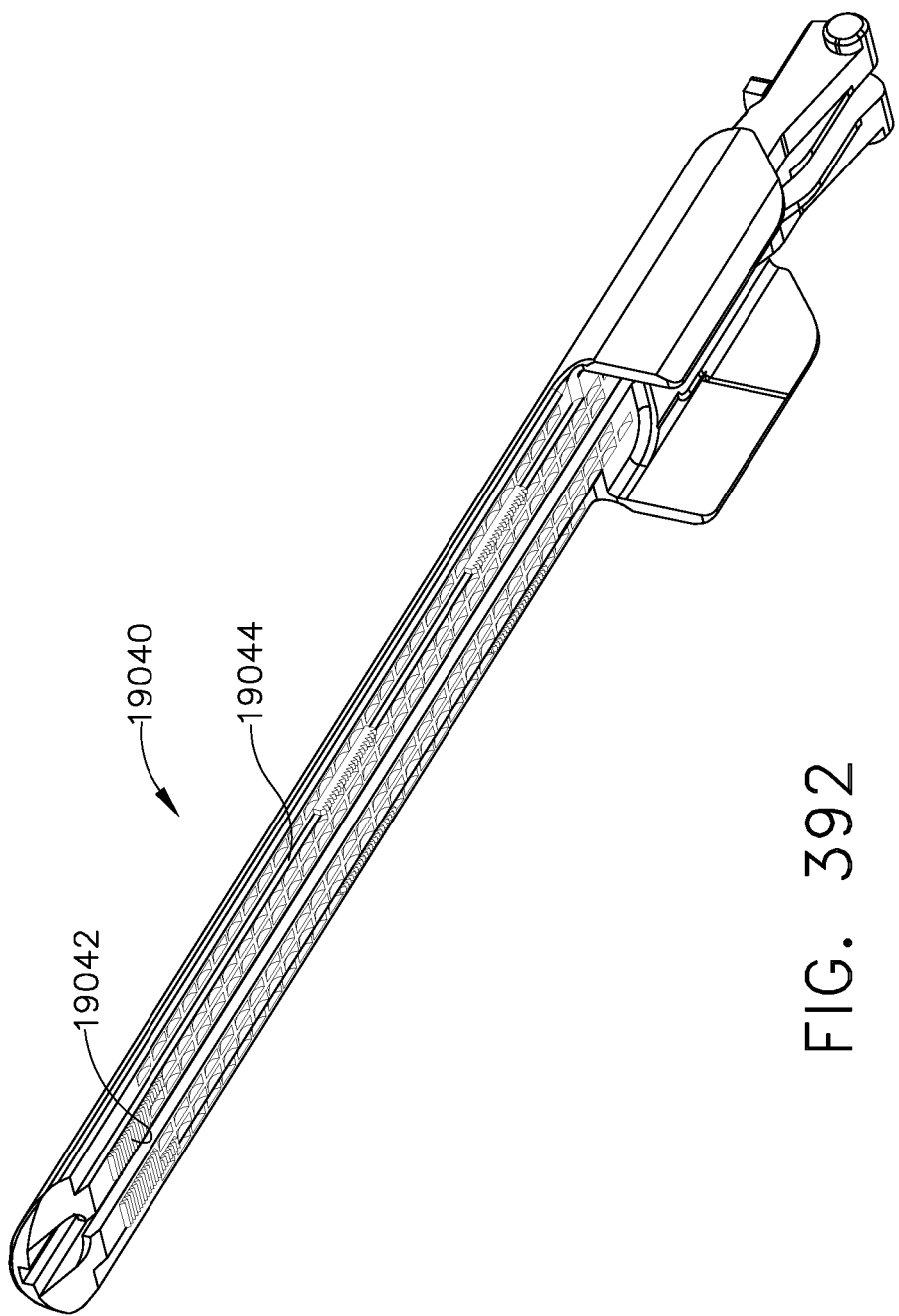
Figure 393:
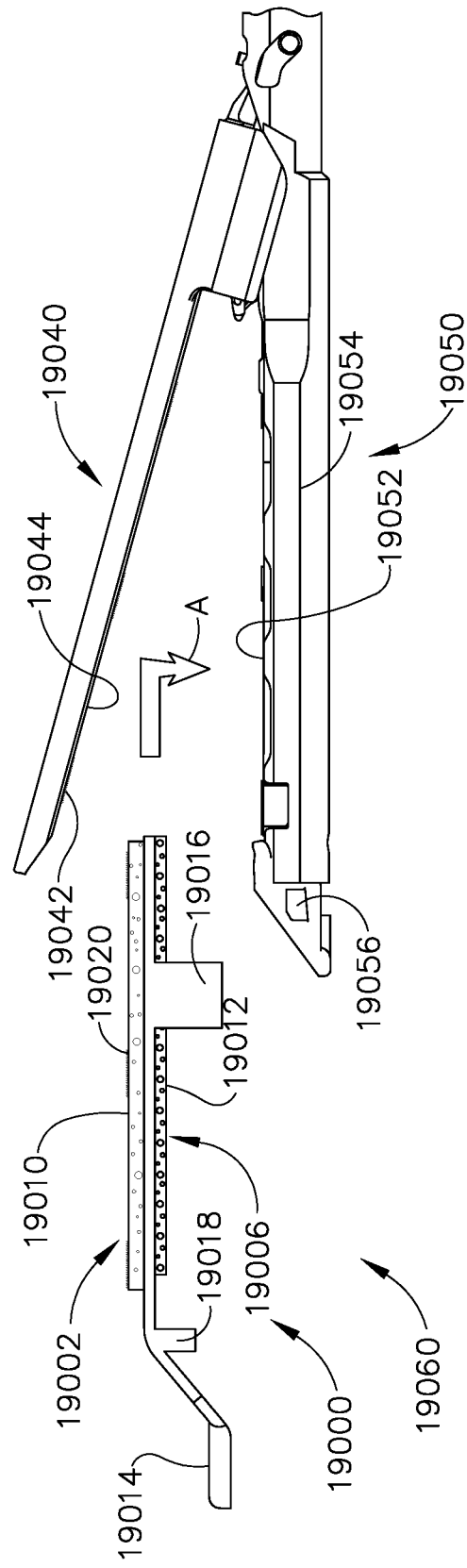
Figure 396:
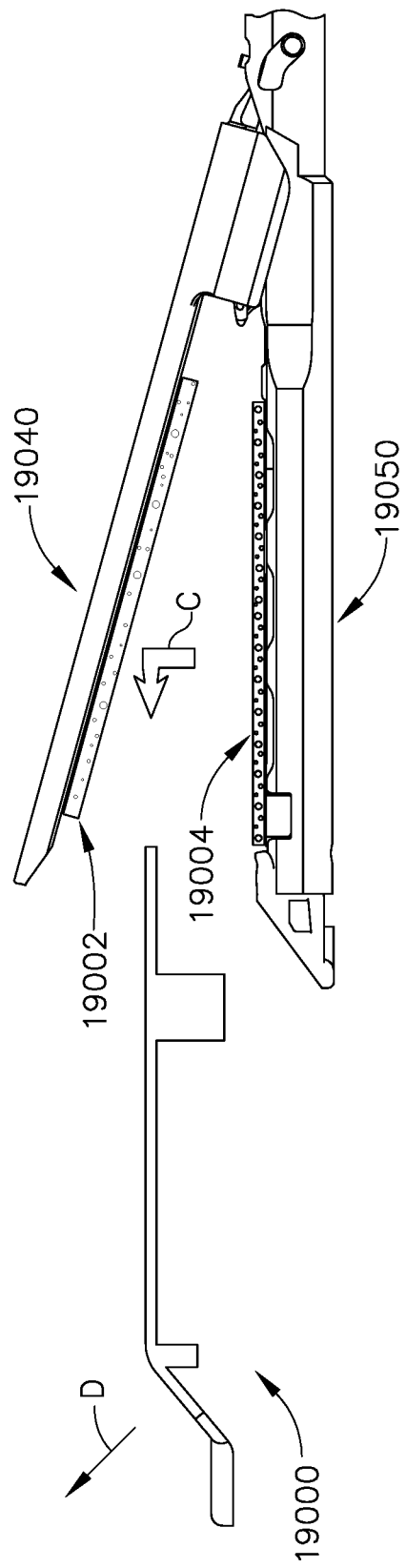
Figure 397:
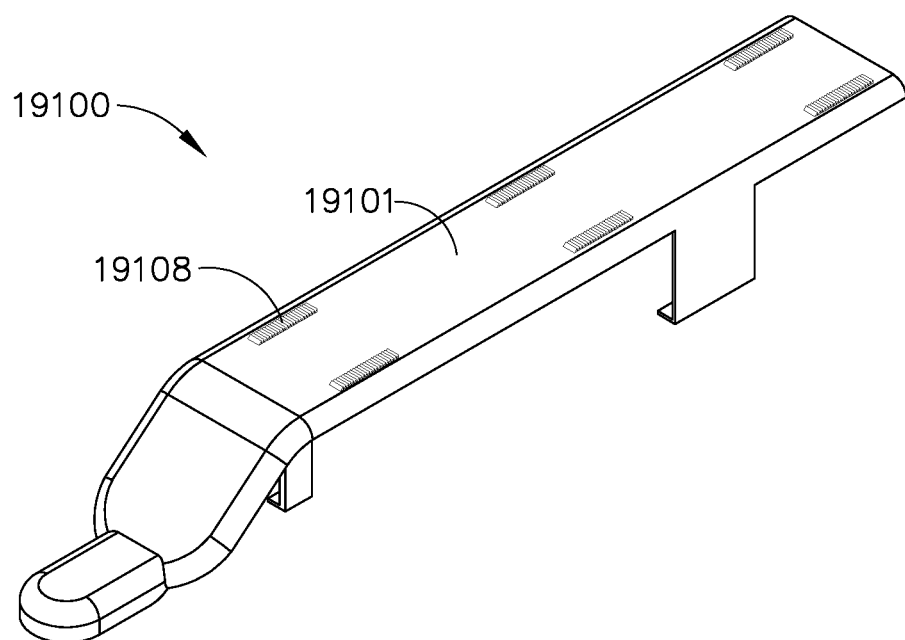
Figure 400:
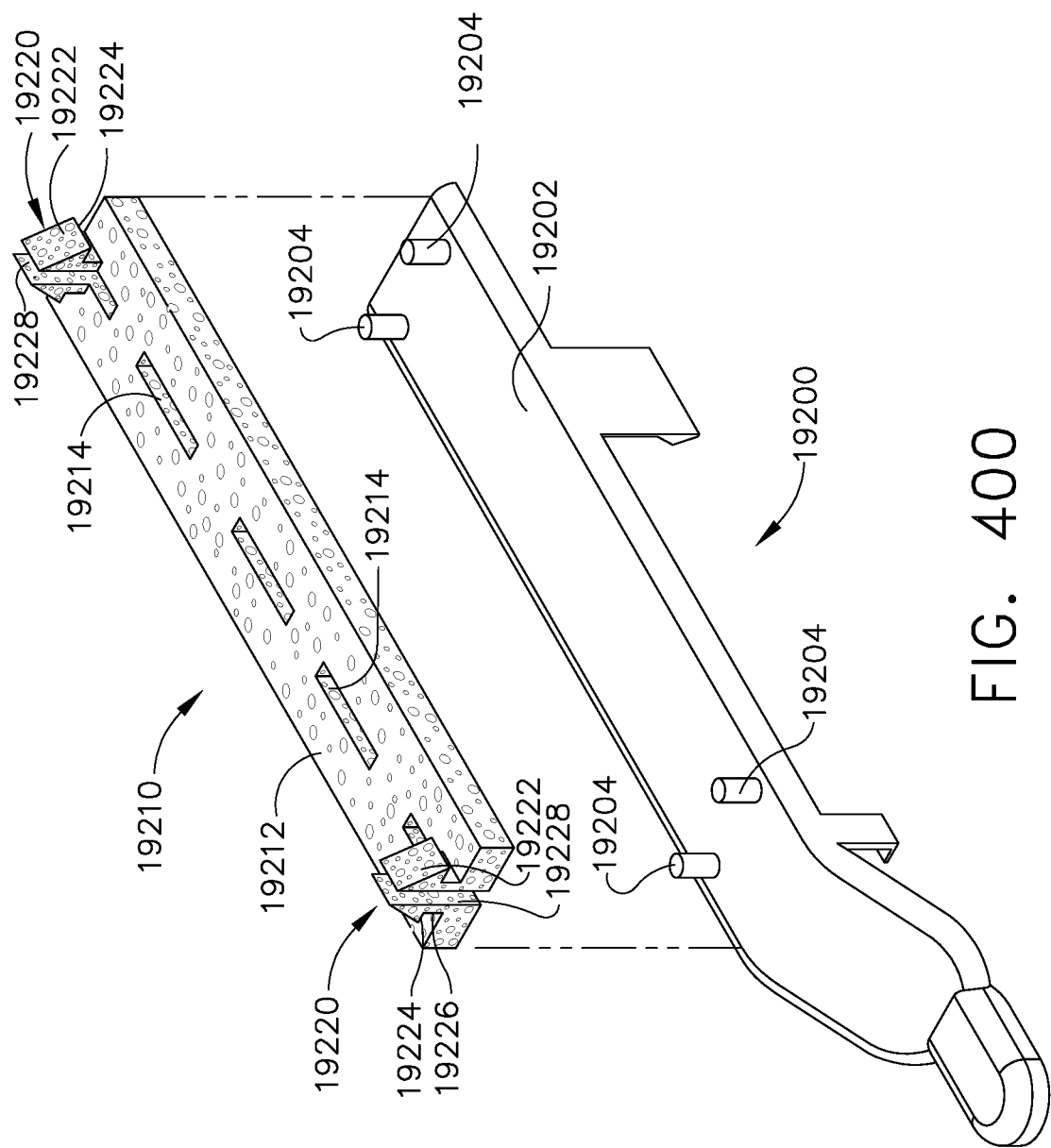
Figure 401:
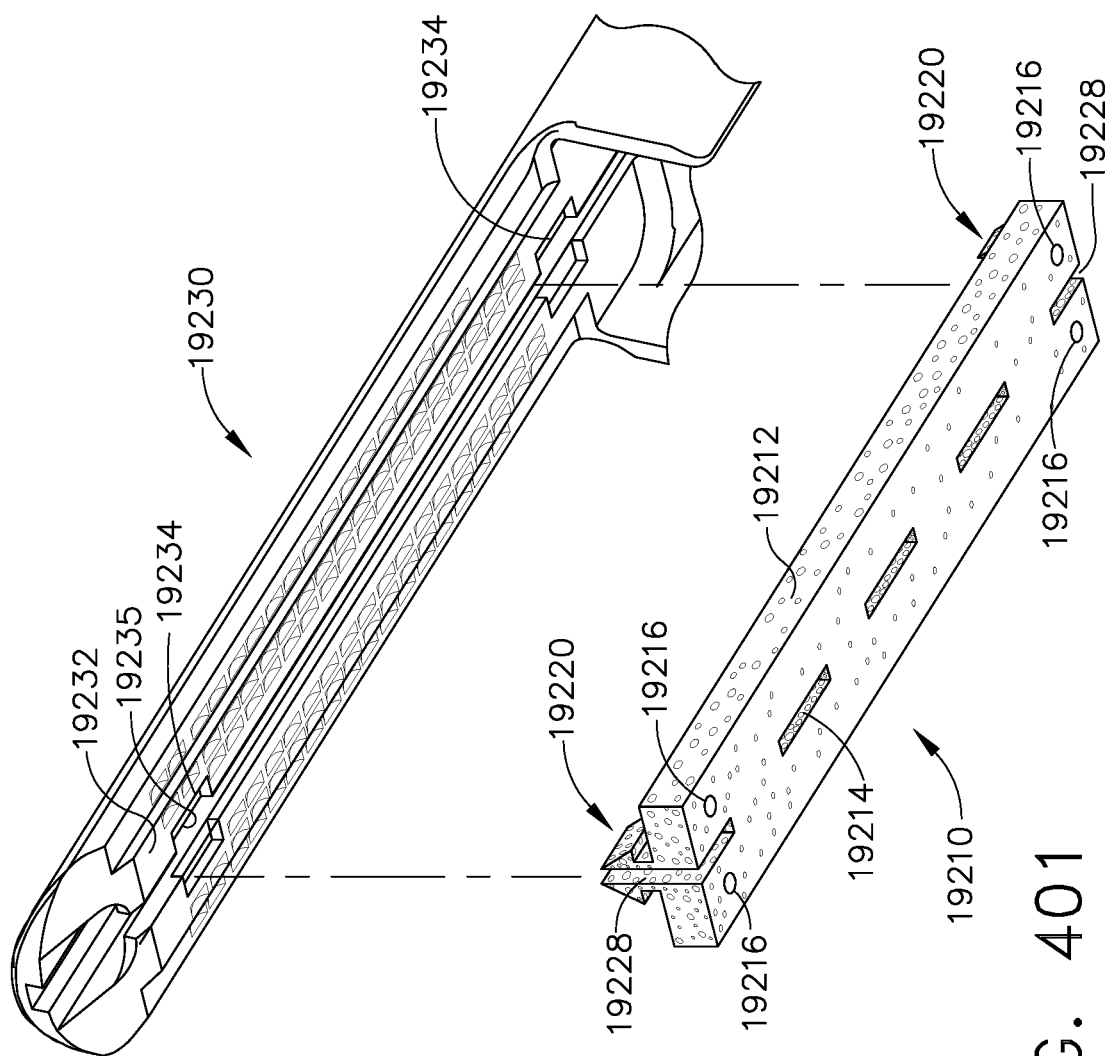
Figure 402:
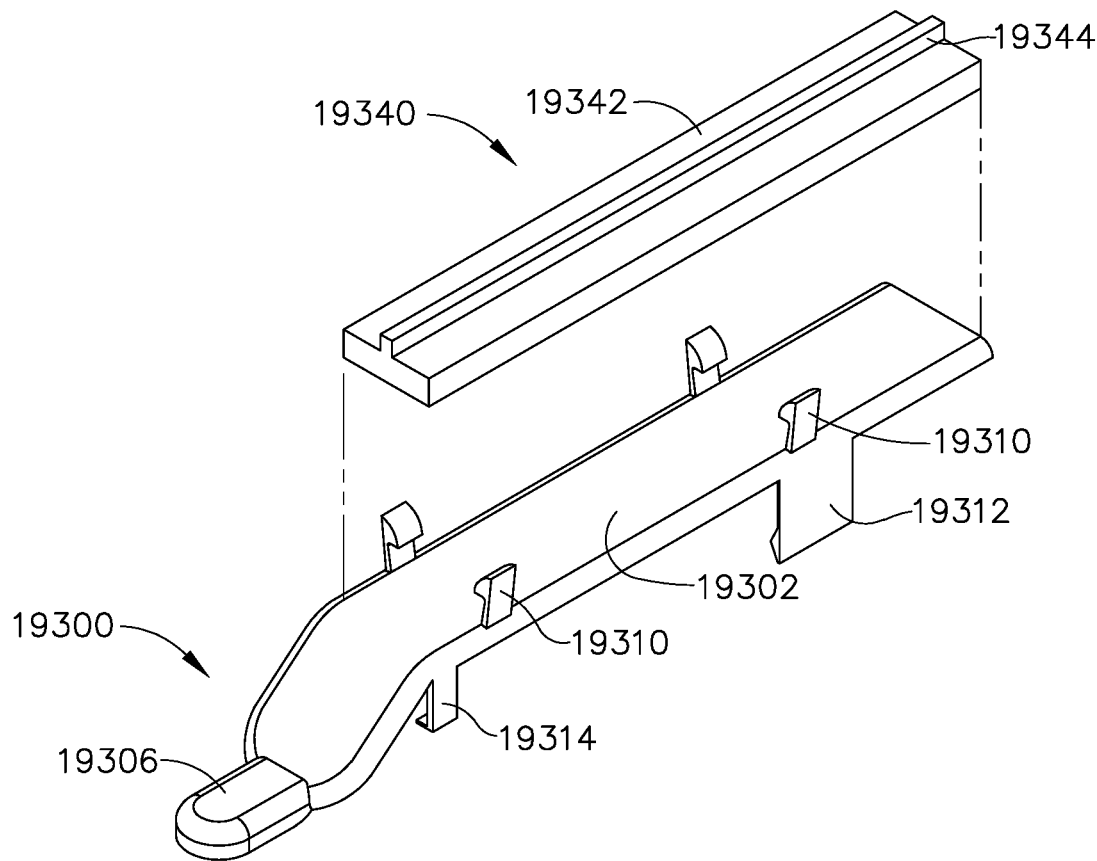
Figure 403:
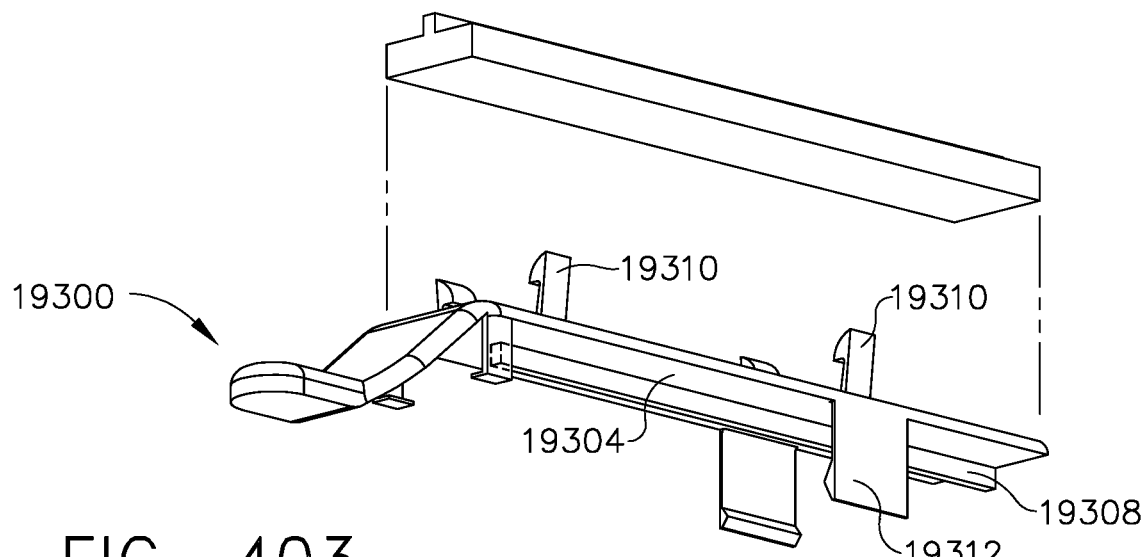
Figure 404:
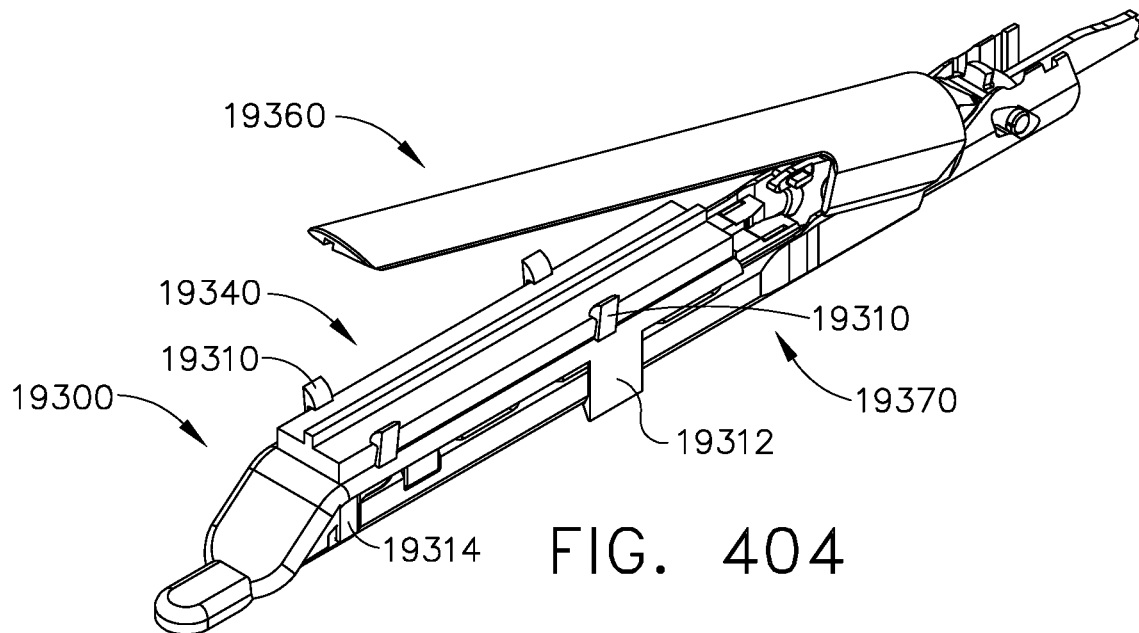
Figure 405:
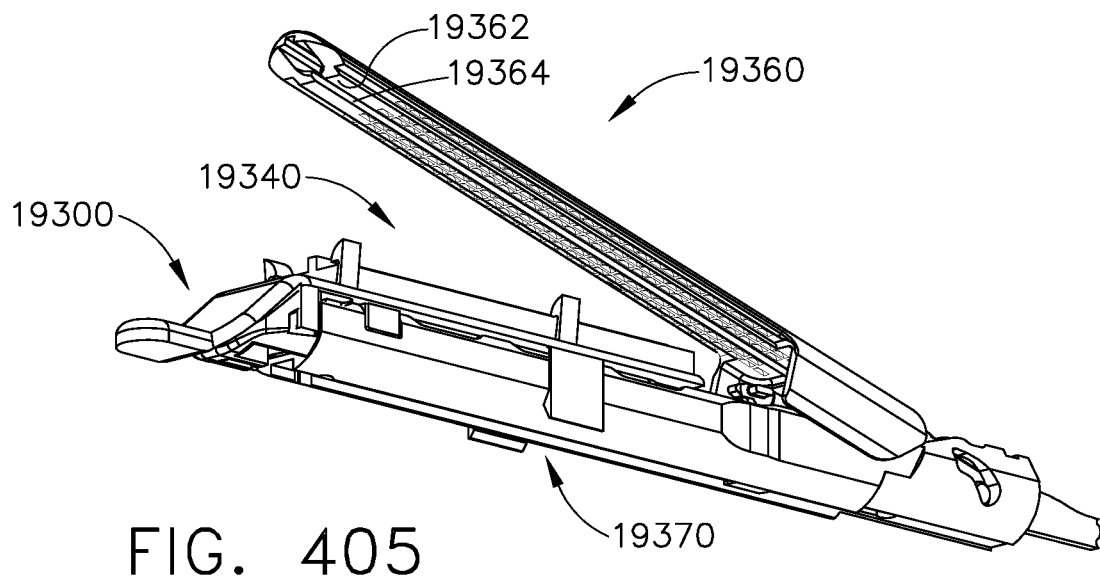
Figure 406:
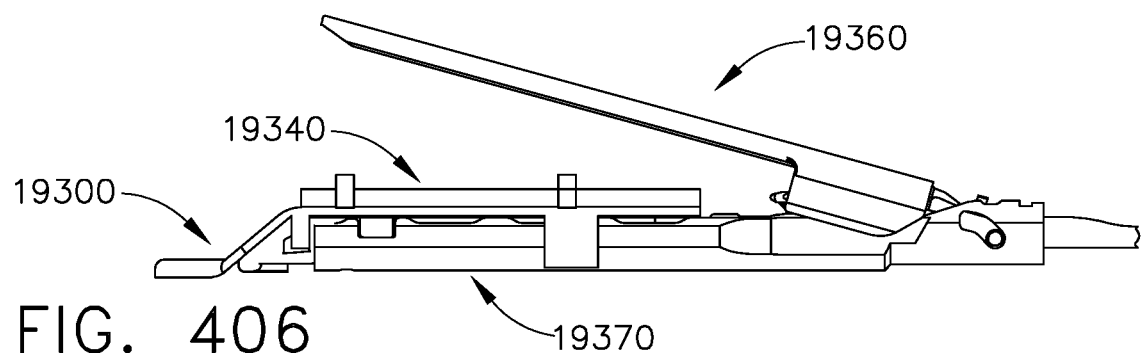
Figure 407:
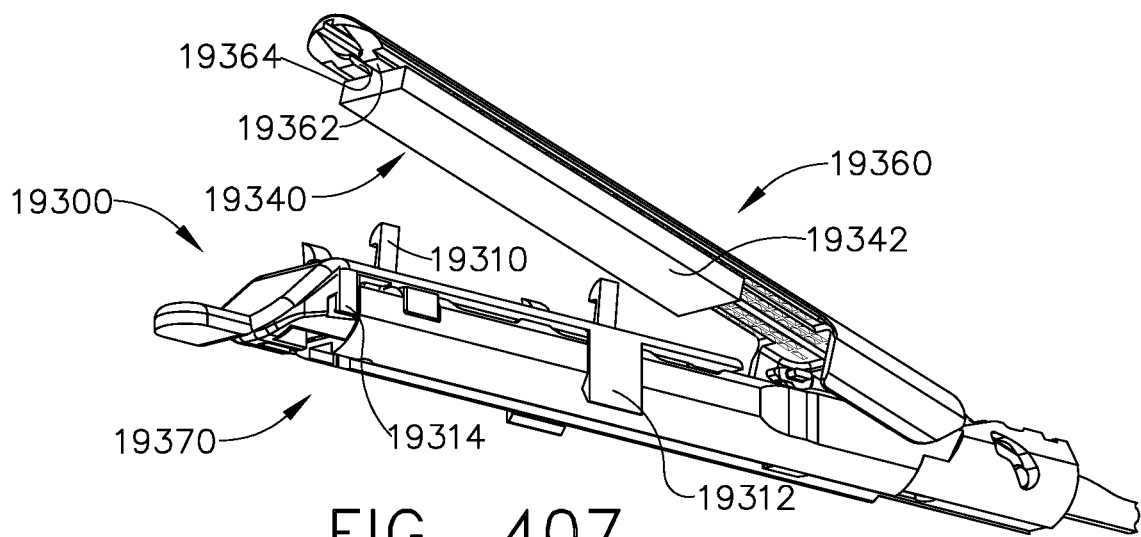
Figure 408:
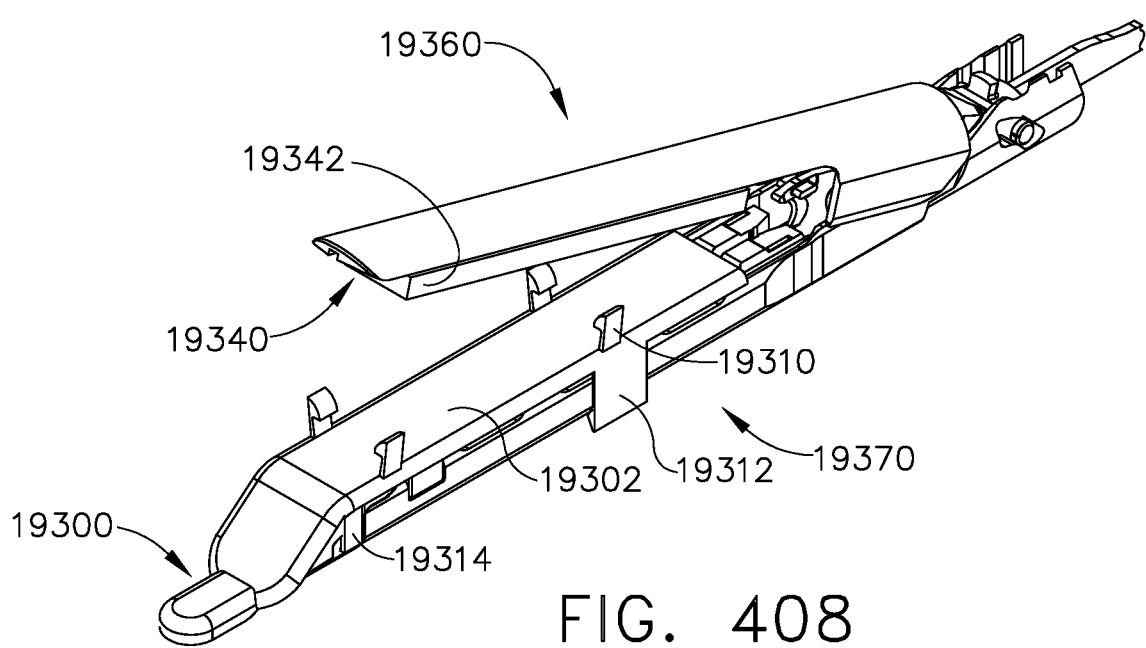
Figure 409:
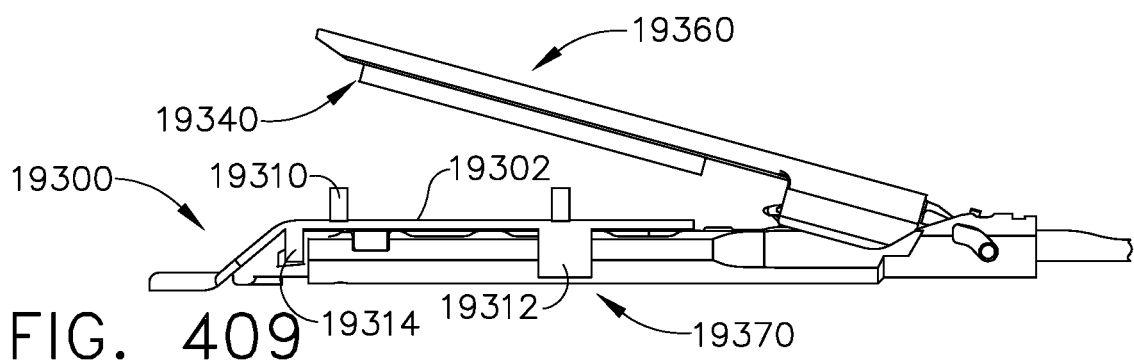
Figure 410:
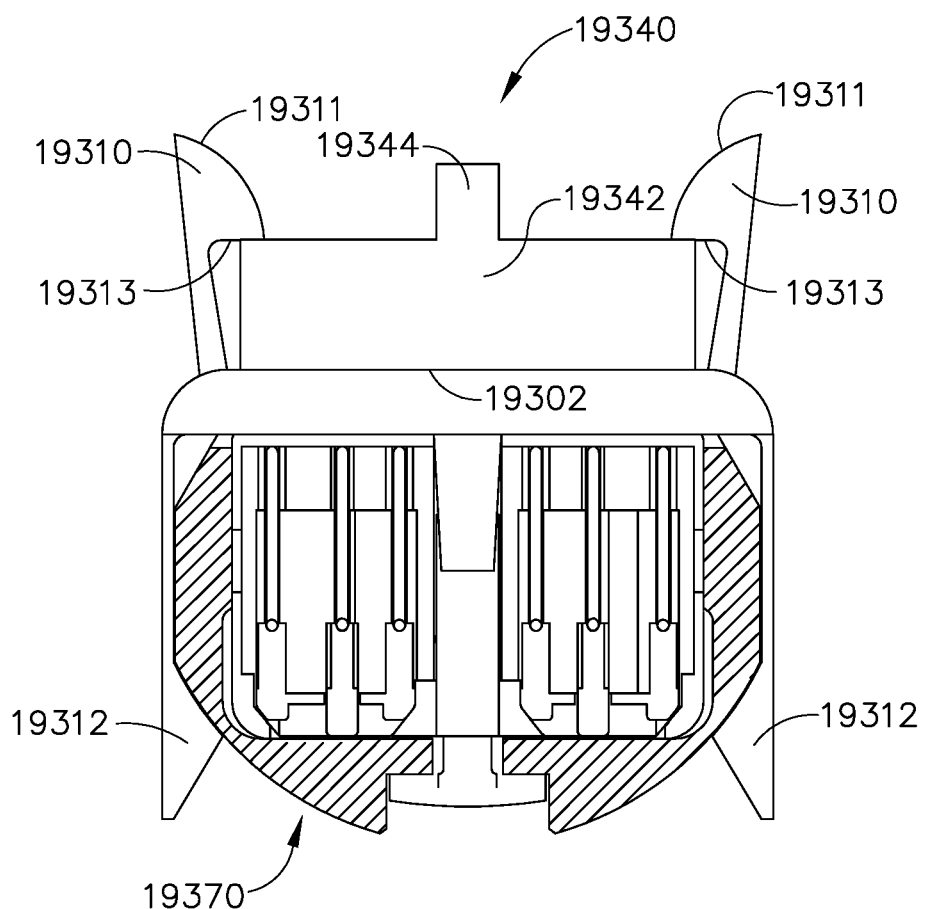
Figure 411:
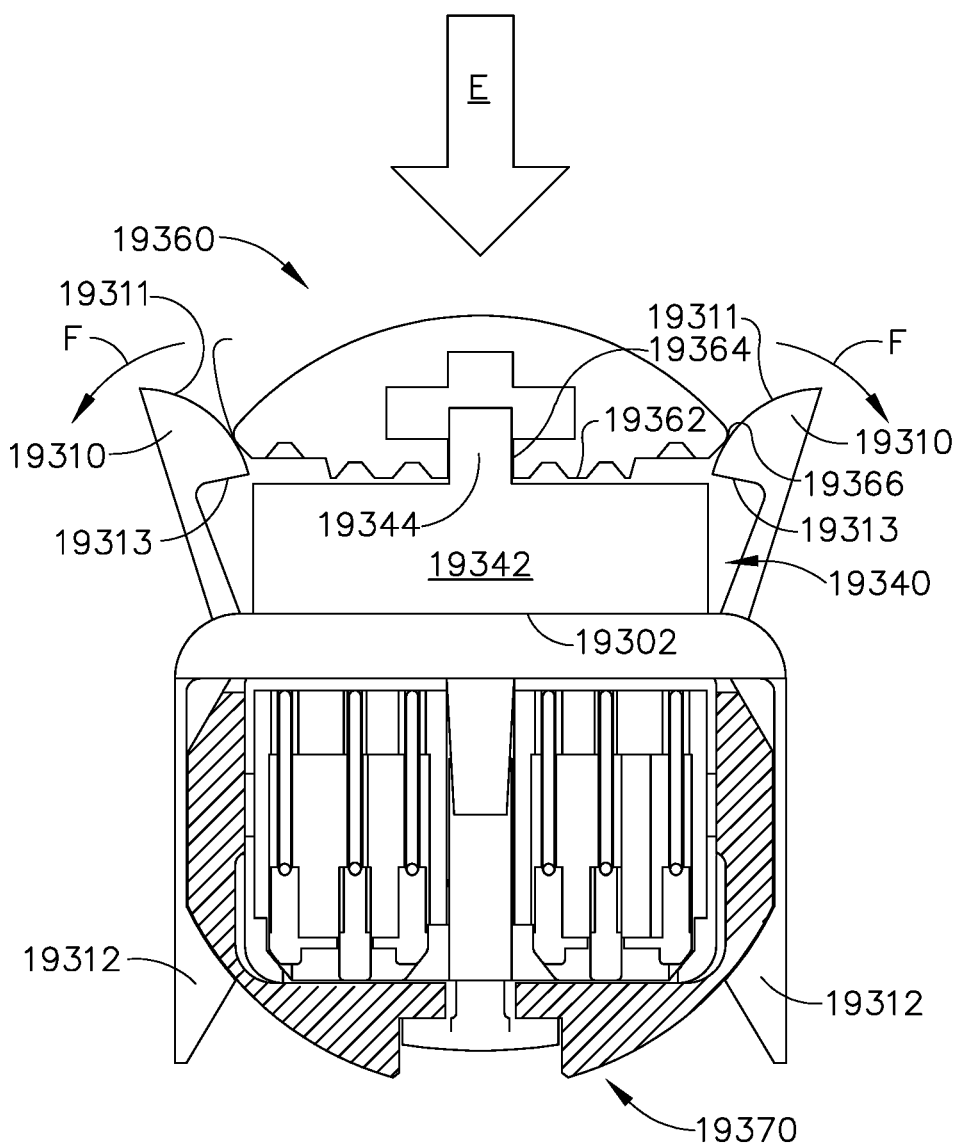
Figure 412:
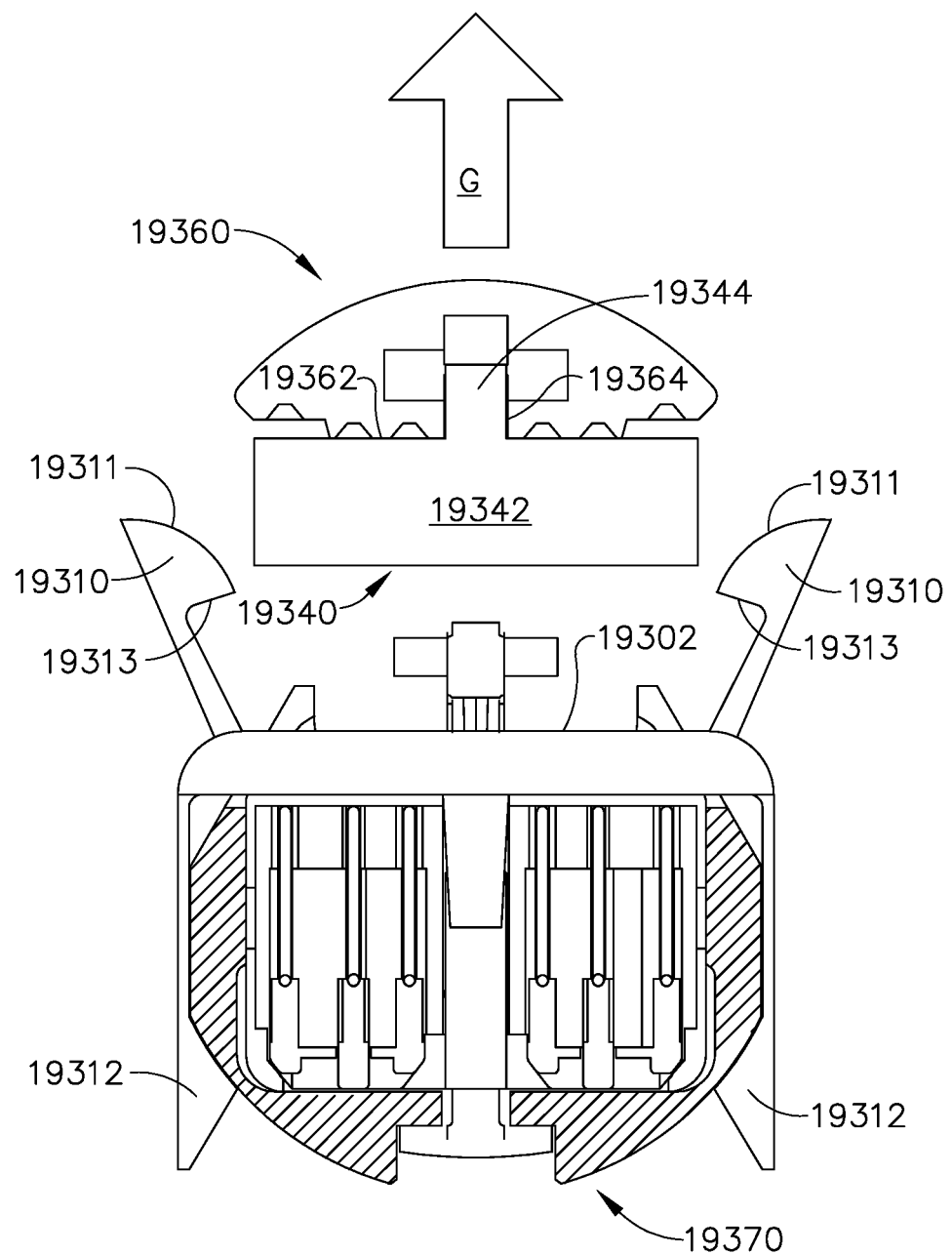
Figure 413:
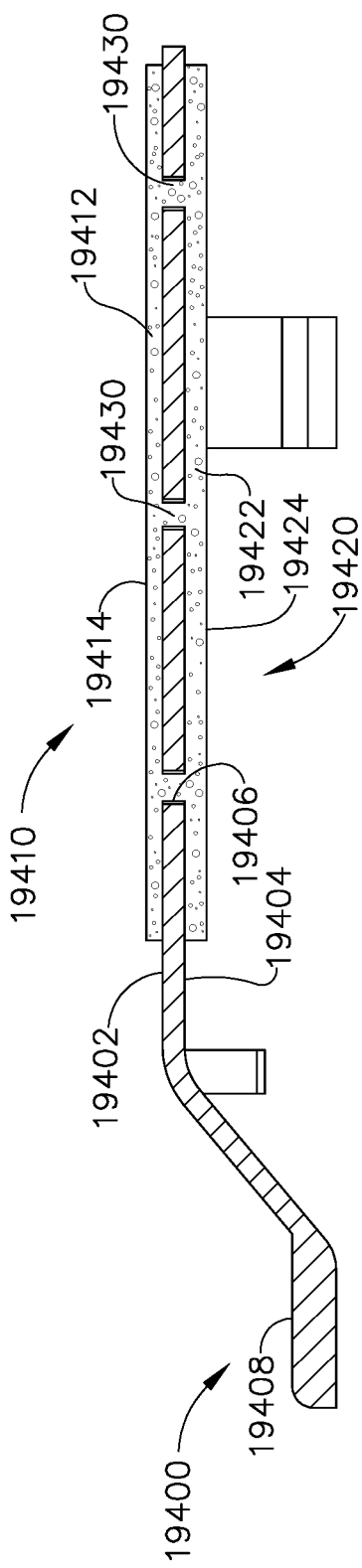
Figure 414:
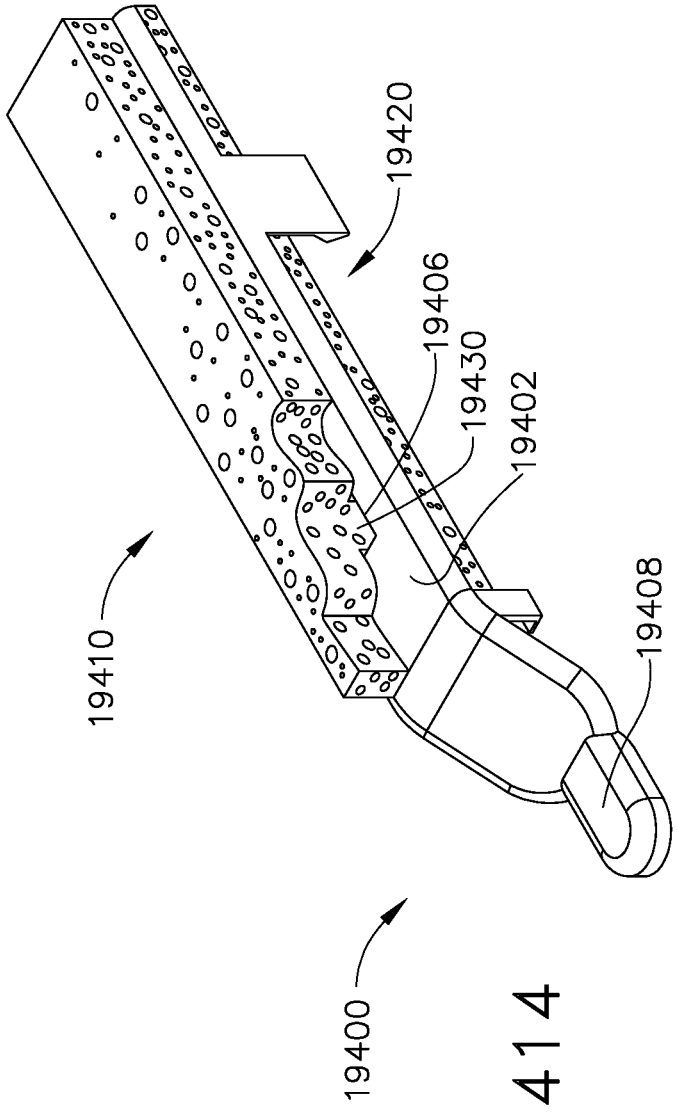
Figure 418:
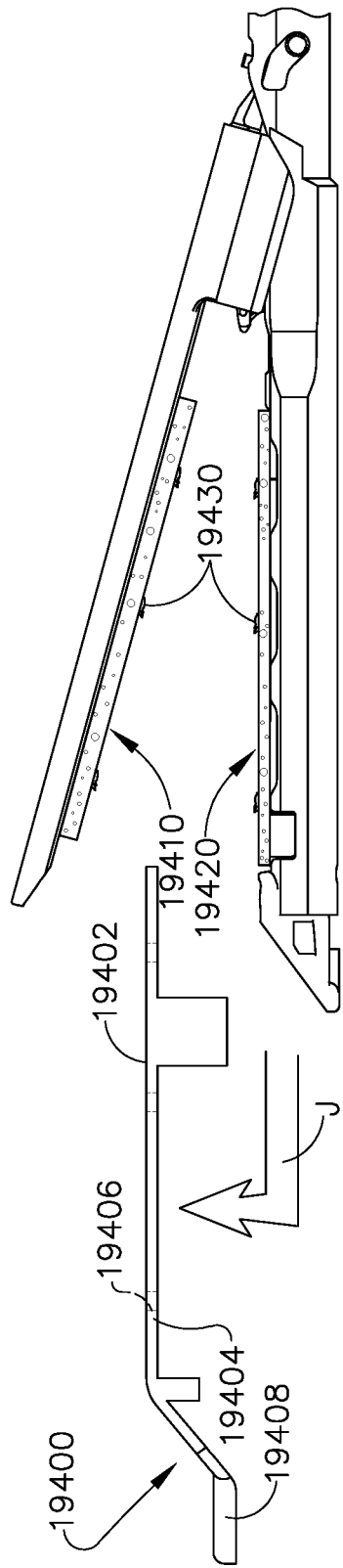
Figure 419:
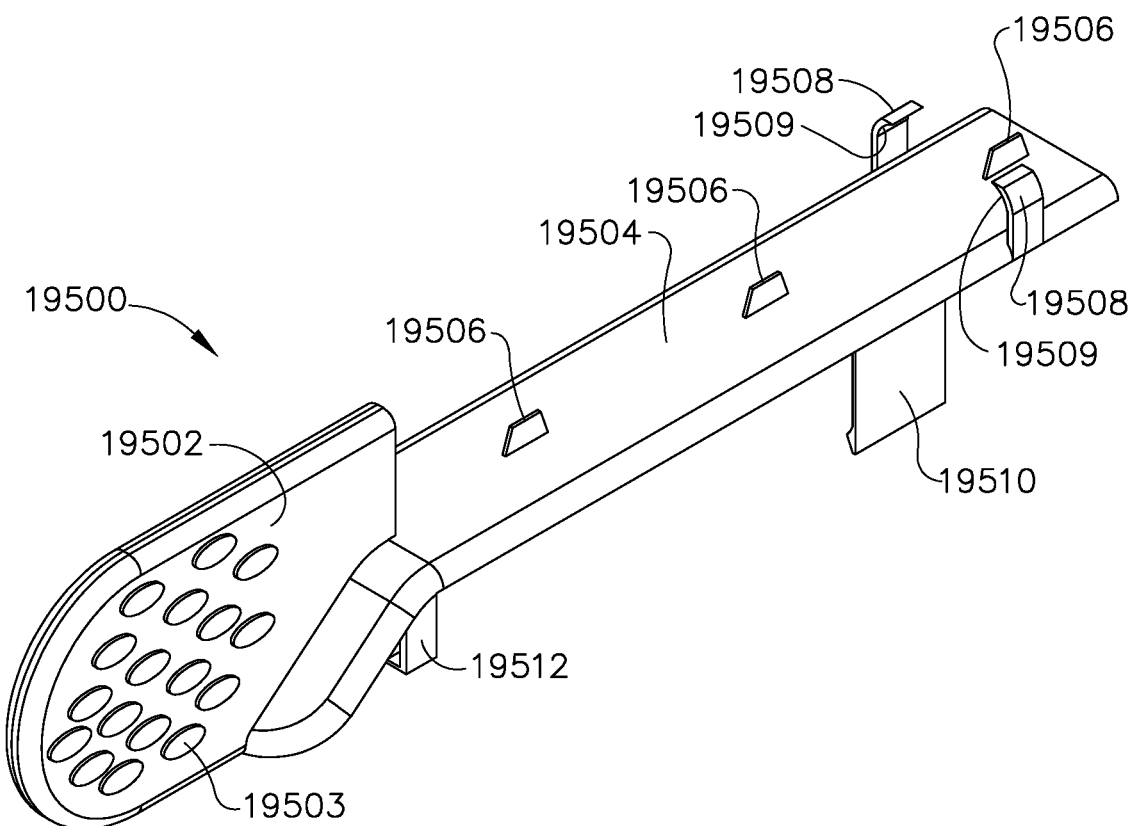
Figure 420:
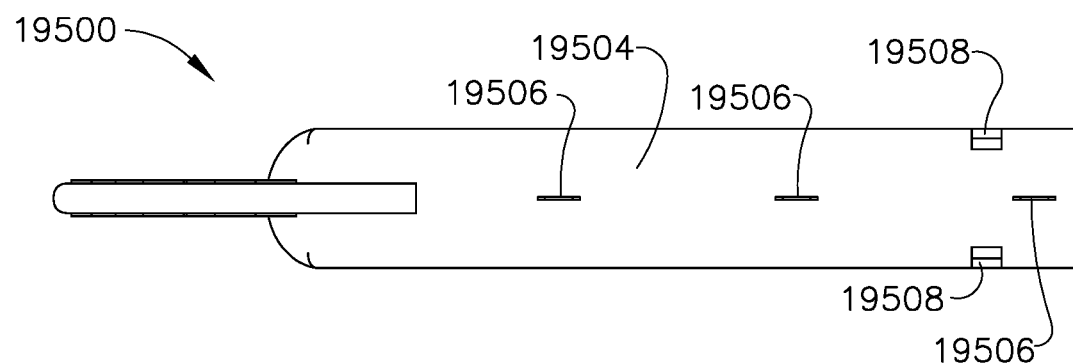
Figure 421:
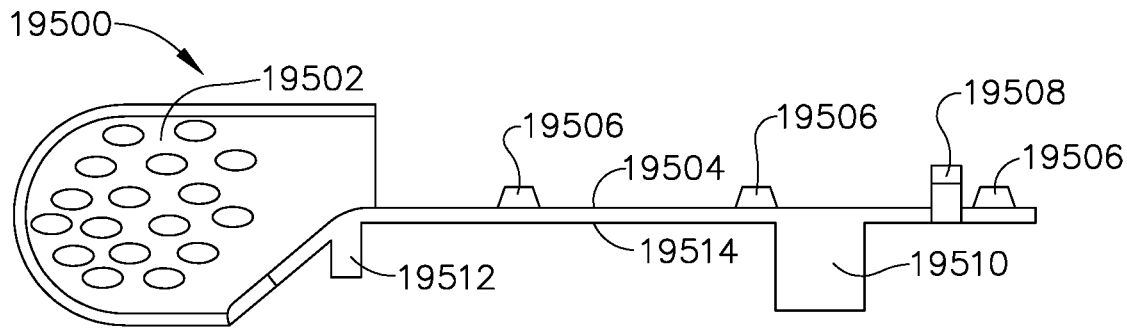
Figure 422:
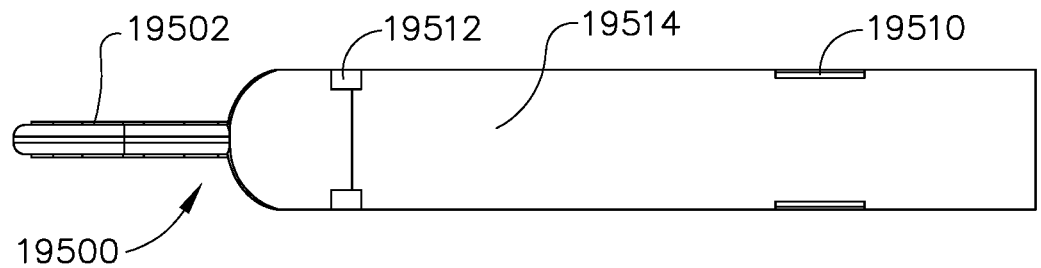
Figure 423:
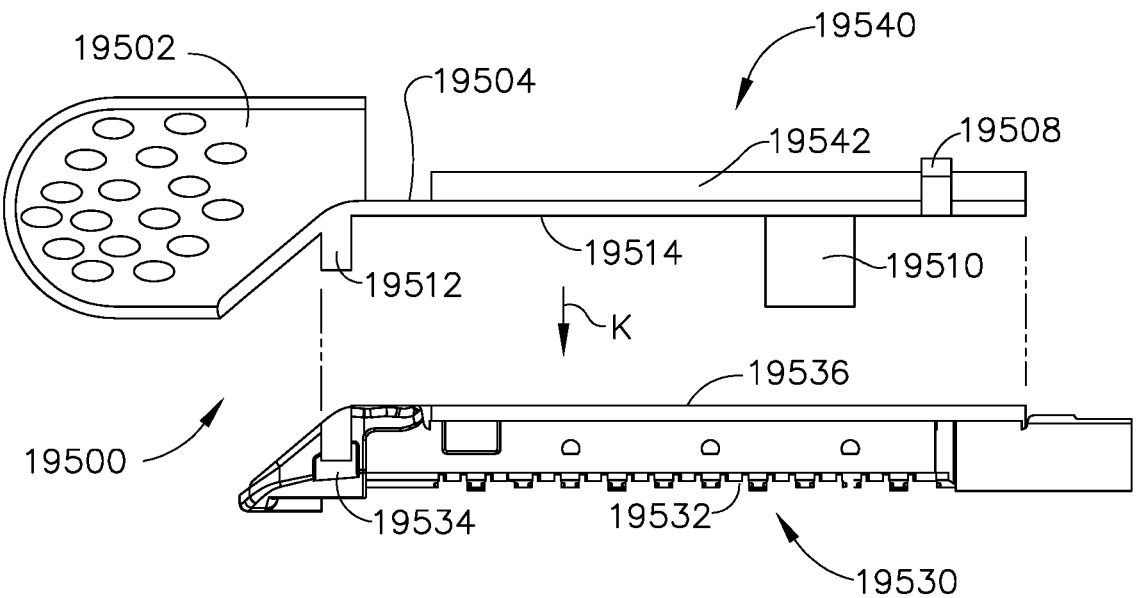
Figure 430:
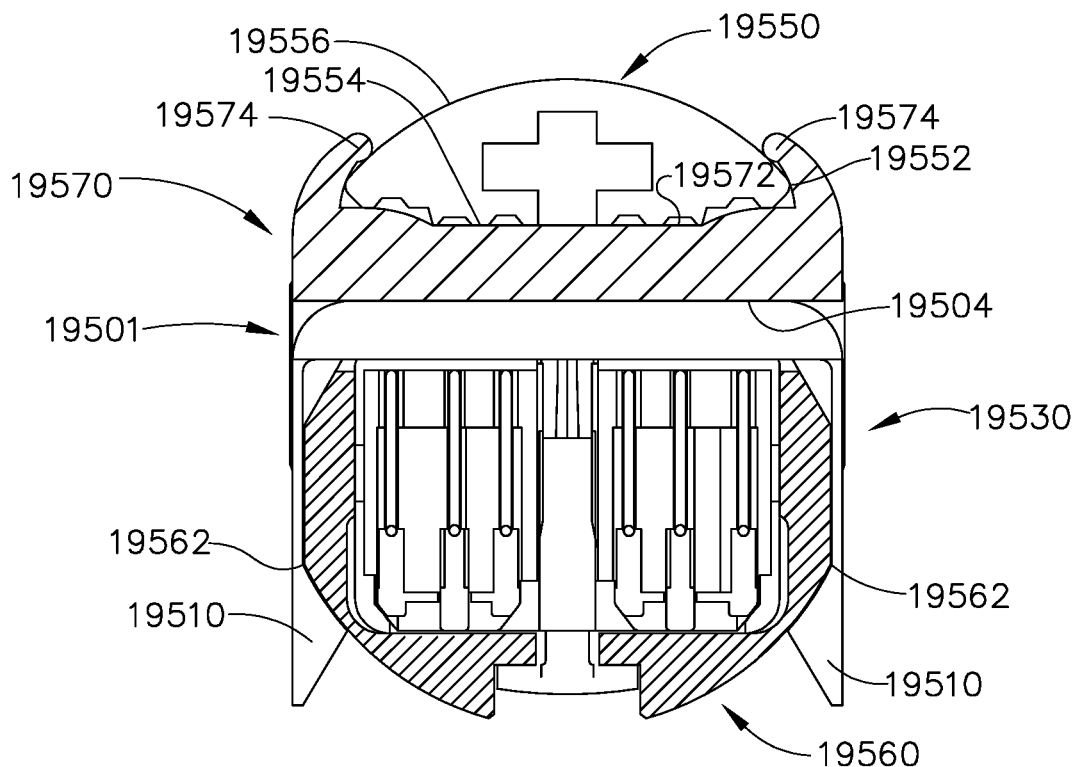
Figure 431:
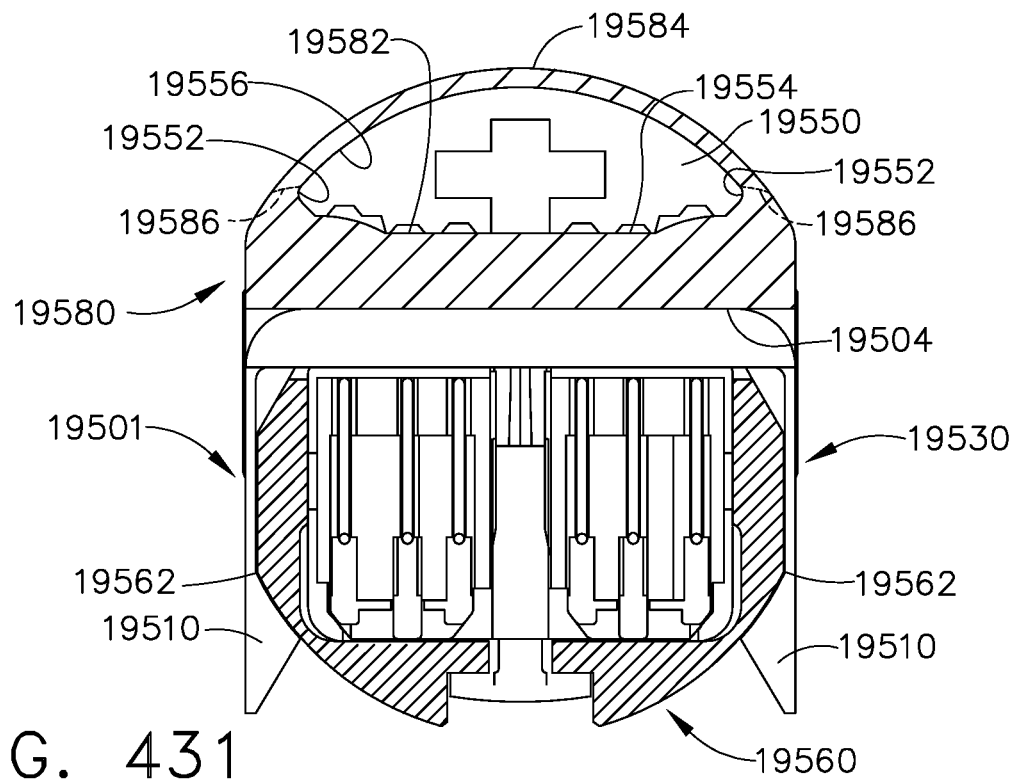
Figure 432:
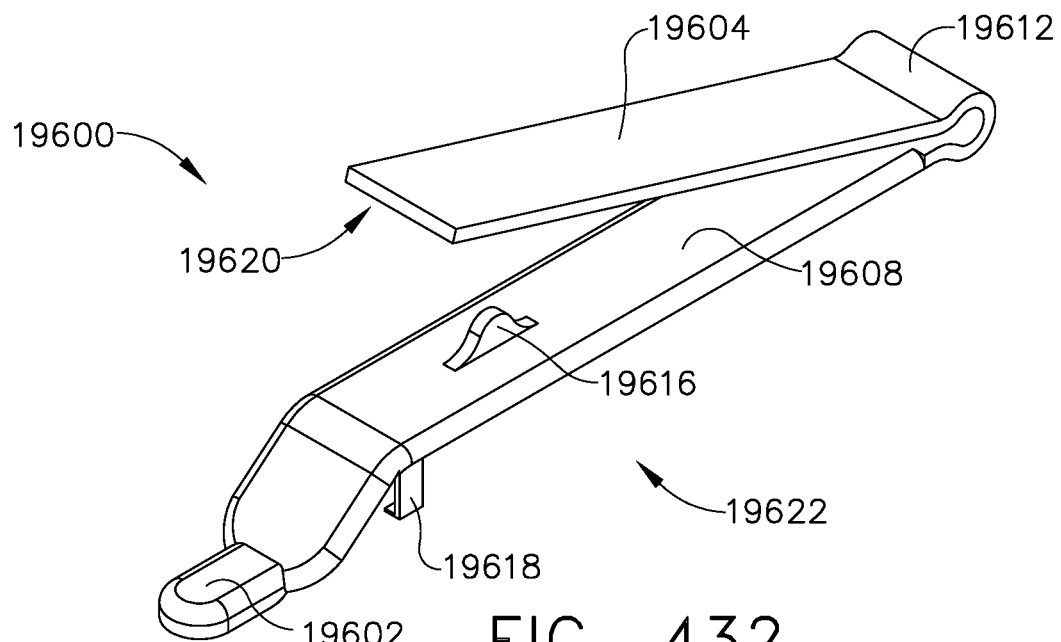
Figure 433:
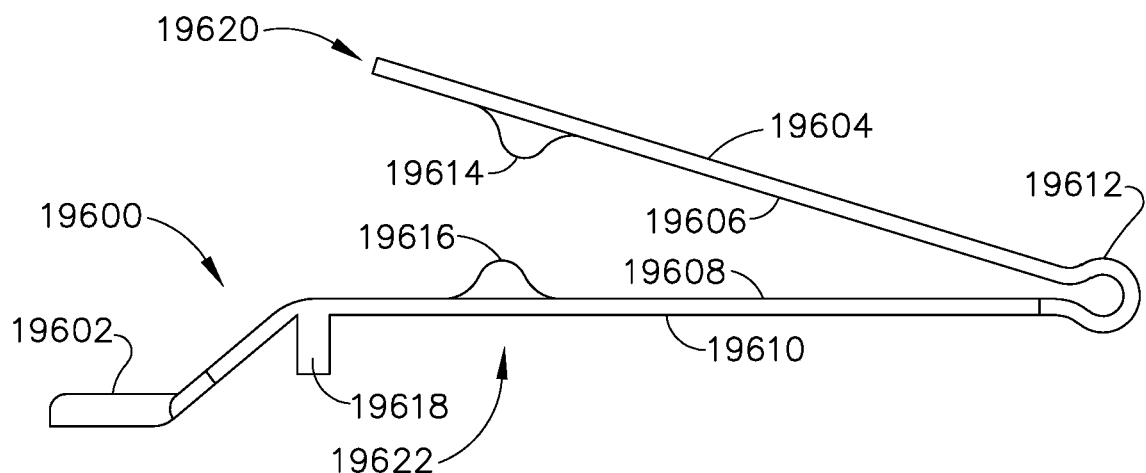
Figure 436:
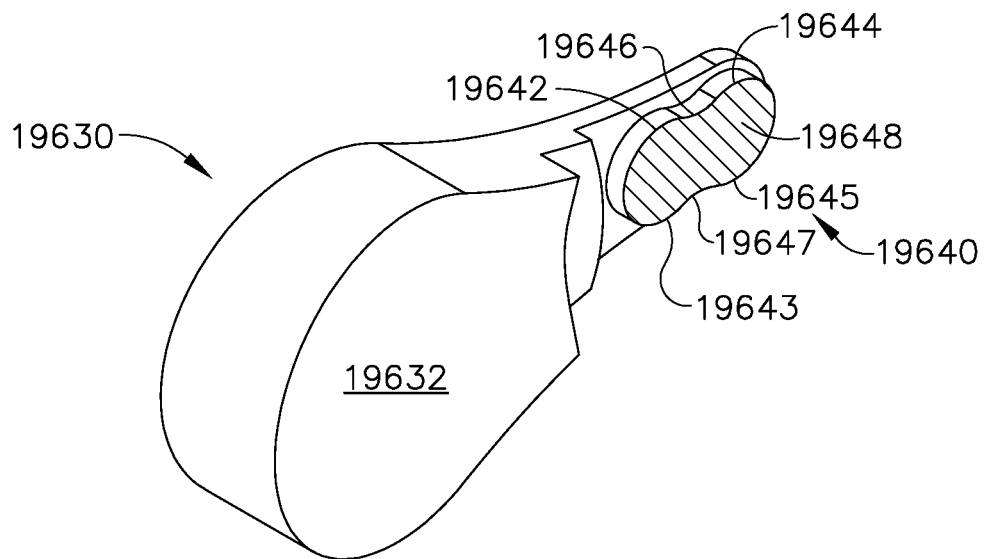
Figure 437:
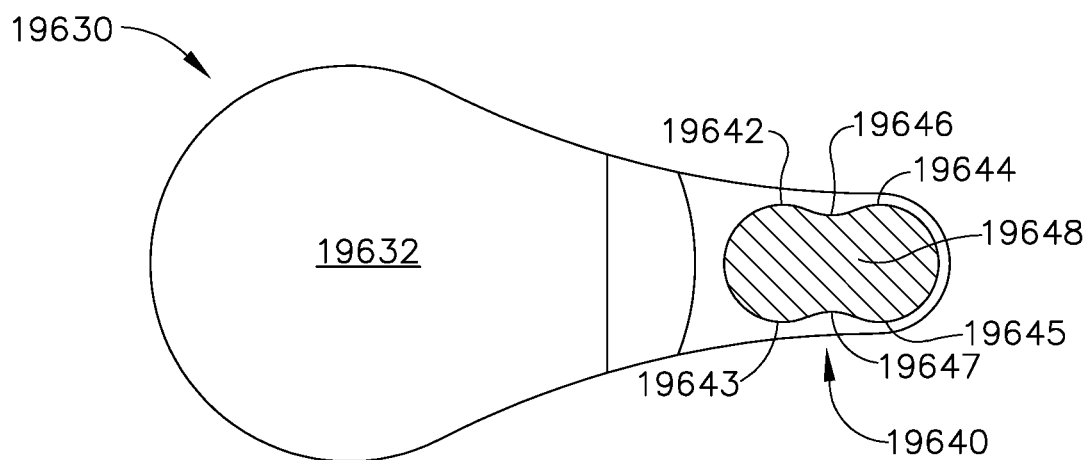
Figure 438:
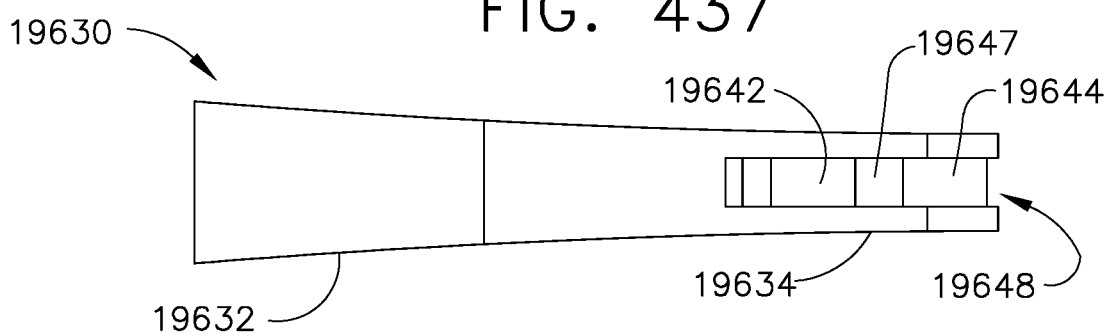
Figure 439:
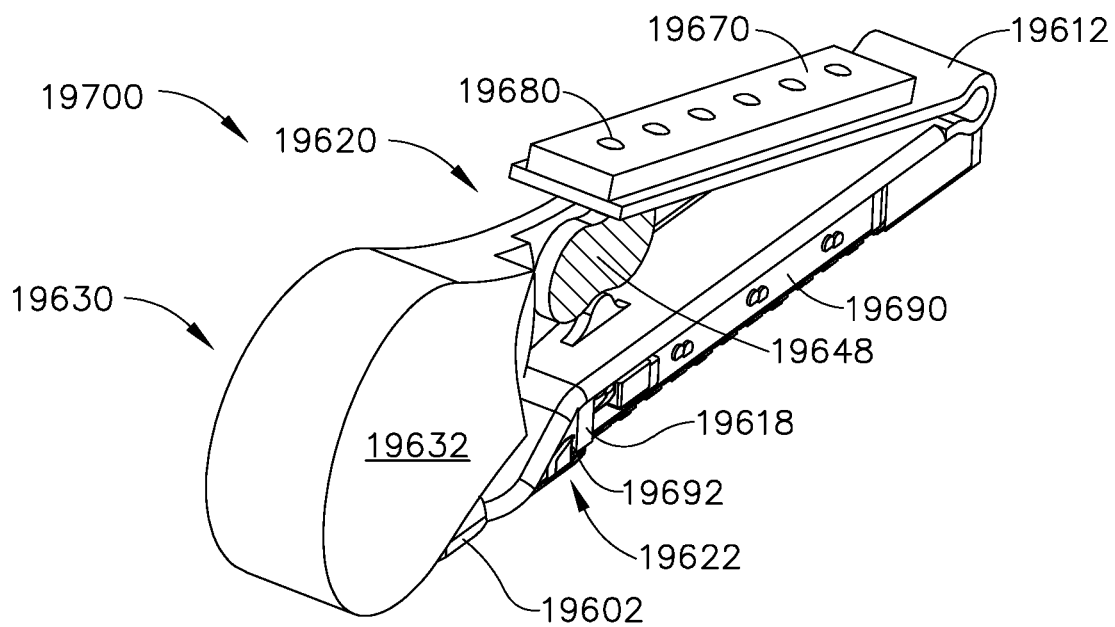
Figure 440:
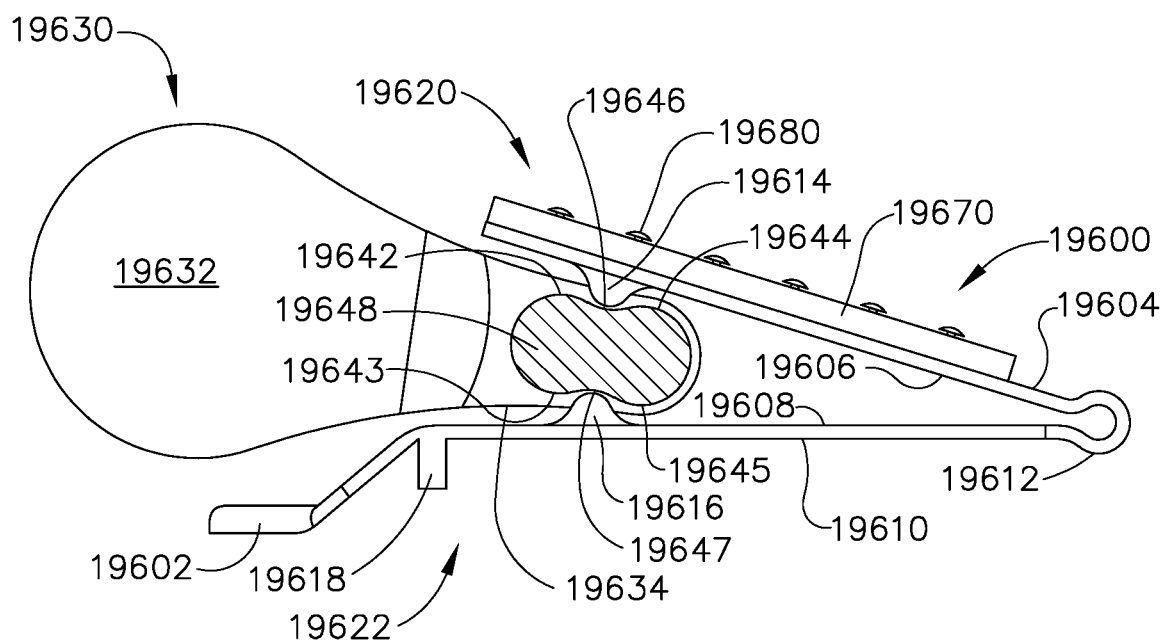
Figure 445:
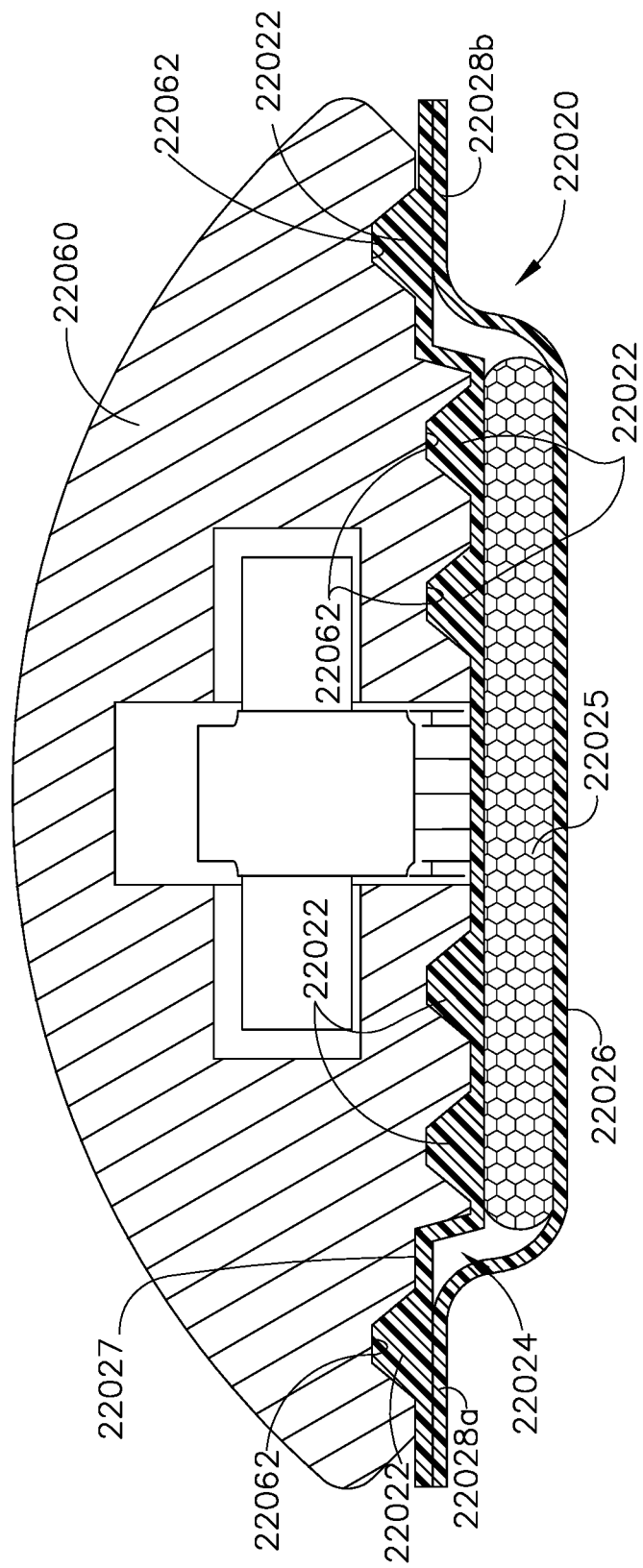
Figure 446:
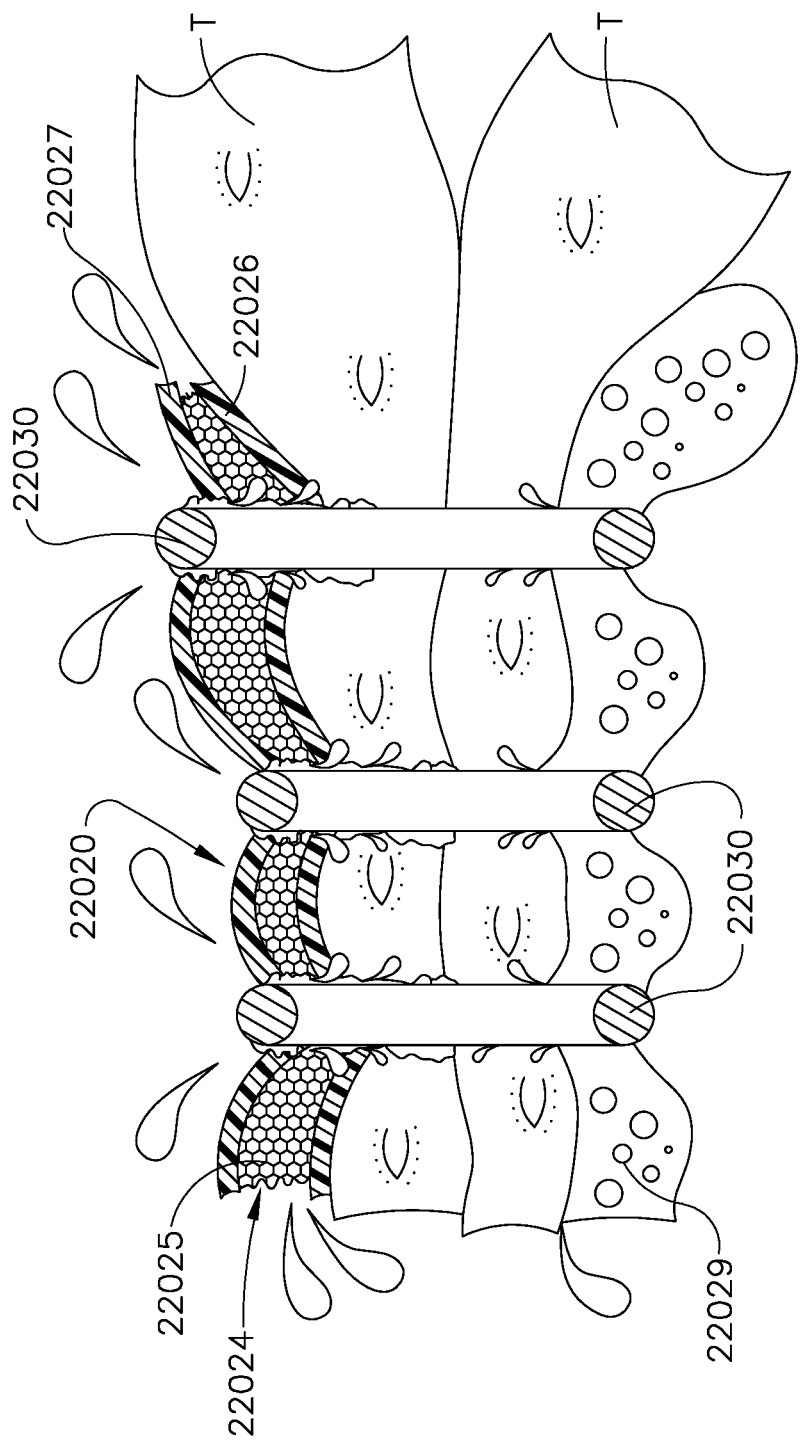
Figure 447:
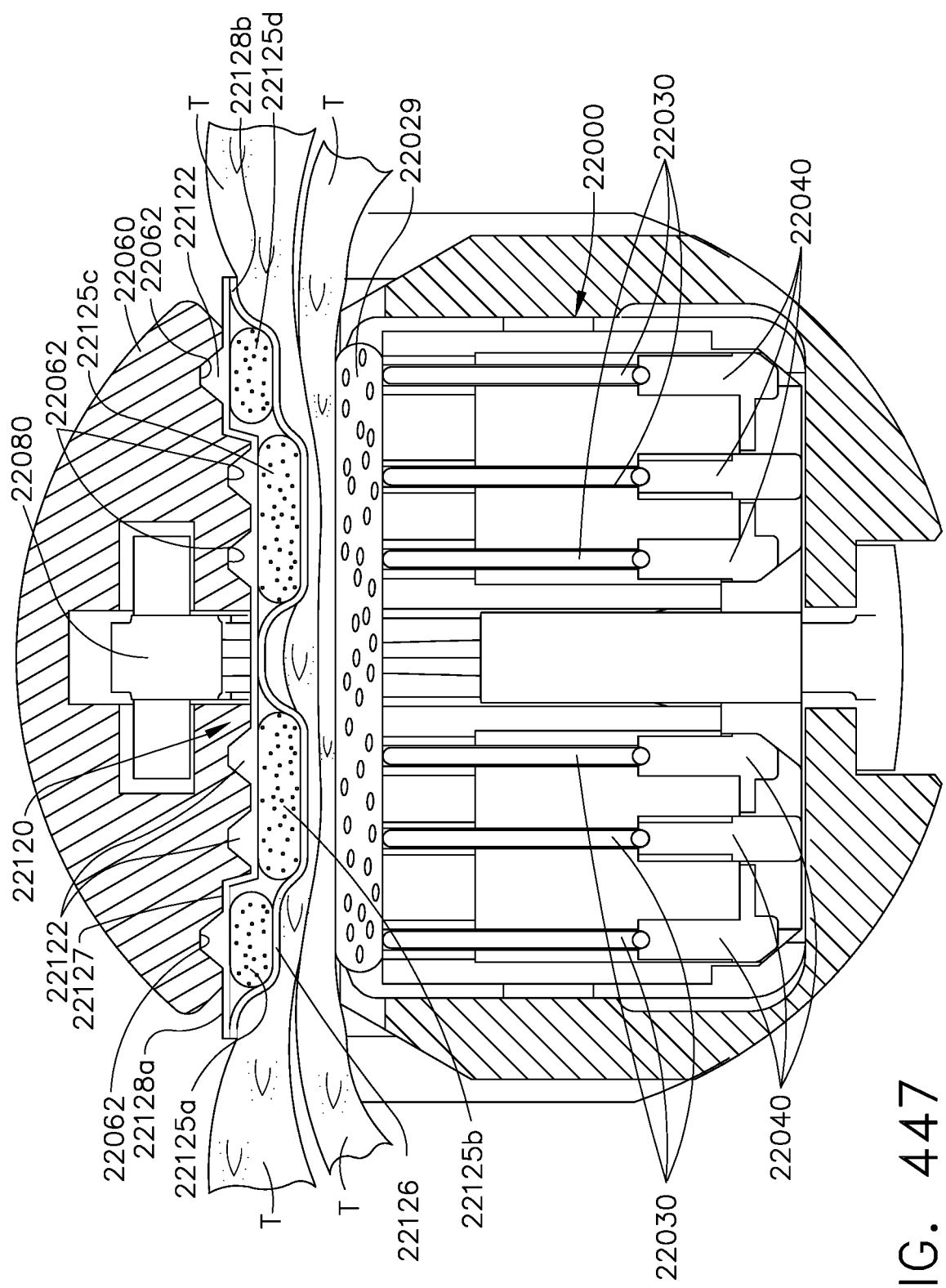
Figure 448:
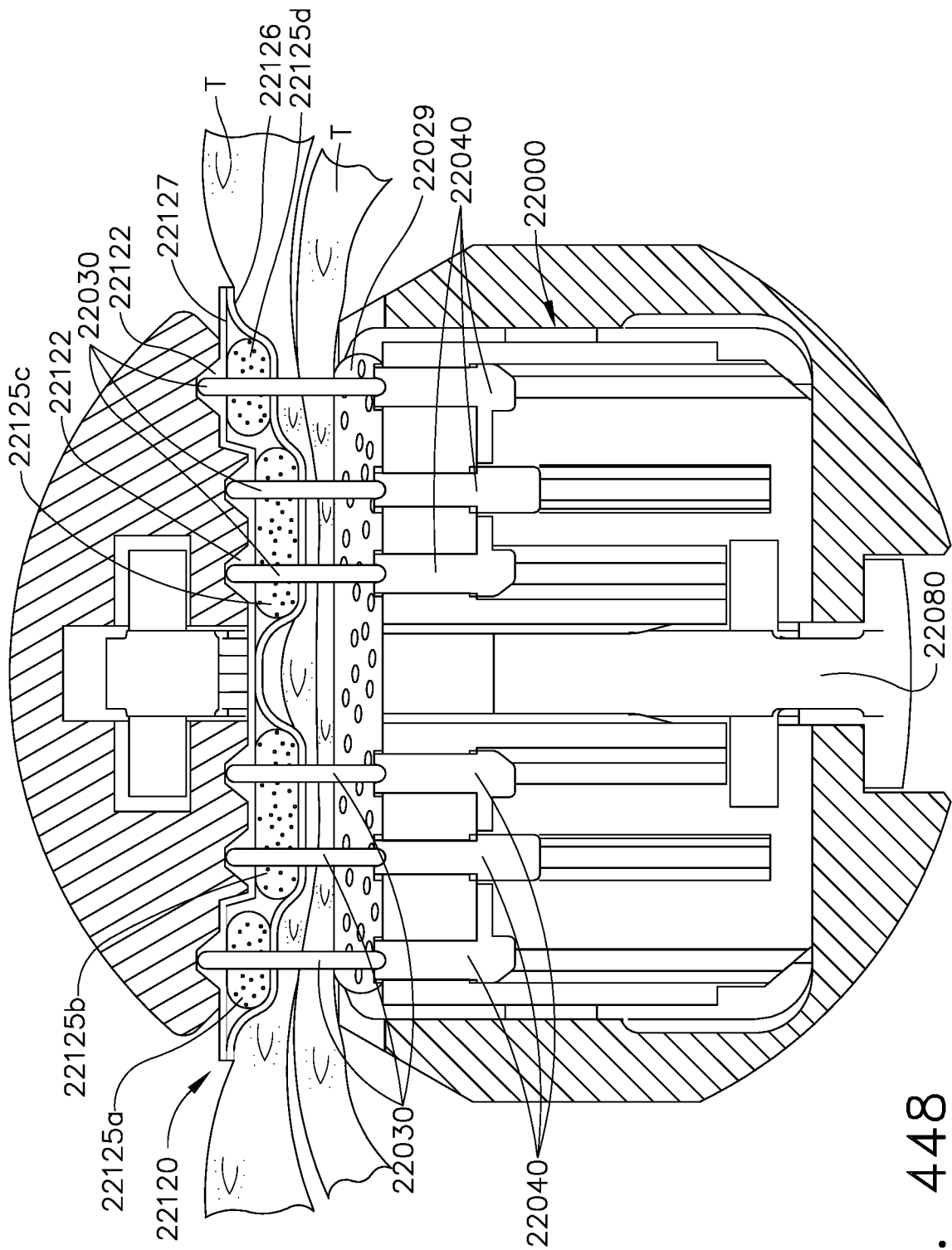
Figure 450:
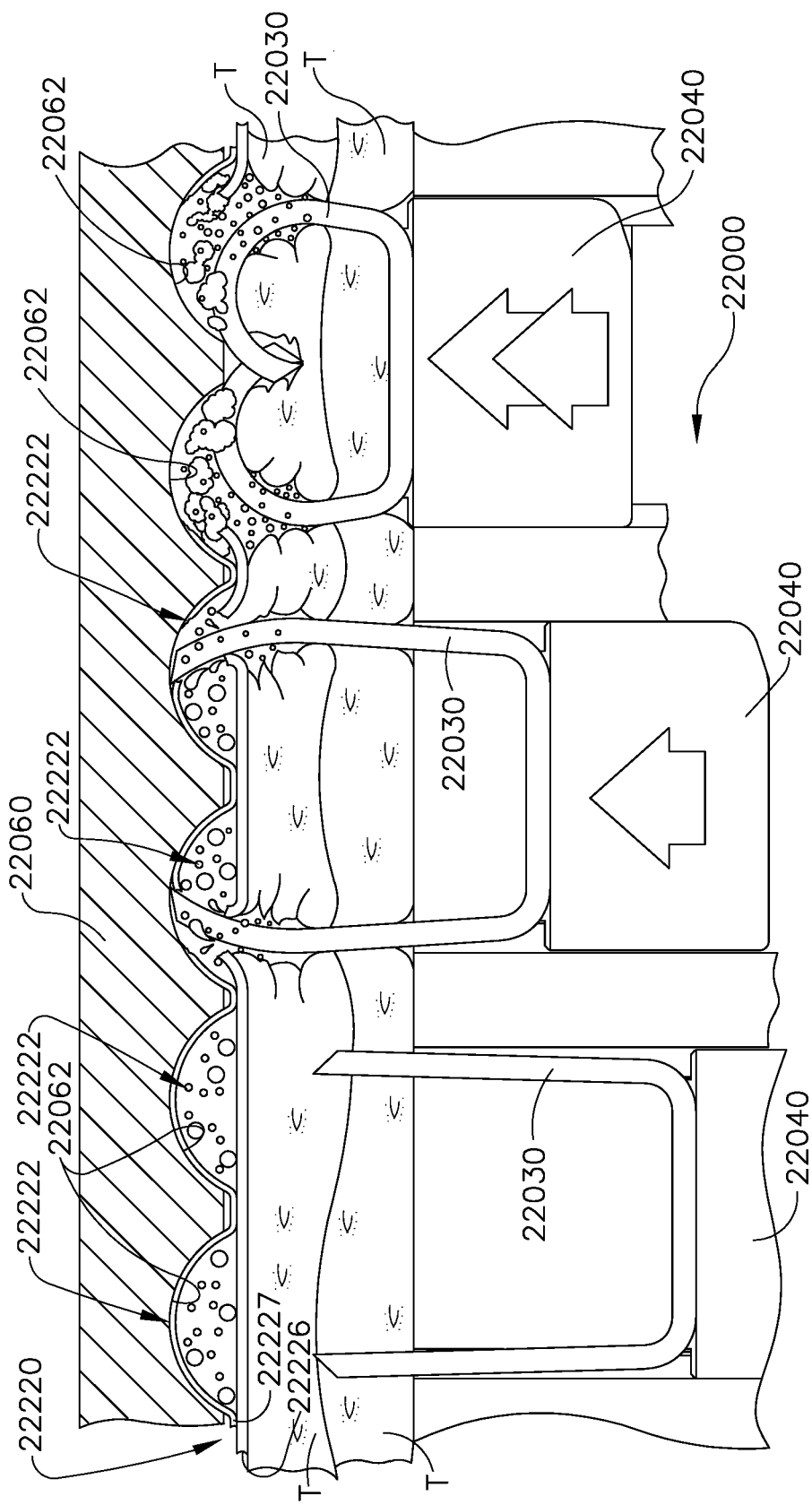
Figure 451:
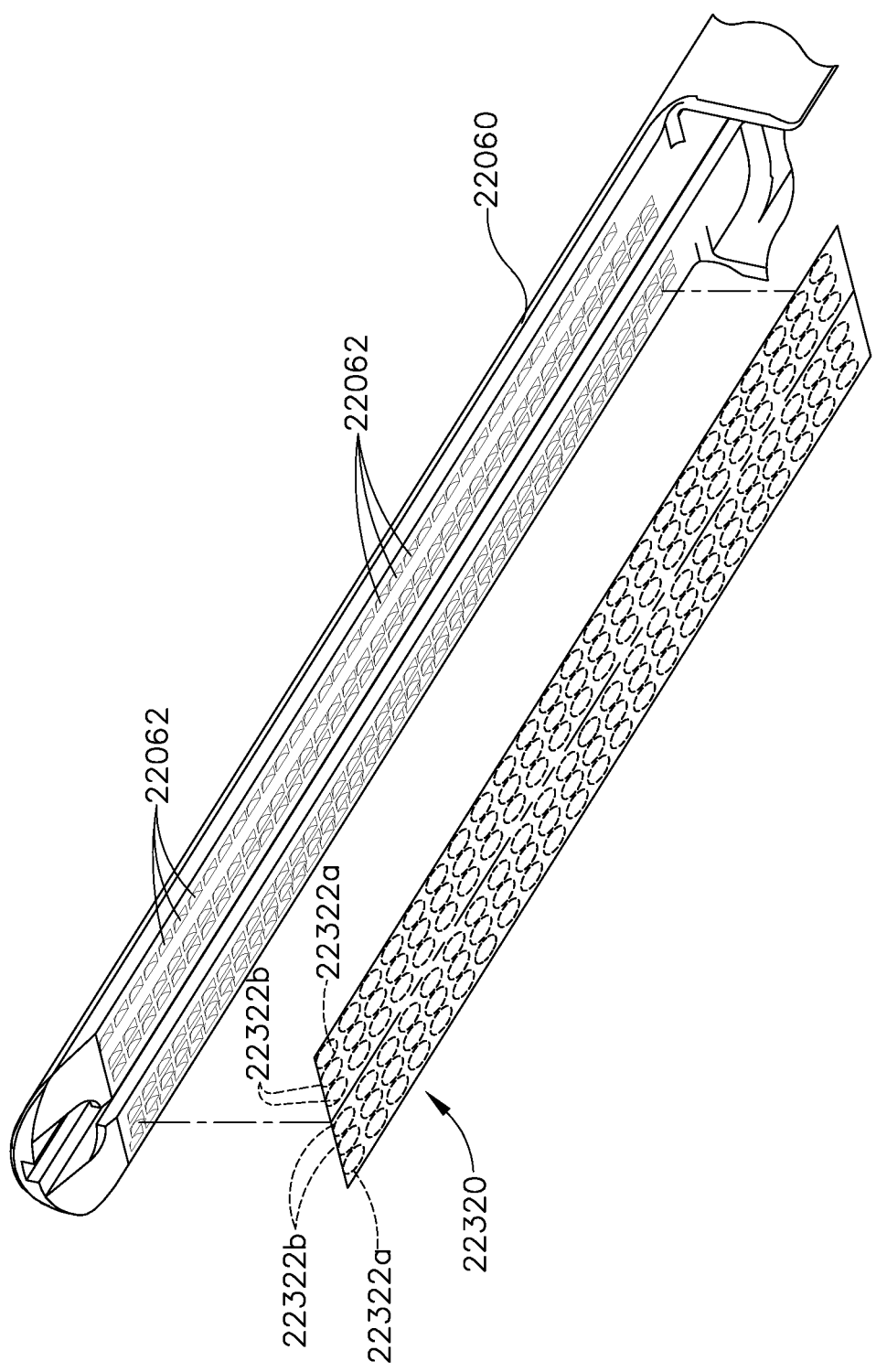
Figure 452:
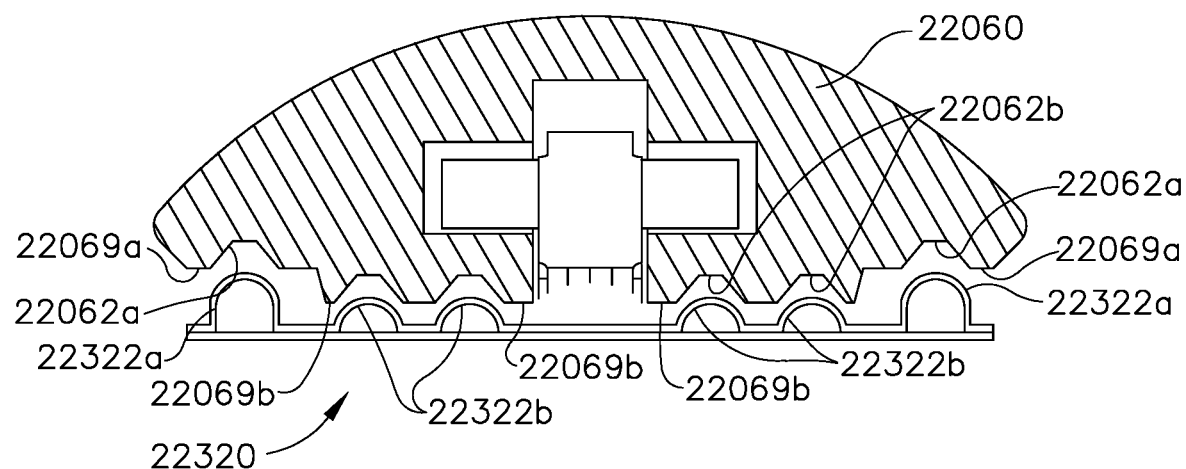
Figure 453:
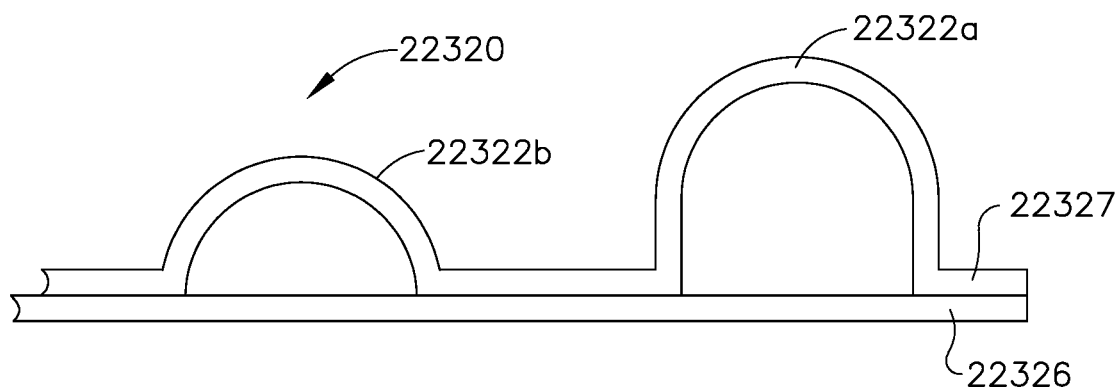
Figure 454:
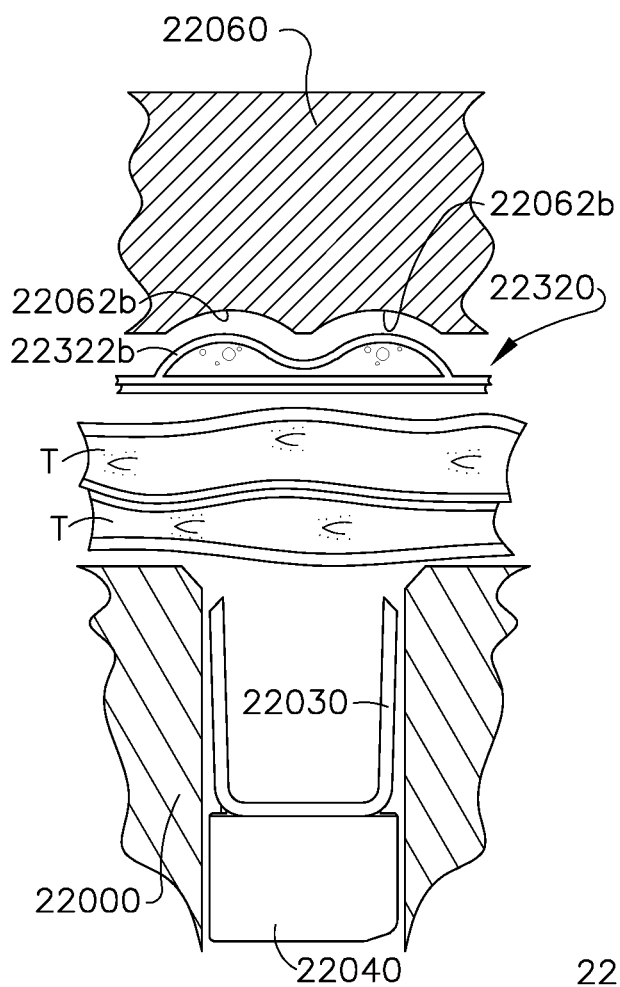
Figure 455:
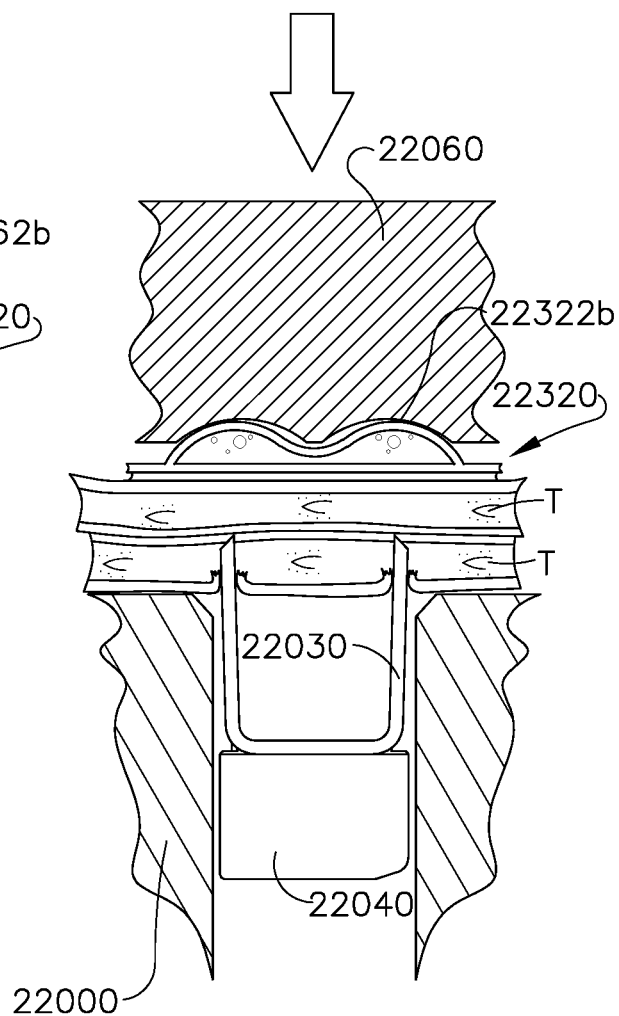
Figure 456:
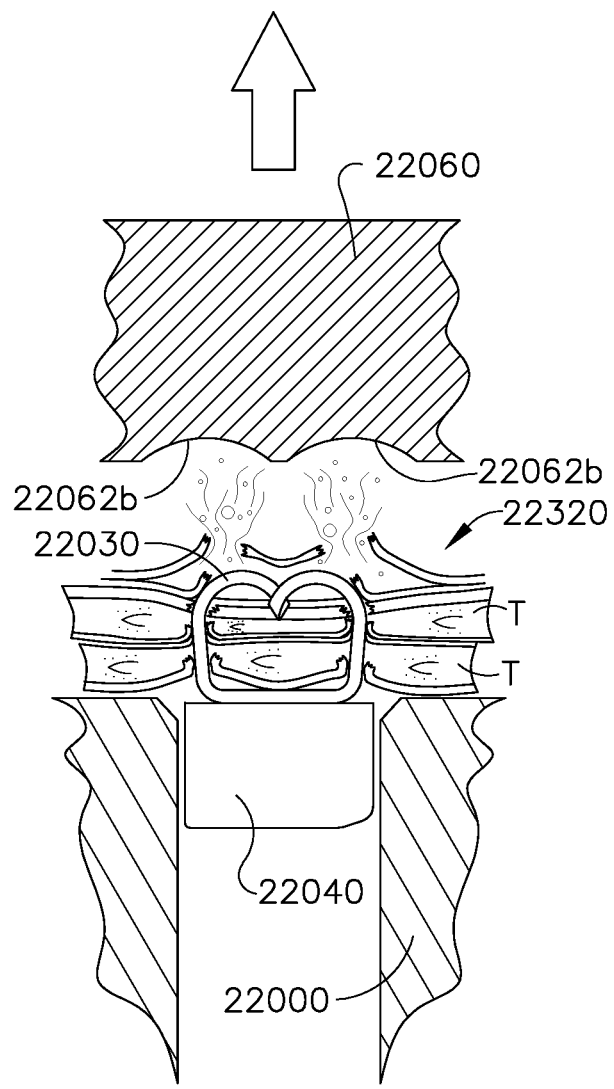
Figure 457:
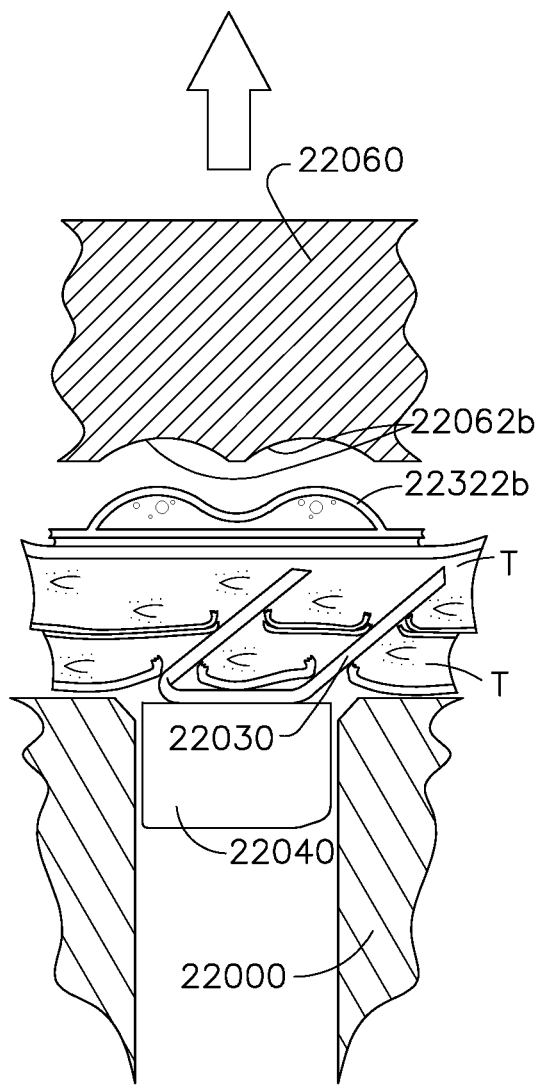
Figure 458:
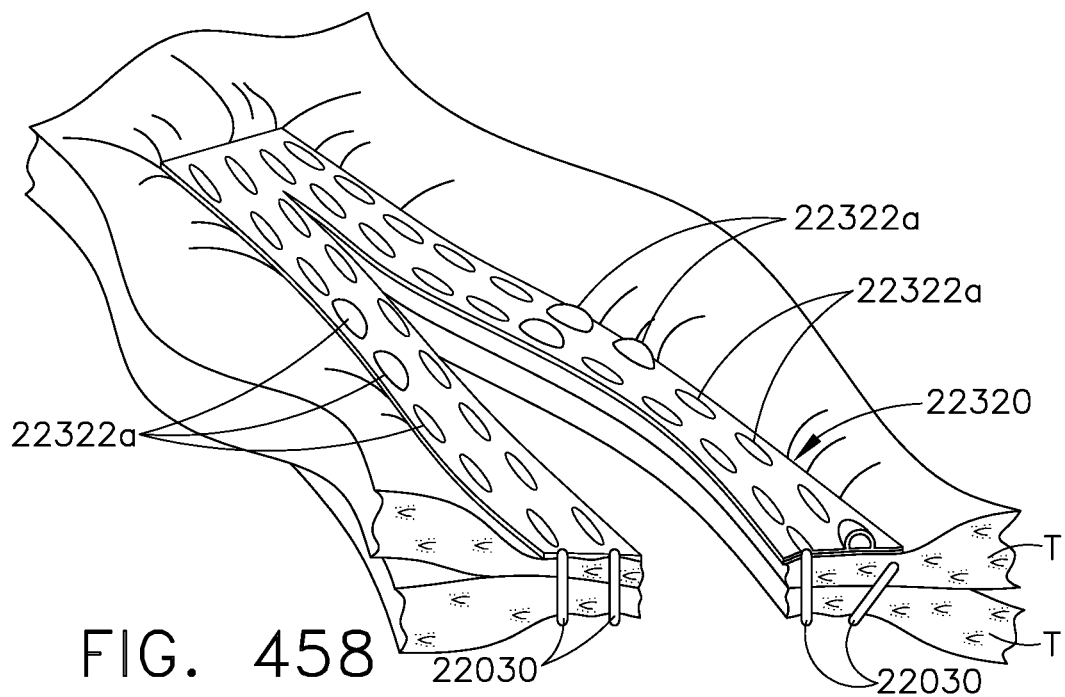
Figure 459:
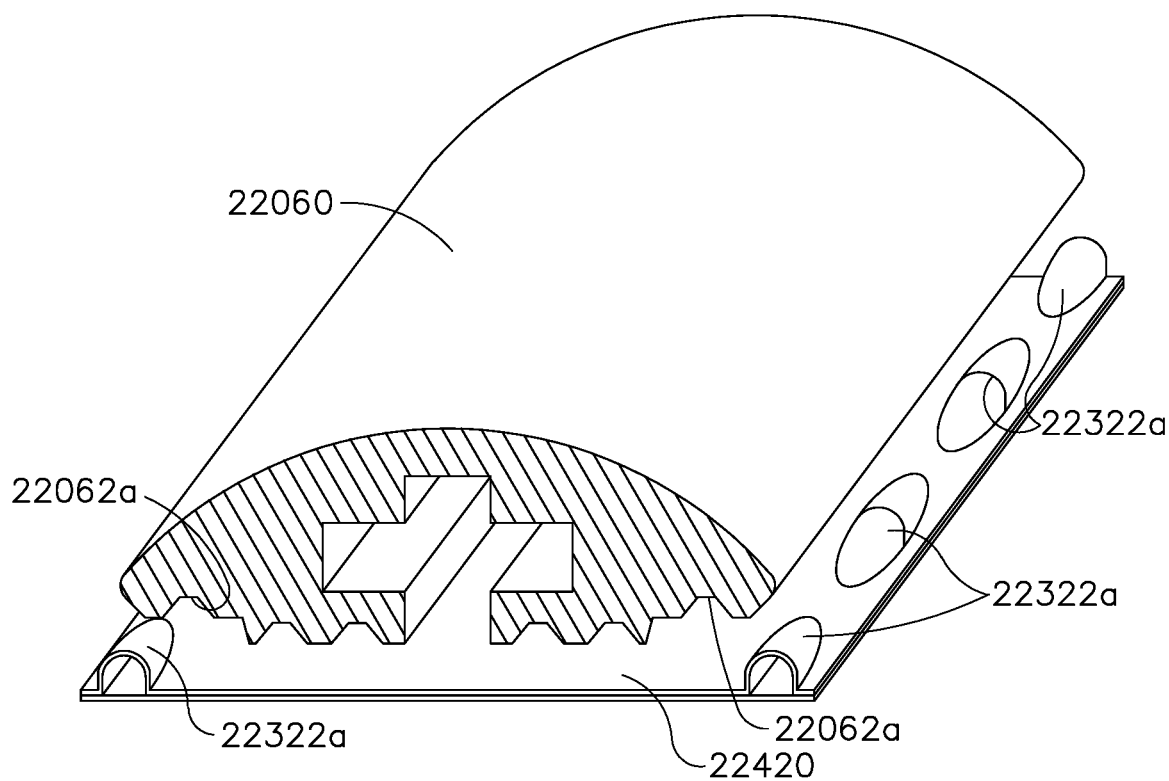
Figure 460:
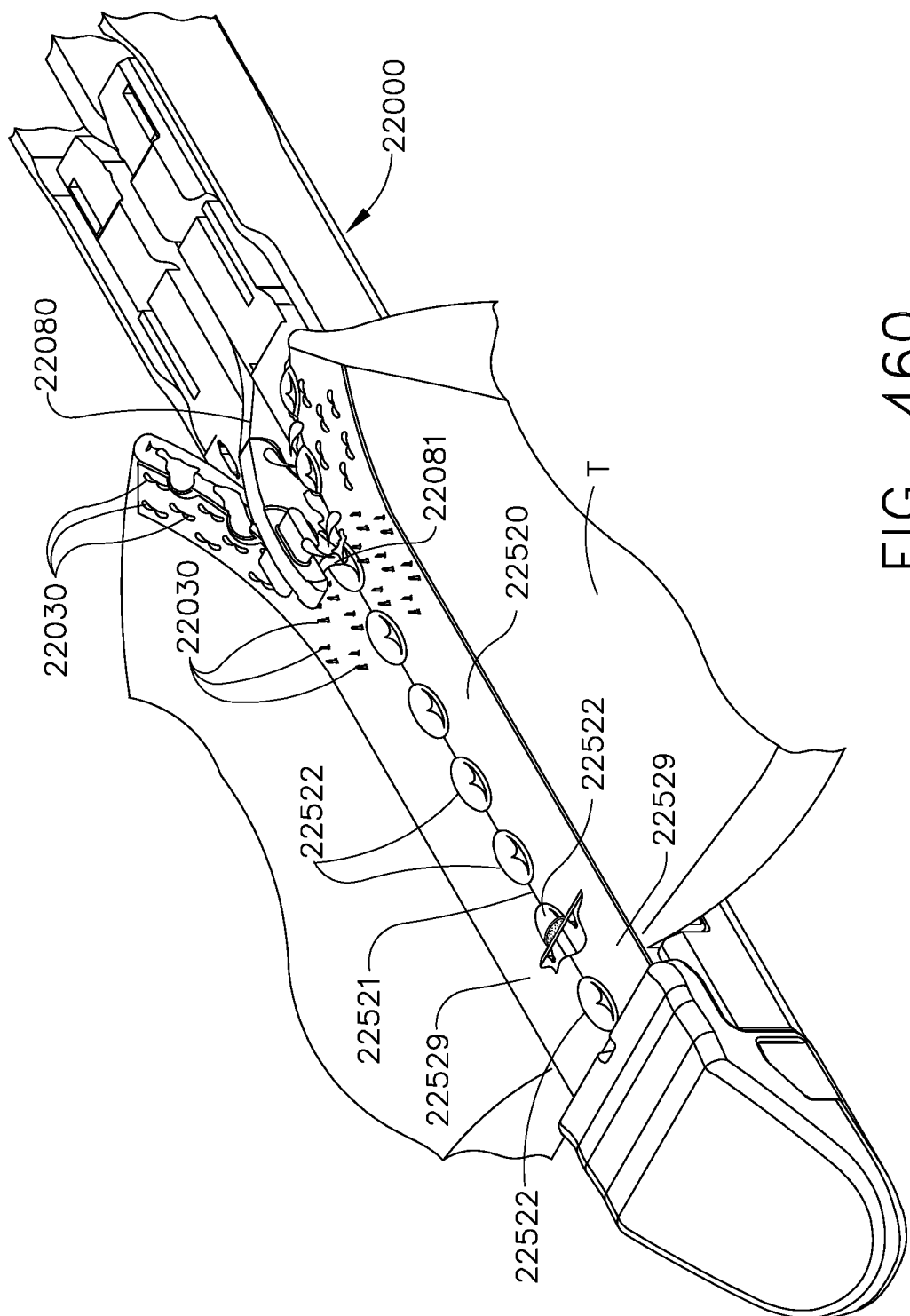
Figure 461:
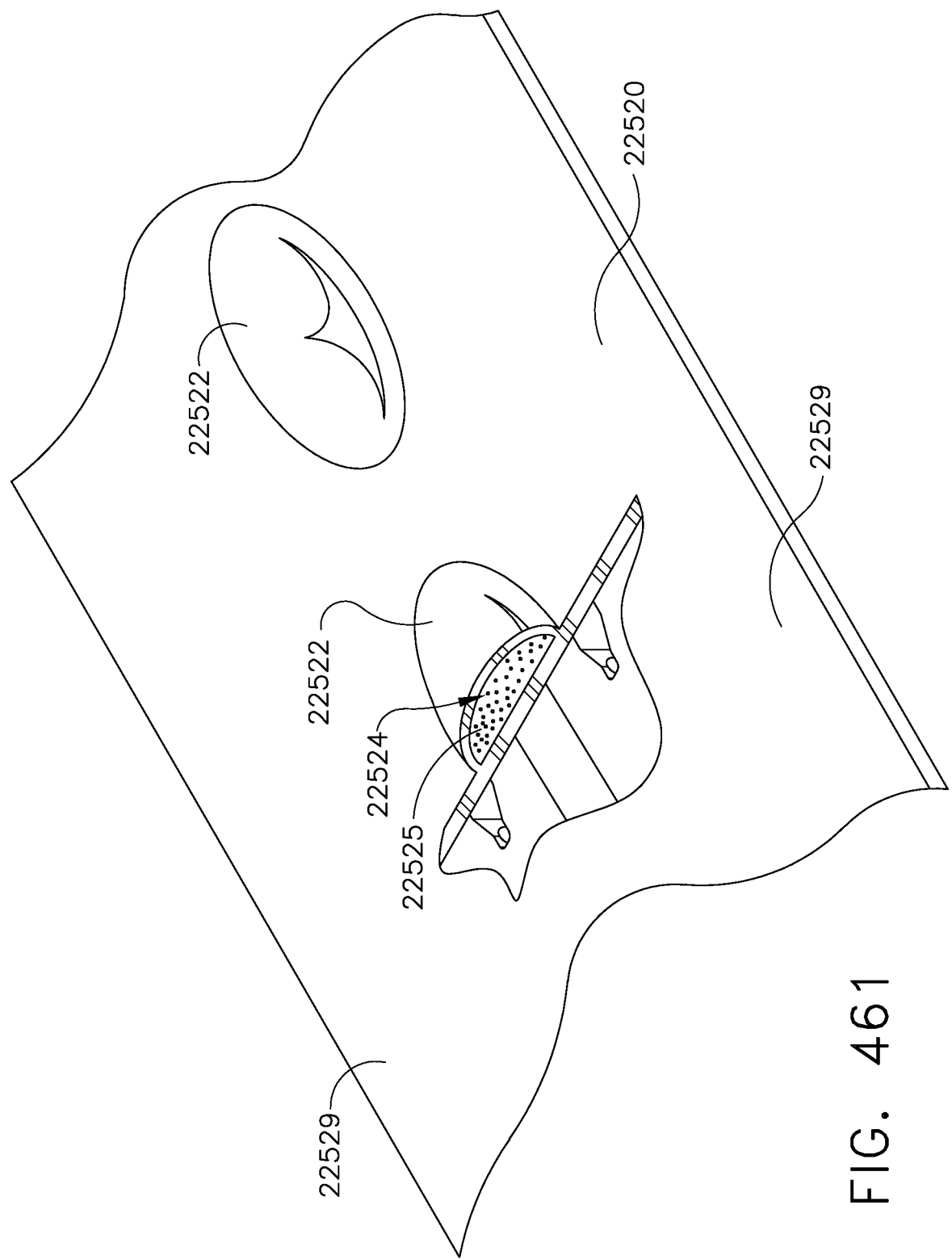
Figure 462:
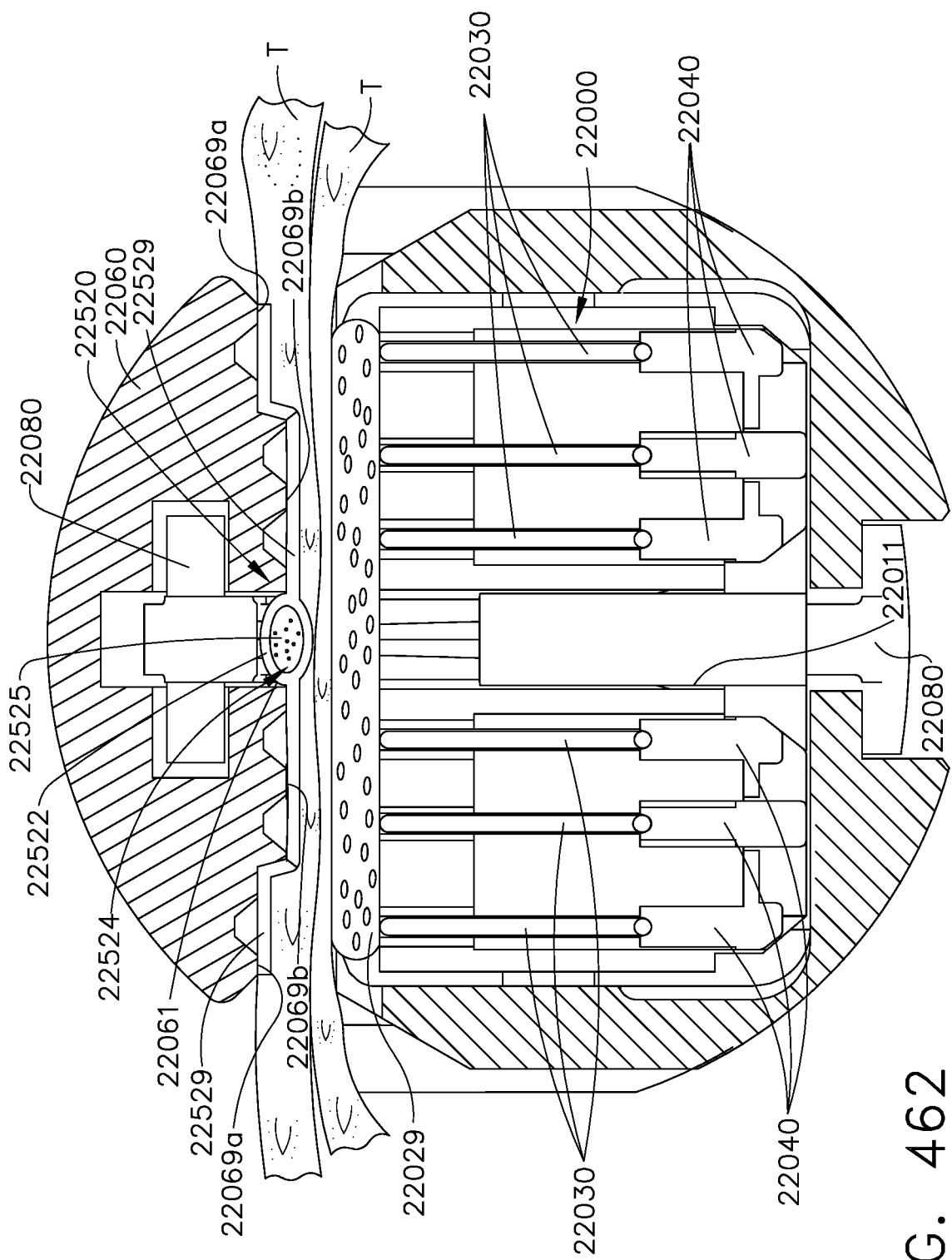
Figure 465:
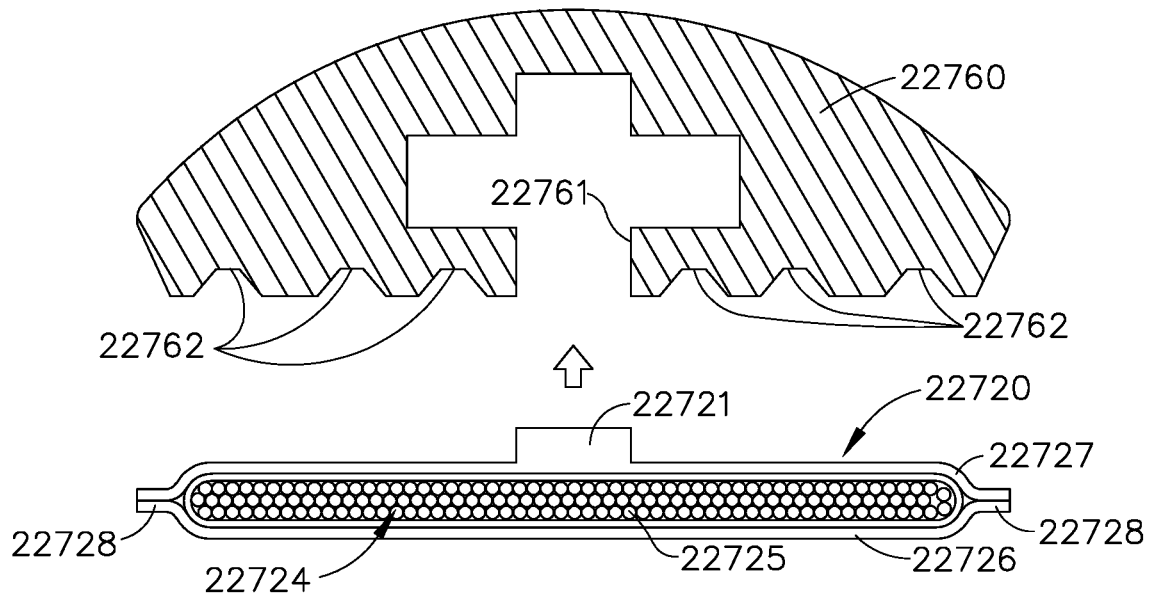
Figure 466:
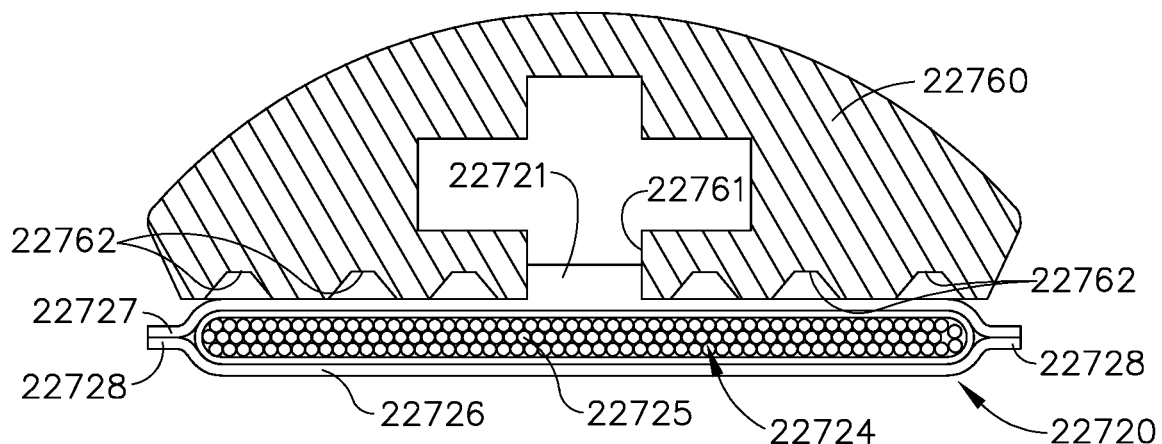
Figure 467:
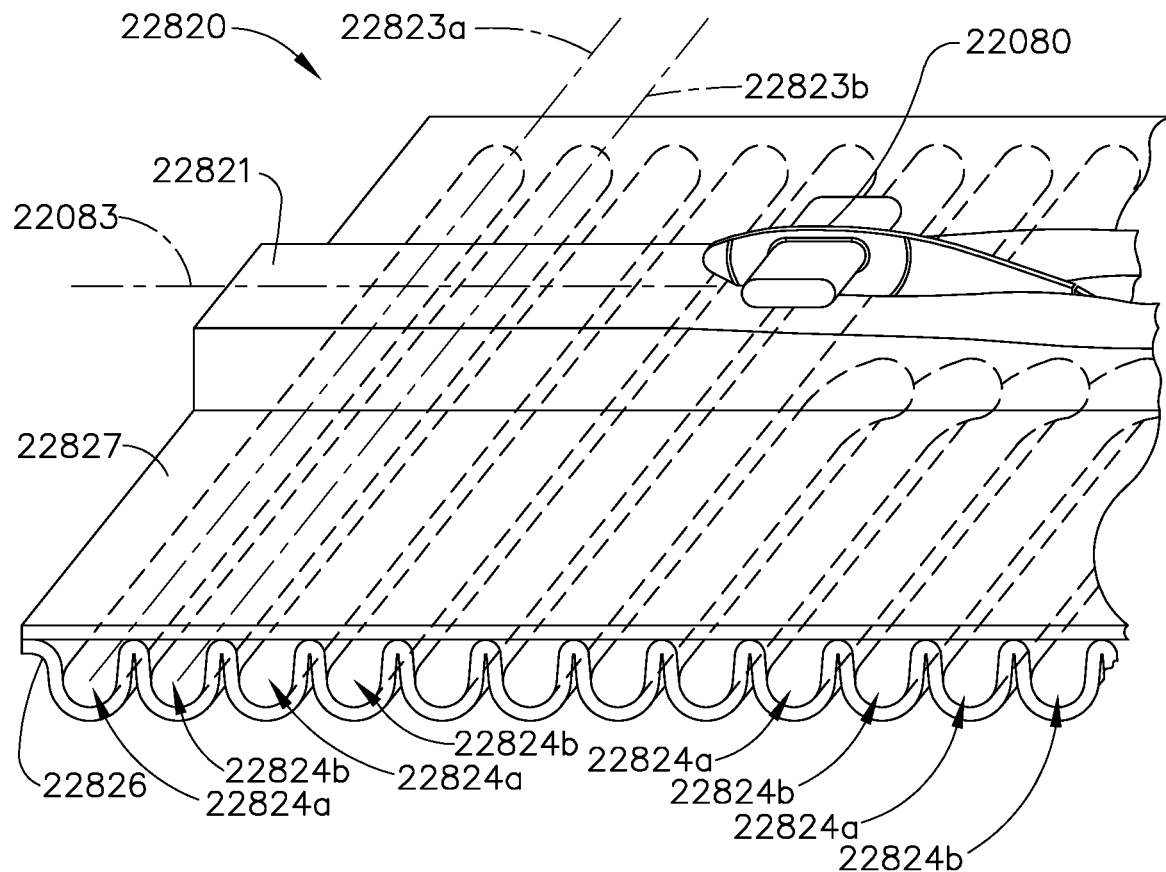
Figure 468:
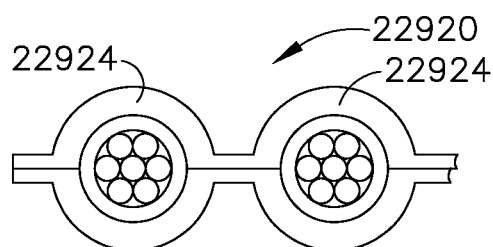
Figure 469:
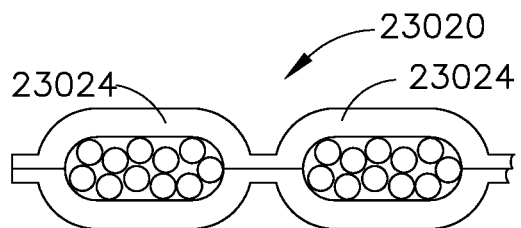
Figure 470:
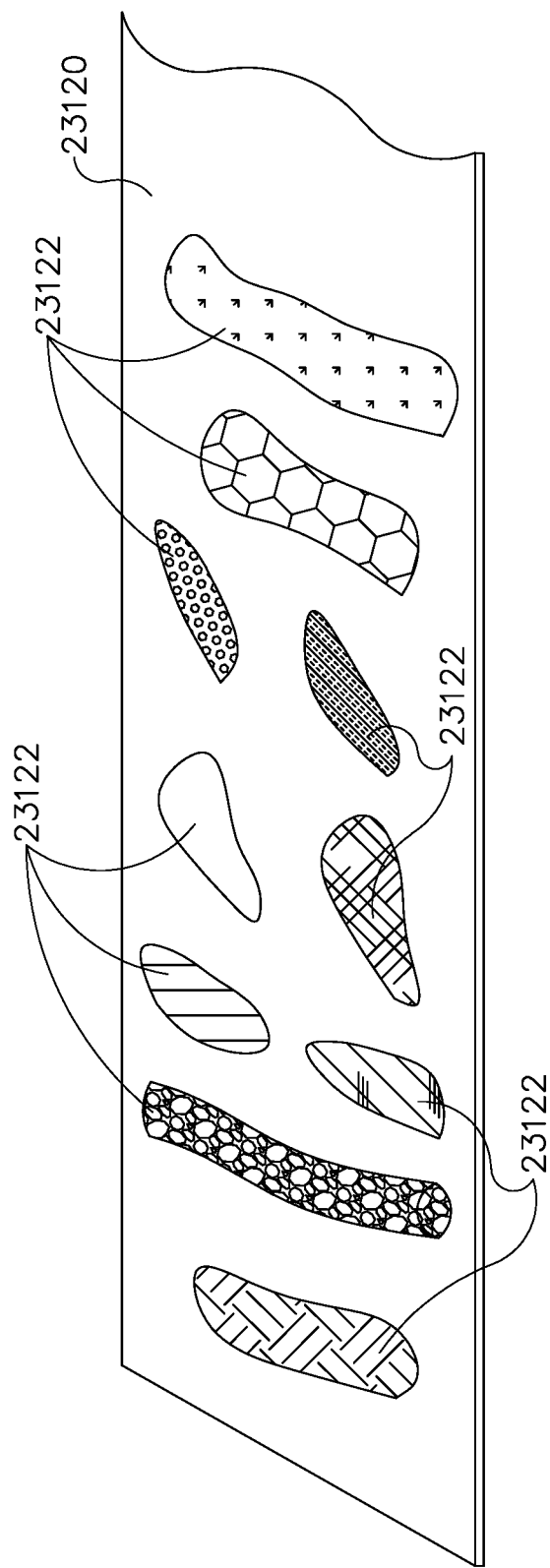
Figure 471:
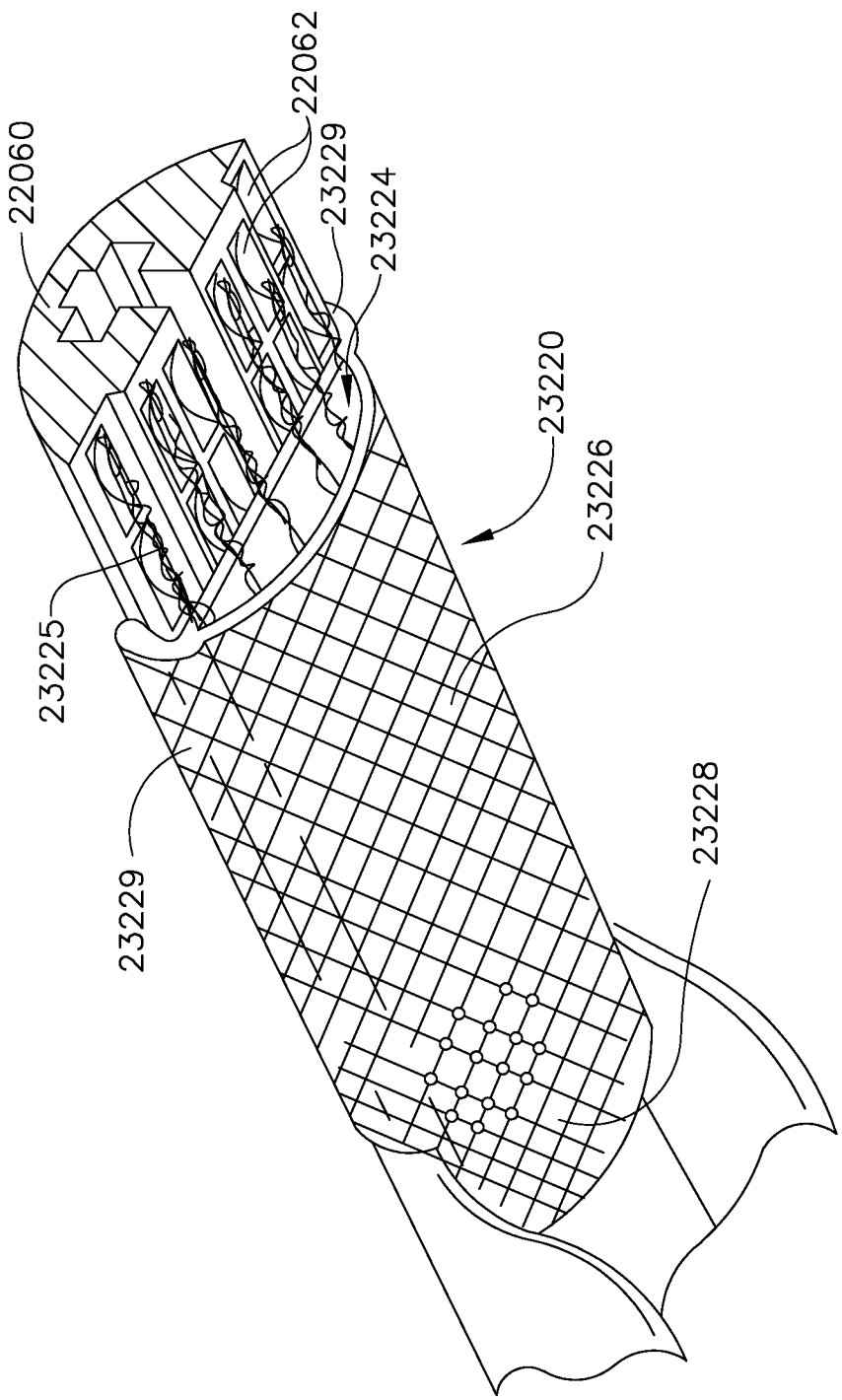
Figure 481:
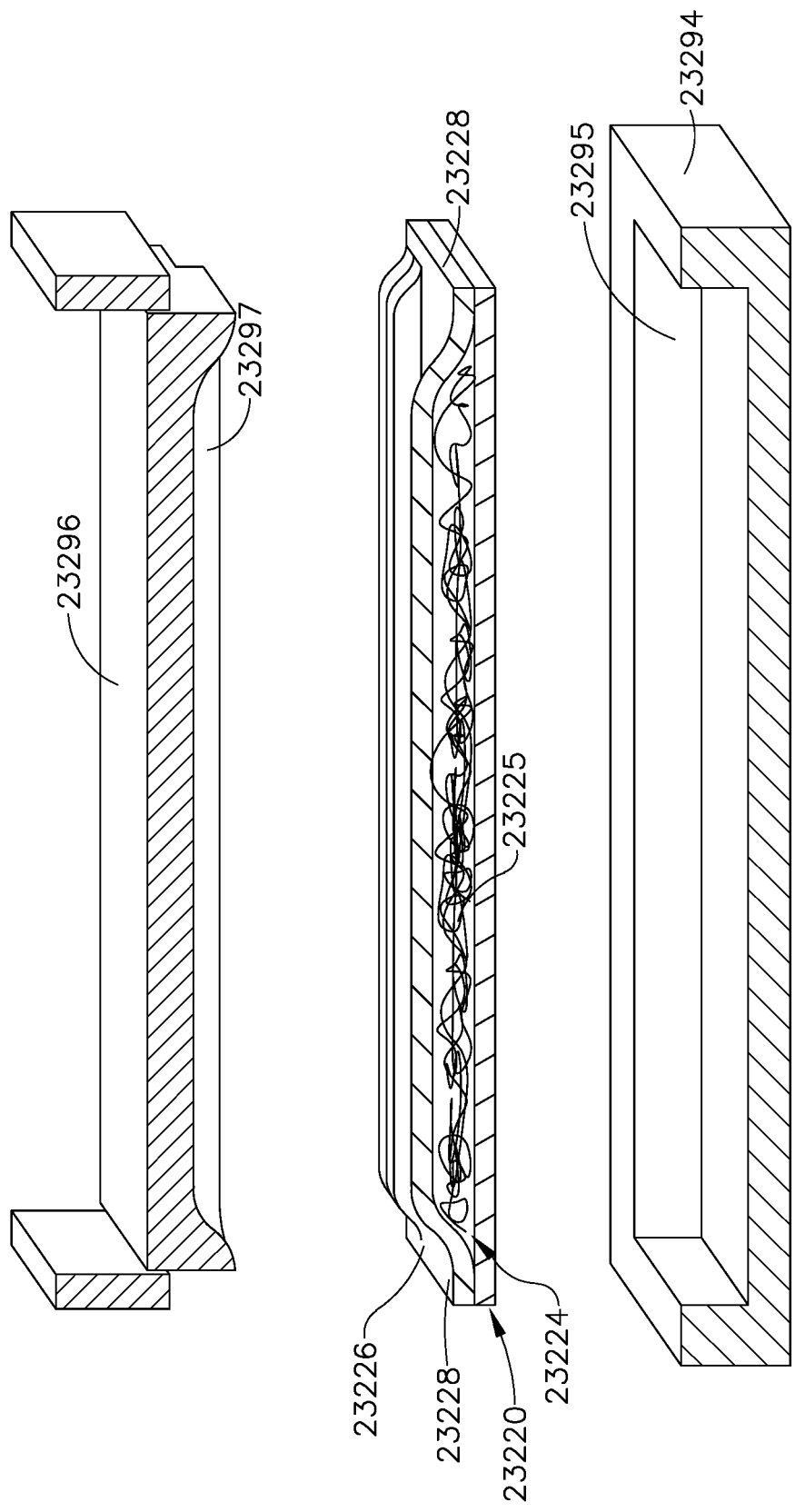
Figure 482:
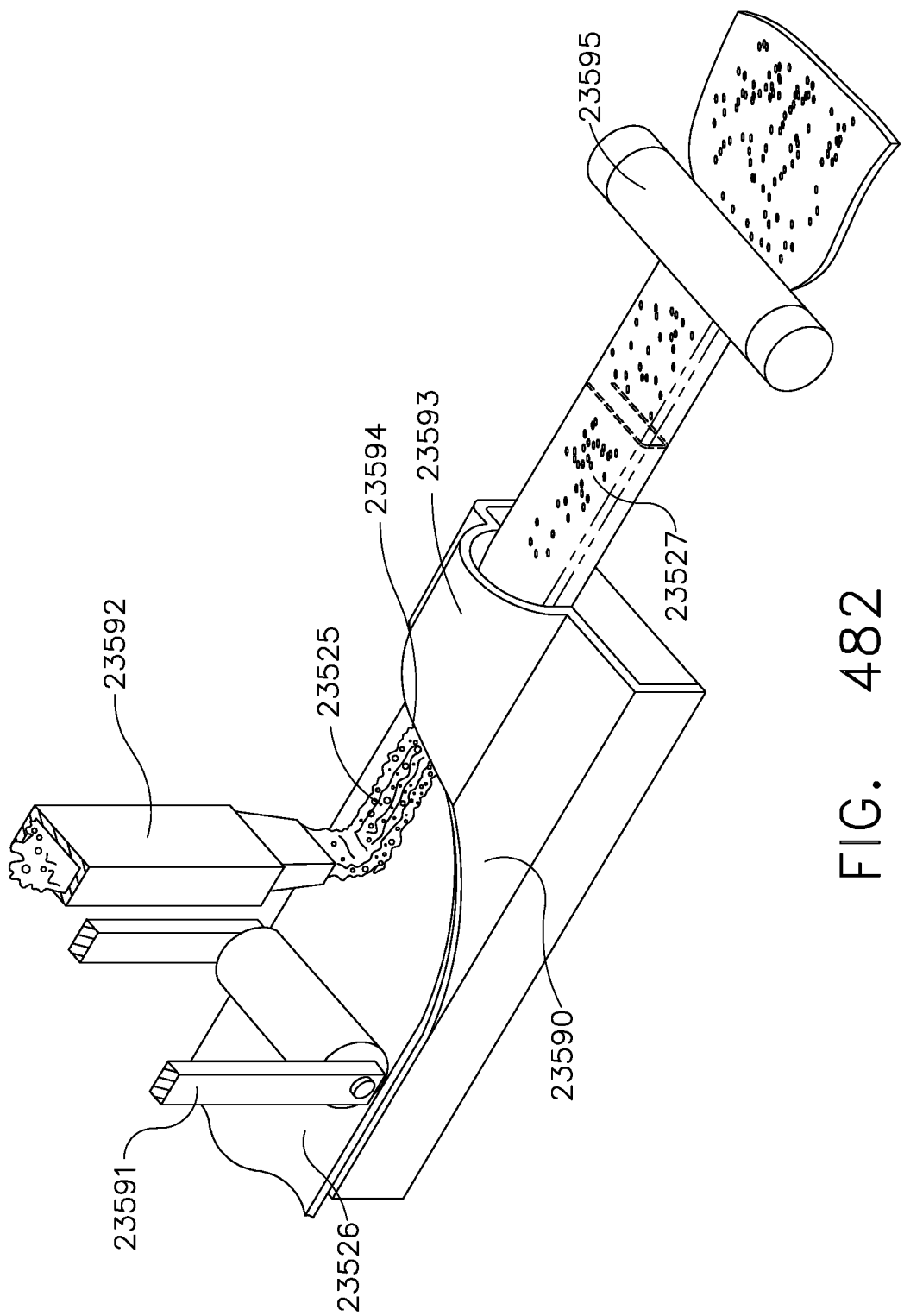
Figure 483:
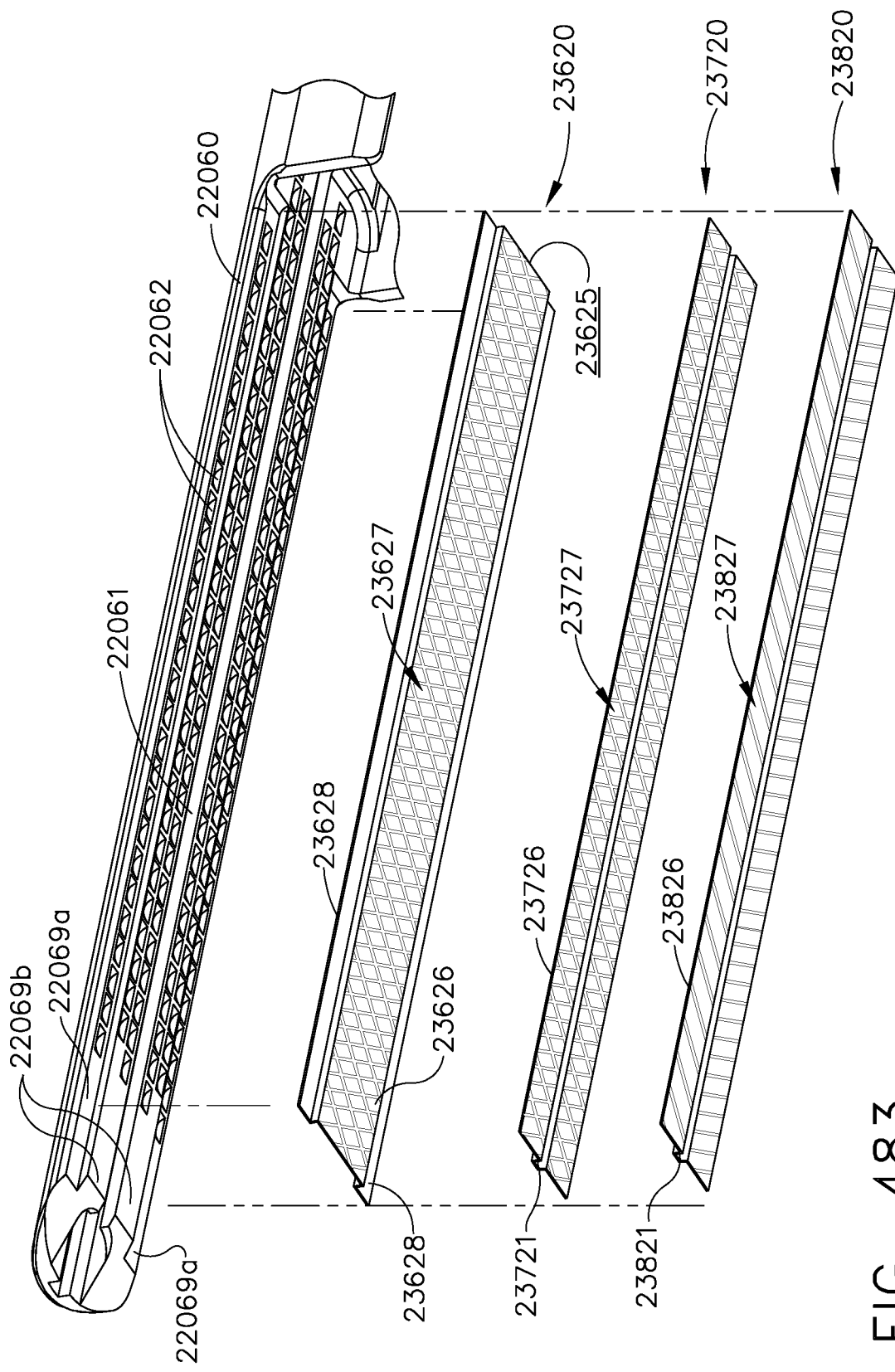
Figure 484:
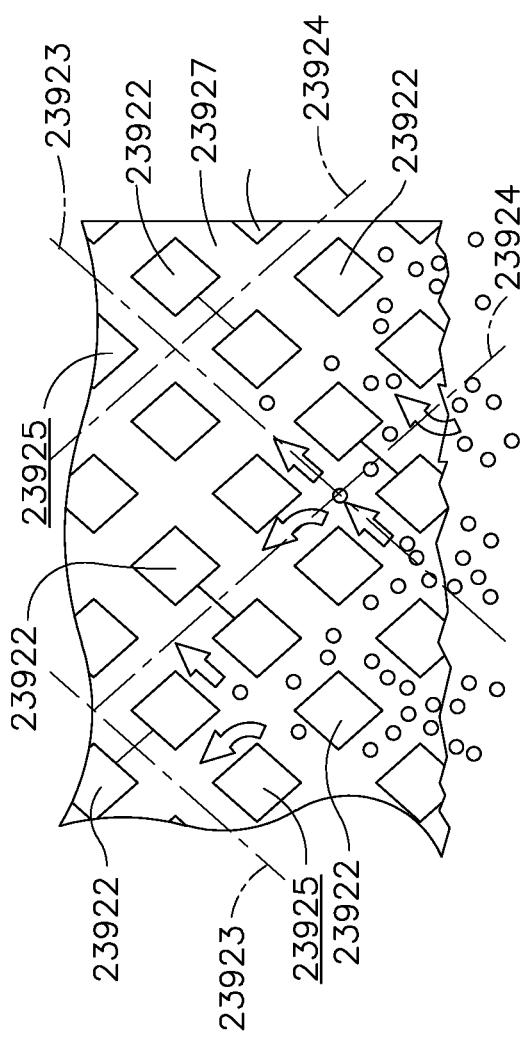
Figure 485:
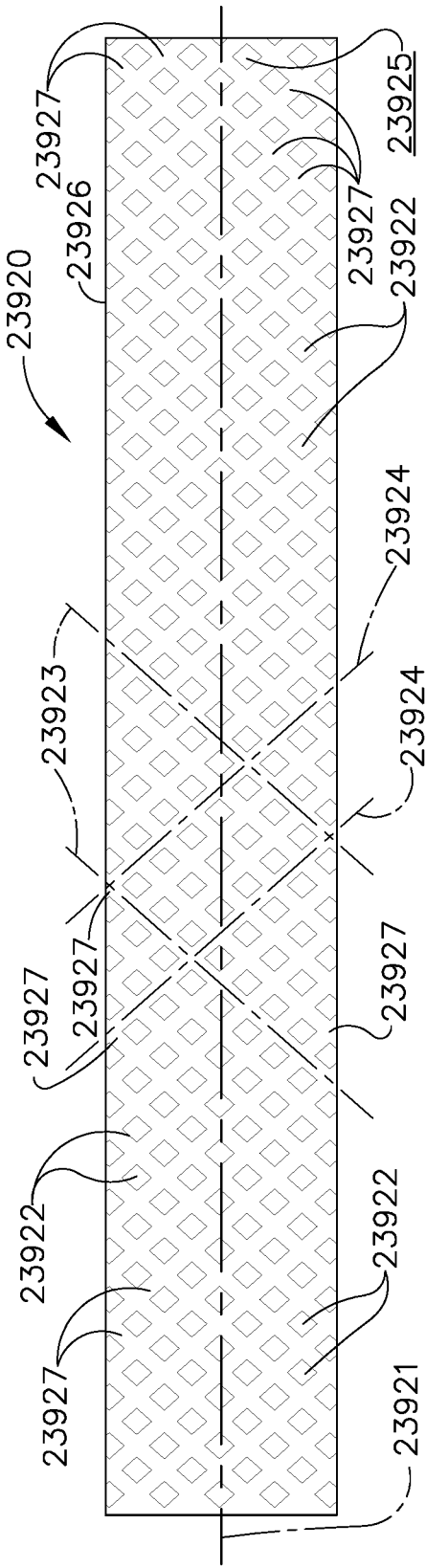
Figure 486:
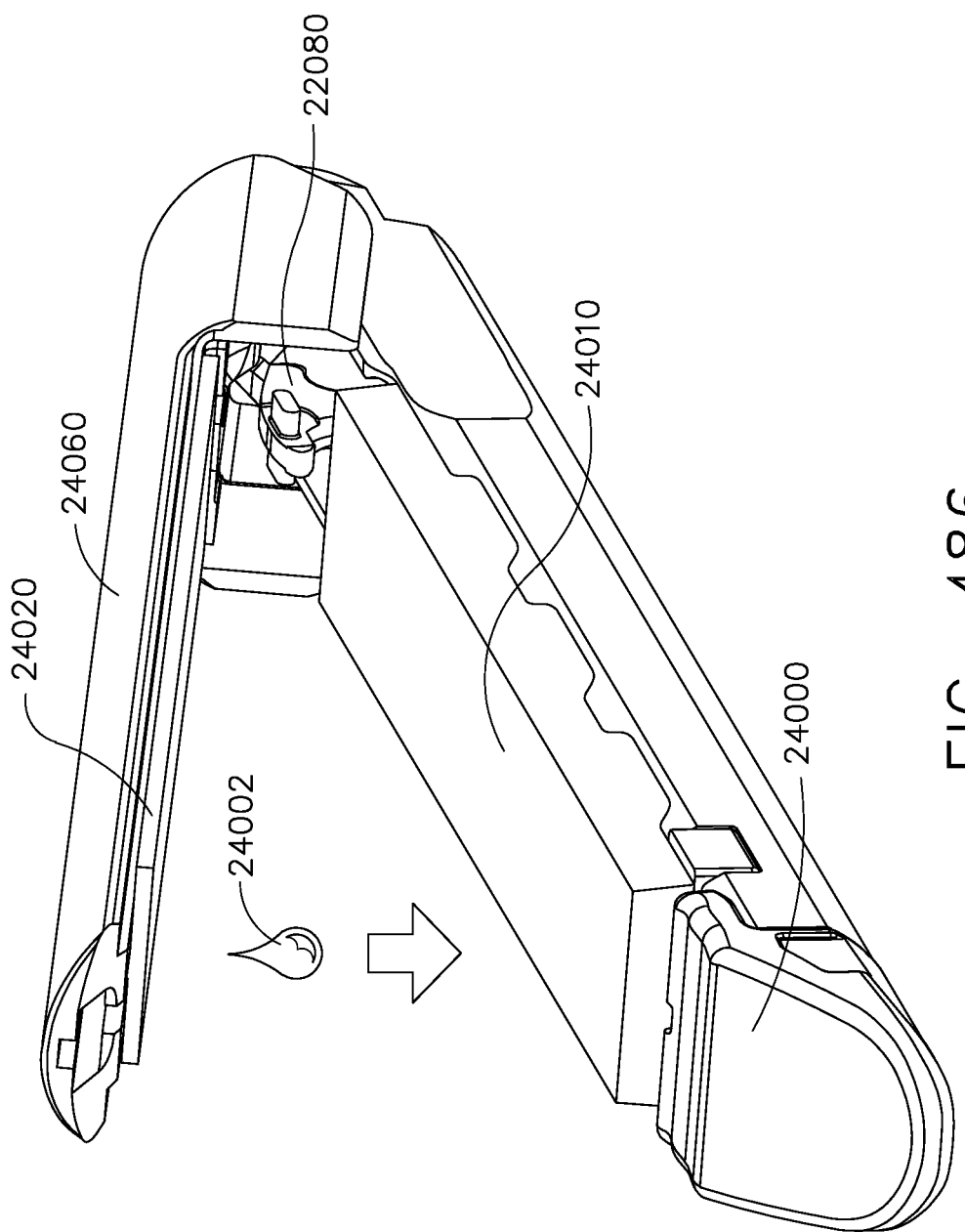
Figure 487:
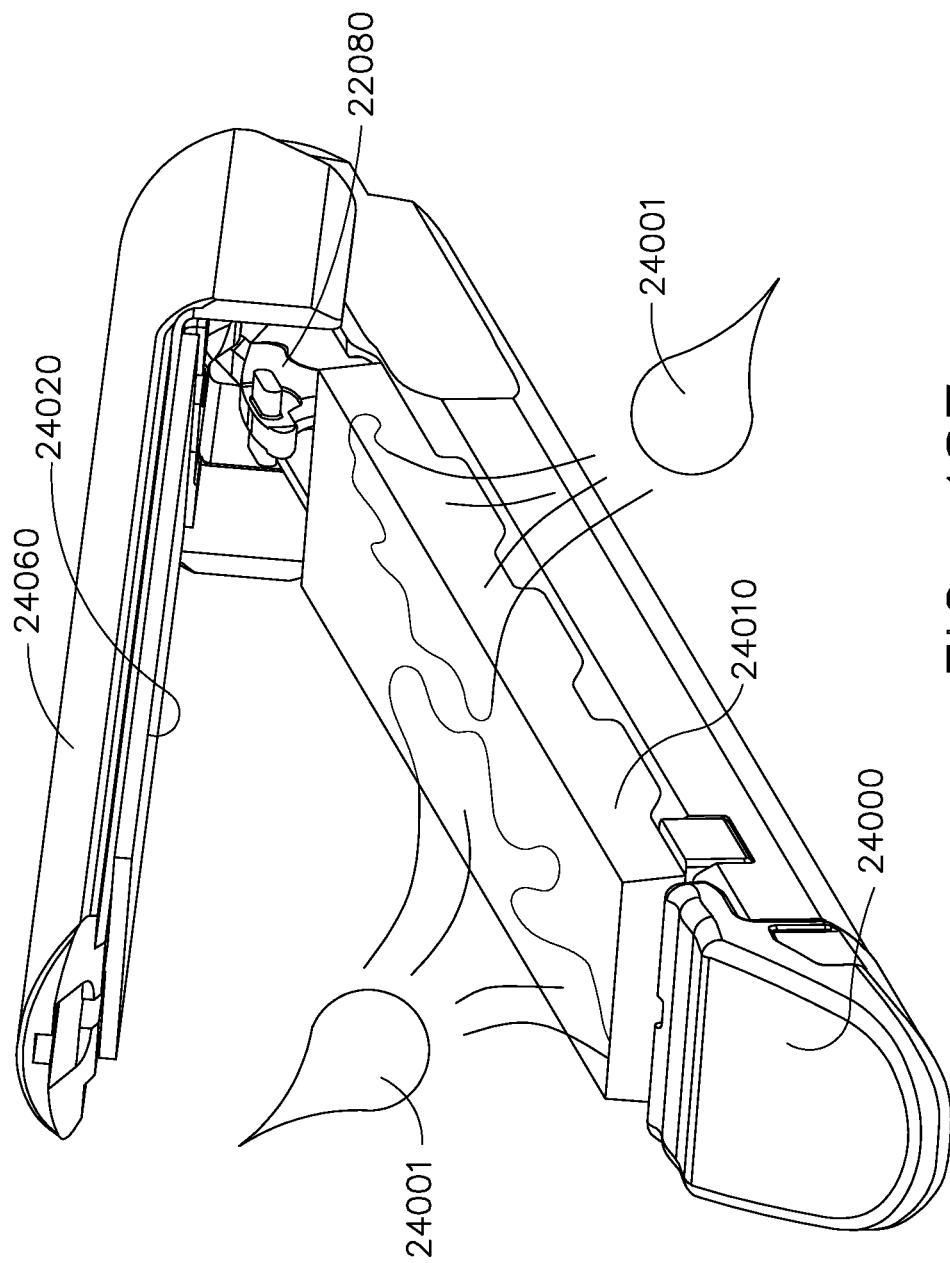
Figure 488:
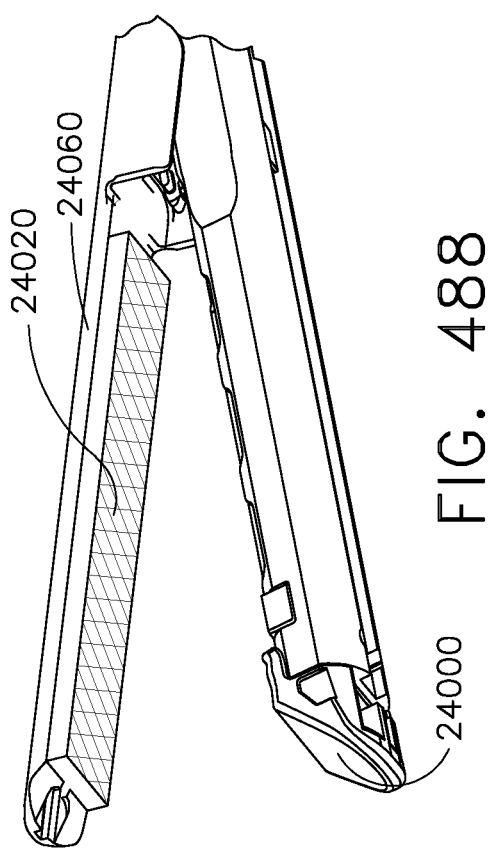
Figure 489:
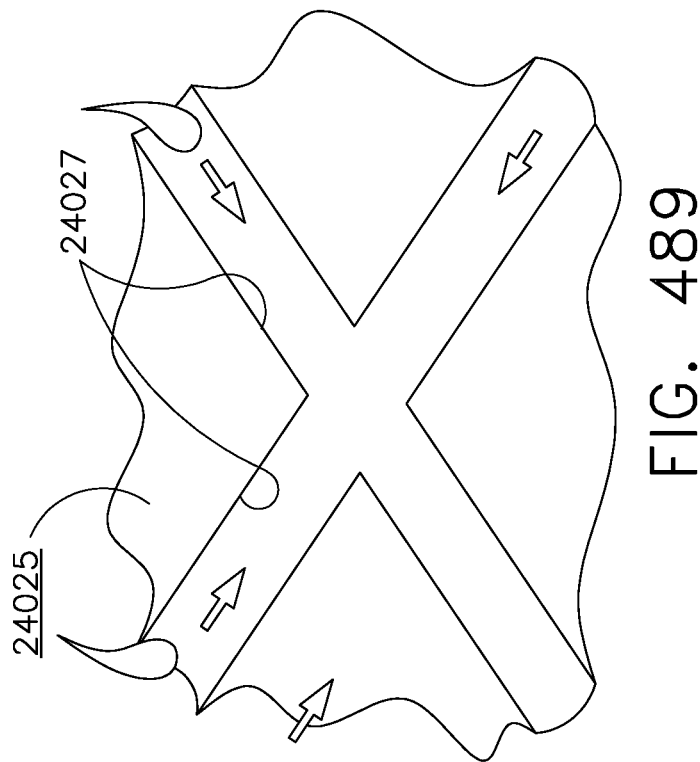
Figure 490:
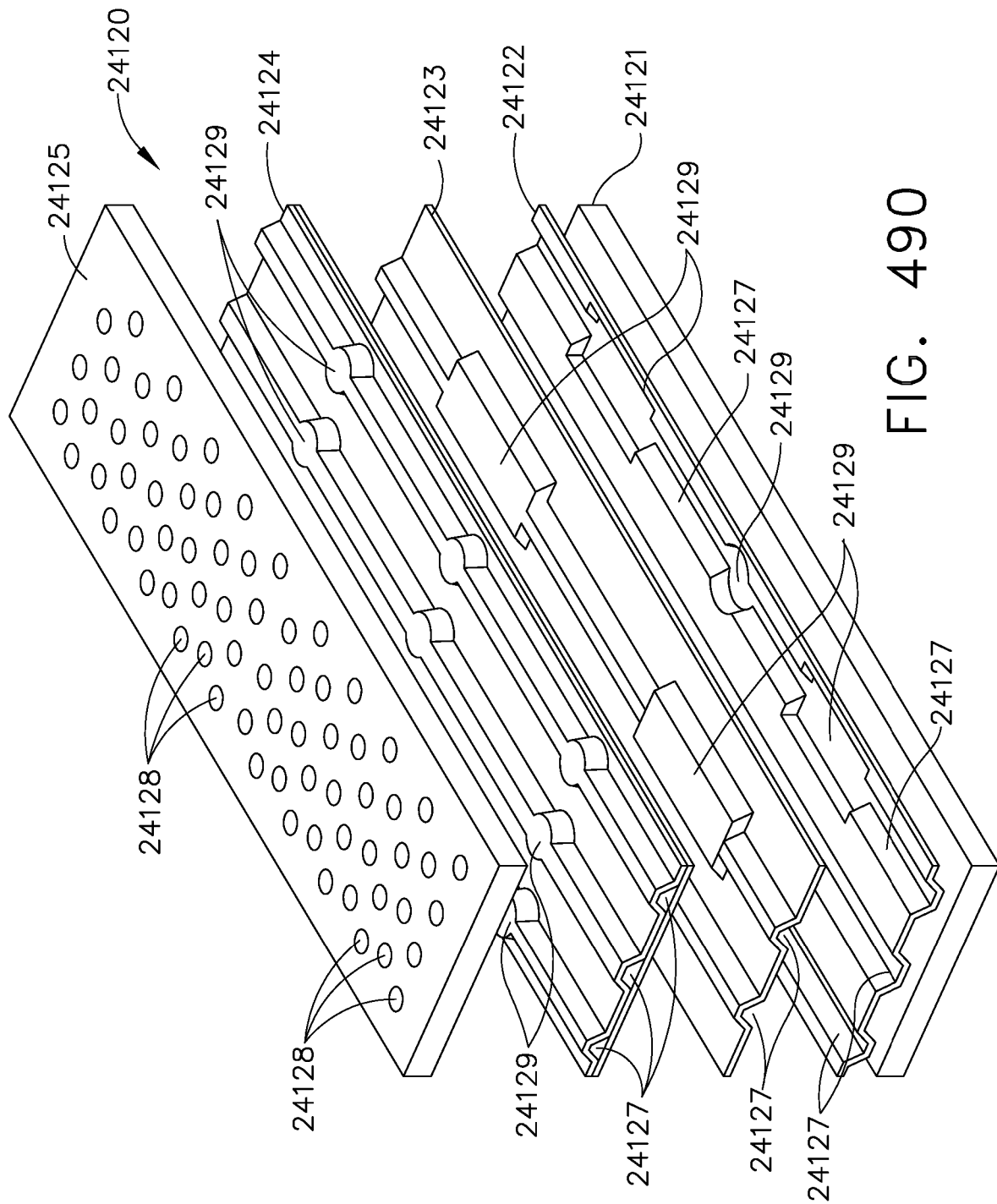
Figure 496:
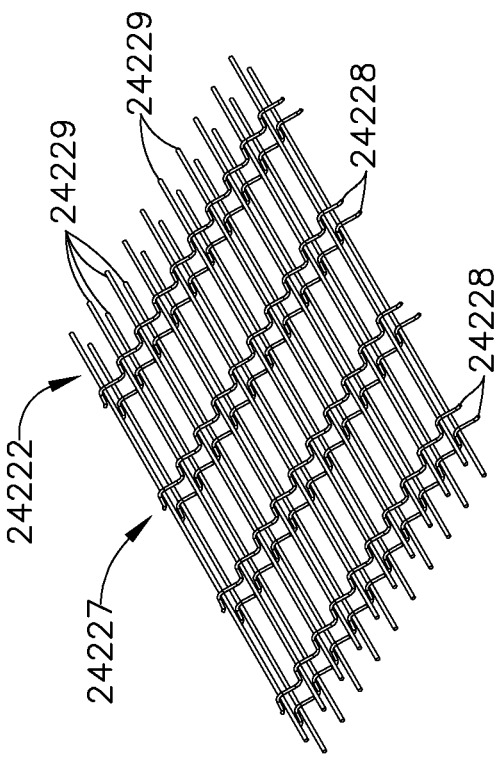
Figure 495:
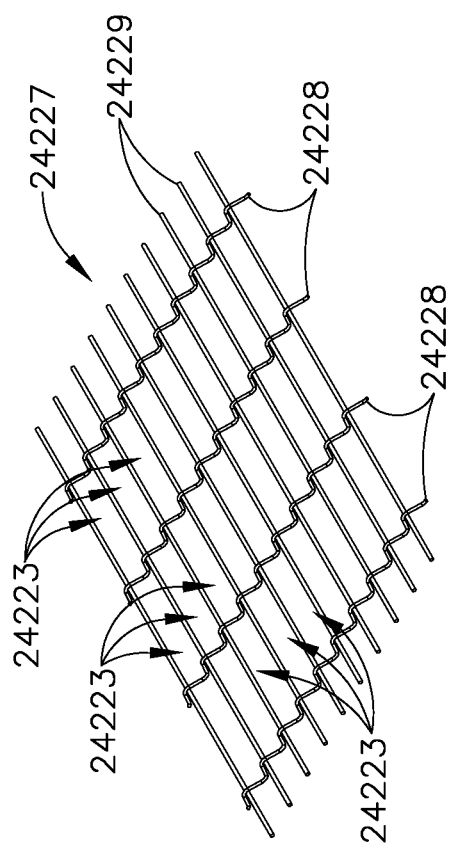
Figure 497:
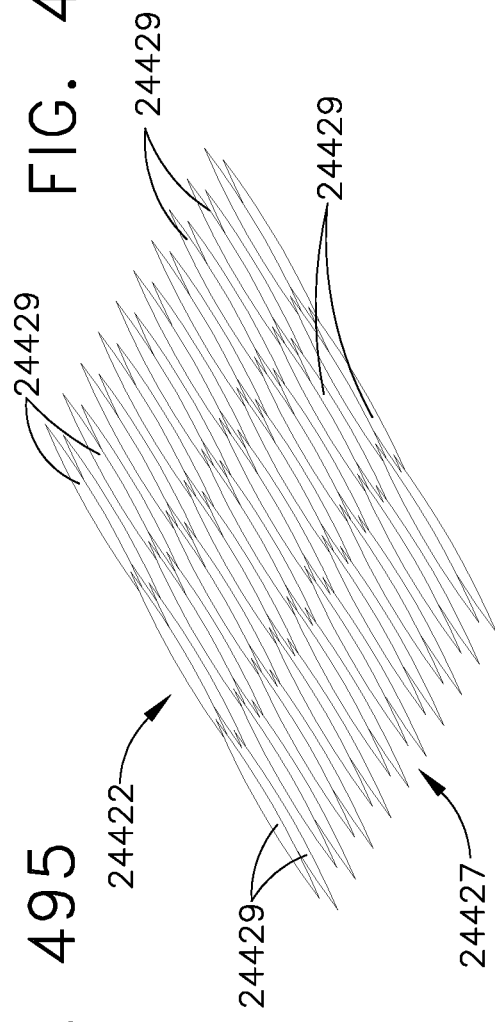
Figure 504:
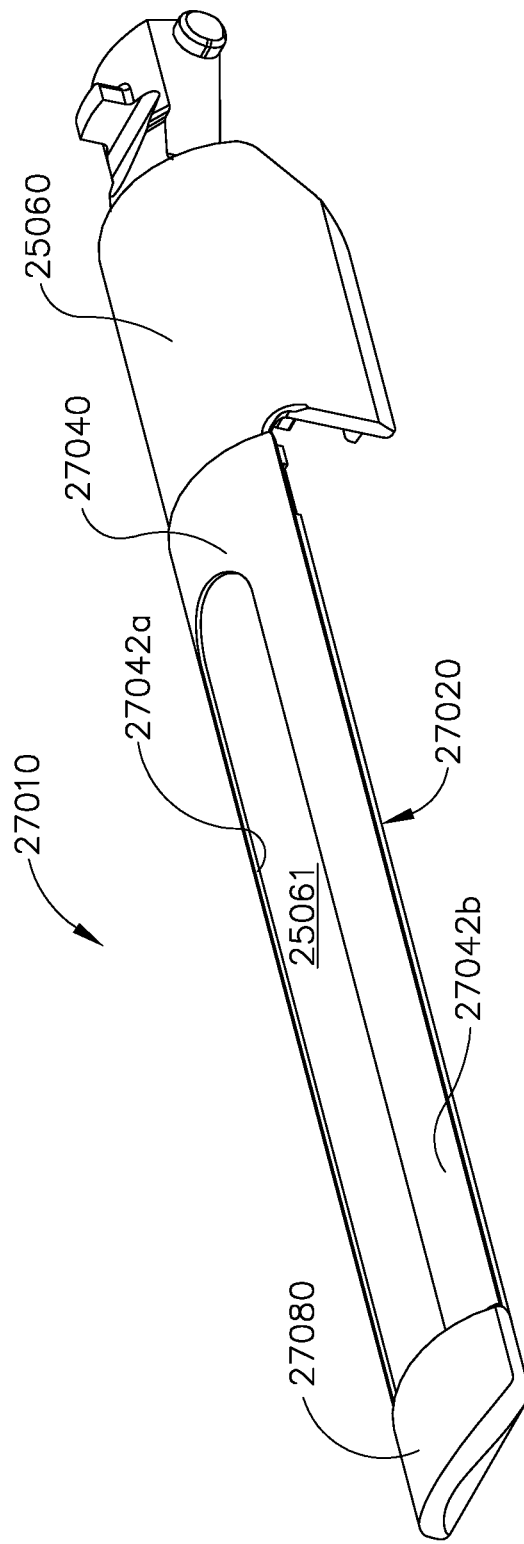
Figure 515:
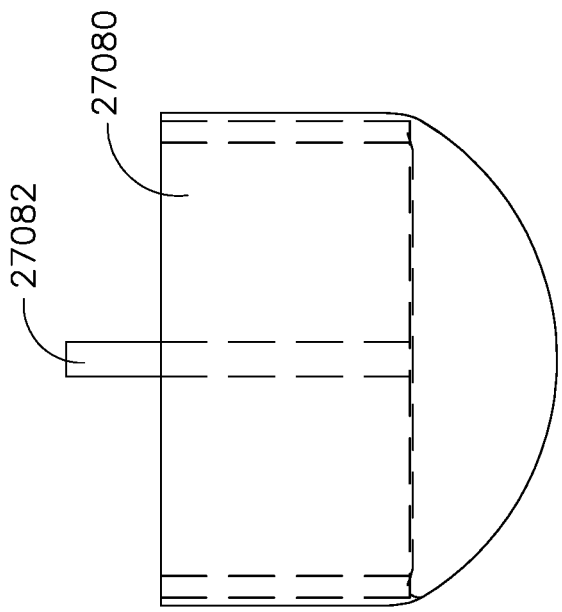
Figure 517:
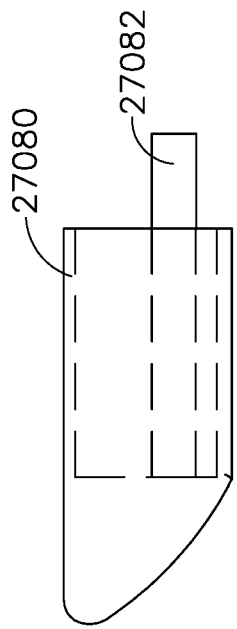
Figure 516:
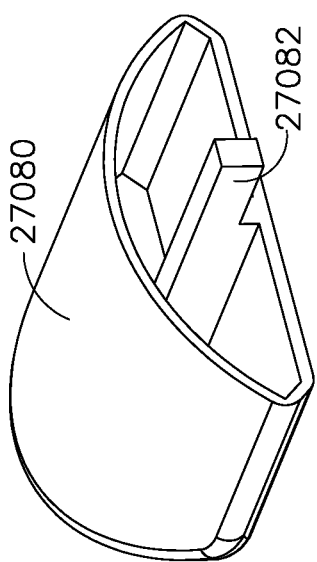
Figure 518:
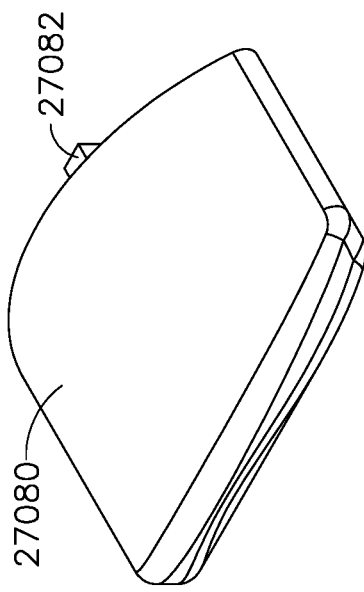
Figure 519:
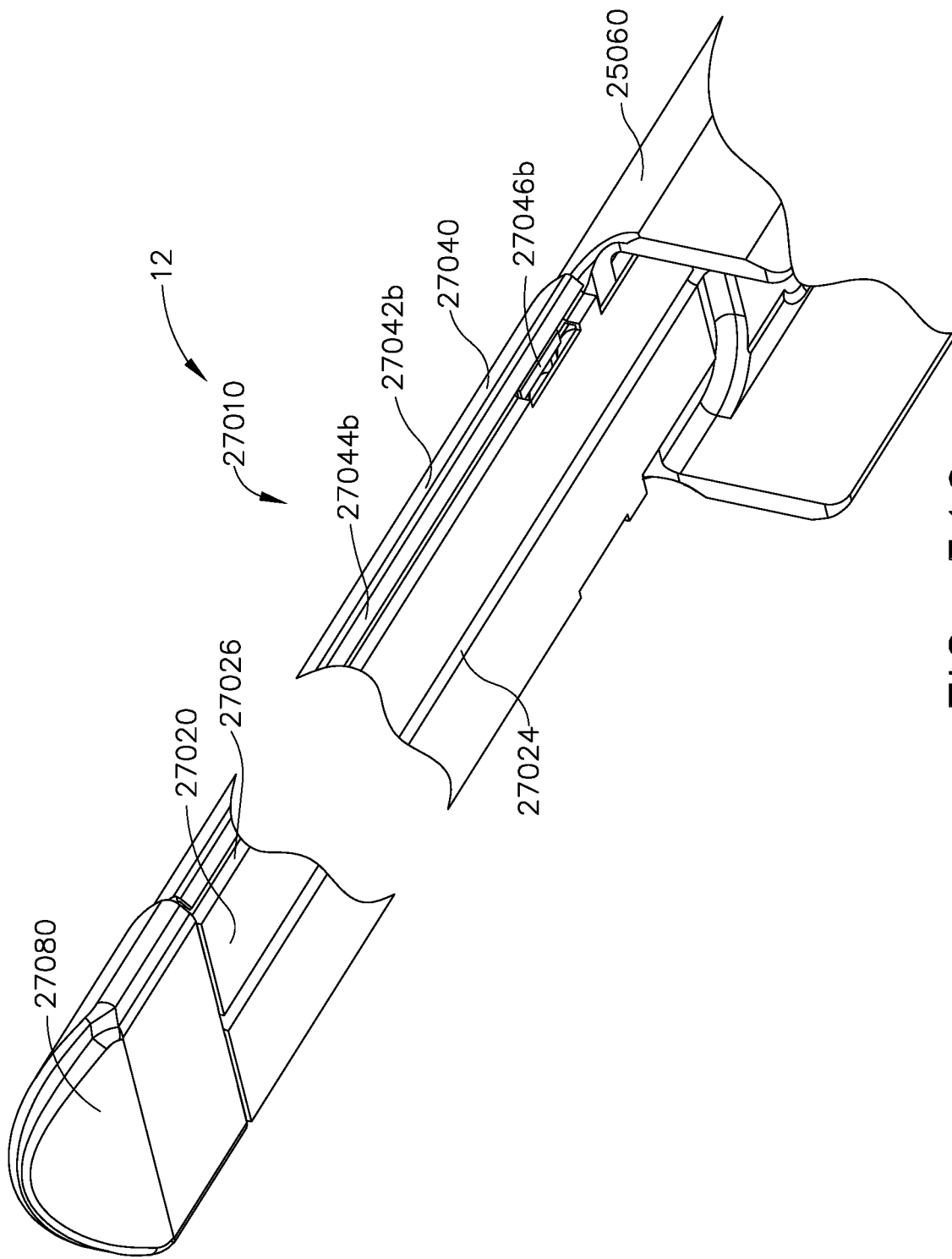
Figure 520:
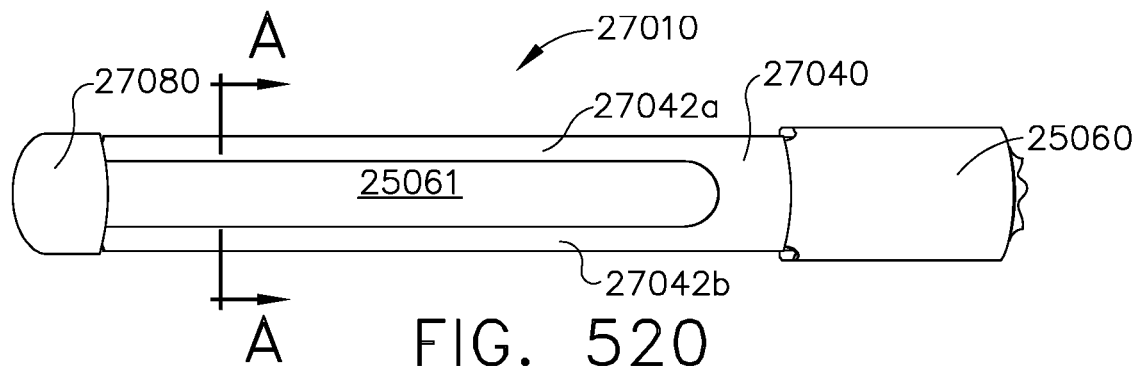
Figure 521:
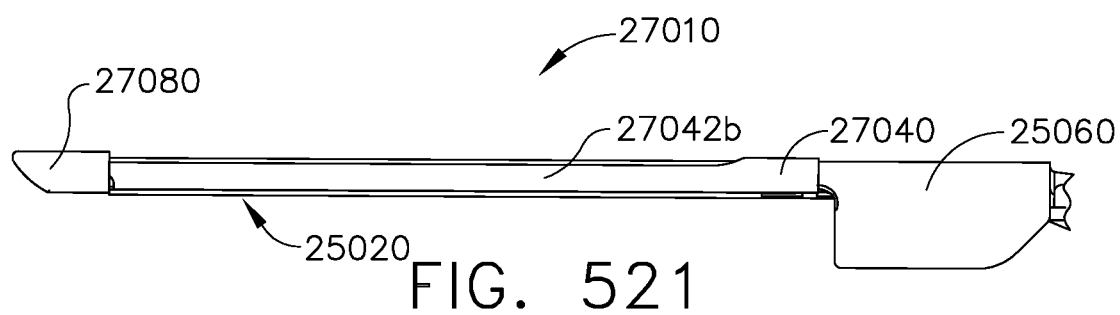
Figure 522:
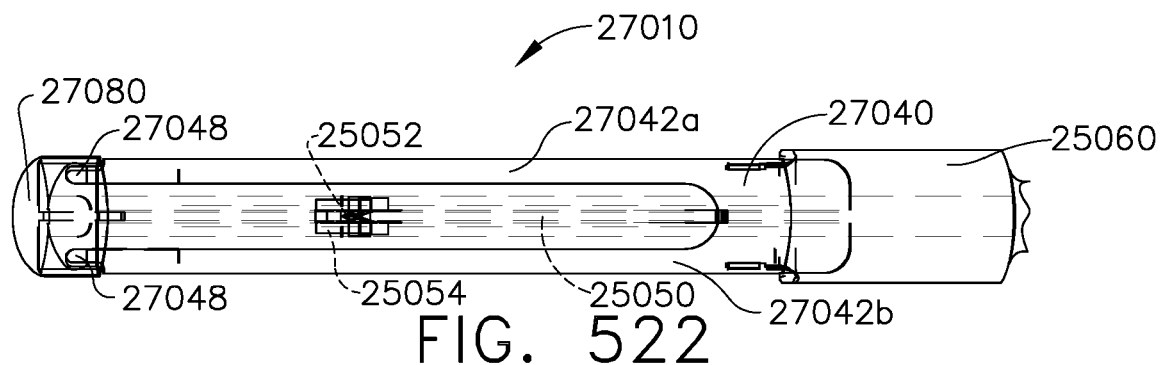
Figure 523:
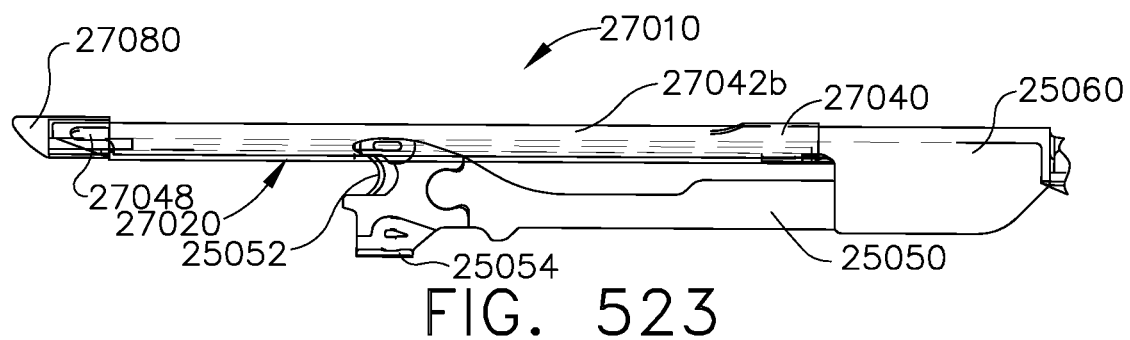
Figure 524:
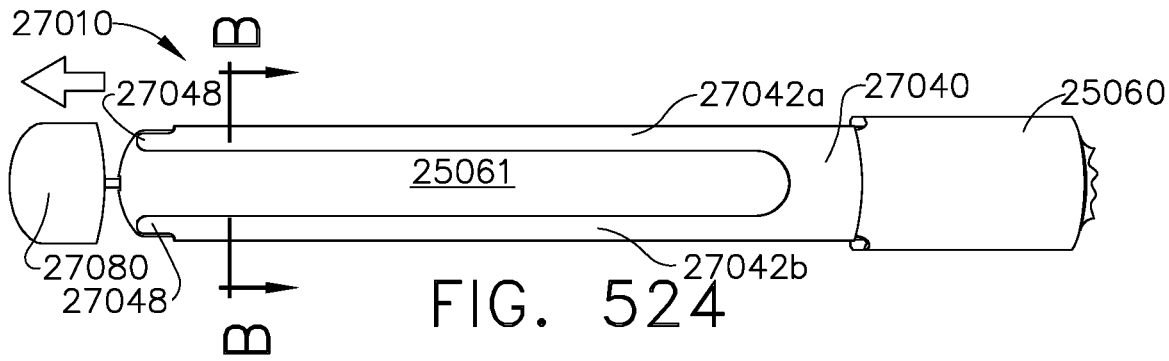
Figure 525:
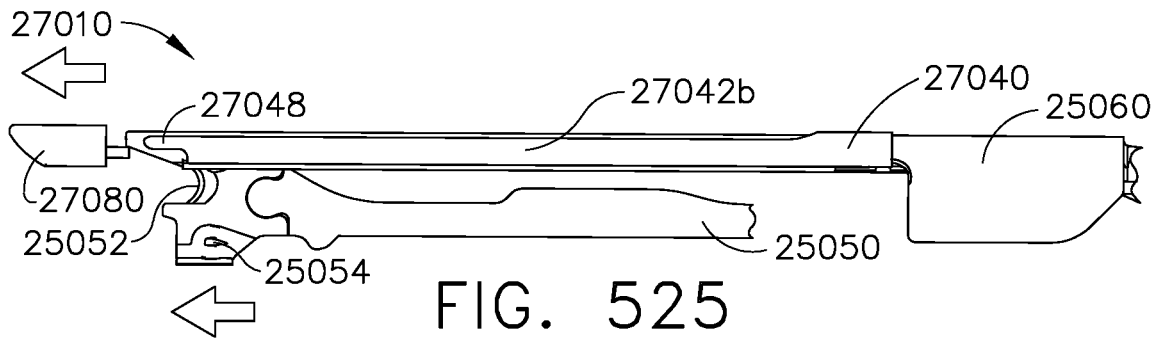
Figure 526:
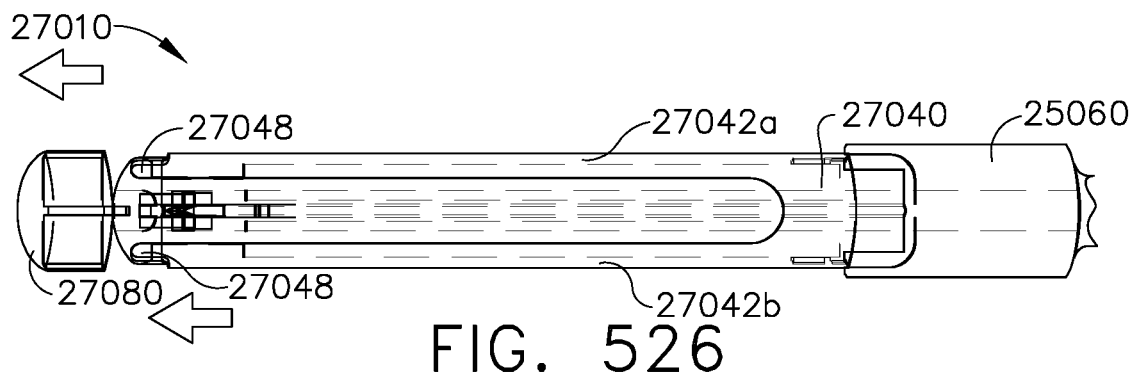
Figure 527:
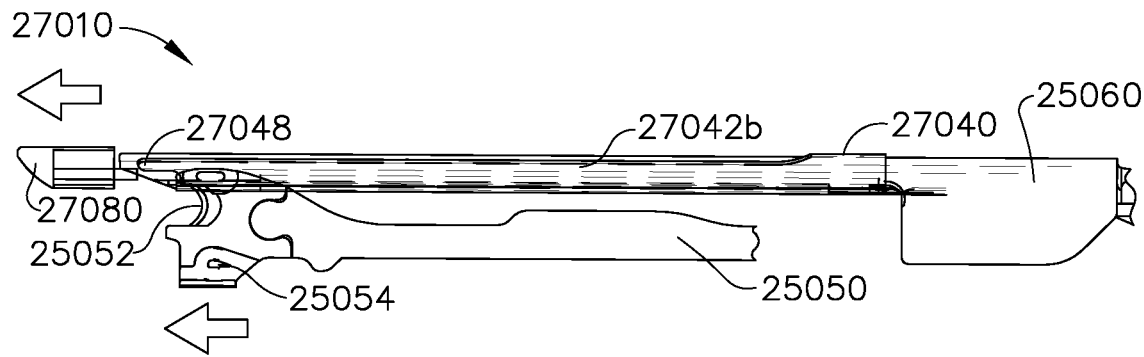
Figure 528:
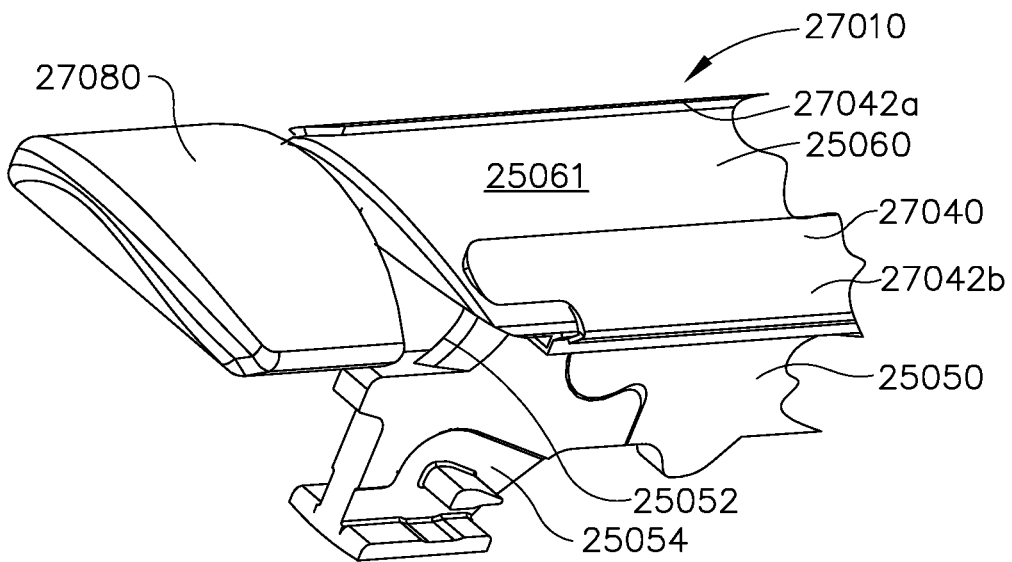
Figure 529:
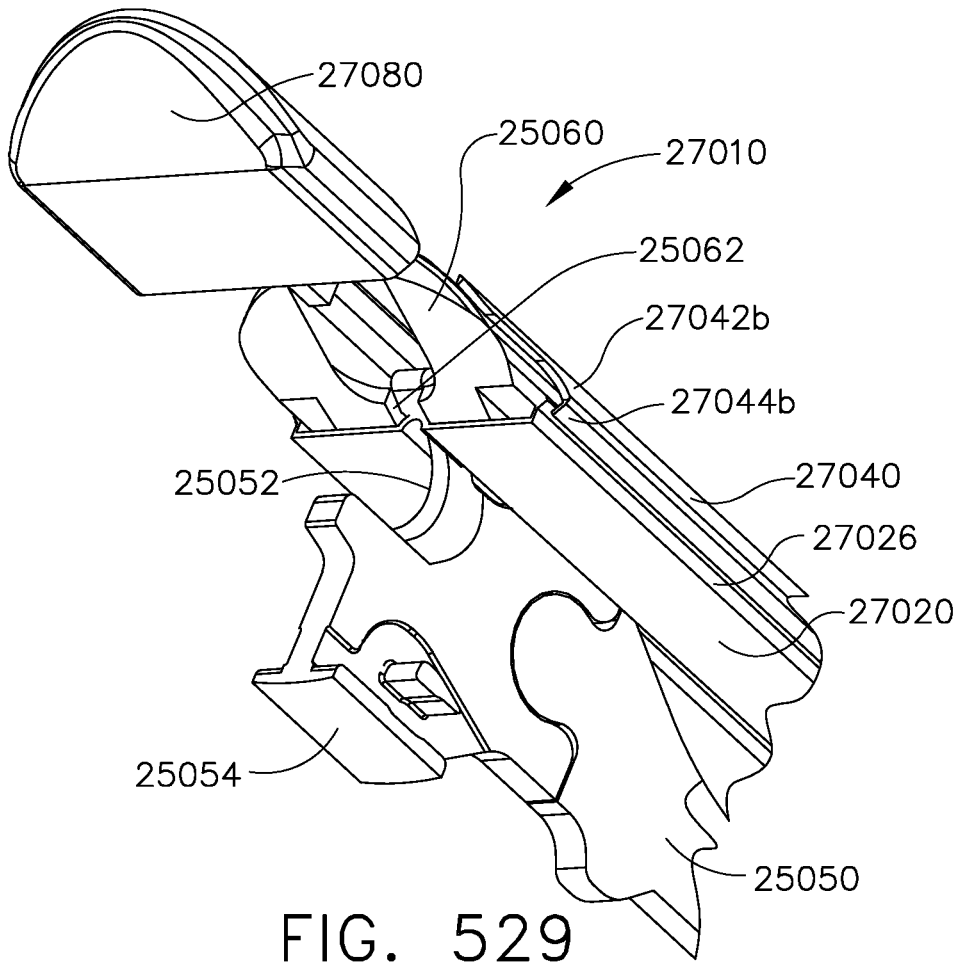
Figure 535:
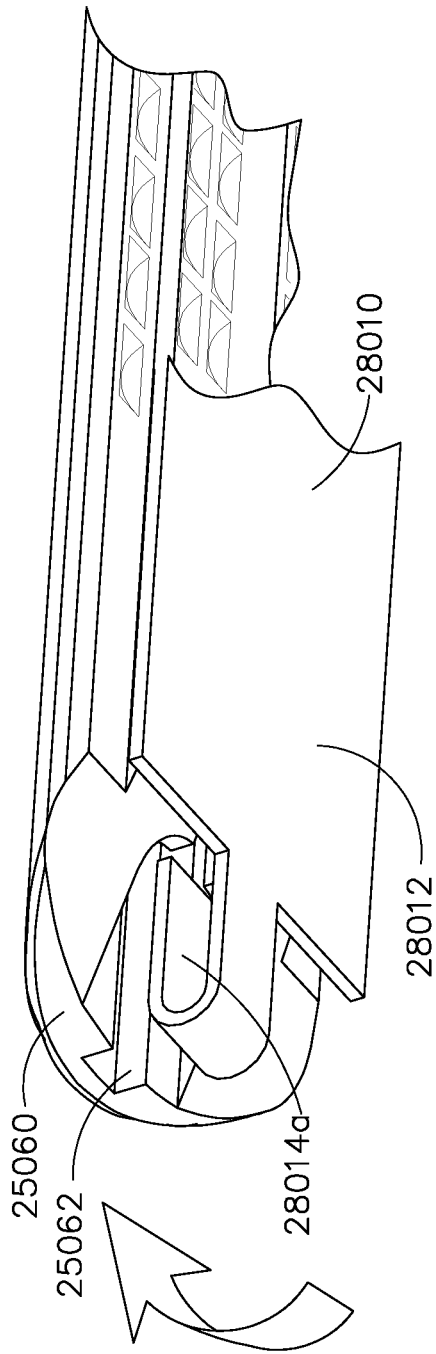
Figure 536:
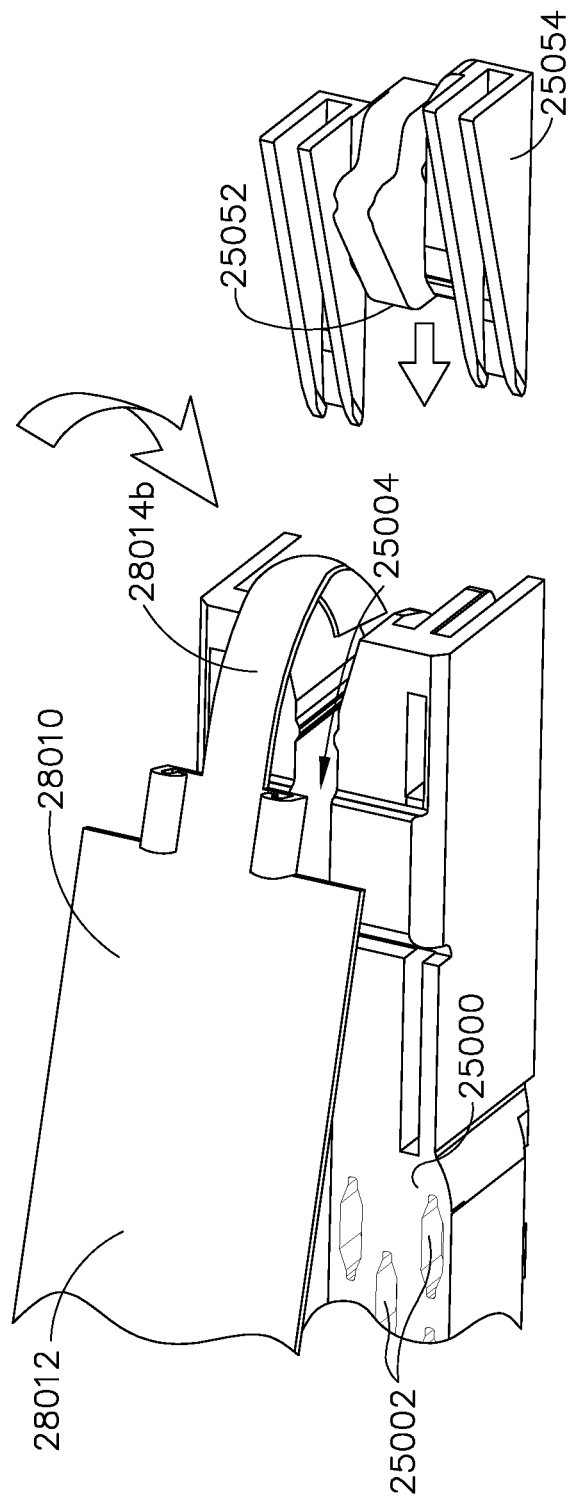
Figure 539:
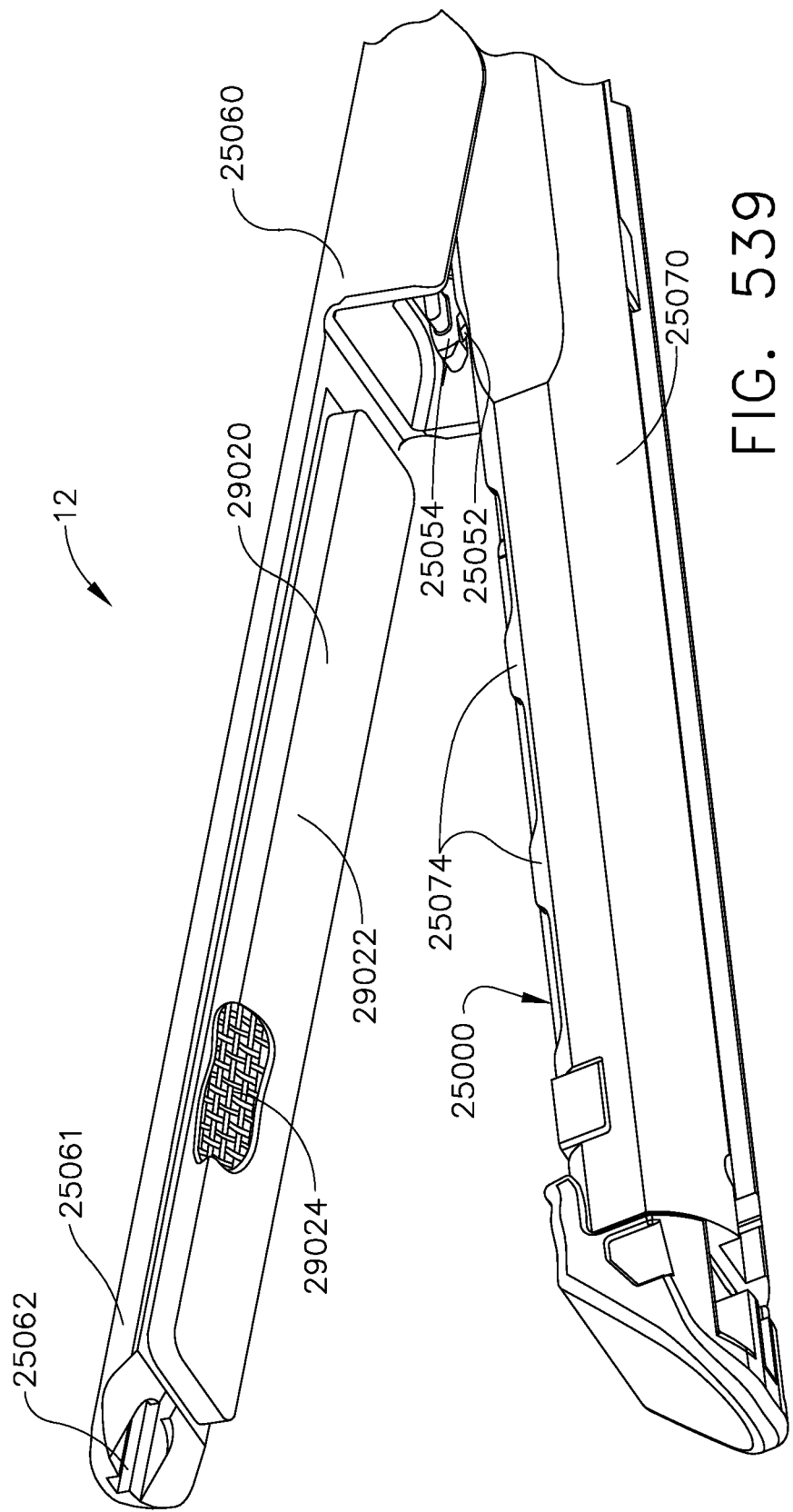
Figure 543:
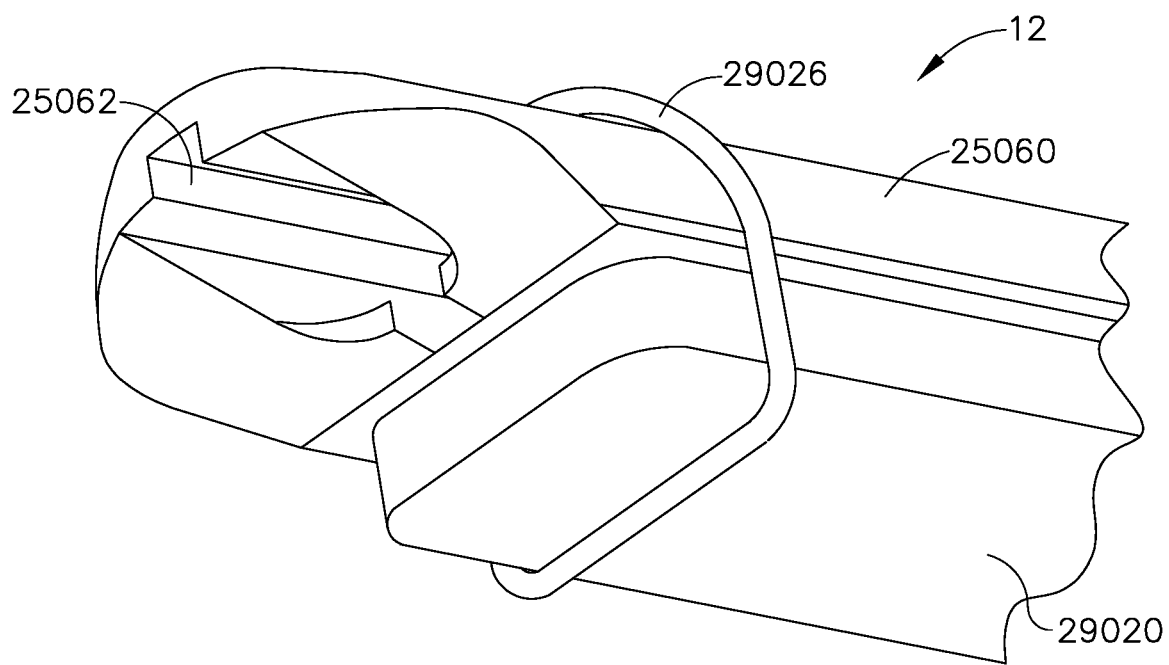
Figure 544:
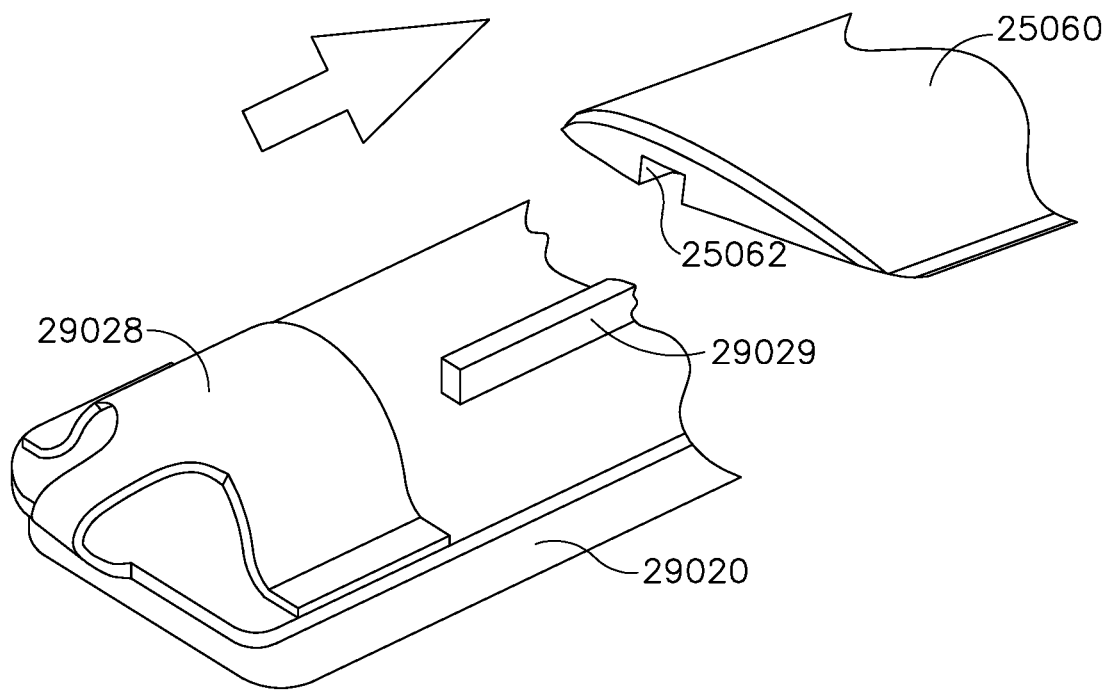
Figure 545:
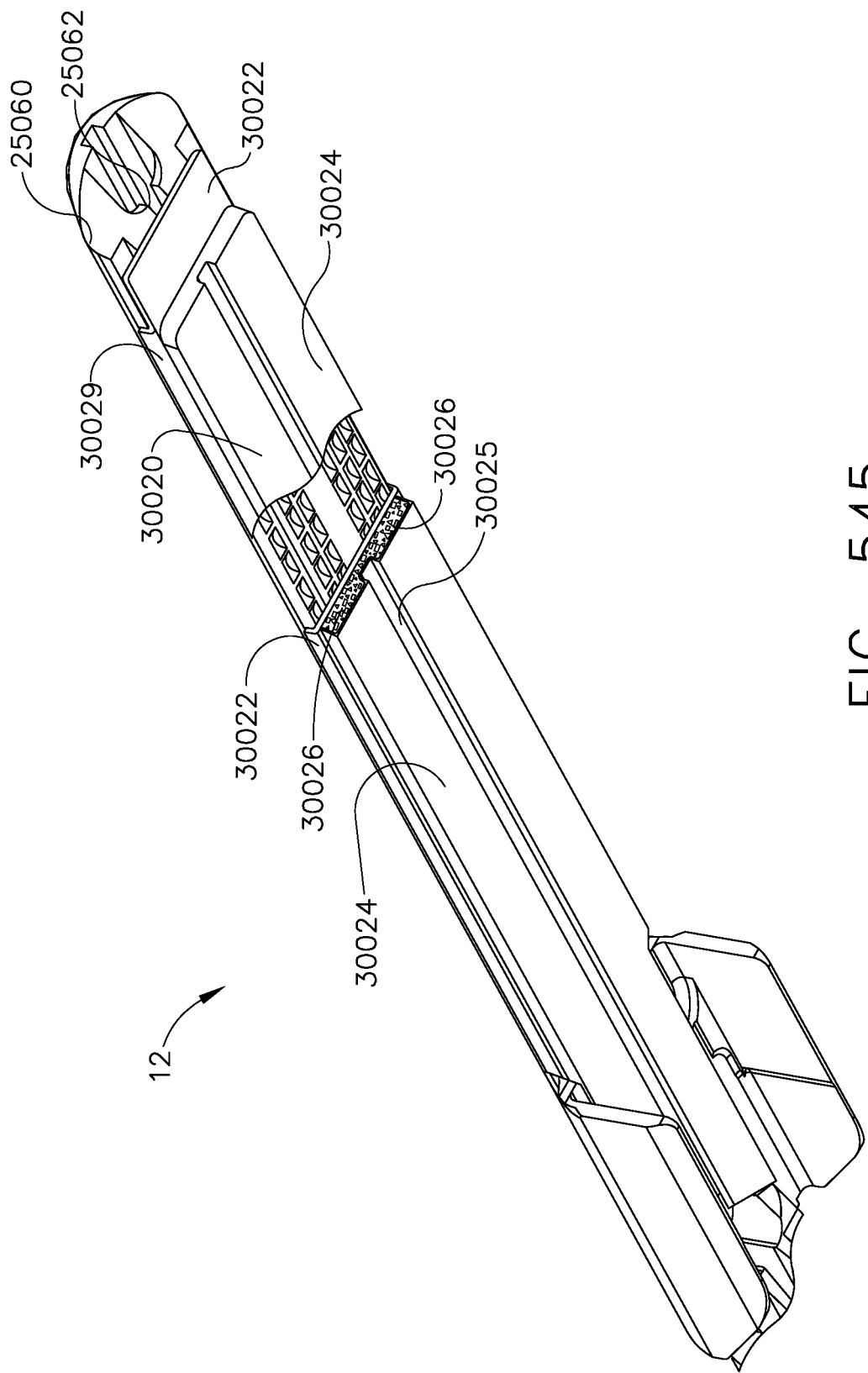
Figure 546:
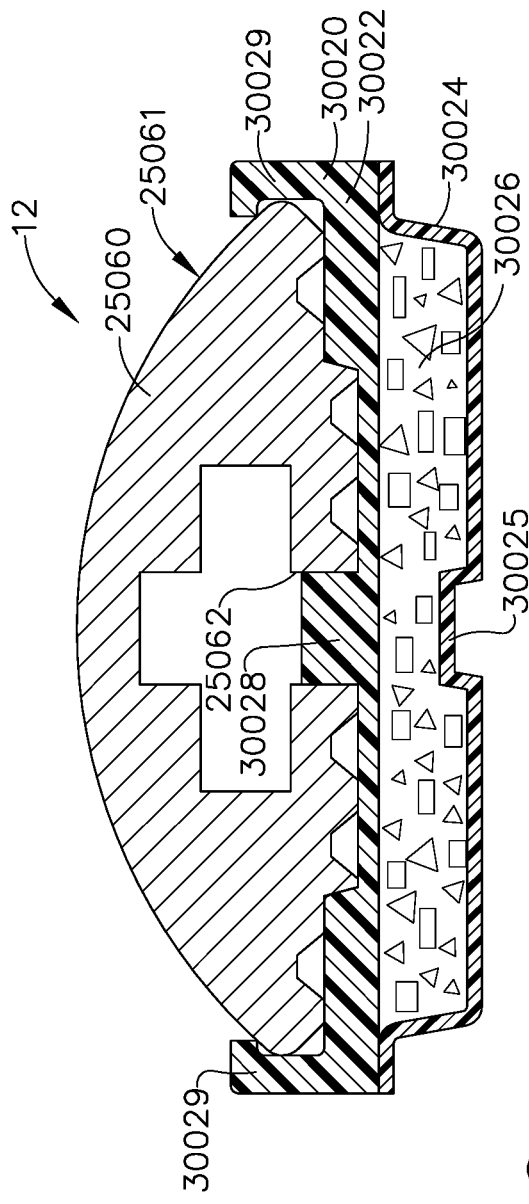
Figure 547:
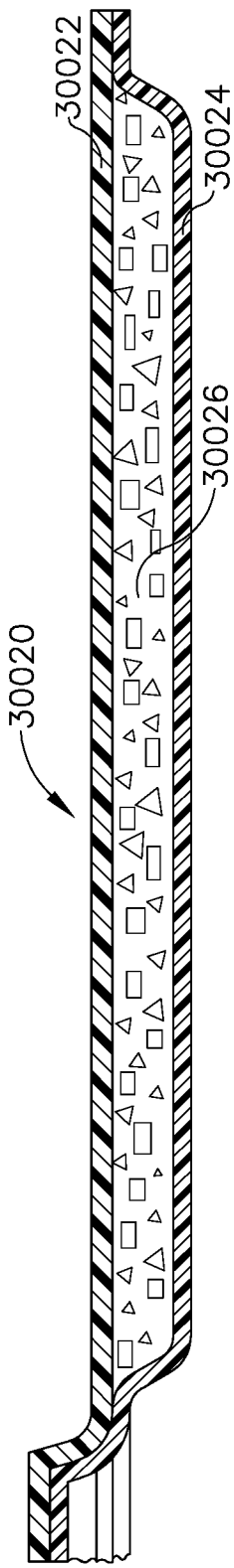
Figure 548:
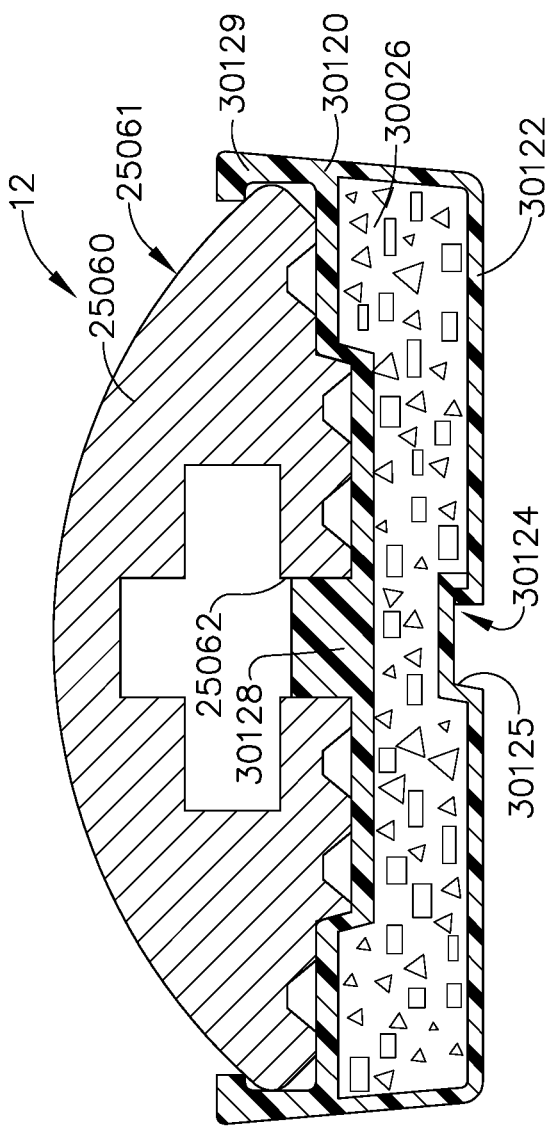
Figure 549:
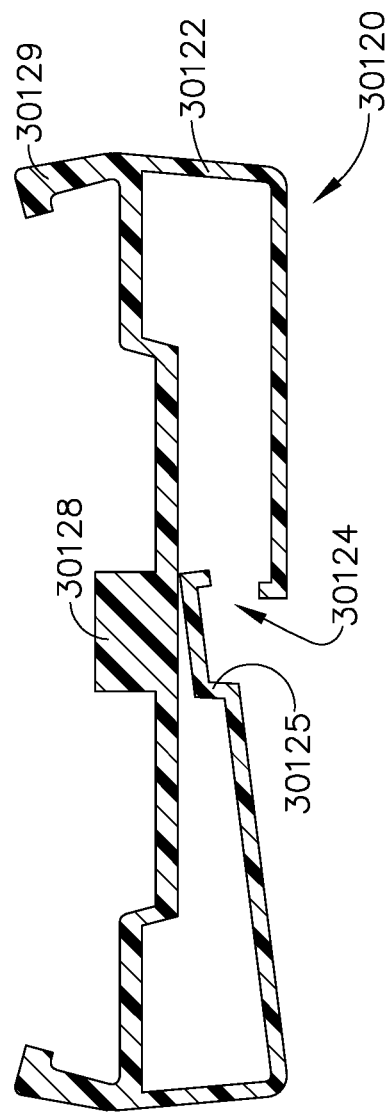
Figure 550:
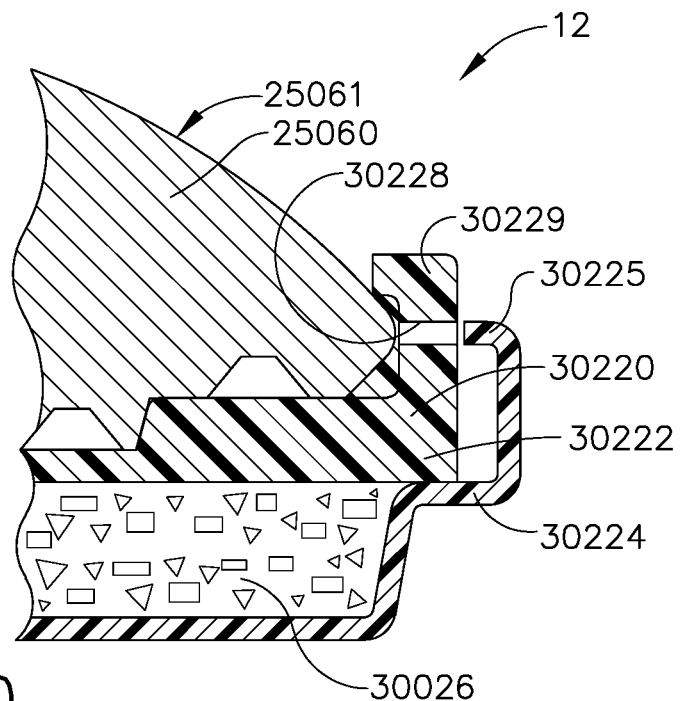
Figure 551:
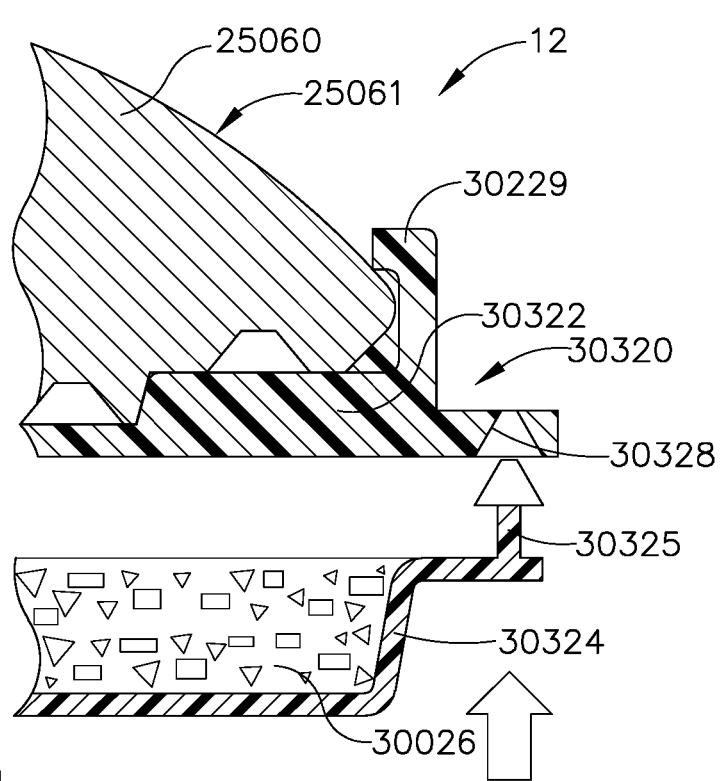
Figure 552:
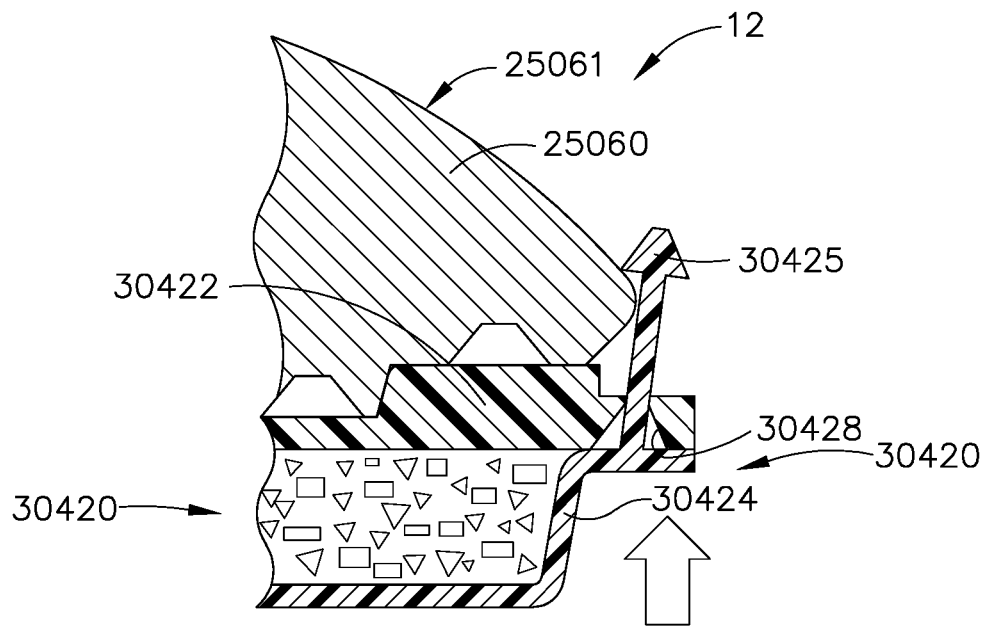
Figure 553:
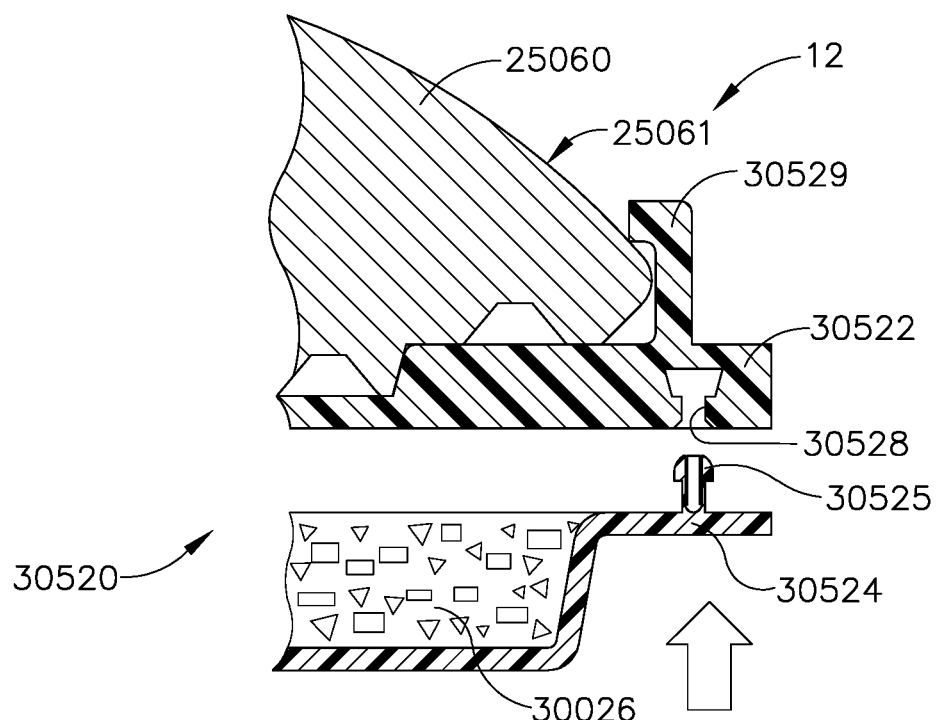
Figure 554:
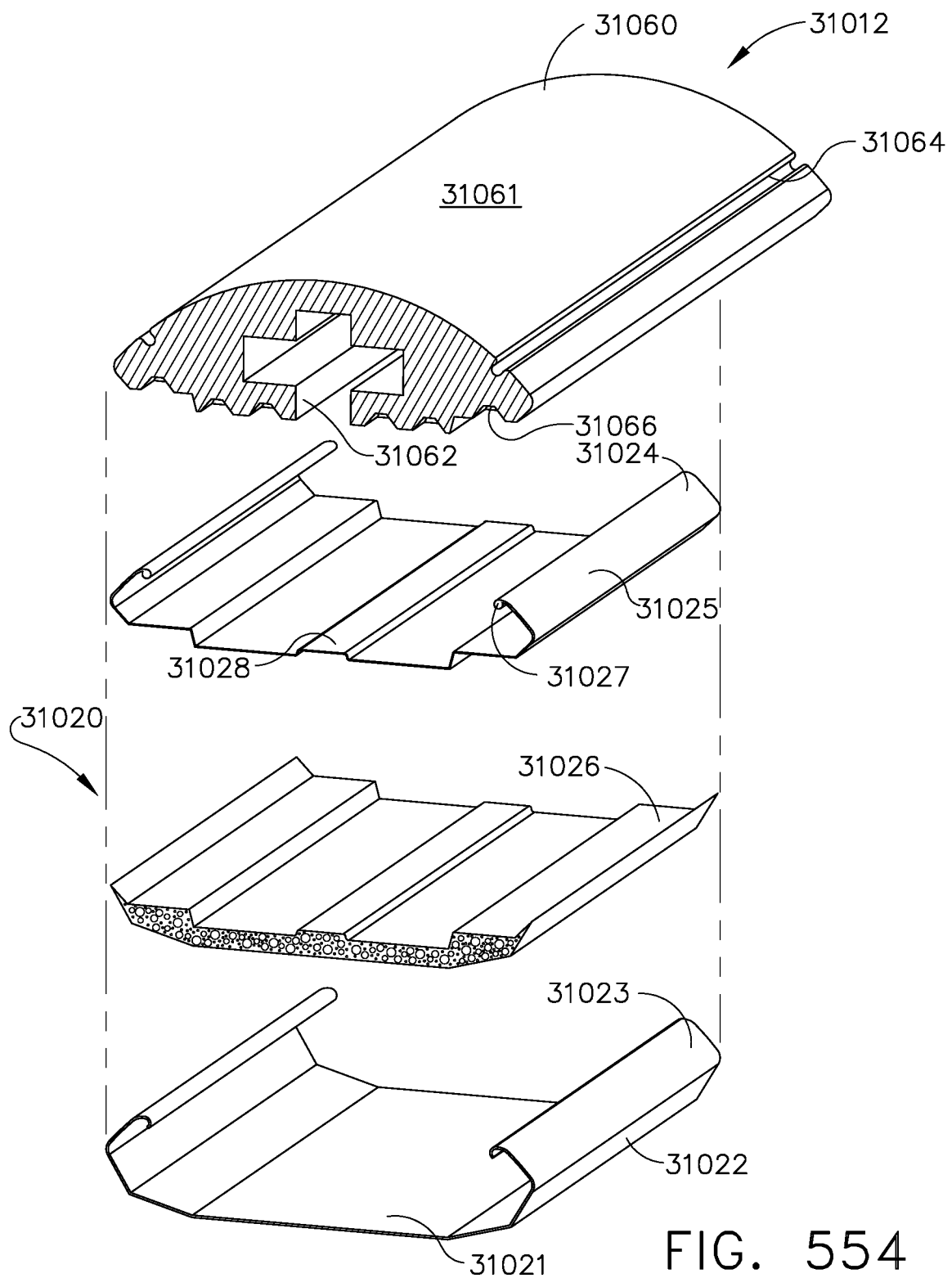
Figure 555:
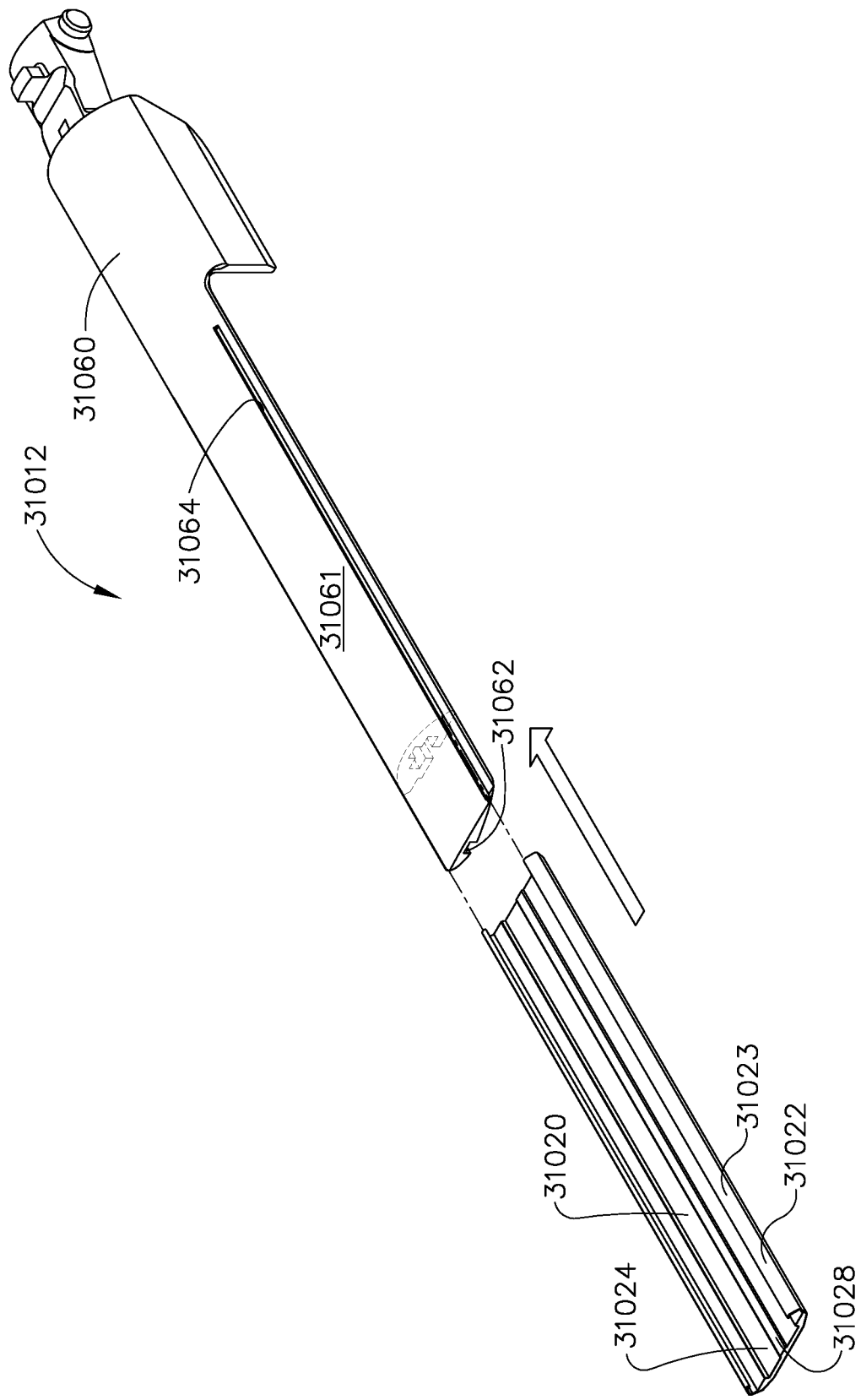
Figure 556:
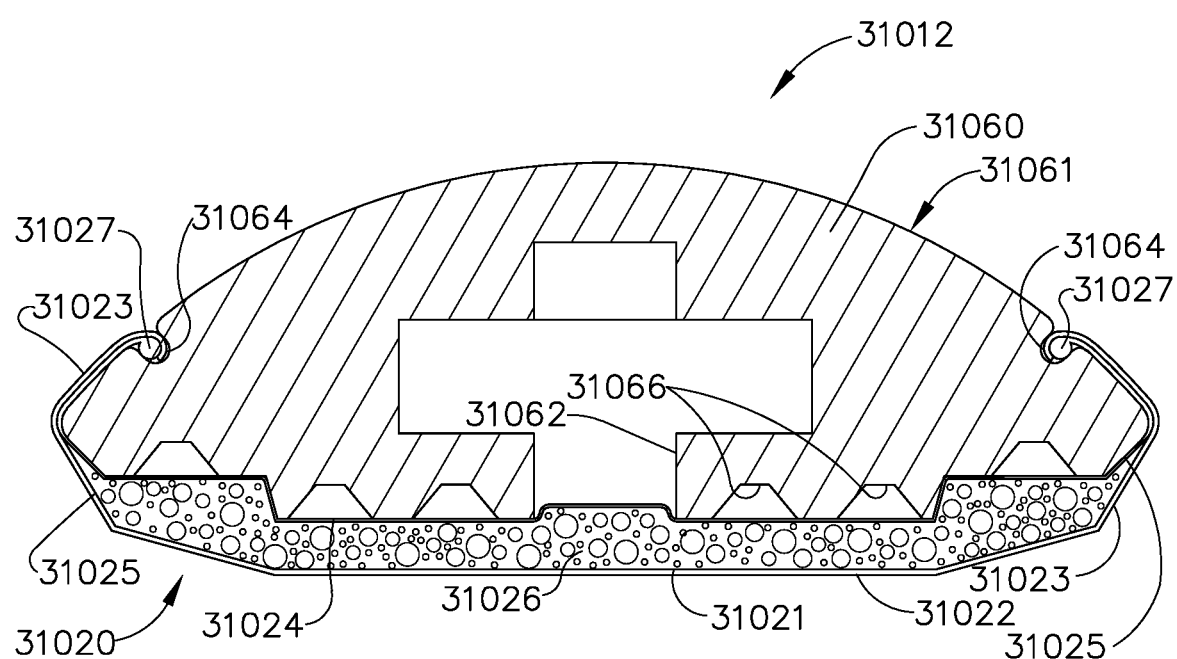
Figure 557:
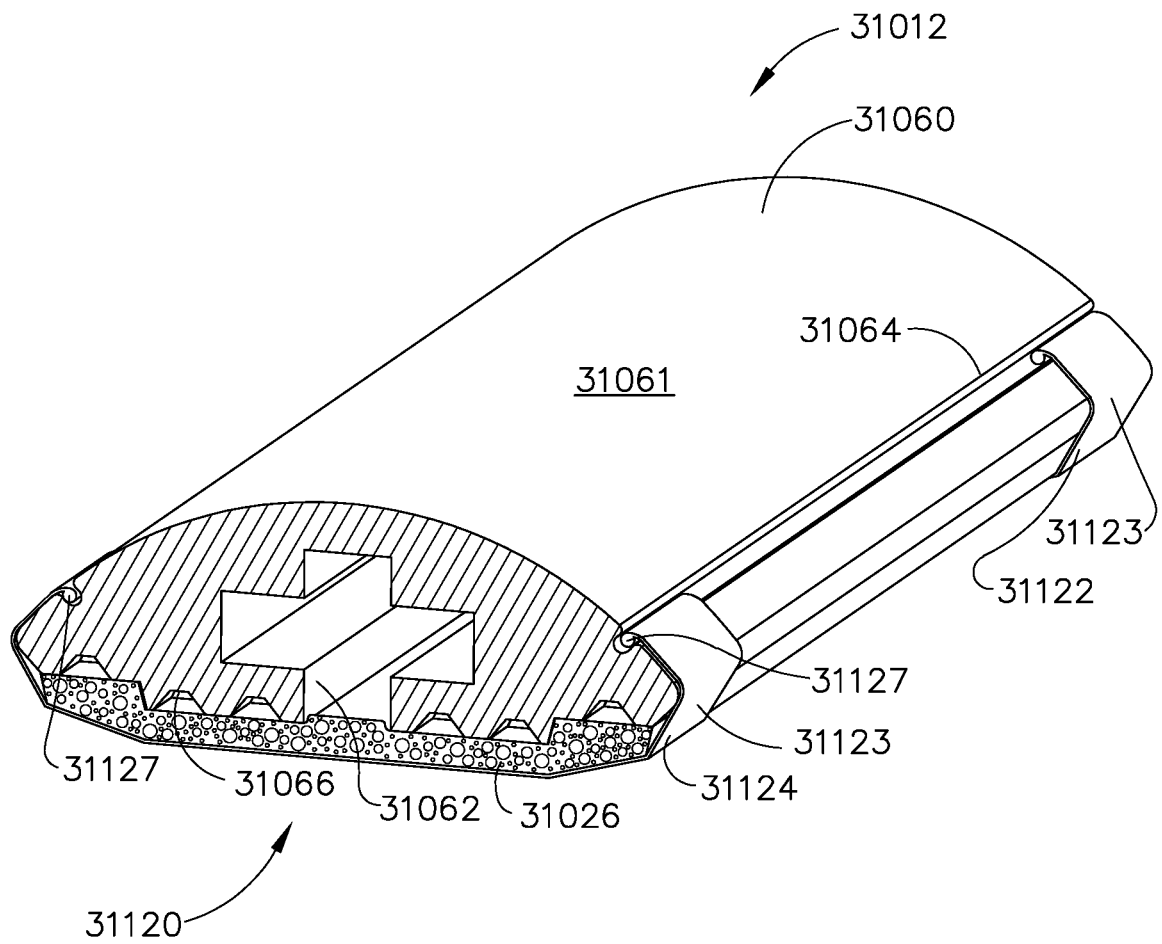
Figure 558:
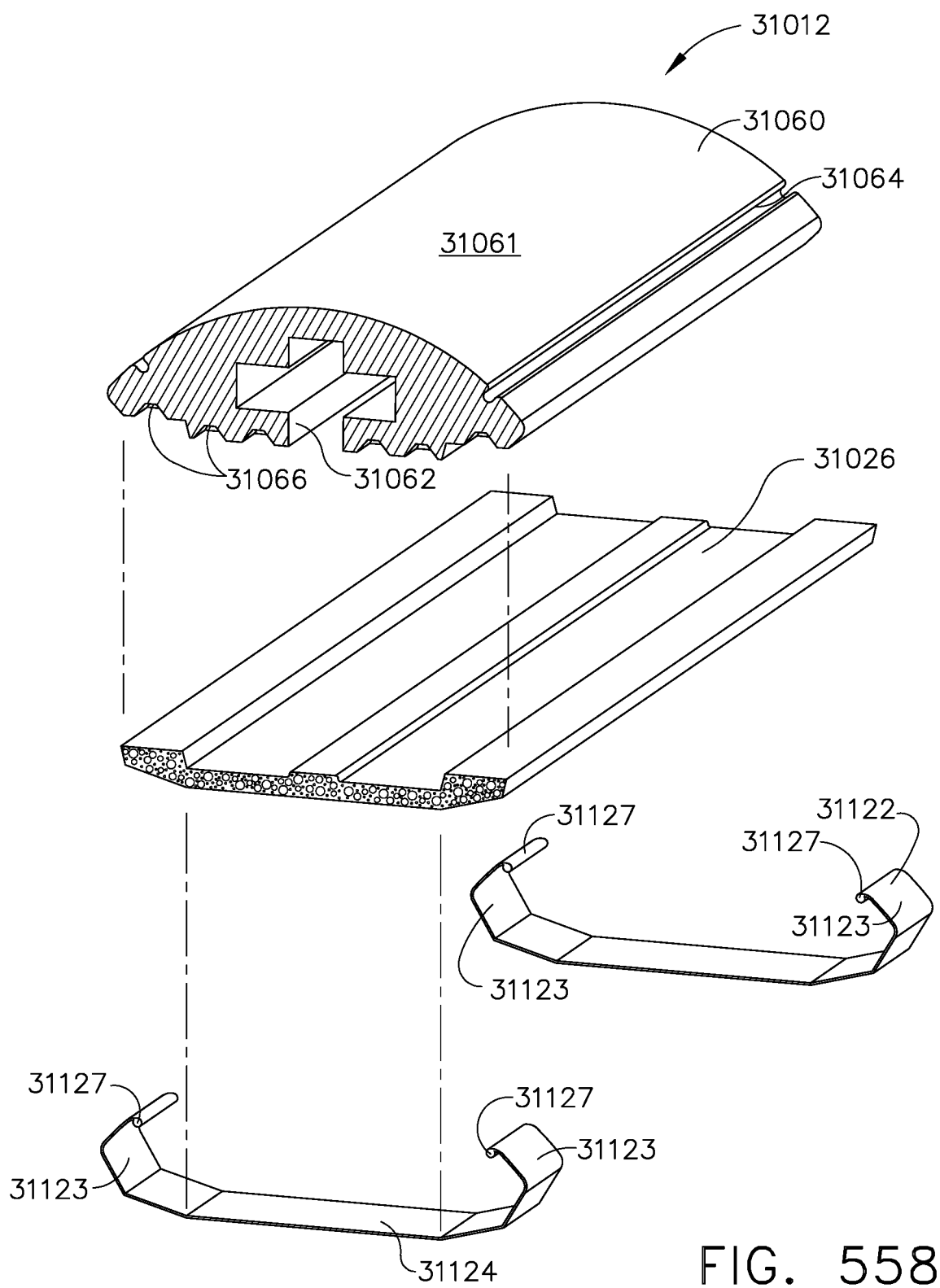
Figure 564:
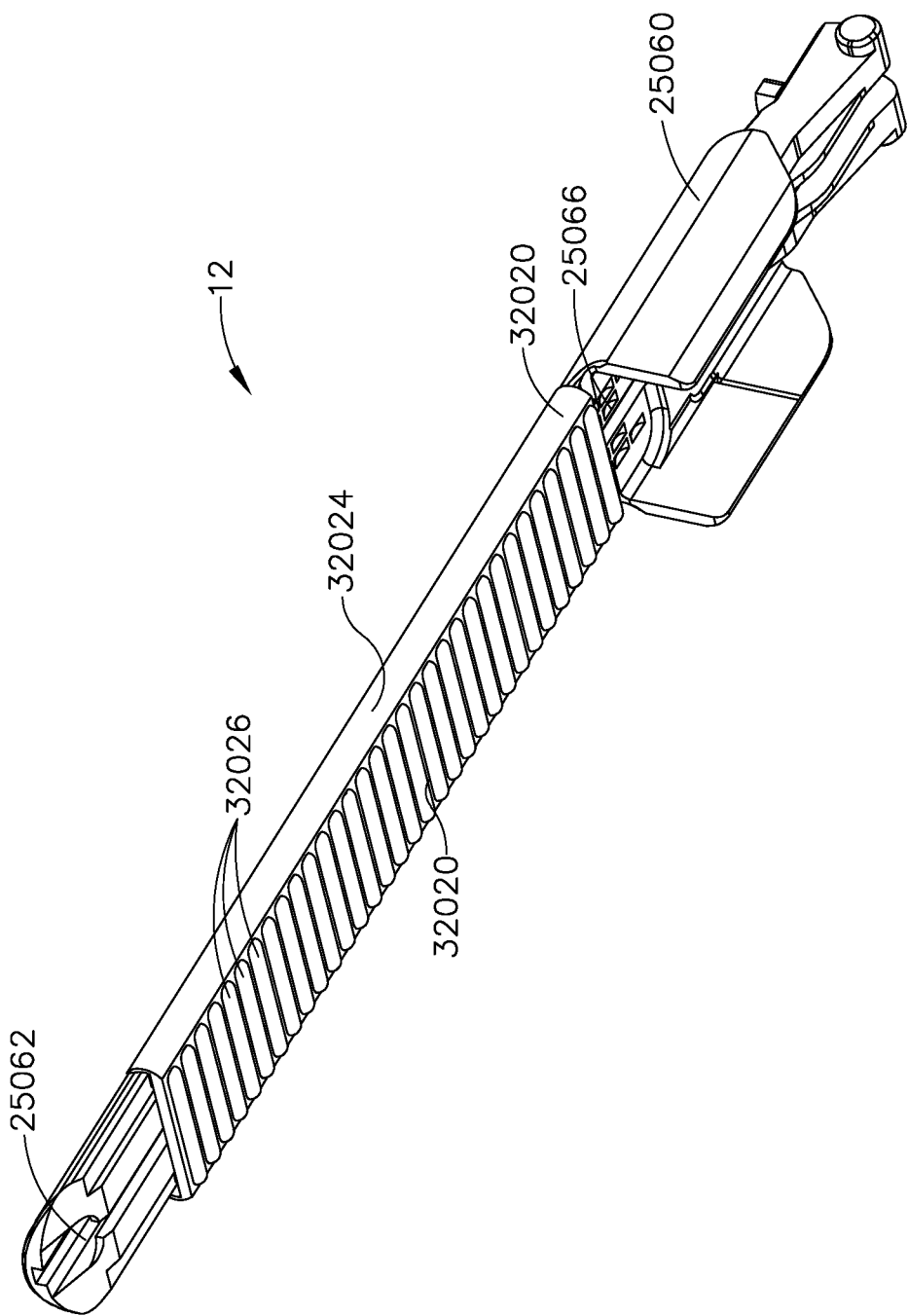
Figure 565:
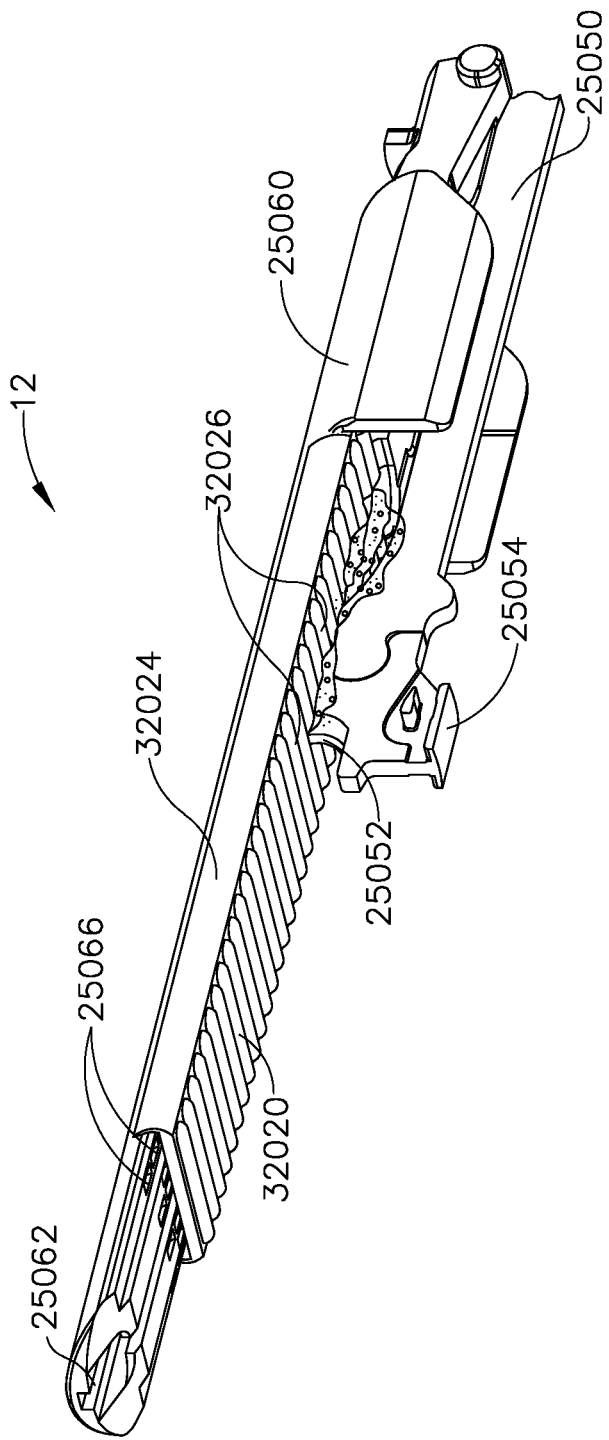
Figure 566:
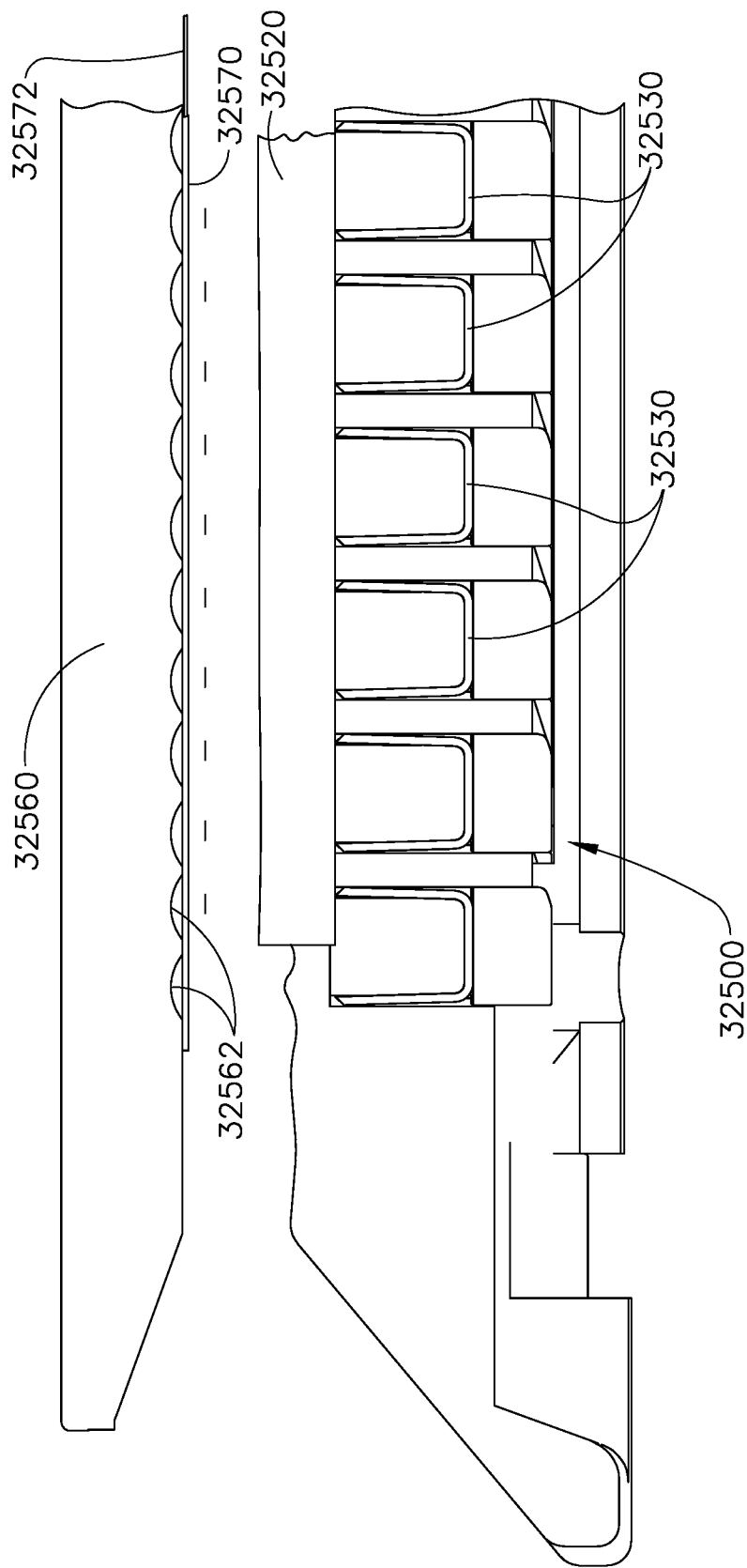
Figure 567:
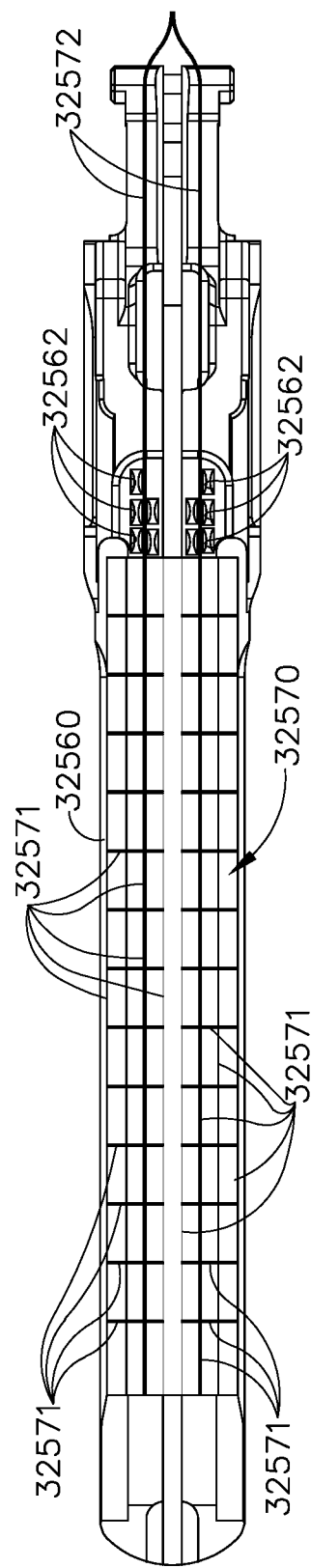
Figure 568:
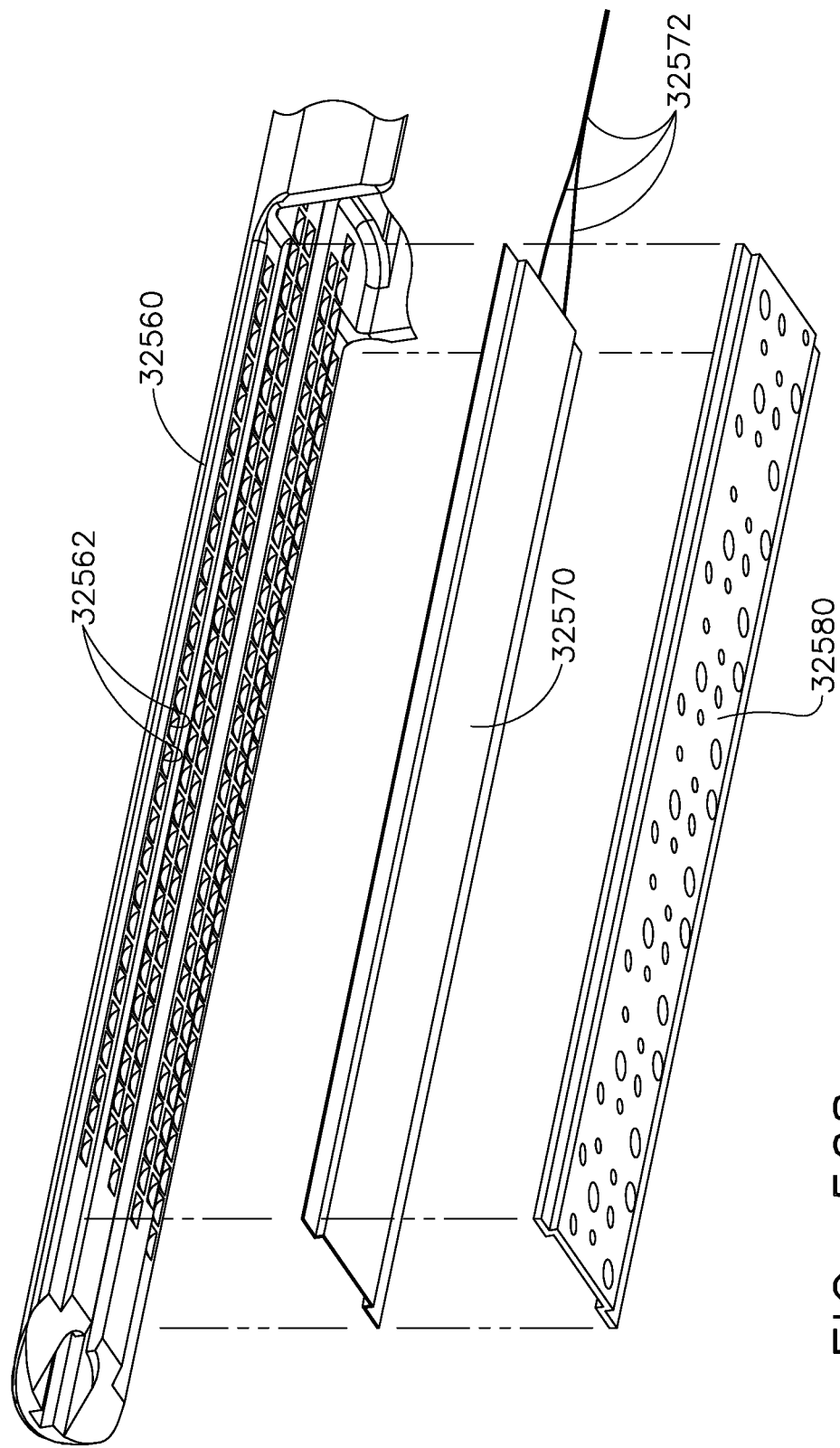
Figure 569A:
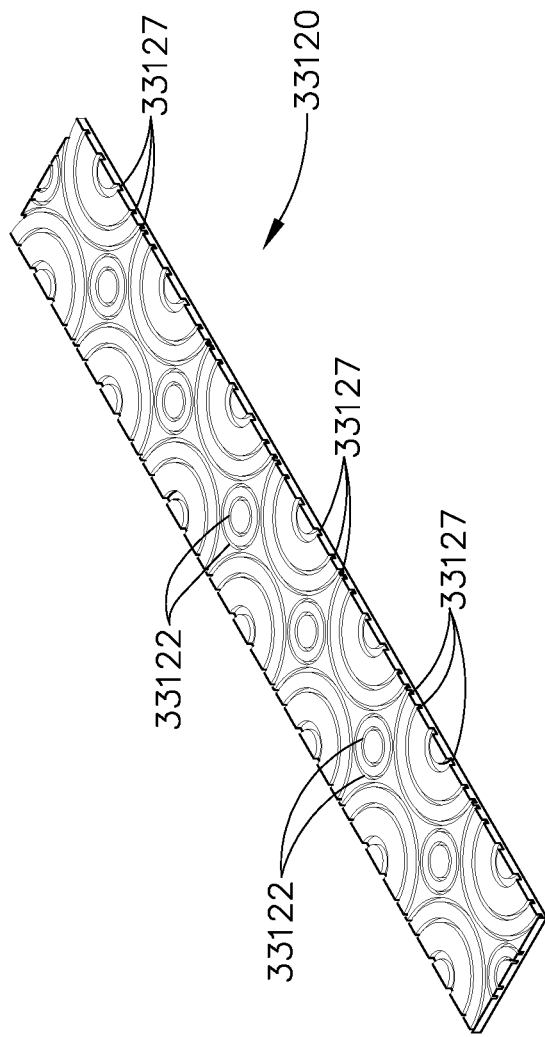
Figure 570A:
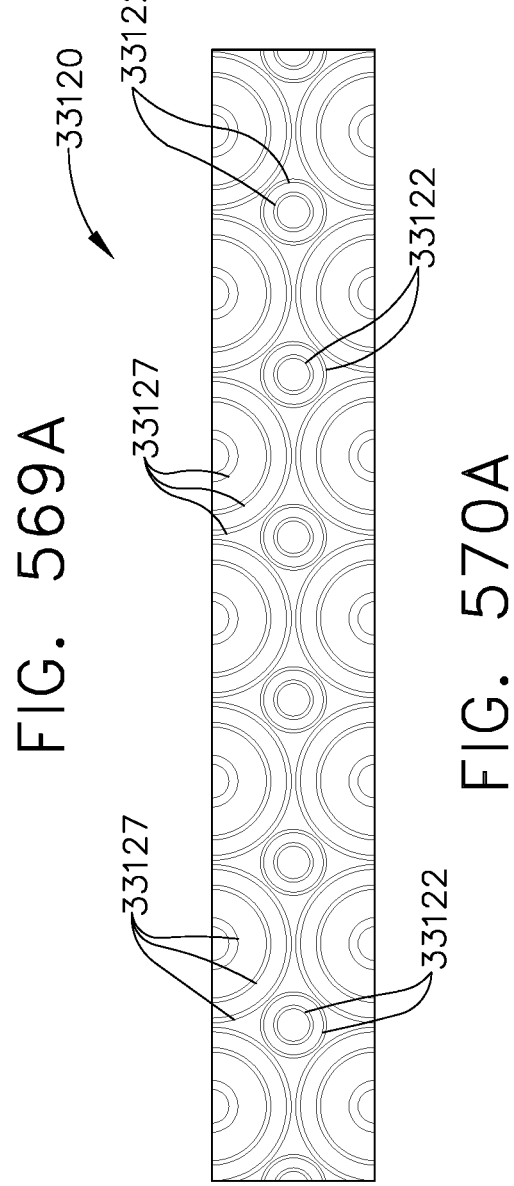
Figure 571:
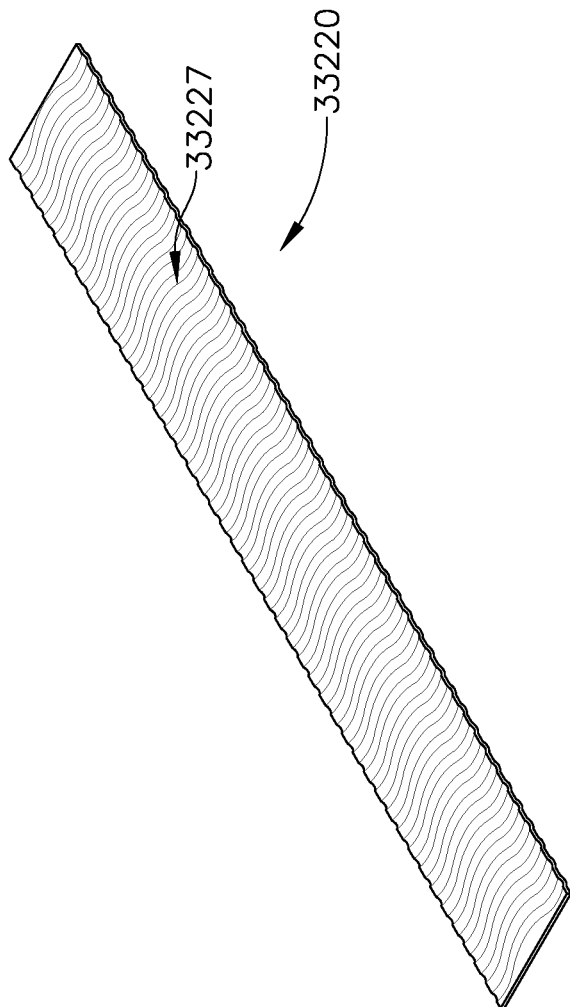
Figure 572:
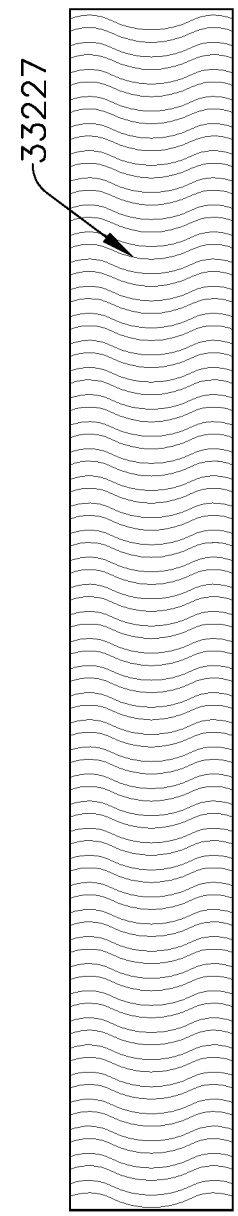
Figure 573:
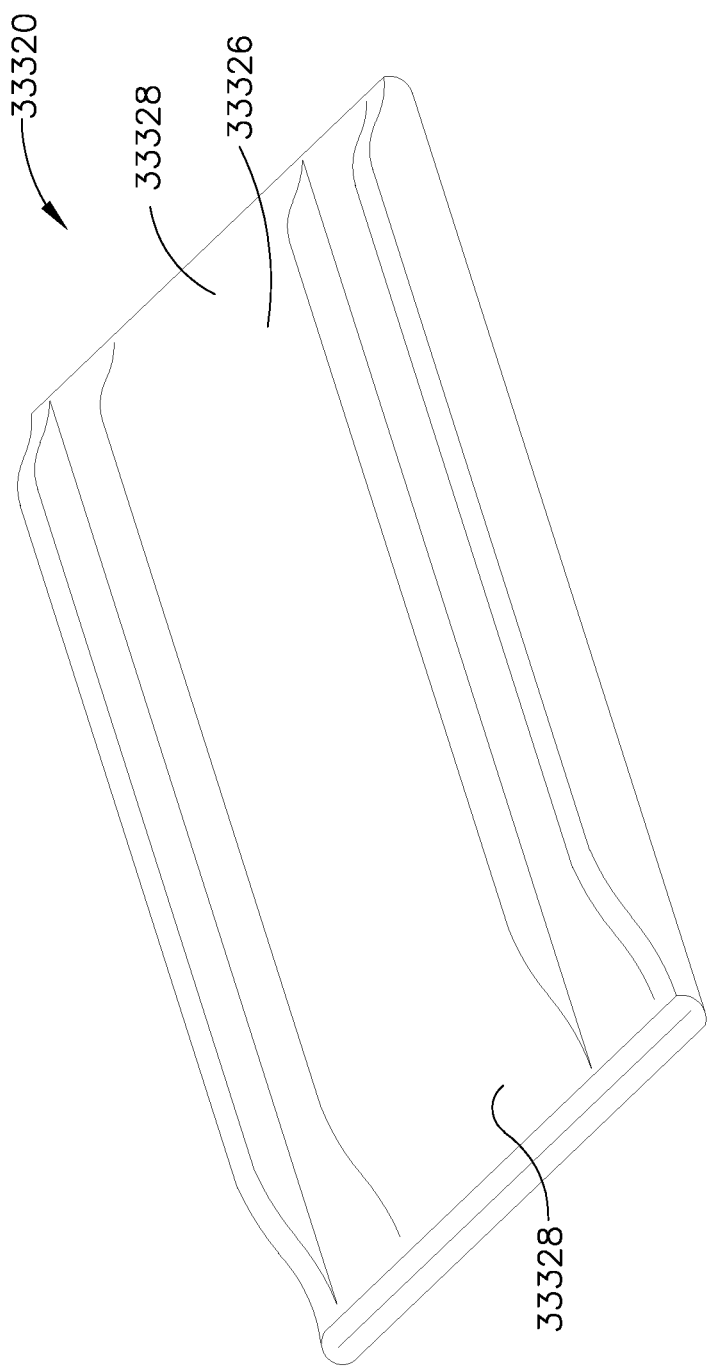
Figure 574:
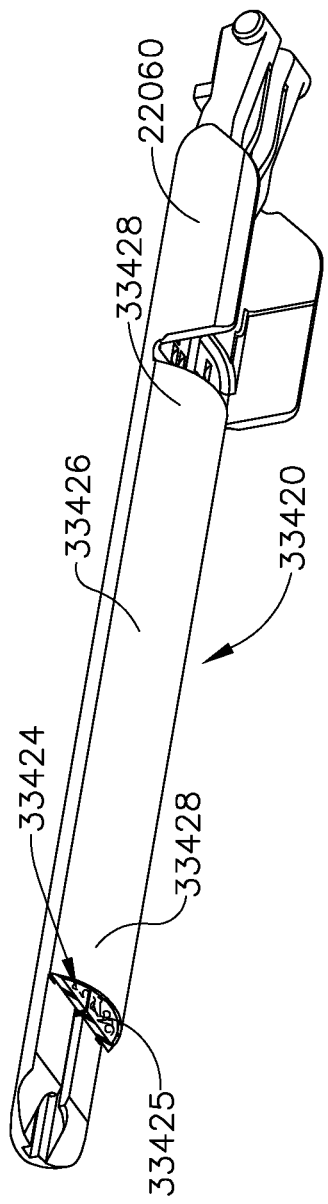
Figure 576:
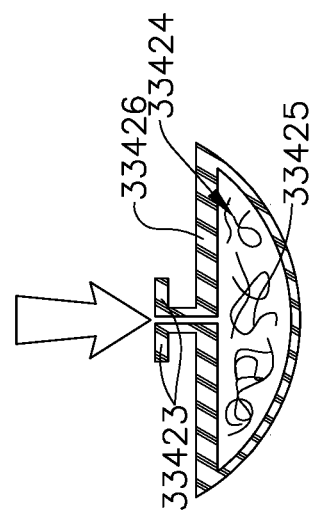
Figure 575:
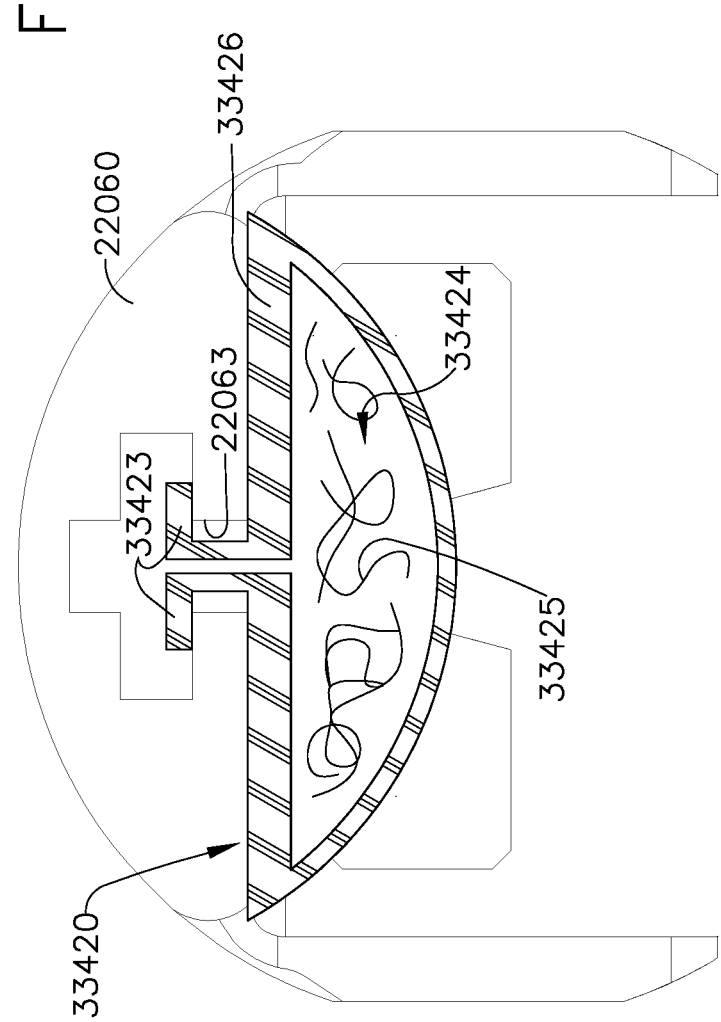
Figure 584:
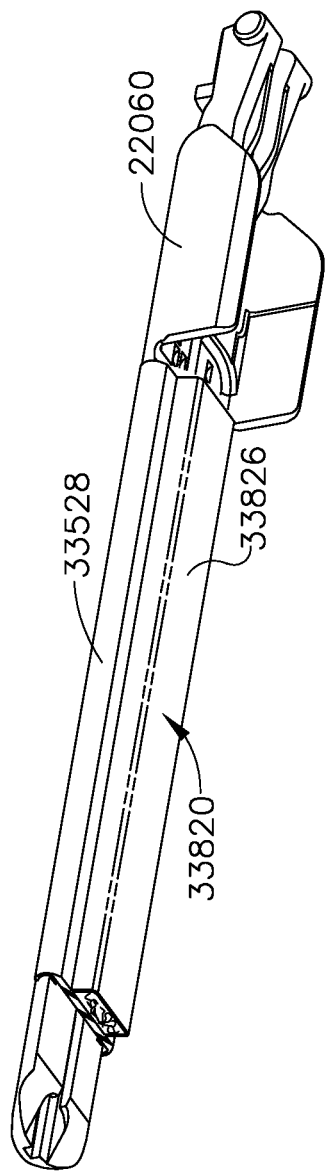
Figure 585:
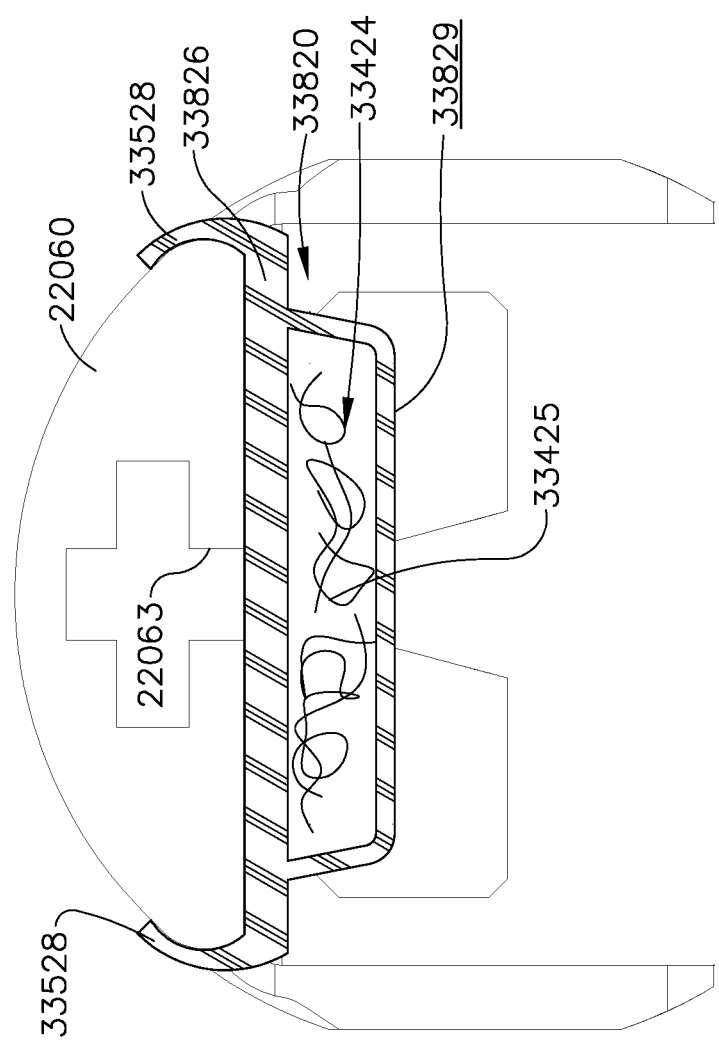

FIG. 122 is a bottom perspective view of the fastening system arrangement of FIG. 121;

FIG. 123 is a partial perspective view of the fastening system arrangement of FIG. 121;

FIG. 124 is a partial cross-sectional view of the fastening system arrangement of FIG. 121;

FIG. 125 is an elevational view of an end effector in accordance with at least one embodiment comprising a jaw in an open position, a retention matrix and a plurality of protective caps positioned in the jaw, and a staple cartridge positioned in a staple cartridge channel;

FIG. 126 is an elevational view of the end effector of FIG. 125 in a closed position;

FIG. 127 is an elevational view of the end effector of FIG. 125 in a fired position;

FIG. 128 is an elevational view of the retention matrix and protective caps of FIG. 125 assembled to the staple cartridge of FIG. 125;

FIG. 129 is a detail view of the arrangement of FIG. 128;

FIG. 130 is an elevational view of the end effector of FIG. 125 illustrating the jaw in an open position with thinner tissue positioned between the retention matrix and the staple cartridge;

FIG. 131 is an elevational view of the end effector of FIG. 125 illustrating the jaw in a closed position against the thinner tissue of FIG. 130;

FIG. 132 is an elevational view of the end effector of FIG. 125 illustrating the jaw in a fired position to capture the thinner tissue of FIG. 130 between the retention matrix and the staple cartridge;

FIG. 133 is an elevational view of the retention matrix and the protective caps of FIG. 125 assembled to the staple cartridge of FIG. 125 with the thin tissue of FIG. 130 positioned therebetween;

FIG. 134 is a detail view of the arrangement of FIG. 133;

FIG. 135 is a cross-sectional view of a protective cap positioned on the tip of a staple leg in accordance with at least one alternative embodiment;

FIG. 136 is a perspective view of a plurality of protective caps embedded within a sheet of material;

FIG. 137 is a perspective view of a jaw comprising a plurality of recesses configured to receive a plurality of protective caps therein;

FIG. 138 is a detail view of a portion of a jaw comprising a sheet covering the protective caps positioned within the jaw of FIG. 137;

FIG. 139 is a cross-sectional view of a protective cap positioned on a tip of a staple leg in accordance with at least one alternative embodiment wherein the protective cap comprises an interior forming surface;

FIG. 140 is another cross-sectional view of the protective cap of FIG. 139 illustrating the staple leg being deformed against the forming surface;

FIG. 141 is a top view of an alternative embodiment of a retention matrix comprising a plurality of connected matrix elements;

FIG. 142 is a top view of an alternative embodiment of a retention matrix comprising a plurality of connected matrix elements;

FIG. 143 is a top view of an alternative embodiment of a retention matrix comprising a plurality of connected matrix elements;

FIG. 144 is a top view of an alternative embodiment of an array of retention matrices comprising a plurality of connected matrix elements;

FIG. 145 is a top view of an alternative embodiment of a retention matrix comprising a plurality of connected matrix elements;

FIG. 146 is a partial exploded view of a jaw comprising a retention matrix including a compressible cover;

FIG. 147 is a detail view of the retention matrix of FIG. 146;

FIG. 148 is a partial cross-sectional view of a fastening system comprising a retention matrix including a compressible layer and a plurality of cells encapsulating one or more medicaments;

FIG. 149 is a diagram illustrating staple legs which have pierced the cells of FIG. 148 as they are being engaged with the retention matrix;

FIG. 150 is a partial cross-sectional view of a fastening system comprising a retention matrix including a compressible layer;

FIG. 151 is an elevational view of a fastener cartridge insertion assembly comprising a holder, a first fastener cartridge, and a second fastener cartridge;

FIG. 152 is an elevational view of an end effector of a surgical stapler comprising a first jaw and a second jaw, the second jaw being illustrated in an open configuration;

FIG. 153 is an elevational view of the end effector of FIG. 152 illustrating the second jaw in a closed configuration and the fastener cartridge insertion assembly of FIG. 151 being used to load the first jaw with the first cartridge and the second jaw with the second cartridge;

FIG. 154 is an elevational view of the loaded end effector of FIG. 153 illustrating the cartridge insertion assembly removed from the end effector, the second jaw in an open configuration once again, and tissue positioned intermediate the first jaw and the second jaw;

FIG. 155 is an elevational view of the loaded end effector of FIG. 154 in a fired configuration;

FIG. 156 is an elevational view of the first cartridge and the second cartridge in an implanted condition;

FIG. 157 is an elevational view of the end effector of FIG. 152 illustrating a portion of the first cartridge still engaged with the first jaw in accordance with at least one embodiment;

FIG. 158 is an elevational view of an alternative embodiment of a fastener cartridge insertion assembly comprising a holder, a first fastener cartridge, and a second fastener cartridge;

FIG. 159 is an elevational view of the fastener cartridge insertion assembly of FIG. 158 being used to load a first jaw of an end effector with the first cartridge and a second jaw with the second cartridge;

FIG. 160 is a cross-sectional view of the loaded end effector of FIG. 159;

FIG. 161 is a perspective view of a surgical stapler comprising a bottom jaw and a top jaw in accordance with at least one embodiment illustrated with portions of the surgical stapler removed;

FIG. 162 is a perspective view of the surgical stapler of FIG. 161 with the top jaw removed;

FIG. 163 is a perspective view of a slidable anvil system of the top jaw of the surgical stapler of FIG. 161 comprising a first slidable anvil and a second slidable anvil;

FIG. 164 is an end view of the slidable anvil system of FIG. 163;

FIG. 165 is a top view of the slidable anvil system of FIG. 163;

FIG. 166 is a diagram illustrating the slidable anvil system of FIG. 163 in an unfired condition;

FIG. 167 is a diagram illustrating the first slidable anvil of the slidable anvil system of FIG. 163 in an unfired position and staples positioned within the bottom jaw in an undeployed position;

FIG. 168 is a diagram illustrating the staples in the bottom jaw in a deployed configuration and the first slidable anvil of FIG. 167 being pulled proximally to deform a first group of staple legs of the staples;

FIG. 169 is a diagram illustrating the first group of staples of FIG. 168 deformed to a fully deformed state;

FIG. 170 is a diagram illustrating the second slidable anvil of the slidable anvil system of FIG. 163 being pushed distally to deform a second group of staple legs;

FIG. 171 is a partial perspective view of an anvil comprising a plurality of forming pockets in at least one embodiment;

FIG. 172 is a cross-sectional end view of the anvil of FIG. 171;

FIG. 173 is a diagram illustrating a first step in manufacturing the forming pockets of FIG. 171;

FIG. 174 is a diagram illustrating a second step in manufacturing the forming pockets of FIG. 171;

FIG. 175 is a top view of the forming pocket arrangement of the anvil of FIG. 171;

FIG. 176 is a diagram illustrating a first step of a manufacturing process for producing an anvil;

FIG. 177 is a diagram illustrating a second step in the manufacturing process of FIG. 176;

FIG. 178 is a diagram illustrating a third step in the manufacturing process of FIG. 176;

FIG. 179 is a left front perspective view of a surgical stapling and severing instrument with a handle portion including a link triggered automatic retraction and a ratcheting manual retraction mechanism;

FIG. 180 is a right aft perspective view of the surgical stapling and severing instrument of FIG. 179 with a portion of an elongate shaft cut away and a right half shell of a handle housing removed to expose an automatic end-of-firing travel retraction mechanism and a manual firing retraction mechanism;

FIG. 181 is a right aft perspective disassembled view of the handle portion and an elongate shaft of the surgical stapling and severing instrument of FIG. 179;

FIG. 182 is a right aft perspective view of the surgical stapling and severing instrument of FIG. 31 with a right half shell and outer portions of the implement portion removed to expose the closure and firing mechanisms in an initial state;

FIG. 183 is a right side view in elevation of the partially disassembled surgical stapling and severing instrument of FIG. 182;

FIG. 184 is a right aft perspective view of the partially disassembled surgical stapling and severing instrument of FIG. 182 with a closure mechanism closed and clamped and the side pawl firing mechanism completing a first stroke and with a manual retraction mechanism removed to expose a distal link of the linked rack that triggers automatic retraction of the firing mechanism;

FIG. 185 is a right aft perspective view of the partially disassembled surgical stapling and severing instrument of FIG. 183 with the side pawl firing mechanism disengaged and the distal link approaching automatic retraction;

FIG. 186 is left side view in elevation of the partially disassembled surgical stapling and severing instrument of FIG. 183 in an initial state of end effector open and anti-backup mechanism engaged;

FIG. 187 is a left side detail view of the right half shell and an anti-backup release lever of the handle portion of FIG. 186;

FIG. 188 is a left side detail view in elevation of the disassembled surgical stapling and severing instrument of FIG. 179 with the closure trigger clamped, the firing trigger performing a final stroke and the distal link positioned to trip automatic retraction;

FIG. 189 is a left side detail in elevation of the disassembled surgical stapling and severing instrument of FIG. 188 immediately after the distal link has actuated and locked forward the anti-backup release lever, allowing the linked rack to retract;

FIG. 190 is a right disassembled perspective view of the idler and aft gears and manual retraction lever and ratcheting pawl of a manual retraction mechanism of the surgical stapling and severing instrument of FIG. 179;

FIG. 191 is a right perspective view of the manual retraction mechanism of FIG. 190 with the manual retraction lever partially cut away to expose a smaller diameter ratchet gear on the aft gear engaging the ratcheting pawl;

FIG. 192 is a partially disassembled left side view in elevation of a surgical stapling and severing instrument of FIG. 179 with the anti-backup mechanism engaged to a fully fired linked rack that is disconnected from a combination tension/compression spring prior to actuation of the manual retraction lever of FIG. 190;

FIG. 193 is a partially disassembled left side view in elevation of the surgical stapling and severing instrument of FIG. 192 with hidden portions of the anti-backup release lever, aft gear, and manual firing release lever shown in phantom;

FIG. 194 is a partially disassembled left side view in elevation of the surgical stapling and severing instrument of FIG. 193 after actuation of the manual firing release lever has manually retracted the link rack;

FIG. 195 is a partially disassembled left side view in elevation of the surgical stapling and severing instrument of FIG. 194 with the linked rack omitted depicting the manual firing release lever disengaging the anti-backup mechanism;

FIG. 196 is a left side detail view of an alternative anti-backup release lever and handle housing for the surgical stapling and severing instrument of FIG. 179;

FIG. 197 is a left perspective disassembled view of the alternative anti-backup release lever, aft gear axle, and automatic retraction cam wheel of FIG. 196;

FIG. 198 is a right side view in elevation of the alternative anti-backup release mechanism of FIG. 196 with the linked rack in a retracted position and the anti-backup release lever proximally positioned with the anti-backup plate engaged to the firing rod;

FIG. 198A is a right detail side view in elevation of the aft gear, automatic retraction cam wheel and distal-most link of FIG. 198;

FIG. 199 is a right side view in elevation of the anti-backup release mechanism of FIG. 198 after a first firing stroke;

FIG. 199A is a right detail side view in elevation of the aft gear, automatic retraction cam wheel and a second link of FIG. 199;

FIG. 200 is a right side view in elevation of the anti-backup release mechanism of FIG. 199 after a second firing stroke;

FIG. 200A is a right detail side view in elevation of the aft gear, automatic retraction cam wheel and third link of FIG. 200;

FIG. 201 is a right detail side view in elevation of the anti-backup release mechanism of FIG. 200 after a third firing and final stroke;

FIG. 201A is a right detail side view in elevation of the aft gear, automatic retraction cam wheel and proximal-most fourth link of FIG. 201;

FIG. 202 is a right side view in elevation of the automatic release mechanism of FIG. 201 after a further firing stroke causes the automatic retraction cam wheel to distally slide and lock the anti-backup release lever, disengaging the anti-backup mechanism;

FIG. 203 is a left, front perspective view of an open staple applying assembly with a right half portion of a replaceable staple cartridge included in a staple channel;

FIG. 204 is an exploded perspective view of the staple applying assembly of FIG. 203 with a complete replaceable staple cartridge and an nonarticulating shaft configuration;

FIG. 205 is a perspective view of a two-piece knife and firing bar ("E-beam") of the staple applying assembly of FIG. 203;

FIG. 206 is a perspective view of a wedge sled of a staple cartridge of a staple applying assembly;

FIG. 207 is a left side view in elevation taken in longitudinal cross section along a centerline line 207-207 of the staple applying assembly of FIG. 203;

FIG. 208 is a perspective view of the open staple applying assembly of FIG. 203 without the replaceable staple cartridge, a portion of the staple channel proximate to a middle pin of two-piece knife and firing bar, and without a distal portion of a staple channel;

FIG. 209 is a front view in elevation taken in cross section along line 209-209 of the staple applying assembly of FIG. 203 depicting internal staple drivers of the staple cartridge and portions of the two-piece knife and firing bar;

FIG. 210 is a left side view in elevation taken generally along the longitudinal axis of line 207-207 of a closed staple applying assembly of FIG. 203 to include center contact points between the two-piece knife and wedge sled but also laterally offset to show staples and staple drivers within the staple cartridge;

FIG. 211 is a left side detail view in elevation of the staple applying assembly of FIG. 210 with the two-piece knife retracted slightly more as typical for staple cartridge replacement;

FIG. 212 is a left side detail view in elevation of the staple applying assembly of FIG. 211 with the two-piece knife beginning to fire, corresponding to the configuration depicted in FIG. 210;

FIG. 213 is a left side cross-sectional view in elevation of the closed staple applying assembly of FIG. 210 after the two-piece knife and firing bar has distally fired;

FIG. 214 is a left side cross-sectional view in elevation of the closed staple applying assembly of FIG. 213 after firing of the staple cartridge and retraction of the two-piece knife;

FIG. 215 is a left side cross-sectional detail view in elevation of the staple applying assembly of FIG. 214 with the two-piece knife allowed to drop into a lockout position;

FIG. 216 is a perspective view of a staple cartridge comprising a rigid support portion and a compressible tissue thickness compensator for use with a surgical stapling instrument in accordance with at least one embodiment of the invention;

FIG. 217 is a partially exploded view of the staple cartridge of FIG. 216;

FIG. 218 is a fully exploded view of the staple cartridge of FIG. 216;

FIG. 219 is another exploded view of the staple cartridge of FIG. 216 without a warp covering the tissue thickness compensator;

FIG. 220 is a perspective view of a cartridge body, or support portion, of the staple cartridge of FIG. 216;

FIG. 221 is a top perspective view of a sled movable within the staple cartridge of FIG. 216 to deploy staples from the staple cartridge;

FIG. 222 is a bottom perspective view of the sled of FIG. 221;

FIG. 223 is an elevational view of the sled of FIG. 221;

FIG. 224 is a top perspective view of a driver configured to support one or more staples and to be lifted upwardly by the sled of FIG. 221 to eject the staples from the staple cartridge;

FIG. 225 is a bottom perspective view of the driver of FIG. 224;

FIG. 226 is a wrap configured to at least partially surround a compressible tissue thickness compensator of a staple cartridge;

FIG. 227 is a partial cut away view of a staple cartridge comprising a rigid support portion and a compressible tissue thickness compensator illustrated with staples being moved from an unfired position to a fired position during a first sequence;

FIG. 228 is an elevational view of the staple cartridge of FIG. 227;

FIG. 229 is a detail elevational view of the staple cartridge of FIG. 227;

FIG. 230 is a cross-sectional end view of the staple cartridge of FIG. 227;

FIG. 231 is a bottom view of the staple cartridge of FIG. 227;

FIG. 232 is a detail bottom view of the staple cartridge of FIG. 227;

FIG. 233 is a longitudinal cross-sectional view of an anvil in a closed position and a staple cartridge comprising a rigid support portion and a compressible tissue thickness compensator illustrated with staples being moved from an unfired position to a fired position during a first sequence;

FIG. 234 is another cross-sectional view of the anvil and the staple cartridge of FIG. 233 illustrating the anvil in an open position after the firing sequence has been completed;

FIG. 235 is a partial detail view of the staple cartridge of FIG. 233 illustrating the staples in an unfired position;

FIG. 236 is a cross-sectional elevational view of a staple cartridge comprising a rigid support portion and a compressible tissue thickness compensator illustrating the staples in an unfired position;

FIG. 237 is a detail view of the staple cartridge of FIG. 236;

FIG. 238 is an elevational view of an anvil in an open position and a staple cartridge comprising a rigid support portion and a compressible tissue thickness compensator illustrating the staples in an unfired position;

FIG. 239 is an elevational view of an anvil in a closed position and a staple cartridge comprising a rigid support portion and a compressible tissue thickness compensator illustrating the staples in an unfired position and tissue captured between the anvil and the tissue thickness compensator;

FIG. 240 is a detail view of the anvil and staple cartridge of FIG. 239;

FIG. 241 is an elevational view of an anvil in a closed position and a staple cartridge comprising a rigid support portion and a compressible tissue thickness compensator illustrating the staples in an unfired position illustrating thicker tissue positioned between the anvil and the staple cartridge;

FIG. 242 is a detail view of the anvil and staple cartridge of FIG. 241;

FIG. 243 is an elevational view of the anvil and staple cartridge of FIG. 241 illustrating tissue having different thicknesses positioned between the anvil and the staple cartridge;

FIG. 244 is a detail view of the anvil and staple cartridge of FIG. 241 as illustrated in FIG. 243;

FIG. 245 is a diagram illustrating a tissue thickness compensator which is compensating for different tissue thickness captured within different staples;

FIG. 246 is a diagram illustrating a tissue thickness compensator applying a compressive pressure to one or more vessels that have been transected by a staple line;

FIG. 247 is a diagram illustrating a circumstance wherein one or more staples have been improperly formed;

FIG. 248 is a diagram illustrating a tissue thickness compensator which could compensate for improperly formed staples;

FIG. 249 is a diagram illustrating a tissue thickness compensator positioned in a region of tissue in which multiple staples lines have intersected;

FIG. 250 is a diagram illustrating tissue captured within a staple;

FIG. 251 is a diagram illustrating tissue and a tissue thickness compensator captured within a staple;

FIG. 252 is a diagram illustrating tissue captured within a staple;

FIG. 253 is a diagram illustrating thick tissue and a tissue thickness compensator captured within a staple;

FIG. 254 is a diagram illustrating thin tissue and a tissue thickness compensator captured within a staple;

FIG. 255 is a diagram illustrating tissue having an intermediate thickness and a tissue thickness compensator captured within a staple;

FIG. 256 is a diagram illustrating tissue having another intermediate thickness and a tissue thickness compensator captured within a staple;

FIG. 257 is a diagram illustrating thick tissue and a tissue thickness compensator captured within a staple;

FIG. 258 is a partial cross-sectional view of an end effector of a surgical stapling instrument illustrating a firing bar and staple-firing sled in a retracted, unfired position;

FIG. 259 is another partial cross-sectional view of the end effector of FIG. 258 illustrating the firing bar and the staple-firing sled in a partially advanced position;

FIG. 260 is a cross-sectional view of the end effector of FIG. 258 illustrating the firing bar in a fully advanced, or fired, position;

FIG. 261 is a cross-sectional view of the end effector of FIG. 258 illustrating the firing bar in a retracted position after being fired and the staple-firing sled left in its fully fired position;

FIG. 262 is a detail view of the firing bar in the retracted position of FIG. 261;

FIG. 263 is a partial cross-sectional view of an end effector of a surgical stapling instrument including a staple cartridge comprising a tissue thickness compensator and staples at least partially positioned therein;

FIG. 264 is another partial cross-sectional view of the end effector of FIG. 263 illustrating the staples at least partially moved and/or rotated relative to an anvil positioned opposite the staple cartridge;

FIG. 265 is a partial cross-sectional view of an end effector of a surgical stapling instrument in accordance with at least one embodiment;

FIG. 266 is a partial cross-sectional view of an end effector in accordance with at least one alternative embodiment;

FIG. 267 is a partial cross-sectional view of an end effector in accordance with another alternative embodiment;

FIG. 268 is a perspective view of an end effector of a surgical stapling instrument in accordance with at least one embodiment;

FIG. 269 is a partial cross-sectional view of the end effector of FIG. 268 illustrated in a flexed condition;

FIG. 270 is a partial cross-sectional view of the end effector of FIG. 269 in a released condition;

FIG. 271 is a perspective view of an end effector comprising a tissue thickness compensator sock;

FIG. 272 is a rear perspective of the tissue thickness compensator sock in FIG. 271;

FIG. 273 is a perspective view of an end effector comprising a plurality of rails extending from a support portion and a tissue thickness compensator having a longitudinal cavity defined therein;

FIG. 274 is a perspective view of the tissue thickness compensator of FIG. 273;

FIG. 275 is a perspective view of an end effector comprising a plurality of teeth extending from a support portion and a tissue thickness compensator engaged therewith;

FIG. 276 is a perspective view of an anvil comprising a pocket array in accordance with at least one embodiment;

FIG. 277 is a partial detail view of the anvil of FIG. 276;

FIG. 278 is a partial longitudinal cross-sectional view of the anvil of FIG. 276;

FIG. 279 is a transverse cross-sectional view of the anvil of FIG. 276;

FIG. 280 is an elevational view of a fired staple comprising a substantially B-shaped configuration;

FIG. 281 is an elevational view of a fired staple comprising one leg deformed inwardly and one leg deformed outwardly;

FIG. 282 is an elevational view of a fired staple comprising both legs formed outwardly;

FIG. 283 is a partial perspective view of a support portion of a staple cartridge comprising detachable and/or displaceable staple leg guides;

FIG. 284 is a partial cross-sectional view of the staple cartridge of FIG. 283 illustrating staples being deployed from the staple cartridge;

FIG. 285 is a detail view of the cross-sectional view of FIG. 284 after the staple cartridge has been fired;

FIG. 286 is an exploded view of a staple cartridge including a tissue thickness compensator comprising voids defined therein;

FIG. 287 is a diagram illustrating the tissue thickness compensator of FIG. 286 implanted against tissue;

FIG. 288 is another diagram illustrating the tissue thickness compensator of FIG. 286 implanted against tissue;

FIG. 289 is a cross-sectional perspective view of a staple cartridge comprising lateral retention members extending from a support portion thereof configured to hold a tissue thickness compensator in position;

FIG. 290 is a cross-sectional view of the staple cartridge of FIG. 289 being utilized to staple tissue;

FIG. 291 is another cross-sectional view of the staple cartridge of FIG. 289 illustrating the support portion being moved away from the implanted tissue thickness compensator;

FIG. 292 is a cross-sectional perspective view of a staple cartridge comprising lateral retention members configured to hold a tissue thickness compensator to a support portion;

FIG. 293 is a cross-sectional view of the staple cartridge of FIG. 292 being utilized to staple tissue;

FIG. 294 is another cross-sectional view of the staple cartridge of FIG. 292 illustrating the support portion being moved away from the implanted tissue thickness compensator;

FIG. 295 is a cross-sectional detail view of a retainer holding a tissue thickness compensator to a support portion of a staple cartridge in accordance with at least one embodiment;

FIG. 296 is partial cut-away view of a staple cartridge comprising staple drivers having different heights in accordance with at least one embodiment;

FIG. 296A is a diagram illustrating the staple drivers of FIG. 296 and staples having different unfired heights supported thereon;

FIG. 297 is a diagram illustrating a tissue thickness compensator comprising a varying thickness, staple drivers having different heights, and staples having different unformed heights;

FIG. 298 is a diagram illustrating the staples and the tissue thickness compensator of FIG. 297 implanted to tissue;

FIG. 299 is a partial cross-sectional view of a staple cartridge comprising a tissue thickness compensator comprising a varying thickness in accordance with at least one embodiment;

FIG. 300 is a cross-sectional view of an end effector of a surgical stapling instrument in an open configuration;

FIG. 301 is cross-sectional view of the end effector of FIG. 300 illustrated in a partially-fired configuration;

FIG. 302 is a cross-sectional view of the end effector of FIG. 300 illustrated in a re-opened configuration;

FIG. 303 is a cross-sectional view of an end effector of a surgical stapling instrument comprising staple drivers having different heights and a contoured deck surface in accordance with at least one embodiment;

FIG. 304 is a cross-sectional view of an end effector of a surgical stapling instrument comprising staple drivers having different heights and a stepped deck surface in accordance with at least one embodiment;

FIG. 305 is a perspective view of a staple cartridge being loaded into an effector of a surgical stapling instrument utilizing a staple cartridge applicator;

FIG. 306 is a bottom perspective view of the staple cartridge applicator of FIG. 305;

FIG. 307 is a side view of the staple cartridge applicator of FIG. 305 assembled to a staple cartridge;

FIG. 308 is a cross-sectional view of the assembly of FIG. 307;

FIG. 309 is a perspective view of a staple cartridge applicator assembly further including an upper tissue thickness compensator positioned on the top surface of the staple cartridge applicator in accordance with at least one embodiment;

FIG. 310 is an exploded view of the upper tissue thickness compensator and the staple cartridge applicator of FIG. 309;

FIG. 310A is an exploded view of a staple cartridge applicator assembly comprising a pull member configured to detach an upper tissue thickness compensator adhered to the staple cartridge applicator;

FIG. 311 is a partial exploded view of a staple cartridge applicator assembly in accordance with at least one alternative embodiment;

FIG. 312 is a perspective view of a staple cartridge applicator assembly comprising an upper tissue thickness compensator including a plurality of retention features extending therefrom and a staple cartridge comprising a lower tissue thickness compensator;

FIG. 313 is an elevational view of the staple cartridge applicator assembly of FIG. 312 positioned within a staple cartridge channel and an anvil being closed onto the staple cartridge applicator assembly;

FIG. 314 is an elevational view of the anvil of FIG. 313 in a re-opened position and the staple cartridge applicator of FIG. 312 being removed from the end effector;

FIG. 314A is a cross-sectional view of tissue positioned intermediate the upper tissue thickness compensator and the lower tissue thickness compensator of FIG. 312;

FIG. 314B is a cross-sectional view illustrating the upper tissue thickness compensator and the lower tissue thickness compensator stapled to the tissue and severed by a cutting member;

FIG. 315 is a diagram illustrating a tissue thickness compensator being inserted into an anvil in accordance with at least one embodiment;

FIG. 316 is a cross-sectional view of the tissue thickness compensator of FIG. 315;

FIG. 317 is an exploded view of a tissue thickness compensator and an anvil in accordance with at least one alternative embodiment;

FIG. 318 is a perspective view of staple cartridge applicator assembly comprising an upper tissue thickness compensator configured to be attached to an anvil in accordance with at least one embodiment;

FIG. 319 is an elevational view of the staple cartridge applicator assembly of FIG. 318 positioned within a staple cartridge channel and an anvil being moved toward the upper tissue thickness compensator;

FIG. 320 illustrates the staple cartridge applicator of FIG. 318 being removed from the end effector after the upper tissue thickness compensator has been engaged with the anvil;

FIG. 321 is a cross-sectional end view of the anvil being moved toward the upper tissue thickness compensator of FIG. 318;

FIG. 322 is a cross-sectional end view of the anvil engaged with the upper tissue thickness compensator;

FIG. 323 is a cross-sectional view of an end effector of a surgical stapling instrument comprising a staple cartridge including a segmentable tissue thickness compensator attached to a support portion of the staple cartridge by a plurality of fasteners;

FIG. 324 is a cross-sectional view of the end effector of FIG. 323 illustrating a firing member in a partially-fired position;

FIG. 325 is a cross-sectional view of the end effector of FIG. 323 illustrating the support portion being moved away from the partially-implanted tissue thickness compensator;

FIG. 326 is a partial perspective view of the support portion of FIG. 323;

FIG. 327 is a perspective view of a staple-deploying sled in accordance with at least one embodiment;

FIG. 328 is an elevational view of the sled of FIG. 327;

FIG. 329 is a perspective view of an end effector of a surgical stapling instrument comprising a staple cartridge including a tissue thickness compensator and a plurality of staple guides positioned on the tissue thickness compensator;

FIG. 330 is a partial cross-sectional view of the tissue thickness compensator and the staple guides of FIG. 329 in an unfired configuration;

FIG. 331 is a partial cross-sectional view of the tissue thickness compensator and the staple guides of FIG. 329 in a fired configuration;

FIG. 332 is a cross-sectional view of a staple cartridge comprising a tissue thickness compensator and a support portion in accordance with at least one embodiment;

FIG. 333 is a partial cross-sectional view of a tissue thickness compensator, a staple guide layer, and a staple in an unfired position;

FIG. 334 is a partial cross-sectional view of a tissue thickness compensator, a staple guide layer, and a staple in an unfired position in accordance with at least one alternative embodiment;

FIG. 335 is a partial cross-sectional view of a tissue thickness compensator, a staple guide layer, and a staple in an unfired position in accordance with at least one alternative embodiment;

FIG. 336 is a partial cross-sectional view of a tissue thickness compensator, a staple guide layer, and a staple in an unfired position in accordance with at least one alternative embodiment;

FIG. 337 is a partial cross-sectional view of a tissue thickness compensator, a staple guide layer, and a staple in an unfired position in accordance with at least one alternative embodiment;

FIG. 338 is a partial cross-sectional view of a tissue thickness compensator, a staple guide layer, and a staple in an unfired position in accordance with at least one alternative embodiment;

FIG. 339 is a partial cross-sectional view of a tissue thickness compensator, a staple guide layer, and a staple in an unfired position in accordance with at least one alternative embodiment;

FIG. 340 is a detail view of a region surrounding a tip of the staple of FIG. 339;

FIG. 341 is a partial cross-sectional view of a tissue thickness compensator, a staple guide layer, and a staple in an unfired position in accordance with at least one alternative embodiment;

FIG. 342 is a detail view of a region surrounding a tip of the staple of FIG. 341;

FIG. 343 is a partial cross-sectional view of a tissue thickness compensator, a staple guide layer, and a staple in an unfired position in accordance with at least one alternative embodiment;

FIG. 344 is a perspective view of a staple guide layer and a plurality of staples in an unfired position in accordance with at least one alternative embodiment;

FIG. 345 is an end view of a tissue thickness compensator configured to be used with a circular surgical stapler;

FIG. 346 is a perspective view of the tissue thickness compensator and the circular surgical stapler of FIG. 345;

FIG. 347 is an end view of a tissue thickness compensator configured to be used with a circular surgical stapler in accordance with at least one alternative embodiment;

FIG. 348 is a perspective view of the tissue thickness compensator and the circular surgical stapler of FIG. 347;

FIG. 349 is an end view of a tissue thickness compensator configured to be used with a circular surgical stapler;

FIG. 350 is an end view of the tissue thickness compensator of FIG. 349 in a partially expanded configuration;

FIG. 351 is an elevational view of a surgical stapling instrument comprising a staple cartridge in accordance with at least one embodiment;

FIG. 352 is an end view of the surgical stapling instrument of FIG. 351 positioned relative to tissue;

FIG. 353 is an end view of the surgical stapling instrument of FIG. 351 further comprising a tissue thickness compensator positioned between the staple cartridge and the tissue;

FIG. 354 is a partial perspective view of staples deployed into tissue from the surgical stapling instrument of FIG. 351 without a tissue thickness compensator;

FIG. 355 is a partial perspective view of staples deployed into tissue from the surgical stapling instrument of FIG. 351 with a tissue thickness compensator;

FIG. 356 is a partial cross-sectional view of the end effector of the surgical stapling instrument of FIG. 351 comprising an anvil plate in a first position;

FIG. 357 is a partial cross-sectional view of the end effector of the surgical stapling instrument of FIG. 351 illustrating the anvil plate of FIG. 356 in a second position;

FIG. 358 is a cross-sectional view of an end effector of a surgical stapling instrument comprising a staple cartridge including a gap setting element;

FIG. 359 is a perspective view illustrating a firing member cutting the gap setting element of FIG. 358 at the end of firing stroke of the firing member;

FIG. 360 is a cross-sectional view of an end effector of a surgical stapling instrument comprising a staple cartridge including a flexible nose;

FIG. 361 is a cross-sectional view of the end effector of FIG. 360 illustrating the nose in a flexed configuration;

FIG. 362 is a cross-sectional view of an end effector of a surgical stapling instrument comprising a staple cartridge including a slidable portion;

FIG. 363 is a cross-sectional view of the end effector of FIG. 362 illustrating the slidable portion slid distally;

FIG. 364 is a cross-sectional view of an end effector of a surgical stapling instrument comprising a support portion comprising an inclined deck surface and a tissue thickness compensator comprising a varying thickness;

FIG. 365 is a cross-sectional view of an end effector of a surgical stapling instrument comprising a support portion comprising an inclined deck surface and a tissue thickness compensator comprising a uniform thickness;

FIG. 366 is a perspective view of a staple cartridge comprising a tissue thickness compensator having a varying thickness;

FIG. 367 is an end view of the staple cartridge of FIG. 366;

FIG. 368 is a cross-sectional perspective view of a tissue thickness compensator comprising longitudinal layers;

FIG. 369 is a cross-sectional perspective view of a tissue thickness compensator comprising a plurality of layers in accordance with at least one alternative embodiment;

FIG. 370 is a perspective view of a disposable loading unit comprising retention members configured to releasably hold a tissue thickness compensator thereto;

FIG. 371 is a perspective view of a tissue thickness compensator including retention members configured to releasably hold the tissue thickness compensator to a disposable loading unit;

FIG. 372 is a perspective view of the tissue thickness compensator of FIG. 371 attached to a disposable loading unit;

FIG. 373 is an end view of the disposable loading unit of FIG. 372;

FIG. 374 is a perspective view of a tissue thickness compensator including retention members configured to releasably hold the tissue thickness compensator to a disposable loading unit;

FIG. 375 is a perspective view of the tissue thickness compensator of FIG. 374 attached to a disposable loading unit;

FIG. 376 is an end view of the disposable loading unit of FIG. 375;

FIG. 377 is a perspective view of a tissue thickness compensator including a retention member configured to releasably hold the tissue thickness compensator to a disposable loading unit;

FIG. 378 is a perspective view of the tissue thickness compensator of FIG. 377 attached to a disposable loading unit;

FIG. 379 is a perspective view of a tissue thickness compensator applicator positioned within an effector of a disposable loading unit;

FIG. 380 is a top perspective view of the tissue thickness compensator applicator of FIG. 379;

FIG. 381 is a bottom perspective view of the tissue thickness compensator applicator of FIG. 379;

FIG. 382 is a perspective view of a tissue thickness compensator applicator positioned within an effector of a disposable loading unit in accordance with at least one alternative embodiment;

FIG. 383 is a top perspective view of the tissue thickness compensator applicator of FIG. 382;

FIG. 384 is a bottom perspective view of the tissue thickness compensator applicator of FIG. 382;

FIG. 385 is an elevational view of a disposable loading unit including a pivotable jaw configured to support a staple cartridge;

FIG. 386 is a cross-sectional view of a staple cartridge comprising a tissue thickness compensator attached to a support portion of the staple cartridge in accordance with at least one embodiment;

FIG. 387 is a cross-sectional view of a staple cartridge comprising a tissue thickness compensator attached to a support portion of the staple cartridge in accordance with at least one embodiment;

FIG. 388 is a cross-sectional view of a staple cartridge comprising a tissue thickness compensator attached to a support portion of the staple cartridge in accordance with at least one embodiment;

FIG. 389 is a perspective view of the tissue thickness compensator of FIG. 387;

FIG. 390 is an exploded view of a retainer assembly including a retainer and two tissue thickness compensators in accordance with at least one embodiment;

FIG. 391 is a perspective view of the retainer assembly shown in FIG. 390;

FIG. 392 is a perspective view of an anvil with which the retainer assembly of FIG. 390 may be used;

FIG. 393 is an illustration depicting the retainer assembly shown in FIG. 390 being inserted in an end effector of a surgical stapler which includes an anvil and a staple cartridge;

FIG. 394 is a side view of the retainer assembly shown in FIG. 390 engaged with the staple cartridge of FIG. 393;

FIG. 395 is a side view of the retainer assembly shown in FIG. 390 engaged with the staple cartridge and the anvil of FIG. 393 illustrating the anvil in a closed position;

FIG. 396 is a side view of the retainer assembly of FIG. 390 being removed from the end effector of FIG. 393;

FIG. 397 is a perspective view of a retainer;

FIG. 398 is a side view of the retainer of FIG. 397 with tissue thickness compensators attached to bottom and top surfaces thereof illustrating one of the tissue thickness compensators engaged with a staple cartridge in a surgical stapler comprising an anvil;

FIG. 399 is a side view illustrating the anvil of FIG. 398 in a closed position;

FIG. 400 is an exploded perspective view of a retainer and a tissue thickness compensator in accordance with at least one embodiment;

FIG. 401 is an exploded perspective view of the tissue thickness compensator of FIG. 400 and an anvil of a surgical stapler;

FIG. 402 is an exploded top perspective view of a retainer and a tissue thickness compensator in accordance with at least one embodiment;

FIG. 403 is an exploded bottom perspective view of the retainer and tissue thickness compensator of FIG. 402;

FIG. 404 is a top perspective view of the retainer and tissue thickness compensator of FIG. 402 engaged with a surgical stapler;

FIG. 405 is a bottom perspective view of the retainer and tissue thickness compensator of FIG. 402 engaged with the surgical stapler of FIG. 404;

FIG. 406 is a side view of the retainer and tissue thickness compensator of FIG. 402 engaged with the surgical stapler of FIG. 404;

FIG. 407 is a bottom perspective view of the retainer and tissue thickness compensator of FIG. 402 illustrating the tissue thickness compensator attached to the anvil of the surgical stapler of FIG. 404;

FIG. 408 is a top perspective view of the retainer and tissue thickness compensator of FIG. 402 illustrating the tissue thickness compensator attached to the anvil of FIG. 407;

FIG. 409 is a side view of the tissue thickness compensator of FIG. 402 attached to the anvil of FIG. 407;

FIG. 410 is a cross-sectional view of the retainer and tissue thickness compensator of FIGS. 402 and 403 attached to a staple cartridge and channel of a surgical stapler;

FIG. 411 is a cross-sectional view of the retainer and tissue thickness compensator of FIGS. 402 and 403 attached to the staple cartridge and channel of the surgical stapler of FIG. 410 illustrating an anvil of the surgical stapler engaged with the tissue thickness compensator;

FIG. 412 is a cross-sectional view of the tissue thickness compensator of FIG. 402 attached to the anvil of the surgical stapler and being moved away from the retainer;

FIG. 413 is a side cross-sectional view of a retainer assembly comprising a retainer, tissue thickness compensators mounted on first and second surfaces of the retainer, and connectors passing through holes in the retainer in accordance with at least one embodiment;

FIG. 414 is a perspective view of the retainer assembly of FIG. 413 illustrated with a portion of a tissue thickness compensator removed for the purposes of illustration;

FIG. 415 is a side view of the retainer assembly of FIG. 413 engaged with a surgical stapler comprising an anvil illustrated in an open position;

FIG. 416 is a side view of the retainer assembly of FIG. 413 and the anvil of FIG. 415 illustrated in a closed position;

FIG. 417 is a side view of the retainer assembly of FIG. 413 illustrating the retainer being removed from between the tissue thickness compensators of the retainer assembly;

FIG. 418 is a side view of the retainer removed from the tissue thickness compensators of FIG. 413;

FIG. 419 is a perspective view of a retainer configured to engage an anvil of a surgical stapler in accordance with at least one embodiment;

FIG. 420 is a top view of the retainer of FIG. 419;

FIG. 421 is a side view of the retainer of FIG. 419;

FIG. 422 is a bottom view of the retainer of FIG. 419;

FIG. 423 illustrates a retainer assembly comprising the retainer of FIG. 419 and a tissue thickness compensator being attached to a staple cartridge for a surgical stapler;

FIG. 424 illustrates the retainer assembly and staple cartridge of FIG. 423 engaging an anvil of an end effector of a surgical stapler;

FIG. 425 illustrates the retainer assembly and staple cartridge of FIG. 423 engaging the anvil of the end effector of the surgical stapler of FIG. 424;

FIG. 426 illustrates the retainer assembly and staple cartridge of FIG. 423 engaged on the anvil of the surgical stapler of FIG. 424;

FIG. 427 illustrates the retainer assembly and staple cartridge of FIG. 423 engaged on the anvil of the surgical stapler of FIG. 424 and the anvil being moved into a closed position;

FIG. 428 illustrates the anvil of the surgical stapler of FIG. 424 in an open position with the tissue thickness compensator attached thereto and the retainer engaged with the staple cartridge channel of the surgical stapler;

FIG. 429 illustrates the retainer of FIG. 423 engaged with the staple cartridge channel of the surgical stapler of FIG. 424 and the anvil in an open position;

FIG. 430 is a cross-sectional view of a retainer including a tissue thickness compensator comprising protrusions or wings configured to engage an anvil of a surgical stapler;

FIG. 431 is a cross-sectional view of a retainer including a tissue thickness compensator comprising a sock configured to engage an anvil of a surgical stapler;

FIG. 432 is a perspective view of a retainer that includes two plates connected by a hinge according to at least one embodiment;

FIG. 433 is a side view of the retainer of FIG. 432;

FIG. 434 is a rear perspective view of an embodiment of an insertion tool configured for use with the retainer of FIG. 432;

FIG. 435 is a top perspective view of the insertion tool of FIG. 434;

FIG. 436 is a rear perspective view of the insertion tool of FIG. 434 with a portion of the insertion tool removed for purposes of illustration;

FIG. 437 is a side view of the insertion tool of FIG. 434 with a portion of the insertion tool removed for purposes of illustration;

FIG. 438 is a top view of the insertion tool of FIG. 434;

FIG. 439 is a perspective view of a retainer assembly comprising the retainer of FIG. 432, a tissue thickness compensator positioned on the retainer, a staple cartridge positioned on the retainer, and the insertion tool of FIG. 434 engaged with the retainer, wherein a portion of the insertion tool is removed for purposes of illustration;

FIG. 440 is a side view of a retainer assembly comprising the retainer of FIG. 432, a tissue thickness compensator positioned on the retainer, and the insertion tool of FIG. 434 engaged with the retainer, wherein a portion of the insertion tool is removed for purposes of illustration;

FIG. 441 illustrates the retainer assembly of FIG. 439 being inserted into a surgical instrument comprising an anvil and a staple cartridge channel, wherein a portion of the insertion tool is removed for the purposes of illustration;

FIG. 442 illustrates the retainer assembly of FIG. 439 being inserted into a surgical instrument comprising an anvil and a staple cartridge channel, wherein a portion of the insertion tool is removed for the purposes of illustration;

FIG. 443 illustrates the insertion tool of FIG. 434 being moved relative to the retainer to engage the staple cartridge in the staple cartridge channel and to engage the tissue thickness compensator with the anvil, wherein a portion of the insertion tool is removed for the purposes of illustration;

FIG. 444 illustrates the insertion tool of FIG. 434 being moved relative to the retainer to disengage the retainer from the tissue thickness compensator and from the staple cartridge, wherein a portion of the insertion tool is removed for the purposes of illustration;

FIG. 445 is a cross-sectional view of a tissue thickness compensator attached to an anvil of a surgical stapling instrument in accordance with at least one embodiment;

FIG. 446 is a diagram illustrating deformed staples at least partially capturing the tissue thickness compensator of FIG. 445 therein;

FIG. 447 is a cross-sectional view of an end effector of a surgical stapling instrument including a staple cartridge comprising a first tissue thickness compensator and an anvil comprising a second tissue thickness compensator in accordance with at least one embodiment;

FIG. 448 is a cross-sectional view of the end effector of FIG. 447 illustrating staples from the staple cartridge moved from an unfired position to a fired position;

FIG. 449 is a perspective view of a tissue thickness compensator attached to an anvil of an end effector wherein the tissue thickness compensator comprises a plurality of capsules in accordance with at least one embodiment;

FIG. 449A is a partial perspective view of the tissue thickness compensator of FIG. 449;

FIG. 450 is a cross-sectional view of staples being moved from an unfired position to a fired position to puncture the capsules of the tissue thickness compensator of FIG. 449;

FIG. 451 is an exploded view of an anvil and a tissue thickness compensator in accordance with at least one embodiment;

FIG. 452 is a cross-sectional view of an anvil comprising a plurality of staple forming pockets and a tissue thickness compensator comprising a plurality of capsules aligned with the forming pockets in accordance with at least one embodiment;

FIG. 453 is a detail view of the capsules of the tissue thickness compensator of FIG. 452;

FIG. 454 is a diagram illustrating the anvil and the tissue thickness compensator of FIG. 452 positioned relative to tissue which is to be stapled by staples from a staple cartridge positioned on the opposite side of the tissue;

FIG. 455 is a diagram illustrating the anvil of FIG. 452 moved toward the staple cartridge of FIG. 454 and staples partially fired from the staple cartridge;

FIG. 456 is a diagram illustrating the staples of FIG. 455 in a fully-fired configuration and the capsules of the tissue thickness compensator of FIG. 452 in a ruptured state;

FIG. 457 is a diagram illustrating a staple of FIG. 455 in a misfired condition;

FIG. 458 is a diagram illustrating the staples of FIG. 455 in a fully-fired configuration and the tissue thickness compensator of FIG. 452 in at least partially transected condition;

FIG. 459 is a cross-sectional perspective view of an alternative embodiment of a tissue thickness compensator in accordance with at least one embodiment;

FIG. 460 is a perspective view of an alternative embodiment of a tissue thickness compensator comprising a plurality of capsules aligned with a cutting member of a surgical stapling instrument;

FIG. 461 is a detail view of the capsules of FIG. 460;

FIG. 462 is a cross-sectional view of the tissue thickness compensator of FIG. 460 comprising a plurality of capsules aligned with a knife slot of an anvil of a surgical stapling instrument;

FIGS. 463 and 464 illustrate an alternative embodiment of a tissue thickness compensator being attached to an anvil;

FIG. 465 is a cross-sectional exploded view of an anvil and a compensator in accordance with at least one embodiment;

FIG. 466 illustrates the compensator of FIG. 465 attached to the anvil;

FIG. 467 is a partial perspective view of a tissue thickness compensator and a cutting member incising the tissue thickness compensator in accordance with at least one embodiment;

FIG. 468 is a partial cross-sectional view of an alternative embodiment of a tissue thickness compensator in accordance with at least one embodiment;

FIG. 469 is a partial cross-sectional view of another alternative embodiment of a tissue thickness compensator in accordance with at least one embodiment;

FIG. 470 is an illustration depicting a tissue thickness compensator comprising a plurality of irregular and/or asymmetrical cavities in accordance with various embodiments;

FIG. 471 is a partial cut-away view of a tissue thickness compensator attached to an anvil of a surgical stapling instrument in accordance with at least one embodiment;

FIG. 472 is a perspective view of a seamless extruded casing, or outer tube, of a tissue thickness compensator in accordance with at least one embodiment;

FIG. 473 is a perspective view of another seamless extruded casing, or outer tube, of a tissue thickness compensator in accordance with at least one embodiment;

FIG. 474 is a perspective view of oxidized regenerated cellulose fibers;

FIG. 475 is a perspective view of oxidized regenerated cellulose fibers which are shorter than the fibers of FIG. 474;

FIG. 476 is a diagram illustrating the fibers of FIG. 474 being woven into a strand utilizing the fibers of FIG. 475;

FIG. 477 depicts the strand of FIG. 476 being fluffed and at least partially cut;

FIG. 478 depicts a grasper inserted through a casing, or outer tube, of a tissue thickness compensator and positioned to grasp the strand of FIG. 476;

FIG. 479 illustrates the grasper of FIG. 478 being withdrawn from the casing and the strand of FIG. 476 being pulled through the casing;

FIG. 480 illustrates the casing and the strand of FIG. 479 being segmented;

FIG. 481 illustrates the ends of the casing being heat-welded and/or sealed;

FIG. 482 illustrates a process for creating a tissue thickness compensator without lateral seams;

FIG. 483 illustrates an anvil of a surgical stapling instrument and a plurality of compensators which can be selectively attached to the anvil, wherein each of the compensators comprises an array of capillary channels;

FIG. 484 is a plan view of a compensator configured to be attached to an anvil;

FIG. 485 is a detail view of a portion of the compensator of FIG. 484;

FIG. 486 is a perspective view of an end effector of a surgical stapling instrument;

FIG. 487 is another perspective view of the end effector of FIG. 486 illustrating a fluid being placed on a tissue thickness compensator of the end effector;

FIG. 488 is another perspective view of the end effector of FIG. 488 illustrating a compensator attached to an anvil of the end effector;

FIG. 489 is a detail view of an array of capillary channels on the compensator of FIG. 488;

FIG. 490 is an exploded view of a compensator comprising a plurality of layers in accordance with at least one embodiment;

FIG. 491 is an exploded view of a compensator and an anvil of a surgical stapling instrument in accordance with at least one embodiment;

FIG. 492 is a partial cross-sectional view of the compensator and the anvil of FIG. 491;

FIG. 493 is an exploded view of a compensator comprising a cellular ingrowth matrix in accordance with at least one embodiment;

FIG. 494 is a perspective view of the compensator of FIG. 493;

FIG. 495 is a perspective view of a fibrous layer of material for a compensator;

FIG. 496 is a perspective view of a plurality of fibrous layers stacked on one another in accordance with at least one embodiment;

FIG. 497 is a perspective view of another plurality of fibrous layers stacked on one another in accordance with at least one embodiment;

FIG. 498 is a perspective view of a fibrous layer of material for a compensator;

FIG. 499 is a perspective view of a plurality of fibrous layers stacked on one another wherein the fibers are arranged in different directions in accordance with at least one embodiment;

FIG. 500 is a perspective view of another plurality of fibrous layers stacked on one another in accordance with at least one embodiment;

FIG. 501 is a perspective view of an end effector insert and an end effector of a surgical instrument in accordance with at least one embodiment;

FIG. 502 is an elevational view of a tissue thickness compensator positioned in an end effector of a surgical instrument in accordance with at least one embodiment;

FIG. 503 is an elevational view of a tissue thickness compensator positioned in the end effector of the surgical instrument in accordance with at least one embodiment;

FIG. 504 is a perspective view of a sleeve positioned on an anvil for the end effector of the surgical instrument in accordance with at least one embodiment;

FIG. 505 is a plan view of a pronged portion of the sleeve of FIG. 504;

FIG. 506 is an elevational view of the pronged portion of the sleeve of FIG. 504;

FIG. 507 is an end view of the pronged portion of the sleeve of FIG. 504;

FIG. 508 is a perspective view of the pronged portion of the sleeve of FIG. 504;

FIG. 509 is a plan view of a tissue compensator of a sleeve in accordance with at least one embodiment;

FIG. 510 is a perspective view of the tissue compensator of FIG. 509;

FIG. 511 is an elevational view of the tissue compensator of FIG. 509;

FIG. 512 is a plan view of a tissue compensator of a sleeve in accordance with at least one embodiment;

FIG. 513 is a perspective view of the tissue compensator of FIG. 512;

FIG. 514 is an elevational view of the tissue compensator of FIG. 512;

FIG. 515 is a perspective view of a nose of the sleeve of FIG. 504;

FIG. 516 is another perspective view of the nose of FIG. 515;

FIG. 517 is a plan view of the nose of FIG. 515 depicting the inner geometry in phantom lines;

FIG. 518 is an elevational view of the nose of FIG. 515 depicting the inner geometry in phantom lines;

FIG. 519 is another perspective view of the sleeve of FIG. 504 positioned on the anvil;

FIG. 520 is a plan view of the sleeve of FIG. 504 positioned on the anvil;

FIG. 521 is an elevational view of the sleeve of FIG. 504 positioned on the anvil;

FIG. 522 is a plan view of the sleeve of FIG. 504 positioned on the anvil depicting a translating firing bar shown in phantom lines;

FIG. 523 is an elevational view of the sleeve of FIG. 504 positioned on the anvil depicting a translating firing bar shown in phantom lines;

FIG. 524 is a plan view of the sleeve of FIG. 504 positioned on the anvil depicting the release of the nose from the sleeve;

FIG. 525 is an elevational view of the sleeve of FIG. 504 positioned on the anvil depicting the release of the nose from the sleeve;

FIG. 526 is a plan view of the sleeve of FIG. 504 positioned on the anvil depicting the firing bar in phantom lines and the release of the nose from the sleeve;

FIG. 527 is an elevational view of the sleeve of FIG. 504 positioned on the anvil depicting the firing bar in phantom lines and the release of the nose from the sleeve;

FIG. 528 is a partial perspective view of the sleeve, the anvil, and the firing bar of FIG. 526;

FIG. 529 is another partial perspective view of the sleeve, the anvil, and the firing bar of FIG. 526;

FIG. 530 is an elevational cross-sectional view of the sleeve and the anvil of FIG. 504;

FIG. 531 is an elevational cross-sectional view of the anvil of FIG. 504 depicting the release of the tissue compensator from the sleeve;

FIG. 532 is a plan view of an end effector insert in accordance with at least one embodiment;

FIG. 533 is an elevational view of the end effector insert of FIG. 532;

FIG. 534 is a perspective view of the end effector insert of FIG. 534;

FIG. 535 is a partial perspective view of the end effector insert of FIG. 532 depicting the end effector insert engaging the anvil of the end effector of a surgical instrument;

FIG. 536 is a partial perspective view of the end effector insert of FIG. 532 depicting the end effector insert engaging the staple cartridge of the end effector of a surgical instrument;

FIG. 537 is an elevational view of the end effector insert of FIG. 532 depicting the end effector insert engaging the end effector of a surgical instrument;

FIG. 538 is an elevational view of the end effector insert of FIG. 532 positioned in the end effector of a surgical instrument;

FIG. 539 is a perspective view of a tissue thickness compensator positioned in the end effector of a surgical instrument in accordance with at least one embodiment illustrated with a portion of the tissue thickness compensator cut away;

FIG. 540 is a perspective view of the tissue thickness compensator of FIG. 539 secured to the anvil of the end effector by a static charge;

FIG. 541 is a perspective view of the tissue thickness compensator of FIG. 539 secured to the anvil of the end effector by suction elements;

FIG. 542 is a perspective view of the tissue thickness compensator of FIG. 539 secured to the anvil of the end effector by hook and loop fasteners;

FIG. 543 is a partial perspective view of the tissue thickness compensator of FIG. 539 secured to the anvil of the end effector by a band;

FIG. 544 is a partial perspective view of the tissue thickness compensator of FIG. 539 secured to the anvil of the end effector by a sock at the distal end of the tissue thickness compensator;

FIG. 545 is a perspective partial cross-sectional view of a tissue thickness compensator secured to the anvil of the end effector of a surgical instrument in accordance with at least one embodiment;

FIG. 546 is an elevational cross-sectional view of the tissue thickness compensator of FIG. 545;

FIG. 547 is another elevational cross-sectional view of the tissue thickness compensator of FIG. 545;

FIG. 548 is an elevational cross-sectional view of a tissue thickness compensator secured to the anvil of the end effector of a surgical instrument depicting a latch in a closed position in accordance with at least one embodiment;

FIG. 549 is an elevational cross-sectional view the tissue thickness compensator of FIG. 548 depicting the latch in the open position;

FIG. 550 is an elevational cross-sectional view of a tissue thickness compensator secured to the anvil of the end effector of a surgical instrument in accordance with at least one embodiment;

FIG. 551 is an elevational cross-sectional view of a tissue thickness compensator secured to the anvil of the end effector of a surgical instrument in accordance with at least one embodiment;

FIG. 552 is an elevational cross-sectional view of a tissue thickness compensator secured to the anvil of the end effector of a surgical instrument in accordance with at least one embodiment;

FIG. 553 is an elevational cross-sectional view of a tissue thickness compensator secured to the anvil of the end effector of the surgical instrument in accordance with at least one embodiment;

FIG. 554 is a perspective cross-sectional exploded view of a tissue thickness compensator secured to an anvil of an end effector of the surgical instrument in accordance with at least one embodiment;

FIG. 555 is a perspective view of the tissue thickness compensator of FIG. 554 depicting movement of the tissue thickness compensator towards the anvil;

FIG. 556 is an elevational cross-sectional view of the tissue thickness compensator of FIG. 554 engaged with the anvil;

FIG. 557 is a perspective cross-sectional view of a tissue thickness compensator secured to the anvil of the end effector of a surgical instrument in accordance with at least one embodiment;

FIG. 558 is a perspective cross-sectional exploded view of the tissue thickness compensator and the anvil of FIG. 557;

FIG. 559 is an elevational view of a tissue thickness compensator in accordance with at least one embodiment;

FIG. 560 is a perspective view of the tissue thickness compensator of FIG. 559;

FIG. 561 is another perspective of the tissue thickness compensator of FIG. 559;

FIG. 562 is a perspective view of the tissue thickness compensator of FIG. 559 depicting movement of the tissue thickness compensator towards the anvil of the end effector of a surgical instrument;

FIG. 563 is a plan cross-sectional view of the tissue thickness compensator of FIG. 559 positioned on the anvil;

FIG. 564 is a perspective view of the tissue thickness compensator of FIG. 559 positioned on the anvil;

FIG. 565 is a perspective view of the tissue thickness compensator of FIG. 559 positioned on the anvil illustrating a cutting element severing the tissue thickness compensator;

FIG. 566 is a cross-sectional elevational view of an end effector of a surgical stapling instrument comprising an anvil and a chargeable layer in accordance with at least one embodiment;

FIG. 567 is a bottom view of the anvil and the chargeable layer of FIG. 566;

FIG. 568 is an exploded view of the anvil and the chargeable layer of FIG. 566 and a tissue thickness compensator releasably attachable to the chargeable layer;

FIG. 569 is a perspective view of a tissue thickness compensator in accordance with at least one embodiment;

FIG. 570 is a plan view of the tissue thickness compensator of FIG. 569;

FIG. 569A is a perspective view of a tissue thickness compensator in accordance with at least one alternative embodiment;

FIG. 570A is a plan view of the tissue thickness compensator of FIG. 569A;

FIG. 571 is a perspective view of a tissue thickness compensator in accordance with at least one alternative embodiment;

FIG. 572 is a plan view of the tissue thickness compensator of FIG. 571;

FIG. 573 is a perspective view of a tissue thickness compensator in accordance with at least one embodiment;

FIG. 574 is a perspective view of a tissue thickness compensator attached to an anvil in accordance with at least one embodiment;

FIG. 575 is a cross-sectional view of the anvil and the tissue thickness compensator of FIG. 574;

FIG. 576 is a cross-sectional view of the tissue thickness compensator of FIG. 574;

FIG. 577 is a perspective view of a tissue thickness compensator attached to an anvil in accordance with at least one alternative embodiment;

FIG. 578 is a cross-sectional view of the anvil and the tissue thickness compensator of FIG. 577;

FIG. 579 is a cross-sectional view of the tissue thickness compensator of FIG. 577 in an open configuration;

FIG. 580 is a perspective view of a tissue thickness compensator attached to an anvil in accordance with at least one alternative embodiment;

FIG. 581 is a cross-sectional view of the anvil and the tissue thickness compensator of FIG. 580;

FIG. 582 is a perspective view of a tissue thickness compensator attached to an anvil in accordance with at least one alternative embodiment;

FIG. 583 is a cross-sectional view of the anvil and the tissue thickness compensator of FIG. 582;

FIG. 584 is a perspective view of a tissue thickness compensator attached to an anvil in accordance with at least one alternative embodiment;

FIG. 585 is a cross-sectional view of the anvil and the tissue thickness compensator of FIG. 584;

FIG. 586 is a perspective view of a tissue thickness compensator attached to an anvil in accordance with at least one alternative embodiment; and FIG. 587 is a cross-sectional view of the anvil and the tissue thickness compensator of FIG. 586.

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

The Applicant of the present application also owns the U.S. patent applications identified below which are each herein incorporated by reference in their respective entirety:

U.S. patent application Ser. No. 12/894,311, entitled SURGICAL INSTRUMENTS WITH RECONFIGURABLE SHAFT SEGMENTS, now U.S. Pat. No. 8,763,877;

U.S. patent application Ser. No. 12/894,340, entitled SURGICAL STAPLE CARTRIDGES SUPPORTING NON-LINEARLY ARRANGED STAPLES AND SURGICAL STAPLING INSTRUMENTS WITH COMMON STAPLE-FORMING POCKETS, U.S. Pat. No. 8,899,463;

U.S. patent application Ser. No. 12/894,327, entitled JAW CLOSURE ARRANGEMENTS FOR SURGICAL INSTRUMENTS, now U.S. Pat. No. 8,978,956;

U.S. patent application Ser. No. 12/894,351, entitled SURGICAL CUTTING AND FASTENING INSTRUMENTS WITH SEPARATE AND DISTINCT FASTENER DEPLOYMENT AND TISSUE CUTTING SYSTEMS, now U.S. Pat. No. 9,113,864;

U.S. patent application Ser. No. 12/894,338, entitled IMPLANTABLE FASTENER CARTRIDGE HAVING A NON-UNIFORM ARRANGEMENT, now U.S. Pat. No. 8,864,007;

U.S. patent application Ser. No. 12/894,369, entitled IMPLANTABLE FASTENER CARTRIDGE COMPRISING A SUPPORT RETAINER, now U.S. Patent Application Publication No. 2012/0080344.

U.S. patent application Ser. No. 12/894,312, entitled IMPLANTABLE FASTENER CARTRIDGE COMPRISING MULTIPLE LAYERS, now U.S. Pat. No. 8,925,782;

U.S. patent application Ser. No. 12/894,377, entitled SELECTIVELY ORIENTABLE IMPLANTABLE FASTENER CARTRIDGE, now U.S. Pat. No. 8,393,514;

U.S. patent application Ser. No. 12/894,339, entitled SURGICAL STAPLING INSTRUMENT WITH COMPACT ARTICULATION CONTROL ARRANGEMENT, now U.S. Pat. No. 8,840,003;

U.S. patent application Ser. No. 12/894,360, entitled SURGICAL STAPLING INSTRUMENT WITH A VARIABLE STAPLE FORMING SYSTEM, now U.S. Pat. No. 9,113,862;

U.S. patent application Ser. No. 12/894,322, entitled SURGICAL STAPLING INSTRUMENT WITH INTERCHANGEABLE STAPLE CARTRIDGE ARRANGEMENTS, now U.S. Pat. No. 8,740,034;

U.S. patent application Ser. No. 12/894,350, entitled SURGICAL STAPLE CARTRIDGES WITH DETACHABLE SUPPORT STRUCTURES AND SURGICAL STAPLING INSTRUMENTS WITH SYSTEMS FOR PREVENTING ACTUATION MOTIONS WHEN A CARTRIDGE IS NOT PRESENT, now U.S. Patent Application Publication No. 2012/0080478;

U.S. patent application Ser. No. 12/894,383, entitled IMPLANTABLE FASTENER CARTRIDGE COMPRISING BIOABSORBABLE LAYERS, now U.S. Pat. No. 8,752,699;

U.S. patent application Ser. No. 12/894,389, entitled COMPRESSIBLE FASTENER CARTRIDGE, now U.S. Pat. No. 8,740,037;

U.S. patent application Ser. No. 12/894,345, entitled FASTENERS SUPPORTED BY A FASTENER CARTRIDGE SUPPORT, now U.S. Pat. No. 8,783,542;

U.S. patent application Ser. No. 12/894,306, entitled COLLAPSIBLE FASTENER CARTRIDGE, now U.S. Pat. No. 9,044,227;

U.S. patent application Ser. No. 12/894,318, entitled FASTENER SYSTEM COMPRISING A PLURALITY OF CONNECTED RETENTION MATRIX ELEMENTS, now U.S. Pat. No. 8,814,024;

U.S. patent application Ser. No. 12/894,330, entitled FASTENER SYSTEM COMPRISING A RETENTION MATRIX AND AN ALIGNMENT MATRIX, now U.S. Pat. No. 8,757,465;

U.S. patent application Ser. No. 12/894,361, entitled FASTENER SYSTEM COMPRISING A RETENTION MATRIX, now U.S. Pat. No. 8,529,600;

U.S. patent application Ser. No. 12/894,367, entitled FASTENING INSTRUMENT FOR DEPLOYING A FASTENER SYSTEM COMPRISING A RETENTION MATRIX, now U.S. Pat. No. 9,033,203;

U.S. patent application Ser. No. 12/894,388, entitled FASTENER SYSTEM COMPRISING A RETENTION MATRIX AND A COVER, now U.S. Pat. No. 8,474,677; U.S. patent application Ser. No. 12/894,376, entitled FASTENER SYSTEM COMPRISING A PLURALITY OF FASTENER CARTRIDGES, now U.S. Pat. No. 9,044,228;

U.S. patent application Ser. No. 13/097,865, entitled SURGICAL STAPLER ANVIL COMPRISING A PLURALITY OF FORMING POCKETS, now U.S. Pat. No. 9,295,464; U.S. patent application Ser. No. 13/097,936, entitled TISSUE THICKNESS COMPENSATOR FOR A SURGICAL STAPLER, now U.S. Pat. No. 8,657,176;

U.S. patent application Ser. No. 13/097,954, entitled STAPLE CARTRIDGE COMPRISING A VARIABLE THICKNESS COMPRESSIBLE PORTION, now U.S. Patent Application Publication No. 2012/0080340;

U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336;

U.S. patent application Ser. No. 13/097,928, entitled TISSUE THICKNESS COMPENSATOR COMPRISING DETACHABLE PORTIONS, now U.S. Pat. No. 8,746,535;

U.S. patent application Ser. No. 13/097,891, entitled TISSUE THICKNESS COMPENSATOR FOR A SURGICAL STAPLER COMPRISING AN ADJUSTABLE ANVIL, now U.S. Pat. No. 8,864,009;

U.S. patent application Ser. No. 13/097,948, entitled STAPLE CARTRIDGE COMPRISING AN ADJUSTABLE DISTAL PORTION, now U.S. Pat. No. 8,978,954;

U.S. patent application Ser. No. 13/097,907, entitled COMPRESSIBLE STAPLE CARTRIDGE ASSEMBLY, now U.S. Pat. No. 9,301,755;

U.S. patent application Ser. No. 13/097,861, entitled TISSUE THICKNESS COMPENSATOR COMPRISING PORTIONS HAVING DIFFERENT PROPERTIES, now U.S. Pat. No. 9,113,865;

U.S. patent application Ser. No. 13/097,869, entitled STAPLE CARTRIDGE LOADING ASSEMBLY, now U.S. Pat. No. 8,857,694;

U.S. patent application Ser. No. 13/097,917, entitled COMPRESSIBLE STAPLE CARTRIDGE COMPRISING ALIGNMENT MEMBERS, now U.S. Pat. No. 8,777,004;

U.S. patent application Ser. No. 13/097,873, entitled STAPLE CARTRIDGE COMPRISING A RELEASABLE PORTION, now U.S. Pat. No. 8,740,038;

U.S. patent application Ser. No. 13/097,938, entitled STAPLE CARTRIDGE COMPRISING COMPRESSIBLE DISTORTION RESISTANT COMPONENTS, now U.S. Pat. No. 9,016,542;

U.S. patent application Ser. No. 13/097,924, entitled STAPLE CARTRIDGE COMPRISING A TISSUE THICKNESS COMPENSATOR, now U.S. Pat. No. 9,168,038;

U.S. patent application Ser. No. 13/242,029, entitled SURGICAL STAPLER WITH FLOATING ANVIL, now U.S. Pat. No. 8,893,949;

U.S. patent application Ser. No. 13/242,066, entitled CURVED END EFFECTOR FOR A STAPLING INSTRUMENT, now U.S. Patent Application Publication No. 2012/0080498;

U.S. patent application Ser. No. 13/242,086, entitled STAPLE CARTRIDGE INCLUDING COLLAPSIBLE DECK, now U.S. Pat. No. 9,055,941;

U.S. patent application Ser. No. 13/241,912, entitled STAPLE CARTRIDGE INCLUDING COLLAPSIBLE DECK ARRANGEMENT, now U.S. Pat. No. 9,050,084;

U.S. patent application Ser. No. 13/241,922, entitled SURGICAL STAPLER WITH STATIONARY STAPLE DRIVERS, now U.S. Pat. No. 9,216,019;

U.S. patent application Ser. No. 13/241,637, entitled SURGICAL INSTRUMENT WITH TRIGGER ASSEMBLY FOR GENERATING MULTIPLE ACTUATION MOTIONS, now U.S. Pat. No. 8,789,741; and U.S. patent application Ser. No. 13/241,629, entitled SURGICAL INSTRUMENT WITH SELECTIVELY ARTICULATABLE END EFFECTOR, now U.S. Patent Application Publication No. 2012/0074200.

The Applicant of the present application also owns the U.S. patent applications identified below which were filed on Mar. 28, 2012, and which are each herein incorporated by reference in their respective entirety:

U.S. patent application Ser. No. 13/433,096, entitled TISSUE THICKNESS COMPENSATOR COMPRISING A PLURALITY OF CAPSULES, now U.S. Pat. No. 9,301,752;

U.S. patent application Ser. No. 13/433,103, entitled TISSUE THICKNESS COMPENSATOR COMPRISING A PLURALITY OF LAYERS, now U.S. Pat. No. 9,433,419;

U.S. patent application Ser. No. 13/433,098, entitled EXPANDABLE TISSUE THICKNESS COMPENSATOR, now U.S. Pat. No. 9,301,753;

U.S. patent application Ser. No. 13/433,102, entitled TISSUE THICKNESS COMPENSATOR COMPRISING A RESERVOIR, now U.S. Pat. No. 9,232,941;

U.S. patent application Ser. No. 13/433,136, entitled TISSUE THICKNESS COMPENSATOR COMPRISING AT LEAST ONE MEDICAMENT, now U.S. Pat. No. 9,839,420;

U.S. patent application Ser. No. 13/433,141, entitled TISSUE THICKNESS COMPENSATOR COMPRISING CONTROLLED RELEASE AND EXPANSION, now U.S. Patent Application Publication No. 2012/0241493;

U.S. patent application Ser. No. 13/433,144, entitled TISSUE THICKNESS COMPENSATOR COMPRISING FIBERS TO PRODUCE A RESILIENT LOAD, now U.S. Pat. No. 9,277,919;

U.S. patent application Ser. No. 13/433,148, entitled TISSUE THICKNESS COMPENSATOR COMPRISING STRUCTURE TO PRODUCE A RESILIENT LOAD, now U.S. Pat. No. 9,220,500;

U.S. patent application Ser. No. 13/433,155, entitled TISSUE THICKNESS COMPENSATOR COMPRISING RESILIENT MEMBERS, now U.S. Pat. No. 9,480,476;

U.S. patent application Ser. No. 13/433,163, entitled METHODS FOR FORMING TISSUE THICKNESS COMPENSATOR ARRANGEMENTS FOR SURGICAL STAPLERS, now U.S. Patent Application Publication No. 2012/0248169;

U.S. patent application Ser. No. 13/433,167, entitled TISSUE THICKNESS COMPENSATORS, now U.S. Pat. No. 9,220,501;

U.S. patent application Ser. No. 13/433,175, entitled LAYERED TISSUE THICKNESS COMPENSATOR, now U.S. Pat. No. 9,332,974;

U.S. patent application Ser. No. 13/433,179, entitled TISSUE THICKNESS COMPENSATORS FOR CIRCULAR SURGICAL STAPLERS, now U.S. Pat. No. 9,364,233;

U.S. patent application Ser. No. 13/433,115, entitled TISSUE THICKNESS COMPENSATOR COMPRISING CAPSULES DEFINING A LOW PRESSURE ENVIRONMENT, now U.S. Pat. No. 9,204,880;

U.S. patent application Ser. No. 13/433,118, entitled TISSUE THICKNESS COMPENSATOR COMPRISED OF A PLURALITY OF MATERIALS, now U.S. Pat. No. 9,414,838;

U.S. patent application Ser. No. 13/433,135, entitled MOVABLE MEMBER FOR USE WITH A TISSUE THICKNESS COMPENSATOR, now U.S. Pat. No. 9,517,063;

U.S. patent application Ser. No. 13/433,129, entitled TISSUE THICKNESS COMPENSATOR COMPRISING A PLURALITY OF MEDICAMENTS, now U.S. Pat. No. 9,211,120;

U.S. patent application Ser. No. 13/433,140, entitled TISSUE THICKNESS COMPENSATOR AND METHOD FOR MAKING THE SAME, now U.S. Pat. No. 9,241,714;

U.S. patent application Ser. No. 13/433,147, entitled TISSUE THICKNESS COMPENSATOR COMPRISING CHANNELS, now U.S. Pat. No. 9,351,730;

U.S. patent application Ser. No. 13/433,126, entitled TISSUE THICKNESS COMPENSATOR COMPRISING TISSUE INGROWTH FEATURES, now U.S. Pat. No. 9,320,523; and U.S. patent application Ser. No. 13/433,132, entitled DEVICES AND METHODS FOR ATTACHING TISSUE THICKNESS COMPENSATING MATERIALS TO SURGICAL STAPLING INSTRUMENTS, now U.S. Patent Application Publication No. 2013/0256373.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 1:
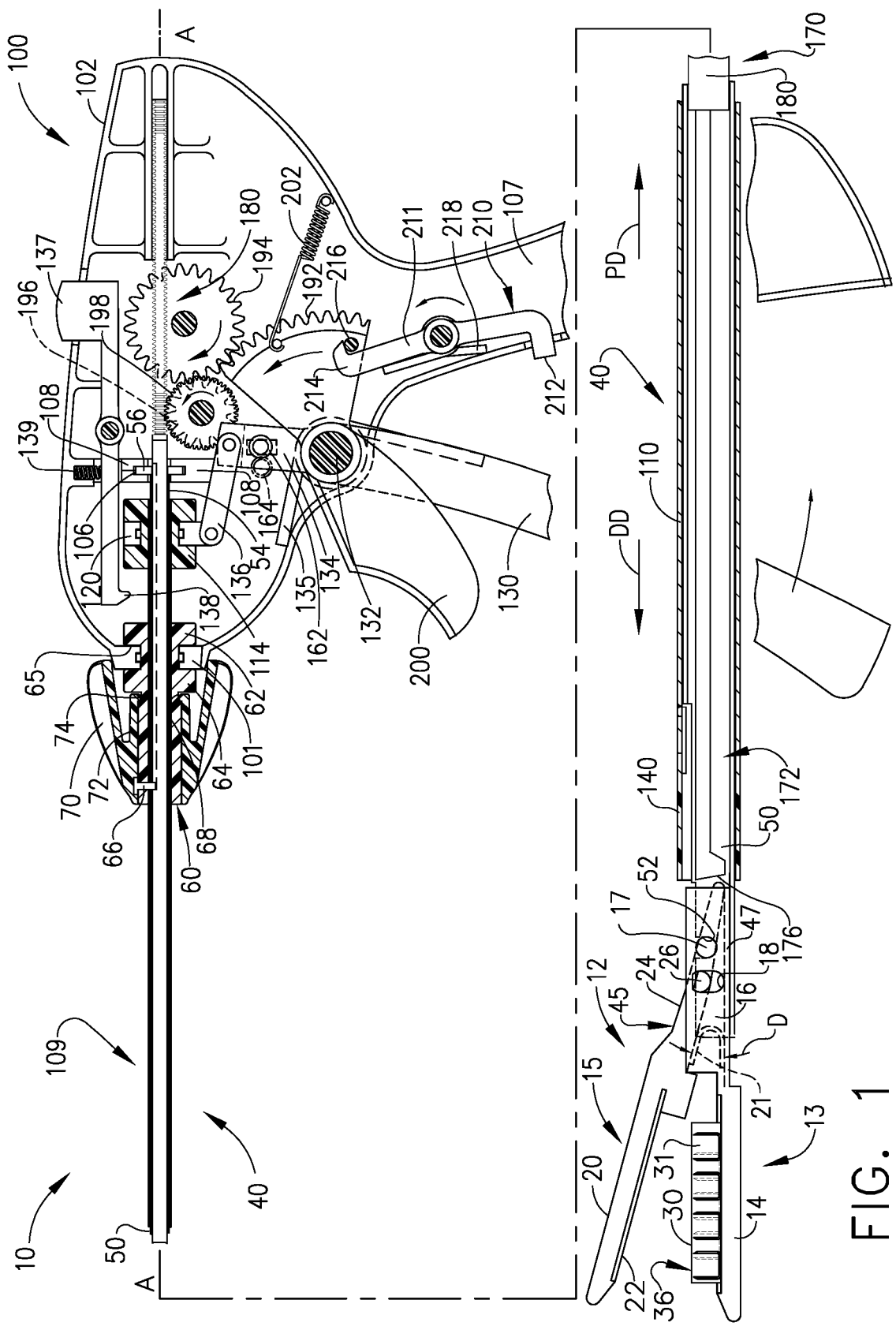
FIG. 1 is a cross-sectional view of a surgical instrument embodiment.

Turning to the Drawings wherein like numerals denote like components throughout the several views, FIG. 1 depicts a surgical instrument 10 that is capable of practicing several unique benefits. The surgical stapling instrument 10 is designed to manipulate and/or actuate various forms and sizes of end effectors 12 that are operably attached thereto. In the embodiment depicted in FIGS. 1-1E, for example, the end effector 12 includes an elongated channel 14 that forms a lower jaw 13 of the end effector 12. The elongated channel 14 is configured to support an "implantable" staple cartridge 30 and also movably support an anvil 20 that functions as an upper jaw 15 of the end effector 12.

In various embodiments, the elongated channel 14 may be fabricated from, for example, 300 & 400 Series, 17-4 & 17-7 stainless steel, titanium, etc. and be formed with spaced side walls 16. The anvil 20 may be fabricated from, for example, 300 & 400 Series, 17-4 & 17-7 stainless steel, titanium, etc. and have a staple forming undersurface, generally labeled as 22 that has a plurality of staple forming pockets 23 formed therein. See FIGS. 1B-1E. In addition, the anvil 20 has a bifurcated ramp assembly 24 that protrudes proximally therefrom. An anvil pin 26 protrudes from each lateral side of the ramp assembly 24 to be received within a corresponding slot or opening 18 in the side walls 16 of the elongated channel 14 to facilitate its movable or pivotable attachment thereto.

Figure 1A:
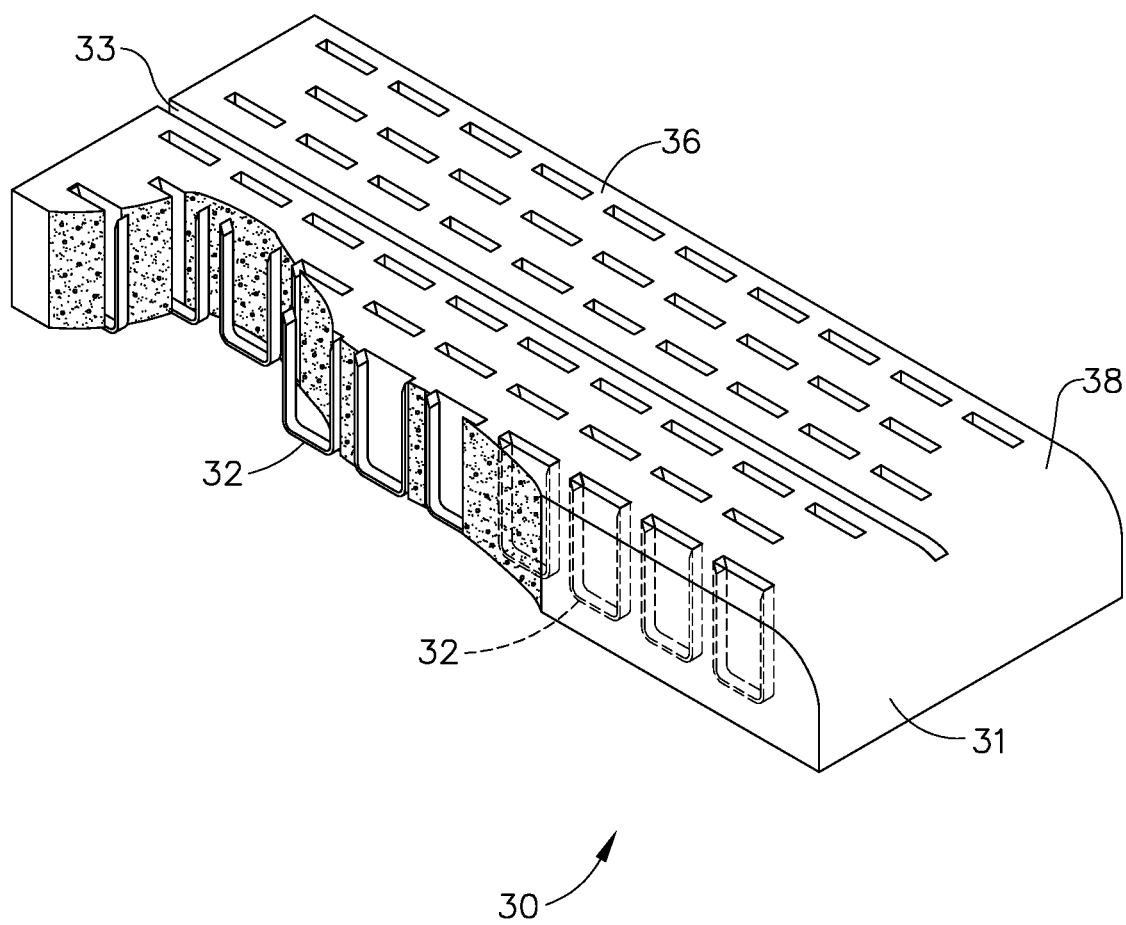
FIG. 1A is a perspective view of one embodiment of an implantable staple cartridge.

Various forms of implantable staple cartridges may be employed with the various embodiments of the surgical instruments disclosed herein. Specific staple cartridge configurations and constructions will be discussed in further detail below. However, in the embodiment depicted in FIG. 1A, an implantable staple cartridge 30 is shown. In at least one embodiment, the staple cartridge 30 has a body portion 31 that consists of a compressible hemostat material such as, for example, oxidized regenerated cellulose ("ORC") or a bio-absorbable foam in which lines of unformed metal staples 32 are supported. In at least some embodiments, in order to prevent the staple from being affected and the hemostat material from being activated during the introduction and positioning process, the entire cartridge may be coated or wrapped in a biodegradable film 38 such as a polydioxanon film sold under the trademark PDS® or with a Polyglycerol sebacate (PGS) film or other biodegradable films formed from PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured. The body 31 of staple cartridge 30 is sized to be removably supported within the elongated channel 14 as shown such that each staple 32 therein is aligned with corresponding staple forming pockets 23 in the anvil when the anvil 20 is driven into forming contact with the staple cartridge 30.

In use, once the end effector 12 has been positioned adjacent the target tissue, the end effector 12 is manipulated to capture or clamp the target tissue between an upper face 36 of the staple cartridge 30 and the staple forming surface 22 of the anvil 20. The staples 32 are formed by moving the anvil 20 in a path that is substantially parallel to the elongated channel 14 to bring the staple forming surface 22 and, more particularly, the staple forming pockets 23 therein into substantially simultaneous contact with the upper face 36 of the staple cartridge 30. As the anvil 20 continues to move into the staple cartridge 30, the legs 34 of the staples 32 contact a corresponding staple forming pocket 23 in anvil 20 which serves to bend the staple legs 34 over to form the staples 32 into a "B shape". Further movement of the anvil 20 toward the elongated channel 14 will further compress and form the staples 32 to a desired final formed height "FF".

The above-described staple forming process is generally depicted in FIGS. 1B-1E. For example, FIG. 1B illustrates the end effector 12 with target tissue "T" between the anvil 20 and the upper face 36 of the implantable staple cartridge 30. FIG. 1C illustrates the initial clamping position of the anvil 20 wherein the anvil has 20 been closed onto the target tissue "T" to clamp the target tissue "T" between the anvil 20 and the upper face 36 of the staple cartridge 30. FIG. 1D illustrates the initial staple formation wherein the anvil 20 has started to compress the staple cartridge 30 such that the legs 34 of the staples 32 are starting to be formed by the staple forming pockets 23 in the anvil 20. FIG. 1E illustrates the staple 32 in its final formed condition through the target tissue "T" with the anvil 20 removed for clarity purposes. Once the staples 32 have been formed and fastened to the target tissue "T", the surgeon will move the anvil 20 to the open position to enable the cartridge body 31 and the staples 32 to remain affixed to the target tissue while the end effector 12 is being withdrawn from the patient. The end effector 12 forms all of the staples simultaneously as the two jaws 13, 15 are clamped together. The remaining "crushed" body materials 31 act as both a hemostat (the ORC) and a staple line reinforcement (PGA, PDS or any of the other film compositions mentioned above 38). Also, since the staples 32 never have to leave the cartridge body 31 during forming, the likelihood of the staples 32 being malformed during forming is minimized. As used herein the term "implantable" means that, in addition to the staples, the cartridge body materials that support the staples will also remain in the patient and may eventually be absorbed by the patient's body. Such implantable staple cartridges are distinguishable from prior cartridge arrangements that remain positioned within the end effector in their entirety after they have been fired.

In various implementations, the end effector 12 is configured to be coupled to an elongated shaft assembly 40 that protrudes from a handle assembly 100. The end effector 12 (when closed) and the elongated shaft assembly 40 may have similar cross-sectional shapes and be sized to operably pass through a trocar tube or working channel in another form of access instrument. As used herein, the term "operably pass" means that the end effector and at least a portion of the elongated shaft assembly may be inserted through or passed through the channel or tube opening and can be manipulated therein as needed to complete the surgical stapling procedure. In some embodiments, when in a closed position, the jaws 13 and 15 of the end effector 12 may provide the end effector with a roughly circular cross-sectional shape that facilitates its passage through a circular passage/opening. However, the end effectors of various embodiments of the present invention, as well as the elongated shaft assembly embodiments, could conceivably be provided with other cross-sectional shapes that could otherwise pass through access passages and openings that have non-circular cross-sectional shapes. Thus, an overall size of a cross-section of a closed end effector will be related to the size of the passage or opening through which it is intended to pass. Thus, one end effector for example, may be referred to as a "5 mm" end effector which means it can operably pass through an opening that is at least approximately 5 mm in diameter.

In various embodiments, the elongated shaft assembly 40 may have an outer diameter that is substantially the same as the outer diameter of the end effector 12 when in a closed position. For example, a 5 mm end effector may be coupled to an elongated shaft assembly 40 that has 5 mm cross-sectional diameter. However, as the present Detailed Description proceeds, it will become apparent that various embodiments of the present may be effectively used in connection with different sizes of end effectors. For example, a 10 mm end effector may be attached to an elongated shaft that has a 5 mm cross-sectional diameter. Conversely, for those applications wherein a 10 mm or larger access opening or passage is provided, the elongated shaft assembly 40 may have a 10 mm (or larger) cross-sectional diameter, but may also be able to actuate a 5 mm or 10 mm end effector. Accordingly, the outer shaft 40 may have an outer diameter that is the same as or is different from the outer diameter of a closed end effector 12 attached thereto.

As depicted, the elongated shaft assembly 40 extends distally from the handle assembly 100 in a generally straight line to define a longitudinal axis A-A. In various embodiments, for example, the elongated shaft assembly 40 may be approximately 9-16 inches (229-406 mm) long. However, the elongated shaft assembly 40 may be provided in other lengths and, in other embodiments, may have joints therein or be otherwise configured to facilitate articulation of the end effector 12 relative to other portions of the shaft or handle assembly as will be discussed in further detail below. In various embodiments, the elongated shaft assembly 40 includes a spine member 50 that extends from the handle assembly 100 to the end effector 12. The proximal end of the elongated channel 14 of the end effector 12 has a pair of retention trunnions 17 protruding therefrom that are sized to be received within corresponding trunnion openings or cradles 52 that are provided in a distal end of the spine member 50 to enable the end effector 12 to be removably coupled the elongated shaft assembly 40. The spine member 50 may be fabricated from, for example, 6061 or 7075 aluminum, stainless steel, titanium, etc.

In various embodiments, the handle assembly 100 comprises a pistol grip-type housing that may be fabricated in two or more pieces for assembly purposes. For example, the handle assembly 100 as shown comprises a right hand case member 102 and a left hand case member (not illustrated) that are molded or otherwise fabricated from a polymer or plastic material and are designed to mate together. Such case members may be attached together by snap features, pegs and sockets molded or otherwise formed therein and/or by adhesive, screws, etc. The spine member 50 has a proximal end 54 that has a flange 56 formed thereon. The flange 56 is configured to be rotatably supported within a groove 106 formed by mating ribs 108 that protrude inwardly from each of the case members 102, 104. Such arrangement facilitates the attachment of the spine member 50 to the handle assembly 100 while enabling the spine member 50 to be rotated relative to the handle assembly 100 about the longitudinal axis A-A in a 360° path.

As can be further seen in FIG. 1, the spine member 50 passes through and is supported by a mounting bushing 60 that is rotatably affixed to the handle assembly 100. The mounting bushing 60 has a proximal flange 62 and a distal flange 64 that define a rotational groove 65 that is configured to rotatably receive a nose portion 101 of the handle assembly 100 therebetween. Such arrangement enables the mounting bushing 60 to rotate about longitudinal axis A-A relative to the handle assembly 100. The spine member 50 is non-rotatably pinned to the mounting bushing 60 by a spine pin 66. In addition, a rotation knob 70 is attached to the mounting bushing 60. In one embodiment, for example, the rotation knob 70 has a hollow mounting flange portion 72 that is sized to receive a portion of the mounting bushing 60 therein. In various embodiments, the rotation knob 70 may be fabricated from, for example, glass or carbon filled Nylon, polycarbonate, Ultem®, etc. and is affixed to the mounting bushing 60 by the spine pin 66 as well. In addition, an inwardly protruding retention flange 74 is formed on the mounting flange portion 72 and is configured to extend into a radial groove 68 formed in the mounting bushing 60. Thus, the surgeon may rotate the spine member 50 (and the end effector 12 attached thereto) about longitudinal axis A-A in a 360° path by grasping the rotation knob 70 and rotating it relative to the handle assembly 100.

In various embodiments, the anvil 20 is retained in an open position by an anvil spring 21 and/or another biasing arrangement. The anvil 20 is selectively movable from the open position to various closed or clamping and firing positions by a firing system, generally designated as 109. The firing system 109 includes a "firing member" 110 which, in various embodiments, comprises a hollow firing tube 110. The hollow firing tube 110 is axially movable on the spine member 50 and thus forms the outer portion of the elongated shaft assembly 40. The firing tube 110 may be fabricated from a polymer or other suitable material and have a proximal end that is attached to a firing yoke 114 of the firing system 109. In various embodiments for example, the firing yoke 114 may be over-molded to the proximal end of the firing tube 110. However, other fastener arrangements may be employed.

As can be seen in FIG. 1, the firing yoke 114 may be rotatably supported within a support collar 120 that is configured to move axially within the handle assembly 100. In various embodiments, the support collar 120 has a pair of laterally extending fins that are sized to be slidably received within fin slots formed in the right and left hand case members. Thus, the support collar 120 may slide axially within the handle housing 100 while enabling the firing yoke 114 and firing tube 110 to rotate relative thereto about the longitudinal axis A-A. In various embodiments, a longitudinal slot is provided through the firing tube 110 to enable the spine pin 66 to extend therethrough into the spine member 50 while facilitating the axial travel of the firing tube 110 on the spine member 50.

The firing system 109 further comprises a firing trigger 130 which serves to control the axial travel of the firing tube 110 on the spine member 50. See FIG. 1. Such axial movement in the distal direction of the firing tube 110 into firing interaction with the anvil 20 is referred to herein as "firing motion". As can be seen in FIG. 1, the firing trigger 130 is movably or pivotally coupled to the handle assembly 100 by a pivot pin 132. A torsion spring 135 is employed to bias the firing trigger 130 away from the pistol grip portion 107 of the handle assembly 100 to an un-actuated "open" or starting position. As can be seen in FIG. 1, the firing trigger 130 has an upper portion 134 that is movably attached to (pinned) firing links 136 that are movably attached to (pinned) the support collar 120. Thus, movement of the firing trigger 130 from the starting position (FIG. 1) toward an ending position adjacent the pistol grip portion 107 of the handle assembly 100 will cause the firing yoke 114 and the firing tube 110 to move in the distal direction "DD". Movement of the firing trigger 130 away from the pistol grip portion 107 of the handle assembly 100 (under the bias of the torsion spring 135) will cause the firing yoke 114 and firing tube 110 to move in the proximal direction "PD" on the spine member 50.

Various embodiments of the present invention may be employed with different sizes and configurations of implantable staple cartridges. For example, the surgical instrument 10, when used in connection with a first firing adapter 140, may be used with a 5 mm end effector 12 that is approximately 20 mm long (or in other lengths) which supports an implantable staple cartridge 30. Such end effector size may be particularly well-suited, for example, to complete relatively fine dissection and vascular transactions. However, as will be discussed in further detail below, the surgical instrument 10 may also be employed, for example, in connection with other sizes of end effectors and staple cartridges by replacing the first firing adapter 140 with a second firing adapter. In still other embodiments, the elongated shaft assembly 40 may configured to be attached to only one form or size of end effector.

One method of removably coupling the end effector 12 to the spine member 50 will now be explained. The coupling process is commenced by inserting the retention trunnions 17 on the elongated channel 14 into the trunnion cradles 52 in the spine member 50. Thereafter, the surgeon advances the firing trigger 130 toward the pistol grip 107 of the housing assembly 100 to distally advance the firing tube 110 and the first firing adapter 140 over a proximal end portion 47 of the elongated channel 14 to thereby retain the trunnions 17 in their respective cradles 52. Such position of the first firing adapter 140 over the trunnions 17 is referred to herein as the "coupled position". Various embodiments of the present invention may also have an end effector locking assembly for locking the firing trigger 130 in position after an end effector 12 has been attached to the spine member 50.

More specifically, one embodiment of the end effector locking assembly 160 includes a retention pin 162 that is movably supported in the upper portion 134 of the firing trigger 130. As discussed above, the firing tube 110 must initially be advanced distally to the coupled position wherein the first firing adapter 140 retains the retention trunnions 17 of the end effector 12 in the trunnion cradles 52 in the spine member 50. The surgeon advances the firing adapter 140 distally to the coupled position by pulling the firing trigger 130 from the starting position toward the pistol grip 107. As the firing trigger 130 is initially actuated, the retention pin 162 is moved distally until the firing tube 110 has advanced the first firing adapter 140 to the coupled position at which point the retention pin 162 is biased into a locking cavity 164 formed in the case member. In various embodiments, when the retention pin 162 enters into the locking cavity 164, the pin 162 may make an audible "click" or other sound, as well as provide a tactile indication to the surgeon that the end effector 12 has been "locked" onto the spine member 50. In addition, the surgeon cannot inadvertently continue to actuate the firing trigger 130 to start to form staples 32 in the end effector 12 without intentionally biasing the retention pin 162 out of the locking cavity 164. Similarly, if the surgeon releases the firing trigger 130 when in the coupled position, it is retained in that position by the retention pin 162 to prevent the firing trigger 130 from returning to the starting position and thereby releasing the end effector 12 from the spine member 50.

Various embodiments of the present invention may further include a firing system lock button 137 that is pivotally attached to the handle assembly 100. In one form, the firing system lock button 137 has a latch 138 formed on a distal end thereof that is oriented to engage the firing yoke 114 when the firing release button is in a first latching position. As can be seen in FIG. 1, a latch spring 139 serves to bias the firing system lock button 137 to the first latching position. In various circumstances, the latch 138 serves to engage the firing yoke 114 at a point where the position of the firing yoke 114 on the spine member 50 corresponds to a point wherein the first firing adapter 140 is about to distally advance up the clamping ramp 28 on the anvil 20. It will be understood that, as the first firing adapter 140 advances axially up the clamping ramp 28, the anvil 20 will move in a path such that its staple forming surface portion 22 is substantially parallel to the upper face 36 of the staple cartridge 30.

After the end effector 12 has been coupled to the spine member 50, the staple forming process is commenced by first depressing the firing system lock button 137 to enable the firing yoke 114 to be further moved distally on the spine member 50 and ultimately compress the anvil 20 into the staple cartridge 30. After depressing the firing system lock button 137, the surgeon continues to actuate the firing trigger 130 towards the pistol grip 107 thereby driving the first staple collar 140 up the corresponding staple forming ramp 29 to force the anvil 20 into forming contact with the staples 32 in the staple cartridge 30. The firing system lock button 137 prevents the inadvertent forming of the staples 32 until the surgeon is ready to start that process. In this embodiment, the surgeon must depress the firing system lock button 137 before the firing trigger 130 may be further actuated to begin the staple forming process.

The surgical instrument 10 may be solely used as a tissue stapling device if so desired. However, various embodiments of the present invention may also include a tissue cutting system, generally designated as 170. In at least one form, the tissue cutting system 170 comprises a knife member 172 that may be selectively advanced from an un-actuated position adjacent the proximal end of the end effector 12 to an actuated position by actuating a knife advancement trigger 200. The knife member 172 is movably supported within the spine member 50 and is attached or otherwise protrudes from a knife rod 180. The knife member 172 may be fabricated from, for example, 420 or 440 stainless steel with a hardness of greater than 38HRC (Rockwell Hardness C-scale) and have a tissue cutting edge 176 formed on the distal end 174 thereof and be configured to slidably extend through a slot in the anvil 20 and a centrally disposed slot 33 in the staple cartridge 30 to cut through tissue that is clamped in the end effector 12. In various embodiments, the knife rod 180 extends through the spine member 50 and has a proximal end portion which drivingly interfaces with a knife transmission that is operably attached to the knife advance trigger 200. In various embodiments, the knife advance trigger 200 is attached to pivot pin 132 such that it may be pivoted or otherwise actuated without actuating the firing trigger 130. In various embodiments, a first knife gear 192 is also attached to the pivot pin 132 such that actuation of the knife advance trigger 200 also pivots the first knife gear 192. A firing return spring 202 is attached between the first knife gear 192 and the handle housing 100 to bias the knife advancement trigger 200 to a starting or un-actuated position.

Various embodiments of the knife transmission also include a second knife gear 194 that is rotatably supported on a second gear spindle and in meshing engagement with the first knife gear 192. The second knife gear 194 is in meshing engagement with a third knife gear 196 that is supported on a third gear spindle. Also supported on the third gear spindle 195 is a fourth knife gear 198. The fourth knife gear 198 is adapted to drivingly engage a series of annular gear teeth or rings on a proximal end of the knife rod 180. Thus, such arrangement enables the fourth knife gear 198 to axially drive the knife rod 180 in the distal direction "DD" or proximal direction "PD" while enabling the firing rod 180 to rotate about longitudinal axis A-A with respect to the fourth knife gear 198. Accordingly, the surgeon may axially advance the firing rod 180 and ultimately the knife member 172 distally by pulling the knife advancement trigger 200 towards the pistol grip 107 of the handle assembly 100.

Various embodiments of the present invention further include a knife lockout system 210 that prevents the advancement of the knife member 172 unless the firing trigger 130 has been pulled to the fully fired position. Such feature will therefore prevent the activation of the knife advancement system 170 unless the staples have first been fired or formed into the tissue. As can be seen in FIG. 1, various implementations of the knife lockout system 210 comprise a knife lockout bar 211 that is pivotally supported within the pistol grip portion 107 of the handle assembly 100. The knife lockout bar 211 has an activation end 212 that is adapted to be engaged by the firing trigger 130 when the firing trigger 130 is in the fully fired position. In addition, the knife lockout bar 211 has a retaining hook 214 on its other end that is adapted to hookingly engage a latch rod 216 on the first cut gear 192. A knife lock spring 218 is employed to bias the knife lockout bar 211 to a "locked" position wherein the retaining hook 214 is retained in engagement with the latch rod 216 to thereby prevent actuation of the knife advancement trigger 200 unless the firing trigger 130 is in the fully fired position.

After the staples have been "fired" (formed) into the target tissue, the surgeon may depress the firing trigger release button 167 to enable the firing trigger 130 to return to the starting position under the bias of the torsion spring 135 which enables the anvil 20 to be biased to an open position under the bias of spring 21. When in the open position, the surgeon may withdraw the end effector 12 leaving the implantable staple cartridge 30 and staples 32 behind. In applications wherein the end effector was inserted through a passage, working channel, etc. the surgeon will return the anvil 20 to the closed position by activating the firing trigger 130 to enable the end effector 12 to be withdrawn out through the passage or working channel. If, however, the surgeon desires to cut the target tissue after firing the staples, the surgeon activates the knife advancement trigger 200 in the above-described manner to drive the knife bar 172 through the target tissue to the end of the end effector. Thereafter, the surgeon may release the knife advancement trigger 200 to enable the firing return spring 202 to cause the firing transmission to return the knife bar 172 to the starting (un-actuated) position. Once the knife bar 172 has been returned to the starting position, the surgeon may open the end effector jaws 13, 15 to release the implantable cartridge 30 within the patient and then withdraw the end effector 12 from the patient. Thus, such surgical instruments facilitate the use of small implantable staple cartridges that may be inserted through relatively smaller working channels and passages, while providing the surgeon with the option to fire the staples without cutting tissue or if desired to also cut tissue after the staples have been fired.

Various unique and novel embodiments of the present invention employ a compressible staple cartridge that supports staples in a substantially stationary position for forming contact by the anvil. In various embodiments, the anvil is driven into the unformed staples wherein, in at least one such embodiment, the degree of staple formation attained is dependent upon how far the anvil is driven into the staples. Such an arrangement provides the surgeon with the ability to adjust the amount of forming or firing pressure applied to the staples and thereby alter the final formed height of the staples. In other various embodiments of the present invention, surgical stapling arrangements can employ staple driving elements which can lift the staples toward the anvil. Such embodiments are described in greater detail further below.

In various embodiments, with regard to the embodiments described in detail above, the amount of firing motion that is applied to the movable anvil is dependent upon the degree of actuation of the firing trigger. For example, if the surgeon desires to attain only partially formed staples, then the firing trigger is only partially depressed inward towards the pistol grip 107. To attain more staple formation, the surgeon simply compresses the firing trigger further which results in the anvil being further driven into forming contact with the staples. As used herein, the term "forming contact" means that the staple forming surface or staple forming pockets have contacted the ends of the staple legs and have started to form or bend the legs over into a formed position. The degree of staple formation refers to how far the staple legs have been folded over and ultimately relates to the forming height of the staple as referenced above. Those of ordinary skill in the art will further understand that, because the anvil 20 moves in a substantially parallel relationship with respect to the staple cartridge as the firing motions are applied thereto, the staples are formed substantially simultaneously with substantially the same formed heights.

Figure 2:
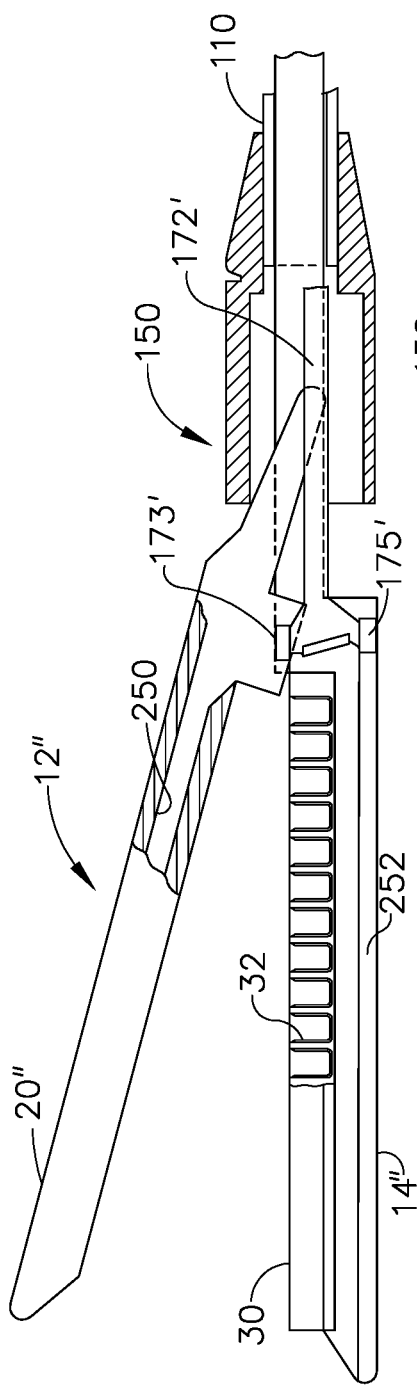
FIG. 2 is a partial cross-sectional side view of another end effector coupled to a portion of a surgical instrument with the end effector supporting a surgical staple cartridge and with the anvil thereof in an open position.
Figure 3:
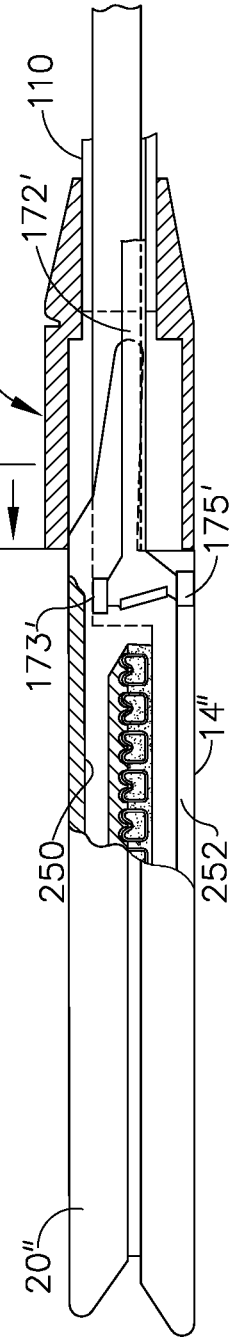
FIG. 3 is another partial cross-sectional side view of the end effector of FIG. 2 in a closed position.

FIGS. 2 and 3 illustrate an alternative end effector 12" that is similar to the end effector 12' described above, except with the following differences that are configured to accommodate a knife bar 172'. The knife bar 172' is coupled to or protrudes from a knife rod 180 and is otherwise operated in the above described manner with respect to the knife bar 172. However, in this embodiment, the knife bar 172' is long enough to traverse the entire length of the end effector 12" and therefore, a separate distal knife member is not employed in the end effector 12". The knife bar 172' has an upper transverse member 173' and a lower transverse member 175' formed thereon. The upper transverse member 173' is oriented to slidably transverse a corresponding elongated slot 250 in anvil 20" and the lower transverse member 175' is oriented to traverse an elongated slot 252 in the elongated channel 14" of the end effector 12". A disengagement slot (not shown) is also provided in the anvil 20" such that when the knife bar 172' has been driven to an ending position within end effector 12", the upper transverse member 173' drops through the corresponding slot to enable the anvil 20" to move to the open position to disengage the stapled and cut tissue. The anvil 20" may be otherwise identical to anvil 20 described above and the elongated channel 14" may be otherwise identical to elongated channel 14 described above.

Figure 4:
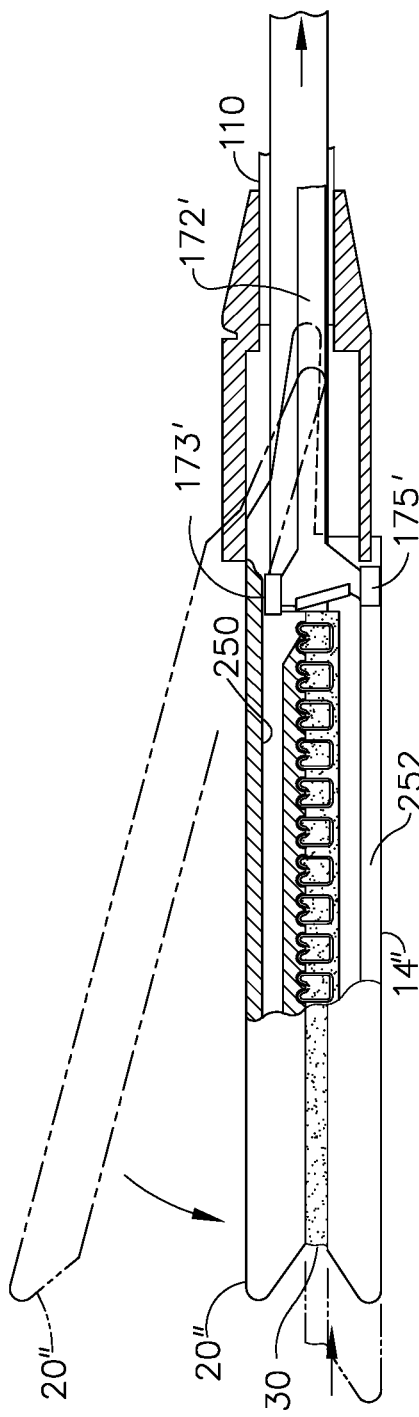
FIG. 4 is another partial cross-sectional side view of the end effector of FIGS. 2 and 3 as the knife bar is starting to advance through the end effector.
Figure 5:
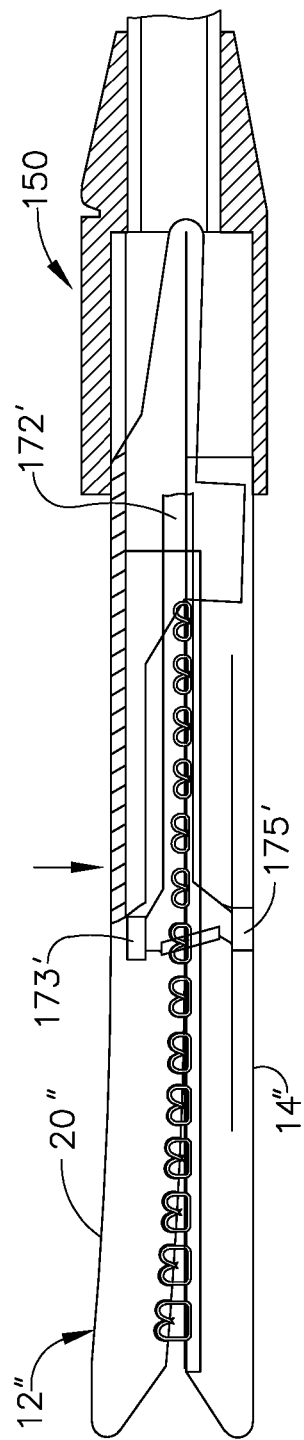
FIG. 5 is another partial cross-sectional side view of the end effector of FIGS. 2-4 with the knife bar partially advanced therethrough.

In these embodiments, the anvil 20" is biased to a fully open position (FIG. 2) by a spring or other opening arrangement (not shown). The anvil 20" is moved between the open and fully clamped positions by the axial travel of the firing adapter 150 in the manner described above. Once the firing adapter 150 has been advanced to the fully clamped position (FIG. 3), the surgeon may then advance the knife bar 172" distally in the manner described above. If the surgeon desires to use the end effector as a grasping device to manipulate tissue, the firing adapter may be moved proximally to allow the anvil 20" to move away from the elongated channel 14" as represented in FIG. 4 in broken lines. In this embodiment, as the knife bar 172" moves distally, the upper transverse member 173' and the lower transverse member 175' draw the anvil 20" and elongated channel 14" together to achieve the desired staple formation as the knife bar 172" is advanced distally through the end effector 12". See FIG. 5. Thus, in this embodiment, staple formation occurs simultaneously with tissue cutting, but the staples themselves may be sequentially formed as the knife bar 172" is driven distally.

The unique and novel features of the various surgical staple cartridges and the surgical instruments of the present invention enable the staples in those cartridges to be arranged in one or more linear or non-linear lines. A plurality of such staple lines may be provided on each side of an elongated slot that is centrally disposed within the staple cartridge for receiving the tissue cutting member therethrough. In one arrangement, for example, the staples in one line may be substantially parallel with the staples in adjacent line(s) of staples, but offset therefrom. In still other embodiments, one or more lines of staples may be non-linear in nature. That is, the base of at least one staple in a line of staples may extend along an axis that is substantially transverse to the bases of other staples in the same staple line. For example, as will be discussed in further detail below, in alternative embodiments, the lines of staples on each side of the elongated slot may have a zigzag appearance. Such non-linear staple arrangements may attain better tissue fastening results with less staples than various linear staple arrangements employed in prior staple cartridges.

Figure 6:
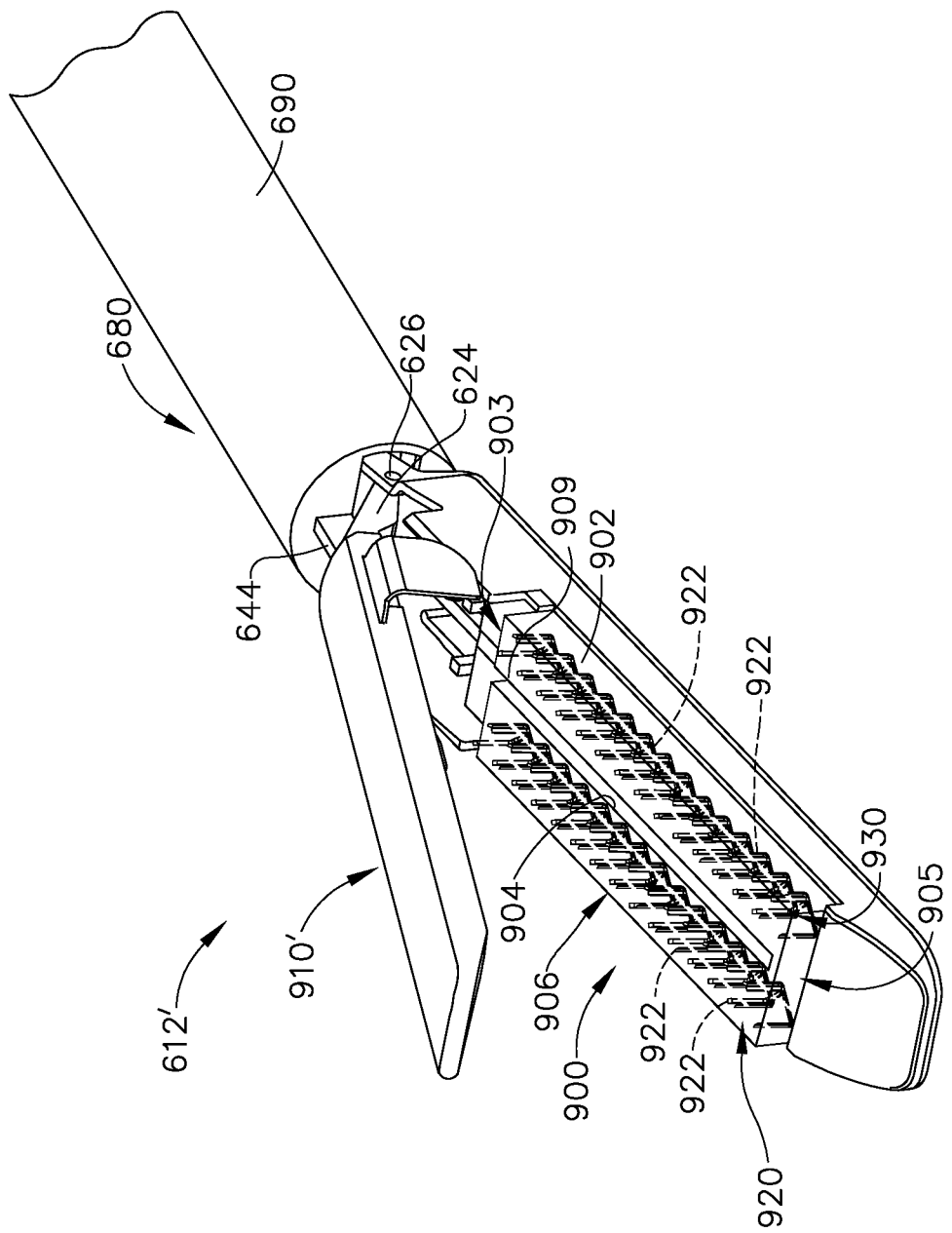
FIG. 6 is a perspective view of an alternative staple cartridge embodiment installed in a surgical cutting and stapling device.

FIG. 6 illustrates use of a surgical staple cartridge embodiment 900 in an end effector embodiment 612'. As can be seen in FIGS. 6 and 7, an embodiment of the surgical staple cartridge 900 has a cartridge body 902 that has a centrally disposed elongated slot 904 extending through a proximal end 903 to an area adjacent a distal end 905. The elongated slot 904 is configured to permit a knife body to axially move therethrough during a tissue cutting operation in the manner described above. In at least one embodiment, the cartridge body 902 consists of a compressible hemostat material such as, for example, oxidized regenerated cellulose ("ORC") or a bio-absorbable foam fabricated from, for example, PGA (Polyglycolic acid, sold under the trademark Vicryl), PCL (polycaprolactone), PLA or PLLA (Polyactic acid), PDS, (Polydioxanone), PHA (polyhydroxyalkanoate), PGCL (poliglecaprone 25, sold under the trademark Monocryl) or a composite of PGA, PCL, PLA and PDS in which lines 920, 930 of unformed staples 922 are supported. However, the cartridge body 902 may be fabricated from other materials that serve to support the unformed staples 922 in a desired orientation such that they may be compressed as the anvil 910' is brought into contact therewith. As with various other embodiments described above, the staple cartridge 900 is implantable and is left attached to the stapled tissue after the stapling procedure has been completed. In at least some embodiments, in order to prevent the staples 922 from being affected and the hemostat material from being activated during the introduction and positioning process, the entire cartridge 900 may be coated or wrapped in a biodegradable film 906 such as a polydioxanon film sold under the trademark PDS® or with a Polyglycerol sebacate (PGS) film or other biodegradable films fabricated from, for example, PGA (Polyglycolic acid, marketed under the trademark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured. The cartridge body 902 of staple cartridge 900 is sized to be removably supported within the elongated channel of the end effector 612'.

In the embodiment depicted in FIGS. 6, 10, and 11, the surgical staple cartridge 900 operably supports a first line 920 of staples 922 on one lateral side 907 of the elongated slot 904 and a second line 930 of staples 922 on the other lateral side 909 of the elongated slot 904. In various embodiments, the staples 922 may be fabricated from a metal material such as, for example, Titanium, Titanium alloys (e.g., 6Al-4V Titanium, 3al-2.5V Titanium), Stainless Steel, etc. and have a staple base 924 and two upstanding staple legs 926 protruding therefrom. Each staple leg 926 may have a tissue-piercing tip 928 formed thereon. In the first line 920 of staples 922, the staple base 924 of at least one staple 922 overlaps the staple base of another staple 922. In a preferred embodiment, the staple base 924 of each staple 922 overlaps the staple bases 924 of two adjacent staples 922, except for the base 924 of the last staple 922 on each end of the first staple line 920. See FIG. 10. Thus, the first staple line 920 has a substantially non-linear shape. More particularly, when viewed from above, the first staple line 920 has a substantially zigzag appearance.

As can be seen in FIG. 9, the anvil 90 has two sequential longitudinal staple forming pockets 912 that each has a substantial zigzag shape that corresponds to the shape of the first line 920 of staples 922 such that, when the anvil 910 is brought into forming contact with the staples 922, the legs 926 thereof are formed as shown in FIG. 11. Thus, the distal leg of one staple shares the same pocket as the proximal leg of the next staple longitudinally. Such arrangement allows for a denser pocket pattern, even to a point where the staples themselves interact (e.g., are folded over one another). In prior staple pocket arrangements, in general, there has to be between 0.005 and 0.015 inches of metal/space from one set of pockets to the next. This embodiment of the present invention, however, has a spacing arrangement from 0 to 0.02 inches of interference/overlap (essentially a –0.020") because one staple mates with the next staple, for example. Such arrangements allow for 15-30% more staples in the same space. Furthermore, when the staples interlock, there is less need for multiple lateral rows of staples. Prior arrangements commonly employ three rows on each side of the tissue cut line to prevent the existing of an open path through which blood may pass. Lines of interlocking staples are less likely to leave paths through which blood may pass. Another distinct advantage provided by the various interlocking staple arrangements of the present invention relates to improved "burst strength" which relates to the amount of force required to tear a staple line open.

Another staple forming pocket arrangement may comprise a common staple forming pocket. As used herein, the term "common staple forming pocket" means that one forming pocket can form all of the staples in a single line of staples as opposed to prior anvil designs wherein a discrete forming pocket is provided for each leg of each staple to be formed.

FIG. 12 illustrates yet another staple embodiment 922' wherein the base 924' has an offset portion 929 to facilitate a tighter overlap of the bases 924'. As indicated above, the staple cartridge 900 has a second line 930 of staples 922 supported on a second lateral side 909 of the elongated slot 904. The second line 930 of staples 922 is substantially identical to the first line 920 of staples 922. Thus, the anvil 910 has a second common staple forming pocket 912 that corresponds to the second line of staples 930 for forming contact therewith. In alternative embodiments, however, the second line 930 of staples 922 may differ from the first line 920 of staples in shape and, perhaps, number of staples.

FIG. 8 illustrates a surgical staple cartridge 900' that is substantially identical to the staple cartridge 900 described above, with the exception of the lines 920', 930' of staples 922 supported therein. For example, in this embodiment, the line 920' of staples 922 are arranged relative to each other such that a base axis S-S of at least one staple base 924 is substantially transverse to the base axis S-S of the staple base 924 of at least one other adjacent staple 922. Such predetermined pattern of staples, when viewed from above, comprises a substantially zigzag arrangement. In the embodiment depicted in FIG. 13, the respective bases 924 of staples 922 may additionally have a base support member 927 overmolded thereon as shown. In various embodiments, the base support member 927 may be fabricated from, for example, non-absorbable plastic such as Polyether ether ketone "PEEK" or absorbable plastic such as, for example, Polyglycolic acid "PGA", Polylactic acid "PLA" or "PLLA", Polydioxanone "PDS", PCL (polycaprolactone), PHA (polyhydroxyalkanoate), PGCL (poliglecaprone 25, sold under the trademark Monocryl) or various composite mixes if PGS, PDS, PLA, PGA, and PCL. The base support members 927 facilitate interlocking between the staples without making the staples themselves overlap. Thus, such arrangements could form staples with "B" shapes or inverted "W" shapes without the legs of the staples themselves overlapping. However, the crowns are connected by the base support members so they act like overlapping staples. Such arrangements allow the combined pockets to have two discrete paths for each leg.

The embodiment depicted in FIG. 14 employs a staple line 920" wherein the legs 926 of adjacent staples 922 are coupled together by a coupler portion 929 molded or otherwise attached thereto. Each coupler portion 929 may be fabricated from, for example, Polyether ether ketone "PEEK" or absorbable plastic such as, for example, Polyglycolic acid "PGA", Polylactic acid "PLA" or "PLLA", Polydioxanone "PDS", PCL (polycaprolactone), PHA (polyhydroxyalkanoate), PGCL (poliglecaprone 25, sold under the trademark Monocryl) or various composite mixes if PGS, PDS, PLA, PGA, and PCL. Such staple line 920" has substantial zigzag appearance when viewed from above. While the various surgical staple cartridge embodiments 900, 900' have been explained with reference to use with the end effector 612', it will be understood that the staple cartridges 900, 900' may be effectively employed with the various other end effectors and surgical instruments described hereinabove, with appropriate staple forming pocket arrangements being provided in the anvils of those instruments in order to achieved the desired amount of staple formation upon movement of the anvils into forming contact with the staples.

Figure 15:
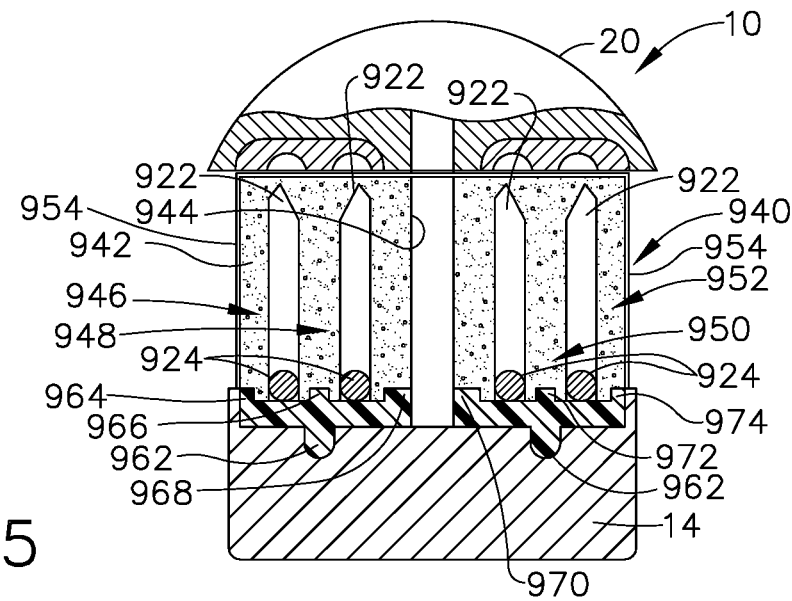
FIG. 15 is a cross-sectional view of an end effector supporting a staple cartridge.
Figure 16:
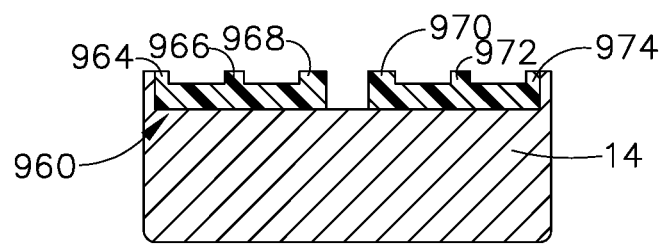
FIG. 16 is a cross-sectional view of the elongated channel portion of the end effector of FIG. 15 after the implantable staple cartridge body portion and staples have been removed therefrom.

FIGS. 15 and 16 illustrate another surgical staple cartridge 940 embodiment supported in an elongated channel 14 of a surgical instrument 10. In at least one embodiment, the surgical staple cartridge 940 includes a cartridge body 942 that has a centrally disposed elongated slot 944 extending at least partially therethrough. The elongated slot 944 is configured to permit a knife body of the surgical instrument 10 to axially move therethrough during a tissue cutting operation in the manner described above. In various embodiments, the cartridge body 942 consists of a compressible hemostat material such as, for example, oxidized regenerated cellulose ("ORC") or a bio-absorbable foam of the types described above or below in which lines 946, 948, 950, 952 of unformed staples 922 are supported. In at least some embodiments, in order to prevent the staples 922 from being affected and the hemostat material from being activated during the introduction and positioning process, the entire cartridge 940 may be coated or wrapped in a biodegradable film 954 such as a polydioxanon film sold under the trademark PDS® or with a Polyglycerol sebacate (PGS) film or other biodegradable films fabricated from, for example, PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured.

In the embodiment depicted in FIG. 15, the cartridge 940 further includes a cartridge support member 960 that is coupled to the cartridge body 942. In various embodiments, the cartridge support member 960 may be fabricated from a rigid material such as, for example, Titanium, Stainless Steel, Aluminum, any alloy of the foregoing, etc. and may be partially embedded within the cartridge body 942. In various embodiments, the cartridge support member 960 may be held in place by, for example, film 954. In still other embodiments wherein a limited bond is desired, sporadic use of cyanoacylate could be used to "glue" the two components together. In yet other embodiments, the cartridge body 942 may be heated and "welded" or "fused" to the cartridge support member 960. In various embodiments, the cartridge support member 960 forms at least a portion of the bottom surface of the cartridge body 942 for mating with the elongated channel 14. In at least one embodiment, the cartridge support member 960 has one or more snap features 962 protruding therefrom for releasably coupling the cartridge support member 960 to the elongated channel 14. Other forms of snap features/fastener arrangements may be employed for releasably coupling the cartridge support member 960 to the elongated channel 14.

Figure 17:
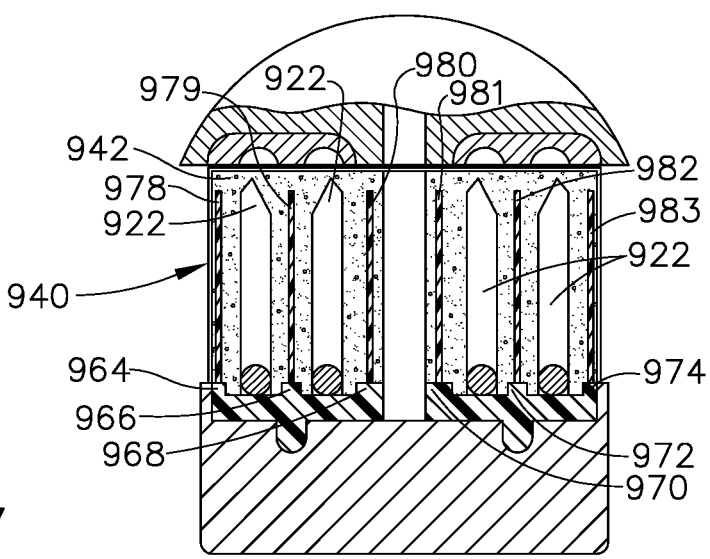
FIG. 17 is a cross-sectional view of an end effector supporting another staple cartridge.

In various embodiments, the cartridge support member 960 has a series of support ridges 964, 966, 968, 970, 972, 974, 976 formed thereon to provide some lateral support to the bases 924 of the staples 922 in the staple lines 946, 948, 950, 952 as shown in FIG. 15. Thus, in at least some embodiments, the support ridges are substantially coextensive with the staple lines. FIG. 17 illustrates an alternative staple cartridge embodiment 940' that is substantially identical to cartridge 940, except for the inclusion of upstanding fin portions 978, 979, 980, 981, 982, 983 that protrude from the support ridges 964, 966, 968, 970, 972, 976, respectively to provide additional lateral support to the staples 922. In various embodiments, the fin portions may be integrally formed with the cartridge support member 960 and have a height that is about ½ or less of the height of the cartridge. Thus, in various embodiments, for example, any standing features supporting the foam cannot extend above the maximum compression height of the foam. Thus, if the cartridge is designed, for example, to compress to ⅓ of its original height when fired, the fins would between 66% of the uncompressed height, all the way down to 10% of uncompressed height.

In use, once the staples 922 have been formed through contact with the anvil 20 in the manner described above, the anvil 20 is opened and the end effector 12 is pulled away from the stapled tissue. As the end effector 12 is pulled away from the stapled tissue, the cartridge body 942 remains fastened to the stapled tissue and is then separated from the cartridge support member 960 which remains coupled to the elongated channel 14. In various embodiments, the cartridge support member 960 is provided with a color that differs from the color of the material comprising the cartridge body 942 as well as the color of the elongated channel 14. Such arrangement provides the surgeon with an easily recognizable indication that no staple cartridge is present within the end effector. Thus, the surgeon will not inadvertently attempt to reinsert/use the end effector without first installing a new staple cartridge therein. To do so, the surgeon simply disconnects the snap features of the cartridge support member 960 from the elongated channel 14 to enable the cartridge support member 960 of a new staple cartridge 940 to be placed therein. While the staple cartridges 940, 940' have been explained with reference to surgical instrument 10, it will be understood that those cartridges may be effectively employed with many of the other surgical instrument embodiments disclosed herein without departing from the spirit and scope of the present invention.

In various embodiments, a staple cartridge can comprise a cartridge body and a plurality of staples stored within the cartridge body. In use, the staple cartridge can be introduced into a surgical site and positioned on a side of the tissue being treated. In addition, a staple-forming anvil can be positioned on the opposite side of the tissue. In various embodiments, the anvil can be carried by a first jaw and the staple cartridge can be carried by a second jaw, wherein the first jaw and/or the second jaw can be moved toward the other. Once the staple cartridge and the anvil have been positioned relative to the tissue, the staples can be ejected from the staple cartridge body such that the staples can pierce the tissue and contact the staple-forming anvil. Once the staples have been deployed from the staple cartridge body, the staple cartridge body can then be removed from the surgical site. In various embodiments disclosed herein, a staple cartridge, or at least a portion of a staple cartridge, can be implanted with the staples. In at least one such embodiment, as described in greater detail further below, a staple cartridge can comprise a cartridge body which can be compressed, crushed, and/or collapsed by the anvil when the anvil is moved from an open position into a closed position. When the cartridge body is compressed, crushed, and/or collapsed, the staples positioned within the cartridge body can be deformed by the anvil. Alternatively, the jaw supporting the staple cartridge can be moved toward the anvil into a closed position. In either event, in various embodiments, the staples can be deformed while they are at least partially positioned within the cartridge body. In certain embodiments, the staples may not be ejected from the staple cartridge while, in some embodiments, the staples can be ejected from the staple cartridge along with a portion of the cartridge body.

Referring now to FIGS. 18A-18D, a compressible staple cartridge, such as staple cartridge 1000, for example, can comprise a compressible, implantable cartridge body 1010 and, in addition, a plurality of staples 1020 positioned in the compressible cartridge body 1010, although only one staple 1020 is depicted in FIGS. 18A-18D. FIG. 18A illustrates the staple cartridge 1000 supported by a staple cartridge support, or staple cartridge channel, 1030, wherein the staple cartridge 1000 is illustrated in an uncompressed condition. In such an uncompressed condition, the anvil 1040 may or may not be in contact with the tissue T. In use, the anvil 1040 can be moved from an open position into contact with the tissue T as illustrated in FIG. 18B and position the tissue T against the cartridge body 1010. Even though the anvil 1040 can position the tissue T against a tissue-contacting surface 1019 of staple cartridge body 1010, referring again to FIG. 18B, the staple cartridge body 1010 may be subjected to little, if any, compressive force or pressure at such point and the staples 1020 may remain in an unformed, or unfired, condition. As illustrated in FIGS. 18A and 18B, the staple cartridge body 1010 can comprise one or more layers and the staple legs 1021 of staples 1020 can extend upwardly through these layers. In various embodiments, the cartridge body 1010 can comprise a first layer 1011, a second layer 1012, a third layer 1013, wherein the second layer 1012 can be positioned intermediate the first layer 1011 and the third layer 1013, and a fourth layer 1014, wherein the third layer 1013 can be positioned intermediate the second layer 1012 and the fourth layer 1014. In at least one embodiment, the bases 1022 of the staples 1020 can be positioned within cavities 1015 in the fourth layer 1014 and the staple legs 1021 can extend upwardly from the bases 1022 and through the fourth layer 1014, the third layer 1013, and the second layer 1012, for example. In various embodiments, each deformable leg 1021 can comprise a tip, such as sharp tip 1023, for example, which can be positioned in the second layer 1012, for example, when the staple cartridge 1000 is in an uncompressed condition. In at least one such embodiment, the tips 1023 may not extend into and/or through the first layer 1011, wherein, in at least one embodiment, the tips 1023 may not protrude through the tissue-contacting surface 1019 when the staple cartridge 1000 is in an uncompressed condition. In certain other embodiments, the sharp tips 1023 may be positioned in the third layer 1013, and/or any other suitable layer, when the staple cartridge is in an uncompressed condition. In various alternative embodiments, a cartridge body of a staple cartridge may have any suitable number of layers such as less than four layers or more than four layers, for example.

In various embodiments, as described in greater detail below, the first layer 1011 can be comprised of a buttress material and/or plastic material, such as polydioxanone (PDS) and/or polyglycolic acid (PGA), for example, and the second layer 1012 can be comprised of a bioabsorbable foam material and/or a compressible hemostatic material, such as oxidized regenerated cellulose (ORC), for example. In various embodiments, one or more of the first layer 1011, the second layer 1012, the third layer 1013, and the fourth layer 1014 may hold the staples 1020 within the staple cartridge body 1010 and, in addition, maintain the staples 1020 in alignment with one another. In various embodiments, the third layer 1013 can be comprised of a buttress material, or a fairly incompressible or inelastic material, which can be configured to hold the staple legs 1021 of the staples 1020 in position relative to one another. Furthermore, the second layer 1012 and the fourth layer 1014, which are positioned on opposite sides of the third layer 1013, can stabilize, or reduce the movement of, the staples 1020 even though the second layer 1012 and the fourth layer 1014 can be comprised of a compressible foam or elastic material. In certain embodiments, the staple tips 1023 of the staple legs 1021 can be at least partially embedded in the first layer 1011. In at least one such embodiment, the first layer 1011 and the third layer 1013 can be configured to co-operatively and firmly hold the staple legs 1021 in position. In at least one embodiment, the first layer 1011 and the third layer 1013 can each be comprised of a sheet of bioabsorbable plastic, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example, and the second layer 1012 and the fourth layer 1014 can each be comprised of at least one hemostatic material or agent.

Although the first layer 1011 can be compressible, the second layer 1012 can be substantially more compressible than the first layer 1011. For example, the second layer 1012 can be about twice as compressible, about three times as compressible, about four times as compressible, about five times as compressible, and/or about ten times as compressible, for example, as the first layer 1011. Stated another way, the second layer 1012 may compress about two times, about three times, about four times, about five times, and/or about ten times as much as first layer 1011, for a given force. In certain embodiments, the second layer 1012 can be between about twice as compressible and about ten times as compressible, for example, as the first layer 1011. In at least one embodiment, the second layer 1012 can comprise a plurality of air voids defined therein, wherein the amount and/or size of the air voids in the second layer 1012 can be controlled in order to provide a desired compressibility of the second layer 1012. Similar to the above, although the third layer 1013 can be compressible, the fourth layer 1014 can be substantially more compressible than the third layer 1013. For example, the fourth layer 1014 can be about twice as compressible, about three times as compressible, about four times as compressible, about five times as compressible, and/or about ten times as compressible, for example, as the third layer 1013. Stated another way, the fourth layer 1014 may compress about two times, about three times, about four times, about five times, and/or about ten times as much as third layer 1013, for a given force. In certain embodiments, the fourth layer 1014 can be between about twice as compressible and about ten times as compressible, for example, as the third layer 1013. In at least one embodiment, the fourth layer 1014 can comprise a plurality of air voids defined therein, wherein the amount and/or size of the air voids in the fourth layer 1014 can be controlled in order to provide a desired compressibility of the fourth layer 1014. In various circumstances, the compressibility of a cartridge body, or cartridge body layer, can be expressed in terms of a compression rate, i.e., a distance in which a layer is compressed for a given amount of force. For example, a layer having a high compression rate will compress a larger distance for a given amount of compressive force applied to the layer as compared to a layer having a lower compression rate. This being said, the second layer 1012 can have a higher compression rate than the first layer 1011 and, similarly, the fourth layer 1014 can have a higher compression rate than the third layer 1013. In various embodiments, the second layer 1012 and the fourth layer 1014 can be comprised of the same material and can comprise the same compression rate. In various embodiments, the second layer 1012 and the fourth layer 1014 can be comprised of materials having different compression rates. Similarly, the first layer 1011 and the third layer 1013 can be comprised of the same material and can comprise the same compression rate. In certain embodiments, the first layer 1011 and the third layer 1013 can be comprised of materials having different compression rates.

As the anvil 1040 is moved toward its closed position, the anvil 1040 can contact tissue T and apply a compressive force to the tissue T and the staple cartridge 1000, as illustrated in FIG. 18C. In such circumstances, the anvil 1040 can push the top surface, or tissue-contacting surface 1019, of the cartridge body 1010 downwardly toward the staple cartridge support 1030. In various embodiments, the staple cartridge support 1030 can comprise a cartridge support surface 1031 which can be configured to support the staple cartridge 1000 as the staple cartridge 1000 is compressed between the cartridge support surface 1031 and the tissue-contacting surface 1041 of anvil 1040. Owing to the pressure applied by the anvil 1040, the cartridge body 1010 can be compressed and the anvil 1040 can come into contact with the staples 1020. More particularly, in various embodiments, the compression of the cartridge body 1010 and the downward movement of the tissue-contacting surface 1019 can cause the tips 1023 of the staple legs 1021 to pierce the first layer 1011 of cartridge body 1010, pierce the tissue T, and enter into forming pockets 1042 in the anvil 1040. As the cartridge body 1010 is further compressed by the anvil 1040, the tips 1023 can contact the walls defining the forming pockets 1042 and, as a result, the legs 1021 can be deformed or curled inwardly, for example, as illustrated in FIG. 18C. As the staple legs 1021 are being deformed, as also illustrated in FIG. 18C, the bases 1022 of the staples 1020 can be in contact with or supported by the staple cartridge support 1030. In various embodiments, as described in greater detail below, the staple cartridge support 1030 can comprise a plurality of support features, such as staple support grooves, slots, or troughs 1032, for example, which can be configured to support the staples 1020, or at least the bases 1022 of the staples 1020, as the staples 1020 are being deformed. As also illustrated in FIG. 18C, the cavities 1015 in the fourth layer 1014 can collapse as a result of the compressive force applied to the staple cartridge body 1010. In addition to the cavities 1015, the staple cartridge body 1010 can further comprise one or more voids, such as voids 1016, for example, which may or may not comprise a portion of a staple positioned therein, that can be configured to allow the cartridge body 1010 to collapse. In various embodiments, the cavities 1015 and/or the voids 1016 can be configured to collapse such that the walls defining the cavities and/or walls deflect downwardly and contact the cartridge support surface 1031 and/or contact a layer of the cartridge body 1010 positioned underneath the cavities and/or voids.

Upon comparing FIG. 18B and FIG. 18C, it is evident that the second layer 1012 and the fourth layer 1014 have been substantially compressed by the compressive pressure applied by the anvil 1040. It may also be noted that the first layer 1011 and the third layer 1013 have been compressed as well. As the anvil 1040 is moved into its closed position, the anvil 1040 may continue to further compress the cartridge body 1010 by pushing the tissue-contacting surface 1019 downwardly toward the staple cartridge support 1030. As the cartridge body 1010 is further compressed, the anvil 1040 can deform the staples 1020 into their completely-formed shape as illustrated in FIG. 18D. Referring to FIG. 18D, the legs 1021 of each staple 1020 can be deformed downwardly toward the base 1022 of each staple 1020 in order to capture at least a portion of the tissue T, the first layer 1011, the second layer 1012, the third layer 1013, and the fourth layer 1014 between the deformable legs 1021 and the base 1022. Upon comparing FIGS. 18C and 18D, it is further evident that the second layer 1012 and the fourth layer 1014 have been further substantially compressed by the compressive pressure applied by the anvil 1040. It may also be noted upon comparing FIGS. 18C and 18D that the first layer 1011 and the third layer 1013 have been further compressed as well. After the staples 1020 have been completely, or at least sufficiently, formed, the anvil 1040 can be lifted away from the tissue T and the staple cartridge support 1030 can be moved away, and/or detached from, the staple cartridge 1000. As depicted in FIG. 18D, and as a result of the above, the cartridge body 1010 can be implanted with the staples 1020. In various circumstances, the implanted cartridge body 1010 can support the tissue along the staple line. In some circumstances, a hemostatic agent, and/or any other suitable therapeutic medicament, contained within the implanted cartridge body 1010 can treat the tissue over time. A hemostatic agent, as mentioned above, can reduce the bleeding of the stapled and/or incised tissue while a bonding agent or tissue adhesive can provide strength to the tissue over time. The implanted cartridge body 1010 can be comprised of materials such as ORC (oxidized regenerated cellulous), protein matrix, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain circumstances, the cartridge body 1010 can comprise an antibiotic and/or anti-microbial material, such as colloidal silver and/or triclosan, for example, which can reduce the possibility of infection in the surgical site.

In various embodiments, the layers of the cartridge body 1010 can be connected to one another. In at least one embodiment, the second layer 1012 can be adhered to the first layer 1011, the third layer 1013 can be adhered to the second layer 1012, and the fourth layer 1014 can be adhered to the third layer 1013 utilizing at least one adhesive, such as fibrin and/or protein hydrogel, for example. In certain embodiments, although not illustrated, the layers of the cartridge body 1010 can be connected together by interlocking mechanical features. In at least one such embodiment, the first layer 1011 and the second layer 1012 can each comprise corresponding interlocking features, such as a tongue and groove arrangement and/or a dovetail joint arrangement, for example. Similarly, the second layer 1012 and the third layer 1013 can each comprise corresponding interlocking features while the third layer 1013 and the fourth layer 1014 can each comprise corresponding interlocking features. In certain embodiments, although not illustrated, the staple cartridge 1000 can comprise one or more rivets, for example, which can extend through one or more layers of the cartridge body 1010. In at least one such embodiment, each rivet can comprise a first end, or head, positioned adjacent to the first layer 1011 and a second head positioned adjacent to the fourth layer 1014 which can be either assembled to or formed by a second end of the rivet. Owing to the compressible nature of the cartridge body 1010, in at least one embodiment, the rivets can compress the cartridge body 1010 such that the heads of the rivets can be recessed relative to the tissue-contacting surface 1019 and/or the bottom surface 1018 of the cartridge body 1010, for example. In at least one such embodiment, the rivets can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain embodiments, the layers of the cartridge body 1010 may not be connected to one another other than by the staples 1020 contained therein. In at least one such embodiment, the frictional engagement between the staple legs 1021 and the cartridge body 1010, for example, can hold the layers of the cartridge body 1010 together and, once the staples have been formed, the layers can be captured within the staples 1020. In certain embodiments, at least a portion of the staple legs 1021 can comprise a roughened surface or rough coating which can increase the friction forces between the staples 1020 and the cartridge body 1010.

As described above, a surgical instrument can comprise a first jaw including the staple cartridge support 1030 and a second jaw including the anvil 1040. In various embodiments, as described in greater detail further below, the staple cartridge 1000 can comprise one or more retention features which can be configured to engage the staple cartridge support 1030 and, as a result, releasably retain the staple cartridge 1000 to the staple cartridge support 1030. In certain embodiments, the staple cartridge 1000 can be adhered to the staple cartridge support 1030 by at least one adhesive, such as fibrin and/or protein hydrogel, for example. In use, in at least one circumstance, especially in laparoscopic and/or endoscopic surgery, the second jaw can be moved into a closed position opposite the first jaw, for example, such that the first and second jaws can be inserted through a trocar into a surgical site. In at least one such embodiment, the trocar can define an approximately 5 mm aperture, or cannula, through which the first and second jaws can be inserted. In certain embodiments, the second jaw can be moved into a partially-closed position intermediate the open position and the closed position which can allow the first and second jaws to be inserted through the trocar without deforming the staples 1020 contained in the staple cartridge body 1010. In at least one such embodiment, the anvil 1040 may not apply a compressive force to the staple cartridge body 1010 when the second jaw is in its partially-closed intermediate position while, in certain other embodiments, the anvil 1040 can compress the staple cartridge body 1010 when the second jaw is in its partially-closed intermediate position. Even though the anvil 1040 can compress the staple cartridge body 1010 when it is in such an intermediate position, the anvil 1040 may not sufficiently compress the staple cartridge body 1010 such that the anvil 1040 comes into contact with the staples 1020 and/or such that the staples 1020 are deformed by the anvil 1040. Once the first and second jaws have been inserted through the trocar into the surgical site, the second jaw can be opened once again and the anvil 1040 and the staple cartridge 1000 can be positioned relative to the targeted tissue as described above.

Figure 19A:
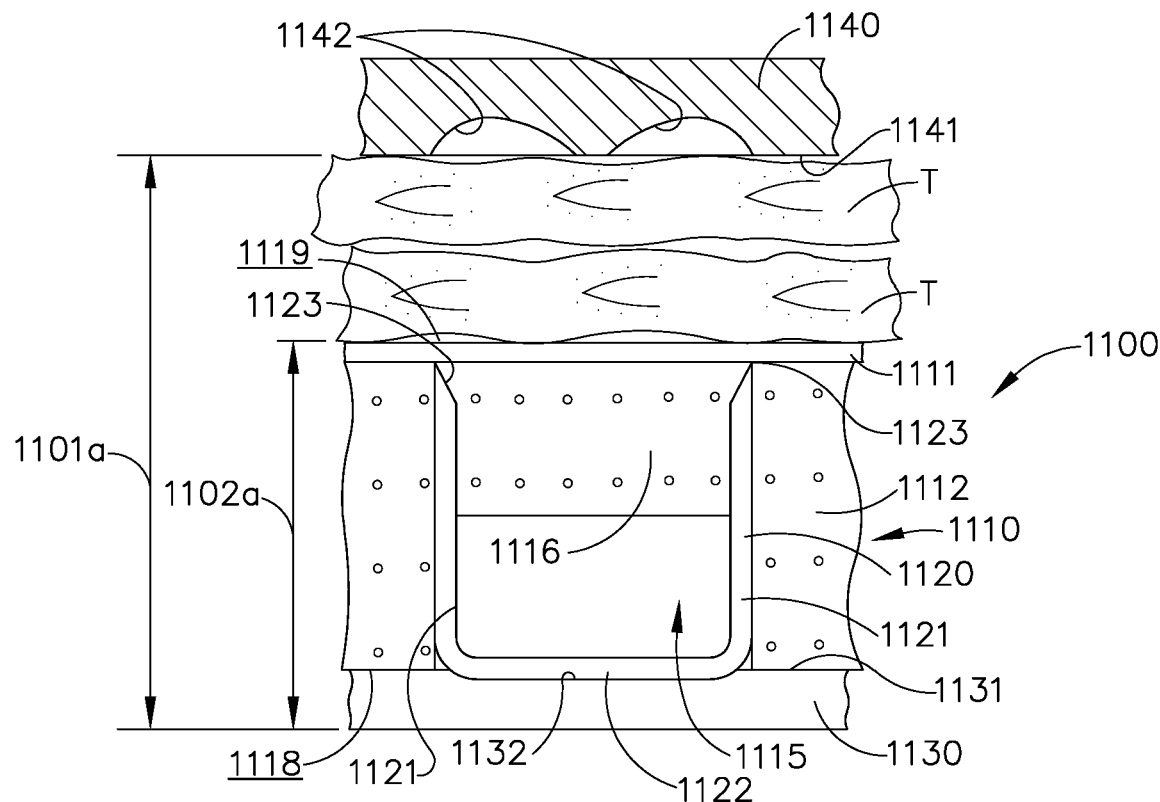
FIG. 19A is a diagram illustrating a staple positioned in a crushable staple cartridge body.
Figure 19B:
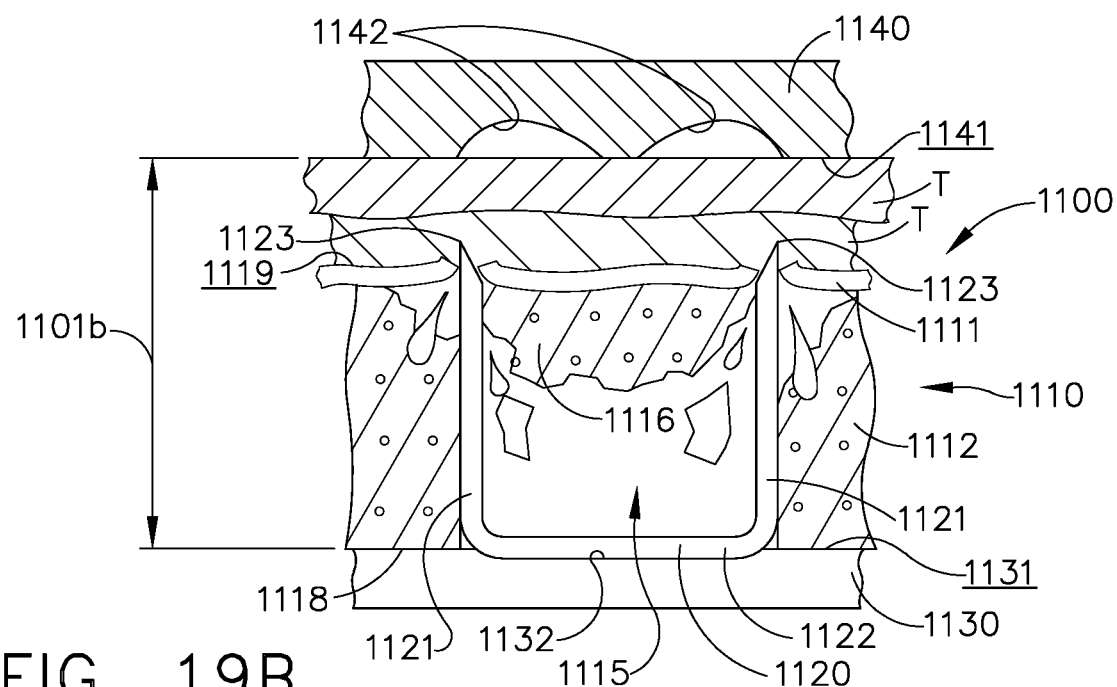
FIG. 19B is a diagram illustrating the crushable staple cartridge body of FIG. 19A being crushed by an anvil.
Figure 19C:
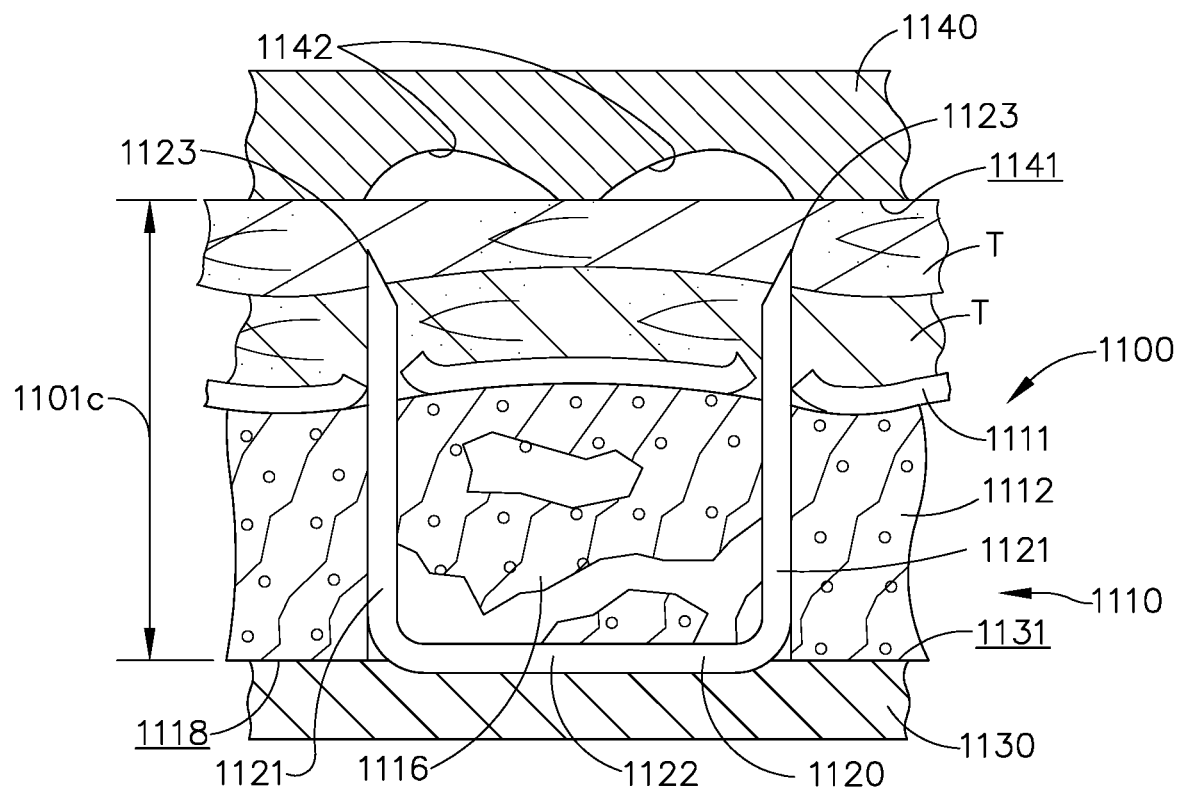
FIG. 19C is a diagram illustrating the crushable staple cartridge body of FIG. 19A being further crushed by the anvil.

In various embodiments, referring now to FIGS. 19A-19D, an end effector of a surgical stapler can comprise an implantable staple cartridge 1100 positioned intermediate an anvil 1140 and a staple cartridge support 1130. Similar to the above, the anvil 1140 can comprise a tissue-contacting surface 1141, the staple cartridge 1100 can comprise a tissue-contacting surface 1119, and the staple cartridge support 1130 can comprise a support surface 1131 which can be configured to support the staple cartridge 1100. Referring to FIG. 19A, the anvil 1140 can be utilized to position the tissue T against the tissue contacting surface 1119 of staple cartridge 1100 without deforming the staple cartridge 1100 and, when the anvil 1140 is in such a position, the tissue-contacting surface 1141 can be positioned a distance 1101*a* away from the staple cartridge support surface 1131 and the tissue-contacting surface 1119 can be positioned a distance 1102*a* away from the staple cartridge support surface 1131. Thereafter, as the anvil 1140 is moved toward the staple cartridge support 1130, referring now to FIG. 19B, the anvil 1140 can push the top surface, or tissue-contacting surface 1119, of staple cartridge 1100 downwardly and compress the first layer 1111 and the second layer 1112 of cartridge body 1110. As the layers 1111 and 1112 are compressed, referring again to FIG. 19B, the second layer 1112 can be crushed and the legs 1121 of staples 1120 can pierce the first layer 1111 and enter into the tissue T. In at least one such embodiment, the staples 1120 can be at least partially positioned within staple cavities, or voids, 1115 in the second layer 1112 and, when the second layer 1112 is compressed, the staple cavities 1115 can collapse and, as a result, allow the second layer 1112 to collapse around the staples 1120. In various embodiments, the second layer 1112 can comprise cover portions 1116 which can extend over the staple cavities 1115 and enclose, or at least partially enclose, the staple cavities 1115. FIG. 19B illustrates the cover portions 1116 being crushed downwardly into the staple cavities 1115. In certain embodiments, the second layer 1112 can comprise one or more weakened portions which can facilitate the collapse of the second layer 1112. In various embodiments, such weakened portions can comprise score marks, perforations, and/or thin cross-sections, for example, which can facilitate a controlled collapse of the cartridge body 1110. In at least one embodiment, the first layer 1111 can comprise one or more weakened portions which can facilitate the penetration of the staple legs 1121 through the first layer 1111. In various embodiments, such weakened portions can comprise score marks, perforations, and/or thin cross-sections, for example, which can be aligned, or at least substantially aligned, with the staple legs 1121.

Figure 19D:
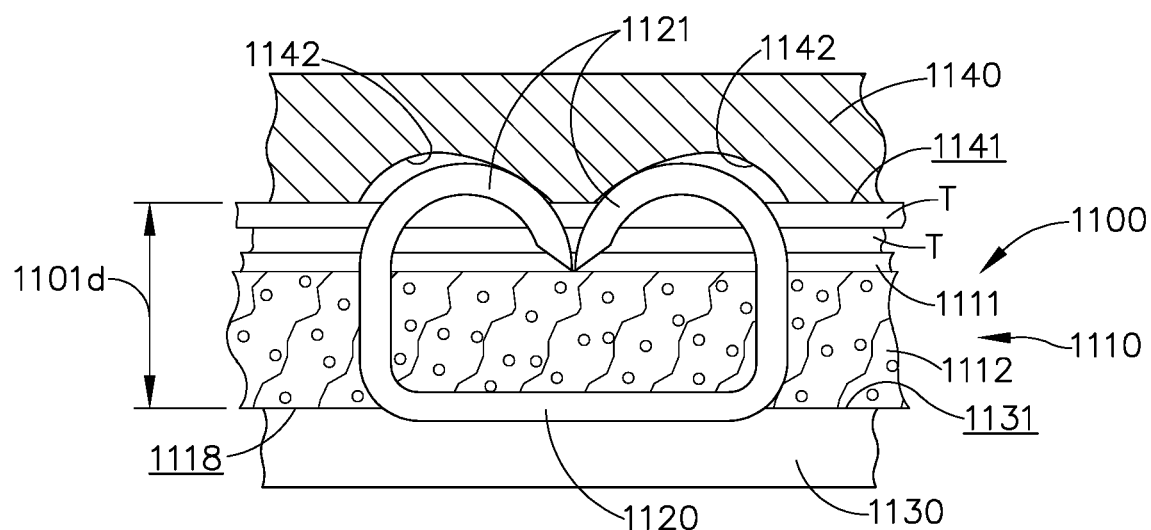
FIG. 19D is a diagram illustrating the staple of FIG. 19A in a fully formed configuration and the crushable staple cartridge of FIG. 19A in a fully crushed condition.

When the anvil 1140 is in a partially closed, unfired position, referring again to FIG. 19A, the anvil 1140 can be positioned a distance 1101*a* away from the cartridge support surface 1131 such that a gap is defined therebetween. This gap can be filled by the staple cartridge 1100, having a staple cartridge height 1102*a*, and the tissue T. As the anvil 1140 is moved downwardly to compress the staple cartridge 1100, referring again to FIG. 19B, the distance between the tissue contacting surface 1141 and the cartridge support surface 1131 can be defined by a distance 1101*b* which is shorter than the distance 1101*a*. In various circumstances, the gap between the tissue-contacting surface 1141 of anvil 1140 and the cartridge support surface 1131, defined by distance 1101*b*, may be larger than the original, undeformed staple cartridge height 1102*a*. As the anvil 1140 is moved closer to the cartridge support surface 1131, referring now to FIG. 19C, the second layer 1112 can continue to collapse and the distance between the staple legs 1121 and the forming pockets 1142 can decrease. Similarly, the distance between the tissue-contacting surface 1141 and the cartridge support surface 1131 can decrease to a distance 1101*c* which, in various embodiments, may be greater than, equal to, or less than the original, undeformed cartridge height 1102*a*. Referring now to FIG. 19D, the anvil 1140 can be moved into a final, fired position in which the staples 1120 have been fully formed, or at least formed to a desired height. In such a position, the tissue-contacting surface 1141 of anvil 1140 can be a distance 1101*d* away from the cartridge support surface 1131, wherein the distance 1101*d* can be shorter than the original, undeformed cartridge height 1102*a*. As also illustrated in FIG. 19D, the staple cavities 1115 may be fully, or at least substantially, collapsed and the staples 1120 may be completely, or at least substantially, surrounded by the collapsed second layer 1112. In various circumstances, the anvil 1140 can be thereafter moved away from the staple cartridge 1100. Once the anvil 1140 has been disengaged from the staple cartridge 1100, the cartridge body 1110 can at least partially re-expand in various locations, i.e., locations intermediate adjacent staples 1120, for example. In at least one embodiment, the crushed cartridge body 1110 may not resiliently re-expand. In various embodiments, the formed staples 1120 and, in addition, the cartridge body 1110 positioned intermediate adjacent staples 1120 may apply pressure, or compressive forces, to the tissue T which may provide various therapeutic benefits.

As discussed above, referring again to the embodiment illustrated in FIG. 19A, each staple 1120 can comprise staple legs 1121 extending therefrom. Although staples 1120 are depicted as comprising two staple legs 1121, various staples can be utilized which can comprise one staple leg or, alternatively, more than two staple legs, such as three staple legs or four staple legs, for example. As illustrated in FIG. 19A, each staple leg 1121 can be embedded in the second layer 1112 of the cartridge body 1110 such that the staples 1120 are secured within the second layer 1112. In various embodiments, the staples 1120 can be inserted into the staple cavities 1115 in cartridge body 1110 such that the tips 1123 of the staple legs 1121 enter into the cavities 1115 before the bases 1122. After the tips 1123 have been inserted into the cavities 1115, in various embodiments, the tips 1123 can be pressed into the cover portions 1116 and incise the second layer 1112. In various embodiments, the staples 1120 can be seated to a sufficient depth within the second layer 1112 such that the staples 1120 do not move, or at least substantially move, relative to the second layer 1112. In certain embodiments, the staples 1120 can be seated to a sufficient depth within the second layer 1112 such that the bases 1122 are positioned or embedded within the staple cavities 1115. In various other embodiments, the bases 1122 may not be positioned or embedded within the second layer 1112. In certain embodiments, referring again to FIG. 19A, the bases 1122 may extend below the bottom surface 1118 of the cartridge body 1110. In certain embodiments, the bases 1122 can rest on, or can be directly positioned against, the cartridge support surface 1130. In various embodiments, the cartridge support surface 1130 can comprise support features extending therefrom and/or defined therein wherein, in at least one such embodiment, the bases 1122 of the staples 1120 may be positioned within and supported by one or more support grooves, slots, or troughs, 1132, for example, in the staple cartridge support 1130, as described in greater detail further below.

Further to the above, referring now to FIG. 20, the bases 1122 of the staples 1120 can be positioned directly against the support surface 1131 of staple cartridge support 1130. In various embodiments, including embodiments where the staple bases 1122 comprise circular or arcuate bottom surfaces 1124, for example, the staple bases 1122 may move or slide along the staple cartridge support surface 1131. Such sliding can occur when the anvil 1140 is pressed against the tips 1123 of the staple legs 1121 during the staple forming process. In certain embodiments, as described above and referring now to FIG. 21, the staple cartridge support 1130 can comprise one or more support slots 1132 therein which can be configured to eliminate, or at least reduce, the relative movement between the staple bases 1122 and the cartridge support surface 1131. In at least one such embodiment, each support slot 1132 can be defined by a surface contour which matches, or at least substantially matches, the contour of the bottom surface of the staple positioned therein. For example, the bottom surface 1124 of the base 1122 depicted in FIG. 21 can comprise a circular, or at least substantially circular, surface and the support slot 1132 can also comprise a circular, or at least substantially circular, surface. In at least one such embodiment, the surface defining the slot 1132 can be defined by a radius of curvature which is greater than or equal to a radius of curvature which defines bottom surface 1124. Although the slots 1132 may assist in preventing or reducing relative sliding movement between the staples 1120 and the staple cartridge support 1130, the slots 1132 may also be configured to prevent or reduce relative rotational movement between the staples 1120 and the staple cartridge support 1130. More particularly, in at least one embodiment, the slots 1132 can be configured to closely receive the bases 1122 in order to prevent or reduce the rotation of the staples 1120 about axes 1129, for example, such that the staples 1120 do not rotate or twist when they are being deformed.

In various embodiments, further to the above, each staple 1120 can be formed from a round, or an at least substantially round, wire. In certain embodiments, the legs and the base of each staple can be formed from a wire having a non-circular cross-section, such as a rectangular cross-section, for example. In at least one such embodiment, the staple cartridge support 1130 can comprise corresponding non-circular slots, such as rectangular slots, for example, configured to receive the bases of such staples. In various embodiments, referring now to FIG. 22, each staple 1120 can comprise a crown, such as a crown 1125, for example, overmolded onto a base 1122 wherein each crown 1125 can be positioned within a support slot in the staple cartridge support 1130. In at least one such embodiment, each crown 1125 can comprise a square and/or rectangular cross-section, for example, which can be configured to be received within square and/or rectangular slots 1134, for example, in the staple cartridge support 1130. In various embodiments, the crowns 1125 can be comprised of a bioabsorbable plastic, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example, and can be formed around the bases 1122 of the staples 1120 by an injection molding process, for example. Various crowns and methods for forming various crowns are disclosed in U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, filed on Sep. 29, 2006, now U.S. Pat. No. 7,794,475, the entire disclosure of which is incorporated be reference herein. Referring again to FIG. 22, the slots 1134 can further comprise lead-ins, or bevels, 1135 which can be configured to facilitate the insertion of the crowns 1125 into the slots 1134. In various embodiments, the bases and/or crowns of the staples 1120 may be positioned within the slots 1134 when the staple cartridge 1100 is assembled to the staple cartridge support 1130. In certain embodiments, the crowns 1125 of the staples 1120 may be aligned with the slots 1134 when the staple cartridge 1100 is assembled to the staple cartridge support 1130. In at least one such embodiment, the crowns 1125 may not enter into the slots 1134 until a compressive force is applied to the staple legs 1121 and the bases and/or crowns of the staples 1120 are pushed downwardly into the slots 1134.

Figure 23:
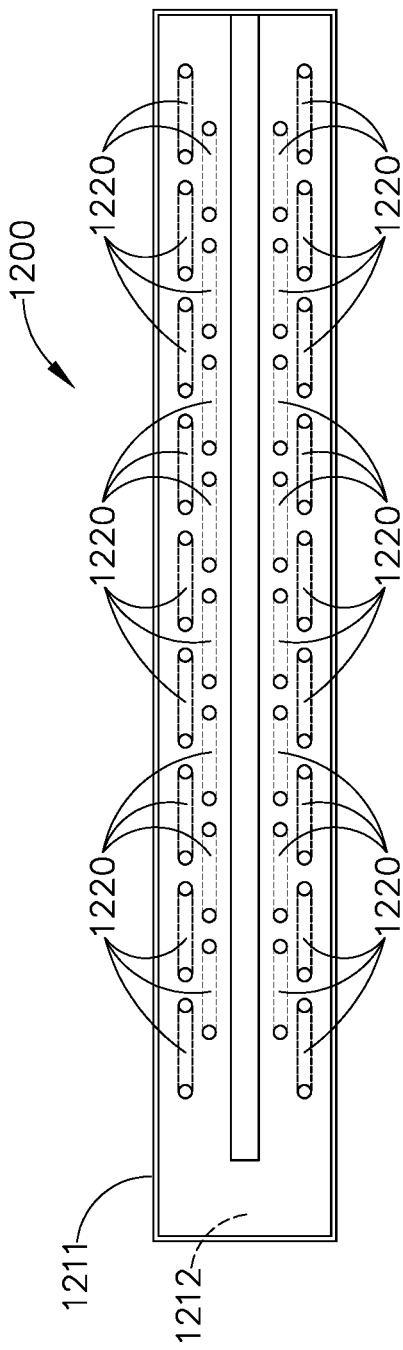
FIG. 23 is a top view of a staple cartridge in accordance with at least one embodiment comprising staples embedded in a collapsible staple cartridge body.
Figure 24:
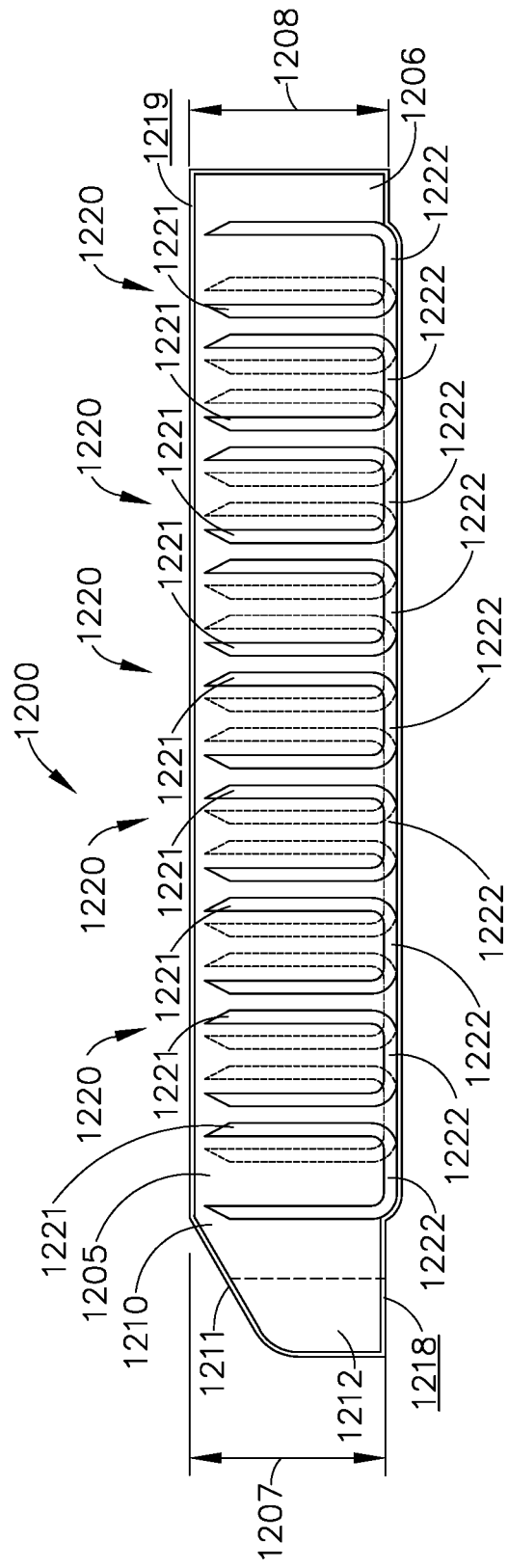
FIG. 24 is an elevational view of the staple cartridge of FIG. 23.

In various embodiments, referring now to FIGS. 23 and 24, a staple cartridge, such as staple cartridge 1200, for example, can comprise a compressible, implantable cartridge body 1210 comprising an outer layer 1211 and an inner layer 1212. Similar to the above, the staple cartridge 1200 can comprise a plurality of staples 1220 positioned within the cartridge body 1210. In various embodiments, each staple 1220 can comprise a base 1222 and one or more staple legs 1221 extending therefrom. In at least one such embodiment, the staple legs 1221 can be inserted into the inner layer 1212 and seated to a depth in which the bases 1222 of the staples 1220 abut and/or are positioned adjacent to the bottom surface 1218 of the inner layer 1212, for example. In the embodiment depicted in FIGS. 23 and 24, the inner layer 1212 does not comprise staple cavities configured to receive a portion of the staples 1220 while, in other embodiments, the inner layer 1212 can comprise such staple cavities. In various embodiments, further to the above, the inner layer 1212 can be comprised of a compressible material, such as bioabsorbable foam and/or oxidized regenerated cellulose (ORC), for example, which can be configured to allow the cartridge body 1210 to collapse when a compressive load is applied thereto. In various embodiments, the inner layer 1212 can be comprised of a lyophilized foam comprising polylactic acid (PLA) and/or polyglycolic acid (PGA), for example. The ORC may be commercially available under the trade name Surgicel and can comprise a loose woven fabric (like a surgical sponge), loose fibers (like a cotton ball), and/or a foam. In at least one embodiment, the inner layer 1212 can be comprised of a material including medicaments, such as freeze-dried thrombin and/or fibrin, for example, contained therein and/or coated thereon which can be water-activated and/or activated by fluids within the patient's body, for example. In at least one such embodiment, the freeze-dried thrombin and/or fibrin can be held on a Vicryl (PGA) matrix, for example. In certain circumstances, however, the activatable medicaments can be unintentionally activated when the staple cartridge 1200 is inserted into a surgical site within the patient, for example. In various embodiments, referring again to FIGS. 23 and 24, the outer layer 1211 can be comprised of a water impermeable, or at least substantially water impermeable, material such that liquids do not come into contact with, or at least substantially contact, the inner layer 1212 until after the cartridge body 1210 has been compressed and the staple legs have penetrated the outer layer 1211 and/or after the outer layer 1211 has been incised in some fashion. In various embodiments, the outer layer 1211 can be comprised of a buttress material and/or plastic material, such as polydioxanone (PDS) and/or polyglycolic acid (PGA), for example. In certain embodiments, the outer layer 1211 can comprise a wrap which surrounds the inner layer 1212 and the staples 1220. More particularly, in at least one embodiment, the staples 1220 can be inserted into the inner layer 1212 and the outer layer 1211 can be wrapped around the sub-assembly comprising the inner layer 1212 and the staples 1220 and then sealed.

Figure 25:
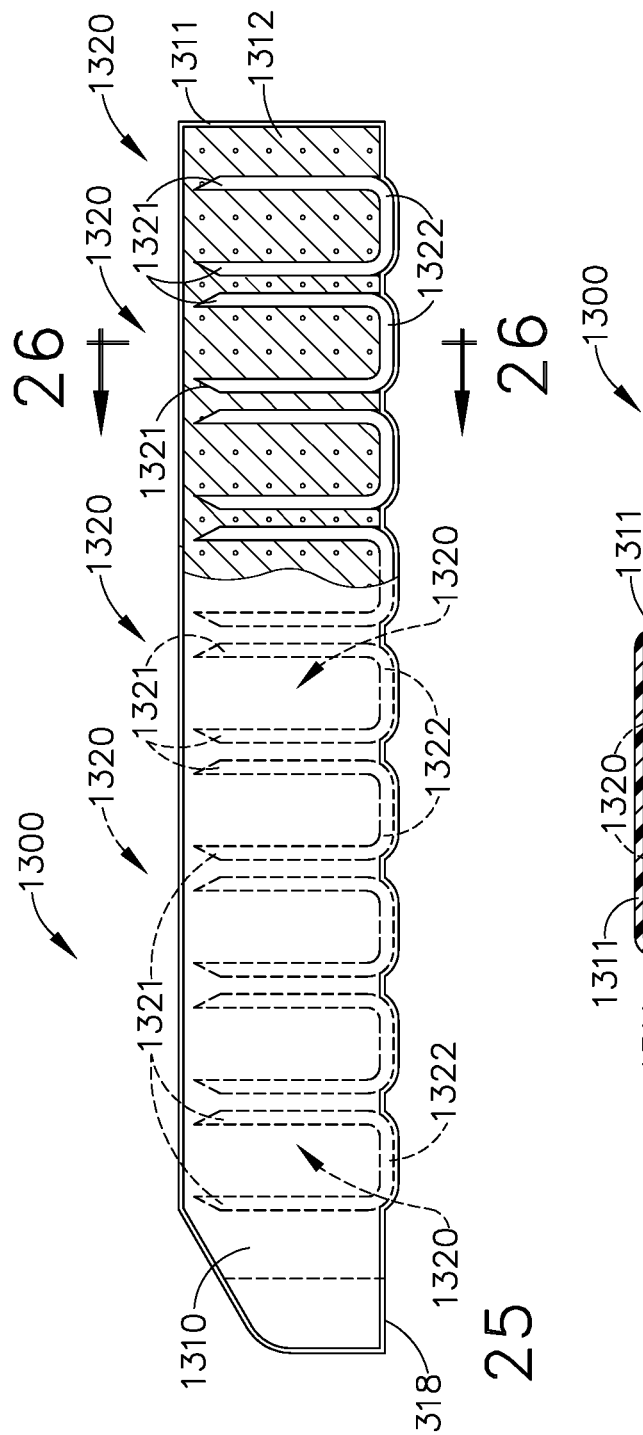
FIG. 25 is an elevational view of a staple cartridge in accordance with at least one embodiment comprising a protective layer surrounding staples positioned within a collapsible staple cartridge body.
Figure 26:
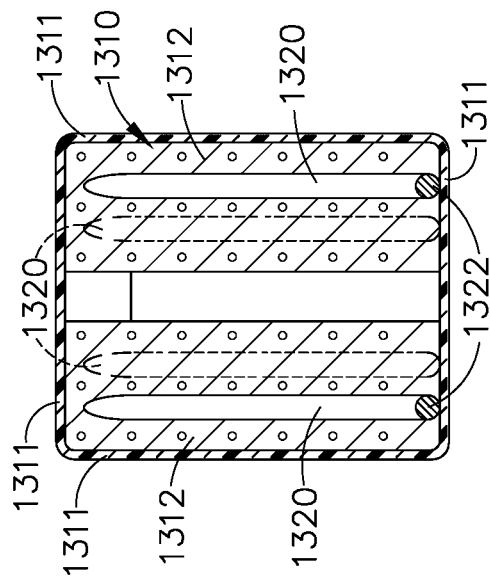
FIG. 26 is a cross-sectional view of the staple cartridge of FIG. 25 taken along line 26-26 in FIG. 25.

In various embodiments, referring now to FIGS. 25 and 26, a staple cartridge, such as staple cartridge 1300, for example, can comprise a compressible, implantable cartridge body 1310 including an outer layer 1311 and an inner layer 1312. Similar to the above, the staple cartridge 1300 can further comprise staples 1320 positioned within the cartridge body 1310 wherein each staple 1320 can comprise a base 1322 and one or more legs 1321 extending therefrom. Similar to staple cartridge 1200, the bases 1322 of staples 1320 can extend below the bottom surface 1318 of the inner layer 1312 and the outer layer 1311 can surround the bases 1322. In at least one such embodiment, the outer layer 1311 can be sufficiently flexible so as to envelop each staple base 1322 such that the outer layer 1311 conforms to the contour of the bases 1322. In at least one alternative embodiment, referring again to FIG. 24, the outer layer 1211 can be sufficiently rigid such that it extends around the bases 1222 without conforming to each base 1222. In any event, in various embodiments, the outer layer 1311 can be positioned intermediate the bases 1322 of staples 1320 and a staple cartridge support surface, such as support surfaces 1031 or 1131, for example, supporting the staple cartridge 1300. In at least one such embodiment, the outer layer 1311 can be positioned intermediate the bases 1322 and support slots, such as slots 1032 or 1132, for example, defined in the staple cartridge support surface. In at least one such embodiment, further to the above, the outer layer 1311 can be configured to limit the movement of the bases 1322 and/or increase the coefficient of friction between the bases 1322 and the staple cartridge support surface and/or support slots in order to reduce relative movement therebetween. In various alternative embodiments, referring now to FIGS. 27 and 28, the outer layer of a staple cartridge, such as staple cartridge 1400, for example, may not entirely surround the staples positioned therein. In at least one such embodiment, an outer layer 1411 of a compressible, implantable cartridge body 1410 may be assembled to the inner layer 1412 before the staple legs 1421 of staples 1420 are inserted into the cartridge body 1410. As a result of the above, the bases 1422 of staples 1420 may extend outside of the outer layer 1411 and, in at least one such embodiment, the bases 1422 may be positioned directly into the support slots 1032 or 1132 within the staple cartridge support surfaces 1031 or 1131, for example. In various embodiments, the staple legs 1421 may incise the outer layer 1411 when they are inserted therethrough. In various circumstances, the holes created by the staple legs 1421 may closely surround the staple legs 1421 such that very little, if any, fluid can leak between the staple legs 1421 and the outer layer 1411 which can reduce the possibility of, or prevent, the medicament contained within the staple cartridge body 1410 from being activated and/or leaking out of the cartridge body 1410 prematurely.

As discussed above, referring again to FIGS. 23 and 24, the legs 1221 of the staples 1220 can be embedded within the cartridge body 1210 and the bases 1222 of staples 1220 may extend outwardly from the bottom surface 1218 of the inner layer 1212. In various embodiments, further to the above, the inner layer 1212 may not comprise staple cavities configured to receive the staples 1220. In various other embodiments, referring now to FIGS. 29 and 30, a staple cartridge, such as staple cartridge 1500, for example, may comprise a compressible, implantable cartridge body 1510 comprising staple cavities 1515 which can be configured to receive at least a portion of the staples 1520 therein. In at least one such embodiment, a top portion of the staple legs 1521 of the staples 1520 may be embedded in the inner layer 1512 while a bottom portion of the staple legs 1521, and the bases 1522, may be positioned within the staple cavities 1515. In certain embodiments, the bases 1522 may be entirely positioned in the staple cavities 1515 while, in some embodiments, the bases 1522 may at least partially extend below the bottom surface 1518 of the inner layer 1512. Similar to the above, the outer layer 1511 may enclose the inner layer 1512 and the staples 1520 positioned therein. In certain other embodiments, referring now to FIG. 31, a staple cartridge 1600 may comprise staples 1620 positioned within staple cavities 1615 in a compressible, implantable cartridge body 1610 wherein at least a portion of the staples 1620 are not enclosed by the outer layer 1611. In at least one such embodiment, each staple 1620 can comprise staple legs 1621 which are at least partially embedded in the inner layer 1612 and, in addition, bases 1622 which extend outwardly around the outer layer 1611.

In various embodiments, referring now to FIGS. 32 and 33, a staple cartridge, such as staple cartridge 1700, for example, can comprise a compressible, implantable cartridge body 1710 and a plurality of staples 1720 at least partially positioned within the cartridge body 1710. The cartridge body 1710 can comprise an outer layer 1711, an inner layer 1712, and, in addition, an alignment matrix 1740 which can be configured to align and/or retain the staples 1720 in position within the cartridge body 1710. In at least one embodiment, the inner layer 1712 can comprise a recess 1741 which can be configured to receive the alignment matrix 1740 therein. In various embodiments, the alignment matrix 1140 can be press-fit within the recess 1741 and/or otherwise suitably secured to the inner layer 1712 utilizing at least one adhesive, such as fibrin and/or protein hydrogel, for example. In at least one embodiment, the recess 1741 can be configured such that the bottom surface 1742 of alignment matrix 1740 is aligned, or at least substantially aligned, with the bottom surface 1718 of the inner layer 1712. In certain embodiments, the bottom surface 1742 of the alignment matrix can be recessed with respect to and/or extend from the bottom surface 1718 of the second layer 1712. In various embodiments, each staple 1720 can comprise a base 1722 and one or more legs 1721 extending from the base 1722, wherein at least a portion of the staple legs 1721 can extend through the alignment matrix 1740. The alignment matrix 1740 can further comprise a plurality of apertures and/or slots, for example, extending therethrough which can be configured to receive the staple legs 1721 therein. In at least one such embodiment, each aperture can be configured to closely receive a staple leg 1721 such that there is little, if any, relative movement between the staple leg 1721 and the sidewalls of the aperture. In certain embodiments, the alignment matrix apertures may not extend entirely through the alignment matrix 1740 and the staple legs 1721 may be required to incise the alignment matrix 1740 as the staple legs 1721 are pushed therethrough.

In various embodiments, the alignment matrix 1740 can be comprised of a molded plastic body which, in at least one embodiment, can be stiffer or less compressible than the inner layer 1712 and/or the outer layer 1711. In at least one such embodiment, the alignment matrix 1740 can be comprised of a plastic material and/or any other suitable material, such as polydioxanone (PDS) and/or polyglycolic acid (PGA), for example. In certain embodiments, the alignment matrix 1740 can be assembled to the inner layer 1712 and the staple legs 1721 can thereafter be inserted through the alignment matrix 1740 and embedded into the inner layer 1712. In various embodiments, the bottom surface 1742 of the alignment matrix 1740 can comprise one or more grooves, slots, or troughs, for example, which can be configured to at least partially receive the bases 1722 of the staples 1720. Similar to the above, the outer layer 1711 can then be placed around the subassembly comprising the inner layer 1712, the alignment matrix 1740, and the staples 1720. Alternatively, the outer layer 1711 can be placed around a subassembly comprising the inner layer 1712 and the alignment matrix 1740 wherein the staples 1720 can be thereafter inserted through the outer layer 1711, the alignment matrix 1740, and the inner layer 1712. In any event, as a result of the above, the inner layer 1712, the alignment matrix 1740, and/or the outer layer 1711 can be configured to retain the staples 1720 in position until and/or after they are deformed by an anvil as described above. In at least one such embodiment, the alignment matrix 1740 can serve to hold the staples 1720 in place before the staple cartridge 1700 is implanted within a patient and, in addition, secure the tissue along the staple line after the staple cartridge 1700 has been implanted. In at least one embodiment, the staples 1720 may be secured within the alignment matrix 1740 without being embedded in the inner layer 1712 and/or the outer layer 1711, for example.

Figure 34:
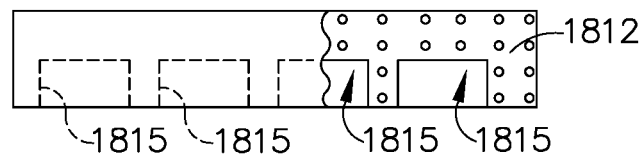
FIG. 34 is partial cut-away view of an inner layer of a compressible staple cartridge body.
Figure 35:
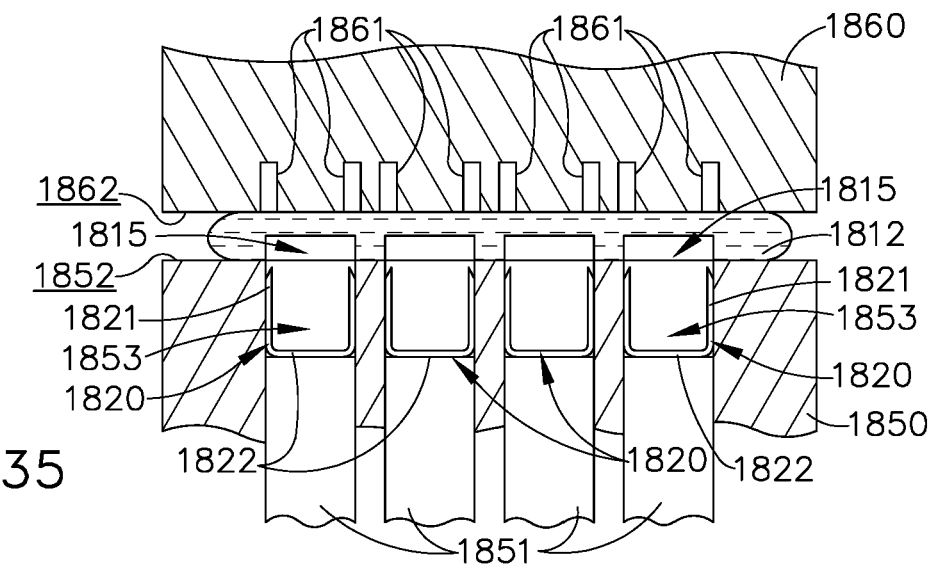
FIG. 35 is a diagram illustrating the inner layer of FIG. 34 compressed between a transfer plate and a support plate.
Figure 36:
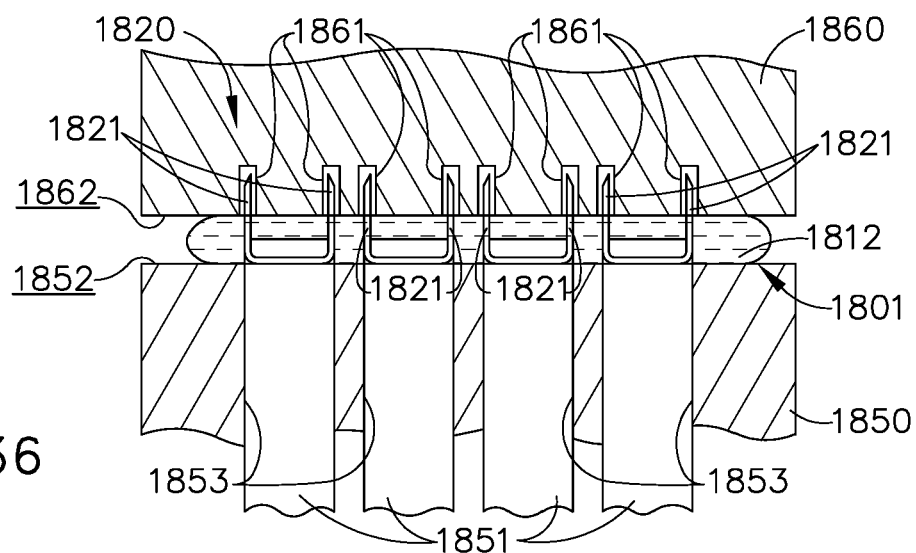
FIG. 36 is a diagram illustrating staples being inserted into the compressed inner layer of FIG. 35.

In various embodiments, referring now to FIGS. 34-40, a staple cartridge, such as staple cartridge 1800, for example, can be assembled by compressing an inner layer 1812, inserting staples, such as staples 1820, for example, into the inner layer 1812, and wrapping the inner layer 1812 with an outer layer 1811. Referring primarily to FIG. 34, a compressible inner layer 1812 is illustrated as comprising a plurality of staple cavities 1815 defined therein, although other embodiments are envisioned in which the inner layer 1812 does not comprise staple cavities, as described above. Referring now to FIG. 35, the compressible inner layer 1812 can be positioned intermediate a transfer plate 1850 and a support plate 1860 and compressed between the compression surfaces 1852 and 1862 thereof, respectively. As illustrated in FIG. 35, the top and bottom surfaces of the inner layer 1812 can be compressed toward one another and, in response thereto, the inner layer 1812 can bulge outwardly in the lateral directions. In certain embodiments, the inner layer 1812 can be compressed to a height which is approximately one-third of its original height, for example, and can have a height or thickness between approximately 0.06" and approximately 0.08" in its compressed state, for example. As also illustrated in FIG. 35, the transfer plate 1850 can further comprise a plurality of staples, such as staples 1820, for example, positioned within a plurality of staple wells 1853. In addition, the transfer plate 1850 can further comprise a plurality of drivers 1851 which can be configured to push the staples 1820 upwardly and out of the staple wells 1853. Referring now to FIG. 36, the drivers 1851 can be utilized to push the staple legs 1821 of the staples 1820 into and through the compressed inner layer 1812. In various embodiments, the drivers 1851 can be configured such that the top surfaces thereof are positioned flush, or at least nearly flush, with the compression surface 1852 of the transfer plate 1850 when the staples 1820 have been fully deployed from the staple wells 1853 of transfer plate 1850. In certain embodiments, as also illustrated in FIG. 36, the support plate 1860 can comprise a plurality of receiving apertures 1861 which can be configured to receive the staple legs 1821, or at least the tips of the staple legs 1821, after they are pushed through the inner layer 1812. The receiving apertures 1861, or the like, may be necessitated in embodiments where the inner layer 1812 has been compressed to a height which is shorter than the height of the staples 1820 and, thus, when the staples 1820 have been fully ejected from the staple wells 1853, the staple legs 1821 may protrude from the top surface of the compressed inner layer 1812. In certain other embodiments, the inner layer 1812 may be compressed to a height which is taller than the height of the staples 1820 and, as a result, the receiving apertures 1861 in support plate 1860 may be unnecessary.

Figure 37:
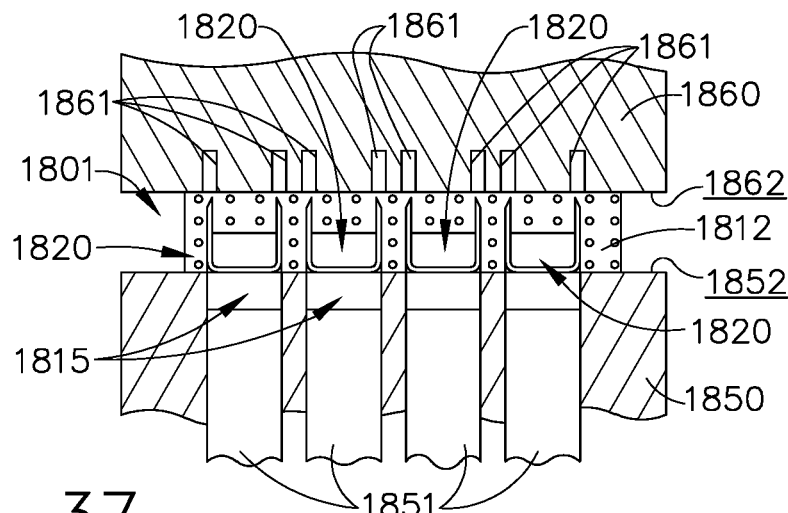
FIG. 37 is a diagram of the support plate of FIG. 35 being removed away from the inner layer.
Figure 38:
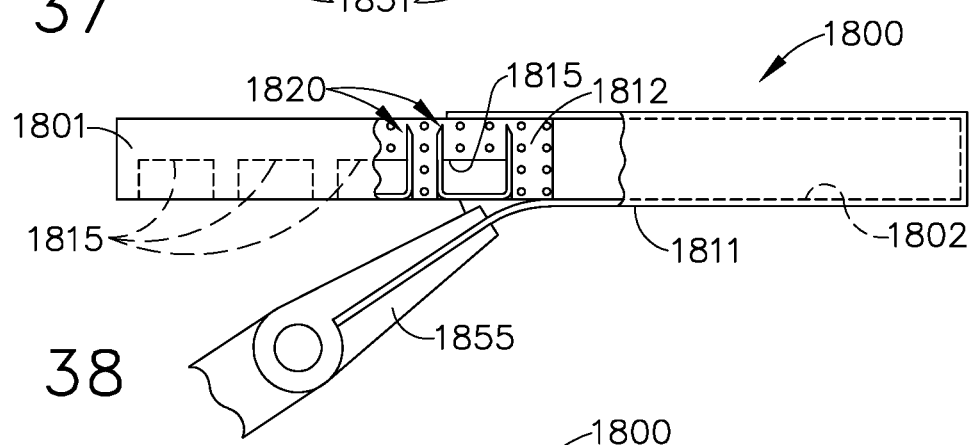
FIG. 38 is a diagram of a subassembly comprising the inner layer of FIG. 34 and the staples of FIG. 36 being inserted into an outer layer.
Figure 39:
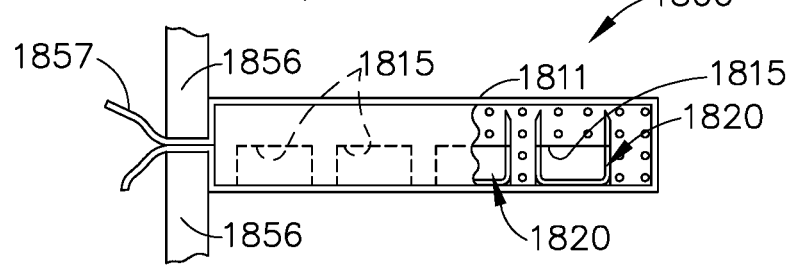
FIG. 39 is a diagram illustrating the outer layer of FIG. 38 being sealed to form a sealed staple cartridge.
Figure 40:
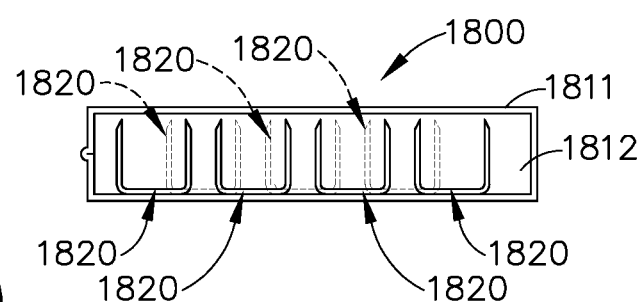
FIG. 40 is a cross-sectional view of the sealed staple cartridge of FIG. 39.

After the staples 1820 have been inserted into the inner layer 1812, referring now to FIG. 37, the support plate 1860 can be moved away from the transfer plate 1850 in order to allow the inner layer 1812 to decompress. In such circumstances, the inner layer 1812 can resiliently re-expand to its original, or at least near-original, uncompressed height. As the inner layer 1812 re-expands, the height of the inner layer 1812 can increase such that it exceeds the height of the staples 1820 and such that the staple legs 1821 of the staples 1820 no longer protrude from the top surface of the inner layer 1812. In various circumstances, the receiving apertures 1861 can be configured to hold the staple legs 1821 in position at least until the support plate 1860 has been sufficiently moved away such that the legs 1821 are no longer positioned within the receiving apertures 1861. In such circumstances, the receiving apertures 1861 can assist in maintaining the relative alignment of the staples 1820 within the inner layer 1812 as it re-expands. In various circumstances, the inner layer 1812 and the staples 1820 positioned therein can comprise a subassembly 1801 which, referring now to FIG. 38, can be inserted into an outer layer 1811, for example. In at least one such embodiment, the outer layer 1811 can comprise a cavity 1802 defined therein which can be configured to receive the subassembly 1801 therein. In various circumstances, a tool, such as pliers 1855, for example, can be utilized to pull the outer layer 1811 onto the subassembly 1801. Once the subassembly 1801 has been sufficiently positioned within the outer layer 1811, referring now to FIG. 39, the outer layer 1811 can be sealed. In various embodiments, the outer layer 1811 can be sealed utilizing the application of heat energy to a portion thereof. More particularly, in at least one embodiment, the outer layer 1811 can be comprised of a plastic material wherein the open end of the outer layer 1811 can be heat-staked by one or more heated elements, or irons, 1856 in order to bond and/or seal the perimeter of the open end of the outer layer 1811 together. In at least one such embodiment, referring now to FIG. 40, an excess portion 1857 of the outer layer 1811 can be removed and the staple cartridge 1800 can then be used as described herein.

As described above, a staple cartridge can be positioned within and/or secured to a staple cartridge attachment portion. In various embodiments, referring now to FIGS. 41 and 42, a staple cartridge attachment portion can comprise a staple cartridge channel, such as staple cartridge channel 1930, for example, which can be configured to receive at least a portion of a staple cartridge, such as staple cartridge 1900, for example, therein. In at least one embodiment, the staple cartridge channel 1930 can comprise a bottom support surface 1931, a first lateral support wall 1940, and a second lateral support wall 1941. In use, the staple cartridge 1900 can be positioned within the staple cartridge channel 1930 such that the staple cartridge 1900 is positioned against and/or adjacent to the bottom support surface 1931 and positioned intermediate the first lateral support wall 1940 and the second lateral support wall 1941. In certain embodiments, the first lateral support wall 1940 and the second lateral support wall 1941 can define a lateral gap therebetween. In at least one such embodiment, the staple cartridge 1900 can comprise a lateral width 1903 which is the same as and/or wider than the lateral gap defined between the support walls 1940 and 1941 such that a compressible, implantable cartridge body 1910 of the staple cartridge 1900 can fit securely between the walls 1940 and 1941. In certain other embodiments, the lateral width 1903 of the staple cartridge 1900 can be shorter than the gap defined between the first and second side walls 1940 and 1941. In various embodiments, at least a portion of the walls 1940 and 1941 and the bottom support surface 1931 can be defined by a stamped metal channel while, in at least one embodiment, at least a portion of the lateral support wall 1940 and/or lateral support wall 1941 can be comprised of a flexible material, such as an elastomeric material, for example. Referring primarily to FIG. 41, the first side wall 1940 and the second side wall 1941 of the staple cartridge channel 1930 can each be comprised of a rigid portion 1933 extending upwardly from the bottom support surface 1931 and a flexible portion 1934 extending upwardly from the rigid portions 1933.

In various embodiments, further to the above, the cartridge body 1910 of staple cartridge 1900 can be comprised of one or more compressible layers, such as first layer 1911 and second layer 1912, for example. When the cartridge body 1910 is compressed against the bottom support surface 1931 by an anvil, as described above, the side portions of the cartridge body 1910 can expand laterally. In embodiments where the staple cartridge 1930 is comprised of rigid side walls, the lateral expansion of the cartridge body 1910 can be prevented, or at least limited, by the rigid side walls and, as a result, a significant amount of internal pressure, or stress, can be developed within the cartridge body 1910. In embodiments where at least a portion of the staple cartridge 1930 is comprised of flexible side walls, the flexible side walls can be configured to flex laterally and permit the side portions of the cartridge body 1910 to expand laterally, thereby reducing the internal pressure, or stress, generated within the cartridge body 1910. In embodiments where the cartridge channel does not comprise lateral side walls, or comprises lateral sidewalls which are relatively shorter than the staple cartridge, the side portions of the staple cartridge may expand laterally uninhibited, or at least substantially uninhibited. In any event, referring now to FIG. 42, a staple cartridge channel 2030 can comprise lateral sidewalls 2040 and 2041 which can be entirely comprised of a flexible material, such as an elastomeric material, for example. The staple cartridge channel 2030 can further comprise lateral slots 2033 extending along the sides of the bottom support surface 2031 of the staple cartridge channel 2030 which can be configured to receive and secure at least a portion of the lateral sidewalls 2040 and 2041 therein. In certain embodiments, the lateral side walls 2040 and 2041 can be secured in the slots 2033 via a snap-fit and/or press-fit arrangement while, in at least some embodiments, the lateral side walls 2040 and 2041 can be secured in the slots 2033 by one or more adhesives. In at least one embodiment, the sidewalls 2040 and 2041 may be detachable from the bottom support surface 2031 during use. In any event, a compressible, implantable cartridge body 2010 can be detached and/or disengaged from the lateral side walls 2040 and 2041 when the cartridge body 2010 is implanted with the staples 2020.

In various embodiments, referring now to FIG. 43, a surgical instrument can comprise a shaft 2150 and an end effector extending from the distal end of the shaft 2150. The end effector can comprise, similar to the above, a staple cartridge channel 2130, an anvil 2140 movable between an open position and a closed position, and a staple cartridge 2100 positioned intermediate the staple cartridge channel 2130 and the anvil 2140. Also similar to the above, the staple cartridge 2100 can comprise a compressible, implantable cartridge body 2110 and a plurality of staples 2120 positioned in the cartridge body 2110. In various embodiments, the staple cartridge channel 2130 can comprise, one, a bottom support surface 2131 against which the staple cartridge 2100 can be positioned, two, a distal end 2135 and, three, a proximal end 2136. In at least one embodiment, as illustrated in FIG. 43, the staple cartridge 2100 can comprise a first end 2105 which can be positionable in the distal end 2135 of the staple cartridge channel 2130 and a second end 2106 which can be positionable in the proximal end 2136 of the staple cartridge channel 2130. In various embodiments, the distal end 2135 of the staple cartridge channel 2130 can comprise at least one distal retention feature, such as a retention wall 2137, for example, and, similarly, the proximal end 2136 can comprise at least one proximal retention feature, such as a retention wall 2138, for example. In at least one such embodiment, the distal retention wall 2137 and the proximal retention wall 2138 can define a gap therebetween which can be equal to or less than the length of the staple cartridge 2100 such that the staple cartridge 2100 can fit securely within the staple cartridge channel 2130 when the staple cartridge 2100 is inserted therein.

In various embodiments, referring again to FIGS. 23 and 24, a staple cartridge, such as staple cartridge 1200, for example, can comprise a flat, or at least substantially flat, tissue-contacting surface 1219. In at least one such embodiment, the staple cartridge body 1210 of staple cartridge 1200 can comprise a first end 1205 which can be defined by a first height, or thickness, 1207 and a second end 1206 which can be defined by a second height, or thickness, 1208, wherein the first height 1207 can be equal to, or at least substantially equal to, the second height 1208. In certain embodiments, the cartridge body 1210 can comprise a constant, or at least substantially constant, height, or thickness, between the first end 1205 and the second end 1206. In at least one such embodiment, the tissue-contacting surface 1219 can be parallel, or at least substantially parallel, to the bottom surface 1218 of the cartridge body 1210. In various embodiments, referring once again to FIG. 43, the first end 2105 of the cartridge body 2110 of staple cartridge 2100 can be defined by a first height 2107 which is different than a second height 2108 of the second end 2106. In the illustrated embodiment, the first height 2107 is larger than the second height 2108, although the second height 2108 could be larger than the first height 2107 in alternative embodiments. In various embodiments, the height of the cartridge body 2110 can decrease linearly and/or geometrically between the first end 2105 and the second end 2106. In at least one such embodiment, the tissue-contacting surface 2119, which extends between the first end 2105 and the second end 2106, can be oriented along an angle defined therebetween. In at least one such embodiment, the tissue-contacting surface 2119 may not be parallel to the bottom surface 2118 of the cartridge body 2110 and/or parallel to the support surface 2131 of the staple cartridge channel 2130.

In various embodiments, referring again to FIGS. 43 and 44, the anvil 2140 can comprise a tissue-contacting surface 2141 which can be parallel, or at least substantially parallel, to the support surface 2131 of the staple cartridge channel 2130 when the anvil 2140 is in a closed position, as illustrated in FIG. 44. When the anvil 2140 is in a closed position, the anvil 2140 can be configured to compress the first end 2105 of the staple cartridge 2100 more than the second end 2106 owing to the taller height of the first end 2105 and the shorter height of the second end 2106. In some circumstances, including circumstances where the tissue T positioned intermediate the tissue contacting surfaces 2119 and 2141 has a constant, or at least substantially constant, thickness, the pressure generated within the tissue T and the cartridge 2100 can be greater at the distal end of the end effector than the proximal end of the end effector. More particularly, when the tissue T between the anvil 2140 and the staple cartridge 2100 has a substantially constant thickness, the tissue T positioned intermediate the distal end 2145 of the anvil 2140 and the first end 2105 of the staple cartridge 2100 can be more compressed than the tissue T positioned intermediate the proximal end 2146 of the anvil 2140 and the second end 2106 of the staple cartridge 2100. In various embodiments, a pressure gradient can be generated within the tissue T between the proximal end and the distal end of the end effector. More particularly, in at least one embodiment, when the tissue T between the anvil 2140 and the staple cartridge 2100 has a substantially constant thickness and the height of the staple cartridge 2100 decreases linearly from the distal end to the proximal end of the end effector, the pressure within the tissue T can decrease linearly from the distal end of the end effector to the proximal end of the end effector. Similarly, in at least one embodiment, when the tissue T between the anvil 2140 and the staple cartridge 2100 has a substantially constant thickness and the height of the staple cartridge 2100 decreases geometrically from the distal end to the proximal end of the end effector, the pressure within the tissue T can decrease geometrically from the distal end of the end effector to the proximal end of the end effector.

In various embodiments, referring again to FIG. 43, the tissue T positioned intermediate the staple cartridge 2100 and the anvil 2140 may not have a constant thickness throughout. In at least one such circumstance, the tissue T positioned between the proximal end 2146 of the anvil 2140 and the second end 2106 of the staple cartridge 2100 may be thicker than the tissue T positioned between the distal end 2145 of the anvil 2140 and the first end 2105 of the staple cartridge 2100. In such circumstances, as a result, the thicker tissue T may be generally positioned above the shorter proximal end 2106 of the staple cartridge 2100 and the thinner tissue T may be generally positioned above the taller distal end 2105. In use, the firing collar 2152 of the shaft 2150 can be advanced distally along the shaft spine 2151 such that the firing collar 2152 engages the cam portion 2143 of the anvil 2140 and rotates the anvil 2140 toward the staple cartridge 2100 as illustrated in FIG. 44. Once the anvil 2140 has been rotated into a fully-closed position, the tissue T may be compressed between the tissue-contacting surfaces 2119 and 2141 and, even though the height of the staple cartridge 2100 may not be constant between the proximal and distal ends of the end effector, the pressure or compressive forces applied to the tissue T may be constant, or at least substantially constant, thereacross. More particularly, as the thinner tissue T may be associated with the taller height of the staple cartridge 2100 and the thicker tissue T may be associated with the shorter height of the staple cartridge 2100, the cumulative, or summed, height of the tissue T and the staple cartridge 2100 may be constant, or at least substantially constant, between the proximal and distal ends of the end effector and, as a result, the compression of this cumulative height by the anvil 2140 may be constant, or at least substantially constant, thereacross.

Figure 45:
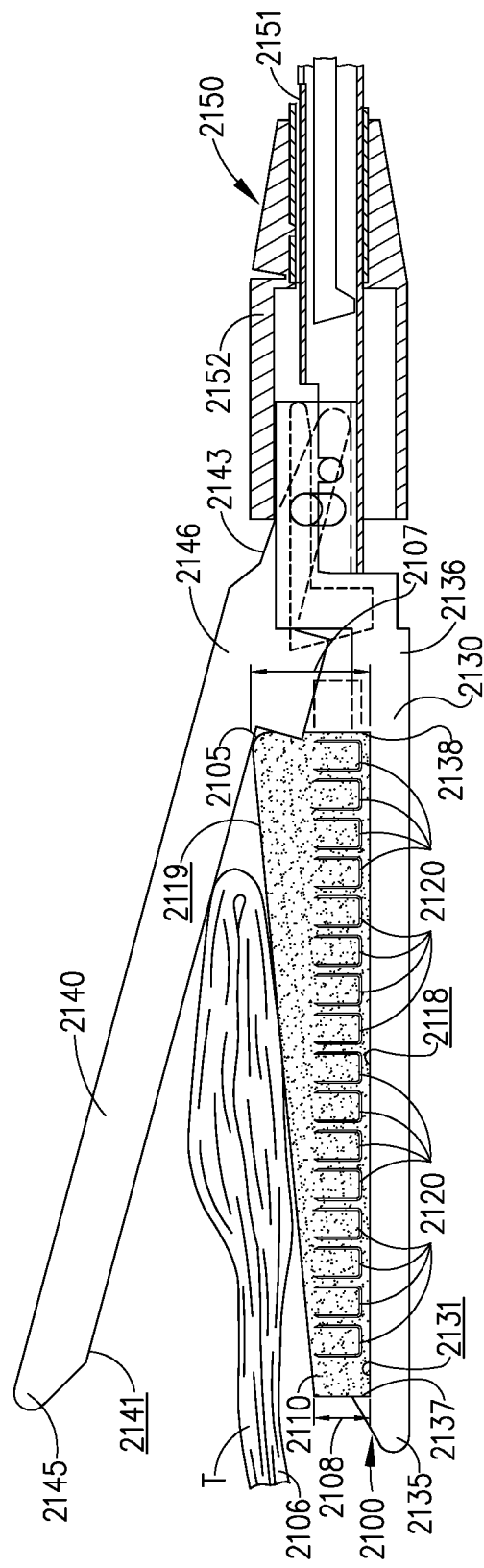
FIG. 45 is an elevational view of the end effector of FIG. 43 illustrating the staple cartridge of FIG. 43 positioned within the staple cartridge channel in an alternative manner.

In various embodiments, referring again to FIGS. 43 and 44, the staple cartridge 2100 can comprise an asymmetrical configuration. In at least one such embodiment, for example, the height of the staple cartridge 2100 at the first end 2105 thereof may be higher than the height of the staple cartridge 2100 at the second end 2106 thereof. In certain embodiments, the staple cartridge 2100 and/or the staple cartridge channel 2130 can comprise one or more alignment and/or retention features which can be configured to assure that the staple cartridge 2100 can only be positioned within the staple cartridge channel 2130 in one orientation, i.e., an orientation in which the first end 2105 is positioned in the distal end 2135 of the staple cartridge channel 2130 and the second end 2106 is positioned in the proximal end 2136. In various alternative embodiments, the staple cartridge 2100 and/or the staple cartridge channel 2130 can comprise one or more alignment and/or retention features which can be configured to permit the staple cartridge 2100 to be positioned within the staple cartridge channel 2130 in more than one orientation. Referring now to FIG. 45, for example, the staple cartridge 2100 can be positioned within the staple cartridge channel 2130 such that the first end 2105 of the staple cartridge 2100 can be positioned in the proximal end 2136 of the staple cartridge channel 2130 and the second end 2106 can be positioned in the distal end 2135. In various embodiments, as a result, the shorter height of the staple cartridge 2100 can be positioned proximate the distal retention wall 2137 and the taller height of the staple cartridge 2100 can be positioned proximate to the proximal retention wall 2138. In at least one such embodiment, the staple cartridge 2100 can be suitably arranged to apply a constant, or at least substantially constant, clamping pressure to tissue T having a thicker portion within the distal end of the end effector and a thinner portion within the proximal end of the end effector. In various embodiments, the staple cartridge 2100, for example, can be selectively oriented within the staple cartridge channel 2130. In at least one such embodiment, the alignment and/or retention features of the staple cartridge 2100 can be symmetrical and a surgeon can selectively orient the staple cartridge 2100 within the staple cartridge channel 2130 in the orientations depicted in FIG. 43 and FIG. 45, for example.

Further to the above, the implantable cartridge body 2110 can comprise a longitudinal axis 2109 which, when the staple cartridge 2100 is positioned in the staple cartridge channel 2130, can extend between the proximal and distal ends of the end effector. In various embodiments, the thickness of the cartridge body 2110 can generally decrease and/or generally increase between the first end 2105 and the second end 2106 along the longitudinal axis 2109. In at least one such embodiment, the distance, or height, between the bottom surface 2118 and the tissue-contacting surface 2119 can generally decrease and/or generally increase between the first end 2105 and the second end 2106. In certain embodiments, the thickness of the cartridge body 2110 can both increase and decrease along the longitudinal axis 2109. In at least one such embodiment, the thickness of the cartridge body 2110 can comprise one or more portions which increase in thickness and one or more portions which can decrease in thickness. In various embodiments, the staple cartridge 2100 can comprise a plurality of staples 2120 positioned therein. In use, as described above, the staples 2120 can be deformed when the anvil 2140 is moved into a closed position. In certain embodiments, each staple 2120 can have the same, or at least substantially the same, height. In at least one such embodiment, the height of a staple can be measured from the bottom of the base of the staple to the top, or tip, of the tallest leg of the staple, for example.

In various embodiments, the staples within a staple cartridge can have different staple heights. In at least one such embodiment, a staple cartridge can comprise a first group of staples having a first staple height which are positioned in a first portion of a compressible cartridge body and a second group of staples having a second staple height which are positioned in a second portion of the compressible cartridge body. In at least one embodiment, the first staple height can be taller than the second staple height and the first group of staples can be positioned in the first end 2105 of the staple cartridge 2100 while the second group of staples can be positioned in the second end 2106. Alternatively, the taller first group of staples can be positioned in the second end 2106 of the staple cartridge 2100 while the shorter second group of staples can be positioned in the first end 2105. In certain embodiments, a plurality of staple groups, each group having a different staple height, can be utilized. In at least one such embodiment, a third group having an intermediate staple height can be positioned in the cartridge body 2110 intermediate the first group of staples and the second group of staples. In various embodiments, each staple within a staple row in the staple cartridge can comprise a different staple height. In at least one embodiment, the tallest staple within a staple row can be positioned on a first end of a staple row and the shortest staple can be positioned on an opposite end of the staple row. In at least one such embodiment, the staples positioned intermediate the tallest staple and the shortest staple can be arranged such that the staple heights descend between the tallest staple and the shortest staple, for example.

Figure 46:
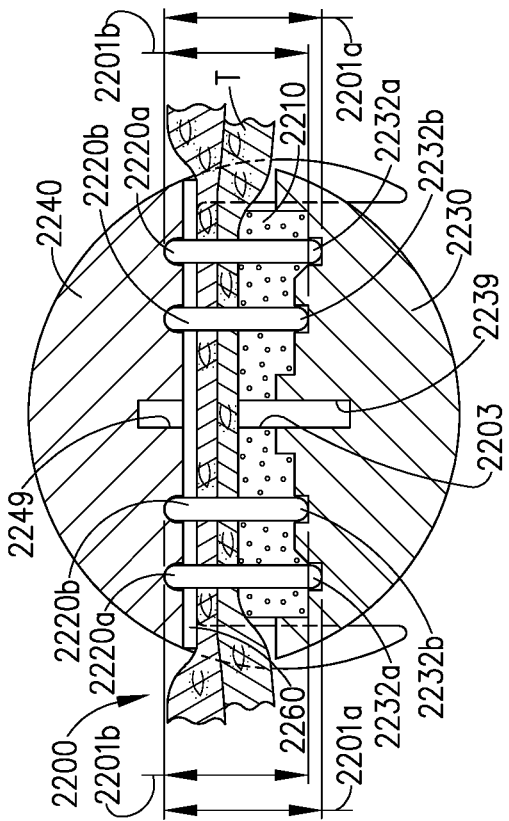
FIG. 46 is a cross-sectional view of an end effector of a surgical stapler comprising a compressible staple cartridge positioned within a staple cartridge channel and a piece of buttress material attached to an anvil.
Figure 47:
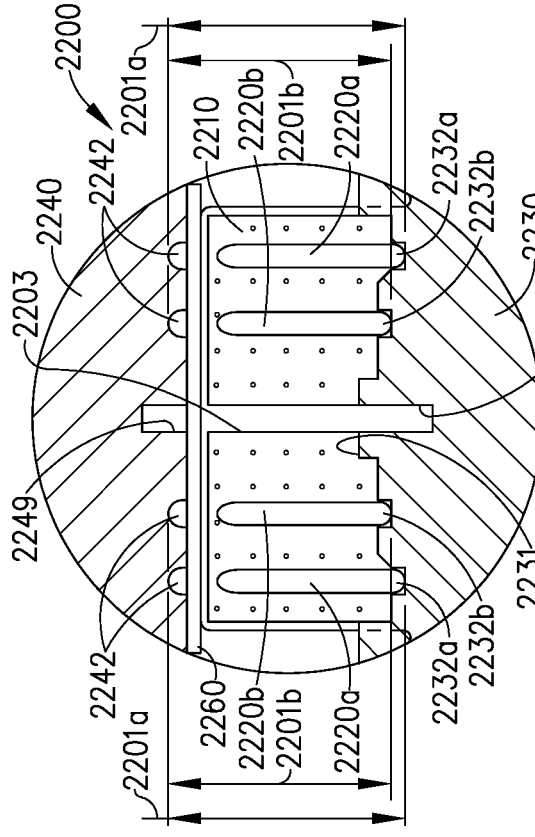
FIG. 47 is a cross-sectional view of the end effector of FIG. 46 illustrating the anvil in a closed position.

In various embodiments, referring now to FIG. 46, an end effector of a surgical stapler can comprise an anvil 2240, a staple cartridge channel 2230, and a staple cartridge 2200 supported by the staple cartridge channel 2230. The staple cartridge 2200 can comprise a compressible, implantable cartridge body 2210 and a plurality of staples, such as staples 2220a and staples 2220b, for example, positioned therein. In various embodiments, the staple cartridge channel 2230 can comprise a cartridge support surface 2231 and a plurality of staple support slots, such as support slots 2232a and 2232b, for example, defined therein. In at least one such embodiment, the staple cartridge 2200 can comprise two outer rows of staples 2220a and two inner rows of staples 2220b, wherein the support slots 2232a can be configured to support the staples 2220a and the support slots 2232b can be configured to support the staples 2220b. Referring to FIGS. 46 and 47, the anvil 2240 can comprise a plurality of staple forming pockets 2242 defined therein which can be configured to receive and deform the staples 2220a and 2220b when the anvil 2240 is moved toward the staple cartridge 2200. In at least one such embodiment, the bottom surfaces of the support slots 2232a can be a first distance 2201a away from the top surfaces of the staple forming pockets 2242 while the bottom surfaces of the support slots 2232b can be a second distance 2201b away from the top surfaces of the staple forming pockets 2242. In at least one such embodiment, the support slots 2232b are positioned closer to the anvil 2240 owing to the raised step in the support surface 2231 in which they are defined. Owing to the different distances 2201a and 2201b, in various embodiments, the outer rows of staples 2220a and the inner rows of staples 2220b can be deformed to different formed heights. In various circumstances, staples deformed to different formed heights can apply different clamping pressures or forces to the tissue T being stapled. In addition to the above, the staples can begin with different unformed staple heights. In at least one such embodiment, referring again to FIG. 46, the outer staples 2220a can have an initial, unformed height which is greater than the initial, unformed height of the inner staples 2220b. As illustrated in FIGS. 46 and 47, the inner staples 2220b, which have a shorter unformed height than the outer staples 2220a, can also have a shorter formed height than the outer staples 2220b. In various alternative embodiments, the inner staples 2220b may have a taller unformed height than the outer staples 2220a yet have a shorter deformed staple height than the outer staples 2220a.

In various embodiments, further to the above, the anvil 2240 can be moved into a closed position, as illustrated in FIG. 47, in order to compress the cartridge body 2210 and deform the staples 2220a and 2220b. In certain embodiments, a surgical stapler comprising the end effector depicted in FIGS. 46 and 47, for example, can further comprise a cutting member which can be configured to transect the tissue T positioned intermediate the anvil 2240 and the staple cartridge 2200. In at least one such embodiment, the anvil 2240, the staple cartridge channel 2230 and/or the staple cartridge 2200 can define a slot configured to slidably receive a cutting member therein. More particularly, the anvil 2240 can comprise a slot portion 2249, the staple cartridge channel 2230 can comprise a slot portion 2239, and the staple cartridge 2200 can comprise a slot portion 2203 which can be aligned, or at least substantially aligned, with one another when the anvil 2240 is in a closed, or at least substantially closed, position. In various embodiments, the cutting member can be moved from the proximal end of the end effector toward the distal end of the end effector after the anvil 2240 has been closed and the staples 2220a, 2220b have been deformed. In at least one embodiment, the cutting member can be moved independently of the staple deformation process. In certain embodiments, the cutting member can be advanced at the same time that the staples are being deformed. In any event, in at least one embodiment, the cutting member can be configured to incise the tissue along a path positioned intermediate the inner rows of staples 2220b.

In various embodiments, as illustrated in FIG. 47, the inner staples 2220b can be formed to a shorter height than the outer staples 2220a wherein the inner staples 2220b can apply a larger clamping pressure or force to the tissue adjacent to the cut line created by the cutting member. In at least one such embodiment, the larger clamping pressure or force created by the inner staples 2220b can provide various therapeutic benefits such as reducing bleeding from the incised tissue T while the smaller clamping pressure created by the outer staples 2220a can provide flexibility within the stapled tissue. In various embodiments, referring again to FIGS. 46 and 47, the anvil 2240 can further comprise at least one piece of buttress material, such as buttress material 2260, for example, attached thereto. In at least one such embodiment, the legs of the staples 2220a, 2220b can be configured to incise the buttress material 2260 and/or pass through apertures in the buttress material 2260 when the staple cartridge 2200 is compressed by the anvil 2240 and thereafter contact the staple forming pockets 2242 in the anvil 2240. As the legs of the staples 2220a, 2220b are being deformed, the legs can contact and/or incise the buttress material 2260 once again. In various embodiments, the buttress material 2260 can improve the hemostasis of and/or provide strength to the tissue being stapled.

Figure 48:
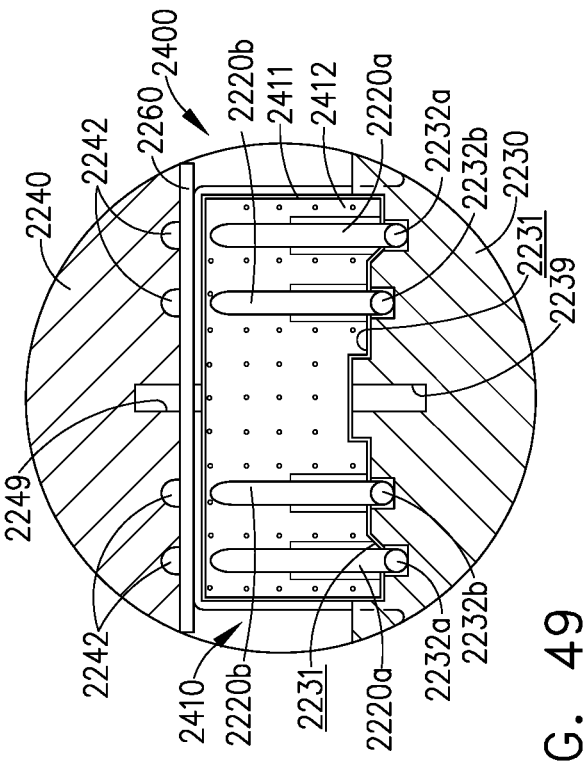
FIG. 48 is a cross-sectional view of an alternative embodiment of an end effector of a surgical stapler comprising a staple cartridge comprising a water impermeable layer.
Figure 49:
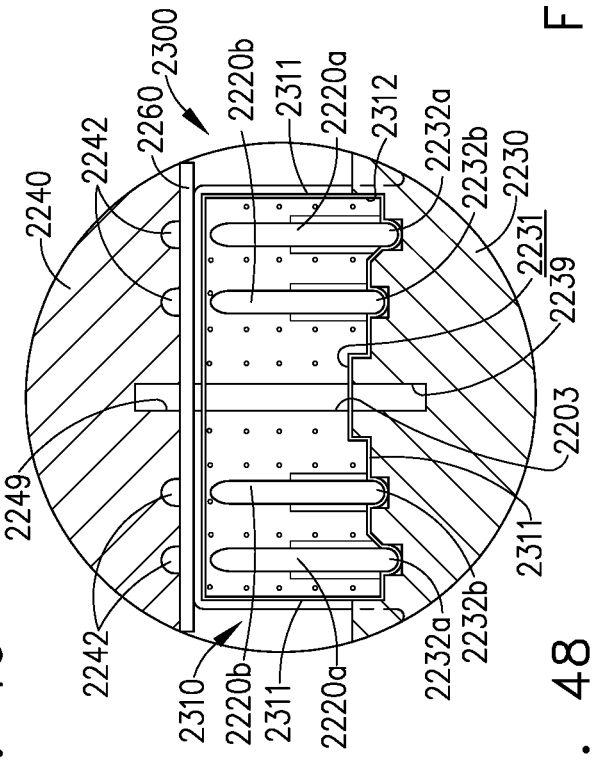
FIG. 49 is a cross-sectional view of another alternative embodiment of an end effector of a surgical stapler.

In various embodiments, referring again to FIGS. 46 and 47, the bottom surface of the cartridge body 2210 can comprise a stepped contour which matches, or at least substantially matches, the stepped contour of the cartridge support surface 2231. In certain embodiments, the bottom surface of the cartridge body 2210 can deform to match, or at least substantially match, the contour of the cartridge support surface 2231. In various embodiments, referring now to FIG. 48, an end effector, similar to the end effector depicted in FIG. 46, for example, can comprise a staple cartridge 2300 positioned therein. The staple cartridge 2300 can comprise a compressible, implantable body 2310 comprising an inner layer 2312 and an outer layer 2311 wherein, further to the above, the outer layer 2311 can be comprised of a water impermeable material in at least one embodiment. In various embodiments, the outer layer 2311 can extend around the staples 2220a, 2220b and can be positioned intermediate the staples 2220a, 2220b and the support slots 2232a, 2232b, respectively. In various embodiments, referring now to FIG. 49, an end effector, similar to the end effector depicted in FIG. 46, for example, can comprise a staple cartridge 2400 positioned therein. Similar to the staple cartridge 2300, the compressible, implantable cartridge body 2410 of staple cartridge 2400 can comprise an inner layer 2412 and an outer layer 2411; however; in at least one embodiment, the cartridge body 2410 may not comprise a cutting member slot therein. In at least one such embodiment, the cutting member may be required to incise the inner layer 2412 and/or the outer layer 2411, for example, as it is advanced through the staple cartridge.

Figure 50:
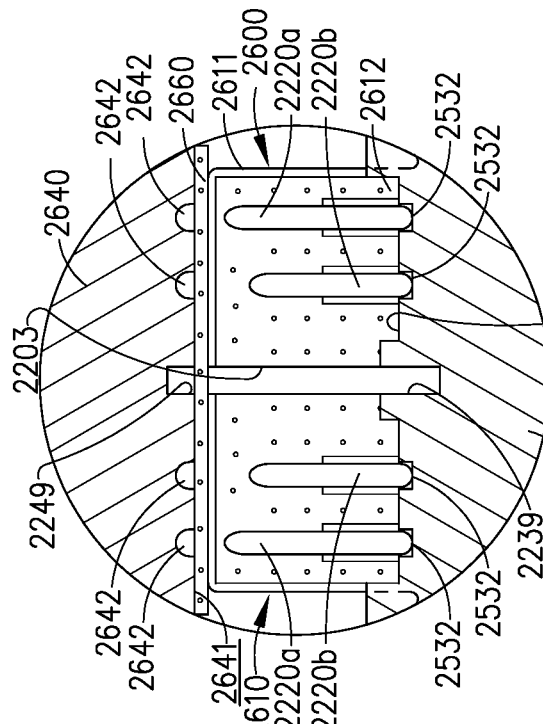
FIG. 50 is a cross-sectional view of an alternative embodiment of an end effector of a surgical stapler comprising a stepped anvil and a staple cartridge comprising a stepped cartridge body.

In various embodiments, referring now to FIG. 50, an end effector of a surgical stapler can comprise an anvil 2540, a staple cartridge channel 2530, and a staple cartridge 2500 positioned in the staple cartridge channel 2530. Similar to the above, the staple cartridge 2500 can comprise a compressible, implantable cartridge body 2510, outer rows of staples 2220a, and inner rows of staples 2220b. The staple cartridge channel 2530 can comprise a flat, or an at least substantially flat, cartridge support surface 2531 and staple support slots 2532 defined therein. The anvil 2540 can comprise a stepped surface 2541 and a plurality of staple forming pockets, such as forming pockets 2542a and 2542b, for example, defined therein. Similar to the above, the forming pockets 2542a and the support slots 2532 can define a distance therebetween which is greater than the distance between the forming pockets 2452b and the support slots 2532. In various embodiments, the anvil 2540 can further comprise a piece of buttress material 2560 attached to the stepped surface 2541 of the anvil 2540. In at least one such embodiment, the buttress material 2560 can conform, or at least substantially conform, to the stepped surface 2541. In various embodiments, the buttress material 2560 can be removably attached to the surface 2541 by at least one adhesive, such as fibrin and/or protein hydrogel, for example. In certain embodiments, the cartridge body 2510 can also comprise a stepped profile which, in at least one embodiment, parallels, or at least substantially parallels, the stepped surface 2541 of the anvil 2540. More particularly, in at least one embodiment, the anvil 2540 can comprise steps 2548 extending toward the staple cartridge 2500 wherein the steps 2548 can comprise a step height which equals, or at least substantially equals, the step height of the steps 2508 extending from the cartridge body 2510. In at least one such embodiment, as a result of the above, the amount of the compressible cartridge body 2510 that can be captured in the first staples 2220a can be different than the amount of the compressible cartridge body 2510 that can be captured in the second staples 2220b, for example.

Figure 51:
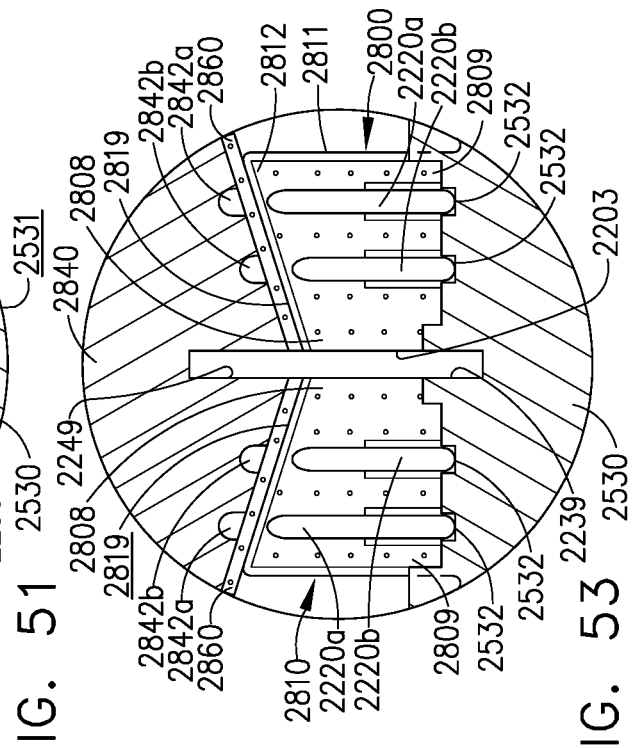
FIG. 51 is a cross-sectional view of another alternative embodiment of an end effector of a surgical stapler.

In various embodiments, referring now to FIG. 51, an end effector can comprise an anvil 2640, a staple cartridge channel 2530, and a staple cartridge 2600 positioned therebetween. The staple cartridge 2600 can comprise a compressible, implantable cartridge body 2610 including an inner layer 2612, an outer layer 2611, and a plurality of staples, such as staples 2220a and 2200b, for example, positioned therein. In various embodiments, the anvil 2640 can comprise a plurality of staple forming pockets 2642 in surface 2641 and the staple cartridge channel 2530 can comprise a plurality of staple forming slots 2532 defined in the support surface 2531. As illustrated in FIG. 51, the anvil surface 2641 can be parallel, or at least substantially parallel, to the cartridge support surface 2531 wherein each forming pocket 2642 can be positioned an equal, or at least substantially equal, distance away from an opposing and corresponding staple support slot 2532. In various embodiments, the staple cartridge 2600 can comprise staples having the same, or at least substantially the same, initial, unformed staple height and, in addition, the same, or at least substantially the same, formed staple height. In certain other embodiments, the outer rows of staples can comprise staples 2220a and the inner rows of staples can comprise staples 2220b wherein, as discussed above, the staples 2220a and 2220b can have different unformed staple heights. When the anvil 2640 is moved toward the staple cartridge 2600 into a closed position, the staples 2220a and 2220b can be formed such that they have the same, or at least substantially the same, formed staple height. In at least one such embodiment, as a result of the above, the formed outer staples 2220a and the inner staples 2220b may have the same, or at least substantially the same, amount of compressible cartridge body 2610 contained therein; however, as the outer staples 2220a have a taller unformed staple height than the inner staples 2220b and may have the same formed staple height nonetheless, a greater clamping pressure can be generated in the outer staples 2220a than the inner staples 2220b, for example.

Figure 52:
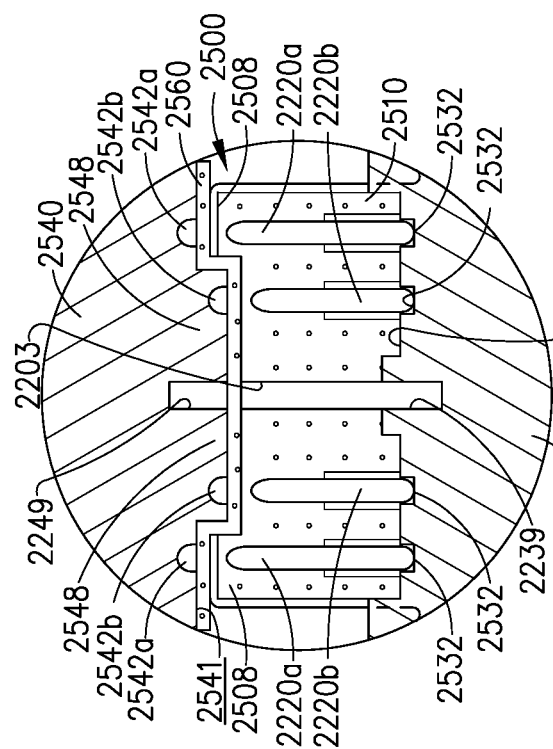
FIG. 52 is a cross-sectional view of an alternative embodiment of an end effector of a surgical stapler comprising inclined tissue-contacting surfaces.

In various embodiments, referring now to FIG. 52, an end effector of a surgical stapler can comprise an anvil 2740, a staple cartridge channel 2530, and a staple cartridge 2700 positioned within the staple cartridge channel 2530. Similar to the above, the staple cartridge 2700 can comprise a compressible, implantable cartridge body 2710 comprising an inner layer 2712, an outer layer 2711, and a plurality of staples, such as staples 2220a and 2220b, for example, positioned therein. In at least one embodiment, the thickness of the cartridge body 2710 can vary across its width. In at least one such embodiment, the cartridge body 2710 can comprise a center portion 2708 and side portions 2709, wherein the center portion 2708 can comprise a thickness which is greater than the thickness of the side portions 2709. In various embodiments, the thickest portion of the cartridge body 2710 can be located at the center portion 2708 while the thinnest portion of the cartridge body 2710 can be located at the side portions 2709. In at least one such embodiment, the thickness of the cartridge body 2710 can decrease gradually between the center portion 2708 and the side portions 2709. In certain embodiments, the thickness of the cartridge body 2710 can decrease linearly and/or geometrically between the center portion 2708 and the side portions 2709. In at least one such embodiment, the tissue-contacting surface 2719 of cartridge body 2710 can comprise two inclined, or angled, surfaces which slope downwardly from the center portion 2708 toward the side portions 2709. In various embodiments, the anvil 2740 can comprise two inclined, or angled, surfaces which parallel, or at least substantially parallel, the inclined tissue-contacting surfaces 2719. In at least one embodiment, the anvil 2740 can further comprise at least one piece of buttress material 2760 attached to the inclined surfaces of the anvil 2740.

In various embodiments, further to the above, the inner rows of staples in the staple cartridge 2700 can comprise the taller staples 2220a and the outer rows of staples can comprise the shorter staples 2220b. In at least one embodiment, the taller staples 2220a can be positioned within and/or adjacent to the thicker center portion 2708 while the staples 2220b can be positioned within and/or adjacent to the side portions 2709. In at least one such embodiment, as a result of the above, the taller staples 2220a can capture more material of the implantable cartridge body 2710 than the shorter staples 2220b. Such circumstances could result in the staples 2220a applying a greater clamping pressure to the tissue T than the staples 2220b. In certain embodiments, even though the taller staples 2220a may capture more material of the cartridge body 2710 therein than the shorter staples 2220b, the taller staples 2220a may have a taller formed staple height than the shorter staples 2220b owing to the inclined arrangement of the staple forming pockets 2742a and 2742b. Such considerations can be utilized to achieve a desired clamping pressure within the tissue captured by the staples 2220a and 2220b wherein, as a result, the clamping pressure in the staples 2220a can be greater than, less than, or equal to the clamping pressure applied to the tissue by the staples 2220b, for example. In various alternative embodiments to the end effector illustrated in FIG. 52, the shorter staples 2220b can be positioned within and/or adjacent to the thicker center portion 2708 of the cartridge body 2710 and the taller staples 2220a can be positioned within and/or adjacent to the thinner side portions 2709. Furthermore, although the staple cartridge 2700 is depicted as comprising inner and outer rows of staples, the staple cartridge 2700 may comprise additional rows of staples, such as staple rows positioned intermediate the inner and outer rows of staples, for example. In at least one such embodiment, the intermediate staple rows can comprise staples having an unformed staple height which is intermediate the unformed staple heights of the staples 2220a and 2220b and a formed staple height which is intermediate the formed staple heights of the staples 2220a and 2220b, for example.

Figure 53:
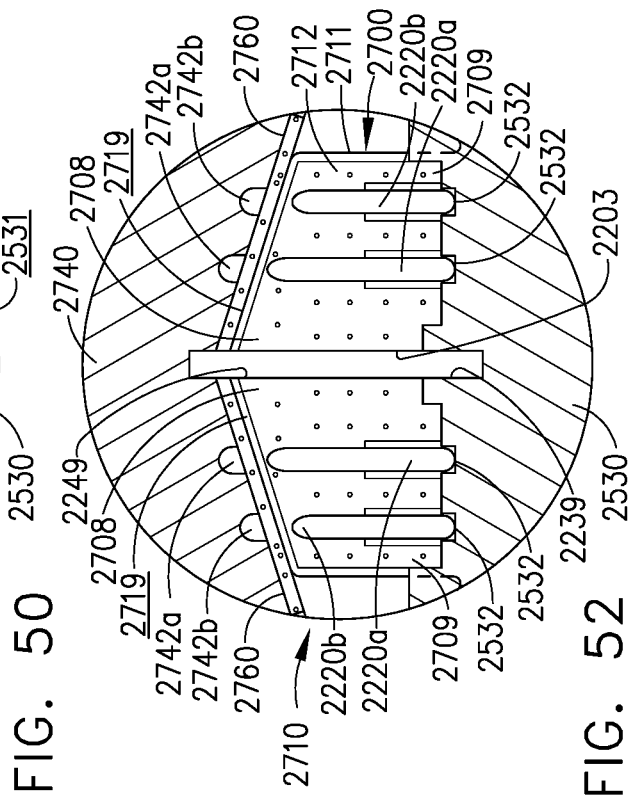
FIG. 53 is a cross-sectional view of another alternative embodiment of an end effector of a surgical stapler comprising inclined tissue-contacting surfaces.

In various embodiments, referring now to FIG. 53, an end effector of a surgical stapler can comprise an anvil 2840, a staple cartridge channel 2530, and a staple cartridge 2800 positioned within the staple cartridge channel 2530. Similar to the above, the staple cartridge 2800 can comprise a compressible, implantable cartridge body 2810 comprising an inner layer 2812, an outer layer 2811, and a plurality of staples, such as staples 2220a and 2220b, for example, positioned therein. In at least one embodiment, the thickness of the cartridge body 2810 can vary across its width. In at least one such embodiment, the cartridge body 2810 can comprise a center portion 2808 and side portions 2809, wherein the center portion 2808 can comprise a thickness which is less than the thickness of the side portions 2809. In various embodiments, the thinnest portion of the cartridge body 2810 can be located at the center portion 2808 while the thickest portion of the cartridge body 2810 can be located at the side portions 2809. In at least one such embodiment, the thickness of the cartridge body 2810 can increase gradually between the center portion 2808 and the side portions 2809. In certain embodiments, the thickness of the cartridge body 2810 can increase linearly and/or geometrically between the center portion 2808 and the side portions 2809. In at least one such embodiment, the tissue-contacting surface 2819 of cartridge body 2810 can comprise two inclined, or angled, surfaces which slope upwardly from the center portion 2808 toward the side portions 2809. In various embodiments, the anvil 2840 can comprise two inclined, or angled, surfaces which parallel, or at least substantially parallel, the inclined tissue-contacting surfaces 2819. In at least one embodiment, the anvil 2840 can further comprise at least one piece of buttress material 2860 attached to the inclined surfaces of the anvil 2840. In various embodiments, further to the above, the outer rows of staples in the staple cartridge 2800 can comprise the taller staples 2220a and the inner rows of staples can comprise the shorter staples 2220b. In at least one embodiment, the taller staples 2220a can be positioned within and/or adjacent to the thicker side portions 2809 while the staples 2220b can be positioned within and/or adjacent to the center portion 2808. In at least one such embodiment, as a result of the above, the taller staples 2220a can capture more material of the implantable cartridge body 2810 than the shorter staples 2220b.

Figure 54:
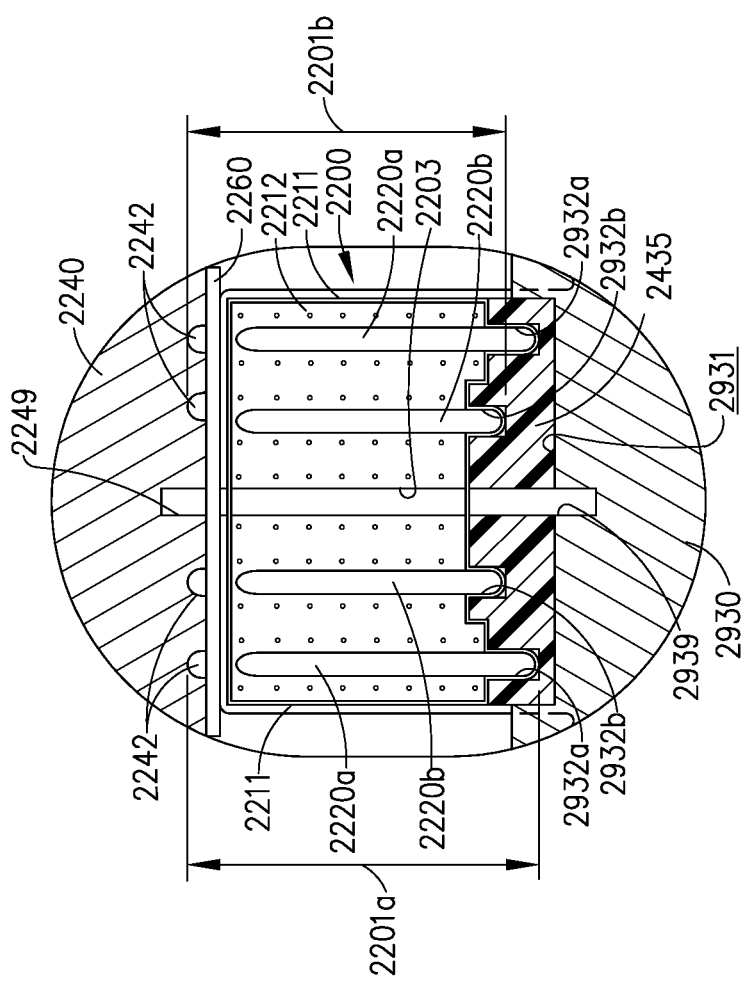
FIG. 54 is a cross-sectional view of an alternative embodiment of an end effector of a surgical stapler comprising a support insert configured to support a staple cartridge.

As described above with regard to the embodiment of FIG. 46, for example, the staple cartridge channel 2230 can comprise a stepped support surface 2231 which can be configured to support the staples 2220a and 2220b at different heights with respect the anvil 2240. In various embodiments, the staple cartridge channel 2230 can be comprised of metal and the steps in the support surface 2231 may be formed in the support surface 2231 by a grinding operation, for example. In various embodiments, referring now to FIG. 54, an end effector of a surgical instrument can comprise a staple cartridge channel 2930 comprising a support insert 2935 positioned therein. More particularly, in at least one embodiment, the staple cartridge channel 2930 can be formed such that it has a flat, or at least substantially flat, support surface 2931, for example, which can be configured to support the insert 2935 which comprises the stepped surfaces for supporting the staples 2220a and 2220b of the staple cartridge 2200 at different heights. In at least one such embodiment, the insert 2935 can comprise a flat, or at least substantially flat, bottom surface which can be positioned against the support surface 2931. The insert 2935 can further comprise support slots, grooves, or troughs 2932a and 2932b which can be configured to support the staples 2220a and 2220b, respectively, at different heights. Similar to the above, the insert 2935 can comprise a knife slot 2939 defined therein which can be configured to permit a cutting member to pass therethrough. In various embodiments, the staple cartridge channel 2930 can be comprised of the same material as or a different material than the support insert 2935. In at least one embodiment, the staple cartridge channel 2930 and the support insert 2935 can both be comprised of metal, for example, while, in other embodiments, the staple cartridge channel 2930 can be comprised of metal, for example, and the support insert 2935 can be comprised of plastic, for example. In various embodiments, the support insert 2935 can be fastened and/or welded into the staple cartridge channel 2930. In certain embodiments, the support insert 2935 can be snap-fit and/or press-fit into the staple cartridge channel 2930. In at least one embodiment the support insert 2935 can be secured in the staple cartridge channel 2930 using an adhesive.

In various embodiments, referring now to FIG. 55, an end effector of a surgical stapler can comprise an anvil 3040, a staple cartridge channel 3030, and a compressible, implantable staple cartridge 3000 positioned in the staple cartridge channel 3030. Similar to the above, the anvil 3040 can comprise a plurality of staple-forming pockets 3042 defined therein and a knife slot 3049 which can be configured to slidably receive a cutting member therein. Also similar to the above, the staple cartridge channel 3030 can comprise a plurality of staple support slots 3032 defined therein and a knife slot 3039 which can also be configured to slidably receive a cutting member therein. In various embodiments, the staple cartridge 3000 can comprise a first layer 3011, a second layer 3012, and a plurality of staples, such as staples 3020a and 3020b, for example, positioned therein. In at least one embodiment, the staples 3020a can comprise an unformed staple height which is taller than the unformed staple height of the staples 3020b. In various embodiments, the first layer 3011 can be comprised of a first compressible material and the second layer 3012 can be comprised of a second compressible material. In certain embodiments, the first compressible material can be compressed at a rate which is higher than the second compressible material while, in certain other embodiments, the first compressible material can be compressed at a rate which is lower than the second compressible material. In at least one embodiment, the first compressible material can be comprised of a resilient material which can comprise a first spring rate and the second compressible material can be comprised of a resilient material which can comprise a second spring rate which is different than the first spring rate. In various embodiments, the first compressible material can comprise a spring rate which is greater than the spring rate of the second compressible material. In certain other embodiments, the first compressible material can comprise a spring rate which is less than the spring rate of the second compressible material. In various embodiments, the first compressible layer can comprise a first stiffness and the second compressible layer can comprise a second stiffness, wherein the first stiffness is different than the second stiffness. In various embodiments, the first compressible layer can comprise a stiffness which is greater than the stiffness of the second compressible layer. In certain other embodiments, the first compressible layer can comprise a stiffness which is less than the stiffness of the second compressible layer.

In various embodiments, referring again to FIG. 55, the second layer 3012 of the staple cartridge 3000 can comprise a constant, or at least substantially constant, thickness across the width thereof. In at least one embodiment, the first layer 3011 can comprise a thickness which varies across the width thereof. In at least one such embodiment, the first layer 3011 can comprise one or more steps 3008 which can increase the thickness of the cartridge body 3010 in certain portions of the cartridge body 3010, such as the center portion, for example. Referring again to FIG. 55, the shorter staples 3020b can be positioned in or aligned with the steps 3008, i.e., the thicker portions of the cartridge body 3010, and the taller staples 3020a can be positioned in or aligned with the thinner portions of the cartridge body 3010. In various embodiments, as a result of the thicker and thinner portions of the cartridge body 3010, the stiffness of the cartridge body 3010 can be greater along the inner rows of staples 3020b than the outer rows of staples 3020a. In various embodiments, the first layer 3011 can be connected to the second layer 3012. In at least one such embodiment, the first layer 3011 and the second layer 3012 can comprise interlocking features which can retain the layers 3011 and 3012 together. In certain embodiments, the first layer 3011 can comprise a first laminate and the second layer 3012 can comprise a second laminate, wherein the first laminate can be adhered to the second laminate by one or more adhesives. In various embodiments, the staple cartridge 3000 can comprise a knife slot 3003 which can be configured to slidably receive a cutting member therein.

In various embodiments, referring now to FIG. 56, a staple cartridge 3100 can comprise a compressible, implantable cartridge body 3110 comprising a single layer of compressible material and, in addition, a plurality of staples, such as staples 3020b, for example, positioned therein. In at least one embodiment, the thickness of the cartridge body 3110 can vary across the width thereof. In at least one such embodiment, the cartridge body 3110 can comprise steps 3108 extending along the side portions thereof. In various embodiments, referring now to FIG. 57, a staple cartridge 3200 can comprise a compressible, implantable cartridge body 3210 comprising a single layer of compressible material and, in addition, a plurality of staples, such as staples 3020b, for example, positioned therein. In at least one embodiment, the thickness of the cartridge body 3210 can vary across the width thereof. In at least one such embodiment, the cartridge body 3210 can comprise steps 3208 extending along the center portion thereof. In various embodiments, referring now to FIG. 58, a staple cartridge 3300 can comprise a compressible, implantable cartridge body 3310 wherein, similar to the above, the thickness of the cartridge body 3310 can vary across the width thereof. In at least one embodiment, the thickness of the cartridge body 3310 can increase geometrically between the side portions and the center portion of the cartridge body 3310. In at least one such embodiment, the thickness of the cartridge body 3310 can be defined by an arcuate or curved profile and can comprise an arcuate or curved tissue-contacting surface 3319. In certain embodiments, the thickness of the cartridge body 3310, and the contour of the tissue-contacting surface 3319, can be defined by one radius of curvature or, alternatively, by several radiuses of curvature, for example. In various embodiments, referring now to FIG. 59, a staple cartridge 3400 can comprise a compressible, implantable cartridge body 3410 wherein the thickness of the cartridge body 3410 can increase linearly, or at least substantially linearly, between the side portions and the center portion of the cartridge body 3410.

Figure 60:
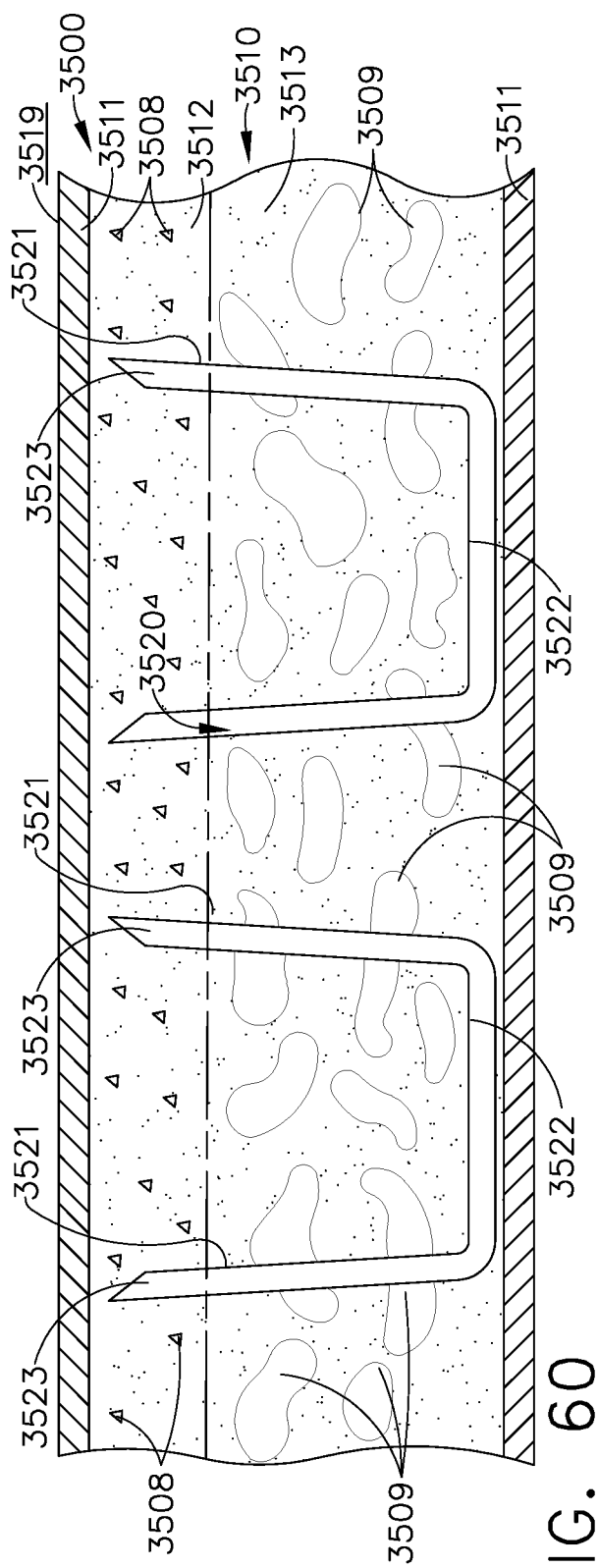
FIG. 60 is a cross-sectional view of a compressible staple cartridge comprising staples and at least one medicament stored therein.
Figure 61:
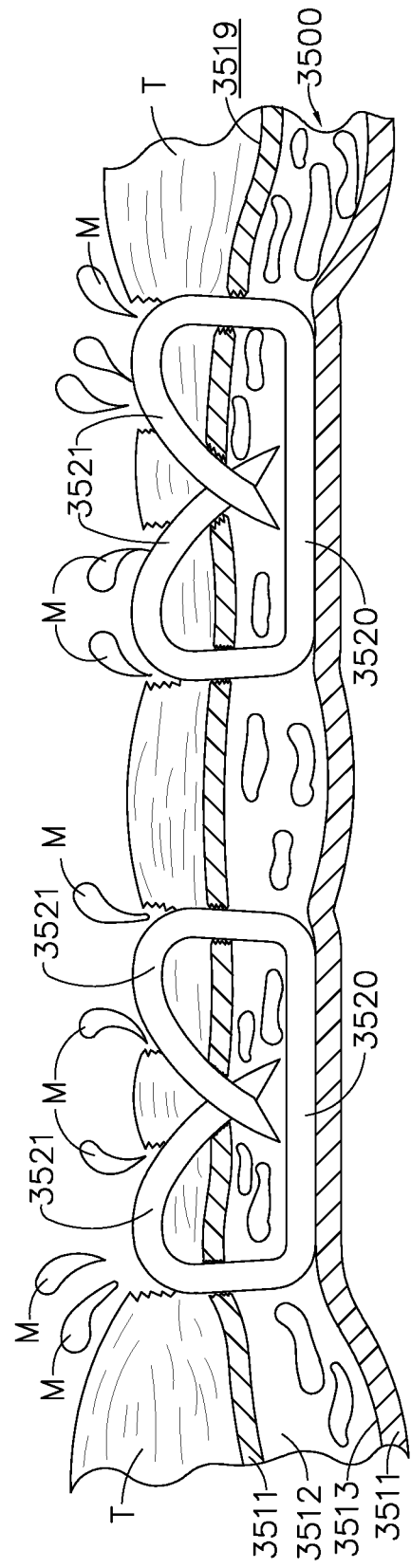
FIG. 61 is a diagram illustrating the compressible staple cartridge of FIG. 60 after it has been compressed and the staples contained therein have been deformed.

In various embodiments, referring now to FIG. 60, a staple cartridge 3500 can comprise a compressible, implantable cartridge body 3510 and a plurality of staples 3520 positioned therein. The implantable cartridge body 3510 can comprise a first inner layer 3512, a second inner layer 3513, and an outer layer 3511. In at least one embodiment, the first inner layer 3512 can comprise a first thickness and the second inner layer 3513 can comprise a second thickness wherein the second inner layer 3513 can be thicker than the first inner layer 3512. In at least one alternative embodiment, the first inner layer 3512 can be thicker than the second inner layer 3513. In another alternative embodiment, the first inner layer 3512 can have the same, or at least substantially the same, thickness as the second inner layer 3513. In certain embodiments, each staple 3520 can comprise a base 3522 and one or more deformable legs 3521 extending from the base 3522. In various embodiments, each leg 3521 can comprise a tip 3523 which is embedded in the first inner layer 3511 and, in addition, each base 3522 of the staples 3520 can be embedded in the second inner layer 3512. In at least one embodiment, the first inner layer 3512 and/or the second inner layer 3513 can comprise at least one medicament stored therein and, in various embodiments, the outer layer 3511 can encapsulate and seal the first inner layer 3512 and the second inner layer 3513 such that the medicament does not flow out of the staple cartridge body 3510 until after the outer layer 3511 has been punctured by the staples 3520. More particularly, further to the above, an anvil can be pushed downwardly against tissue positioned against the tissue-contacting surface 3519 of staple cartridge 3500 such that the cartridge body 3510 is compressed and the surface 3519 is moved downwardly toward, and at least partially below, the staple tips 3523 such that the tips 3523 rupture or puncture the outer layer 3511. After the outer layer 3511 has been breached by the staple legs 3521, the at least one medicament M can flow out of the cartridge body 3510 around the staple legs 3521. In various circumstances, additional compression of the cartridge body 3510 can squeeze additional medicament M out of the cartridge body 3510 as illustrated in FIG. 61.

In various embodiments, referring again to FIG. 60, the outer layer 3511 can comprise a water impermeable, or at least substantially impermeable, wrap which can configured to, one, keep the medicament from prematurely flowing out of the staple cartridge 3500 and, two, prevent fluids within a surgical site, for example, from prematurely entering into the staple cartridge 3500. In certain embodiments, the first inner layer 3512 can comprise a first medicament stored, or absorbed, therein and the second inner layer 3513 can comprise a second medicament stored, or absorbed, therein, wherein the second medicament can be different than the first medicament. In at least one embodiment, an initial compression of the cartridge body 3510, which causes the rupture of the outer layer 3511, can generally express the first medicament out of the first inner layer 3512 and a subsequent compression of the cartridge body 3510 can generally express the second medicament out of the second inner layer 3513. In such embodiments, however, portions of the first medicament and the second medicament may be expressed simultaneously although a majority of the medicament that is initially expressed can be comprised of the first medicament and a majority of the medicament subsequently expressed thereafter can be comprised of the second medicament. In certain embodiments, further to the above, the first inner layer 3512 can be comprised of a more compressible material than the second inner layer 3513 such that the initial compression forces or pressure, which can be lower than the subsequent compression forces or pressure, can cause a larger initial deflection within the first inner layer 3512 than the second inner layer 3513. This larger initial deflection within the first inner layer 3512 can cause a larger portion of the first medicament to be expressed from the first inner layer 3512 than the second medicament from the second inner layer 3513. In at least one embodiment, the first inner layer 3512 can be more porous and/or more flexible than the second inner layer 3513. In at least one such embodiment, the first inner layer 3512 can comprise a plurality of pores, or voids, 3508 defined therein and the second inner layer 3513 can comprise a plurality of pores, or voids, 3509 defined therein wherein, in various embodiments, the pores 3508 can be configured to store the first medicament in the first inner layer 3512 and the pores 3509 can be configured to store the second medicament in the second inner layer 3513. In certain embodiments, the size and density of the pores 3508 within the first inner layer 3512 and the pores 3509 within the second inner layer 3513 can be selected so as to provide a desired result described herein.

In various embodiments, referring again to FIGS. 60 and 61, the outer layer 3511, the first inner layer 3512, and/or the second inner layer 3513 can be comprised of a bioabsorbable material. In at least one embodiment, the first inner layer 3512 can be comprised of a first bioabsorbable material, the second inner layer 3513 can be comprised of a second bioabsorbable material, and the outer layer 3511 can be comprised of a third bioabsorbable material, wherein the first bioabsorbable material, the second bioabsorbable material, and/or the third bioabsorbable material can be comprised of different materials. In certain embodiments, the first bioabsorbable material can be bioabsorbed at a first rate, the second bioabsorbable material can be bioabsorbed at a second rate, and the third bioabsorbable material can be bioabsorbed at a third rate, wherein the first rate, the second rate, and/or the third rate can be different. In at least one such embodiment, when a material is bioabsorbed at a particular rate, such a rate can be defined as the amount of material mass that is absorbed by a patient's body over a unit of time. As it is known, the bodies of different patients may absorb different materials at different rates and, thus, such rates may be expressed as average rates in order to account for such variability. In any event, a faster rate may be a rate in which more mass is bioabsorbed for a unit of time than a slower rate. In various embodiments, referring again to FIGS. 60 and 61, the first inner layer 3512 and/or the second inner layer 3513 can be comprised of a material which bioabsorbs faster than the material comprising the outer layer 3511. In at least one such embodiment, the first inner layer 3512 and/or the second inner layer 3513 can be comprised of a bioabsorbable foam, tissue sealant, and/or hemostatic material, such as oxidized regenerated cellulose (ORC), for example, and the outer layer 3511 can be comprised of a buttress material and/or plastic material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In such embodiments, the first inner layer 3512 and/or the second inner layer 3513 can immediately treat the tissue and can reduce bleeding from the tissue, for example, wherein the outer layer 3514 can provide longer-term structural support and can be bioabsorbed at a slower rate.

Owing to the slower rate of bioabsorbability of the outer layer 3511, further to the above, the outer layer 3511 can buttress or structurally reinforce the tissue within the staple line as it heals. In certain embodiments, one of the first inner layer 3512 and the second inner layer 3513 can be comprised of a material which can be bioabsorbed faster than the other such that, in at least one embodiment, one of the layers can provide an initial release of a therapeutic material and the other layer can provide a sustained release of the same therapeutic material and/or a different therapeutic material. In at least one such embodiment, the rate in which a therapeutic material can be released from a layer 3512, 3513 can be a function of the bioabsorbability of the substrate layer in which the medicament is absorbed or dispersed. For example, in at least one embodiment, the substrate comprising the first inner layer 3512 can be bioabsorbed faster than the substrate comprising the second inner layer 3513 and, as a result, a medicament can be release from the first inner layer 3512 faster than the second inner layer 3513, for example. In various embodiments, as described herein, one or more of the layers 3511, 3512, and 3513 of the cartridge body 3510 can be adhered to one another by at least one adhesive, such as fibrin and/or protein hydrogel, for example. In certain embodiments, the adhesive can be water soluble and can be configured to release the connection between the layers as the staple cartridge 3500 is being implanted and/or some time thereafter. In at least one such embodiment, the adhesive can be configured to bioabsorb faster than the outer layer 3511, the first inner layer 3512, and/or the second inner layer 3513.

Figure 62:
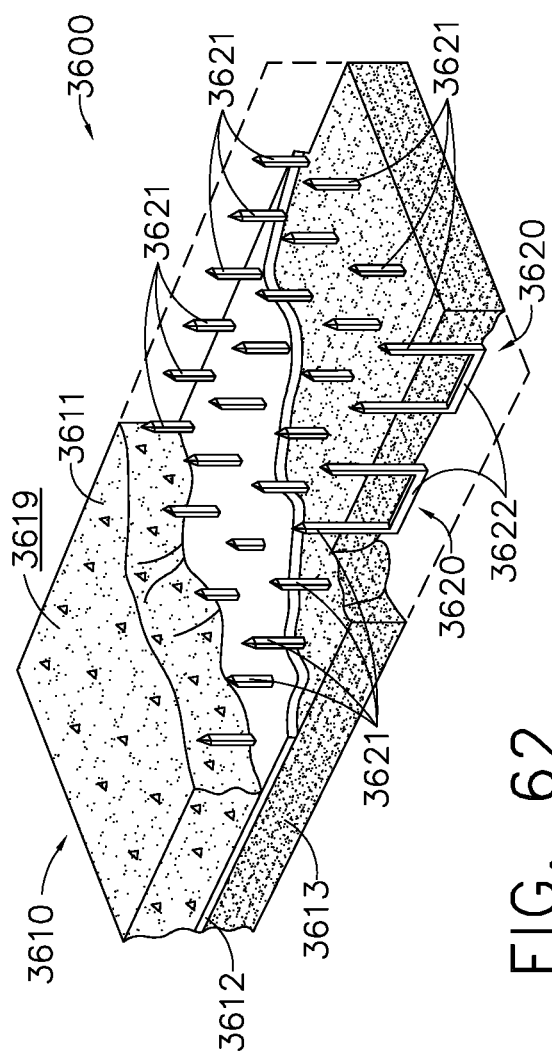
FIG. 62 is a partial cut-away view of a staple cartridge in accordance with at least one embodiment.
Figure 63:
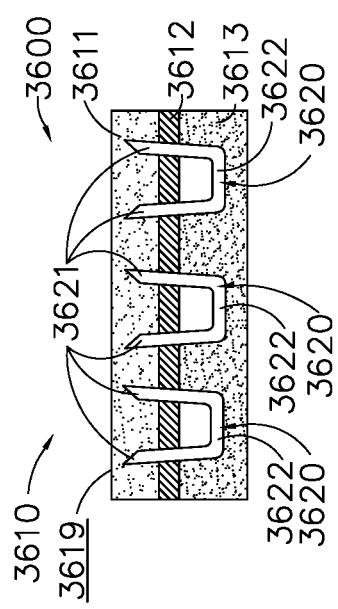
FIG. 63 is a cross-sectional view of the staple cartridge of FIG. 62.

In various embodiments, referring now to FIGS. 62 and 63, a staple cartridge, such as staple cartridge 3600, for example, can comprise a cartridge body 3610 including a compressible first layer 3611, a second layer 3612 attached to the first layer 3611, and a removable compressible layer 3613 attached to the second layer 3612. In at least one such embodiment, the first layer 3611 can be comprised of a compressible foam material, the second layer 3612 can comprise a laminate material adhered to the first layer 3611 utilizing one or more adhesives, and the third layer 3613 can comprise a compressible foam material removably adhered to the second layer 3612 utilizing one or more adhesives, for example. In various embodiments, the staple cartridge 3600 can further comprise a plurality of staples, such as staples 3620, for example, positioned in the cartridge body 3610. In at least one such embodiment, each staple 3620 can comprise a base 3622 positioned in the third layer 3613 and one or more deformable legs 3621 extending upwardly from the base 3622 through the second layer 3612 and into the first layer 3611, for example. In use, further to the above, the top surface 3619 of the staple cartridge body 3610 can be pushed downwardly by an anvil until the staple legs 3621 penetrate through the top surface 3619 and the targeted tissue and contact the anvil. After the staple legs 3621 have been sufficiently deformed, the anvil can be moved away from the staple cartridge 3600 such that the compressible layers thereof can at least partially re-expand. In various circumstances, the insertion of the staples through the tissue can cause the tissue to bleed. In at least one embodiment, the third layer 3613 can be comprised of an absorbent material, such as protein hydrogel, for example, which can draw blood away from the stapled tissue. In addition to or in lieu of the above, the third layer 3613 can be comprised of a hemostatic material and/or tissue sealant, such as freeze-dried thrombin and/or fibrin, for example, which can be configured to reduce the bleeding from the tissue. In certain embodiments, the third layer 3613 may provide a structural support to the first layer 3611 and the second layer 3612 wherein the third layer 3613 may be comprised of a bioabsorbable material and/or a non-bioabsorbable material. In any event, in various embodiments, the third layer 3613 can be detached from the second layer 3612 after the staple cartridge 3610 has been implanted. In embodiments where the third layer 3613 comprises an implantable-quality material, the surgeon can elect whether to remove the third layer 3613 of the cartridge body 3610. In at least one embodiment, the third layer 3613 can be configured to be removed from the second layer 3612 in one piece.

Figure 64:
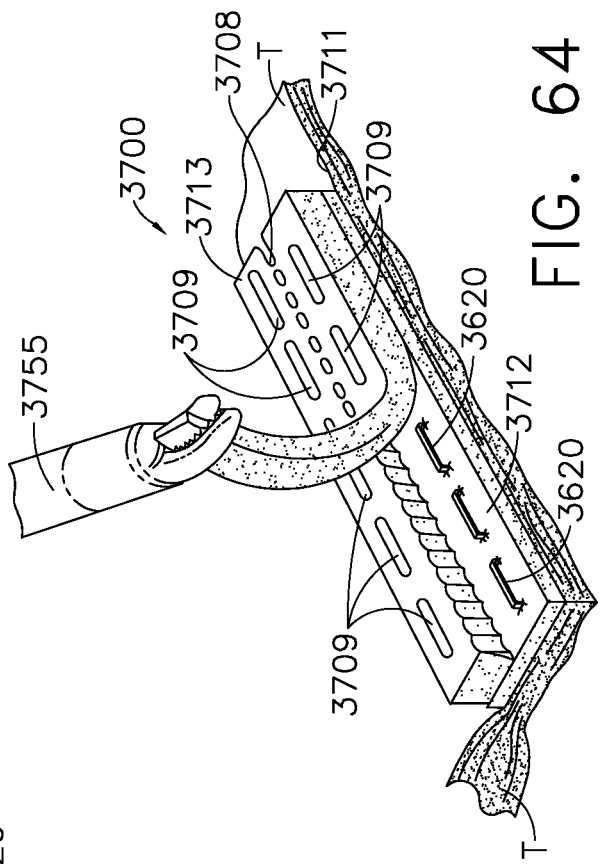
FIG. 64 is a perspective view of an implanted staple cartridge in accordance with at least one alternative embodiment.
Figure 65:
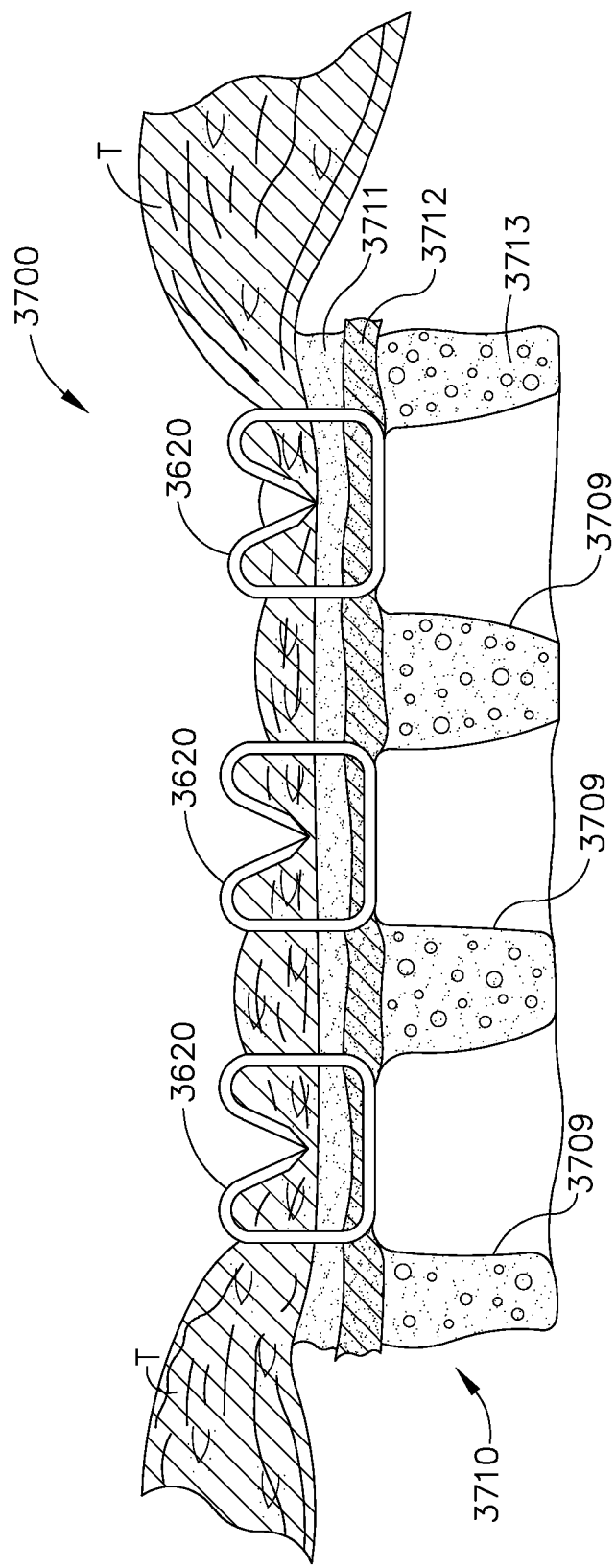
FIG. 65 is a cross-sectional view of the implanted staple cartridge of FIG. 64.

In various embodiments, the first layer 3611 can be comprised of a first foam material and the third layer 3613 can be comprised of a second foam material which can be different than the first foam material. In at least one embodiment, the first foam material can have a first density and the second foam material can have a second density wherein the first density can be different than the second density. In at least one such embodiment, the second density can be higher than the first density wherein, as a result, the third layer 3613 may be less compressible, or have a lower compression rate, than the first layer 3611. In at least one alternative embodiment, the first density can be higher than the second density wherein, as a result, the first layer 3611 may be less compressible, or have a lower compression rate, than the third layer 3613. In various embodiments, referring now to FIGS. 64 and 65, a staple cartridge 3700, similar to the staple cartridge 3600, can comprise a cartridge body 3710 comprising a first compressible foam layer 3711, a second layer 3712 attached to the first layer 3711, and a detachable third compressible foam layer 3713 removably attached to the second layer 3712. In at least one such embodiment, the third layer 3713 can comprise a plurality of staple receiving slots, or cut-outs, 3709 which can each be configured to receive at least a portion of a staple 3620, such as a staple base 3622, for example, therein. In certain embodiments, the staples 3620 can be configured to slide within the staple receiving slots 3709 or, stated another way, the third layer 3713 can be configured to slide relative to the staples 3620 when the staple cartridge 3700 is positioned against the targeted tissue and compressed by an anvil, for example. In at least one embodiment, the receiving slots 3709 can be configured such that there is clearance between the staples 3620 and the side walls of the receiving slots 3709. In at least one such embodiment, as a result of the above, the staples 3620 may not capture a portion of the third layer 3713 therein when the staples 3620 are deformed, as illustrated in FIGS. 64 and 65. In certain other embodiments, the ends of the staple receiving slots 3709 adjacent to the second layer 3712 can be closed by a portion of the third layer 3713 and, as a result, at least a portion of the third layer 3713 can be captured within the staples 3620 when they are deformed. In any event, the third layer 3713 can comprise one or more perforations and/or score marks 3708, for example, which can be configured to permit the third layer 3713 to be removed from the second layer 3712 in two or more pieces as illustrated in FIG. 64. In FIG. 64, one of the pieces of the third layer 3713 is illustrated as being removed by a tool 3755. In various embodiments, the perforations 3708 can be arranged along a line positioned intermediate a first row of staples and a second row of staples.

In various embodiments, referring again to FIGS. 64 and 65, the bases 3622 of the staples 3620 can be positioned within the receiving slots 3709 wherein, in at least one embodiment, the side walls of the receiving slots 3709 can be configured to contact and releasable retain the staple legs 3621 in position. In certain embodiments, although not illustrated, the third layer 3713 can comprise an elongated slot surrounding all of the staples within a staple line. In at least one such embodiment, a staple cartridge comprising four staple rows, for example, can comprise an elongate slot aligned with each staple row in the bottom layer of the staple cartridge. Further to the above, at least a portion of the staple cartridge 3600 and/or the staple cartridge 3700 can be implanted within a patient and at least a portion of the staple cartridge can be removable from the patient. In at least one embodiment, referring again to FIGS. 64 and 65, the first layer 3711 and the second layer 3712 can be captured within the staples 3620 and can be implanted with the staples 3620, whereas the third layer 3713 can be optionally removed or detached from the staple cartridge 3700. In various circumstances, the removal of a portion of the implanted staple cartridge can reduce the amount of material that the patient's body has to reabsorb which can provide various therapeutic benefits. In the event that a portion of a staple cartridge is detached and removed, such as by a laparoscopic tool 3755, for example, the detached staple cartridge portion can be removed from the surgical site through a trocar, such as a trocar having a 5 mm aperture, for example. In certain embodiments, a cartridge body can comprise more than one layer that can be removed. For example, the cartridge body 3710 can comprise a fourth layer wherein the third layer of 3713 of the cartridge body 3710 can be comprised of a hemostatic material and the fourth layer can be comprised of a support layer. In at least one such embodiment, a surgeon can remove the support layer and then elect whether to remove the hemostatic layer, for example.

In various embodiments, referring now to FIG. 66, a staple cartridge, such as staple cartridge 3800, for example, can comprise a cartridge body 3810 including an outer layer 3811 and an inner layer 3812. The inner layer 3812 can be comprised of a compressible foam material and the outer layer 3811 can be at leas partially wrapped around the inner layer 3812. In at least one embodiment, the outer layer 3811 can comprise a first portion 3811a configured to be positioned on a first side of the inner layer 3812 and a second portion 3811b configured to be positioned on a second side of the inner layer 3812 wherein the first portion 3811a and the second portion 3811b can be connected by a flexible hinge, such as hinge 3809, for example. In at least one such embodiment, at least one adhesive, such as fibrin and/or protein hydrogel, for example, can be applied to the first side and/or the second side of the inner layer 3812 in order to secure the portions of the outer layer 3811 thereto. In various embodiments, the outer layer 3811 can comprise one or more fastening members extending therefrom. In at least one such embodiment, the outer layer 3811 can comprise a plurality of deformable legs 3821 extending from one side of the outer layer 3811 which can be seated in the compressible inner layer 3812. In at least one such embodiment, the legs 3821 may not protrude from the second side of the inner layer 3812 while, in at least one alternative embodiment, the legs 3821 may at least partially protrude from the inner layer 3812. When the compressible cartridge body 3810 is compressed, in use, the legs 3821 can be configured to pierce the inner layer 3812 and the second portion 3811b of the outer layer 3811. In certain embodiments, the second portion 3811b of the outer layer 3811 can comprise apertures, such as apertures 3808, for example defined therein which can be configured to receive the staple legs 3821. In certain embodiments, at least portions of the staple cartridge 3800 can comprise a knife slot 3803 which can be configured to slidably receive a cutting member therein. In at least one such embodiment, the knife slot 3803 may not extend entirely through the thickness of the cartridge body 3810 and, as a result, the cutting member may incise the cartridge body 3810 as it is moved relative thereto.

In various embodiments, referring now to FIG. 67, a staple cartridge 3900 can comprise, similar to staple cartridge 3800, a cartridge body 3910 including an inner layer 3812 and an outer layer 3811, wherein the outer layer 3811 can comprise a first portion 3811a positioned adjacent to the first side of the inner layer 3812 and a second portion 3811b positioned adjacent to the second side of the inner layer 3812. In at least one embodiment, similar to the above, the outer layer 3811 can comprise one or more fastening members extending therefrom. In at least one such embodiment, the outer layer 3811 can comprise a plurality of deformable legs 3921 extending from one side of the outer layer 3811 which can be seated in the compressible inner layer 3812. In certain embodiments, each deformable leg 3921 can comprise at least one hook or barb 3923 protruding therefrom which can be configured to engage the second portion 3811b of the outer layer 3811 and, as a result, retain the outer layer 3811 to the inner layer 3812. In at least one such embodiment, the barbs 3923 can be configured to protrude from the second side of the inner layer 3812 and extend through the apertures 3808 in the second portion 3811b of the outer layer 3811 such that the barbs 3923 can engage the outside surface of the outer layer 3811 and lock the outer layer 3811 to the inner layer 3812. In order to construct the staple cartridge 3900, the inner layer 3812 may be at least partially compressed in order to cause the barbs to protrude therefrom and enter into the apertures 3808. In at least one such embodiment, the staple cartridge 3900 can be at least partially pre-compressed when it is inserted into a staple cartridge, for example. In certain embodiments, further to the above, at least a portion of the legs 3921 can be embedded within the first portion 3811a of the outer layer 3811 wherein, in at least one embodiment, the outer layer 3811 can be comprised of a plastic material, such as polydioxanone (PDS) and/or polyglycolic acid (PGA), for example, and the plastic material can be overmolded around at least a portion of the legs 3921.

In various embodiments, referring now to FIGS. 68-72, a staple cartridge, such as staple cartridge 4000, for example, can comprise a cartridge body 4010 including a compressible first layer 4011 and a second layer 4012 and, in addition, a plurality of staples 4020 positioned within the cartridge body 4010. In certain embodiments, referring to FIG. 70, each staple 4020 can comprise a base 4022 and at least one deformable leg 4023 extending from the base 4022. In at least one embodiment, referring to FIG. 68, the staple cartridge 4000 can be positioned between a staple cartridge channel 4030 and an anvil 4040 of an end effector of a surgical stapler wherein the second layer 4012 of the cartridge body 4010 and/or the bases 4022 of the staples 4020 can be positioned against the staple cartridge channel 4030. In various embodiments, referring now to FIG. 69, the second layer 4012 can comprise a layer of pledgets 4060 interconnected to one another by a pledget support frame 4061. In at least one such embodiment, the pledgets 4060 and the pledget support frame 4061 can be comprised of a molded plastic material, such as polyglycolic acid (PGA), for example. Each pledget 4060 can comprise one or more apertures or slots 4062 which can be configured to receive a staple leg 4021 extending therethrough as illustrated in FIGS. 70 and 71. Each pledget 4060 can further comprise a receiving slot 4063 defined therein which can be configured to receive a base 4022 of a staple 4020. In various embodiments, referring again to FIG. 69, the pledgets 4060 and/or pledget support fame 4061 can comprise a plurality of score marks, perforations, or the like which can be configured to allow the pledgets 4060 to become detached from the pledget support frame 4061 at a desired location. Similarly, referring to FIG. 71, one or more pledgets 4060 can be connected to one another along a line comprising perforations and/or score marks 4064, for example. In use, the compressible foam layer 4011 can be positioned against the targeted tissue T and the cartridge body 4010 can be compressed by the anvil 4040 such that the anvil 4040 can deform the staples 4020. When the staples 4020 are deformed, the staple legs 4021 of each staple 4020 can capture the tissue T, a portion of the first layer 4011, and a pledget 4060 within the deformed staple. When the staple cartridge channel 4030 is moved away from the implanted staple cartridge 4060, for example, the pledget support frame 4061 can be detached from the pledgets 4060 and/or the pledgets 4060 can be detached from one another. In certain circumstances, the pledgets 4060 can be detached from the frame 4061 and/or each other when the staples 4020 are being deformed by the anvil 4040 as described above.

Figure 73:
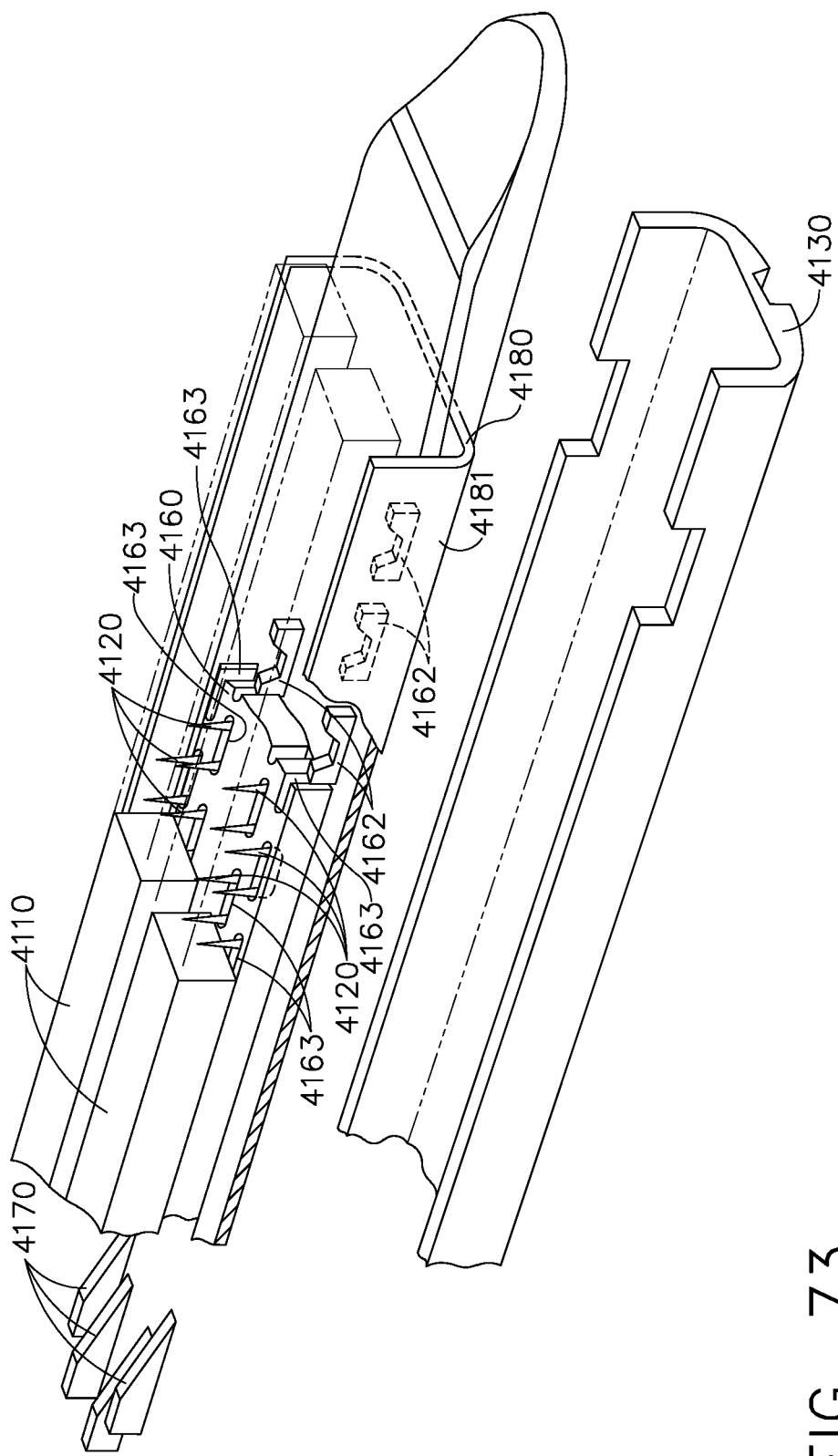
FIG. 73 is an exploded perspective view of an alternative embodiment of a compressible staple cartridge comprising staples therein and a system for driving the staples against an anvil.
Figure 73A:
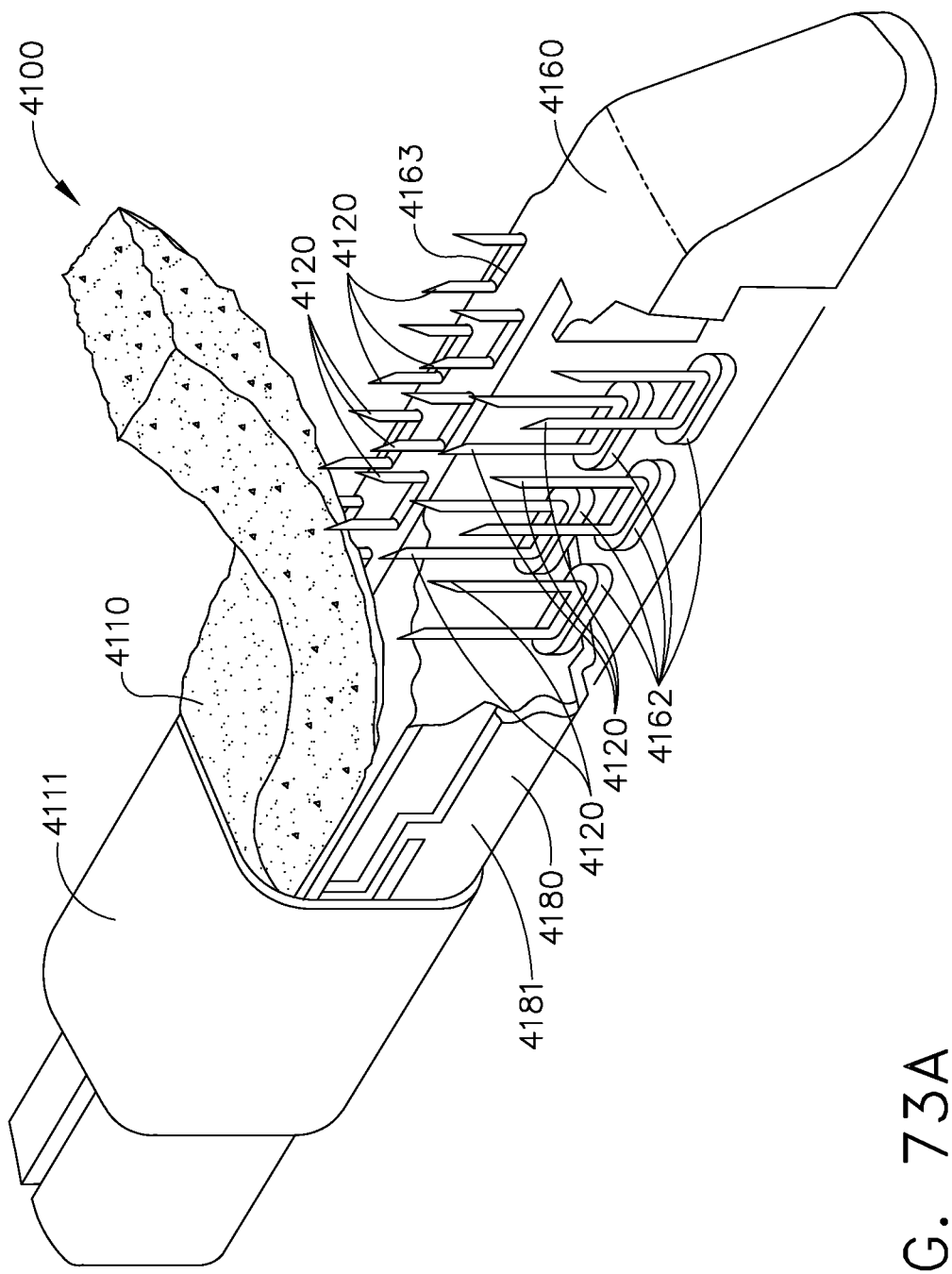
FIG. 73A is a partial cut-away view of an alternative embodiment of the staple cartridge of FIG. 73.
Figure 74:
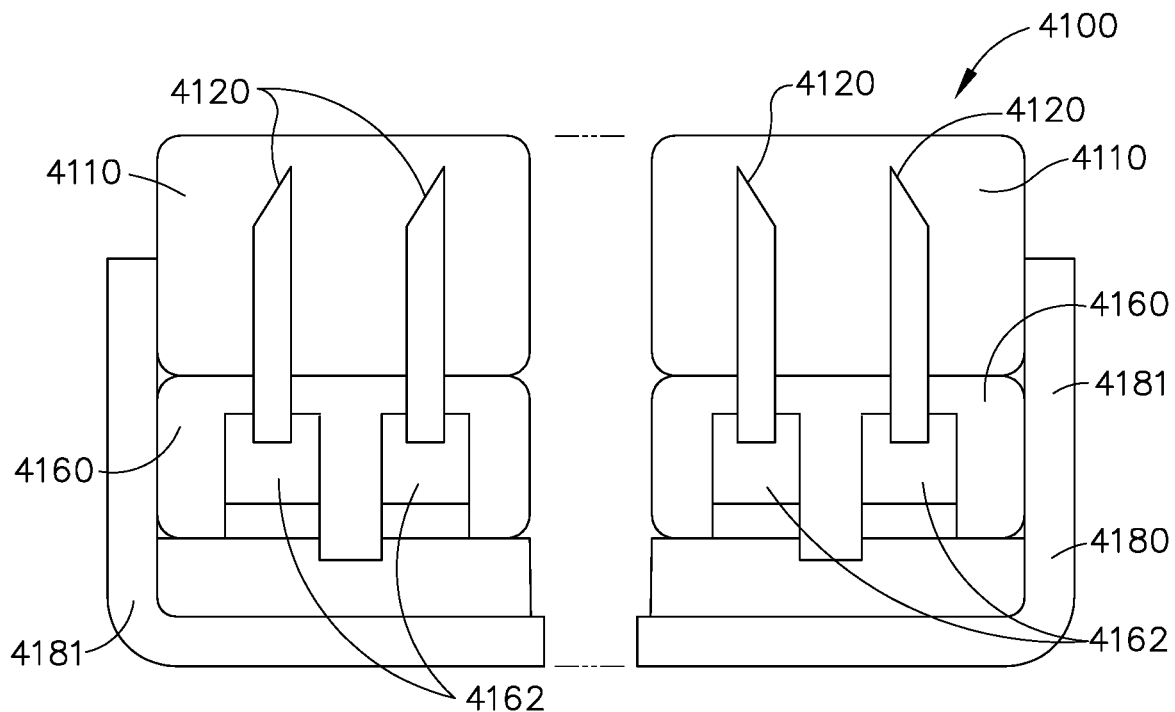
FIG. 74 is a cross-sectional view of the staple cartridge of FIG. 73.
Figure 75:
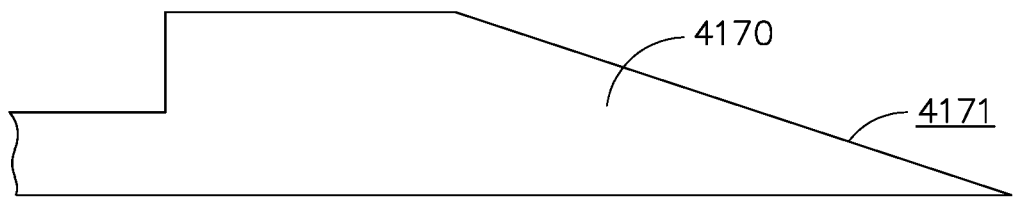
FIG. 75 is an elevational view of a sled configured to traverse the staple cartridge of FIG. 73 and move the staples to toward the anvil.

In various embodiments described herein, the staples of a staple cartridge can be fully formed by an anvil when the anvil is moved into a closed position. In various other embodiments, referring now to FIGS. 73-76, the staples of a staple cartridge, such as staple cartridge 4100, for example, can be deformed by an anvil when the anvil is moved into a closed position and, in addition, by a staple driver system which moves the staples toward the closed anvil. The staple cartridge 4100 can comprise a compressible cartridge body 4110 which can be comprised of a foam material, for example, and a plurality of staples 4120 at least partially positioned within the compressible cartridge body 4110. In various embodiments, the staple driver system can comprise a driver holder 4160, a plurality of staple drivers 4162 positioned within the driver holder 4160, and a staple cartridge pan 4180 which can be configured to retain the staple drivers 4162 in the driver holder 4160. In at least one such embodiment, the staple drivers 4162 can be positioned within one or more slots 4163 in the driver holder 4160 wherein the sidewalls of the slots 4163 can assist in guiding the staple drivers 4162 upwardly toward the anvil. In various embodiments, the staples 4120 can be supported within the slots 4163 by the staple drivers 4162 wherein, in at least one embodiment, the staples 4120 can be entirely positioned in the slots 4163 when the staples 4120 and the staple drivers 4162 are in their unfired positions. In certain other embodiments, at least a portion of the staples 4120 can extend upwardly through the open ends 4161 of slots 4163 when the staples 4120 and staple drivers 4162 are in their unfired positions. In at least one such embodiment, referring primarily now to FIG. 74, the bases of the staples 4120 can be positioned within the driver holder 4160 and the tips of the staples 4120 can be embedded within the compressible cartridge body 4110. In certain embodiments, approximately one-third of the height of the staples 4120 can be positioned within the driver holder 4160 and approximately two-thirds of the height of the staples 4120 can be positioned within the cartridge body 4110. In at least one embodiment, referring to FIG. 73A, the staple cartridge 4100 can further comprise a water impermeable wrap or membrane 4111 surrounding the cartridge body 4110 and the driver holder 4160, for example.

Figure 76:
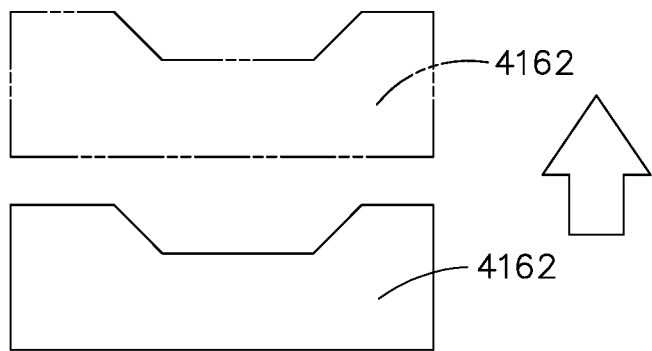
FIG. 76 is a diagram of a staple driver which can be lifted toward the anvil by the sled of FIG. 75.

In use, the staple cartridge 4100 can be positioned within a staple cartridge channel, for example, and the anvil can be moved toward the staple cartridge 4100 into a closed position. In various embodiments, the anvil can contact and compress the compressible cartridge body 4110 when the anvil is moved into its closed position. In certain embodiments, the anvil may not contact the staples 4120 when the anvil is in its closed position. In certain other embodiments, the anvil may contact the legs of the staples 4120 and at least partially deform the staples 4120 when the anvil is moved into its closed position. In either event, the staple cartridge 4100 can further comprise one or more sleds 4170 which can be advanced longitudinally within the staple cartridge 4100 such that the sleds 4170 can sequentially engage the staple drivers 4162 and move the staple drivers 4162 and the staples 4120 toward the anvil. In various embodiments, the sleds 4170 can slide between the staple cartridge pan 4180 and the staple drivers 4162. In embodiments where the closure of the anvil has started the forming process of the staples 4120, the upward movement of the staples 4120 toward the anvil can complete the forming process and deform the staples 4120 to their fully formed, or at least desired, height. In embodiments where the closure of the anvil has not deformed the staples 4120, the upward movement of the staples 4120 toward the anvil can initiate and complete the forming process and deform the staples 4120 to their fully formed, or at least desired, height. In various embodiments, the sleds 4170 can be advanced from a proximal end of the staple cartridge 4100 to a distal end of the staple cartridge 4100 such that the staples 4120 positioned in the proximal end of the staple cartridge 4100 are fully formed before the staples 4120 positioned in the distal end of the staple cartridge 4100 are fully formed. In at least one embodiment, referring to FIG. 75, the sleds 4170 can each comprise at least one angled or inclined surface 4711 which can be configured to slide underneath the staple drivers 4162 and lift the staple drivers 4162 as illustrated in FIG. 76.

In various embodiments, further to the above, the staples 4120 can be formed in order to capture at least a portion of the tissue T and at least a portion of the compressible cartridge body 4110 of the staple cartridge 4100 therein. After the staples 4120 have been formed, the anvil and the staple cartridge channel 4130 of the surgical stapler can be moved away from the implanted staple cartridge 4100. In various circumstances, the cartridge pan 4180 can be fixedly engaged with the staple cartridge channel 4130 wherein, as a result, the cartridge pan 4180 can become detached from the compressible cartridge body 4110 as the staple cartridge channel 4130 is pulled away from the implanted cartridge body 4110. In various embodiments, referring again to FIG. 73, the cartridge pan 4180 can comprise opposing side walls 4181 between which the cartridge body 4110 can be removably positioned. In at least one such embodiment, the compressible cartridge body 4110 can be compressed between the side walls 4181 such that the cartridge body 4110 can be removably retained therebetween during use and releasably disengaged from the cartridge pan 4180 as the cartridge pan 4180 is pulled away. In at least one such embodiment, the driver holder 4160 can be connected to the cartridge pan 4180 such that the driver holder 4160, the drivers 4162, and/or the sleds 4170 can remain in the cartridge pan 4180 when the cartridge pan 4180 is removed from the surgical site. In certain other embodiments, the drivers 4162 can be ejected from the driver holder 4160 and left within the surgical site. In at least one such embodiment, the drivers 4162 can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, the drivers 4162 can be attached to the staples 4120 such that the drivers 4162 are deployed with the staples 4120. In at least one such embodiment, each driver 4162 can comprise a trough configured to receive the bases of the staples 4120, for example, wherein, in at least one embodiment, the troughs can be configured to receive the staple bases in a press-fit and/or snap-fit manner.

In certain embodiments, further to the above, the driver holder 4160 and/or the sleds 4170 can be ejected from the cartridge pan 4180. In at least one such embodiment, the sleds 4170 can slide between the cartridge pan 4180 and the driver holder 4160 such that, as the sleds 4170 are advanced in order to drive the staple drivers 4162 and staples 4120 upwardly, the sleds 4170 can move the driver holder 4160 upwardly out of the cartridge pan 4180 as well. In at least one such embodiment, the driver holder 4160 and/or the sleds 4170 can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, the sleds 4170 can be integrally formed and/or attached to a drive bar, or cutting member, which pushes the sleds 4170 through the staple cartridge 4100. In such embodiments, the sleds 4170 may not be ejected from the cartridge pan 4180 and may remain with the surgical stapler while, in other embodiments in which the sleds 4170 are not attached to the drive bar, the sleds 4170 may be left in the surgical site. In any event, further to the above, the compressibility of the cartridge body 4110 can allow thicker staple cartridges to be used within an end effector of a surgical stapler as the cartridge body 4110 can compress, or shrink, when the anvil of the stapler is closed. In certain embodiments, as a result of the staples being at least partially deformed upon the closure of the anvil, taller staples, such as staples having an approximately 0.18" staple height, for example, could be used, wherein approximately 0.12" of the staple height can be positioned within the compressible layer 4110 and wherein the compressible layer 4110 can have an uncompressed height of approximately 0.14", for example.

Figure 82:
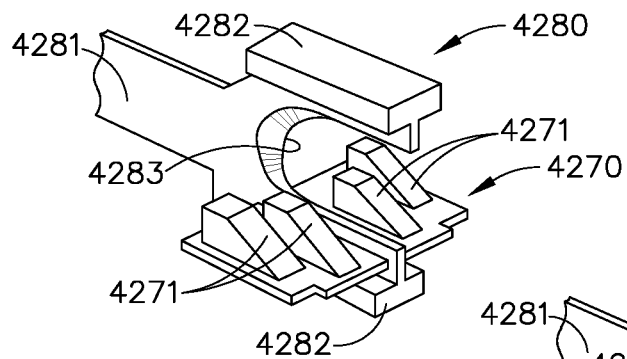
FIG. 82 is a perspective view of a sled and cutting member assembly.
Figure 83:
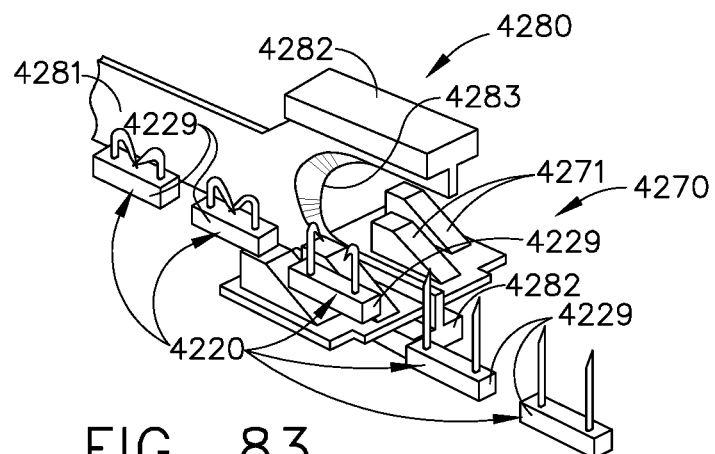
FIG. 83 is a diagram of the sled and cutting member assembly of FIG. 82 being used to lift the staples of the staple cartridge of FIG. 77.

In various embodiments, referring now to FIGS. 77-80, a staple cartridge, such as staple cartridge 4200, for example, can comprise a compressible cartridge body 4210, a plurality of staples 4220 positioned therein, and a plurality of flexible lateral support members 4234. In various embodiments, referring now to FIG. 78, the staple cartridge 4200 can be positioned intermediate an anvil 4240 and a staple cartridge channel 4230 wherein, in at least one embodiment, the lateral support members 4234 can be attached to the staple cartridge channel 4230. When the anvil 4240 is moved downwardly to compress the cartridge body 4210 and at least partially deform the staples 4220, as illustrated in FIG. 79, the side portions of the cartridge body 4210 can bulge laterally and push the lateral support members 4234 outwardly. In at least one such embodiment, the lateral support members 4234 can be attached to the cartridge body 4210 and, when the cartridge body 4210 bulges laterally as described above, the lateral support members 4234 can detach from the cartridge body 4210 as illustrated in FIG. 79. In at least one embodiment, the lateral support members 4234 can be adhered to the cartridge body 4210 utilizing at least one adhesive, such as fibrin and/or protein hydrogel, for example. Similar to the above, the closing of the anvil 4240 may only partially deform the staples 4220, wherein the formation of the staples 4220 can be completed by the advancement of one or more sleds 4270 through the staple cartridge 4200 as illustrated in FIG. 80. In various embodiments, referring now to FIGS. 82 and 83, the sleds 4270 can be advanced from a proximal end of the staple cartridge 4200 to a distal end of the staple cartridge 4200 by a cutting member 4280. In at least one such embodiment, the cutting member 4280 can comprise a cutting element, or knife, 4283, which can be advanced through the tissue T and/or the compressible cartridge body 4210. In certain embodiments, the cutting member 4280 can comprise camming members 4282 which can travel along the outside surfaces of the jaws 4230 and 4240 and move or hold the jaws in position. In various embodiments, as a result of the above, the staples 4220 can be formed into their final shapes at the same time, or at least substantially the same time, as the tissue T is incised. In at least one such embodiment, the sleds 4270 can be positioned distally with respect to the knife 4283 such that the tissue T is only incised when the proceeding portion of the tissue has been fully stapled, for example.

In various embodiments, referring again to FIGS. 82 and 83, the sleds 4270 can comprise separate slidable members which are advanced together by the cutting member 4280. In at least one such embodiment, the sleds 4270 can be contained within the staple cartridge 4200 and the cutting member 4280 can be advanced into the staple cartridge 4200 by a firing bar 4281 such that the cutting member 4280 engages the sleds 4270 and advances the sleds 4270 distally. In certain embodiments, the sleds 4270 can be connected to one another. In either event, each sled 4270 can comprise an angled surface, or cam, 4271 which can be configured to lift the staples 4220 aligned within a staple row. In certain embodiments, the angled surfaces 4271 can be integrally formed with the cutting member 4280. In at least one embodiment, referring again to FIGS. 82 and 83, each staple 4200 can comprise a base, at least one deformable member extending from the base, and a crown 4229 overmolded onto and/or positioned around at least a portion of the base and/or the deformable members of the staple 4200. In various embodiments, such crowns 4229 can be configured to be driven directly by a sled 4270, for example. More particularly, in at least one embodiment, the crowns 4229 of staples 4220 can be configured such that the angled surfaces 4271 of the sleds 4270 can slide underneath and directly contact the crowns 4229 without a staple driver positioned therebetween. In such embodiments, each crown 4229 can comprise at least one co-operating angled or inclined surface which can be engaged by an angled surface 4271 of the sleds 4270 such that the co-operating angled surfaces can drive the staples 4220 upwardly when the sleds 4270 are slid underneath the staples 4220.

In various embodiments, referring now to FIG. 81, a staple cartridge, such as staple cartridge 4300, for example, can comprise a compressible body 4310 and a plurality of staples 4320 positioned within the compressible body 4310. Similar to the above, the staple cartridge 4300 can comprise flexible lateral supports 4334 which can be attached to a staple cartridge channel and/or adhered to the compressible body 4310. In addition to the above, the flexible lateral supports 4334 can be connected together by one or more struts, or connection members, 4335 which can be configured to hold the lateral supports 4334 together. In use, the connection members 4335 can be configured to prevent, or at least inhibit, the lateral supports 4334 from becoming prematurely detached from the cartridge body 4310. In certain embodiments, the connection members 4335 can be configured to hold the lateral supports 4334 together after the staple cartridge 4300 has been compressed by an anvil. In such embodiments, the lateral supports 4334 can resist the lateral bulging, or displacement, of the lateral portions of the cartridge body 4310. In certain embodiments, a cutting member, such as cutting member 4280, for example, can be configured to transect the connection members 4335 as the cutting member 4280 is moved distally within the cartridge body 4310. In at least one such embodiment, the cutting member 4280 can be configured to push one or more sleds, such as sleds 4270, for example, distally in order to form the staples 4320 against an anvil. The sleds 4270 can lead the cutting edge 4283 such that the cutting member 4280 does not transect a connection member 4335 until the staples 4320 adjacent to that connection member 4335 have been fully formed, or at least formed to a desired height. In various circumstances, the connection members 4335, in co-operation with the lateral supports 4334, can prevent, or at least reduce, the lateral movement of the compressible cartridge body 4310 and, concurrently, prevent, or at least reduce, the lateral movement of the staples 4320 positioned within the cartridge body 4310. In such circumstances, the connection members 4335 can hold the staples 4320 in position until after they are deformed and the connection members 4335 can be thereafter cut to release the lateral portions of the cartridge body 4310. As mentioned above, the lateral supports 4334 can be connected to the staple cartridge channel and, as a result, can be removed from the surgical site with the staple cartridge channel after the staple cartridge 4300 has been implanted. In certain embodiments, the lateral supports 4334 can be comprised of an implantable material and can be left within a surgical site. In at least one embodiment, the connection members 4335 can be positioned intermediate the cartridge body 4310 and the tissue T and, after the connection members 4335 have been detached from the lateral supports 4334, the connections members 4335 can remain implanted in the patient. In at least one such embodiment, the connection members 4335 can be comprised of an implantable material and, in certain embodiments, the connection members 4335 can be comprised of the same material as the lateral supports 4334, for example. In various embodiments, the connection members 4335 and/or lateral supports 4334 can be comprised of a flexible bioabsorbable material such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, a connection member can comprise a sheet of material connecting the lateral supports 4334. In certain embodiments, a staple cartridge can comprise connection members extending across the top surface of the cartridge body 4310 and, in addition, connection members extending around the bottom surface of the cartridge body 4310.

Figure 84:
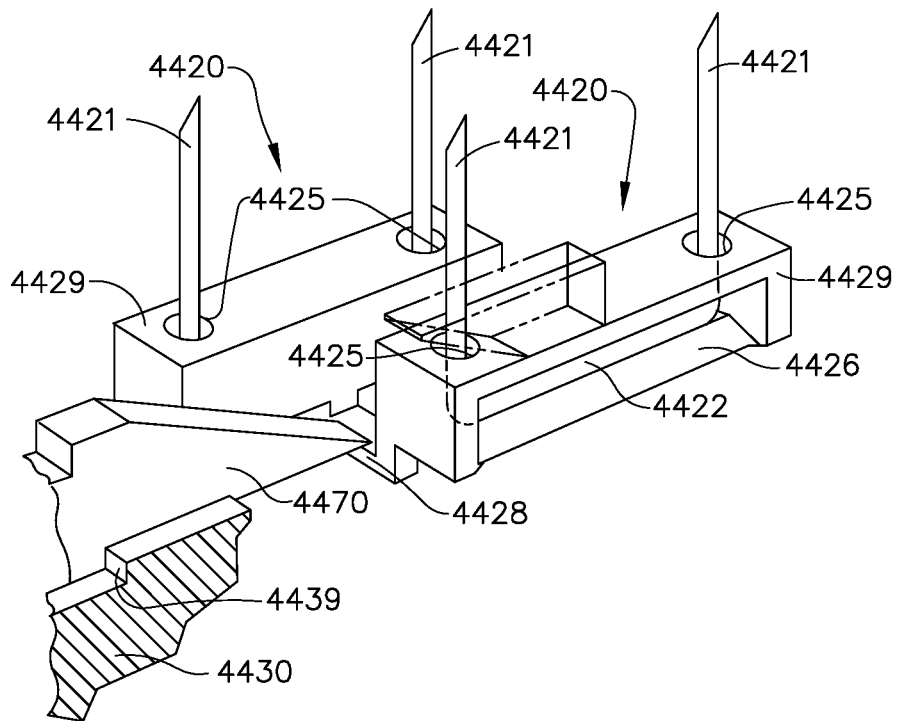
FIG. 84 is a diagram illustrating a sled configured to engage and lift staples toward an anvil and a lock-out system configured to selectively permit the sled to move distally.
Figures 85A, 85B, 85C:
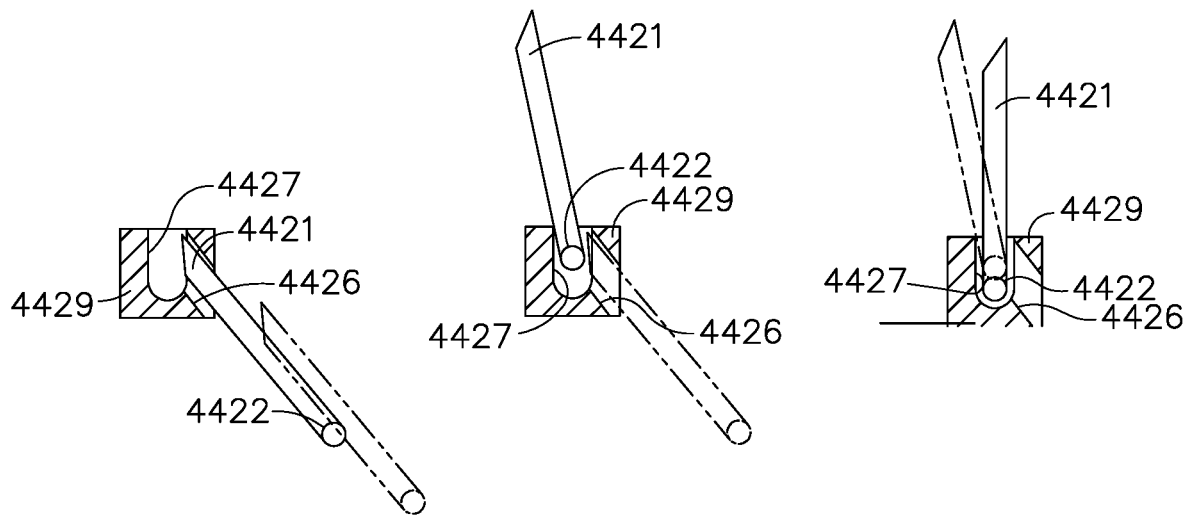
FIGS. 85A-85C illustrate the progression of a staple being inserted into a staple crown.

In various embodiments, referring now to FIG. 84, a staple cartridge can comprise staples, such as staples 4420, for example, which can comprise a wire portion inserted into a crown portion. In at least one embodiment, the wire portion can be comprised of metal, such as titanium and/or stainless steel, for example, and/or plastic, such as polydioxanone (PDS) and/or polyglycolic acid (PGA), for example. In at least one embodiment, the crown portion can be comprised of metal, such as titanium and/or stainless steel, for example, and/or plastic, such as polydioxanone (PDS) and/or polyglycolic acid (PGA), for example. In certain embodiments, the wire portion of each staple 4420 can comprise a base 4422 and deformable legs 4421 extending from the base 4422 wherein the crown portion of each staple 4420 can comprise a crown 4429 which can be configured to receive at least a portion of a base 4422 therein. In order to assemble the portions of each staple 4420, referring now to FIGS. 85A-85C, the legs 4421 of the wire portion can be inserted into an opening 4426 in a crown 4429 wherein the opening 4426 can be configured to guide the legs 4421 into a base chamber 4427. The wire portion can be further inserted into the crown 4429 such that the legs 4421 exit the base chamber 4427 and the base 4422 of the wire portion enters into the base chamber 4427. In at least one such embodiment, the base chamber 4427 can be configured such that the wire portion is rotated within the crown 4429 as the base 4422 enters into the base chamber 4427 such that the staple legs 4421 are pointed in an upward, or at least substantially upward, direction. In various embodiments, referring again to FIG. 84, the crown 4429 can comprise exit holes 4425 which can be configured to receive the staple legs 4421 therein.

In various embodiments, further to the above, a surgical stapler can comprise a sled 4470 configured to transverse the staple cartridge 4400 and staple cartridge channel 4430 and move the staples 4420 contained within the cartridge body 4410 toward an anvil. In various circumstances, the sled 4470 can be moved from a proximal end of the staple cartridge channel 4430 to a distal end of the cartridge channel 4430 in order to implant the cartridge body 4410 and the staples 4420. In certain circumstances, the sled 4470 can be retracted or returned to the proximal end of the cartridge channel 4430 and another staple cartridge 4400 can be inserted into the cartridge channel 4430. Once the new staple cartridge 4400 has been positioned within the cartridge channel 4430, the sled 4470 can be advanced distally once again. In various embodiments, the surgical stapler may comprise one or more lock-out features which can prevent the sled 4470 from being advanced distally once again without a new staple cartridge 4400 being positioned within the cartridge channel 4430. In at least one such embodiment, referring again to FIG. 84, the staple cartridge channel 4430 can comprise a lock-out shoulder 4439 which can be configured to prevent, or at least limit, the distal movement of the sled 4470. More particularly, the sled 4470 can be configured to abut the shoulder 4439 unless the sled 4470 is at least partially lifted upwardly over the shoulder 4439 by a lift feature 4428, for example, extending between the proximal-most staples 4420 within a staple cartridge 4400. Stated another way, absent the presence of the proximal-most staples 4420 in a new staple cartridge 4400, the sled 4470 cannot be advanced. Thus, when an expended staple cartridge 4400 is present within the cartridge channel 4430, or no staple cartridge 4400 is present in the cartridge channel 4430 at all, the sled 4470 cannot be advanced within the cartridge channel 4430.

Figure 86:
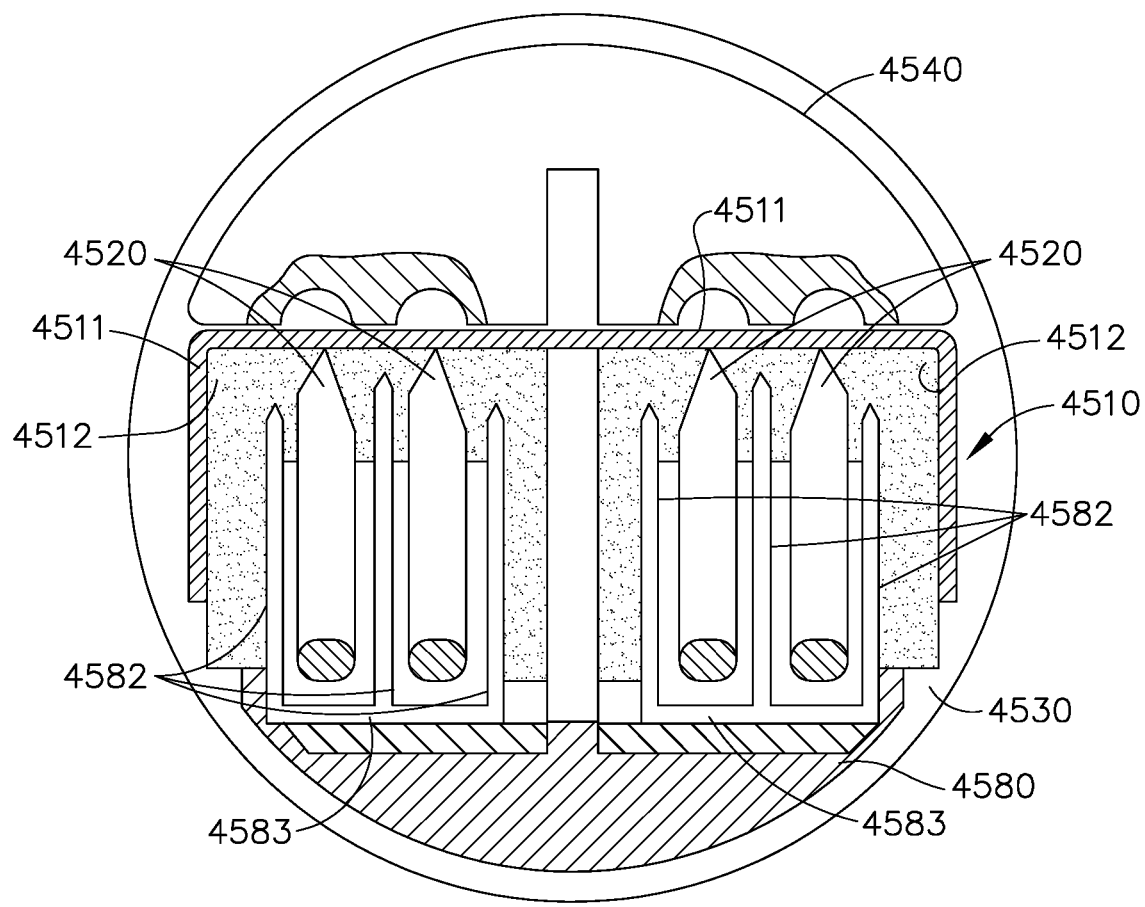
FIG. 86 is a cross-sectional view of a staple cartridge comprising a support pan or retainer.

Further to the above, referring now to FIG. 86, a staple cartridge, such as staple cartridge 4500, for example, can be positioned within a staple cartridge channel 4530 and can comprise a compressible cartridge body 4510, a plurality of staples 4520 positioned within the cartridge body 4510, and a cartridge pan, or retainer, 4580. In various embodiments, the compressible cartridge body 4510 can comprise an outer layer 4511 and an inner layer 4512 wherein, in at least one embodiment, the outer layer 4511 can sealingly enclose the inner layer 4512. In at least one such embodiment, the outer layer 4511 can extend between the inner layer 4512 and the cartridge pan 4580. In certain other embodiments, the outer layer 4511 may only partially surround the inner layer 4512 and, in at least one such embodiment, the outer layer 4511 and the cartridge pan 4580 can co-operate to encompass, or at least substantially encompass, the inner layer 4512. In various embodiments, further to the above, the staples 4520 can be supported by the cartridge pan 4580 wherein the cartridge pan 4580 can comprise one or more staple support channels configured to support the staples 4520. In certain embodiments, the cartridge pan 4580 can be attached to the cartridge body 4510 wherein, in at least one such embodiment, the cartridge body 4510 can be compressed laterally between opposing side walls of the cartridge pan 4580. In various embodiments, the side walls of the cartridge pan 4580 can support the cartridge body 4510 laterally and, in at least one such embodiment, the cartridge pan 4580 can comprise one or more walls, or fins, 4582 extending upwardly from the bottom support 4583 into the cartridge body 4510. In at least one such embodiment, the cartridge body 4510 can comprise one or more slots, or channels, therein which can be configured to receive and/or interlock with the walls 4582. In various embodiments, the walls 4582 can extend partially, or almost entirely, through the cartridge body 4510. In at least one such embodiment, the walls 4582 can extend longitudinally through the staple cartridge 4500 between a first row of staples 4520 and a second row of staples 4520.

In various embodiments, the cartridge body 4510 and/or the cartridge pan 4580 can comprise co-operating retention features which can provide a snap-fit between the cartridge pan 4580 and the cartridge body 4510. In certain embodiments, the staple cartridge 4500 can be positioned within the cartridge channel 4530 such that the cartridge pan 4580 is positioned against and/or attached to the cartridge channel 4530. In at least one embodiment, the cartridge pan 4580 can be detachably coupled to the cartridge channel 4530 such that, after the staple cartridge 4500 has been compressed by the anvil 4540 and the staples 4520 have been deformed, the cartridge pan 4580 can detach from the cartridge channel 4530 and can be implanted with the cartridge body 4510. In at least one such embodiment, the cartridge pan 4580 can be comprised of a bioabsorbable material such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain embodiments, a surgical stapler can further comprise a firing mechanism and/or driver which can be slid intermediate the staple cartridge channel 4530 and a bottom drive surface on the cartridge pan 4580 which can be configured to lift or eject the cartridge pan 4580 from the cartridge channel 4530. In certain embodiments, the cartridge body 4510 can be detachably coupled to the cartridge pan 4580 such that, after the staple cartridge 4500 has been compressed by the anvil 4540 and the staples 4520 have been deformed, the cartridge body 4510 can detach from the cartridge pan 4580. In at least one such embodiment, the cartridge pan 4580 can remain fixedly engaged with the cartridge channel 4530 such that the cartridge pan 4580 is removed from the surgical site with the cartridge channel 4530. In certain embodiments, a surgical stapler can further comprise a firing mechanism and/or driver which can be slid intermediate the staple cartridge pan 4580 and a bottom drive surface on the cartridge body 4510 which can be configured to lift or eject the cartridge body 4510 from the cartridge pan 4580. In at least one such embodiment, the staple cartridge 4500 can further comprise staple drivers positioned intermediate the cartridge pan 4580 and the staples 4520 such that, as the firing mechanism is slid distally, the staple drivers and the staples 4520 can be driven upwardly toward the anvil. In at least one such embodiment, the staple drivers can be at least partially embedded within the compressible cartridge body 4510.

In various embodiments, similar to the above, the staple cartridge 4500 can comprise a lock-out feature which can be configured to prevent, or at least limit, the distal movement of a cutting member unless a unfired staple cartridge 4500 has been positioned within the staple cartridge channel 4530. In certain embodiments, the staple cartridge pan 4580 can comprise a surface which lifts the cutting member upwardly and over a locking surface within the staple cartridge channel 4530, for example. In the event that a staple cartridge 4500 comprising a cartridge pan 4580 is not present in the cartridge channel 4530, the cutting member cannot be advanced. In at least one embodiment, the proximal-most staples, and/or any other suitable staples, within a staple cartridge 4500 can comprise a lifting surface which can sufficiently lift the cutting member over the locking surface. In addition to or in lieu of the above, various portions of the staple cartridge 4500 can be comprised of materials having different colors. In such embodiments, a surgeon may be able to visually identify when an unfired and/or fired staple cartridge is present in the staple cartridge channel 4530. In at least one such embodiment, the outer layer 4511 of the cartridge body 4510 may have a first color, the cartridge pan 4580 may have a second color, and the staple cartridge channel 4530 may have a third color. In the event that the surgeon sees the first color, the surgeon may know that an unfired cartridge 4500 is present in the staple cartridge channel 4530; in the event that the surgeon sees the second color, the surgeon may know that a fired cartridge 4500 is present in the staple cartridge channel 4530 and that the remaining cartridge pan 4580 needs to be removed; and in the event that the surgeon sees the third color, the surgeon may know that no portion of a staple cartridge 4500 remains within the cartridge channel 4530.

In various embodiments, referring now to FIG. 87, a staple cartridge, such as staple cartridge 4600, for example, can comprise a compressible, implantable cartridge body 4610 and a plurality of staples 4620 positioned therein. The cartridge body 4610 can comprise an outer layer 4611 and an inner layer 4612. In certain embodiments, the inner layer 4612 can comprise a plurality of pockets, such as pockets, or cavities, 4615, for example, defined therein which can facilitate the collapse of the cartridge body 4610. In at least one such embodiment, the inner layer 4612 can comprise a corrugated, or honeycomb-configured, lattice which can be configured to withstand a compressive force, or pressure, as long as the compressive force, or pressure, does not exceed a certain threshold value. When the threshold value has not been exceeded, the inner layer 4612 can deform at a linear, or at least substantially linear, rate with respect to the compressive force, or pressure, being applied. After the compressive force, or pressure, has exceeded the threshold value, the inner layer 4612 can suddenly succumb to large deflections and collapse, or buckle, as a result of the compressive load. In various embodiments, the lattice of the inner layer 4612 can be comprised of a plurality of sub-layers 4612*a* which can be connected together. In at least one embodiment, each sub-layer 4612*a* can comprise a plurality of alternating furrows and ridges, or waves, which can be aligned with the alternating furrows and ridges of an adjacent sub-layer 4612*a*. In at least one such embodiment, the furrows of a first sub-layer 4612*a* can be positioned adjacent to the ridges of a second sub-layer 4612*a* and, similarly, the ridges of the first sub-layer 4612*a* can be positioned adjacent to the furrows of the second sub-layer 4612*a*. In various embodiments, the adjacent sub-layers 4612*a* can be adhered to one another and/or the outer layer 4611 by at least one adhesive, such as fibrin and/or protein hydrogel, for example. FIG. 88 illustrates the staple cartridge 4600 after the cartridge body 4610 has been collapsed and the staples 4620 have been deformed in order to capture and hold tissue T against the cartridge body 4610.

In various embodiments, referring now to FIGS. 89-91, a staple cartridge, such as staple cartridge 4700, for example, can comprise a compressible, implantable cartridge body 4710 and a plurality of staples 4720 positioned within the cartridge body 4710. Similar to the above, the cartridge body 4710 can comprise an outer layer 4711 and an inner layer 4712, wherein the inner layer 4712 can comprise a plurality of sub-layers 4712a. Also similar to the above, each sub-layer 4712a can comprise alternating furrows 4717 and ridges 4718 which can be aligned with one another to define pockets, or cavities, 4715 therebetween. In at least one such embodiment, the furrows 4717 and/or the ridges 4718 can extend along axes which are parallel to one another and/or parallel to a longitudinal axis 4709. In various embodiments, the staples 4720 can be aligned in a plurality of staple rows which can extend along axes which are parallel to one another and/or parallel to the longitudinal axis 4709. In various alternative embodiments, referring again to FIGS. 87 and 88, the staples 4620 contained in the cartridge body 4600 can extend along axes which are traverse or perpendicular with respect to the axes defined by the furrows and ridges of the sub-layers 4612a. Referring again to FIGS. 89-91, the staples 4720 can extend through the furrows 4717 and the ridges 4718 wherein friction forces between the staples 4720 and the sub-layers 4712a can hold the staples 4720 within the cartridge body 4710. In certain embodiments, the plurality of sub-layers 4712a can be comprised of a buttress material and/or plastic material, such as polydioxanone (PDS) and/or polyglycolic acid (PGA), for example, which can be configured to hold the staples 4720 in an upright orientation, for example, and/or hold the staples 4720 in alignment with respect to each other as illustrated in FIGS. 89 and 90. FIG. 91 illustrates the staple cartridge 4700 after the cartridge body 4710 has been collapsed and the staples 4720 have been deformed in order to capture and hold tissue T against the cartridge body 4710.

In various embodiments, referring again to FIGS. 89-91, the cartridge body 4710 can resiliently or elastically collapse when it is compressed. In at least one such embodiment, the waves formed within each sub-layer 4712a by the furrows 4717 and the ridges 4718 can be flattened, or at least substantially flattened, when the cartridge body 4710 is compressed which can collapse, or at least substantially collapse, the cavities 4715 defined therebetween. In various circumstances, the cartridge body 4710, or at least portions of the cartridge body 4710, can resiliently or elastically re-expand after the compressive force, or pressure, has been removed from the cartridge body 4710. In at least one such embodiment, the connections between the furrows 4717 and the ridges 4718 of adjacent sub-layers 4712a can remain intact, or at least substantially intact, when the cartridge body 4710 is compressed such that, after the compression force has been removed from the cartridge body 4710, the sub-layers 4712a can bias themselves away from each other and, as a result, at least partially re-expand the cartridge body 4710. In certain embodiments, the cartridge body 4710 can be plastically deformed, or crushed, when it is compressed and, as a result, the cartridge body 4710 may not re-expand after the compressive force, or pressure, has been removed from the cartridge body 4710. In certain embodiments, referring now to FIG. 92, a staple cartridge, such as staple cartridge 4800, for example, can comprise a crushable cartridge body 4810 comprising an outer layer 4811 and an inner layer 4812, wherein the inner layer 4812 can comprise a corrugated, honeycomb-configured, lattice having a plurality of pockets, or cavities, 4815 defined therein. In various embodiments, the walls defining the lattice of inner layer 4812 can comprise one or more weakened, or thin, cross-sections 4819 which can be configured to allow the walls defining the lattice to break when the cartridge body 4810 is compressed. In such circumstances, the cartridge body 4810 can be crushed when the staple cartridge 4800 is implanted.

Figure 94:
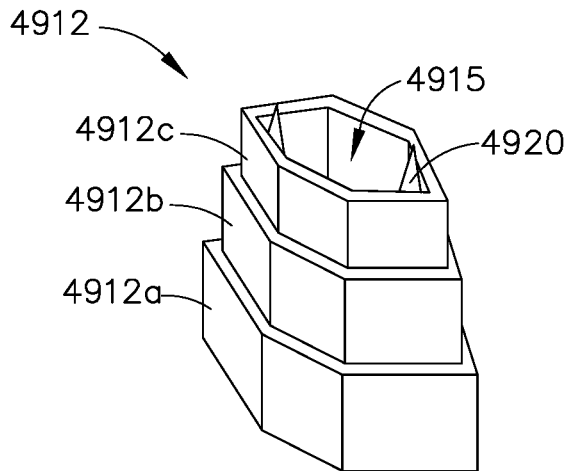
FIG. 94 is a perspective view of a collapsible element of FIG. 93 in an uncollapsed state.
Figure 95:
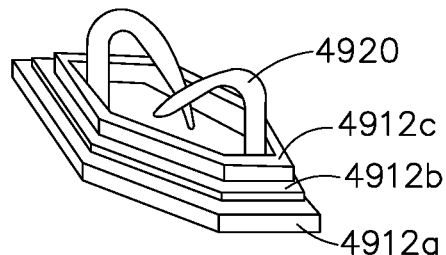
FIG. 95 is a perspective view of the collapsible element of FIG. 94 in a collapsed state.
Figure 93:
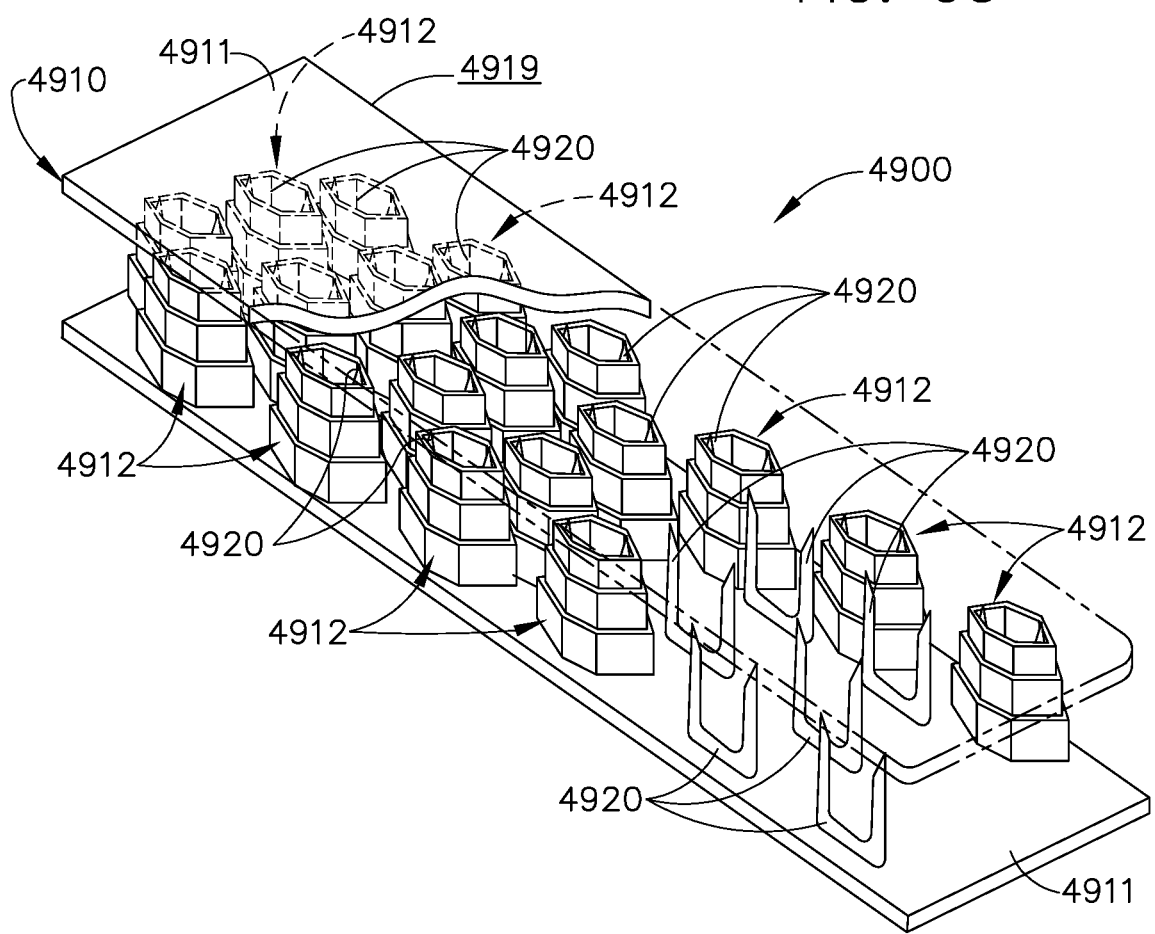
FIG. 93 is a partial cut-away view of a collapsible staple cartridge in accordance with at least one embodiment comprising a plurality of collapsible elements.

In various embodiments, referring now to FIGS. 93-95, a staple cartridge, such as staple cartridge 4900, for example, can comprise a cartridge body 4910 comprising an outer layer 4911 and a plurality of collapsible elements 4912 positioned intermediate top and bottom portions of the outer layer 4911, for example. Referring primarily to FIGS. 93 and 94, the staple cartridge 4900 can further comprise a plurality of staples 4920, wherein each staple 4920 can be positioned in a collapsible element 4912. More particularly, each collapsible element 4912 can comprise a first portion 4912a, a second portion 4012b, and a third portion 4012c which can co-operate to define a cavity 4915 therein which is configured to receive a staple 4920. In use, further to the above, the staple cartridge 4900 can be positioned within a staple cartridge channel and a compressive force can be applied to the tissue contacting surface 4919 in order to compress the cartridge body 4910. As the tissue contacting surface 4919 is moved downwardly, the collapsible elements 4912 can collapse. In such circumstances, the second portion 4912b of each collapsible element 4912 can collapse into a corresponding first portion 4912a and, similarly, the third portion 4912c of each collapsible element 4912 can collapse into a corresponding second portion 4912b. As the cartridge body 4910 is compressed and the collapsible elements 4912 are collapsed, the staples 4920 positioned within the collapsible elements 4912 can be deformed, as illustrated in FIG. 95. In various embodiments, the second portion 4912b of each collapsible element 4912 can be frictionally engaged and/or press-fit within a corresponding first portion 4912a such that, once the compressive force applied to the collapsible element 4912 exceeds the retention force retaining the first portion 4912a and the second portion 4912b in their extended position (FIG. 94), the first portion 4912a and the second portion 4912b can begin to slide relative to one another. Similarly, the third portion 4912c of each collapsible element 4912 can be frictionally engaged and/or press-fit within a corresponding second portion 4912b such that, once the compressive force applied to the collapsible element 4912 exceeds the retention force retaining the second portion 4912b and the third portion 4912c in their extended position (FIG. 94), the second portion 4912b and the third portion 4912c can begin to slide relative to one another.

In many embodiments described herein, a staple cartridge can comprise a plurality of staples therein. In various embodiments, such staples can be comprised of a metal wire deformed into a substantially U-shaped configuration having two staple legs. Other embodiments are envisioned in which staples can comprise different configurations such as two or more wires that have been joined together having three or more staple legs. In various embodiments, the wire, or wires, used to form the staples can comprise a round, or at least substantially round, cross-section. In at least one embodiment, the staple wires can comprise any other suitable cross-section, such as square and/or rectangular cross-sections, for example. In certain embodiments, the staples can be comprised of plastic wires. In at least one embodiment, the staples can be comprised of plastic-coated metal wires. In various embodiments, a cartridge can comprise any suitable type of fastener in addition to or in lieu of staples. In at least one such embodiment, such a fastener can comprise pivotable arms which are folded when engaged by an anvil. In certain embodiments, two-part fasteners could be utilized. In at least one such embodiment, a staple cartridge can comprise a plurality of first fastener portions and an anvil can comprise a plurality of second fastener portions which are connected to the first fastener portions when the anvil is compressed against the staple cartridge. In certain embodiments, as described above, a sled or driver can be advanced within a staple cartridge in order to complete the forming process of the staples. In certain embodiments, a sled or driver can be advanced within an anvil in order to move one or more forming members downwardly into engagement with the opposing staple cartridge and the staples, or fasteners, positioned therein.

In various embodiments described herein, a staple cartridge can comprise four rows of staples stored therein. In at least one embodiment, the four staple rows can be arranged in two inner staple rows and two outer staple rows. In at least one such embodiment, an inner staple row and an outer staple row can be positioned on a first side of a cutting member, or knife, slot within the staple cartridge and, similarly, an inner staple row and an outer staple row can be positioned on a second side of the cutting member, or knife, slot. In certain embodiments, a staple cartridge may not comprise a cutting member slot; however, such a staple cartridge may comprise a designated portion configured to be incised by a cutting member in lieu of a staple cartridge slot. In various embodiments, the inner staple rows can be arranged within the staple cartridge such that they are equally, or at least substantially equally, spaced from the cutting member slot. Similarly, the outer staple rows can be arranged within the staple cartridge such that they are equally, or at least substantially equally, spaced from the cutting member slot. In various embodiments, a staple cartridge can comprise more than or less than four rows of staples stored within a staple cartridge. In at least one embodiment, a staple cartridge can comprise six rows of staples. In at least one such embodiment, the staple cartridge can comprise three rows of staples on a first side of a cutting member slot and three rows of staples on a second side of the cutting member slot. In certain embodiments, a staple cartridge may comprise an odd number of staple rows. For example, a staple cartridge may comprise two rows of staples on a first side of a cutting member slot and three rows of staples on a second side of the cutting member slot. In various embodiments, the staple rows can comprise staples having the same, or at least substantially the same, unformed staple height. In certain other embodiments, one or more of the staple rows can comprise staples having a different unformed staple height than the other staples. In at least one such embodiment, the staples on a first side of a cutting member slot may have a first unformed height and the staples on a second side of a cutting member slot may have a second unformed height which is different than the first height, for example.

In various embodiments, referring now to FIGS. 96A-96D, an end effector of a surgical stapler can comprise a cartridge attachment portion, such as staple cartridge channel 5030, for example, a fastener cartridge removably positioned in the staple cartridge channel 5030, such as staple cartridge 5000, for example, and a jaw 5040 positioned opposite the staple cartridge 5000 and the staple cartridge channel 5030. The staple cartridge 5000 can comprise a compressible body 5010 and a plurality of staples 5020, and/or any other suitable fasteners, at least partially positioned in the compressible body 5010. In at least one such embodiment, each staple 5020 can comprise a base 5022 and, in addition, legs 5021 extending upwardly from the base 5022, wherein at least a portion of the legs 5021 can be embedded in the cartridge body 5010. In various embodiments, the compressible body 5010 can comprise a top, or tissue-contacting, surface 5019 and a bottom surface 5018, wherein the bottom surface 5018 can be positioned against and supported by a support surface 5031 of the staple cartridge channel 5030. Similar to the above, the support surface 5031 can comprise a plurality of support slots 5032 (FIG. 96D), for example, defined therein which can be configured to receive and support the bases 5022 of the staples 5020. In various embodiments, the end effector of the surgical stapler can further comprise a retention matrix, such as retention matrix 5050, for example, which can be configured to engage the staples 5020 and capture tissue therebetween. In at least one such embodiment, the retention matrix 5050 can be removably mounted to the jaw 5040. In use, once the staple cartridge 5000 has been positioned within the staple cartridge channel 5030, the jaw 5040, and the retention matrix 5050 attached thereto, can be moved toward the staple cartridge 5000 and the staple cartridge channel 5030. In at least one embodiment, the jaw 5040 can be moved downwardly along an axis 5099 such that the jaw 5040 and the staple cartridge channel 5030 remain parallel, or at least substantially parallel, to one another as the jaw 5040 is closed. More particularly, in at least one such embodiment, the jaw 5040 can be closed in a manner such that a tissue-contacting surface 5051 of the retention matrix 5050 is parallel, or at least substantially parallel, to the tissue-contacting surface 5019 of the staple cartridge 5000 as the jaw 5040 is moved toward the staple cartridge 5000.

Figure 96B:
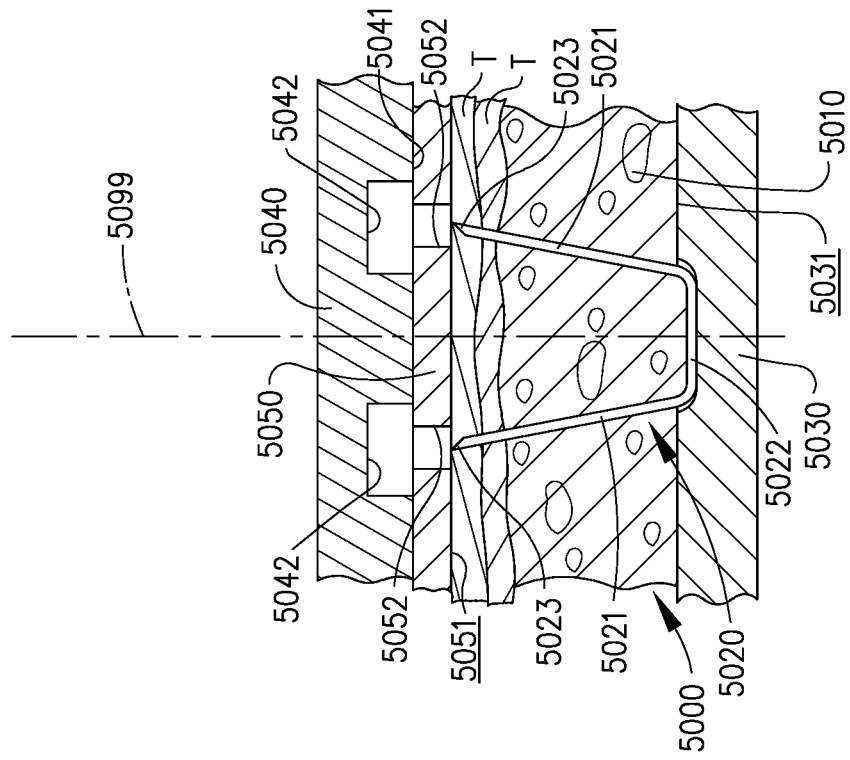
FIG. 96B is a partial cross-sectional view of the end effector of FIG. 96A illustrating the jaw being moved toward the staple cartridge channel, the staple cartridge being compressed by the anvil and the retention matrix, and a staple at least partially extending through tissue positioned intermediate the retention matrix and the staple cartridge.
Figure 96A:
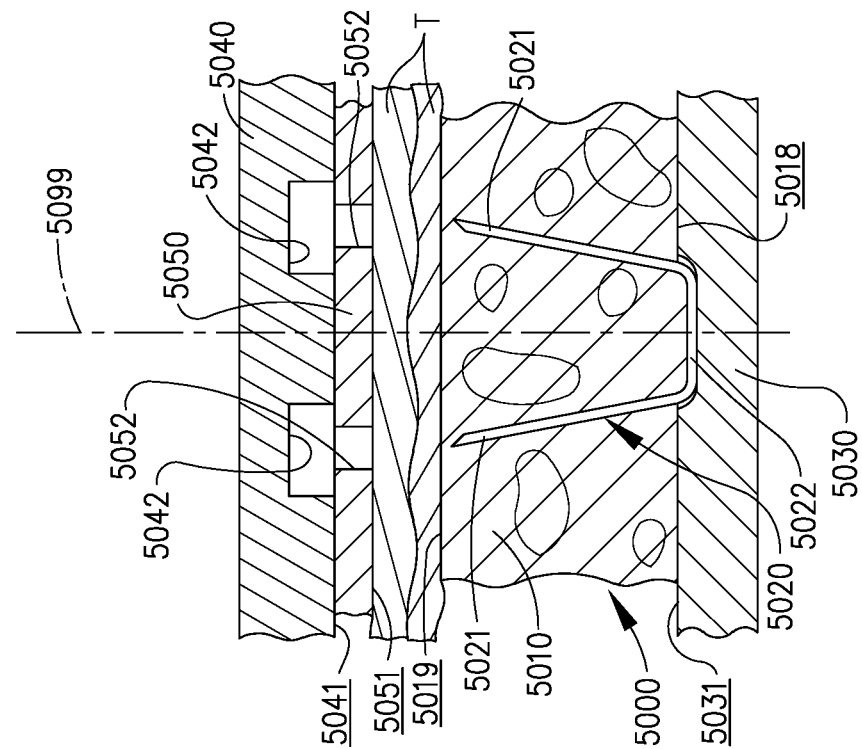
FIG. 96A is a partial cross-sectional view of an end effector of a surgical stapling instrument comprising a jaw, a staple cartridge channel positioned opposite the jaw, and a staple cartridge positioned within the staple cartridge channel, wherein the jaw comprises a retention matrix attached thereto.

In various embodiments, referring now to FIG. 96A, the retention matrix 5050 can be detachably secured to the jaw 5040 such that there is little, if any, relative movement between the retention matrix 5050 and the jaw 5040 when the retention matrix 5050 is attached to the jaw 5040. In at least one embodiment, the jaw 5040 can comprise one or more retention features which can be configured to hold the retention matrix 5050 in position. In at least one such embodiment, the retention matrix 5050 can be snap-fit and/or press-fit into the jaw 5040. In certain embodiments, the retention matrix 5050 can be adhered to the jaw 5040 utilizing at least one adhesive. In any event, the jaw 5040 can be moved into a position in which the retention matrix 5050 is in contact with the tissue T and the tissue T is positioned against the tissue-contacting surface 5019 of the staple cartridge 5000. When the tissue T is positioned against the staple cartridge 5000 by the jaw 5040, the compressible body 5010 of the staple cartridge 5000 may or may not be compressed by the jaw 5040. In either circumstance, in various embodiments, the legs 5021 of the staples 5200 may not protrude through the tissue-contacting surface 5019 of the staple cartridge 5000 as illustrated in FIG. 96A. Furthermore, as also illustrated in FIG. 96A, the jaw 5040 can hold the tissue T against the compressible body 5010 without engaging the retention matrix 5050 with the staples 5020. Such embodiments can permit a surgeon to open and close the jaw 5040 multiple times in order to obtain a desired positioning of the end effector within a surgical site, for example, without damaging the tissue T. Other embodiments are envisioned, however, where the staple tips 5023 can protrude from the tissue-contacting surface 5019 prior to the cartridge body 5010 being compressed by the anvil 5040. Once the end effector has been suitably positioned, referring now to FIG. 96B, the jaw 5040 can be moved downwardly toward the staple cartridge channel 5030 such that the compressible body 5010 is compressed by the anvil 5040 and such that the tissue-contacting surface 5019 is pushed downwardly relative to the staples 5020. As the tissue-contacting surface 5019 is pushed downwardly, the tips 5023 of the staple legs 5021 can pierce the tissue-contacting surface 5019 and pierce at least a portion of the tissue T. In such circumstances, the retention matrix 5050 may be positioned above the staples 5020 such that the retention apertures 5052 of retention matrix 5050 are aligned, or at least substantially aligned, with the tips 5023 of the staple legs 5021.

As the retention matrix 5050 is pushed downwardly along the axis 5099, referring now to FIG. 96C, the staple legs 5021 of staples 5020 can enter into the retention apertures 5052. In various embodiments, the staple legs 5021 can engage the side walls of the retention apertures 5052. In certain embodiments, as described in greater detail below, the retention matrix 5050 can comprise one or more retention members extending into and/or around the retention apertures 5052 which can engage the staple legs 5021. In either event, the staple legs 5021 can be retained in the retention apertures 5052. In various circumstances, the tips 5023 of the staple legs 5021 can enter into the retention apertures 5052 and can frictionally engage the retention members and/or the side walls of the apertures 5052. As the retention matrix 5050 is pushed toward the bases 5022 of the staples 5020, the staple legs 5021 can slide relative to the side walls and/or the retention members. As a result of the above, sliding friction forces can be created between the staple legs 5021 and the retention matrix 5050 wherein such sliding friction forces can resist the insertion of the retention matrix 5050 onto the staples 5020. In various embodiments, the sliding friction forces between the retention matrix 5050 and the staples 5020 can be constant, or at least substantially constant, as the retention matrix 5050 is slid downwardly along the staple legs 5021 of the staples 5020. In certain embodiments, the sliding friction forces may increase and/or decrease as the retention matrix 5050 is slid downwardly along the staple legs 5021 owing to variations in geometry of the staple legs 5021, the retention apertures 5052, and/or the retention members extending into and/or around the retention apertures 5052, for example. In various embodiments, the insertion of the retention matrix 5050 onto the staples 5020 can also be resisted by the compressible body 5010 of the staple cartridge 5000. More particularly, the compressible body 5010 can be comprised of an elastic material, for example, which can apply a resistive force to the retention matrix 5050 which increases as the distance in which the compressible body 5010 is compressed increases. In at least one such embodiment, the increase in the resistive force generated by the cartridge body 5010 can be linearly proportional, or at least substantially linearly proportional, with respect to the distance in which the cartridge body 5010 is compressed. In certain embodiments, the increase in the resistive force generated by the cartridge body 5010 can be geometrically proportional with respect to the distance in which the cartridge body 5010 is compressed.

In various embodiments, further to the above, a sufficient firing force can be applied to the jaw 5040 and the retention matrix 5050 in order to overcome the resistive and friction forces described above. In use, the retention matrix 5050 can be seated to any suitable depth with respect to the staples 5020. In at least one embodiment, the retention matrix 5050 can be seated to a depth with respect to the bases 5022 of the staples 5020 in order to secure two or more layers of tissue together and generate compressive forces, or pressure, within the tissue. In various circumstances, the system comprising the retention matrix 5050 and the staples 5020 can allow a surgeon to select the amount of compressive forces, or pressure, that is applied the tissue by selecting the depth in which the retention matrix 5050 is seated. For example, the retention matrix 5050 can be pushed downwardly toward the staple bases 5022 of the staples 5020 until the retention matrix 5050 is seated a certain depth 5011 away from the bottom of the support slots 5032, wherein a shorter depth 5011 can result in higher compressive forces, or pressure, being applied to the tissue T than a taller depth 5011 which can result in lower compressive forces, or pressure, being applied to the tissue T. In various embodiments, the compressive forces, or pressures, applied to the tissue T can be linearly proportional, or at least substantially linearly proportional, to the depth 5011 in which the retention matrix 5050 is seated. In various circumstances, the compressive forces, or pressure, applied to the tissue T can depend on the thickness of the tissue T positioned between the retention matrix 5050 and the staple cartridge 5020. More particularly, for a given distance 5011, the presence of thicker tissue T can result in higher compression forces, or pressure, than the presence of thinner tissue T.

In various circumstances, further to the above, a surgeon can adjust the depth in which the retention matrix 5050 is seated in order to account for thicker and/or thinner tissue positioned within the end effector and to apply a certain or predetermined pressure to the tissue T regardless of the tissue thickness. For example, the surgeon can seat the retention matrix 5050 to a shorter depth 5011 when fastening thinner tissue T or a taller depth 5011 when fastening thicker tissue T in order to arrive at the same, or at least substantially the same, compression pressure within the tissue. In certain embodiments, further to the above, a surgeon can selectively determine the amount of compressive pressure to apply to the tissue T positioned between the retention matrix 5050 and the staple cartridge 5010. In various circumstances, a surgeon can engage the retention matrix 5050 with the staples 5020 and position the retention matrix 5050 a first distance away from the bases 5022 of the staples 5020 in order to apply a first compressive pressure to the tissue. The surgeon can alternatively position the retention matrix 5050 a second distance away from the bases 5022, which is shorter than the first distance, in order to apply a second compressive pressure to the tissue which is greater than the first pressure. The surgeon can alternatively position the retention matrix 5050 a third distance away from the bases 5022, which is shorter than the second distance, in order to apply a third compressive pressure to the tissue which is greater than the second pressure. In various embodiments, the fastening system comprising the retention matrix 5050 and the staples 5020 can be configured to permit a surgeon to apply a wide range of compressive pressures to the targeted tissue.

In various embodiments, referring now to FIG. 96D, the staple legs 5021 can be inserted through the retention matrix 5050 such that the staple leg tips 5023 extend above the top surface of the retention matrix 5050. In at least one embodiment, referring again to FIG. 96C, the jaw 5040 can further comprise clearance apertures 5042 defined therein which can be configured to receive the staple leg tips 5023 as they pass through the retention apertures 5052 in the retention matrix 5050. In at least one such embodiment, the clearance apertures 5042 can be aligned with the retention apertures 5052 such that the legs 5021 do not contact the jaw 5040. In various embodiments, the clearance apertures 5042 can have a sufficient depth such that the staple legs 5021 do not contact the jaw 5040 regardless of the distance in which the retention matrix 5050 is seated. After the retention matrix 5050 has been engaged with the staples 5020 and seated to a desired position, referring now to FIG. 96D, the staple cartridge channel 5030 and the jaw 5040 can be moved away from the tissue T. More particularly, the staple cartridge channel 5030 can be detached from the implanted staple cartridge 5000 and the anvil 5040 can be detached from the implanted retention matrix 5050. As the jaw 5040 is moved away from the retention matrix 5050 and the staple supports 5032 are moved away from the staple bases 5022, the distance 5011 between the retention matrix 5050 and the bottom of the bases 5022 can be maintained even though the jaw 5040 and the staple cartridge channel 5030 are no longer providing support thereto. In various embodiments, the static friction forces between the staple legs 5021 and the retention matrix 5050 can be sufficient to maintain the retention matrix 5050 in position despite a biasing force being applied to the retention matrix 5050 by the compressed cartridge body 5010 and/or the compressed tissue T. In at least one such embodiment, the cartridge body 5010 can be comprised of a resilient material which, when compressed, can apply an elastic biasing force to the retention matrix 5050 and the staples 5020 in a manner which tends to push the retention matrix 5050 and the staples 5020 apart, although such movement is opposed by the frictional engagement between the staple legs 5021 and the retention matrix 5050.

Figure 97:
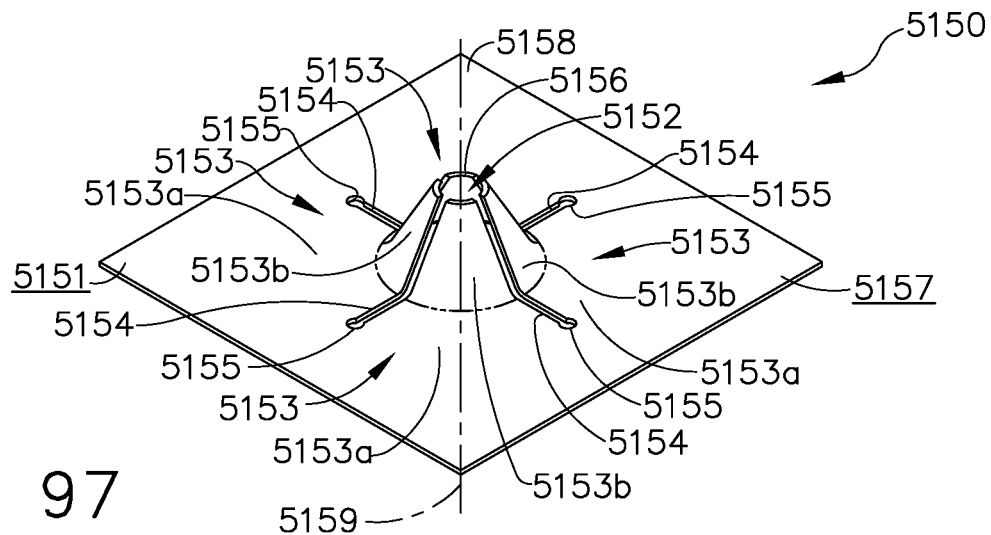
FIG. 97 is a perspective view of a retention aperture of a retention matrix in accordance with at least one alternative embodiment comprising a plurality of retention members configured to engage a fastener leg extending therethrough.

In various embodiments, as described above, a retention matrix can comprise a plurality of retention apertures, wherein each retention aperture can be configured to receive a leg of a fastener therein. In at least one embodiment, referring now to FIG. 97, a portion of a retention matrix 5150 is illustrated therein which can comprise a retention aperture 5152 defined by a perimeter 5156. In various embodiments, the perimeter 5156 of the aperture 5152 can comprise a circular, or at least substantially circular, profile and/or any other suitable profile. In certain embodiments, the retention matrix 5150 can comprise one or more retention members, such as retention members 5153, for example, which extend into the aperture 5152 and can be configured to engage a fastener leg when the fastener leg is inserted therethrough. In at least one such embodiment, each retention member 5153 can comprise a cantilever which extends inwardly toward a center axis 5159, i.e., toward the center of the aperture 5152. In various embodiments, each cantilever can comprise a first end which is attached to the retention matrix body 5158 and a second end which forms the perimeter 5156 of the retention aperture 5152. In certain embodiments, the perimeter 5156 of a retention aperture 5152 can be defined by a first diameter, or width, and a fastener leg can be defined by a second diameter, or width, wherein the second diameter can be larger than the first diameter. In at least one such embodiment, the fastener leg can be configured to contact and deflect one or more of the retention members 5153 in order to increase the diameter of the retention aperture 5152 as the fastener leg is being inserted therethrough. In certain embodiments, further to the above, the fastener leg can define a perimeter which is larger than the perimeter 5156 of the retention aperture 5152 such that the fastener leg can expand the perimeter 5156 when the fastener leg is inserted therein.

In various embodiments, referring again to FIG. 97, the aperture 5152 can be defined by the deformable members 5153, wherein each deformable member 5153 can be configured to deflect relative to, or independently of, the other deformable members 5153. In at least one such embodiment, adjacent deformable members 5153 can be separated by slots 5154 which can be configured to permit each deformable member 5153 to flex relative to the others. In certain embodiments, each slot 5154 can comprise a first end 5155 in the retention matrix body 5158, a second end opening into the retention aperture 5152, and a constant, or at least substantially constant, width extending between the first end 5155 and the second end. In various other embodiments, the width of each slot 5154 may not be constant and each slot 5154 may increase and/or decrease in width between the first and second ends thereof. In certain embodiments, the first ends 5155 of the slots 5154 can comprise an enlarged portion, such as a circular portion, which can provide, one, strain relief to the bases of the deformable members 5153 attached to the retention matrix body 5158 and, two, means for increasing the flexibility of the deformable members 5153. In various embodiments, the geometry of the deformable members 5153, and/or slots 5154, can be selected so as to provide the deformable members 5153 with a desired flexibility. In certain embodiments, for example, the slots 5154 can be lengthened in order to create longer deformable members 5153 which can be more flexible than deformable members 5153 having a shorter length. In at least one embodiment, the width of each deformable member 5153 can be selected so as to provide a desired flexibility thereof. More particularly, deformable members having a thinner width can be more flexible than deformable members having a thicker width. In certain embodiments, referring again to FIG. 97, the first ends of the cantilevers of deformable members 5153 attached to the retention matrix body 5158 can be wider than the second ends of the cantilevers. In at least one such embodiment, the cantilevers can be tapered in a linear, or at least substantially linear, manner between the first and second ends thereof.

In various embodiments, referring again to FIG. 97, the retention matrix body 5158 can comprise a flat, or at least substantially flat, sheet of material having a tissue-contacting surface 5151 and a top surface 5157. In at least one such embodiment, the tissue-contacting surface 5151 and the top surface 5157 can be parallel, or at least substantially parallel, to one another. In various embodiments, each deformable member 5153 can comprise a first portion 5153a and a second portion 5153b, wherein the first portion 5153a can extend in a first direction and the second portion 5153b can extend in a different, or second, direction. In at least one such embodiment, the retention matrix body 5158 can define a plane and the first portions 5153a of the deformable members 5153 can lie within such a plane. In various embodiments, the second portions 5153b of the deformable members 5153 can extend at an angle relative to the first portions 5153a. In at least one such embodiment, the second portions 5153b can extend in directions which are pointed away from the top surface 5157 of the retention matrix body 5158 and, in certain embodiments, the second portions 5153b can converge toward the central axis 5159 of the retention aperture 5152. In any event, in various embodiments, the second portions 5153b can be configured to deflect away from the central axis 5159 when the fastener leg is inserted therethrough. In embodiments where a staple leg 5021 of a staple 5020 is inserted into a retention aperture 5152, the deformable members 5153 can deform in a direction which is generally away from the bases 5122 of the staples 5120. In certain embodiments, as a result, the deformable members 5153 can deflect in a general direction which is the same as, or at least substantially the same as, the direction in which the staple legs 5021 are being inserted.

In various embodiments, referring again to FIG. 97, the second portions 5153b of the deformable members 5153 can each comprise a sharp tip, for example, which can be configured to slide against a staple leg 5021 as the staple leg 5021 is inserted therein. The sharp tips of the second portions 5153b can also be configured to bite into the staple leg 5021 in the event that the staple leg 5021 were to be pulled in the opposite direction, i.e., in a direction which would remove the staple leg 5021 from the retention aperture 5052. In certain circumstances, the second portions 5153b can be inclined at an angle relative to the side of the staple leg 5021 which is greater than 90 degrees and, as a result, the second portions 5153b may dig, or burrow, into the side of the staple leg 5021 when the staple leg 5021 experiences a force which tends to withdraw the staple leg 5021 from the retention aperture 5052. In certain embodiments, the staple legs 5021 can comprise indentations and/or concavities, such as microindentations, for example, in the surfaces thereof which can be configured to receive the tips of the deformable members 5053, for example, therein. In at least one such embodiment, the tips of the deformable members 5053 can catch in and burrow into the indentations in the staple legs 5021 when a withdrawing force is applied to the staple legs 5021. In various embodiments, as a result of the burrowing of the second portions 5153b into the staple legs 5021, forces acting to remove the staple legs 5021 from the retention apertures 5022 may only seat the second portions 5153b deeper into the staple legs 5021 and increase the force required to remove the staple legs 5021. Furthermore, owing to the upward inclination of the second portions 5153b, in at least one embodiment, the second portions 5153b can be more permissive to the insertion of a staple leg 5021 within a retention aperture 5152 and more resistive to withdrawal of the staple leg 5021. In at least one embodiment, as a result, the force required to insert a staple leg 5021 into a retention aperture 5022 may be less than the force required to remove the staple leg 5021 from the retention aperture 5022. In various embodiments, the force needed to remove the staple leg 5021 from the retention aperture 5022 can be approximately 50 percent greater than the force needed to insert the staple leg 5021 into the retention aperture 5022, for example. In various other embodiments, the force needed to remove the staple leg 5021 may between approximately 10 percent and approximately 100 percent greater than the force needed to insert the staple leg 5021, for example. In certain embodiments, the force needed to remove the staple leg 5021 may be approximately 100 percent, approximately 150 percent, approximately 200 percent, and/or greater than approximately 200 percent larger than the force needed to insert the staple leg 5021, for example.

Figure 98:
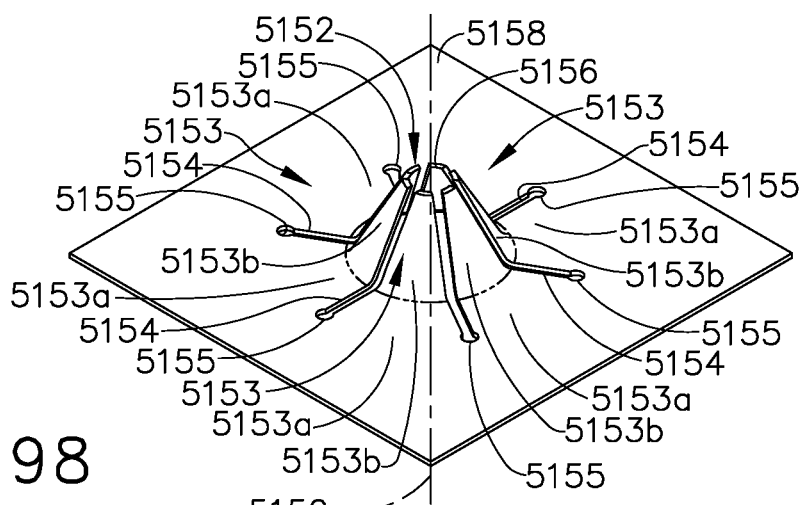
FIG. 98 is a perspective view of a retention aperture of a retention matrix in accordance with at least one alternative embodiment comprising six retention members.
Figure 99:
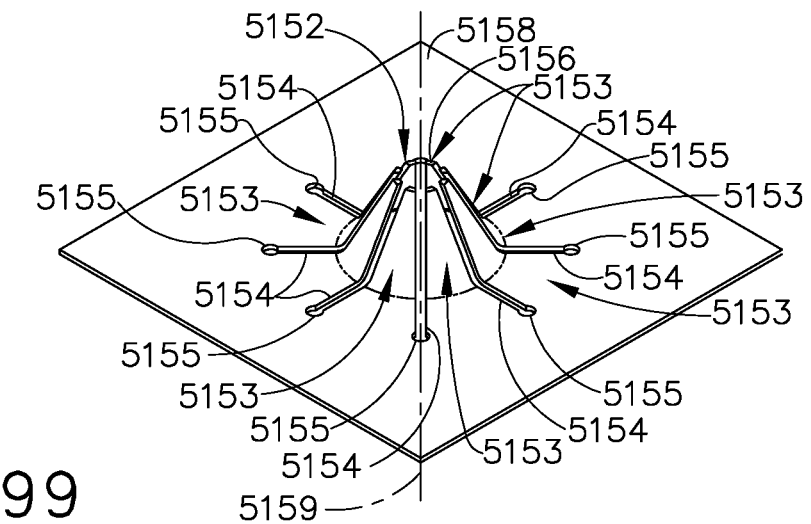
FIG. 99 is a perspective view of a retention aperture of a retention matrix in accordance with at least one alternative embodiment comprising eight retention members.
Figure 100:
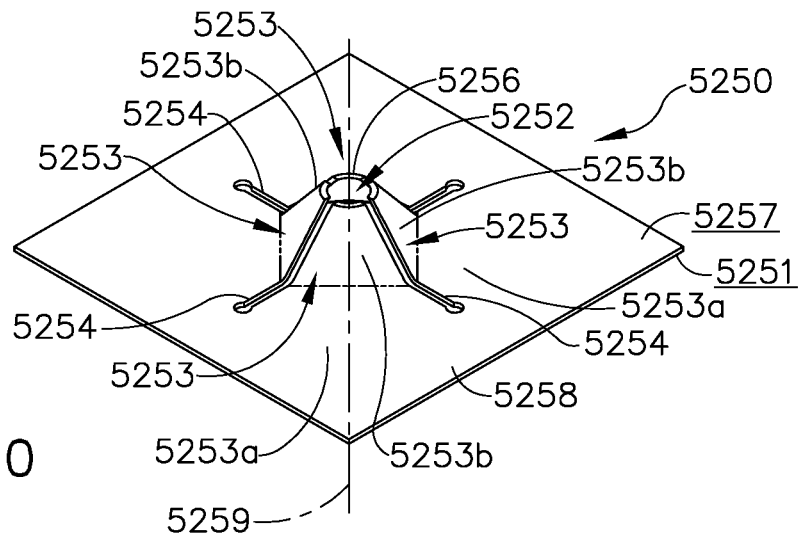
FIG. 100 is a perspective view of a retention aperture of a retention matrix in accordance with at least one alternative embodiment comprising a plurality of retention members configured to engage a fastener leg extending therethrough.

In certain embodiments, referring again to FIG. 97, the second portions 5153b can be arranged circumferentially around the aperture 5152 and can define a pocket therebetween. More particularly, the second portions 5153b can define a pocket 5160 which can be configured to receive the tip of the fastener leg when it is inserted into the retention aperture 5152. In various embodiments, the second portions 5153b of the deformable members 5153 can comprise an annular, or an at least substantially annular, contour which can co-operatively define an annular, or at least substantially annular, profile of the pocket 1560, for example. In at least one such embodiment, the second portions 5153b can define a conical or frustoconical pocket. In various embodiments, the pocket can be defined by a suitable number of deformable members, such as four deformable members 5153 (FIG. 97), six deformable members 5153 (FIG. 98), or eight deformable members 5153 (FIG. 99), for example. In certain embodiments, referring now to FIG. 100, the deformable members of a retention matrix, such as retention matrix 5250, for example, can form a pyramidal shape, or an at least substantially pyramidal shape, for example. In various embodiments, a retention matrix 5250 can comprise a plurality of retention apertures, such as retention aperture 5252, for example, which can be defined by a perimeter 5256. In various embodiments, the perimeter 5256 can comprise a polygonal, or at least substantially polygonal, profile and/or any other suitable profile. In certain embodiments, the retention matrix 5250 can comprise one or more retention members, such as retention members 5253, for example, which extend into the aperture 5252 and can be configured to engage a fastener leg when the fastener leg is inserted therethrough. In at least one such embodiment, each retention member 5253 can comprise a cantilever which extends inwardly toward a center axis 5259, i.e., toward the center of the aperture 5252. In various embodiments, each cantilever can comprise a first end which is attached to the retention matrix body 5258 and a second end which forms the perimeter 5256 of the retention aperture 5252. In certain embodiments, the perimeter 5256 of a retention aperture 5252 can be defined by a first diameter, or width, and a fastener leg can be defined by a second diameter, or width, wherein the second diameter can be larger than the first diameter. In at least one such embodiment, the fastener leg can be configured to contact and deflect one or more of the retention members 5253 in order to increase the diameter of the retention aperture 5252 as the fastener leg is being inserted therethrough. In certain embodiments, further to the above, the fastener leg can define a perimeter which is larger than the perimeter 5256 of the retention aperture 5252 such that the fastener leg can expand the perimeter 5256 when the fastener leg is inserted therein.

Figure 101:
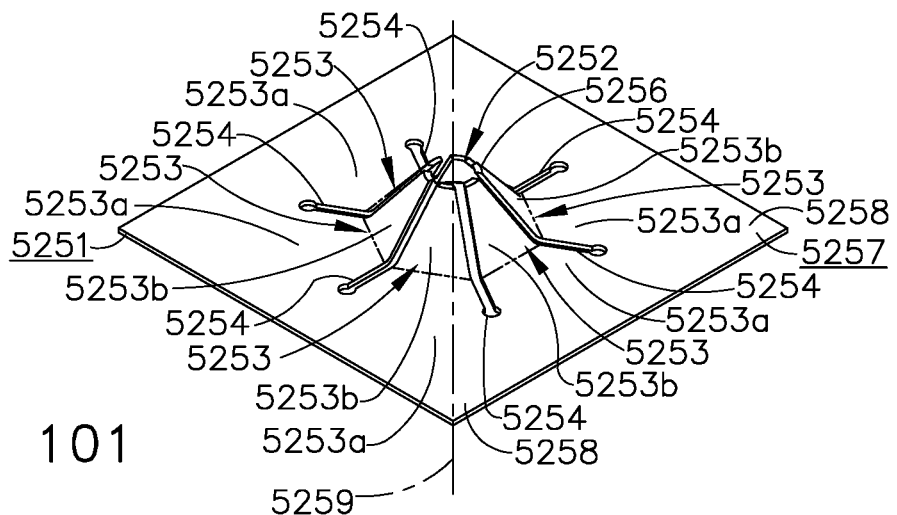
FIG. 101 is a perspective view of a retention aperture of a retention matrix in accordance with at least one alternative embodiment comprising six retention members.
Figure 102:
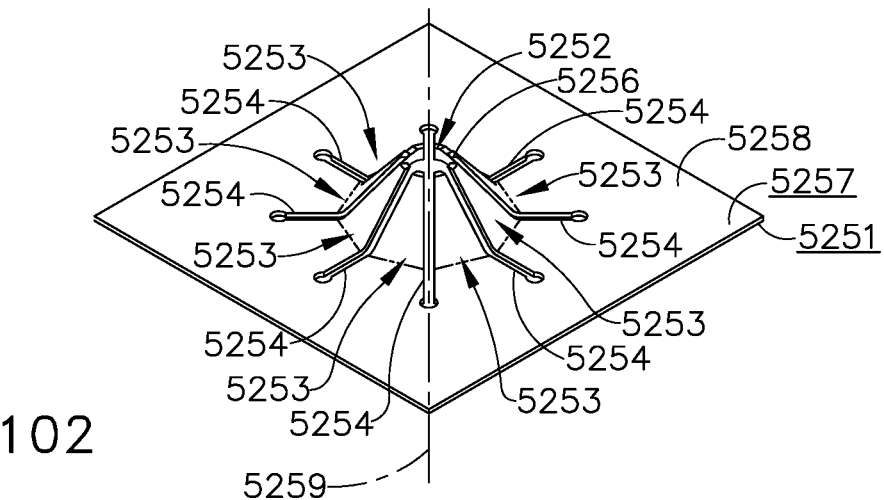
FIG. 102 is a perspective view of a retention aperture of a retention matrix in accordance with at least one alternative embodiment comprising eight retention members.

In various embodiments, referring again to FIG. 100, the aperture 5252 can be defined by the deformable members 5253, wherein each deformable member 5253 can be configured to deflect relative to, or independently of, the other deformable members 5253. In at least one such embodiment, adjacent deformable members 5253 can be separated by slots 5254 which can be configured to permit each deformable member 5253 to flex relative to the others. In various embodiments, the retention matrix body 5258 can comprise a flat, or at least substantially flat, sheet of material having a tissue-contacting surface 5251 and a top surface 5257. In at least one such embodiment, the tissue-contacting surface 5251 and the top surface 5257 can be parallel, or at least substantially parallel, to one another. In various embodiments, each deformable member 5253 can comprise a first portion 5253a and a second portion 5253b, wherein the first portion 5253a can extend in a first direction and the second portion 5253b can extend in a different, or second, direction. In at least one such embodiment, the retention matrix body 5258 can define a plane and the first portions 5253a of the deformable members 5253 can lie within such a plane. In various embodiments, the second portions 5253b of the deformable members 5253 can extend at an angle relative to the first portions 5253a. In at least one such embodiment, the second portions 5253b can extend in directions which are pointed away from the top surface 5257 of the retention matrix body 5258 and, in certain embodiments, the second portions 5253b can converge toward the central axis 5259 of the retention aperture 5252. In any event, in various embodiments, the second portions 5253b can be configured to deflect away from the central axis 5259 when the fastener leg is inserted therethrough. In certain embodiments, referring again to FIG. 100, the second portions 5253b can be arranged circumferentially around the aperture 5252 and can define a pocket therebetween. More particularly, the second portions 5253b can define a pocket which can be configured to receive the tip of the fastener leg when it is inserted into the retention aperture 5252. In various embodiments, the second portions 5253b of the deformable members 5253 can define a polygonal, or an at least substantially polygonal, pocket, for example. In various embodiments, the pocket can be defined by a suitable number of deformable members, such as four deformable members 5253 (FIG. 100) which can define a square, six deformable members 5253 (FIG. 101) which can define a hexagon, or eight deformable members 5253 (FIG. 102) which can define an octagon, for example.

Figure 103:
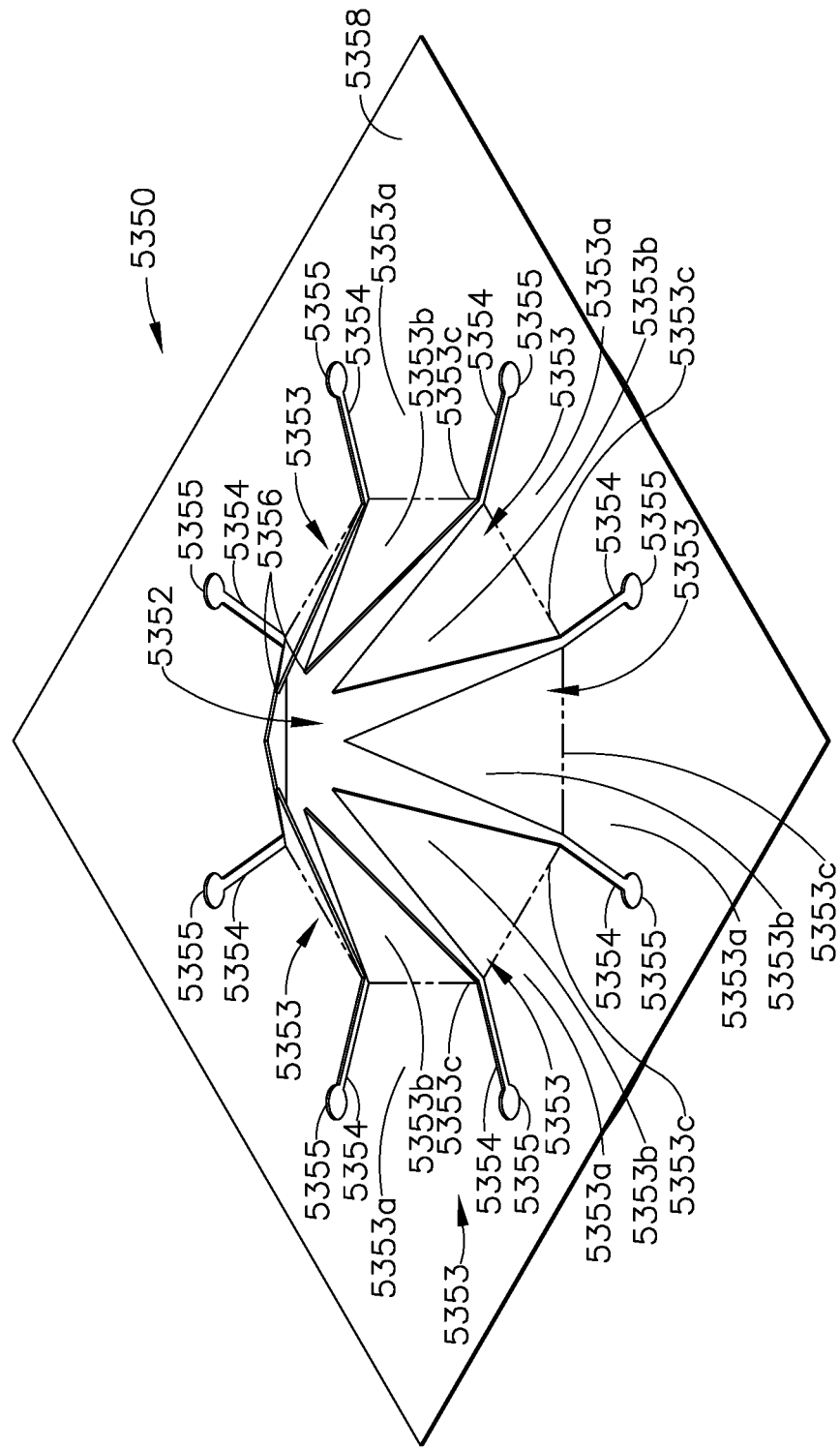
FIG. 103 is a perspective view of a retention aperture of a retention matrix in accordance with at least one alternative embodiment comprising a plurality of retention members that have been stamped from a sheet of metal.
Figure 104:
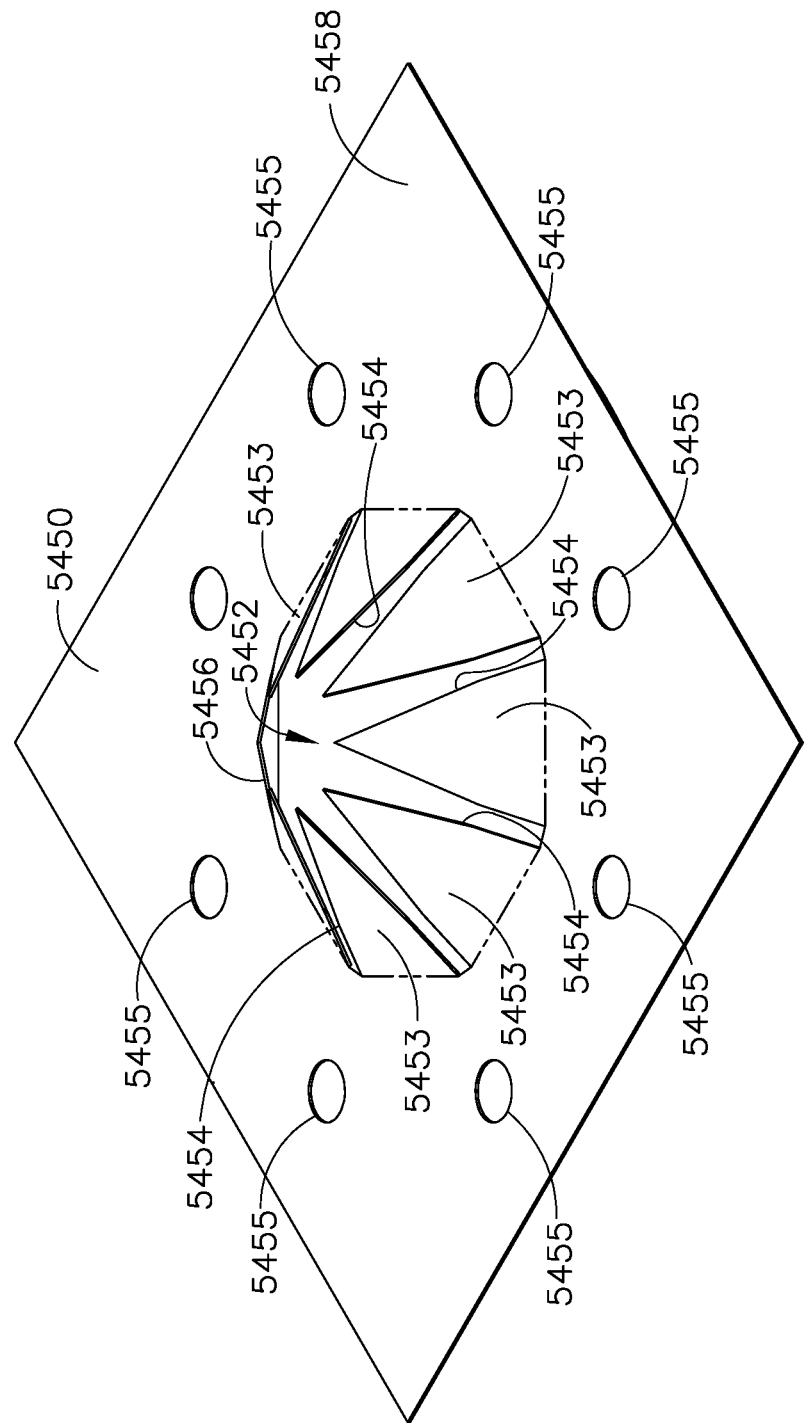
FIG. 104 is a perspective view of a retention aperture of a retention matrix in accordance with at least one alternative embodiment comprising a plurality of apertures extending around the perimeter of the retention aperture.

In various embodiments, referring now to FIG. 103, a retention matrix, such as retention matrix 5350, for example, can be formed from a flat, or an at least substantially flat, sheet of material such as titanium and/or stainless steel, for example. In at least one such embodiment, a plurality of apertures 5352 can be formed in the body 5358 of the retention matrix 5350 by one or more stamping processes. The sheet of material can be positioned in a stamping die which, when actuated, can punch out certain portions of the material in order to form slots 5354, apertures 5355 of slots 5354, and/or the perimeter 5356 of the retention aperture 5352, for example. The stamping die can also be configured to bend the deformable members 5353 in a suitable configuration. In at least one such embodiment, the stamping die can deform the second portions 5353*b* upwardly relative to the first portions 5353*a* along a crease line 5353*c*. In various embodiments, referring now to FIG. 104, a retention matrix, such as retention matrix 5450, for example, can comprise a plurality of retention apertures 5452. Similar to the above, the perimeter 5456 of each retention aperture 5452 can be defined by a plurality of deformable members 5453 separated by slots, or slits, 5454. In at least one such embodiment, the entirety of each deformable member 5453 can be bent upwardly wherein the free ends of the cantilevers comprising the deformable members 5453 can define the perimeter 5456. In various embodiments, the retention matrix 5450 can comprise a plurality of apertures 5455 surrounding, or at least substantially surrounding, the retention aperture 5452. In at least one such embodiment, the apertures 5455 can be arranged in a circular array surrounding or enclosing a perimeter defined by the fixed ends of the cantilevers of the deformable members 5453. In certain embodiments, each aperture 5455 can comprise a circular, or at least substantially circular, perimeter and/or any other suitable perimeter. In use, the apertures 5455 can provide, one, strain relief to the bases of the deformable members 5453 attached to the retention matrix body 5458 and, two, means for increasing the flexibility of the deformable members 5453. In various embodiments, larger apertures 5455 can provide more flexibility to the deformable members 5453 as compared to smaller apertures 5455. Furthermore, apertures 5455 which are closer to the deformable members 5453 can provide more flexibility as compared to apertures 5455 which are further away.

Figure 105:
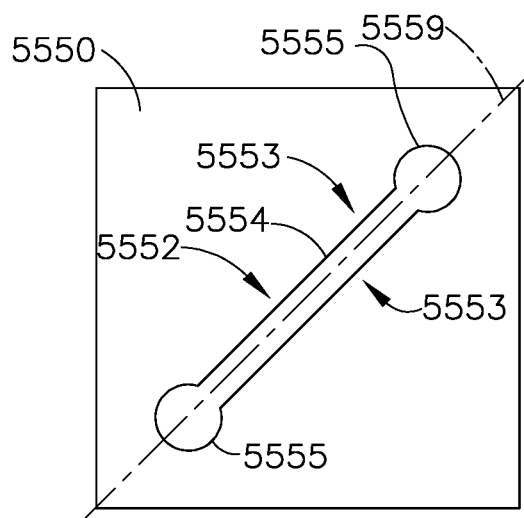
FIG. 105 is a top view of a retention aperture of a retention matrix in accordance with at least one alternative embodiment.
Figure 106:
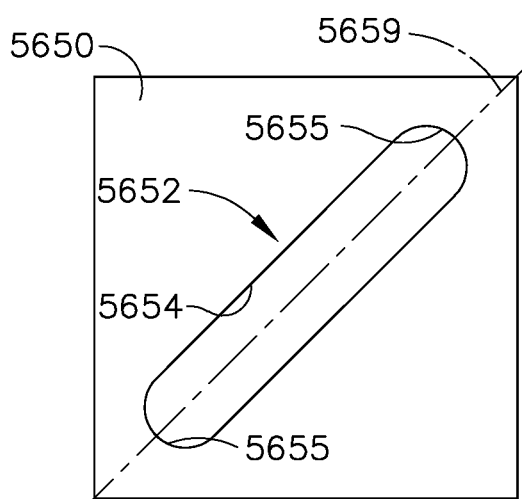
FIG. 106 is a top view of a retention aperture of a retention matrix in accordance with at least one alternative embodiment.

In various embodiments, referring now to FIG. 105, a retention matrix, such as retention matrix 5550, for example, can comprise a plurality of retention apertures 5552. Each retention aperture 5552 can comprise an elongate slot 5554 having enlarged circular, or at least substantially circular, ends 5555. In at least one such embodiment, the ends 5555 can be defined by a diameter which is wider than the slot 5554. In certain embodiments, the elongate slot 5554 and the ends 5555 can positioned along, and/or centered along, a longitudinal axis 5559. In various embodiments, the slot 5554 and the ends 5555 can define two opposing tabs 5553 which can be configured to engage a leg of a fastener and deflect as the fastener leg is inserted therethrough. In at least one embodiment, ends 5555 having a larger perimeter, or diameter, can define longer tabs 5553 which can be more flexible than tabs 5553 defined by ends 5555 having a smaller perimeter, or diameter. In various embodiments, the ends 5555 can have the same perimeter and diameter and, in at least one such embodiment, each tab 5553 can be symmetrical about an axis which is perpendicular, or at least substantially perpendicular, to the longitudinal axis 5559. Alternatively, the ends 5555 can have different perimeters and/or diameters wherein, in at least one embodiment, each tab 5553 may not be symmetrical about its axis. In at least one such alternative embodiment, the tabs 5553 may twist about their axes as the fastener leg is inserted through the retention aperture 5552. In various embodiments, referring now to FIG. 106, a retention matrix, such as retention matrix 5650, for example, can comprise a plurality of retention apertures 5652. Each retention aperture 5652 can comprise an elongate slot 5654 comprising circular, or at least substantially circular, ends 5655. In at least one such embodiment, the elongate slot 5654 and the ends 5655 can be positioned along, and/or centered along, a longitudinal axis 5659. In various embodiments, each end 5655 can be defined by a diameter which is the same as, or at least substantially the same as, the width of the slot 5654.

Figure 107:
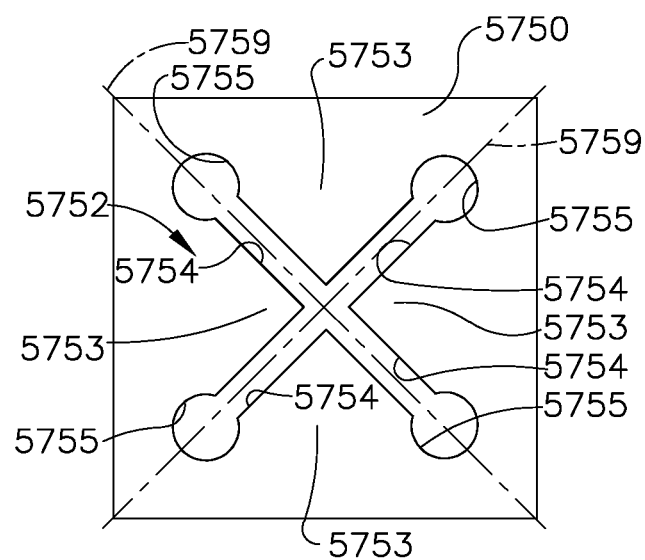
FIG. 107 is a top view of a retention aperture of a retention matrix in accordance with at least one alternative embodiment.
Figure 108:
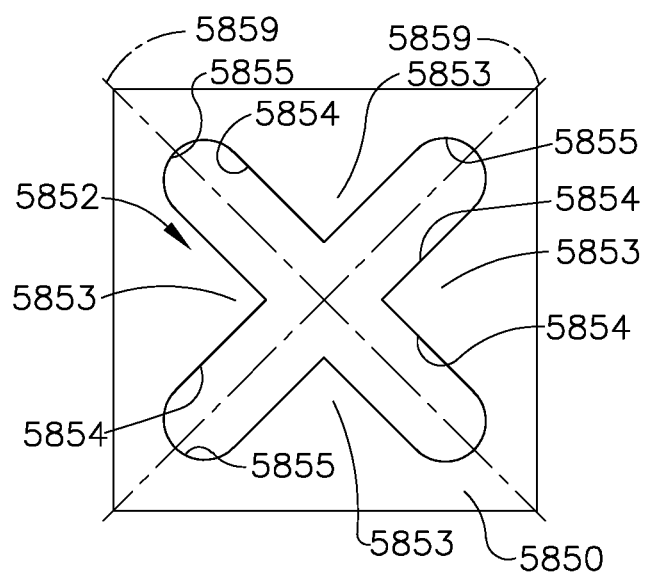
FIG. 108 is a top view of a retention aperture of a retention matrix in accordance with at least one alternative embodiment.

In various embodiments, referring now to FIG. 107, a retention matrix, such as retention matrix 5750, for example, can comprise a plurality of retention apertures 5752. Each retention aperture 5752 can comprise a plurality of slots, such as slots 5754, for example, having enlarged ends 5755. In at least one such embodiment, the slots 5754 and the ends 5755 can be positioned along and/or centered along longitudinal axes 5759. In various embodiments, the axes 5759 can extend in directions which are perpendicular or transverse to one another. In certain embodiments, the slots 5754 and the ends 5755 can define four tabs 5753, for example, which can be configured to engage a fastener leg and deflect when the fastener leg is inserted through the retention aperture 5752. In at least one embodiment, each tab 5753 can comprise a triangular, or at least substantially triangular, configuration, such as an equilateral triangle, for example. In various other embodiments, referring now to FIG. 108, a retention matrix, such as retention matrix 5850, for example, can comprise a plurality of retention apertures 5852. Each retention aperture 5852 can comprise a plurality of slots, such as slots 5854, for example, having ends 5855, wherein the slots 5854 and the ends 5855 can be positioned along and/or centered along longitudinal axes 5859. In various embodiments, the axes 5859 can extend in directions which are perpendicular or transverse to one another. In certain embodiments, the slots 5854 and the ends 5855 can define tabs 5853 which can be configured to engage a fastener leg and deflect when the fastener leg is inserted through the retention aperture 5852. In at least one embodiment, each tab 5853 can comprise an arcuate profile. More particularly, each tab 5853 can comprise a curved end, as opposed to a pointed end depicted in FIG. 105, which can be configured to contact the fastener leg.

Figure 109:
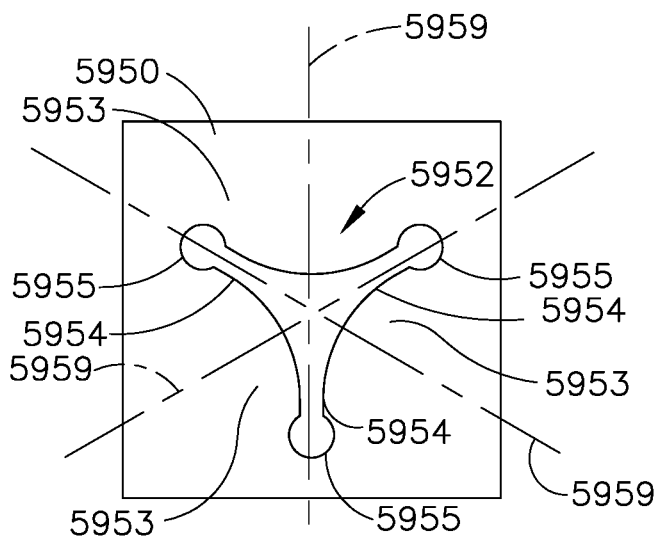
FIG. 109 is a top view of a retention aperture of a retention matrix in accordance with at least one alternative embodiment.

In various embodiments, referring now to FIG. 109, a retention matrix, such as retention matrix 5950, for example, can comprise a plurality of retention apertures 5952. Each retention aperture 5952 can comprise a plurality of slots, such as slots 5954, for example, wherein each slot 5954 can extend along, and/or can be centered along, an axis 5959. In various embodiments, the axes 5959 can be transverse to each other and, in at least one such embodiment, the axes 5959 can be arranged such that all of the axes 5959 extend through a center of the retention aperture 5952 and are spaced equidistantly, or at least substantially equidistantly, from each other. In at least one embodiment, each slot 5954 can comprise an open end facing the center of the retention aperture 5952 and a second, or closed, end 5955 at the opposite end of the slot 5954. Similar to the above, the slots

Figure 110:
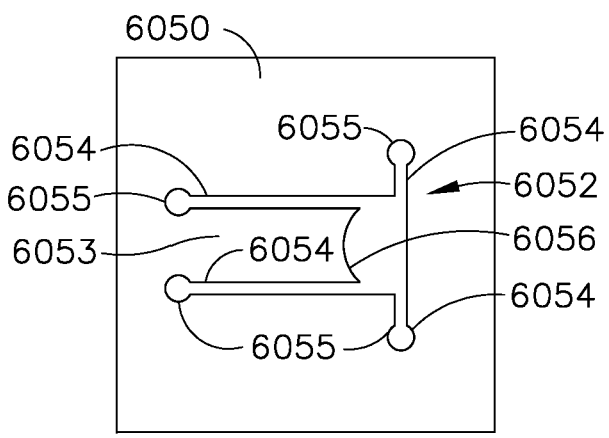

5954 and the ends 5955 can define three tabs 5953, for example, which can be configured to engage a fastener leg and deflect when the fastener leg is inserted into the retention aperture 5952. In various embodiments, each tab 5953 can comprise an arcuate configuration extending between adjacent ends 5955 of the slots 5954. In various embodiments, referring now to FIG. 110, a retention matrix, such as retention matrix 6050, for example, can comprise a plurality of retention apertures 6052. Each retention aperture 6052 can comprise a tab 6053 which can be configured to engage a fastener leg and to deflect when the fastener leg is inserted into the retention aperture 6052. In at least one such embodiment, the tab 6053 can comprise a base fixed to the retention matrix body 6058 and a free end comprising an arcuate or curved profile 6056 which can be configured to contact the fastener leg. In certain embodiments, the fastener leg can be a staple leg comprised of a round wire wherein the curved profile 6056 can be configured to match, or at least substantially match, a curved outer surface of the round wire.

Figure 111:
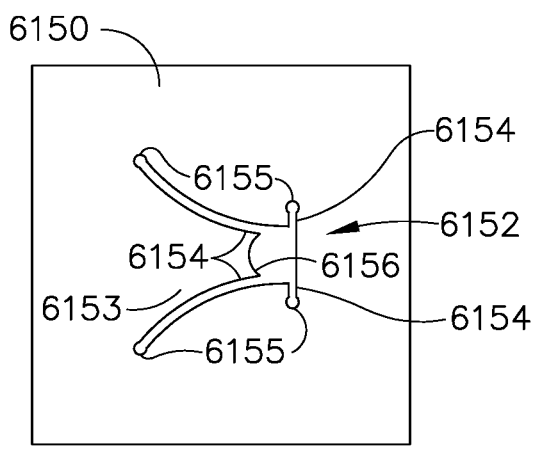

In various embodiments, referring again to FIG. 110, the retention matrix body 6058 can comprise a plurality of slots 6054 and apertures 6055 which can be configured to define the tab 6053 and various portions of the retention aperture 6052. In at least one embodiment, the tab 6053 can comprise a rectangular configuration comprising parallel, or at least substantially parallel, sides. In certain embodiments, referring now to FIG. 111, a retention matrix, such as retention matrix 6150, for example, can comprise a plurality of retention apertures 6152. Each retention aperture 6152 can comprise a tab 6153 which can be configured to engage a fastener leg and to deflect when the fastener leg is inserted into the retention aperture 6152. In at least one such embodiment, the tab 6153 can comprise a base fixed to the retention matrix body 6158 and a free end comprising an arcuate or curved profile 6156 which can be configured to contact the fastener leg. In various embodiments, the retention matrix body 6158 can comprise a plurality of slots 6154 and apertures 6155 which can be configured to define the tab 6153 and various portions of the retention aperture 6152. In at least one embodiment, the tab 6153 can comprise a tapered configuration comprising arcuate sides. In at least one such embodiment, the tab 6153 can taper geometrically with the base being wider than the free end, for example.

Figure 119:
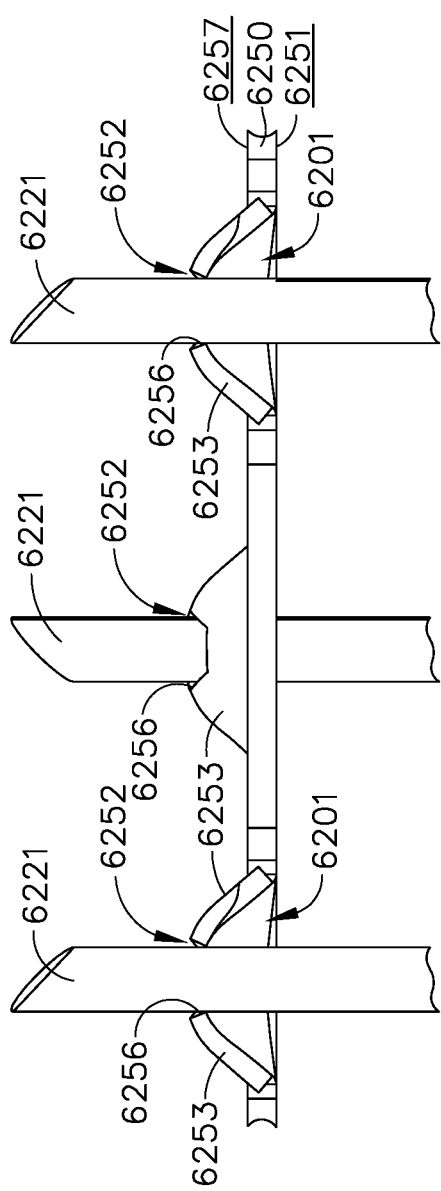
Figure 120:
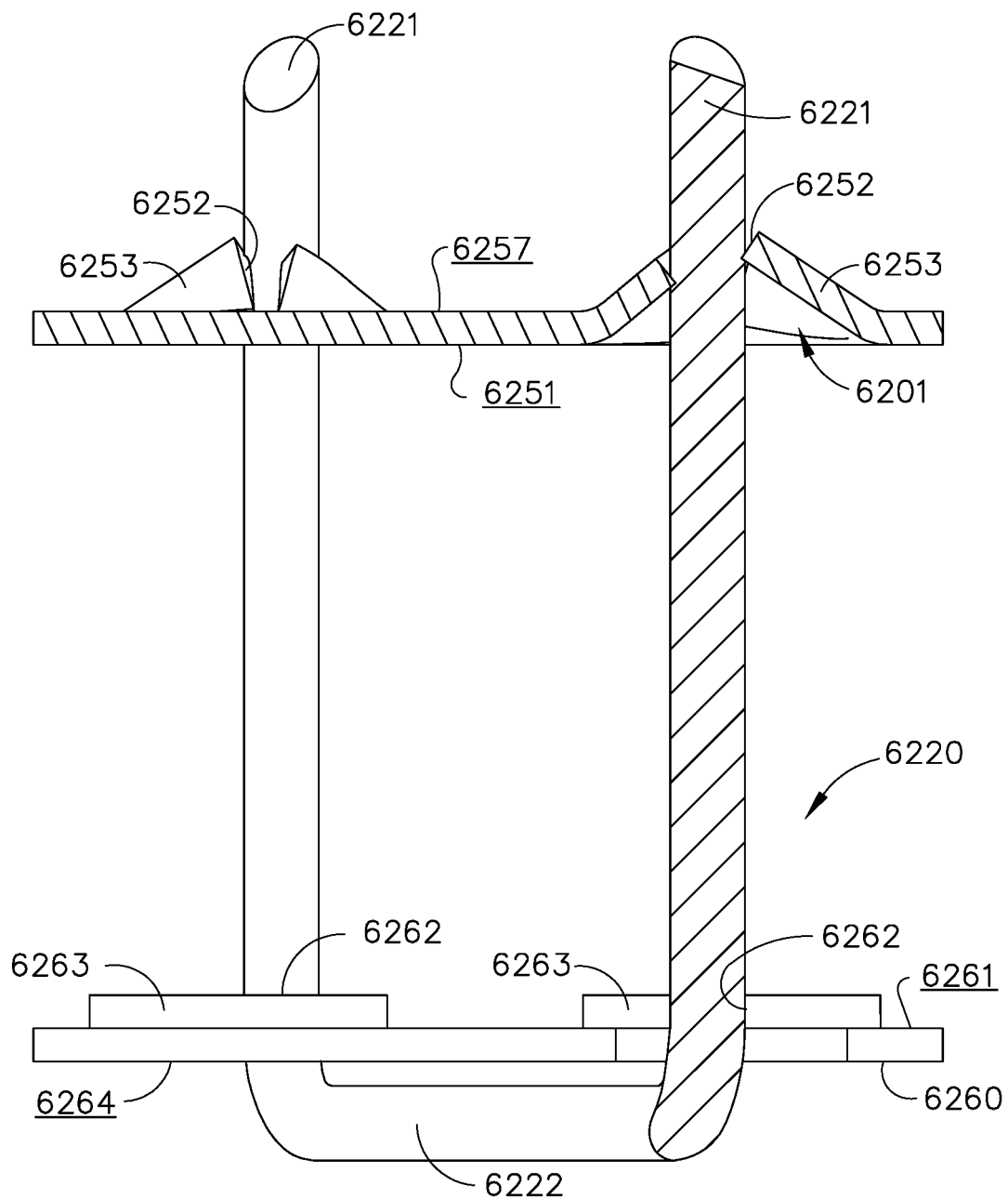

In various embodiments, as described above, a fastening system can comprise a plurality of staples comprising staple legs which are inserted through a plurality of retention apertures in a retention matrix. In certain embodiments, as described in greater detail below, the staples can be held in a first jaw and the retention matrix can be held in a second jaw, wherein at least one of the first jaw and the second jaw can be moved toward the other. In various circumstances, the staples positioned within the first jaw can be secured therein such that the staple legs are aligned with the retention apertures when the retention matrix is engaged with the staple legs. In certain embodiments, referring to FIGS. 112 and 113, a fastener system can comprise a staple cartridge 6200, for example, positioned in a first jaw of a surgical stapler and a retention matrix 6250, for example, positioned in a second jaw of the surgical stapler. Referring now to FIGS. 119 and 120, further to the above, the retention matrix 6250 can comprise a plurality of retention apertures 6252, wherein each retention aperture 6252 can comprise a perimeter 6256 defined by one or more deflectable members 6253. In at least one such embodiment, further to the above, the deflectable members 6253 defining each aperture 6252 can define a pocket 6201. In various embodiments, each pocket 6201 can comprise a curved and/or concave surface, for example, which can be configured to guide a tip of a staple leg into the aperture 6252 in the event that the staple leg is misaligned with the retention aperture 6252 and initially contacts the deflectable members 6253 and/or the tissue-contacting surface 6251, for example.

Figure 115:
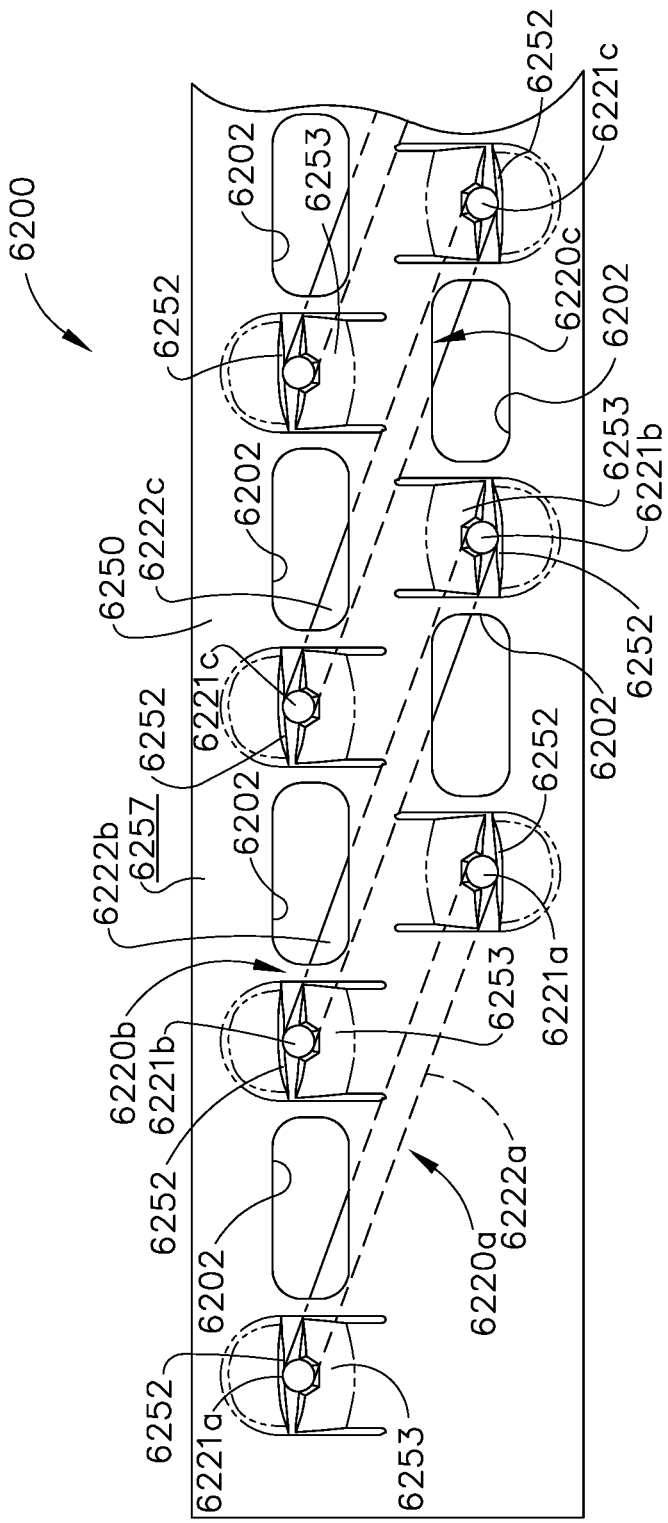
Figure 116:
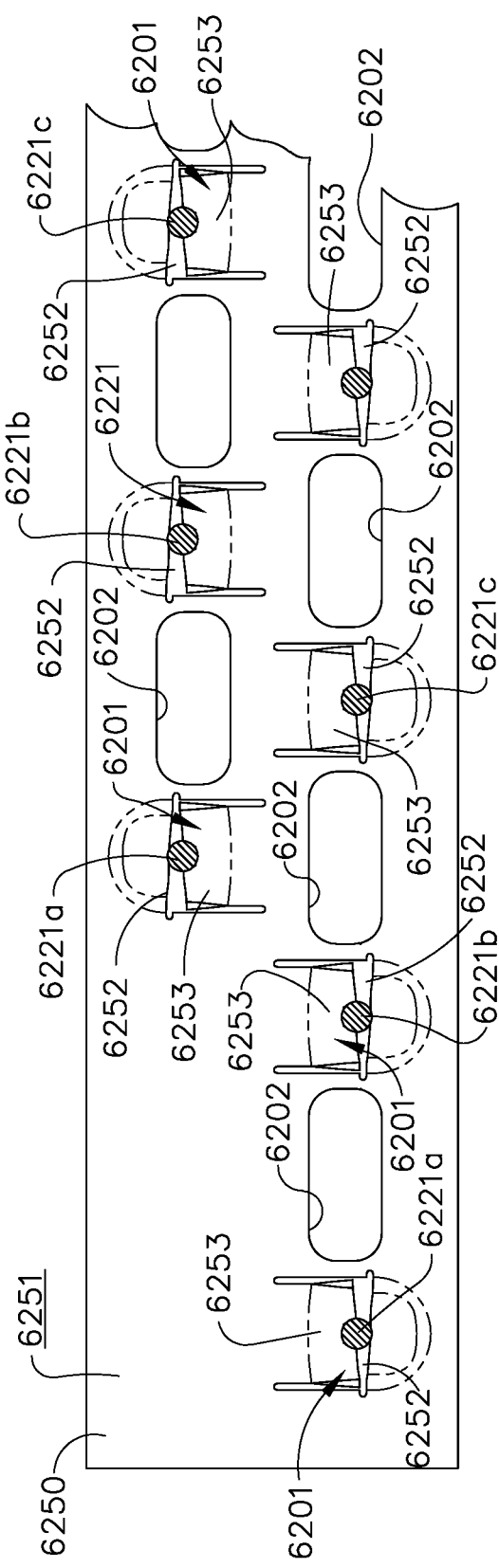

In various embodiments, further to the above, the fastening system can further comprise a plurality of staples 6220 comprising staple legs 6221 which can be inserted through the retention apertures 6252 in the retention matrix 6250. In at least one such embodiment, each staple 6220 can comprise a substantially U-shaped configuration, for example, comprising a base 6222 from which the staple legs 6221 can extend upwardly. In various embodiments, referring now to FIGS. 115 and 116, the retention apertures 6252 in the retention matrix 6250 can be arranged in two parallel, or at least substantially parallel, longitudinal rows, for example, which can extend along, or parallel to, a longitudinal axis of the retention matrix. In certain embodiments, the retention apertures 6252 in a first row can be offset, or staggered, with respect to the retention apertures 6252 in a second row. In at least one such embodiment, each staple 6220 can comprise a first staple leg 6221 positioned in a retention aperture 6252 in the first row of and a second staple leg 6221 positioned in a retention aperture 6252 in the second row wherein, as a result, the bases 6222 can extend in a direction which is transverse to the longitudinal axis of the retention matrix 6250. In at least one such embodiment, the staples 6220 can be parallel, or at least substantially parallel, to one another. More particularly, a base 6222*a* of a staple 6220*a* be parallel to, or at least substantially parallel to, a base 6222*b* of a staple 6220*b* which can be parallel to, or at least substantially parallel to, a base 6222*c* of a staple 6220*c*, for example. In at least one embodiment, the staple legs 6221*a* of staple 6220*a* can define a plane which is parallel to, or at least substantially parallel to, a plane defined by the staple legs 6221*b* of staple 6220*b* which can be parallel to, or at least substantially parallel to, a plane defined by the staple legs 6221 of staple 6220*c*, for example.

Figure 112:
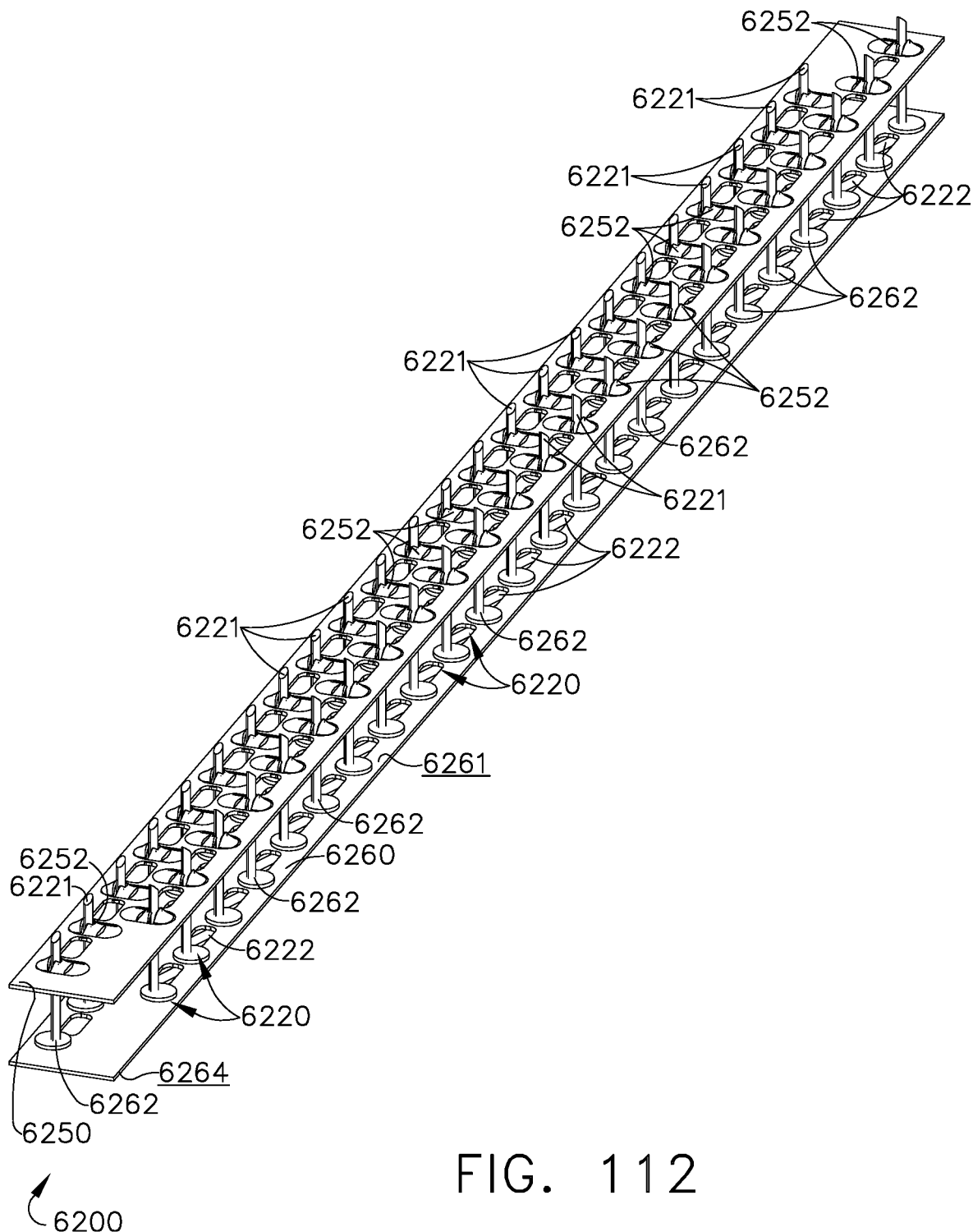
Figure 113:
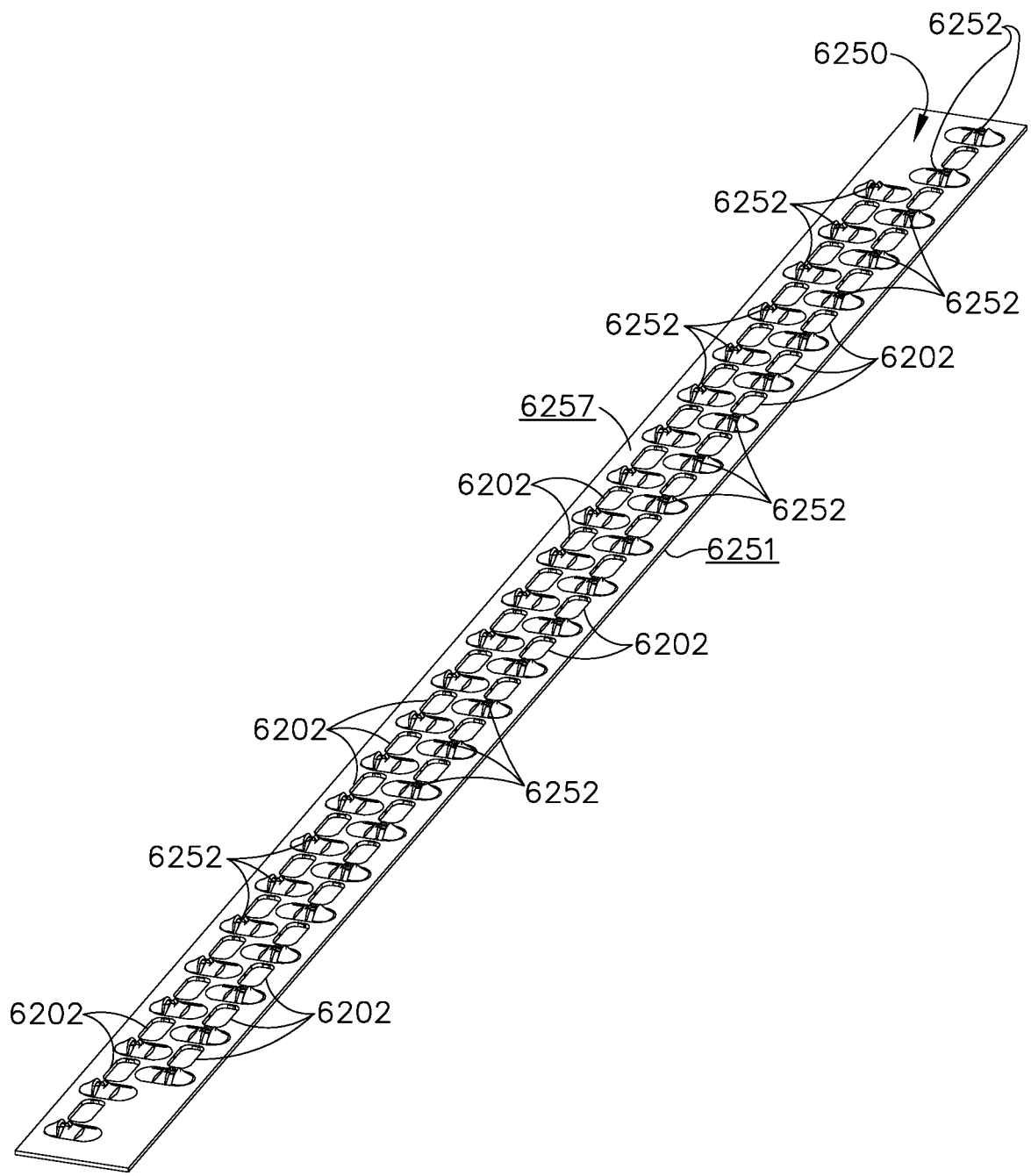
Figure 114:
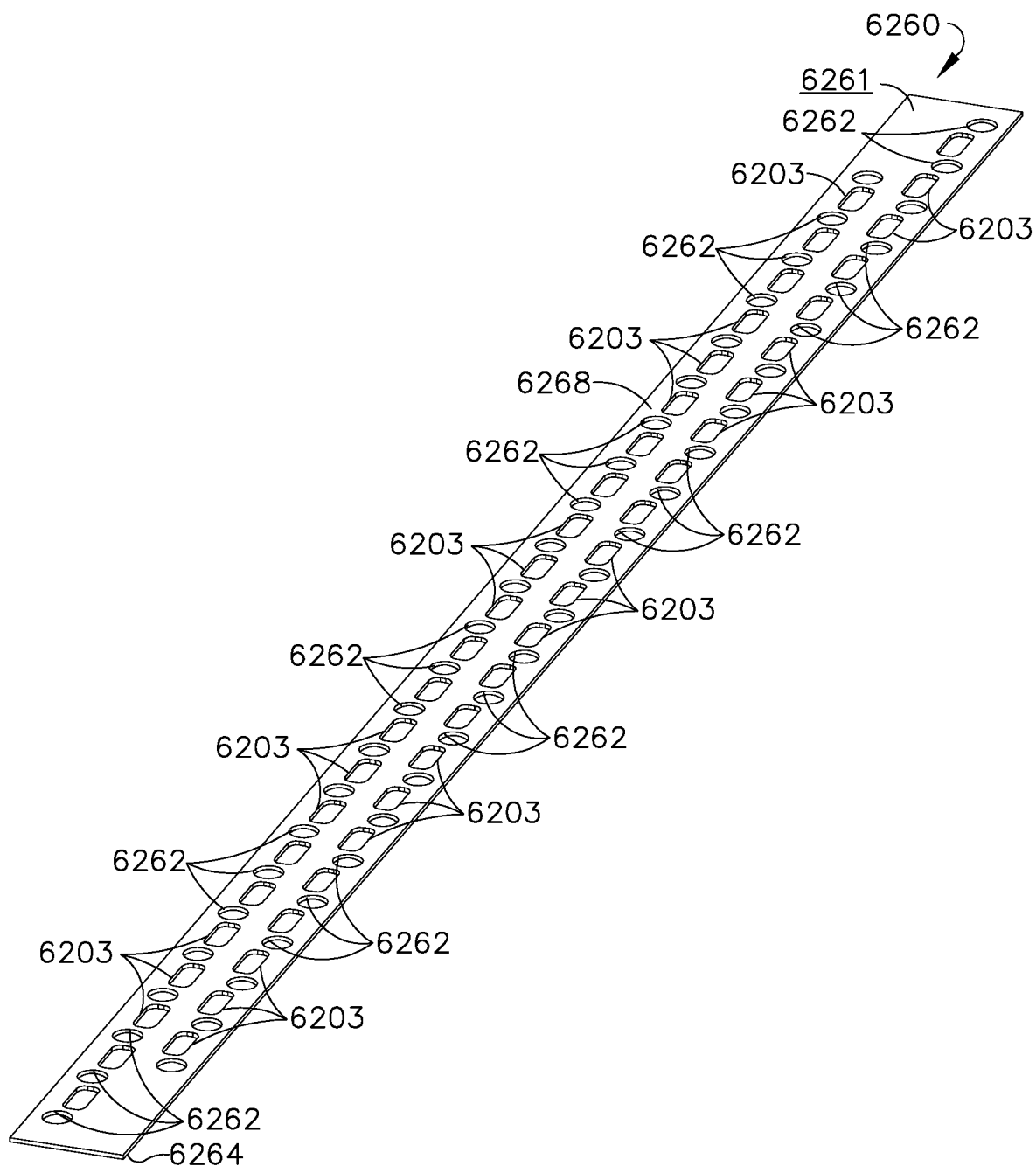
Figure 117:
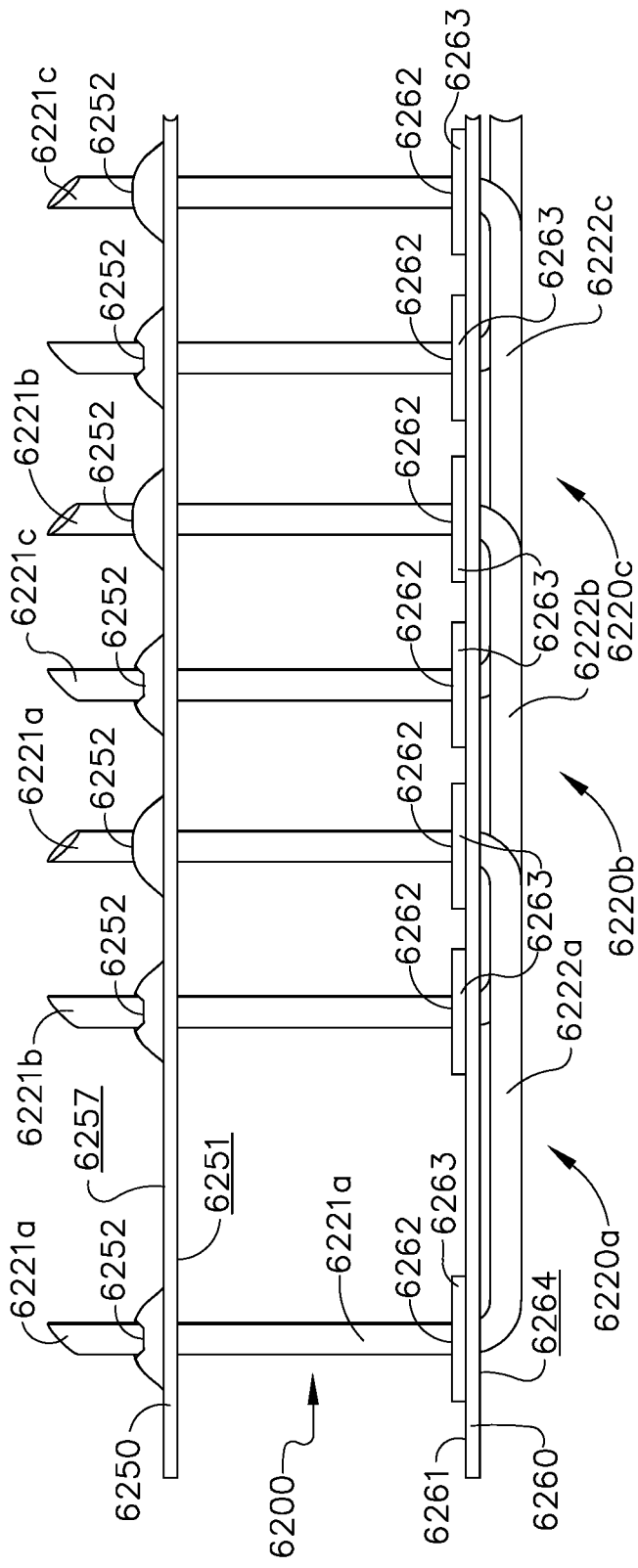
Figure 118:
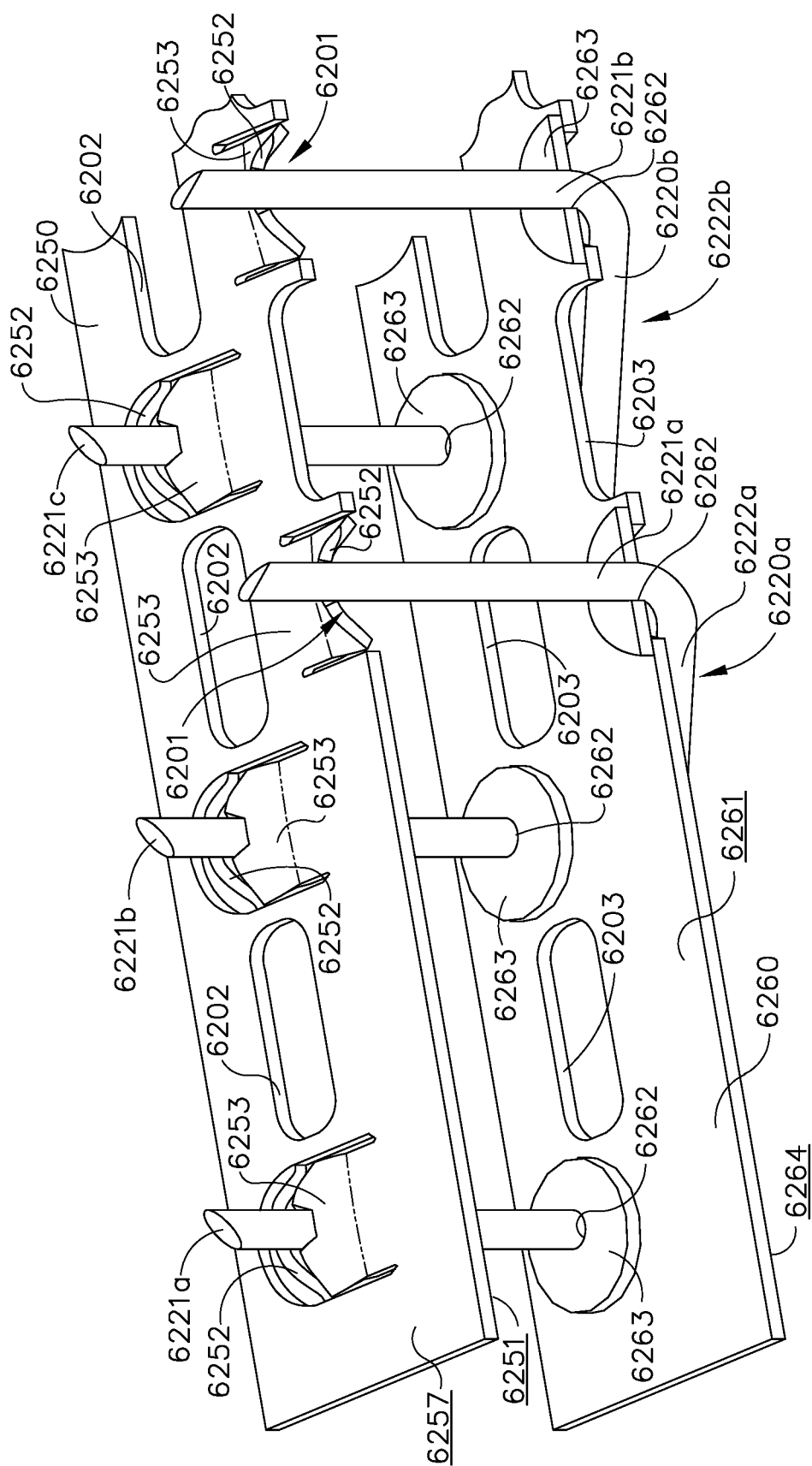

In various embodiments, referring now to FIGS. 112 and 114, the staple cartridge 6200 can comprise a plurality of staples 6220 and, in addition, an alignment matrix 6260 comprising a plurality of alignment guides, such as slots, grooves, and/or apertures, for example, which can be configured to align the staples 6220. In various circumstances, the alignment matrix 6260 can be configured such that the staple legs 6221 of the staples 6220 are aligned with the retention apertures 6252 in the retention matrix 6250 before the retention matrix 6250 is engaged with the staple legs 6221. In various embodiments, referring now to FIGS. 117 and 118, the alignment matrix 6260 can comprise a plurality of alignment apertures 6262 which can be configured to closely receive the staple legs 6221 of the staples 6220. In at least one such embodiment, each staple 6220 can comprise a base 6222 and two staple legs 6221 extending from the base 6222 wherein the bases 6222 of the staples 6220 can extend around a bottom surface 6264 of the retention matrix 6260 and the staple legs 6221 can extend upwardly through the alignment apertures 6262. In certain embodiments, each alignment aperture 6262 can be circular, or at least substantially circular, and can be defined by a diameter which is equal to or slightly larger than the diameter of the staple leg 6221 extending therethrough. In various embodiments, the alignment matrix 6260 can further comprise a plurality of raised members 6263 which can extend upwardly from the top surface 6261 of the alignment matrix 6260 and surround, or at least partially surround, the alignment apertures 6262. In certain embodiments, the raised members 6263 can provide for longer alignment apertures 6262 wherein, in various circumstances, longer apertures 6262 can provide more control over the alignment of the staple legs 6221 than shorter apertures 6262.

In use, in various embodiments, a first jaw supporting the staple cartridge 6200 can be positioned on one side of the tissue that is to be stapled and a second jaw supporting the retention matrix 6250 can be positioned on the other side of the tissue. Once the jaws have been suitably positioned relative to the tissue, in certain embodiments, the second jaw and the retention matrix 6250 can be moved toward the staple cartridge 6200. As the staple legs 6221 are being inserted through the retention apertures 6252 of the retention matrix 6250, in various embodiments, a tissue-contacting, or bottom, surface 6251 of the retention matrix 6250 can contact the tissue and press the tissue against the tissue-contacting, or top, surface 6261 of the alignment matrix 6260. In various other embodiments, as described in greater detail further below, the staple cartridge 6200 can further comprise a compressible cartridge body positioned above the top surface 6261 of the alignment matrix 6260, for example, which can contact the tissue. In certain embodiments, referring again to FIGS. 114 and 118, the alignment matrix 6260 can further comprise one or more apertures 6203 defined therein which, when the alignment matrix 6260 is positioned against tissue, can be configured to receive a portion of the tissue therein. In embodiments where a compressible cartridge body is positioned above and/or against the alignment matrix 6260, a portion of the compressible cartridge body can enter into the apertures 6203 when the cartridge body is compressed. Similarly, the retention matrix 6250 can comprise a plurality of apertures 6202 which can be configured to receive at least a portion of the tissue therein when the retention matrix 6250 is positioned against the tissue.

As the staple legs 6221 of the staples 6220 are inserted through the retention apertures 6252 of the retention matrix 6250, further to the above, the tips of the staple legs 6221 may protrude upwardly from the top surface 6257 of the retention matrix 6250. In various circumstances, as described above, the tips of the staple legs 6221 may remain unbent after they have been inserted through the retention apertures 6252. In certain embodiments, referring now to FIGS. 121-124, a fastening system comprising the staple cartridge 6200 and the retention matrix 6250 may further comprise a plurality of protective caps or covers, such as caps 6270, for example, which can be assembled to the staple legs 6221 protruding above the retention matrix 6250. In various embodiments, each cap 6270 can entirely, or at least partially, cover the sharp end of a staple leg 6221 such that the sharp end does not contact tissue positioned adjacent thereto. In at least one embodiment, referring now to FIG. 124, each cap 6270 can comprise an aperture 6271 defined therein which can be configured to closely receive a tip of a staple leg 6221 therein. In various embodiments, the caps 6270 can be comprised of an elastomeric material, such as silicone, polyisoprene, sanoprene, and/or natural rubber, for example. In at least one embodiment, the aperture 6271 can comprise a perimeter or diameter which is smaller than the perimeter or diameter of the staple leg 6221 inserted therein. In at least one such embodiment, the aperture 6271 in the protective cap 6270 can expand in order to receive the staple leg 6221 therein. In various alternative embodiments, the caps 6270 may not comprise apertures and the tips of the staple legs 6221 can be configured to incise the caps 6270 as the legs 6221 are inserted therein. In any event, in various embodiments, each cap 6270 can be seated onto a staple leg 6221 until the base 6272 of the cap 6270 abuts, or is positioned adjacent to, the top surface 6257 of the retention matrix 6250. In various circumstances, the caps 6270 can be configured such that they are seated snugly onto the tips of the staple legs 6221 such that they are not easily removed therefrom. In certain embodiments, each cap 6270 can comprise a conical, or at least substantially conical, outer surface, for example. In various embodiments, the caps 6270 can comprise any suitable shape, such as shapes comprising a parabolic, or at least substantially parabolic, outer surface, for example.

In various embodiments, the fastener system described above, for example, could be deployed using the surgical stapler depicted in FIGS. 125-127, for example. In various embodiments, the end effector can comprise a first jaw, or staple cartridge channel, 6230 which can be configured to support the staple cartridge 6200 therein and a second jaw 6240 which can be configured to support the retention matrix 6250 and the plurality of protective caps 6270. Referring primarily to FIG. 125, which illustrates the second jaw 6240 in an open configuration, the jaws 6230 and 6240 can be positioned relative to tissue T such that the tissue T is positioned intermediate the retention matrix 6250 and the staple cartridge 6200. In various embodiments, as discussed above, the staple cartridge 6200 can further comprise a compressible cartridge body, such as cartridge body 6210, for example, in which the staples 6220 and the alignment matrix 6260 can be positioned. In at least one such embodiment, the tissue T can be positioned against a top surface of the cartridge body 6210. In certain embodiments, the second jaw 6240 can comprise a plurality of recesses, or apertures, 6245 configured to receive the plurality of protective caps 6270 and, in addition, one or more retention features, or retainers, which can be configured to hold the retention matrix 6250 in position over the caps 6270. In at least one such embodiment, the retention matrix 6250 can be configured to retain the caps 6270 in the apertures 6245. In various embodiments, referring now to FIG. 137, each aperture 6245 can be configured to receive a portion of, or the entirety of, a cap 6270 therein. In certain embodiments, the apertures 6245 can be sufficiently sized and configured such that the caps 6270 can be secured therein by at least one of a press-fit and/or snap fit arrangement, for example. In some embodiments, at least one adhesive could be utilized to secure the caps 6270 in the apertures 6245. In at least one such embodiment, such an adhesive could be selected such that caps 6270 can detach from the second jaw 6240 after the caps 6270 have been engaged with the staple legs 6221 and the second jaw 6240 is moved away from the implanted fastener assembly. In certain embodiments, referring now to FIG. 138, the second jaw 6240 can further comprise at least one cover sheet 6246 which can be assembled to the second jaw 6240 and can extend over and retain the caps 6270 in the apertures 6245. In at least one such embodiment, at least a portion of the cover sheet 6246 can be secured to the jaw 6240 utilizing at least one adhesive, for example. In use, in at least one embodiment, the cover sheet 6246 can be at least partially detached from the jaw 6240 before the end effector is inserted into a surgical site. In certain embodiments, the cover sheet 6246 can be comprised of an implantable material, such as PDS and/or PGA, for example, which can be incised by the staple legs 6221 as the staple legs 6221 emerge from the retention matrix 6250. In at least one such embodiment, the cover sheet 6246 can be secured in the fastening system intermediate the covers 6270 and the retention matrix 6250.

Further to the above, referring now to FIG. 126, the jaw 6240 can be moved from an open position to a closed position in which the tissue T is positioned against the retention matrix 6250 and the cartridge body 6210. In such a position, the retention matrix 6250 may not yet be engaged with the staples 6220. In various embodiments, the jaw 6240 can be moved between its open position and its closed position by an actuator 6235. In at least one such embodiment, the jaw 6240 can comprise a distal pin 6243 and a proximal pin 6244 extending therefrom, wherein the distal pin 6243 can slide vertically, or at least substantially vertically, within a distal slot 6233 defined in the cartridge channel 6230, and wherein the proximal pin 6244 can slide vertically, or at least substantially vertically, within a proximal slot 6234 which is also defined in the staple cartridge channel 6230. In use, the actuator 6235 can be retracted proximally in order to drive the pins 6243 and 6244 into the upper ends of their respective slots 6233 and 6234 as illustrated in FIG. 126. In at least one such embodiment, the actuator 6235 can comprise a distal drive slot 6236 and a proximal drive slot 6237, wherein the sidewalls of the drive slots 6236 and 6237 can be configured to contact the distal pin 6243 and the proximal pin 6244, respectively, and drive the pins 6243 and 6244 upwardly as the actuator 6235 is moved proximally. More particularly, as the actuator 6235 is moved proximally, the distal pin 6243 can slide up an inclined first portion 6236a of the distal drive slot 6236 into an intermediate, or second, portion 6236b and, similarly, the proximal pin 6244 can slide up an inclined first portion 6237a of the distal drive slot 6237 into an intermediate, or second, portion 6237b. As the pins 6243 and 6244 are both moved upwardly, the jaw 6240 can be rotated downwardly toward the tissue T into a closed position.

Further to the above, referring now to FIG. 127, the actuator 6235 can be pulled further proximally in order to push the second jaw 6240 downwardly toward the first jaw 6230, compress the cartridge body 6210, and engage the retention matrix 6250 and the plurality of protective caps 6270 with the staple legs of the staples 6220. In at least one such embodiment, the additional proximal movement of the actuator 6235 can cause the sidewalls of the drive slots 6236 and 6237 to contact the pins 6243 and 6244, respectively, and drive the pins 6243 and 6244 downwardly toward the bottom ends of the slots 6233 and 6234, respectively. In such circumstances, the actuator 6235 can be pulled proximally such that, one, the distal pin 6243 exits the second portion 6236b of the drive slot 6236 and enters into an inclined third portion 6236c and, similarly, the proximal pin 6244 exits the second portion 6237b of the drive slot 6237 and enters into an inclined third portion 6237c. As the pins 6243 and 6244 are both moved downwardly, the second jaw 6240 can move downwardly toward the first jaw 6230 into a fired position. In at least one such embodiment, the second jaw 6240 can be moved downwardly such that the retention matrix 6250 remains parallel, or at least substantially parallel, to the top surface of the cartridge body 6210 and/or parallel, or at least substantially parallel, to the alignment matrix 6260. In any event, once the retention matrix 6250 and the protective caps 6270 have been engaged with the staple legs 6221 of the staples 6220, as illustrated in FIG. 129, the second jaw 6240 can be returned to an open, or an at least substantially open, position. In at least one such embodiment, the actuator 6235 can be pushed distally in order to drive the pins 6243 and 6244 to the top ends of the slots 6233 and 6234, respectively, and then driven downwardly toward the bottom ends of the slots 6233 and 6234 once the pins have passed through the intermediate portions 6236b and 6237b of the respective drive slots 6236 and 6237. Once the second jaw 6240 has been opened, the first jaw 6230 can be detached from the implanted staple cartridge 6200 and the first and second jaws 6230, 6240 can be removed away from the implanted fastener assembly, as illustrated in FIG. 128.

Referring to FIG. 127 once again, the reader will note that the pins 6243 and 6244 are not illustrated as being seated in the very bottoms of their respective slots 6233 and 6234 even though the retention matrix 6250 and the caps 6270 have been engaged with the staple legs 6221. Such circumstances can arise when thick tissue T is positioned between the retention matrix 6250 and the cartridge body 6210. In circumstances where thinner tissue T is positioned between the retention matrix 6250 and the cartridge body 6210, referring now to FIG. 130, the pins 6243 and 6244 can be drive further downwardly into their respective slots 6233 and 6234 as illustrated in FIG. 132. In general, in at least one such embodiment, the actuator 6235 can be pulled proximally in order to drive the pins 6243 and 6244 upwardly and downwardly through the progressions described above and illustrated in FIGS. 130-132 and, owing to the thinner tissue T, the retention matrix 6250 and the protective caps 6270 can be driven further onto the staple legs 6221 of the staples 6220, as illustrated in FIGS. 133 and 134. In various embodiments, as a result of the adjustability afforded by the retention matrix 6250, the same, or at least substantially the same, compressive pressure can be obtained in the fastened tissue regardless of whether the tissue captured within the end effector is thick or thin. In certain embodiments, the adjustability afforded by the retention matrix 6250 can allow a surgeon can select whether to apply a larger compressive pressure or a smaller compressive pressure to the tissue by selecting the depth to which the retention matrix 6250 is seated. In at least one such embodiment, the range in which the retention matrix 6250 can be seated onto the staple legs 6221 can be determined by the lengths, or ranges, of the slots 6233 and 6234, for example.

In various embodiments, as described above, the protective caps 6270 can be comprised of a soft or flexible material, for example, which can be configured to grip the ends of the staple legs 6221. In certain embodiments, the protective caps 6270 can be comprised of a bioabsorbable plastic, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example, and/or a biocompatible metal, such as titanium and/or stainless steel, for example. As illustrated in FIG. 124, in at least one embodiment, each cap 6270 can be unconnected to the other caps 6270. In certain other embodiments, one or more caps 6270 can be mounted to the retention matrix 6250. In at least one such embodiment, the caps 6270 can be connected to the retention matrix 6250 by at least one adhesive, for example, wherein the apertures 6271 in the caps 6270 can be aligned, or at least substantially aligned, with the retention apertures 6252 in the retention matrix 6270. In various embodiments, referring now to FIG. 135, a protective cap, such as a cap 6370, for example, can define an inner cavity, or dome, 6374 which can be configured to receive a tip of a staple leg 6221, for example, therein. In at least one such embodiment, the cap 6370 can comprise a bottom 6372 and an aperture 6371 extending through the bottom 6372. In various embodiments, the aperture 6371 can be defined by one or more deflectable members 6373 which can be configured to deflect when the staple leg 6221 is inserted therethrough. In certain embodiments, two or more caps 6370, for example, can be connected together to form an array of caps 6370. In at least one such embodiment, referring now to FIG. 136, a plurality of caps 6370 can be connected together by a sheet of material 6375. In certain embodiments, the sheet 6375 can be sufficiently rigid in order to maintain a desired arrangement and/or alignment of the caps 6370. In at least one embodiment, the caps 6370 can be comprised of a biocompatible metal, such as titanium and/or stainless steel, for example, and the sheet 6375 can be comprised of a bioabsorbable plastic, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, a sheet 6375 can be comprised of a bioabsorbable material including an antimicrobial agent, such as colloidal silver and/or triclosan, for example, stored and/or dispersed therein which can be released as the sheet 6375 is bioabsorbed, for example.

In various embodiments, further to the above, the sheet 6375 can be injection molded around the caps 6370 utilizing an injection molding process, for example, such that the caps 6370 are embedded in the sheet 6375. In certain other embodiments, the sheet 6375 can be molded utilizing an injection molding process, for example, wherein apertures 6376 can be formed in the sheet 6375 during the injection molding process and/or after the injection molding process utilizing a stamping process, for example. In either event, the caps 6370 can be inserted into and secured in the apertures 6376 utilizing a press-fit and/or snap-fit interconnection and/or at least one adhesive. In certain embodiments, each cap 6370 can comprise an annular groove surrounding, or at least partially surrounding, the perimeter of the cap 6370 which can be configured to receive the perimeter of an aperture 6376 therein. In certain embodiments, the sheet 6375 can be comprised of a flexible and/or pliable material which can permit relative movement between the caps 6370. In at least one such embodiment, the flexible sheet 6375 can be comprised of a rubber, plastic, and/or silicone material, for example, and the caps 6370 can be comprised of a rigid material, such as metal, for example. In at least one such embodiment, similar to the above, the flexible material can be molded around the caps 6370. In certain embodiments, the caps 6370 can be pressed into a pre-molded sheet 6375, for example. In various embodiments, the durometer of the flexible material can be selected to provide a desired stiffness of the sheet 6375. In certain embodiments, the sheet 6375 can be configured such that it comprises a flexible band. In any event, the sheet 6375 can facilitate the assembly of the caps 6370 into an end effector as a plurality of the caps 6370 can be positioned and/or aligned simultaneously within the end effector. Furthermore, the sheet 6375 connecting the caps 6370, once implanted, can strengthen or bolster the tissue along the staple line, for example. In addition to or in lieu of a sheet connecting the caps 6370, the caps 6370 can be connected together by a plurality of links. In at least one such embodiment, such links can be flexible and can permit relative movement between the caps 6370.

In various embodiments, referring now to FIGS. 139 and 140, a protective cap, such as cap 6470, for example, can comprise a forming surface which can be configured to deform a tip of a staple leg. In at least one such embodiment, the cap 6470 can comprise a base 6472 which can include an aperture 6471 extending therethrough. In various embodiments, the aperture 6471 can be configured to closely receive a staple leg, such as a staple leg 6221, for example, therein. In at least one embodiment, the aperture 6471 can be defined by a diameter or perimeter which can be equal to or larger than the diameter or perimeter of the staple leg 6221. In various embodiments, the cap 6470 can further comprise a cavity, or dome, 6474 which can be configured to receive the tip of the staple leg 6221 as it is inserted into the cap 6470. Referring primarily to FIG. 140, the cap 6470 can further comprise an anvil, or forming surface, 6473 which can be configured to deflect and deform the staple leg 6221. In various circumstances, the forming surface 6473 can be curved and/or concave, for example, and can be configured to curl the staple leg 6221 as it is inserted into the cap 6470. In certain embodiments, the staple leg 6221 can be sufficiently deformed such that it cannot be withdrawn through the aperture 6471 and, as a result, the cap 6470 can become locked to the staple leg 6221. In at least one such embodiment, the base 6472 of the cap 6470 can define a lip extending around the aperture 6471 which can prevent the deformed staple leg 6221 from being removed from the cavity 6474. In various circumstances, as a result of the above, one or more caps 6470 can prevent, or inhibit, a retention matrix, such as retention matrix 6250, for example, from backing up or being disengaged from the staples 6220. In various embodiments, although not illustrated, the cap 6470 can be symmetrically, or at least substantially symmetrically, formed, and the aperture 6471 can be located along a central axis 6479 extending through the cap 6470. In various alternative embodiments, referring again to FIG. 139, the aperture 6471 can be offset with respect to the central axis 6479. In at least one such embodiment, the offset aperture 6471 can allow the staple leg 6221 to contact a side of the forming surface 6473 and curl over to the other side of the forming surface 6473 instead of contacting the center of the forming surface 6473, as may occur in embodiments comprising a centered aperture 6471 mentioned above.

In various embodiments, as discussed above, a retention matrix, such as retention matrix 6250, for example, can be comprised of a sheet of material and a plurality of retention apertures 6252 extending therethrough. In at least some embodiments, the sheet of material comprising the retention matrix 6250 can be rigid or substantially inflexible. In certain other embodiments, a retention matrix can be comprised of an array of retention matrix elements and a plurality of flexible connectors, or links, connecting the retention matrix elements. In various embodiments, referring now to FIG. 141, a retention matrix, or a portion of retention matrix, 6550 can comprise a plurality of element bodies 6505 which can be connected together by one or more connecting links 6507. In at least one embodiment, each element body 6505 can comprise a plurality of deformable members 6553 which define a retention aperture 6552 therein. In certain embodiments, the element bodies 6505 and the connecting links 6507 of a retention matrix 6550 can be integrally formed and can comprise a unitary piece of material. In various embodiments, the retention matrix 6550 can be stamped or cast, for example, from a metal material, such as titanium and/or stainless steel, for example. In at least one embodiment, the retention matrix 6550 can be comprised of plastic, such as polyetheretherketone (PEEK), polypropylene which is marketed under the trade name Prolene, polyester, polyethylene terephthalate which is marketed under the trade names Ethibond and Mersilene, polyvinylidene fluoride, polyvinylidene fluoride-co-hexafluoropropylene, poly hexafluoropropylene-VDF which is marketed under the trade name Pronova, and/or long-chain aliphatic polymers Nylon 6 and Nylon 6,6 which are marketed under the trade names Ethilon & Nurolon, for example, and can be formed by an injection molding process, for example. In certain embodiments, the element bodies 6505 may not be integrally formed with the connecting links 6507. In various embodiments, a plurality of singular element bodies 6505 can be produced which are subsequently connected together and embedded in a retention matrix. In at least one such embodiment, the element bodies 6505 can be stamped from a metal material, such as titanium and/or stainless steel, for example, and placed in a plastic injection mold wherein a plastic material can be injected into the mold to form, one, a rim 6506 of material surrounding, or at least partially surrounding, the element bodies 6505 and, two, connecting links 6507 extending from the rims 6506. In certain other embodiments, one or more connector lattices can be formed comprising apertures defined within a plurality of rims 6506 wherein each such aperture can be configured to receive an element body 6505 therein. In at least one embodiment, each element body 6505 can comprise a circular, or at least substantially circular, outer perimeter and, similarly, each rim 6506 can define a circular, or at least substantially circular, aperture therein, wherein the diameter of the aperture can be equal to or smaller than the diameter of the element body 6505. In at least one such embodiment, the element bodies 6505 can be press-fit or embedded into the apertures in the rims 6505. In certain embodiments, the element bodies 6505 can be secured in the apertures utilizing at least one adhesive.

In various embodiments, further to the above, a retention matrix can comprise a plurality of element bodies 6505 and a plurality of connecting links 6507 which can connect the element bodies 6505 in any suitable array, such as those illustrated in FIGS. 142-145, for example. Regardless of the pattern of the array, in various embodiments, the connecting links 6507 can be configured to allow the element bodies 6505 and the retention apertures 6552 to move relative to one another. In at least one such embodiment, the lattice of element bodies 6505 and connecting links 6507 comprising the retention matrix 6550, once engaged with tissue, can be configured to stretch, twist, contract, and/or otherwise flex in order to permit at least some movement within the tissue yet, at the same time, resist larger movements thereof. In various embodiments, each connecting link 6507 can comprise a flexible member configured to stretch, twist, and/or contract in order to permit the retention matrix 6550 to flex intermediate the matrix retention elements 6505, for example. Referring again to FIG. 141, each link 6507 extending from a rim 6506 can be defined by a width which is narrower than the width of the element body 6505 and/or the rim 6506. In certain embodiments, referring to FIGS. 142-145, one or more links 6507 can comprise straight portions which extend along a line between adjacent element bodies 6506, for example. In at least one such embodiment, each link 6507 can comprise a first end attached to a first rim 6506 and a second end attached to a second rim 6506. In certain embodiments, referring once again to FIG. 141, two or more links 6507 can be connected to one another. In at least one such embodiment, two or more links 6507 can be connected at an intermediate hinge 6509, for example. In various embodiments, the hinge 6509 can comprise a reduction in cross-sectional thickness in one or more directions as compared to the cross-sectional thickness of the links 6507 which can permit the connected links 6507 to move relative to each other, for example. In certain embodiments, the retention matrix 6550 can further comprise hinges 6508 which can connect the links 6507 to the rims 6506 and permit relative movement between the links 6507 and the rims 6506. Similar to hinges 6509, hinges 6508 can comprise a reduction in cross-sectional thickness in one or more directions as compared to the cross-sectional thickness of the links 6507, for example.

In various embodiments, further to the above, the connected links 6507 can extend in different directions. In at least one such embodiment, a first link 6507 can extend in a first direction and a second link 6507 can extend in a second direction, wherein the first direction can be different than the second direction. In certain embodiments, the first link 6507 can extend along a first line and the second link 6507 can extend along a second line, wherein the first line and the second line can intersect each other at an angle, such as approximately 30 degrees, approximately 45 degrees, approximately 60 degrees, and/or approximately 90 degrees, for example. In various embodiments, the hinges 6508 and/or hinges 6509 can comprise living hinges which can permit the links 6507 to move relative to each other a number of times without breaking. In certain embodiments, the hinges 6508 and/or hinges 6509 can comprise frangible, or easily-breakable, portions which can break when flexed too far and/or flexed too many times. In at least one such embodiment, such frangible portions can permit one or more portions of the retention matrix 6550 to break away from another portion of the retention matrix 6550. In various embodiments, the hinges 6508 and/or hinges 6509, for example, can comprise sections of the retention matrix 6550 which are easier to incise than the other portions of the retention matrix 6550. More particularly, an implanted retention matrix, and the tissue fastened by the implanted retention matrix, may oftentimes by incised by a cutting member for various reasons and, in order to facilitate such cross-cutting, the hinges 6508 and/or hinges 6509 can provide avenues, or thin sections, through which a cutting member can more easily pass through the retention matrix 6550, for example. In various embodiments, further to the above, the connecting links 6507 can comprise one or more coined features or material upsets, for example, defined therein which can facilitate the bending, breakage, and/or incision of the connecting links 6507.

In various embodiments, a retention matrix can comprise a plurality of retention matrix elements, such as matrix element bodies 6505, for example, which can be embedded in a flexible sheet, or band, of material. In at least one embodiment, a flexible sheet of material can be formed from a bioabsorbable, elastomeric material, such as silicone, for example, wherein the flexible sheet can be produced with a plurality of apertures defined therein. In at least one such embodiment, a solid flexible sheet can be molded and a plurality of apertures can be punched out of the flexible sheet. In various alternative embodiments, the flexible sheet can be molded and the apertures defined therein can be formed during the molding process. In either event, the retention matrix elements 6505, for example, can be inserted into and retained within the flexible sheet. In certain other embodiments, similar to the above, the flexible sheet can be formed around the matrix elements 6505. In at least one embodiment, the flexible sheet can be comprised of a woven mesh, for example, and/or any other suitable material. Such a woven mesh, further to the above, may be easy to cross-cut.

In various embodiments, referring now to FIGS. 146 and 147, a fastener system comprising a retention matrix, such as retention matrix 6250, for example, can further comprise a cover, such as cover 6670, for example, which can cover the tips of the staple legs 6221 when they extend above the top surface 6257 of the retention matrix 6250. In various embodiments, the cover 6670 can be attached to the retention matrix 6250. In certain embodiments, the cover 6670 and/or the retention matrix 6250 can comprise retention features which can be configured to retain the cover 6670 to the retention matrix 6250. In at least one embodiment, at least one adhesive can be utilized to adhere the cover 6670 to the retention matrix 6250. In at least one embodiment, the cover 6670 can be comprised of a single layer, although the cover 6670 is illustrated as comprising two layers as described in greater detail further below. In various embodiments, referring primarily to FIG. 147, the tips of the staple legs 6221 can extend through a bottom surface 6673 of the cover 6670; however, the cover 6670 can comprise a sufficient thickness such that the staple tips do not extend through the top surface 6675 of the cover 6670. In at least one such embodiment, as a result, the tips of the staple legs 6221 may not protrude from the cover 6670. In various embodiments, the cover 6670 can comprise a plurality of layers. In at least one such embodiment, the cover 6670 can comprise a first layer 6671 and a second layer 6672. In at least one embodiment, the first layer 6671 and the second layer 6672 can be attached to one another wherein, in at least one embodiment, the second layer 6672 can comprise a bottom surface 6676 which is adhered to the first layer 6671. In various embodiments, the first layer 6671 and the second layer 6672 can comprise different thicknesses while, in certain embodiments, they can comprise the same thickness. In at least one embodiment, the first layer 6671 and the second layer 6672 can comprise substantially the same width and/or length. In alternative embodiments, the layers 6671 and 6672 can comprise different widths and/or lengths.

In various embodiments, further to the above, the first layer 6671 can be comprised of a compressible foam, mesh material, and/or hydrogel, for example, which can be incised by the staple legs 6211. In at least one embodiment, the second layer 6672 can be comprise of a tougher material, or skin, such as PGA and/or PDS, for example, and/or any suitable buttress material. In at least one such embodiment, the staple legs 6221 can be configured to penetrate the first layer 6671; however, in various embodiments, the staple legs 6221 may be unable to penetrate the second layer 6672. In certain embodiments, the second layer 6672 can be comprised of a material having a sufficient resiliency and/or toughness which can permit the second layer 6672 to be contacted and displaced by the staple leg 6221 but not be incised, or only marginally incised, by the staple tip of the staple leg 6221. Although not illustrated, a cover can comprise more than two layers wherein one or more of such layers may be penetration-resistant. In use, in at least one such embodiment, the retention matrix 6250 can be positioned against the tissue to be fastened and pushed downwardly such that the staple legs 6221 of the staples 6220 are pushed through the tissue T and the retention apertures 6252 in the retention matrix 6250 and enter into the first layer 6271 of the cover 6270. In various embodiments, the tips of the staple legs 6221 may not enter, or at least substantially enter, into the second layer 6272 of the cover 6270. After the retention matrix 6250 has been suitably positioned, the jaw 6240 can be opened and the cover 6670 and the retention matrix 6250 can detach from the jaw 6240 as illustrated in FIG. 146. As illustrated in FIG. 146, a jaw 6640 can be configured to hold more than one retention matrix 6250 and cover 6670. In at least one such embodiment, the jaw 6640 can comprise two channels 6679 which each can be configured to receive a cover 6670 therein and a retention matrix 6250 positioned thereover such that the tissue-contacting surface 6251 of each retention matrix 6250 depends downwardly from the bottom of the jaw 6240. In at least one such embodiment, a retention matrix 6250 and a cover 6270 can be housed in the jaw 6640 on each side of a knife slot 6678. In use, both retention matrices 6250 and covers 6670 can be deployed simultaneously and/or to the same depth with respect to opposing staple cartridges, such as cartridges 6200, for example, positioned thereacross. Thereafter, in various embodiments, the fastened tissue can be incised along a cutting line by a cutting member that traverses the knife slot 6678 wherein the jaw 6640 can then be re-opened. In certain embodiments, the covers 6670 may not be attached to the retention matrix 6250. In at least one such embodiment, the covers 6670 can be positioned in the channels 6679 and can be retained in the channels 6679 by the retention matrices 6250 which can be secured to the jaw 6640. In various embodiments, the each retention matrix 6250 can be wider and/or longer than their respective covers 6670 such that the retention matrices 6250 can retain the entirety of their covers 6670 in position. In certain embodiments, each retention matrix 6250 can comprise the same width and/or length as their respective cover 6670, for example.

In various embodiments, as described above, a fastener system can comprise a layer of material which can be attached to a retention matrix, such as retention matrix 6250, for example. In at least one embodiment, referring now to FIG. 150, a layer of material 6870 can be attached to the bottom surface 6251 of the retention matrix 6250. In certain embodiments, the layer 6870 and/or the retention matrix 6250 can comprise retention features which can be configured to retain the layer 6870 to the retention matrix 6250. In at least one embodiment, at least one adhesive can be utilized to adhere the layer 6870 to the retention matrix 6250. In any event, the layer 6870 can comprise a bottom, or tissue-contacting, surface 6873 which can be configured to contact the tissue T when the retention matrix 6250 is moved downwardly toward the staples 6220 to engage the retention apertures 6252 with the staple legs 6221. In at least one such embodiment, the layer 6870 can be comprised of a compressible material, such as a bioabsorbable foam, for example, which can be compressed between the bottom surface 6251 of the retention matrix 6250 and the tissue T. In various embodiments, the layer 6870 can further comprise at least one medicament stored and/or absorbed therein which can be expressed from the layer 6870 as the layer 6870 is compressed. In at least one embodiment, the medicament can comprise at least one tissue sealant, hemostatic agent, and/or anti-microbial material, such as ionized silver and/or triclosan, for example. In various embodiments, the compression of the layer 6870 can squeeze the medicament from the layer 6870 such that the entirety of, or at least a significant portion of, the surface of the tissue T is covered with the medicament. Furthermore, as the layer 6870 is compressed and the staple legs 6221 penetrate the tissue T and the layer 6870, the medicament can flow down the staple legs 6221 and treat the tissue that has just been incised by the staple legs 6221, for example. In various embodiments, the body of the retention matrix 6250 can comprise a first layer which is comprised of a biocompatible material, such as titanium and/or stainless steel, for example, and the bottom layer 6870 can comprise a second layer comprised of a bioabsorbable material, such as oxidized regenerated cellulose (ORC), biologically active agents like fibrin and/or thrombin (either in their liquid state or freeze dried), glycerin, absorbable porcine gelatin in either flue or foam configurations, and/or anti-microbials, such as ionized silver and/or triclosan, for example. Additional bioabsorbable materials can comprise Surgicel Nu-Knit, Surgicel Fibrillar, collagen/ORC which is a hybrid with a built in collagen matrix and is marketed under the trade name Promogran, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. Although only one layer 6870 is illustrated in FIG. 150, any suitable number of layers could be used. In at least one embodiment, a first layer comprising a first medicament could be attached to the retention matrix 6250 and a second layer comprising a second, or different, medicament could be attached to the first layer. In at least one such embodiment, a plurality of layers could be used wherein each layer can comprise a different medicament and/or a different combination of medicaments contained therein.

In various embodiments, referring now to FIG. 148, a fastener system can comprise a layer of material 6770 attached to the bottom surface 6251 of the retention matrix 6250. In certain embodiments, the layer 6770 and/or the retention matrix 6250 can comprise retention features which can be configured to retain the layer 6770 to the retention matrix 6250. In at least one embodiment, at least one adhesive can be utilized to adhere the layer 6770 to the retention matrix 6250. In any event, the layer 6770 can comprise a bottom, or tissue-contacting, surface 6773 which can be configured to contact the tissue T when the retention matrix 6250 is moved downwardly toward the staples 6220 to engage the retention apertures 6252 with the staple legs 6221. In at least one such embodiment, the layer 6770 can be comprised of a compressible material, such as a bioabsorbable foam, for example, which can be compressed between the surface 6251 of the retention matrix 6250 and the tissue T. In various embodiments, the layer 6770 can further comprise one or more encapsulations, or cells, 6774 which can be configured to store at least one medicament therein. In certain embodiments, referring to FIG. 149, the encapsulations 6774 can be aligned, or at least substantially aligned, with the retention apertures 6252 such that, when the staple legs 6221 are pushed through the tissue T and the layer 6770, the staple legs 6221 can puncture and/or otherwise rupture the encapsulations 6774. After the encapsulations 6774 have been ruptured, the at least one medicament M stored in the encapsulations 6774 can flow out onto the tissue T. In at least one such embodiment, the medicament M can comprise a fluid which can flow or wick down the staple legs 6221 and treat the tissue T that was just incised by the staple legs. As a result of the above, the medicament stored within the encapsulations 6774 can provide a localized treatment to the tissue. In certain embodiments, the encapsulations 6774 in the sheet 6770 can comprise different medicaments stored therein. For example, a first group of encapsulations 6774 can comprise a first medicament, or a first combination of medicaments, stored therein and a second group of encapsulations can comprise a different medicament, or a different combination of medicaments, stored therein. In various embodiments, the layer 6770 can be comprised of a flexible silicone sheet and the encapsulations 6774 can represent voids in the silicone sheet. In at least one such embodiment, the silicone sheet can comprise two layers that can be attached to one another wherein the encapsulations 6774 can be defined between the two layers. In various embodiments, the layer 6770 can comprise one or more thin sections or weakened portions, such as partial perforations, for example, which can facilitate the incision of the layer 6770 and the rupture of the encapsulations 6774 by the legs 6221. In certain embodiments, at least a portion of the encapsulations 6774 can be positioned within domes 6777, wherein the domes 6777 can extend upwardly from the sheet 6770. In at least one such embodiment, the domes 6777 and/or at least a portion of the encapsulations 6774 can be positioned within the pockets 6201 formed within the retention matrix 6250. In certain embodiments, the encapsulations 6774 may comprise discrete cells which are unconnected to each other. In certain other embodiments, one or more of the encapsulations 6774 can be in fluid communication with each other via one or more passageways, conduits, and/or channels, for example, extending through the layer 6770. The disclosure of U.S. Pat. No. 7,780,685, entitled ADHESIVE AND MECHANICAL FASTENER, which issued on Aug. 24, 2010, is hereby incorporated by reference in its entirety.

In various embodiments, further to the above, a staple cartridge comprising a cartridge body, staples, and/or an alignment matrix therein can be loaded into a first jaw of an end effector and, similarly, a retention matrix and/or one or more covers can be loaded into a second jaw of the end effector. In certain embodiments, referring now to FIG. 151, an instrument, such as cartridge loader 6990, for example, can be used to insert two or more fastener cartridges into an end effector at the same. In at least one embodiment, the cartridge loader 6990 can comprise a handle 6991 and a cartridge carrier 6992, wherein the cartridge carrier 6992 can comprise a first retention portion configured to retain the cartridge body 6210 of the staple cartridge 6200 thereto and, in addition, a second retention portion configured to retain a cartridge body 6980 which supports, one, a plurality of protective caps 6270 therein and, two, a retention matrix 6250 along the bottom surface thereof, for example. In various embodiments, the first and second retention portions can each comprise one or more retention members configured to releasably engage the cartridge bodies 6210 and 6980. In use, referring now to FIGS. 152 and 153, an end effector can comprise a first, or bottom, jaw 6230 and a second, or top, jaw 6940, wherein the staple cartridge 6200 can be loaded into the first jaw 6230 and the cartridge body 6980 can be loaded into the second jaw 6940. In various circumstances, the top jaw 6940 can be rotated from an open position (FIG. 152) to a closed position (FIG. 153) by an actuator 6235, wherein the operation of the actuator 6235 is described above and is not repeated herein for the sake of brevity. Once the top jaw 6940 is in its closed position, referring now to FIG. 153, the distal end 6993 of the cartridge carrier 6992 can be inserted into the end effector such that the staple cartridge 6200 is slid through the distal end 6938 of the first jaw 6930 and into a first attachment portion, or channel, 6939 in the first jaw 6230. Similarly, the distal end 6993 of the cartridge carrier 6992 can be inserted into the end effector such that the cartridge body 6980 is slid through the distal end 6948 of the second jaw 6940 and into a second attachment portion, or channel, 6949 in the second jaw 6940. A surgeon, or other clinician, holding the handle 6991 of the cartridge loader 6990 can push the staple cartridge 6200 and the cartridge body 6980 through the channels 6939 and 6949, respectively, until the staple cartridge 6200 and the cartridge body 6980 are fully seated therein.

As the staple cartridge 6200 and the cartridge body 6980 are being seated, the staple cartridge 6200 and the cartridge body 6980 can each engage one or more retention portions in their respective jaws 6230 and 6940, as described in greater detail further below. In any event, once the staple cartridge 6200 and the cartridge body 6980 have been seated, referring now to FIG. 154, the cartridge loader 6990 can be detached from the staple cartridge 6200 and the cartridge body 6980 and removed from the end effector. In at least one such embodiment, the retention force holding the staple cartridge 6200 in the first jaw 6230 can be greater than the retention force holding the staple cartridge 6200 to the cartridge carrier 6992 such that, as the cartridge carrier 6992 is pulled distally out of the end effector, the staple cartridge 6200 can remain behind in the first jaw 6230. Similarly, the retention force holding the cartridge body 6980 in the second jaw 6940 can be greater than the retention force holding the cartridge body 6940 to the cartridge carrier 6992 such that, as the cartridge carrier 6992 is pulled distally out of the end effector, the cartridge body 6940 can remain behind in the second jaw 6940. Once the cartridge loader 6990 has been removed from the end effector, the loaded first jaw 6230 and the loaded second jaw 6940 can be positioned relative to the tissue T that is to be stapled. Referring now to FIG. 155, the second jaw 6940 can be moved from an open position (FIG. 154) to a fired position (FIG. 155) in order to engage the retention matrix 6250 and the plurality of protective caps 6270 carried by the cartridge body 6980 with the staples 6220 positioned within the staple cartridge 6200.

Referring now to FIGS. 156 and 157, the second jaw 6940 can be re-opened and the plurality of protective caps 6270 and the retention matrix 6250 can detach from the cartridge body 6980 such that the caps 6270 and the retention matrix 6250 can remain engaged with the tissue T and the staple cartridge 6200. In at least one embodiment, the cartridge body 6980 can comprise a plurality of pockets in which the plurality of caps 6270 can be removably positioned and one or more retention slots configured to removably retain the retention matrix 6250 thereto. In various embodiments, the retention members of the second jaw 6940 engaged with the cartridge body 6980 can retain the cartridge body 6980 in the second jaw 6940 after the second jaw 6940 has been opened. In certain embodiments, the cartridge body 6980 can be configured to tear as the second jaw 6940 is opened such that a portion of the cartridge body 6980 is implanted with the caps 6270 and the retention matrix 6250 and a portion of the cartridge body 6980 remains in the second jaw 6940. Similarly, referring again to FIGS. 156 and 157, the retention members of the first jaw 6230 engaged with the cartridge body 6210 can retain the cartridge body 6210 in the first jaw 6230 after the second jaw 6940 has been opened. In certain embodiments, the cartridge body 6210 can be configured to tear as the first jaw 6230 is pulled away from the implanted cartridge 6200 such that a portion of the cartridge body 6210 is implanted with the staples 6220 and alignment matrix 6260 and a portion of the cartridge body 6210 remains in the first jaw 6230. In various embodiments, referring now to FIGS. 158-160, a staple cartridge, such as staple cartridge 6900, for example, can comprise one or more longitudinal retention slots 6913 extending along the length of the cartridge body 6910 which, when the staple cartridge 6900 is inserted into a jaw 6930, for example, can be configured to receive one or more longitudinal retention rails 6916 extending from the jaw 6930 therein. In use, in at least one embodiment, an end of the retention slots 6913 can be aligned with the distal ends of the retention rails 6916 before the staple cartridge 6900 is slid through the distal end 6938 of the retention channel 6939, for example.

In various embodiments, referring again to FIG. 160, the jaw 6940 can comprise two retention channels 6949, wherein each retention channel 6949 can be configured to receive a cartridge body 6980 comprising a plurality of caps 6270 and a retention matrix 6250 therein. In certain embodiments, each cartridge body 6980 can comprise one or more longitudinal retention shoulders 6917 which can be configured to be slid along one or more longitudinal retention rails 6918 of the second jaw 6940 as the cartridge bodies 6980 are inserted into their respective retention channels 6949 in jaw 6940. In various embodiments, the retention rails 6918 and the retention shoulders 6917 can co-operate to retain the cartridge body 6980 in the second jaw 6940 as the cartridge bodies 6980 are detached from the caps 6270 and the retention matrix 6250 stored therein. In various embodiments, referring now to FIG. 159, the second jaw 6940 can further comprise one or more distal bumps, or retention members, 6915 extending therefrom which can be configured to removably lock the cartridge bodies 6980 in their respective retention channels. In at least one such embodiment, the second jaw 6940 can comprise a distal bump 6915 configured and positioned relative to each retention channel 6949 such that each cartridge body 6980 can flex around the bumps 6915 as the cartridge bodies 6980 are being inserted into the channels 6949 wherein, just as the cartridge bodies 6915 are being fully seated in the channels 6949, the distal ends of the cartridge bodies 6980 can clear and snap over the bumps 6915. In order to remove the cartridge bodies 6980 after they have been expended, as described above, the cartridge bodies 6980 can be pulled back over the bumps 6915 and removed from the retention channels 6949. Similar to the above, the first jaw 6930 can comprise one or more distal retention bumps 6914 extending therefrom which can be configured to be received in one or more retention grooves, or slots, 6912 (FIG. 158) in the cartridge body 6910 when the staple cartridge 6900 has been fully seated.

In various embodiments, further to the above, a first fastener cartridge comprising a plurality of first fasteners positioned therein can be positioned in a first jaw of a surgical fastening device and a second fastener cartridge comprising a plurality of second fasteners positioned therein can be positioned in a second jaw of the surgical fastening device. In use, the first jaw and/or the second jaw can be moved toward the other in order to engage the first fasteners with the second fasteners and secure tissue therebetween. In certain embodiments, the first fastener cartridge and the second fastener cartridge can be engaged with each other as the first fasteners are engaged with the second fasteners. In at least one embodiment, the body of the first fastener cartridge can be comprised of a first compressible material and the body of the second fastener cartridge can be comprised of a second compressible material, wherein the first body and/or the second body can be compressed against the tissue being fastened. After the tissue has been fastened, the first jaw can be moved away from the implanted first fastener cartridge and the second jaw can be moved away from the implanted second fastener cartridge. Thereafter, the first jaw can be reloaded with another first fastener cartridge, or the like, and the second jaw can be reloaded with another second fastener cartridge, or the like, and the surgical fastening instrument can be reused. While staples can be used in some embodiments, other embodiments are envisioned comprising other types of fasteners, such as two-part fasteners which are locked together when they are engaged with one another, for example. In at least one such embodiment, the first fastener cartridge can comprise a first storage portion for storing the first fastener portions and the second fastener cartridge can comprise a second storage portion for storing the second fastener portions. In various embodiments, the fastening systems described herein can utilize fasteners comprising any suitable type of material and/or form. In certain embodiments, the fasteners can comprise penetrating members. Such penetrating members could be comprised of a polymer, a composite, and/or a multi-layered substrate, for example. An example of a multi-layered substrate could be a wire or a sheet substrate with an elastomeric or polymeric coating. It could be a thin sheet formed such that penetrating members are oriented perpendicular, or at least substantially perpendicular, to the connecting member. The penetrating members could comprise a rectangular profile, semi-circular profile, and/or any beam profile. In various embodiments, the fasteners described herein can be manufactured utilizing any suitable process, such as a wire extruding process, for example. Another possibility is the use of microfabrication to create hollow penetrating members. These penetrating members could be fabricated from a process which is different than a wire extruded process and could use a combination of materials.

As described above, the tips of staple legs protruding through a retention matrix can be covered by one or more caps and/or covers. In certain embodiments, the tips of the staple legs can be deformed after they have been inserted through the retention matrix. In at least one embodiment, a jaw holding the retention matrix can further comprise anvil pockets positioned above and/or aligned with the retention apertures which can be configured to deform the staple legs as they protrude above the retention matrix. In various embodiments, the staple legs of each staple can be curled inwardly toward each other and/or toward the center of the staple, for example. In certain other embodiments, one or more of the staple legs of a staple can be curled outwardly away from the other staple legs and/or away from the center of the staple. In various embodiments, regardless of the direction in which the staple legs are curled, the tips of the staple legs can contact the body of the retention matrix and may not re-enter the tissue that has been fastened by the staples. In at least one embodiment, the deformation of the staple legs after they have passed through the retention matrix can lock the retention matrix in position.

In various embodiments, referring now to FIGS. 161 and 162, a surgical stapling instrument, such as surgical stapler 7000, for example, can comprise a first jaw 7030 and a second jaw 7040, wherein the second jaw 7040 can be moved toward and away from the first jaw 7030 by the movement of actuator 6235. The operation of actuator 6235 is described above and is not repeated herein for the sake of brevity. In various embodiments, the first jaw 7030 can comprise a distal end 7031 and a proximal end 7032, wherein the first jaw 7030 can define a channel extending between the distal end 7031 and the proximal end 7032 which is configured to receive a staple cartridge. For the purposes of illustration, the cartridge body of such a staple cartridge is not depicted in FIG. 161, although such a staple cartridge can comprise a cartridge body, staples 6220 positioned within the cartridge body, and staple drivers 7012 positioned underneath the staples 6220. In certain embodiments, although not illustrated in FIG. 161 for the sake of clarity, the second jaw 7040 can be configured to hold a retention matrix, such as retention matrix 6250, for example, over the staples 6220 and/or move the retention matrix into engagement with the legs of the staples 6220 as described above. In at least one embodiment, the surgical stapler 7000 can further comprise a sled 7010 positioned in the first jaw 7030 which can be slid from the distal end 7031 of the first jaw 7030 toward the proximal end 7032, for example, and lift the staple drivers 7012, and the staple 6220 supported thereon, toward the retention matrix and the second jaw 7040. In various other embodiments, the sled 7010 can be moved from the proximal end 7032 toward the distal end 7031 in order to deploy the staples 6020, for example. In at least one embodiment, the sled 7010 can comprise one or more inclined ramps, or cams, 7011 which can be configured to slide underneath the staple drivers 7012 and lift the staple drivers 7012 upwardly. In various embodiments, the surgical stapler 7000 can further comprise a pull, or push, rod operably coupled to the sled 7010 which can be moved proximally and/or distally by an actuator located on a handle and/or shaft of the surgical stapler 7000, for example.

In various embodiments, referring again to FIG. 161, the second jaw 7040 of the surgical stapler 7000 can comprise a frame 7041, a distal end 7048, and a proximal end 7049 positioned opposite the distal end 7048. In certain embodiments, the second jaw 7040 can further comprise a guide system comprising one or more guide rails, such as guide rails 7045 and 7046, for example, extending along the longitudinal axis of the frame 7041 which, as described in greater detail further below, can be configured to guide one or more anvils, or cams, which can engage and deform the staple legs of the staples 6220 after the staple legs 6221 of the staples 6220 have passed through the retention matrix. In at least one such embodiment, the guide rails 7045 and 7046 can comprise a guide wire or cable which extends along a top portion or surface of the frame 7041, around a distal post 7047, and back along the top portion or surface of the frame 7041, for example. In various embodiments, as mentioned above and referring primarily now to FIGS. 163 and 165, the second jaw 7040 can further comprise one or more anvils, or cams, such as first anvil 7050 and second anvil 7060, for example, which can be moved longitudinally along the second jaw 7040 in order to deform the legs of the staples 6220 after they have passed through the retention matrix. In at least one embodiment, the surgical stapler 7000 can further comprise a first anvil driver, or actuator, 7051 connected to and/or operably coupled to the first anvil 7050 which can be configured to pull the first anvil 7050 proximally and/or push the first anvil 7050 distally. Similarly, in at least one embodiment, the surgical stapler 7000 can further comprise a second anvil driver, or actuator, connected to and/or operably coupled to the second anvil 7060 which can be configured to push the second anvil 7060 distally and/or pull the second anvil 7060 proximally. In various embodiments, the first anvil 7050 can comprise guide slots 7052 and the second anvil 7060 can comprise guide slots 7062 which can each be configured to slidably receive guide rail 7045 or guide rail 7046 therein. In at least one such embodiment, the guide rails 7045 and 7046 can be closely received within the guide slots 7052 and 7062 such that relative lateral, or side-to-side, movement therebetween can be prevented, or at least limited.

In certain embodiments, further to the above, the first anvil 7050 can be pulled proximally and the second anvil 7060 can be pulled distally. In at least one embodiment, referring to FIG. 161, the guide rails 7045 and 7046 and the distal post 7047 can comprise a pulley system configured to pull the second anvil 7060 distally and/or pull the second anvil 7060 proximally. In at least one such embodiment, the guide rail 7045 and the guide rail 7046 can comprise a continuous wire or cable extending around the distal post 7047, wherein a portion of the continuous wire can be pulled in order to cycle the wire around the distal post 7047. In various embodiments, the guide rail 7046, for example, can be mounted to the second anvil 7060 such that, when the continuous cable is cycled in a first direction, the second anvil 7060 can be pulled distally toward the distal end 7048 of the jaw 7040 and, when the continuous cable is cycled in a second, or opposite, direction, the second anvil 7060 can be pulled proximally toward the proximal end 7049. In at least one embodiment, referring now to FIG. 163, the guide rail 7046 can be secured within a guide slot 7062 such that a pulling force can be transmitted therebetween. In at least one such embodiment, the guide rail 7045 can be configured to slide within the other guide slot 7062. In various embodiments, the first anvil 7050 may operate independently of the second anvil 7060 and the pulley system and the guide slots 7052 defined in the first anvil 7050 may be configured to slidably receive the guide rails 7045 and 7046 such that relative movement is permitted therebetween. In various embodiments, the continuous cable comprising guide rails 7045 and 7046 can be sufficiently flexible in order to accommodate the opening and closing of the top jaw 7040. The continuous cable can also be sufficiently flexible in order to accommodate the vertical movement of the second anvil 7060 toward and away from the bottom jaw 7030, which is described in greater detail further below.

In various embodiments, referring again to FIGS. 163 and 165, the first anvil 7050 can comprise cam followers 7055 extending therefrom which can be configured to ride in one or more cam slots, or guide slots, such as cam slot 7070 (FIG. 166), for example, defined in the frame 7041 of the second jaw 7040. More particularly, in at least one embodiment, the frame 7041 can comprise a first cam slot 7070 extending longitudinally along a first side of the frame 7041 and a second cam 7070 extending longitudinally along a second, or opposite, side of the frame 7041, wherein the cam followers 7055 extending from a first side of the first anvil 7050 can ride in the first cam slot 7070 and the cam followers 7055 extending from a second side of the first anvil 7050 can ride in the second cam slot 7070. In at least one such embodiment, the contours of each cam slot 7070 can be identical, or at least substantially identical, and can be aligned, or at least substantially aligned, with one another. Similarly, in various embodiments, the second anvil 7060 can comprise cam followers 7065 extending therefrom which can be configured to ride in the cam slots 7070 (FIG. 166) defined in the frame 7041 of the second jaw 7040. More particularly, in at least one embodiment, the cam followers 7065 extending from a first side of the second anvil 7060 can ride in the first cam slot 7070 and the cam followers 7065 extending from a second side of the second anvil 7060 can ride in the second cam slot 7070. In use, the cam followers 7055 of the first anvil 7050 and the cam followers 7065 of the second anvil 7060 can slide within the cam slots 7070 such that first anvil 7050 and the second anvil 7060 follow the contours of the cam slots 7070 as the first anvil 7050 and the second anvil 7060 are pulled proximally and/or pushed distally. In various embodiments, each cam slot 7070 can comprise a plurality of dwell, or upper, portions 7071 and a plurality of driver, or lower, portions 7072 which can be configured to move the anvils 7050 and 7060 vertically, i.e., toward and away from the bottom jaw 7030, at the same time that the anvils 7050 and 7060 are being moved longitudinally, i.e., between the distal end 7048 and the proximal end 7049 of the frame 7041, as described in greater detail further below.

When the surgical stapler 7000 is in an unfired condition, referring to FIG. 166, the first anvil 7050 can be positioned at the distal end 7048 of the frame 7041 and the second anvil 7060 can be positioned at the proximal end 7049 of the frame 7041; furthermore, referring now to FIG. 167, the staples 6220 positioned in the first jaw 7030 may not yet be inserted into the tissue T and/or the retention matrix positioned thereabove when the surgical stapler 7000 is in an unfired condition. In use, referring now to FIG. 168, the staples 6220 can be driven upwardly within the staple cavities 7033 of a staple cartridge by the staple drivers 7012 and, in addition, the first anvil 7050 can be moved proximally from the distal end 7048 of the frame 7041 toward the distal end 7049 in order to engage the staple legs 6221 of the staples 6220. In at least one embodiment, the staples 6220 can be driven upwardly before the first anvil 7050 is engaged with the staple legs 6221 thereof. In various embodiments, all of the staples 6220 may be deployed upwardly by the sled 7010 before the first anvil 7050 is advanced into contact with the staple legs 6221 or, alternatively, the sled 7010 may be moved proximally at the same time that the first anvil 7050 is moved proximally, although the sled 7010 may sufficiently lead the first anvil 7050 in order to deploy the staples 6220 ahead of the first anvil 7050. In various embodiments, as illustrated in FIG. 168, the cam slots 7070 can be configured and arranged such that the forming surfaces, such as forming, or camming, surfaces 7053 and 7054, for example, of the first cam 7050 can contact at least some of the staple legs 6221 when the first cam 7050 is passing through a dwell, or upper, position. In various circumstances, the cam followers 7055 of the first anvil 7050 can each be positioned in a dwell portion 7071 of the cam slots 7070 such that the forming surfaces 7053 and 7054 are in a raised position and such that the staple legs 6221 are only partially deformed when the anvil 7050 passes thereby in the dwell position. As the first cam 7050 is moved further along the cam slots 7070, as illustrated in FIG. 169, the cam followers 7055 of the first anvil 7050 can be driven into driven, or lower, portions 7072 of the cam slots 7070 such that the forming surfaces 7053 and 7054 are moved vertically downwardly toward the staple legs 6021 in order to drive the staple legs 6021 into their finally formed configurations. Thereafter, as the first anvil 7050 is progressed further along the cam slots 7070, the first anvil 7050 can be driven vertically upwardly into another set of dwell portions 7071 of the cam slots 7070. As illustrated in FIGS. 168 and 169, the reader will note that the first anvil 7050 may only engage some of the staple legs and not others. In at least one such embodiment, the first anvil 7050 can be configured to only deform a group of staple legs comprising the distal staple legs 6221 of the staples 6220, for example. In at least one such embodiment, the first anvil 7050 can be configured to deform the distal staple legs 6221 toward the center of the staples 6220. In various embodiments, each proximal staple leg 6221 can be contacted twice by the first anvil 7050, i.e., by a first forming surface 7053 and by a second forming surface 7054 aligned with the first forming surface 7053. In at least one such embodiment, the first forming surfaces 7053 can deform the distal staple legs 6221 into a partially-deformed configuration when the first anvil 7050 is in a dwell, or upper, position and the second forming surfaces 7054 can deform the distal staple legs 6221 into a fully-formed configuration when the first anvil 7050 is moved into a driven, or lower, position. In various embodiments, referring now to FIGS. 163 and 164, the first anvil 7050 can comprise a plurality of first forming surfaces 7053 and a plurality of second forming surfaces 7054 in order to deform the distal staple legs 6221 of staples 6220 when the staple legs 6221 are arranged in more than one row or line. In various embodiments, as described in greater detail further below, the proximal staple legs 6221 of the staples 6020 can be deformed by the second anvil 7060, for example.

In various embodiments, further to the above, the first anvil 7050 can be moved from the distal end 7048 of the frame 7041 to the proximal end 7049 in order to deform all of the distal staple legs 6221 of the staples 6220. As the reader will note, the first anvil 7050 can be moved up and down relative to the undeformed proximal staple legs 6221 and, in order to accommodate such relative movement, in various embodiments, the first anvil 7050 can comprise one or more clearance slots 7057 (FIG. 165) which can be configured to receive the unbent proximal staple legs 6221 as the first anvil 7050 bends the distal staple legs 6221. Similarly, referring again to FIG. 163, the second anvil 7060 can comprise a clearance slot 7067 which can be configured to accommodate the vertical movement of the first cam actuator 7051 which moves up and down as the first anvil 7050 is moved between its dwell and driven positions as described above. After all of the distal staple legs 6221 have been bent, in at least one embodiment, the second anvil 7060 can be moved from the proximal end 7049 of the frame 7041 to the distal end 7048 by the anvil actuator 7061. Similar to the above, referring now to FIG. 170, the cam followers 7065 of the second anvil 7060 can slide within the cam slots 7070 such that the second anvil 7060 is moved between dwell, or upper, positions and driven, or lower, positions in order to deform the proximal staple legs 6221 inwardly toward the centers of the staples 6220, for example. Similar to the above, the second anvil 7060 can comprise a plurality of first forming, or camming, surfaces 7063 and a plurality of second forming, or camming, surfaces 7064 which can each be configured to at least partially deform and/or completely deform one or more of the proximal staple legs 6021. Referring again to FIG. 164, the second anvil 7060 can comprise a plurality of first forming surface 7063 and a plurality of second forming surfaces 7064 which can be configured to deform the proximal staple legs 6221 of staples 6220 arranged in a plurality of rows, or lines, for example. As also illustrated in FIG. 164, the first forming surfaces 7063 and the second forming surfaces 7064 of the second anvil 7060 may not be aligned with the first forming surfaces 7053 and the second forming surfaces 7054 of the first anvil 7050 wherein, as a result, the proximal legs 6221 of the staples 6220 may be positioned in different rows, or lines, than the distal legs 6221 of the staples 6220. As the reader will also note, the second anvil 7060 can push the first anvil 7050 as the second anvil 7060 is moved distally. In at least one such embodiment, the second anvil 7060 can push the first anvil 7050 back into the distal end 7048 of the frame 7041 such that the first anvil 7050 can be returned to its initial, or unfired, position. After all of the proximal staple legs 6221 of the staples 6220 have been deformed, the second anvil 7060 can be retracted proximally and returned to its initial, or unfired, position. In this way, the surgical stapler 7000 can be reset such that a new staple cartridge can be positioned in the first jaw 7030 and a new retention matrix can be positioned in the second jaw 7040 in order to use the surgical stapler 7000 once again.

In various embodiments, as described above, a surgical stapler can comprise two or more anvils which can travel longitudinally in order to engage the legs of a plurality of staples in a transverse direction. In certain embodiments, a surgical stapler can comprise an anvil which is moved proximally, for example, in order to deform a first group of staple legs and distally, for example, in order to deform a second group of staple legs. In at least one such embodiment, such an anvil can comprise forming surfaces facing proximally and forming surfaces facing distally, for example.

In various embodiments, referring now to FIG. 171, an anvil, such as anvil 7140, for example, can comprise a bottom, or tissue-contacting, surface 7141 and a plurality of forming pockets 7142 defined therein. In at least one embodiment, the anvil 7140 can comprise more than one plate, such as pocket plates 7143, for example, which can be welded into a frame 7144. In at least one such embodiment, each pocket plate 7143 can be positioned in a plate channel 7145 in the frame 7144 and welded to the frame 7144 through a weld slot 7146 extending through the frame 7144 in order to form a longitudinal weld 7147. In various circumstances, the longitudinal weld 7147 can comprise a continuous weld extending along the entire length of the weld slot 7146 or a series of spaced-apart spot welds extending along the length thereof, for example. In various embodiments, each pocket plate 7143 can comprise two or more plate portions that have been welded together. In at least one such embodiment, each pocket plate 7143 can comprise a first plate portion 7143a and a second plate portion 7143b which can be welded together along a seam 7148. In various embodiments, the first plate portion 7143a and the second plate portion 7143b of each plate 7143 can be welded together before the plates 7143 are welded into the plate channels 7145 in the frame 7144. In at least one such embodiment, the first plate portion 7143a and the second plate portion 7143b can comprise co-operating profiles, such as the toothed profiles illustrated in FIG. 171, for example, which can be fitted together to form a tight seam 7148. In at least one embodiment, each plate 7143 can comprise a height of approximately 0.02", for example, which can be taller than the depth of the plate channels 7145 such that the tissue-contacting surfaces 7141 thereof extend from the frame 7044 of the anvil 7040. In certain embodiments, referring now to FIG. 172, the plates 7143 can be connected together by at least one weld 7149 at the distal ends of the plates 7143, for example.

As illustrated in FIGS. 171 and 172, each pocket plate 7143 can comprise a plurality of forming pockets 7142 defined therein. In various embodiments, the forming pockets 7142 can be formed in the plates 7143 by any suitable manufacturing process, such as a grinding process and/or electrode-burning process, for example. In at least one such embodiment, referring now to FIGS. 173 and 174, each forming pocket 7142 can be manufactured by first forming a deep well 7150, then forming an arcuate or curved surface 7151 surrounding the deep well 7150, and then forming a staple leg guide groove 7152 in the curved surface 7151, for example. In various other embodiments, these steps can be performed in any suitable order. In various embodiments, referring now to FIG. 175, the staple forming pockets 7142 can be formed such that the inner edges 7153 of the forming pockets are separated by a consistent, or at least substantially consistent, gap 7154. In at least one such embodiment, the gap 7154 can be approximately 0.008", for example. Furthermore, in at least one such embodiment, the forming pockets 7142 can be positioned along two or more rows, or lines, the centerlines of which can be separated by a consistent, or at least substantially consistent, spacing 7155. In at least one such embodiment, the spacing 7155 between the centerlines can be approximately 0.035", for example. In various embodiments, referring again to FIG. 175, each forming pocket 7142 can taper between a narrow width 7156 and a wide width 7157. In at least one such embodiment, the narrow width 7156 can be approximately 0.045" and the wide width 7157 can be approximately 0.075", for example. In various embodiments, the plates 7143 can be comprised of the same material as the frame 7144. In at least one such embodiment, the plates 7143 and the frame 7144 can both be comprised of stainless steel, such as a 300 series or a 400 series stainless steel, for example, and/or titanium, for example. In various other embodiments, the plates 7143 and the frame 7144 can be comprised of different materials. In at least one such embodiment, the plates 7143 can be comprised of a ceramic material, for example, and the frame 7144 can be comprised of a stainless steel and/or titanium, for example. In various circumstances, depending on the materials used, at least one brazing process could be used to secure the plates 7143 in the frame 7144 in addition to or in lieu of the welding processes described above, for example.

In various embodiments, referring now to FIGS. 176-178, an anvil 7240 can comprise a frame 7244 and a plurality of pocket plates 7243 which can be inserted into the frame 7244. Similar to the above, each pocket plate 7243 can comprise a plurality of forming pockets 7242 defined therein. In at least one embodiment, the anvil frame 7244 can comprise retention slots 7246 defined therein which can each be configured to receive a retention rail 7247 extending from a pocket plate 7243. In order to assemble the pocket plates 7243 to the anvil frame 7244, the side walls 7245 of the anvil frame 7244 can be flexed or splayed outwardly, as illustrated in FIG. 177, in order to widen the retention slots 7246 such that each retention slot 7246 can receive a retention rail 7247 of a pocket plate 7243 therein. Once the retention rails 7247 have been positioned in the retention slots 7246, the side walls 7245 can be released, as illustrated in FIG. 178, thereby allowing the frame 7244 to resiliently contract and/or return to its unflexed state. In such circumstances, the retention slots 7246 can contract and thereby capture the retention rails 7247 therein. In certain embodiments, the retention rails 7247 and/or the retention slots 7246 can comprise one or more co-operating tapered surfaces which, after the flexed retention slots 7246 have been released, can form a taper-lock engagement which can retain the retention rails 7247 in the retention slots 7246. Similar to the above, the pocket plates 7243 can be comprised of the same material as or a different material than the frame 7244. In at least one such embodiment, the plates 7243 can be comprised of a ceramic material, for example, and the frame 7244 can be comprised of a stainless steel and/or titanium, for example. In various circumstances, depending on the materials used, at least one brazing process and/or at least one welding process, for example, could be used to secure the plates 7243 in the frame 7244.

In FIGS. 179 and 180, a surgical stapling and severing instrument 8010 can comprise an anvil 8014 which may be repeatably opened and closed about its pivotal attachment to an elongate staple channel 8016. A staple applying assembly 8012 can comprise the anvil 8014 and the channel 8016, wherein the assembly 8012 can be proximally attached to the elongate shaft 8018 forming an implement portion 8022. When the staple applying assembly 8012 is closed, or at least substantially closed, the implement portion 8022 can present a sufficiently small cross-section suitable for inserting the staple applying assembly 8012 through a trocar. In various embodiments, the assembly 8012 can be manipulated by a handle 8020 connected to the shaft 8018. The handle 8020 can comprise user controls such as a rotation knob 8030 that rotates the elongate shaft 8018 and staple applying assembly 8012 about a longitudinal axis of the shaft 8018. A closure trigger 8026, which can pivot in front of a pistol grip 8036 about a closure trigger pin 8152 (FIG. 181) engaged laterally across the handle housing 8154, can be depressed to close the staple applying assembly 8012. In various embodiments, a closure release button 8038 can be outwardly presented on the handle 8020 when the closure trigger 8026 is clamped such that the release button 8038 can be depressed to unclamp the closure trigger 8026 and open the staple applying assembly 8012, as described in greater detail below. A firing trigger 8034, which can pivot in front of the closure trigger 8026, can cause the staple applying assembly 8012 to simultaneously sever and staple tissue clamped therein. In various circumstances, as described in greater detail below, multiple firing strokes can be employed using the firing trigger 8034 to reduce the amount of force required to be applied by the surgeon's hand per stroke. In certain embodiments, the handle 8020 can comprise rotatable right and/or left indicator wheels 8040, 8041 (FIG. 181) which can indicate the firing progress. For instance, full firing travel may require three full firing strokes of firing trigger 8034 and thus the indicator wheels 8040, 8041 can rotate up to one-third of a revolution each per stroke of firing trigger 8034. As described in greater detail below, a manual firing release lever 8042 can allow the firing system to be retracted before full firing travel has been completed, if desired, and, in addition, the firing release lever 8042 can allow a surgeon, or other clinician, to retract the firing system in the event that the firing system binds and/or fails.

With reference to FIGS. 179 and 181, the elongate shaft 8018 can comprise an outer structure including a longitudinally reciprocating closure tube 8024 that pivots the anvil 8014 toward its close position in response to the proximal depression of the closure trigger 8026 of handle 8020. The elongate channel 8018 can be connected to the handle 8020 by a frame 8028 (FIG. 181) that is internal to the closure tube 8024. The frame 8028 can be rotatably engaged to the handle 8020 so that the rotation of the rotation knob 8030 (FIG. 179) can rotate the implement portion 8022. With particular reference to FIG. 181, the rotation knob 8030 can be comprised of two half-shells which can include one or more inward projections 8031 that can extend through one or more elongate side openings 8070 in the closure tube 8024 and engage the frame 8028. As a result of the above, the rotation knob 8030 and the frame 8028 can be rotated together, or synchronously, such that the rotated position of knob 8030 determines the rotated position of the implement portion 8022. In various embodiments, the longitudinal length of the longer opening 8070 is sufficiently long to allow the longitudinal closure motion, and opening motion, of the closure tube 8024. With regard to generating the closure motion of closure tube 8024, referring primarily to FIGS. 181 and 183, an upper portion 8160 of the closure trigger 8026 can push forward a closure yoke 8162 via a closure link 8164. The closure link 8164 is pivotally attached at its distal end by a closure yoke pin 8166 to the closure yoke 8162 and is pivotally attached at its proximal end by a closure link pin 8168. In various embodiments, the closure trigger 8026 can be urged to an open position by a closure trigger tension spring 8246 that is connected proximally to the upper portion 8160 of the closure trigger 8026 and a handle housing 8154 formed by right and left half shells 8156, 8158. The tension force applied by the tension spring 8246 can be overcome by a closing force applied to the closure trigger 8026 in order to advance the yoke 8162, closure link 8164, and the closure tube 8024 distally.

As the closure trigger 8026 is actuated, or depressed, as described above, the closure release button 8038 can be positioned such that the surgeon, or other clinician, can push the closure release button 8038, if desired, and allow the closure trigger 8026, and the rest of the surgical instrument, to return to an unactuated state. In various embodiments, the closure release button 8038 can be connected to a pivoting locking arm 8172 by a central lateral pivot 8173 such that motion can be transferred between the release button 8038 and the locking arm 8172. Referring again to FIG. 181, a compression spring 8174 can bias the closure release button 8038 proximally, i.e., clockwise about the central lateral pivot 8173 as viewed from the right and the upper portion 8160 of the closure trigger 8026 can include a proximal crest 8170 with an aft notch 8171. As the closure trigger 8026 is depressed, the pivoting locking arm 8172 can ride upon the proximal crest 8170 and when the closure trigger 8026 reaches its fully depressed position, it should be appreciated that the aft notch 8171 is presented below the pivoting locking arm 8172 which drops into and locks against the aft notch 8171 under the urging of the compression spring 8174. At such point, manual depression of the closure release button 8038 rotates the pivoting locking arm 8172 upward and out of aft notch 8171 thereby unlocking the closure trigger 8026 and allowing the closure trigger 8026 to be returned to its unclamped position.

Once the closure trigger 8026 is proximally clamped, as discussed above, the firing trigger 8034 can be drawn toward the pistol grip 8036 in order to advance a firing rod 8032 distally from the handle 8020. In various embodiments, the firing trigger 8034 can pivot about a firing trigger pin 8202 that laterally traverses and is engaged with the right and left half shells 8156, 8158 of the handle 8020. The firing trigger 8034, when actuated, can advance a linked transmission firing mechanism 8150. The linked transmission firing mechanism 8150 can be urged into a retracted, unfired, position by a spring 8184 that is, one, attached to the pistol grip 8036 of the handle 8020 and, two, attached to one of the links, for example, of the linked transmission firing mechanism 8150 as described in greater detail below. The spring 8184 can comprise a nonmoving end 8186 connected to the housing 8154 and a moving end 8188 connected to a proximal end 8190 of a steel band 8192. A distally-disposed end 8194 of the steel band 8192 can be attached to an attachment feature 8195 on a front link 8196a of a plurality of links 8196a-8196d that form a linked rack 8200. Linked rack 8200 can be flexible such that it can readily retract into the pistol grip 8036 and minimize the length of the handle 8020 and yet form a straight rigid rack assembly that may transfer a significant firing force to and/or through the firing rod 8032. As described in greater detail below, the firing trigger 8034 can be engaged with a first link 8196a during a first actuation of the firing trigger 8034, engaged with a second link 8196b during a second actuation of the firing trigger 8034, engaged with a third link 8196c during a third actuation of the firing trigger 8034, and engaged with a fourth link 8196d during a fourth actuation of the firing trigger 8034, wherein each actuation of the firing trigger 8034 can advance the linked rack 8200 distally an incremental amount. In various embodiments, further to the above, the multiple strokes of firing trigger 1034 can rotate the right and left indicator gauge wheels 1040, 1041 to indicate the distance in which the linked rack 8200 has been advanced.

Referring now to FIGS. 181 and 183, an anti-backup mechanism 8250 can prevent the combination tension/compression spring 8184 from retracting the linked rack 8200 between firing strokes. In various embodiments, a coupling slide tube 8131 abuts the first link 8196a and connects to the firing rod 8032 to communicate the firing motion. The firing rod 8032 extends proximally out of a proximal end of the frame 8028 and through a through hole 8408 of an anti-backup plate 8266. The through hole 8408 is sized to slidingly receive the firing rod 8032 when perpendicularly aligned but to bind when tipped. A lower tab attachment 8271 extends proximally from a lower lip of the proximal end of the frame 8028, extending through an aperture 8269 on a lower edge of the anti-backup plate 8266. This lower tab attachment 8271 draws the lower portion of the anti-backup plate 8266 proximate to the frame 8028 so that the anti-backup plate 8266 is perpendicular when the firing rod 8032 is distally advanced and allowed to tip top aft into a binding state when the firing rod 8032 attempts to retract. An anti-backup compression spring 8264 is distally constrained by the proximal end of the frame 8028 and proximally abuts a top portion of the anti-backup plate 8266, biasing the anti-backup plate 8266 to a locking state. Opposing the spring bias, an anti-backup cam tube 8268 slidingly encompasses the coupling slide tube 8131 and abuts the anti-backup plate 8266. A proximally projecting anti-backup yoke 8256 attached to the anti-backup cam tube 8268 extends overtop of the closure yoke 8162.

Referring to FIG. 181, a link triggered automatic retraction mechanism 8289 is incorporated into the surgical stapling and severing instrument 8010 to cause knife retraction at the end of full firing travel. To that end, the distal link 8196d includes a tang 8290 that projects upwardly when the distal link 8196d is advanced into rack channel 8291 (FIG. 181) formed in the closure yoke 8162. This tang 8290 is aligned to activate a bottom proximal cam 8292 on an anti-backup release lever 8248 (FIG. 186). With particular reference to FIGS. 186 and 187, structures formed in the right and left half shells 8156, 8158 constrain movement of the anti-backup release lever 8248. A pin receptacle 8296 and circular pin 8293 formed respectively between right and left half shells 8156, 8158 is received through a longitudinally elongate aperture 8294 formed in the anti-backup release lever 8248 distal to the bottom proximal cam 8292, thus allowing longitudinal translation as well as rotation about the circular pin 8293. In the right half shell 8156, a proximally open channel 8295 includes a proximal horizontal portion 8295a that communicates with an upwardly and distally angled portion 8295b that receives a rightward aft pin 8297 (FIG. 187) near the proximal end of the anti-backup release lever 8248, thus imparting an upward rotation as the anti-backup release lever 8248 reaches the distal most portion of its translation. A blocking structure formed in the right half shell 8156 proximal to the anti-backup release lever 8248 prevents proximal movement thereof once assembled to maintain rightward aft pin 8297 in the proximally open channel 8295.

Further to the above, as depicted in FIGS. 187 and 188, a distal end 8254 of the anti-backup release lever 8248 thus is urged distally and downwardly, causing a rightward front pin 8298 to drop into distally open step structure 8299 formed in the right half shell 8156, which is urged into this engagement by a compression spring 8300 (FIG. 188) hooked to a leftward hook 8301 on the anti-backup release lever 8248 between the rightward front pin 8298 and the longitudinally elongate aperture 8294. The other end of the compression spring 8300 is attached to a hook 8302 (FIGS. 186, 188, 189) formed in the right half shell 8156 in a more proximal and lower position just above the closure yoke 8266. The compression spring 8300 thus pulls the distal end 8254 of the anti-backup release lever 8248 down and aft, which results in the rightward front pin 8298 locking into the distally open step structure 8299 when distally advanced. Thus, once tripped, referring to FIG. 189, the anti-backup release lever 8248 remains forward holding the anti-backup plate 8266 perpendicularly and thus allowing the linked rack 8200 to be retracted. When the closure yoke 8266 is subsequently retracted when unclamping the end effector 8012, an upwardly projecting reset tang 8303 on the closure yoke 8266 contacts a bottom distal cam 8305 of the anti-backup release lever 8248, lifting the rightward front pin 8298 out of the distally open step structure 8299 so that the anti-backup compression spring 8264 can proximally push the anti-backup cam tube 8268 and the anti-backup release lever 8248 to their retracted positions (FIG. 186).

In various embodiments, referring to FIGS. 179 and 189, the firing trigger 8034 can be operably engaged to the linked rack 8200 in any suitable manner. With particular reference to FIGS. 180 and 185, the firing trigger 8034 pivots about a firing trigger pin 8202 that is connected to the housing 8154. An upper portion 8204 of the firing trigger 8034 moves distally about the firing trigger pin 8202 as the firing trigger 8034 is depressed towards pistol grip 8036, stretching a proximally placed firing trigger tension spring 8206 (FIG. 181) proximally connected between the upper portion 8204 of the firing trigger 8034 and the housing 8154. The upper portion 8204 of the firing trigger 8034 engages the linked rack 8200 during each firing trigger depression via a spring biased side pawl mechanism 8210. When the firing trigger is released, the side pawl mechanism is disengaged from the linked rack 8200 and the firing trigger can be returned to an undepressed, or unfired, position. In use, a ramped right-side track formed by a proximally and rightwardly facing beveled surface 8284 in each of the links 8196a-8196d is engaged by a side pawl assembly 8285. In particular, a pawl slide 8270 (FIGS. 181 and 183) has right and left lower guides 8272 that slide respectively in a left track 8274 (FIG. 181) formed in the closure yoke 8266 below the rack channel 8291 and a right track 8275 in a closure yoke rail 8276 that parallels rack channel 8291 and is attached to a rack channel cover 8277 that closes a rightwardly open portion of the rack channel 8291 in the closure yoke 8266 that is distal to the travel of the pawl slide 8270. In FIGS. 181, 182, and 185, a compression spring 8278 is attached between a hook 8279 on a top proximal position on the closure yoke rail 8276 and a hook 8280 on a distal right-side of the pawl slide 8270, which keeps the pawl slide 8270 drawn proximally into contact with the upper portion 8204 of the firing trigger 8034.

With particular reference to FIG. 181, a pawl block 8318 sits on the pawl slide 8270 pivoting about a vertical aft pin 8320 that passes through a left proximal corner of pawl block 8318 and pawl slide 8270. A kick-out block recess 8322 is formed on a distal portion of a top surface of the block 8318 to receive a kick-out block 8324 pivotally pinned therein by a vertical pin 8326 whose bottom tip extends into a pawl spring recess 8328 on a top surface of the pawl slide 8270. A pawl spring 8330 in the pawl spring recess 8328 extends to the right of the vertical front pin 8326 urging the pawl block 8318 to rotate counterclockwise when viewed from above into engagement with the ramped right-side track 8282. A small coil spring 8332 in the kick-out block recess 8322 urges the kick-out block 8324 to rotate clockwise when viewed from above, its proximal end urged into contact with a contoured lip 8334 formed in the closure yoke 8266 above the rack channel 8291. As shown in FIG. 184, the stronger mechanical advantage of the pawl spring 8330 over the small coil spring 8332 means that the pawl block 8318 tends toward engagement with the kick-out block 8324 rotated clockwise. In FIG. 185, as the firing trigger 8034 is fully depressed and begins to be release, the kick-out block 8324 encounters a ridge 8336 in the contoured lip 8334 as the pawl slide 8270 retracts, forcing the kick-out block 8324 to rotate clockwise when viewed from above and thereby kicking out the pawl block 8318 from engagement with the linked rack 8200. The shape of the kick-out block recess 8322 stops the clockwise rotation of the kick-out block 8324 to a perpendicular orientation to the contoured lip 8334 maintaining this disengagement during the full retraction and thereby eliminating a ratcheting noise.

In FIGS. 181, 183, 190, and 195, the surgical stapling and severing instrument 8010 can include a manual retraction mechanism 8500 that provides for a manual release of the firing mechanism, manual retraction, and in one version (FIGS. 196-202) further performs automatic retraction at the end of full firing travel. Referring now to FIGS. 181, 190, and 191, in particular, a front idler gear 8220 is engaged with a toothed upper, left surface 8222 of the linked rack 8200 wherein the front idler gear 8220 also engages an aft idler gear 8230 having a smaller right-side ratchet gear 8231. Both the front idler gear 8220 and aft idler gear 8230 are rotatably connected to the handle housing 8154 respectively on front idler axle 8232 and aft idler axle 8234. Each end of the aft axle 8232 extend through the respective right and left housing half shells 8156, 8158 and are attached to the left and right indicator gauge wheels 8040, 8041 and, since the aft axle 8234 is free spinning in the handle housing 8154 and has a keyed engagement to the aft gear 8230, the indicator gauge wheels 8040, 8041 rotate with the aft gear 8230. The gear relationship between the linked rack 8200, idler gear 8220 and aft gear 8230 may be advantageously selected so that the toothed upper surface 8222 has tooth dimensions that are suitably strong and that the aft gear 8230 makes no more than one revolution during the full firing travel of the linked transmission firing mechanism 8150. In addition to gear mechanism 8502 visually indicating the firing travel, or progress, the gear mechanism 8502 can also be used to manual retract the knife. In various embodiments, the smaller right-side ratchet gear 8231 of the aft idler gear 8230 extends into a hub 8506 of the manual retraction lever 8042, specifically aligned with a vertical longitudinally-aligned slot 8508 (FIG. 190) bisecting the hub 8506. A lateral through hole 8510 of the hub 8506 communicates with an upper recess 8512. A front portion 8514 is shaped to receive a proximally directed locking pawl 8516 that pivots about a rightward lateral pin 8518 formed in a distal end of the upper recess 8512. An aft portion 8520 is shaped to receive an L-shaped spring tab 8522 that urges the locking pawl 8516 downward into engagement with the right-side smaller ratchet gear 8231. A hold-up structure 8524 (FIGS. 186 and 193) projects from the right half shell 8156 into the upper recess 8512 holding up the locking pawl 8516 from engaging the smaller right-side ratchet gear 8231 when the manual retraction lever 8042 is down (FIG. 193). A coil spring 8525 (FIG. 181) urges the manual retraction lever 8042 down.

In use, as depicted in FIGS. 192 and 193, the combination tension/compression spring 8184 may become disconnected with the linked rack distally positioned. In FIGS. 194 and 195, as the manual retraction lever 8042 is raised, the locking pawl 8516 rotates clockwise and no longer is held up by the hold-up structure 8524 and engages the smaller right-side ratcheting gear 8231, rotating the aft idler gear 8230 clockwise when viewed from the left. Thus, the forward idler gear 8220 responds counterclockwise retracting the linked rack 8200. In addition, a rightward curved ridge 8510 projects out from the hub 8506, sized to contact and distally move the anti-backup release lever 8248 to release the anti-backup mechanism 8250 as the manual retraction lever 8042 is rotated.

In FIGS. 196-202, an automatic retraction mechanism 8600 for a surgical stapling and severing instrument 8010*a* can incorporate automatic retraction at the end of full firing travel into a front idler gear 8220*a* having a tooth 8602 that moves within a circular groove 8604 in a cam wheel 8606 until encountering a blockage 8608 after nearly a full rotation corresponding to three firing strokes. In such circumstances, rightward ridge 8610 is rotated upward into contact a bottom cam recess 8612 to distally move an anti-backup release lever 8248*a*. With particular reference to FIG. 197, the anti-backup release lever 8248*a* includes the distal end 8254 that operates as previously described. The circular pin 8293 and pin receptacle 8296 formed between right and left half shells 8156, 8158 is received through a generally rectangular aperture 8294*a* formed in the anti-backup release lever 8248*a* aft of the bottom cam 8192, thus allowing longitudinal translation as well as downward locking motion of the distal end 8254 of the anti-backup release lever 8248*a*. In the right half shell 8156, a horizontal proximally open channel 8295*a* receives the rightward aft pin 8297 near the proximal end of the anti-backup release lever 8248*a*.

In operation, before firing in FIGS. 198, 198A, the linked rack 8200 and the anti-backup cam tube 8268 are in a retracted position, locking the anti-backup mechanism 8250 as the anti-backup compression spring 8264 proximally tips the anti-backup plate 8266. The automatic retraction mechanism 8600 is at an initial state with the anti-backup release lever 8248*a* retracted with link 8196*a* in contact with the forward idler gear 8220*a*. The tooth 8602 is at a six o'clock position with full travel of the circular groove 8604 progressing counterclockwise thereof with the rightward ridge 8610 just proximal to the tooth 8602. In FIGS. 199, 199A, one firing stroke has occurred moving up one distal link 8196*b* into contact with the forward idler gear 8220*a*. The tooth 8602 has progressed one third of a turn through the circular groove 8604 of the immobile cam wheel 8606. In FIGS. 200, 200A, a second firing stroke has occurred moving up one more link 8196*c* into contact with the forward idler gear 8220*a*. The tooth 8602 has progressed two thirds of a turn through the circular groove 8604 of the immobile cam wheel 8606. In FIGS. 201, 201A, a third firing stroke has occurred moving up one distal link 8196*d* into contact with the forward idler gear 8220*a*. The tooth 8602 has progressed fully around the circular groove 8604 into contact with the blockage 8608 initiating counterclockwise rotation (when viewed from the right) of the cam wheel 8606 bringing the rightward ridge 8608 into contact with the anti-backup release lever 8248*a*. In FIG. 202, the anti-backup release lever 8248*a* has moved distally in response thereto, locking the rightward front pin 8298 into the distally open step structure 8299 and releasing the anti-backup mechanism 8250. Similar surgical stapling instruments are disclosed in U.S. Pat. No. 7,083,075, which issued on Aug. 1, 2006, the entire disclosure of which is incorporated by reference herein.

Referring to FIG. 203, the staple applying assembly 9012 of a surgical stapling instrument 9010 accomplishes the functions of clamping onto tissue, driving staples and severing tissue by two distinct motions transferred longitudinally down the shaft 9016 relative to a shaft frame 9070. This shaft frame 9070 is proximally attached to a handle of a surgical stapling instrument and is coupled thereto for rotation about a longitudinal axis. An illustrative multistroke handle for the surgical stapling and severing instrument is described in greater detail in the co-owned U.S. patent application entitled SURGICAL STAPLING INSTRUMENT INCORPORATING A MULTISTROKE FIRING POSITION INDICATOR AND RETRACTION MECHANISM, Ser. No. 10/674,026, now U.S. Pat. No. 7,364,061, the disclosure of which is hereby incorporated by reference in its entirety. Other applications consistent with the present invention may incorporate a single firing stroke, such as described in commonly owned U.S. patent application SURGICAL STAPLING INSTRUMENT HAVING SEPARATE DISTINCT CLOSING AND FIRING SYSTEMS, Ser. No. 10/441,632, now U.S. Pat. No. 7,000,818, the disclosure of which is hereby incorporated by reference in its entirety.

With particular reference to FIG. 204, the distal end of the shaft frame 9070 is attached to the staple channel 9018. The anvil 9022 has a proximal pivoting end 9072 that is pivotally received within a proximal end 9074 of the staple channel 9018, just distal to its engagement to the shaft frame 9070. When the anvil 9022 is pivoted downwardly, the anvil 9022 moves a tissue contacting surface 9028 and forming pockets 9026 toward an opposing staple cartridge, described in greater detail further below. The pivoting end 9072 of the anvil 9022 includes a closure feature 9076 proximate but distal to its pivotal attachment with the staple channel 9018. Thus, a closure tube 9078, whose distal end includes a horseshoe aperture 9080 that engages this closure feature 9076, selectively imparts an opening motion to the anvil 9022 during proximal longitudinal motion and a closing motion to the anvil 9022 during distal longitudinal motion of the closure tube 9078 sliding over the shaft frame 9070 in response to a closure trigger, similar to the above. The shaft frame 9070 encompasses and guides a firing motion from the handle through a longitudinally reciprocating, two-piece knife and firing bar 9090. In particular, the shaft frame 9070 includes a longitudinal firing bar slot 9092 that receives a proximal portion of the two-piece knife and firing bar 9090, specifically a laminate tapered firing bar 9094. It should be appreciated that the laminated tapered firing bar 9094 may be substituted with a solid firing bar and/or any other suitable materials.

An E-beam 9102 is the distal portion of the two-piece knife and firing bar 9090, which facilitates separate closure and firing as well as spacing of the anvil 9022 from the elongate staple channel 9018 during firing. With particular reference to FIGS. 204 and 205, in addition to any attachment treatment such as brazing or an adhesive, the knife and firing bar 9090 are formed of a female vertical attachment aperture 9104 proximally formed in the E-beam 9102 that receives a corresponding male attachment member 9106 distally presented by the laminated tapered firing bar 9094, allowing each portion to be formed of a selected material and process suitable for their disparate functions (e.g., strength, flexibility, friction). The E-beam 9102 may be advantageously formed of a material having suitable material properties for forming a pair of top pins 9110, a pair of middle pins 9112 and a bottom pin or foot 9114, as well as being able to acquire a sharp cutting edge 9116. In addition, integrally formed and proximally projecting top guide 9118 and middle guide 9120 bracketing each vertical end of the cutting edge 9116 further define a tissue staging area 9122 assisting in guiding tissue to the sharp cutting edge 9116 prior to being severed. The middle guide 9120 also serves to engage and fire the staple applying apparatus 9012 by abutting a stepped central member 9124 of a wedge sled 9126 (FIG. 206) that effects staple formation by the staple applying assembly 9012, as described in greater detail below. Forming these features (e.g., top pins 9110, middle pins 9112, and bottom foot 9114) integrally with the E-beam 9102 facilitates manufacturing at tighter tolerances relative to one another as compared to being assembled from a plurality of parts, ensuring desired operation during firing and/or effective interaction with various lockout features of the staple applying assembly 9012.

In FIGS. 207 and 208, the staple applying assembly 9012 is shown open, with the E-beam 9102 fully retracted. During assembly, the lower foot 9114 of the E-beam 9102 is dropped through a widened hole 9130 in the staple channel 9018 and the E-beam 9102 is then advanced such that the E-beam 9102 slides distally along a lower track 9132 formed in the staple channel 9018. In particular, the lower track 9132 includes a narrow slot 9133 that opens up as a widened slot 9134 on an undersurface of the staple channel 9018 to form an inverted T-shape in lateral cross section, as depicted particularly in FIGS. 208 and 209, which communicates with the widened hole 9130. Once assembled, the components proximally coupled to the laminate tapered firing bar 9094 do not allow the lower foot 9114 to proximally travel again to the widened hole 9130 to permit disengagement. Referring to FIG. 210, the laminate tapered firing bar 9094 facilitates insertion of the staple applying assembly 9012 through a trocar. In particular, a more distal, downward projection 9136 raises the E-beam 9102 when fully retracted. This is accomplished by placement of the downward projection 9136 at a point where it cams upwardly on a proximal edge of the widened hole 9130 in the staple channel 9018. Referring now to FIG. 211, the laminate tapered firing bar 9094 also enhances operation of certain lockout features that may be incorporated into the staple channel 9018 by including a more proximal upward projection 9138 that is urged downwardly by the shaft frame 9070 during an initial portion of the firing travel. In particular, a lateral bar 9140 is defined between a pair of square apertures 9142 in the shaft frame 9070 (FIG. 204). A clip spring 9144 that encompasses the lateral bar 9140 downwardly urges a portion of the laminate tapered firing bar 9094 projecting distally out of the longitudinal firing bar slot 9092, which ensures certain advantageous lockout features are engaged when appropriate. This urging is more pronounced or confined solely to that portion of the firing travel when the upward projection 9138 contacts the clip spring 9144.

In FIGS. 207 and 208, the E-beam 9102 is retracted with the top pins 9110 thereof residing within an anvil pocket 9150 near the pivoting proximal end of the anvil 9022. A downwardly open vertical anvil slot 9152 (FIG. 203) laterally widens in the anvil 9022 into an anvil internal track 9154 that captures the top pins 9110 of the E-beam 9102 as they distally advance during firing, as depicted in FIGS. 210 and 211, affirmatively spacing the anvil 9022 from the staple channel 9018. Thus, with the E-beam 9102 retracted, the surgeon is able to repeatably open and close the staple applying assembly 9012 until satisfied with the placement and orientation of tissue captured therein for stapling and severing, yet the E-beam 9102 assists in proper positioning of tissue even for a staple applying assembly 9012 of reduced diameter and correspondingly reduced rigidity. In FIGS. 203, 204, 206, 207, 209, and 215, the staple applying assembly 9012 is shown with the replaceable staple cartridge 9020 that includes the wedge sled 9126. Longitudinally aligned and parallel plurality of downwardly open wedge slots 9202 (FIG. 209) receive respective wedges 9204 integral to the wedge sled 9126. In FIGS. 209-211, the wedge sled 9126 thus cams upwardly a plurality of staple drivers 9206 that are vertically slidable within staple driver recesses 9208. In this illustrative version, each staple driver 9206 includes two vertical prongs, each translating upwardly into a respective staple hole 9210, or cavity 9024, to upwardly force out and deform a staple 9023 resting thereupon against a staple forming surface 9214 (FIG. 211) of the anvil 9022. A central firing recess 9216 (FIG. 204) defined within the staple cartridge 9020 proximate to the staple channel 9018 allows the passage of the bottom, horizontal portion 9218 (FIG. 206) of the wedge sled 9126 as well as the middle pins 9112 of the E-beam 9102. Specifically, a staple cartridge tray 9220 (FIGS. 204, 209) attaches to and underlies a polymer staple cartridge body 9222 that has the staple driver recesses 9208, staple holes 9210, and central firing recess 9216 formed therein. As staples 9023 are thus formed to either side, the sharp cutting edge 9116 enters a vertical through slot 9230 passing through the longitudinal axis of the staple cartridge 9020, excepting only a most distal end thereof.

Firing the staple applying assembly 9012 begins as depicted in FIG. 211 with the two-piece knife and firing bar 9090 proximally drawn until the downward projection 9136 cams the middle guide 9120 on the E-beam 9102 upward and aft, allowing a new staple cartridge 9020 to be inserted into the staple channel 9018 when the anvil 9022 is open as depicted in FIGS. 203 and 207. In FIG. 212, the two-piece knife and firing bar 9090 has been distally advanced a small distance, allowing the downward projection 9136 to drop into the widened hole 9130 of the lower track 9132 under the urging of the clip spring 9144 against the upward projection 9138 of the laminate tapered firing bar 9094. The middle guide 9120 prevents further downward rotation by resting upon the stepped central member 9124 of the wedge sled 9126, thus maintaining the middle pin 9112 of the E-beam within the central firing recess 9216. In FIG. 213, the two-piece knife and firing bar 9090 has been distally fired, advancing the wedge sled 9126 to cause formation of staples 9023 while severing tissue 9242 clamped between the anvil 9022 and staple cartridge 9020 with the sharp cutting edge 9116. Thereafter, in FIG. 214, the two-piece knife and firing bar 9090 is retracted, leaving the wedge sled 9126 distally positioned. In FIG. 215, the middle pin 9112 is allowed to translate down into a lockout recess 9240 formed in the staple channel 9018 (also see FIGS. 208, 211). Thus, the operator would receive a tactile indication as the middle pin 9112 encounters the distal edge of the lockout recess 9240 when the wedge sled 9126 (not shown in FIG. 215) is not proximally positioned (i.e., missing staple cartridge 9020 or spent staple cartridge 9020). Similar surgical stapling instruments are disclosed in U.S. Pat. No. 7,380,696, which issued on Jun. 3, 2008, the entire disclosure of which is incorporated by reference herein.

In various embodiments, as described above, a staple cartridge can comprise a cartridge body including a plurality of staple cavities defined therein. The cartridge body can comprise a deck and a top deck surface wherein each staple cavity can define an opening in the deck surface. As also described above, a staple can be positioned within each staple cavity such that the staples are stored within the cartridge body until they are ejected therefrom. Prior to being ejected from the cartridge body, in various embodiments, the staples can be contained with the cartridge body such that the staples do not protrude above the deck surface. As the staples are positioned below the deck surface, in such embodiments, the possibility of the staples becoming damaged and/or prematurely contacting the targeted tissue can be reduced. In various circumstances, the staples can be moved between an unfired position in which they do not protrude from the cartridge body and a fired position in which they have emerged from the cartridge body and can contact an anvil positioned opposite the staple cartridge. In various embodiments, the anvil, and/or the forming pockets defined within the anvil, can be positioned a predetermined distance above the deck surface such that, as the staples are being deployed from the cartridge body, the staples are deformed to a predetermined formed height. In some circumstances, the thickness of the tissue captured between the anvil and the staple cartridge may vary and, as a result, thicker tissue may be captured within certain staples while thinner tissue may be captured within certain other staples. In either event, the clamping pressure, or force, applied to the tissue by the staples may vary from staple to staple or vary between a staple on one end of a staple row and a staple on the other end of the staple row, for example. In certain circumstances, the gap between the anvil and the staple cartridge deck can be controlled such that the staples apply a certain minimum clamping pressure within each staple. In some such circumstances, however, significant variation of the clamping pressure within different staples may still exist.

In various embodiments described herein, a staple cartridge can comprise means for compensating for the thickness of the tissue captured within the staples deployed from the staple cartridge. In various embodiments, referring to FIG. 216, a staple cartridge, such as staple cartridge 10000, for example, can include a rigid first portion, such as support portion 10010, for example, and a compressible second portion, such as tissue thickness compensator 10020, for example. In at least one embodiment, referring primarily to FIG. 218, the support portion 10010 can comprise a cartridge body, a top deck surface 10011, and a plurality of staple cavities 10012 wherein, similar to the above, each staple cavity 10012 can define an opening in the deck surface 10011. A staple 10030, for example, can be removably positioned in each staple cavity 10012. In at least one such embodiment, referring primarily to FIG. 245 and as described in greater detail below, each staple 10030 can comprise a base 10031 and one or more legs 10032 extending from the base 10031. Prior to the staples 10030 being deployed, as also described in greater detail below, the bases 10031 of the staples 10030 can be supported by staple drivers positioned within the support portion 10010 and, concurrently, the legs 10032 of the staples 10030 can be at least partially contained within the staple cavities 10012. In various embodiments, the staples 10030 can be deployed between an unfired position and a fired position such that the legs 10032 move through the tissue thickness compensator 10020, penetrate through a top surface of the tissue thickness compensator 10020, penetrate the tissue T, and contact an anvil positioned opposite the staple cartridge 10000. As the legs 10032 are deformed against the anvil, the legs 10032 of each staple 10030 can capture a portion of the tissue thickness compensator 10020 and a portion of the tissue T within each staple 10030 and apply a compressive force to the tissue. Further to the above, the legs 10032 of each staple 10030 can be deformed downwardly toward the base 10031 of the staple to form a staple entrapment area 10039 in which the tissue T and the tissue thickness compensator 10020 can be captured. In various circumstances, the staple entrapment area 10039 can be defined between the inner surfaces of the deformed legs 10032 and the inner surface of the base 10031. The size of the entrapment area for a staple can depend on several factors such as the length of the legs, the diameter of the legs, the width of the base, and/or the extent in which the legs are deformed, for example.

In previous embodiments, a surgeon was often required to select the appropriate staples having the appropriate staple height for the tissue being stapled. For example, a surgeon could select tall staples for use with thick tissue and short staples for use with thin tissue. In some circumstances, however, the tissue being stapled did not have a consistent thickness and, thus, some staples were unable to achieve the desired fired configuration. For example, FIG. 250 illustrates a tall staple used in thin tissue. Referring now to FIG. 251, when a tissue thickness compensator, such as tissue thickness compensator 10020, for example, is used with thin tissue, for example, the larger staple may be formed to a desired fired configuration.

Owing to the compressibility of the tissue thickness compensator, the tissue thickness compensator can compensate for the thickness of the tissue captured within each staple. More particularly, referring now to FIGS. 245 and 246, a tissue thickness compensator, such as tissue thickness compensator 10020, for example, can consume larger and/or smaller portions of the staple entrapment area 10039 of each staple 10030 depending on the thickness and/or type of tissue contained within the staple entrapment area 10039. For example, if thinner tissue T is captured within a staple 10030, the tissue thickness compensator 10020 can consume a larger portion of the staple entrapment area 10039 as compared to circumstances where thicker tissue T is captured within the staple 10030. Correspondingly, if thicker tissue T is captured within a staple 10030, the tissue thickness compensator 10020 can consume a smaller portion of the staple entrapment area 10039 as compared to the circumstances where thinner tissue T is captured within the staple 10030. In this way, the tissue thickness compensator can compensate for thinner tissue and/or thicker tissue and assure that a compressive pressure is applied to the tissue irrespective, or at least substantially irrespective, of the tissue thickness captured within the staples. In addition to the above, the tissue thickness compensator 10020 can compensate for different types, or compressibilities, of tissues captured within different staples 10030. Referring now to FIG. 246, the tissue thickness compensator 10020 can apply a compressive force to vascular tissue T which can include vessels V and, as a result, restrict the flow of blood through the less compressible vessels V while still applying a desired compressive pressure to the surrounding tissue T. In various circumstances, further to the above, the tissue thickness compensator 10020 can also compensate for malformed staples. Referring to FIG. 247, the malformation of various staples 10030 can result in larger staple entrapment areas 10039 being defined within such staples. Owing to the resiliency of the tissue thickness compensator 10020, referring now to FIG. 248, the tissue thickness compensator 10020 positioned within malformed staples 10030 may still apply a sufficient compressive pressure to the tissue T even though the staple entrapment areas 10039 defined within such malformed staples 10030 may be enlarged. In various circumstances, the tissue thickness compensator 10020 located intermediate adjacent staples 10030 can be biased against the tissue T by properly-formed staples 10030 surrounding a malformed staple 10030 and, as a result, apply a compressive pressure to the tissue surrounding and/or captured within the malformed staple 10030, for example. In various circumstances, a tissue thickness compensator can compensate for different tissue densities which can arise due to calcifications, fibrous areas, and/or tissue that has been previously stapled or treated, for example.

In various embodiments, a fixed, or unchangeable, tissue gap can be defined between the support portion and the anvil and, as a result, the staples may be deformed to a predetermined height regardless of the thickness of the tissue captured within the staples. When a tissue thickness compensator is used with these embodiments, the tissue thickness compensator can adapt to the tissue captured between the anvil and the support portion staple cartridge and, owing to the resiliency of the tissue thickness compensator, the tissue thickness compensator can apply an additional compressive pressure to the tissue. Referring now to FIGS. 252-257, a staple 10030 has been formed to a predefined height H. With regard to FIG. 252, a tissue thickness compensator has not been utilized and the tissue T consumes the entirety of the staple entrapment area 10039. With regard to FIG. 259, a portion of a tissue thickness compensator 10020 has been captured within the staple 10030, compressed the tissue T, and consumed at least a portion of the staple entrapment area 10039. Referring now to FIG. 254, thin tissue T has been captured within the staple 10030. In this embodiment, the compressed tissue T has a height of approximately ⅔H and the compressed tissue thickness compensator 10020 has a height of approximately ⅞H, for example. Referring now to FIG. 255, tissue T having an intermediate thickness has been captured within the staple 10030. In this embodiment, the compressed tissue T has a height of approximately ⅘H and the compressed tissue thickness compensator 10020 has a height of approximately ⅝H, for example. Referring now to FIG. 256, tissue T having an intermediate thickness has been captured within the staple 10030. In this embodiment, the compressed tissue T has a height of approximately ⅔H and the compressed tissue thickness compensator 10020 has a height of approximately ⅓H, for example. Referring now to FIG. 255, thick tissue T has been captured within the staple 10030. In this embodiment, the compressed tissue T has a height of approximately ⅝H and the compressed tissue thickness compensator 10020 has a height of approximately ⅑H, for example. In various circumstances, the tissue thickness compensator can comprise a compressed height which comprises approximately 10% of the staple entrapment height, approximately 20% of the staple entrapment height, approximately 30% of the staple entrapment height, approximately 40% of the staple entrapment height, approximately 50% of the staple entrapment height, approximately 60% of the staple entrapment height, approximately 70% of the staple entrapment height, approximately 80% of the staple entrapment height, and/or approximately 90% of the staple entrapment height, for example.

In various embodiments, the staples 10030 can comprise any suitable unformed height. In certain embodiments, the staples 10030 can comprise an unformed height between approximately 2 mm and approximately 4.8 mm, for example. The staples 10030 can comprise an unformed height of approximately 2.0 mm, approximately 2.5 mm, approximately 3.0 mm, approximately 3.4 mm, approximately 3.5 mm, approximately 3.8 mm, approximately 4.0 mm, approximately 4.1 mm, and/or approximately 4.8 mm, for example. In various embodiments, the height H to which the staples can be deformed can be dictated by the distance between the deck surface 10011 of the support portion 10010 and the opposing anvil. In at least one embodiment, the distance between the deck surface 10011 and the tissue-contacting surface of the anvil can be approximately 0.097", for example. The height H can also be dictated by the depth of the forming pockets defined within the anvil. In at least one embodiment, the forming pockets can have a depth measured from the tissue-contacting surface, for example. In various embodiments, as described in greater detail below, the staple cartridge 10000 can further comprise staple drivers which can lift the staples 10030 toward the anvil and, in at least one embodiment, lift, or "overdrive", the staples above the deck surface 10011. In such embodiments, the height H to which the staples 10030 are formed can also be dictated by the distance in which the staples 10030 are overdriven. In at least one such embodiment, the staples 10030 can be overdriven by approximately 0.028", for example, and can result in the staples 10030 being formed to a height of approximately 0.189", for example. In various embodiments, the staples 10030 can be formed to a height of approximately 0.8 mm, approximately 1.0 mm, approximately 1.5 mm, approximately 1.8 mm, approximately 2.0 mm, and/or approximately 2.25 mm, for example. In certain embodiments, the staples can be formed to a height between approximately 2.25 mm and approximately 3.0 mm, for example. Further to the above, the height of the staple entrapment area of a staple can be determined by the formed height of the staple and the width, or diameter, of the wire comprising the staple. In various embodiments, the height of the staple entrapment area 10039 of a staple 10030 can comprise the formed height H of the staple less two diameter widths of the wire. In certain embodiments, the staple wire can comprise a diameter of approximately 0.0089", for example. In various embodiments, the staple wire can comprise a diameter between approximately 0.0069" and approximately 0.0119", for example. In at least one exemplary embodiment, the formed height H of a staple 10030 can be approximately 0.189" and the staple wire diameter can be approximately 0.0089" resulting in a staple entrapment height of approximately 0.171", for example.

In various embodiments, further to the above, the tissue thickness compensator can comprise an uncompressed, or pre-deployed, height and can be configured to deform to one of a plurality of compressed heights. In certain embodiments, the tissue thickness compensator can comprise an uncompressed height of approximately 0.125", for example. In various embodiments, the tissue thickness compensator can comprise an uncompressed height of greater than or equal to approximately 0.080", for example. In at least one embodiment, the tissue thickness compensator can comprise an uncompressed, or pre-deployed, height which is greater than the unfired height of the staples. In at least one embodiment, the uncompressed, or pre-deployed, height of the tissue thickness compensator can be approximately 10% taller, approximately 20% taller, approximately 30% taller, approximately 40% taller, approximately 50% taller, approximately 60% taller, approximately 70% taller, approximately 80% taller, approximately 90% taller, and/or approximately 100% taller than the unfired height of the staples, for example. In at least one embodiment, the uncompressed, or pre-deployed, height of the tissue thickness compensator can be up to approximately 100% taller than the unfired height of the staples, for example. In certain embodiments, the uncompressed, or pre-deployed, height of the tissue thickness compensator can be over 100% taller than the unfired height of the staples, for example. In at least one embodiment, the tissue thickness compensator can comprise an uncompressed height which is equal to the unfired height of the staples. In at least one embodiment, the tissue thickness compensator can comprise an uncompressed height which is less than the unfired height of the staples. In at least one embodiment, the uncompressed, or pre-deployed, height of the thickness compensator can be approximately 10% shorter, approximately 20% shorter, approximately 30% shorter, approximately 40% shorter, approximately 50% shorter, approximately 60% shorter, approximately 70% shorter, approximately 80% shorter, and/or approximately 90% shorter than the unfired height of the staples, for example. In various embodiments, the compressible second portion can comprise an uncompressed height which is taller than an uncompressed height of the tissue T being stapled. In certain embodiments, the tissue thickness compensator can comprise an uncompressed height which is equal to an uncompressed height of the tissue T being stapled. In various embodiments, the tissue thickness compensator can comprise an uncompressed height which is shorter than an uncompressed height of the tissue T being stapled.

As described above, a tissue thickness compensator can be compressed within a plurality of formed staples regardless of whether thick tissue or thin tissue is captured within the staples. In at least one exemplary embodiment, the staples within a staple line, or row, can be deformed such that the staple entrapment area of each staple comprises a height of approximately 2.0 mm, for example, wherein the tissue T and the tissue thickness compensator can be compressed within this height. In certain circumstances, the tissue T can comprise a compressed height of approximately 1.75 mm within the staple entrapment area while the tissue thickness compensator can comprise a compressed height of approximately 0.25 mm within the staple entrapment area, thereby totaling the approximately 2.0 mm staple entrapment area height, for example. In certain circumstances, the tissue T can comprise a compressed height of approximately 1.50 mm within the staple entrapment area while the tissue thickness compensator can comprise a compressed height of approximately 0.50 mm within the staple entrapment area, thereby totaling the approximately 2.0 mm staple entrapment area height, for example. In certain circumstances, the tissue T can comprise a compressed height of approximately 1.25 mm within the staple entrapment area while the tissue thickness compensator can comprise a compressed height of approximately 0.75 mm within the staple entrapment area, thereby totaling the approximately 2.0 mm staple entrapment area height, for example. In certain circumstances, the tissue T can comprise a compressed height of approximately 1.0 mm within the staple entrapment area while the tissue thickness compensator can comprise a compressed height of approximately 1.0 mm within the staple entrapment area, thereby totaling the approximately 2.0 mm staple entrapment area height, for example. In certain circumstances, the tissue T can comprise a compressed height of approximately 0.75 mm within the staple entrapment area while the tissue thickness compensator can comprise a compressed height of approximately 1.25 mm within the staple entrapment area, thereby totaling the approximately 2.0 mm staple entrapment area height, for example. In certain circumstances, the tissue T can comprise a compressed height of approximately 1.50 mm within the staple entrapment area while the tissue thickness compensator can comprise a compressed height of approximately 0.50 mm within the staple entrapment area, thereby totaling the approximately 2.0 mm staple entrapment area height, for example. In certain circumstances, the tissue T can comprise a compressed height of approximately 0.25 mm within the staple entrapment area while the tissue thickness compensator can comprise a compressed height of approximately 1.75 mm within the staple entrapment area, thereby totaling the approximately 2.0 mm staple entrapment area height, for example.

In various embodiments, further to the above, the tissue thickness compensator can comprise an uncompressed height which is less than the fired height of the staples. In certain embodiments, the tissue thickness compensator can comprise an uncompressed height which is equal to the fired height of the staples. In certain other embodiments, the tissue thickness compensator can comprise an uncompressed height which is taller than the fired height of the staples. In at least one such embodiment, the uncompressed height of a tissue thickness compensator can comprise a thickness which is approximately 110% of the formed staple height, approximately 120% of the formed staple height, approximately 130% of the formed staple height, approximately 140% of the formed staple height, approximately 150% of the formed staple height, approximately 160% of the formed staple height, approximately 170% of the formed staple height, approximately 180% of the formed staple height, approximately 190% of the formed staple height, and/or approximately 200% of the formed staple height, for example. In certain embodiments, the tissue thickness compensator can comprise an uncompressed height which is more than twice the fired height of the staples. In various embodiments, the tissue thickness compensator can comprise a compressed height which is from approximately 85% to approximately 150% of the formed staple height, for example. In various embodiments, as described above, the tissue thickness compensator can be compressed between an uncompressed thickness and a compressed thickness. In certain embodiments, the compressed thickness of a tissue thickness compensator can be approximately 10% of its uncompressed thickness, approximately 20% of its uncompressed thickness, approximately 30% of its uncompressed thickness, approximately 40% of its uncompressed thickness, approximately 50% of its uncompressed thickness, approximately 60% of its uncompressed thickness, approximately 70% of its uncompressed thickness, approximately 80% of its uncompressed thickness, and/or approximately 90% of its uncompressed thickness, for example. In various embodiments, the uncompressed thickness of the tissue thickness compensator can be approximately two times, approximately ten times, approximately fifty times, and/or approximately one hundred times thicker than its compressed thickness, for example. In at least one embodiment, the compressed thickness of the tissue thickness compensator can be between approximately 60% and approximately 99% of its uncompressed thickness. In at least one embodiment, the uncompressed thickness of the tissue thickness compensator can be at least 50% thicker than its compressed thickness. In at least one embodiment, the uncompressed thickness of the tissue thickness compensator can be up to one hundred times thicker than its compressed thickness. In various embodiments, the compressible second portion can be elastic, or at least partially elastic, and can bias the tissue T against the deformed legs of the staples. In at least one such embodiment, the compressible second portion can resiliently expand between the tissue T and the base of the staple in order to push the tissue T against the legs of the staple. In certain embodiments, discussed in further detail below, the tissue thickness compensator can be positioned intermediate the tissue T and the deformed staple legs. In various circumstances, as a result of the above, the tissue thickness compensator can be configured to consume any gaps within the staple entrapment area.

In various embodiments, the tissue thickness compensator may comprise a polymeric composition. The polymeric composition may comprise one or more synthetic polymer and/or one or more non-synthetic polymer. The synthetic polymer may comprise a synthetic absorbable polymer and/or a synthetic non-absorbable polymer. In various embodiments, the polymeric composition may comprise a biocompatible foam, for example. The biocompatible foam may comprise a porous, open cell foam and/or a porous, closed cell foam, for example. The biocompatible foam can have a uniform pore morphology or may have a gradient pore morphology (i.e. small pores gradually increasing in size to large pores across the thickness of the foam in one direction). In various embodiments, the polymeric composition may comprise one or more of a porous scaffold, a porous matrix, a gel matrix, a hydrogel matrix, a solution matrix, a filamentous matrix, a tubular matrix, a composite matrix, a membranous matrix, a biostable polymer, and a biodegradable polymer, and combinations thereof. For example, the tissue thickness compensator may comprise a foam reinforced by a filamentous matrix or may comprise a foam having an additional hydrogel layer that expands in the presence of bodily fluids to further provide the compression on the tissue. In various embodiments, a tissue thickness compensator could also be comprised of a coating on a material and/or a second or third layer that expands in the presence of bodily fluids to further provide the compression on the tissue. Such a layer could be a hydrogel that could be a synthetic and/or naturally derived material and could be either biodurable and/or biodegradable, for example. In certain embodiments, a tissue thickness compensator could be reinforced with fibrous non-woven materials or fibrous mesh type elements, for example, that can provide additional flexibility, stiffness, and/or strength. In various embodiments, a tissue thickness compensator that has a porous morphology which exhibits a gradient structure such as, for example, small pores on one surface and larger pores on the other surface. Such morphology could be more optimal for tissue in-growth or hemostatic behavior. Further, the gradient could be also compositional with a varying bio-absorption profile. A short term absorption profile may be preferred to address hemostasis while a long term absorption profile may address better tissue healing without leakages.

Examples of non-synthetic polymers include, but are not limited to, lypholized polysaccharide, glycoprotein, elastin, proteoglycan, gelatin, collagen, and oxidized regenerated cellulose (ORC). Examples of synthetic absorbable polymers include, but are not limited to, poly(lactic acid) (PLA), poly(L-lactic acid) (PLLA), polycaprolactone (PCL), polyglycolic acid (PGA), poly(trimethylene carbonate) (TMC), polyethylene terephthalate (PET), polyhydroxyalkanoate (PHA), a copolymer of glycolide and ε-caprolactone (PGCL), a copolymer of glycolide and-trimethylene carbonate, poly(glycerol sebacate) (PGS), polydioxanone, poly(orthoesters), polyanhydrides, polysaccharides, poly(ester-amides), tyrosine-based polyarylates, tyrosine-based polyiminocarbonates, tyrosine-based polycarbonates, poly(D,L-lactide-urethane), poly(B-hydroxybutyrate), poly(E-caprolactone), polyethyleneglycol (PEG), poly[bis(carboxylatophenoxy)phosphazene], poly(amino acids), pseudo-poly(amino acids), absorbable polyurethanes, and combinations thereof. In various embodiments, the polymeric composition may comprise from approximately 50% to approximately 90% by weight of the polymeric composition of PLLA and approximately 50% to approximately 10% by weight of the polymeric composition of PCL, for example. In at least one embodiment, the polymeric composition may comprise approximately 70% by weight of PLLA and approximately 30% by weight of PCL, for example. In various embodiments, the polymeric composition may comprise from approximately 55% to approximately 85% by weight of the polymeric composition of PGA and 15% to 45% by weight of the polymeric composition of PCL, for example. In at least one embodiment, the polymeric composition may comprise approximately 65% by weight of PGA and approximately 35% by weight of PCL, for example. In various embodiments, the polymeric composition may comprise from approximately 90% to approximately 95% by weight of the polymeric composition of PGA and approximately 5% to approximately 10% by weight of the polymeric composition of PLA, for example.

In various embodiments, the synthetic absorbable polymer may comprise a bioabsorbable, biocompatible elastomeric copolymer. Suitable bioabsorbable, biocompatible elastomeric copolymers include but are not limited to copolymers of epsilon-caprolactone and glycolide (preferably having a mole ratio of epsilon-caprolactone to glycolide of from about 30:70 to about 70:30, preferably 35:65 to about 65:35, and more preferably 45:55 to 35:65); elastomeric copolymers of epsilon-caprolactone and lactide, including L-lactide, D-lactide blends thereof or lactic acid copolymers (preferably having a mole ratio of epsilon-caprolactone to lactide of from about 35:65 to about 65:35 and more preferably 45:55 to 30:70) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of epsilon-caprolactone and p-dioxanone (preferably having a mole ratio of epsilon-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. In one embodiment, the elastomeric copolymer is a copolymer of glycolide and epsilon-caprolactone. In another embodiment, the elastomeric copolymer is a copolymer of lactide and epsilon-caprolactone.

The disclosures of U.S. Pat. No. 5,468,253, entitled ELASTOMERIC MEDICAL DEVICE, which issued on Nov. 21, 1995, and U.S. Pat. No. 6,325,810, entitled FOAM BUTTRESS FOR STAPLING APPARATUS, which issued on Dec. 4, 2001, are hereby incorporated by reference in their respective entireties.

In various embodiments, the synthetic absorbable polymer may comprise one or more of 90/10 poly(glycolide-L-lactide) copolymer, commercially available from Ethicon, Inc. under the trade designation VICRYL (polyglactic 910), polyglycolide, commercially available from American Cyanamid Co. under the trade designation DEXON, polydioxanone, commercially available from Ethicon, Inc. under the trade designation PDS, poly(glycolide-trimethylene carbonate) random block copolymer, commercially available from American Cyanamid Co. under the trade designation MAXON, 75/25 poly(glycolide-E-caprolactone-poliglecaprolactone 25) copolymer, commercially available from Ethicon under the trade designation MONOCRYL, for example.

Examples of synthetic non-absorbable polymers include, but are not limited to, foamed polyurethane, polypropylene (PP), polyethylene (PE), polycarbonate, polyamides, such as nylon, polyvinylchloride (PVC), polymethylmetacrylate (PMMA), polystyrene (PS), polyester, polyetheretherketone (PEEK), polytetrafluoroethylene (PTFE), polytrifluorochloroethylene (PTFCE), polyvinylfluoride (PVF), fluorinated ethylene propylene (FEP), polyacetal, polysulfone, and combinations thereof. The synthetic non-absorbable polymers may include, but are not limited to, foamed elastomers and porous elastomers, such as, for example, silicone, polyisoprene, and rubber. In various embodiments, the synthetic polymers may comprise expanded polytetrafluoroethylene (ePTFE), commercially available from W. L. Gore & Associates, Inc. under the trade designation GORE-TEX Soft Tissue Patch and co-polyetherester urethane foam commercially available from Polyganics under the trade designation NASOPORE.

The polymeric composition of a tissue thickness compensator may be characterized by percent porosity, pore size, and/or hardness, for example. In various embodiments, the polymeric composition may have a percent porosity from approximately 30% by volume to approximately 99% by volume, for example. In certain embodiments, the polymeric composition may have a percent porosity from approximately 60% by volume to approximately 98% by volume, for example. In various embodiments, the polymeric composition may have a percent porosity from approximately 85% by volume to approximately 97% by volume, for example. In at least one embodiment, the polymeric composition may comprise approximately 70% by weight of PLLA and approximately 30% by weight of PCL, for example, and can comprise approximately 90% porosity by volume, for example. In at least one such embodiment, as a result, the polymeric composition would comprise approximately 10% copolymer by volume. In at least one embodiment, the polymeric composition may comprise approximately 65% by weight of PGA and approximately 35% by weight of PCL, for example, and can have a percent porosity from approximately 93% by volume to approximately 95% by volume, for example. In various embodiments, the polymeric composition may comprise a greater than 85% porosity by volume. The polymeric composition may have a pore size from approximately 5 micrometers to approximately 2000 micrometers, for example. In various embodiments, the polymeric composition may have a pore size between approximately 10 micrometers to approximately 100 micrometers, for example. In at least one such embodiment, the polymeric composition can comprise a copolymer of PGA and PCL, for example. In certain embodiments, the polymeric composition may have a pore size between approximately 100 micrometers to approximately 1000 micrometers, for example. In at least one such embodiment, the polymeric composition can comprise a copolymer of PLLA and PCL, for example. According to certain aspects, the hardness of a polymeric composition may be expressed in terms of the Shore Hardness, which can defined as the resistance to permanent indentation of a material as determined with a durometer, such as a Shore Durometer. In order to assess the durometer value for a given material, a pressure is applied to the material with a durometer indenter foot in accordance with ASTM procedure D2240-00, entitled, STANDARD TEST METHOD FOR RUBBER PROPERTY-DUROMETER HARDNESS, the entirety of which is incorporated herein by reference. The durometer indenter foot may be applied to the material for a sufficient period of time, such as 15 seconds, for example, wherein a reading is then taken from the appropriate scale. Depending on the type of scale being used, a reading of 0 can be obtained when the indenter foot completely penetrates the material, and a reading of 100 can be obtained when no penetration into the material occurs. This reading is dimensionless. In various embodiments, the durometer may be determined in accordance with any suitable scale, such as Type A and/or Type OO scales, for example, in accordance with ASTM D2240-00. In various embodiments, the polymeric composition of a tissue thickness compensator may have a Shore A hardness value from approximately 4 A to approximately 16 A, for example, which is approximately 45 OO to approximately 65 OO on the Shore OO range. In at least one such embodiment, the polymeric composition can comprise a PLLA/PCL copolymer or a PGA/PCL copolymer, for example. In various embodiments, the polymeric composition of a tissue thickness compensator may have a Shore A Hardness value of less than 15 A. In various embodiments, the polymeric composition of a tissue thickness compensator may have a Shore A Hardness value of less than 10 A. In various embodiments, the polymeric composition of a tissue thickness compensator may have a Shore A Hardness value of less than 5 A. In certain embodiments, the polymeric material may have a Shore OO composition value from approximately 35 OO to approximately 75 OO, for example.

In various embodiments, the polymeric composition may have at least two of the above-identified properties. In various embodiments, the polymeric composition may have at least three of the above-identified properties. The polymeric composition may have a porosity from 85% to 97% by volume, a pore size from 5 micrometers to 2000 micrometers, and a Shore A hardness value from 4 A to 16 A and Shore OO hardness value from 45 OO to 65 OO, for example. In at least one embodiment, the polymeric composition may comprise 70% by weight of the polymeric composition of PLLA and 30% by weight of the polymeric composition of PCL having a porosity of 90% by volume, a pore size from 100 micrometers to 1000 micrometers, and a Shore A hardness value from 4 A to 16 A and Shore OO hardness value from 45 OO to 65 OO, for example. In at least one embodiment, the polymeric composition may comprise 65% by weight of the polymeric composition of PGA and 35% by weight of the polymeric composition of PCL having a porosity from 93% to 95% by volume, a pore size from 10 micrometers to 100 micrometers, and a Shore A hardness value from 4 A to 16 A and Shore OO hardness value from 45 OO to 65 OO, for example.

In various embodiments, the polymeric composition may comprise a pharmaceutically active agent. The polymeric composition may release a therapeutically effective amount of the pharmaceutically active agent. In various embodiments, the pharmaceutically active agent may be released as the polymeric composition is desorbed/absorbed. In various embodiments, the pharmaceutically active agent may be released into fluid, such as, for example, blood, passing over or through the polymeric composition. Examples of pharmaceutically active agents may include, but are not limited to, hemostatic agents and drugs, such as, for example, fibrin, thrombin, and oxidized regenerated cellulose (ORC); anti-inflammatory drugs, such as, for example, diclofenac, aspirin, naproxen, sulindac, and hydrocortisone; antibiotic and antimicrobial drug or agents, such as, for example, triclosan, ionic silver, ampicillin, gentamicin, polymyxin B, chloramphenicol; and anticancer agents, such as, for example, cisplatin, mitomycin, adriamycin.

In various embodiments, referring now to FIG. 216, a staple cartridge, such as staple cartridge 10000, for example, can comprise a support portion 10010 and a compressible tissue thickness compensator 10020. Referring now to FIGS. 218-220, the support portion 10010 can comprise a deck surface 10011 and a plurality of staple cavities 10012 defined within the support portion 10010. Each staple cavity 10012 can be sized and configured to removably store a staple, such as a staple 10030, for example, therein. The staple cartridge 10000 can further comprise a plurality of staple drivers 10040 which can each be configured to support one or more staples 10030 within the staple cavities 10012 when the staples 10030 and the staple drivers 10040 are in their unfired positions. In at least one such embodiment, referring primarily to FIGS. 224 and 225, each staple driver 10040 can comprise one or more cradles, or troughs, 10041, for example, which can be configured to support the staples and limit relative movement between the staples 10030 and the staple drivers 10040. In various embodiments, referring again to FIG. 218, the staple cartridge 10000 can further comprise a staple-firing sled 10050 which can be moved from a proximal end 10001 to a distal end 10002 of the staple cartridge in order to sequentially lift the staple drivers 10040 and the staples 10030 from their unfired positions toward an anvil positioned opposite the staple cartridge 10000. In certain embodiments, referring primarily to FIGS. 218 and 220, each staple 10030 can comprise a base 10031 and one or more legs 10032 extending from the base 10031 wherein each staple can be at least one of substantially U-shaped and substantially V-shaped, for example. In at least one embodiment, the staples 10030 can be configured such that the tips of the staple legs 10032 are recessed with respect to the deck surface 10011 of the support portion 10010 when the staples 10030 are in their unfired positions. In at least one embodiment, the staples 10030 can be configured such that the tips of the staple legs 10032 are flush with respect to the deck surface 10011 of the support portion 10010 when the staples 10030 are in their unfired positions. In at least one embodiment, the staples 10030 can be configured such that the tips of the staple legs 10032, or at least some portion of the staple legs 10032, extend above the deck surface 10011 of the support portion 10010 when the staples 10030 are in their unfired positions. In such embodiments, the staple legs 10032 can extend into and can be embedded within the tissue thickness compensator 10020 when the staples 10030 are in their unfired positions. In at least one such embodiment, the staple legs 10032 can extend above the deck surface 10011 by approximately 0.075", for example. In various embodiments, the staple legs 10032 can extend above the deck surface 10011 by a distance between approximately 0.025" and approximately 0.125", for example. In certain embodiments, further to the above, the tissue thickness compensator 10020 can comprise an uncompressed thickness between approximately 0.08" and approximately 0.125", for example.

In use, further to the above and referring primarily to FIG. 233, an anvil, such as anvil, 10060, for example, can be moved into a closed position opposite the staple cartridge 10000. As described in greater detail below, the anvil 10060 can position tissue against the tissue thickness compensator 10020 and, in various embodiments, compress the tissue thickness compensator 10020 against the deck surface 10011 of the support portion 10010, for example. Once the anvil 10060 has been suitably positioned, the staples 10030 can be deployed, as also illustrated in FIG. 233. In various embodiments, as mentioned above, the staple-firing sled 10050 can be moved from the proximal end 10001 of the staple cartridge 10000 toward the distal end 10002, as illustrated in FIG. 234. As the sled 10050 is advanced, the sled 10050 can contact the staple drivers 10040 and lift the staple drivers 10040 upwardly within the staple cavities 10012. In at least one embodiment, the sled 10050 and the staple drivers 10040 can each comprise one or more ramps, or inclined surfaces, which can co-operate to move the staple drivers 10040 upwardly from their unfired positions. In at least one such embodiment, referring to FIGS. 221-225, each staple driver 10040 can comprise at least one inclined surface 10042 and the sled 10050 can comprise one or more inclined surfaces 10052 which can be configured such that the inclined surfaces 10052 can slide under the inclined surface 10042 as the sled 10050 is advanced distally within the staple cartridge. As the staple drivers 10040 are lifted upwardly within their respective staple cavities 10012, the staple drivers 10040 can lift the staples 10030 upwardly such that the staples 10030 can emerge from their staple cavities 10012 through openings in the staple deck 10011. During an exemplary firing sequence, referring primarily to FIGS. 227-229, the sled 10050 can first contact staple 10030a and begin to lift the staple 10030a upwardly. As the sled 10050 is advanced further distally, the sled 10050 can begin to lift staples 10030b, 10030c, 10030d, 10030e, and 10030f, and any other subsequent staples, in a sequential order. As illustrated in FIG. 229, the sled 10050 can drive the staples 10030 upwardly such that the legs 10032 of the staples contact the opposing anvil, are deformed to a desired shape, and ejected therefrom the support portion 10010. In various circumstances, the sled 10030 can move several staples upwardly at the same time as part of a firing sequence. With regard to the firing sequence illustrated in FIG. 229, the staples 10030a and 10030b have been moved into their fully fired positions and ejected from the support portion 10010, the staples 10030c and 10030d are in the process of being fired and are at least partially contained within the support portion 10010, and the staples 10030e and 10030f are still in their unfired positions.

As discussed above, and referring to FIG. 235, the staple legs 10032 of the staples 10030 can extend above the deck surface 10011 of the support portion 10010 when the staples 10030 are in their unfired positions. With further regard to this firing sequence illustrated in FIG. 229, the staples 10030e and 10030f are illustrated in their unfired position and their staple legs 10032 extend above the deck surface 10011 and into the tissue thickness compensator 10020. In various embodiments, the tips of the staple legs 10032, or any other portion of the staple legs 10032, may not protrude through a top tissue-contacting surface 10021 of the tissue thickness compensator 10020 when the staples 10030 are in their unfired positions. As the staples 10030 are moved from their unfired positions to their fired positions, as illustrated in FIG. 229, the tips of the staple legs can protrude through the tissue-contacting surface 10032. In various embodiments, the tips of the staple legs 10032 can comprise sharp tips which can incise and penetrate the tissue thickness compensator 10020. In certain embodiments, the tissue thickness compensator 10020 can comprise a plurality of apertures which can be configured to receive the staple legs 10032 and allow the staple legs 10032 to slide relative to the tissue thickness compensator 10020. In certain embodiments, the support portion 10010 can further comprise a plurality of guides 10013 extending from the deck surface 10011. The guides 10013 can be positioned adjacent to the staple cavity openings in the deck surface 10011 such that the staple legs 10032 can be at least partially supported by the guides 10013. In certain embodiments, a guide 10013 can be positioned at a proximal end and/or a distal end of a staple cavity opening. In various embodiments, a first guide 10013 can be positioned at a first end of each staple cavity opening and a second guide 10013 can be positioned at a second end of each staple cavity opening such that each first guide 10013 can support a first staple leg 10032 of a staple 10030 and each second guide 10013 can support a second staple leg 10032 of the staple. In at least one embodiment, referring to FIG. 235, each guide 10013 can comprise a groove or slot, such as groove 10016, for example, within which a staple leg 10032 can be slidably received. In various embodiments, each guide 10013 can comprise a cleat, protrusion, and/or spike that can extend from the deck surface 10011 and can extend into the tissue thickness compensator 10020. In at least one embodiment, as discussed in greater detail below, the cleats, protrusions, and/or spikes can reduce relative movement between the tissue thickness compensator 10020 and the support portion 10010. In certain embodiments, the tips of the staple legs 10032 may be positioned within the guides 10013 and may not extend above the top surfaces of the guides 10013 when the staples 10030 are in their unfired position. In at least such embodiment, the guides 10013 can define a guide height and the staples 10030 may not extend above this guide height when they are in their unfired position.

In various embodiments, a tissue thickness compensator, such as tissue thickness compensator 10020, for example, can be comprised of a single sheet of material. In at least one embodiment, a tissue thickness compensator can comprise a continuous sheet of material which can cover the entire top deck surface 10011 of the support portion 10010 or, alternatively, cover less than the entire deck surface 10011. In certain embodiments, the sheet of material can cover the staple cavity openings in the support portion 10010 while, in other embodiments, the sheet of material can comprise openings which can be aligned, or at least partially aligned, with the staple cavity openings. In various embodiments, a tissue thickness compensator can be comprised of multiple layers of material. In some embodiments, referring now to FIG. 217, a tissue thickness compensator can comprise a compressible core and a wrap surrounding the compressible core. In certain embodiments, a wrap 10022 can be configured to releasably hold the compressible core to the support portion 10010. In at least one such embodiment, the support portion 10010 can comprise one or more projections, such as projections 10014 (FIG. 220), for example, extending therefrom which can be received within one or more apertures and/or slots, such as apertures 10024, for example, defined in the wrap 10022. The projections 10014 and the apertures 10024 can be configured such that the projections 10014 can retain the wrap 10022 to the support portion 10010. In at least one embodiment, the ends of the projections 10014 can be deformed, such as by a heat-stake process, for example, in order to enlarge the ends of the projections 10014 and, as a result, limit the relative movement between the wrap 10022 and the support portion 10010. In at least one embodiment, the wrap 10022 can comprise one or more perforations 10025 which can facilitate the release of the wrap 10022 from the support portion 10010, as illustrated in FIG. 217. Referring now to FIG. 226, a tissue thickness compensator can comprise a wrap 10222 including a plurality of apertures 10223, wherein the apertures 10223 can be aligned, or at least partially aligned, with the staple cavity openings in the support portion 10010. In certain embodiments, the core of the tissue thickness compensator can also comprise apertures which are aligned, or at least partially aligned, with the apertures 10223 in the wrap 10222. In other embodiments, the core of the tissue thickness compensator can comprise a continuous body and can extend underneath the apertures 10223 such that the continuous body covers the staple cavity openings in the deck surface 10011.

In various embodiments, as described above, a tissue thickness compensator can comprise a wrap for releasably holding a compressible core to the support portion 10010. In at least one such embodiment, referring to FIG. 218, a staple cartridge can further comprise retainer clips 10026 which can be configured to inhibit the wrap, and the compressible core, from prematurely detaching from the support portion 10010. In various embodiments, each retainer clip 10026 can comprise apertures 10028 which can be configured to receive the projections 10014 extending from the support portion 10010 such that the retainer clips 10026 can be retained to the support portion 10010. In certain embodiments, the retainer clips 10026 can each comprise at least one pan portion 10027 which can extend underneath the support portion 10010 and can support and retain the staple drivers 10040 within the support portion 10010. In certain embodiments, as described above, a tissue thickness compensator can be removably attached to the support portion 10010 by the staples 10030. More particularly, as also described above, the legs of the staples 10030 can extend into the tissue thickness compensator 10020 when the staples 10030 are in their unfired position and, as a result, releasably hold the tissue thickness compensator 10020 to the support portion 10010. In at least one embodiment, the legs of the staples 10030 can be in contact with the sidewalls of their respective staple cavities 10012 wherein, owing to friction between the staple legs 10032 and the sidewalls, the staples 10030 and the tissue thickness compensator 10020 can be retained in position until the staples 10030 are deployed from the staple cartridge 10000. When the staples 10030 are deployed, the tissue thickness compensator 10020 can be captured within the staples 10030 and held against the stapled tissue T. When the anvil is thereafter moved into an open position to release the tissue T, the support portion 10010 can be moved away from the tissue thickness compensator 10020 which has been fastened to the tissue. In certain embodiments, an adhesive can be utilized to removably hold the tissue thickness compensator 10020 to the support portion 10010. In at least one embodiment, a two-part adhesive can be utilized wherein, in at least one embodiment, a first part of the adhesive can be placed on the deck surface 10011 and a second part of the adhesive can be placed on the tissue thickness compensator 10020 such that, when the tissue thickness compensator 10020 is placed against the deck surface 10011, the first part can contact the second part to active the adhesive and detachably bond the tissue thickness compensator 10020 to the support portion 10010. In various embodiments, any other suitable means could be used to detachably retain the tissue thickness compensator to the support portion of a staple cartridge.

In various embodiments, further to the above, the sled 10050 can be advanced from the proximal end 10001 to the distal end 10002 to fully deploy all of the staples 10030 contained within the staple cartridge 10000. In at least one embodiment, referring now to FIGS. 258-262, the sled 10050 can be advanced distally within a longitudinal cavity 10016 within the support portion 10010 by a firing member, or knife bar, 10052 of a surgical stapler. In use, the staple cartridge 10000 can be inserted into a staple cartridge channel in a jaw of the surgical stapler, such as staple cartridge channel 10070, for example, and the firing member 10052 can be advanced into contact with the sled 10050, as illustrated in FIG. 258. As the sled 10050 is advanced distally by the firing member 10052, the sled 10050 can contact the proximal-most staple driver, or drivers, 10040 and fire, or eject, the staples 10030 from the cartridge body 10010, as described above. As illustrated in FIG. 258, the firing member 10052 can further comprise a cutting edge 10053 which can be advanced distally through a knife slot in the support portion 10010 as the staples 10030 are being fired. In various embodiments, a corresponding knife slot can extend through the anvil positioned opposite the staple cartridge 10000 such that, in at least one embodiment, the cutting edge 10053 can extend between the anvil and the support portion 10010 and incise the tissue and the tissue thickness compensator positioned therebetween. In various circumstances, the sled 10050 can be advanced distally by the firing member 10052 until the sled 10050 reaches the distal end 10002 of the staple cartridge 10000, as illustrated in FIG. 260. At such point, the firing member 10052 can be retracted proximally. In some embodiments, the sled 10050 can be retracted proximally with the firing member 10052 but, in various embodiments, referring now to FIG. 261, the sled 10050 can be left behind in the distal end 10002 of the staple cartridge 10000 when the firing member 10052 is retracted. Once the firing member 10052 has been sufficiently retracted, the anvil can be re-opened, the tissue thickness compensator 10020 can be detached from the support portion 10010, and the remaining non-implanted portion of the expended staple cartridge 10000, including the support portion 10010, can be removed from the staple cartridge channel 10070.

After the expended staple cartridge 10000 has been removed from the staple cartridge channel, further to the above, a new staple cartridge 10000, or any other suitable staple cartridge, can be inserted into the staple cartridge channel 10070. In various embodiments, further to the above, the staple cartridge channel 10070, the firing member 10052, and/or the staple cartridge 10000 can comprise co-operating features which can prevent the firing member 10052 from being advanced distally a second, or subsequent, time without a new, or unfired, staple cartridge 10000 positioned in the staple cartridge channel 10070. More particularly, referring again to FIG. 258, as the firing member 10052 is advanced into contact with the sled 10050 and, when the sled 10050 is in its proximal unfired position, a support nose 10055 of the firing member 10052 can be positioned on and/or over a support ledge 10056 on the sled 10050 such that the firing member 10052 is held in a sufficient upward position to prevent a lock, or beam, 10054 extending from the firing member 10052 from dropping into a lock recess defined within the staple cartridge channel. As the lock 10054 will not drop into the lock recess, in such circumstances, the lock 10054 may not abut a distal sidewall 10057 of the lock recess as the firing member 10052 is advanced. As the firing member 10052 pushes the sled 10050 distally, the firing member 10052 can be supported in its upward firing position owing to the support nose 10055 resting on the support ledge 10056. When the firing member 10052 is retracted relative to the sled 10050, as discussed above and illustrated in FIG. 261, the firing member 10052 can drop downwardly from its upward position as the support nose 10055 is no longer resting on the support ledge 10056 of the sled 10050. In at least one such embodiment, the surgical staple can comprise a spring 10058, and/or any other suitable biasing element, which can be configured to bias the firing member 10052 into its downward position. Once the firing member 10052 has been completely retracted, as illustrated in FIG. 262, the firing member 10052 cannot be advanced distally through the spent staple cartridge 10000 once again. More particularly, the firing member 10052 can't be held in its upper position by the sled 10050 as the sled 10050, at this point in the operating sequence, has been left behind at the distal end 10002 of the staple cartridge 10000. Thus, as mentioned above, in the event that the firing member 10052 is advanced once again without replacing the staple cartridge, the lock beam 10054 will contact the sidewall 10057 of the lock recess which will prevent the firing member 10052 from being advanced distally into the staple cartridge 10000 once again. Stated another way, once the spent staple cartridge 10000 has been replaced with a new staple cartridge, the new staple cartridge will have a proximally-positioned sled 10050 which can hold the firing member 10052 in its upper position and allow the firing member 10052 to be advanced distally once again.

As described above, the sled 10050 can be configured to move the staple drivers 10040 between a first, unfired position and a second, fired position in order to eject staples 10030 from the support portion 10010. In various embodiments, the staple drivers 10040 can be contained within the staple cavities 10012 after the staples 10030 have been ejected from the support portion 10010. In certain embodiments, the support portion 10010 can comprise one or more retention features which can be configured to block the staple drivers 10040 from being ejected from, or falling out of, the staple cavities 10012. In various other embodiments, the sled 10050 can be configured to eject the staple drivers 10040 from the support portion 10010 with the staples 10030. In at least one such embodiment, the staple drivers 10040 can be comprised of a bioabsorbable and/or biocompatible material, such as Ultem, for example. In certain embodiments, the staple drivers can be attached to the staples 10030. In at least one such embodiment, a staple driver can be molded over and/or around the base of each staple 10030 such that the driver is integrally formed with the staple. U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, filed on Sep. 29, 2006, now U.S. Pat. No. 7,794,475, is hereby incorporated by reference in its entirety.

In various circumstances, further to the above, a compressible tissue thickness compensator can move, twist, and/or deflect relative to the underlying rigid support portion of a staple cartridge. In various embodiments, the support portion, and/or any other suitable portion of the staple cartridge, can comprise one or more features configured to limit relative movement between the tissue thickness compensator and the support portion. As described above, at least a portion of the staples 10030 can extend above the deck surface 10011 of the support portion 10010 wherein, in certain circumstances, referring now to FIGS. 263 and 264, lateral forces applied to a tissue thickness compensator 10120, for example, can be resisted by the staples 10030 and/or the cleats 10013 extending from the support portion 10010, for example. In various circumstances, the staples 10030 may tilt and/or bend within the staple cavities 10012 while resisting the lateral movement of the tissue thickness compensator 10120 wherein, in various embodiments, the staple cavities 10012 and the staples 10030 can be sized and configured to maintain the relative alignment between the legs 10032 of the staples 10030 and the forming pockets 10062 in the opposing anvil 10060 such that the staples 10000 are properly formed during the staple forming process. In various embodiments, the staples 10030 and/or the cleats 10013 can be configured to prevent or at least limit lateral distortion within the tissue thickness compensator 10020, as illustrated in FIG. 264. In at least one such embodiment, the staples 10030 and/or cleats 10013, for example, can be configured to stiffen, or limit the lateral and/or longitudinal movement of, a first, or tissue-contacting, surface 10021 of the tissue thickness compensator relative to a second, or bottom, surface 10029. In various embodiments, a staple cartridge, and/or a staple cartridge channel in which the staple cartridge is positioned, can comprise at least one distortion minimizing member which can extend upwardly to limit the lateral and/or longitudinal movement, or distortion, of a tissue thickness compensator. A wrap at least partially surrounding a tissue thickness compensator, as discussed above, may also prevent, or at least limit, the lateral and/or longitudinal movement, or distortion, of the tissue thickness compensator.

In various embodiments, referring again to FIGS. 263 and 264, a tissue thickness compensator, such as tissue thickness compensator 10120, for example, can comprise a core 10128 and a skin 10122. The skin 10122 and the compressible core 10128 can be comprised of different materials or, alternatively, of the same material. In either event, the skin 10122 can have a higher density than the core 10128. In circumstances where the skin 10122 comprises the top of the tissue thickness compensator 10120, the tips of the staple legs 10032 can be embedded in the skin 10122. In embodiments wherein a skin comprises the bottom of the tissue thickness compensator 10120, the staple legs 10032 can extend through the skin and into the core. In either event, the skin of the tissue thickness compensator can assist in holding the staple legs 10032 in alignment with the forming pockets 10062 of the anvil 10060. In various embodiments, the skin 10122 can comprise a density which is approximately 10% greater than the density of the core 10128, approximately 20% greater than the density of the core 10128, approximately 30% greater than the density of the core 10128, approximately 40% greater than the density of the core 10128, approximately 50% greater than the density of the core 10128, approximately 60% greater than the density of the core 10128, approximately 70% greater than the density of the core 10128, approximately 80% greater than the density of the core 10128, approximately 90% greater than the density of the core 10128, and/or approximately 100% greater than the density of the core 10128, for example. In various embodiments, the skin 10122 can comprise a density which is more than the density of the core 10128 and less than twice the density of the core 10128, for example. In various embodiments, the skin 10122 can comprise a density which is over twice the density of the core 10128, for example. In various embodiments, further to the above, the skin 10122 and the core 10128 can be formed, or manufactured, simultaneously. In at least one such embodiment, a fluid comprising any suitable material disclosed herein can be poured into a dish or mold and, while the fluid solidifies, the fluid can form a skin, or layer, which has a higher density than the remainder of the material. In various embodiments, multiple layers within a material can be formed by utilizing a process in which one or more subsequent layers of material are poured onto a previously cured layer. In certain embodiments, two or more layers can be bonded to each other with an adhesive, for example. In some embodiments, two or more layers can be attached to each other by one or more fasteners and/or one or more mechanical interlocking features, for example. In at least one such embodiment, adjacent layers can be connected together by one or more dovetail joints, for example. In certain embodiments, the skin can comprise a sealed surface which can prevent, or at least limit, the flow of fluid therethrough. In certain other embodiments, the skin can comprise an open cell porous structure, for example.

In various embodiments, further to the above, the skin can be cut off of the tissue thickness compensator. In at least one embodiment, the tissue thickness compensator can be cut from a larger block of material such that the tissue thickness compensator does not comprise a skin. In at least one such embodiment, the tissue thickness compensator can be comprised of a homogenous, or at least substantially homogeneous, material, comprising large pores, for example.

In various embodiments, a staple cartridge can comprise a plurality of staple cavities each containing a staple positioned therein wherein the staple cavities can be arranged in a plurality of rows, and wherein an anvil positioned opposite the staple cartridge can comprise a plurality of forming pockets which correspond to the staple cavities in the staple cartridge. Stated another way, the anvil can comprise a plurality of forming pocket rows wherein each forming pocket can be positioned opposite a staple cavity in the staple cartridge. In various embodiments, each forming pocket can comprise two forming cups configured to receive the staple legs 10032 of a staple 10030 wherein each forming cup is configured to receive a staple leg 10032 and form or curl the staple leg 10032 toward the other staple leg 10032, for example. In various circumstances, the legs 10032 may miss or not properly enter into the forming cups and, as a result, the staple legs 10032 may become malformed during the firing sequence. In various embodiments described herein, an anvil can comprise an array, or grid, of forming pockets which are each configured to receive and form a staple leg. In at least one such embodiment, the array of forming pockets can comprise a quantity of forming pockets that exceeds the quantity of staples contained within the staple cartridge. In at least one embodiment, a staple cartridge can comprise six longitudinal rows of staple cavities, for example, wherein the anvil can comprise six rows of forming pockets aligned with the six rows of staple cavities and, in addition, forming pockets positioned intermediate the rows of forming pockets. For example, on one side of the anvil, the anvil can comprise a first row of forming pockets which can be positioned over a first row of staple cavities, a second row of forming pockets which can be positioned over a second row of staple cavities that is adjacent to the first row of staple cavities, and, in addition, a row of forming pockets positioned intermediate the first row of forming pockets and the second row of forming pockets. In various embodiments, referring now to FIGS. 276-279, an anvil 10260 can comprise six rows of forming pockets 10261 which can be configured to be placed over six corresponding rows of staple cavities in the staple cartridge 10200. In at least one such embodiment, rows of intermediate forming pockets 10262 can be positioned intermediate and/or adjacent to the rows of forming pockets 10261. In certain embodiments, referring now to FIGS. 277, 278, and 280, each forming pocket 10261 and 10262 can comprise two forming cups, wherein each forming cup can comprise a distal portion 10263 which can be configured to form or curl a staple leg 10032 proximally and a proximal portion 10264 which can be configured to form or curl a staple leg 10032 distally. In various other circumstances, the staples 10030 can be formed in a variety of other ways. For example, a staple 10030 can be formed such that one leg 10032 is formed outwardly and the other leg 10032 is formed inwardly (FIG. 281), or such that both legs 10032 are formed outwardly (FIG. 282) depending on, one, which forming cups that the staple legs 10032 enter into and/or, two, whether the legs 10032 enter into the proximal portion 10263 or the distal portion 10064 of each forming cup, for example.

In various embodiments, further to the above, each forming pocket 10261 and/or forming pocket 10262 can comprise a triangular or diamond-like shape, for example. In at least one embodiment, each distal portion 10263 and/or each proximal portion 10264 of the forming pockets can comprise a triangular shape wherein, in at least one such embodiment, the triangular shapes of the distal portions 10263 and the proximal portions 10264 can be arranged such that they have vertices pointing in opposite directions. In certain embodiments, an anvil can comprise an array of substantially square forming pockets, for example. In at least one such embodiment, the forming surface of each square forming pocket can comprise an arcuate surface that extends between the sides of the square. In some embodiments, an anvil can comprise an array of circular or spherical dimples, for example. In various embodiments, further to the above, the forming pockets 10261 can be positioned along one or more lines and, similarly, the forming pockets 10262 can also be positioned along one or more lines. In various other embodiments, the forming pockets 10261 and/or the forming pockets 10262 can be arranged in one or more circular rows. In at least one such embodiment, the forming pockets 10261 can be arranged along a primary circumference and the forming pockets 10262 can be arranged along a different circumference. In various embodiments, the primary circumference and the different circumference can be concentric, or at least substantially concentric. In certain embodiments, the forming pockets 10262 can be arranged along an inner circumference positioned radially inwardly with respect to the primary circumference and/or an outer circumference positioned radially outwardly with respect to the primary circumference, for example. In various embodiments, the primary circumference can be defined by a primary diameter, the inner circumference can be defined by an inner diameter, and the outer circumference can be defined by an outer diameter. In at least one such embodiment, the inner diameter can be shorter than the primary diameter and the outer diameter can be longer than the primary diameter.

In various embodiments, as described above, an anvil can be moved from an open position to a closed position in order to compress tissue against the tissue thickness compensator of a staple cartridge, such as tissue thickness compensator 10020, for example. In various circumstances, the tissue thickness compensator can be positioned adjacent to the support portion of the staple cartridge prior to the tissue thickness compensator being positioned relative to the tissue. In certain embodiments, the tissue thickness compensator 10020 can be in a position in which it abuts the support portion 10018 prior to the anvil being moved into its closed position. In certain other embodiments, the tissue thickness compensator 10020 can be in a position in which a gap is present between the tissue thickness compensator 10020 and the support portion 10018. In at least one such embodiment, the anvil can displace the tissue and the tissue thickness compensator 10020 downwardly until the tissue thickness compensator 10020 abuts the support portion 10018 wherein, at such point, the anvil can be moved into is closed position and generate compression within the tissue. In the event that a surgeon is not satisfied with the positioning of the tissue between the anvil and the staple cartridge, the surgeon can open the anvil, adjust the position of the anvil and the staple cartridge, and close the anvil once again. Owing to such positioning and re-positioning of the staple cartridge relative to the tissue, in various circumstances, the distal end of the tissue thickness compensator 10020 may become dislodged from the support portion 10010, for example. In some such circumstances, the distal end of the tissue thickness compensator 10020 can contact the tissue and peel away from, or roll relative to, the support portion 10010. In various embodiments, as described in greater detail below, a staple cartridge can comprise one or more features configured to releasably retain a tissue thickness compensator to an underlying support portion of the staple cartridge In various embodiments, referring now to FIG. 265, a staple cartridge 10300 can comprise a support portion 10310, a tissue thickness compensator 10320 supported by the support portion 10310, and a distal end 10302 which includes a nose 10303 configured to releasably hold a distal end 10325 of the tissue thickness compensator 10320 in position. In at least one embodiment, the nose 10303 can comprise a slot 10305 configured to receive the distal end 10325 of the tissue thickness compensator 10320. In various embodiments, the distal end 10325 can be compressed, or wedged, within the slot 10305 such that the distal end 10325 can be held in place as the staple cartridge 10300 is positioned relative to the tissue. In at least one such embodiment, the slot 10305 can be oriented in a direction which is parallel, or at least substantially parallel, to the deck surface 10311 of the support portion 10310. In various embodiments, the slot 10305 can be horizontal with respect to the deck surface 10311. In various other embodiments, referring now to FIG. 266, a staple cartridge 10400 can comprise a support portion, a tissue thickness compensator 10420 supported by support portion, and a distal end 10402 which includes a nose 10403 configured to releasably hold the distal end 10425 of the tissue thickness compensator 10420 in position. In at least one embodiment, the distal end 10425 can comprise a projection extending therefrom and the nose 10403 can comprise a vertical slot 10405 configured to receive the projection of the distal end 10425. In various embodiments, the distal end 10425, and/or the projection extending therefrom, can be compressed, or wedged, within the slot 10405 such that the distal end 10425 can be held in place as the staple cartridge 10400 is positioned relative to the tissue. In certain embodiments, the tissue thickness compensator 10420 can comprise a slot, such as slot 10429, for example, which can be configured to receive at least a portion of the nose 10403 therein. In at least one embodiment, the slot 10405 can be oriented in a direction which is perpendicular, or at least substantially perpendicular, to the deck surface 10411 of the support portion. In various embodiments, referring now to FIG. 267, a staple cartridge 10500 can comprise a support portion, a tissue thickness compensator 10520 supported by the support portion, and a distal end 10502 which includes a nose configured to releasably hold the distal end 10525 of the tissue thickness compensator 10520 in position. In at least one embodiment, the nose can comprise a vertical slot 10505 configured to receive the distal end 10525 of the tissue thickness compensator 10520. In various embodiments, the distal end 10525 can be compressed, or wedged, within the slot 10505 such that the distal end 10525 can be held in place as the staple cartridge 10500 is positioned relative to the tissue.

In various embodiments, referring again to FIG. 265, the tissue thickness compensator 10320 can comprise a top surface 10324 which can be positioned above the top surface 10304 of the nose 10303. Another exemplary embodiment in which the top surface of a tissue thickness compensator is positioned above the nose of the staple cartridge is illustrated in FIG. 238, wherein the top surface 10721 of the tissue thickness compensator 10720 is positioned above the top surface 10004 of the nose 10003, for example. In use, referring once again to FIG. 265, tissue can slide over the top surface 10304 of the nose 10303 and, in some circumstance, the tissue can contact the distal end 10325 of the tissue thickness compensator 10320 and can apply a force to the tissue thickness compensator 10320 tending to peel the tissue thickness compensator 10320 away from the support portion 10310. In the embodiments described herein, this peel force can be resisted by the portion of the distal end 10325 wedged within the nose 10303. In any event, once the tissue has been suitably positioned relative to the staple cartridge 13000, an anvil can be rotated into a closed position to compress the tissue and the tissue thickness compensator 10320 against the support portion 10310. In at least one such embodiment, the anvil can be rotated into a position in which the anvil contacts the top surface 10304 of the nose 10303 and, as a result, the anvil can be prevented from rotating further. In various circumstances, owing to the top surface 10324 of the tissue thickness compensator 10320 being positioned above the top surface 10304 of the nose 10303, the top surface 10324 can be pushed downwardly toward the support portion 10310 as the anvil is being closed and, in some circumstances, the top surface 10324 can be pushed below the top surface 10304 of the nose 10303, for example. After the staples contained within the staple cartridge 10300 have been deployed and the tissue thickness compensator 10320 has been incised, as described herein, the support portion 10310 and the nose 10303 can be moved away from the tissue thickness compensator 10320 such that the distal end 10325 of the tissue thickness compensator 10320 can slide out of the slot 10305.

As described above, an anvil, such as anvil 10060, for example, can be rotated into a closed position in which the anvil 10060 contacts the top nose surface 10004 of a staple cartridge, such as staple cartridge 10000, for example. Once the anvil has reached its closed position, the amount in which a tissue thickness compensator, such as tissue thickness compensator 10020, for example, is compressed will depend on, among other things, the uncompressed thickness, or height, of the tissue thickness compensator and the thickness of the tissue. Referring now to FIGS. 236 and 237, a tissue thickness compensator 10920 can comprise a top surface which is flush, or at least substantially flush, with the top surface 10004 of the nose 10003. In such embodiments, the top surface of the tissue thickness compensator 10920 can be pushed below the top surface 10004 of the nose 10003. Referring now to FIGS. 241 and 242, a tissue thickness compensator, such as tissue thickness compensator 10820, for example, can comprise a top surface 10821 which is positioned below the top nose surface 10004 prior to the tissue thickness compensator 10820 being compressed by the tissue T and anvil 10060. In the circumstances where the tissue T is relatively thin, as illustrated in FIGS. 239 and 240, the tissue thickness compensator 10920 may undergo relatively little compression. Referring now to FIGS. 241 and 242, the tissue thickness compensator 10820 may undergo a larger compression when the tissue T is relatively thicker. In the circumstances where the tissue T has both thin sections and thicker sections, as illustrated in FIGS. 243 and 244, the tissue thickness compensator 10820 may be compressed a larger amount when it is positioned under the thicker tissue T and a lesser amount when it is positioned under the thinner tissue T, for example. In this way, as described above, the tissue thickness compensator can compensate for different tissue thicknesses.

In various embodiments, referring now to FIGS. 268-270, a surgical stapling instrument can comprise, one, a cartridge channel 16670 configured to receive a staple cartridge 16600 and, two, an anvil 16660 pivotably coupled to the cartridge channel 16670. The staple cartridge 16600 can comprise a support portion 16610 and a tissue thickness compensator 16620 wherein a distal end 16625 of the tissue thickness compensator 16620 can be releasably held to the support portion 16610 by a nose 16603 at the distal end 16602 of the staple cartridge 16600. In at least one embodiment, the nose 16603 can comprise a slot 16605 and can be comprised of a flexible material. In use, referring primarily to FIG. 269, the nose 16603 can be flexed downwardly in order to expand the opening of slot 16605. In certain embodiments, the nose 16603 can comprise notches or cut-outs 16606 which can be configured to permit the nose 16603 to flex downwardly. In any event, in various circumstances, the expanded opening of the slot 16605 can facilitate the insertion of the distal end 16625 of the tissue thickness compensator 16620 into the slot 16605. Once the tissue thickness compensator 16620 has been suitably positioned, the nose 16603 can be released and, owing to the resiliency of the material comprising the nose 16603, the nose 16603 can return, or at least substantially return, to its unflexed condition and trap the distal end 16625 of the tissue thickness compensator 16620 against the deck surface 16611, as illustrated in FIG. 270. In use, similar to the above, the distal end 16625 can be pulled out of the slot 16605 when the support portion 16610 is moved away from the stapled tissue. In various circumstances, the flexible nose 16603 can be configured to deflect as the tissue thickness compensator 16620 is detached from the support portion 16610. In various embodiments, referring again to FIG. 270, the tissue thickness compensator 16620 can comprise a top surface 16621 which is aligned, or at least substantially aligned, with a top surface 16604 of the nose 16603.

In various embodiments, referring to FIG. 271, a surgical stapling instrument can comprise, one, a channel 10770 configured to receive a staple cartridge 10700 and, two, an anvil 10760 rotatably coupled to the channel 10770. The staple cartridge 10700 can comprise a support portion 10710 and a tissue thickness compensator 10720. In various embodiments, the tissue thickness compensator 10720 can be held in position by a nose sock 10703 which can be slid over the support portion 10710. In at least one embodiment, referring primarily to FIG. 272, the nose sock 10703 can comprise one or more side slots 10707 which can be configured to removably receive one or more attachment rails extending along the support portion 10710, for example. In various embodiments, the tissue thickness compensator 10720 can be positioned intermediate the side slots 10707. In certain embodiments, the nose sock 10703 can further comprise a distal end 10702 and a cavity 10706 defined in the distal end 10702 wherein the cavity 10706 can also be configured to receive at least a portion of the support portion 10710, for example, therein. In use, the nose sock 10703 can be slid onto the support portion 10710 in a distal to proximal direction. In various embodiments, the tissue thickness compensator 10720 can be removably mounted to the nose sock 10703 such that, after staples have been fired through the tissue thickness compensator 10720, the tissue thickness compensator 10720 can detach from the nose sock 10703 as the support portion 10710 and the nose sock 10703 are moved away from the tissue thickness compensator 10720. In various embodiments, the top surface 10721 of the tissue thickness compensator 10720 can be positioned below the top surface 10704 of the nose 10703.

In various embodiments, referring now to FIGS. 273 and 274, a surgical stapling instrument can comprise, one, a staple cartridge channel 11070 configured to receive a staple cartridge 11000 and, two, an anvil 11060 rotatably coupled to the channel 11070. The staple cartridge 11000 can comprise a support portion 11010 and a tissue thickness compensator 11020. In various embodiments, the tissue thickness compensator 11020 can be held in position by a one or more longitudinal rails 11019 extending from the deck 11011 of the support portion 11010. In at least one embodiment, the longitudinal rails 11019 can be embedded within the tissue thickness compensator 11020. In certain embodiments, referring primarily to FIG. 274, the tissue thickness compensator 11020 can comprise a longitudinal recess 11029 which can be configured to receive the longitudinal rails 11019. In at least one such embodiment, the recess 11029 can be sized and configured to receive the rails 11019 in a press-fit arrangement, for example. Such features, further to the above, can be configured to prevent, or at least limit, relative lateral movement between the tissue thickness compensator 11020 and the support portion 11010 and, in addition, limit the pre-mature release of the tissue thickness compensator 11020 from the support portion 11010, for example. In various embodiments, referring now to FIG. 275, a surgical stapling instrument can comprise, one, a staple cartridge channel 11170 configured to receive a staple cartridge 11100 and, two, an anvil 11160 rotatably coupled to the channel 11170. The staple cartridge 11100 can comprise a support portion 11110 and a tissue thickness compensator 11120. In various embodiments, the tissue thickness compensator 11120 can be held in position by one or more longitudinal rows of spikes, or teeth, 11119 extending from the deck 11111 of the support portion 11110. In at least one embodiment, the longitudinal rows of spikes 11119 can be embedded within the tissue thickness compensator 11120.

With regard to the embodiment illustrated in FIG. 273, further to the above, the tissue thickness compensator 11020 of the staple cartridge 11000 can be progressively released from the support portion 11010 as the staples are ejected from the staple cavities 10012 defined therein. More particularly, further to the above, the staples positioned in the staple cavities 10012 can be ejected sequentially between the proximal end 11001 of the staple cartridge 11000 and the distal end 11002 of the staple cartridge 11000 such that, as the staples are being ejected, the staples can apply an upward biasing force to the tissue thickness compensator 11020 which acts to push the tissue thickness compensator 11020 off of the rails 11019. In such circumstances, the proximal end 11006 of the tissue thickness compensator 11020 can be released from the support portion 11010 as the staples are ejected from the proximal-most staple cavities 10012. The tissue thickness compensator 11020 can then be progressively released from the support portion 11010 as the staples are progressively ejected from the support portion 11010 between the proximal end 11001 and the distal end 11002 of the staple cartridge 11000. When the staples positioned within the distal-most staple cavities 10012 are ejected from the support portion 11010, the distal end 11007 of the tissue thickness compensator 11020 can be released from the support portion 11010. With regard to the embodiment illustrated in FIG. 275, the tissue thickness compensator 11120 can be progressively released from the spikes 1119 extending from the support portion 11110 as the staples are progressively ejected from the staple cartridge between the proximal end 11101 and the distal end 11102.

As discussed above, a tissue thickness compensator can be progressively released from the support portion of a staple cartridge as the staples are progressively ejected from the support portion and contact the tissue thickness compensator. In various embodiments, the legs of the staple, such as staple legs 10032, for example, may be able to pass through the tissue thickness compensator without releasing the tissue thickness compensator from the support portion. In such embodiments, the tissue thickness compensator may remain engaged with the support portion until the bases of the staples, such as bases 10031, contact the tissue thickness compensator and push it upwardly. In various embodiments, however, cleats and/or other retention features extending from the support portion, for example, may oppose the release of the tissue thickness compensator from the support portion. In certain embodiments, as described in greater detail below, a support portion can comprise retention features which can be configured to progressively release a tissue thickness compensator from the support portion as the staples are progressively fired from the staple cartridge. Referring now to FIG. 283, a staple cartridge, such as staple cartridge 11200, for example, can comprise a support portion 11210 including retention features 11213 which can be configured to releasably hold a tissue thickness compensator 11220 (FIG. 284) to the support portion 11210. In various embodiments, the retention features 11213 can be positioned at the ends of each staple cavity 11212, for example, wherein each retention feature 11213 can comprise a guide groove 11216 defined therein which is configured to slidably receive a staple leg 10032 of a staple 10030. In such embodiments, both the staple legs 10032 and the retention features 11213 can be configured to releasably retain the tissue thickness compensator 11220 to the support portion 11210. In use, referring now to FIG. 284, staple drivers 10040 contained within the support portion 11210 can be driven upwardly by a sled 10050, as described above, wherein the staple drivers 10040 can be configured to contact the retention features 11213, at least partially detach the retention features 11213 from the support portion 11210, and displace the retention features 11213 outwardly and away from the staples 10030 and the staple cavities 11212. When the retention features 11213 are detached from the support portion 11210 and/or displaced outwardly, as illustrated in FIG. 284, the retention features 11213 may no longer be able to retain the tissue thickness compensator 11220 to the support portion 11210 and, as a result, the tissue thickness compensator 11220 can be released from the support portion 11210. Similar to the above, the tissue thickness compensator 11220 can be progressively released from the support portion 11210 as the staples 10030 are progressively ejected from the staple cartridge toward an anvil, such as anvil 11260, for example. In various embodiments, the staple drivers 10040 may contact the retention features 11213 when the top surfaces of the staple drivers 10040 become co-planar, or at least substantially co-planar, with the deck surface 11211 of the support portion 11210, for example. In such embodiments, the tissue thickness compensator 11220 may be released from the support portion 11210 at the same time as and/or just before the staples 10030 are formed to their fully-formed, or fully-fired, configuration. In at least one such embodiment, referring primarily to FIG. 285, the drivers 10040 can be overdriven such that they are pushed above the deck surface 11211 to fully form the staples 10030 and, during the process of being overdriven, break the retention features 11213 away from the support portion 11210. In various embodiments, referring again to FIG. 284, the retention features 11213 may extend over, or overhang, into the staple cavities 11212 prior to being detached or displaced outwardly such that the drivers 10040 can contact the retention features 11213 just as the drivers 10040 reach the deck surface 11211. In any event, once the tissue thickness compensator 11220 has been released from the support portion 11210, referring now to FIG. 285, the support portion 11210 can be moved away from the implanted tissue thickness compensator 11220.

As described above, a compressible tissue thickness compensator of a staple cartridge can be progressively released from a support portion, or cartridge body, of the staple cartridge as the staples are fired, or deployed, from the staple cartridge. In various circumstances, such a release can comprise a progressive loosening of the tissue thickness compensator from the support portion wherein, in some circumstances, a complete detachment of the tissue thickness compensator from the support portion may not occur until the anvil is opened and the support portion is moved away from the implanted tissue thickness compensator. In various embodiments, referring now to FIG. 289, a staple cartridge, such as staple cartridge 11300, for example, can comprise a tissue thickness compensator 11320 which is releasably retained to a support portion 11310. In at least one embodiment, the support portion 11310 can comprise a plurality of retention members 11313 extending therefrom which are configured to releasably compress and hold the longitudinal sides of the tissue thickness compensator 11320 to the support portion 11310. In at least one such embodiment, each retention member 11313 can comprise an inwardly-facing channel or slot 11316 which can be configured to receive the longitudinal sides of the tissue thickness compensator 11320 therein. In various circumstances, a plurality of retention members 11313 can extend along a first longitudinal side of the support portion 11310 and a plurality of retention members 11313 can extend along a second longitudinal side of the support portion 11310 wherein, in certain circumstances, the retention members 11313 can be configured to prevent, or at least limit, relative lateral movement between the tissue thickness compensator 11320 and the support portion 11310 and, in addition, prevent, or at least limit, the premature release of the tissue thickness compensator 11320 from the support portion 11310. In various embodiments, the retention members 11313 can be integrally formed with the support portion 11310 and, in at least one embodiment, referring to FIG. 290, the retention members 11313 can be configured to detach, or at least partially detach, from the support portion 11310 in order to allow the tissue thickness compensator 11320 to detach from the support portion 11310, as illustrated in FIG. 291, for example. In certain embodiments, an anvil, such as anvil 11360, for example, can be configured to compress the tissue thickness compensator 11320 and, in response to pressure generated within the tissue thickness compensator 11320, the tissue thickness compensator 11320 can expand laterally to at least partially detach, or disengage, the retention members 11313 from the tissue thickness compensator 11320. In various embodiments, the advancement of a knife member, discussed above, through the anvil 11360 and the staple cartridge 11300 can deploy the staples contained therein and, simultaneously, squeeze the anvil 11360 and the staple cartridge 11300 closer to one another which can apply an added compressive pressure to the tissue thickness compensator 11320 and thereby cause the retention members 11313 to sequentially detach as the knife member passes through the staple cartridge 11300.

In various embodiments, referring now to FIGS. 292-294, a staple cartridge, such as staple cartridge 11400, for example, can comprise a tissue thickness compensator 11420 removably attached to a support portion 11410. In at least one embodiment, the staple cartridge 11400 can comprise one or more retainer bars 11413 which can be configured to hold the longitudinal sides of the tissue thickness compensator 11420 to the deck surface 11411. In at least one such embodiment, each retainer bar 11413 can comprise opposing arms 11418 which can define a channel 11416 therebetween. In such embodiments, one of the arms 11418 can be configured to extend over the tissue thickness compensator 11420 and the other arm 11418 can be configured to extend under a lip 11419 extending from the support portion 11410. Referring primarily to FIG. 292, the channel 11416 of each retainer bar 11413 can be sized and configured to apply a compressive force to the longitudinal sides of the tissue thickness compensator 11420 prior to the staple cartridge 11400 being used. During use, referring primarily to FIG. 293, the staple cartridge 11400 can be positioned within a staple cartridge channel and, once the staple cartridge 11400 has been suitably positioned, an anvil, such as anvil 11460, for example, can be moved into a position in which it can compress the tissue thickness compensator 11420. Similar to the above, the thickness tissue compensator 11420, when compressed, can expand laterally, or outwardly, and, as a result, detach the retainer bars 11413 from the staple cartridge 11400. In certain other embodiments, the closing of the anvil 11460 may not detach, or may not completely detach, the retainer bars 11413 from the staple cartridge. In at least one such embodiment, the advancement of a firing bar, described above, through the staple cartridge 11400 can deploy the staples 10030 from the support portion 11410 and, simultaneously, squeeze the anvil 11460 and the staple cartridge 11400 closer together to apply a compressive force to the tissue thickness compensator 11420 that is sufficient to cause the tissue thickness compensator 11420 to expand laterally and detach the retainer bars 11413 from the staple cartridge 11400. Once the retainer bars 11413 have been detached from the staple cartridge 11400, referring to FIG. 294, the support portion 11410 can be moved away from the implanted tissue thickness compensator 11420 and removed from the surgical site. In certain alternative embodiments, referring now to FIG. 295, a staple cartridge 11400' can comprise retainer bars 11413' which, similar to the above, can comprise arms 11418' extending therefrom. In at least one such embodiment, each of the arms 11418' can comprise a wedge-lock bevel 11417' which can be configured to releasably latch the retainer bars 11413' to the staple cartridge 11400'. More particularly, in at least one embodiment, the support portion 11410' of the staple cartridge 11400' can comprise undercuts 11419' which, in co-operation with the wedge-lock bevels 11417', can be configured to releasably retain the retainer bars 11413' to the staple cartridge 11400 and inhibit the tissue thickness compensator 11420 from being prematurely detached from the support portion 11410'. During use, similar to the above, the retainer bars 11413' can be detached from the staple cartridge 11400' when a sufficient compressive force is applied to the tissue thickness compensator 11420, for example.

In various circumstances, as described above and referring again to FIGS. 259 and 260, the sled 10050 of the staple cartridge 10000 and the firing member 10052 of a surgical stapling instrument can be moved from the proximal end 10001 of the staple cartridge 10000 to the distal end 10002 (FIG. 219) of the staple cartridge 10000 in order to deploy the staples 10030 from the support portion 10010. In at least one such circumstance, each staple 10030 can be moved from an unfired position to a fired position and ejected from the support portion 10010 to capture the entirety of the tissue thickness compensator 10020 against the tissue positioned between the anvil 10060 and the staple cartridge 10000. In certain circumstances, a surgeon may not need to fire all of the staples 10030 from the staple cartridge 10000 and the surgeon may stop the progression of the sled 10050 and the firing bar 10052 at a point located intermediate the proximal end 10001 and the distal end 10002 of the staple cartridge 10000. In such circumstances, the tissue thickness compensator 10020 may only be partially implanted to the tissue T and, in order to detach the unimplanted portion of the tissue thickness compensator 10020 from the support portion 10010, the surgeon can pull the support portion 10010 away from the partially implanted tissue thickness compensator 10020 such that the unimplanted portion peels or pulls off of the support portion 10010. While such embodiments are suitable in various circumstances, an improvement is illustrated in FIGS. 300-302 wherein a tissue thickness compensator, such as tissue thickness compensator 11520 of staple cartridge 11500, for example, can comprise a plurality of connected segments which can be configured to detach from one another. In at least one such embodiment, the tissue thickness compensator 11520 can comprise a first, or proximal-most, segment 11520a, a second segment 11520b removably connected to the first segment 11520a, a third segment 11520c removably connected to the second segment 11520b, a fourth segment 11520d removably connected to the third segment 11520c, and a fifth segment 11520e removably connected to the fourth segment 11520d, for example. In various embodiments, the tissue thickness compensator 11520 can comprise at least one thin section 11529 positioned intermediate any two adjacent segments 11520a-11520e which can be configured to define a predetermined rupture or separation point in which the tissue thickness compensator segments can separate from one another. In certain embodiments, a tissue thickness compensator can include any suitable arrangement of perforations, thin sections, and/or any other means for creating a separation point within the tissue thickness compensator. Referring primarily to FIG. 301, an anvil 11560 is illustrated in a closed position and the firing member 10052 is illustrated as having been partially advanced through the staple cartridge 11500 such that the staples 10030 underlying the first segment 11520a, the second segment 11520b, and the third segment 11520c have been fired to capture the tissue thickness compensator 11520 against the tissue T. In such a position, the firing member 10052 has not yet been advanced to deploy the staples 10030 underlying the fourth segment 11520d and the fifth segment 11520e, for example. Referring now to FIG. 302, the anvil 11560 has been moved into an open position and the support portion 11510 of the staple cartridge 11500 has been moved away from the portion of the tissue thickness compensator 11520 that has been implanted. As illustrated in FIG. 302, the thin section 11529 (FIG. 300) located intermediate the third segment 11520c and the fourth segment 11520d has allowed the unimplanted portion of the tissue thickness compensator 11520 to separate from the implanted portion.

In various embodiments, further to the above, a staple cartridge can comprise a plurality of fasteners configured to releasably hold a tissue thickness compensator to a support portion of the staple cartridge. In certain embodiments, the support portion can comprise a plurality of apertures defined in the deck surface, for example, wherein the fasteners can extend through the tissue thickness compensator and can be releasably retained in the support portion apertures. In use, the fasteners can be progressively released from the support portion as the staples are progressively ejected from the support portion. In at least one such embodiment, the fasteners can be implanted with the tissue thickness compensator and, in at least one embodiment, the fasteners can be comprised of at least one bioabsorbable material, for example. In certain embodiments, the fasteners can detach from the support portion after the tissue thickness compensator has been at least partially implanted and as the support portion is moved away from the implanted tissue thickness compensator. In various embodiments, referring now to FIGS. 323-325, a staple cartridge, such as staple cartridge 11600, for example, can comprise a tissue thickness compensator 11620 releasably mounted to a support portion 11610 by a plurality of fasteners 11613. Each fastener 11613 can comprise a first end 11618 embedded within and/or otherwise engaged with the tissue thickness compensator 11620, a second end 11618 engaged with the support portion 11610, and a connector 11616 which connects the first end 11618 to the second end 11618. In various embodiments, the fasteners 11613 can extend through a knife slot 11615 defined in the support portion 11610. In use, the firing member 10052, described above, can move a knife edge through the knife slot 11615 in the support portion 11610 and incise the fasteners 11613 in order to release the tissue thickness compensator 11620 from the support portion 11610. In at least one such embodiment, the firing bar 10052 can be advanced from a proximal end 11601 of the staple cartridge 11600 to a distal end 11602 of the staple cartridge 11600 in order to, one, advance the sled 10050 distally and progressively fire the staples 10030, as discussed above, and, two, progressively incise and/or break the fasteners 11613 to progressively release the tissue thickness compensator 11620 from the support portion 11610. In certain embodiments, similar to the above, the tissue thickness compensator 11620 can comprise a plurality of detachable segments 11620a-11620e which can each be held to support portion 11610 by one or more fasteners 11613, for example. In the event that the firing member 10052 is stopped intermediate the proximal end 11601 and the distal end 11602 of the staple cartridge 11600, as illustrated in FIG. 324, the fasteners 11613 can assist in holding the unimplanted portion of the tissue thickness compensator 11620 to the support portion 11610 after the anvil 11660 is opened and the support portion 11610 is moved away from the tissue T, as illustrated in FIG. 325. In various embodiments, further to the above, the cutting edge 10053 of the firing member 10052 can be configured to incise and/or break the fasteners 11613. In certain alternative embodiments, referring now to FIGS. 327 and 328, a staple-deploying sled, such as sled 11650, for example, can comprise a knife edge 11653 which can be configured to incise the connectors 11616 of the fasteners 11613 as the sled 11650 traverses the staple cartridge 11600. In at least one such embodiment, each connector 11616 can comprise a cylindrical member extending between the T-shaped ends 11618 of the fasteners 11613 wherein the knife edge 11653 can comprise a concave profile 11653 which can be configured to receive the cylindrical connector 11616, for example.

As discussed above, a staple cartridge can be loaded into a staple cartridge channel of a surgical stapling instrument. In various circumstances, a surgeon, or other clinician, may insert the staple cartridge into the staple cartridge channel by placing a downward force onto the staple cartridge to lock the staple cartridge in place. In some such circumstances, the clinician may place their thumb, for example, on the top surface of the staple cartridge to apply such a downward force. In various embodiments, the top surface of the staple cartridge may comprise the top surface of a tissue thickness compensator wherein, as described above, the tissue thickness compensator can be compressible and, in certain embodiments, the downward force applied to tissue thickness compensator can cause the tissue thickness compensator to compress to the point in which the clinician's thumb comes into contact with the tips of the staples stored within the support portion. In various embodiments, a staple cartridge applicator can be utilized to insert a staple cartridge into a staple cartridge channel which can be configured to prevent, or at least limit, the possibility of the clinician touching the staples in the staple cartridge. After the staple cartridge has been suitably positioned within the staple cartridge channel, as described in greater detail below, the applicator can be detached from the staple cartridge.

In certain embodiments, referring now to FIGS. 305 and 306, a staple cartridge applicator can comprise a rigid cover, such as cover 10080, for example, which can be attached to a staple cartridge 10000. Further to the above, the cover 10080 can be configured to prevent, or at least inhibit, a clinician's thumb, for example, from contacting the tips of the staples 10030 positioned within the staple cartridge 10000 when the staple cartridge 10000 is inserted into a staple cartridge channel. Referring now to FIGS. 307 and 308, the cover 10080 can extend over the top surface 10021, or at least a portion of the top surface 10021, of the tissue thickness compensator 10020 and can include, one, a bottom surface 10081 which can extend over and/or abut the tissue thickness compensator 10020 and, two, a top surface 10082 which can provide a pushing surface for the clinician to apply a downward force thereto, for example. In use, the clinician can grab a handle portion 10084 of the cover 10080, align the support portion 10010 of the staple cartridge 10000 with the staple cartridge channel, and at least partially insert the staple cartridge 10000 within the staple cartridge channel. Thereafter, the clinician can completely seat the staple cartridge 10000 in the staple cartridge channel by applying the downward force to the top surface 10082 of the cover 10880 which can, in various embodiments, transmit the downward force directly to the support portion 10010. In at least one such embodiment, the cover 10080 can comprise proximal supports 10087 which can extend downwardly and contact the deck surface 10011 of the support portion. In certain embodiments, the cover 10080 can further comprise a distal support portion 10083 which can be configured to abut the nose 10003. When a downward force is applied the cover 10080, the downward force can be transmitted through the proximal supports 10087 and/or the distal support portion 10083 without transmitting, or at least without substantially transmitting, the downward force to the support portion 10010 through the tissue thickness compensator 10020. In various circumstances, as a result of the above, the clinician may not directly contact the tissue thickness compensator 10020. Also as a result of the above, the cover 10080 may not compress, or at least substantially compress, the tissue thickness compensator 10020 as the staple cartridge 10000 is being inserted into the staple cartridge channel. In various embodiments, a cover can comprise any suitable number of supports which are configured to transmit a downward force to the support portion without transmitting, or at least substantially transmitting, the downward force through the tissue thickness compensator. In certain embodiments, the supports can extend around the distal end, the proximal end, and/or the longitudinal sides of the tissue thickness compensator. In some embodiments, the supports can extend through the tissue thickness compensator. In at least one such embodiment, the supports can extend through apertures within the tissue thickness compensator and abut the deck of the support portion. In certain embodiments, at least some of the supports may not be in contact with the deck before the downward force is applied to the cover; however, in various embodiments, the cover can be configured to flex, or move, downwardly until the supports contact the deck of the support portion. At such point, the downward flexure, or movement, of the cover can be impeded, or at least substantially impeded, from flexing further.

As described above, the cover 10080 can be attached to the staple cartridge 10000 and can be used to manipulate the position of the staple cartridge 10000. In various embodiments, the cover 10080 can comprise any suitable number of gripping members which can be configured to releasably hold the cover 10080 to the support portion 10010 of the staple cartridge 10000, for example. In at least one such embodiment, the cover 10080 can further comprise one or more retention members, such as latch arms 10088 and/or 10089, for example. In various embodiments, the latch arms 10089 can be configured to extend around the sides of the nose 10003 and engage the bottom surface 10009 (FIG. 306) of the nose 10003. Similarly, the latch arms 10088 can extend around the sides of lock projections 10008 extending from the support portion 10010 and engage the bottom surfaces of the lock projections 10008. These latch arms, in various embodiments, can be configured to position the cover 10080 over the zone or region in which the staples are stored within the support portion 10010. In any event, once the staple cartridge 10000 has been suitably positioned, the cover 10080 can be detached from the staple cartridge 10000. In at least one embodiment, the clinician can apply an upward lifting force to the handle 10084 in order to detach the distal end of the cover 10080 from the distal end 10002 of the staple cartridge 10000. In at least one such embodiment, the latch arms 10088 and 10089 can flex outwardly as the handle 10084 is lifted upwardly such that the latch arms 10088 and 10089 can flex around the lock projections 10008 and the nose 10003, respectively. Thereafter, the proximal end of the cover 10080 can be lifted away from the proximal end 10001 of the staple cartridge and the cover 10080 can be moved away from the staple cartridge 10000.

In certain embodiments, referring now to FIGS. 309 and 310, a staple cartridge applicator, such as staple cartridge applicator 10680, for example, can be configured to position an upper tissue thickness compensator, such as tissue thickness compensator 10690, for example, relative to an anvil in addition to positioning a staple cartridge, such as staple cartridge 10600, for example, within a staple cartridge channel. Similar to the above, the applicator 10680 can comprise latch arms 10688 which can be releasably engaged with lock projections 10608 extending from a support portion 10610 of the staple cartridge 10600 such that the applicator 10680 can be maintained in position over a tissue thickness compensator 10620 of the staple cartridge 10600. In various embodiments, the upper tissue thickness compensator 10690 can be removably attached to the staple cartridge applicator 10680 such that the anvil of a surgical instrument, such as anvil 10060, for example, can be closed onto the applicator 10680, engage the tissue thickness compensator 10690, and detach the tissue thickness compensator 10690 from the applicator 10680. In various embodiments, the tissue thickness compensator 10690 and/or the anvil 10060 can comprise one or more retention features which can be configured to releasably hold the tissue thickness compensator 10690 to the anvil 10060. In at least one such embodiment, the tissue thickness compensator 10690 can comprise a longitudinal rail 10695, for example, extending from the top surface 10691 of the tissue thickness compensator 10690 which can be received within a longitudinal knife slot 10065 defined within the anvil 10060. In various embodiments, the tissue thickness compensator 10690 and the longitudinal rail 10695 can be comprised of any suitable compressible material, such as those described in the this patent application, for example, wherein the longitudinal rail 10695 can be compressed and/or wedged within the knife slot 10065, for example. Once the anvil 10060 has been engaged with the tissue thickness compensator 10690, the anvil 10060 can be returned to an open position and, in such circumstances, the tissue thickness compensator 10690 can detach from the applicator 10680. Thereafter, the applicator 10680 can be detached from the staple cartridge 10600 such that the anvil 10060 and the staple cartridge 10600 can be positioned relative to the tissue that is to be stapled and/or incised. In use, a staple-deploying sled, such as sled 10050 (FIG. 236), for example, can be advanced distally through the staple cartridge 10600 by a firing member 10052 (FIG. 236), for example, in order to eject the staples from the staple cartridge 10060, as outlined above. As the staples are deformed, each staple can capture a portion of the tissue thickness compensator 10690 against the top surface of the tissue and a portion of the tissue thickness compensator 10620 against the bottom surface of the tissue. At the same time, the firing member 10052 can advance a knife edge 10053 (FIG. 236) through the tissue thickness compensator 10620 and/or the tissue thickness compensator 10690 wherein, in at least one embodiment, the knife edge 10053 can be advanced through the longitudinal rail 10695 in order to incise the rail 10695 and progressively detach the tissue thickness compensator 10690 from the anvil 10060. After the staples have been deployed, the anvil 10060 can be re-opened and moved away from the implanted tissue thickness compensator 10690 and, similarly, the support portion 10610 of the staple cartridge 10600 can be moved away from the implanted tissue thickness compensator 10620. In various embodiments, further to the above, the tissue thickness compensator 10620 and/or the tissue thickness compensator 10690 can comprise a plurality of detachable segments which can be configured to separate from one another in the event that only portions of the tissue thickness compensators 10620 and 10690 are implanted by the staples.

In various embodiments, further to the above, the applicator 10680 can comprise one or more retention features which can be configured to releasably hold the tissue thickness compensator 10690 to the applicator 10680. In at least one such embodiment, referring primarily to FIG. 310, the applicator 10680 can comprise a longitudinal retention rail 10685 which can be configured to be received in a longitudinal retention slot 10694 defined in the bottom surface 10692 of the tissue thickness compensator 10690 in a press-fit manner, for example. In various circumstances, the retention rail 10685 and the retention slot 10694 can be configured to retain the tissue thickness compensator 10690 to the applicator 10680 until a sufficient upward lifting force is applied to the tissue thickness compensator 10690 by the anvil 10060, as described above. In at least one such embodiment, the retention rail 10685 extending from the applicator 10680 can further comprise end stops 10686 positioned at the proximal and distal ends of the retention rail 10685 which can be configured to prevent, or at least limit, relative longitudinal movement between the tissue thickness compensator 10690 and the applicator 10680. In certain embodiments, referring again to FIG. 310, one or more adhesives, such as longitudinal adhesive strips 10693, for example, can be placed on the contact surface 10691 of the tissue thickness compensator 10690 such that, when the anvil 10060 contacts the tissue thickness compensator 10690, as described above, the adhesive can releasably attach the tissue thickness compensator 10690 to the anvil 10060. In various embodiments, one or more adhesives can be utilized in addition to or in lieu of the compressible retention features described above, for example. In certain embodiments, one or more adhesives can be utilized to releasably hold a tissue thickness compensator to a staple cartridge applicator. In at least one embodiment, referring now to FIG. 310A, the cover 10080, for example, can include one or more adhesive pads 12185 which can be configured to releasably retain an upper tissue thickness compensator, such as tissue thickness compensator 12190, for example, to the top surface 10082 of the cover 10080. In at least one such embodiment, similar to the embodiments described above, an anvil can be closed onto to the tissue thickness compensator 12190 to engage the longitudinal retention rail 12195 of the tissue thickness compensator 12190. In certain embodiments, a release mechanism can be positioned intermediate the tissue thickness compensator 12190 and the cover 10080 which can be utilized to break the adhesive bonds holding the tissue thickness compensator 12190 to the cover 10080 and detach the tissue thickness compensator 12190 from the cover 10080. In at least one embodiment, the release mechanism can comprise a pull tab 12196 and a loop 12197 wherein the loop 12197 can comprise first and second ends which are attached to the pull tab 12196. The loop 12197 can comprise a suture, for example, which can define a perimeter which circumscribes the adhesive pads 12185 such that, when the pull tab 12196 is pulled distally, the suture can slide between the tissue thickness compensator 12190 and the cover 10080 and contact the tissue pads 12185. In such circumstances, the suture can at least one of separate the adhesive pads 12185 from the tissue thickness compensator 12190, separate the adhesive pads 12185 from the cover 10080, and/or sever the adhesive pads 12185, for example.

In various embodiments, referring now to FIG. 311, a staple cartridge can comprise a support portion 10710, for example, which, similar to the above, can comprise a longitudinal knife slot 10715 extending therethrough. In at least one such embodiment, a staple cartridge applicator, such as applicator 10780, for example, can comprise a longitudinal retention and alignment member 10786 which can extend into the knife slot 10715 in the support portion 10710. In certain embodiments, the retention member 10786 can be configured to engage the sidewalls of the knife slot 10715 in a press-fit manner, for example, such that the applicator 10780 can be releasably retained to the support portion 10710. In various embodiments, although not illustrated, a first portion of a tissue thickness compensator can be positioned on a first side of the retention member 10786 and a second portion of the tissue thickness compensator can be positioned on an opposite, or second, side of the retention member 10786. Similar to the above, the first and second portions of the tissue thickness compensator can be mounted to the support portion 10710 of the staple cartridge via retention members 10013, for example. Also similar to the above, an upper tissue thickness compensator 10790 can be removably mounted to the applicator 10780 via a longitudinal retention member 10785 extending from the loading surface 10782 of the applicator 10780 wherein the retention member 10785 can be releasably press-fit into a longitudinal slot 10794 defined in the bottom surface 10792 of the tissue thickness compensator 10790, for example. In various embodiments, also similar to the above, the tissue thickness compensator 10790 can further comprise a longitudinal retention member 10795 extending from the top surface 10791 of the tissue thickness compensator 10790 which can be releasably retained in the longitudinal knife slot 10065 defined in the anvil 10060, for example. In at least one such embodiment, the longitudinal retention member 10795 can comprise a wedge-shaped cross-section comprising a top portion which is larger than a bottom portion, wherein the bottom portion can attach the retention member 10795 to the tissue thickness compensator 10790, for example.

In various embodiments, referring now to FIGS. 312 and 313, a staple cartridge 10800 comprising a support portion 10810 and a tissue thickness compensator 10820 can be loaded into a staple cartridge channel with a staple cartridge applicator 10880, for example. Similar to the above, the staple cartridge applicator 10880 can also be configured to position an upper tissue thickness compensator 10890, for example, relative to an anvil, such as anvil 10060, for example, such that, when the anvil 10060 is closed, the anvil 10060 can contact and engage the tissue thickness compensator 10890. In at least one embodiment, the tissue thickness compensator 10890 can comprise a plurality of retention legs 10895 extending from the top surface 10891 of the tissue thickness compensator 10890 which can be configured to be engage the anvil 10060 and releasably retain the tissue thickness compensator 10890 to the anvil 10060. In at least one such embodiment, the legs 10895 can be arranged in a longitudinal row wherein each leg 10895 can comprise at least one foot configured to enter into and engage the knife slot 10065 defined in the anvil 10060. In certain embodiments, some of the feet of legs 10895 can extend in one direction while other feet can extend in another direction. In at least one embodiment, some of the feet can extend in opposite directions. In any event, once the anvil 10060 has been engaged with the tissue thickness compensator 10890, referring now to FIGS. 313 and 314, the anvil 10060 can be reopened and the clinician can move the staple cartridge applicator 10880 away from the tissue thickness compensators 10820 and 10890. Thereafter, referring to FIG. 314A, the upper tissue thickness compensator 10890 can be positioned on a first side of the targeted tissue and the tissue thickness compensator 10820, which can comprise a lower tissue thickness compensator, can be positioned on a second side of the tissue. After the tissue thickness compensators 10820 and 10890 have been suitably positioned, referring now to FIG. 314B, a knife edge of a firing member, such as knife edge 10053, for example, can be advanced through the tissue and the tissue thickness compensators. In various embodiments, referring now to FIG. 318, a staple cartridge applicator, such as applicator 12280, for example, can comprise a tissue thickness compensator 12290 detachably mounted thereto which can be, similar to the above, inserted into a staple cartridge channel, as illustrated in FIG. 319, and engaged by the anvil 10060 when the anvil 10060 is moved into a closed position. In at least one such embodiment, the tissue thickness compensator 12290 can comprise a plurality of retention members 12295 extending upwardly from the top surface 12291 of the tissue thickness compensator 12290 wherein each retention member 12295 can comprise a plurality of flexible legs 12296 which can be configured to be inserted into the knife slot 10065 in the anvil 10060. Referring primarily to FIGS. 321 and 322, the flexible legs 12296 of each retention member 12295 can be separated by a gap 12298 such that, as the legs 12296 are inserted into the knife slot 10065, the legs 12296 can flex inwardly and then resiliently return outwardly once the enlarged feet of the flexible legs 12296 have passed through the knife slot 10065. In various embodiments, the enlarged feet of the flexible legs 12296 can flex behind opposing retention lips 12297 defined in the anvil 10060 and, as a result of the interaction of the legs 12296 and the lips 12297, the tissue thickness compensator 12290 can be retained to the anvil 10060. Thereafter, the staple cartridge applicator 12280 can be moved away from the tissue thickness compensator 12290, as illustrated in FIG. 320. In use, once the tissue thickness compensator 12290 has been implanted against the tissue by staples deployed from staple cartridge 10000, for example, the anvil 10060 can be re-opened and, as the anvil 10060 is moved away from the implanted tissue thickness compensator 12290, the legs 12296 of the retention members 12995 can flex inwardly such that they can be pulled out of the knife slot 10065.

In various embodiments, referring now to FIGS. 315 and 316, a tissue thickness compensator, such as tissue thickness compensator 11990, for example, can be loaded longitudinally into an anvil, such as anvil 11960, for example. More particularly, in at least one embodiment, the tissue thickness compensator 11990 can comprise one or more longitudinal rails 11995 which can be inserted into a distal opening in a knife slot 11965 of the anvil 11960 and then pushed proximally until the tissue thickness compensator 11990 has been properly seated in the anvil 11960. In at least one such embodiment, each rail 11995 can comprise a longitudinal retention foot 11996 which can be positioned behind a longitudinal retention lip 11997 which at least partially defines the knife slot 11965, for example. As illustrated in FIG. 316, the feet 11996 can extend in opposite directions in order to be positioned behind retention lips 11997 positioned on the opposite sides of the knife slot 11965. In various embodiments, a longitudinal gap 11998 can be defined between the rails 11995 which can be configured to permit the rails 11995 to flex inwardly toward one another when the tissue thickness compensator 11990 is detached from the anvil 11960. In certain embodiments, referring now to FIG. 317, a tissue thickness compensator, such as tissue thickness compensator 12090, for example, can comprise one or more lock arms 12098 which can extend around the sides of an anvil, such as anvil 12060, for example. In use, the lock arms 12098 can engage the anvil 12060 and releasably retain the tissue thickness compensator 12090 to the anvil 12060. In at least one such embodiment, the anvil 12060 can comprise one or more notches, or lock shoulders, 12097, for example, which can each be configured to receive a foot extending from a lock arm 12098. In use, the arms 12098 can flex outwardly and detach from the anvil 12060 when the anvil 12060 is moved away from the tissue thickness compensator 12090 after the tissue thickness compensator 12090 has been at least partially implanted.

As described above, a surgical stapling instrument can comprise a staple cartridge channel configured to receive a staple cartridge, an anvil rotatably coupled to the staple cartridge channel, and a firing member comprising a knife edge which is movable relative to the anvil and the staple cartridge channel. In use, a staple cartridge can be positioned within the staple cartridge channel and, after the staple cartridge has been at least partially expended, the staple cartridge can be removed from the staple cartridge channel and replaced with a new staple cartridge. In some such embodiments, the staple cartridge channel, the anvil, and/or the firing member of the surgical stapling instrument may be re-used with the replacement staple cartridge. In certain other embodiments, a staple cartridge may comprise a part of a disposable loading unit assembly which can include a staple cartridge channel, an anvil, and/or a firing member, for example, which can be replaced along with the staple cartridge as part of replacing the disposable loading unit assembly. Certain disposable loading unit assemblies are disclosed in U.S. patent application Ser. No. 12/031,817, entitled END EFFECTOR COUPLING ARRANGEMENTS FOR A SURGICAL CUTTING AND STAPLING INSTRUMENT, which was filed on Feb. 15, 2008, now U.S. Patent Application Publication No. 2009/0206131, the entire disclosure of which is incorporated by reference herein. Referring now to FIG. 370, a disposable loading unit, such as disposable loading unit 12500, for example, can comprise a support portion 12510, an anvil 12560 rotatably coupled to the support portion 12510, and an elongate shaft 12570 extending from the support portion 12510. Similar to the staple cartridges described herein, the support portion 12510 can comprise a plurality of staple cavities 10012 and a staple, such as a staple 10030, for example, positioned in each staple cavity 10012, for example. The disposable loading unit 12500 can further comprise a firing member 12552 which can be advanced distally in order to move the anvil 12560 from an open position, as illustrated in FIG. 370, to a closed position. In various embodiments, the disposable loading unit 12500 can further comprise a tissue thickness compensator 12520 positioned on and/or attached to the support portion 12510 wherein, when the anvil 12560 is in its closed position, the anvil 12560 can be positioned opposite the tissue thickness compensator 12520 and, in some embodiments, the anvil 12560 can at least partially compress the tissue thickness compensator 12520 when the anvil 12560 is in its closed position. In either event, the firing member 12552 can be advanced further in order to eject the staples from the support portion 12510. As the staples are ejected, the staples can be deformed by the anvil 12560 and trap at least a portion of the tissue thickness compensator 12520 therein. Thereafter, the firing member 12552 can be retracted proximally, the anvil 12560 can be re-opened, and the support portion 12510 can be moved away from the implanted tissue thickness compensator 12520.

In various embodiments, further to the above, the tissue thickness compensator 12520 can be detachably mounted to the support portion 12510. In at least one such embodiment, the support portion 12510 can comprise a longitudinal retention rail 12526 mounted to each side thereof wherein each rail 12526 can comprise one or more apertures 12528 which can be configured to receive at least a portion of the tissue thickness compensator 12520 therein. Once the tissue thickness compensator 12520 has been at least partially implanted, the tissue thickness compensator 12520 can pull out of the apertures 12528 as the support portion 12510 is moved away. In various embodiments, referring now to FIGS. 371-373, a disposable loading unit 12600 can comprise a support portion 12610, a tissue thickness compensator 12620 detachably mounted to the support portion 12610, and one or more retention rails 12626 which can be configured to extend under the tissue thickness compensator 12620 and mount the tissue thickness compensator 12620 to the support portion 12610. Each retention rail 12626 can comprise a plurality of retention hooks 12628, for example, which can be engaged to the support portion 12610 via retention slots 12614, for example, defined in the support portion 12610. In use, in at least one such embodiment, the tissue thickness compensator 12620 can be configured to detach from the retention rails 12626 after the tissue thickness compensator 12620 has been at least partially implanted and the support portion 12610 is moved away from the tissue thickness compensator 12620. In various embodiments, referring now to FIGS. 374-376, a disposable loading unit 12700 can comprise one or more retention rails 12726 which can each comprise a bottom bar 12725 which can extend under the tissue thickness compensator 12720 and a top bar 12727 which can extend over the top surface 12621 of the tissue thickness compensator 12620. In certain embodiments, the tissue thickness compensator 12620 can be at least partially compressed between the top bars 12727 and the bottom bars 12725 such that the retention rails 12726 can releasably hold the tissue thickness compensator 12620 relative to the support portion 12610. In at least one such embodiment, each retention rail 12726 can comprise one or more retention hooks 12728 which can be engaged with the support portion 12610 to retain the retention rails 12726 to the support portion 12610.

In various embodiments, referring now to FIGS. 377 and 378, a disposable loading unit 12800 can comprise a retention member 12822 which can be configured to mount a tissue thickness compensator 12620 to the support portion 12610. In at least one such embodiment, the retention member 12822 can comprise a sheet of material positioned against the deck surface 12611 of the support portion wherein the tissue thickness compensator 12620 can be attached to the sheet of material by at least one adhesive, for example. The retention member 12822 can further comprise a longitudinal retention rail 12825 configured to extend downwardly into a knife slot 12615 defined in the support portion 12610. In at least one such embodiment, the retention rail 12825 can be sized and configured such that it is compressed between the sidewalls of the knife slot 12615. In use, the firing member 12552 can comprise a knife edge which can pass through the knife slot 12615 as the firing member 12552 is advanced distally and transect the tissue thickness compensator 12620 and the retention rail 12825 longitudinally. Also, in use, the staples ejected from the support portion 12610 can penetrate the retention member 12822, the tissue thickness compensator 12820, and the tissue positioned between the tissue thickness compensator 12820 and the anvil 12560. In various embodiments, the retention member 12822 can be comprised of a biocompatible and/or bioabsorbable material. In certain embodiments, the retention member 12822 can be comprised of a sufficiently compressible material to comprise a tissue thickness compensator underlying the tissue thickness compensator 12620. In various embodiments, referring now to FIGS. 379-381, a disposable loading unit 12900 can comprise a loading assembly including a bottom portion 12922 which can be removably attached to the support portion 12610, a top portion 12990 which can be removably attached to the anvil 12560, and a flexible joint 12991 connecting the bottom portion 12922 and the top portion 12990. Similar to the above, a longitudinal retention rail 12825 can extend downwardly from the bottom portion 12922 and into the knife slot 12615 defined in the support portion 12610 such that the bottom portion 12922 can be releasably retained to the support portion 12610. Similarly, a longitudinal retention rail 12995 can extend upwardly from the top portion 12990 into a knife slot defined in the anvil 12560 such that the top portion 12990 can be releasably retained to the anvil 12560. As illustrated in FIGS. 380 and 381, a tissue thickness compensator 12620 can be mounted to the bottom portion 12922 of the loading assembly wherein, in order to position the tissue thickness compensator 12620 relative to the support portion 12610, a clinician could flex the top portion 12990 and the bottom portion 12922 toward one another, position the loading assembly between the anvil 12560 and the support portion 12610, and release the flexed loading assembly such that it can resiliently expand and bias the top portion 12990 against the anvil 12560 and the bottom portion 12922 against the support portion 12610. In at least one embodiment, referring now to FIGS. 382-384, the loading assembly can further comprise one or more latch hooks, such as latch hooks 12994, for example, extending therefrom which can be configured to releasably connect the top portion 12990 to the anvil 12560 and/or releasably connect the bottom portion 12922 to the support portion 12610.

In various embodiments, referring now to FIG. 385, a disposable loading unit 15900, for example, can comprise an anvil 15960 and a staple cartridge channel 15970 wherein the staple cartridge channel 15970 can rotate relative to the anvil 15960. In at least one such embodiment, the anvil 15960 may not be able to rotate. In certain embodiments, tissue can be positioned between the anvil 15960 and the staple cartridge channel 15970 and, thereafter, the staple cartridge channel 15970 can be rotated toward the tissue to clamp the tissue against the anvil. In at least one such embodiment, the disposable loading unit 15900 can further comprise a tissue thickness compensator 15920 which can be configured to contact the tissue.

As discussed above and referring to FIG. 332, a staple cartridge, such as staple cartridge 10000, for example, can comprise a support portion 10010 and a tissue thickness compensator 10020 wherein a plurality of staples 10030 can be at least partially stored in the support portion 10010 and can extend into the tissue thickness compensator 10020 when the staples 10030 are in their unfired position. In various embodiments, the tips of the staples 10030 do not protrude from the tissue thickness compensator 10020 when the staples 10030 are in their unfired positions. As the staples 10030 are moved from their unfired positions to their fired positions by the staple drivers 10040, as discussed above, the tips of the staples 10030 can penetrate through the tissue thickness compensator 10020 and/or penetrate through the upper layer, or skin, 10022. In certain alternative embodiments, the tips of the staples 10030 can protrude through the top surface of the tissue thickness compensator 10020 and/or skin 10022 when the staples 10030 are in their unfired position. In either event, the staples 10030, as they extend upwardly out of the support portion 10010 prior to being deployed, may tilt and/or deflect relative to the support portion, as also discussed above. In various embodiments, referring now to FIG. 329, a staple cartridge, such as staple cartridge 13000, for example, can comprise a plurality of guide members, or retainers, which can be configured to limit relative movement between the support portion 13010 and the tips of the staples positioned therein. Referring primarily to FIG. 330, the staple cartridge 13000 can comprise a tissue thickness compensator 13020 mounted to a support portion 13010 and, in addition, a plurality of pledgets 13022 attached to the top surface 13021 of the tissue thickness compensator 13020. In various embodiments, each pledget 13022 can comprise a plurality of apertures 13029 defined therein which can be configured to slidably receive and/or guide the legs 13022 of a staple 13030 therein. In addition to or in lieu of the apertures, a pledget can comprise any suitable opening such as a slot, guide, and/or groove, for example, which can be configured to slidably receive and/or guide the legs 13022. In certain embodiments, as illustrated in FIG. 330, the tips of the staple legs 13032 can be positioned within the apertures 13029 when the staples 13030 are in their unfired positions. In at least one such embodiment, the tips of the staple legs 13032 can protrude above the pledgets 13022 when the staples are in their unfired position. In certain other embodiments, the tips of the staple legs 13032 may be positioned just below the pledgets 13022 when the staples 13030 are in their unfired positions such that, when the staples 13030 are moved upwardly through the tissue thickness compensator 13020, the staple legs 13032 can enter into the apertures 13029 of the pledgets 13022 and slide therethrough. In any event, when the legs 13032 of the staples 13030 are positioned within the pledgets, the lateral and/or longitudinal movement of the staple legs 13032 can be limited without preventing the upward movement of the staple legs 13032 when the staples 13030 are deployed. When the staples 13030 are deployed, referring now to FIG. 331, the staple legs 13032 can slide upwardly through the pledgets 13022 to penetrate the tissue T, contact an anvil positioned opposite the staple cartridge 13030, and deform downwardly to capture the tissue T and the tissue thickness compensator 13030 therein.

In various embodiments, further to the above, the pledgets 13022 can be attached to the tissue thickness compensator 13020 utilizing at least one biocompatible and/or bioabsorbable adhesive, for example. In certain embodiments, the pledgets 13022, and/or a retention member extending from each pledget, can be at least partially embedded within the tissue thickness compensator 13020. In at least one such embodiment, the tissue thickness compensator 13020 can comprise pockets defined therein which are configured to at least partially receive a pledget 13022. In certain embodiments, the tissue thickness compensator 13020 can be integrally molded, or formed around, the pledgets 13022 during a molding manufacturing process. In various embodiments, the pledgets 13022 may comprise discrete retainers that can move independently of one another. In at least one embodiment, referring primarily to FIG. 330, each pledget 13022 can comprise interlocking and/or keyed features which can be configured to permit and, to a certain extent, limit relative lateral and longitudinal movement between the pledgets 13022. In at least one such embodiment, each pledget 13022 can comprise a projection 13026 and one or more recesses 13027, for example, wherein the projection 13026 of a first pledget 13022 can be positioned within and/or aligned with respect to the recesses of 13027 of adjacent second and third pledgets 13022. In various embodiments, gaps can be present between adjacent pledgets 13022 which can permit the pledgets 13022 to move or slide relative to one another until they contact an adjacent pledget 13022. In certain embodiments, the pledgets 13022 can be loosely interconnected. In various embodiments, the pledgets 13022 can be detachably connected to one another. In at least one such embodiment, the pledgets 13022 can be manufactured as a sheet of interconnected pledgets wherein, when a sufficient force is applied to the sheet, one or more of the pledgets 13022 can break away from the others. In certain embodiments, referring again to FIG. 329, a first sheet 13024 of pledgets 13022 can be positioned on a first side of a longitudinal slot 13025 and a second sheet 13024 of pledgets 13022 can be positioned on a second side of slot 13025. In at least one embodiment, further to the above, the longitudinal slot 13025 extending through the tissue thickness compensator 13020 can be configured to facilitate the passage of a knife edge of a firing member through the tissue thickness compensator 13020 and, as the firing member passes thereby, the firing member can apply a compressive force to the sheets 13024 and separate or singulate at least some of the pledgets 13022.

In various embodiments, the pledgets 13022 can be comprised of a biocompatible and/or bioabsorbable plastic, for example. In certain embodiments, the pledgets 13022 can be comprised of a solid material, a semi-solid material, and/or a flexible material, for example. In certain embodiments, the pledgets 13022 can be embedded within a tissue thickness compensator such that the pledgets 13022 move with the tissue thickness compensator. In at least one such embodiment, the pledgets 13022 can be sufficiently flexible such that they can flex with the top surface of the tissue thickness compensator. In certain embodiments, the pledgets 13022 can be configured to remain embedded in the tissue thickness compensator while, in certain other embodiments, the pledgets 13022 can be configured to pop out of, or detach from, the tissue thickness compensator. In various embodiments, the pledges 13022 can comprise a top surface which is flush with the top surface of the tissue thickness compensator. In certain embodiments, the top surfaces of the pledgets 13022 can be positioned above and/or below the top surface of the tissue thickness compensator. In various embodiments, the top surfaces of the pledgets 13022 can be disposed such that they are visible when viewing the top surface of the tissue thickness compensator while, in other embodiments, the top surfaces of the pledgets 13022 can be positioned below a layer of the tissue thickness compensator, for example. In certain embodiments, guide features can be molded into the top surface of a tissue thickness compensator, for example. In at least one such embodiment, the tissue thickness compensator may not comprise a composite material and may comprise a unitary piece of material, for example.

In various embodiments, referring now to FIG. 338, a staple cartridge can comprise a tissue thickness compensator 13620 and a skin, or top layer, 13621, for example. In at least one such embodiment, one or more pledgets, or retainers, 13622, for example, can be embedded in the skin 13621. In certain embodiments, each retainer 13622 can comprise one or more apertures 13629 defined therein which can be configured to receive the staple legs 13032 of staples 13030 therein when the staples 13030 are in their unfired position, as illustrated in FIG. 338. In use, further to the above, the staple legs 10032 can slide through the apertures 13629 when the staples 13030 are moved from their unfired position to their fired position until the bases 13031 of the staples 13030 contact the tissue thickness compensator 13620 and compress at least a portion of the tissue thickness compensator 13620 against the bottom surfaces of the pledgets 13622, for example. In various embodiments, referring now to FIG. 333, a staple cartridge can comprise a tissue thickness compensator 13120 and a skin, or top layer, 13122, for example. In at least one such embodiment, the tissue thickness compensator 13120 can comprise conical bumps, projections, and/or protrusions 13128, for example, which can extend upwardly from the top surface 13121 of the tissue thickness compensator 13120. The projections 13128 can be configured to receive and envelop the tips of the staple legs 13032 of the staples 13030 when the staples 13030 are in their unfired position, as illustrated in FIG. 333. The top layer 13122 can also comprise conical bumps, projections, and/or protrusions 13129 which can be aligned, or at least substantially aligned, with the projections 13128. In use, the staple legs 10032 can penetrate the projections 13128 and 13129 and emerge from the tissue thickness compensator 13120. In various embodiments, referring now to FIG. 337, a staple cartridge can comprise a tissue thickness compensator 13520 and a skin, or top layer, 13522, for example. In at least one such embodiment, the skin 13522 can comprise conical bumps, projections, and/or protrusions 13529, for example, which can extend upwardly from the top surface 13521 of the tissue thickness compensator 13520. Similar to the above, the projections 13529 can be configured to receive and envelop the tips of the staple legs 13032 of the staples 13030 when the staples 13030 are in their unfired position, as illustrated in FIG. 337. In use, the staple legs 10032 can penetrate the projections 13529 and emerge from the skin 13522.

In various embodiments, referring now to FIG. 334, a staple cartridge can comprise a tissue thickness compensator 13220 and a skin, or top layer, 13222, for example. In at least one such embodiment, the tissue thickness compensator 13220 can comprise conical dimples and/or recesses 13128, for example, which can extend downwardly into the top surface 13221 of the tissue thickness compensator 13220. In various embodiments, the tips of the staple legs 13032 can extend through the recesses 13128 when the staples 13030 are in their unfired position, as illustrated in FIG. 334. In at least one embodiment, the top layer 13222 can also comprise conical dimples and/or recesses 13229 which can be aligned, or at least substantially aligned, with the recesses 13228. In various embodiments, referring now to FIG. 335, a staple cartridge can comprise a tissue thickness compensator 13320 and a skin, or top layer, 13322, for example. In at least one such embodiment, the skin 13320 can comprise thick portions 13329 which can extend downwardly into the top surface 13321 of the tissue thickness compensator 13320. In various circumstances, the thick portions 13329 can be configured to receive at least a portion of the staple legs 13032 of the staples 13030 therein when the staples 13030 are in their unfired position, as illustrated in FIG. 335. In such embodiments, the thick portions 13329 can hold the staple legs 13032 in position such that the legs 13032 are aligned, or at least substantially aligned, with the staple-forming pockets of an anvil positioned opposite the tissue thickness compensator 13320. In various embodiments, referring now to FIG. 336, a staple cartridge can comprise a tissue thickness compensator 13420 and a skin, or top layer, 13422, for example. In at least one such embodiment, the skin 13422 can comprise thick portions 13429 which can extend upwardly from the top surface 13421 of the tissue thickness compensator 13420. In various circumstances, the thick portions 13429 can be configured to receive at least a portion of the staple legs 13032 of the staples 13030 therein when the staples 13030 are in their unfired position, as illustrated in FIG. 336. In such embodiments, the thick portions 13429 can hold the staple legs 13032 in position such that the legs 13032 are aligned, or at least substantially aligned, with the staple-forming pockets of an anvil positioned opposite the tissue thickness compensator 13420.

In various embodiments, referring now to FIGS. 339 and 340, a staple cartridge can comprise a tissue thickness compensator 13720 and a skin, or top layer, 13721, for example. In at least one such embodiment, the tissue thickness compensator 13720 can comprise pyramidal and/or stepped bumps, projections, and/or protrusions 13728, for example, which can extend upwardly from the top surface 13721 of the tissue thickness compensator 13720. The projections 13728 can be configured to receive and envelop the tips of the staple legs 13032 of the staples 13030 when the staples 13030 are in their unfired position, as illustrated in FIG. 340. Similarly, the top layer 13721 can comprise pyramidal and/or stepped bumps, projections, and/or protrusions 13729 which can be aligned, or at least substantially aligned, with the projections 13728. In various embodiments, the skin 13721 can further comprise one or more teeth 13727 extending upwardly from the projections 13729 which can be configured to engage tissue positioned against the top layer 13721 and prevent, or at least limit, relative lateral and/or longitudinal movement between the tissue, the top layer 13721, and/or the tips of the staple legs 13032. In use, the staple legs 13032 can penetrate the projections 13728 and 13729 and emerge from the tissue thickness compensator 13720 when the staples 13030 are moved from their unfired positions to their fired positions. In various embodiments, referring now to FIGS. 341 and 342, a staple cartridge can comprise a tissue thickness compensator 13820 and a skin, or top layer, 13821, for example. In at least one such embodiment, the tissue thickness compensator 13820 can comprise pyramidal and/or stepped bumps, projections, and/or protrusions 13828, for example, which can extend upwardly from the top surface 13821 of the tissue thickness compensator 13820. The projections 13828 can be configured to receive and envelop the tips of the staple legs 13032 of the staples 13030 when the staples 13030 are in their unfired position, as illustrated in FIG. 342. Similarly, the top layer 13821 can comprise pyramidal and/or stepped bumps, projections, and/or protrusions 13829 which can be aligned, or at least substantially aligned, with the projections 13828. In various embodiments, the top layer 13821 can further comprise one or more teeth 13827 extending downwardly into the tissue thickness compensator 13820 which can be configured to prevent, or at least limit, relative lateral and/or longitudinal movement between the top layer 13821 and the tissue thickness compensator 13820, for example. In use, the staple legs 10032 can penetrate the projections 13828 and 13829 and emerge from the tissue thickness compensator 13820 when the staples 13030 are moved from their unfired positions and their fired positions.

In various embodiments, referring now to FIG. 343, a staple cartridge can comprise a tissue thickness compensator, such as tissue thickness compensator 13920, for example, which can include ridges 13923 and valleys 13924 defined therein wherein, in at least one embodiment, the valleys 13924 can be defined between the ridges 13923. In various embodiments, each ridge 13923 can comprise the same height, substantially the same height, or different heights. Similarly, each valley 13924 can comprise the same depth, substantially the same depth, or different depths. In various embodiments, a plurality of staples 13030 can be at least partially stored within the tissue thickness compensator 13920 such that the tips of the staples 13030 can be positioned within the ridges 13923. In at least one such embodiment, the staple legs 13032 of the staples 13030 may not protrude from the tissue thickness compensator 13920 and/or a skin, or top layer, 13921 attached to the tissue thickness compensator 13920, for example, when the staples 13030 are stored in their unfired position. In various embodiments, the ridges 13923 and/or the valleys 13924 can extend laterally across the staple cartridge. In at least one such embodiment, the staple cartridge can comprise a longitudinal knife slot wherein the ridges 13923 and the valleys 13924 can extend in a direction which is transverse and/or perpendicular to the knife slot. In various circumstances, the ridges 13923 can be configured to hold the tips of the staple legs 13032 in position until the staples 13030 are moved from their unfired position into their fired position. In various embodiments, referring now to FIG. 344, a tissue thickness compensator, and/or a skin covering a tissue thickness compensator, can comprise longitudinal ridges and/or valleys. In at least one such embodiment, a tissue thickness compensator can comprise a top surface defined by ridges 14023 and valleys 14024, wherein the valleys 14024 can be defined between the ridges 14023, for example. In various embodiments, the tissue thickness compensator can comprise a skin 14021 which can include a plurality of apertures 14029 defined therein which can each be configured to receive a staple leg 13032. In certain embodiments, the apertures 14029 can be defined in the ridges 14023 wherein the tips of the staple legs 13032 may be positioned below the peaks 14028 of the ridges 14029, positioned flush with the peaks 14028, and/or positioned above the peaks 14028. In certain embodiments, in addition to or in lieu of the above, the apertures 14029 can be defined in the valleys 14024, for example. In certain embodiments, each aperture can be surrounded, or at least partially surrounded, by an embossment, for example, which can strengthen the skin and/or tissue thickness compensator surrounding the apertures. In any event, further to the above, the skin 14021 can be attached to a tissue thickness compensator in any suitable manner, including using at least one adhesive, for example.

As described above and referring again to FIG. 233, a surgical stapling instrument can comprise an anvil, such as anvil 10060, for example, which can be moved between an open position and a closed position in order to compress tissue T against the tissue thickness compensator 10020 of a staple cartridge 10000, for example. In various circumstances, the anvil 10060 can be rotated toward the staple cartridge 10000 until its downward movement is stopped by some portion of the staple cartridge 10000 and/or some portion of the channel in which the staple cartridge 10000 is positioned. In at least one such circumstance, the anvil 10060 can be rotated downwardly until its downward movement is resisted by the nose 10003 of the staple cartridge 10000 and/or the tissue T positioned intermediate the nose 10003 and the staple cartridge 10000. In some circumstances, the anvil 10060 may sufficiently compress the tissue thickness compensator 10020 to permit the tissue T to contact the tips of the staples 10030. In certain circumstances, depending on the thickness of the tissue T, the anvil 10060 may sufficiently compress the tissue thickness compensator 10020 such that the anvil 10060 comes into contact with the staples 10030 by the time the anvil 10060 has reached its fully closed position. Stated another way, in such circumstances, the anvil 10060 may deform the staples 10030 prior to the firing member 10052 being advanced into the staple cartridge 10000 to fire the staples 10030. Such circumstances may be acceptable in certain embodiments; however, referring now to FIGS. 358 and 359, other embodiments are envisioned in which a distal gap-setting element, such as element 10059, for example, can be utilized to limit the distance in which the anvil 10060 can be closed prior to the firing bar 10052 being advanced into the staple cartridge 10000. In various embodiments, the element 10059 can extend upwardly from the top surface 10021 of the tissue thickness compensator 10020 such that the downward movement of the anvil 10060 can be arrested as the tissue T is compressed against the element 10059 and a resistive force is generated therebetween. In use, as described above, the firing member 10052 can be advanced distally into the staple cartridge 10000 toward the distal end 10002 of the staple cartridge 10000 in order to eject the staples 10030 from the support portion 10010. Simultaneously, the firing member 10052 can engage the anvil 10060 and position the anvil 10060 a desired distance from the deck surface 10011 (FIG. 218) of the support portion 10010 over the staples 10030 being formed. In this way, the firing member 10052 can control the distance, or gap, between the tissue-contacting surface of the anvil 10060 and the deck surface 10011 at a particular location, wherein this particular location can be advanced distally as the firing member 10052 is advanced distally. In various circumstances, this gap distance may be shorter than the gap between the anvil 10060 and the deck surface 10011 being controlled or dictated by the distal gap-setting element 10059 at the distal end of the tissue thickness compensator 10020. In various embodiments, referring now to FIG. 359, the knife edge 10053 of the firing member 10052 can be configured to transect the distal gap-setting element 10059 when the firing member 10052 reaches the distal end of the tissue thickness compensator 10020 such that, after the element 10059 has been transected, the firing member 10052 can pull the anvil 10060 downwardly toward the support portion 10010 and close the gap to the desired gap height when firing the staples 10030 at the distal end of the staple cartridge 10000. In certain alternative embodiments, a distal gap-setting element can be configured to collapse as the firing member approaches the distal end of the staple cartridge. In at least one such embodiment, the distal gap-setting element can comprise a column which can provide resistance to the anvil as described above and then suddenly buckle once the buckling strength of the gap-setting element has been reached when the firing member approaches the distal end of the staple cartridge. In at least one embodiment, this buckling force can be approximately 10 lbf, for example. In certain embodiments, a gap setting element can be configured to drop downwardly into the deck of the support portion when a force exceeding a predetermined amount is applied to the gap setting element, for example. In certain other embodiments, the distal gap can be controlled by the nose of the staple cartridge. In at least one such embodiment, the downward movement of the anvil 10060 can be limited by the nose until the firing member has reached the distal end of the cartridge wherein, at such point, the compressive force applied to the nose can cause the nose to collapse. In certain embodiments, the nose can comprise a cavity defined by cavity walls which can allow the cavity to collapse once the compressive force applied thereto has exceed a predetermined force. In at least one such embodiment, the cavity can be defined by collapsible walls.

In various embodiments, as described above, an anvil, such as anvil 10060, for example, can be moved between an open position and a closed position in order to compress a tissue thickness compensator between the anvil and the support portion of a staple cartridge. In certain circumstances, referring now to FIGS. 360 and 361, the tissue thickness compensator of a staple cartridge, such as tissue thickness compensator 14120 of staple cartridge 14100, for example, may expand laterally and/or longitudinally when the tissue thickness compensator 14120 is compressed against a support portion 14110 of the staple cartridge 14100. In certain embodiments, the ends and/or sides of the tissue thickness compensator 14120 may not be constrained by the support portion 14110 and/or the anvil 10060 and, as a result, the tissue thickness compensator 14120 can expand in those directions without generating a compressive pressure, or at least an undesirable compressive pressure, within the tissue thickness compensator 14120. In such embodiments, a firing member, such as firing member 10052 (FIG. 236), for example, passing through the tissue thickness compensator 14120 may not be unduly impeded by an undesirable compressive pressure within the tissue thickness compensator 14120, for example. In certain other embodiments, referring again to FIG. 360, the distal end 14125 of the tissue thickness compensator 14120 may be constrained by the nose 14103 of the staple cartridge 14100, for example. In this particular embodiment, similar to the above, the distal end 14125 of the tissue thickness compensator 14120 may be constrained by the nose 14103 in order to reduce the possibility of the tissue thickness compensator 14120 from becoming prematurely detached from the support portion 14110. In any event, as a result of the above, a large internal pressure can be generated within the distal end 14125 which can impede the advancement of the firing member 10052, especially when the firing member 10052 reaches the distal end 14125. More particularly, in certain circumstances, the firing member 10052 can push, plow, and/or displace the tissue thickness compensator 14120 distally as it transects the tissue thickness compensator 14120 and, as a result, an even larger internal pressure can be created within the distal end 14125 of the tissue thickness compensator 14120. In order to at least partially dissipate this pressure within the tissue thickness compensator 14120, the nose 14103 can be comprised of a flexible material which can allow the nose 14103 to flex distally, for example, and create additional space for the tissue thickness compensator 14120. In certain embodiments, referring now to FIGS. 362 and 363, the nose of a staple cartridge can comprise a portion which can slide distally. More particularly, the nose 14203 of the staple cartridge 14200 can comprise a slidable portion 14204 which can be slidably connected to the nose 14203 such that, when the anvil 10060 is closed and/or the firing member 10052 is advanced into the distal end of the staple cartridge 14200, the slidable portion 14204 can slide distally and create additional room for the tissue thickness compensator 14200 and at least partially alleviate the internal pressure therein. In at least one embodiment, one of the nose 14203 and the slidable portion 14204 can comprise one or more rails and the other of the nose 14203 and the slidable portion 14204 can comprise one or more channels configured to slidably receive the rails therein. In at least one such embodiment, the channels and rails can be configured to co-operatively limit the movement of the slidable portion 14204 to a longitudinal distal path, for example.

In various circumstances, further to the above, certain staples, such as the distal-most staples within a staple cartridge, for example, can capture a larger portion of a tissue thickness compensator than the proximal staples within the staple cartridge. In such circumstances, as a result, a large clamping pressure can be applied to the tissue captured within the distal staples as compared to the proximal staples. These circumstances can arise when at least a portion of the tissue thickness compensator is shifted to and/or gathered at the distal end of the staple cartridge during use, as described above, even though the tissue thickness compensator may be comprised of a substantially homogenous material having a substantially constant thickness. In various circumstances, it may be desirable for certain staples to apply a higher clamping pressure to the tissue than other staples wherein, in various embodiments, a support portion and/or a tissue thickness compensator can be constructed and arranged to control which staples may apply the higher clamping pressure to the tissue and which staples may apply a lower clamping pressure to the tissue. Referring now to FIG. 364, a staple cartridge 14300 can comprise a support portion 14310 and, in addition, a tissue thickness compensator 14320 positioned on the deck surface 14311 of the support portion 14310. As compared to other embodiments disclosed in this application which comprise a support portion 14310 having a flat, or at least substantially flat, deck surface, the deck surface 14311 can be inclined and/or declined between the distal end 14305 and the proximal end 14306 of the support portion 14310. In at least one embodiment, the deck surface 14311 of the support portion 14310 can comprise a deck height at its distal end 14305 which is shorter than the deck height at its proximal end 14306. In at least one such embodiment, the staples 10030 at the distal end of the staple cartridge 14300 can extend above the deck surface 14311 a larger distance than the staples 10030 at the proximal end. In various alterative embodiments, the deck surface of a support portion can comprise a height at its distal end which is taller than its height at its proximal end. Referring again to FIG. 364, the tissue thickness compensator 14320 may comprise a thickness which is different along the longitudinal length thereof. In various embodiments, the tissue thickness compensator 14320 can comprise a thickness at its distal end 14325 which is thicker than its proximal end 14326, for example. In at least one such embodiment, the tissue thickness compensator 14322 can comprise a bottom surface 14322 which can be inclined or declined to match, or at least substantially match, the inclined or declined deck surface 14311 of the support portion 14310. As a result, the top, or tissue-contacting, surface 14321 of the tissue thickness compensator 14320 can comprise a flat, or at least substantially flat, surface upon which the tissue T can be positioned. In any event, as the tissue thickness compensator 14320 is thicker at its distal end 14325, the distal staples 10030 can capture a larger portion of the tissue thickness compensator 14320 therein than the proximal staples 10030 and, as a result, the distal staples 10030 can apply a larger compressive force to the tissue T, especially when the gap distance between the anvil 10060 and the deck surface 14311 is constant, or at least substantially constant, at the proximal and distal ends of the staple cartridge. In certain circumstances, however, the anvil 10060 may not reach a fully closed position and, as a result, the gap distance between the anvil 10060 and the deck surface 14311 may be larger at the distal end of the staple cartridge 14300 than the proximal end. In various circumstances, the distal staples 10030 may not be fully formed and, as a result, the distal staples 10030 may not apply the desired clamping pressure to the tissue T. In the embodiments where the tissue thickness compensator is thicker at the distal end of the staple cartridge, the tissue thickness compensator may compensate for the underforming of the staples and apply a sufficient pressure to the tissue T.

In various embodiments, referring now to FIG. 365, a staple cartridge, such as staple cartridge 14400, for example, can comprise a support portion 14410 and, in addition, a tissue thickness compensator 14420 positioned on the deck surface 14411 of the support portion 14410. Similar to the above, the deck surface 14411 can be inclined and/or declined such that, in at least one embodiment, the distal end 14405 of the support portion 14410 can have a deck height which is shorter than the deck height at the proximal end 14406, for example. In certain embodiments, the tissue thickness compensator 14420 can comprise a constant, or at least substantially constant, thickness along the length thereof and, as a result, the top, or tissue-contacting, surface 14421 of the tissue thickness compensator 14420 may parallel, or at least substantially parallel, the contour of the deck surface 14411. In various embodiments, the staples 10030 of the staple cartridge 14400 can be completely embedded within the tissue thickness compensator 14420 and the support portion 14410 when the staples 10030 are in their unfired position. In certain embodiments, the staples 10030 positioned at the proximal end of the staple cartridge 14400 may be completely embedded within the tissue thickness compensator 14420 and the support portion 14410 when the staples 10030 are in their unfired position whereas, due to the declined slope of the deck 14411 and top surface 14421, the tips of certain staples 10030, including the staples 10030 positioned at the distal end of the staple cartridge 14400, can protrude through the top surface 14421 of the tissue thickness compensator 14420 when the staples 10030 are in their unfired position.

In various embodiments, as described above, a tissue thickness compensator can be comprised of a single material wherein the entirety of the tissue thickness compensator can have the same, or at least substantially the same, material properties, such as density, stiffness, spring rate, durometer, and/or elasticity, for example, throughout. In various other embodiments, referring now to FIG. 368, a tissue thickness compensator, such as tissue thickness compensator 14520, for example, can comprise a plurality of materials or layers of materials. In at least one embodiment, the tissue thickness compensator 14520 can comprise a first, or central, layer 14520*a*, second, or intermediate, layers 14520*b* attached to the first layer 14520*a* on opposite sides thereof, and a third, or outer layer 14520*c* attached to each of the second layers 14520*b*. In certain embodiments, the intermediate layers 14520*b* can be attached to the central layer 14520*a* utilizing at least one adhesive and, similarly, the outer layers 14520*c* can be attached the second layers 14520 utilizing at least one adhesive. In addition to or in lieu of an adhesive, the layers 14520*a*-14520*c* can be held together by one or more interlocking features and/or fasteners, for example. In any event, the inner layer 14520*a* can be comprised of a first material having a first set of material properties, the intermediate layers 14520*b* can be comprised of a second material having a second set of material properties, and the outer layers 14520*c* can be comprised of a third material having a third set of material properties, for example. These sets of material properties can include density, stiffness, spring rate, durometer, and/or elasticity, for example. In certain embodiments, a staple cartridge can comprise six rows of staples 10030, for example, wherein a row of staples 10030 can be at least partially positioned in each of the outer layers 14520*c* and each of the inner layers 14520*b*, for example, and wherein two rows of staples 10030 can be at least partially positioned with the inner layer 14520*a*. In use, similar to the above, the staples 10030 can be ejected from the staple cartridge such that the staple legs 10032 of the staples 10030 penetrate the top surface 14521 of the tissue thickness compensator 14520, penetrate tissue positioned against the top surface 14521 by an anvil, and then contact the anvil such that the legs 10032 are deformed to capture the tissue thickness compensator 14520 and the tissue within the staples 10030. Also similar to the above, the tissue thickness compensator 14520 can be transected by a firing member as the firing member is advanced through the staple cartridge. In at least one such embodiment, the firing member can transect the inner layer 14520*a*, and the tissue, along a path defined by axis 14529, for example.

In various embodiments, further to the above, the rows of staples 10030 positioned within the inner layer 14520*a* can comprise the staple rows which are closest to the edges of the transected tissue. Correspondingly, the rows of staples 10030 positioned within the outer layers 14520*c* can comprise the staple rows which are furthest away from the edges of the transected tissue. In certain embodiments, the first material comprising the inner layer 14520*a* may comprise a density which is higher than the density of the second material comprising the intermediate layers 14520*b* and, similarly, the density of the second material may be higher than the density of the third material comprising the outer layers 14520*c*, for example. In various circumstances, as a result, larger compressive forces can be created within the staples 10030 positioned within the inner layer 14520*a* as compared to the compressive forces generated within the staples 10030 positioned within the intermediate layers 14520*b* and the outer layers 14520*c*. Similarly, larger compressive forces can be created within the staples 10030 positioned within the intermediate layers 14520b as compared to compressive forces created within the staples 10030 positioned within the outer layers 14520c, for example. In various alternative embodiments, the first material comprising the inner layer 14520a may comprise a density which is lower than the density of the second material comprising the intermediate layers 14520b and, similarly, the density of the second material may be lower than the density of the third material comprising the outer layers 14520c, for example. In various circumstances, as a result, larger compressive forces can be created within the staples 10030 positioned within the outer layers 14520c as compared to the compressive forces created within the staples 10030 positioned within the intermediate layers 14520b and the inner layer 14520a. Similarly, larger compressive forces can be created within the staples 10030 positioned within the intermediate layers 14520b as compared to the compressive forces created within the staples 10030 positioned within the inner layer 14520a, for example. In various other embodiments, any other suitable arrangement of layers, materials, and/or material properties could be utilized. In any event, in various embodiments, the layers 14520a-14520c of the tissue thickness compensator 14520 can be configured to remain attached to one another after they have been implanted. In certain other embodiments, the layers 14520a-14520c of the tissue thickness compensator 14520 can be configured to detach from one another after they have been implanted. In at least one such embodiment, the layers 14520a-14520c can be bonded together utilizing one or more bioabsorbable adhesives which can initially hold the layers together and then allow the layers to release from one another over time.

As described above, a tissue thickness compensator of a staple cartridge, such as tissue thickness compensator 14520, for example, can comprise a plurality of longitudinal layers. In various other embodiments, referring now to FIG. 369, a staple cartridge can comprise a tissue thickness compensator, such as tissue thickness compensator 14620, for example, which can comprise a plurality of horizontal layers. In at least one such embodiment, the tissue thickness compensator 14620 can comprise a first, or bottom, layer 14620a, a second, or intermediate, layer 14620b attached to the bottom layer 14620a, and a third, or top, layer 14620c attached to the intermediate layer 14620b. In various embodiments, the first layer 14620a can comprise a flat, or substantially flat, bottom surface 14626a and a triangular, or pyramidal, top surface 14625a, for example. In at least one such embodiment, the second layer 14620b can comprise a triangular, or pyramidal, bottom surface 14626b which can be configured to parallel and abut the top surface 14625a of the first layer 14620a. Similar to the above, the second layer 14620b can comprise a triangular, or pyramidal, top surface 14625b which can parallel and abut a bottom triangular, or pyramidal, bottom surface 14626c of the third layer 14620c, for example. In various embodiments, the top surface of the third layer 14626c can comprise a flat, or at least substantially flat, tissue-contacting surface 14621. Also similar to the above, the tissue thickness compensator 14620 can be configured to at least partially store six rows of staples, such as staples 10030, for example, therein wherein a firing member can transect the tissue thickness compensator 14620 between the two innermost staple rows along a path extending through axis 14629, for example. Similar to the above, each layer 14620a, 14620b, and 14620c can be comprised of a different material which can comprise different material properties and, as a result of the triangular, or pyramidal, configuration of the layers 14620a-14620c, the tissue thickness compensator 14620 can have different overall properties at various locations therewithin. For example, the outermost rows of staples 10030 may capture more of the third layer 14620c than the first layer 14620a therein whereas the innermost rows of staples 10030 may capture less of the third layer 14620c than the first layer 14620a and, as a result, the tissue thickness compensator 14620 may compress the tissue captured within the outermost staples 10030 differently than the tissue captured within the innermost staples 10030, for example, even though the tissue thickness compensator 14620 may have the same, or at least substantially the same, overall thickness thereacross.

In various embodiments, referring now to FIG. 286, a tissue thickness compensator of a staple cartridge, such as tissue thickness compensator 14720 of staple cartridge 14700, for example, can comprise voids, pockets, channels, and/or grooves, for example, defined therein which can vary the thickness of the tissue thickness compensator 14720. In at least one such embodiment, the tissue thickness compensator 14720 can be positioned against the deck surface 14711 of a support portion 14710 of the staple cartridge 14700 such that voids 14723 defined in the bottom surface 14722 of the tissue thickness compensator 14720 can overlie certain staple cavities 10012, but not others. In various embodiments, the voids 14723 can extend transversely to the knife slot 14715 of the support portion 14710, perpendicular to the knife slot 14715, and/or parallel to the knife slot 14715, for example. In certain embodiments, the voids 14723 can define a tread pattern in the bottom surface 14722 of the tissue thickness compensator 14720. In any event, when staples, such as staples 10030, for example, are deployed from the support portion 14710, referring now to FIGS. 287 and 288, certain staples 10030 can capture the tissue thickness compensator 14720 within a region containing a void 14723 while other staples 10030 can capture the tissue thickness compensator 14720 within a region positioned intermediate the voids 14723. In addition to or in lieu of the above, the tissue thickness compensator 14720 can comprise voids, pockets, channels, and/or grooves, for example, defined in the top, or tissue-contacting, surface 14721. In certain embodiments, referring now to FIGS. 366 and 367, a staple cartridge 14800 can comprise a tissue thickness compensator 14820 which can include a plurality of treads 14823 extending at least one of upwardly from a top surface 14821 of the tissue thickness compensator 14820, inwardly toward a central groove 14825, and/or distally toward the distal end of the staple cartridge 14800, for example. In at least one such embodiment, the treads 14823 can be separated by channels, slots, and/or grooves, such as channels 14824, for example. In various circumstances, as a result of the above, the overall thickness of the tissue thickness compensator can vary between staple rows and/or vary between the staples within a staple row. In certain circumstances, the treads, or thick portions, can be constructed and arranged such that they can flow in a desire direction, such as inwardly, for example, when the tissue thickness compensator is compressed.

In various embodiments, referring now to FIG. 303, a staple cartridge, such as staple cartridge 14900, for example, can comprise a support portion 14910 and, in addition, a tissue thickness compensator 14920 positioned against the support portion 14910. Similar to the above, the support portion 14910 can comprise staple drivers which can be lifted upwardly by a staple-deploying sled in order to lift staples, such as staples 10030, for example, at least partially positioned within the support portion 14910 toward an anvil, such as anvil 10060, for example, positioned opposite the staple cartridge 14900. In certain embodiments, the support portion 14910 can comprise six rows of staple cavities, such as two outer rows of staple cavities, two inner rows of staple cavities, and two intermediate rows of staple cavities positioned intermediate the inner rows and the outer rows, for example, wherein the anvil 10060 can comprise six rows of forming pockets 10062 aligned, or at least substantially aligned, with the staple cavities. In various embodiments, the inner rows of staple cavities can include staple drivers 14940a positioned therein, the intermediate rows of staple cavities can include staple drivers 14940b positioned therein, and the outer rows of staple cavities can include staple drivers 14940c positioned therein, wherein each of the staple drivers 14940a can include a cradle 14949a configured to support a staple 10030, wherein each of the staple drivers 14940b can include a cradle 14949b configured to support a staple 10030, and wherein each of the staple drivers 14940c can include a cradle 14949c configured to support a staple 10030. In their unfired positions, i.e., when the staple drivers 14940a-14940c are sitting on driver supports 14926 which extend underneath the support portion 14910, the cradles 14949a of the staple drivers 14940a can be positioned closer to the anvil 10060 than the cradles 14949b of the staple drivers 14940b and the cradles 14949c of the staple drivers 14940c. In such a position, a first forming distance can be defined between the cradles 14949a and the forming pockets 10062 positioned over the cradles 14949a, a second forming distance can be defined between the cradles 14949b and the forming pockets 10062 positioned over the cradles 14949b, and a third forming distance can be defined between the cradles 14949c and the forming pockets 10062 positioned over the cradles 14949c, wherein, in various embodiments, the first forming distance can be shorter than the second forming distance and the second forming distance can be shorter than the third forming distance, for example. When the staple drivers 14940a-14940c are moved from their unfired positions (FIG. 303) to their fired positions, each staple driver 14940a-14940c can be moved upwardly an equal, or an at least substantially equal, distance toward the anvil 10060 by the staple-deploying sled such that the first drivers 14940a drive their respective staples 10030 to a first formed height, the second drivers 14940b drive their respective staples 10030 to a second formed height, and the third drivers 14940c drive their respective staples 10030 to a third formed height, wherein the first formed height can be shorter than the second formed height and the second formed height can be shorter than the third formed height, for example. Various other embodiments are envisioned in which the first staple drivers 14940a are displaced upwardly a first distance, the second staple drivers 14940b are displaced upwardly a second distance, and the third staple drivers 14940c are displaced upwardly a third distance, wherein one or more of the first distance, the second distance, and the third distance can be different.

In various embodiments, referring again to FIG. 303, the deck surface 14911 of the support portion 14910 can vary in height with respect to the tissue-contacting surface 10061 of the anvil 10060. In certain embodiments, this height variation can occur laterally and, in at least one embodiment, the height of the deck surface 14911 surrounding the inner rows of staple cavities can be higher than the deck surface 14911 surrounding the outer rows of staple cavities, for example. In various embodiments, the bottom surface 14922 of the tissue thickness compensator 14920 can be configured to parallel, or at least substantially parallel, the deck surface 14911 of the support portion 14910. Further to the above, the tissue thickness compensator 14920 can also vary in thickness wherein, in at least one embodiment, the top, or tissue-contacting, surface 14921 of the tissue thickness compensator 14920 can slope inwardly from the outside or lateral edges thereof. In at least one such embodiment, as a result of the above, the tissue thickness compensator 14920 can be thinner in a region positioned over the inner rows of staple cavities and thicker in a region positioned over the outer rows of staple cavities, for example. In various embodiments, referring now to FIG. 304, the deck surface of a support portion 15010 can comprise a stepped deck surface, for example, wherein the highest steps of the stepped surface can surround the inner rows of staple cavities and the lowest steps of the stepped surface can surround the outer rows of staple cavities, for example. In at least one such embodiment, steps having an intermediate height can surround the intermediate rows of staple cavities. In certain embodiments, a tissue thickness compensator, such as tissue thickness compensator 15020, for example, can comprise a bottom surface which can parallel and abut the deck surface of the support portion 15010. In at least one embodiment, the top, or tissue-contacting, surface 15021 of the tissue thickness compensator can comprise an arcuate, parabolic, and/or curved surface, for example, which, in at least one such embodiment, can extend from a first lateral side of the tissue thickness compensator 15020 to a second lateral side of the tissue thickness compensator 15020 with an apex aligned, or at least substantially aligned, with the center of the staple cartridge 15000, for example. In various embodiments, referring now to FIG. 299, a staple cartridge 15300, for example, can comprise a support portion 15310, a plurality of staple drivers 15340 movably positioned within staple cavities defined in the support portion 15310, and a tissue thickness compensator 15320 positioned above the deck surface 15311 of the support portion 15310. The staple cartridge 15300 can further comprise one or more bottom pan portions 15326 which can be attached to the support portion 15310 and extend around the bottom of the support portion 15310 and support the drivers 15340, and staples 15330, in their unfired positions. As a staple-deploying sled is advanced through the staple cartridge, the sled can also be supported by the bottom pan portions 15326 as the sled lifts the staple drivers 15340 and the staples 15330 upwardly through the tissue thickness compensator 15320. In at least one embodiment, the tissue thickness compensator 15320 can comprise a first, or inner, portion 15322a positioned over an inner row of staple cavities, a second, or intermediate portion 15322b positioned over an intermediate row of staple cavities, and a third, or outer, portion 15322c positioned over a row of staple cavities, wherein the inner portion 15322a can be thicker than the intermediate portion 15322b and the intermediate portion 15322b can be thicker than the outer portion 15322c, for example. In at least one embodiment, the tissue thickness compensator 15320 can comprise longitudinal channels, for example, defined therein which can create the thinner portions 15322b and 15322c of the tissue thickness compensator 15320. In various alternative embodiments, the longitudinal channels can be defined in the top surface and/or the bottom surface of a tissue thickness compensator. In at least one embodiment, the top surface 15321 of the tissue thickness compensator 15320 can comprise a flat, or at least substantially flat, surface, for example.

In various embodiments, referring now to FIG. 296, a staple cartridge can comprise a tissue thickness compensator, such as tissue thickness compensator 15120, for example, which can comprise a plurality of portions having different thicknesses. In at least one embodiment, the tissue thickness compensator 15120 can comprise a first, or inner, portion 15122*a* which can have a first thickness, second, or intermediate, portions 15122*b* extending from the first portion 15122*b* which can each have a second thickness, and third, or outer, portions 15122*c* extending from the second portions 15122*b* which can each have a third thickness. In at least one such embodiment, the third thickness can be thicker than the second thickness and the second thickness can be thicker than the first thickness, for example, although any suitable thicknesses could be utilized in various other embodiments. In various embodiments, the portions 15122*a*-15122*c* of the tissue thickness compensator 15120 can comprise steps having different thickness. In at least one embodiment, similar to the above, a staple cartridge can comprise several rows of staples 10030 and a plurality of staple drivers having different heights which can deform the staples 10030 to different formed heights. Also similar to the above, the staple cartridge can comprise first staple drivers 15140*a* which can drive the staples 10030 supported thereon to a first formed height, second staple drivers 15140*b* which can drive the staples 10030 supported thereon to a second formed height, and third staple drivers which can drive the staples 10030 supported thereon to a third formed height, wherein the first formed height can be shorter than the second formed height and the second formed height can be shorter than the third formed height, for example. In various embodiments, as illustrated in FIG. 296, each staple 10030 can comprise the same, or substantially the same, unformed, or unfired, height. In certain other embodiments, referring now to FIG. 296A, the first drivers 15140*a*, the second drivers 15140*b*, and/or the third drivers 15140*c* can support staples having different unformed heights. In at least one such embodiment, the first staple drivers 15140*a* can support staples 15130*a* having a first unformed height, the second staple drivers 15140*b* can support staples 15130*b* having a second unformed height, and the third staple drivers 15140*c* can support staples 15130*c* having a third unformed height, wherein the first unformed height can be shorter than the second unformed height and the second unformed height can be shorter than the third unformed height, for example. In various embodiments, referring again to FIG. 296A, the tips of the staples 15130*a*, 15130*b*, and/or 15130*c* can lie, or at least substantially lie, in the same plane while, in other embodiments, the tips of the staples 15130*a*, 15130*b*, and/or 15130*c* may not lie in same plane. In certain embodiments, referring now to FIG. 297, a staple cartridge can include a tissue thickness compensator 15220 having a plurality of portions having different thickness which can be implanted against the tissue T by the staples 15130*a*, 15130*b*, and 15130*c*, as described above. In at least one embodiment, referring now to FIG. 298, the staples 15130*a*, 15130*b*, and/or 15130*c* can be deformed to different formed heights wherein the first staples 15130*a* can be formed to a first formed height, the second staples 15130*b* can be formed to a second formed height, and the third staples 15130*c* can be formed to a third formed height, and wherein the first formed height can be shorter than the second formed height and the second formed height can be shorter than the third formed height, for example. Other embodiments are envisioned in which the staples 15130*a*, 15130*b*, and 15130*c* can be formed to any suitable formed heights and/or any relative formed heights.

In various embodiments, as described above, the anvil of a surgical stapling instrument can be moved between an open position and a closed position. In such circumstances, the tissue-contacting surface of the anvil can be moved into its final, or forming, position as the anvil is moved into its closed position. Once the anvil is in its closed position, in certain embodiments, the tissue-contacting surface may no longer be adjustable. In certain other embodiments, referring now to FIG. 351, a surgical stapler, such as surgical stapler 15500, for example, can comprise an anvil channel 15560 and an adjustable tissue-contacting anvil adjustment plate 15561 positioned within the anvil channel 15560. In such embodiments, the anvil plate 15561 can be raised and/or lowered within the anvil channel 15560 in order to adjust the position of the tissue-contacting surface of the anvil plate 15561 relative to a staple cartridge positioned opposite the anvil plate 15561. In various embodiments, the surgical stapler 15500 can comprise an adjustment slide 15564 which, referring to FIGS. 356 and 357, can be slid intermediate the anvil channel 15560 and the anvil plate 15561 in order to control the distance between the anvil plate 15561 and the staple cartridge. In certain embodiments, referring again to FIGS. 351 and 352, the surgical stapler 15500 can further comprise an actuator 15562 coupled to the adjustment slide 15564 which can be slid proximally in order to slide the adjustment slide 15564 proximally and/or slid distally in order to slide the adjustment slide 15564 distally. In various embodiments, referring again to FIGS. 356 and 357, the actuator 15562 can be slid between two or more pre-defined positions in order to adjust the anvil plate 15561 between two or more positions, respectively. In at least one embodiment, such pre-defined positions can be demarcated on the surgical stapler 15500 as demarcations 15563 (FIG. 351), for example. In certain embodiments, referring to FIG. 357, the adjustment slide 15564 can comprise a plurality of support surfaces, such as first support surface 15565*a*, second support surface 15565*b*, and third support surface 15565*c*, for example, which can be aligned with a plurality of plate positioning surfaces, such as first positioning surface 15569*a*, second positioning surface 15569*b*, and third positioning surface 15569*c*, respectively, on the backside of the anvil plate 15561 in order to position the anvil plate 15561 in a first position. In order to position the anvil plate 15561 in a second position, the actuator 15562 and the slide 15564 can be slid proximally, for example, in order to realign the support surfaces 15565*a*-15565*c* of the slide 15564 relative to the positioning surfaces 15569*a*-15569*c* of the anvil plate 15561. More particularly, referring to FIG. 356, the slide 15564 can be slid distally such that the first support surface 15565*a* of the slide 15564 can be positioned behind the second positioning surface 15569*b* of the anvil plate 15561 and such that the second support surface 15565*b* of the slide 15564 can be positioned behind the third positioning surface 15569*c* of the anvil plate 15561 in order to move the anvil plate 15561 closer to the staple cartridge. When the anvil plate 15561 is moved from its first position to its second position, in such circumstances, the adjustable anvil plate 15561 can further compress the tissue T positioned between the anvil plate 15561 and the staple cartridge. In addition to the above, the formed height of the staples can be controlled by the position of the anvil plate 15561 relative to the staple cartridge as the forming pockets defined in the anvil plate 15561 will move closer to and/or further away from the staple cartridge when the anvil plate 15561 is adjusted. Although only two positions are discussed above, the slide 15564 can be slid into a suitable number of positions to move the anvil plate 15561 closer to and/or away from the staple cartridge. In any event, once the anvil plate 15561 has been suitably positioned, a staple-deploying sled 15550 can be slid distally within the staple cartridge in order to lift staple drivers 15540 and staples 15530 toward the anvil plate 15561 and staple the tissue T, as illustrated in FIG. 354. Similar surgical staplers are disclosed in U.S. patent application Ser. No. 13/036,647, entitled SURGICAL STAPLING INSTRUMENT, which was filed on Feb. 28, 2011, now U.S. Pat. No. 8,561,870, the entire disclosure of which is incorporated by reference herein.

In various embodiments, referring now to FIG. 353, a staple cartridge can be positioned within a staple cartridge channel 15570 of the surgical stapler 15500 which can comprise a tissue thickness compensator, such as tissue thickness compensator 15520, for example. When the anvil plate 15561 is moved toward the staple cartridge, as described above, the anvil plate 15561 can compress the tissue thickness compensator 15520 and/or the tissue T positioned intermediate the anvil plate 15561 and the tissue thickness compensator 15520. As the staples 15530 are deployed from the staple cartridge, referring to FIG. 355, the staples 15530 can compress and implant the tissue thickness compensator 15520 against the tissue T. In various embodiments, when the anvil plate 15561 is positioned against the slide 15564 and tissue has not yet been placed between the anvil plate 15561 and the tissue thickness compensator 15520, a gap can be defined between the anvil plate 15561 and the top surface 15521 of the tissue thickness compensator 15520 when the anvil plate 15561 is in a first position. When the anvil plate 15561 is moved into a second position, the anvil plate 15561 can contact the tissue thickness compensator 15520. In various alternative embodiments, when the anvil plate 15561 is positioned against the slide 15564 and tissue has not yet been placed between the anvil plate 15561 and the tissue thickness compensator 15520, a gap can be defined between the anvil plate 15561 and the top surface 15521 of the tissue thickness compensator 15520 when the anvil plate 15561 is in a first position and/or a second position. In at least one such embodiment, the anvil plate 15561 may not come into contact with the tissue thickness compensator 15520. In further alternative embodiments, when the anvil plate 15561 is positioned against the slide 15564 and tissue has not yet been placed between the anvil plate 15561 and the tissue thickness compensator 15520, the anvil plate 15561 can be in contact with the top surface 15521 of the tissue thickness compensator 15520 regardless of whether the anvil plate 15561 is in a first position and/or a second position, for example. Although only two positions for the anvil plate 15611 are described herein, the anvil plate 15611 may be positioned, or indexed, into any suitable number of positions.

In various embodiments, as a result of the above, a surgical stapling instrument can comprise means for adjusting the formed height of the staples which can, in various circumstance, compensate for different tissue thicknesses. In addition, the surgical stapling instrument can comprise other means for compensating for different tissue thicknesses and/or thickness variations within the tissue, for example. In at least one such embodiment, the anvil plate 15561 can be adjusted upwardly, or away, from the opposing staple cartridge to increase the formed, or fired, height of the staples. Correspondingly, the anvil plate 15561 can be adjusted downwardly, or toward, the opposing staple cartridge to decrease the formed, or fired, height of the staples. In various embodiments, the adjustment of the anvil plate 15561, for example, can adjust the gap between the forming pockets defined in the anvil plate 15561 and the fired height of the staple drivers or, more specifically, the fired height of the staple driver cradles, for example. Even with such a capacity to adjust the formed height of the staples to account for thicker and/or thinner tissue, for example, a tissue thickness compensator can also compensate for thicker and/or thinner tissue and/or compensate for thickness variations within the tissue, as described above. In such embodiments, a surgeon can be afforded with several compensation means within the same surgical stapling instrument.

As described above and illustrated in several embodiments, a surgical stapling instrument can utilize a staple cartridge having a linear arrangement of staple cavities and staples wherein a firing member can be advanced distally through the staple cartridge to deploy the staples from the staple cavities. In certain embodiments, a staple cartridge can comprise rows of staple cavities and staples which are curved. In at least one embodiment, referring now to FIGS. 345 and 346, a surgical stapling instrument, such as stapler 15600, for example, can comprise one or more circular or annular rows of staple cavities defined in a circular or annular support portion 15610. Such circular staple rows can comprise a circular row of inner staple cavities 15612 and a circular row of outer staple cavities 15613, for example. In at least one such embodiment, the circular rows of staple cavities can surround a circular or annular aperture 15615 defined in the stapler 15600 which can house a circular or annular knife movably positioned therein. In use, tissue can be positioned against the deck surface 15611 of the support portion 15610 and an anvil (not illustrated) can be assembled to the surgical stapler 15600 via an actuator extending through and/or positioned within the aperture 15615 such that, when the actuator is actuated, the anvil can be clamped toward the support portion 15610 and compress the tissue against the deck surface 15611. Once the tissue has been sufficiently compressed, the staples positioned within the staple cavities 15612 and 15613 can be ejected from the support portion 15610 and through the tissue such that the staples can contact the anvil and be sufficiently deformed to capture the tissue therein. As the staples are being fired and/or after the staples have been fired, the circular knife can be advanced to transect the tissue. Thereafter, the anvil can be moved away from the support portion 15610 and/or detached from the surgical stapler 15600 such that the anvil and the surgical stapler 15600 can be removed from the surgical site. Such surgical staplers 15600 and such surgical techniques, in various embodiments, can be utilized to join two portions of a large intestine, for example. In various circumstances, the circular staple lines may be configured to hold the portions of the large intestine together while the tissue heals and, at the same time, permit the portions of the large intestine to resiliently expand. Similar surgical stapling instruments and surgical techniques are disclosed in U.S. Pat. No. 5,285,945, entitled SURGICAL ANASTOMOSIS STAPLING INSTRUMENT, which issued on Feb. 15, 1994, the entire disclosure of which is incorporated by reference herein.

In various embodiments, further to the above, a tissue thickness compensator may be positioned against and/or attached to the support portion 15610 of the surgical stapler 15600, for example. In at least one embodiment, the tissue thickness compensator can be comprised of a circular or annular ring of material comprising an inner radius and an outer radius, for example. In certain circumstances, tissue can be positioned against this ring of material and, when the anvil is used to move the tissue toward the support portion 15610, the tissue thickness compensator can be compressed between the tissue and the deck surface 15611. During use, the staples can be fired through the tissue thickness compensator and the tissue such that the staples can contact the anvil and deform to their fired position to capture portions of the tissue and the tissue thickness compensator within the staples. In various circumstances, further to the above, the ring of material comprising the tissue thickness compensator must be sufficiently resilient to permit the portions of the large intestine surrounding the staple lines to expand. In various embodiments, referring again to FIGS. 345 and 346, a flexible tissue thickness compensator 15620 can comprise a circular or annular flexible inner ring 15624, for example, which, in at least one embodiment, can define a circular or annular aperture 15625. In certain embodiments, the inner ring 15624 may be configured such that it is not captured within staples deployed from the surgical stapler 15600; rather, in at least one embodiment, the inner ring 15624 may be positioned radially inwardly with respect to the inner row of staple cavities 15612. In at least one such embodiment, the tissue thickness compensator 15620 can comprise a plurality of tags, such as inner tags 15622 and outer tags 15623, for example, extending therefrom such that the tags can be at least partially captured within the staples as they are being deformed. More particularly, referring primarily to FIG. 345, each inner tag 15622 can comprise a head which is positioned over a staple cavity 15612 defined in the surgical stapler 15600 wherein the head can be attached to the inner ring 15624 by a neck 15626, for example, and, similarly, each outer tag 15623 can comprise a head which is positioned over a staple cavity 15613 defined in the surgical stapler 15600 wherein the head can be attached to the inner ring 15624 by a neck 15627, for example. In various embodiments, the heads of the inner tags 15622 and the outer tags 15623 can comprise any suitable shape, such as round, oval, and/or elliptical, for example. The necks 15626 and/or 15627 can also comprise any suitable shape wherein, in at least one embodiment, the necks 15627 connecting the heads of the outer tags 15623 to the inner ring 15624 can be configured to extend between adjacent inner staple cavities 15612 in the support portion 15610 such that the necks 15627 are not captured within the staples deployed from the inner staple cavities 15612.

In various embodiments, referring now to FIGS. 347 and 348, a flexible tissue thickness compensator 15720 can comprise a circular or annular flexible outer ring 15724, for example. In certain embodiments, the outer ring 15724 may be configured such that it is not captured within staples deployed from the surgical stapler 15600; rather, in at least one embodiment, the outer ring 15724 may be positioned radially outwardly with respect to the outer row of staple cavities 15613. In at least one such embodiment, the tissue thickness compensator 15720 can comprise a plurality of tags, such as inner tags 15622 and outer tags 15623, for example, extending therefrom such that the tags can be at least partially captured within the staples as they are being deformed. More particularly, referring primarily to FIG. 347, each inner tag 15622 can comprise a head which is positioned over a staple cavity 15612 defined in the surgical stapler 15600 wherein the head can be attached to the outer ring 15724 by a neck 15726, for example, and, similarly, each outer tag 15623 can comprise a head which is positioned over a staple cavity 15613 defined in the surgical stapler 15600 wherein the head can be attached to the outer ring 15724 by a neck 15727, for example. In various embodiments, the heads of the inner tags 15622 and the outer tags 15623 can comprise any suitable shape, such as round, oval, and/or elliptical, for example. The necks 15726 and/or 15727 can also comprise any suitable shape wherein, in at least one embodiment, the necks 15726 connecting the heads of the inner tags 15622 to the outer ring 15724 can be configured to extend between adjacent outer staple cavities 15613 such that the necks 15726 are not captured within the staples deployed from the outer staple cavities 15613. In certain alternative embodiments, a tissue thickness compensator can comprise a circular or annular flexible inner ring, a circular or annular flexible outer ring, and, in addition, a plurality of tags which can be connected to the inner ring and/or the outer ring. In at least one embodiment, certain tags can be connected to the inner ring and certain other tags can be connected to the outer ring. In certain embodiments, at least some of the tags can be connected to both the inner ring and the outer ring. In any event, further to the above, the inner ring 15624 of the tissue thickness compensator 15620, the outer ring 15724 of the tissue thickness compensator 15720, and/or any other suitable tissue thickness compensator, can be configured to resiliently expand and/or contract in order to accommodate the expansion and/or contraction of the tissue that it has been implanted against. Furthermore, although various embodiments are described herein as comprising circular or annular support rings, a tissue thickness compensator can comprise any suitably-shaped support structure for connecting the tags thereto. In various embodiments, further to the above, the circular knife advanced by the surgical stapler to cut the tissue captured between the anvil and the support portion can also cut the buttress material. In at least one such embodiment, the knife can separate the inner support ring from the tags by cutting the necks thereof, for example.

In various embodiments, further to the above, a tissue thickness compensator can comprise detachable and/or relatively movable positions which can be configured to allow the tissue thickness compensator to expand and/or contract in order to accommodate the movement of the tissue that it has been implanted against. Referring now to FIGS. 349 and 350, a circular or annular tissue thickness compensator 15820 can be positioned against and/or supported by the deck surface 15611 of the surgical stapler 15600 which can be held in an unexpanded position (FIG. 349) as it is being implanted against the tissue and, after the tissue thickness compensator 15820 has been implanted, the tissue thickness compensator 15820 can be configured to expand outwardly, as illustrated in FIG. 350. In various embodiments, the tissue thickness compensator 15820 can comprise a plurality of arcuate portions 15822 which can be connected together by an inner ring 15824, for example. In at least one embodiment, the arcuate portions 15822 can be separated from one another by seams 15828. In at least one other embodiment, the arcuate portions 15822 may be connected to one another wherein, in at least one such embodiment, an arrangement of perforations may permit the arcuate portions 15822 to separate from one another. In either event, in various embodiments, the arcuate portions 15822 can each comprise interlocking features, such as projections 15826 and notches 15823, for example, which can co-operate to limit relative movement between the arcuate portions 15822 prior to the tissue thickness compensator 15820 being implanted. Further to the above, each arcuate portion 15822 can be connected to the inner ring 15824 by one or more connectors 15827, for example, which can be configured to releasably hold the arcuate portions 15822 in position. After the staples, such as staples 10030, for example, stored within the support portion 15610 have been utilized to implant the tissue thickness compensator 15620 against the tissue, referring primarily to FIG. 350, the connectors 15827 can detach from the inner ring 15824 and allow the tissue thickness compensator 15820 to at least partially expand to accommodate movement within the underlying tissue. In various circumstances, all of the arcuate portions 15822 may detach from the inner ring 15824 while, in other circumstances, only some of the arcuate portions 15822 may detach from the inner ring 15824. In certain alternative embodiments, the arcuate portions 15822 can be connected by flexible sections which can permit the arcuate portions 15822 to move relative to each other but not detach from one another. In at least one such embodiment, the flexible sections may not receive staples therein and can be configured to stretch and/or contract to accommodate the relative movement of the arcuate portions 15822. In the embodiment illustrated in FIGS. 349 and 350, the tissue thickness compensator 15820 can comprise eight arcuate portions 15822, for example. In certain other embodiments, a tissue thickness compensator can comprise any suitable number of arcuate portions, such as two or more arcuate portions, for example.

Further to the above, a tissue thickness compensator 15620, 15720, and/or 15820, for example, can be configured to compensate for thicker and/or thinner tissue captured between the anvil and the support portion 15610 of the surgical instrument 15600. In various embodiments, similar to the above, the formed, or fired, height of the staples can be adjusted by moving the anvil toward and/or away from the support portion 15610. More particularly, the anvil can be moved closer to the support portion 15610 to decrease the formed height of the staples while, correspondingly, the anvil can be moved further away from the support portion 15610 to increase the formed height of the staples. In such embodiments, as a result, a surgeon can adjust the anvil away from the support portion 15610 to account for thick tissue and toward the support portion 15610 to account for thin tissue. In various other circumstances, the surgeon may decide not to adjust the anvil at all and rely on the tissue thickness compensator to account for the thinner and/or thicker tissue. In various embodiments, as a result, the surgical instrument 15600 can comprise at least two means for compensating for different tissue thicknesses and/or variations in the tissue thickness.

In various embodiments, as described above, a tissue thickness compensator can be attached to a support portion of a staple cartridge. In certain embodiments, the bottom surface of the tissue thickness compensator can comprise one of a layer of hooks or a layer of loops while a deck surface on the support portion can comprise the other one of the layer of hooks and the layer of loops. In at least one such embodiment, the hooks and the loops can be configured to engage one another and releasably retain the tissue thickness compensator to the support portion. In various embodiments, each hook can comprise an enlarged head extending from a neck, for example. In certain embodiments, a plurality of pads comprising the loops, for example, can be bonded to the bottom surface of the tissue thickness compensator while a plurality of pads comprising the hooks can be bonded to the deck surface of the support portion. In at least one embodiment, the support portion can comprise one or more apertures and/or recesses, for example, which can be configured to receive an insert therein comprising hooks and/or loops. In addition to or in lieu of the above, a tissue thickness compensator can be removably mounted to an anvil utilizing such hook and loop arrangements, for example. In various embodiments, the hooks and loops can comprise fibrous surfaces, for example.

In various embodiments, as described above, a staple cartridge can comprise a support portion and a tissue thickness compensator attached to the support portion. In certain embodiments, as also described above, the support portion can comprise a longitudinal slot configured to receive a cutting member therein and the tissue thickness compensator can comprise a retention member that can be retained in the longitudinal slot. In at least one embodiment, referring now to FIG. 386, a staple cartridge 16000 can comprise a support portion 16010 including a deck surface 16011 and a longitudinal slot 16015. The staple cartridge 16000 can further comprise a tissue thickness compensator 16020 positioned above the deck surface 16011. In various embodiments, the tissue thickness compensator 16020 can include a longitudinal retention member 16025 which extends downwardly into the longitudinal slot 16015. In at least one such embodiment, the retention member 16025 can be pressed into the slot 16015 such that the interaction between the retention member 16025 and the slot 16015 can resist relative movement between the support portion 16010 and the tissue thickness compensator 16020. In various embodiments, the body of the tissue thickness compensator 16020 can be comprised of a first material and the retention member 16025 can be comprised of a second, or different, material. In certain embodiments, the body of the tissue thickness compensator 16020 can be comprised of a material having a first durometer and the retention member 16025 can be comprised of a material having a second durometer, wherein the second durometer can be higher than the first durometer, for example. In use, in at least one embodiment, the staples 10030 can be pushed upwardly by staple drivers 10040 such that the tips of the staples 10030 can push through the body of the tissue thickness compensator 16020 and emerge from the tissue contacting surface 16021 and capture at least a portion of the tissue thickness compensator 16020 against the targeted tissue. In various embodiments, a cutting member passing through the slot 16015 can transect the retention member 16025 as the staples 10030 are being deployed. Once the tissue thickness compensator 16020 has been implanted, in various embodiments, the retention member 16025 can be pulled out of the slot 16015. In certain other embodiments, the body of the tissue thickness compensator 16020 can be configured to detach from the retention member 16025.

Referring now to FIGS. 387 and 389, a staple cartridge 17000 can comprise a support portion 17010 including a deck surface 17011 and a longitudinal slot 17015. The staple cartridge 17000 can further comprise a tissue thickness compensator 17020 positioned above the deck surface 17011. In various embodiments, the tissue thickness compensator 17020 can include a longitudinal retention member 17025 which extends downwardly into the longitudinal slot 17015. In at least one such embodiment, the retention member 17025 can be pressed into the slot 17015 such that the interaction between the retention member 17025 and the slot 17015 can resist relative movement between the support portion 17010 and the tissue thickness compensator 17020. In various embodiments, the retention member 17025 can extend through the entirety of the tissue thickness compensator 17020 to the top surface 17021 thereof wherein body portions 17024 of the tissue thickness compensator 17020 can be attached to opposite sides of the retention member 17025. In at least one such embodiment, the retention member 17025 can also be configured to resist the lateral deflection, for example, of the tissue thickness compensator 17020. In various embodiments, the body portions 17024 can be comprised of a first material and the retention member 17025 can be comprised of a second, or different, material. In certain embodiments, the body portions 17024 can be comprised of a material having a first durometer and the retention member 17025 can be comprised of a material having a second durometer, wherein the second durometer can be higher than the first durometer, for example. In various embodiments, further to the above, a cutting member passing through the slot 17015 can transect the retention member 17025 as the staples 10030 are being deployed. Once the tissue thickness compensator 17020 has been implanted, in various embodiments, the retention member 17025 can be pulled out of the slot 17015. In certain other embodiments, the body portions 17024 can be configured to detach from the retention member 17025.

Referring now to FIG. 388, a staple cartridge 18000 can comprise a support portion 18010 including a deck surface 18011 and a longitudinal slot 18015. The staple cartridge 18000 can further comprise a tissue thickness compensator 18020 positioned above the deck surface 18011. In various embodiments, the tissue thickness compensator 18020 can include a longitudinal retention member 18025 which extends downwardly into the longitudinal slot 18015. In at least one such embodiment, the retention member 18025 can be pressed into the slot 18015 such that the interaction between the retention member 18025 and the slot 18015 can resist relative movement between the support portion 18010 and the tissue thickness compensator 18020. In various embodiments, the retention member 18025 can extend through the entirety of the tissue thickness compensator 18020 to the top surface 18021 thereof wherein body portions 18024 of the tissue thickness compensator 18020 can be attached to opposite sides of the retention member 18025. In at least one embodiment, the retention member 18025 can comprise an enlarged portion 18026 which can be received in a cavity 18016 defined in the slot 18015. In at least one such embodiment, the enlarged portion 18026 can resist the withdrawal of the retention member 18025 from the slot 18015.

In various embodiments, referring now to FIG. 445, a tissue thickness compensator, such as tissue thickness compensator 22020, for example, can be attached to an anvil of a surgical stapling instrument, such as anvil 22060, for example. The tissue thickness compensator 22020 can include, in at least one embodiment, a cavity 22024 defined between a first film 22026 and a second film 22027, wherein at least portions of the first film 22026 are attached to the second film 22027. In at least one such embodiment, the first film 22026 can be attached to the second film 22027 along lateral seams 22028a and 22028b, for example. In various embodiments, the first film 22026 can be attached to the second film 22027 along a sealed perimeter in order to sealingly enclose the cavity 22024. In certain embodiments, the first film 22026 and the second film 22027 can be thermally welded along the lateral seams 22028a, 22028b and/or any other seams connecting the films 22026 and 22027, for example. Referring again to FIG. 445, the anvil 22060 can comprise a plurality of staple forming pockets 22062 which can each be configured to receive and deform the leg of staple wherein, in at least one embodiment, the second film 22027 can comprise projections 22022 which can extend into the forming pockets 22062. In certain embodiments, the projections 22022 can be sized and configured such that they fit snugly within the forming pockets 22062 and can retain the tissue thickness compensator 22020 to the anvil 22060. In the illustrated embodiment, the anvil 22060 can comprise six rows of forming pockets 22062 wherein the tissue thickness compensator 22020 can similarly comprise six rows of projections 22022 which are aligned with the forming pockets 22062, for example. Other embodiments comprising more than or less than six rows of forming pockets 22062 and/or projections 22022 could be utilized. In certain embodiments, one or more adhesives could be utilized to retain the tissue thickness compensator 22020 to the anvil 20060.

As discussed above, the tissue thickness compensator 22020 can comprise a cavity 22024 defined therein. In various embodiments, the cavity 22024 can extend longitudinally along the anvil 22060. Referring again to FIG. 445, the tissue thickness compensator 22020 can comprise a compressible material positioned within the cavity 22024. In at least one embodiment, referring now to FIG. 446, staples, such as staples 22030, for example, can be ejected from a staple cartridge such that the staples 22030 penetrate the tissue T and then penetrate the tissue thickness compensator 22020 before contacting the anvil 22060. As the legs of the staples 22030 are deformed by the anvil 22060, in various embodiments, the legs can be turned downwardly to repenetrate the tissue thickness compensator 22020 once again. In any event, once the staples 22030 have penetrated the tissue thickness compensator 22020, one or more fluids contained in the cavity 22024, for example, can flow or weep out of the tissue thickness compensator 22020 and onto the tissue T. In certain embodiments, the cavity 22024 can comprise one or more powders contained therein which can escape the cavity 22024 once the tissue thickness compensator 22020 has been at least partially ruptured by the staples 22030, for example. In various embodiments, a material 22025 positioned within the cavity 22024 can be compressed or squeezed within the staples 22030 when the staples 22030 are deformed into their fired configurations such that, in at least one embodiment, a fluid stored within the material 22025 can be expressed from the material 22025, for example. In various embodiments, referring again to FIG. 446, the staples 22030 can also be configured to capture a tissue thickness compensator, such as compensator 22029, for example, removably attached to the staple cartridge against the other side of the tissue T.

In various embodiments, further to the above, the material 22025 can comprise freeze-dried thrombin, freeze-dried fibrin, and/or small fiber non-woven oxidized regenerated cellulose, for example. In certain embodiments, the material 22025 can comprise a compressed powder wafer. In at least one embodiment, the sealed cavity 22024 can comprise an internal atmosphere having a pressure below that of the atmosphere surrounding the tissue thickness compensator 22020. In such an embodiment, the pressure difference between the atmosphere in the internal cavity 22024 and the atmosphere can cause the films 22027 and 22028 to be drawn inwardly. When the internal cavity 22024 is ruptured by the staples 22030, as described above, the vacuum within the internal cavity 22024 can equalize with the surrounding atmosphere and the material 22025 can escape the internal cavity 22024, as also described above. In such circumstances, the tissue thickness compensator 22020 can expand and apply a compressive force to the tissue T captured within the staples 20030. In embodiments in which the material 22025 is vacuum-packed within the tissue thickness compensator 22020, the material 22025 can expand after the internal cavity 22024 has been punctured. In certain embodiments, the films 22026, 22027 can be comprised of a bioabsorbable material and can be configured to dissolve once placed in the patient. In at least one such embodiment, each film 22026, 22027 can be comprised of a layer, or laminate, which is between approximately 0.25 mils and approximately 0.50 mils thick, for example. In any event, further to the above, the tissue thickness compensator 22020, including the material 22025, can be transected by a cutting element as the staples 22030 are fired from their staple cartridge.

In certain embodiments, referring again to FIG. 445, the cavity 22024 and the material 22025 of the tissue thickness compensator 22020 can be positioned underneath the inner four rows of staple forming pockets 22062 while the seams 22028a, 22028b can be positioned underneath the outer rows of forming pockets 22062. In such embodiments, the staples in the outer rows of staples may not engage the material 22025 and, thus, they may not capture the material 22025 therein. Rather, such staples may only capture the films 22026 and 22027 along seams 22028a, 22028b. In various alternative embodiments, referring now to FIGS. 447 and 448, a tissue thickness compensator 22120 can comprise, similar to the above, a first film 22126, a second film 22127, and a plurality of materials 22125a-d captured between the first film 22126 and the second film 22127. In at least one such embodiment, referring primarily to FIG. 447, the first material 22125a can be aligned with an outer row of staples 22030 in staple cartridge 22000 and an outer row of staple cavities 22062 in anvil 22060, the second material 22125b and the third material 22125c can each be aligned with two inner rows of staples 22030 and staple cavities 22062, and the fourth material 22126d can be aligned with another outer row of staples 22030 and staple cavities 22062. In such an embodiment, referring now to FIG. 448, all of the staples 22030 can be arranged such that they can capture at least one of the materials 22125a-22125d therein. As illustrated in FIGS. 447 and 448, further to the above, the staples 22030 can be lifted upwardly between an unfired position and a fired position by staple drivers 22040 positioned within the staple cartridge 22000.

In various embodiments, referring again to FIGS. 447 and 448, the layers 22126 and 22127 can define one or more sealed cavities in which the materials 22125a-d can be positioned. In at least one embodiment, the layers 22126 and 22127 can be sealed together along a perimeter which can include lateral seams 22128a and 22128b, for example, utilizing any suitable process, such as thermal and/or laser welding, for example. In certain embodiments, each of the materials 22125a-22125d can be sealed within separate cavities while, in other embodiments, two or more of the materials 22125a-22125d can be sealed within the same cavity. In various embodiments, the materials 22125a-22125d can be comprised of the same material or materials while, in other embodiments, one or more of the materials 22125a-22125d can be comprised of different materials. In at least one embodiment, one or more of the materials 22125a-22125d can be comprised of sodium sterate and/or LAE, for example. In certain embodiments, the materials 22125a-22125d can comprise a lubricant. In such embodiments, the legs of the staples 22030 can be exposed to the lubricant when the staple legs penetrate the materials 22125a-22125d of the tissue thickness compensator 22120. After the legs pass through the tissue thickness compensator 22120, the legs can contact the anvil 22060 wherein the lubricant can reduce the coefficient of friction, and the friction forces, between the staple legs and the anvil 22060. In such circumstances, the force needed to fire the staples 22030 can be reduced. Owing to the position of the tissue thickness compensator 22120 against the anvil 22060, in at least one embodiment, the staple legs of the staples 22030 can contact the anvil 22060 directly after exiting the tissue thickness compensator 22120 thereby reducing the possibility that the lubricant may be wiped off the staple legs before they contact the anvil 22060. Similarly, the staple legs of the staples 22030 can contact the anvil 22060 directly after being exposed to one or medicaments in the tissue thickness compensator 22120 thereby reducing the possibility that medicaments may be wiped off the staple legs before they re-enter the tissue T. In some circumstances, the staple legs can re-enter the tissue thickness compensator 22120 as the staple legs are being deformed downwardly such that the staple legs can be re-exposed to the medicaments before re-entering the tissue T, for example. In various embodiments, similar to the above, the second film 22127 can comprise a plurality of projections 22122, for example, which can be snugly received within the staple cavities 22062 in order to retain the tissue thickness compensator 22120 to the anvil 22060, for example.

In various embodiments, referring now to FIGS. 449 and 450, an end effector of a surgical stapling instrument can comprise a tissue thickness compensator, such as compensator 22220, for example, which can comprise a plurality of cavities 22222 aligned with the staple forming pockets 22062 of the anvil 22060. In at least one embodiment, the compensator 22220 can be comprised of a first, or bottom, layer 22226 and a second, or top, layer 22227 wherein the first layer 22226 and/or the second layer 22227 can comprise a plurality of raised portions or partial bubbles which can define the cavities 22222. As illustrated in FIG. 449, the compensator 22220 can be attached to the anvil 22060 such that the cavities 22222 are aligned, or at least substantially aligned, with the staple forming pockets 22062 of the anvil 22060. In various embodiments, each cavity 22222 can include one or more medicaments contained therein, such as, for example, oxidized regenerated cellulose, calcium, and/or alginate. In use, in certain embodiments, each cavity 22222 can be in a sealed, unpunctured state prior to being punctured by the staples 22030 ejected from the staple cartridge 22000, for example. After the legs of the staples 22030 have passed through the tissue T, referring now to FIG. 450, each staple leg can pierce and penetrate the first layer 22226 and enter into a cavity 22222 where the staple leg can then pass through one or more medicaments contained therein before piercing and penetrating the second layer 22227. Similar to the above, the legs of the staples 22030 can then contact the anvil 22060.

In various embodiments, the cavities 22222 can maintain the one or more medicaments stored therein in a dry or an at least substantially dry state before being ruptured. After a cavity 22222 has been ruptured, a fluid, such as blood, for example, can enter into the cavity 22222 and mix with the one or more medicaments. In at least one embodiment, the mixture of the fluid with a medicament can cause the medicament to expand within the cavity 22222 wherein, in at least one such embodiment, the medicament can comprise at least one hydrogel, for example. In certain embodiments, the medicament can comprise at least one haemostatic material, for example. In various embodiments, the first layer 22226 and/or the second layer 22227 can be comprised of a flexible material which can stretch to accommodate the expansion of the medicament. In at least one embodiment, the layers 22226, 22227 can be comprised of a CAP/GLY material, for example. In any event, the expansion of the medicament can apply a compressive force to the tissue T captured within and/or positioned around the staples 22030, for example. In various circumstances, the expansion of the medicament can cause the cavities 22222 to burst. In certain embodiments, a first group of cavities 22222 can comprise a first medicament therein while a second group of cavities 22222 can comprise a second medicament therein, for example. In at least one such embodiment, the first medicament can be configured to expand a first amount and/or at a first rate while the second medicament can be configured to expand a second amount and/or at a second rate, for example, wherein the first amount can be different than the second amount and/or the first rate can be different than the second rate. Further to the above, in various embodiments, one or more cavities 22222 can include two or more medicaments stored in each cavity wherein the medicaments can comprise a first medicament and a second medicament, for example. In certain embodiments, a cavity 22222 can maintain the first medicament and the second medicament in a dry, or an at least substantially dry, state before being ruptured. After the cavity 22222 has been ruptured, as described above, blood, for example, can enter into the cavity 22222 and mix with the first and second medicaments wherein, in at least one embodiment, the first and second medicaments can form a gel which expands.

In various embodiments, referring now to FIGS. 451-453, a tissue thickness compensator, such as compensator 22320, for example, can comprise a plurality of first cavities 22322a and a plurality of second cavities 22322b which can be aligned with staple forming pockets 22062a and 22062b, respectively. In at least one embodiment, referring primarily to FIG. 452, the staple forming pockets 22062a and 22062b may be defined in separate stepped surfaces on the anvil 22060. More particularly, the forming pockets 22062a can be defined in first surfaces 22069a of anvil 22060 and the forming pockets 22062b can be defined in second surfaces 22069b wherein the first surfaces 22069a can be positioned offset, or higher, with respect to the second surfaces 22069b, for example. In various embodiments, the first cavities 22322a of the tissue thickness compensator 22320 can be larger than the second cavities 22322b wherein, in at least one such embodiment, the first cavities 22322a can extend higher than the second cavities 22322b. As a result of the above, the first cavities 22322a can extend upwardly into the first staple forming pockets 22062a while, concurrently, the second cavities 22322b can extend upwardly into the second staple forming pockets 22062b. In various embodiments, each of the first cavities 22322a can be configured to contain a larger quantity of a medicament than the second cavities 22322b, for example. In other embodiments, the first cavities 22322a and the second cavities 22322b can contain the same, or at least substantially the same, amount of medicament therein even though the cavities 22322a and 22322b may have different sizes.

In various embodiments, further to the above, the first cavities 22322a can be arranged in certain rows while the second cavities 22322b can be arranged in different rows. In certain embodiments, a tissue thickness compensator can comprise cavities aligned with each forming pocket while, in other embodiments, referring to FIG. 459, a tissue thickness compensator, such as compensator 22420, for example, may comprise cavities aligned with only some of the forming pockets. In various embodiments, referring again to FIG. 452, the compensator 22320 can be attached to the anvil 22060. In at least one embodiment, the cavities 22322a and/or the cavities 22322b can be configured such that fit snugly within staple forming pockets 22062a and/or 22062b, respectively. In certain embodiments, the compensator 22320 can be assembled to the anvil 22060 such that the second layer 22327 of the compensator 22320 is positioned against the second surfaces 22069b of the anvil 22060. In certain other embodiments, referring now to FIGS. 454 and 455, the compensator 22320 can be positioned adjacent to the anvil 22060 such that the compensator 22320 can abut the anvil 22060 when the anvil 22060 is displaced toward the staple cartridge 22000 to compress the tissue T therebetween. Once the staples 22030 have been fired from the staple cartridge 22000 and deformed by the anvil 22060, referring now to FIG. 456, the compensator 22320 can be trapped against the tissue T by the staples 22030 and the anvil 22060 can be moved away from the compensator 22320. In certain circumstances, referring now to FIG. 457, one or more of the staples 22030 may not be properly deformed by the anvil 22030. In such circumstances, referring now to FIG. 458, the cavities in the tissue thickness compensator which overlie the misfired or misformed staples may not be pierced when the staples are fired. In at least one such embodiment, the tissue thickness compensator may be comprised of a bioabsorbable material which can dissolve and subsequently release the medicament contained in the unpierced cavities.

In various embodiments, further to the above, the first cavities 22322a and/or the second cavities 22322b of the tissue thickness compensator 22320 can comprise a gas, such as air, carbon dioxide, and/or nitrogen, for example, sealed therein. In certain embodiments, the cavities 22322a and/or 22322b can comprise bubbles which can be popped when the staples 22030 are fired through the cavities 22322a and 22322b to release the gas contained therein. In at least one embodiment, such popping can provide an audio feedback to the surgeon that the cavities 22322a and 22322b are being ruptured. In some circumstances, however, some of the staples 22030 may be misfired, as described above, and the cavities 22322a and 22322b associated therewith may not be popped. In various circumstances, the surgeon can scan the stapled tissue for any unpopped bubbles, or cavities 22322a and 22322b, and determine whether any corrective action needs to be taken.

As discussed above, referring now to FIG. 460, a surgical stapling instrument can comprise a firing member, such as firing member 22080, for example, which can include a cutting member, or cutting edge, 22081 which can be advanced through the tissue T and one or more tissue thickness compensators as the firing member 22080 is advanced through the cartridge 22000 to deploy the staples 22030 therefrom. In various embodiments, referring primarily to FIG. 462, a compensator, such as compensator 22520, for example, can be attached to the anvil 22060 of the surgical stapling instrument wherein the anvil 22060 can include a knife slot 22061 sized and configured to receive at least a portion of the cutting member 22081. Similarly, the staple cartridge 22000 can comprise a knife slot 22011 which can also be sized and configured to receive at least a portion of the cutting member 22081. In various embodiments, referring again to FIG. 460, the compensator 22520 can comprise one or more cavities, such as cavities 22522, for example, positioned along a cutting line 22521 of the compensator 22520 wherein the cavities 22522 can be aligned with the knife slot 22061 defined in the anvil 22060. As the cutting member 22081 is progressed distally through the staple cartridge 22000 to deploy the staples 22030, the cutting member 22081 can incise the tissue T and the cavities 22522 of the compensator 22520. Similar to the above, referring primarily to FIG. 461, each cavity 22522 can define a sealed cavity 22524 which can contain one or more medicaments 22525 therein. In at least one embodiment, one or more of the cavities 22522 can be configured to contain a fluid which can be released when the cavities 22522 are at least partially incised by the cutting member 22081. In various circumstances, the cutting member 22081 can sequentially incise the cavities 22522 and, as a result, sequentially release the medicaments contained therein.

In various embodiments, referring primarily to FIG. 462, the compensator 22520 can comprise lateral projections, or wings, 22529 that extend along the sides thereof. In at least one embodiment, the projections 22529 can be secured to the anvil surfaces 22069a and/or anvil surfaces 22069b utilizing one or more adhesives, for example. In certain embodiments, the projections 22522 can be sized and configured to fit snugly within the knife slot 22061 of the anvil 22060 such that, in at least one such embodiment, the projections 22522 can retain the compensator 22520 to the anvil 22060. In various embodiments, the lateral projections 22529 can be sized and configured such that they extend over, or overlie, the staple forming pockets 22062*b* and/or the staple forming pockets 22062*a*. In certain other embodiments, referring now to FIGS. 463 and 464, a compensator 22620 can comprise lateral projections 22629 that do not extend over, or overlie, the staple forming pockets 22062*a* and 22062*b* of the anvil 22060 and/or any other staple forming pockets, for example. In at least one such embodiment, the compensator 22620 may not be captured within a staple 22030 ejected from the staple cartridge 22030. In any event, referring again to FIG. 460, the cutting member 22081 can transect the compensator 22520 as the compensator 22520 is being secured to the tissue T by the staples 22030. In such embodiments, the compensator 22520 can detach from the anvil 22060 and remain with the tissue T. Referring again to the compensator 22620 illustrated in FIGS. 463 and 464, the staples 22030 may not secure the compensator 22620 to the anvil 22060 and, in at least one embodiment, may remain attached to the anvil 22060 after the cutting member 22081 has transected the compensator 22620.

In various embodiment, referring now to FIGS. 465 and 466, an end effector of a surgical stapling instrument can comprise a tissue thickness compensator, such as compensator 22720, for example, which can be attached to, or can be configured to be attached to, an anvil, such as anvil 22760, among others. In at least one embodiment, similar to the above, the anvil 22760 can comprise a plurality of staple forming pockets 22762 and a longitudinal knife slot 22761 configured to receive a cutting member therein as the cutting member is advanced through the end effector. In certain embodiments, the compensator 22720 can comprise a first film layer 22726 and a second film layer 22727 which can be attached to one another to define a cavity 22724. In at least one such embodiment, the first film layer 22726 can be attached to the second film layer 22727 along a sealed outer perimeter 22728 wherein the sealed outer perimeter 22728 can contain at least one medicament 22725 in the cavity 22724, for example. As illustrated in FIG. 466, the cavity 22724 and the medicament 22725 can extend under all of the staple cavities 22762 and, in at least one embodiment, the sealed perimeter 22728 can be positioned laterally with respect to the outermost staple cavities 22762. In various embodiments, the compensator 22720 can further comprise a longitudinal rib 22721, for example, which can be configured to extend upwardly into the knife slot 22761. In at least one such embodiment, the rib 22721 can be sized and configured to fit snugly within the knife slot 22761 in order to secure the compensator 22720 to the anvil 22760. In certain embodiments, the rib 22721 can be configured to align or center the compensator 22720 with the anvil 22760. Similarly, referring to FIG. 467, a tissue thickness compensator 22820 can comprise a retention rib 22821 which can be positioned within the knife slot 22761, for example, in order to secure the compensator 22820 to the anvil 22760. Referring again to FIG. 466, as a cutting member is advanced through the knife slot 22761, in various circumstances, the cutting member can transect the rib 22721 and release the compensator 22720 from the anvil 22760. Such a cutting member is depicted in FIG. 467 as part of firing member 22080, for example.

In various embodiments, referring again to FIG. 467, the tissue thickness compensator 22820 can comprise a first layer 22826 and a second layer 22827 which can be configured and arranged to define a plurality of first packets 22824*a* and a plurality of second packets 22824*b*. In at least one embodiment, each of the first packets 22824*a* can be configured to contain a first medicament and each of the second packets 22824*b* can be configured to contain a second medicament, wherein the second medicament can be different than the first medicament. In various embodiments, the first packets 22824*a* and the second packets 22824*b* can be arranged in an alternating arrangement. In at least one such embodiment, the first packets 22824*a* and the second packets 22824*b* can extend laterally across the tissue thickness compensator 22820 such that a second packet 22824*b* is positioned intermediate two first packets 22824*a* and a first packet 22824*a* is positioned intermediate two second packets 22824*b*, for example. As the cutting member 22080 is progressed through the compensator 22820, as illustrated in FIG. 467, the cutting member 22080 can transect a first packet 22824*a*, followed by a second packet 22824*b*, followed by a first packet 22824*a*, followed by a second packet 22824*b*, and so forth. Correspondingly, in such embodiments, the cutting member 22080 can sequentially release the first medicament contained in a first packet 22824*a* and the second medicament contained in a second packet 22824*b* in an alternating arrangement, for example. In embodiments where the first packets 22824*a* and the second packets 22824*b* are positioned adjacent to one another, the first medicament can be configured to mix with the second medicament when they are released from their respective first packets 22824*a* and second packets 22824*b*. In at least one such embodiment, the advancement of the cutting member through the compensator 22820 can mix the first medicament with the second medicament.

In various embodiments, further to the above, the first medicament can comprise a first powder while the second medicament can comprise a second powder. In at least one embodiment, the first medicament and/or the second medicament can be comprised of a haemostatic material, oxidized regenerated cellulose, alginate, and/or calcium, for example. In certain embodiments, the first medicament and/or the second medicament can comprise a fluid. In at least one embodiment, one or more of the first packets 22824*a* and/or one or more of the second packets 22824*b* can comprise a lubricant which can reduce the force needed to advance the firing member 22080 through the compensator 22820 and/or the tissue T. In various embodiments, the first film layer 22826 and/or the second film layer 22827 can be comprised of a bioabsorbable material, such as PDS, for example. In certain embodiments, the first film layer 22826 and the second film layer 22827 can be attached to one another such that the first packets 22824*a* are sealed from the second packets 22824*b* prior to being incised by the firing member 22080. In certain embodiments, the first packets 22824*a* and/or the second packets 22825*b* can comprise a certain burst strength in order to withstand a certain burst pressure. More particularly, when an anvil, such as anvil 22760, for example, moves the compensator 22820 toward a staple cartridge positioned opposite the anvil 22760, the packets 22824*a*, 22824*b* can be positioned against the tissue positioned intermediate the packets 22824*a*, 22824*b* and the staple cartridge wherein the anvil 22760 can then be pushed, or clamped, downwardly toward the staple cartridge in order to compress the tissue positioned therebetween. In such circumstances, the packets 22824*a*, 22824*b* may be subjected to compressive pressures. In some circumstances, it may be desirable for the packets 22824a and/or packets 22824b to remain intact until they are incised by the cutting member 22080 and/or punctured by staples fired from the staple cartridge. In certain other circumstances, it may be desirable for the packets 22824a and/or the packets 22824b to burst from the compressive clamping load applied thereto.

As discussed above, the first packets 22824a and the second packets 22842b can extend laterally across the compensator 22820. In various embodiments, the first packets 22824a can extend along transverse axes 22823a while the second packets 22824b can extend along transverse axes 22823b, for example. In at least one embodiment, the first axes 22823a and/or the second axes 22823b can be perpendicular, or at least substantially perpendicular, to a longitudinal axis 22083 of the compensator 22820. In at least one such embodiment, the longitudinal axis 22083 can define the cutting path of the firing member 22080. In certain embodiments, the first axes 22823a and/or the second axes 22823b may not be perpendicular to the longitudinal axis 22083 and may be skew with respect to the longitudinal axis 22083. In various embodiments, as discussed above, the first packets 22824a and the second packets 22824b can be arranged in an alternating arrangement. In certain other embodiments, any other suitable arrangement of the first packets 22824a and the second packets 22824b may be utilized. For instance, a sequence of packets arranged in a tissue thickness compensator could include a first packet 22824a, a second packet 22824b, a second packet 22824b, and a first packet 22824a. In certain embodiments, a tissue thickness compensator can further comprise a plurality of third packets comprising a third medicament which is different than the first medicament and the second medicament. In at least one such embodiment, the first packets, the second packets, and the third packets can be arranged in an alternating arrangement. For instance, a sequence of packets arranged in a tissue thickness compensator could include a first packet, followed by a second packet, which is followed by a third packet, for example.

In various embodiments, referring again to FIG. 467, the first packets 22824a and/or the second packets 22824b of the tissue thickness compensator 22820 can define U-shaped, or at least substantially U-shaped, cross-sections, for example. In certain embodiments, referring now to FIG. 468, the packets 22924 of a tissue thickness compensator 22920 can define circular, or at least substantially circular, cross-sections, for example. In some embodiments, referring now to FIG. 469, the packets 23024 of a tissue thickness compensator 23020 can define oval and/or elliptical cross-sections, for example. In various embodiments, referring again to FIG. 467, the first cavities 22824a and the second cavities 22824b can comprise symmetrical, or at least nearly symmetrical, configurations which are defined in parallel, or at least substantially parallel, rows. In certain other embodiments, referring now to FIG. 470, a tissue thickness compensator, such as compensator 23120, for example, can comprise asymmetrical cavities 23122 defined therein which can have an irregular and/or non-repeating pattern, for example. In at least one such embodiment, each of the cavities 23122 can contain one or more different medicaments therein.

In various embodiments, referring now to FIG. 471, a tissue thickness compensator, such as tissue thickness compensator 23220, for example, can comprise a casing 23226 which defines a cavity 23224 therein and a material 23225 positioned within the cavity 23224. In certain embodiments, the casing 23226 can be comprised of a resorbable polymer, PDS, PGA, PLLA, Cap Gly, and/or PCL, for example, while the material 23225 could be comprised of a haemostatic agent, oxidized regenerated cellulose, Hercules, fibrin, and/or thrombin, for example, which can take any suitable form such as a powder, a fiber, and/or a gel, for example. In at least one embodiment, the casing 23226 can be manufactured utilizing an extrusion process. In such embodiments, the casing 23226 can comprise a constant, or an at least substantially constant, cross-section along the length thereof which can be created without having to weld a seam together. In at least one such embodiment, the cavity 23224 can be defined by a sidewall extending around the entire perimeter thereof without openings defined therein. In certain embodiments, the casing 23226 can be comprised of a mesh and/or a straw-like material having openings defined therein. In at least one embodiment, openings can be cut in the casing 23226 by a laser cutting process and/or a die cutting process, for example.

As part of manufacturing the material 23225, referring now to FIGS. 474-476, a yarn strand can be created utilizing fibers and/or a fibrous material, such as oxidized regenerated cellulose, for example. In certain embodiments, longer fibers 23325, depicted in FIG. 474, and shorter fibers 23425, depicted in FIG. 475, can be mixed together as illustrated in FIG. 476 to form the yarn strand of material 23225. In various embodiments, the yarn strand can be drawn and/or placed under tension in order to stretch the fibers contained therein in a longitudinal direction. In certain embodiments, referring now to FIG. 477, the yarn strand of material 23225 can be fluffed by graspers 23290 which can grasp and twist the material 23225 to increase the volume of the yarn strand. In at least one such embodiment, the graspers 23290 can fluff the material 23225 as the yarn strand is moving relative to the graspers 23290, for example. In some embodiments, referring again to FIG. 477, cutting members 23291 could be utilized to make small incisions and/or micro-cuts, for example, in the yarn strand of material 23225. Similar to the above, the cutting members 23291 can cut the material 23225 as the yarn strand is moving relative to the cutting members 23291. In certain embodiments, the yarn strand of material 23225 can be fluffed before the above-described incisions are made while, in other embodiments, the yarn strand of material 23225 could be incised before it is fluffed.

Once the yarn strand of material 23225 has been suitably prepared, the material 23225 can be positioned within the casing 23226. In at least one embodiment, referring now to FIG. 478, two or more casings 23226 could be formed together as part of an extrusion process, discussed above, wherein the casings 23226 can be connected together as part of a tube 23227. In various embodiments, the yarn strand of material 23225 can be positioned within, or drawn into, the cavity 23224 defined in the tube 23227. In at least one embodiment, the yarn strand of material 23225 can be positioned adjacent to and/or within a first open end 23221 of the cavity 23224 wherein a grasper 23292 can be inserted through a second open end 23222 of the cavity 23224. The grasper 23292 can then be pushed through the cavity 23224 until the jaws 23292a of the grasper 23292 pass through, and/or are positioned relative to, the first open end 23222 such that grasper jaws 23292a can be manipulated to grasp the yarn strand of material 23225. In certain embodiments, a grasper may comprise a hook member, for example, which can be configured to grasp the yarn strand of material 23225. In any event, once the grasper 23292 has sufficiently grasped the yarn strand of material 23225, the grasper 23292 can be drawn back into the cavity 23224 in order to pull the yarn strand of material 23225 into the cavity 23224. In various embodiments, the grasper 23292 can be configured to twist the yarn strand of material 23225 before, during, and/or after the yarn strand is pulled into the tube 23227.

Once the yarn strand of material 23225 has been suitably positioned within the tube 23227, the grasper 23292 can be operated to release the yarn strand of material 23225. In various embodiments, the yarn strand can be released before the yarn strand has been pulled through the second open end 23222 of the tube 23227 while, in other embodiments, the yarn strand can be released after the yarn strand has been pulled through the second open end 23222, as illustrated in FIG. 479. In certain circumstances, the yarn strand can be pulled through the second open end 23222 such that, when the yarn strand is released, the yarn strand can shrink, or spring back, into the tube 23227 through the second open end 23222. In various circumstances, the yarn strand can be cut at a location adjacent to the first open end 23221 such that, similar to the above, the yarn strand can shrink, or spring back, into the tube 23227 through the first open end 23222. In various circumstances, further to the above, the grasper 23292 can apply a tension force to the yarn strand of material 23225 such that when the grasper 23292 releases the yarn strand and/or when the yarn strand is cut, the tension force within the yarn strand can be relieved thereby allowing the yarn strand to contract.

Once the yarn strand of material 23225 has been sufficiently positioned within the tube 23227, referring now to FIG. 480, the tube 23227 and the material 23225 can be cut into a plurality of segments, wherein each segment can be made into a tissue thickness compensator 23220, for example. In various embodiments, the cavity 23224 extending through the cover 23226 of each such segment can comprise an open end on opposite ends thereof. In at least one such embodiment, one or both of the open ends can be closed and/or sealed by a heat-staking, heat-welding, and/or laser welding process, for example. Referring to FIG. 481, a segment comprising a cover 23226 and a portion of the material 23225 therein can be positioned within a die configured to close and/or seal the open ends of the cover 23226. More particularly, in at least one embodiment, the die can comprise a base 23294 and a movable portion 23296, for example, wherein the segment can be positioned within a cavity 23295 defined in the base 23294. Once positioned, the movable portion 23296 can be moved downwardly to apply a force to the segment. In various embodiments, heat can be applied to the segment via the base 23294 and/or the movable portion 23296 wherein the heat and/or the force applied to the segment can distort the cover 23226. More specifically, in at least one embodiment, the movable portion 23296 can define a pocket 23297 which can be contoured to apply a clamping force to certain portions of the cover 23226, such as the open ends thereof, in order to close, flatten, and/or neck down such portions of the tissue thickness compensator 23220. For instance, the pocket 23297 can be configured to form the closed ends 23228 of the tissue thickness compensator 23220 and flatten the portion of the tissue thickness compensator 23220 positioned intermediate the closed ends 23228. After the tissue thickness compensator 23220 has been suitably formed, the movable portion 23296 can be moved to an open position and the tissue thickness compensator 23220 can be removed from the die. In various embodiments, the tissue thickness compensator 23220 can then be positioned in a cooling container wherein the compensator 23220 can be permitted to cool to room temperature and/or any other suitable temperature.

In certain alternative embodiments, further to the above, the tube 23227 can be positioned within a heat-forming die after the material 23225 has been positioned therein. After the tube 23227, and the material 23225 positioned therein, have been formed, the tube 23227 and the material 23225 can then be segmented into a plurality of tissue thickness compensators 23220, for example. In various embodiments, referring again to FIG. 471, the tissue thickness compensator 23220 can comprise lateral wings, or clips, 23229 which can be configured to be attached to the anvil 22060, for example. In at least one such embodiment, the lateral wings 23229 can be formed in the cover 23226 when the tissue thickness compensator 23220 is formed between the die portions 23294 and 23296, as described above. Referring now to FIG. 472, a tissue thickness compensator 23320 can comprise lateral wings 23329 extending from cover 23326. In certain embodiments, referring now to FIG. 473, a tissue thickness compensator 23420 can comprise a cover 23426 having one or more lateral flexible joints 23428, for example, which can permit the cover 23426 to flex and flatten when it is subjected to a compressive pressure in the heat-forming die described above. In various embodiments, as a result of the above, the tissue thickness compensator 23220 may not comprise lateral seams. In such embodiments, referring again to FIG. 471, the material 23225 may extend to the lateral edges of the anvil 22060, for example.

As described above, a yarn strand can be pulled through a tube and then cut to length to form one or more tissue thickness compensators. In various embodiments, further to the above, a yarn strand can be pulled or pushed through a tube utilizing a rigid strand of material. In at least one embodiment, a rigid strand of polymer material, such as PCL, for example, can be heated above its glass transition temperature and stretched into a deformed shape. In at least one such embodiment, the rigid strand can comprise an undeformed serpentine shape which, when stretched into its deformed shape, can comprise a straight, or at least substantially straight, shape, for example. Thereafter, the rigid strand can be cooled below the glass transition temperature of the material while the rigid strand is constrained so that the rigid strand can maintain its deformed shape. Once the rigid strand is in its deformed shape, in various embodiments, ORC fibers, for example, can be formed around the rigid strand. In certain embodiments, an ORC yarn strand, for example, can be wound around, flocked, and/or folded over the rigid strand. Alternatively, the rigid strand can be inserted into ORC fibers, for example. In certain embodiments, the rigid strand can comprise a sticky surface which can be rolled and/or dipped within the ORC fibers. In any event, the rigid strand and the ORC fibers can then be inserted into a tube, similar to the above, and reheated above the glass transition temperature of the rigid strand. In such circumstances, the rigid strand can be unconstrained, or at least substantially unconstrained, and can be permitted to return, or at least substantially return, to its original undeformed shape. In at least one such embodiment, the rigid strand can contract when returning to its original shape and retract the ORC fibers into the tube. In certain embodiments, the center of the tube can be clamped to hold the rigid strand and the ORC fibers in the center of the tube as the rigid tube contracts. Similar to the above, the ends of the tube can be sealed to enclose the rigid strand and the ORC fibers therein.

In various embodiments, referring now to FIG. 573, a tissue thickness compensator 33320 can comprise a shell 33326, a compressible core positioned within the shell 33326, and closed ends 33328 which can be configured to contain the compressible core within the shell 33326. In at least one embodiment, further to the above, the shell 33326 can be produced from a continuous extruding process and can comprise a continuous cross-sectional shape along the length thereof. In certain embodiments, referring now to FIGS. 574-576, a tissue thickness compensator 33420 can comprise a shell 33426, a cavity 33424 defined in the shell 33426, and a core 33425 positioned within the cavity 33424. In at least one such embodiment, the shell 33426 can comprise a film body formed from a continuous extruded shape and the core 33425 can comprise a fibrous medicament core, such as ORC, for example. In at least one embodiment, the shell 33426 can comprise one or more flexible legs 33423 which can be configured to extend into a knife slot 22063 defined in the anvil 22060 and releasably retain the tissue thickness compensator 33420 to the anvil 22060. In certain embodiments, referring now to FIGS. 577-579, a tissue thickness compensator 33520 can comprise a shell 33526, a cavity 33524 defined in the shell 33526, and a core 33425 positioned within the cavity 33524. In at least one such embodiment, the shell 33526 can comprise a film body formed from a continuous extruded shape and the core 33425 can comprise a fibrous medicament core, such as ORC, for example. In at least one embodiment, the shell 33526 can comprise one or more retention members 33528 which can be configured to extend around the outside surface of the anvil 22060 and releasably retain the tissue thickness compensator 33520 to the anvil 22060. In at least one such embodiment, referring primarily to FIG. 579, the shell 33526 can comprise movable portions 33527 and a gap 33523 defined between the movable portions 33527 wherein, after the tissue thickness compensator 33520 has detached from the anvil 22060, the movable portions 33527 can spring open to expose the core 33425 contained therein. In certain embodiments, referring now to FIGS. 580-581, a tissue thickness compensator 33620 can comprise a shell 33626, a cavity 33424 defined in the shell 33626, and a core 33425 positioned within the cavity 33424. In at least one such embodiment, the shell 33626 can comprise a film body formed from a continuous extruded shape and the core 33425 can comprise a fibrous medicament core, such as ORC, for example. In at least one embodiment, the shell 33626 can comprise a thin section 33623 which can be aligned with the knife slot 22063 defined in the anvil 22060 such that a cutting member passing through the tissue thickness compensator 33620 can pass through the thin section 33623 and reduce the force or energy needed to transect the tissue thickness compensator 33620. In certain embodiments, referring now to FIGS. 582-583, a tissue thickness compensator 33720 can comprise a shell 33726, a cavity 33424 defined in the shell 33726, and a core 33425 positioned within the cavity 33424. In at least one such embodiment, the shell 33726 can comprise a film body formed from a continuous extruded shape and the core 33425 can comprise a fibrous medicament core, such as ORC, for example. In at least one embodiment, the shell 33726 can comprise one or more retention members 33723 which can be configured to wrap around the outside surface of the anvil 22060 and releasably retain the tissue thickness compensator 33720 to the anvil 22060. In certain embodiments, referring now to FIGS. 584-585, a tissue thickness compensator 33820 can comprise a shell 33826, a cavity 33424 defined in the shell 33826, and a core 33425 positioned within the cavity 33424. In at least one such embodiment, the shell 33826 can comprise a film body formed from a continuous extruded shape and the core 33425 can comprise a fibrous medicament core, such as ORC, for example. In at least one embodiment, the shell 33826 can comprise a substantially rectangular cavity 33424 and a substantially flat tissue contacting surface 33829 as opposed to the arcuate cavity 33424 and tissue contacting surface depicted in FIG. 583, for example. In certain embodiments, referring now to FIGS. 586-587, a tissue thickness compensator 33920 can comprise a shell 33926, a plurality of cavities 33924 defined in the shell 33926, and a core 33925 positioned within each of the cavities 33924. In at least one such embodiment, the shell 33926 can comprise a film body formed from a continuous extruded shape and the cores 33925 can each comprise a fibrous medicament core, such as ORC, for example. In certain embodiments, the cores 33925 can be comprised of different materials. In at least one embodiment, the shell 33926 can comprise one or more retention members 33923 which can be configured to extend into the knife slot 22063 of the anvil 22060.

Referring now to FIG. 482, a tissue thickness compensator can be formed utilizing a folding process. In various embodiments, a material 23525, such as oxidized regenerated cellulose, for example, can be placed on a cover sheet 23526 which can be folded and then sealed in order to encapsulate the material 23525. In at least one such embodiment, the cover sheet 23526 can be comprised of cap gly, for example. In certain embodiments, a continuous process can be utilized in which the cover sheet 23526 can be passed under a hopper 23592 which is configured to dispense the material 23525 onto the cover sheet 23526. In at least one such embodiment, the cover sheet 23526 can be flattened between a roller 23591 and an anvil 23590 before the material 23525 is placed onto the cover sheet 23526. In certain embodiments, the material 23525 may be placed on one side, or half, of the cover sheet 23526 wherein the other side, or half, of the cover sheet 23526 can be folded, or flipped, over the material 23525. Before, during, and/or after the material 23525 has been placed on the cover sheet 23526, the cover sheet 23526 can be folded, or at least partially folded. In various embodiments, the anvil 23590, for example, can comprise a cam surface 23594 which can be configured to lift an edge or side of the longitudinally moving cover sheet 23526 and then fold the cover sheet 23526 in half, for example. In at least one embodiment, the cam surface 23594 can comprise a three-dimensional cam, or barrel cam, which progressively lifts and turns a portion of the cover sheet 23526 as the cover sheet 23526 passes by the cam surface 23594.

After the cover sheet 23526 has been folded over the material 23525, the folded cover sheet 23526 and the material 23525 positioned therein can pass through a die 23593 which can, in at least one embodiment, compress and/or compact the folded cover sheet 23526 and the material 23525 to form a tube 23527. In certain embodiments, the edges of the folded cover sheet 23526 can be sealed closed utilizing any suitable process such as thermal welding and/or laser welding, for example. In various embodiments, the tube 23527 can be further flattened by one or more rollers 23595, for example, before the sidewall of the tube 23527 has been sealed. In certain embodiments, the tube 23527 can be further flattened by one or more rollers after the sidewall of the tube 23527 has been sealed. In any event, the tube 23527 can be segmented into portions to create separate tissue thickness compensators. In various embodiments, the ends of the tissue thickness compensators can be sealed utilizing any suitable process such as thermal welding and/or laser welding, for example, while, in other embodiments, one or both of the ends of the tissue thickness compensator can remain in an open configuration, for example.

In various embodiments, referring now to FIG. 483, a compensator can be attached to an anvil, such as anvil 22060, for example, wherein the compensator can be configured to store at least one medicament therein. In at least one embodiment, a compensator 23620 can comprise a central body portion 23626 and lateral attachment portions 23628 which can be configured to be attached to the anvil 22060. In certain embodiments, the compensator 23620 can further comprise an array of capillary channels 23627 defined in a tissue contacting surface 23625 of the compensator 23620 wherein the capillary channels 23627 can be configured to store one or medicaments therein. In at least one such embodiment, the medicament can comprise a fluid which, owing to fluid tension forces, can be retained between the sidewalls of the capillary channels 23627. In various circumstances, the medicament can be applied to the compensator 23620 before the compensator 23620 is attached to the anvil 22060 while, in some circumstances, the medicament can be applied to the compensator 23620 after it has been attached to the anvil 22060, for example. In any event, the compensator 23620 can be configured to contact tissue positioned between the anvil 22060 and a staple cartridge positioned opposite the anvil 22060 wherein the medicament stored in the capillary channels 23627 can flow onto the tissue. In various circumstances, the medicament can flow within the capillary channels 23627.

In various embodiments, referring again to the compensator 23620 illustrated in FIG. 483, the array of capillary channels 23627 can be constructed and arranged in a cross-hatched pattern wherein a first quantity of channels 23627 can extend in a first direction and a second quantity of channels 23627 can extend in a second direction. In at least one embodiment, the first quantity of channels 23627 can intersect and can be in fluid communication with the second quantity of channels 23627. Referring now to FIG. 484, a compensator 23920 can comprise a body 23926 which includes an array of capillary channels 23927 defined in a tissue-contacting surface 23925. In various embodiments, the channels 23927 can be defined along linear paths while, in certain embodiments, the channels 23927 can be defined along non-linear paths. In at least one embodiment, a first quantity of channels 23927 can extend along axes 23923 while a second quantity of channels 23927 can extend along axes 23924, for example, wherein the axes 23923 can extend in different directions than the axes 23924. In various embodiments, the axes 23923 can be perpendicular, or at least substantially perpendicular, to the axes 23924 wherein, in at least one embodiment, the channels 23627 can define islands 23922 therebetween. In at least one such embodiment, the top surfaces of the islands 23922 can define the tissue contacting surface 23925 of the compensator 23920. In various embodiments, the compensator 23920 can comprise a longitudinal axis 23921 and the channels 23627 can extend in directions which are transverse or skew with respect to the longitudinal axis 23921. In certain embodiments, referring again to FIG. 483, a compensator 23720 can comprise a body 23726 and a plurality of capillary channels 23727 defined in the body 23726. In at least one embodiment, the compensator 23720 can further comprise a longitudinal channel 23721 which can be in fluid communication with the capillary channels 23727. In various embodiments, one or medicaments can be stored in the longitudinal channel 23721 wherein the medicaments can flow between the channel 23721 and the capillary channels 23727, for example. In at least one embodiment, the channel 23721 can define a longitudinal protrusion which can extend upwardly into a longitudinal knife slot 22061 defined in the anvil 22060.

As discussed above, referring again to FIG. 483, an array of capillary channels defined in a compensator can comprise a cross-hatched pattern. In various other embodiments, however, an array of capillary channels can comprise any suitable shape or configuration. For example, referring to compensator 23820 illustrated in FIG. 483, the channels 23827 defined in the body 23826 of the compensator 23820 can comprise parallel, diagonal channels which converge toward and/or diverge away from a central channel 23821, for example. Referring now to FIG. 487, an end effector of a surgical stapling instrument can include a staple cartridge 24000 including a tissue thickness compensator 24010 wherein, in at least one embodiment, the tissue thickness compensator 24010 can include at least one medicament, such as medicament 24001, for example, therein and/or thereon. Referring now to FIG. 488, a compensator 24020 attached to an anvil 24060, for example, can be moved into a closed position in order to place the compensator 24020 in contact with the tissue thickness compensator 24010. In such circumstances, the medicament 24001, for example, can be transferred from the tissue thickness compensator 24010 to the compensator 24020. In at least one embodiment, referring now to FIG. 489, the compensator 24020 can comprise a tissue contacting surface 24025 which can be brought into contact with the tissue thickness compensator 24010 wherein, in certain embodiments, the medicament 24001 can flow into capillary channels 24027 defined in the tissue contacting surface 24025. In certain embodiments, referring now to FIG. 486, the compensator 24020 can include at least one medicament, such as medicament 24002, for example, thereon and/or therein which can be transferred from the compensator 24020 to the tissue thickness compensator 24010.

In various embodiments, referring now to FIGS. 569 and 570, a tissue thickness compensator 33020 can comprise a plurality of channels and/or wells defined in the surface thereof. In at least one embodiment, the tissue thickness compensator 33020 can comprise a longitudinal channel 33026 that extends along a longitudinal axis defined through the tissue thickness compensator 33020. In at least one such embodiment, the end of the longitudinal channel 33026 can be in fluid communication with the perimeter of the tissue thickness compensator 33020. The tissue thickness compensator 33020 can further comprise a plurality of wells 33022 and, in addition, a plurality of diagonal channels 33024 which are in fluid communication with the wells 33022 and the longitudinal channel 33026. In certain embodiments, the tissue thickness compensator 33020 can further comprise a plurality of inlet-outlet channels 33027 which can be in fluid communication with the wells 33022 and the perimeter of the tissue thickness compensator 33020. In various embodiments, as a result of the above, fluids can flow into and/or out of the tissue thickness compensator 33020 before, during, and/or after it has been implanted against a patient's tissue. In certain embodiments, the pattern of channels 33024, 33026, and 33027 and the wells 33022 defined in the tissue-contacting surface 33025 of the tissue thickness compensator 33020 can define gripping edges which can be configured to contact the tissue and limit slipping between the tissue thickness compensator 33020 and the tissue. Referring now to the alternative embodiment illustrated in FIGS. 569A and 570A, a tissue thickness compensator 33120 can comprise a plurality of circular channels defined in the surface thereof. In various embodiments, the tissue thickness compensator 33120 can comprise concentric circular channels 33127 which comprise openings defined in the perimeter of the tissue thickness compensator 33120. Similar to the above, fluids can flow into and/or out of the tissue thickness compensator 33120 through the channels 33127. In at least one embodiment, the tissue thickness compensator 33120 can comprise concentric circular channels 33122 which may not include openings defined in the perimeter of the tissue thickness compensator 33120. Referring now to the alternative embodiment illustrated in FIGS. 571 and 572, a tissue thickness compensator 33220 can comprise a plurality of ridges 33227 extending therefrom which can be configured to grip tissue that is positioned against the tissue thickness compensator 33220. In at least one embodiment, the ridges 33227 can be straight while, in some embodiments, the ridges 33227 can comprise a curved contour, for example. Although the ridges and channels described above may be useful for tissue thickness compensators, in various embodiments, such ridges and channels could be utilized with any suitable bioabsorbable and/or biocompatible layer.

In various embodiments, a compensator can be comprised of a plurality of layers. In at least one embodiment, the compensator can comprise a first layer and a second layer attached to the first layer, for example. In certain embodiments, the first layer can comprise a tissue contacting surface and a plurality of capillary channels defined in the tissue contacting surface. In at least one embodiment, the first layer can also comprise capillary channels defined in a side which faces the second layer and faces opposite the tissue contacting surface. In certain embodiments, the second layer can comprise capillary channels defined therein. In at least one embodiment, wells can be defined between the first layer and the second layer of the compensator. In various embodiments, the capillary channels can be formed in the layers of the compensator utilizing any suitable process, such as during a molding process in which the layers are formed and/or during a heat-staking process, for example. In at least one embodiment, a heat-staking process can be utilized to attach the layers of the compensator to one another, for example. In at least one such embodiment, the layers can be comprised of a material which can become deformable when heat is applied thereto, such as CAP/GLY (36/64), for example. In any event, in various embodiments, the capillary channels defined in the tissue contacting surface of the compensator can define gripping surfaces therebetween which can improve the grip, or control, that can be applied to tissue positioned between the anvil and the staple cartridge of the surgical stapling instrument. Stated another way, the capillary channels defined in the tissue-contacting surface of a compensator can decrease the area in which the compensator can contact the tissue. In such circumstances, the smaller contact area can result in higher contact pressures between the compensator and the tissue for a given force. In various circumstances, the higher contact pressures can reduce slipping between the compensator and the tissue.

In various embodiments, one or medicaments can be positioned within the capillary channels and/or voids defined within and/or between the first layer and the second layer. In certain embodiments, the plurality of layers comprising a compensator can comprise a pack of therapeutic layers, or therapies. For instance, a first layer can be comprised of a first medicament and a second layer can be comprised of a second medicament, wherein the first medicament can be different than the second medicament. In at least one such embodiment, capillary channels defined in the first layer can store a third medicament and capillary channels defined in the second layer can store a fourth medicament, wherein the first, second, third, and/or fourth medicaments can be different, for example. In at least one embodiment, the first, second, third, and/or fourth medicaments can be different, for example. In various embodiments, referring now to FIG. 490, a compensator 24120 can comprise a plurality of layers, such as layers 24121-24125, for example. In at least one embodiment, the first layer 24121 and/or the fifth layer 24125 can comprise a flat sheet of material between which the second layer 24122, the third layer 24123, and/or the fourth layer 24124 can be sandwiched. In various embodiments, one or more of the layers 24121-24125 can comprise one or more channels 24127 defined therein. In at least one embodiment, the channels 24127 can extend from one end of the compensator 24120 to the other end and, in certain embodiments, the channels 24127 can extend between one side of the compensator 24120 to the other. In certain other embodiments, the channels 24127 can extend in any suitable direction between any suitable sides and/or ends of the compensator 24120. In various embodiments, referring now to FIGS. 493 and 494, a compensator 24820 can comprise two or more inner layers 24827 which can define lateral channels 24822, for example, which extend from one side of the compensator 24820 to the other. In certain embodiments, referring again to FIG. 490, the channels 24127 defined in one of the layers 24121-24125 can be aligned with the channels defined in a layer positioned adjacent thereto. In some embodiments, the channels 24127 defined in one of the layers 24121-24125 can face, or open toward, a flat surface on a layer positioned adjacent thereto. In various embodiments, referring again to FIG. 490, one or more of the layers 24121-24125 can comprise at least one well 24129 defined therein. In at least one embodiment, the wells 24129 can be in fluid communication with one or more of the channels 24127 defined in the layer. Similar to the above, the wells 24129 can comprise an opening which opens toward, or faces, an adjacent layer wherein the adjacent layer can cover the opening.

In various embodiments, further to the above, the channels 24127 and/or the wells 24129 can be configured to contain one or medicaments therein. In at least one embodiment, the channels 24127 can comprise one or more open ends which can permit a medicament to flow out of the channels 24127. Similarly, in at least one embodiment, the channels 24127 can include one or more openings which can be configured to permit a fluid, such as blood, for example, to flow into the channels 24127. In such embodiments, the fluid can flow into the compensator 24120, absorb at least a portion of a medicament and/or a layer 24121-24125, and then flow out of the compensator 24120. Referring again to FIGS. 493 and 494, the compensator 24820 can comprise apertures 24828 defined in outer layers 24826, for example. In various embodiments, referring again to FIG. 490, the layers 24121-24125 can be comprised of any suitable material, such as a bioabsorbable polymer, PLA, and/or PGA, for example. In certain embodiments, all of the layers 24121-24125 can be comprised of the same material. In certain other embodiments, one or more of the layers 24121-24125 could be comprised of different materials. In various embodiments, one or more of the layers 24121-24125 can include through holes 24128 extending therethrough which can be configured to permit fluids, such as blood, for example, to flow into the channels 24127, wells 24126, and/or between two or more of the layers 24121-21135, for example. In certain embodiments, one or more of the layers 24121-24125 can be connected to each other utilizing a heat-welding and/or laser-welding process, for example. In such embodiments, the fluid, or fluids, flowing into the compensator 24120 can dissolve the welded portions of the layers 24121-24125 and permit the layers 24121-24125 to separate and/or delaminate. In certain embodiments, one or more of the layers 24121-24125 can be comprised of a material which dissolves at a faster rate and/or a slower rate than the material, or materials, comprising the other layers 24121-24125. In at least one such embodiment, the inner layers 24122-24124 of the compensator 24120 can be comprised of a material which dissolves at a faster rate than the material, or materials, which comprise the outer layers 24121 and 24125, for example. In such embodiments, the compensator 24120 can maintain a consistent, or at least substantially consistent, general shape while the interior of the compensator 24120 is dissolved away. In certain other embodiments, the outermost layers of a compensator can be comprised of a material which dissolves at a faster rate than the material, or materials, which comprise the innermost layers of the compensator, for example. In various embodiments, the layers can comprise sheets of material having a thickness between approximately 1 mil and approximately 4 mils, for example.

In various embodiments, referring now to FIGS. 491 and 492, a compensator, such as compensator 24220, for example, can comprise a support layer 24226 which can be configured to be attached to an anvil, such as anvil 22060, for example, and/or a staple cartridge. In certain embodiments, the compensator 24220 can further comprise a scaffold 24222 attached to the support layer 24226 wherein the scaffold 24222 can comprise a plurality of scaffold layers 24227. In at least one embodiment, the scaffold can comprise a three-dimensional structural matrix, for example. In various embodiments, each of the scaffold layers 24227 can be comprised of a plurality of fibers. In at least one embodiment, referring now to FIG. 495, each scaffold layer 24227 can be comprised of a fiber weave including a first plurality of fibers 24228 extending in a first direction and a second plurality of fibers 24229 extending in a second, or different, direction. In certain embodiments, each fiber weave can comprise a plurality of pockets, or cavities, 24223 wherein the layers 24227, the fibers 24228, 24229, and the cavities 24223 can define a matrix favorable to tissue and cellular ingrowth. In various embodiments, the fibers 24228, 24229, and/or any other suitable fibers, can be comprised of a bioabsorbable material. In at least one embodiment, the fibers can be comprised of a haemostatic agent, bound active agents such as those that are biologically and/or pharmacologically active, and/or support members, for example, which can be interweaved with one another. In any event, the material of the fibers can be selected to induce a desirable biologic response such as cellular migration into the scaffold 24222, ECM secretion, and/or the proliferation of structural support cells, for example.

In various embodiments, further to the above, the support layer 24226 can be configured to structurally support the scaffold 24222. In at least one embodiment, the scaffold 24222 can be attached to the support layer 24226 utilizing one or more bioabsorbable adhesives, for example. Similarly, in certain embodiments, the support layer 24226 can be attached to an anvil or a staple cartridge utilizing one or more biocompatible adhesives, for example. In various embodiments, the layers 24227 of the scaffold 24222 can be arranged, or stacked, in any suitable manner. In certain embodiments, each layer 24227 can comprise a pattern of fibers wherein the layers 24227 can be arranged in the scaffold 24222 such that the patterns of the layers 24227 are aligned with each other. In at least one embodiment, referring to FIG. 496, the layers 24227 can be stacked on one another such that the fibers 24228 in a first layer 24227 are aligned with the fibers 24228 in a second layer 24227. Likewise, the layers 24227 can be stacked on one another such that the fibers 24229 in the first layer 24227 are aligned with the fibers 24229 in the second layer 24227. In certain embodiments, referring now to FIG. 497, a scaffold 24422 can comprise a plurality of scaffold layers 24427 wherein the fibers 24429 in each scaffold layer 24427 are oriented in the same direction, such as a longitudinal direction, for example. In certain embodiments, referring now to FIG. 499, each scaffold layer 24227 can comprise a pattern of fibers wherein the layers 24227 can be arranged in a scaffold 24322 such that the patterns of the layers 24227 are not aligned with each other. In at least one embodiment, the layers 24227 can be stacked on one another such that the fibers 24228 in a first layer 24227 extend in a direction which is transverse to or oblique with the fibers 24228 in a second layer 24227. Likewise, the layers 24227 can be stacked on one another such that the fibers 24229 in the first layer 24227 extend in a direction which is transverse to or oblique with the fibers 24229 in the second layer 24227. In certain embodiments, referring now to FIG. 500, a scaffold 24522 can comprise a plurality of scaffold layers 24427 which are oriented such that the fibers 24229 in each scaffold layer 24427 are oriented in different directions, for example.

In various embodiments, further to the above, a first scaffold layer 24227 of a scaffold 24222, for example, can be comprised of a first material while a second scaffold layer 24227 of the scaffold 24222 can be comprised of a second, or different, material. In at least one embodiment, the first material can comprise a first medicament while the second material can comprise a second, or different, medicament, for example. In various embodiments, further to the above, a first scaffold layer 24227 of a scaffold 24222, for example, can comprise a first medicament absorbed into the fibers thereof while a second scaffold layer 24227 of the scaffold 24222 can comprise a second, or different, medicament absorbed into the fibers thereof, for example. In at least one embodiment, the first material can comprise a first medicament while the second material can comprise a second, or different, medicament, for example. In certain embodiments, a scaffold can comprise any suitable number of layers having any suitable density of fibers which are comprised of any suitable number of materials.

Tissue thickness compensators may be installed in a surgical device, such as a surgical cutting and stapling device, for example, utilizing a retainer. The retainer can include a gripping surface and enable a surgeon, nurse, technician, or other person to align one or more of the tissue thickness compensators with features of the surgical instrument, such as an anvil and/or a staple cartridge, for example. In various embodiments, the retainer may include features that align the one or more tissue thickness compensators by engaging a staple cartridge of the surgical instrument. In certain embodiments, the retainer may include features that align one or more tissue thickness compensators by engaging an anvil of a surgical instrument. In certain embodiments, a staple cartridge for the surgical instrument may be included with the retainer and engaging the retainer with the surgical instrument can install the staple cartridge in the surgical instrument and align one or more of the tissue thickness compensators. After the tissue thickness compensators have been aligned with and attached to the surgical instrument, the retainer may be detached from the tissue thickness compensators and then removed from the surgical instrument.

FIGS. 390-396 illustrate an embodiment of a retainer 19000 that may be used to attach a first tissue thickness compensator 19002 to an anvil 19040 and a second tissue thickness compensator 19004 to a staple cartridge 19050 of a surgical stapler, for example. A retainer assembly 19060 can be provided which includes the retainer 19000, the first tissue thickness compensator 19002, and the second tissue thickness compensator 19004. In use, generally, the retainer assembly 19060 may be inserted between the anvil 19040 and a channel configured to support the staple cartridge 19050. Thereafter, the anvil 19040 can be closed. By closing the anvil 19040, the anvil 19040 can push downwardly onto the first tissue thickness compensator 19002 such that the first tissue thickness compensator 19002 may be attached to the anvil 19040. In at least one embodiment, closing the anvil 19040 pushes downwardly on the retainer 19000 and seats the staple cartridge 19050 into the channel of the surgical instrument. When the anvil 19040 is reopened, the first tissue thickness compensator 19002 can detach from the retainer 19000 and when the retainer 19000 is subsequently removed from the surgical device, the retainer 19000 can detach from the second tissue thickness compensator 19004. The surgical device is then ready for use with the first tissue thickness compensator 19002 attached to the anvil 19040 and the second tissue thickness compensator 19004 attached to the staple cartridge 19050.

Referring to FIG. 390, the retainer 19000 may include a grip 19014 by which a person, such as a surgeon, nurse, or technician preparing surgical instruments may grasp the retainer 19000. The retainer 19000 may include a first surface 19001 on which a first tissue thickness compensator 19002 may be positioned and an opposing second surface 19003 on which a second tissue thickness compensator 19004 may be positioned. In various embodiments, one or more adhesives can be applied to the first surface 19001 and/or the second surface 19003 for attaching the first and second tissue thickness compensators 19002 and 19004 thereto. The retainer 19000 also may include clips that can engage a staple cartridge 19050 of the surgical device, for example. In at least one embodiment, referring to FIG. 393, the retainer 19000 may include distal clips 19108 configured to engage a recess 19056 at a distal end of the staple cartridge 19050 and/or proximal clips 19106 configured engage a ridge or edge 19054 on the staple cartridge 19050.

Referring to FIG. 390, in various embodiments, the first tissue thickness compensator 19002 may include a retainer-facing surface 19006 and an anvil-facing surface 19010. The retainer-facing surface 19006 can be attached to the first surface 19001 of the retainer 19000 by adhesives and/or engagement features, for example. The anvil-facing surface 19010 may include at least one adhesive thereon which can attach the first tissue thickness compensator 19002 to the anvil 19040 of the surgical device. For example, the adhesive can comprise an activatable adhesive that may adhere to a staple forming surface 19044 (FIG. 392) of the anvil 19040.

Referring to FIGS. 390 and 392-395, the anvil-facing surface 19010 of the first tissue thickness compensator may include engagement features 19020 that engage similar engagement features 19042 on the anvil 19040. Thus, in various embodiments, a first retention force can retain the first tissue thickness compensator 19002 to the retainer 19000 and a second retention force can retain the first tissue thickness compensator 19002 to the anvil 19040. In various embodiments, the second retention force can be greater than the first retention force such that the first tissue thickness compensator 19002 can remain attached to the anvil 19040 and separate from the retainer 19000 when the retainer 19000 is removed from the end effector.

Referring again to FIG. 390, the second tissue thickness compensator 19004 may include a retainer-facing surface 19008 and a staple-cartridge-facing surface 19012. The retainer-facing surface 19006 can be attached to the first surface 19001 of the retainer 19000 by one or more adhesives and/or engagement features. The staple-cartridge-facing surface 19012 may include an adhesive thereon which can attach the second tissue thickness compensator 19004 to the staple cartridge 19050 of the surgical device. For example, referring to FIG. 393, the adhesive may adhere the second tissue thickness compensator 19004 to a staple deck 19052 of the staple cartridge 19050. The staple-cartridge-facing surface 19012 also may include engagement features that engage co-operating engagement features on the staple cartridge 19050. Thus, in various embodiments, a first retention force can retain the second tissue thickness compensator 19004 to the retainer 19000 and a second retention force can retain the second tissue thickness compensator 19004 to the staple cartridge 19050. In various embodiments, the second retention force can be greater than the first retention force such that the second tissue thickness compensator 19004 can remain attached to the staple cartridge 19050 and separate from the retainer 19000 when the retainer 19000 is removed from the end effector.

As shown in FIG. 393, the retainer assembly 19060 may be attached to a staple cartridge 19050 as indicated by arrow A. As described above, distal clips 19018 on the retainer 19000 may engage a recess 19056 in the staple cartridge and proximal clips 19016 on the retainer may engage the edge or ridge 19054 on the staple cartridge 19050. At such point, the retainer 19000 is attached to the staple cartridge 19050, as shown in FIG. 394, and the second tissue thickness compensator 19004 can be attached to the staple cartridge 19050. As shown in FIG. 395, closure of the anvil 19040 of the surgical device in the direction of arrow B may bring a surface 19044 of the anvil, such as a staple-forming surface and/or a tissue contacting surface, for example, into contact with the first tissue thickness compensator 19002. As described above, the anvil 19040 contacting the first tissue thickness compensator 19002 can cause the first tissue thickness compensator 19002 to become attached to the anvil 19040.

After the retainer assembly 19060 has been attached to the staple cartridge 19050 and the anvil 19040 has been closed, the first tissue thickness compensator 19002 can be attached to the anvil 19040 and the second tissue thickness compensator 19004 can be attached to the staple cartridge 19050. As described above, the retention force retaining the first tissue thickness compensator 19002 to the retainer 19000 can be less than the retention force holding the first tissue thickness compensator 19002 to the anvil 19040. Thus, when the anvil 19040 is reopened, the first tissue thickness compensator 19002 can detach from the retainer 19000 and remain with the anvil 19040, as shown in FIG. 396. As also described above, the retention force retaining the second tissue thickness compensator 19004 to the retainer 19000 can be less than the retention force holding the first tissue thickness compensator 19004 to the staple cartridge 19050. Thus, when the retainer 19000 is removed in the directions of arrows C and D in FIG. 396, the retainer 19000 can detach from the second tissue thickness compensator 19004. The surgical stapler shown in FIG. 396 includes the first tissue thickness compensator 19002 attached to the anvil 19040 and the second tissue thickness compensator 19004 attached to the staple cartridge 19050 and is ready for use.

FIGS. 390-396 show the retainer 19000 being used with a first tissue thickness compensator 19002 and a second tissue thickness compensator 19004. In various embodiments, the retainer 19000 may also be used with only one of the first tissue thickness compensator 19002 and the second tissue thickness compensator 19004. For example, the first tissue thickness compensator 19002 may be omitted.

FIGS. 397-399 show an embodiment of a retainer 19100 that can include engagement features 19108 on a surface 19101. As shown in FIGS. 398 and 399, the engagement features 19108 on the retainer 19100 engage co-operating engagement features 19109 on a first tissue thickness compensator 19102.

FIGS. 400-401 show an embodiment of a retainer 19200 that may include a surface 19202 configured to align and attach a tissue thickness compensator 19210 to an anvil 19230. The retainer 19200 may include alignment pegs 19204 extending from the surface 19202. The retainer 19200 shown in FIGS. 400 and 401 includes four alignment pegs 19204, but more or fewer alignment pegs 19204 may be present. Referring to FIG. 401, the tissue thickness compensator 19210 can include a body 19212 that includes holes 19216 that can be located such that they that correspond to the locations of the alignment pegs 19204 extending from the retainer 19200. Each hole 19216 in the tissue thickness compensator 19210 fits over an alignment peg 19204, and owing to a close fit between the holes 19216 and the pegs 19204, the tissue thickness compensator 19210 can be aligned with the retainer 19200. In various embodiments, each hole 19216 may be slightly smaller than its corresponding peg 19204 such that each hole 19216 stretches when placed on its peg 19204. Such stretching can hold the holes 19216 on the pegs 19204. In certain embodiments, each hole 19216 may include an adhesive therein to create a releasable bond between the pegs 19204 and the tissue thickness compensator 19210.

The tissue thickness compensator 19220 may include tabs 19220 extending from a body 19212 of the tissue thickness compensator 19220 which can be configured to be received by slots 19234 in an anvil 19230. In various embodiments, the slots 19234 in the anvil 19230 may be located in a staple forming surface 19232, for example. After the retainer 19200 has been attached to a staple cartridge, similar to the embodiments described above, the anvil 19230 can be closed against the tissue thickness compensator 19210 on the retainer 19200. As the anvil 19230 is closed, referring to FIG. 401, the tabs 19220 on the tissue thickness compensator 19210 can engage the slots 19234, thereby attaching the tissue thickness compensator 19210 to the anvil 19230. Referring primarily to FIG. 400, each tab 19220 may include a tapered portion 19222 that guides the tab 19220 into the slots 19234 of the anvil 19230. The tapered portion 19222 can include sloped walls and may increase in cross-sectional area along the length thereof. A base portion 19226 of each tab 19220 may have a smaller cross-sectional area than the largest cross-sectional area of the tapered portion 19222. In various embodiments, the tapered portion 19222 may comprise a lock surface 19224 wherein, when a tab 19220 enters a slot 19234, the lock surface 19224 can catch on a lip 19235 in the slot 19234. As a result, the lock surface 19224 can hold the tab 19220 within the slot 19234 and thereby hold the tissue thickness compensator 19210 to the anvil 19230. Slots 19228 defined in the tissue thickness compensator 19210 and extending between the tabs 19220 can enable the tabs 19220 to flex inwardly and fit within the slots 19234. In various embodiments, the tabs 19220 being held with the slots 19234 can define a first retention force that retains the tissue thickness compensator 19210 to the anvil 19230 and the holes 19216 in the tissue thickness compensator 19210 being held on the pegs 19204 can define a second retention force. In various embodiments, the first retention force can be greater than the second retention force such that the tissue thickness compensator 19210 can remain attached to the anvil 19230 and separate from the retainer 19200 when the retainer 19200 is removed from the end effector.

The body 19212 of the tissue thickness compensator 19210 in FIGS. 400 and 401 also may define slots 19214 therewithin. The slots 19214 may be aligned along a longitudinal axis of the tissue thickness compensator 19210. For example, the slots 19214 may be arranged on a longitudinal axis such that the slots 19214 are aligned with a longitudinal path of a cutting blade of the surgical device when the tissue thickness compensator 19210 is attached to an anvil 19230. The slots 19214 may reduce the amount of energy required by the cutting blade to cut through the tissue thickness compensator 19210.

FIGS. 402-412 show an embodiment of a retainer 19300 that includes clips 19310 which are configured to retain a tissue thickness compensator 19340 on a first surface 19302 of the retainer 19300. When an anvil 19360 is closed on the retainer 19300, similar to the above, the anvil 19360 can push and displace the clips 19310 outwardly and, as a result, disengage the retainer 19300 from the tissue thickness compensator 19340. In various embodiments, the tissue thickness compensator 19340 can attach to the anvil 19360 when the anvil 19360 is pressed against the tissue thickness compensator 19340 and moved away from the retainer 19300 when the anvil 19360 is reopened.

The retainer 19300 may include staple cartridge mounting clips 19312 and 19314 which can be similar to those described above with respect to FIGS. 390-399. In addition to the first surface 19302 described above, the retainer 19300 also may include a second surface 19304 that may be configured to carry a second tissue thickness compensator. In various embodiments, the second surface 19304 may include an alignment feature, such as, for example, a raised ridge 19308. The raised ridge 19308 may engage a slot in a second tissue thickness compensator and/or a slot in a staple cartridge 19370, for example.

Referring to FIGS. 404-406, in use, the retainer 19300 may be attached to a staple cartridge 19370 by clips 19314 and 19312. The first tissue thickness compensator 19340 can be positioned on the first surface 19302 at the retainer 19300 and can be held in place by clips 19310. Referring primarily to FIGS. 410-412, each clip includes a flat 19313 that can clamp the first tissue thickness compensator 19340 against the first surface 19302 of the retainer 19300. Each clip 19310 can include an inward-facing tapered or curved surface 19311. As the anvil 19360 moves in the direction of arrow E, referring to FIG. 411, edges 19366 of the anvil 19360 can contact the inward-facing curved surfaces 19311 of the clips 19310. As the anvil 19360 continues to move in the direction of arrow E, interference between the edges 19366 of the anvil 19360 and the curved surfaces 19311 of the clips 19310 can push the clips 19310 outwardly in the direction of arrow F, as illustrated in FIG. 411. As the clips 19310 move in the direction of arrow F, the first tissue thickness compensator 19340 is freed from the flats 19313 of the clips 19310.

As the anvil 19360 continues to move in the direction of arrow E, it also contacts and attaches to the tissue thickness compensator 19340. For example, as the anvil 19360 moves in the direction of arrow E, an engagement feature, such as, for example, a raised ridge 19344, on the tissue thickness compensator 19340 engages a channel 19364 in the anvil 19360. The raised ridge 19344 may be configured to have an interference fit with the channel 19364 such that the tissue thickness compensator 19340 becomes attached to the anvil 19360. The tissue thickness compensator 19340 may include an adhesive that adheres to surfaces of the anvil 19360. In at least one embodiment, the raised ridge 19344 may include an adhesive that adheres to surfaces of the channel 19364. Likewise, surfaces of the body 19342 of the tissue thickness compensator 19340 may include an adhesive that adheres to a surface 19362 of the anvil 19360. After the tissue thickness compensator 19340 is attached to the anvil 19360, the tissue thickness compensator 19340 can lift from the retainer 19300 and remain with the anvil 19360 as the anvil 19360 returns to its open position by moving in the direction of arrow G, as illustrated in FIG. 412.

FIG. 413 shows a cross-sectional side view of an embodiment of a retainer 19400. A first tissue thickness compensator 19410 is positioned on a first side 19402 of the retainer 19400 and a second tissue thickness compensator 19420 is positioned on an opposing second side 19404 of the retainer 19400. The retainer 19400 defines one or more holes 19406 extending therethrough. The first tissue thickness compensator 19410 and the second tissue thickness compensator 19420 are connected through the holes by connectors 19430 which extend through the holes 19406. In various embodiments, the first tissue thickness compensator 19410, the second tissue thickness compensator 19420, and the connectors 19430 all may be formed of a unitary material. For example, the first tissue thickness compensator 19410, the second tissue thickness compensator 19420, and the connectors 19430 may be overmolded onto the retainer 19400. In various other embodiments, the connectors 19430 may be formed as part of one of the tissue thickness compensators, such as, for example, the first tissue thickness compensator 19410. The connectors 19430 may be passed through the holes 19406 and then attached to the remaining tissue thickness compensator, such as, for example, the second tissue thickness compensator 19420. The connectors 19430 may be attached to the second tissue thickness compensator 19420, for example, by using an adhesive or by using an interference fit between an end of the connector and a receiving port (not shown) in the second tissue thickness compensator 19420. In various embodiments, the connectors 19430 may be separate components that are placed into the holes 19406 and to which the first tissue thickness compensator 19410 and the second tissue thickness compensator 19410 may be attached, for example, by using adhesives or interference fits between ends of the connectors 19430 and receiving ports in the first tissue thickness compensator 19410 and the second tissue thickness compensator 19420.

After the retainer 19400 has been placed on a staple cartridge 19450, for example, an anvil 19440 of the surgical device can be moved in the direction of arrow H into a closed position. An adhesive and/or engagement features on a surface 19414 of the first tissue thickness compensator 19410 can attach the first tissue thickness compensator 19410 to the anvil 19440 when the anvil 19440 closes. Likewise, an adhesive and/or engagement features on a surface 19424 of the second tissue thickness compensator 19420 can attach the second tissue thickness compensator 19420 to the staple cartridge 19450. After the anvil 19440 is closed and the first and second tissue thickness compensators 19410 and 19420 are attached to the anvil 19440 and staple cartridge 19450, respectively, the retainer 19400 may be pulled in the direction of arrow I (FIG. 417) to remove the retainer 19400 from between the first tissue thickness compensator 19410 and the second tissue thickness compensator 19420 and to break the connectors 19430. As shown in FIG. 418, after the connectors 19430 are broken and the retainer 19400 has been removed, the anvil 19440 may be reopened, and the first tissue thickness compensator 19410 will be attached to the anvil 19440 and the second tissue thickness compensator 19420 will be attached to the staple cartridge 19450.

In various embodiments, a proximal portion 19407 of each hole 19406 in the retainer 19400 may include a cutting edge. When the retainer is pulled in the direction of arrow I (FIG. 417), a pulling force is transmitted through the proximal portion 19407 of the holes 19406 to break the connectors. A cutting edge at the proximal portion 19407 of each hole 19406 will concentrate the transmitted force on a relatively small area of each connector. As a result, the connectors will break more easily and a lower pulling force may be required to remove the retainer 19400 from between the first tissue thickness compensator 19410 and the second tissue thickness compensator 19420.

As described above, a retainer assembly can comprise a retainer positioned between a first tissue thickness compensator and a second tissue thickness compensator wherein, after the two tissue thickness compensators have been inserted into and attached to an end effector of a surgical instrument, the retainer can be pulled from between the tissue thickness compensators and removed from the end effector. In certain embodiments, the retainer can provide a barrier between the first and second tissue thickness compensators. Once the retainer is removed from between the first and second tissue thickness compensators, substances in and/or on the first tissue thickness compensator can react with substances in and/or on the second tissue thickness compensator, for example. In some embodiments, one or both of the tissue thickness compensators can include a film that can encase substances within the tissue thickness compensators. In certain embodiments, the films can be attached to the retainer wherein, when the retainer is pulled from between the tissue thickness compensators, as described above, the retainer can pull the films away from the tissue thickness compensators to expose the substances contained therein. At such point, the substances within each of the tissue thickness compensators can interact with each other.

FIGS. 419-429 illustrate an embodiment of a retainer that engages an anvil of a surgical device, such as, for example, a surgical stapler. The retainer may align a first tissue thickness compensator with the anvil and a second tissue thickness compensator with a staple cartridge. Closing the anvil causes the first tissue thickness compensator to attach to the anvil and the second tissue thickness compensator to attach to the staple cartridge. The retainer also may carry the staple cartridge with a tissue thickness compensator optionally disposed between the retainer and the staple cartridge. Closing the anvil causes the staple cartridge to attach to a channel of the surgical stapler and causes the first tissue thickness compensator to attach to the anvil.

FIGS. 419-422 show an embodiment of a retainer 19500. The retainer 19500 includes a grip 19502 by which a surgeon, nurse, technician, or other person may manipulate the retainer 19500. The grip 19502 may include a textured surface, such as raised portions 19503, for example, which may provide a better gripping surface. In various embodiments, the retainer 19500 can include a surface 19504 on which a tissue thickness compensator may be mounted. The surface 19504 may include one or more projections 19506 wherein the projections 19506 may engage recesses in the tissue thickness compensator and align the tissue thickness compensator relative to the surface 19504 of the retainer 19500. The recesses in the tissue thickness compensator may be slightly smaller than the projections 19506 such that, when engaged with the recesses, the projections 19506 can hold the tissue thickness compensator to the surface 19504. In various embodiments, the projections 19506 may pass through holes in the tissue thickness compensator and engage a slot, such as, a cutting blade slot 19558 in anvil 19550 shown in FIG. 424, thereby aligning the tissue thickness compensator with the retainer 19500 and also providing additional alignment of the retainer 19500 with the anvil 19550. The tissue thickness compensator 19540 may include an adhesive and/or engagement features, described above, on a surface 19542 for attaching the tissue thickness compensator to an anvil 19550.

As shown in FIG. 423, in various embodiments, a staple cartridge 19530 may be attached to the retainer 19500. The staple cartridge 19530 can be attached to the retainer 19500 by clips 19510 and 19512 extending from the retainer 19500. Clips 19512 on the retainer 19500 can engage a slot 19534 in the staple cartridge 19530. Clips 19510 of the retainer 19500 can surround the bottom 19532 of the staple cartridge 19532. In various embodiments, a second tissue thickness compensator may be attached to the staple cartridge 19530. In at least one embodiment, a second tissue thickness compensator may be attached to a staple deck 19536 of the staple cartridge 19530.

As shown in FIGS. 424 and 425, a retainer assembly 19590 comprising the retainer 19500, a tissue thickness compensator 19540, and a staple cartridge 19530, can slide onto the anvil 19550 of a surgical device, such as a surgical stapler, in the direction of arrow L. The guide tabs 19508 on the retainer 19500 can surround edges 19552 of the anvil 19550 and position the retainer assembly 19590 relative to the anvil 19550. After the retainer assembly 19590 is engaged on the anvil 19550, as shown in FIGS. 426 and 427, the anvil can be closed in the direction of arrow M. Closure of the anvil 19550 can position the staple cartridge 19530 in a channel 19560 of the surgical device. In at least one embodiment, closure of the anvil 19550 can cause the clips 19510 extending from the retainer 19500 to engage a ridge 19562 of the channel 19560 in order to securely position the staple cartridge 19530 in the channel 19560. When the anvil 19550 is reopened in the direction of arrow N, referring now to FIGS. 428 and 429, the tissue thickness compensator 19540 can remain attached to the anvil 19550 and separates from the retainer 19500. The retainer 19500 then can be removed from the surgical instrument in the direction of arrow O (FIGS. 428 and 429) leaving the staple cartridge 19530 in the channel 19560 of the surgical device and a tissue thickness compensator 19540 attached to the anvil 19550.

FIGS. 430 and 431 show examples of two alternative embodiments of tissue thickness compensators 19570 and 19580, respectively. FIG. 430 is a cross-sectional view of a tissue thickness compensator 19570 attached to a retainer 19501 wherein the tissue thickness compensator 19570 can include protrusions 19574 which can contact edges 19552 of the anvil 19550 and partially surround an exterior surface 19556 of the anvil 19550. In various embodiments, the protrusions can grip the anvil 19550 and/or be attached to the anvil 19550 utilizing one or more adhesives. In order to release the tissue thickness compensator 19570 from the anvil 19550 after the compensator 19570 has been implanted against a patient's tissue, the protrusions 19574 can flex outwardly from the anvil 19550 thereby enabling the tissue thickness compensator 19570 to be pulled away from the anvil 19550. FIG. 431 is a cross-sectional view of a tissue thickness compensator 19580 attached to the retainer 19501 shown in FIG. 430. The tissue thickness compensator 19580 includes a sock 19584 that can surround the anvil 19550 to align the tissue thickness compensator 19580 with the anvil 19550 and/or to retain the tissue thickness compensator 19580 on the anvil 19550. In various embodiments, the sock 19584 can retain the tissue thickness compensator 19580 on the anvil 19550. In order to detach the sock 19584 from the anvil 19550, in various embodiments, the tissue thickness compensator 19580 can tear away from the sock 19584 at perforations 19586, for example. Thus, the sock 19584 can remain on the anvil 19550 while the remainder of the tissue thickness compensator 19580 can remain stapled to the patient tissue.

In certain embodiments, a tissue thickness compensator, such as tissue thickness compensator 19570, for example, can include an interior portion that comprises a biocompatible substance positioned therein. In various embodiments, the biocompatible substance can include an anti-inflammatory, a coagulant, and/or an antibiotic, for example. In various embodiments, a body, such as a wafer, for example can be inserted into the interior portion within the tissue thickness compensator. In at least one such embodiment, the wafer may be inserted through an open end of the tissue thickness compensator into a cavity defined therein. In certain embodiments, the wafer may be held within the cavity of the tissue thickness compensator by an interference fit. In certain embodiments, steps for assembling the wafer into the tissue thickness compensator can include a first step of heating the tissue thickness compensator such that the tissue thickness compensator expands. When the tissue thickness compensator expands, in various embodiments, the cavity defined therein can also expand. When the tissue thickness compensator is in an expanded state, according to a second step, the wafer may be inserted into the cavity. Then, as the tissue thickness compensator cools, according to a third step, the cavity can shrink onto the wafer and hold the wafer in place within the cavity.

FIGS. 432-444 illustrate an embodiment of a retainer comprising a separate insertion tool. The insertion tool can be used to insert an assembly into a surgical instrument, such as a surgical stapler, for example. The insertion tool can also press a staple cartridge and one or more tissue thickness compensators of the retainer assembly into position within the surgical instrument. Referring to FIGS. 432 and 433, a retainer 19600 may include a first plate 19620 and a second plate 19622. The first plate 19620 and the second plate 19622 may be connected by a hinge 19612. The hinge 19612 can position the first plate 19620 at an angle relative to the second plate 19622 and can also enable the first plate 19620 to rotate relative to the second plate 19622 about the hinge 19612.

In various embodiments, the first plate 19620 can include an outward-facing surface 19604 and an inward-facing surface 19606. Likewise, the second plate 19622 may include an outward-facing surface 19610 and an inward-facing surface 19608. In at least one embodiment, the inward-facing surface 19606 of the first plate 19620 may include a cam protrusion 19614. Similarly, the inward-facing surface 19608 of the second plate 19622 may include a cam protrusion 19616. Referring to FIGS. 439-444, outward-facing surface 19604 of the first plate may include a tissue thickness compensator positioned thereon. Outward-facing surface 19601 of the second plate 19622 may also include a tissue thickness compensator positioned thereon. The tissue thickness compensators may be attached to the outer surfaces 19604 and 19610 using adhesives, engagement features, and/or other suitable attachment means, such as, for example, retention members 12295 described above with respect to FIGS. 318-322. In various embodiments, the retainer 19600 can include clips 19618 extending from the second plate 19622 which can be configured to engage a staple cartridge 19690, as shown in FIGS. 439 and 441-444.

Referring now to FIGS. 434-438, an insertion tool 19630 can include a first end 19632 and a second end 19634. The first end 19632 can be large enough to be gripped by a surgeon, nurse, and/or technician, for example. In various embodiments, the second end 19634 defines a cavity 19640 wherein the cavity can include a cam 19648 positioned therein. A first side of the cam 19648 may include a first lobe 19642, a second lobe 19644, and a first anti-lobe 19646 positioned therebetween. A second side of the cam 19648 can include a third lobe 19643, a fourth lobe 19645, and a second anti-lobe 19647 positioned therebetween. In at least one such embodiment, the lobes and the anti-lobes can be arranged in a mirror-image manner. In other words, the first lobe 19642 may be arranged on the first side of the cam 19648 directly opposite the third lobe 19643 on the second side of the cam 19648. Likewise, the second lobe 19644 may be arranged on the first side of the cam 19648 directly opposite the fourth lobe 19645 on the second side of the cam 19648. Further, the first anti-lobe 19464 may be arranged on the first side of the cam 19648 directly opposite the second anti-lobe 19647 on the second side of the cam 19648.

In use, the second end 19634 of the insertion tool 19630 is placed between the first plate 19620 and the second plate 19622 of the retainer 19600 such that the cam protrusion 19614 on the first plate 19620 is engaged with anti-lobe 19646 and cam protrusion 19616 on the second plate 19622 is engaged with anti-lobe 19647, for example. As shown in FIGS. 441 and 442, an insertion assembly 19700, which includes the retainer 19600, the insertion tool 19630, one or more tissue thickness compensators, and staple cartridge 19690 can be inserted into a surgical instrument. The surgical instrument, such as a surgical stapler, may include a channel 19740, which is configured to receive the staple cartridge 19690, and an anvil 19720. The insertion assembly 19700 can be inserted into the surgical instrument in the direction of arrow P (FIG. 442) to lock the staple cartridge 19690 into the channel 19740. In such a position, the cams 19614 and 19616 can be aligned with the anti-lobes 19646 and 19647, respectively.

After the staple cartridge 19690 is locked into the channel 19740, as shown in FIG. 443, the insertion tool 19600 can continue to be moved in the direction of arrow Q relative to the surgical instrument. Further movement of the insertion tool 19600 in the direction of arrow Q can align the first lobe 19642 with the first cam protrusion 19614 and the third lobe 19634 with the second cam protrusion 19616. Such an alignment can cause the retainer plates 19620 and 19622 to rotate away from each other about the hinge 19612 in the direction of arrow R (FIG. 443). In such circumstances, the retainer plate 19620 and the tissue thickness compensator 19670 can move toward the anvil 19720 and the retainer plate 19622 can move toward and contact the anvil 19720. In various embodiments, as a result of the above, the tissue thickness compensator 19670 can be seated on the anvil 19720. After the tissue thickness compensator 19670 is attached to the anvil 19720, the insertion tool 19630 may be retracted or moved in the direction of arrow S (shown in FIG. 444). Movement of the insertion tool 19630 in the direction of arrow S can causes the cam protrusions 19614 an 19616 to disengage from the first lobe 19642 and the third lobe 19643, respectively, and become re-aligned with the first anti-lobe 19646 and the second anti-lobe 19647, respectively. In various embodiments, the second lobe 19642 and the fourth lobe 19645 can abut the cam protrusions 19614 and 19616, respectively, and, in at least one embodiment, can prevent the insertion tool 19630 from completely separating from the retainer 19600. With the cam protrusions 19614 and 19616 realigned with the anti-lobes 19646 and 19647, the first plate 19620 can at least partially rotate toward the second plate 19622 about the hinge 19612 and away from the anvil 19720. The retainer 19600 can also be detached from the channel 19740, in various embodiments, and then removed in the direction of arrow S leaving the tissue thickness compensator 19670 attached to the anvil 19720, for example.

In the embodiments described herein, a retainer assembly can be utilized to install one or more tissue thickness compensators into an end effector of a surgical stapling instrument. In certain embodiments, a retainer assembly can install layers besides tissue thickness compensators into a surgical instrument. In at least one embodiment, the layers may include an absorbable material and/or a biocompatible material, for example.

Referring to FIG. 501, an end effector 12 can be configured to receive an end effector insert 25002. In various embodiments, the end effector 12 can comprise a lower jaw 25070 and an anvil 25060 that is configured to pivot relative to the lower jaw 25070. In some embodiments, the end effector insert 25002 can comprise a staple cartridge 25000 that is pivotably connected to an anvil insert 25004. The end effector 12 can be configured to receive the end effector insert 25002 such that the staple cartridge 25000 fits within a staple cartridge channel 25072 of the lower jaw 25070, for example, and the anvil insert 25004 contacts the anvil 25060, for example. In various embodiments, the lower jaw 25070 can comprise a plurality of securing members 25074 configured to secure the staple cartridge 25000 to the staple cartridge channel 25072. In some embodiments, the anvil insert 25004 can comprise at least one retaining protrusion configured to engage at least one retaining groove in the anvil 25060. The anvil insert 25004 can be configured to correspondingly pivot towards the staple cartridge 25000 when the anvil 25060 pivots towards the lower jaw 25070, as described in greater detail herein.

Referring still to FIG. 501, the end effector insert 25002 can further comprise a retainer 25010. In various embodiments, the retainer 25010 can securely engage at least one of the staple cartridge 25000 and the anvil insert 25004. In at least one embodiment, the retainer 25010 can comprise at least one securing clip 25012 that can clip, engage, snap, clamp, and/or hook the staple cartridge 25000. As illustrated in FIG. 501, the retainer 25010 can comprise two securing clips 25012 on each longitudinal side thereof, for example. In at least one such embodiment, the securing clips 25012 can be configured to clip onto a portion of the staple cartridge 25000, for example. In various embodiments, a tissue thickness compensator can be held in position relative to the end effector insert 25002 by the retainer 25010. For example, a tissue thickness compensator can be positioned between the retainer 25010 and the staple cartridge 25000.

In various embodiments, when an operator is inserting the end effector insert 25002 into the end effector 12, the retainer 25010 can provide a solid or substantially solid element for the operator to grasp. Furthermore, the retainer 25010 can prevent premature deformation of a tissue thickness compensator that is confined by the retainer 25010, for example. In various embodiments, the retainer 25010 can be removed from the end effector 12 prior to utilizing the end effector 12 to cut and/or fasten tissue. In other embodiments, the retainer 25010 can remain positioned in the end effector 12. For example, the retainer 25010 can be transected by the cutting element 25052 (FIG. 536) as staples are fired from staples cavities 25002 (FIG. 536) in the staple cartridge 25000. In various embodiments, the retainer 25010 can comprise a polymeric composition, such as a bioabsorbable, biocompatible elastomeric polymer, for example. The retainer 25010 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the retainer 25010 can comprise at least one therapeutic agent such as a pharmaceutically active agent or medicament.

Referring to FIG. 502, an end effector 26012 can comprise an anvil 26060 and a lower jaw 26070. In various embodiments, a tissue compensator 26020 can be releasably secured to the anvil 26060, the lower jaw 26070, and/or both the anvil 26060 and the lower jaw 26070. For example, a first tissue compensator 26020 can be releasably secured to a staple cartridge 26000 in the lower jaw 26070 and a second tissue compensator 26022 can be releasably secured to the anvil 26060. In various embodiments, the first and second tissue compensators 26020, 26022 can be deformable and/or resilient, similar to at least one tissue thickness compensator described herein. For example, the first and second tissue compensators 26020, 26022 can comprise a polymeric composition, such as a bioabsorbable, biocompatible elastomeric polymer, for example. The first and second tissue compensators 26020, 26022 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the first and second tissue compensators 26020, 26022 can comprise at least one therapeutic agent such as a pharmaceutically active agent or medicament.

In some embodiments, the tissue compensator 26020, 26022 can comprise a firm or substantially firm tip 26024, 26026. For example, a first tip 26024 can be positioned at the distal end of the first tissue compensator 26020 and a second tip 26026 can be positioned at the distal end of the second tissue compensator 26022. In various embodiments, the tips 26024, 26026 may prevent or limit premature deformation of the tissue compensators 26020, 26022. For example, the tips 26024, 26026 can protect the tissue compensators 26020, 26022 when the tissue compensators 26020, 26022 are moved through a trocar and/or maneuvered around a patient's tissue, for example. Similarly, referring to FIG. 503, the end effector 12 can comprise a first tissue compensator 25020 releasably secured to the staple cartridge 25000 in the lower jaw 25070 and a second tissue compensator 25022 releasably secured to the anvil 25060. In various embodiments, a tip 25026 can be positioned at the distal end of the second tissue compensator 25022. The tip 25026 can be positioned adjacent to a deformable and/or resilient portion of the tissue compensator 25022. In some embodiments, the tip 25026 can extend over and/or around a portion of the tissue compensator 25022, such that the tip 25026 protects the distal end and an intermediate portion of the tissue compensator 25022.

Referring to FIGS. 504-531, a sleeve 27010 can be configured to engage the anvil 25060 of the end effector 12 of a surgical instrument, for example. In various embodiments, the sleeve 27010 can comprise a pronged portion 27040 (FIGS. 505-508), a nose 27080 (FIGS. 515-518) and a compensator 27120 (FIGS. 509-511). In some embodiments, the sleeve 27010 can be configured to release a compensator 27020 when a translating firing bar 25052 (FIG. 525) approaches the distal end of the end effector 12.

In various embodiments, the compensator 27020 can be deformable and/or resilient, similar to at least one tissue thickness compensator described herein. For example, the compensator 27020 can comprise a polymeric composition, such as a bioabsorbable, biocompatible elastomeric polymer, for example. The compensator 27020 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the compensator 27020 can comprise at least one therapeutic agent such as a pharmaceutically active agent or medicament. Referring primarily to FIG. 504, the pronged portion 27040 can be positioned on and/or around an outer surface 25061 of the anvil 25060. In various embodiments, the nose 27080 of the sleeve 27010 can be positioned at and/or around a distal portion of the anvil 25060. In some embodiments, the compensator 27020 can be positioned on and/or around an inner surface of the anvil 25060.

Referring still to FIG. 504, the pronged portion 27040 can comprise at least one prong 27042a. In various embodiments, as illustrated in FIGS. 505-508, the pronged portion 27040 can comprise a first prong 27042a and a second prong 27042b. The prongs 27042a, 27042b can be symmetrical or substantially symmetrical, for example. In some embodiments, the first prong 27042a can be asymmetrical relative to the second prong 27042b. In various embodiments, the first and/or second prongs 27042a, 27042b can narrow at the distal end thereof. For example, each prong 27042a, 27042b can comprise a narrowed end 27048. Referring primarily to FIG. 507, the pronged portion 27040 can be contoured, for example. In various embodiments, referring again to FIG. 504, the contour of the pronged portion 27040 can match or substantially match a contour of the outer surface 25061 of the anvil 25060, for example. Referring primarily to FIGS. 507 and 508, the pronged portion 27040 can also comprise at least one catch 27044a extending from the first prong 27042a. In some embodiments, a first catch 27044a can be positioned on a first side of the pronged portion 27040 and a second catch 27044b can be positioned on a second side of the pronged portion 27040. In various embodiments, the catches 27044a, 27044b can be positioned at or near the proximal end of the pronged portion 27040, for example. In some embodiments, the catches 27044a, 27044b can be positioned at or near the distal end of the pronged portion 27040, such as along the first and/or second prongs 27042a, 27042b, for example. In various embodiments, the catches 27044a, 27044b can extend along a substantial length of the pronged portion 27040 and/or along a shorter length of the pronged portion 27040. In some embodiments, a plurality of catches 27044a, 27044b can be positioned along each longitudinal side of the pronged portion, for example. Referring primarily to FIG. 508, the first catch 27044a can comprise a first catch extension 27046a and/or the second catch 27044b can comprise a second catch extension 27046b. In various embodiments, the first catch extension 27046a can protrude from at least a portion of the catch 27044a and the second catch extension 27046b can protrude from at least a portion of the catch 27044b, for example. Further, the first catch extension 27046a and the second catch extension 27046b can each be configured to engage a gap 27128 (FIG. 510) in the compensator 27020, as described in greater detail herein.

Referring now to FIG. 530, the compensator 27020 for the sleeve 27010 can comprise a longitudinal protrusion 27024 and an edge 27026 on each longitudinal side of the compensator 27020. In various embodiments, the compensator 27020 can be positioned adjacent to an inner surface 25063 of the anvil 25060. Further, when the sleeve 27010 is positioned on the anvil 25060, the longitudinal protrusion 27024 can be substantially aligned with and/or positioned within a longitudinal slot 25062 in the anvil 25060. The edges 27026 of the compensator 27020 can at least partially wrap around the anvil 25060 towards the outer surface 25061 thereof. Referring primarily to FIGS. 509-511, a compensator 27120 for a sleeve 27110 can comprise a body 27122 having a longitudinal protrusion 27124 that extends along at least a portion of the body 27122. The longitudinal protrusion 27124 can define a longitudinal path along the midline of the body 27122, for example. In various embodiments, the longitudinal protrusion 27124 can be received by the longitudinal slot 25062 (FIG. 530) in the anvil 25060 when the sleeve 27110 is positioned on the anvil 25060. Referring primarily to FIG. 511, the longitudinal protrusion 27124 can comprise a rounded projection. For example, the cross-section of the longitudinal protrusion 27124 can form an arc and/or partial ring. In other embodiments, the longitudinal protrusion 27124 can comprise an angular and/or stepped projection. The compensator 27120 can further comprise an edge 27126, which can be straight, bent, fluted, wavy, and/or zigzagged, for example. In various embodiments, the edge 27126 can comprise gaps 27128 that can be configured to receive the catch extensions 27046a, 27046b (FIG. 508) when the assembled sleeve 27110 is positioned on the anvil 25060. The catch extensions 27046a, 27046b can fit through the gap 27128 to engage the anvil 25060 such that the catch extensions 27046a, 27046b help to secure the sleeve 27110 to the anvil 25060, for example.

Referring primarily to FIGS. 512-514, a compensator 27220 for a sleeve 27210 can comprise a body 27222 comprising a longitudinal protrusion 27224 extending along at least a portion of the body 27222. In various embodiments, similar to the above, the longitudinal protrusion 27224 can be received by the longitudinal slot 25062 (FIG. 531) in the anvil 25060 when the sleeve 27210 is positioned on the anvil 25060. Referring primarily to FIG. 514, the longitudinal protrusion 27224 can comprise an angular projection such that the cross-section of the protrusion 70224 forms a substantially rectangular shape. The compensator 27220 can further comprise an edge 27226, which can be straight, bent, fluted, wavy, and/or zigzagged, for example. In various embodiments, the edge 27226 can comprise gaps 27228 that can be configured to receive the catch extensions 27046a, 27046b (FIG. 508) when the assembled sleeve 27210 is positioned on the anvil 25060. The catch extensions 27046a, 27046b can fit through the gaps 27228 and engage the anvil 25060 such that the catch extensions 27046a, 27046b help to secure the sleeve 27210 to the anvil 25060, for example. In various embodiments, the compensator 27220 can further comprise a plurality of ribs 27229 that laterally traverse the body 27222 of the compensator 27220. The ribs 27229 can support the body 27222 of the compensator 27220 when the sleeve 27210 is positioned on the anvil 25060 and/or when the compensator 27220 contacts tissue.

Referring to FIGS. 515-519, the nose 27080 of the sleeve 27010 can comprise an alignment ridge 27082 that can be substantially aligned with the longitudinal slot 25062 (FIG. 530) in the anvil 25060. When the alignment ridge 27082 is aligned with the longitudinal slot 25062 and when the sleeve 27010 is positioned on the anvil 25060, the nose 27082 can at least partially surround a distal portion of the pronged portion 27040 of the sleeve 27010. For example, the narrowed end 27048 of each prong 27042a, 27042b can be positioned within the nose 27080 when the sleeve 27010 is positioned on the anvil 25060. As described in greater detail herein, the nose 27080 can flex the prongs 27042a, 27042b closer together and/or downward when the pronged portion 27042 is engaged with the nose 27080. Furthermore, as illustrated in FIG. 519, when the narrowed ends 27048 of the pronged portion 27040 are positioned within the nose 27080, the catches 27044a, 27044b on the pronged portion 27040 can engage the edges 27026 of the compensator 27020, for example. As a result of such engagement, the compensator 27010 can be secured to the anvil 25060.

Referring to FIGS. 520-524, when the nose 27080 is engaged with the pronged portion 27040 of the sleeve 27010, the compensator 27020 can be secured to the anvil 25060. The nose 27080 can remain engaged with the pronged portion 27040 as the firing bar 25050 translates along a portion of the longitudinal slot 25062 in the anvil 25060. Referring now to FIGS. 524-529, when the cutting element 25052 on the firing bar 25050, and/or any other suitable portion of the firing bar 25050, such as retaining flange 25054, for example, approaches the distal end of the anvil 25060, the firing bar 25050 can disengage the nose 27080 from the pronged portion 27040. The firing bar 25050 can, for example, contact the nose 27080 and push the nose 27080 off of the anvil 25060 such that the nose 27080 becomes disconnected from the pronged portion 27040 of the sleeve 27010. Referring now to FIG. 531, when the nose 27080 is disengaged with the pronged portion 27040, the first and second prongs 27042a, 27042b can be configured to flex away from the anvil 25060. For example, when the pronged portion 27070 is engaged with the nose 27080, the prongs 27042a, 27042b can be flexed closer together and/or downwards towards the anvil 25060 and held in such a position by the nose 27080. In various embodiments, the prongs 27042a, 27042b can be held under a spring load by the nose 27080 such that the prongs 27042a, 27042b seek to rebound to a neutral configuration once the nose 27080 is disengaged from the prongs 27042a, 27042b. In other embodiments, the prongs 27042a, 27042b can be sufficiently deformable such that the prongs 27042a, 27042b can be deformed or splayed outwardly by the firing bar 25050 once the nose 27080 is disengaged therefrom. When the prongs 27042a, 27042b move away from the anvil 25060, the catches 27044a, 27044b along a longitudinal side of each prong 27042a, 27042b can disengage the compensator 27020, which can allow the compensator 27020 to be released from the anvil 25060.

Referring to FIGS. 532-538, the end effector 12 of a surgical instrument, for example, can be configured to receive an end effector insert 28010. In various embodiments, the end effector insert 28010 can comprise a compensator body 28012 and at least one clip 28014a, 28014b. In various embodiments, the end effector insert 28010 can comprise a proximal clip 28014b at the proximal end of the compensator body 28012 and a distal clip 28014a at the distal end of the compensator body 28012, for example. Referring primarily to FIG. 535, the distal clip 28014a can be secured to the anvil 25060 of the end effector 12 at or near the distal end of the anvil 25060. For example, the distal clip 28014a can be substantially aligned with and/or partially positioned within the longitudinal slot 25062 of the anvil 25060. Referring primarily to FIG. 536, the proximal clip 28014b can be secured to a staple cartridge 25000 in the lower jaw 25070 of the end effector 12 (FIG. 537). The proximal clip 28014b can be secured to the staple cartridge 25000 at or near the proximal end of the staple cartridge 25000. For example, the proximal clip 28014b can be substantially aligned with and/or positioned within a longitudinal slot 25004 in the staple cartridge 25000.

Referring now to FIGS. 537 and 538, the end effector insert 28010 can be inserted into the end effector 12 of a surgical instrument. In various embodiments, at least a portion of the end effector insert 28010, such as the compensator body 28012, distal clips 28014*a*, and/or proximal clip 28014*b*, can be deformable and/or resilient, for example. When the end effector insert 28010 is inserted into the end effector 12, the distal and/or the proximal clips 28014*a*, 28014*b* can bend or flex. When the clips 28014*a*, 28014*b* are flexed, for example, the clips 28014*a*, 28014*b* can seek to return to their initial, undeformed configuration and can generate a corresponding springback or restoring force, for example. In various embodiments, when the end effector insert 28010 is positioned within the end effector 12, the end effector insert 28010 can apply a spring load to the end effector 12. In some embodiments, the end effector insert 28010 can be solid or substantially solid such that an operator can grasp the insert 28010 when the operator is inserting the end effector insert 28010 and staple cartridge 25000 into the end effector 12.

In some embodiments, the end effector insert 28010 can be removed from the end effector 12 prior to cutting and/or fastening operations of the end effector 12. In other embodiments, the end effector insert 28010 can remain positioned in the end effector 12 during cutting and/or firing operations. For example, the end effector insert 28010 can be transected by the cutting element 25052 as staples are fired from their staples cavities 25002 (FIG. 536) in the staple cartridge 25000. In various embodiments, the end effector insert 28010 can comprise a tissue thickness compensation material, similar to at least one of the tissue thickness compensators described herein. For example, the end effector insert 28010 can comprise a polymeric composition, such as a bioabsorbable, biocompatible elastomeric polymer, for example. The end effector insert 28010 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the end effector insert 28010 can comprise at least one therapeutic agent such as a pharmaceutically active agent or medicament.

Referring to FIGS. 539-544, a tissue thickness compensator 29020 can be positioned in the end effector 12 of a surgical instrument. The tissue thickness compensator 29020 can be substantially similar to at least one of the tissue thickness compensators described herein. For example, the tissue thickness compensator 29020 can be sufficiently deformable and resilient such that deformation of the tissue thickness compensator 29020 generates a springback or restoring force. In various embodiments, referring primarily to FIG. 540, a static charge can attract the tissue thickness compensator 29020 to the anvil 25060 of the end effector 12 such that the static charge secures the tissue thickness compensator 29020 to the anvil 25060. In various embodiments, the static charge can be neutralized such that the anvil 25060 releases the tissue thickness compensator 29020. Additionally or alternatively, referring now to FIG. 541, the tissue thickness compensator 29020 can be secured to the anvil 25060 by at least one suction element 29022. For example, a plurality of micro-suction elements 29022 on a surface of the tissue thickness compensator 29020 can releasably secure the tissue thickness compensator 29020 to the anvil 25060. Additionally or alternatively, referring to FIG. 542, hook and loop fasteners 29024 can secure the tissue thickness compensator 29020 to the anvil 25060. For example, a surface of the tissue thickness compensator 29020 can comprise a plurality of hook fasteners 29024*a* and a surface of the anvil 25060 can comprise a plurality of loop fasteners 29024*b*, for example. The hook fasteners 29024*a* can engage the loop fasteners 29024*b* such that the tissue thickness compensator 29020 is releasably secured to the anvil 25060.

Additionally or alternatively, referring now to FIG. 543, the tissue thickness compensator 29020 can be secured to the anvil 25060 by a band 29026. In some embodiments, the band 29026 can comprise an elastomeric polymer and/or can be tied or knotted around the anvil 25060. When the band 29026 is removed from the anvil 25060, the tissue thickness compensator 29020 can be released from the anvil 25060. To facilitate removal of the band 29026, it can be stretched and/or cut, for example. In various embodiments, a plurality of bands 29026 can secure the tissue thickness compensator 29020 to the anvil 25060. Alternatively or additionally, referring now to FIG. 544, the tissue thickness compensator 29020 can be secured to the anvil 25060 by a sock 29028 positioned at the distal end of the tissue thickness compensator 29020. The sock 29028 can be configured to receive the distal end of the anvil 25060 therein, for example. In some embodiments, an alignment ledge 29029 on the tissue thickness compensator 29020 can be aligned with and/or positioned within the longitudinal slot 25062 in the anvil 25060. For example, the alignment ledge 29029 can slide within the longitudinal slot 25062 as the tissue thickness compensator 29020 is positioned on and/or removed from the anvil 25060.

Referring to FIGS. 545-547, a tissue thickness compensator 30020 can be positioned on the anvil 25060 of the end effector 12 of the surgical instrument. In various embodiments, the tissue thickness compensator 30020 can comprise a body 30022 and a pocket 30024. In at least one embodiment, a compensator material 30026 can be retained between the body 30022 and the pocket 30024, for example. In some embodiments, the compensator material 30026 can comprise a bioabsorbable polymer, such as, for example, lyophilized polysaccharide, glycoprotein, elastin, proteoglycan, gelatin, collagen, and/or oxidized regenerated cellulose (ORC), for example. Additionally or alternatively, the compensator material 30026 can comprise at least one therapeutic agent such as a pharmaceutically active agent or medicament. In various embodiments, the tissue thickness compensator 30020 can be deformable and/or resilient, similar to at least one tissue thickness compensator described herein. For example, the tissue thickness compensator 30020 can comprise a polymeric composition, such as a bioabsorbable, biocompatible elastomeric polymer, for example. The tissue thickness compensator 30020 can further comprise a bioabsorbable polymer, such as, for example, lyophilized polysaccharide, glycoprotein, elastin, proteoglycan, gelatin, collagen, and/or oxidized regenerated cellulose (ORC), for example.

Referring primarily to FIG. 546, the body 30022 of the tissue thickness compensator 30020 can comprise an alignment element 30028 that can be received within the longitudinal slot 25062 of the anvil 25060 when the tissue thickness compensator 30020 is secured to the anvil 25060. In some embodiments, the body 30022 can comprise a stepped thickness such that the geometry of the body 30022 substantially corresponds with the geometry of the anvil 25060. Further, in various embodiments, the body 30022 can comprise longitudinal flanges 30029. In at least one such embodiment, a longitudinal flange 30029 can extend along each longitudinal side of the body 30022 of the tissue thickness compensator 30020, for example. In various embodiments, the longitudinal flanges 30029 can at least partially wrap around the anvil 25060 to secure the tissue thickness compensator 30020 to the anvil 25060. Further, the longitudinal flanges 30029 can be sufficiently resilient such that the longitudinal flanges 30029 can flex to accommodate and/or engage the anvil 25060, for example. In various embodiments, the longitudinal flanges 30029 can exert a clamping force on the anvil 25060 when the flanges 30029 engage the anvil 25060. In some embodiments, the pocket 30024 can comprise an indentation 30025. When the tissue thickness compensator 30020 is secured to the anvil 25060, the indentation 30025 can be substantially aligned with the longitudinal slot 25062 in the anvil 25060, for example. In various embodiments, the tissue thickness compensator 30020 can be thinner at the indentation 30025 such that the translating cutting element 25052 (FIG. 536) severs the tissue thickness compensator 30020 where it is thinner.

Referring now to FIGS. 548 and 549, a tissue thickness compensator 30120 can comprise a body 30122 that is configured to retain compensation material 30026 therein. In various embodiments, the tissue thickness compensator 30120 can comprise an alignment element 30128, an indentation 30125, and/or longitudinal flanges 30129, similar to at least one of the embodiments described herein. In some embodiments, the tissue thickness compensator 30120 can also comprise a latch 30124 that can be moved between an open position and a closed position. When the latch 30124 is in the closed position, as illustrated in FIG. 548, the compensation material 30026 can be enclosed within the body 30122 of the tissue thickness compensator 30120 and, when the latch 30124 is in the open position, as illustrated in FIG. 549, the compensation material 30026 can escape from the body 30122. Similar to at least one of the tissue thickness compensators described herein, the tissue thickness compensator 30120 can be deformable and/or resilient. For example, the tissue thickness compensator 30120 can comprise a polymeric composition, such as a bioabsorbable, biocompatible elastomeric polymer, for example. The tissue thickness compensator 30120 can further comprise a bioabsorbable polymer, such as, for example, lyophilized polysaccharide, glycoprotein, elastin, proteoglycan, gelatin, collagen, and/or oxidized regenerated cellulose (ORC), for example. Owing to the resiliency of the tissue thickness compensator 30120, at least a portion of the body 30122 can be flexed to move the latch 30124 between the open position and the closed position. In at least one embodiment, the body 30122 of the tissue thickness compensator 30120 can remain attached to the anvil when the anvil is removed from the surgical site. In at least one such embodiment, the body 30122 can be configured to tear away from any staples that may have captured the body 30122 therein.

Referring to FIG. 550, a tissue thickness compensator 30220 can comprise a body 30222 and a pocket 30224. The compensator material 30026 can be retained between the body 30222 and the pocket 30224, for example. In various embodiments, the tissue thickness compensator 30220 can comprise an alignment element, an indentation, and/or longitudinal flanges 30229, similar to at least one of the embodiments described herein. Further, at least one longitudinal flange 30229 can comprise a groove, or slot, 30228, which can be configured to receive a tab 30225 extending from the pocket 30224 of the tissue thickness compensator 30220. In such an embodiment, engagement of the groove 30228 and the tab 30225 can connect the body 30222 and the pocket 30224. Further, in such an embodiment, the groove 30028 and tab 30025 connection can enclose and/or retain the compensation material 30026 within the tissue thickness compensator 30220. Referring now to FIG. 551, in various embodiments, a pocket 30324 of a tissue thickness compensator 30320 can comprise an anchor 30325 extending therefrom. Further, the tissue thickness compensator 30320 can comprise a body 30322 having an opening 30328. In various embodiments, the anchor 30325 can extend from the pocket 30324 to engage the opening 30328 in the body 30322. In such an arrangement, the pocket 30324 and the body 30222 can encase the compensation material 30026 therebetween. In at least one embodiment, the tissue thickness compensator 30320 can further comprise one or more flanges 30229 which can be mounted to the anvil in order to retain the body 30322 to the anvil.

Referring now to FIG. 552, a tissue thickness compensator 30420 can comprise a body 30422 and a pocket 30424. In various embodiments, the compensation material 30026 can be retained between the body 30422 and the pocket 30424 of the tissue thickness compensator 30420. In some embodiments, the body 30422 can comprise an orifice 30428 and the pocket 30424 can comprise an anchor 30425. The anchor 30425 can extend from the pocket 30424 and through the orifice 30428 of the body 30422, for example. In various embodiments, the anchor 30425 can engage the anvil 25060 when the tissue thickness compensator 30420 is secured to the anvil 25060, for example. The anchor 30525 can be sufficiently deformable and resilient such that the anchor 30425 flexes when it engages the anvil 25060. Further, in some embodiments, the flexed anchor 30425 can apply a clamping force to the anvil 25060 to secure or assist in securing the tissue thickness compensator 30420 to the anvil 25060. In other embodiments, an anchor may not extend completely through an orifice in the compensator body. Referring to FIG. 553, an anchor 30525 on a pocket 30524 of a tissue thickness compensator 30520 can engage an orifice 30528 in a body 30522 of the tissue thickness compensator 30520. In various embodiments, the anchor 30525 can engage the orifice 30528 to secure the pocket 30524 to the body 30522. For example, the orifice 30528 can comprise a necked portion that extends to a socket. The anchor 30525 can comprise securing edge, which can pass through the necked portion and engage the socket to secure the anchor 20525 within the orifice 30528. Similar to at least one of the embodiments described herein, the tissue thickness compensator 30520 can also comprise an alignment element, an indentation, and/or longitudinal flanges 30529, for example.

Referring to FIGS. 554-556, a tissue thickness compensator 31020 can be configured to engage an anvil 31060 of an end effector 31012 of a surgical instrument. In various embodiments, the tissue thickness compensator 31020 can comprise an outer film 31022, an inner film 31024 and a compensation material 31026 positioned therebetween. In various embodiments, the tissue thickness compensator 31020 can be deformable and/or resilient, similar to at least one of the tissue thickness compensators described herein. For example, the compensation material 31026 can comprise a polymeric composition, such as a bioabsorbable, biocompatible elastomeric polymer, for example. The tissue thickness compensator 31020 can further comprise a bioabsorbable polymer such as, for example, lyophilized polysaccharide, glycoprotein, elastin, proteoglycan, gelatin, collagen, and/or oxidized regenerated cellulose (ORC), for example. In some embodiments, the tissue thickness compensator 31020 can comprise at least one therapeutic agent such as a pharmaceutically active agent or medicament. In various embodiments, the compensation material 31206 of the tissue thickness compensator 31020 can comprise a therapeutic agent.

The inner film 31024 can be positioned adjacent to staple forming pockets 31066 in the anvil 31060, for example. Referring primarily to FIG. 554, the inner film 31024 can comprise a stepped geometry such that the geometry of the inner film 31024 substantially corresponds to the geometry of the anvil 31060. The inner film 31024 can further comprise an alignment ridge 31028, which can be substantially aligned with and/or parallel to a longitudinal slot 31062 in the anvil 31060, for example. As described in greater detail herein, the inner film 31024 can comprise an inner flange 31025 extending from each longitudinal side of the inner film 31024 and terminating in a catch 31027. The outer film 31022 can comprise a body 31021 and at least one outer flange 31023, for example. In various embodiments, an outer flange 31023 can extend from each longitudinal side of the body 31021, for example. In various embodiments, the outer flange 31023 can be secured to the inner flange 31025 such that the compensation material 31026 is retained between the outer film 31022 and the inner film 31024.

Referring primarily to FIG. 556, the anvil 31060 can comprise an outer surface 31061 and at least one groove 31064 along at least a portion of the outer surface 31061. In various embodiments, a catch 31027 on the inner flange 31025 of the inner film 31024 can be positioned within a groove 31064. Referring to FIG. 555, for example, the tissue thickness compensator 31020 can be slid around the anvil 31060. In various embodiments, the grooves 31064 on the anvil 31060 can extend to the distal end of the anvil 31060. In such embodiments, the catches 31027 of the tissue thickness compensator 31020 can slide into the grooves 31064 and along a length of the tissue thickness compensator 31020.

In various embodiments, referring now to FIGS. 557 and 558, a tissue thickness compensator 31120 can comprise a compensation material 31026 and at least one connector 31124. Each connector 31124 can extend around the compensation material 31026 and can terminate in a catch 31127 on opposite ends thereof. In various embodiments, the catches 31127 can be positioned within the grooves 31064 of the anvil 31060 to fasten the tissue thickness compensator 31120 to the anvil 31060. In various embodiments, the grooves 31164 on the anvil 31060 can extend to the distal end of the anvil 31060. In such embodiments, the catches 31127 of the connectors 31124 can slide into the grooves 31064. In other embodiments, the connectors 31224 can be resilient such that they can flex and snap around the anvil 31060. In use, the connectors 31224 can hold the compensation material 31026 in place until the compensation material 31026 detaches from the anvil 31060. In certain circumstances, the connectors 31224 can remain attached to the anvil 31060 and can be removed from the surgical site with the anvil. In certain other circumstances, the connectors 31224 can detach from the anvil 31060 and can be implanted with the compensation material 31026.

Referring to FIGS. 559-565, a tissue thickness compensator 32020 can comprise a body portion 32022, at least one longitudinal flange 32024, and at least one pocket 32026. In various embodiments, the tissue thickness compensator 31020 can be deformable and/or resilient, similar to at least one of the tissue thickness compensators described herein. For example, the compensation material 31026 can comprise a polymeric composition such as a bioabsorbable, biocompatible elastomeric polymer, for example. The tissue thickness compensator 31020 can further comprise a bioabsorbable polymer such as, for example, lyophilized polysaccharide, glycoprotein, elastin, proteoglycan, gelatin, collagen, and/or oxidized regenerated cellulose (ORC), for example. In various embodiments, the longitudinal flange 32024 can extend along each longitudinal side of the body portion 32022. Referring primarily to FIG. 562, the longitudinal flanges 32024 of the tissue thickness compensator 32020 can be configured to engage the anvil 25060. For example, the tissue thickness compensator 32020 can slide onto the anvil 25060 and the longitudinal flanges 32024 and can at least partially wrap around a portion of the anvil 25060. In such embodiments, the flanges 32024 can secure the tissue thickness compensator 32020 to the anvil 25060, for example. In various embodiments, when the tissue thickness compensator 32020 is secured to the anvil, the body portion 32022 of the tissue thickness compensator 32020 can overlap staple forming pockets 25066 on the inner surface of the anvil 25060.

Further to the above, in various embodiments, a plurality of pockets 32026 can laterally traverse the body portion 32022. Referring primarily to FIG. 563, the plurality of pockets 32026 can comprise at least one therapeutic agent such as a pharmaceutically active agent or medicament. In various embodiments, a plurality of first pockets 32026a can comprise a first therapeutic agent or combination thereof and a plurality of second pockets 32026b can comprise a second therapeutic agent or combination thereof. The first pockets 32026a and the second pockets 32026b can be alternatingly positioned along the body portion 32022, for example. Further, in various embodiments, when the first therapeutic agent is released from the first pocket 32026a and the second therapeutic agent is released from the second pocket 32026b, the first and second therapeutic agents can be configured to react with each other. Referring to FIG. 565, the pockets 32026 can release the therapeutic agent(s) retained therein when the cutting element 25052 on the firing bar 25050 translates along the longitudinal slot 25062 in the anvil 25060, for example.

In various embodiments, referring now to FIG. 566, an end effector of a surgical stapling instrument can comprise an anvil 32560 and a staple cartridge 32500 comprising a tissue thickness compensator 32520. Similar to the above, the staple cartridge 32500 can comprise a plurality of staples 32530 at least partially contained therein which can be ejected therefrom to capture the tissue thickness compensator 32520 therein. Also similar to the above, the staples 32530 can penetrate the tissue thickness compensator 32520 and contact staple forming pockets 32562 defined in the anvil 32560. In certain embodiments, referring now to FIG. 568, the anvil 32560 can further comprise a layer 32570 attached thereto which can be configured to retain a tissue thickness compensator 32580 to the anvil 32560. In at least one such embodiment, the layer 32570 can comprise a chargeable layer which can be configured to hold and/or generate an electrostatic charge and attract the tissue thickness compensator 32580 thereto. More specifically, in various embodiments, Van der Waals molecular forces, whether actively or passively actuated, for example, can hold the tissue thickness compensator 32580 to the layer 32570. In certain embodiments, the chargeable layer 32570 can be in electrical communication with a handle of the surgical stapling instrument which can comprise a control configured to selectively couple the chargeable layer 32570 with a power source and, as a result, allow an electrostatic charge to be selectively generated within the chargeable layer 32570. In at least one such embodiment, the chargeable layer 32570 can comprise conductive electrodes embedded within a polymer, for example. In any event, the statically-charged layer 32570 can attract oppositely-charged particles in the tissue thickness compensator 32580 and hold the tissue thickness compensator 32580 to the anvil. In certain embodiments, referring now to FIG. 567, the chargeable layer 32570 can comprise a grid, or lattice, of conductors 32571 which are in electrical communication with one another. In at least one such embodiment, the conductors can be positioned and arranged such that they surround the staple forming pockets 32562 defined in the anvil 32560. In such embodiments, staples 32530 can be ejected from the staple cartridge 32500 and then deformed by the anvil 32560 without capturing the conductors 32571 therein. In various circumstances, the chargeable layer 32570 can be uncoupled from the power source after the staples 32530 have been engaged with the tissue thickness compensator 32580 such that the electrostatic charge in the layer 32570 can dissipate. In certain other circumstances, the chargeable layer 32570 can be uncoupled from the power source prior to the staples 32530 being fired. In any event, as the electrostatic charge dissipates, the anvil 32560 can be re-opened and the layer 32570 can be moved away from the tissue thickness compensator 32580. In some embodiments, the electrostatic charge may need to dissipate completely before the layer 32570 can be detached from the tissue thickness compensator 32580 while, in other embodiments, the layer 32570 can be detached from the tissue thickness compensator 32580 before the electrostatic charge in the layer 32570 has completely dissipated. In certain embodiments, as a result of the above, the tissue thickness compensator 32580 can be attached to the anvil 32560 without the use of a chemical adhesive.

In various embodiments, further to the above, the layer 32570 can also provide feedback capability to the handle of the surgical stapling instrument. In at least one such embodiment, the layer 32570 can be pressure sensitive and can be configured to detect the clamping pressure being applied thereto by the anvil 32560, for example.

In various embodiments, further to the above, a tissue thickness compensator can be comprised of a biocompatible material. The biocompatible material, such as, a foam, may comprise tackifiers, surfactants, fillers, cross-linkers, pigments, dyes, antioxidants and other stabilizers and/or combinations thereof to provide desired properties to the material. In certain embodiments, a biocompatible foam may comprise a surfactant. The surfactant may be applied to the surface of the material and/or dispersed within the material. Without wishing to be bound to any particular theory, the surfactant applied to the biocompatible material may reduce the surface tension of the fluids contacting the material. For example, the surfactant may reduce the surface tension of water contacting the material to accelerate the penetration of water into the material. In various embodiments, the water may act as a catalyst. The surfactant may increase the hydrophilicity of the material.

In various embodiments, the surfactant may comprise an anionic surfactant, a cationic surfactant, and/or a non-ionic surfactant. Examples surfactants include, but are not limited to polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, and polyoxamers, and combinations thereof. In at least one embodiment, the surfactant may comprise a copolymer of polyethylene glycol and polypropylene glycol. In at least one embodiment, the surfactant may comprise a phospholipid surfactant. The phospholipid surfactant may provide antibacterial stabilizing properties and/or disperse other materials in the biocompatible material. In various embodiments, the tissue thickness compensator may comprise at least one medicament. The tissue thickness compensator may comprise one or more of the natural materials, non-synthetic materials, and/or synthetic materials described herein. In certain embodiments, the tissue thickness compensator may comprise a biocompatible foam comprising gelatin, collagen, hyaluronic acid, oxidized regenerated cellulose, polyglycolic acid, polycaprolactone, polylactic acid, polydioxanone, polyhydroxyalkanoate, poliglecaprone, and combinations thereof. In certain embodiments, the tissue thickness compensator may comprise a film comprising the at least one medicament. In certain embodiments, the tissue thickness compensator may comprise a biodegradable film comprising the at least one medicament. In certain embodiments, the medicament may comprise a liquid, gel, and/or powder. In various embodiments, the medicaments may comprise anticancer agents, such as, for example, cisplatin, mitomycin, and/or adriamycin.

In various embodiments, the tissue thickness compensator may comprise a biodegradable material to provide controlled elution or release of the at least one medicament as the biodegradable material degrades. In various embodiments, the biodegradable material may degrade may decompose, or loses structural integrity, when the biodegradable material contacts an activator, such as, for example an activator fluid. In various embodiments, the activator fluid may comprise saline or any other electrolyte solution, for example. The biodegradable material may contact the activator fluid by conventional techniques, including, but not limited to spraying, dipping, and/or brushing. In use, for example, a surgeon may dip an end effector and/or a staple cartridge comprising the tissue thickness compensator comprising the at least one medicament into an activator fluid comprising a salt solution, such as sodium chloride, calcium chloride, and/or potassium chloride. The tissue thickness compensator may release the medicament as the tissue thickness compensator degrades. In certain embodiments, the elution or release of the medicament from the tissue thickness compensator may be characterized by a rapid initial elution or release rate and a slower sustained elution or release rate.

In various embodiments, a tissue thickness compensator, for example, can be comprised of a biocompatible material which may comprise an oxidizing agent. In various embodiments, the oxidizing agent may be an organic peroxide and/or an inorganic peroxide. Examples of oxidizing agents may include, but are not limited to, hydrogen peroxide, urea peroxide, calcium peroxide, and magnesium peroxide, and sodium percarbonate. In various embodiments, the oxidizing agent may comprise peroxygen-based oxidizing agents and hypohalite-based oxidizing agents, such as, for example, hydrogen peroxide, hypochlorous acid, hypochlorites, hypocodites, and percarbonates. In various embodiments, the oxidizing agent may comprise alkali metal chlorites, hypochlorites and perborates, such as, for example, sodium chlorite, sodium hypochlorite and sodium perborate. In certain embodiments, the oxidizing agent may comprise vanadate. In certain embodiments, the oxidizing agent may comprise ascorbic acid. In certain embodiments, the oxidizing agent may comprise an active oxygen generator. In various embodiments, a tissue scaffold may comprise the biocompatible material comprising an oxidizing agent.

In various embodiments, the biocompatible material may comprise a liquid, gel, and/or powder. In certain embodiments, the oxidizing agent may comprise microparticles and/or nanoparticles, for example. For example, the oxidizing agent may be milled into microparticles and/or nanoparticles. In certain embodiments, the oxidizing agent may be incorporated into the biocompatible material by suspending the oxidizing agent in a polymer solution. In certain embodiments, the oxidizing agent may be incorporated into the biocompatible material during the lyophilization process. After lyophylization, the oxidizing agent may be attached to the cell walls of the biocompatible material to interact with the tissue upon contact. In various embodiments, the oxidizing agent may not be chemically bonded to the biocompatible material. In at least one embodiment, a percarbonate dry power may be embedded within a biocompatible foam to provide a prolonged biological effect by the slow release of oxygen. In at least one embodiment, a percarbonate dry power may be embedded within a polymeric fiber in a non-woven structure to provide a prolonged biological effect by the slow release of oxygen. In various embodiments, the biocompatible material may comprise an oxidizing agent and a medicament, such as, for example, doxycycline and ascorbic acid.

In various embodiments, the biocompatible material may comprise a rapid release oxidizing agent and/or a slower sustained release oxidizing agent. In certain embodiments, the elution or release of the oxidizing agent from the biocompatible material may be characterized by a rapid initial elution or release rate and a slower sustained elution or release rate. In various embodiments, the oxidizing agent may generate oxygen when the oxidizing agent contacts bodily fluid, such as, for example, water. Examples of bodily fluids may include, but are not limited to, blood, plasma, peritoneal fluid, cerebral spinal fluid, urine, lymph fluid, synovial fluid, vitreous fluid, saliva, gastrointestinal luminal contents, and/or bile. Without wishing to be bound to any particular theory, the oxidizing agent may reduce cell death, enhance tissue viability and/or maintain the mechanical strength of the tissue to tissue that may be damaged during cutting and/or stapling.

In various embodiments, the biocompatible material may comprise at least one microparticle and/or nanoparticle. The biocompatible material may comprise one or more of the natural materials, non-synthetic materials, and synthetic materials described herein. In various embodiments, the biocompatible material may comprise particles having a mean diameter of about 10 nm to about 100 nm and/or about 10 µm to about 100 µm, such as, for example, 45-50 nm and/or 45-50 µm. In various embodiments, the biocompatible material may comprise biocompatible foam comprising at least one microparticle and/or nanoparticle embedded therein. The microparticle and/or nanoparticle may not be chemically bonded to the biocompatible material. The microparticle and/or nanoparticle may provide controlled release of the medicament. In certain embodiments, the microparticle and/or nanoparticle may comprise at least one medicament. In certain embodiments, the microparticle and/or nanoparticle may comprise a hemostatic agent, an antimicrobial agent, and/or an oxidizing agent, for example. In certain embodiments, the tissue thickness compensator may comprise a biocompatible foam comprising an hemostatic agent comprising oxidized regenerated cellulose, an antimicrobial agent comprising doxycline and/or Gentamicin, and/or an oxidizing agent comprising a percarbant. In various embodiments, the microparticle and/or nanoparticle may provide controlled release of the medicament up to three days, for example.

In various embodiments, the microparticle and/or nanoparticle may be embedded in the biocompatible material during a manufacturing process. For example, a biocompatible polymer, such as, for example, a PGA/PCL, may contact a solvent, such as, for example, dioxane to form a mixture. The biocompatible polymer may be ground to form particles. Dry particles, with or without ORC particles, may be contacted with the mixture to form a suspension. The suspension may be lyophilized to form a biocompatible foam comprising PGA/PCL having dry particles and/or ORC particles embedded therein.

In various embodiments, the tissue thickness compensators or layers disclosed herein can be comprised of an absorbable polymer, for example. In certain embodiments, a tissue thickness compensator can be comprised of foam, film, fibrous woven, fibrous non-woven PGA, PGA/PCL (Poly(glycolic acid-co-caprolactone)), PLA/PCL (Poly(lactic acid-co-polycaprolactone)), PLLA/PCL, PGA/TMC (Poly(glycolic acid-co-trimethylene carbonate)), PDS, PEPBO or other absorbable polyurethane, polyester, polycarbonate, Polyorthoesters, Polyanhydrides, Polyesteramides, and/or Polyoxaesters, for example. In various embodiments, a tissue thickness compensator can be comprised of PGA/PLA (Poly(glycolic acid-co-lactic acid)) and/or PDS/PLA (Poly(p-dioxanone-co-lactic acid)), for example. In various embodiments, a tissue thickness compensator can be comprised of an organic material, for example. In certain embodiments, a tissue thickness compensator can be comprised of Carboxymethyl Cellulose, Sodium Alginate, Cross-linked Hyaluronic Acid, and/or Oxidized regenerated cellulose, for example. In various embodiments, a tissue thickness compensator can comprise a durometer in the 3-7 Shore A (30-50 Shore OO) ranges with a maximum stiffness of 15 Shore A (65 Shore OO), for example. In certain embodiments, a tissue thickness compensator can undergo 40% compression under 3 lbf load, 60% compression under 6 lbf load, and/or 80% compression under 20 lbf load, for example. In certain embodiments, one or more gasses, such as air, nitrogen, carbon dioxide, and/or oxygen, for example, can be bubbled through and/or contained within the tissue thickness compensator. In at least one embodiment, a tissue thickness compensator can comprise beads therein which comprise between approximately 50% and approximately 75% of the material stiffness comprising the tissue thickness compensator.

In various embodiments, a tissue thickness compensator can comprise hyaluronic acid, nutrients, fibrin, thrombin, platelet rich plasma, Sulfasalazine (Azulfidine®)-5ASA+ Sulfapyridine diazo bond))-prodrug-colonic bacterial (Azoreductase), Mesalamine (5ASA with different prodrug configurations for delayed release), Asacol® (5ASA+Eudragit-S coated—pH>7 (coating dissolution)), Pentasa® (5ASA+ethylcellulose coated—time/pH dependent slow release), Mesasal® (5ASA+Eudragit-L coated—pH>6), Olsalazine (5ASA+5ASA—colonic bacterial (Azoreductase)), Balsalazide (5ASA+4Aminobenzoyl-B-alanine)-colonic bacterial (Azoreductase)), Granulated mesalamine, Lialda (delay and SR formulation of mesalamine), HMPL-004 (herbal mixture that may inhibit TNF-alpha, interleukin-1 beta, and nuclear-kappa B activation), CCX282-B (oral chemokine receptor antagonist that interferes with trafficking of T lymphocytes into the intestinal mucosa), Rifaximin (nonabsorbable broad-spectrum antibiotic), Infliximab, murine chymieric (monoclonal antibody directed against TNF-alpha-approved for reducing signs/symptoms and maintaining clinical remission in adult/pediatric patients with moderate/severe luminal and fistulizing Crohn's disease who have had inadequate response to conventional therapy), Adalimumab, Total Human IgG1 (anti-TNF-alpha monoclonal antibody—approved for reducing signs/symptoms of Crohn's disease, and for the induction and maintenance of clinical remission in adult patients with moderate/severe active Crohn's disease with inadequate response to conventional therapies, or who become intolerant to Infliximab), Certolizumab pegoll, humanized anti-TNF FAB' (monoclonal antibody fragment linked to polyethylene glycol—approved for reducing signs/symptoms of Crohn's disease and for the induction and maintenance of response in adult patients w/moderate/severe disease with inadequate response to conventional therapies), Natalizumab, First non-TNF-alpha inhibitor (biologic compound approved for Crohn's disease), Humanized monoclonal IgG4 antibody (directed against alpha-4 integrin—FDA approved for inducing and maintaining clinical response and remission in patients with moderate/severe disease with evidence of inflammation and who have had inadequate response to or are unable to tolerate conventional Crohn's therapies and inhibitors of TNF-alpha), concomitant Immunomodulators potentially given with Infliximab, Azathioprine 6-Mercaptopurine (purine synthesis inhibitor—prodrug), Methotrexate (binds dihydrofolate reductase (DHFR) enzyme that participates in tetrahydrofolate synthesis, inhibits all purine synthesis), Allopurinol and Thioprine therapy, PPI, H2 for acid suppression to protect the healing line, C-Diff—Flagyl, Vancomycin (fecal translocation treatment; probiotics; repopulation of normal endoluminal flora), and/or Rifaximin (treatment of bacterial overgrowth (notably hepatic encephalopathy); not absorbed in GI tract with action on intraluminal bacteria), for example.

As described herein, a tissue thickness compensator can compensate for variations in the thickness of tissue that is captured within the staples ejected from a staple cartridge and/or contained within a staple line, for example. Stated another way, certain staples within a staple line can capture thick portions of the tissue while other staples within the staple line can capture thin portions of the tissue. In such circumstances, the tissue thickness compensator can assume different heights or thicknesses within the staples and apply a compressive force to the tissue captured within the staples regardless of whether the captured tissue is thick or thin. In various embodiments, a tissue thickness compensator can compensate for variations in the hardness of the tissue. For instance, certain staples within a staple line can capture highly compressible portions of the tissue while other staples within the staple line can capture portions of the tissue which are less compressible. In such circumstances, the tissue thickness compensator can be configured to assume a smaller height within the staples that have captured tissue having a lower compressibility, or higher hardness, and, correspondingly, a larger height within the staples that have captured tissue having a higher compressibility, or lower hardness, for example. In any event, a tissue thickness compensator, regardless of whether it compensates for variations in tissue thickness and/or variations in tissue hardness, for example, can be referred to as a 'tissue compensator' and/or as a 'compensator', for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An implantable layer for use with a surgical stapler, the implantable layer comprising:
   a first layer comprising a first side, wherein the first side comprises an opening;
   a second layer comprising a second side, wherein the second side extends at least partially through the opening to hold the second layer relative to the first layer, and wherein a pocket is defined between the first layer and the second layer; and
   a bioabsorbable material in the pocket.

2. The implantable layer of claim 1, wherein the surgical stapler comprises a jaw comprising a longitudinal slot, wherein the implantable layer further comprises a longitudinal ridge extending from the first layer, and wherein the longitudinal ridge is receivable by the longitudinal slot of the jaw to align the implantable layer with the jaw.

3. The implantable layer of claim 2, wherein the first side of the first layer comprises a flange to at least partially wrap around an outer surface of the jaw to attach the implantable layer to the jaw.

4. The implantable layer of claim 3, wherein the jaw comprises a longitudinal groove defined in the outer surface, and wherein at least a portion of the flange is receivable in the longitudinal groove.

5. The implantable layer of claim 3, wherein the opening comprises a slot extending through the flange, and wherein the second side comprises a tab insertable into the slot.

6. The implantable layer of claim 1, wherein the opening comprises an orifice extending through the first side of the first layer, and wherein the second side comprises an anchor insertable into the orifice.

7. The implantable layer of claim 6, wherein the surgical stapler comprises a jaw, and wherein the anchor is insertable through the orifice to at least partially wrap around an outer surface of the jaw.

8. The implantable layer of claim 1, wherein the surgical stapler comprises an anvil, wherein the anvil comprises a stepped staple forming surface, and wherein the first layer comprises a stepped profile that complements the stepped staple forming surface.

9. The implantable layer of claim 1, wherein the second layer comprises a latch movable between an open position and a closed position, and wherein the bioabsorbable material is insertable into the pocket when the latch is in the open position.

10. The implantable layer of claim 1, wherein the bioabsorbable material comprises a polyurethane-based foam.

11. A surgical stapling system, comprising:
an end effector comprising a jaw; and
an implantable layer attachable to the jaw, wherein the implantable layer comprises:
a first layer comprising a first side, wherein the first side comprises an opening;
a second layer comprising a second side, wherein the second side extends at least partially through the opening to hold the second layer relative to the first layer, and wherein a pocket is defined between the first layer and the second layer; and
a bioabsorbable material in the pocket.

12. The surgical stapling system of claim 11, wherein the jaw comprises a longitudinal slot, wherein the implantable layer further comprises a longitudinal ridge extending from the first layer, and wherein the longitudinal ridge is receivable by the longitudinal slot of the jaw to align the implantable layer with the jaw.

13. The surgical stapling system of claim 12, wherein the second layer comprises a latch movable between an open position and a closed position, and wherein the bioabsorbable material is insertable into the pocket when the latch is in the open position.

14. The surgical stapling system of claim 11, wherein the first side of the first layer comprises a flange to at least partially wrap around an outer surface of the jaw to attach the implantable layer to the jaw.

15. The surgical stapling system of claim 14, wherein the jaw comprises a longitudinal groove defined in the outer surface, and wherein at least a portion of the flange is receivable in the longitudinal groove.

16. The surgical stapling system of claim 15, wherein the opening comprises a slot extending through the flange, and wherein the second side comprises a tab insertable into the slot.

17. The surgical stapling system of claim 11, wherein the opening comprises an orifice extending through the first side of the first layer, and wherein the second side comprises an anchor insertable into the orifice.

18. The stapling surgical system of claim 17, wherein the anchor is insertable through the orifice to at least partially wrap around an outer surface of the jaw.

19. The surgical stapling system of claim 11, wherein the jaw comprises an anvil comprising a stepped staple forming surface, and wherein the first layer comprises a stepped profile that compliments the stepped staple forming surface.

20. An implantable layer attachable to a jaw of a surgical stapling device, the implantable layer comprising:
a first layer comprising a first side, wherein the first side comprises an opening;
a second layer comprising a second side; and
a connection interface, wherein the second side extends at least partially through the opening at the connection interface to hold the second layer relative to the first layer, and wherein a pocket is defined between the first layer and the second layer.

* * * * *